(12) United States Patent
Evdokimov et al.

(10) Patent No.: US 7,507,568 B2
(45) Date of Patent: Mar. 24, 2009

(54) THREE DIMENSIONAL COORDINATES OF HPTPBETA

(75) Inventors: Artem Gennady Evdokimov, Loveland, OH (US); Matthew Eugene Pokross, Loveland, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 193 days.

(21) Appl. No.: 10/634,027

(22) Filed: Aug. 4, 2003

(65) Prior Publication Data

US 2004/0077065 A1 Apr. 22, 2004

Related U.S. Application Data

(60) Provisional application No. 60/413,547, filed on Sep. 25, 2002.

(51) Int. Cl.
*C12N 9/14* (2006.01)
*G01N 31/00* (2006.01)
(52) U.S. Cl. ............................. 435/195; 436/4
(58) Field of Classification Search ............... None
See application file for complete search history.

(56) References Cited

U.S. PATENT DOCUMENTS

| 6,589,758 B1 | 7/2003 | Zhu |
| 2004/0204863 A1 | 10/2004 | Kim et al. |

FOREIGN PATENT DOCUMENTS

| WO | WO 00/65085 A1 | 11/2000 |
| WO | WO 00/65088 | 11/2000 |
| WO | WO 02/26774 A2 | 4/2002 |

OTHER PUBLICATIONS

Cohen et al. Molecular Modeling Software and Methods for Medicinal Chemistry. J. Med. Chem. 1990, 33 (3), 883-894.*
Dean et al. BioEssays, 1994, 16(9):683-687.*
Bartlett et al., "Molecular Recognition in Chemical and Biological Problems," Special Pub., Royal Chem. Soc., 78, 182-196 Caveat: A Program to Facilitate the Structure-derived Design of Biologically Active Molecules (Apr. 1989).
Böhm, "The Computer Program LUDI: A New Method for the Novo Design of Enzyme Inhibitors," *J. Computer-Aided Molecular Design*, 6:61-78 (1992).
Goodford, "A Computational Procedure for Determining Energetically Favorable Binding Sites on Biologically Important Macromolecules," *J. Med. Chem.*, 28(7):849-857 (1985).
Goodsell et al., "Automated Docking of Substrates to Proteins by Simulated Annealing," *Proteins: Structure, Function and Genetics*, 8:195-202 (1990).
Jones et al., "Molecular Recognition of Receptor Sites Using a Genetic Algorithm with a Description of Desolvation," *J. Mol. Biol.*, 245:43-53 (1995).
Kruegar et al., "Structural Diversity and Evolution of Human Receptor-Like Portein Tyrosine Phosphatases," *EMBO Journal*, 9(10):3241-3252 (1990).
Kuntz et al., "A Geometric Approach to Macromolecule—Ligand Interactions," *J. Mol. Biol.*, 161:269-288 (1982).
Martin, "3D Database Searching in Drug Design," *J. Med. Chem.*, 35(12):2145-2154 (1992).
Miranker et al., "Functionality Maps of Binding Sites: A Multiple Copy Simultaneous Search Method," *Proteins: Structure, Function and Genetics*, 11:29-34 (1991).
Navaza, "AMoRe: An Automated Package for Molecular Replacement," *Acta Cryst.* A50:157-163 (1994).
Nishibata et al., "Automatic Creation of Drug Candidate Structures Based on Receptor Structure. Starting Point for Artificial Lead Generation," *Tetrahedron*, 47(43):8985-8990 (1991).
Collaborative Computational Project, No. 4, "The CCP4 Suite: Programs for Prtein Crystallography," *Acta Cryst.*, D50:760-763 (1994).

* cited by examiner

*Primary Examiner*—Suzanne M. Noakes
(74) *Attorney, Agent, or Firm*—Ballard Spahr Andrews & Ingersoll, LLP

(57) ABSTRACT

The crystal structures of catalytic domain of HPTPbeta, both ligand-bound and ligan-free are described. These structures are useful in computer aided drug design for identifying compounds that bind or activate HPTPbeta and thereby modulate angiogenesis mediated disorders or diseases.

10 Claims, 304 Drawing Sheets

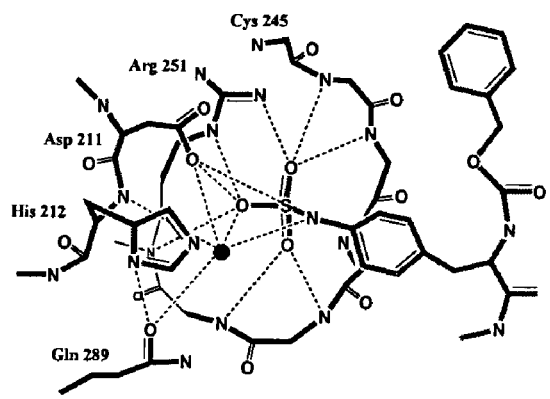
(a)
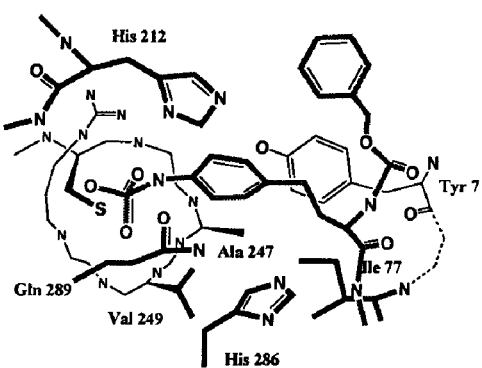
(b)
FIGURE 4

| | | | | | | | | | |
|---|---|---|---|---|---|---|---|---|---|
| CRYST1 | | 61.890 | | 71.535 | 70.345 | 90.00 | 93.25 | 90.00 | |
| ATOM | 1 | N | LYS | A | 19 | 12.885 | 20.303 | 21.460 | 1.000106.97 |
| ATOM | 2 | CA | LYS | A | 19 | 12.939 | 19.537 | 20.223 | 1.000 85.75 |
| ATOM | 3 | CB | LYS | A | 19 | 13.192 | 20.422 | 19.007 | 1.000 87.72 |
| ATOM | 4 | CG | LYS | A | 19 | 11.902 | 20.923 | 18.320 | 1.000 95.27 |
| ATOM | 5 | CD | LYS | A | 19 | 12.014 | 20.782 | 16.801 | 1.000 99.48 |
| ATOM | 6 | CE | LYS | A | 19 | 10.663 | 21.012 | 16.143 | 1.000100.17 |
| ATOM | 7 | NZ | LYS | A | 19 | 10.303 | 22.523 | 16.035 | 1.000102.13 |
| ATOM | 8 | C | LYS | A | 19 | 14.027 | 18.457 | 20.298 | 1.000 78.84 |
| ATOM | 9 | O | LYS | A | 19 | 15.217 | 18.783 | 20.327 | 1.000 93.11 |
| ATOM | 10 | N | THR | A | 20 | 13.573 | 17.224 | 20.310 | 1.000 69.90 |
| ATOM | 11 | CA | THR | A | 20 | 14.257 | 15.957 | 20.169 | 1.000 59.58 |
| ATOM | 12 | CB | THR | A | 20 | 13.713 | 15.258 | 18.900 | 1.000 45.21 |
| ATOM | 13 | OG1 | THR | A | 20 | 14.633 | 14.309 | 18.358 | 1.000 57.38 |
| ATOM | 14 | CG2 | THR | A | 20 | 13.489 | 16.286 | 17.795 | 1.000 64.36 |
| ATOM | 15 | C | THR | A | 20 | 15.771 | 16.101 | 20.107 | 1.000 59.34 |
| ATOM | 16 | O | THR | A | 20 | 16.304 | 16.833 | 19.272 | 1.000 83.31 |
| ATOM | 17 | N | SER | A | 21 | 16.471 | 15.408 | 20.994 | 1.000 53.48 |
| ATOM | 18 | CA | SER | A | 21 | 17.903 | 15.206 | 20.988 | 1.000 46.96 |
| ATOM | 19 | CB | SER | A | 21 | 18.353 | 14.742 | 19.581 | 1.000 47.66 |
| ATOM | 20 | OG | SER | A | 21 | 19.770 | 14.620 | 19.599 | 1.000 58.97 |
| ATOM | 21 | C | SER | A | 21 | 18.784 | 16.398 | 21.346 | 1.000 41.17 |
| ATOM | 22 | O | SER | A | 21 | 18.538 | 17.534 | 20.963 | 1.000 47.65 |
| ATOM | 23 | N | CYS | A | 22 | 19.843 | 16.085 | 22.080 | 1.000 41.72 |
| ATOM | 24 | CA | CYS | A | 22 | 20.898 | 16.977 | 22.509 | 1.000 43.91 |
| ATOM | 25 | CB | CYS | A | 22 | 20.566 | 17.726 | 23.798 | 1.000 41.39 |
| ATOM | 26 | SG | CYS | A | 22 | 19.635 | 19.259 | 23.584 | 1.000109.59 |
| ATOM | 27 | C | CYS | A | 22 | 22.183 | 16.174 | 22.752 | 1.000 37.65 |
| ATOM | 28 | O | CYS | A | 22 | 22.505 | 15.999 | 23.925 | 1.000 36.88 |
| ATOM | 29 | N | PRO | A | 23 | 22.822 | 15.731 | 21.680 | 1.000 42.64 |
| ATOM | 30 | CA | PRO | A | 23 | 24.007 | 14.873 | 21.736 | 1.000 46.23 |
| ATOM | 31 | CB | PRO | A | 23 | 24.238 | 14.461 | 20.277 | 1.000 45.02 |
| ATOM | 32 | CG | PRO | A | 23 | 23.012 | 14.867 | 19.533 | 1.000 44.64 |
| ATOM | 33 | CD | PRO | A | 23 | 22.447 | 16.037 | 20.280 | 1.000 45.34 |
| ATOM | 34 | C | PRO | A | 23 | 25.254 | 15.595 | 22.253 | 1.000 49.52 |
| ATOM | 35 | O | PRO | A | 23 | 25.409 | 16.802 | 22.079 | 1.000 43.06 |
| ATOM | 36 | N | ILE | A | 24 | 26.145 | 14.847 | 22.897 | 1.000 50.39 |
| ATOM | 37 | CA | ILE | A | 24 | 27.396 | 15.350 | 23.436 | 1.000 45.58 |
| ATOM | 38 | CB | ILE | A | 24 | 27.299 | 15.718 | 24.926 | 1.000 45.32 |
| ATOM | 39 | CG1 | ILE | A | 24 | 26.035 | 16.480 | 25.330 | 1.000 43.71 |
| ATOM | 40 | CD1 | ILE | A | 24 | 25.222 | 15.741 | 26.376 | 1.000 43.61 |
| ATOM | 41 | CG2 | ILE | A | 24 | 28.545 | 16.488 | 25.350 | 1.000 57.16 |
| ATOM | 42 | C | ILE | A | 24 | 28.517 | 14.327 | 23.296 | 1.000 43.32 |
| ATOM | 43 | O | ILE | A | 24 | 28.322 | 13.140 | 23.537 | 1.000 46.87 |
| ATOM | 44 | N | LYS | A | 25 | 29.713 | 14.766 | 22.907 | 1.000 49.84 |
| ATOM | 45 | CA | LYS | A | 25 | 30.820 | 13.808 | 22.815 | 1.000 50.13 |
| ATOM | 46 | CB | LYS | A | 25 | 31.917 | 14.375 | 21.922 | 1.000 59.09 |
| ATOM | 47 | CG | LYS | A | 25 | 31.444 | 14.757 | 20.527 | 1.000 65.03 |
| ATOM | 48 | CD | LYS | A | 25 | 32.307 | 14.074 | 19.471 | 1.000 71.18 |
| ATOM | 49 | CE | LYS | A | 25 | 31.469 | 13.255 | 18.493 | 1.000 72.46 |
| ATOM | 50 | NZ | LYS | A | 25 | 32.328 | 12.452 | 17.576 | 1.000 73.47 |
| ATOM | 51 | C | LYS | A | 25 | 31.346 | 13.486 | 24.204 | 1.000 52.08 |

FIGURE 7

| | | | | | | | | | |
|---|---|---|---|---|---|---|---|---|---|
| ATOM | 52 | O | LYS | A | 25 | 31.294 | 14.340 | 25.095 | 1.000 53.68 |
| ATOM | 53 | N | ILE | A | 26 | 31.849 | 12.274 | 24.434 | 1.000 52.14 |
| ATOM | 54 | CA | ILE | A | 26 | 32.275 | 11.942 | 25.793 | 1.000 63.74 |
| ATOM | 55 | CB | ILE | A | 26 | 32.817 | 10.504 | 25.904 | 1.000 65.16 |
| ATOM | 56 | CG1 | ILE | A | 26 | 34.316 | 10.370 | 25.624 | 1.000 65.92 |
| ATOM | 57 | CD1 | ILE | A | 26 | 34.847 | 8.970 | 25.852 | 1.000 69.50 |
| ATOM | 58 | CG2 | ILE | A | 26 | 32.016 | 9.561 | 25.016 | 1.000 68.17 |
| ATOM | 59 | C | ILE | A | 26 | 33.335 | 12.911 | 26.307 | 1.000 70.34 |
| ATOM | 60 | O | ILE | A | 26 | 33.411 | 13.146 | 27.515 | 1.000 67.42 |
| ATOM | 61 | N | ASN | A | 27 | 34.141 | 13.465 | 25.406 | 1.000 74.12 |
| ATOM | 62 | CA | ASN | A | 27 | 35.231 | 14.350 | 25.799 | 1.000 78.44 |
| ATOM | 63 | CB | ASN | A | 27 | 36.116 | 14.679 | 24.588 | 1.000 86.40 |
| ATOM | 64 | CG | ASN | A | 27 | 36.877 | 15.980 | 24.768 | 1.000 90.22 |
| ATOM | 65 | OD1 | ASN | A | 27 | 37.854 | 16.044 | 25.515 | 1.000 84.42 |
| ATOM | 66 | ND2 | ASN | A | 27 | 36.432 | 17.033 | 24.084 | 1.000 85.29 |
| ATOM | 67 | C | ASN | A | 27 | 34.740 | 15.649 | 26.423 | 1.000 75.19 |
| ATOM | 68 | O | ASN | A | 27 | 35.473 | 16.309 | 27.170 | 1.000 89.55 |
| ATOM | 69 | N | GLN | A | 28 | 33.507 | 16.048 | 26.126 | 1.000 67.31 |
| ATOM | 70 | CA | GLN | A | 28 | 33.008 | 17.350 | 26.550 | 1.000 57.01 |
| ATOM | 71 | CB | GLN | A | 28 | 32.497 | 18.097 | 25.313 | 1.000 54.35 |
| ATOM | 72 | CG | GLN | A | 28 | 32.204 | 19.571 | 25.517 | 1.000 59.01 |
| ATOM | 73 | CD | GLN | A | 28 | 32.233 | 20.351 | 24.213 | 1.000 66.07 |
| ATOM | 74 | OE1 | GLN | A | 28 | 31.315 | 21.121 | 23.907 | 1.000 69.78 |
| ATOM | 75 | NE2 | GLN | A | 28 | 33.291 | 20.154 | 23.427 | 1.000 81.02 |
| ATOM | 76 | C | GLN | A | 28 | 31.894 | 17.263 | 27.581 | 1.000 51.77 |
| ATOM | 77 | O | GLN | A | 28 | 31.322 | 18.300 | 27.939 | 1.000 55.71 |
| ATOM | 78 | N | PHE | A | 29 | 31.566 | 16.061 | 28.051 | 1.000 50.17 |
| ATOM | 79 | CA | PHE | A | 29 | 30.395 | 15.896 | 28.910 | 1.000 48.12 |
| ATOM | 80 | CB | PHE | A | 29 | 29.984 | 14.424 | 29.031 | 1.000 47.45 |
| ATOM | 81 | CG | PHE | A | 29 | 28.679 | 14.209 | 29.760 | 1.000 51.71 |
| ATOM | 82 | CD1 | PHE | A | 29 | 27.473 | 14.198 | 29.076 | 1.000 47.01 |
| ATOM | 83 | CE1 | PHE | A | 29 | 26.272 | 14.005 | 29.732 | 1.000 44.54 |
| ATOM | 84 | CZ | PHE | A | 29 | 26.254 | 13.826 | 31.104 | 1.000 53.70 |
| ATOM | 85 | CE2 | PHE | A | 29 | 27.448 | 13.826 | 31.808 | 1.000 58.73 |
| ATOM | 86 | CD2 | PHE | A | 29 | 28.641 | 14.016 | 31.134 | 1.000 58.31 |
| ATOM | 87 | C | PHE | A | 29 | 30.633 | 16.505 | 30.293 | 1.000 48.21 |
| ATOM | 88 | O | PHE | A | 29 | 29.805 | 17.313 | 30.723 | 1.000 51.21 |
| ATOM | 89 | N | GLU | A | 30 | 31.725 | 16.100 | 30.932 | 1.000 50.97 |
| ATOM | 90 | CA | GLU | A | 30 | 32.118 | 16.617 | 32.243 | 1.000 40.77 |
| ATOM | 91 | CB | GLU | A | 30 | 33.518 | 16.157 | 32.627 | 1.000 48.14 |
| ATOM | 92 | CG | GLU | A | 30 | 33.957 | 16.520 | 34.038 | 1.000 61.37 |
| ATOM | 93 | CD | GLU | A | 30 | 34.375 | 15.319 | 34.871 | 1.000 63.56 |
| ATOM | 94 | OE1 | GLU | A | 30 | 34.907 | 14.350 | 34.287 | 1.000 58.37 |
| ATOM | 95 | OE2 | GLU | A | 30 | 34.180 | 15.327 | 36.108 | 1.000 52.10 |
| ATOM | 96 | C | GLU | A | 30 | 32.029 | 18.136 | 32.196 | 1.000 42.41 |
| ATOM | 97 | O | GLU | A | 30 | 31.394 | 18.780 | 33.026 | 1.000 53.55 |
| ATOM | 98 | N | GLY | A | 31 | 32.650 | 18.719 | 31.167 | 1.000 41.84 |
| ATOM | 99 | CA | GLY | A | 31 | 32.510 | 20.160 | 31.001 | 1.000 40.41 |
| ATOM | 100 | C | GLY | A | 31 | 31.063 | 20.531 | 30.754 | 1.000 48.99 |
| ATOM | 101 | O | GLY | A | 31 | 30.515 | 21.443 | 31.373 | 1.000 50.79 |
| ATOM | 102 | N | HIS | A | 32 | 30.407 | 19.821 | 29.826 | 1.000 45.73 |
| ATOM | 103 | CA | HIS | A | 32 | 29.036 | 20.224 | 29.519 | 1.000 40.05 |

FIGURE 8

```
ATOM    104  CB   HIS A  32      28.481  19.370  28.368  1.000  44.33
ATOM    105  CG   HIS A  32      26.991  19.509  28.268  1.000  46.74
ATOM    106  ND1  HIS A  32      26.393  20.629  27.736  1.000  49.67
ATOM    107  CE1  HIS A  32      25.081  20.489  27.779  1.000  47.50
ATOM    108  NE2  HIS A  32      24.803  19.318  28.328  1.000  46.49
ATOM    109  CD2  HIS A  32      25.985  18.688  28.642  1.000  48.61
ATOM    110  C    HIS A  32      28.128  20.126  30.738  1.000  36.48
ATOM    111  O    HIS A  32      27.213  20.935  30.894  1.000  47.25
ATOM    112  N    PHE A  33      28.355  19.146  31.611  1.000  37.04
ATOM    113  CA   PHE A  33      27.466  18.940  32.760  1.000  45.61
ATOM    114  CB   PHE A  33      27.679  17.531  33.322  1.000  44.57
ATOM    115  CG   PHE A  33      26.836  17.160  34.514  1.000  38.23
ATOM    116  CD1  PHE A  33      25.506  17.531  34.598  1.000  30.80
ATOM    117  CE1  PHE A  33      24.748  17.191  35.702  1.000  28.41
ATOM    118  CZ   PHE A  33      25.308  16.468  36.737  1.000  30.68
ATOM    119  CE2  PHE A  33      26.635  16.088  36.669  1.000  27.11
ATOM    120  CD2  PHE A  33      27.378  16.436  35.564  1.000  28.82
ATOM    121  C    PHE A  33      27.652  19.998  33.837  1.000  49.01
ATOM    122  O    PHE A  33      26.723  20.391  34.548  1.000  35.78
ATOM    123  N    MET A  34      28.873  20.503  33.990  1.000  55.36
ATOM    124  CA   MET A  34      29.145  21.595  34.918  1.000  48.73
ATOM    125  CB   MET A  34      30.612  22.002  34.804  1.000  50.55
ATOM    126  CG   MET A  34      31.589  20.956  35.319  1.000  44.00
ATOM    127  SD   MET A  34      31.900  21.178  37.082  1.000  69.37
ATOM    128  CE   MET A  34      32.522  19.553  37.528  1.000 157.91
ATOM    129  C    MET A  34      28.257  22.797  34.629  1.000  45.46
ATOM    130  O    MET A  34      27.672  23.409  35.524  1.000  51.08
ATOM    131  N    LYS A  35      28.169  23.133  33.343  1.000  42.34
ATOM    132  CA   LYS A  35      27.337  24.249  32.905  1.000  41.76
ATOM    133  CB   LYS A  35      27.357  24.341  31.387  1.000  48.16
ATOM    134  CG   LYS A  35      28.744  24.409  30.774  1.000  54.19
ATOM    135  CD   LYS A  35      28.745  25.343  29.558  1.000  56.45
ATOM    136  CE   LYS A  35      27.969  26.621  29.849  1.000  59.03
ATOM    137  NZ   LYS A  35      26.532  26.499  29.466  1.000  63.17
ATOM    138  C    LYS A  35      25.902  24.093  33.401  1.000  52.49
ATOM    139  O    LYS A  35      25.341  25.000  34.019  1.000  58.86
ATOM    140  N    LEU A  36      25.323  22.927  33.122  1.000  45.81
ATOM    141  CA   LEU A  36      23.967  22.608  33.538  1.000  38.58
ATOM    142  CB   LEU A  36      23.651  21.126  33.313  1.000  45.57
ATOM    143  CG   LEU A  36      23.288  20.682  31.901  1.000  50.85
ATOM    144  CD1  LEU A  36      24.233  21.277  30.870  1.000  57.32
ATOM    145  CD2  LEU A  36      23.292  19.159  31.799  1.000  59.71
ATOM    146  C    LEU A  36      23.753  22.921  35.011  1.000  35.30
ATOM    147  O    LEU A  36      22.857  23.679  35.382  1.000  53.13
ATOM    148  N    GLN A  37      24.585  22.311  35.857  1.000  36.39
ATOM    149  CA   GLN A  37      24.427  22.527  37.292  1.000  46.18
ATOM    150  CB   GLN A  37      25.238  21.504  38.085  1.000  56.71
ATOM    151  CG   GLN A  37      26.311  20.782  37.289  1.000  59.65
ATOM    152  CD   GLN A  37      26.681  19.440  37.891  1.000  59.86
ATOM    153  OE1  GLN A  37      27.412  18.655  37.285  1.000  76.78
ATOM    154  NE2  GLN A  37      26.190  19.165  39.092  1.000  59.17
ATOM    155  C    GLN A  37      24.844  23.938  37.696  1.000  53.32
```

FIGURE 9

| | | | | | | | | | |
|---|---|---|---|---|---|---|---|---|---|
| ATOM | 156 | O | GLN | A | 37 | 24.407 | 24.448 | 38.730 | 1.000 47.35 |
| ATOM | 157 | N | ALA | A | 38 | 25.684 | 24.560 | 36.876 | 1.000 58.65 |
| ATOM | 158 | CA | ALA | A | 38 | 26.173 | 25.905 | 37.151 | 1.000 68.20 |
| ATOM | 159 | CB | ALA | A | 38 | 27.038 | 26.387 | 35.992 | 1.000 88.29 |
| ATOM | 160 | C | ALA | A | 38 | 25.055 | 26.906 | 37.416 | 1.000 68.67 |
| ATOM | 161 | O | ALA | A | 38 | 24.003 | 26.933 | 36.777 | 1.000 57.74 |
| ATOM | 162 | N | ASP | A | 39 | 25.301 | 27.778 | 38.394 | 1.000 72.20 |
| ATOM | 163 | CA | ASP | A | 39 | 24.314 | 28.796 | 38.736 | 1.000 74.27 |
| ATOM | 164 | CB | ASP | A | 39 | 23.909 | 29.628 | 37.527 | 1.000 85.74 |
| ATOM | 165 | CG | ASP | A | 39 | 25.044 | 30.402 | 36.878 | 1.000 97.59 |
| ATOM | 166 | OD1 | ASP | A | 39 | 24.958 | 30.635 | 35.641 | 1.000113.10 |
| ATOM | 167 | OD2 | ASP | A | 39 | 26.039 | 30.750 | 37.574 | 1.000105.88 |
| ATOM | 168 | C | ASP | A | 39 | 23.087 | 28.123 | 39.343 | 1.000 66.70 |
| ATOM | 169 | O | ASP | A | 39 | 21.999 | 28.689 | 39.281 | 1.000 73.27 |
| ATOM | 170 | N | SER | A | 40 | 23.298 | 26.947 | 39.907 | 1.000 64.44 |
| ATOM | 171 | CA | SER | A | 40 | 22.275 | 26.159 | 40.578 | 1.000 64.68 |
| ATOM | 172 | CB | SER | A | 40 | 21.396 | 27.050 | 41.465 | 1.000 55.65 |
| ATOM | 173 | OG | SER | A | 40 | 22.105 | 28.171 | 41.962 | 1.000 78.01 |
| ATOM | 174 | C | SER | A | 40 | 21.376 | 25.400 | 39.603 | 1.000 62.90 |
| ATOM | 175 | O | SER | A | 40 | 20.184 | 25.716 | 39.507 | 1.000 51.42 |
| ATOM | 176 | N | ASN | A | 41 | 21.912 | 24.422 | 38.883 | 1.000 60.85 |
| ATOM | 177 | CA | ASN | A | 41 | 21.172 | 23.654 | 37.894 | 1.000 61.49 |
| ATOM | 178 | CB | ASN | A | 41 | 20.165 | 22.694 | 38.532 | 1.000 61.83 |
| ATOM | 179 | CG | ASN | A | 41 | 20.762 | 21.620 | 39.402 | 1.000 69.08 |
| ATOM | 180 | OD1 | ASN | A | 41 | 21.917 | 21.225 | 39.250 | 1.000 80.40 |
| ATOM | 181 | ND2 | ASN | A | 41 | 19.957 | 21.130 | 40.339 | 1.000 78.07 |
| ATOM | 182 | C | ASN | A | 41 | 20.361 | 24.555 | 36.966 | 1.000 67.15 |
| ATOM | 183 | O | ASN | A | 41 | 19.289 | 24.130 | 36.528 | 1.000 80.59 |
| ATOM | 184 | N | TYR | A | 42 | 20.825 | 25.767 | 36.685 | 1.000 63.68 |
| ATOM | 185 | CA | TYR | A | 42 | 19.955 | 26.712 | 35.995 | 1.000 58.60 |
| ATOM | 186 | CB | TYR | A | 42 | 20.581 | 28.109 | 35.929 | 1.000 62.78 |
| ATOM | 187 | CG | TYR | A | 42 | 19.713 | 29.057 | 35.134 | 1.000 60.11 |
| ATOM | 188 | CD1 | TYR | A | 42 | 18.414 | 29.333 | 35.553 | 1.000 62.46 |
| ATOM | 189 | CE1 | TYR | A | 42 | 17.603 | 30.195 | 34.844 | 1.000 61.51 |
| ATOM | 190 | CZ | TYR | A | 42 | 18.099 | 30.785 | 33.705 | 1.000 62.86 |
| ATOM | 191 | OH | TYR | A | 42 | 17.300 | 31.648 | 32.990 | 1.000 84.83 |
| ATOM | 192 | CE2 | TYR | A | 42 | 19.378 | 30.523 | 33.263 | 1.000 60.46 |
| ATOM | 193 | CD2 | TYR | A | 42 | 20.186 | 29.658 | 33.976 | 1.000 59.75 |
| ATOM | 194 | C | TYR | A | 42 | 19.631 | 26.234 | 34.584 | 1.000 44.43 |
| ATOM | 195 | O | TYR | A | 42 | 18.468 | 26.109 | 34.216 | 1.000 44.77 |
| ATOM | 196 | N | LEU | A | 43 | 20.701 | 25.982 | 33.847 | 1.000 40.94 |
| ATOM | 197 | CA | LEU | A | 43 | 20.603 | 25.447 | 32.499 | 1.000 53.15 |
| ATOM | 198 | CB | LEU | A | 43 | 21.973 | 25.359 | 31.837 | 1.000 60.19 |
| ATOM | 199 | CG | LEU | A | 43 | 22.899 | 26.570 | 31.920 | 1.000 67.43 |
| ATOM | 200 | CD1 | LEU | A | 43 | 23.839 | 26.600 | 30.724 | 1.000 71.66 |
| ATOM | 201 | CD2 | LEU | A | 43 | 22.126 | 27.871 | 32.003 | 1.000 79.71 |
| ATOM | 202 | C | LEU | A | 43 | 19.934 | 24.068 | 32.542 | 1.000 55.94 |
| ATOM | 203 | O | LEU | A | 43 | 18.895 | 23.893 | 31.904 | 1.000 56.22 |
| ATOM | 204 | N | LEU | A | 44 | 20.523 | 23.138 | 33.277 | 1.000 55.33 |
| ATOM | 205 | CA | LEU | A | 44 | 20.043 | 21.785 | 33.466 | 1.000 57.43 |
| ATOM | 206 | CB | LEU | A | 44 | 20.668 | 21.151 | 34.719 | 1.000 58.28 |
| ATOM | 207 | CG | LEU | A | 44 | 20.333 | 19.672 | 34.935 | 1.000 58.45 |

FIGURE 10

| | | | | | | | | | |
|---|---|---|---|---|---|---|---|---|---|
| ATOM | 208 | CD1 | LEU | A | 44 | 21.583 | 18.890 | 35.306 | 1.000 66.34 |
| ATOM | 209 | CD2 | LEU | A | 44 | 19.259 | 19.509 | 35.999 | 1.000 64.52 |
| ATOM | 210 | C | LEU | A | 44 | 18.522 | 21.721 | 33.618 | 1.000 58.45 |
| ATOM | 211 | O | LEU | A | 44 | 17.875 | 20.876 | 33.005 | 1.000 62.57 |
| ATOM | 212 | N | SER | A | 45 | 18.022 | 22.636 | 34.428 | 1.000 58.88 |
| ATOM | 213 | CA | SER | A | 45 | 16.634 | 22.760 | 34.841 | 1.000 54.60 |
| ATOM | 214 | CB | SER | A | 45 | 16.564 | 23.645 | 36.093 | 1.000 50.24 |
| ATOM | 215 | OG | SER | A | 45 | 15.228 | 23.927 | 36.463 | 1.000 55.87 |
| ATOM | 216 | C | SER | A | 45 | 15.745 | 23.315 | 33.743 | 1.000 57.32 |
| ATOM | 217 | O | SER | A | 45 | 14.548 | 23.027 | 33.655 | 1.000 57.44 |
| ATOM | 218 | N | LYS | A | 46 | 16.303 | 24.131 | 32.849 | 1.000 62.62 |
| ATOM | 219 | CA | LYS | A | 46 | 15.432 | 24.625 | 31.776 | 1.000 66.95 |
| ATOM | 220 | CB | LYS | A | 46 | 15.937 | 25.962 | 31.242 | 1.000 74.26 |
| ATOM | 221 | CG | LYS | A | 46 | 16.359 | 26.942 | 32.327 | 1.000 76.81 |
| ATOM | 222 | CD | LYS | A | 46 | 15.163 | 27.555 | 33.036 | 1.000 76.98 |
| ATOM | 223 | CE | LYS | A | 46 | 13.919 | 27.533 | 32.159 | 1.000 77.01 |
| ATOM | 224 | NZ | LYS | A | 46 | 13.910 | 28.669 | 31.183 | 1.000 76.61 |
| ATOM | 225 | C | LYS | A | 46 | 15.324 | 23.574 | 30.673 | 1.000 58.56 |
| ATOM | 226 | O | LYS | A | 46 | 14.244 | 23.378 | 30.116 | 1.000 75.22 |
| ATOM | 227 | N | GLU | A | 47 | 16.436 | 22.917 | 30.384 | 1.000 47.55 |
| ATOM | 228 | CA | GLU | A | 47 | 16.525 | 21.820 | 29.431 | 1.000 50.54 |
| ATOM | 229 | CB | GLU | A | 47 | 17.934 | 21.229 | 29.416 | 1.000 51.00 |
| ATOM | 230 | CG | GLU | A | 47 | 18.207 | 20.220 | 28.322 | 1.000 54.12 |
| ATOM | 231 | CD | GLU | A | 47 | 19.602 | 19.627 | 28.395 | 1.000 52.91 |
| ATOM | 232 | OE1 | GLU | A | 47 | 20.500 | 20.053 | 27.631 | 1.000 41.94 |
| ATOM | 233 | OE2 | GLU | A | 47 | 19.799 | 18.714 | 29.229 | 1.000 49.31 |
| ATOM | 234 | C | GLU | A | 47 | 15.509 | 20.738 | 29.790 | 1.000 49.73 |
| ATOM | 235 | O | GLU | A | 47 | 14.803 | 20.208 | 28.939 | 1.000 39.85 |
| ATOM | 236 | N | TYR | A | 48 | 15.448 | 20.426 | 31.086 | 1.000 44.02 |
| ATOM | 237 | CA | TYR | A | 48 | 14.563 | 19.352 | 31.531 | 1.000 41.02 |
| ATOM | 238 | CB | TYR | A | 48 | 14.890 | 18.965 | 32.971 | 1.000 38.64 |
| ATOM | 239 | CG | TYR | A | 48 | 13.922 | 17.993 | 33.599 | 1.000 36.61 |
| ATOM | 240 | CD1 | TYR | A | 48 | 13.950 | 16.650 | 33.247 | 1.000 34.64 |
| ATOM | 241 | CE1 | TYR | A | 48 | 13.073 | 15.745 | 33.809 | 1.000 36.45 |
| ATOM | 242 | CZ | TYR | A | 48 | 12.153 | 16.179 | 34.738 | 1.000 35.24 |
| ATOM | 243 | OH | TYR | A | 48 | 11.285 | 15.269 | 35.288 | 1.000 36.83 |
| ATOM | 244 | CE2 | TYR | A | 48 | 12.098 | 17.506 | 35.108 | 1.000 34.92 |
| ATOM | 245 | CD2 | TYR | A | 48 | 12.983 | 18.405 | 34.535 | 1.000 38.27 |
| ATOM | 246 | C | TYR | A | 48 | 13.112 | 19.774 | 31.382 | 1.000 42.44 |
| ATOM | 247 | O | TYR | A | 48 | 12.227 | 18.943 | 31.170 | 1.000 37.58 |
| ATOM | 248 | N | GLU | A | 49 | 12.839 | 21.077 | 31.488 | 1.000 34.93 |
| ATOM | 249 | CA | GLU | A | 49 | 11.443 | 21.484 | 31.313 | 1.000 36.05 |
| ATOM | 250 | CB | GLU | A | 49 | 11.210 | 22.881 | 31.875 | 1.000 45.26 |
| ATOM | 251 | CG | GLU | A | 49 | 11.239 | 22.953 | 33.390 | 1.000 56.89 |
| ATOM | 252 | CD | GLU | A | 49 | 10.271 | 21.998 | 34.053 | 1.000 65.15 |
| ATOM | 253 | OE1 | GLU | A | 49 | 10.722 | 21.031 | 34.704 | 1.000 61.85 |
| ATOM | 254 | OE2 | GLU | A | 49 | 9.047 | 22.220 | 33.926 | 1.000 85.66 |
| ATOM | 255 | C | GLU | A | 49 | 11.065 | 21.406 | 29.835 | 1.000 40.11 |
| ATOM | 256 | O | GLU | A | 49 | 9.884 | 21.429 | 29.488 | 1.000 45.25 |
| ATOM | 257 | N | GLU | A | 50 | 12.071 | 21.304 | 28.972 | 1.000 34.88 |
| ATOM | 258 | CA | GLU | A | 50 | 11.897 | 21.219 | 27.536 | 1.000 34.15 |
| ATOM | 259 | CB | GLU | A | 50 | 13.225 | 21.224 | 26.784 | 1.000 47.42 |

FIGURE 11

| ATOM | 260 | CG | GLU | A | 50 | 14.193 | 22.357 | 27.039 | 1.000 | 58.31 |
| ATOM | 261 | CD | GLU | A | 50 | 15.395 | 22.299 | 26.111 | 1.000 | 72.71 |
| ATOM | 262 | OE1 | GLU | A | 50 | 15.705 | 21.201 | 25.592 | 1.000 | 84.88 |
| ATOM | 263 | OE2 | GLU | A | 50 | 16.034 | 23.355 | 25.892 | 1.000 | 89.36 |
| ATOM | 264 | C | GLU | A | 50 | 11.172 | 19.927 | 27.145 | 1.000 | 41.10 |
| ATOM | 265 | O | GLU | A | 50 | 10.637 | 19.814 | 26.042 | 1.000 | 48.55 |
| ATOM | 266 | N | LEU | A | 51 | 11.214 | 18.984 | 28.077 | 1.000 | 37.69 |
| ATOM | 267 | CA | LEU | A | 51 | 10.671 | 17.650 | 27.907 | 1.000 | 34.93 |
| ATOM | 268 | CB | LEU | A | 51 | 11.632 | 16.647 | 28.554 | 1.000 | 32.69 |
| ATOM | 269 | CG | LEU | A | 51 | 12.990 | 16.479 | 27.869 | 1.000 | 27.26 |
| ATOM | 270 | CD1 | LEU | A | 51 | 14.003 | 15.896 | 28.837 | 1.000 | 30.09 |
| ATOM | 271 | CD2 | LEU | A | 51 | 12.860 | 15.598 | 26.636 | 1.000 | 25.80 |
| ATOM | 272 | C | LEU | A | 51 | 9.286 | 17.512 | 28.523 | 1.000 | 39.93 |
| ATOM | 273 | O | LEU | A | 51 | 8.633 | 16.483 | 28.348 | 1.000 | 32.60 |
| ATOM | 274 | N | LYS | A | 52 | 8.856 | 18.542 | 29.242 | 1.000 | 35.85 |
| ATOM | 275 | CA | LYS | A | 52 | 7.628 | 18.496 | 30.017 | 1.000 | 43.68 |
| ATOM | 276 | CB | LYS | A | 52 | 7.282 | 19.881 | 30.584 | 1.000 | 49.99 |
| ATOM | 277 | CG | LYS | A | 52 | 5.828 | 20.014 | 31.009 | 1.000 | 50.93 |
| ATOM | 278 | CD | LYS | A | 52 | 5.552 | 21.383 | 31.613 | 1.000 | 54.40 |
| ATOM | 279 | CE | LYS | A | 52 | 4.187 | 21.908 | 31.183 | 1.000 | 52.01 |
| ATOM | 280 | NZ | LYS | A | 52 | 4.061 | 23.372 | 31.421 | 1.000 | 52.88 |
| ATOM | 281 | C | LYS | A | 52 | 6.440 | 17.978 | 29.211 | 1.000 | 41.72 |
| ATOM | 282 | O | LYS | A | 52 | 5.749 | 17.087 | 29.712 | 1.000 | 40.74 |
| ATOM | 283 | N | ASP | A | 53 | 6.241 | 18.521 | 28.018 | 1.000 | 35.76 |
| ATOM | 284 | CA | ASP | A | 53 | 5.074 | 18.259 | 27.196 | 1.000 | 33.00 |
| ATOM | 285 | CB | ASP | A | 53 | 4.640 | 19.524 | 26.440 | 1.000 | 35.62 |
| ATOM | 286 | CG | ASP | A | 53 | 4.134 | 20.637 | 27.333 | 1.000 | 39.83 |
| ATOM | 287 | OD1 | ASP | A | 53 | 4.039 | 21.790 | 26.856 | 1.000 | 41.69 |
| ATOM | 288 | OD2 | ASP | A | 53 | 3.834 | 20.393 | 28.518 | 1.000 | 48.93 |
| ATOM | 289 | C | ASP | A | 53 | 5.283 | 17.142 | 26.177 | 1.000 | 29.06 |
| ATOM | 290 | O | ASP | A | 53 | 4.349 | 16.827 | 25.426 | 1.000 | 22.95 |
| ATOM | 291 | N | VAL | A | 54 | 6.459 | 16.533 | 26.120 | 1.000 | 26.91 |
| ATOM | 292 | CA | VAL | A | 54 | 6.661 | 15.454 | 25.148 | 1.000 | 23.54 |
| ATOM | 293 | CB | VAL | A | 54 | 8.059 | 14.818 | 25.272 | 1.000 | 30.36 |
| ATOM | 294 | CG1 | VAL | A | 54 | 8.120 | 13.547 | 24.435 | 1.000 | 21.06 |
| ATOM | 295 | CG2 | VAL | A | 54 | 9.154 | 15.791 | 24.855 | 1.000 | 31.51 |
| ATOM | 296 | C | VAL | A | 54 | 5.617 | 14.348 | 25.309 | 1.000 | 29.36 |
| ATOM | 297 | O | VAL | A | 54 | 5.350 | 13.848 | 26.409 | 1.000 | 28.89 |
| ATOM | 298 | N | GLY | A | 55 | 5.015 | 13.988 | 24.188 | 1.000 | 23.19 |
| ATOM | 299 | CA | GLY | A | 55 | 4.021 | 12.953 | 24.067 | 1.000 | 23.74 |
| ATOM | 300 | C | GLY | A | 55 | 2.731 | 13.216 | 24.816 | 1.000 | 35.64 |
| ATOM | 301 | O | GLY | A | 55 | 1.917 | 12.289 | 24.916 | 1.000 | 34.29 |
| ATOM | 302 | N | ARG | A | 56 | 2.535 | 14.432 | 25.331 | 1.000 | 26.60 |
| ATOM | 303 | CA | ARG | A | 56 | 1.351 | 14.736 | 26.122 | 1.000 | 26.13 |
| ATOM | 304 | CB | ARG | A | 56 | 1.587 | 15.960 | 27.020 | 1.000 | 28.53 |
| ATOM | 305 | CG | ARG | A | 56 | 2.477 | 15.672 | 28.222 | 1.000 | 31.24 |
| ATOM | 306 | CD | ARG | A | 56 | 1.970 | 14.486 | 29.030 | 1.000 | 31.18 |
| ATOM | 307 | NE | ARG | A | 56 | 2.866 | 14.160 | 30.136 | 1.000 | 39.70 |
| ATOM | 308 | CZ | ARG | A | 56 | 2.724 | 14.463 | 31.417 | 1.000 | 41.60 |
| ATOM | 309 | NH1 | ARG | A | 56 | 1.683 | 15.139 | 31.879 | 1.000 | 33.99 |
| ATOM | 310 | NH2 | ARG | A | 56 | 3.650 | 14.082 | 32.292 | 1.000 | 42.42 |
| ATOM | 311 | C | ARG | A | 56 | 0.123 | 14.966 | 25.250 | 1.000 | 24.97 |

FIGURE 12

| | | | | | | | | | |
|---|---|---|---|---|---|---|---|---|---|
| ATOM | 312 | O | ARG | A | 56 | -0.957 | 15.301 | 25.741 | 1.000 29.55 |
| ATOM | 313 | N | ASN | A | 57 | 0.258 | 14.781 | 23.944 | 1.000 24.28 |
| ATOM | 314 | CA | ASN | A | 57 | -0.895 | 14.909 | 23.064 | 1.000 33.49 |
| ATOM | 315 | CB | ASN | A | 57 | -0.474 | 15.189 | 21.611 | 1.000 33.93 |
| ATOM | 316 | CG | ASN | A | 57 | 0.605 | 14.218 | 21.162 | 1.000 35.19 |
| ATOM | 317 | OD1 | ASN | A | 57 | 1.492 | 13.907 | 21.957 | 1.000 42.76 |
| ATOM | 318 | ND2 | ASN | A | 57 | 0.547 | 13.751 | 19.918 | 1.000 35.98 |
| ATOM | 319 | C | ASN | A | 57 | -1.720 | 13.635 | 23.056 | 1.000 35.77 |
| ATOM | 320 | O | ASN | A | 57 | -2.865 | 13.607 | 22.617 | 1.000 32.52 |
| ATOM | 321 | N | GLN | A | 58 | -1.139 | 12.529 | 23.521 | 1.000 35.76 |
| ATOM | 322 | CA | GLN | A | 58 | -1.864 | 11.271 | 23.295 | 1.000 30.59 |
| ATOM | 323 | CB | GLN | A | 58 | -0.851 | 10.129 | 23.178 | 1.000 29.64 |
| ATOM | 324 | CG | GLN | A | 58 | 0.201 | 10.442 | 22.108 | 1.000 28.67 |
| ATOM | 325 | CD | GLN | A | 58 | 1.406 | 9.527 | 22.230 | 1.000 31.92 |
| ATOM | 326 | OE1 | GLN | A | 58 | 2.330 | 9.754 | 23.023 | 1.000 40.11 |
| ATOM | 327 | NE2 | GLN | A | 58 | 1.386 | 8.474 | 21.427 | 1.000 22.80 |
| ATOM | 328 | C | GLN | A | 58 | -2.899 | 11.017 | 24.373 | 1.000 26.57 |
| ATOM | 329 | O | GLN | A | 58 | -2.814 | 11.505 | 25.494 | 1.000 28.16 |
| ATOM | 330 | N | SER | A | 59 | -3.895 | 10.232 | 23.996 | 1.000 21.64 |
| ATOM | 331 | CA | SER | A | 59 | -5.004 | 9.889 | 24.858 | 1.000 21.49 |
| ATOM | 332 | CB | SER | A | 59 | -6.312 | 9.936 | 24.060 | 1.000 23.13 |
| ATOM | 333 | OG | SER | A | 59 | -6.423 | 8.760 | 23.266 | 1.000 50.75 |
| ATOM | 334 | C | SER | A | 59 | -4.832 | 8.495 | 25.465 | 1.000 27.34 |
| ATOM | 335 | O | SER | A | 59 | -4.113 | 7.652 | 24.915 | 1.000 28.20 |
| ATOM | 336 | N | CYS | A | 60 | -5.510 | 8.289 | 26.585 | 1.000 21.68 |
| ATOM | 337 | CA | CYS | A | 60 | -5.566 | 7.030 | 27.307 | 1.000 19.90 |
| ATOM | 338 | CB | CYS | A | 60 | -4.841 | 7.171 | 28.645 | 1.000 31.73 |
| ATOM | 339 | SG | CYS | A | 60 | -3.240 | 8.002 | 28.554 | 1.000 43.81 |
| ATOM | 340 | C | CYS | A | 60 | -7.008 | 6.595 | 27.556 | 1.000 22.77 |
| ATOM | 341 | O | CYS | A | 60 | -7.341 | 6.204 | 28.678 | 1.000 20.42 |
| ATOM | 342 | N | ASP | A | 61 | -7.852 | 6.663 | 26.540 | 1.000 21.77 |
| ATOM | 343 | CA | ASP | A | 61 | -9.266 | 6.323 | 26.610 | 1.000 30.03 |
| ATOM | 344 | CB | ASP | A | 61 | -9.915 | 6.527 | 25.236 | 1.000 35.37 |
| ATOM | 345 | CG | ASP | A | 61 | -9.894 | 7.936 | 24.695 | 1.000 32.99 |
| ATOM | 346 | OD1 | ASP | A | 61 | -9.618 | 8.909 | 25.426 | 1.000 42.37 |
| ATOM | 347 | OD2 | ASP | A | 61 | -10.171 | 8.083 | 23.481 | 1.000 42.70 |
| ATOM | 348 | C | ASP | A | 61 | -9.529 | 4.890 | 27.073 | 1.000 31.27 |
| ATOM | 349 | O | ASP | A | 61 | -10.375 | 4.669 | 27.946 | 1.000 26.07 |
| ATOM | 350 | N | ILE | A | 62 | -8.840 | 3.896 | 26.517 | 1.000 33.57 |
| ATOM | 351 | CA | ILE | A | 62 | -9.017 | 2.497 | 26.889 | 1.000 26.85 |
| ATOM | 352 | CB | ILE | A | 62 | -8.021 | 1.572 | 26.166 | 1.000 27.84 |
| ATOM | 353 | CG1 | ILE | A | 62 | -7.987 | 1.728 | 24.650 | 1.000 25.02 |
| ATOM | 354 | CD1 | ILE | A | 62 | -9.326 | 1.502 | 23.982 | 1.000 31.68 |
| ATOM | 355 | CG2 | ILE | A | 62 | -8.284 | 0.124 | 26.574 | 1.000 22.54 |
| ATOM | 356 | C | ILE | A | 62 | -8.822 | 2.256 | 28.381 | 1.000 32.08 |
| ATOM | 357 | O | ILE | A | 62 | -9.608 | 1.599 | 29.071 | 1.000 30.72 |
| ATOM | 358 | N | ALA | A | 63 | -7.724 | 2.812 | 28.896 | 1.000 25.21 |
| ATOM | 359 | CA | ALA | A | 63 | -7.448 | 2.650 | 30.321 | 1.000 24.51 |
| ATOM | 360 | CB | ALA | A | 63 | -6.138 | 3.336 | 30.687 | 1.000 24.25 |
| ATOM | 361 | C | ALA | A | 63 | -8.585 | 3.208 | 31.168 | 1.000 32.19 |
| ATOM | 362 | O | ALA | A | 63 | -8.795 | 2.776 | 32.302 | 1.000 36.44 |
| ATOM | 363 | N | LEU | A | 64 | -9.309 | 4.183 | 30.622 | 1.000 29.54 |

FIGURE 13

| ATOM | 364 | CA  | LEU | A | 64 | -10.325 | 4.890  | 31.389 | 1.000 | 31.43 |
|------|-----|-----|-----|---|----|---------|--------|--------|-------|-------|
| ATOM | 365 | CB  | LEU | A | 64 | -10.486 | 6.331  | 30.884 | 1.000 | 27.77 |
| ATOM | 366 | CG  | LEU | A | 64 | -9.333  | 7.259  | 31.283 | 1.000 | 27.38 |
| ATOM | 367 | CD1 | LEU | A | 64 | -9.308  | 8.494  | 30.399 | 1.000 | 15.84 |
| ATOM | 368 | CD2 | LEU | A | 64 | -9.456  | 7.608  | 32.760 | 1.000 | 25.15 |
| ATOM | 369 | C   | LEU | A | 64 | -11.663 | 4.180  | 31.315 | 1.000 | 27.53 |
| ATOM | 370 | O   | LEU | A | 64 | -12.640 | 4.639  | 31.902 | 1.000 | 25.88 |
| ATOM | 371 | N   | LEU | A | 65 | -11.712 | 3.063  | 30.594 | 1.000 | 24.50 |
| ATOM | 372 | CA  | LEU | A | 65 | -13.005 | 2.371  | 30.555 | 1.000 | 29.09 |
| ATOM | 373 | CB  | LEU | A | 65 | -12.934 | 1.238  | 29.534 | 1.000 | 26.20 |
| ATOM | 374 | CG  | LEU | A | 65 | -12.633 | 1.726  | 28.112 | 1.000 | 32.04 |
| ATOM | 375 | CD1 | LEU | A | 65 | -12.556 | 0.568  | 27.137 | 1.000 | 26.24 |
| ATOM | 376 | CD2 | LEU | A | 65 | -13.692 | 2.740  | 27.692 | 1.000 | 42.91 |
| ATOM | 377 | C   | LEU | A | 65 | -13.380 | 1.876  | 31.948 | 1.000 | 36.19 |
| ATOM | 378 | O   | LEU | A | 65 | -12.506 | 1.424  | 32.690 | 1.000 | 34.08 |
| ATOM | 379 | N   | PRO | A | 66 | -14.658 | 1.985  | 32.302 | 1.000 | 38.51 |
| ATOM | 380 | CA  | PRO | A | 66 | -15.156 | 1.575  | 33.618 | 1.000 | 45.55 |
| ATOM | 381 | CB  | PRO | A | 66 | -16.682 | 1.595  | 33.438 | 1.000 | 41.37 |
| ATOM | 382 | CG  | PRO | A | 66 | -16.895 | 2.654  | 32.411 | 1.000 | 38.85 |
| ATOM | 383 | CD  | PRO | A | 66 | -15.733 | 2.545  | 31.463 | 1.000 | 39.79 |
| ATOM | 384 | C   | PRO | A | 66 | -14.718 | 0.173  | 34.026 | 1.000 | 45.91 |
| ATOM | 385 | O   | PRO | A | 66 | -14.329 | -0.049 | 35.171 | 1.000 | 40.19 |
| ATOM | 386 | N   | GLU | A | 67 | -14.780 | -0.764 | 33.090 | 1.000 | 39.45 |
| ATOM | 387 | CA  | GLU | A | 67 | -14.412 | -2.143 | 33.370 | 1.000 | 36.99 |
| ATOM | 388 | CB  | GLU | A | 67 | -14.780 | -3.022 | 32.170 | 1.000 | 40.26 |
| ATOM | 389 | CG  | GLU | A | 67 | -13.872 | -2.765 | 30.975 | 1.000 | 51.03 |
| ATOM | 390 | CD  | GLU | A | 67 | -14.478 | -3.329 | 29.706 | 1.000 | 62.19 |
| ATOM | 391 | OE1 | GLU | A | 67 | -15.190 | -4.351 | 29.789 | 1.000 | 95.02 |
| ATOM | 392 | OE2 | GLU | A | 67 | -14.229 | -2.750 | 28.629 | 1.000 | 48.12 |
| ATOM | 393 | C   | GLU | A | 67 | -12.929 | -2.311 | 33.685 | 1.000 | 41.35 |
| ATOM | 394 | O   | GLU | A | 67 | -12.555 | -3.306 | 34.309 | 1.000 | 49.39 |
| ATOM | 395 | N   | ASN | A | 68 | -12.105 | -1.357 | 33.266 | 1.000 | 44.36 |
| ATOM | 396 | CA  | ASN | A | 68 | -10.668 | -1.381 | 33.488 | 1.000 | 35.22 |
| ATOM | 397 | CB  | ASN | A | 68 | -9.938  | -0.853 | 32.244 | 1.000 | 30.80 |
| ATOM | 398 | CG  | ASN | A | 68 | -10.071 | -1.799 | 31.070 | 1.000 | 26.82 |
| ATOM | 399 | OD1 | ASN | A | 68 | -10.219 | -3.004 | 31.263 | 1.000 | 30.94 |
| ATOM | 400 | ND2 | ASN | A | 68 | -10.021 | -1.271 | 29.849 | 1.000 | 25.55 |
| ATOM | 401 | C   | ASN | A | 68 | -10.240 | -0.570 | 34.706 | 1.000 | 35.99 |
| ATOM | 402 | O   | ASN | A | 68 | -9.074  | -0.612 | 35.110 | 1.000 | 34.21 |
| ATOM | 403 | N   | ARG | A | 69 | -11.151 | 0.170  | 35.325 | 1.000 | 40.53 |
| ATOM | 404 | CA  | ARG | A | 69 | -10.796 | 1.005  | 36.475 | 1.000 | 35.31 |
| ATOM | 405 | CB  | ARG | A | 69 | -12.060 | 1.688  | 36.993 | 1.000 | 47.65 |
| ATOM | 406 | CG  | ARG | A | 69 | -11.878 | 3.089  | 37.547 | 1.000 | 59.36 |
| ATOM | 407 | CD  | ARG | A | 69 | -12.710 | 3.262  | 38.819 | 1.000 | 65.36 |
| ATOM | 408 | NE  | ARG | A | 69 | -12.615 | 2.076  | 39.666 | 1.000 | 69.47 |
| ATOM | 409 | CZ  | ARG | A | 69 | -13.019 | 1.980  | 40.923 | 1.000 | 75.71 |
| ATOM | 410 | NH1 | ARG | A | 69 | -13.586 | 3.018  | 41.542 | 1.000 | 91.00 |
| ATOM | 411 | NH2 | ARG | A | 69 | -12.880 | 0.832  | 41.575 | 1.000 | 74.09 |
| ATOM | 412 | C   | ARG | A | 69 | -10.114 | 0.205  | 37.572 | 1.000 | 33.70 |
| ATOM | 413 | O   | ARG | A | 69 | -9.102  | 0.634  | 38.135 | 1.000 | 41.23 |
| ATOM | 414 | N   | GLY | A | 70 | -10.641 | -0.976 | 37.890 | 1.000 | 34.09 |
| ATOM | 415 | CA  | GLY | A | 70 | -10.030 | -1.844 | 38.877 | 1.000 | 29.32 |

FIGURE 14

```
ATOM    416  C    GLY A  70      -8.645  -2.304  38.476 1.000 33.87
ATOM    417  O    GLY A  70      -7.861  -2.788  39.293 1.000 29.15
ATOM    418  N    LYS A  71      -8.269  -2.166  37.200 1.000 28.62
ATOM    419  CA   LYS A  71      -6.975  -2.730  36.805 1.000 28.56
ATOM    420  CB   LYS A  71      -7.145  -3.327  35.403 1.000 26.54
ATOM    421  CG   LYS A  71      -8.206  -4.431  35.340 1.000 22.84
ATOM    422  CD   LYS A  71      -8.540  -4.715  33.880 1.000 25.18
ATOM    423  CE   LYS A  71      -9.766  -5.603  33.744 1.000 26.92
ATOM    424  NZ   LYS A  71     -10.179  -5.703  32.310 1.000 25.36
ATOM    425  C    LYS A  71      -5.825  -1.737  36.871 1.000 24.24
ATOM    426  O    LYS A  71      -4.670  -2.046  36.565 1.000 23.92
ATOM    427  N    ASN A  72      -6.078  -0.506  37.292 1.000 21.36
ATOM    428  CA   ASN A  72      -5.019   0.485  37.438 1.000 22.33
ATOM    429  CB   ASN A  72      -5.431   1.802  36.760 1.000 17.72
ATOM    430  CG   ASN A  72      -5.773   1.557  35.299 1.000 20.67
ATOM    431  OD1  ASN A  72      -4.968   1.023  34.534 1.000 19.13
ATOM    432  ND2  ASN A  72      -6.981   1.935  34.901 1.000 22.56
ATOM    433  C    ASN A  72      -4.691   0.708  38.904 1.000 22.55
ATOM    434  O    ASN A  72      -5.548   0.952  39.747 1.000 27.49
ATOM    435  N    ARG A  73      -3.410   0.626  39.238 1.000 24.79
ATOM    436  CA   ARG A  73      -2.989   0.857  40.612 1.000 22.71
ATOM    437  CB   ARG A  73      -1.523   0.471  40.761 1.000 19.16
ATOM    438  CG   ARG A  73      -1.003   0.559  42.185 1.000 20.59
ATOM    439  CD   ARG A  73       0.456   0.114  42.254 1.000 16.95
ATOM    440  NE   ARG A  73       0.546  -1.347  42.281 1.000 17.30
ATOM    441  CZ   ARG A  73       0.282  -2.041  43.387 1.000 28.69
ATOM    442  NH1  ARG A  73      -0.073  -1.406  44.500 1.000 20.46
ATOM    443  NH2  ARG A  73       0.372  -3.371  43.383 1.000 26.38
ATOM    444  C    ARG A  73      -3.227   2.314  40.990 1.000 29.57
ATOM    445  O    ARG A  73      -3.731   2.609  42.070 1.000 23.74
ATOM    446  N    TYR A  74      -2.864   3.229  40.095 1.000 22.89
ATOM    447  CA   TYR A  74      -3.188   4.640  40.292 1.000 19.10
ATOM    448  CB   TYR A  74      -1.941   5.487  40.496 1.000 29.90
ATOM    449  CG   TYR A  74      -0.889   4.936  41.434 1.000 28.85
ATOM    450  CD1  TYR A  74      -0.948   5.169  42.802 1.000 29.68
ATOM    451  CE1  TYR A  74       0.019   4.668  43.655 1.000 32.91
ATOM    452  CZ   TYR A  74       1.064   3.920  43.146 1.000 32.73
ATOM    453  OH   TYR A  74       2.029   3.415  43.989 1.000 28.80
ATOM    454  CE2  TYR A  74       1.156   3.672  41.791 1.000 20.37
ATOM    455  CD2  TYR A  74       0.182   4.186  40.957 1.000 22.57
ATOM    456  C    TYR A  74      -4.007   5.110  39.095 1.000 33.71
ATOM    457  O    TYR A  74      -3.753   4.819  37.920 1.000 23.30
ATOM    458  N    ASN A  75      -5.062   5.861  39.410 1.000 33.95
ATOM    459  CA   ASN A  75      -6.019   6.213  38.358 1.000 32.58
ATOM    460  CB   ASN A  75      -7.389   6.458  39.014 1.000 35.23
ATOM    461  CG   ASN A  75      -7.716   5.300  39.947 1.000 42.60
ATOM    462  OD1  ASN A  75      -7.925   5.491  41.144 1.000 68.26
ATOM    463  ND2  ASN A  75      -7.745   4.087  39.403 1.000 39.56
ATOM    464  C    ASN A  75      -5.533   7.385  37.534 1.000 30.63
ATOM    465  O    ASN A  75      -6.101   7.736  36.497 1.000 26.15
ATOM    466  N    ASN A  76      -4.440   8.015  37.962 1.000 28.76
ATOM    467  CA   ASN A  76      -3.897   9.102  37.150 1.000 28.13
```

FIGURE 15

| ATOM | 468 | CB  | ASN | A | 76 | -3.719 | 10.374 | 37.979 | 1.000 | 27.74 |
| ATOM | 469 | CG  | ASN | A | 76 | -2.648 | 10.200 | 39.041 | 1.000 | 28.93 |
| ATOM | 470 | OD1 | ASN | A | 76 | -2.497 | 9.101  | 39.573 | 1.000 | 29.34 |
| ATOM | 471 | ND2 | ASN | A | 76 | -1.937 | 11.284 | 39.321 | 1.000 | 29.63 |
| ATOM | 472 | C   | ASN | A | 76 | -2.570 | 8.694  | 36.526 | 1.000 | 29.10 |
| ATOM | 473 | O   | ASN | A | 76 | -1.851 | 9.557  | 36.015 | 1.000 | 33.33 |
| ATOM | 474 | N   | ILE | A | 77 | -2.273 | 7.392  | 36.558 | 1.000 | 24.17 |
| ATOM | 475 | CA  | ILE | A | 77 | -1.095 | 6.908  | 35.830 | 1.000 | 23.94 |
| ATOM | 476 | CB  | ILE | A | 77 | 0.024  | 6.496  | 36.797 | 1.000 | 28.53 |
| ATOM | 477 | CG1 | ILE | A | 77 | 0.575  | 7.663  | 37.624 | 1.000 | 24.03 |
| ATOM | 478 | CD1 | ILE | A | 77 | 1.451  | 7.212  | 38.776 | 1.000 | 35.26 |
| ATOM | 479 | CG2 | ILE | A | 77 | 1.137  | 5.798  | 36.041 | 1.000 | 21.08 |
| ATOM | 480 | C   | ILE | A | 77 | -1.457 | 5.760  | 34.900 | 1.000 | 22.75 |
| ATOM | 481 | O   | ILE | A | 77 | -1.618 | 4.597  | 35.282 | 1.000 | 17.56 |
| ATOM | 482 | N   | LEU | A | 78 | -1.605 | 6.108  | 33.621 | 1.000 | 16.56 |
| ATOM | 483 | CA  | LEU | A | 78 | -2.172 | 5.202  | 32.641 | 1.000 | 12.89 |
| ATOM | 484 | CB  | LEU | A | 78 | -3.616 | 5.616  | 32.310 | 1.000 | 17.17 |
| ATOM | 485 | CG  | LEU | A | 78 | -4.457 | 6.017  | 33.522 | 1.000 | 22.43 |
| ATOM | 486 | CD1 | LEU | A | 78 | -5.794 | 6.590  | 33.075 | 1.000 | 27.35 |
| ATOM | 487 | CD2 | LEU | A | 78 | -4.637 | 4.813  | 34.431 | 1.000 | 17.32 |
| ATOM | 488 | C   | LEU | A | 78 | -1.415 | 5.213  | 31.326 | 1.000 | 17.93 |
| ATOM | 489 | O   | LEU | A | 78 | -0.846 | 6.221  | 30.922 | 1.000 | 18.95 |
| ATOM | 490 | N   | PRO | A | 79 | -1.459 | 4.086  | 30.640 | 1.000 | 21.12 |
| ATOM | 491 | CA  | PRO | A | 79 | -0.773 | 3.971  | 29.355 | 1.000 | 18.86 |
| ATOM | 492 | CB  | PRO | A | 79 | -0.858 | 2.470  | 29.068 | 1.000 | 18.12 |
| ATOM | 493 | CG  | PRO | A | 79 | -2.148 | 2.076  | 29.721 | 1.000 | 21.28 |
| ATOM | 494 | CD  | PRO | A | 79 | -2.184 | 2.858  | 31.011 | 1.000 | 17.43 |
| ATOM | 495 | C   | PRO | A | 79 | -1.532 | 4.694  | 28.253 | 1.000 | 19.81 |
| ATOM | 496 | O   | PRO | A | 79 | -2.761 | 4.633  | 28.249 | 1.000 | 19.07 |
| ATOM | 497 | N   | TYR | A | 80 | -0.784 | 5.317  | 27.355 | 1.000 | 16.14 |
| ATOM | 498 | CA  | TYR | A | 80 | -1.338 | 5.843  | 26.117 | 1.000 | 15.09 |
| ATOM | 499 | CB  | TYR | A | 80 | -0.216 | 6.508  | 25.313 | 1.000 | 20.99 |
| ATOM | 500 | CG  | TYR | A | 80 | 0.350  | 7.734  | 25.993 | 1.000 | 20.29 |
| ATOM | 501 | CD1 | TYR | A | 80 | -0.494 | 8.670  | 26.577 | 1.000 | 20.64 |
| ATOM | 502 | CE1 | TYR | A | 80 | 0.019  | 9.796  | 27.206 | 1.000 | 20.96 |
| ATOM | 503 | CZ  | TYR | A | 80 | 1.385  | 9.986  | 27.243 | 1.000 | 21.66 |
| ATOM | 504 | OH  | TYR | A | 80 | 1.903  | 11.103 | 27.859 | 1.000 | 23.51 |
| ATOM | 505 | CE2 | TYR | A | 80 | 2.239  | 9.071  | 26.671 | 1.000 | 18.25 |
| ATOM | 506 | CD2 | TYR | A | 80 | 1.722  | 7.946  | 26.047 | 1.000 | 21.75 |
| ATOM | 507 | C   | TYR | A | 80 | -1.988 | 4.755  | 25.277 | 1.000 | 23.46 |
| ATOM | 508 | O   | TYR | A | 80 | -1.471 | 3.635  | 25.187 | 1.000 | 23.99 |
| ATOM | 509 | N   | ASP | A | 81 | -3.125 | 5.040  | 24.637 | 1.000 | 22.91 |
| ATOM | 510 | CA  | ASP | A | 81 | -3.735 | 4.027  | 23.780 | 1.000 | 19.34 |
| ATOM | 511 | CB  | ASP | A | 81 | -5.033 | 4.518  | 23.120 | 1.000 | 24.22 |
| ATOM | 512 | CG  | ASP | A | 81 | -6.080 | 4.908  | 24.143 | 1.000 | 34.31 |
| ATOM | 513 | OD1 | ASP | A | 81 | -6.296 | 4.128  | 25.094 | 1.000 | 27.78 |
| ATOM | 514 | OD2 | ASP | A | 81 | -6.688 | 5.992  | 24.010 | 1.000 | 35.52 |
| ATOM | 515 | C   | ASP | A | 81 | -2.769 | 3.610  | 22.678 | 1.000 | 18.44 |
| ATOM | 516 | O   | ASP | A | 81 | -2.722 | 2.439  | 22.278 | 1.000 | 24.18 |
| ATOM | 517 | N   | ALA | A | 82 | -2.002 | 4.573  | 22.161 | 1.000 | 16.71 |
| ATOM | 518 | CA  | ALA | A | 82 | -1.164 | 4.229  | 21.008 | 1.000 | 21.74 |
| ATOM | 519 | CB  | ALA | A | 82 | -0.654 | 5.520  | 20.373 | 1.000 | 25.83 |

FIGURE 16

| | | | | | | | | | |
|---|---|---|---|---|---|---|---|---|---|
| ATOM | 520 | C | ALA | A | 82 | -0.010 | 3.300 | 21.338 | 1.000 26.28 |
| ATOM | 521 | O | ALA | A | 82 | 0.556 | 2.660 | 20.439 | 1.000 24.04 |
| ATOM | 522 | N | THR | A | 83 | 0.447 | 3.140 | 22.584 | 1.000 19.03 |
| ATOM | 523 | CA | THR | A | 83 | 1.625 | 2.280 | 22.757 | 1.000 14.68 |
| ATOM | 524 | CB | THR | A | 83 | 2.853 | 3.095 | 23.225 | 1.000 22.79 |
| ATOM | 525 | OG1 | THR | A | 83 | 2.464 | 3.852 | 24.374 | 1.000 18.61 |
| ATOM | 526 | CG2 | THR | A | 83 | 3.308 | 4.096 | 22.168 | 1.000 17.97 |
| ATOM | 527 | C | THR | A | 83 | 1.412 | 1.199 | 23.799 | 1.000 22.48 |
| ATOM | 528 | O | THR | A | 83 | 2.380 | 0.580 | 24.254 | 1.000 20.29 |
| ATOM | 529 | N | ARG | A | 84 | 0.144 | 1.005 | 24.159 | 1.000 18.73 |
| ATOM | 530 | CA | ARG | A | 84 | -0.176 | 0.106 | 25.257 | 1.000 22.92 |
| ATOM | 531 | CB | ARG | A | 84 | -1.621 | 0.347 | 25.683 | 1.000 27.10 |
| ATOM | 532 | CG | ARG | A | 84 | -2.650 | -0.247 | 24.721 | 1.000 21.68 |
| ATOM | 533 | CD | ARG | A | 84 | -4.047 | 0.092 | 25.236 | 1.000 25.76 |
| ATOM | 534 | NE | ARG | A | 84 | -5.071 | -0.515 | 24.395 | 1.000 31.14 |
| ATOM | 535 | CZ | ARG | A | 84 | -5.698 | -1.652 | 24.648 | 1.000 28.06 |
| ATOM | 536 | NH1 | ARG | A | 84 | -5.426 | -2.351 | 25.741 | 1.000 15.53 |
| ATOM | 537 | NH2 | ARG | A | 84 | -6.608 | -2.073 | 23.781 | 1.000 24.30 |
| ATOM | 538 | C | ARG | A | 84 | 0.032 | -1.353 | 24.874 | 1.000 25.02 |
| ATOM | 539 | O | ARG | A | 84 | -0.089 | -1.712 | 23.702 | 1.000 21.04 |
| ATOM | 540 | N | VAL | A | 85 | 0.337 | -2.204 | 25.856 | 1.000 14.13 |
| ATOM | 541 | CA | VAL | A | 85 | 0.491 | -3.624 | 25.512 | 1.000 14.38 |
| ATOM | 542 | CB | VAL | A | 85 | 1.464 | -4.344 | 26.455 | 1.000 9.78 |
| ATOM | 543 | CG1 | VAL | A | 85 | 1.425 | -5.848 | 26.218 | 1.000 17.73 |
| ATOM | 544 | CG2 | VAL | A | 85 | 2.881 | -3.814 | 26.306 | 1.000 12.51 |
| ATOM | 545 | C | VAL | A | 85 | -0.863 | -4.313 | 25.593 | 1.000 24.23 |
| ATOM | 546 | O | VAL | A | 85 | -1.573 | -4.163 | 26.594 | 1.000 24.70 |
| ATOM | 547 | N | LYS | A | 86 | -1.270 | -5.081 | 24.590 | 1.000 22.80 |
| ATOM | 548 | CA | LYS | A | 86 | -2.572 | -5.741 | 24.686 | 1.000 22.12 |
| ATOM | 549 | CB | LYS | A | 86 | -3.307 | -5.564 | 23.347 | 1.000 31.33 |
| ATOM | 550 | CG | LYS | A | 86 | -3.256 | -4.147 | 22.803 | 1.000 27.28 |
| ATOM | 551 | CD | LYS | A | 86 | -3.691 | -4.077 | 21.352 | 1.000 33.19 |
| ATOM | 552 | CE | LYS | A | 86 | -4.193 | -2.688 | 20.990 | 1.000 43.70 |
| ATOM | 553 | NZ | LYS | A | 86 | -4.520 | -2.549 | 19.542 | 1.000 37.64 |
| ATOM | 554 | C | LYS | A | 86 | -2.483 | -7.222 | 25.020 | 1.000 24.22 |
| ATOM | 555 | O | LYS | A | 86 | -1.658 | -7.961 | 24.475 | 1.000 27.05 |
| ATOM | 556 | N | LEU | A | 87 | -3.358 | -7.682 | 25.911 | 1.000 23.05 |
| ATOM | 557 | CA | LEU | A | 87 | -3.530 | -9.107 | 26.143 | 1.000 23.37 |
| ATOM | 558 | CB | LEU | A | 87 | -4.250 | -9.392 | 27.460 | 1.000 24.62 |
| ATOM | 559 | CG | LEU | A | 87 | -3.733 | -8.696 | 28.711 | 1.000 27.34 |
| ATOM | 560 | CD1 | LEU | A | 87 | -4.614 | -9.032 | 29.904 | 1.000 20.48 |
| ATOM | 561 | CD2 | LEU | A | 87 | -2.284 | -9.078 | 28.973 | 1.000 32.54 |
| ATOM | 562 | C | LEU | A | 87 | -4.360 | -9.720 | 25.020 | 1.000 26.94 |
| ATOM | 563 | O | LEU | A | 87 | -5.318 | -9.094 | 24.555 | 1.000 38.77 |
| ATOM | 564 | N | SER | A | 88 | -4.021 | -10.925 | 24.581 | 1.000 33.75 |
| ATOM | 565 | CA | SER | A | 88 | -4.872 | -11.557 | 23.567 | 1.000 42.66 |
| ATOM | 566 | CB | SER | A | 88 | -4.317 | -12.913 | 23.154 | 1.000 46.57 |
| ATOM | 567 | OG | SER | A | 88 | -4.765 | -13.947 | 24.014 | 1.000 59.78 |
| ATOM | 568 | C | SER | A | 88 | -6.292 | -11.680 | 24.113 | 1.000 52.63 |
| ATOM | 569 | O | SER | A | 88 | -6.499 | -11.777 | 25.325 | 1.000 40.47 |
| ATOM | 570 | N | ASN | A | 89 | -7.274 | -11.656 | 23.225 | 1.000 65.95 |
| ATOM | 571 | CA | ASN | A | 89 | -8.680 | -11.790 | 23.586 | 1.000 71.68 |

FIGURE 17

```
ATOM    572  CB  ASN A  89      -9.528 -11.132  22.496 1.000 75.26
ATOM    573  CG  ASN A  89      -8.793 -11.244  21.163 1.000 78.86
ATOM    574  OD1 ASN A  89      -7.806 -10.546  20.946 1.000 71.99
ATOM    575  ND2 ASN A  89      -9.271 -12.122  20.293 1.000 90.92
ATOM    576  C   ASN A  89      -9.057 -13.256  23.738 1.000 79.05
ATOM    577  O   ASN A  89      -8.808 -14.039  22.811 1.000 73.71
ATOM    578  N   VAL A  90      -9.633 -13.639  24.875 1.000 87.92
ATOM    579  CA  VAL A  90      -9.929 -15.052  25.128 1.000 94.68
ATOM    580  CB  VAL A  90      -8.920 -15.629  26.140 1.000 89.31
ATOM    581  CG1 VAL A  90      -7.494 -15.497  25.590 1.000 54.27
ATOM    582  CG2 VAL A  90      -9.031 -14.923  27.491 1.000100.28
ATOM    583  C   VAL A  90     -11.354 -15.293  25.619 1.000102.19
ATOM    584  O   VAL A  90     -12.315 -14.798  25.014 1.000100.56
ATOM    585  N   ASP A  91     -11.498 -16.059  26.693 1.000105.22
ATOM    586  CA  ASP A  91     -12.783 -16.447  27.271 1.000108.70
ATOM    587  CB  ASP A  91     -12.578 -17.068  28.656 1.000107.42
ATOM    588  CG  ASP A  91     -13.530 -18.205  28.939 1.000106.43
ATOM    589  OD1 ASP A  91     -13.926 -18.900  27.974 1.000113.61
ATOM    590  OD2 ASP A  91     -13.894 -18.413  30.116 1.000 86.41
ATOM    591  C   ASP A  91     -13.743 -15.268  27.371 1.000115.28
ATOM    592  O   ASP A  91     -13.390 -14.223  27.924 1.000126.76
ATOM    593  N   ASP A  92     -14.952 -15.429  26.834 1.000116.43
ATOM    594  CA  ASP A  92     -15.914 -14.333  26.741 1.000116.50
ATOM    595  CB  ASP A  92     -16.500 -13.952  28.090 1.000111.11
ATOM    596  CG  ASP A  92     -17.029 -15.093  28.929 1.000103.39
ATOM    597  OD1 ASP A  92     -17.835 -15.908  28.441 1.000 70.91
ATOM    598  OD2 ASP A  92     -16.639 -15.180  30.116 1.000105.06
ATOM    599  C   ASP A  92     -15.224 -13.122  26.103 1.000121.44
ATOM    600  O   ASP A  92     -14.846 -13.211  24.935 1.000119.15
ATOM    601  N   ASP A  93     -15.077 -12.068  26.886 1.000124.91
ATOM    602  CA  ASP A  93     -14.260 -10.887  26.698 1.000127.04
ATOM    603  CB  ASP A  93     -13.201 -11.126  25.615 1.000127.70
ATOM    604  CG  ASP A  93     -13.710 -10.960  24.174 1.000128.89
ATOM    605  OD1 ASP A  93     -14.877 -11.323  23.869 1.000136.07
ATOM    606  OD2 ASP A  93     -12.928 -10.464  23.315 1.000126.93
ATOM    607  C   ASP A  93     -15.055  -9.617  26.384 1.000125.66
ATOM    608  O   ASP A  93     -15.775  -9.536  25.388 1.000112.27
ATOM    609  N   PRO A  94     -14.884  -8.640  27.272 1.000123.81
ATOM    610  CA  PRO A  94     -15.331  -7.253  27.126 1.000114.77
ATOM    611  CB  PRO A  94     -15.751  -6.908  28.554 1.000118.39
ATOM    612  CG  PRO A  94     -14.893  -7.760  29.440 1.000121.09
ATOM    613  CD  PRO A  94     -14.224  -8.799  28.586 1.000123.81
ATOM    614  C   PRO A  94     -14.172  -6.360  26.685 1.000 99.08
ATOM    615  O   PRO A  94     -14.080  -5.961  25.527 1.000 69.91
ATOM    616  N   CYS A  95     -13.294  -6.071  27.635 1.000 91.61
ATOM    617  CA  CYS A  95     -11.981  -5.485  27.441 1.000 80.21
ATOM    618  CB  CYS A  95     -11.883  -4.014  27.797 1.000 80.05
ATOM    619  SG  CYS A  95     -10.319  -3.186  27.438 1.000 75.64
ATOM    620  C   CYS A  95     -10.991  -6.285  28.303 1.000 67.30
ATOM    621  O   CYS A  95     -10.299  -5.735  29.149 1.000 48.15
ATOM    622  N   SER A  96     -10.993  -7.580  28.030 1.000 62.04
ATOM    623  CA  SER A  96     -10.102  -8.548  28.645 1.000 49.24
```

FIGURE 18

| | | | | | | | | | |
|---|---|---|---|---|---|---|---|---|---|
| ATOM | 624 | CB | SER | A | 96 | -10.644 | -9.959 | 28.392 | 1.000 47.34 |
| ATOM | 625 | OG | SER | A | 96 | -10.772 | -10.165 | 26.989 | 1.000 35.99 |
| ATOM | 626 | C | SER | A | 96 | -8.689 | -8.404 | 28.091 | 1.000 40.83 |
| ATOM | 627 | O | SER | A | 96 | -7.762 | -9.091 | 28.530 | 1.000 43.79 |
| ATOM | 628 | N | ASP | A | 97 | -8.519 | -7.503 | 27.119 | 1.000 33.54 |
| ATOM | 629 | CA | ASP | A | 97 | -7.200 | -7.260 | 26.543 | 1.000 26.97 |
| ATOM | 630 | CB | ASP | A | 97 | -7.333 | -6.817 | 25.088 | 1.000 24.79 |
| ATOM | 631 | CG | ASP | A | 97 | -7.611 | -5.353 | 24.842 | 1.000 31.75 |
| ATOM | 632 | OD1 | ASP | A | 97 | -7.973 | -4.566 | 25.740 | 1.000 34.88 |
| ATOM | 633 | OD2 | ASP | A | 97 | -7.473 | -4.920 | 23.667 | 1.000 32.46 |
| ATOM | 634 | C | ASP | A | 97 | -6.406 | -6.227 | 27.331 | 1.000 19.31 |
| ATOM | 635 | O | ASP | A | 97 | -5.239 | -6.008 | 27.001 | 1.000 32.90 |
| ATOM | 636 | N | TYR | A | 98 | -7.001 | -5.563 | 28.319 | 1.000 21.87 |
| ATOM | 637 | CA | TYR | A | 98 | -6.317 | -4.446 | 28.958 | 1.000 24.52 |
| ATOM | 638 | CB | TYR | A | 98 | -7.294 | -3.441 | 29.604 | 1.000 22.29 |
| ATOM | 639 | CG | TYR | A | 98 | -6.556 | -2.288 | 30.277 | 1.000 21.76 |
| ATOM | 640 | CD1 | TYR | A | 98 | -6.012 | -1.275 | 29.489 | 1.000 23.46 |
| ATOM | 641 | CE1 | TYR | A | 98 | -5.324 | -0.202 | 30.044 | 1.000 12.80 |
| ATOM | 642 | CZ | TYR | A | 98 | -5.184 | -0.152 | 31.415 | 1.000 16.57 |
| ATOM | 643 | OH | TYR | A | 98 | -4.516 | 0.900 | 32.001 | 1.000 20.04 |
| ATOM | 644 | CE2 | TYR | A | 98 | -5.710 | -1.138 | 32.234 | 1.000 21.65 |
| ATOM | 645 | CD2 | TYR | A | 98 | -6.388 | -2.192 | 31.652 | 1.000 22.47 |
| ATOM | 646 | C | TYR | A | 98 | -5.329 | -4.852 | 30.045 | 1.000 23.39 |
| ATOM | 647 | O | TYR | A | 98 | -5.609 | -5.609 | 30.964 | 1.000 28.32 |
| ATOM | 648 | N | ILE | A | 99 | -4.143 | -4.250 | 29.978 | 1.000 19.82 |
| ATOM | 649 | CA | ILE | A | 99 | -3.247 | -4.242 | 31.130 | 1.000 21.08 |
| ATOM | 650 | CB | ILE | A | 99 | -2.185 | -5.354 | 31.091 | 1.000 21.45 |
| ATOM | 651 | CG1 | ILE | A | 99 | -1.169 | -5.304 | 32.224 | 1.000 13.12 |
| ATOM | 652 | CD1 | ILE | A | 99 | -0.466 | -6.601 | 32.573 | 1.000 15.73 |
| ATOM | 653 | CG2 | ILE | A | 99 | -1.481 | -5.344 | 29.737 | 1.000 24.91 |
| ATOM | 654 | C | ILE | A | 99 | -2.593 | -2.867 | 31.218 | 1.000 17.86 |
| ATOM | 655 | O | ILE | A | 99 | -2.362 | -2.161 | 30.235 | 1.000 23.00 |
| ATOM | 656 | N | ASN | A | 100 | -2.271 | -2.426 | 32.429 | 1.000 17.97 |
| ATOM | 657 | CA | ASN | A | 100 | -1.523 | -1.168 | 32.506 | 1.000 16.53 |
| ATOM | 658 | CB | ASN | A | 100 | -1.696 | -0.583 | 33.904 | 1.000 15.17 |
| ATOM | 659 | CG | ASN | A | 100 | -1.169 | 0.837 | 33.940 | 1.000 17.63 |
| ATOM | 660 | OD1 | ASN | A | 100 | -0.087 | 1.081 | 33.409 | 1.000 19.68 |
| ATOM | 661 | ND2 | ASN | A | 100 | -1.931 | 1.727 | 34.566 | 1.000 19.64 |
| ATOM | 662 | C | ASN | A | 100 | -0.064 | -1.408 | 32.144 | 1.000 20.69 |
| ATOM | 663 | O | ASN | A | 100 | 0.784 | -1.727 | 32.977 | 1.000 13.39 |
| ATOM | 664 | N | ALA | A | 101 | 0.246 | -1.268 | 30.851 | 1.000 11.73 |
| ATOM | 665 | CA | ALA | A | 101 | 1.586 | -1.586 | 30.370 | 1.000 13.46 |
| ATOM | 666 | CB | ALA | A | 101 | 1.737 | -3.096 | 30.235 | 1.000 16.17 |
| ATOM | 667 | C | ALA | A | 101 | 1.842 | -0.930 | 29.026 | 1.000 14.30 |
| ATOM | 668 | O | ALA | A | 101 | 0.883 | -0.739 | 28.277 | 1.000 15.61 |
| ATOM | 669 | N | SER | A | 102 | 3.088 | -0.603 | 28.708 | 1.000 17.77 |
| ATOM | 670 | CA | SER | A | 102 | 3.385 | 0.102 | 27.472 | 1.000 18.13 |
| ATOM | 671 | CB | SER | A | 102 | 3.627 | 1.593 | 27.759 | 1.000 13.36 |
| ATOM | 672 | OG | SER | A | 102 | 2.735 | 2.076 | 28.738 | 1.000 20.39 |
| ATOM | 673 | C | SER | A | 102 | 4.623 | -0.444 | 26.786 | 1.000 23.90 |
| ATOM | 674 | O | SER | A | 102 | 5.568 | -0.832 | 27.475 | 1.000 22.19 |
| ATOM | 675 | N | TYR | A | 103 | 4.639 | -0.454 | 25.452 | 1.000 16.79 |

FIGURE 19

| ATOM | 676 | CA  | TYR | A | 103 | 5.871  | -0.877 | 24.793 | 1.000 | 10.43 |
| ATOM | 677 | CB  | TYR | A | 103 | 5.619  | -1.287 | 23.347 | 1.000 | 16.27 |
| ATOM | 678 | CG  | TYR | A | 103 | 4.840  | -2.567 | 23.157 | 1.000 | 15.11 |
| ATOM | 679 | CD1 | TYR | A | 103 | 5.421  | -3.802 | 23.412 | 1.000 | 18.80 |
| ATOM | 680 | CE1 | TYR | A | 103 | 4.704  | -4.978 | 23.232 | 1.000 | 22.75 |
| ATOM | 681 | CZ  | TYR | A | 103 | 3.396  | -4.922 | 22.798 | 1.000 | 19.98 |
| ATOM | 682 | OH  | TYR | A | 103 | 2.689  | -6.094 | 22.625 | 1.000 | 16.85 |
| ATOM | 683 | CE2 | TYR | A | 103 | 2.797  | -3.704 | 22.536 | 1.000 | 14.29 |
| ATOM | 684 | CD2 | TYR | A | 103 | 3.517  | -2.540 | 22.714 | 1.000 | 12.99 |
| ATOM | 685 | C   | TYR | A | 103 | 6.847  | 0.293  | 24.853 | 1.000 | 19.42 |
| ATOM | 686 | O   | TYR | A | 103 | 6.398  | 1.440  | 24.787 | 1.000 | 21.35 |
| ATOM | 687 | N   | ILE | A | 104 | 8.143  | 0.039  | 24.983 | 1.000 | 20.28 |
| ATOM | 688 | CA  | ILE | A | 104 | 9.090  | 1.151  | 25.068 | 1.000 | 18.75 |
| ATOM | 689 | CB  | ILE | A | 104 | 9.522  | 1.444  | 26.516 | 1.000 | 25.72 |
| ATOM | 690 | CG1 | ILE | A | 104 | 8.372  | 1.673  | 27.507 | 1.000 | 19.54 |
| ATOM | 691 | CD1 | ILE | A | 104 | 7.657  | 2.991  | 27.243 | 1.000 | 24.18 |
| ATOM | 692 | CG2 | ILE | A | 104 | 10.466 | 2.640  | 26.556 | 1.000 | 25.08 |
| ATOM | 693 | C   | ILE | A | 104 | 10.321 | 0.843  | 24.229 | 1.000 | 18.91 |
| ATOM | 694 | O   | ILE | A | 104 | 10.899 | -0.236 | 24.356 | 1.000 | 21.99 |
| ATOM | 695 | N   | PRO | A | 105 | 10.719 | 1.777  | 23.376 | 1.000 | 25.40 |
| ATOM | 696 | CA  | PRO | A | 105 | 11.854 | 1.513  | 22.482 | 1.000 | 23.49 |
| ATOM | 697 | CB  | PRO | A | 105 | 11.761 | 2.641  | 21.457 | 1.000 | 25.41 |
| ATOM | 698 | CG  | PRO | A | 105 | 11.030 | 3.747  | 22.133 | 1.000 | 26.30 |
| ATOM | 699 | CD  | PRO | A | 105 | 10.166 | 3.121  | 23.187 | 1.000 | 24.38 |
| ATOM | 700 | C   | PRO | A | 105 | 13.165 | 1.602  | 23.249 | 1.000 | 24.84 |
| ATOM | 701 | O   | PRO | A | 105 | 13.255 | 2.321  | 24.246 | 1.000 | 19.70 |
| ATOM | 702 | N   | GLY | A | 106 | 14.176 | 0.872  | 22.788 | 1.000 | 21.42 |
| ATOM | 703 | CA  | GLY | A | 106 | 15.485 | 1.020  | 23.423 | 1.000 | 28.59 |
| ATOM | 704 | C   | GLY | A | 106 | 16.527 | 1.498  | 22.425 | 1.000 | 30.55 |
| ATOM | 705 | O   | GLY | A | 106 | 16.222 | 2.089  | 21.395 | 1.000 | 20.21 |
| ATOM | 706 | N   | ASN | A | 107 | 17.796 | 1.244  | 22.710 | 1.000 | 32.09 |
| ATOM | 707 | CA  | ASN | A | 107 | 18.884 | 1.677  | 21.850 | 1.000 | 26.56 |
| ATOM | 708 | CB  | ASN | A | 107 | 20.219 | 1.386  | 22.552 | 1.000 | 28.73 |
| ATOM | 709 | CG  | ASN | A | 107 | 20.932 | 2.668  | 22.930 | 1.000 | 36.73 |
| ATOM | 710 | OD1 | ASN | A | 107 | 20.436 | 3.454  | 23.736 | 1.000 | 67.71 |
| ATOM | 711 | ND2 | ASN | A | 107 | 22.095 | 2.891  | 22.331 | 1.000 | 51.19 |
| ATOM | 712 | C   | ASN | A | 107 | 18.828 | 0.985  | 20.497 | 1.000 | 33.29 |
| ATOM | 713 | O   | ASN | A | 107 | 19.161 | 1.589  | 19.469 | 1.000 | 31.37 |
| ATOM | 714 | N   | ASN | A | 108 | 18.394 | -0.282 | 20.495 | 1.000 | 25.02 |
| ATOM | 715 | CA  | ASN | A | 108 | 18.476 | -1.030 | 19.241 | 1.000 | 37.28 |
| ATOM | 716 | CB  | ASN | A | 108 | 19.377 | -2.255 | 19.480 | 1.000 | 49.51 |
| ATOM | 717 | CG  | ASN | A | 108 | 20.794 | -1.843 | 19.847 | 1.000 | 47.25 |
| ATOM | 718 | OD1 | ASN | A | 108 | 21.555 | -1.301 | 19.041 | 1.000 | 51.78 |
| ATOM | 719 | ND2 | ASN | A | 108 | 21.149 | -2.103 | 21.097 | 1.000 | 32.89 |
| ATOM | 720 | C   | ASN | A | 108 | 17.157 | -1.472 | 18.642 | 1.000 | 41.66 |
| ATOM | 721 | O   | ASN | A | 108 | 17.148 | -1.922 | 17.485 | 1.000 | 47.43 |
| ATOM | 722 | N   | PHE | A | 109 | 16.007 | -1.389 | 19.306 | 1.000 | 28.44 |
| ATOM | 723 | CA  | PHE | A | 109 | 14.782 | -1.693 | 18.557 | 1.000 | 26.26 |
| ATOM | 724 | CB  | PHE | A | 109 | 14.575 | -3.179 | 18.334 | 1.000 | 25.58 |
| ATOM | 725 | CG  | PHE | A | 109 | 14.889 | -4.154 | 19.423 | 1.000 | 33.48 |
| ATOM | 726 | CD1 | PHE | A | 109 | 13.866 | -4.796 | 20.113 | 1.000 | 34.64 |
| ATOM | 727 | CE1 | PHE | A | 109 | 14.130 | -5.705 | 21.121 | 1.000 | 41.36 |

FIGURE 20

| ATOM | 728 | CZ | PHE | A | 109 | 15.442 | -5.997 | 21.459 | 1.000 | 37.10 |
| ATOM | 729 | CE2 | PHE | A | 109 | 16.469 | -5.365 | 20.782 | 1.000 | 39.85 |
| ATOM | 730 | CD2 | PHE | A | 109 | 16.198 | -4.452 | 19.778 | 1.000 | 33.66 |
| ATOM | 731 | C | PHE | A | 109 | 13.572 | -1.059 | 19.243 | 1.000 | 30.59 |
| ATOM | 732 | O | PHE | A | 109 | 13.663 | -0.571 | 20.375 | 1.000 | 28.48 |
| ATOM | 733 | N | ARG | A | 110 | 12.446 | -1.068 | 18.531 | 1.000 | 21.36 |
| ATOM | 734 | CA | ARG | A | 110 | 11.262 | -0.340 | 18.981 | 1.000 | 27.72 |
| ATOM | 735 | CB | ARG | A | 110 | 10.239 | -0.271 | 17.833 | 1.000 | 27.18 |
| ATOM | 736 | CG | ARG | A | 110 | 10.751 | 0.480 | 16.614 | 1.000 | 42.55 |
| ATOM | 737 | CD | ARG | A | 110 | 10.188 | 1.893 | 16.543 | 1.000 | 49.91 |
| ATOM | 738 | NE | ARG | A | 110 | 11.080 | 2.835 | 17.214 | 1.000 | 61.23 |
| ATOM | 739 | CZ | ARG | A | 110 | 10.772 | 4.078 | 17.551 | 1.000 | 65.49 |
| ATOM | 740 | NH1 | ARG | A | 110 | 9.569 | 4.569 | 17.287 | 1.000 | 60.40 |
| ATOM | 741 | NH2 | ARG | A | 110 | 11.681 | 4.823 | 18.164 | 1.000 | 70.08 |
| ATOM | 742 | C | ARG | A | 110 | 10.581 | -0.929 | 20.206 | 1.000 | 31.32 |
| ATOM | 743 | O | ARG | A | 110 | 10.063 | -0.191 | 21.048 | 1.000 | 19.57 |
| ATOM | 744 | N | ARG | A | 111 | 10.536 | -2.256 | 20.315 | 1.000 | 31.03 |
| ATOM | 745 | CA | ARG | A | 111 | 9.825 | -2.858 | 21.447 | 1.000 | 28.45 |
| ATOM | 746 | CB | ARG | A | 111 | 8.752 | -3.826 | 20.971 | 1.000 | 24.30 |
| ATOM | 747 | CG | ARG | A | 111 | 7.678 | -3.274 | 20.054 | 1.000 | 26.60 |
| ATOM | 748 | CD | ARG | A | 111 | 6.895 | -4.443 | 19.432 | 1.000 | 26.88 |
| ATOM | 749 | NE | ARG | A | 111 | 5.494 | -4.083 | 19.259 | 1.000 | 39.04 |
| ATOM | 750 | CZ | ARG | A | 111 | 4.427 | -4.851 | 19.403 | 1.000 | 38.77 |
| ATOM | 751 | NH1 | ARG | A | 111 | 4.532 | -6.128 | 19.745 | 1.000 | 39.25 |
| ATOM | 752 | NH2 | ARG | A | 111 | 3.226 | -4.319 | 19.199 | 1.000 | 38.01 |
| ATOM | 753 | C | ARG | A | 111 | 10.821 | -3.575 | 22.352 | 1.000 | 27.13 |
| ATOM | 754 | O | ARG | A | 111 | 10.716 | -4.761 | 22.672 | 1.000 | 22.92 |
| ATOM | 755 | N | GLU | A | 112 | 11.827 | -2.801 | 22.753 | 1.000 | 24.46 |
| ATOM | 756 | CA | GLU | A | 112 | 12.921 | -3.388 | 23.527 | 1.000 | 20.04 |
| ATOM | 757 | CB | GLU | A | 112 | 14.147 | -2.484 | 23.425 | 1.000 | 26.41 |
| ATOM | 758 | CG | GLU | A | 112 | 15.469 | -3.181 | 23.658 | 1.000 | 27.73 |
| ATOM | 759 | CD | GLU | A | 112 | 16.662 | -2.423 | 23.112 | 1.000 | 26.53 |
| ATOM | 760 | OE1 | GLU | A | 112 | 17.767 | -2.676 | 23.628 | 1.000 | 22.28 |
| ATOM | 761 | OE2 | GLU | A | 112 | 16.520 | -1.592 | 22.191 | 1.000 | 24.96 |
| ATOM | 762 | C | GLU | A | 112 | 12.523 | -3.597 | 24.976 | 1.000 | 14.90 |
| ATOM | 763 | O | GLU | A | 112 | 13.092 | -4.442 | 25.668 | 1.000 | 19.62 |
| ATOM | 764 | N | TYR | A | 113 | 11.540 | -2.823 | 25.426 | 1.000 | 12.89 |
| ATOM | 765 | CA | TYR | A | 113 | 11.084 | -2.956 | 26.807 | 1.000 | 16.51 |
| ATOM | 766 | CB | TYR | A | 113 | 11.619 | -1.873 | 27.733 | 1.000 | 20.74 |
| ATOM | 767 | CG | TYR | A | 113 | 13.078 | -1.515 | 27.619 | 1.000 | 26.13 |
| ATOM | 768 | CD1 | TYR | A | 113 | 13.516 | -0.557 | 26.718 | 1.000 | 18.47 |
| ATOM | 769 | CE1 | TYR | A | 113 | 14.856 | -0.215 | 26.600 | 1.000 | 15.41 |
| ATOM | 770 | CZ | TYR | A | 113 | 15.762 | -0.861 | 27.419 | 1.000 | 20.13 |
| ATOM | 771 | OH | TYR | A | 113 | 17.101 | -0.557 | 27.351 | 1.000 | 18.27 |
| ATOM | 772 | CE2 | TYR | A | 113 | 15.348 | -1.814 | 28.327 | 1.000 | 21.37 |
| ATOM | 773 | CD2 | TYR | A | 113 | 14.015 | -2.150 | 28.439 | 1.000 | 19.35 |
| ATOM | 774 | C | TYR | A | 113 | 9.561 | -2.892 | 26.883 | 1.000 | 12.89 |
| ATOM | 775 | O | TYR | A | 113 | 8.890 | -2.269 | 26.069 | 1.000 | 17.48 |
| ATOM | 776 | N | ILE | A | 114 | 9.052 | -3.550 | 27.919 | 1.000 | 15.07 |
| ATOM | 777 | CA | ILE | A | 114 | 7.656 | -3.353 | 28.290 | 1.000 | 16.69 |
| ATOM | 778 | CB | ILE | A | 114 | 6.820 | -4.639 | 28.237 | 1.000 | 20.07 |
| ATOM | 779 | CG1 | ILE | A | 114 | 6.471 | -5.095 | 26.816 | 1.000 | 12.15 |

FIGURE 21

| ATOM | 780 | CD1 | ILE | A | 114 | 6.039 | -6.546 | 26.725 | 1.000 | 8.94 |
|---|---|---|---|---|---|---|---|---|---|---|
| ATOM | 781 | CG2 | ILE | A | 114 | 5.565 | -4.473 | 29.088 | 1.000 | 8.30 |
| ATOM | 782 | C | ILE | A | 114 | 7.694 | -2.763 | 29.700 | 1.000 | 14.06 |
| ATOM | 783 | O | ILE | A | 114 | 8.303 | -3.348 | 30.598 | 1.000 | 21.26 |
| ATOM | 784 | N | VAL | A | 115 | 7.089 | -1.596 | 29.869 | 1.000 | 14.01 |
| ATOM | 785 | CA | VAL | A | 115 | 7.062 | -0.937 | 31.174 | 1.000 | 13.47 |
| ATOM | 786 | CB | VAL | A | 115 | 7.364 | 0.562 | 31.033 | 1.000 | 21.33 |
| ATOM | 787 | CG1 | VAL | A | 115 | 6.907 | 1.314 | 32.276 | 1.000 | 36.92 |
| ATOM | 788 | CG2 | VAL | A | 115 | 8.848 | 0.796 | 30.787 | 1.000 | 22.96 |
| ATOM | 789 | C | VAL | A | 115 | 5.679 | -1.158 | 31.777 | 1.000 | 17.22 |
| ATOM | 790 | O | VAL | A | 115 | 4.690 | -0.963 | 31.064 | 1.000 | 14.66 |
| ATOM | 791 | N | THR | A | 116 | 5.582 | -1.561 | 33.041 | 1.000 | 12.85 |
| ATOM | 792 | CA | THR | A | 116 | 4.240 | -1.763 | 33.594 | 1.000 | 13.54 |
| ATOM | 793 | CB | THR | A | 116 | 3.847 | -3.242 | 33.400 | 1.000 | 21.30 |
| ATOM | 794 | OG1 | THR | A | 116 | 2.453 | -3.453 | 33.671 | 1.000 | 12.82 |
| ATOM | 795 | CG2 | THR | A | 116 | 4.622 | -4.140 | 34.364 | 1.000 | 10.46 |
| ATOM | 796 | C | THR | A | 116 | 4.203 | -1.329 | 35.050 | 1.000 | 19.71 |
| ATOM | 797 | O | THR | A | 116 | 5.232 | -0.961 | 35.629 | 1.000 | 17.41 |
| ATOM | 798 | N | GLN | A | 117 | 3.030 | -1.346 | 35.671 | 1.000 | 15.37 |
| ATOM | 799 | CA | GLN | A | 117 | 2.879 | -0.940 | 37.068 | 1.000 | 16.82 |
| ATOM | 800 | CB | GLN | A | 117 | 1.431 | -0.504 | 37.325 | 1.000 | 15.09 |
| ATOM | 801 | CG | GLN | A | 117 | 0.408 | -1.602 | 37.048 | 1.000 | 19.18 |
| ATOM | 802 | CD | GLN | A | 117 | -1.027 | -1.187 | 37.299 | 1.000 | 20.69 |
| ATOM | 803 | OE1 | GLN | A | 117 | -1.353 | -0.007 | 37.405 | 1.000 | 25.69 |
| ATOM | 804 | NE2 | GLN | A | 117 | -1.921 | -2.158 | 37.408 | 1.000 | 18.66 |
| ATOM | 805 | C | GLN | A | 117 | 3.256 | -2.108 | 37.959 | 1.000 | 19.79 |
| ATOM | 806 | O | GLN | A | 117 | 3.305 | -3.228 | 37.431 | 1.000 | 16.87 |
| ATOM | 807 | N | GLY | A | 118 | 3.513 | -1.947 | 39.253 | 1.000 | 17.49 |
| ATOM | 808 | CA | GLY | A | 118 | 3.594 | -3.168 | 40.078 | 1.000 | 15.99 |
| ATOM | 809 | C | GLY | A | 118 | 2.238 | -3.855 | 40.061 | 1.000 | 17.56 |
| ATOM | 810 | O | GLY | A | 118 | 1.217 | -3.179 | 40.257 | 1.000 | 18.31 |
| ATOM | 811 | N | PRO | A | 119 | 2.182 | -5.164 | 39.834 | 1.000 | 24.40 |
| ATOM | 812 | CA | PRO | A | 119 | 0.885 | -5.845 | 39.699 | 1.000 | 30.48 |
| ATOM | 813 | CB | PRO | A | 119 | 1.272 | -7.296 | 39.388 | 1.000 | 31.82 |
| ATOM | 814 | CG | PRO | A | 119 | 2.683 | -7.227 | 38.899 | 1.000 | 29.01 |
| ATOM | 815 | CD | PRO | A | 119 | 3.310 | -6.102 | 39.686 | 1.000 | 21.75 |
| ATOM | 816 | C | PRO | A | 119 | 0.033 | -5.781 | 40.966 | 1.000 | 34.89 |
| ATOM | 817 | O | PRO | A | 119 | 0.531 | -5.756 | 42.091 | 1.000 | 19.13 |
| ATOM | 818 | N | LEU | A | 120 | -1.288 | -5.753 | 40.778 | 1.000 | 30.42 |
| ATOM | 819 | CA | LEU | A | 120 | -2.231 | -5.801 | 41.886 | 1.000 | 18.88 |
| ATOM | 820 | CB | LEU | A | 120 | -3.467 | -4.949 | 41.613 | 1.000 | 22.55 |
| ATOM | 821 | CG | LEU | A | 120 | -3.264 | -3.439 | 41.494 | 1.000 | 24.74 |
| ATOM | 822 | CD1 | LEU | A | 120 | -4.202 | -2.849 | 40.458 | 1.000 | 19.55 |
| ATOM | 823 | CD2 | LEU | A | 120 | -3.482 | -2.766 | 42.842 | 1.000 | 27.98 |
| ATOM | 824 | C | LEU | A | 120 | -2.690 | -7.241 | 42.099 | 1.000 | 25.27 |
| ATOM | 825 | O | LEU | A | 120 | -2.588 | -8.006 | 41.139 | 1.000 | 22.48 |
| ATOM | 826 | N | PRO | A | 121 | -3.160 | -7.550 | 43.298 | 1.000 | 32.56 |
| ATOM | 827 | CA | PRO | A | 121 | -3.719 | -8.872 | 43.596 | 1.000 | 22.33 |
| ATOM | 828 | CB | PRO | A | 121 | -4.528 | -8.621 | 44.871 | 1.000 | 23.26 |
| ATOM | 829 | CG | PRO | A | 121 | -3.777 | -7.531 | 45.557 | 1.000 | 29.77 |
| ATOM | 830 | CD | PRO | A | 121 | -3.184 | -6.660 | 44.477 | 1.000 | 30.93 |
| ATOM | 831 | C | PRO | A | 121 | -4.638 | -9.339 | 42.476 | 1.000 | 23.80 |

FIGURE 22

| | | | | | | | | | |
|---|---|---|---|---|---|---|---|---|---|
| ATOM | 832 | O | PRO | A | 121 | -4.596 | -10.483 | 42.026 | 1.000 34.64 |
| ATOM | 833 | N | GLY | A | 122 | -5.453 | -8.405 | 41.983 | 1.000 24.62 |
| ATOM | 834 | CA | GLY | A | 122 | -6.344 | -8.742 | 40.887 | 1.000 23.65 |
| ATOM | 835 | C | GLY | A | 122 | -5.751 | -8.605 | 39.505 | 1.000 23.11 |
| ATOM | 836 | O | GLY | A | 122 | -6.478 | -8.836 | 38.533 | 1.000 28.12 |
| ATOM | 837 | N | THR | A | 123 | -4.480 | -8.246 | 39.320 | 1.000 20.65 |
| ATOM | 838 | CA | THR | A | 123 | -3.939 | -8.167 | 37.962 | 1.000 21.61 |
| ATOM | 839 | CB | THR | A | 123 | -3.544 | -6.732 | 37.551 | 1.000 26.10 |
| ATOM | 840 | OG1 | THR | A | 123 | -2.505 | -6.195 | 38.380 | 1.000 23.39 |
| ATOM | 841 | CG2 | THR | A | 123 | -4.762 | -5.828 | 37.710 | 1.000 18.68 |
| ATOM | 842 | C | THR | A | 123 | -2.713 | -9.052 | 37.765 | 1.000 24.76 |
| ATOM | 843 | O | THR | A | 123 | -2.184 | -9.097 | 36.653 | 1.000 25.68 |
| ATOM | 844 | N | LYS | A | 124 | -2.249 | -9.744 | 38.806 | 1.000 23.64 |
| ATOM | 845 | CA | LYS | A | 124 | -1.015 | -10.520 | 38.633 | 1.000 29.85 |
| ATOM | 846 | CB | LYS | A | 124 | -0.485 | -10.990 | 39.979 | 1.000 33.93 |
| ATOM | 847 | CG | LYS | A | 124 | -1.476 | -11.566 | 40.964 | 1.000 33.84 |
| ATOM | 848 | CD | LYS | A | 124 | -0.857 | -11.618 | 42.358 | 1.000 31.42 |
| ATOM | 849 | CE | LYS | A | 124 | -1.630 | -12.583 | 43.246 | 1.000 29.23 |
| ATOM | 850 | NZ | LYS | A | 124 | -0.899 | -12.844 | 44.518 | 1.000 57.02 |
| ATOM | 851 | C | LYS | A | 124 | -1.209 | -11.674 | 37.656 | 1.000 25.22 |
| ATOM | 852 | O | LYS | A | 124 | -0.283 | -12.089 | 36.954 | 1.000 23.70 |
| ATOM | 853 | N | ASP | A | 125 | -2.412 | -12.221 | 37.545 | 1.000 18.28 |
| ATOM | 854 | CA | ASP | A | 125 | -2.657 | -13.219 | 36.515 | 1.000 12.12 |
| ATOM | 855 | CB | ASP | A | 125 | -4.097 | -13.722 | 36.640 | 1.000 22.43 |
| ATOM | 856 | CG | ASP | A | 125 | -4.249 | -14.657 | 37.831 | 1.000 27.90 |
| ATOM | 857 | OD1 | ASP | A | 125 | -3.285 | -14.704 | 38.618 | 1.000 29.09 |
| ATOM | 858 | OD2 | ASP | A | 125 | -5.301 | -15.311 | 37.945 | 1.000 33.37 |
| ATOM | 859 | C | ASP | A | 125 | -2.450 | -12.633 | 35.120 | 1.000 23.84 |
| ATOM | 860 | O | ASP | A | 125 | -1.964 | -13.280 | 34.191 | 1.000 23.80 |
| ATOM | 861 | N | ASP | A | 126 | -2.855 | -11.375 | 34.973 | 1.000 22.66 |
| ATOM | 862 | CA | ASP | A | 126 | -2.745 | -10.631 | 33.732 | 1.000 16.52 |
| ATOM | 863 | CB | ASP | A | 126 | -3.480 | -9.297 | 33.831 | 1.000 25.64 |
| ATOM | 864 | CG | ASP | A | 126 | -4.972 | -9.394 | 33.608 | 1.000 41.42 |
| ATOM | 865 | OD1 | ASP | A | 126 | -5.419 | -10.439 | 33.084 | 1.000 47.26 |
| ATOM | 866 | OD2 | ASP | A | 126 | -5.703 | -8.435 | 33.953 | 1.000 43.25 |
| ATOM | 867 | C | ASP | A | 126 | -1.274 | -10.385 | 33.422 | 1.000 17.37 |
| ATOM | 868 | O | ASP | A | 126 | -0.798 | -10.492 | 32.297 | 1.000 16.89 |
| ATOM | 869 | N | PHE | A | 127 | -0.544 | -10.017 | 34.473 | 1.000 17.74 |
| ATOM | 870 | CA | PHE | A | 127 | 0.871 | -9.707 | 34.284 | 1.000 21.41 |
| ATOM | 871 | CB | PHE | A | 127 | 1.493 | -9.263 | 35.604 | 1.000 21.46 |
| ATOM | 872 | CG | PHE | A | 127 | 3.004 | -9.193 | 35.632 | 1.000 22.78 |
| ATOM | 873 | CD1 | PHE | A | 127 | 3.643 | -8.020 | 35.266 | 1.000 12.05 |
| ATOM | 874 | CE1 | PHE | A | 127 | 5.024 | -7.924 | 35.292 | 1.000 16.72 |
| ATOM | 875 | CZ | PHE | A | 127 | 5.790 | -9.004 | 35.682 | 1.000 21.66 |
| ATOM | 876 | CE2 | PHE | A | 127 | 5.172 | -10.189 | 36.044 | 1.000 19.24 |
| ATOM | 877 | CD2 | PHE | A | 127 | 3.794 | -10.266 | 36.036 | 1.000 18.50 |
| ATOM | 878 | C | PHE | A | 127 | 1.578 | -10.931 | 33.700 | 1.000 25.45 |
| ATOM | 879 | O | PHE | A | 127 | 2.374 | -10.786 | 32.784 | 1.000 21.87 |
| ATOM | 880 | N | TRP | A | 128 | 1.280 | -12.107 | 34.243 | 1.000 21.42 |
| ATOM | 881 | CA | TRP | A | 128 | 1.958 | -13.350 | 33.864 | 1.000 15.43 |
| ATOM | 882 | CB | TRP | A | 128 | 1.695 | -14.415 | 34.942 | 1.000 17.74 |
| ATOM | 883 | CG | TRP | A | 128 | 2.565 | -14.200 | 36.157 | 1.000 13.35 |

FIGURE 23

| | | | | | | | | | |
|---|---|---|---|---|---|---|---|---|---|
| ATOM | 884 | CD1 | TRP | A | 128 | 2.171 | -14.021 | 37.449 | 1.000 18.06 |
| ATOM | 885 | NE1 | TRP | A | 128 | 3.264 | -13.857 | 38.263 | 1.000 16.29 |
| ATOM | 886 | CE2 | TRP | A | 128 | 4.398 | -13.927 | 37.497 | 1.000 13.72 |
| ATOM | 887 | CD2 | TRP | A | 128 | 3.999 | -14.142 | 36.169 | 1.000 15.37 |
| ATOM | 888 | CE3 | TRP | A | 128 | 4.986 | -14.251 | 35.178 | 1.000 20.85 |
| ATOM | 889 | CZ3 | TRP | A | 128 | 6.319 | -14.148 | 35.521 | 1.000 13.01 |
| ATOM | 890 | CH2 | TRP | A | 128 | 6.684 | -13.932 | 36.859 | 1.000 20.19 |
| ATOM | 891 | CZ2 | TRP | A | 128 | 5.744 | -13.822 | 37.849 | 1.000 22.48 |
| ATOM | 892 | C | TRP | A | 128 | 1.529 | -13.783 | 32.480 | 1.000 11.86 |
| ATOM | 893 | O | TRP | A | 128 | 2.310 | -14.288 | 31.668 | 1.000 21.55 |
| ATOM | 894 | N | LYS | A | 129 | 0.267 | -13.551 | 32.155 | 1.000 16.27 |
| ATOM | 895 | CA | LYS | A | 129 | -0.214 | -13.821 | 30.798 | 1.000 20.73 |
| ATOM | 896 | CB | LYS | A | 129 | -1.732 | -13.626 | 30.741 | 1.000 17.81 |
| ATOM | 897 | CG | LYS | A | 129 | -2.314 | -13.971 | 29.375 | 1.000 25.97 |
| ATOM | 898 | CD | LYS | A | 129 | -3.752 | -13.477 | 29.289 | 1.000 37.98 |
| ATOM | 899 | CE | LYS | A | 129 | -4.458 | -14.085 | 28.083 | 1.000 38.08 |
| ATOM | 900 | NZ | LYS | A | 129 | -4.700 | -15.547 | 28.280 | 1.000 56.47 |
| ATOM | 901 | C | LYS | A | 129 | 0.480 | -12.919 | 29.785 | 1.000 24.29 |
| ATOM | 902 | O | LYS | A | 129 | 0.862 | -13.346 | 28.692 | 1.000 28.21 |
| ATOM | 903 | N | MET | A | 130 | 0.668 | -11.651 | 30.143 | 1.000 19.69 |
| ATOM | 904 | CA | MET | A | 130 | 1.478 | -10.735 | 29.351 | 1.000 15.73 |
| ATOM | 905 | CB | MET | A | 130 | 1.576 | -9.342 | 29.996 | 1.000 13.64 |
| ATOM | 906 | CG | MET | A | 130 | 2.430 | -8.380 | 29.162 | 1.000 18.33 |
| ATOM | 907 | SD | MET | A | 130 | 2.476 | -6.702 | 29.808 | 1.000 23.04 |
| ATOM | 908 | CE | MET | A | 130 | 3.483 | -6.962 | 31.274 | 1.000 22.96 |
| ATOM | 909 | C | MET | A | 130 | 2.897 | -11.282 | 29.166 | 1.000 14.42 |
| ATOM | 910 | O | MET | A | 130 | 3.384 | -11.324 | 28.034 | 1.000 21.88 |
| ATOM | 911 | N | VAL | A | 131 | 3.537 | -11.664 | 30.266 | 1.000 11.85 |
| ATOM | 912 | CA | VAL | A | 131 | 4.902 | -12.202 | 30.262 | 1.000 21.55 |
| ATOM | 913 | CB | VAL | A | 131 | 5.372 | -12.557 | 31.682 | 1.000 18.65 |
| ATOM | 914 | CG1 | VAL | A | 131 | 6.598 | -13.458 | 31.679 | 1.000 16.39 |
| ATOM | 915 | CG2 | VAL | A | 131 | 5.688 | -11.303 | 32.508 | 1.000 13.87 |
| ATOM | 916 | C | VAL | A | 131 | 4.984 | -13.418 | 29.333 | 1.000 26.29 |
| ATOM | 917 | O | VAL | A | 131 | 5.892 | -13.533 | 28.500 | 1.000 16.82 |
| ATOM | 918 | N | TRP | A | 132 | 4.026 | -14.334 | 29.437 | 1.000 24.10 |
| ATOM | 919 | CA | TRP | A | 132 | 3.985 | -15.531 | 28.598 | 1.000 23.86 |
| ATOM | 920 | CB | TRP | A | 132 | 2.902 | -16.495 | 29.121 | 1.000 27.36 |
| ATOM | 921 | CG | TRP | A | 132 | 2.771 | -17.754 | 28.310 | 1.000 30.80 |
| ATOM | 922 | CD1 | TRP | A | 132 | 1.818 | -18.027 | 27.370 | 1.000 36.86 |
| ATOM | 923 | NE1 | TRP | A | 132 | 2.017 | -19.278 | 26.835 | 1.000 36.99 |
| ATOM | 924 | CE2 | TRP | A | 132 | 3.115 | -19.844 | 27.424 | 1.000 30.56 |
| ATOM | 925 | CD2 | TRP | A | 132 | 3.613 | -18.914 | 28.359 | 1.000 24.79 |
| ATOM | 926 | CE3 | TRP | A | 132 | 4.745 | -19.267 | 29.094 | 1.000 24.86 |
| ATOM | 927 | CZ3 | TRP | A | 132 | 5.332 | -20.499 | 28.890 | 1.000 26.51 |
| ATOM | 928 | CH2 | TRP | A | 132 | 4.813 | -21.405 | 27.955 | 1.000 24.87 |
| ATOM | 929 | CZ2 | TRP | A | 132 | 3.706 | -21.089 | 27.215 | 1.000 30.31 |
| ATOM | 930 | C | TRP | A | 132 | 3.747 | -15.207 | 27.129 | 1.000 29.34 |
| ATOM | 931 | O | TRP | A | 132 | 4.450 | -15.695 | 26.237 | 1.000 17.82 |
| ATOM | 932 | N | GLU | A | 133 | 2.744 | -14.379 | 26.835 | 1.000 23.54 |
| ATOM | 933 | CA | GLU | A | 133 | 2.415 | -14.062 | 25.448 | 1.000 23.03 |
| ATOM | 934 | CB | GLU | A | 133 | 1.100 | -13.274 | 25.422 | 1.000 27.10 |
| ATOM | 935 | CG | GLU | A | 133 | -0.095 | -14.176 | 25.718 | 1.000 30.65 |

FIGURE 24

```
ATOM    936  CD  GLU A 133      -1.396 -13.399  25.736 1.000 35.26
ATOM    937  OE1 GLU A 133      -1.363 -12.159  25.561 1.000 34.94
ATOM    938  OE2 GLU A 133      -2.444 -14.049  25.925 1.000 35.41
ATOM    939  C   GLU A 133       3.490 -13.262  24.735 1.000 27.45
ATOM    940  O   GLU A 133       3.689 -13.428  23.528 1.000 24.03
ATOM    941  N   GLN A 134       4.197 -12.382  25.449 1.000 21.95
ATOM    942  CA  GLN A 134       5.207 -11.554  24.787 1.000 17.30
ATOM    943  CB  GLN A 134       5.310 -10.184  25.466 1.000 17.87
ATOM    944  CG  GLN A 134       3.998  -9.411  25.524 1.000 15.39
ATOM    945  CD  GLN A 134       3.647  -8.841  24.163 1.000 19.03
ATOM    946  OE1 GLN A 134       4.481  -8.152  23.584 1.000 36.10
ATOM    947  NE2 GLN A 134       2.453  -9.133  23.668 1.000 27.56
ATOM    948  C   GLN A 134       6.576 -12.214  24.782 1.000 21.51
ATOM    949  O   GLN A 134       7.556 -11.579  24.396 1.000 32.24
ATOM    950  N   ASN A 135       6.677 -13.476  25.207 1.000 20.76
ATOM    951  CA  ASN A 135       7.974 -14.146  25.117 1.000 19.02
ATOM    952  CB  ASN A 135       8.406 -14.179  23.644 1.000 24.87
ATOM    953  CG  ASN A 135       7.566 -15.129  22.810 1.000 36.12
ATOM    954  OD1 ASN A 135       7.515 -16.331  23.072 1.000 34.91
ATOM    955  ND2 ASN A 135       6.895 -14.604  21.788 1.000 45.85
ATOM    956  C   ASN A 135       9.026 -13.459  25.974 1.000 21.43
ATOM    957  O   ASN A 135      10.193 -13.337  25.602 1.000 20.37
ATOM    958  N   VAL A 136       8.620 -12.988  27.148 1.000 16.96
ATOM    959  CA  VAL A 136       9.529 -12.287  28.047 1.000 15.79
ATOM    960  CB  VAL A 136       8.719 -11.486  29.093 1.000 11.80
ATOM    961  CG1 VAL A 136       9.587 -11.074  30.260 1.000  9.82
ATOM    962  CG2 VAL A 136       8.053 -10.279  28.431 1.000 16.29
ATOM    963  C   VAL A 136      10.440 -13.264  28.760 1.000 18.01
ATOM    964  O   VAL A 136       9.900 -14.252  29.262 1.000 28.46
ATOM    965  N   HIS A 137      11.747 -13.025  28.820 1.000 17.89
ATOM    966  CA  HIS A 137      12.634 -13.889  29.610 1.000 21.67
ATOM    967  CB  HIS A 137      13.724 -14.513  28.743 1.000 30.48
ATOM    968  CG  HIS A 137      13.253 -15.380  27.621 1.000 42.06
ATOM    969  ND1 HIS A 137      14.124 -16.077  26.808 1.000 53.39
ATOM    970  CE1 HIS A 137      13.449 -16.758  25.899 1.000 51.26
ATOM    971  NE2 HIS A 137      12.159 -16.533  26.088 1.000 49.27
ATOM    972  CD2 HIS A 137      12.018 -15.676  27.154 1.000 48.02
ATOM    973  C   HIS A 137      13.263 -13.116  30.766 1.000 19.36
ATOM    974  O   HIS A 137      13.818 -13.683  31.703 1.000 19.33
ATOM    975  N   ASN A 138      13.190 -11.780  30.748 1.000 23.51
ATOM    976  CA  ASN A 138      13.772 -11.010  31.842 1.000 19.39
ATOM    977  CB  ASN A 138      15.045 -10.301  31.351 1.000 21.07
ATOM    978  CG  ASN A 138      16.123 -11.316  30.999 1.000 26.12
ATOM    979  OD1 ASN A 138      16.514 -11.460  29.841 1.000 27.41
ATOM    980  ND2 ASN A 138      16.606 -12.026  32.011 1.000 23.04
ATOM    981  C   ASN A 138      12.811  -9.974  32.413 1.000 21.29
ATOM    982  O   ASN A 138      12.180  -9.217  31.666 1.000 16.20
ATOM    983  N   ILE A 139      12.718  -9.937  33.737 1.000 17.13
ATOM    984  CA  ILE A 139      11.859  -8.987  34.435 1.000 16.53
ATOM    985  CB  ILE A 139      10.693  -9.655  35.187 1.000 17.07
ATOM    986  CG1 ILE A 139       9.711 -10.424  34.296 1.000 17.67
ATOM    987  CD1 ILE A 139       8.911 -11.494  35.031 1.000 15.33
```

FIGURE 25

| | | | | | | | | | |
|---|---|---|---|---|---|---|---|---|---|
| ATOM | 988 | CG2 | ILE | A | 139 | 9.941 | -8.625 | 36.020 | 1.000 12.08 |
| ATOM | 989 | C | ILE | A | 139 | 12.694 | -8.169 | 35.412 | 1.000 17.79 |
| ATOM | 990 | O | ILE | A | 139 | 13.465 | -8.707 | 36.203 | 1.000 21.50 |
| ATOM | 991 | N | VAL | A | 140 | 12.560 | -6.852 | 35.353 | 1.000 19.27 |
| ATOM | 992 | CA | VAL | A | 140 | 13.298 | -5.966 | 36.242 | 1.000 20.43 |
| ATOM | 993 | CB | VAL | A | 140 | 14.088 | -4.892 | 35.469 | 1.000 23.29 |
| ATOM | 994 | CG1 | VAL | A | 140 | 14.892 | -4.018 | 36.427 | 1.000 15.96 |
| ATOM | 995 | CG2 | VAL | A | 140 | 14.965 | -5.563 | 34.419 | 1.000 15.64 |
| ATOM | 996 | C | VAL | A | 140 | 12.331 | -5.254 | 37.179 | 1.000 17.79 |
| ATOM | 997 | O | VAL | A | 140 | 11.385 | -4.619 | 36.709 | 1.000 15.65 |
| ATOM | 998 | N | MET | A | 141 | 12.596 | -5.376 | 38.473 | 1.000 19.78 |
| ATOM | 999 | CA | MET | A | 141 | 11.718 | -4.726 | 39.452 | 1.000 23.36 |
| ATOM | 1000 | CB | MET | A | 141 | 11.016 | -5.796 | 40.283 | 1.000 25.59 |
| ATOM | 1001 | CG | MET | A | 141 | 10.199 | -5.282 | 41.461 | 1.000 21.23 |
| ATOM | 1002 | SD | MET | A | 141 | 9.408 | -6.648 | 42.325 | 1.000 27.56 |
| ATOM | 1003 | CE | MET | A | 141 | 8.617 | -5.832 | 43.707 | 1.000 31.17 |
| ATOM | 1004 | C | MET | A | 141 | 12.541 | -3.772 | 40.294 | 1.000 27.26 |
| ATOM | 1005 | O | MET | A | 141 | 13.509 | -4.208 | 40.923 | 1.000 19.70 |
| ATOM | 1006 | N | VAL | A | 142 | 12.179 | -2.487 | 40.299 | 1.000 22.95 |
| ATOM | 1007 | CA | VAL | A | 142 | 12.981 | -1.529 | 41.061 | 1.000 23.51 |
| ATOM | 1008 | CB | VAL | A | 142 | 13.642 | -0.457 | 40.171 | 1.000 24.01 |
| ATOM | 1009 | CG1 | VAL | A | 142 | 14.774 | -1.104 | 39.384 | 1.000 28.07 |
| ATOM | 1010 | CG2 | VAL | A | 142 | 12.631 | 0.200 | 39.250 | 1.000 26.62 |
| ATOM | 1011 | C | VAL | A | 142 | 12.151 | -0.832 | 42.134 | 1.000 24.80 |
| ATOM | 1012 | O | VAL | A | 142 | 12.092 | 0.396 | 42.186 | 1.000 24.92 |
| ATOM | 1013 | N | THR | A | 143 | 11.544 | -1.654 | 42.968 | 1.000 32.06 |
| ATOM | 1014 | CA | THR | A | 143 | 10.713 | -1.262 | 44.092 | 1.000 31.60 |
| ATOM | 1015 | CB | THR | A | 143 | 9.303 | -0.845 | 43.629 | 1.000 34.01 |
| ATOM | 1016 | OG1 | THR | A | 143 | 8.553 | -0.296 | 44.720 | 1.000 32.56 |
| ATOM | 1017 | CG2 | THR | A | 143 | 8.489 | -2.040 | 43.150 | 1.000 19.73 |
| ATOM | 1018 | C | THR | A | 143 | 10.608 | -2.414 | 45.081 | 1.000 32.84 |
| ATOM | 1019 | O | THR | A | 143 | 10.735 | -3.579 | 44.697 | 1.000 27.98 |
| ATOM | 1020 | N | GLN | A | 144 | 10.371 | -2.074 | 46.348 | 1.000 33.83 |
| ATOM | 1021 | CA | GLN | A | 144 | 9.992 | -3.090 | 47.327 | 1.000 31.46 |
| ATOM | 1022 | CB | GLN | A | 144 | 10.464 | -2.772 | 48.733 | 1.000 28.66 |
| ATOM | 1023 | CG | GLN | A | 144 | 11.964 | -2.806 | 48.954 | 1.000 39.24 |
| ATOM | 1024 | CD | GLN | A | 144 | 12.357 | -2.317 | 50.339 | 1.000 47.09 |
| ATOM | 1025 | OE1 | GLN | A | 144 | 12.240 | -3.049 | 51.324 | 1.000 40.08 |
| ATOM | 1026 | NE2 | GLN | A | 144 | 12.828 | -1.075 | 50.438 | 1.000 32.97 |
| ATOM | 1027 | C | GLN | A | 144 | 8.469 | -3.184 | 47.268 | 1.000 30.87 |
| ATOM | 1028 | O | GLN | A | 144 | 7.859 | -2.272 | 46.701 | 1.000 27.64 |
| ATOM | 1029 | N | CYS | A | 145 | 7.887 | -4.240 | 47.815 | 1.000 32.97 |
| ATOM | 1030 | CA | CYS | A | 145 | 6.434 | -4.376 | 47.762 | 1.000 27.50 |
| ATOM | 1031 | CB | CYS | A | 145 | 6.053 | -5.820 | 48.082 | 1.000 24.78 |
| ATOM | 1032 | SG | CYS | A | 145 | 6.485 | -6.965 | 46.749 | 1.000 32.93 |
| ATOM | 1033 | C | CYS | A | 145 | 5.746 | -3.404 | 48.716 | 1.000 29.39 |
| ATOM | 1034 | O | CYS | A | 145 | 4.579 | -3.052 | 48.520 | 1.000 29.75 |
| ATOM | 1035 | N | VAL | A | 146 | 6.480 | -2.988 | 49.733 | 1.000 32.17 |
| ATOM | 1036 | CA | VAL | A | 146 | 6.060 | -2.022 | 50.744 | 1.000 32.69 |
| ATOM | 1037 | CB | VAL | A | 146 | 5.547 | -2.672 | 52.039 | 1.000 35.63 |
| ATOM | 1038 | CG1 | VAL | A | 146 | 4.981 | -1.619 | 52.989 | 1.000 28.22 |
| ATOM | 1039 | CG2 | VAL | A | 146 | 4.490 | -3.724 | 51.746 | 1.000 39.32 |

FIGURE 26

| ATOM | 1040 | C   | VAL | A | 146 | 7.238  | -1.119 | 51.101 | 1.000 | 24.56 |
| ATOM | 1041 | O   | VAL | A | 146 | 8.312  | -1.600 | 51.466 | 1.000 | 30.54 |
| ATOM | 1042 | N   | GLU | A | 147 | 7.053  | 0.184  | 50.987 | 1.000 | 26.82 |
| ATOM | 1043 | CA  | GLU | A | 147 | 8.128  | 1.123  | 51.322 | 1.000 | 34.58 |
| ATOM | 1044 | CB  | GLU | A | 147 | 8.516  | 1.929  | 50.080 | 1.000 | 36.31 |
| ATOM | 1045 | CG  | GLU | A | 147 | 8.591  | 1.048  | 48.834 | 1.000 | 43.83 |
| ATOM | 1046 | CD  | GLU | A | 147 | 9.589  | 1.535  | 47.809 | 1.000 | 42.03 |
| ATOM | 1047 | OE1 | GLU | A | 147 | 9.517  | 2.715  | 47.414 | 1.000 | 36.27 |
| ATOM | 1048 | OE2 | GLU | A | 147 | 10.460 | 0.748  | 47.383 | 1.000 | 38.56 |
| ATOM | 1049 | C   | GLU | A | 147 | 7.682  | 2.020  | 52.466 | 1.000 | 43.00 |
| ATOM | 1050 | O   | GLU | A | 147 | 6.842  | 2.895  | 52.262 | 1.000 | 36.39 |
| ATOM | 1051 | N   | LYS | A | 148 | 8.228  | 1.770  | 53.651 | 1.000 | 53.50 |
| ATOM | 1052 | CA  | LYS | A | 148 | 7.803  | 2.440  | 54.874 | 1.000 | 50.57 |
| ATOM | 1053 | CB  | LYS | A | 148 | 8.242  | 3.904  | 54.859 | 1.000 | 53.82 |
| ATOM | 1054 | CG  | LYS | A | 148 | 9.487  | 4.175  | 55.693 | 1.000 | 55.76 |
| ATOM | 1055 | CD  | LYS | A | 148 | 9.736  | 5.666  | 55.836 | 1.000 | 61.51 |
| ATOM | 1056 | CE  | LYS | A | 148 | 11.217 | 5.994  | 55.917 | 1.000 | 64.59 |
| ATOM | 1057 | NZ  | LYS | A | 148 | 11.582 | 7.165  | 55.066 | 1.000 | 54.71 |
| ATOM | 1058 | C   | LYS | A | 148 | 6.291  | 2.327  | 55.068 | 1.000 | 40.10 |
| ATOM | 1059 | O   | LYS | A | 148 | 5.588  | 3.337  | 55.119 | 1.000 | 40.70 |
| ATOM | 1060 | N   | GLY | A | 149 | 5.792  | 1.102  | 55.161 | 1.000 | 31.76 |
| ATOM | 1061 | CA  | GLY | A | 149 | 4.396  | 0.812  | 55.408 | 1.000 | 38.69 |
| ATOM | 1062 | C   | GLY | A | 149 | 3.455  | 1.021  | 54.249 | 1.000 | 45.94 |
| ATOM | 1063 | O   | GLY | A | 149 | 2.303  | 0.575  | 54.255 | 1.000 | 42.79 |
| ATOM | 1064 | N   | ARG | A | 150 | 3.889  | 1.707  | 53.188 | 1.000 | 44.38 |
| ATOM | 1065 | CA  | ARG | A | 150 | 2.967  | 1.932  | 52.076 | 1.000 | 37.05 |
| ATOM | 1066 | CB  | ARG | A | 150 | 3.179  | 3.306  | 51.450 | 1.000 | 43.59 |
| ATOM | 1067 | CG  | ARG | A | 150 | 2.273  | 4.410  | 51.971 | 1.000 | 52.87 |
| ATOM | 1068 | CD  | ARG | A | 150 | 2.530  | 5.696  | 51.196 | 1.000 | 65.25 |
| ATOM | 1069 | NE  | ARG | A | 150 | 1.626  | 6.786  | 51.559 | 1.000 | 75.91 |
| ATOM | 1070 | CZ  | ARG | A | 150 | 1.738  | 8.024  | 51.087 | 1.000 | 82.71 |
| ATOM | 1071 | NH1 | ARG | A | 150 | 2.708  | 8.322  | 50.240 | 1.000 | 99.14 |
| ATOM | 1072 | NH2 | ARG | A | 150 | 0.886  | 8.969  | 51.456 | 1.000 | 75.70 |
| ATOM | 1073 | C   | ARG | A | 150 | 3.144  | 0.849  | 51.015 | 1.000 | 31.26 |
| ATOM | 1074 | O   | ARG | A | 150 | 4.266  | 0.643  | 50.541 | 1.000 | 26.56 |
| ATOM | 1075 | N   | VAL | A | 151 | 2.039  | 0.197  | 50.671 | 1.000 | 26.68 |
| ATOM | 1076 | CA  | VAL | A | 151 | 2.035  | -0.861 | 49.673 | 1.000 | 27.32 |
| ATOM | 1077 | CB  | VAL | A | 151 | 0.713  | -1.647 | 49.660 | 1.000 | 35.52 |
| ATOM | 1078 | CG1 | VAL | A | 151 | 0.755  | -2.776 | 48.637 | 1.000 | 33.72 |
| ATOM | 1079 | CG2 | VAL | A | 151 | 0.441  | -2.202 | 51.049 | 1.000 | 18.61 |
| ATOM | 1080 | C   | VAL | A | 151 | 2.298  | -0.281 | 48.288 | 1.000 | 28.80 |
| ATOM | 1081 | O   | VAL | A | 151 | 1.563  | 0.579  | 47.806 | 1.000 | 38.64 |
| ATOM | 1082 | N   | LYS | A | 152 | 3.371  | -0.759 | 47.674 | 1.000 | 33.79 |
| ATOM | 1083 | CA  | LYS | A | 152 | 3.788  | -0.282 | 46.358 | 1.000 | 32.44 |
| ATOM | 1084 | CB  | LYS | A | 152 | 5.272  | 0.088  | 46.373 | 1.000 | 29.41 |
| ATOM | 1085 | CG  | LYS | A | 152 | 5.626  | 1.158  | 47.393 | 1.000 | 38.23 |
| ATOM | 1086 | CD  | LYS | A | 152 | 4.469  | 2.111  | 47.631 | 1.000 | 43.28 |
| ATOM | 1087 | CE  | LYS | A | 152 | 4.900  | 3.566  | 47.538 | 1.000 | 49.33 |
| ATOM | 1088 | NZ  | LYS | A | 152 | 3.834  | 4.403  | 46.910 | 1.000 | 76.06 |
| ATOM | 1089 | C   | LYS | A | 152 | 3.528  | -1.344 | 45.298 | 1.000 | 30.77 |
| ATOM | 1090 | O   | LYS | A | 152 | 3.227  | -1.024 | 44.149 | 1.000 | 33.84 |
| ATOM | 1091 | N   | CYS | A | 153 | 3.648  | -2.611 | 45.697 | 1.000 | 27.03 |

FIGURE 27

| ATOM | 1092 | CA  | CYS | A | 153 | 3.476  | -3.698  | 44.729 | 1.000 | 27.81 |
| ATOM | 1093 | CB  | CYS | A | 153 | 4.776  | -3.878  | 43.946 | 1.000 | 27.07 |
| ATOM | 1094 | SG  | CYS | A | 153 | 4.790  | -5.091  | 42.611 | 1.000 | 26.17 |
| ATOM | 1095 | C   | CYS | A | 153 | 3.064  | -4.986  | 45.420 | 1.000 | 26.82 |
| ATOM | 1096 | O   | CYS | A | 153 | 3.553  | -5.324  | 46.490 | 1.000 | 27.44 |
| ATOM | 1097 | N   | ASP | A | 154 | 2.155  | -5.742  | 44.804 | 1.000 | 34.85 |
| ATOM | 1098 | CA  | ASP | A | 154 | 1.828  | -7.062  | 45.322 | 1.000 | 37.76 |
| ATOM | 1099 | CB  | ASP | A | 154 | 0.584  | -7.638  | 44.645 | 1.000 | 29.89 |
| ATOM | 1100 | CG  | ASP | A | 154 | 0.099  | -8.911  | 45.316 | 1.000 | 34.93 |
| ATOM | 1101 | OD1 | ASP | A | 154 | -0.148 | -9.919  | 44.627 | 1.000 | 38.18 |
| ATOM | 1102 | OD2 | ASP | A | 154 | -0.042 | -8.917  | 46.557 | 1.000 | 47.22 |
| ATOM | 1103 | C   | ASP | A | 154 | 3.010  | -8.017  | 45.130 | 1.000 | 40.61 |
| ATOM | 1104 | O   | ASP | A | 154 | 3.825  | -7.877  | 44.216 | 1.000 | 30.25 |
| ATOM | 1105 | N   | HIS | A | 155 | 3.097  | -8.993  | 46.020 | 1.000 | 32.47 |
| ATOM | 1106 | CA  | HIS | A | 155 | 4.072  | -10.070 | 45.914 | 1.000 | 30.20 |
| ATOM | 1107 | CB  | HIS | A | 155 | 4.312  | -10.721 | 47.282 | 1.000 | 28.22 |
| ATOM | 1108 | CG  | HIS | A | 155 | 5.365  | -11.788 | 47.244 | 1.000 | 30.06 |
| ATOM | 1109 | ND1 | HIS | A | 155 | 6.655  | -11.595 | 47.686 | 1.000 | 32.04 |
| ATOM | 1110 | CE1 | HIS | A | 155 | 7.357  | -12.700 | 47.514 | 1.000 | 31.07 |
| ATOM | 1111 | NE2 | HIS | A | 155 | 6.557  | -13.606 | 46.980 | 1.000 | 35.21 |
| ATOM | 1112 | CD2 | HIS | A | 155 | 5.311  | -13.064 | 46.793 | 1.000 | 27.75 |
| ATOM | 1113 | C   | HIS | A | 155 | 3.531  | -11.053 | 44.879 | 1.000 | 30.27 |
| ATOM | 1114 | O   | HIS | A | 155 | 2.745  | -11.922 | 45.253 | 1.000 | 34.64 |
| ATOM | 1115 | N   | TYR | A | 156 | 3.914  | -10.897 | 43.613 | 1.000 | 24.90 |
| ATOM | 1116 | CA  | TYR | A | 156 | 3.234  | -11.590 | 42.521 | 1.000 | 22.68 |
| ATOM | 1117 | CB  | TYR | A | 156 | 3.093  | -10.621 | 41.340 | 1.000 | 22.68 |
| ATOM | 1118 | CG  | TYR | A | 156 | 4.387  | -10.046 | 40.818 | 1.000 | 21.15 |
| ATOM | 1119 | CD1 | TYR | A | 156 | 5.101  | -10.741 | 39.844 | 1.000 | 20.48 |
| ATOM | 1120 | CE1 | TYR | A | 156 | 6.286  | -10.236 | 39.348 | 1.000 | 18.15 |
| ATOM | 1121 | CZ  | TYR | A | 156 | 6.755  | -9.037  | 39.824 | 1.000 | 18.02 |
| ATOM | 1122 | OH  | TYR | A | 156 | 7.933  | -8.545  | 39.322 | 1.000 | 19.23 |
| ATOM | 1123 | CE2 | TYR | A | 156 | 6.070  | -8.320  | 40.786 | 1.000 | 19.56 |
| ATOM | 1124 | CD2 | TYR | A | 156 | 4.883  | -8.836  | 41.274 | 1.000 | 17.13 |
| ATOM | 1125 | C   | TYR | A | 156 | 3.905  | -12.870 | 42.063 | 1.000 | 25.52 |
| ATOM | 1126 | O   | TYR | A | 156 | 3.550  | -13.447 | 41.027 | 1.000 | 22.83 |
| ATOM | 1127 | N   | TRP | A | 157 | 4.881  | -13.356 | 42.825 | 1.000 | 33.11 |
| ATOM | 1128 | CA  | TRP | A | 157 | 5.531  | -14.623 | 42.504 | 1.000 | 31.82 |
| ATOM | 1129 | CB  | TRP | A | 157 | 6.985  | -14.383 | 42.092 | 1.000 | 32.50 |
| ATOM | 1130 | CG  | TRP | A | 157 | 7.827  | -13.805 | 43.197 | 1.000 | 31.35 |
| ATOM | 1131 | CD1 | TRP | A | 157 | 8.582  | -14.486 | 44.110 | 1.000 | 27.90 |
| ATOM | 1132 | NE1 | TRP | A | 157 | 9.208  | -13.611 | 44.960 | 1.000 | 24.08 |
| ATOM | 1133 | CE2 | TRP | A | 157 | 8.866  | -12.330 | 44.607 | 1.000 | 25.03 |
| ATOM | 1134 | CD2 | TRP | A | 157 | 8.000  | -12.414 | 43.503 | 1.000 | 28.13 |
| ATOM | 1135 | CE3 | TRP | A | 157 | 7.500  | -11.231 | 42.944 | 1.000 | 23.89 |
| ATOM | 1136 | CZ3 | TRP | A | 157 | 7.880  | -10.030 | 43.502 | 1.000 | 22.95 |
| ATOM | 1137 | CH2 | TRP | A | 157 | 8.743  | -9.975  | 44.602 | 1.000 | 25.46 |
| ATOM | 1138 | CZ2 | TRP | A | 157 | 9.251  | -11.113 | 45.172 | 1.000 | 27.53 |
| ATOM | 1139 | C   | TRP | A | 157 | 5.490  | -15.556 | 43.706 | 1.000 | 28.64 |
| ATOM | 1140 | O   | TRP | A | 157 | 5.361  | -15.056 | 44.828 | 1.000 | 33.96 |
| ATOM | 1141 | N   | PRO | A | 158 | 5.623  | -16.858 | 43.503 | 1.000 | 30.31 |
| ATOM | 1142 | CA  | PRO | A | 158 | 5.666  | -17.787 | 44.640 | 1.000 | 33.91 |
| ATOM | 1143 | CB  | PRO | A | 158 | 5.597  | -19.170 | 44.009 | 1.000 | 24.17 |

FIGURE 28

```
ATOM   1144  CG   PRO A 158       5.988 -18.987  42.583  1.000  30.62
ATOM   1145  CD   PRO A 158       5.757 -17.553  42.215  1.000  28.57
ATOM   1146  C    PRO A 158       6.990 -17.602  45.391  1.000  42.64
ATOM   1147  O    PRO A 158       8.051 -17.797  44.790  1.000  41.28
ATOM   1148  N    ALA A 159       6.903 -17.227  46.657  1.000  44.31
ATOM   1149  CA   ALA A 159       8.044 -16.897  47.500  1.000  52.40
ATOM   1150  CB   ALA A 159       7.567 -16.083  48.701  1.000  39.50
ATOM   1151  C    ALA A 159       8.838 -18.094  48.000  1.000  52.74
ATOM   1152  O    ALA A 159       9.922 -17.935  48.572  1.000  69.24
ATOM   1153  N    ASP A 160       8.338 -19.307  47.809  1.000  51.47
ATOM   1154  CA   ASP A 160       9.110 -20.487  48.190  1.000  60.84
ATOM   1155  CB   ASP A 160       8.266 -21.507  48.945  1.000  68.39
ATOM   1156  CG   ASP A 160       7.989 -21.175  50.394  1.000  75.02
ATOM   1157  OD1  ASP A 160       8.838 -20.519  51.035  1.000  88.56
ATOM   1158  OD2  ASP A 160       6.913 -21.574  50.891  1.000  76.88
ATOM   1159  C    ASP A 160       9.663 -21.134  46.924  1.000  53.11
ATOM   1160  O    ASP A 160       9.452 -20.618  45.827  1.000  52.42
ATOM   1161  N    GLN A 161      10.327 -22.273  47.064  1.000  49.61
ATOM   1162  CA   GLN A 161      10.738 -23.062  45.911  1.000  54.59
ATOM   1163  CB   GLN A 161      11.818 -24.073  46.306  1.000  56.30
ATOM   1164  CG   GLN A 161      13.239 -23.547  46.201  1.000  55.95
ATOM   1165  CD   GLN A 161      13.450 -22.701  44.959  1.000  53.24
ATOM   1166  OE1  GLN A 161      13.368 -23.208  43.842  1.000  49.06
ATOM   1167  NE2  GLN A 161      13.724 -21.415  45.153  1.000  41.80
ATOM   1168  C    GLN A 161       9.543 -23.794  45.301  1.000  51.44
ATOM   1169  O    GLN A 161       9.666 -24.493  44.295  1.000  52.78
ATOM   1170  N    ASP A 162       8.381 -23.641  45.922  1.000  45.89
ATOM   1171  CA   ASP A 162       7.149 -24.258  45.482  1.000  51.10
ATOM   1172  CB   ASP A 162       6.101 -24.204  46.603  1.000  57.35
ATOM   1173  CG   ASP A 162       5.884 -22.779  47.078  1.000  65.40
ATOM   1174  OD1  ASP A 162       6.698 -21.916  46.685  1.000  69.28
ATOM   1175  OD2  ASP A 162       4.914 -22.539  47.823  1.000  75.26
ATOM   1176  C    ASP A 162       6.603 -23.596  44.219  1.000  49.85
ATOM   1177  O    ASP A 162       7.291 -22.878  43.496  1.000  53.02
ATOM   1178  N    SER A 163       5.331 -23.884  43.972  1.000  41.47
ATOM   1179  CA   SER A 163       4.634 -23.472  42.768  1.000  32.87
ATOM   1180  CB   SER A 163       4.486 -24.685  41.840  1.000  32.47
ATOM   1181  OG   SER A 163       3.800 -25.721  42.529  1.000  31.33
ATOM   1182  C    SER A 163       3.257 -22.894  43.072  1.000  32.86
ATOM   1183  O    SER A 163       2.679 -23.132  44.135  1.000  30.48
ATOM   1184  N    LEU A 164       2.739 -22.138  42.115  1.000  28.27
ATOM   1185  CA   LEU A 164       1.390 -21.603  42.172  1.000  23.14
ATOM   1186  CB   LEU A 164       1.320 -20.222  42.813  1.000  23.52
ATOM   1187  CG   LEU A 164       1.908 -20.041  44.206  1.000  37.76
ATOM   1188  CD1  LEU A 164       1.918 -18.560  44.569  1.000  36.50
ATOM   1189  CD2  LEU A 164       1.141 -20.859  45.236  1.000  38.57
ATOM   1190  C    LEU A 164       0.833 -21.459  40.757  1.000  28.03
ATOM   1191  O    LEU A 164       1.613 -21.308  39.816  1.000  24.57
ATOM   1192  N    TYR A 165      -0.492 -21.480  40.677  1.000  28.64
ATOM   1193  CA   TYR A 165      -1.157 -21.136  39.432  1.000  28.93
ATOM   1194  CB   TYR A 165      -2.517 -21.817  39.316  1.000  22.72
ATOM   1195  CG   TYR A 165      -2.482 -23.276  38.942  1.000  18.62
```

FIGURE 29

```
ATOM   1196  CD1 TYR A 165      -2.328  -24.260  39.911  1.000  25.83
ATOM   1197  CE1 TYR A 165      -2.294  -25.603  39.581  1.000  25.94
ATOM   1198  CZ  TYR A 165      -2.418  -25.987  38.262  1.000  26.30
ATOM   1199  OH  TYR A 165      -2.393  -27.324  37.926  1.000  27.99
ATOM   1200  CE2 TYR A 165      -2.577  -25.035  37.287  1.000  21.27
ATOM   1201  CD2 TYR A 165      -2.606  -23.693  37.627  1.000  22.96
ATOM   1202  C   TYR A 165      -1.349  -19.620  39.364  1.000  30.51
ATOM   1203  O   TYR A 165      -1.633  -19.005  40.383  1.000  27.58
ATOM   1204  N   TYR A 166      -1.205  -19.047  38.185  1.000  24.74
ATOM   1205  CA  TYR A 166      -1.612  -17.675  37.914  1.000  24.22
ATOM   1206  CB  TYR A 166      -0.422  -16.731  37.786  1.000  24.27
ATOM   1207  CG  TYR A 166       0.394  -16.584  39.057  1.000  25.75
ATOM   1208  CD1 TYR A 166       0.075  -15.624  40.015  1.000  21.51
ATOM   1209  CE1 TYR A 166       0.820  -15.483  41.177  1.000  23.56
ATOM   1210  CZ  TYR A 166       1.899  -16.316  41.394  1.000  24.64
ATOM   1211  OH  TYR A 166       2.646  -16.197  42.543  1.000  25.20
ATOM   1212  CE2 TYR A 166       2.244  -17.280  40.464  1.000  21.31
ATOM   1213  CD2 TYR A 166       1.492  -17.401  39.306  1.000  28.88
ATOM   1214  C   TYR A 166      -2.449  -17.749  36.642  1.000  28.89
ATOM   1215  O   TYR A 166      -1.923  -17.886  35.535  1.000  28.35
ATOM   1216  N   GLY A 167      -3.775  -17.705  36.793  1.000  30.71
ATOM   1217  CA  GLY A 167      -4.586  -17.861  35.583  1.000  35.47
ATOM   1218  C   GLY A 167      -4.383  -19.271  35.038  1.000  34.48
ATOM   1219  O   GLY A 167      -4.521  -20.213  35.826  1.000  29.66
ATOM   1220  N   ASP A 168      -4.072  -19.391  33.760  1.000  25.86
ATOM   1221  CA  ASP A 168      -3.860  -20.665  33.082  1.000  23.07
ATOM   1222  CB  ASP A 168      -4.216  -20.560  31.601  1.000  22.17
ATOM   1223  CG  ASP A 168      -5.719  -20.526  31.403  1.000  30.38
ATOM   1224  OD1 ASP A 168      -6.422  -20.536  32.432  1.000  44.55
ATOM   1225  OD2 ASP A 168      -6.178  -20.501  30.246  1.000  52.57
ATOM   1226  C   ASP A 168      -2.411  -21.110  33.207  1.000  28.96
ATOM   1227  O   ASP A 168      -1.997  -22.187  32.785  1.000  35.10
ATOM   1228  N   LEU A 169      -1.617  -20.229  33.816  1.000  33.00
ATOM   1229  CA  LEU A 169      -0.197  -20.558  33.927  1.000  32.77
ATOM   1230  CB  LEU A 169       0.652  -19.326  33.571  1.000  25.71
ATOM   1231  CG  LEU A 169       0.116  -18.558  32.353  1.000  24.37
ATOM   1232  CD1 LEU A 169       0.491  -17.088  32.434  1.000  31.21
ATOM   1233  CD2 LEU A 169       0.634  -19.191  31.076  1.000  35.13
ATOM   1234  C   LEU A 169       0.190  -21.063  35.306  1.000  20.10
ATOM   1235  O   LEU A 169      -0.332  -20.698  36.352  1.000  25.85
ATOM   1236  N   ILE A 170       1.186  -21.938  35.253  1.000  23.95
ATOM   1237  CA  ILE A 170       1.792  -22.432  36.482  1.000  30.46
ATOM   1238  CB  ILE A 170       1.748  -23.965  36.556  1.000  29.06
ATOM   1239  CG1 ILE A 170       2.820  -24.536  37.485  1.000  31.61
ATOM   1240  CD1 ILE A 170       2.381  -24.474  38.935  1.000  36.97
ATOM   1241  CG2 ILE A 170       1.824  -24.585  35.175  1.000  61.97
ATOM   1242  C   ILE A 170       3.229  -21.924  36.541  1.000  27.52
ATOM   1243  O   ILE A 170       3.980  -22.051  35.579  1.000  28.50
ATOM   1244  N   LEU A 171       3.581  -21.324  37.663  1.000  33.56
ATOM   1245  CA  LEU A 171       4.899  -20.758  37.889  1.000  23.37
ATOM   1246  CB  LEU A 171       4.752  -19.251  38.120  1.000  35.18
ATOM   1247  CG  LEU A 171       5.997  -18.414  37.823  1.000  43.60
```

FIGURE 30

| ATOM | 1248 | CD1 | LEU | A | 171 | 5.642 | -17.121 | 37.111 | 1.000 | 63.91 |
| --- | --- | --- | --- | --- | --- | --- | --- | --- | --- | --- |
| ATOM | 1249 | CD2 | LEU | A | 171 | 6.736 | -18.133 | 39.121 | 1.000 | 45.12 |
| ATOM | 1250 | C | LEU | A | 171 | 5.591 | -21.435 | 39.061 | 1.000 | 27.57 |
| ATOM | 1251 | O | LEU | A | 171 | 5.001 | -21.717 | 40.109 | 1.000 | 26.54 |
| ATOM | 1252 | N | GLN | A | 172 | 6.879 | -21.712 | 38.886 | 1.000 | 33.32 |
| ATOM | 1253 | CA | GLN | A | 172 | 7.659 | -22.398 | 39.914 | 1.000 | 32.37 |
| ATOM | 1254 | CB | GLN | A | 172 | 7.941 | -23.825 | 39.432 | 1.000 | 29.07 |
| ATOM | 1255 | CG | GLN | A | 172 | 8.747 | -24.687 | 40.384 | 1.000 | 30.68 |
| ATOM | 1256 | CD | GLN | A | 172 | 9.108 | -26.026 | 39.763 | 1.000 | 33.95 |
| ATOM | 1257 | OE1 | GLN | A | 172 | 9.084 | -26.176 | 38.543 | 1.000 | 34.24 |
| ATOM | 1258 | NE2 | GLN | A | 172 | 9.436 | -27.007 | 40.589 | 1.000 | 42.96 |
| ATOM | 1259 | C | GLN | A | 172 | 8.953 | -21.663 | 40.192 | 1.000 | 26.84 |
| ATOM | 1260 | O | GLN | A | 172 | 9.698 | -21.353 | 39.268 | 1.000 | 27.43 |
| ATOM | 1261 | N | MET | A | 173 | 9.304 | -21.339 | 41.437 | 1.000 | 32.50 |
| ATOM | 1262 | CA | MET | A | 173 | 10.597 | -20.678 | 41.595 | 1.000 | 30.97 |
| ATOM | 1263 | CB | MET | A | 173 | 10.693 | -19.860 | 42.883 | 1.000 | 29.94 |
| ATOM | 1264 | CG | MET | A | 173 | 12.132 | -19.396 | 43.134 | 1.000 | 34.61 |
| ATOM | 1265 | SD | MET | A | 173 | 12.197 | -18.091 | 44.380 | 1.000 | 57.02 |
| ATOM | 1266 | CE | MET | A | 173 | 12.001 | -19.065 | 45.860 | 1.000 | 24.26 |
| ATOM | 1267 | C | MET | A | 173 | 11.719 | -21.715 | 41.612 | 1.000 | 36.84 |
| ATOM | 1268 | O | MET | A | 173 | 11.649 | -22.640 | 42.427 | 1.000 | 50.73 |
| ATOM | 1269 | N | LEU | A | 174 | 12.703 | -21.541 | 40.741 | 1.000 | 29.04 |
| ATOM | 1270 | CA | LEU | A | 174 | 13.805 | -22.491 | 40.663 | 1.000 | 33.35 |
| ATOM | 1271 | CB | LEU | A | 174 | 14.272 | -22.638 | 39.215 | 1.000 | 28.88 |
| ATOM | 1272 | CG | LEU | A | 174 | 13.322 | -23.341 | 38.253 | 1.000 | 37.78 |
| ATOM | 1273 | CD1 | LEU | A | 174 | 13.953 | -23.473 | 36.869 | 1.000 | 27.40 |
| ATOM | 1274 | CD2 | LEU | A | 174 | 12.907 | -24.710 | 38.769 | 1.000 | 40.70 |
| ATOM | 1275 | C | LEU | A | 174 | 14.990 | -22.089 | 41.532 | 1.000 | 40.05 |
| ATOM | 1276 | O | LEU | A | 174 | 15.816 | -22.939 | 41.869 | 1.000 | 47.76 |
| ATOM | 1277 | N | SER | A | 175 | 15.096 | -20.812 | 41.884 | 1.000 | 40.28 |
| ATOM | 1278 | CA | SER | A | 175 | 16.267 | -20.331 | 42.611 | 1.000 | 36.37 |
| ATOM | 1279 | CB | SER | A | 175 | 17.521 | -20.496 | 41.750 | 1.000 | 41.94 |
| ATOM | 1280 | OG | SER | A | 175 | 17.651 | -19.439 | 40.814 | 1.000 | 42.50 |
| ATOM | 1281 | C | SER | A | 175 | 16.120 | -18.877 | 43.028 | 1.000 | 33.27 |
| ATOM | 1282 | O | SER | A | 175 | 15.231 | -18.146 | 42.597 | 1.000 | 31.30 |
| ATOM | 1283 | N | GLU | A | 176 | 17.016 | -18.426 | 43.908 | 1.000 | 21.04 |
| ATOM | 1284 | CA | GLU | A | 176 | 16.840 | -17.086 | 44.444 | 1.000 | 28.91 |
| ATOM | 1285 | CB | GLU | A | 176 | 15.621 | -17.013 | 45.373 | 1.000 | 31.33 |
| ATOM | 1286 | CG | GLU | A | 176 | 15.576 | -15.684 | 46.108 | 1.000 | 33.37 |
| ATOM | 1287 | CD | GLU | A | 176 | 14.525 | -15.568 | 47.187 | 1.000 | 40.95 |
| ATOM | 1288 | OE1 | GLU | A | 176 | 14.831 | -15.906 | 48.350 | 1.000 | 66.50 |
| ATOM | 1289 | OE2 | GLU | A | 176 | 13.390 | -15.121 | 46.900 | 1.000 | 42.21 |
| ATOM | 1290 | C | GLU | A | 176 | 18.075 | -16.657 | 45.225 | 1.000 | 35.17 |
| ATOM | 1291 | O | GLU | A | 176 | 18.353 | -17.212 | 46.288 | 1.000 | 48.02 |
| ATOM | 1292 | N | SER | A | 177 | 18.794 | -15.685 | 44.683 | 1.000 | 30.91 |
| ATOM | 1293 | CA | SER | A | 177 | 20.036 | -15.232 | 45.282 | 1.000 | 28.08 |
| ATOM | 1294 | CB | SER | A | 177 | 21.182 | -15.290 | 44.263 | 1.000 | 26.33 |
| ATOM | 1295 | OG | SER | A | 177 | 21.340 | -16.639 | 43.844 | 1.000 | 59.53 |
| ATOM | 1296 | C | SER | A | 177 | 19.908 | -13.811 | 45.804 | 1.000 | 28.71 |
| ATOM | 1297 | O | SER | A | 177 | 19.678 | -12.900 | 45.008 | 1.000 | 21.80 |
| ATOM | 1298 | N | VAL | A | 178 | 20.078 | -13.672 | 47.112 | 1.000 | 28.75 |
| ATOM | 1299 | CA | VAL | A | 178 | 20.081 | -12.360 | 47.739 | 1.000 | 33.94 |

FIGURE 31

| | | | | | | | | | |
|---|---|---|---|---|---|---|---|---|---|
| ATOM | 1300 | CB | VAL | A | 178 | 19.564 | -12.385 | 49.185 | 1.000 36.90 |
| ATOM | 1301 | CG1 | VAL | A | 178 | 19.530 | -10.966 | 49.740 | 1.000 26.11 |
| ATOM | 1302 | CG2 | VAL | A | 178 | 18.191 | -13.032 | 49.252 | 1.000 38.71 |
| ATOM | 1303 | C | VAL | A | 178 | 21.492 | -11.768 | 47.753 | 1.000 37.69 |
| ATOM | 1304 | O | VAL | A | 178 | 22.404 | -12.390 | 48.298 | 1.000 42.82 |
| ATOM | 1305 | N | LEU | A | 179 | 21.605 | -10.603 | 47.149 | 1.000 36.54 |
| ATOM | 1306 | CA | LEU | A | 179 | 22.772 | -9.738 | 47.125 | 1.000 37.72 |
| ATOM | 1307 | CB | LEU | A | 179 | 23.086 | -9.250 | 45.709 | 1.000 40.59 |
| ATOM | 1308 | CG | LEU | A | 179 | 23.817 | -10.254 | 44.811 | 1.000 42.47 |
| ATOM | 1309 | CD1 | LEU | A | 179 | 24.258 | -11.454 | 45.634 | 1.000 49.20 |
| ATOM | 1310 | CD2 | LEU | A | 179 | 22.942 | -10.672 | 43.638 | 1.000 27.98 |
| ATOM | 1311 | C | LEU | A | 179 | 22.522 | -8.547 | 48.041 | 1.000 36.64 |
| ATOM | 1312 | O | LEU | A | 179 | 21.375 | -8.338 | 48.461 | 1.000 39.97 |
| ATOM | 1313 | N | PRO | A | 180 | 23.523 | -7.750 | 48.377 | 1.000 35.66 |
| ATOM | 1314 | CA | PRO | A | 180 | 23.219 | -6.610 | 49.254 | 1.000 37.77 |
| ATOM | 1315 | CB | PRO | A | 180 | 24.584 | -5.934 | 49.447 | 1.000 38.49 |
| ATOM | 1316 | CG | PRO | A | 180 | 25.553 | -7.049 | 49.201 | 1.000 37.57 |
| ATOM | 1317 | CD | PRO | A | 180 | 24.950 | -7.802 | 48.031 | 1.000 30.63 |
| ATOM | 1318 | C | PRO | A | 180 | 22.228 | -5.644 | 48.617 | 1.000 33.86 |
| ATOM | 1319 | O | PRO | A | 180 | 21.382 | -5.100 | 49.338 | 1.000 33.02 |
| ATOM | 1320 | N | GLU | A | 181 | 22.328 | -5.430 | 47.303 | 1.000 29.48 |
| ATOM | 1321 | CA | GLU | A | 181 | 21.557 | -4.357 | 46.678 | 1.000 30.49 |
| ATOM | 1322 | CB | GLU | A | 181 | 22.501 | -3.428 | 45.911 | 1.000 33.66 |
| ATOM | 1323 | CG | GLU | A | 181 | 23.039 | -2.275 | 46.752 | 1.000 42.87 |
| ATOM | 1324 | CD | GLU | A | 181 | 24.282 | -1.678 | 46.120 | 1.000 51.54 |
| ATOM | 1325 | OE1 | GLU | A | 181 | 25.233 | -2.443 | 45.850 | 1.000 75.46 |
| ATOM | 1326 | OE2 | GLU | A | 181 | 24.303 | -0.455 | 45.890 | 1.000 75.08 |
| ATOM | 1327 | C | GLU | A | 181 | 20.471 | -4.855 | 45.741 | 1.000 31.78 |
| ATOM | 1328 | O | GLU | A | 181 | 19.651 | -4.082 | 45.245 | 1.000 30.15 |
| ATOM | 1329 | N | TRP | A | 182 | 20.469 | -6.158 | 45.486 | 1.000 30.83 |
| ATOM | 1330 | CA | TRP | A | 182 | 19.412 | -6.733 | 44.667 | 1.000 29.29 |
| ATOM | 1331 | CB | TRP | A | 182 | 19.582 | -6.376 | 43.197 | 1.000 28.58 |
| ATOM | 1332 | CG | TRP | A | 182 | 20.858 | -6.827 | 42.567 | 1.000 33.11 |
| ATOM | 1333 | CD1 | TRP | A | 182 | 21.167 | -8.066 | 42.078 | 1.000 32.78 |
| ATOM | 1334 | NE1 | TRP | A | 182 | 22.451 | -8.067 | 41.577 | 1.000 29.50 |
| ATOM | 1335 | CE2 | TRP | A | 182 | 22.991 | -6.819 | 41.738 | 1.000 29.38 |
| ATOM | 1336 | CD2 | TRP | A | 182 | 22.021 | -6.010 | 42.354 | 1.000 28.84 |
| ATOM | 1337 | CE3 | TRP | A | 182 | 22.313 | -4.676 | 42.637 | 1.000 26.83 |
| ATOM | 1338 | CZ3 | TRP | A | 182 | 23.561 | -4.198 | 42.293 | 1.000 27.97 |
| ATOM | 1339 | CH2 | TRP | A | 182 | 24.508 | -5.021 | 41.679 | 1.000 32.03 |
| ATOM | 1340 | CZ2 | TRP | A | 182 | 24.250 | -6.333 | 41.391 | 1.000 35.86 |
| ATOM | 1341 | C | TRP | A | 182 | 19.363 | -8.248 | 44.842 | 1.000 29.75 |
| ATOM | 1342 | O | TRP | A | 182 | 20.270 | -8.854 | 45.409 | 1.000 29.69 |
| ATOM | 1343 | N | THR | A | 183 | 18.273 | -8.804 | 44.338 | 1.000 23.29 |
| ATOM | 1344 | CA | THR | A | 183 | 17.984 | -10.221 | 44.437 | 1.000 22.15 |
| ATOM | 1345 | CB | THR | A | 183 | 16.812 | -10.506 | 45.397 | 1.000 23.41 |
| ATOM | 1346 | OG1 | THR | A | 183 | 17.155 | -10.024 | 46.694 | 1.000 26.52 |
| ATOM | 1347 | CG2 | THR | A | 183 | 16.567 | -12.004 | 45.501 | 1.000 25.62 |
| ATOM | 1348 | C | THR | A | 183 | 17.630 | -10.771 | 43.063 | 1.000 22.12 |
| ATOM | 1349 | O | THR | A | 183 | 16.748 | -10.228 | 42.399 | 1.000 27.35 |
| ATOM | 1350 | N | ILE | A | 184 | 18.333 | -11.820 | 42.662 | 1.000 22.30 |
| ATOM | 1351 | CA | ILE | A | 184 | 18.088 | -12.437 | 41.360 | 1.000 23.94 |

FIGURE 32

| | | | | | | | | | |
|---|---|---|---|---|---|---|---|---|---|
| ATOM | 1352 | CB | ILE | A | 184 | 19.396 | -12.675 | 40.592 | 1.000 25.30 |
| ATOM | 1353 | CG1 | ILE | A | 184 | 20.199 | -11.396 | 40.326 | 1.000 22.21 |
| ATOM | 1354 | CD1 | ILE | A | 184 | 21.601 | -11.696 | 39.831 | 1.000 22.92 |
| ATOM | 1355 | CG2 | ILE | A | 184 | 19.170 | -13.392 | 39.270 | 1.000 24.72 |
| ATOM | 1356 | C | ILE | A | 184 | 17.317 | -13.730 | 41.564 | 1.000 27.42 |
| ATOM | 1357 | O | ILE | A | 184 | 17.775 | -14.657 | 42.235 | 1.000 27.72 |
| ATOM | 1358 | N | ARG | A | 185 | 16.108 | -13.816 | 41.000 | 1.000 24.23 |
| ATOM | 1359 | CA | ARG | A | 185 | 15.404 | -15.097 | 41.120 | 1.000 17.59 |
| ATOM | 1360 | CB | ARG | A | 185 | 14.007 | -14.943 | 41.706 | 1.000 21.98 |
| ATOM | 1361 | CG | ARG | A | 185 | 13.946 | -14.608 | 43.191 | 1.000 30.13 |
| ATOM | 1362 | CD | ARG | A | 185 | 12.698 | -13.806 | 43.506 | 1.000 29.20 |
| ATOM | 1363 | NE | ARG | A | 185 | 12.608 | -13.366 | 44.885 | 1.000 25.63 |
| ATOM | 1364 | CZ | ARG | A | 185 | 12.669 | -12.112 | 45.309 | 1.000 25.06 |
| ATOM | 1365 | NH1 | ARG | A | 185 | 12.832 | -11.112 | 44.455 | 1.000 24.55 |
| ATOM | 1366 | NH2 | ARG | A | 185 | 12.570 | -11.850 | 46.607 | 1.000 24.44 |
| ATOM | 1367 | C | ARG | A | 185 | 15.324 | -15.729 | 39.740 | 1.000 18.32 |
| ATOM | 1368 | O | ARG | A | 185 | 15.468 | -15.034 | 38.737 | 1.000 27.89 |
| ATOM | 1369 | N | GLU | A | 186 | 15.083 | -17.033 | 39.702 | 1.000 27.54 |
| ATOM | 1370 | CA | GLU | A | 186 | 14.806 | -17.688 | 38.433 | 1.000 33.52 |
| ATOM | 1371 | CB | GLU | A | 186 | 15.931 | -18.640 | 38.027 | 1.000 37.26 |
| ATOM | 1372 | CG | GLU | A | 186 | 15.709 | -19.229 | 36.633 | 1.000 44.30 |
| ATOM | 1373 | CD | GLU | A | 186 | 16.999 | -19.785 | 36.063 | 1.000 50.45 |
| ATOM | 1374 | OE1 | GLU | A | 186 | 16.974 | -20.303 | 34.930 | 1.000 68.14 |
| ATOM | 1375 | OE2 | GLU | A | 186 | 18.035 | -19.694 | 36.755 | 1.000 45.57 |
| ATOM | 1376 | C | GLU | A | 186 | 13.496 | -18.471 | 38.501 | 1.000 35.05 |
| ATOM | 1377 | O | GLU | A | 186 | 13.271 | -19.227 | 39.448 | 1.000 27.73 |
| ATOM | 1378 | N | PHE | A | 187 | 12.649 | -18.294 | 37.488 | 1.000 21.89 |
| ATOM | 1379 | CA | PHE | A | 187 | 11.434 | -19.091 | 37.427 | 1.000 24.39 |
| ATOM | 1380 | CB | PHE | A | 187 | 10.188 | -18.203 | 37.533 | 1.000 26.13 |
| ATOM | 1381 | CG | PHE | A | 187 | 10.245 | -17.205 | 38.663 | 1.000 34.20 |
| ATOM | 1382 | CD1 | PHE | A | 187 | 10.669 | -15.907 | 38.444 | 1.000 31.66 |
| ATOM | 1383 | CE1 | PHE | A | 187 | 10.727 | -14.979 | 39.465 | 1.000 27.66 |
| ATOM | 1384 | CZ | PHE | A | 187 | 10.352 | -15.353 | 40.737 | 1.000 25.23 |
| ATOM | 1385 | CE2 | PHE | A | 187 | 9.926 | -16.645 | 40.980 | 1.000 26.99 |
| ATOM | 1386 | CD2 | PHE | A | 187 | 9.875 | -17.565 | 39.952 | 1.000 33.63 |
| ATOM | 1387 | C | PHE | A | 187 | 11.345 | -19.910 | 36.138 | 1.000 22.76 |
| ATOM | 1388 | O | PHE | A | 187 | 11.934 | -19.600 | 35.113 | 1.000 22.84 |
| ATOM | 1389 | N | LYS | A | 188 | 10.568 | -20.964 | 36.254 | 1.000 24.79 |
| ATOM | 1390 | CA | LYS | A | 188 | 10.099 | -21.834 | 35.200 | 1.000 26.88 |
| ATOM | 1391 | CB | LYS | A | 188 | 10.353 | -23.309 | 35.515 | 1.000 29.96 |
| ATOM | 1392 | CG | LYS | A | 188 | 10.069 | -24.234 | 34.340 | 1.000 40.94 |
| ATOM | 1393 | CD | LYS | A | 188 | 10.185 | -25.699 | 34.726 | 1.000 36.57 |
| ATOM | 1394 | CE | LYS | A | 188 | 8.857 | -26.229 | 35.244 | 1.000 36.18 |
| ATOM | 1395 | NZ | LYS | A | 188 | 9.078 | -27.265 | 36.298 | 1.000 55.70 |
| ATOM | 1396 | C | LYS | A | 188 | 8.602 | -21.591 | 35.044 | 1.000 24.40 |
| ATOM | 1397 | O | LYS | A | 188 | 7.885 | -21.601 | 36.049 | 1.000 27.61 |
| ATOM | 1398 | N | ILE | A | 189 | 8.141 | -21.364 | 33.822 | 1.000 23.95 |
| ATOM | 1399 | CA | ILE | A | 189 | 6.710 | -21.109 | 33.659 | 1.000 28.81 |
| ATOM | 1400 | CB | ILE | A | 189 | 6.449 | -19.639 | 33.313 | 1.000 35.20 |
| ATOM | 1401 | CG1 | ILE | A | 189 | 4.972 | -19.306 | 33.080 | 1.000 43.59 |
| ATOM | 1402 | CD1 | ILE | A | 189 | 4.692 | -17.815 | 33.127 | 1.000 51.14 |
| ATOM | 1403 | CG2 | ILE | A | 189 | 7.290 | -19.208 | 32.121 | 1.000 19.65 |

FIGURE 33

| | | | | | | | | |
|---|---|---|---|---|---|---|---|---|
| ATOM | 1404 | C | ILE | A | 189 | 6.141 | -22.040 | 32.594 1.000 30.63 |
| ATOM | 1405 | O | ILE | A | 189 | 6.820 | -22.278 | 31.600 1.000 34.60 |
| ATOM | 1406 | N | CYS | A | 190 | 4.945 | -22.551 | 32.839 1.000 36.44 |
| ATOM | 1407 | CA | CYS | A | 190 | 4.195 | -23.466 | 32.001 1.000 38.23 |
| ATOM | 1408 | CB | CYS | A | 190 | 3.935 | -24.832 | 32.645 1.000 36.83 |
| ATOM | 1409 | SG | CYS | A | 190 | 5.333 | -25.621 | 33.465 1.000 54.28 |
| ATOM | 1410 | C | CYS | A | 190 | 2.836 | -22.854 | 31.647 1.000 40.07 |
| ATOM | 1411 | O | CYS | A | 190 | 2.035 | -22.528 | 32.524 1.000 34.54 |
| ATOM | 1412 | N | GLY | A | 191 | 2.596 | -22.714 | 30.348 1.000 38.67 |
| ATOM | 1413 | CA | GLY | A | 191 | 1.317 | -22.192 | 29.891 1.000 47.19 |
| ATOM | 1414 | C | GLY | A | 191 | 0.665 | -23.168 | 28.937 1.000 57.83 |
| ATOM | 1415 | O | GLY | A | 191 | 1.108 | -24.313 | 28.810 1.000 57.59 |
| ATOM | 1416 | N | GLU | A | 192 | -0.394 | -22.733 | 28.252 1.000 68.94 |
| ATOM | 1417 | CA | GLU | A | 192 | -0.950 | -23.669 | 27.264 1.000 77.08 |
| ATOM | 1418 | CB | GLU | A | 192 | -2.249 | -23.139 | 26.671 1.000 79.72 |
| ATOM | 1419 | CG | GLU | A | 192 | -3.488 | -23.931 | 27.082 1.000 83.44 |
| ATOM | 1420 | CD | GLU | A | 192 | -4.763 | -23.113 | 27.103 1.000 88.99 |
| ATOM | 1421 | OE1 | GLU | A | 192 | -4.760 | -21.996 | 27.669 1.000 97.81 |
| ATOM | 1422 | OE2 | GLU | A | 192 | -5.784 | -23.582 | 26.555 1.000 83.85 |
| ATOM | 1423 | C | GLU | A | 192 | 0.137 | -23.932 | 26.222 1.000 79.08 |
| ATOM | 1424 | O | GLU | A | 192 | 0.449 | -23.046 | 25.419 1.000 84.98 |
| ATOM | 1425 | N | GLU | A | 193 | 0.712 | -25.136 | 26.276 1.000 80.23 |
| ATOM | 1426 | CA | GLU | A | 193 | 1.810 | -25.537 | 25.407 1.000 88.15 |
| ATOM | 1427 | CB | GLU | A | 193 | 1.859 | -27.061 | 25.268 1.000 82.57 |
| ATOM | 1428 | CG | GLU | A | 193 | 2.981 | -27.559 | 24.373 1.000 74.69 |
| ATOM | 1429 | CD | GLU | A | 193 | 4.340 | -27.361 | 25.023 1.000 75.38 |
| ATOM | 1430 | OE1 | GLU | A | 193 | 4.581 | -27.990 | 26.075 1.000 64.29 |
| ATOM | 1431 | OE2 | GLU | A | 193 | 5.153 | -26.581 | 24.488 1.000 79.60 |
| ATOM | 1432 | C | GLU | A | 193 | 1.682 | -24.896 | 24.026 1.000100.09 |
| ATOM | 1433 | O | GLU | A | 193 | 0.956 | -25.403 | 23.166 1.000118.96 |
| ATOM | 1434 | N | GLN | A | 194 | 2.383 | -23.782 | 23.814 1.000102.10 |
| ATOM | 1435 | CA | GLN | A | 194 | 2.277 | -23.101 | 22.520 1.000107.47 |
| ATOM | 1436 | CB | GLN | A | 194 | 1.451 | -21.819 | 22.686 1.000110.48 |
| ATOM | 1437 | CG | GLN | A | 194 | 0.039 | -22.092 | 23.245 1.000111.93 |
| ATOM | 1438 | CD | GLN | A | 194 | -0.952 | -20.989 | 22.858 1.000112.96 |
| ATOM | 1439 | OE1 | GLN | A | 194 | -0.959 | -20.485 | 21.724 1.000119.77 |
| ATOM | 1440 | NE2 | GLN | A | 194 | -1.812 | -20.629 | 23.805 1.000105.14 |
| ATOM | 1441 | C | GLN | A | 194 | 3.653 | -22.834 | 21.928 1.000110.55 |
| ATOM | 1442 | O | GLN | A | 194 | 4.374 | -23.775 | 21.570 1.000118.12 |
| ATOM | 1443 | N | LEU | A | 195 | 4.067 | -21.573 | 21.796 1.000108.99 |
| ATOM | 1444 | CA | LEU | A | 195 | 5.409 | -21.363 | 21.238 1.000106.04 |
| ATOM | 1445 | CB | LEU | A | 195 | 5.601 | -19.930 | 20.752 1.000103.44 |
| ATOM | 1446 | CG | LEU | A | 195 | 6.025 | -19.764 | 19.285 1.000101.76 |
| ATOM | 1447 | CD1 | LEU | A | 195 | 6.636 | -18.390 | 19.041 1.000 93.51 |
| ATOM | 1448 | CD2 | LEU | A | 195 | 7.000 | -20.865 | 18.871 1.000 83.67 |
| ATOM | 1449 | C | LEU | A | 195 | 6.462 | -21.736 | 22.276 1.000109.72 |
| ATOM | 1450 | O | LEU | A | 195 | 7.662 | -21.740 | 21.977 1.000128.83 |
| ATOM | 1451 | N | ASP | A | 196 | 6.020 | -22.054 | 23.495 1.000104.75 |
| ATOM | 1452 | CA | ASP | A | 196 | 6.956 | -22.505 | 24.521 1.000 97.46 |
| ATOM | 1453 | CB | ASP | A | 196 | 7.139 | -21.463 | 25.616 1.000 94.37 |
| ATOM | 1454 | CG | ASP | A | 196 | 6.470 | -20.133 | 25.358 1.000 89.89 |
| ATOM | 1455 | OD1 | ASP | A | 196 | 5.236 | -20.089 | 25.182 1.000 80.93 |

FIGURE 34

| ATOM | 1456 | OD2 | ASP | A | 196 | 7.206 | -19.119 | 25.348 | 1.000 | 73.17 |
| --- | --- | --- | --- | --- | --- | --- | --- | --- | --- | --- |
| ATOM | 1457 | C | ASP | A | 196 | 6.498 | -23.822 | 25.150 | 1.000 | 96.72 |
| ATOM | 1458 | O | ASP | A | 196 | 5.391 | -24.300 | 24.896 | 1.000 | 103.69 |
| ATOM | 1459 | N | ALA | A | 197 | 7.366 | -24.390 | 25.976 | 1.000 | 95.34 |
| ATOM | 1460 | CA | ALA | A | 197 | 7.113 | -25.628 | 26.703 | 1.000 | 92.76 |
| ATOM | 1461 | CB | ALA | A | 197 | 7.661 | -26.824 | 25.949 | 1.000 | 80.95 |
| ATOM | 1462 | C | ALA | A | 197 | 7.715 | -25.535 | 28.106 | 1.000 | 92.67 |
| ATOM | 1463 | O | ALA | A | 197 | 6.986 | -25.567 | 29.100 | 1.000 | 101.36 |
| ATOM | 1464 | N | HIS | A | 198 | 9.035 | -25.410 | 28.190 | 1.000 | 90.04 |
| ATOM | 1465 | CA | HIS | A | 198 | 9.720 | -25.190 | 29.464 | 1.000 | 83.32 |
| ATOM | 1466 | CB | HIS | A | 198 | 10.618 | -26.370 | 29.813 | 1.000 | 84.18 |
| ATOM | 1467 | CG | HIS | A | 198 | 11.844 | -26.074 | 30.617 | 1.000 | 84.25 |
| ATOM | 1468 | ND1 | HIS | A | 198 | 11.839 | -25.834 | 31.968 | 1.000 | 86.44 |
| ATOM | 1469 | CE1 | HIS | A | 198 | 13.071 | -25.609 | 32.389 | 1.000 | 85.15 |
| ATOM | 1470 | NE2 | HIS | A | 198 | 13.884 | -25.681 | 31.348 | 1.000 | 81.36 |
| ATOM | 1471 | CD2 | HIS | A | 198 | 13.141 | -25.969 | 30.232 | 1.000 | 81.88 |
| ATOM | 1472 | C | HIS | A | 198 | 10.489 | -23.876 | 29.379 | 1.000 | 70.03 |
| ATOM | 1473 | O | HIS | A | 198 | 11.664 | -23.784 | 29.023 | 1.000 | 64.25 |
| ATOM | 1474 | N | ARG | A | 199 | 9.790 | -22.781 | 29.701 | 1.000 | 58.16 |
| ATOM | 1475 | CA | ARG | A | 199 | 10.431 | -21.480 | 29.568 | 1.000 | 50.11 |
| ATOM | 1476 | CB | ARG | A | 199 | 9.498 | -20.464 | 28.903 | 1.000 | 50.90 |
| ATOM | 1477 | CG | ARG | A | 199 | 10.292 | -19.446 | 28.092 | 1.000 | 53.59 |
| ATOM | 1478 | CD | ARG | A | 199 | 9.616 | -18.087 | 28.108 | 1.000 | 48.39 |
| ATOM | 1479 | NE | ARG | A | 199 | 8.377 | -18.120 | 27.322 | 1.000 | 42.37 |
| ATOM | 1480 | CZ | ARG | A | 199 | 7.502 | -17.120 | 27.427 | 1.000 | 43.29 |
| ATOM | 1481 | NH1 | ARG | A | 199 | 7.751 | -16.096 | 28.241 | 1.000 | 31.50 |
| ATOM | 1482 | NH2 | ARG | A | 199 | 6.398 | -17.186 | 26.709 | 1.000 | 24.97 |
| ATOM | 1483 | C | ARG | A | 199 | 10.900 | -20.944 | 30.918 | 1.000 | 37.10 |
| ATOM | 1484 | O | ARG | A | 199 | 10.201 | -21.106 | 31.914 | 1.000 | 28.73 |
| ATOM | 1485 | N | LEU | A | 200 | 12.079 | -20.336 | 30.889 | 1.000 | 29.92 |
| ATOM | 1486 | CA | LEU | A | 200 | 12.757 | -19.865 | 32.087 | 1.000 | 35.35 |
| ATOM | 1487 | CB | LEU | A | 200 | 14.196 | -20.394 | 32.149 | 1.000 | 38.39 |
| ATOM | 1488 | CG | LEU | A | 200 | 14.295 | -21.881 | 32.511 | 1.000 | 51.57 |
| ATOM | 1489 | CD1 | LEU | A | 200 | 15.401 | -22.134 | 33.523 | 1.000 | 73.84 |
| ATOM | 1490 | CD2 | LEU | A | 200 | 12.963 | -22.382 | 33.052 | 1.000 | 69.62 |
| ATOM | 1491 | C | LEU | A | 200 | 12.762 | -18.343 | 32.153 | 1.000 | 31.71 |
| ATOM | 1492 | O | LEU | A | 200 | 13.040 | -17.681 | 31.155 | 1.000 | 29.83 |
| ATOM | 1493 | N | ILE | A | 201 | 12.446 | -17.820 | 33.333 | 1.000 | 23.61 |
| ATOM | 1494 | CA | ILE | A | 201 | 12.371 | -16.376 | 33.510 | 1.000 | 23.62 |
| ATOM | 1495 | CB | ILE | A | 201 | 10.962 | -15.892 | 33.903 | 1.000 | 25.57 |
| ATOM | 1496 | CG1 | ILE | A | 201 | 9.858 | -16.232 | 32.898 | 1.000 | 30.41 |
| ATOM | 1497 | CD1 | ILE | A | 201 | 10.310 | -16.192 | 31.459 | 1.000 | 26.58 |
| ATOM | 1498 | CG2 | ILE | A | 201 | 10.964 | -14.395 | 34.171 | 1.000 | 23.03 |
| ATOM | 1499 | C | ILE | A | 201 | 13.332 | -15.933 | 34.604 | 1.000 | 22.99 |
| ATOM | 1500 | O | ILE | A | 201 | 13.382 | -16.507 | 35.688 | 1.000 | 27.49 |
| ATOM | 1501 | N | ARG | A | 202 | 14.088 | -14.886 | 34.299 | 1.000 | 19.58 |
| ATOM | 1502 | CA | ARG | A | 202 | 14.960 | -14.324 | 35.320 | 1.000 | 17.66 |
| ATOM | 1503 | CB | ARG | A | 202 | 16.361 | -14.091 | 34.768 | 1.000 | 25.08 |
| ATOM | 1504 | CG | ARG | A | 202 | 17.450 | -14.797 | 35.562 | 1.000 | 39.27 |
| ATOM | 1505 | CD | ARG | A | 202 | 18.605 | -15.183 | 34.654 | 1.000 | 48.88 |
| ATOM | 1506 | NE | ARG | A | 202 | 19.385 | -16.289 | 35.220 | 1.000 | 55.89 |
| ATOM | 1507 | CZ | ARG | A | 202 | 19.961 | -17.201 | 34.435 | 1.000 | 60.48 |

FIGURE 35

```
ATOM  1508  NH1  ARG A 202    19.812  -17.100  33.119  1.000  50.30
ATOM  1509  NH2  ARG A 202    20.666  -18.191  34.965  1.000  77.85
ATOM  1510  C    ARG A 202    14.343  -13.023  35.826  1.000  22.83
ATOM  1511  O    ARG A 202    13.885  -12.219  35.007  1.000  22.73
ATOM  1512  N    HIS A 203    14.345  -12.858  37.136  1.000  18.38
ATOM  1513  CA   HIS A 203    13.794  -11.690  37.815  1.000  21.09
ATOM  1514  CB   HIS A 203    12.701  -12.145  38.770  1.000  22.13
ATOM  1515  CG   HIS A 203    11.824  -11.117  39.389  1.000  24.48
ATOM  1516  ND1  HIS A 203    12.146  -10.463  40.554  1.000  20.07
ATOM  1517  CE1  HIS A 203    11.186   -9.616  40.875  1.000  23.08
ATOM  1518  NE2  HIS A 203    10.240   -9.697  39.959  1.000  27.63
ATOM  1519  CD2  HIS A 203    10.611  -10.629  39.022  1.000  25.25
ATOM  1520  C    HIS A 203    14.894  -10.952  38.579  1.000  27.02
ATOM  1521  O    HIS A 203    15.541  -11.548  39.447  1.000  18.53
ATOM  1522  N    PHE A 204    15.086   -9.691  38.246  1.000  21.78
ATOM  1523  CA   PHE A 204    16.068   -8.796  38.840  1.000  16.28
ATOM  1524  CB   PHE A 204    16.891   -8.101  37.742  1.000  16.39
ATOM  1525  CG   PHE A 204    17.526   -9.112  36.813  1.000  27.16
ATOM  1526  CD1  PHE A 204    16.899   -9.466  35.632  1.000  16.95
ATOM  1527  CE1  PHE A 204    17.476  -10.397  34.790  1.000  26.09
ATOM  1528  CZ   PHE A 204    18.686  -10.979  35.123  1.000  31.27
ATOM  1529  CE2  PHE A 204    19.326  -10.639  36.303  1.000  26.75
ATOM  1530  CD2  PHE A 204    18.744   -9.699  37.136  1.000  28.81
ATOM  1531  C    PHE A 204    15.378   -7.752  39.707  1.000  16.41
ATOM  1532  O    PHE A 204    14.748   -6.809  39.223  1.000  24.46
ATOM  1533  N    HIS A 205    15.514   -7.930  41.006  1.000  16.66
ATOM  1534  CA   HIS A 205    14.879   -7.081  41.998  1.000  14.51
ATOM  1535  CB   HIS A 205    14.118   -7.987  42.982  1.000  14.31
ATOM  1536  CG   HIS A 205    13.201   -7.221  43.887  1.000  25.21
ATOM  1537  ND1  HIS A 205    12.631   -7.784  45.009  1.000  24.28
ATOM  1538  CE1  HIS A 205    11.882   -6.885  45.611  1.000  27.88
ATOM  1539  NE2  HIS A 205    11.939   -5.756  44.927  1.000  24.25
ATOM  1540  CD2  HIS A 205    12.761   -5.949  43.845  1.000  28.00
ATOM  1541  C    HIS A 205    15.867   -6.211  42.764  1.000  26.42
ATOM  1542  O    HIS A 205    16.535   -6.668  43.697  1.000  21.37
ATOM  1543  N    TYR A 206    15.950   -4.954  42.359  1.000  25.43
ATOM  1544  CA   TYR A 206    16.705   -3.918  43.045  1.000  26.77
ATOM  1545  CB   TYR A 206    16.849   -2.707  42.142  1.000  30.54
ATOM  1546  CG   TYR A 206    17.810   -1.643  42.603  1.000  30.50
ATOM  1547  CD1  TYR A 206    19.177   -1.758  42.349  1.000  21.06
ATOM  1548  CE1  TYR A 206    20.048   -0.774  42.779  1.000  26.02
ATOM  1549  CZ   TYR A 206    19.551    0.320  43.457  1.000  28.32
ATOM  1550  OH   TYR A 206    20.406    1.309  43.883  1.000  33.26
ATOM  1551  CE2  TYR A 206    18.201    0.452  43.715  1.000  31.83
ATOM  1552  CD2  TYR A 206    17.330   -0.534  43.289  1.000  30.09
ATOM  1553  C    TYR A 206    15.978   -3.521  44.324  1.000  32.60
ATOM  1554  O    TYR A 206    14.893   -2.942  44.266  1.000  27.05
ATOM  1555  N    THR A 207    16.574   -3.858  45.460  1.000  30.86
ATOM  1556  CA   THR A 207    15.870   -3.793  46.729  1.000  34.19
ATOM  1557  CB   THR A 207    16.205   -5.071  47.535  1.000  35.60
ATOM  1558  OG1  THR A 207    17.627   -5.263  47.486  1.000  37.52
ATOM  1559  CG2  THR A 207    15.545   -6.290  46.917  1.000  40.16
```

FIGURE 36

| ATOM | 1560 | C | THR | A | 207 | 16.214 | -2.599 | 47.604 | 1.000 | 42.95 |
| ATOM | 1561 | O | THR | A | 207 | 15.790 | -2.560 | 48.768 | 1.000 | 33.25 |
| ATOM | 1562 | N | VAL | A | 208 | 16.982 | -1.633 | 47.105 | 1.000 | 38.87 |
| ATOM | 1563 | CA | VAL | A | 208 | 17.495 | -0.587 | 47.986 | 1.000 | 42.20 |
| ATOM | 1564 | CB | VAL | A | 208 | 19.001 | -0.829 | 48.254 | 1.000 | 38.89 |
| ATOM | 1565 | CG1 | VAL | A | 208 | 19.208 | -2.188 | 48.913 | 1.000 | 29.05 |
| ATOM | 1566 | CG2 | VAL | A | 208 | 19.810 | -0.734 | 46.973 | 1.000 | 32.10 |
| ATOM | 1567 | C | VAL | A | 208 | 17.304 | 0.826 | 47.464 | 1.000 | 41.85 |
| ATOM | 1568 | O | VAL | A | 208 | 18.055 | 1.725 | 47.850 | 1.000 | 40.55 |
| ATOM | 1569 | N | TRP | A | 209 | 16.329 | 1.095 | 46.602 | 1.000 | 38.83 |
| ATOM | 1570 | CA | TRP | A | 209 | 16.039 | 2.473 | 46.199 | 1.000 | 36.12 |
| ATOM | 1571 | CB | TRP | A | 209 | 15.037 | 2.480 | 45.053 | 1.000 | 31.43 |
| ATOM | 1572 | CG | TRP | A | 209 | 15.042 | 3.683 | 44.170 | 1.000 | 31.44 |
| ATOM | 1573 | CD1 | TRP | A | 209 | 14.710 | 4.963 | 44.509 | 1.000 | 26.97 |
| ATOM | 1574 | NE1 | TRP | A | 209 | 14.840 | 5.788 | 43.417 | 1.000 | 29.65 |
| ATOM | 1575 | CE2 | TRP | A | 209 | 15.261 | 5.047 | 42.342 | 1.000 | 23.71 |
| ATOM | 1576 | CD2 | TRP | A | 209 | 15.399 | 3.717 | 42.779 | 1.000 | 28.34 |
| ATOM | 1577 | CE3 | TRP | A | 209 | 15.821 | 2.749 | 41.862 | 1.000 | 32.82 |
| ATOM | 1578 | CZ3 | TRP | A | 209 | 16.086 | 3.142 | 40.564 | 1.000 | 33.95 |
| ATOM | 1579 | CH2 | TRP | A | 209 | 15.939 | 4.478 | 40.159 | 1.000 | 36.07 |
| ATOM | 1580 | CZ2 | TRP | A | 209 | 15.527 | 5.448 | 41.033 | 1.000 | 22.47 |
| ATOM | 1581 | C | TRP | A | 209 | 15.490 | 3.239 | 47.397 | 1.000 | 36.81 |
| ATOM | 1582 | O | TRP | A | 209 | 14.515 | 2.795 | 48.008 | 1.000 | 32.77 |
| ATOM | 1583 | N | PRO | A | 210 | 16.069 | 4.369 | 47.770 | 1.000 | 34.94 |
| ATOM | 1584 | CA | PRO | A | 210 | 15.624 | 5.061 | 48.987 | 1.000 | 33.09 |
| ATOM | 1585 | CB | PRO | A | 210 | 16.456 | 6.345 | 48.988 | 1.000 | 32.95 |
| ATOM | 1586 | CG | PRO | A | 210 | 17.633 | 6.063 | 48.123 | 1.000 | 34.50 |
| ATOM | 1587 | CD | PRO | A | 210 | 17.160 | 5.078 | 47.088 | 1.000 | 36.07 |
| ATOM | 1588 | C | PRO | A | 210 | 14.140 | 5.412 | 48.940 | 1.000 | 41.55 |
| ATOM | 1589 | O | PRO | A | 210 | 13.515 | 5.321 | 47.882 | 1.000 | 42.95 |
| ATOM | 1590 | N | ASP | A | 211 | 13.590 | 5.820 | 50.081 | 1.000 | 49.64 |
| ATOM | 1591 | CA | ASP | A | 211 | 12.183 | 6.214 | 50.158 | 1.000 | 54.78 |
| ATOM | 1592 | CB | ASP | A | 211 | 11.720 | 6.296 | 51.612 | 1.000 | 55.95 |
| ATOM | 1593 | CG | ASP | A | 211 | 11.048 | 5.030 | 52.100 | 1.000 | 56.96 |
| ATOM | 1594 | OD1 | ASP | A | 211 | 10.660 | 4.976 | 53.286 | 1.000 | 50.78 |
| ATOM | 1595 | OD2 | ASP | A | 211 | 10.905 | 4.079 | 51.306 | 1.000 | 63.04 |
| ATOM | 1596 | C | ASP | A | 211 | 11.959 | 7.551 | 49.457 | 1.000 | 52.82 |
| ATOM | 1597 | O | ASP | A | 211 | 10.896 | 7.882 | 48.937 | 1.000 | 45.02 |
| ATOM | 1598 | N | HIS | A | 212 | 13.020 | 8.351 | 49.446 | 1.000 | 48.03 |
| ATOM | 1599 | CA | HIS | A | 212 | 12.961 | 9.675 | 48.845 | 1.000 | 53.87 |
| ATOM | 1600 | CB | HIS | A | 212 | 12.846 | 10.746 | 49.934 | 1.000 | 72.68 |
| ATOM | 1601 | CG | HIS | A | 212 | 12.681 | 10.177 | 51.311 | 1.000 | 76.92 |
| ATOM | 1602 | ND1 | HIS | A | 212 | 11.458 | 10.093 | 51.935 | 1.000 | 78.57 |
| ATOM | 1603 | CE1 | HIS | A | 212 | 11.610 | 9.555 | 53.133 | 1.000 | 80.63 |
| ATOM | 1604 | NE2 | HIS | A | 212 | 12.890 | 9.277 | 53.307 | 1.000 | 79.40 |
| ATOM | 1605 | CD2 | HIS | A | 212 | 13.578 | 9.660 | 52.180 | 1.000 | 77.05 |
| ATOM | 1606 | C | HIS | A | 212 | 14.197 | 9.908 | 47.986 | 1.000 | 46.17 |
| ATOM | 1607 | O | HIS | A | 212 | 15.310 | 9.572 | 48.392 | 1.000 | 42.06 |
| ATOM | 1608 | N | GLY | A | 213 | 13.992 | 10.472 | 46.799 | 1.000 | 43.66 |
| ATOM | 1609 | CA | GLY | A | 213 | 15.091 | 10.704 | 45.885 | 1.000 | 43.27 |
| ATOM | 1610 | C | GLY | A | 213 | 15.654 | 9.421 | 45.299 | 1.000 | 41.13 |
| ATOM | 1611 | O | GLY | A | 213 | 15.050 | 8.357 | 45.431 | 1.000 | 31.32 |

FIGURE 37

| ATOM | 1612 | N   | VAL | A | 214 | 16.804 | 9.569  | 44.663 | 1.000 | 40.78 |
|------|------|-----|-----|---|-----|--------|--------|--------|-------|-------|
| ATOM | 1613 | CA  | VAL | A | 214 | 17.476 | 8.540  | 43.881 | 1.000 | 37.49 |
| ATOM | 1614 | CB  | VAL | A | 214 | 18.098 | 9.200  | 42.644 | 1.000 | 31.11 |
| ATOM | 1615 | CG1 | VAL | A | 214 | 17.047 | 10.031 | 41.917 | 1.000 | 31.20 |
| ATOM | 1616 | CG2 | VAL | A | 214 | 19.284 | 10.056 | 43.059 | 1.000 | 42.36 |
| ATOM | 1617 | C   | VAL | A | 214 | 18.526 | 7.827  | 44.715 | 1.000 | 45.89 |
| ATOM | 1618 | O   | VAL | A | 214 | 18.953 | 8.384  | 45.729 | 1.000 | 57.46 |
| ATOM | 1619 | N   | PRO | A | 215 | 18.933 | 6.624  | 44.333 | 1.000 | 40.93 |
| ATOM | 1620 | CA  | PRO | A | 215 | 19.764 | 5.782  | 45.188 | 1.000 | 34.00 |
| ATOM | 1621 | CB  | PRO | A | 215 | 20.251 | 4.672  | 44.247 | 1.000 | 42.73 |
| ATOM | 1622 | CG  | PRO | A | 215 | 19.225 | 4.606  | 43.168 | 1.000 | 48.15 |
| ATOM | 1623 | CD  | PRO | A | 215 | 18.636 | 5.975  | 43.041 | 1.000 | 45.87 |
| ATOM | 1624 | C   | PRO | A | 215 | 21.003 | 6.478  | 45.755 | 1.000 | 38.07 |
| ATOM | 1625 | O   | PRO | A | 215 | 21.508 | 7.427  | 45.159 | 1.000 | 36.58 |
| ATOM | 1626 | N   | GLU | A | 216 | 21.427 | 5.942  | 46.886 | 1.000 | 51.41 |
| ATOM | 1627 | CA  | GLU | A | 216 | 22.569 | 6.331  | 47.688 | 1.000 | 59.42 |
| ATOM | 1628 | CB  | GLU | A | 216 | 23.016 | 5.168  | 48.587 | 1.000 | 62.22 |
| ATOM | 1629 | CG  | GLU | A | 216 | 24.008 | 5.566  | 49.666 | 1.000 | 66.95 |
| ATOM | 1630 | CD  | GLU | A | 216 | 25.143 | 4.586  | 49.863 | 1.000 | 69.08 |
| ATOM | 1631 | OE1 | GLU | A | 216 | 24.891 | 3.377  | 50.036 | 1.000 | 49.54 |
| ATOM | 1632 | OE2 | GLU | A | 216 | 26.314 | 5.036  | 49.867 | 1.000 | 70.82 |
| ATOM | 1633 | C   | GLU | A | 216 | 23.739 | 6.782  | 46.818 | 1.000 | 54.66 |
| ATOM | 1634 | O   | GLU | A | 216 | 24.238 | 7.895  | 46.980 | 1.000 | 48.01 |
| ATOM | 1635 | N   | THR | A | 217 | 24.155 | 5.905  | 45.908 | 1.000 | 43.30 |
| ATOM | 1636 | CA  | THR | A | 217 | 25.239 | 6.207  | 44.989 | 1.000 | 40.68 |
| ATOM | 1637 | CB  | THR | A | 217 | 26.492 | 5.353  | 45.264 | 1.000 | 40.90 |
| ATOM | 1638 | OG1 | THR | A | 217 | 26.180 | 3.960  | 45.083 | 1.000 | 41.85 |
| ATOM | 1639 | CG2 | THR | A | 217 | 26.966 | 5.527  | 46.698 | 1.000 | 28.03 |
| ATOM | 1640 | C   | THR | A | 217 | 24.823 | 5.970  | 43.535 | 1.000 | 42.76 |
| ATOM | 1641 | O   | THR | A | 217 | 23.831 | 5.299  | 43.269 | 1.000 | 55.29 |
| ATOM | 1642 | N   | THR | A | 218 | 25.612 | 6.524  | 42.625 | 1.000 | 38.69 |
| ATOM | 1643 | CA  | THR | A | 218 | 25.506 | 6.280  | 41.199 | 1.000 | 46.38 |
| ATOM | 1644 | CB  | THR | A | 218 | 26.407 | 7.242  | 40.399 | 1.000 | 48.77 |
| ATOM | 1645 | OG1 | THR | A | 218 | 27.771 | 7.133  | 40.833 | 1.000 | 31.20 |
| ATOM | 1646 | CG2 | THR | A | 218 | 26.004 | 8.690  | 40.634 | 1.000 | 44.45 |
| ATOM | 1647 | C   | THR | A | 218 | 25.887 | 4.831  | 40.882 | 1.000 | 40.27 |
| ATOM | 1648 | O   | THR | A | 218 | 25.248 | 4.124  | 40.099 | 1.000 | 43.37 |
| ATOM | 1649 | N   | GLN | A | 219 | 26.962 | 4.401  | 41.524 | 1.000 | 36.77 |
| ATOM | 1650 | CA  | GLN | A | 219 | 27.592 | 3.095  | 41.332 | 1.000 | 40.35 |
| ATOM | 1651 | CB  | GLN | A | 219 | 28.841 | 3.052  | 42.215 | 1.000 | 46.27 |
| ATOM | 1652 | CG  | GLN | A | 219 | 29.392 | 1.680  | 42.538 | 1.000 | 60.44 |
| ATOM | 1653 | CD  | GLN | A | 219 | 30.902 | 1.629  | 42.393 | 1.000 | 71.25 |
| ATOM | 1654 | OE1 | GLN | A | 219 | 31.414 | 1.573  | 41.274 | 1.000 | 90.40 |
| ATOM | 1655 | NE2 | GLN | A | 219 | 31.593 | 1.640  | 43.527 | 1.000 | 53.90 |
| ATOM | 1656 | C   | GLN | A | 219 | 26.621 | 1.959  | 41.619 | 1.000 | 37.53 |
| ATOM | 1657 | O   | GLN | A | 219 | 26.618 | 0.907  | 40.977 | 1.000 | 32.61 |
| ATOM | 1658 | N   | SER | A | 220 | 25.739 | 2.146  | 42.596 | 1.000 | 33.04 |
| ATOM | 1659 | CA  | SER | A | 220 | 24.720 | 1.164  | 42.929 | 1.000 | 26.50 |
| ATOM | 1660 | CB  | SER | A | 220 | 23.845 | 1.739  | 44.049 | 1.000 | 29.93 |
| ATOM | 1661 | OG  | SER | A | 220 | 22.837 | 0.814  | 44.413 | 1.000 | 35.63 |
| ATOM | 1662 | C   | SER | A | 220 | 23.860 | 0.792  | 41.727 | 1.000 | 34.98 |
| ATOM | 1663 | O   | SER | A | 220 | 23.745 | -0.378 | 41.354 | 1.000 | 31.36 |

FIGURE 38

| | | | | | | | | | |
|---|---|---|---|---|---|---|---|---|---|
| ATOM | 1664 | N   | LEU | A | 221 | 23.247 |  1.800 | 41.104 | 1.000 | 34.26 |
| ATOM | 1665 | CA  | LEU | A | 221 | 22.404 |  1.571 | 39.940 | 1.000 | 32.25 |
| ATOM | 1666 | CB  | LEU | A | 221 | 21.483 |  2.764 | 39.648 | 1.000 | 25.67 |
| ATOM | 1667 | CG  | LEU | A | 221 | 20.313 |  2.430 | 38.705 | 1.000 | 23.74 |
| ATOM | 1668 | CD1 | LEU | A | 221 | 19.468 |  1.312 | 39.303 | 1.000 | 18.81 |
| ATOM | 1669 | CD2 | LEU | A | 221 | 19.490 |  3.672 | 38.420 | 1.000 | 28.95 |
| ATOM | 1670 | C   | LEU | A | 221 | 23.238 |  1.270 | 38.700 | 1.000 | 36.04 |
| ATOM | 1671 | O   | LEU | A | 221 | 22.797 |  0.534 | 37.806 | 1.000 | 29.22 |
| ATOM | 1672 | N   | ILE | A | 222 | 24.446 |  1.845 | 38.637 | 1.000 | 33.99 |
| ATOM | 1673 | CA  | ILE | A | 222 | 25.231 |  1.532 | 37.445 | 1.000 | 25.77 |
| ATOM | 1674 | CB  | ILE | A | 222 | 26.562 |  2.282 | 37.364 | 1.000 | 24.00 |
| ATOM | 1675 | CG1 | ILE | A | 222 | 26.426 |  3.748 | 36.963 | 1.000 | 25.72 |
| ATOM | 1676 | CD1 | ILE | A | 222 | 27.516 |  4.638 | 37.512 | 1.000 | 30.84 |
| ATOM | 1677 | CG2 | ILE | A | 222 | 27.496 |  1.556 | 36.405 | 1.000 | 31.40 |
| ATOM | 1678 | C   | ILE | A | 222 | 25.511 |  0.027 | 37.382 | 1.000 | 27.84 |
| ATOM | 1679 | O   | ILE | A | 222 | 25.444 | -0.541 | 36.293 | 1.000 | 29.04 |
| ATOM | 1680 | N   | GLN | A | 223 | 25.789 | -0.572 | 38.525 | 1.000 | 25.48 |
| ATOM | 1681 | CA  | GLN | A | 223 | 26.120 | -1.982 | 38.660 | 1.000 | 27.33 |
| ATOM | 1682 | CB  | GLN | A | 223 | 26.628 | -2.245 | 40.091 | 1.000 | 32.58 |
| ATOM | 1683 | CG  | GLN | A | 223 | 28.119 | -1.965 | 40.240 | 1.000 | 37.66 |
| ATOM | 1684 | CD  | GLN | A | 223 | 28.804 | -1.836 | 38.896 | 1.000 | 40.45 |
| ATOM | 1685 | OE1 | GLN | A | 223 | 28.765 | -2.759 | 38.076 | 1.000 | 70.90 |
| ATOM | 1686 | NE2 | GLN | A | 223 | 29.430 | -0.693 | 38.657 | 1.000 | 56.51 |
| ATOM | 1687 | C   | GLN | A | 223 | 24.952 | -2.916 | 38.387 | 1.000 | 25.59 |
| ATOM | 1688 | O   | GLN | A | 223 | 25.071 | -3.940 | 37.712 | 1.000 | 26.61 |
| ATOM | 1689 | N   | PHE | A | 224 | 23.794 | -2.560 | 38.945 | 1.000 | 23.53 |
| ATOM | 1690 | CA  | PHE | A | 224 | 22.586 | -3.328 | 38.637 | 1.000 | 26.71 |
| ATOM | 1691 | CB  | PHE | A | 224 | 21.408 | -2.714 | 39.374 | 1.000 | 23.63 |
| ATOM | 1692 | CG  | PHE | A | 224 | 20.093 | -3.429 | 39.226 | 1.000 | 23.65 |
| ATOM | 1693 | CD1 | PHE | A | 224 | 19.892 | -4.676 | 39.789 | 1.000 | 26.30 |
| ATOM | 1694 | CE1 | PHE | A | 224 | 18.688 | -5.341 | 39.670 | 1.000 | 23.27 |
| ATOM | 1695 | CZ  | PHE | A | 224 | 17.660 | -4.747 | 38.963 | 1.000 | 22.78 |
| ATOM | 1696 | CE2 | PHE | A | 224 | 17.843 | -3.504 | 38.397 | 1.000 | 21.02 |
| ATOM | 1697 | CD2 | PHE | A | 224 | 19.050 | -2.842 | 38.529 | 1.000 | 17.14 |
| ATOM | 1698 | C   | PHE | A | 224 | 22.335 | -3.340 | 37.135 | 1.000 | 29.21 |
| ATOM | 1699 | O   | PHE | A | 224 | 22.212 | -4.385 | 36.497 | 1.000 | 23.28 |
| ATOM | 1700 | N   | VAL | A | 225 | 22.272 | -2.147 | 36.539 | 1.000 | 29.45 |
| ATOM | 1701 | CA  | VAL | A | 225 | 22.003 | -2.057 | 35.103 | 1.000 | 23.17 |
| ATOM | 1702 | CB  | VAL | A | 225 | 22.017 | -0.597 | 34.616 | 1.000 | 27.27 |
| ATOM | 1703 | CG1 | VAL | A | 225 | 22.186 | -0.539 | 33.112 | 1.000 | 19.10 |
| ATOM | 1704 | CG2 | VAL | A | 225 | 20.732 |  0.108 | 35.045 | 1.000 | 33.43 |
| ATOM | 1705 | C   | VAL | A | 225 | 22.985 | -2.871 | 34.273 | 1.000 | 28.40 |
| ATOM | 1706 | O   | VAL | A | 225 | 22.554 | -3.638 | 33.400 | 1.000 | 25.05 |
| ATOM | 1707 | N   | ARG | A | 226 | 24.285 | -2.724 | 34.517 | 1.000 | 31.38 |
| ATOM | 1708 | CA  | ARG | A | 226 | 25.276 | -3.513 | 33.780 | 1.000 | 34.53 |
| ATOM | 1709 | CB  | ARG | A | 226 | 26.705 | -3.147 | 34.173 | 1.000 | 31.80 |
| ATOM | 1710 | CG  | ARG | A | 226 | 27.183 | -1.771 | 33.762 | 1.000 | 33.34 |
| ATOM | 1711 | CD  | ARG | A | 226 | 28.697 | -1.716 | 33.673 | 1.000 | 47.45 |
| ATOM | 1712 | NE  | ARG | A | 226 | 29.241 | -0.365 | 33.600 | 1.000 | 56.24 |
| ATOM | 1713 | CZ  | ARG | A | 226 | 29.961 |  0.232 | 34.542 | 1.000 | 62.79 |
| ATOM | 1714 | NH1 | ARG | A | 226 | 30.261 | -0.370 | 35.686 | 1.000 | 50.14 |
| ATOM | 1715 | NH2 | ARG | A | 226 | 30.401 |  1.471 | 34.354 | 1.000 | 74.65 |

FIGURE 39

| ATOM | 1716 | C | ARG | A | 226 | 25.054 | -5.011 | 34.010 | 1.000 | 23.44 |
| ATOM | 1717 | O | ARG | A | 226 | 25.301 | -5.826 | 33.118 | 1.000 | 30.89 |
| ATOM | 1718 | N | THR | A | 227 | 24.582 | -5.377 | 35.195 | 1.000 | 21.86 |
| ATOM | 1719 | CA | THR | A | 227 | 24.250 | -6.761 | 35.521 | 1.000 | 31.38 |
| ATOM | 1720 | CB | THR | A | 227 | 23.825 | -6.921 | 36.994 | 1.000 | 37.64 |
| ATOM | 1721 | OG1 | THR | A | 227 | 24.903 | -6.608 | 37.874 | 1.000 | 34.53 |
| ATOM | 1722 | CG2 | THR | A | 227 | 23.457 | -8.365 | 37.306 | 1.000 | 22.45 |
| ATOM | 1723 | C | THR | A | 227 | 23.108 | -7.250 | 34.627 | 1.000 | 32.76 |
| ATOM | 1724 | O | THR | A | 227 | 23.237 | -8.240 | 33.912 | 1.000 | 27.21 |
| ATOM | 1725 | N | VAL | A | 228 | 21.985 | -6.526 | 34.679 | 1.000 | 22.99 |
| ATOM | 1726 | CA | VAL | A | 228 | 20.814 | -6.869 | 33.886 | 1.000 | 22.33 |
| ATOM | 1727 | CB | VAL | A | 228 | 19.627 | -5.922 | 34.162 | 1.000 | 22.12 |
| ATOM | 1728 | CG1 | VAL | A | 228 | 18.466 | -6.213 | 33.221 | 1.000 | 17.66 |
| ATOM | 1729 | CG2 | VAL | A | 228 | 19.192 | -6.066 | 35.605 | 1.000 | 18.46 |
| ATOM | 1730 | C | VAL | A | 228 | 21.140 | -6.859 | 32.397 | 1.000 | 21.49 |
| ATOM | 1731 | O | VAL | A | 228 | 20.766 | -7.790 | 31.686 | 1.000 | 22.44 |
| ATOM | 1732 | N | ARG | A | 229 | 21.821 | -5.824 | 31.914 | 1.000 | 19.91 |
| ATOM | 1733 | CA | ARG | A | 229 | 22.183 | -5.792 | 30.489 | 1.000 | 30.48 |
| ATOM | 1734 | CB | ARG | A | 229 | 22.877 | -4.480 | 30.149 | 1.000 | 30.12 |
| ATOM | 1735 | CG | ARG | A | 229 | 23.502 | -4.301 | 28.786 | 1.000 | 28.02 |
| ATOM | 1736 | CD | ARG | A | 229 | 22.590 | -4.596 | 27.614 | 1.000 | 26.85 |
| ATOM | 1737 | NE | ARG | A | 229 | 21.290 | -3.951 | 27.719 | 1.000 | 26.70 |
| ATOM | 1738 | CZ | ARG | A | 229 | 20.267 | -4.199 | 26.913 | 1.000 | 27.29 |
| ATOM | 1739 | NH1 | ARG | A | 229 | 20.394 | -5.079 | 25.930 | 1.000 | 20.12 |
| ATOM | 1740 | NH2 | ARG | A | 229 | 19.110 | -3.573 | 27.076 | 1.000 | 22.84 |
| ATOM | 1741 | C | ARG | A | 229 | 23.041 | -7.010 | 30.156 | 1.000 | 42.31 |
| ATOM | 1742 | O | ARG | A | 229 | 22.988 | -7.552 | 29.053 | 1.000 | 34.86 |
| ATOM | 1743 | N | ASP | A | 230 | 23.842 | -7.483 | 31.114 | 1.000 | 40.71 |
| ATOM | 1744 | CA | ASP | A | 230 | 24.637 | -8.682 | 30.882 | 1.000 | 32.09 |
| ATOM | 1745 | CB | ASP | A | 230 | 25.480 | -9.003 | 32.118 | 1.000 | 31.74 |
| ATOM | 1746 | CG | ASP | A | 230 | 26.543 | -10.044 | 31.824 | 1.000 | 48.14 |
| ATOM | 1747 | OD1 | ASP | A | 230 | 27.577 | -10.046 | 32.528 | 1.000 | 73.82 |
| ATOM | 1748 | OD2 | ASP | A | 230 | 26.357 | -10.865 | 30.899 | 1.000 | 48.16 |
| ATOM | 1749 | C | ASP | A | 230 | 23.761 | -9.882 | 30.547 | 1.000 | 32.41 |
| ATOM | 1750 | O | ASP | A | 230 | 24.000 | -10.629 | 29.598 | 1.000 | 36.42 |
| ATOM | 1751 | N | TYR | A | 231 | 22.720 | -10.093 | 31.342 | 1.000 | 24.93 |
| ATOM | 1752 | CA | TYR | A | 231 | 21.802 | -11.200 | 31.103 | 1.000 | 24.73 |
| ATOM | 1753 | CB | TYR | A | 231 | 20.899 | -11.375 | 32.314 | 1.000 | 25.55 |
| ATOM | 1754 | CG | TYR | A | 231 | 21.532 | -12.058 | 33.498 | 1.000 | 21.52 |
| ATOM | 1755 | CD1 | TYR | A | 231 | 22.248 | -11.325 | 34.429 | 1.000 | 20.07 |
| ATOM | 1756 | CE1 | TYR | A | 231 | 22.826 | -11.956 | 35.516 | 1.000 | 25.25 |
| ATOM | 1757 | CZ | TYR | A | 231 | 22.690 | -13.315 | 35.684 | 1.000 | 23.69 |
| ATOM | 1758 | OH | TYR | A | 231 | 23.272 | -13.934 | 36.770 | 1.000 | 36.60 |
| ATOM | 1759 | CE2 | TYR | A | 231 | 21.981 | -14.060 | 34.765 | 1.000 | 22.85 |
| ATOM | 1760 | CD2 | TYR | A | 231 | 21.406 | -13.431 | 33.678 | 1.000 | 23.77 |
| ATOM | 1761 | C | TYR | A | 231 | 20.940 | -10.997 | 29.866 | 1.000 | 24.62 |
| ATOM | 1762 | O | TYR | A | 231 | 20.658 | -11.948 | 29.137 | 1.000 | 34.40 |
| ATOM | 1763 | N | ILE | A | 232 | 20.502 | -9.768 | 29.602 | 1.000 | 26.34 |
| ATOM | 1764 | CA | ILE | A | 232 | 19.713 | -9.542 | 28.388 | 1.000 | 29.59 |
| ATOM | 1765 | CB | ILE | A | 232 | 19.309 | -8.068 | 28.191 | 1.000 | 19.99 |
| ATOM | 1766 | CG1 | ILE | A | 232 | 18.283 | -7.551 | 29.204 | 1.000 | 21.05 |
| ATOM | 1767 | CD1 | ILE | A | 232 | 18.300 | -6.047 | 29.371 | 1.000 | 26.31 |

FIGURE 40

| ATOM | 1768 | CG2 | ILE | A | 232 | 18.811 | -7.833 | 26.772 | 1.000 | 16.63 |
|---|---|---|---|---|---|---|---|---|---|---|
| ATOM | 1769 | C | ILE | A | 232 | 20.497 | -9.985 | 27.153 | 1.000 | 25.92 |
| ATOM | 1770 | O | ILE | A | 232 | 19.982 | -10.719 | 26.311 | 1.000 | 22.41 |
| ATOM | 1771 | N | ASN | A | 233 | 21.741 | -9.526 | 27.075 | 1.000 | 21.03 |
| ATOM | 1772 | CA | ASN | A | 233 | 22.573 | -9.788 | 25.900 | 1.000 | 32.05 |
| ATOM | 1773 | CB | ASN | A | 233 | 23.931 | -9.102 | 26.027 | 1.000 | 31.19 |
| ATOM | 1774 | CG | ASN | A | 233 | 23.891 | -7.603 | 25.830 | 1.000 | 35.15 |
| ATOM | 1775 | OD1 | ASN | A | 233 | 22.990 | -7.064 | 25.190 | 1.000 | 42.73 |
| ATOM | 1776 | ND2 | ASN | A | 233 | 24.873 | -6.892 | 26.379 | 1.000 | 33.97 |
| ATOM | 1777 | C | ASN | A | 233 | 22.757 | -11.289 | 25.690 | 1.000 | 36.07 |
| ATOM | 1778 | O | ASN | A | 233 | 22.998 | -11.738 | 24.575 | 1.000 | 43.18 |
| ATOM | 1779 | N | ARG | A | 234 | 22.637 | -12.049 | 26.765 | 1.000 | 37.01 |
| ATOM | 1780 | CA | ARG | A | 234 | 22.702 | -13.496 | 26.771 | 1.000 | 31.16 |
| ATOM | 1781 | CB | ARG | A | 234 | 23.407 | -13.992 | 28.046 | 1.000 | 30.18 |
| ATOM | 1782 | CG | ARG | A | 234 | 24.757 | -13.308 | 28.235 | 1.000 | 40.73 |
| ATOM | 1783 | CD | ARG | A | 234 | 25.514 | -13.886 | 29.429 | 1.000 | 52.07 |
| ATOM | 1784 | NE | ARG | A | 234 | 26.704 | -13.084 | 29.729 | 1.000 | 58.87 |
| ATOM | 1785 | CZ | ARG | A | 234 | 27.879 | -13.610 | 30.055 | 1.000 | 65.29 |
| ATOM | 1786 | NH1 | ARG | A | 234 | 28.006 | -14.931 | 30.122 | 1.000 | 53.28 |
| ATOM | 1787 | NH2 | ARG | A | 234 | 28.913 | -12.818 | 30.313 | 1.000 | 60.98 |
| ATOM | 1788 | C | ARG | A | 234 | 21.320 | -14.122 | 26.695 | 1.000 | 30.94 |
| ATOM | 1789 | O | ARG | A | 234 | 21.130 | -15.307 | 26.977 | 1.000 | 24.57 |
| ATOM | 1790 | N | SER | A | 235 | 20.307 | -13.346 | 26.303 | 1.000 | 26.15 |
| ATOM | 1791 | CA | SER | A | 235 | 18.990 | -13.971 | 26.162 | 1.000 | 23.60 |
| ATOM | 1792 | CB | SER | A | 235 | 17.959 | -13.293 | 27.058 | 1.000 | 26.05 |
| ATOM | 1793 | OG | SER | A | 235 | 18.357 | -13.227 | 28.416 | 1.000 | 33.56 |
| ATOM | 1794 | C | SER | A | 235 | 18.533 | -13.913 | 24.704 | 1.000 | 32.45 |
| ATOM | 1795 | O | SER | A | 235 | 17.616 | -13.135 | 24.420 | 1.000 | 33.61 |
| ATOM | 1796 | N | PRO | A | 236 | 19.136 | -14.685 | 23.805 | 1.000 | 44.30 |
| ATOM | 1797 | CA | PRO | A | 236 | 18.740 | -14.662 | 22.393 | 1.000 | 39.17 |
| ATOM | 1798 | CB | PRO | A | 236 | 19.695 | -15.646 | 21.714 | 1.000 | 48.74 |
| ATOM | 1799 | CG | PRO | A | 236 | 20.068 | -16.584 | 22.822 | 1.000 | 52.35 |
| ATOM | 1800 | CD | PRO | A | 236 | 20.220 | -15.667 | 24.009 | 1.000 | 52.02 |
| ATOM | 1801 | C | PRO | A | 236 | 17.312 | -15.175 | 22.233 | 1.000 | 29.65 |
| ATOM | 1802 | O | PRO | A | 236 | 16.908 | -16.104 | 22.941 | 1.000 | 30.54 |
| ATOM | 1803 | N | GLY | A | 237 | 16.590 | -14.544 | 21.309 | 1.000 | 24.46 |
| ATOM | 1804 | CA | GLY | A | 237 | 15.214 | -14.952 | 21.050 | 1.000 | 25.34 |
| ATOM | 1805 | C | GLY | A | 237 | 14.233 | -14.388 | 22.054 | 1.000 | 26.14 |
| ATOM | 1806 | O | GLY | A | 237 | 13.035 | -14.623 | 21.905 | 1.000 | 33.46 |
| ATOM | 1807 | N | ALA | A | 238 | 14.681 | -13.642 | 23.069 | 1.000 | 22.93 |
| ATOM | 1808 | CA | ALA | A | 238 | 13.739 | -13.094 | 24.042 | 1.000 | 17.40 |
| ATOM | 1809 | CB | ALA | A | 238 | 14.491 | -12.542 | 25.253 | 1.000 | 20.22 |
| ATOM | 1810 | C | ALA | A | 238 | 12.860 | -11.987 | 23.485 | 1.000 | 22.13 |
| ATOM | 1811 | O | ALA | A | 238 | 13.305 | -11.162 | 22.683 | 1.000 | 22.14 |
| ATOM | 1812 | N | GLY | A | 239 | 11.599 | -11.944 | 23.922 | 1.000 | 22.60 |
| ATOM | 1813 | CA | GLY | A | 239 | 10.794 | -10.755 | 23.654 | 1.000 | 19.77 |
| ATOM | 1814 | C | GLY | A | 239 | 11.314 | -9.578 | 24.475 | 1.000 | 23.04 |
| ATOM | 1815 | O | GLY | A | 239 | 12.456 | -9.584 | 24.931 | 1.000 | 22.08 |
| ATOM | 1816 | N | PRO | A | 240 | 10.501 | -8.544 | 24.664 | 1.000 | 20.46 |
| ATOM | 1817 | CA | PRO | A | 240 | 10.904 | -7.365 | 25.418 | 1.000 | 18.32 |
| ATOM | 1818 | CB | PRO | A | 240 | 9.645 | -6.478 | 25.441 | 1.000 | 15.24 |
| ATOM | 1819 | CG | PRO | A | 240 | 8.855 | -6.953 | 24.270 | 1.000 | 26.50 |

FIGURE 41

| | | | | | | | | |
|---|---|---|---|---|---|---|---|---|
| ATOM | 1820 | CD | PRO | A | 240 | 9.123 | -8.425 | 24.156 1.000 18.86 |
| ATOM | 1821 | C | PRO | A | 240 | 11.261 | -7.689 | 26.866 1.000 24.79 |
| ATOM | 1822 | O | PRO | A | 240 | 10.775 | -8.644 | 27.466 1.000 18.83 |
| ATOM | 1823 | N | THR | A | 241 | 12.130 | -6.846 | 27.414 1.000 24.76 |
| ATOM | 1824 | CA | THR | A | 241 | 12.452 | -6.849 | 28.822 1.000 19.34 |
| ATOM | 1825 | CB | THR | A | 241 | 13.790 | -6.140 | 29.127 1.000 24.33 |
| ATOM | 1826 | OG1 | THR | A | 241 | 14.851 | -6.786 | 28.430 1.000 21.31 |
| ATOM | 1827 | CG2 | THR | A | 241 | 14.100 | -6.254 | 30.618 1.000 17.13 |
| ATOM | 1828 | C | THR | A | 241 | 11.352 | -6.124 | 29.598 1.000 19.74 |
| ATOM | 1829 | O | THR | A | 241 | 11.073 | -4.964 | 29.314 1.000 18.65 |
| ATOM | 1830 | N | VAL | A | 242 | 10.731 | -6.769 | 30.576 1.000 19.16 |
| ATOM | 1831 | CA | VAL | A | 242 | 9.738 | -6.070 | 31.381 1.000 24.84 |
| ATOM | 1832 | CB | VAL | A | 242 | 8.698 | -7.016 | 32.012 1.000 25.33 |
| ATOM | 1833 | CG1 | VAL | A | 242 | 7.903 | -6.283 | 33.087 1.000 13.96 |
| ATOM | 1834 | CG2 | VAL | A | 242 | 7.778 | -7.573 | 30.936 1.000 18.53 |
| ATOM | 1835 | C | VAL | A | 242 | 10.420 | -5.311 | 32.515 1.000 22.81 |
| ATOM | 1836 | O | VAL | A | 242 | 11.202 | -5.907 | 33.245 1.000 15.62 |
| ATOM | 1837 | N | VAL | A | 243 | 10.114 | -4.032 | 32.656 1.000 16.25 |
| ATOM | 1838 | CA | VAL | A | 243 | 10.607 | -3.200 | 33.733 1.000 14.93 |
| ATOM | 1839 | CB | VAL | A | 243 | 11.507 | -2.058 | 33.233 1.000 19.66 |
| ATOM | 1840 | CG1 | VAL | A | 243 | 12.145 | -1.357 | 34.424 1.000 17.79 |
| ATOM | 1841 | CG2 | VAL | A | 243 | 12.551 | -2.600 | 32.271 1.000 16.83 |
| ATOM | 1842 | C | VAL | A | 243 | 9.437 | -2.590 | 34.489 1.000 18.40 |
| ATOM | 1843 | O | VAL | A | 243 | 8.522 | -2.079 | 33.856 1.000 17.50 |
| ATOM | 1844 | N | HIS | A | 244 | 9.469 | -2.655 | 35.821 1.000 14.50 |
| ATOM | 1845 | CA | HIS | A | 244 | 8.388 | -2.005 | 36.543 1.000 19.33 |
| ATOM | 1846 | CB | HIS | A | 244 | 7.200 | -2.952 | 36.704 1.000 15.76 |
| ATOM | 1847 | CG | HIS | A | 244 | 7.362 | -4.005 | 37.749 1.000 15.99 |
| ATOM | 1848 | ND1 | HIS | A | 244 | 7.060 | -3.783 | 39.076 1.000 16.28 |
| ATOM | 1849 | CE1 | HIS | A | 244 | 7.293 | -4.893 | 39.761 1.000 23.84 |
| ATOM | 1850 | NE2 | HIS | A | 244 | 7.736 | -5.820 | 38.934 1.000 18.37 |
| ATOM | 1851 | CD2 | HIS | A | 244 | 7.785 | -5.289 | 37.665 1.000 12.59 |
| ATOM | 1852 | C | HIS | A | 244 | 8.868 | -1.514 | 37.906 1.000 22.68 |
| ATOM | 1853 | O | HIS | A | 244 | 9.879 | -1.996 | 38.398 1.000 22.27 |
| ATOM | 1854 | N | CYS | A | 245 | 8.127 | -0.563 | 38.448 1.000 22.48 |
| ATOM | 1855 | CA | CYS | A | 245 | 8.229 | -0.136 | 39.836 1.000 22.65 |
| ATOM | 1856 | CB | CYS | A | 245 | 8.861 | 1.241 | 39.990 1.000 16.47 |
| ATOM | 1857 | SG | CYS | A | 245 | 8.219 | 2.535 | 38.895 1.000 26.22 |
| ATOM | 1858 | C | CYS | A | 245 | 6.812 | -0.194 | 40.402 1.000 23.88 |
| ATOM | 1859 | O | CYS | A | 245 | 6.094 | -1.173 | 40.153 1.000 26.38 |
| ATOM | 1860 | N | SER | A | 246 | 6.385 | 0.833 | 41.132 1.000 17.80 |
| ATOM | 1861 | CA | SER | A | 246 | 4.995 | 0.806 | 41.607 1.000 11.67 |
| ATOM | 1862 | CB | SER | A | 246 | 4.853 | 1.726 | 42.821 1.000 26.78 |
| ATOM | 1863 | OG | SER | A | 246 | 3.561 | 1.643 | 43.393 1.000 30.47 |
| ATOM | 1864 | C | SER | A | 246 | 4.033 | 1.208 | 40.501 1.000 11.21 |
| ATOM | 1865 | O | SER | A | 246 | 3.068 | 0.510 | 40.185 1.000 20.25 |
| ATOM | 1866 | N | ALA | A | 247 | 4.286 | 2.377 | 39.909 1.000 15.30 |
| ATOM | 1867 | CA | ALA | A | 247 | 3.455 | 2.947 | 38.871 1.000 13.07 |
| ATOM | 1868 | CB | ALA | A | 247 | 3.302 | 4.446 | 39.102 1.000 23.22 |
| ATOM | 1869 | C | ALA | A | 247 | 4.008 | 2.710 | 37.468 1.000 17.09 |
| ATOM | 1870 | O | ALA | A | 247 | 3.286 | 2.806 | 36.473 1.000 23.76 |
| ATOM | 1871 | N | GLY | A | 248 | 5.300 | 2.413 | 37.353 1.000 15.64 |

FIGURE 42

| | | | | | | | | | |
|---|---|---|---|---|---|---|---|---|---|
| ATOM | 1872 | CA | GLY | A | 248 | 5.920 | 2.177 | 36.056 | 1.000 19.79 |
| ATOM | 1873 | C | GLY | A | 248 | 6.329 | 3.497 | 35.413 | 1.000 28.08 |
| ATOM | 1874 | O | GLY | A | 248 | 6.206 | 3.654 | 34.200 | 1.000 29.60 |
| ATOM | 1875 | N | VAL | A | 249 | 6.828 | 4.410 | 36.242 | 1.000 24.91 |
| ATOM | 1876 | CA | VAL | A | 249 | 7.165 | 5.771 | 35.893 | 1.000 28.97 |
| ATOM | 1877 | CB | VAL | A | 249 | 6.349 | 6.742 | 36.799 | 1.000 36.67 |
| ATOM | 1878 | CG1 | VAL | A | 249 | 4.984 | 6.994 | 36.192 | 1.000 26.78 |
| ATOM | 1879 | CG2 | VAL | A | 249 | 6.223 | 6.201 | 38.219 | 1.000 28.45 |
| ATOM | 1880 | C | VAL | A | 249 | 8.635 | 6.167 | 36.035 | 1.000 29.09 |
| ATOM | 1881 | O | VAL | A | 249 | 9.456 | 5.930 | 35.151 | 1.000 32.80 |
| ATOM | 1882 | N | GLY | A | 250 | 8.941 | 6.823 | 37.144 | 1.000 24.19 |
| ATOM | 1883 | CA | GLY | A | 250 | 10.149 | 7.515 | 37.501 | 1.000 19.59 |
| ATOM | 1884 | C | GLY | A | 250 | 11.344 | 6.573 | 37.577 | 1.000 14.84 |
| ATOM | 1885 | O | GLY | A | 250 | 12.267 | 6.702 | 36.763 | 1.000 27.35 |
| ATOM | 1886 | N | ARG | A | 251 | 11.280 | 5.662 | 38.534 | 1.000 11.74 |
| ATOM | 1887 | CA | ARG | A | 251 | 12.347 | 4.688 | 38.735 | 1.000 15.59 |
| ATOM | 1888 | CB | ARG | A | 251 | 12.096 | 3.823 | 39.969 | 1.000 21.64 |
| ATOM | 1889 | CG | ARG | A | 251 | 11.869 | 4.624 | 41.250 | 1.000 23.80 |
| ATOM | 1890 | CD | ARG | A | 251 | 11.653 | 3.670 | 42.416 | 1.000 23.58 |
| ATOM | 1891 | NE | ARG | A | 251 | 11.390 | 4.352 | 43.679 | 1.000 22.88 |
| ATOM | 1892 | CZ | ARG | A | 251 | 11.100 | 3.675 | 44.791 | 1.000 22.64 |
| ATOM | 1893 | NH1 | ARG | A | 251 | 11.042 | 2.354 | 44.756 | 1.000 26.67 |
| ATOM | 1894 | NH2 | ARG | A | 251 | 10.865 | 4.301 | 45.931 | 1.000 21.50 |
| ATOM | 1895 | C | ARG | A | 251 | 12.517 | 3.790 | 37.513 | 1.000 19.15 |
| ATOM | 1896 | O | ARG | A | 251 | 13.649 | 3.477 | 37.144 | 1.000 23.13 |
| ATOM | 1897 | N | THR | A | 252 | 11.409 | 3.372 | 36.904 | 1.000 18.67 |
| ATOM | 1898 | CA | THR | A | 252 | 11.482 | 2.546 | 35.702 | 1.000 18.13 |
| ATOM | 1899 | CB | THR | A | 252 | 10.103 | 2.014 | 35.289 | 1.000 20.50 |
| ATOM | 1900 | OG1 | THR | A | 252 | 9.706 | 1.005 | 36.228 | 1.000 22.47 |
| ATOM | 1901 | CG2 | THR | A | 252 | 10.127 | 1.333 | 33.924 | 1.000 18.43 |
| ATOM | 1902 | C | THR | A | 252 | 12.101 | 3.351 | 34.562 | 1.000 20.66 |
| ATOM | 1903 | O | THR | A | 252 | 13.001 | 2.852 | 33.877 | 1.000 22.41 |
| ATOM | 1904 | N | GLY | A | 253 | 11.627 | 4.580 | 34.377 | 1.000 19.06 |
| ATOM | 1905 | CA | GLY | A | 253 | 12.124 | 5.407 | 33.276 | 1.000 24.03 |
| ATOM | 1906 | C | GLY | A | 253 | 13.615 | 5.663 | 33.423 | 1.000 26.29 |
| ATOM | 1907 | O | GLY | A | 253 | 14.370 | 5.727 | 32.452 | 1.000 20.33 |
| ATOM | 1908 | N | THR | A | 254 | 14.036 | 5.811 | 34.674 | 1.000 20.94 |
| ATOM | 1909 | CA | THR | A | 254 | 15.433 | 6.059 | 35.011 | 1.000 25.32 |
| ATOM | 1910 | CB | THR | A | 254 | 15.546 | 6.439 | 36.505 | 1.000 23.28 |
| ATOM | 1911 | OG1 | THR | A | 254 | 14.879 | 7.688 | 36.704 | 1.000 19.41 |
| ATOM | 1912 | CG2 | THR | A | 254 | 16.993 | 6.642 | 36.910 | 1.000 22.36 |
| ATOM | 1913 | C | THR | A | 254 | 16.300 | 4.847 | 34.714 | 1.000 22.06 |
| ATOM | 1914 | O | THR | A | 254 | 17.389 | 4.928 | 34.151 | 1.000 27.89 |
| ATOM | 1915 | N | PHE | A | 255 | 15.811 | 3.671 | 35.094 | 1.000 18.65 |
| ATOM | 1916 | CA | PHE | A | 255 | 16.498 | 2.433 | 34.780 | 1.000 13.27 |
| ATOM | 1917 | CB | PHE | A | 255 | 15.709 | 1.219 | 35.277 | 1.000 13.04 |
| ATOM | 1918 | CG | PHE | A | 255 | 16.305 | -0.125 | 34.923 | 1.000 21.43 |
| ATOM | 1919 | CD1 | PHE | A | 255 | 17.222 | -0.717 | 35.783 | 1.000 22.29 |
| ATOM | 1920 | CE1 | PHE | A | 255 | 17.786 | -1.941 | 35.492 | 1.000 24.82 |
| ATOM | 1921 | CZ | PHE | A | 255 | 17.476 | -2.615 | 34.325 | 1.000 20.78 |
| ATOM | 1922 | CE2 | PHE | A | 255 | 16.558 | -2.054 | 33.461 | 1.000 16.57 |
| ATOM | 1923 | CD2 | PHE | A | 255 | 15.987 | -0.836 | 33.778 | 1.000 20.56 |

FIGURE 43

| | | | | | | | | | |
|---|---|---|---|---|---|---|---|---|---|
| ATOM | 1924 | C | PHE | A | 255 | 16.721 | 2.323 | 33.277 | 1.000 23.91 |
| ATOM | 1925 | O | PHE | A | 255 | 17.791 | 1.918 | 32.814 | 1.000 23.04 |
| ATOM | 1926 | N | ILE | A | 256 | 15.665 | 2.620 | 32.511 | 1.000 21.98 |
| ATOM | 1927 | CA | ILE | A | 256 | 15.794 | 2.334 | 31.082 | 1.000 23.48 |
| ATOM | 1928 | CB | ILE | A | 256 | 14.462 | 2.211 | 30.336 | 1.000 22.01 |
| ATOM | 1929 | CG1 | ILE | A | 256 | 13.667 | 0.941 | 30.657 | 1.000 26.28 |
| ATOM | 1930 | CD1 | ILE | A | 256 | 12.210 | 1.020 | 30.221 | 1.000 23.52 |
| ATOM | 1931 | CG2 | ILE | A | 256 | 14.666 | 2.310 | 28.823 | 1.000 17.05 |
| ATOM | 1932 | C | ILE | A | 256 | 16.666 | 3.412 | 30.439 | 1.000 14.97 |
| ATOM | 1933 | O | ILE | A | 256 | 17.470 | 3.058 | 29.575 | 1.000 20.35 |
| ATOM | 1934 | N | ALA | A | 257 | 16.489 | 4.659 | 30.864 | 1.000 16.95 |
| ATOM | 1935 | CA | ALA | A | 257 | 17.365 | 5.725 | 30.354 | 1.000 13.62 |
| ATOM | 1936 | CB | ALA | A | 257 | 16.973 | 7.077 | 30.894 | 1.000 16.03 |
| ATOM | 1937 | C | ALA | A | 257 | 18.811 | 5.373 | 30.689 | 1.000 20.04 |
| ATOM | 1938 | O | ALA | A | 257 | 19.713 | 5.497 | 29.866 | 1.000 24.71 |
| ATOM | 1939 | N | LEU | A | 258 | 19.083 | 4.886 | 31.908 | 1.000 20.59 |
| ATOM | 1940 | CA | LEU | A | 258 | 20.490 | 4.560 | 32.186 | 1.000 25.52 |
| ATOM | 1941 | CB | LEU | A | 258 | 20.723 | 4.299 | 33.673 | 1.000 29.22 |
| ATOM | 1942 | CG | LEU | A | 258 | 22.171 | 4.177 | 34.151 | 1.000 33.36 |
| ATOM | 1943 | CD1 | LEU | A | 258 | 23.069 | 5.186 | 33.453 | 1.000 17.44 |
| ATOM | 1944 | CD2 | LEU | A | 258 | 22.268 | 4.363 | 35.660 | 1.000 32.48 |
| ATOM | 1945 | C | LEU | A | 258 | 20.931 | 3.377 | 31.336 | 1.000 24.80 |
| ATOM | 1946 | O | LEU | A | 258 | 22.020 | 3.447 | 30.768 | 1.000 31.87 |
| ATOM | 1947 | N | ASP | A | 259 | 20.130 | 2.316 | 31.238 | 1.000 19.82 |
| ATOM | 1948 | CA | ASP | A | 259 | 20.524 | 1.155 | 30.439 | 1.000 21.21 |
| ATOM | 1949 | CB | ASP | A | 259 | 19.441 | 0.080 | 30.461 | 1.000 26.62 |
| ATOM | 1950 | CG | ASP | A | 259 | 19.716 | -1.155 | 29.637 | 1.000 33.72 |
| ATOM | 1951 | OD1 | ASP | A | 259 | 20.883 | -1.598 | 29.573 | 1.000 35.74 |
| ATOM | 1952 | OD2 | ASP | A | 259 | 18.758 | -1.719 | 29.046 | 1.000 24.80 |
| ATOM | 1953 | C | ASP | A | 259 | 20.832 | 1.579 | 29.010 | 1.000 21.68 |
| ATOM | 1954 | O | ASP | A | 259 | 21.742 | 1.052 | 28.372 | 1.000 28.89 |
| ATOM | 1955 | N | ARG | A | 260 | 20.070 | 2.539 | 28.506 | 1.000 23.42 |
| ATOM | 1956 | CA | ARG | A | 260 | 20.230 | 3.024 | 27.138 | 1.000 25.06 |
| ATOM | 1957 | CB | ARG | A | 260 | 19.028 | 3.897 | 26.771 | 1.000 28.71 |
| ATOM | 1958 | CG | ARG | A | 260 | 17.920 | 3.218 | 25.983 | 1.000 37.83 |
| ATOM | 1959 | CD | ARG | A | 260 | 17.815 | 3.892 | 24.612 | 1.000 40.41 |
| ATOM | 1960 | NE | ARG | A | 260 | 16.447 | 4.236 | 24.289 | 1.000 39.10 |
| ATOM | 1961 | CZ | ARG | A | 260 | 15.997 | 5.081 | 23.376 | 1.000 37.92 |
| ATOM | 1962 | NH1 | ARG | A | 260 | 16.820 | 5.759 | 22.595 | 1.000 44.18 |
| ATOM | 1963 | NH2 | ARG | A | 260 | 14.682 | 5.235 | 23.257 | 1.000 38.91 |
| ATOM | 1964 | C | ARG | A | 260 | 21.503 | 3.834 | 26.932 | 1.000 28.89 |
| ATOM | 1965 | O | ARG | A | 260 | 22.183 | 3.707 | 25.913 | 1.000 28.43 |
| ATOM | 1966 | N | ILE | A | 261 | 21.850 | 4.713 | 27.878 | 1.000 31.24 |
| ATOM | 1967 | CA | ILE | A | 261 | 23.011 | 5.568 | 27.644 | 1.000 32.00 |
| ATOM | 1968 | CB | ILE | A | 261 | 23.003 | 6.871 | 28.463 | 1.000 30.49 |
| ATOM | 1969 | CG1 | ILE | A | 261 | 23.174 | 6.692 | 29.969 | 1.000 33.74 |
| ATOM | 1970 | CD1 | ILE | A | 261 | 22.668 | 7.864 | 30.782 | 1.000 47.87 |
| ATOM | 1971 | CG2 | ILE | A | 261 | 21.747 | 7.669 | 28.142 | 1.000 38.62 |
| ATOM | 1972 | C | ILE | A | 261 | 24.311 | 4.827 | 27.939 | 1.000 30.43 |
| ATOM | 1973 | O | ILE | A | 261 | 25.293 | 5.061 | 27.228 | 1.000 33.25 |
| ATOM | 1974 | N | LEU | A | 262 | 24.317 | 3.958 | 28.951 | 1.000 22.89 |
| ATOM | 1975 | CA | LEU | A | 262 | 25.541 | 3.189 | 29.202 | 1.000 27.21 |

FIGURE 44

```
ATOM   1976  CB   LEU A 262      25.411   2.219  30.368 1.000 29.63
ATOM   1977  CG   LEU A 262      25.330   2.760  31.793 1.000 38.46
ATOM   1978  CD1  LEU A 262      25.371   1.630  32.815 1.000 28.64
ATOM   1979  CD2  LEU A 262      26.441   3.762  32.059 1.000 34.63
ATOM   1980  C    LEU A 262      25.912   2.424  27.931 1.000 37.42
ATOM   1981  O    LEU A 262      27.090   2.228  27.640 1.000 48.70
ATOM   1982  N    GLN A 263      24.900   1.987  27.183 1.000 40.24
ATOM   1983  CA   GLN A 263      25.151   1.267  25.943 1.000 38.78
ATOM   1984  CB   GLN A 263      23.875   0.706  25.322 1.000 30.36
ATOM   1985  CG   GLN A 263      23.653  -0.767  25.637 1.000 26.81
ATOM   1986  CD   GLN A 263      22.223  -1.212  25.423 1.000 28.10
ATOM   1987  OE1  GLN A 263      21.946  -1.976  24.500 1.000 30.64
ATOM   1988  NE2  GLN A 263      21.304  -0.760  26.273 1.000 33.75
ATOM   1989  C    GLN A 263      25.827   2.190  24.934 1.000 44.56
ATOM   1990  O    GLN A 263      26.667   1.744  24.161 1.000 46.96
ATOM   1991  N    GLN A 264      25.420   3.455  24.977 1.000 42.51
ATOM   1992  CA   GLN A 264      25.954   4.431  24.033 1.000 47.48
ATOM   1993  CB   GLN A 264      25.220   5.773  24.152 1.000 39.34
ATOM   1994  CG   GLN A 264      23.957   5.807  23.303 1.000 37.99
ATOM   1995  CD   GLN A 264      23.060   6.989  23.591 1.000 42.10
ATOM   1996  OE1  GLN A 264      23.477   7.972  24.206 1.000 41.41
ATOM   1997  NE2  GLN A 264      21.814   6.899  23.144 1.000 49.45
ATOM   1998  C    GLN A 264      27.452   4.610  24.256 1.000 50.33
ATOM   1999  O    GLN A 264      28.253   4.493  23.328 1.000 38.61
ATOM   2000  N    LEU A 265      27.777   4.876  25.513 1.000 49.87
ATOM   2001  CA   LEU A 265      29.118   5.176  25.984 1.000 51.23
ATOM   2002  CB   LEU A 265      29.084   5.389  27.503 1.000 48.71
ATOM   2003  CG   LEU A 265      28.256   6.584  27.988 1.000 49.68
ATOM   2004  CD1  LEU A 265      28.263   6.684  29.507 1.000 46.47
ATOM   2005  CD2  LEU A 265      28.757   7.884  27.370 1.000 44.07
ATOM   2006  C    LEU A 265      30.122   4.097  25.607 1.000 59.08
ATOM   2007  O    LEU A 265      31.329   4.351  25.565 1.000 62.01
ATOM   2008  N    ASP A 266      29.656   2.887  25.317 1.000 60.11
ATOM   2009  CA   ASP A 266      30.559   1.815  24.901 1.000 60.82
ATOM   2010  CB   ASP A 266      30.345   0.581  25.776 1.000 68.15
ATOM   2011  CG   ASP A 266      30.603   0.832  27.251 1.000 74.94
ATOM   2012  OD1  ASP A 266      31.286   1.822  27.599 1.000 87.47
ATOM   2013  OD2  ASP A 266      30.117   0.033  28.083 1.000 72.82
ATOM   2014  C    ASP A 266      30.362   1.481  23.428 1.000 56.29
ATOM   2015  O    ASP A 266      30.797   0.449  22.918 1.000 65.03
ATOM   2016  N    SER A 267      29.692   2.373  22.703 1.000 49.36
ATOM   2017  CA   SER A 267      29.450   2.133  21.286 1.000 49.97
ATOM   2018  CB   SER A 267      28.040   1.563  21.092 1.000 47.54
ATOM   2019  OG   SER A 267      28.070   0.147  21.070 1.000 70.07
ATOM   2020  C    SER A 267      29.602   3.403  20.457 1.000 56.45
ATOM   2021  O    SER A 267      29.833   3.345  19.249 1.000 64.11
ATOM   2022  N    LYS A 268      29.457   4.547  21.113 1.000 54.03
ATOM   2023  CA   LYS A 268      29.450   5.851  20.473 1.000 61.77
ATOM   2024  CB   LYS A 268      28.124   6.565  20.747 1.000 73.01
ATOM   2025  CG   LYS A 268      27.792   7.746  19.856 1.000 78.98
ATOM   2026  CD   LYS A 268      26.344   7.687  19.384 1.000 85.20
ATOM   2027  CE   LYS A 268      25.589   8.983  19.679 1.000 87.23
```

FIGURE 45

| | | | | | | | | | |
|---|---|---|---|---|---|---|---|---|---|
| ATOM | 2028 | NZ | LYS | A | 268 | 24.372 | 8.773 | 20.503 | 1.000 77.94 |
| ATOM | 2029 | C | LYS | A | 268 | 30.607 | 6.721 | 20.967 | 1.000 57.67 |
| ATOM | 2030 | O | LYS | A | 268 | 31.288 | 6.352 | 21.923 | 1.000 56.55 |
| ATOM | 2031 | N | ASP | A | 269 | 30.759 | 7.842 | 20.289 | 1.000 51.51 |
| ATOM | 2032 | CA | ASP | A | 269 | 31.664 | 8.925 | 20.619 | 1.000 61.39 |
| ATOM | 2033 | CB | ASP | A | 269 | 32.424 | 9.415 | 19.388 | 1.000 66.41 |
| ATOM | 2034 | CG | ASP | A | 269 | 31.625 | 9.286 | 18.106 | 1.000 74.35 |
| ATOM | 2035 | OD1 | ASP | A | 269 | 32.119 | 8.629 | 17.162 | 1.000 91.04 |
| ATOM | 2036 | OD2 | ASP | A | 269 | 30.505 | 9.842 | 18.044 | 1.000 81.62 |
| ATOM | 2037 | C | ASP | A | 269 | 30.865 | 10.067 | 21.240 | 1.000 58.72 |
| ATOM | 2038 | O | ASP | A | 269 | 31.369 | 11.104 | 21.659 | 1.000 48.76 |
| ATOM | 2039 | N | SER | A | 270 | 29.551 | 9.848 | 21.289 | 1.000 55.39 |
| ATOM | 2040 | CA | SER | A | 270 | 28.687 | 10.847 | 21.910 | 1.000 53.30 |
| ATOM | 2041 | CB | SER | A | 270 | 27.989 | 11.679 | 20.834 | 1.000 46.93 |
| ATOM | 2042 | OG | SER | A | 270 | 27.692 | 10.829 | 19.734 | 1.000 51.09 |
| ATOM | 2043 | C | SER | A | 270 | 27.674 | 10.148 | 22.807 | 1.000 54.77 |
| ATOM | 2044 | O | SER | A | 270 | 27.500 | 8.934 | 22.703 | 1.000 57.87 |
| ATOM | 2045 | N | VAL | A | 271 | 27.031 | 10.915 | 23.668 | 1.000 51.16 |
| ATOM | 2046 | CA | VAL | A | 271 | 26.025 | 10.400 | 24.590 | 1.000 47.16 |
| ATOM | 2047 | CB | VAL | A | 271 | 26.612 | 10.189 | 25.992 | 1.000 43.33 |
| ATOM | 2048 | CG1 | VAL | A | 271 | 27.075 | 11.525 | 26.564 | 1.000 28.98 |
| ATOM | 2049 | CG2 | VAL | A | 271 | 25.609 | 9.523 | 26.918 | 1.000 33.32 |
| ATOM | 2050 | C | VAL | A | 271 | 24.851 | 11.374 | 24.626 | 1.000 51.02 |
| ATOM | 2051 | O | VAL | A | 271 | 25.054 | 12.585 | 24.754 | 1.000 45.80 |
| ATOM | 2052 | N | ASP | A | 272 | 23.639 | 10.841 | 24.484 | 1.000 43.19 |
| ATOM | 2053 | CA | ASP | A | 272 | 22.451 | 11.680 | 24.350 | 1.000 34.67 |
| ATOM | 2054 | CB | ASP | A | 272 | 21.819 | 11.492 | 22.973 | 1.000 34.66 |
| ATOM | 2055 | CG | ASP | A | 272 | 20.791 | 12.553 | 22.633 | 1.000 34.78 |
| ATOM | 2056 | OD1 | ASP | A | 272 | 20.496 | 13.413 | 23.488 | 1.000 35.05 |
| ATOM | 2057 | OD2 | ASP | A | 272 | 20.262 | 12.537 | 21.499 | 1.000 61.92 |
| ATOM | 2058 | C | ASP | A | 272 | 21.450 | 11.367 | 25.450 | 1.000 37.86 |
| ATOM | 2059 | O | ASP | A | 272 | 20.601 | 10.489 | 25.312 | 1.000 33.07 |
| ATOM | 2060 | N | ILE | A | 273 | 21.548 | 12.095 | 26.564 | 1.000 29.66 |
| ATOM | 2061 | CA | ILE | A | 273 | 20.651 | 11.774 | 27.671 | 1.000 30.56 |
| ATOM | 2062 | CB | ILE | A | 273 | 21.245 | 12.212 | 29.019 | 1.000 28.78 |
| ATOM | 2063 | CG1 | ILE | A | 273 | 22.562 | 11.518 | 29.362 | 1.000 24.46 |
| ATOM | 2064 | CD1 | ILE | A | 273 | 23.227 | 12.049 | 30.612 | 1.000 33.99 |
| ATOM | 2065 | CG2 | ILE | A | 273 | 20.228 | 12.016 | 30.134 | 1.000 24.56 |
| ATOM | 2066 | C | ILE | A | 273 | 19.290 | 12.420 | 27.450 | 1.000 36.66 |
| ATOM | 2067 | O | ILE | A | 273 | 18.264 | 11.844 | 27.813 | 1.000 38.74 |
| ATOM | 2068 | N | TYR | A | 274 | 19.301 | 13.608 | 26.845 | 1.000 31.39 |
| ATOM | 2069 | CA | TYR | A | 274 | 18.044 | 14.276 | 26.525 | 1.000 27.62 |
| ATOM | 2070 | CB | TYR | A | 274 | 18.312 | 15.642 | 25.908 | 1.000 26.54 |
| ATOM | 2071 | CG | TYR | A | 274 | 17.119 | 16.489 | 25.551 | 1.000 27.58 |
| ATOM | 2072 | CD1 | TYR | A | 274 | 16.633 | 17.434 | 26.450 | 1.000 29.05 |
| ATOM | 2073 | CE1 | TYR | A | 274 | 15.544 | 18.225 | 26.150 | 1.000 28.10 |
| ATOM | 2074 | CZ | TYR | A | 274 | 14.913 | 18.089 | 24.932 | 1.000 28.89 |
| ATOM | 2075 | OH | TYR | A | 274 | 13.827 | 18.881 | 24.631 | 1.000 40.18 |
| ATOM | 2076 | CE2 | TYR | A | 274 | 15.372 | 17.169 | 24.020 | 1.000 30.70 |
| ATOM | 2077 | CD2 | TYR | A | 274 | 16.469 | 16.377 | 24.331 | 1.000 31.75 |
| ATOM | 2078 | C | TYR | A | 274 | 17.228 | 13.415 | 25.565 | 1.000 30.07 |
| ATOM | 2079 | O | TYR | A | 274 | 16.027 | 13.221 | 25.735 | 1.000 27.79 |

FIGURE 46

```
ATOM   2080  N    GLY A 275      17.908  12.908  24.540 1.000 30.84
ATOM   2081  CA   GLY A 275      17.256  12.132  23.499 1.000 38.31
ATOM   2082  C    GLY A 275      16.611  10.863  24.016 1.000 36.93
ATOM   2083  O    GLY A 275      15.515  10.487  23.605 1.000 33.21
ATOM   2084  N    ALA A 276      17.282  10.176  24.930 1.000 26.01
ATOM   2085  CA   ALA A 276      16.728   8.949  25.490 1.000 26.10
ATOM   2086  CB   ALA A 276      17.753   8.300  26.409 1.000 36.77
ATOM   2087  C    ALA A 276      15.440   9.236  26.248 1.000 26.60
ATOM   2088  O    ALA A 276      14.412   8.600  26.061 1.000 21.84
ATOM   2089  N    VAL A 277      15.510  10.227  27.129 1.000 27.46
ATOM   2090  CA   VAL A 277      14.382  10.602  27.971 1.000 26.38
ATOM   2091  CB   VAL A 277      14.829  11.656  29.004 1.000 27.97
ATOM   2092  CG1  VAL A 277      13.661  12.343  29.687 1.000 33.02
ATOM   2093  CG2  VAL A 277      15.720  10.980  30.043 1.000 17.52
ATOM   2094  C    VAL A 277      13.229  11.103  27.113 1.000 26.05
ATOM   2095  O    VAL A 277      12.060  10.837  27.417 1.000 29.47
ATOM   2096  N    HIS A 278      13.556  11.815  26.043 1.000 20.60
ATOM   2097  CA   HIS A 278      12.558  12.336  25.113 1.000 25.33
ATOM   2098  CB   HIS A 278      13.204  13.259  24.087 1.000 27.86
ATOM   2099  CG   HIS A 278      12.276  13.815  23.054 1.000 25.27
ATOM   2100  ND1  HIS A 278      11.807  13.069  21.994 1.000 24.22
ATOM   2101  CE1  HIS A 278      11.015  13.819  21.244 1.000 24.97
ATOM   2102  NE2  HIS A 278      10.961  15.031  21.773 1.000 23.92
ATOM   2103  CD2  HIS A 278      11.746  15.050  22.900 1.000 22.15
ATOM   2104  C    HIS A 278      11.838  11.214  24.370 1.000 23.01
ATOM   2105  O    HIS A 278      10.650  11.288  24.068 1.000 25.09
ATOM   2106  N    ASP A 279      12.571  10.160  24.059 1.000 20.73
ATOM   2107  CA   ASP A 279      11.994   9.026  23.343 1.000 24.89
ATOM   2108  CB   ASP A 279      13.099   8.159  22.746 1.000 30.17
ATOM   2109  CG   ASP A 279      12.727   7.306  21.558 1.000 30.34
ATOM   2110  OD1  ASP A 279      12.077   7.787  20.605 1.000 26.50
ATOM   2111  OD2  ASP A 279      13.096   6.106  21.539 1.000 33.56
ATOM   2112  C    ASP A 279      11.131   8.228  24.309 1.000 19.27
ATOM   2113  O    ASP A 279      10.059   7.720  23.981 1.000 23.16
ATOM   2114  N    LEU A 280      11.627   8.121  25.541 1.000 17.51
ATOM   2115  CA   LEU A 280      10.848   7.371  26.523 1.000 25.22
ATOM   2116  CB   LEU A 280      11.578   7.273  27.857 1.000 22.56
ATOM   2117  CG   LEU A 280      12.948   6.595  27.878 1.000 30.97
ATOM   2118  CD1  LEU A 280      13.309   6.169  29.294 1.000 16.61
ATOM   2119  CD2  LEU A 280      12.998   5.407  26.930 1.000 39.44
ATOM   2120  C    LEU A 280       9.475   8.027  26.702 1.000 28.43
ATOM   2121  O    LEU A 280       8.472   7.315  26.678 1.000 19.82
ATOM   2122  N    ARG A 281       9.480   9.335  26.877 1.000 27.78
ATOM   2123  CA   ARG A 281       8.364  10.230  27.097 1.000 26.26
ATOM   2124  CB   ARG A 281       8.840  11.690  27.129 1.000 27.59
ATOM   2125  CG   ARG A 281       9.597  12.025  28.413 1.000 35.06
ATOM   2126  CD   ARG A 281       8.645  11.966  29.597 1.000 33.64
ATOM   2127  NE   ARG A 281       9.295  12.376  30.831 1.000 36.75
ATOM   2128  CZ   ARG A 281       9.526  13.626  31.204 1.000 40.89
ATOM   2129  NH1  ARG A 281       9.161  14.636  30.435 1.000 32.39
ATOM   2130  NH2  ARG A 281      10.132  13.874  32.361 1.000 61.48
ATOM   2131  C    ARG A 281       7.302  10.096  26.018 1.000 19.40
```

FIGURE 47

| ATOM | 2132 | O   | ARG | A | 281 | 6.104 | 10.236 | 26.254 | 1.000 | 20.20 |
| ATOM | 2133 | N   | LEU | A | 282 | 7.773 | 9.823  | 24.805 | 1.000 | 20.07 |
| ATOM | 2134 | CA  | LEU | A | 282 | 6.823 | 9.651  | 23.711 | 1.000 | 23.11 |
| ATOM | 2135 | CB  | LEU | A | 282 | 7.523 | 9.589  | 22.353 | 1.000 | 17.59 |
| ATOM | 2136 | CG  | LEU | A | 282 | 7.893 | 10.913 | 21.688 | 1.000 | 27.09 |
| ATOM | 2137 | CD1 | LEU | A | 282 | 8.800 | 10.679 | 20.489 | 1.000 | 27.56 |
| ATOM | 2138 | CD2 | LEU | A | 282 | 6.660 | 11.688 | 21.243 | 1.000 | 20.11 |
| ATOM | 2139 | C   | LEU | A | 282 | 5.974 | 8.404  | 23.913 | 1.000 | 26.60 |
| ATOM | 2140 | O   | LEU | A | 282 | 4.880 | 8.342  | 23.352 | 1.000 | 22.78 |
| ATOM | 2141 | N   | HIS | A | 283 | 6.430 | 7.412  | 24.678 | 1.000 | 25.41 |
| ATOM | 2142 | CA  | HIS | A | 283 | 5.698 | 6.144  | 24.667 | 1.000 | 19.57 |
| ATOM | 2143 | CB  | HIS | A | 283 | 6.688 | 5.008  | 24.336 | 1.000 | 24.33 |
| ATOM | 2144 | CG  | HIS | A | 283 | 7.263 | 5.215  | 22.965 | 1.000 | 22.62 |
| ATOM | 2145 | ND1 | HIS | A | 283 | 6.742 | 4.619  | 21.841 | 1.000 | 26.42 |
| ATOM | 2146 | CE1 | HIS | A | 283 | 7.436 | 4.985  | 20.775 | 1.000 | 25.06 |
| ATOM | 2147 | NE2 | HIS | A | 283 | 8.386 | 5.808  | 21.174 | 1.000 | 24.57 |
| ATOM | 2148 | CD2 | HIS | A | 283 | 8.300 | 5.974  | 22.536 | 1.000 | 21.10 |
| ATOM | 2149 | C   | HIS | A | 283 | 4.956 | 5.861  | 25.961 | 1.000 | 17.31 |
| ATOM | 2150 | O   | HIS | A | 283 | 4.101 | 4.976  | 26.006 | 1.000 | 20.69 |
| ATOM | 2151 | N   | ARG | A | 284 | 5.262 | 6.606  | 27.011 | 1.000 | 16.92 |
| ATOM | 2152 | CA  | ARG | A | 284 | 4.594 | 6.512  | 28.296 | 1.000 | 15.56 |
| ATOM | 2153 | CB  | ARG | A | 284 | 5.038 | 5.279  | 29.091 | 1.000 | 19.52 |
| ATOM | 2154 | CG  | ARG | A | 284 | 4.214 | 5.010  | 30.355 | 1.000 | 16.19 |
| ATOM | 2155 | CD  | ARG | A | 284 | 4.569 | 3.660  | 30.954 | 1.000 | 19.69 |
| ATOM | 2156 | NE  | ARG | A | 284 | 4.009 | 3.428  | 32.282 | 1.000 | 18.76 |
| ATOM | 2157 | CZ  | ARG | A | 284 | 2.892 | 2.731  | 32.492 | 1.000 | 19.76 |
| ATOM | 2158 | NH1 | ARG | A | 284 | 2.214 | 2.207  | 31.475 | 1.000 | 11.48 |
| ATOM | 2159 | NH2 | ARG | A | 284 | 2.439 | 2.553  | 33.726 | 1.000 | 17.29 |
| ATOM | 2160 | C   | ARG | A | 284 | 4.845 | 7.774  | 29.119 | 1.000 | 15.30 |
| ATOM | 2161 | O   | ARG | A | 284 | 5.941 | 8.327  | 29.076 | 1.000 | 25.00 |
| ATOM | 2162 | N   | VAL | A | 285 | 3.834 | 8.221  | 29.846 | 1.000 | 19.78 |
| ATOM | 2163 | CA  | VAL | A | 285 | 3.912 | 9.415  | 30.685 | 1.000 | 26.66 |
| ATOM | 2164 | CB  | VAL | A | 285 | 2.507 | 9.771  | 31.215 | 1.000 | 32.12 |
| ATOM | 2165 | CG1 | VAL | A | 285 | 1.981 | 8.686  | 32.152 | 1.000 | 20.70 |
| ATOM | 2166 | CG2 | VAL | A | 285 | 2.503 | 11.126 | 31.909 | 1.000 | 29.12 |
| ATOM | 2167 | C   | VAL | A | 285 | 4.917 | 9.216  | 31.814 | 1.000 | 20.03 |
| ATOM | 2168 | O   | VAL | A | 285 | 5.153 | 8.085  | 32.242 | 1.000 | 23.27 |
| ATOM | 2169 | N   | HIS | A | 286 | 5.510 | 10.296 | 32.281 | 1.000 | 28.92 |
| ATOM | 2170 | CA  | HIS | A | 286 | 6.440 | 10.404 | 33.382 | 1.000 | 29.32 |
| ATOM | 2171 | CB  | HIS | A | 286 | 5.744 | 10.052 | 34.718 | 1.000 | 33.92 |
| ATOM | 2172 | CG  | HIS | A | 286 | 4.476 | 10.821 | 34.904 | 1.000 | 38.90 |
| ATOM | 2173 | ND1 | HIS | A | 286 | 4.430 | 12.188 | 34.769 | 1.000 | 45.43 |
| ATOM | 2174 | CE1 | HIS | A | 286 | 3.197 | 12.615 | 34.978 | 1.000 | 45.72 |
| ATOM | 2175 | NE2 | HIS | A | 286 | 2.439 | 11.567 | 35.244 | 1.000 | 48.04 |
| ATOM | 2176 | CD2 | HIS | A | 286 | 3.216 | 10.433 | 35.200 | 1.000 | 47.11 |
| ATOM | 2177 | C   | HIS | A | 286 | 7.669 | 9.521  | 33.267 | 1.000 | 24.27 |
| ATOM | 2178 | O   | HIS | A | 286 | 8.292 | 9.259  | 34.303 | 1.000 | 39.87 |
| ATOM | 2179 | N   | MET | A | 287 | 8.054 | 9.038  | 32.087 | 1.000 | 19.82 |
| ATOM | 2180 | CA  | MET | A | 287 | 9.326 | 8.294  | 32.047 | 1.000 | 18.04 |
| ATOM | 2181 | CB  | MET | A | 287 | 9.579 | 7.694  | 30.679 | 1.000 | 19.24 |
| ATOM | 2182 | CG  | MET | A | 287 | 8.566 | 6.647  | 30.239 | 1.000 | 24.10 |
| ATOM | 2183 | SD  | MET | A | 287 | 8.699 | 5.134  | 31.234 | 1.000 | 32.12 |

FIGURE 48

| | | | | | | | | | |
|---|---|---|---|---|---|---|---|---|---|
| ATOM | 2184 | CE | MET | A | 287 | 7.526 | 5.570 | 32.521 | 1.000 32.04 |
| ATOM | 2185 | C | MET | A | 287 | 10.457 | 9.247 | 32.459 | 1.000 32.08 |
| ATOM | 2186 | O | MET | A | 287 | 10.732 | 10.211 | 31.741 | 1.000 32.41 |
| ATOM | 2187 | N | VAL | A | 288 | 11.071 | 8.981 | 33.599 | 1.000 29.73 |
| ATOM | 2188 | CA | VAL | A | 288 | 12.024 | 9.837 | 34.294 | 1.000 22.00 |
| ATOM | 2189 | CB | VAL | A | 288 | 13.229 | 10.233 | 33.436 | 1.000 21.06 |
| ATOM | 2190 | CG1 | VAL | A | 288 | 14.167 | 11.132 | 34.232 | 1.000 28.71 |
| ATOM | 2191 | CG2 | VAL | A | 288 | 13.961 | 8.986 | 32.952 | 1.000 15.73 |
| ATOM | 2192 | C | VAL | A | 288 | 11.269 | 11.073 | 34.787 | 1.000 30.61 |
| ATOM | 2193 | O | VAL | A | 288 | 11.226 | 12.112 | 34.132 | 1.000 31.06 |
| ATOM | 2194 | N | GLN | A | 289 | 10.675 | 10.871 | 35.957 | 1.000 23.90 |
| ATOM | 2195 | CA | GLN | A | 289 | 9.626 | 11.709 | 36.494 | 1.000 28.48 |
| ATOM | 2196 | CB | GLN | A | 289 | 8.735 | 10.869 | 37.427 | 1.000 27.94 |
| ATOM | 2197 | CG | GLN | A | 289 | 7.406 | 11.535 | 37.748 | 1.000 34.50 |
| ATOM | 2198 | CD | GLN | A | 289 | 6.481 | 10.661 | 38.562 | 1.000 30.01 |
| ATOM | 2199 | OE1 | GLN | A | 289 | 6.907 | 9.646 | 39.112 | 1.000 45.90 |
| ATOM | 2200 | NE2 | GLN | A | 289 | 5.209 | 11.026 | 38.655 | 1.000 37.56 |
| ATOM | 2201 | C | GLN | A | 289 | 10.123 | 12.924 | 37.258 | 1.000 36.20 |
| ATOM | 2202 | O | GLN | A | 289 | 9.316 | 13.811 | 37.536 | 1.000 32.67 |
| ATOM | 2203 | N | THR | A | 290 | 11.402 | 12.994 | 37.619 | 1.000 33.43 |
| ATOM | 2204 | CA | THR | A | 290 | 11.857 | 14.147 | 38.382 | 1.000 32.24 |
| ATOM | 2205 | CB | THR | A | 290 | 12.078 | 13.862 | 39.878 | 1.000 27.63 |
| ATOM | 2206 | OG1 | THR | A | 290 | 13.285 | 13.106 | 40.043 | 1.000 42.04 |
| ATOM | 2207 | CG2 | THR | A | 290 | 10.951 | 13.021 | 40.456 | 1.000 35.76 |
| ATOM | 2208 | C | THR | A | 290 | 13.174 | 14.677 | 37.822 | 1.000 42.79 |
| ATOM | 2209 | O | THR | A | 290 | 13.921 | 13.935 | 37.191 | 1.000 31.85 |
| ATOM | 2210 | N | GLU | A | 291 | 13.421 | 15.963 | 38.072 | 1.000 41.73 |
| ATOM | 2211 | CA | GLU | A | 291 | 14.707 | 16.538 | 37.692 | 1.000 33.95 |
| ATOM | 2212 | CB | GLU | A | 291 | 14.749 | 18.032 | 37.980 | 1.000 44.06 |
| ATOM | 2213 | CG | GLU | A | 291 | 16.167 | 18.595 | 38.042 | 1.000 51.27 |
| ATOM | 2214 | CD | GLU | A | 291 | 16.146 | 20.001 | 38.627 | 1.000 50.92 |
| ATOM | 2215 | OE1 | GLU | A | 291 | 16.994 | 20.298 | 39.487 | 1.000 46.66 |
| ATOM | 2216 | OE2 | GLU | A | 291 | 15.255 | 20.769 | 38.205 | 1.000 44.79 |
| ATOM | 2217 | C | GLU | A | 291 | 15.814 | 15.826 | 38.461 | 1.000 26.05 |
| ATOM | 2218 | O | GLU | A | 291 | 16.890 | 15.581 | 37.921 | 1.000 31.12 |
| ATOM | 2219 | N | CYS | A | 292 | 15.513 | 15.486 | 39.714 | 1.000 27.69 |
| ATOM | 2220 | CA | CYS | A | 292 | 16.460 | 14.750 | 40.550 | 1.000 22.15 |
| ATOM | 2221 | CB | CYS | A | 292 | 15.840 | 14.409 | 41.899 | 1.000 28.25 |
| ATOM | 2222 | SG | CYS | A | 292 | 16.996 | 13.623 | 43.050 | 1.000 68.90 |
| ATOM | 2223 | C | CYS | A | 292 | 16.908 | 13.477 | 39.849 | 1.000 29.87 |
| ATOM | 2224 | O | CYS | A | 292 | 18.079 | 13.092 | 39.819 | 1.000 32.69 |
| ATOM | 2225 | N | GLN | A | 293 | 15.924 | 12.801 | 39.246 | 1.000 28.10 |
| ATOM | 2226 | CA | GLN | A | 293 | 16.294 | 11.621 | 38.459 | 1.000 28.74 |
| ATOM | 2227 | CB | GLN | A | 293 | 15.030 | 10.845 | 38.087 | 1.000 25.18 |
| ATOM | 2228 | CG | GLN | A | 293 | 14.509 | 10.017 | 39.250 | 1.000 22.15 |
| ATOM | 2229 | CD | GLN | A | 293 | 13.034 | 9.698 | 39.089 | 1.000 27.52 |
| ATOM | 2230 | OE1 | GLN | A | 293 | 12.412 | 10.175 | 38.141 | 1.000 28.92 |
| ATOM | 2231 | NE2 | GLN | A | 293 | 12.503 | 8.909 | 40.009 | 1.000 24.69 |
| ATOM | 2232 | C | GLN | A | 293 | 17.097 | 12.037 | 37.235 | 1.000 29.57 |
| ATOM | 2233 | O | GLN | A | 293 | 18.056 | 11.373 | 36.831 | 1.000 25.56 |
| ATOM | 2234 | N | TYR | A | 294 | 16.706 | 13.165 | 36.640 | 1.000 27.49 |
| ATOM | 2235 | CA | TYR | A | 294 | 17.399 | 13.690 | 35.469 | 1.000 28.60 |

FIGURE 49

```
ATOM   2236  CB   TYR A 294      16.667  14.921  34.934 1.000 26.37
ATOM   2237  CG   TYR A 294      17.095  15.300  33.540 1.000 27.25
ATOM   2238  CD1  TYR A 294      16.934  14.379  32.509 1.000 37.08
ATOM   2239  CE1  TYR A 294      17.311  14.682  31.218 1.000 37.31
ATOM   2240  CZ   TYR A 294      17.861  15.920  30.951 1.000 39.27
ATOM   2241  OH   TYR A 294      18.234  16.214  29.659 1.000 43.06
ATOM   2242  CE2  TYR A 294      18.030  16.846  31.957 1.000 36.04
ATOM   2243  CD2  TYR A 294      17.648  16.535  33.252 1.000 28.82
ATOM   2244  C    TYR A 294      18.844  14.045  35.798 1.000 26.82
ATOM   2245  O    TYR A 294      19.783  13.828  35.040 1.000 34.04
ATOM   2246  N    VAL A 295      19.062  14.611  36.978 1.000 22.51
ATOM   2247  CA   VAL A 295      20.439  14.894  37.384 1.000 32.33
ATOM   2248  CB   VAL A 295      20.466  15.733  38.675 1.000 34.92
ATOM   2249  CG1  VAL A 295      21.858  15.698  39.282 1.000 36.74
ATOM   2250  CG2  VAL A 295      20.006  17.152  38.372 1.000 28.93
ATOM   2251  C    VAL A 295      21.228  13.612  37.608 1.000 27.09
ATOM   2252  O    VAL A 295      22.364  13.460  37.153 1.000 34.90
ATOM   2253  N    TYR A 296      20.606  12.678  38.319 1.000 26.27
ATOM   2254  CA   TYR A 296      21.232  11.378  38.578 1.000 29.32
ATOM   2255  CB   TYR A 296      20.229  10.492  39.314 1.000 28.67
ATOM   2256  CG   TYR A 296      20.761   9.196  39.861 1.000 35.66
ATOM   2257  CD1  TYR A 296      21.638   9.150  40.937 1.000 33.98
ATOM   2258  CE1  TYR A 296      22.119   7.951  41.431 1.000 32.73
ATOM   2259  CZ   TYR A 296      21.722   6.770  40.842 1.000 33.73
ATOM   2260  OH   TYR A 296      22.187   5.561  41.318 1.000 35.73
ATOM   2261  CE2  TYR A 296      20.853   6.786  39.775 1.000 33.85
ATOM   2262  CD2  TYR A 296      20.376   7.987  39.290 1.000 37.49
ATOM   2263  C    TYR A 296      21.742  10.739  37.295 1.000 27.66
ATOM   2264  O    TYR A 296      22.831  10.150  37.266 1.000 32.42
ATOM   2265  N    LEU A 297      21.015  10.840  36.184 1.000 26.94
ATOM   2266  CA   LEU A 297      21.497  10.174  34.968 1.000 28.80
ATOM   2267  CB   LEU A 297      20.459  10.187  33.846 1.000 24.99
ATOM   2268  CG   LEU A 297      19.141   9.462  34.135 1.000 24.86
ATOM   2269  CD1  LEU A 297      18.119   9.734  33.046 1.000 23.89
ATOM   2270  CD2  LEU A 297      19.357   7.966  34.270 1.000 20.37
ATOM   2271  C    LEU A 297      22.795  10.820  34.495 1.000 33.04
ATOM   2272  O    LEU A 297      23.704  10.129  34.036 1.000 49.72
ATOM   2273  N    HIS A 298      22.879  12.139  34.606 1.000 31.51
ATOM   2274  CA   HIS A 298      24.115  12.850  34.291 1.000 35.13
ATOM   2275  CB   HIS A 298      23.871  14.358  34.261 1.000 40.34
ATOM   2276  CG   HIS A 298      22.964  14.791  33.153 1.000 37.19
ATOM   2277  ND1  HIS A 298      21.598  14.646  33.222 1.000 31.89
ATOM   2278  CE1  HIS A 298      21.052  15.109  32.108 1.000 37.29
ATOM   2279  NE2  HIS A 298      22.021  15.545  31.322 1.000 38.18
ATOM   2280  CD2  HIS A 298      23.228  15.356  31.954 1.000 36.75
ATOM   2281  C    HIS A 298      25.202  12.524  35.310 1.000 29.73
ATOM   2282  O    HIS A 298      26.358  12.314  34.945 1.000 36.94
ATOM   2283  N    GLN A 299      24.848  12.470  36.599 1.000 26.95
ATOM   2284  CA   GLN A 299      25.880  12.104  37.579 1.000 34.87
ATOM   2285  CB   GLN A 299      25.339  12.184  39.001 1.000 34.33
ATOM   2286  CG   GLN A 299      24.925  13.584  39.424 1.000 44.04
ATOM   2287  CD   GLN A 299      24.110  13.598  40.702 1.000 49.76
```

FIGURE 50

| | | | | | | | | | |
|---|---|---|---|---|---|---|---|---|---|
| ATOM | 2288 | OE1 | GLN | A | 299 | 23.289 | 12.715 | 40.953 | 1.000 45.00 |
| ATOM | 2289 | NE2 | GLN | A | 299 | 24.315 | 14.612 | 41.540 | 1.000 34.03 |
| ATOM | 2290 | C | GLN | A | 299 | 26.425 | 10.712 | 37.267 | 1.000 42.34 |
| ATOM | 2291 | O | GLN | A | 299 | 27.602 | 10.424 | 37.494 | 1.000 36.30 |
| ATOM | 2292 | N | CYS | A | 300 | 25.565 | 9.845 | 36.732 | 1.000 40.53 |
| ATOM | 2293 | CA | CYS | A | 300 | 25.967 | 8.486 | 36.389 | 1.000 34.21 |
| ATOM | 2294 | CB | CYS | A | 300 | 24.743 | 7.622 | 36.058 | 1.000 28.55 |
| ATOM | 2295 | SG | CYS | A | 300 | 23.923 | 6.884 | 37.493 | 1.000 33.04 |
| ATOM | 2296 | C | CYS | A | 300 | 26.937 | 8.476 | 35.217 | 1.000 34.71 |
| ATOM | 2297 | O | CYS | A | 300 | 27.937 | 7.754 | 35.210 | 1.000 29.76 |
| ATOM | 2298 | N | VAL | A | 301 | 26.651 | 9.279 | 34.193 | 1.000 43.45 |
| ATOM | 2299 | CA | VAL | A | 301 | 27.534 | 9.265 | 33.021 | 1.000 48.01 |
| ATOM | 2300 | CB | VAL | A | 301 | 26.875 | 9.944 | 31.809 | 1.000 44.81 |
| ATOM | 2301 | CG1 | VAL | A | 301 | 27.860 | 10.046 | 30.650 | 1.000 34.28 |
| ATOM | 2302 | CG2 | VAL | A | 301 | 25.626 | 9.187 | 31.372 | 1.000 34.53 |
| ATOM | 2303 | C | VAL | A | 301 | 28.865 | 9.935 | 33.351 | 1.000 51.69 |
| ATOM | 2304 | O | VAL | A | 301 | 29.937 | 9.511 | 32.918 | 1.000 43.92 |
| ATOM | 2305 | N | ARG | A | 302 | 28.808 | 11.008 | 34.140 | 1.000 49.27 |
| ATOM | 2306 | CA | ARG | A | 302 | 30.013 | 11.730 | 34.519 | 1.000 45.50 |
| ATOM | 2307 | CB | ARG | A | 302 | 29.670 | 12.984 | 35.328 | 1.000 43.11 |
| ATOM | 2308 | CG | ARG | A | 302 | 30.898 | 13.642 | 35.952 | 1.000 44.65 |
| ATOM | 2309 | CD | ARG | A | 302 | 30.517 | 14.426 | 37.200 | 1.000 42.63 |
| ATOM | 2310 | NE | ARG | A | 302 | 30.239 | 13.510 | 38.308 | 1.000 45.99 |
| ATOM | 2311 | CZ | ARG | A | 302 | 29.458 | 13.803 | 39.336 | 1.000 50.62 |
| ATOM | 2312 | NH1 | ARG | A | 302 | 28.871 | 14.992 | 39.398 | 1.000 51.05 |
| ATOM | 2313 | NH2 | ARG | A | 302 | 29.264 | 12.909 | 40.297 | 1.000 48.05 |
| ATOM | 2314 | C | ARG | A | 302 | 30.955 | 10.852 | 35.332 | 1.000 44.54 |
| ATOM | 2315 | O | ARG | A | 302 | 32.162 | 10.831 | 35.095 | 1.000 56.02 |
| ATOM | 2316 | N | ASP | A | 303 | 30.409 | 10.124 | 36.305 | 1.000 44.54 |
| ATOM | 2317 | CA | ASP | A | 303 | 31.292 | 9.270 | 37.105 | 1.000 43.81 |
| ATOM | 2318 | CB | ASP | A | 303 | 30.542 | 8.705 | 38.312 | 1.000 34.49 |
| ATOM | 2319 | CG | ASP | A | 303 | 30.053 | 9.823 | 39.215 | 1.000 37.57 |
| ATOM | 2320 | OD1 | ASP | A | 303 | 30.540 | 10.963 | 39.057 | 1.000 52.86 |
| ATOM | 2321 | OD2 | ASP | A | 303 | 29.183 | 9.594 | 40.078 | 1.000 46.64 |
| ATOM | 2322 | C | ASP | A | 303 | 31.889 | 8.163 | 36.248 | 1.000 48.14 |
| ATOM | 2323 | O | ASP | A | 303 | 33.015 | 7.724 | 36.489 | 1.000 65.82 |
| ATOM | 2324 | N | VAL | A | 304 | 31.151 | 7.703 | 35.241 | 1.000 50.71 |
| ATOM | 2325 | CA | VAL | A | 304 | 31.668 | 6.631 | 34.389 | 1.000 49.88 |
| ATOM | 2326 | CB | VAL | A | 304 | 30.541 | 5.917 | 33.628 | 1.000 51.23 |
| ATOM | 2327 | CG1 | VAL | A | 304 | 30.871 | 5.761 | 32.150 | 1.000 50.73 |
| ATOM | 2328 | CG2 | VAL | A | 304 | 30.277 | 4.561 | 34.263 | 1.000 34.30 |
| ATOM | 2329 | C | VAL | A | 304 | 32.697 | 7.175 | 33.404 | 1.000 41.63 |
| ATOM | 2330 | O | VAL | A | 304 | 33.656 | 6.498 | 33.037 | 1.000 41.23 |
| ATOM | 2331 | N | LEU | A | 305 | 32.489 | 8.413 | 32.981 | 1.000 46.33 |
| ATOM | 2332 | CA | LEU | A | 305 | 33.442 | 9.091 | 32.106 | 1.000 57.09 |
| ATOM | 2333 | CB | LEU | A | 305 | 32.783 | 10.338 | 31.507 | 1.000 52.07 |
| ATOM | 2334 | CG | LEU | A | 305 | 31.872 | 10.008 | 30.314 | 1.000 47.93 |
| ATOM | 2335 | CD1 | LEU | A | 305 | 31.630 | 11.216 | 29.427 | 1.000 48.09 |
| ATOM | 2336 | CD2 | LEU | A | 305 | 32.488 | 8.860 | 29.529 | 1.000 30.69 |
| ATOM | 2337 | C | LEU | A | 305 | 34.728 | 9.439 | 32.849 | 1.000 64.87 |
| ATOM | 2338 | O | LEU | A | 305 | 35.814 | 9.387 | 32.266 | 1.000 58.87 |
| ATOM | 2339 | N | ARG | A | 306 | 34.601 | 9.776 | 34.127 | 1.000 68.65 |

FIGURE 51

```
ATOM   2340  CA   ARG A 306      35.714  10.014  35.032  1.000 66.90
ATOM   2341  CB   ARG A 306      35.210  10.407  36.420  1.000 62.97
ATOM   2342  CG   ARG A 306      34.909  11.889  36.584  1.000 63.46
ATOM   2343  CD   ARG A 306      34.233  12.132  37.927  1.000 63.67
ATOM   2344  NE   ARG A 306      33.867  13.537  38.091  1.000 72.26
ATOM   2345  CZ   ARG A 306      33.178  13.982  39.131  1.000 81.44
ATOM   2346  NH1  ARG A 306      32.786  13.132  40.074  1.000 88.77
ATOM   2347  NH2  ARG A 306      32.874  15.266  39.234  1.000 94.65
ATOM   2348  C    ARG A 306      36.601   8.773  35.157  1.000 69.05
ATOM   2349  O    ARG A 306      37.722   8.751  34.650  1.000 60.08
ATOM   2350  N    ALA A 307      36.073   7.760  35.834  1.000 70.13
ATOM   2351  CA   ALA A 307      36.735   6.475  36.013  1.000 72.89
ATOM   2352  CB   ALA A 307      35.766   5.449  36.576  1.000 79.56
ATOM   2353  C    ALA A 307      37.324   5.984  34.694  1.000 75.87
ATOM   2354  O    ALA A 307      38.449   5.491  34.642  1.000 86.48
ATOM   2355  N    ARG A 308      36.535   6.146  33.635  1.000 72.53
ATOM   2356  CA   ARG A 308      36.980   5.843  32.285  1.000 71.87
ATOM   2357  CB   ARG A 308      35.954   6.318  31.260  1.000 72.41
ATOM   2358  CG   ARG A 308      35.892   5.489  29.991  1.000 75.31
ATOM   2359  CD   ARG A 308      34.468   5.480  29.453  1.000 81.76
ATOM   2360  NE   ARG A 308      34.286   4.508  28.381  1.000 82.26
ATOM   2361  CZ   ARG A 308      33.963   4.835  27.136  1.000 81.15
ATOM   2362  NH1  ARG A 308      33.794   6.106  26.802  1.000 66.44
ATOM   2363  NH2  ARG A 308      33.818   3.879  26.222  1.000 98.94
ATOM   2364  C    ARG A 308      38.316   6.522  31.997  1.000 79.31
ATOM   2365  O    ARG A 308      39.323   6.227  32.636  1.000 93.34
ATOM   2366  N    LYS A 309      38.277   7.433  31.039  1.000 83.39
ATOM   2367  CA   LYS A 309      39.434   8.214  30.626  1.000 85.77
ATOM   2368  CB   LYS A 309      39.029   9.196  29.532  1.000 85.52
ATOM   2369  CG   LYS A 309      37.652   8.903  28.934  1.000 85.90
ATOM   2370  CD   LYS A 309      36.903  10.189  28.611  1.000 87.13
ATOM   2371  CE   LYS A 309      37.828  11.241  28.041  1.000 90.18
ATOM   2372  NZ   LYS A 309      37.294  11.834  26.782  1.000 95.87
ATOM   2373  C    LYS A 309      40.045   8.948  31.819  1.000 88.05
ATOM   2374  O    LYS A 309      39.829  10.143  32.007  1.000 83.82
ATOM   2375  N    LEU A 310      40.812   8.199  32.602  1.000 91.25
ATOM   2376  CA   LEU A 310      41.488   8.642  33.803  1.000 89.65
ATOM   2377  CB   LEU A 310      40.575   8.511  35.031  1.000 89.61
ATOM   2378  CG   LEU A 310      41.209   8.874  36.375  1.000 91.78
ATOM   2379  CD1  LEU A 310      41.928  10.213  36.280  1.000 97.42
ATOM   2380  CD2  LEU A 310      40.167   8.896  37.476  1.000 97.23
ATOM   2381  C    LEU A 310      42.772   7.848  34.034  1.000 88.08
ATOM   2382  O    LEU A 310      42.708   6.719  34.516  1.000 91.11
ATOM   2383  N    LYS B  19      45.803  11.373  51.943  1.000103.56
ATOM   2384  CA   LYS B  19      45.533  10.011  51.483  1.000 77.94
ATOM   2385  CB   LYS B  19      46.473   9.008  52.147  1.000 82.60
ATOM   2386  CG   LYS B  19      46.882   7.835  51.255  1.000 87.87
ATOM   2387  CD   LYS B  19      48.286   7.354  51.584  1.000 91.26
ATOM   2388  CE   LYS B  19      49.120   7.117  50.329  1.000 90.51
ATOM   2389  NZ   LYS B  19      50.584   7.099  50.628  1.000 76.07
ATOM   2390  C    LYS B  19      44.082   9.614  51.751  1.000 64.77
ATOM   2391  O    LYS B  19      43.153  10.321  51.368  1.000 54.90
```

FIGURE 52

```
ATOM   2392  N    THR B  20      43.927   8.473  52.402 1.000 58.60
ATOM   2393  CA   THR B  20      42.644   7.870  52.709 1.000 50.23
ATOM   2394  CB   THR B  20      42.853   6.643  53.618 1.000 48.19
ATOM   2395  OG1  THR B  20      41.626   6.256  54.241 1.000 67.26
ATOM   2396  CG2  THR B  20      43.824   6.994  54.737 1.000 41.73
ATOM   2397  C    THR B  20      41.695   8.862  53.376 1.000 54.14
ATOM   2398  O    THR B  20      42.126   9.839  53.992 1.000 48.50
ATOM   2399  N    SER B  21      40.407   8.579  53.235 1.000 57.41
ATOM   2400  CA   SER B  21      39.308   9.335  53.812 1.000 54.62
ATOM   2401  CB   SER B  21      39.008  10.562  52.951 1.000 57.73
ATOM   2402  OG   SER B  21      38.000  10.316  51.989 1.000 61.68
ATOM   2403  C    SER B  21      38.071   8.452  53.980 1.000 51.70
ATOM   2404  O    SER B  21      38.044   7.306  53.523 1.000 45.33
ATOM   2405  N    CYS B  22      37.038   8.961  54.640 1.000 48.54
ATOM   2406  CA   CYS B  22      35.824   8.195  54.908 1.000 41.60
ATOM   2407  CB   CYS B  22      35.884   7.524  56.281 1.000 46.98
ATOM   2408  SG   CYS B  22      36.813   5.974  56.365 1.000 93.30
ATOM   2409  C    CYS B  22      34.590   9.082  54.851 1.000 38.62
ATOM   2410  O    CYS B  22      34.027   9.443  55.887 1.000 49.86
ATOM   2411  N    PRO B  23      34.143   9.447  53.659 1.000 47.14
ATOM   2412  CA   PRO B  23      32.954  10.304  53.566 1.000 56.35
ATOM   2413  CB   PRO B  23      32.868  10.652  52.085 1.000 55.14
ATOM   2414  CG   PRO B  23      34.157  10.216  51.473 1.000 48.26
ATOM   2415  CD   PRO B  23      34.680   9.104  52.334 1.000 45.23
ATOM   2416  C    PRO B  23      31.720   9.529  54.021 1.000 59.08
ATOM   2417  O    PRO B  23      31.566   8.358  53.677 1.000 63.26
ATOM   2418  N    ILE B  24      30.856  10.175  54.800 1.000 57.72
ATOM   2419  CA   ILE B  24      29.645   9.515  55.274 1.000 57.66
ATOM   2420  CB   ILE B  24      29.730   9.129  56.761 1.000 61.40
ATOM   2421  CG1  ILE B  24      30.656   7.951  57.048 1.000 63.99
ATOM   2422  CD1  ILE B  24      31.645   8.269  58.170 1.000 72.75
ATOM   2423  CG2  ILE B  24      28.346   8.849  57.336 1.000 55.60
ATOM   2424  C    ILE B  24      28.423  10.404  55.073 1.000 56.32
ATOM   2425  O    ILE B  24      28.463  11.607  55.319 1.000 56.42
ATOM   2426  N    LYS B  25      27.336   9.790  54.618 1.000 60.08
ATOM   2427  CA   LYS B  25      26.083  10.506  54.431 1.000 69.15
ATOM   2428  CB   LYS B  25      24.998   9.583  53.874 1.000 82.75
ATOM   2429  CG   LYS B  25      25.033   9.350  52.369 1.000 85.99
ATOM   2430  CD   LYS B  25      24.777   7.874  52.048 1.000 85.92
ATOM   2431  CE   LYS B  25      26.083   7.172  51.689 1.000 85.44
ATOM   2432  NZ   LYS B  25      26.510   7.499  50.285 1.000 80.54
ATOM   2433  C    LYS B  25      25.604  11.112  55.747 1.000 63.20
ATOM   2434  O    LYS B  25      25.591  10.438  56.783 1.000 50.64
ATOM   2435  N    ILE B  26      25.195  12.378  55.680 1.000 54.67
ATOM   2436  CA   ILE B  26      24.670  13.059  56.860 1.000 55.87
ATOM   2437  CB   ILE B  26      24.575  14.581  56.678 1.000 58.65
ATOM   2438  CG1  ILE B  26      23.569  15.042  55.620 1.000 60.19
ATOM   2439  CD1  ILE B  26      23.370  16.547  55.610 1.000 57.06
ATOM   2440  CG2  ILE B  26      25.953  15.157  56.389 1.000 63.31
ATOM   2441  C    ILE B  26      23.291  12.498  57.214 1.000 58.06
ATOM   2442  O    ILE B  26      22.810  12.724  58.319 1.000 56.98
ATOM   2443  N    ASN B  27      22.730  11.784  56.260 1.000 61.16
```

FIGURE 53

| | | | | | | | | | |
|---|---|---|---|---|---|---|---|---|---|
| ATOM | 2444 | CA | ASN | B | 27 | 21.489 | 11.049 | 56.299 | 1.000 59.75 |
| ATOM | 2445 | CB | ASN | B | 27 | 21.008 | 10.743 | 54.876 | 1.000 63.07 |
| ATOM | 2446 | CG | ASN | B | 27 | 20.656 | 12.000 | 54.106 | 1.000 65.31 |
| ATOM | 2447 | OD1 | ASN | B | 27 | 20.305 | 11.913 | 52.930 | 1.000 50.97 |
| ATOM | 2448 | ND2 | ASN | B | 27 | 20.748 | 13.143 | 54.774 | 1.000 75.32 |
| ATOM | 2449 | C | ASN | B | 27 | 21.632 | 9.724 | 57.040 | 1.000 57.11 |
| ATOM | 2450 | O | ASN | B | 27 | 20.646 | 9.183 | 57.534 | 1.000 57.56 |
| ATOM | 2451 | N | GLN | B | 28 | 22.856 | 9.217 | 57.094 | 1.000 57.63 |
| ATOM | 2452 | CA | GLN | B | 28 | 23.130 | 7.930 | 57.717 | 1.000 56.91 |
| ATOM | 2453 | CB | GLN | B | 28 | 23.761 | 6.988 | 56.678 | 1.000 64.21 |
| ATOM | 2454 | CG | GLN | B | 28 | 24.000 | 5.578 | 57.192 | 1.000 66.30 |
| ATOM | 2455 | CD | GLN | B | 28 | 22.771 | 4.698 | 57.075 | 1.000 70.95 |
| ATOM | 2456 | OE1 | GLN | B | 28 | 22.005 | 4.829 | 56.119 | 1.000 74.56 |
| ATOM | 2457 | NE2 | GLN | B | 28 | 22.580 | 3.801 | 58.039 | 1.000 63.57 |
| ATOM | 2458 | C | GLN | B | 28 | 24.053 | 8.043 | 58.917 | 1.000 44.81 |
| ATOM | 2459 | O | GLN | B | 28 | 24.358 | 7.034 | 59.556 | 1.000 48.39 |
| ATOM | 2460 | N | PHE | B | 29 | 24.526 | 9.244 | 59.241 | 1.000 46.88 |
| ATOM | 2461 | CA | PHE | B | 29 | 25.544 | 9.393 | 60.273 | 1.000 36.76 |
| ATOM | 2462 | CB | PHE | B | 29 | 25.849 | 10.882 | 60.532 | 1.000 43.65 |
| ATOM | 2463 | CG | PHE | B | 29 | 27.092 | 11.033 | 61.384 | 1.000 41.38 |
| ATOM | 2464 | CD1 | PHE | B | 29 | 28.348 | 10.939 | 60.813 | 1.000 39.51 |
| ATOM | 2465 | CE1 | PHE | B | 29 | 29.493 | 11.073 | 61.579 | 1.000 39.09 |
| ATOM | 2466 | CZ | PHE | B | 29 | 29.383 | 11.303 | 62.933 | 1.000 38.33 |
| ATOM | 2467 | CE2 | PHE | B | 29 | 28.131 | 11.392 | 63.518 | 1.000 42.37 |
| ATOM | 2468 | CD2 | PHE | B | 29 | 26.995 | 11.257 | 62.747 | 1.000 38.83 |
| ATOM | 2469 | C | PHE | B | 29 | 25.186 | 8.747 | 61.601 | 1.000 37.74 |
| ATOM | 2470 | O | PHE | B | 29 | 26.032 | 8.087 | 62.213 | 1.000 43.72 |
| ATOM | 2471 | N | GLU | B | 30 | 23.960 | 8.933 | 62.080 | 1.000 45.93 |
| ATOM | 2472 | CA | GLU | B | 30 | 23.554 | 8.292 | 63.331 | 1.000 49.96 |
| ATOM | 2473 | CB | GLU | B | 30 | 22.082 | 8.589 | 63.614 | 1.000 61.18 |
| ATOM | 2474 | CG | GLU | B | 30 | 21.655 | 8.277 | 65.041 | 1.000 72.30 |
| ATOM | 2475 | CD | GLU | B | 30 | 22.517 | 8.965 | 66.069 | 1.000 84.23 |
| ATOM | 2476 | OE1 | GLU | B | 30 | 23.748 | 8.742 | 66.082 | 1.000104.41 |
| ATOM | 2477 | OE2 | GLU | B | 30 | 21.962 | 9.740 | 66.892 | 1.000 90.78 |
| ATOM | 2478 | C | GLU | B | 30 | 23.801 | 6.785 | 63.292 | 1.000 53.76 |
| ATOM | 2479 | O | GLU | B | 30 | 24.396 | 6.207 | 64.208 | 1.000 40.13 |
| ATOM | 2480 | N | GLY | B | 31 | 23.348 | 6.160 | 62.207 | 1.000 50.11 |
| ATOM | 2481 | CA | GLY | B | 31 | 23.552 | 4.743 | 61.979 | 1.000 39.81 |
| ATOM | 2482 | C | GLY | B | 31 | 25.024 | 4.352 | 61.975 | 1.000 42.21 |
| ATOM | 2483 | O | GLY | B | 31 | 25.429 | 3.569 | 62.841 | 1.000 48.72 |
| ATOM | 2484 | N | HIS | B | 32 | 25.786 | 4.891 | 61.027 | 1.000 44.34 |
| ATOM | 2485 | CA | HIS | B | 32 | 27.227 | 4.682 | 60.898 | 1.000 44.47 |
| ATOM | 2486 | CB | HIS | B | 32 | 27.848 | 5.622 | 59.865 | 1.000 46.08 |
| ATOM | 2487 | CG | HIS | B | 32 | 29.339 | 5.758 | 59.929 | 1.000 57.10 |
| ATOM | 2488 | ND1 | HIS | B | 32 | 30.199 | 4.924 | 59.241 | 1.000 54.47 |
| ATOM | 2489 | CE1 | HIS | B | 32 | 31.451 | 5.291 | 59.477 | 1.000 52.58 |
| ATOM | 2490 | NE2 | HIS | B | 32 | 31.440 | 6.328 | 60.296 | 1.000 49.52 |
| ATOM | 2491 | CD2 | HIS | B | 32 | 30.140 | 6.650 | 60.573 | 1.000 56.38 |
| ATOM | 2492 | C | HIS | B | 32 | 27.916 | 4.872 | 62.244 | 1.000 43.34 |
| ATOM | 2493 | O | HIS | B | 32 | 28.702 | 4.051 | 62.710 | 1.000 44.29 |
| ATOM | 2494 | N | PHE | B | 33 | 27.608 | 6.001 | 62.884 | 1.000 42.64 |
| ATOM | 2495 | CA | PHE | B | 33 | 28.186 | 6.230 | 64.209 | 1.000 46.60 |

FIGURE 54

| | | | | | | | | | |
|---|---|---|---|---|---|---|---|---|---|
| ATOM | 2496 | CB  | PHE | B | 33 | 27.794 | 7.621  | 64.705 | 1.000 45.66 |
| ATOM | 2497 | CG  | PHE | B | 33 | 28.411 | 8.010  | 66.024 | 1.000 41.60 |
| ATOM | 2498 | CD1 | PHE | B | 33 | 29.639 | 7.503  | 66.418 | 1.000 28.55 |
| ATOM | 2499 | CE1 | PHE | B | 33 | 30.180 | 7.856  | 67.635 | 1.000 34.17 |
| ATOM | 2500 | CZ  | PHE | B | 33 | 29.502 | 8.729  | 68.464 | 1.000 39.16 |
| ATOM | 2501 | CE2 | PHE | B | 33 | 28.282 | 9.249  | 68.088 | 1.000 40.43 |
| ATOM | 2502 | CD2 | PHE | B | 33 | 27.743 | 8.885  | 66.871 | 1.000 46.28 |
| ATOM | 2503 | C   | PHE | B | 33 | 27.742 | 5.122  | 65.157 | 1.000 49.56 |
| ATOM | 2504 | O   | PHE | B | 33 | 28.543 | 4.568  | 65.918 | 1.000 39.50 |
| ATOM | 2505 | N   | MET | B | 34 | 26.451 | 4.782  | 65.110 | 1.000 53.61 |
| ATOM | 2506 | CA  | MET | B | 34 | 25.979 | 3.673  | 65.946 | 1.000 51.72 |
| ATOM | 2507 | CB  | MET | B | 34 | 24.456 | 3.545  | 65.882 | 1.000 51.72 |
| ATOM | 2508 | CG  | MET | B | 34 | 23.750 | 4.565  | 66.777 | 1.000 52.01 |
| ATOM | 2509 | SD  | MET | B | 34 | 22.105 | 4.050  | 67.305 | 1.000 72.48 |
| ATOM | 2510 | CE  | MET | B | 34 | 21.721 | 2.817  | 66.063 | 1.000 45.79 |
| ATOM | 2511 | C   | MET | B | 34 | 26.671 | 2.377  | 65.554 | 1.000 52.65 |
| ATOM | 2512 | O   | MET | B | 34 | 27.064 | 1.601  | 66.433 | 1.000 63.08 |
| ATOM | 2513 | N   | LYS | B | 35 | 26.862 | 2.114  | 64.258 | 1.000 52.00 |
| ATOM | 2514 | CA  | LYS | B | 35 | 27.584 | 0.889  | 63.905 | 1.000 54.31 |
| ATOM | 2515 | CB  | LYS | B | 35 | 27.570 | 0.627  | 62.402 | 1.000 59.44 |
| ATOM | 2516 | CG  | LYS | B | 35 | 26.633 | 1.515  | 61.614 | 1.000 66.12 |
| ATOM | 2517 | CD  | LYS | B | 35 | 26.520 | 1.074  | 60.166 | 1.000 69.40 |
| ATOM | 2518 | CE  | LYS | B | 35 | 25.639 | 2.012  | 59.351 | 1.000 62.69 |
| ATOM | 2519 | NZ  | LYS | B | 35 | 26.251 | 2.293  | 58.019 | 1.000 48.67 |
| ATOM | 2520 | C   | LYS | B | 35 | 29.028 | 0.951  | 64.404 | 1.000 56.64 |
| ATOM | 2521 | O   | LYS | B | 35 | 29.607 | -0.094 | 64.699 | 1.000 47.38 |
| ATOM | 2522 | N   | LEU | B | 36 | 29.564 | 2.163  | 64.485 | 1.000 61.24 |
| ATOM | 2523 | CA  | LEU | B | 36 | 30.933 | 2.424  | 64.902 | 1.000 59.97 |
| ATOM | 2524 | CB  | LEU | B | 36 | 31.323 | 3.874  | 64.594 | 1.000 64.56 |
| ATOM | 2525 | CG  | LEU | B | 36 | 32.434 | 4.056  | 63.557 | 1.000 65.01 |
| ATOM | 2526 | CD1 | LEU | B | 36 | 32.294 | 3.032  | 62.440 | 1.000 65.86 |
| ATOM | 2527 | CD2 | LEU | B | 36 | 32.421 | 5.477  | 63.006 | 1.000 46.61 |
| ATOM | 2528 | C   | LEU | B | 36 | 31.155 | 2.157  | 66.385 | 1.000 58.41 |
| ATOM | 2529 | O   | LEU | B | 36 | 32.238 | 1.731  | 66.790 | 1.000 42.70 |
| ATOM | 2530 | N   | GLN | B | 37 | 30.143 | 2.412  | 67.207 | 1.000 64.59 |
| ATOM | 2531 | CA  | GLN | B | 37 | 30.253 | 2.093  | 68.627 | 1.000 66.89 |
| ATOM | 2532 | CB  | GLN | B | 37 | 29.379 | 3.009  | 69.479 | 1.000 65.39 |
| ATOM | 2533 | CG  | GLN | B | 37 | 29.268 | 4.435  | 68.963 | 1.000 71.01 |
| ATOM | 2534 | CD  | GLN | B | 37 | 29.402 | 5.459  | 70.075 | 1.000 69.30 |
| ATOM | 2535 | OE1 | GLN | B | 37 | 28.554 | 6.349  | 70.194 | 1.000 65.62 |
| ATOM | 2536 | NE2 | GLN | B | 37 | 30.448 | 5.336  | 70.883 | 1.000 67.63 |
| ATOM | 2537 | C   | GLN | B | 37 | 29.858 | 0.639  | 68.887 | 1.000 64.12 |
| ATOM | 2538 | O   | GLN | B | 37 | 30.133 | 0.109  | 69.965 | 1.000 61.41 |
| ATOM | 2539 | N   | ALA | B | 38 | 29.211 | 0.013  | 67.912 | 1.000 61.52 |
| ATOM | 2540 | CA  | ALA | B | 38 | 28.752 | -1.364 | 68.068 | 1.000 61.79 |
| ATOM | 2541 | CB  | ALA | B | 38 | 27.973 | -1.811 | 66.843 | 1.000 61.12 |
| ATOM | 2542 | C   | ALA | B | 38 | 29.924 | -2.304 | 68.328 | 1.000 71.64 |
| ATOM | 2543 | O   | ALA | B | 38 | 31.070 | -1.992 | 68.000 | 1.000 88.33 |
| ATOM | 2544 | N   | ASP | B | 39 | 29.627 | -3.453 | 68.927 | 1.000 75.20 |
| ATOM | 2545 | CA  | ASP | B | 39 | 30.678 | -4.382 | 69.332 | 1.000 79.52 |
| ATOM | 2546 | CB  | ASP | B | 39 | 31.399 | -4.960 | 68.119 | 1.000 83.70 |
| ATOM | 2547 | CG  | ASP | B | 39 | 31.928 | -6.362 | 68.329 | 1.000 85.54 |

FIGURE 55

```
ATOM   2548  OD1 ASP B  39      33.151  -6.572  68.165 1.000  77.07
ATOM   2549  OD2 ASP B  39      31.125  -7.261  68.656 1.000  94.95
ATOM   2550  C   ASP B  39      31.654  -3.661  70.262 1.000  80.16
ATOM   2551  O   ASP B  39      32.866  -3.844  70.171 1.000  82.76
ATOM   2552  N   SER B  40      31.091  -2.847  71.149 1.000  80.57
ATOM   2553  CA  SER B  40      31.845  -2.060  72.117 1.000  88.50
ATOM   2554  CB  SER B  40      32.474  -2.960  73.184 1.000  94.68
ATOM   2555  OG  SER B  40      32.154  -2.503  74.493 1.000 104.32
ATOM   2556  C   SER B  40      32.923  -1.227  71.430 1.000  88.12
ATOM   2557  O   SER B  40      34.120  -1.492  71.558 1.000 101.21
ATOM   2558  N   ASN B  41      32.493  -0.212  70.685 1.000  79.40
ATOM   2559  CA  ASN B  41      33.401   0.680  69.978 1.000  77.46
ATOM   2560  CB  ASN B  41      34.193   1.538  70.973 1.000  73.13
ATOM   2561  CG  ASN B  41      33.910   3.013  70.761 1.000  66.31
ATOM   2562  OD1 ASN B  41      32.852   3.359  70.237 1.000  66.52
ATOM   2563  ND2 ASN B  41      34.853   3.853  71.161 1.000  67.42
ATOM   2564  C   ASN B  41      34.370  -0.080  69.091 1.000  78.31
ATOM   2565  O   ASN B  41      35.499   0.345  68.837 1.000  79.80
ATOM   2566  N   TYR B  42      33.919  -1.239  68.605 1.000  74.28
ATOM   2567  CA  TYR B  42      34.837  -2.034  67.800 1.000  72.73
ATOM   2568  CB  TYR B  42      34.211  -3.377  67.423 1.000  73.56
ATOM   2569  CG  TYR B  42      35.147  -4.228  66.588 1.000  73.21
ATOM   2570  CD1 TYR B  42      36.311  -4.738  67.144 1.000  77.06
ATOM   2571  CE1 TYR B  42      37.173  -5.514  66.388 1.000  78.96
ATOM   2572  CZ  TYR B  42      36.872  -5.773  65.067 1.000  78.31
ATOM   2573  OH  TYR B  42      37.729  -6.541  64.312 1.000  91.83
ATOM   2574  CE2 TYR B  42      35.724  -5.272  64.492 1.000  73.89
ATOM   2575  CD2 TYR B  42      34.868  -4.501  65.256 1.000  72.17
ATOM   2576  C   TYR B  42      35.257  -1.247  66.561 1.000  64.17
ATOM   2577  O   TYR B  42      36.414  -0.843  66.456 1.000  62.76
ATOM   2578  N   LEU B  43      34.312  -1.041  65.653 1.000  59.26
ATOM   2579  CA  LEU B  43      34.589  -0.428  64.362 1.000  59.76
ATOM   2580  CB  LEU B  43      33.310  -0.304  63.528 1.000  63.25
ATOM   2581  CG  LEU B  43      32.890  -1.570  62.775 1.000  63.42
ATOM   2582  CD1 LEU B  43      31.436  -1.480  62.336 1.000  46.05
ATOM   2583  CD2 LEU B  43      33.807  -1.812  61.585 1.000  76.10
ATOM   2584  C   LEU B  43      35.252   0.932  64.522 1.000  54.62
ATOM   2585  O   LEU B  43      36.208   1.237  63.810 1.000  53.46
ATOM   2586  N   LEU B  44      34.760   1.742  65.454 1.000  56.15
ATOM   2587  CA  LEU B  44      35.409   3.030  65.682 1.000  52.24
ATOM   2588  CB  LEU B  44      34.729   3.785  66.826 1.000  48.36
ATOM   2589  CG  LEU B  44      35.293   5.195  67.068 1.000  49.68
ATOM   2590  CD1 LEU B  44      35.267   6.017  65.787 1.000  41.86
ATOM   2591  CD2 LEU B  44      34.522   5.886  68.170 1.000  38.98
ATOM   2592  C   LEU B  44      36.898   2.865  65.975 1.000  48.68
ATOM   2593  O   LEU B  44      37.732   3.549  65.378 1.000  45.89
ATOM   2594  N   SER B  45      37.242   1.962  66.882 1.000  49.23
ATOM   2595  CA  SER B  45      38.619   1.713  67.282 1.000  39.06
ATOM   2596  CB  SER B  45      38.690   0.436  68.127 1.000  39.80
ATOM   2597  OG  SER B  45      39.247   0.727  69.398 1.000  49.93
ATOM   2598  C   SER B  45      39.558   1.552  66.098 1.000  45.56
ATOM   2599  O   SER B  45      40.668   2.082  66.083 1.000  52.78
```

FIGURE 56

| | | | | | | | | | |
|---|---|---|---|---|---|---|---|---|---|
| ATOM | 2600 | N | LYS | B | 46 | 39.087 | 0.795 | 65.113 | 1.000 51.54 |
| ATOM | 2601 | CA | LYS | B | 46 | 39.891 | 0.470 | 63.941 | 1.000 63.73 |
| ATOM | 2602 | CB | LYS | B | 46 | 39.189 | -0.575 | 63.073 | 1.000 74.89 |
| ATOM | 2603 | CG | LYS | B | 46 | 39.589 | -2.009 | 63.395 | 1.000 86.82 |
| ATOM | 2604 | CD | LYS | B | 46 | 39.920 | -2.808 | 62.129 | 1.000 98.47 |
| ATOM | 2605 | CE | LYS | B | 46 | 40.285 | -4.250 | 62.467 | 1.000105.16 |
| ATOM | 2606 | NZ | LYS | B | 46 | 39.701 | -5.221 | 61.446 | 1.000118.97 |
| ATOM | 2607 | C | LYS | B | 46 | 40.196 | 1.720 | 63.115 | 1.000 64.75 |
| ATOM | 2608 | O | LYS | B | 46 | 41.369 | 2.039 | 62.917 | 1.000 80.74 |
| ATOM | 2609 | N | GLU | B | 47 | 39.144 | 2.386 | 62.661 | 1.000 60.32 |
| ATOM | 2610 | CA | GLU | B | 47 | 39.214 | 3.608 | 61.876 | 1.000 57.31 |
| ATOM | 2611 | CB | GLU | B | 47 | 37.861 | 4.317 | 61.829 | 1.000 59.96 |
| ATOM | 2612 | CG | GLU | B | 47 | 37.108 | 4.262 | 60.513 | 1.000 64.86 |
| ATOM | 2613 | CD | GLU | B | 47 | 36.069 | 5.368 | 60.394 | 1.000 62.05 |
| ATOM | 2614 | OE1 | GLU | B | 47 | 35.086 | 5.213 | 59.637 | 1.000 43.75 |
| ATOM | 2615 | OE2 | GLU | B | 47 | 36.243 | 6.408 | 61.066 | 1.000 56.16 |
| ATOM | 2616 | C | GLU | B | 47 | 40.261 | 4.566 | 62.445 | 1.000 52.08 |
| ATOM | 2617 | O | GLU | B | 47 | 40.973 | 5.207 | 61.673 | 1.000 46.49 |
| ATOM | 2618 | N | TYR | B | 48 | 40.331 | 4.643 | 63.772 | 1.000 51.35 |
| ATOM | 2619 | CA | TYR | B | 48 | 41.241 | 5.559 | 64.447 | 1.000 47.41 |
| ATOM | 2620 | CB | TYR | B | 48 | 40.768 | 5.841 | 65.876 | 1.000 43.35 |
| ATOM | 2621 | CG | TYR | B | 48 | 41.664 | 6.800 | 66.628 | 1.000 43.06 |
| ATOM | 2622 | CD1 | TYR | B | 48 | 41.634 | 8.162 | 66.350 | 1.000 43.39 |
| ATOM | 2623 | CE1 | TYR | B | 48 | 42.446 | 9.049 | 67.026 | 1.000 33.55 |
| ATOM | 2624 | CZ | TYR | B | 48 | 43.301 | 8.577 | 67.997 | 1.000 33.43 |
| ATOM | 2625 | OH | TYR | B | 48 | 44.109 | 9.457 | 68.675 | 1.000 39.28 |
| ATOM | 2626 | CE2 | TYR | B | 48 | 43.357 | 7.232 | 68.299 | 1.000 35.45 |
| ATOM | 2627 | CD2 | TYR | B | 48 | 42.538 | 6.354 | 67.609 | 1.000 39.88 |
| ATOM | 2628 | C | TYR | B | 48 | 42.666 | 5.026 | 64.486 | 1.000 44.84 |
| ATOM | 2629 | O | TYR | B | 48 | 43.636 | 5.779 | 64.556 | 1.000 38.45 |
| ATOM | 2630 | N | GLU | B | 49 | 42.798 | 3.704 | 64.448 | 1.000 45.22 |
| ATOM | 2631 | CA | GLU | B | 49 | 44.131 | 3.103 | 64.459 | 1.000 46.18 |
| ATOM | 2632 | CB | GLU | B | 49 | 44.027 | 1.636 | 64.889 | 1.000 60.64 |
| ATOM | 2633 | CG | GLU | B | 49 | 43.562 | 1.476 | 66.331 | 1.000 71.11 |
| ATOM | 2634 | CD | GLU | B | 49 | 44.096 | 2.572 | 67.234 | 1.000 79.66 |
| ATOM | 2635 | OE1 | GLU | B | 49 | 43.360 | 2.978 | 68.161 | 1.000 77.35 |
| ATOM | 2636 | OE2 | GLU | B | 49 | 45.242 | 3.035 | 67.029 | 1.000 85.01 |
| ATOM | 2637 | C | GLU | B | 49 | 44.790 | 3.234 | 63.097 | 1.000 39.20 |
| ATOM | 2638 | O | GLU | B | 49 | 46.009 | 3.355 | 62.975 | 1.000 46.67 |
| ATOM | 2639 | N | GLU | B | 50 | 43.971 | 3.230 | 62.044 | 1.000 35.49 |
| ATOM | 2640 | CA | GLU | B | 50 | 44.513 | 3.352 | 60.694 | 1.000 43.74 |
| ATOM | 2641 | CB | GLU | B | 50 | 43.412 | 3.174 | 59.644 | 1.000 53.39 |
| ATOM | 2642 | CG | GLU | B | 50 | 42.601 | 1.900 | 59.756 | 1.000 64.71 |
| ATOM | 2643 | CD | GLU | B | 50 | 41.686 | 1.654 | 58.577 | 1.000 72.97 |
| ATOM | 2644 | OE1 | GLU | B | 50 | 41.888 | 0.646 | 57.858 | 1.000 85.76 |
| ATOM | 2645 | OE2 | GLU | B | 50 | 40.752 | 2.456 | 58.346 | 1.000 70.73 |
| ATOM | 2646 | C | GLU | B | 50 | 45.205 | 4.698 | 60.485 | 1.000 41.38 |
| ATOM | 2647 | O | GLU | B | 50 | 45.975 | 4.860 | 59.534 | 1.000 49.75 |
| ATOM | 2648 | N | LEU | B | 51 | 44.932 | 5.664 | 61.354 | 1.000 32.56 |
| ATOM | 2649 | CA | LEU | B | 51 | 45.542 | 6.982 | 61.247 | 1.000 33.23 |
| ATOM | 2650 | CB | LEU | B | 51 | 44.611 | 8.073 | 61.767 | 1.000 28.37 |
| ATOM | 2651 | CG | LEU | B | 51 | 43.377 | 8.384 | 60.920 | 1.000 34.19 |

FIGURE 57

| | | | | | | | | | |
|---|---|---|---|---|---|---|---|---|---|
| ATOM | 2652 | CD1 | LEU | B | 51 | 42.246 | 8.901 | 61.799 | 1.000 37.25 |
| ATOM | 2653 | CD2 | LEU | B | 51 | 43.720 | 9.389 | 59.828 | 1.000 48.43 |
| ATOM | 2654 | C | LEU | B | 51 | 46.840 | 7.056 | 62.042 | 1.000 38.45 |
| ATOM | 2655 | O | LEU | B | 51 | 47.503 | 8.091 | 62.030 | 1.000 31.93 |
| ATOM | 2656 | N | LYS | B | 52 | 47.146 | 5.957 | 62.721 | 1.000 40.28 |
| ATOM | 2657 | CA | LYS | B | 52 | 48.274 | 5.912 | 63.641 | 1.000 42.24 |
| ATOM | 2658 | CB | LYS | B | 52 | 48.513 | 4.470 | 64.104 | 1.000 40.97 |
| ATOM | 2659 | CG | LYS | B | 52 | 49.510 | 4.333 | 65.238 | 1.000 42.39 |
| ATOM | 2660 | CD | LYS | B | 52 | 49.041 | 3.361 | 66.306 | 1.000 52.34 |
| ATOM | 2661 | CE | LYS | B | 52 | 49.390 | 3.867 | 67.700 | 1.000 61.04 |
| ATOM | 2662 | NZ | LYS | B | 52 | 50.844 | 4.180 | 67.830 | 1.000 76.71 |
| ATOM | 2663 | C | LYS | B | 52 | 49.556 | 6.482 | 63.033 | 1.000 42.33 |
| ATOM | 2664 | O | LYS | B | 52 | 50.231 | 7.281 | 63.679 | 1.000 51.51 |
| ATOM | 2665 | N | ASP | B | 53 | 49.860 | 6.073 | 61.826 | 1.000 38.71 |
| ATOM | 2666 | CA | ASP | B | 53 | 51.069 | 6.209 | 61.057 | 1.000 45.09 |
| ATOM | 2667 | CB | ASP | B | 53 | 51.162 | 5.010 | 60.082 | 1.000 50.29 |
| ATOM | 2668 | CG | ASP | B | 53 | 49.852 | 4.773 | 59.352 | 1.000 58.20 |
| ATOM | 2669 | OD1 | ASP | B | 53 | 48.816 | 4.532 | 60.008 | 1.000 47.71 |
| ATOM | 2670 | OD2 | ASP | B | 53 | 49.828 | 4.823 | 58.101 | 1.000 71.83 |
| ATOM | 2671 | C | ASP | B | 53 | 51.159 | 7.483 | 60.225 | 1.000 42.44 |
| ATOM | 2672 | O | ASP | B | 53 | 52.242 | 7.872 | 59.785 | 1.000 38.32 |
| ATOM | 2673 | N | VAL | B | 54 | 50.014 | 8.111 | 59.996 | 1.000 33.25 |
| ATOM | 2674 | CA | VAL | B | 54 | 49.943 | 9.247 | 59.080 | 1.000 30.88 |
| ATOM | 2675 | CB | VAL | B | 54 | 48.498 | 9.764 | 58.989 | 1.000 35.26 |
| ATOM | 2676 | CG1 | VAL | B | 54 | 48.409 | 11.060 | 58.194 | 1.000 24.09 |
| ATOM | 2677 | CG2 | VAL | B | 54 | 47.599 | 8.696 | 58.361 | 1.000 22.83 |
| ATOM | 2678 | C | VAL | B | 54 | 50.917 | 10.340 | 59.504 | 1.000 32.17 |
| ATOM | 2679 | O | VAL | B | 54 | 50.929 | 10.809 | 60.638 | 1.000 25.64 |
| ATOM | 2680 | N | GLY | B | 55 | 51.766 | 10.722 | 58.562 | 1.000 36.64 |
| ATOM | 2681 | CA | GLY | B | 55 | 52.749 | 11.767 | 58.654 | 1.000 34.77 |
| ATOM | 2682 | C | GLY | B | 55 | 53.995 | 11.423 | 59.430 | 1.000 30.37 |
| ATOM | 2683 | O | GLY | B | 55 | 54.923 | 12.232 | 59.538 | 1.000 25.00 |
| ATOM | 2684 | N | ARG | B | 56 | 54.036 | 10.221 | 60.001 | 1.000 27.19 |
| ATOM | 2685 | CA | ARG | B | 56 | 55.133 | 9.904 | 60.919 | 1.000 34.78 |
| ATOM | 2686 | CB | ARG | B | 56 | 54.724 | 8.753 | 61.847 | 1.000 36.03 |
| ATOM | 2687 | CG | ARG | B | 56 | 53.643 | 9.120 | 62.851 | 1.000 31.22 |
| ATOM | 2688 | CD | ARG | B | 56 | 54.128 | 10.152 | 63.853 | 1.000 34.70 |
| ATOM | 2689 | NE | ARG | B | 56 | 53.193 | 10.340 | 64.954 | 1.000 46.39 |
| ATOM | 2690 | CZ | ARG | B | 56 | 53.205 | 9.786 | 66.155 | 1.000 39.08 |
| ATOM | 2691 | NH1 | ARG | B | 56 | 54.165 | 8.935 | 66.471 | 1.000 26.47 |
| ATOM | 2692 | NH2 | ARG | B | 56 | 52.270 | 10.066 | 67.063 | 1.000 33.87 |
| ATOM | 2693 | C | ARG | B | 56 | 56.425 | 9.574 | 60.187 | 1.000 37.74 |
| ATOM | 2694 | O | ARG | B | 56 | 57.415 | 9.186 | 60.808 | 1.000 41.64 |
| ATOM | 2695 | N | ASN | B | 57 | 56.415 | 9.743 | 58.871 | 1.000 41.17 |
| ATOM | 2696 | CA | ASN | B | 57 | 57.583 | 9.563 | 58.028 | 1.000 38.70 |
| ATOM | 2697 | CB | ASN | B | 57 | 57.146 | 9.244 | 56.587 | 1.000 42.33 |
| ATOM | 2698 | CG | ASN | B | 57 | 56.145 | 10.235 | 56.026 | 1.000 38.45 |
| ATOM | 2699 | OD1 | ASN | B | 57 | 55.184 | 10.631 | 56.689 | 1.000 47.13 |
| ATOM | 2700 | ND2 | ASN | B | 57 | 56.334 | 10.662 | 54.780 | 1.000 33.73 |
| ATOM | 2701 | C | ASN | B | 57 | 58.478 | 10.794 | 58.001 | 1.000 32.39 |
| ATOM | 2702 | O | ASN | B | 57 | 59.628 | 10.706 | 57.573 | 1.000 32.15 |
| ATOM | 2703 | N | GLN | B | 58 | 57.985 | 11.955 | 58.419 | 1.000 33.50 |

FIGURE 58

| | | | | | | | | | |
|---|---|---|---|---|---|---|---|---|---|
| ATOM | 2704 | CA | GLN | B | 58 | 58.765 | 13.190 | 58.281 | 1.000 32.36 |
| ATOM | 2705 | CB | GLN | B | 58 | 57.838 | 14.389 | 58.063 | 1.000 31.34 |
| ATOM | 2706 | CG | GLN | B | 58 | 57.016 | 14.302 | 56.782 | 1.000 22.41 |
| ATOM | 2707 | CD | GLN | B | 58 | 55.700 | 15.058 | 56.891 | 1.000 23.88 |
| ATOM | 2708 | OE1 | GLN | B | 58 | 54.809 | 14.711 | 57.668 | 1.000 33.63 |
| ATOM | 2709 | NE2 | GLN | B | 58 | 55.545 | 16.114 | 56.113 | 1.000 22.62 |
| ATOM | 2710 | C | GLN | B | 58 | 59.652 | 13.445 | 59.490 | 1.000 25.07 |
| ATOM | 2711 | O | GLN | B | 58 | 59.327 | 13.045 | 60.608 | 1.000 29.18 |
| ATOM | 2712 | N | SER | B | 59 | 60.773 | 14.121 | 59.261 | 1.000 17.59 |
| ATOM | 2713 | CA | SER | B | 59 | 61.737 | 14.383 | 60.317 | 1.000 24.95 |
| ATOM | 2714 | CB | SER | B | 59 | 63.157 | 14.310 | 59.752 | 1.000 30.84 |
| ATOM | 2715 | OG | SER | B | 59 | 63.355 | 15.365 | 58.819 | 1.000 51.69 |
| ATOM | 2716 | C | SER | B | 59 | 61.503 | 15.745 | 60.971 | 1.000 27.35 |
| ATOM | 2717 | O | SER | B | 59 | 60.751 | 16.555 | 60.421 | 1.000 26.25 |
| ATOM | 2718 | N | CYS | B | 60 | 62.142 | 15.962 | 62.108 | 1.000 20.52 |
| ATOM | 2719 | CA | CYS | B | 60 | 62.088 | 17.174 | 62.901 | 1.000 25.62 |
| ATOM | 2720 | CB | CYS | B | 60 | 61.291 | 16.938 | 64.187 | 1.000 32.28 |
| ATOM | 2721 | SG | CYS | B | 60 | 59.563 | 16.490 | 63.935 | 1.000 44.06 |
| ATOM | 2722 | C | CYS | B | 60 | 63.483 | 17.658 | 63.294 | 1.000 26.82 |
| ATOM | 2723 | O | CYS | B | 60 | 63.697 | 17.986 | 64.466 | 1.000 32.10 |
| ATOM | 2724 | N | ASP | B | 61 | 64.399 | 17.692 | 62.342 | 1.000 27.28 |
| ATOM | 2725 | CA | ASP | B | 61 | 65.796 | 18.026 | 62.568 | 1.000 27.04 |
| ATOM | 2726 | CB | ASP | B | 61 | 66.567 | 17.889 | 61.242 | 1.000 38.19 |
| ATOM | 2727 | CG | ASP | B | 61 | 66.412 | 16.519 | 60.605 | 1.000 50.13 |
| ATOM | 2728 | OD1 | ASP | B | 61 | 66.494 | 15.504 | 61.335 | 1.000 46.12 |
| ATOM | 2729 | OD2 | ASP | B | 61 | 66.204 | 16.442 | 59.370 | 1.000 33.84 |
| ATOM | 2730 | C | ASP | B | 61 | 66.010 | 19.431 | 63.103 | 1.000 25.10 |
| ATOM | 2731 | O | ASP | B | 61 | 66.821 | 19.666 | 63.995 | 1.000 32.03 |
| ATOM | 2732 | N | ILE | B | 62 | 65.315 | 20.420 | 62.536 | 1.000 31.05 |
| ATOM | 2733 | CA | ILE | B | 62 | 65.582 | 21.807 | 62.924 | 1.000 30.27 |
| ATOM | 2734 | CB | ILE | B | 62 | 64.816 | 22.824 | 62.061 | 1.000 30.17 |
| ATOM | 2735 | CG1 | ILE | B | 62 | 65.175 | 22.724 | 60.577 | 1.000 33.67 |
| ATOM | 2736 | CD1 | ILE | B | 62 | 66.676 | 22.691 | 60.345 | 1.000 39.64 |
| ATOM | 2737 | CG2 | ILE | B | 62 | 65.010 | 24.244 | 62.584 | 1.000 21.41 |
| ATOM | 2738 | C | ILE | B | 62 | 65.202 | 22.019 | 64.382 | 1.000 32.48 |
| ATOM | 2739 | O | ILE | B | 62 | 65.907 | 22.658 | 65.156 | 1.000 29.08 |
| ATOM | 2740 | N | ALA | B | 63 | 64.048 | 21.444 | 64.738 | 1.000 26.00 |
| ATOM | 2741 | CA | ALA | B | 63 | 63.649 | 21.631 | 66.136 | 1.000 26.52 |
| ATOM | 2742 | CB | ALA | B | 63 | 62.232 | 21.116 | 66.313 | 1.000 16.06 |
| ATOM | 2743 | C | ALA | B | 63 | 64.643 | 20.948 | 67.058 | 1.000 26.00 |
| ATOM | 2744 | O | ALA | B | 63 | 64.789 | 21.266 | 68.235 | 1.000 32.44 |
| ATOM | 2745 | N | LEU | B | 64 | 65.380 | 19.963 | 66.558 | 1.000 29.22 |
| ATOM | 2746 | CA | LEU | B | 64 | 66.274 | 19.228 | 67.458 | 1.000 36.10 |
| ATOM | 2747 | CB | LEU | B | 64 | 66.389 | 17.787 | 66.957 | 1.000 34.83 |
| ATOM | 2748 | CG | LEU | B | 64 | 65.227 | 16.867 | 67.351 | 1.000 34.44 |
| ATOM | 2749 | CD1 | LEU | B | 64 | 65.292 | 15.577 | 66.547 | 1.000 29.17 |
| ATOM | 2750 | CD2 | LEU | B | 64 | 65.242 | 16.616 | 68.853 | 1.000 22.34 |
| ATOM | 2751 | C | LEU | B | 64 | 67.641 | 19.880 | 67.584 | 1.000 38.72 |
| ATOM | 2752 | O | LEU | B | 64 | 68.466 | 19.505 | 68.423 | 1.000 33.43 |
| ATOM | 2753 | N | LEU | B | 65 | 67.910 | 20.882 | 66.752 | 1.000 29.69 |
| ATOM | 2754 | CA | LEU | B | 65 | 69.194 | 21.567 | 66.816 | 1.000 24.50 |
| ATOM | 2755 | CB | LEU | B | 65 | 69.248 | 22.693 | 65.788 | 1.000 23.85 |

FIGURE 59

| | | | | | | | | | |
|---|---|---|---|---|---|---|---|---|---|
| ATOM | 2756 | CG | LEU | B | 65 | 69.163 | 22.287 | 64.320 | 1.000 39.84 |
| ATOM | 2757 | CD1 | LEU | B | 65 | 68.898 | 23.516 | 63.459 | 1.000 38.18 |
| ATOM | 2758 | CD2 | LEU | B | 65 | 70.432 | 21.567 | 63.880 | 1.000 36.27 |
| ATOM | 2759 | C | LEU | B | 65 | 69.438 | 22.122 | 68.218 | 1.000 36.38 |
| ATOM | 2760 | O | LEU | B | 65 | 68.526 | 22.606 | 68.883 | 1.000 40.63 |
| ATOM | 2761 | N | PRO | B | 66 | 70.686 | 22.026 | 68.657 | 1.000 45.15 |
| ATOM | 2762 | CA | PRO | B | 66 | 71.066 | 22.422 | 70.011 | 1.000 54.26 |
| ATOM | 2763 | CB | PRO | B | 66 | 72.601 | 22.452 | 69.931 | 1.000 52.68 |
| ATOM | 2764 | CG | PRO | B | 66 | 72.910 | 21.394 | 68.918 | 1.000 46.70 |
| ATOM | 2765 | CD | PRO | B | 66 | 71.831 | 21.512 | 67.881 | 1.000 44.93 |
| ATOM | 2766 | C | PRO | B | 66 | 70.553 | 23.796 | 70.415 | 1.000 50.86 |
| ATOM | 2767 | O | PRO | B | 66 | 70.105 | 23.966 | 71.552 | 1.000 48.53 |
| ATOM | 2768 | N | GLU | B | 67 | 70.616 | 24.767 | 69.510 | 1.000 51.81 |
| ATOM | 2769 | CA | GLU | B | 67 | 70.250 | 26.137 | 69.872 | 1.000 51.43 |
| ATOM | 2770 | CB | GLU | B | 67 | 70.880 | 27.124 | 68.885 | 1.000 55.34 |
| ATOM | 2771 | CG | GLU | B | 67 | 71.814 | 28.138 | 69.522 | 1.000 71.70 |
| ATOM | 2772 | CD | GLU | B | 67 | 71.302 | 28.794 | 70.787 | 1.000 77.75 |
| ATOM | 2773 | OE1 | GLU | B | 67 | 72.110 | 28.959 | 71.733 | 1.000 81.38 |
| ATOM | 2774 | OE2 | GLU | B | 67 | 70.109 | 29.159 | 70.864 | 1.000 60.23 |
| ATOM | 2775 | C | GLU | B | 67 | 68.745 | 26.354 | 69.938 | 1.000 46.00 |
| ATOM | 2776 | O | GLU | B | 67 | 68.296 | 27.474 | 70.196 | 1.000 48.84 |
| ATOM | 2777 | N | ASN | B | 68 | 67.944 | 25.314 | 69.711 | 1.000 40.69 |
| ATOM | 2778 | CA | ASN | B | 68 | 66.494 | 25.487 | 69.755 | 1.000 36.03 |
| ATOM | 2779 | CB | ASN | B | 68 | 65.825 | 24.980 | 68.477 | 1.000 39.69 |
| ATOM | 2780 | CG | ASN | B | 68 | 66.147 | 25.780 | 67.233 | 1.000 33.61 |
| ATOM | 2781 | OD1 | ASN | B | 68 | 66.504 | 26.952 | 67.287 | 1.000 31.83 |
| ATOM | 2782 | ND2 | ASN | B | 68 | 66.038 | 25.160 | 66.060 | 1.000 31.89 |
| ATOM | 2783 | C | ASN | B | 68 | 65.914 | 24.759 | 70.964 | 1.000 34.09 |
| ATOM | 2784 | O | ASN | B | 68 | 64.719 | 24.859 | 71.235 | 1.000 47.57 |
| ATOM | 2785 | N | ARG | B | 69 | 66.765 | 24.038 | 71.685 | 1.000 36.03 |
| ATOM | 2786 | CA | ARG | B | 69 | 66.306 | 23.202 | 72.792 | 1.000 41.44 |
| ATOM | 2787 | CB | ARG | B | 69 | 67.483 | 22.545 | 73.522 | 1.000 43.89 |
| ATOM | 2788 | CG | ARG | B | 69 | 67.790 | 21.126 | 73.075 | 1.000 54.59 |
| ATOM | 2789 | CD | ARG | B | 69 | 68.623 | 21.108 | 71.802 | 1.000 63.54 |
| ATOM | 2790 | NE | ARG | B | 69 | 68.602 | 19.813 | 71.126 | 1.000 68.27 |
| ATOM | 2791 | CZ | ARG | B | 69 | 69.645 | 18.999 | 71.016 | 1.000 73.48 |
| ATOM | 2792 | NH1 | ARG | B | 69 | 70.812 | 19.341 | 71.551 | 1.000 75.03 |
| ATOM | 2793 | NH2 | ARG | B | 69 | 69.536 | 17.838 | 70.378 | 1.000 71.51 |
| ATOM | 2794 | C | ARG | B | 69 | 65.466 | 23.990 | 73.787 | 1.000 37.64 |
| ATOM | 2795 | O | ARG | B | 69 | 64.448 | 23.486 | 74.260 | 1.000 47.56 |
| ATOM | 2796 | N | GLY | B | 70 | 65.885 | 25.212 | 74.117 | 1.000 32.41 |
| ATOM | 2797 | CA | GLY | B | 70 | 65.107 | 25.974 | 75.086 | 1.000 30.87 |
| ATOM | 2798 | C | GLY | B | 70 | 63.789 | 26.425 | 74.495 | 1.000 31.35 |
| ATOM | 2799 | O | GLY | B | 70 | 62.881 | 26.880 | 75.183 | 1.000 32.44 |
| ATOM | 2800 | N | LYS | B | 71 | 63.642 | 26.301 | 73.172 | 1.000 28.40 |
| ATOM | 2801 | CA | LYS | B | 71 | 62.431 | 26.876 | 72.579 | 1.000 23.17 |
| ATOM | 2802 | CB | LYS | B | 71 | 62.809 | 27.437 | 71.205 | 1.000 24.12 |
| ATOM | 2803 | CG | LYS | B | 71 | 63.920 | 28.476 | 71.318 | 1.000 25.57 |
| ATOM | 2804 | CD | LYS | B | 71 | 64.674 | 28.583 | 70.010 | 1.000 30.17 |
| ATOM | 2805 | CE | LYS | B | 71 | 65.580 | 29.802 | 69.994 | 1.000- 37.46 |
| ATOM | 2806 | NZ | LYS | B | 71 | 66.319 | 29.886 | 68.700 | 1.000 51.92 |
| ATOM | 2807 | C | LYS | B | 71 | 61.296 | 25.876 | 72.492 | 1.000 23.16 |

FIGURE 60

| | | | | | | | | | |
|---|---|---|---|---|---|---|---|---|---|
| ATOM | 2808 | O | LYS | B | 71 | 60.205 | 26.158 | 71.995 | 1.000 27.70 |
| ATOM | 2809 | N | ASN | B | 72 | 61.501 | 24.663 | 72.997 | 1.000 19.21 |
| ATOM | 2810 | CA | ASN | B | 72 | 60.414 | 23.691 | 72.972 | 1.000 21.63 |
| ATOM | 2811 | CB | ASN | B | 72 | 60.918 | 22.370 | 72.375 | 1.000 26.16 |
| ATOM | 2812 | CG | ASN | B | 72 | 61.306 | 22.543 | 70.916 | 1.000 31.09 |
| ATOM | 2813 | OD1 | ASN | B | 72 | 60.465 | 22.945 | 70.109 | 1.000 26.04 |
| ATOM | 2814 | ND2 | ASN | B | 72 | 62.558 | 22.245 | 70.577 | 1.000 24.16 |
| ATOM | 2815 | C | ASN | B | 72 | 59.855 | 23.481 | 74.369 | 1.000 28.90 |
| ATOM | 2816 | O | ASN | B | 72 | 60.603 | 23.340 | 75.333 | 1.000 27.09 |
| ATOM | 2817 | N | ARG | B | 73 | 58.532 | 23.462 | 74.504 | 1.000 29.94 |
| ATOM | 2818 | CA | ARG | B | 73 | 57.950 | 23.251 | 75.827 | 1.000 29.94 |
| ATOM | 2819 | CB | ARG | B | 73 | 56.501 | 23.738 | 75.862 | 1.000 30.13 |
| ATOM | 2820 | CG | ARG | B | 73 | 55.847 | 23.665 | 77.239 | 1.000 26.45 |
| ATOM | 2821 | CD | ARG | B | 73 | 54.393 | 24.129 | 77.156 | 1.000 21.48 |
| ATOM | 2822 | NE | ARG | B | 73 | 54.347 | 25.597 | 77.101 | 1.000 21.98 |
| ATOM | 2823 | CZ | ARG | B | 73 | 54.413 | 26.305 | 78.225 | 1.000 30.47 |
| ATOM | 2824 | NH1 | ARG | B | 73 | 54.514 | 25.676 | 79.390 | 1.000 22.83 |
| ATOM | 2825 | NH2 | ARG | B | 73 | 54.373 | 27.624 | 78.162 | 1.000 37.96 |
| ATOM | 2826 | C | ARG | B | 73 | 58.047 | 21.775 | 76.205 | 1.000 36.82 |
| ATOM | 2827 | O | ARG | B | 73 | 58.212 | 21.428 | 77.375 | 1.000 27.47 |
| ATOM | 2828 | N | TYR | B | 74 | 57.948 | 20.904 | 75.202 | 1.000 27.29 |
| ATOM | 2829 | CA | TYR | B | 74 | 58.101 | 19.470 | 75.416 | 1.000 24.94 |
| ATOM | 2830 | CB | TYR | B | 74 | 56.774 | 18.731 | 75.335 | 1.000 24.22 |
| ATOM | 2831 | CG | TYR | B | 74 | 55.661 | 19.265 | 76.209 | 1.000 31.66 |
| ATOM | 2832 | CD1 | TYR | B | 74 | 55.531 | 18.876 | 77.540 | 1.000 37.63 |
| ATOM | 2833 | CE1 | TYR | B | 74 | 54.513 | 19.366 | 78.342 | 1.000 39.66 |
| ATOM | 2834 | CZ | TYR | B | 74 | 53.601 | 20.258 | 77.818 | 1.000 38.75 |
| ATOM | 2835 | OH | TYR | B | 74 | 52.588 | 20.745 | 78.608 | 1.000 34.40 |
| ATOM | 2836 | CE2 | TYR | B | 74 | 53.695 | 20.668 | 76.503 | 1.000 25.62 |
| ATOM | 2837 | CD2 | TYR | B | 74 | 54.722 | 20.163 | 75.724 | 1.000 27.42 |
| ATOM | 2838 | C | TYR | B | 74 | 59.091 | 18.944 | 74.377 | 1.000 34.07 |
| ATOM | 2839 | O | TYR | B | 74 | 58.878 | 19.078 | 73.170 | 1.000 35.65 |
| ATOM | 2840 | N | ASN | B | 75 | 60.170 | 18.362 | 74.871 | 1.000 32.88 |
| ATOM | 2841 | CA | ASN | B | 75 | 61.260 | 17.890 | 74.027 | 1.000 35.16 |
| ATOM | 2842 | CB | ASN | B | 75 | 62.397 | 17.415 | 74.942 | 1.000 41.15 |
| ATOM | 2843 | CG | ASN | B | 75 | 63.227 | 18.582 | 75.448 | 1.000 49.51 |
| ATOM | 2844 | OD1 | ASN | B | 75 | 64.296 | 18.392 | 76.032 | 1.000 62.29 |
| ATOM | 2845 | ND2 | ASN | B | 75 | 62.756 | 19.808 | 75.230 | 1.000 47.01 |
| ATOM | 2846 | C | ASN | B | 75 | 60.832 | 16.813 | 73.042 | 1.000 27.77 |
| ATOM | 2847 | O | ASN | B | 75 | 61.544 | 16.541 | 72.062 | 1.000 31.84 |
| ATOM | 2848 | N | ASN | B | 76 | 59.676 | 16.191 | 73.248 | 1.000 24.48 |
| ATOM | 2849 | CA | ASN | B | 76 | 59.194 | 15.180 | 72.303 | 1.000 31.98 |
| ATOM | 2850 | CB | ASN | B | 76 | 58.888 | 13.857 | 73.026 | 1.000 39.45 |
| ATOM | 2851 | CG | ASN | B | 76 | 57.794 | 14.002 | 74.065 | 1.000 36.56 |
| ATOM | 2852 | OD1 | ASN | B | 76 | 57.640 | 15.076 | 74.643 | 1.000 29.01 |
| ATOM | 2853 | ND2 | ASN | B | 76 | 57.038 | 12.939 | 74.311 | 1.000 28.69 |
| ATOM | 2854 | C | ASN | B | 76 | 57.964 | 15.646 | 71.535 | 1.000 35.01 |
| ATOM | 2855 | O | ASN | B | 76 | 57.304 | 14.845 | 70.863 | 1.000 26.16 |
| ATOM | 2856 | N | ILE | B | 77 | 57.641 | 16.943 | 71.608 | 1.000 28.11 |
| ATOM | 2857 | CA | ILE | B | 77 | 56.567 | 17.443 | 70.743 | 1.000 30.83 |
| ATOM | 2858 | CB | ILE | B | 77 | 55.318 | 17.839 | 71.534 | 1.000 30.03 |
| ATOM | 2859 | CG1 | ILE | B | 77 | 54.547 | 16.646 | 72.114 | 1.000 33.86 |

FIGURE 61

```
ATOM   2860  CD1 ILE B  77      53.956  16.931  73.479 1.000 23.65
ATOM   2861  CG2 ILE B  77      54.400  18.697  70.690 1.000 34.46
ATOM   2862  C   ILE B  77      57.078  18.622  69.914 1.000 27.23
ATOM   2863  O   ILE B  77      57.193  19.748  70.388 1.000 22.76
ATOM   2864  N   LEU B  78      57.404  18.308  68.668 1.000 23.21
ATOM   2865  CA  LEU B  78      58.101  19.170  67.741 1.000 24.29
ATOM   2866  CB  LEU B  78      59.571  18.763  67.579 1.000 30.93
ATOM   2867  CG  LEU B  78      60.317  18.344  68.845 1.000 29.39
ATOM   2868  CD1 LEU B  78      61.596  17.606  68.496 1.000 30.84
ATOM   2869  CD2 LEU B  78      60.606  19.563  69.702 1.000 39.96
ATOM   2870  C   LEU B  78      57.477  19.158  66.348 1.000 27.34
ATOM   2871  O   LEU B  78      56.883  18.186  65.883 1.000 22.52
ATOM   2872  N   PRO B  79      57.653  20.300  65.695 1.000 26.68
ATOM   2873  CA  PRO B  79      57.097  20.468  64.351 1.000 19.33
ATOM   2874  CB  PRO B  79      57.244  21.974  64.135 1.000 20.00
ATOM   2875  CG  PRO B  79      58.491  22.309  64.892 1.000 17.51
ATOM   2876  CD  PRO B  79      58.384  21.490  66.156 1.000 17.54
ATOM   2877  C   PRO B  79      57.939  19.691  63.351 1.000 18.83
ATOM   2878  O   PRO B  79      59.161  19.657  63.510 1.000 24.06
ATOM   2879  N   TYR B  80      57.287  19.098  62.367 1.000 18.71
ATOM   2880  CA  TYR B  80      57.911  18.548  61.181 1.000 17.89
ATOM   2881  CB  TYR B  80      56.857  17.886  60.297 1.000 30.40
ATOM   2882  CG  TYR B  80      56.167  16.688  60.900 1.000 29.81
ATOM   2883  CD1 TYR B  80      56.876  15.711  61.589 1.000 27.11
ATOM   2884  CE1 TYR B  80      56.247  14.607  62.147 1.000 26.90
ATOM   2885  CZ  TYR B  80      54.885  14.478  62.004 1.000 27.92
ATOM   2886  OH  TYR B  80      54.233  13.393  62.539 1.000 22.86
ATOM   2887  CE2 TYR B  80      54.162  15.432  61.324 1.000 21.67
ATOM   2888  CD2 TYR B  80      54.794  16.532  60.774 1.000 22.55
ATOM   2889  C   TYR B  80      58.600  19.647  60.373 1.000 26.95
ATOM   2890  O   TYR B  80      58.000  20.703  60.137 1.000 29.85
ATOM   2891  N   ASP B  81      59.836  19.401  59.962 1.000 23.42
ATOM   2892  CA  ASP B  81      60.607  20.320  59.148 1.000 23.41
ATOM   2893  CB  ASP B  81      61.878  19.642  58.613 1.000 34.98
ATOM   2894  CG  ASP B  81      62.914  19.322  59.664 1.000 32.41
ATOM   2895  OD1 ASP B  81      62.951  20.053  60.680 1.000 35.92
ATOM   2896  OD2 ASP B  81      63.686  18.346  59.510 1.000 30.60
ATOM   2897  C   ASP B  81      59.795  20.828  57.959 1.000 25.69
ATOM   2898  O   ASP B  81      59.760  22.011  57.634 1.000 33.08
ATOM   2899  N   ALA B  82      59.122  19.915  57.268 1.000 28.44
ATOM   2900  CA  ALA B  82      58.455  20.249  56.015 1.000 30.21
ATOM   2901  CB  ALA B  82      57.984  18.939  55.373 1.000 26.10
ATOM   2902  C   ALA B  82      57.283  21.200  56.164 1.000 29.54
ATOM   2903  O   ALA B  82      56.790  21.814  55.211 1.000 25.55
ATOM   2904  N   THR B  83      56.753  21.363  57.372 1.000 22.96
ATOM   2905  CA  THR B  83      55.542  22.170  57.495 1.000 22.68
ATOM   2906  CB  THR B  83      54.342  21.270  57.845 1.000 29.40
ATOM   2907  OG1 THR B  83      54.667  20.507  59.014 1.000 20.17
ATOM   2908  CG2 THR B  83      54.087  20.287  56.713 1.000 25.89
ATOM   2909  C   THR B  83      55.677  23.231  58.566 1.000 23.50
ATOM   2910  O   THR B  83      54.681  23.841  58.936 1.000 22.92
ATOM   2911  N   ARG B  84      56.897  23.443  59.056 1.000 25.87
```

FIGURE 62

| ATOM | 2912 | CA  | ARG | B | 84 | 57.050 | 24.372 | 60.171 | 1.000 | 26.66 |
| ATOM | 2913 | CB  | ARG | B | 84 | 58.405 | 24.149 | 60.862 | 1.000 | 26.13 |
| ATOM | 2914 | CG  | ARG | B | 84 | 59.618 | 24.541 | 60.040 | 1.000 | 22.35 |
| ATOM | 2915 | CD  | ARG | B | 84 | 60.929 | 24.294 | 60.779 | 1.000 | 26.61 |
| ATOM | 2916 | NE  | ARG | B | 84 | 62.018 | 24.933 | 60.053 | 1.000 | 28.50 |
| ATOM | 2917 | CZ  | ARG | B | 84 | 62.683 | 26.031 | 60.352 | 1.000 | 29.24 |
| ATOM | 2918 | NH1 | ARG | B | 84 | 62.442 | 26.754 | 61.435 | 1.000 | 24.43 |
| ATOM | 2919 | NH2 | ARG | B | 84 | 63.645 | 26.433 | 59.530 | 1.000 | 32.59 |
| ATOM | 2920 | C   | ARG | B | 84 | 56.890 | 25.819 | 59.728 | 1.000 | 22.30 |
| ATOM | 2921 | O   | ARG | B | 84 | 57.133 | 26.183 | 58.583 | 1.000 | 23.04 |
| ATOM | 2922 | N   | VAL | B | 85 | 56.477 | 26.663 | 60.669 | 1.000 | 18.94 |
| ATOM | 2923 | CA  | VAL | B | 85 | 56.405 | 28.101 | 60.424 | 1.000 | 21.51 |
| ATOM | 2924 | CB  | VAL | B | 85 | 55.322 | 28.738 | 61.308 | 1.000 | 18.95 |
| ATOM | 2925 | CG1 | VAL | B | 85 | 55.256 | 30.249 | 61.152 | 1.000 | 24.35 |
| ATOM | 2926 | CG2 | VAL | B | 85 | 53.967 | 28.113 | 60.988 | 1.000 | 12.73 |
| ATOM | 2927 | C   | VAL | B | 85 | 57.776 | 28.707 | 60.699 | 1.000 | 25.23 |
| ATOM | 2928 | O   | VAL | B | 85 | 58.331 | 28.435 | 61.767 | 1.000 | 27.46 |
| ATOM | 2929 | N   | LYS | B | 86 | 58.320 | 29.488 | 59.782 | 1.000 | 19.69 |
| ATOM | 2930 | CA  | LYS | B | 86 | 59.624 | 30.120 | 59.878 | 1.000 | 21.25 |
| ATOM | 2931 | CB  | LYS | B | 86 | 60.321 | 30.044 | 58.509 | 1.000 | 26.66 |
| ATOM | 2932 | CG  | LYS | B | 86 | 60.905 | 28.675 | 58.194 | 1.000 | 33.26 |
| ATOM | 2933 | CD  | LYS | B | 86 | 60.950 | 28.412 | 56.698 | 1.000 | 34.06 |
| ATOM | 2934 | CE  | LYS | B | 86 | 61.685 | 27.121 | 56.377 | 1.000 | 41.77 |
| ATOM | 2935 | NZ  | LYS | B | 86 | 63.000 | 27.368 | 55.715 | 1.000 | 51.25 |
| ATOM | 2936 | C   | LYS | B | 86 | 59.558 | 31.584 | 60.289 | 1.000 | 27.93 |
| ATOM | 2937 | O   | LYS | B | 86 | 58.723 | 32.338 | 59.780 | 1.000 | 31.79 |
| ATOM | 2938 | N   | LEU | B | 87 | 60.431 | 32.027 | 61.194 | 1.000 | 31.15 |
| ATOM | 2939 | CA  | LEU | B | 87 | 60.507 | 33.457 | 61.505 | 1.000 | 28.89 |
| ATOM | 2940 | CB  | LEU | B | 87 | 61.126 | 33.736 | 62.870 | 1.000 | 21.77 |
| ATOM | 2941 | CG  | LEU | B | 87 | 60.472 | 33.041 | 64.066 | 1.000 | 30.37 |
| ATOM | 2942 | CD1 | LEU | B | 87 | 61.312 | 33.206 | 65.321 | 1.000 | 35.12 |
| ATOM | 2943 | CD2 | LEU | B | 87 | 59.066 | 33.577 | 64.279 | 1.000 | 22.71 |
| ATOM | 2944 | C   | LEU | B | 87 | 61.332 | 34.163 | 60.429 | 1.000 | 37.83 |
| ATOM | 2945 | O   | LEU | B | 87 | 62.297 | 33.589 | 59.913 | 1.000 | 30.13 |
| ATOM | 2946 | N   | SER | B | 88 | 60.944 | 35.389 | 60.100 | 1.000 | 36.67 |
| ATOM | 2947 | CA  | SER | B | 88 | 61.678 | 36.147 | 59.095 | 1.000 | 40.88 |
| ATOM | 2948 | CB  | SER | B | 88 | 61.145 | 37.572 | 58.969 | 1.000 | 50.96 |
| ATOM | 2949 | OG  | SER | B | 88 | 61.924 | 38.447 | 59.787 | 1.000 | 71.49 |
| ATOM | 2950 | C   | SER | B | 88 | 63.162 | 36.209 | 59.453 | 1.000 | 53.58 |
| ATOM | 2951 | O   | SER | B | 88 | 63.487 | 36.614 | 60.569 | 1.000 | 59.70 |
| ATOM | 2952 | N   | ASN | B | 89 | 63.971 | 35.800 | 58.503 | 1.000 | 71.44 |
| ATOM | 2953 | CA  | ASN | B | 89 | 65.419 | 35.723 | 58.486 | 1.000 | 85.86 |
| ATOM | 2954 | CB  | ASN | B | 89 | 65.871 | 36.099 | 57.064 | 1.000 | 85.53 |
| ATOM | 2955 | CG  | ASN | B | 89 | 64.906 | 35.515 | 56.046 | 1.000 | 83.74 |
| ATOM | 2956 | OD1 | ASN | B | 89 | 63.714 | 35.820 | 56.022 | 1.000 | 58.06 |
| ATOM | 2957 | ND2 | ASN | B | 89 | 65.435 | 34.646 | 55.196 | 1.000 | 94.70 |
| ATOM | 2958 | C   | ASN | B | 89 | 66.085 | 36.608 | 59.532 | 1.000 | 95.53 |
| ATOM | 2959 | O   | ASN | B | 89 | 66.500 | 37.726 | 59.230 | 1.000 | 106.63 |
| ATOM | 2960 | N   | VAL | B | 90 | 66.182 | 36.108 | 60.760 | 1.000 | 99.91 |
| ATOM | 2961 | CA  | VAL | B | 90 | 66.604 | 36.863 | 61.925 | 1.000 | 106.49 |
| ATOM | 2962 | CB  | VAL | B | 90 | 65.922 | 36.329 | 63.208 | 1.000 | 100.23 |
| ATOM | 2963 | CG1 | VAL | B | 90 | 65.594 | 37.484 | 64.140 | 1.000 | 85.61 |

FIGURE 63

| | | | | | | | | | |
|---|---|---|---|---|---|---|---|---|---|
| ATOM | 2964 | CG2 | VAL | B | 90 | 64.673 | 35.536 | 62.861 | 1.000 93.25 |
| ATOM | 2965 | C | VAL | B | 90 | 68.114 | 36.866 | 62.182 | 1.000113.45 |
| ATOM | 2966 | O | VAL | B | 90 | 68.832 | 35.943 | 61.806 | 1.000122.31 |
| ATOM | 2967 | N | ASP | B | 91 | 68.544 | 37.933 | 62.844 | 1.000114.27 |
| ATOM | 2968 | CA | ASP | B | 91 | 69.897 | 38.277 | 63.228 | 1.000110.66 |
| ATOM | 2969 | CB | ASP | B | 91 | 69.892 | 39.409 | 64.264 | 1.000111.15 |
| ATOM | 2970 | CG | ASP | B | 91 | 71.270 | 40.014 | 64.465 | 1.000110.08 |
| ATOM | 2971 | OD1 | ASP | B | 91 | 71.763 | 40.698 | 63.539 | 1.000108.01 |
| ATOM | 2972 | OD2 | ASP | B | 91 | 71.864 | 39.800 | 65.540 | 1.000107.80 |
| ATOM | 2973 | C | ASP | B | 91 | 70.667 | 37.090 | 63.802 | 1.000103.90 |
| ATOM | 2974 | O | ASP | B | 91 | 70.062 | 36.112 | 64.251 | 1.000107.40 |
| ATOM | 2975 | N | ASP | B | 92 | 71.989 | 37.191 | 63.769 | 1.000 95.56 |
| ATOM | 2976 | CA | ASP | B | 92 | 72.913 | 36.160 | 64.216 | 1.000 92.84 |
| ATOM | 2977 | CB | ASP | B | 92 | 72.475 | 35.573 | 65.557 | 1.000 96.48 |
| ATOM | 2978 | CG | ASP | B | 92 | 73.473 | 35.776 | 66.676 | 1.000 98.09 |
| ATOM | 2979 | OD1 | ASP | B | 92 | 73.609 | 34.872 | 67.529 | 1.000 84.88 |
| ATOM | 2980 | OD2 | ASP | B | 92 | 74.122 | 36.837 | 66.715 | 1.000107.58 |
| ATOM | 2981 | C | ASP | B | 92 | 73.036 | 35.057 | 63.161 | 1.000 91.94 |
| ATOM | 2982 | O | ASP | B | 92 | 74.144 | 34.632 | 62.832 | 1.000 94.07 |
| ATOM | 2983 | N | ASP | B | 93 | 71.901 | 34.619 | 62.650 | 1.000 91.73 |
| ATOM | 2984 | CA | ASP | B | 93 | 71.682 | 33.642 | 61.611 | 1.000 95.04 |
| ATOM | 2985 | CB | ASP | B | 93 | 72.393 | 34.073 | 60.319 | 1.000103.17 |
| ATOM | 2986 | CG | ASP | B | 93 | 71.728 | 35.227 | 59.594 | 1.000106.58 |
| ATOM | 2987 | OD1 | ASP | B | 93 | 70.954 | 34.993 | 58.638 | 1.000104.63 |
| ATOM | 2988 | OD2 | ASP | B | 93 | 71.988 | 36.396 | 59.962 | 1.000107.25 |
| ATOM | 2989 | C | ASP | B | 93 | 72.140 | 32.243 | 62.001 | 1.000 91.99 |
| ATOM | 2990 | O | ASP | B | 93 | 72.871 | 31.598 | 61.239 | 1.000105.20 |
| ATOM | 2991 | N | PRO | B | 94 | 71.753 | 31.714 | 63.147 | 1.000 86.76 |
| ATOM | 2992 | CA | PRO | B | 94 | 72.111 | 30.328 | 63.491 | 1.000 84.05 |
| ATOM | 2993 | CB | PRO | B | 94 | 72.346 | 30.431 | 64.992 | 1.000 81.07 |
| ATOM | 2994 | CG | PRO | B | 94 | 71.549 | 31.600 | 65.461 | 1.000 79.07 |
| ATOM | 2995 | CD | PRO | B | 94 | 70.967 | 32.274 | 64.262 | 1.000 82.73 |
| ATOM | 2996 | C | PRO | B | 94 | 70.930 | 29.403 | 63.184 | 1.000 88.17 |
| ATOM | 2997 | O | PRO | B | 94 | 70.886 | 28.767 | 62.140 | 1.000 95.17 |
| ATOM | 2998 | N | CYS | B | 95 | 70.014 | 29.396 | 64.129 | 1.000 85.15 |
| ATOM | 2999 | CA | CYS | B | 95 | 68.692 | 28.806 | 64.171 | 1.000 71.00 |
| ATOM | 3000 | CB | CYS | B | 95 | 68.676 | 27.559 | 65.048 | 1.000 68.25 |
| ATOM | 3001 | SG | CYS | B | 95 | 70.324 | 27.048 | 65.606 | 1.000 59.08 |
| ATOM | 3002 | C | CYS | B | 95 | 67.724 | 29.872 | 64.691 | 1.000 61.59 |
| ATOM | 3003 | O | CYS | B | 95 | 66.839 | 29.638 | 65.507 | 1.000 45.14 |
| ATOM | 3004 | N | SER | B | 96 | 67.966 | 31.077 | 64.176 | 1.000 54.56 |
| ATOM | 3005 | CA | SER | B | 96 | 67.227 | 32.262 | 64.582 | 1.000 54.51 |
| ATOM | 3006 | CB | SER | B | 96 | 67.962 | 33.527 | 64.131 | 1.000 53.89 |
| ATOM | 3007 | OG | SER | B | 96 | 68.750 | 33.268 | 62.979 | 1.000 64.41 |
| ATOM | 3008 | C | SER | B | 96 | 65.806 | 32.239 | 64.029 | 1.000 47.05 |
| ATOM | 3009 | O | SER | B | 96 | 64.946 | 32.971 | 64.526 | 1.000 50.88 |
| ATOM | 3010 | N | ASP | B | 97 | 65.565 | 31.402 | 63.024 | 1.000 36.23 |
| ATOM | 3011 | CA | ASP | B | 97 | 64.263 | 31.360 | 62.369 | 1.000 27.85 |
| ATOM | 3012 | CB | ASP | B | 97 | 64.461 | 30.914 | 60.911 | 1.000 24.26 |
| ATOM | 3013 | CG | ASP | B | 97 | 64.720 | 29.419 | 60.834 | 1.000 36.82 |
| ATOM | 3014 | OD1 | ASP | B | 97 | 65.206 | 28.822 | 61.819 | 1.000 38.88 |
| ATOM | 3015 | OD2 | ASP | B | 97 | 64.431 | 28.828 | 59.772 | 1.000 52.38 |

FIGURE 64

| ATOM | 3016 | C | ASP | B | 97 | 63.263 | 30.420 | 63.027 | 1.000 | 29.64 |
|---|---|---|---|---|---|---|---|---|---|---|
| ATOM | 3017 | O | ASP | B | 97 | 62.132 | 30.313 | 62.537 | 1.000 | 25.93 |
| ATOM | 3018 | N | TYR | B | 98 | 63.653 | 29.727 | 64.094 | 1.000 | 31.48 |
| ATOM | 3019 | CA | TYR | B | 98 | 62.830 | 28.686 | 64.683 | 1.000 | 27.28 |
| ATOM | 3020 | CB | TYR | B | 98 | 63.708 | 27.639 | 65.426 | 1.000 | 24.83 |
| ATOM | 3021 | CG | TYR | B | 98 | 62.860 | 26.500 | 65.960 | 1.000 | 19.17 |
| ATOM | 3022 | CD1 | TYR | B | 98 | 62.365 | 25.535 | 65.080 | 1.000 | 20.66 |
| ATOM | 3023 | CE1 | TYR | B | 98 | 61.587 | 24.485 | 65.523 | 1.000 | 24.11 |
| ATOM | 3024 | CZ | TYR | B | 98 | 61.285 | 24.380 | 66.864 | 1.000 | 26.77 |
| ATOM | 3025 | OH | TYR | B | 98 | 60.508 | 23.331 | 67.317 | 1.000 | 19.75 |
| ATOM | 3026 | CE2 | TYR | B | 98 | 61.760 | 25.324 | 67.751 | 1.000 | 22.13 |
| ATOM | 3027 | CD2 | TYR | B | 98 | 62.540 | 26.372 | 67.306 | 1.000 | 20.85 |
| ATOM | 3028 | C | TYR | B | 98 | 61.775 | 29.132 | 65.687 | 1.000 | 20.04 |
| ATOM | 3029 | O | TYR | B | 98 | 61.972 | 29.920 | 66.608 | 1.000 | 25.66 |
| ATOM | 3030 | N | ILE | B | 99 | 60.604 | 28.517 | 65.531 | 1.000 | 20.57 |
| ATOM | 3031 | CA | ILE | B | 99 | 59.546 | 28.552 | 66.532 | 1.000 | 19.42 |
| ATOM | 3032 | CB | ILE | B | 99 | 58.577 | 29.720 | 66.314 | 1.000 | 19.96 |
| ATOM | 3033 | CG1 | ILE | B | 99 | 57.447 | 29.790 | 67.336 | 1.000 | 17.02 |
| ATOM | 3034 | CD1 | ILE | B | 99 | 56.771 | 31.140 | 67.413 | 1.000 | 19.58 |
| ATOM | 3035 | CG2 | ILE | B | 99 | 58.013 | 29.694 | 64.897 | 1.000 | 29.56 |
| ATOM | 3036 | C | ILE | B | 99 | 58.773 | 27.240 | 66.500 | 1.000 | 22.92 |
| ATOM | 3037 | O | ILE | B | 99 | 58.543 | 26.677 | 65.428 | 1.000 | 23.59 |
| ATOM | 3038 | N | ASN | B | 100 | 58.373 | 26.722 | 67.665 | 1.000 | 17.01 |
| ATOM | 3039 | CA | ASN | B | 100 | 57.617 | 25.462 | 67.617 | 1.000 | 20.62 |
| ATOM | 3040 | CB | ASN | B | 100 | 57.574 | 24.797 | 68.989 | 1.000 | 22.98 |
| ATOM | 3041 | CG | ASN | B | 100 | 56.990 | 23.404 | 68.998 | 1.000 | 24.77 |
| ATOM | 3042 | OD1 | ASN | B | 100 | 56.001 | 23.116 | 68.319 | 1.000 | 25.34 |
| ATOM | 3043 | ND2 | ASN | B | 100 | 57.571 | 22.496 | 69.786 | 1.000 | 18.32 |
| ATOM | 3044 | C | ASN | B | 100 | 56.226 | 25.777 | 67.081 | 1.000 | 20.30 |
| ATOM | 3045 | O | ASN | B | 100 | 55.361 | 26.152 | 67.888 | 1.000 | 19.79 |
| ATOM | 3046 | N | ALA | B | 101 | 56.067 | 25.654 | 65.760 | 1.000 | 21.42 |
| ATOM | 3047 | CA | ALA | B | 101 | 54.782 | 25.946 | 65.121 | 1.000 | 21.68 |
| ATOM | 3048 | CB | ALA | B | 101 | 54.559 | 27.450 | 65.071 | 1.000 | 13.80 |
| ATOM | 3049 | C | ALA | B | 101 | 54.696 | 25.326 | 63.732 | 1.000 | 26.20 |
| ATOM | 3050 | O | ALA | B | 101 | 55.715 | 25.142 | 63.072 | 1.000 | 18.76 |
| ATOM | 3051 | N | SER | B | 102 | 53.499 | 24.985 | 63.271 | 1.000 | 29.48 |
| ATOM | 3052 | CA | SER | B | 102 | 53.250 | 24.285 | 62.023 | 1.000 | 19.07 |
| ATOM | 3053 | CB | SER | B | 102 | 52.919 | 22.808 | 62.271 | 1.000 | 15.75 |
| ATOM | 3054 | OG | SER | B | 102 | 53.753 | 22.258 | 63.274 | 1.000 | 21.52 |
| ATOM | 3055 | C | SER | B | 102 | 52.073 | 24.879 | 61.259 | 1.000 | 19.78 |
| ATOM | 3056 | O | SER | B | 102 | 51.068 | 25.227 | 61.882 | 1.000 | 21.21 |
| ATOM | 3057 | N | TYR | B | 103 | 52.181 | 24.977 | 59.931 | 1.000 | 17.66 |
| ATOM | 3058 | CA | TYR | B | 103 | 51.017 | 25.426 | 59.166 | 1.000 | 18.10 |
| ATOM | 3059 | CB | TYR | B | 103 | 51.373 | 25.982 | 57.794 | 1.000 | 20.23 |
| ATOM | 3060 | CG | TYR | B | 103 | 52.221 | 27.216 | 57.690 | 1.000 | 18.78 |
| ATOM | 3061 | CD1 | TYR | B | 103 | 51.692 | 28.498 | 57.841 | 1.000 | 22.17 |
| ATOM | 3062 | CE1 | TYR | B | 103 | 52.490 | 29.627 | 57.736 | 1.000 | 21.36 |
| ATOM | 3063 | CZ | TYR | B | 103 | 53.840 | 29.489 | 57.472 | 1.000 | 23.55 |
| ATOM | 3064 | OH | TYR | B | 103 | 54.656 | 30.597 | 57.367 | 1.000 | 21.98 |
| ATOM | 3065 | CE2 | TYR | B | 103 | 54.394 | 28.237 | 57.316 | 1.000 | 20.92 |
| ATOM | 3066 | CD2 | TYR | B | 103 | 53.585 | 27.113 | 57.422 | 1.000 | 26.09 |
| ATOM | 3067 | C | TYR | B | 103 | 50.054 | 24.256 | 58.995 | 1.000 | 16.67 |

FIGURE 65

| | | | | | | | | | |
|---|---|---|---|---|---|---|---|---|---|
| ATOM | 3068 | O | TYR | B | 103 | 50.489 | 23.126 | 58.760 | 1.000 22.66 |
| ATOM | 3069 | N | ILE | B | 104 | 48.756 | 24.521 | 59.088 | 1.000 19.23 |
| ATOM | 3070 | CA | ILE | B | 104 | 47.781 | 23.448 | 58.955 | 1.000 24.34 |
| ATOM | 3071 | CB | ILE | B | 104 | 47.099 | 23.127 | 60.304 | 1.000 32.75 |
| ATOM | 3072 | CG1 | ILE | B | 104 | 48.085 | 22.913 | 61.452 | 1.000 27.91 |
| ATOM | 3073 | CD1 | ILE | B | 104 | 48.886 | 21.643 | 61.328 | 1.000 18.81 |
| ATOM | 3074 | CG2 | ILE | B | 104 | 46.164 | 21.938 | 60.144 | 1.000 20.62 |
| ATOM | 3075 | C | ILE | B | 104 | 46.672 | 23.774 | 57.966 | 1.000 24.01 |
| ATOM | 3076 | O | ILE | B | 104 | 46.080 | 24.847 | 58.018 | 1.000 15.86 |
| ATOM | 3077 | N | PRO | B | 105 | 46.370 | 22.829 | 57.086 | 1.000 25.98 |
| ATOM | 3078 | CA | PRO | B | 105 | 45.332 | 23.074 | 56.078 | 1.000 27.95 |
| ATOM | 3079 | CB | PRO | B | 105 | 45.503 | 21.922 | 55.088 | 1.000 18.03 |
| ATOM | 3080 | CG | PRO | B | 105 | 46.582 | 21.035 | 55.586 | 1.000 21.67 |
| ATOM | 3081 | CD | PRO | B | 105 | 46.944 | 21.482 | 56.973 | 1.000 24.89 |
| ATOM | 3082 | C | PRO | B | 105 | 43.940 | 23.045 | 56.698 | 1.000 28.32 |
| ATOM | 3083 | O | PRO | B | 105 | 43.656 | 22.391 | 57.703 | 1.000 36.85 |
| ATOM | 3084 | N | GLY | B | 106 | 43.011 | 23.768 | 56.085 | 1.000 21.37 |
| ATOM | 3085 | CA | GLY | B | 106 | 41.640 | 23.703 | 56.591 | 1.000 21.21 |
| ATOM | 3086 | C | GLY | B | 106 | 40.757 | 23.172 | 55.465 | 1.000 27.66 |
| ATOM | 3087 | O | GLY | B | 106 | 41.280 | 22.580 | 54.521 | 1.000 21.69 |
| ATOM | 3088 | N | ASN | B | 107 | 39.461 | 23.394 | 55.567 | 1.000 27.43 |
| ATOM | 3089 | CA | ASN | B | 107 | 38.490 | 22.979 | 54.572 | 1.000 35.96 |
| ATOM | 3090 | CB | ASN | B | 107 | 37.085 | 23.184 | 55.152 | 1.000 47.76 |
| ATOM | 3091 | CG | ASN | B | 107 | 36.304 | 21.899 | 55.308 | 1.000 49.77 |
| ATOM | 3092 | OD1 | ASN | B | 107 | 35.075 | 21.945 | 55.229 | 1.000 73.31 |
| ATOM | 3093 | ND2 | ASN | B | 107 | 36.983 | 20.777 | 55.521 | 1.000 41.72 |
| ATOM | 3094 | C | ASN | B | 107 | 38.605 | 23.762 | 53.268 | 1.000 40.01 |
| ATOM | 3095 | O | ASN | B | 107 | 38.170 | 23.268 | 52.227 | 1.000 27.43 |
| ATOM | 3096 | N | ASN | B | 108 | 39.172 | 24.962 | 53.316 | 1.000 47.34 |
| ATOM | 3097 | CA | ASN | B | 108 | 39.181 | 25.892 | 52.194 | 1.000 49.18 |
| ATOM | 3098 | CB | ASN | B | 108 | 38.573 | 27.227 | 52.670 | 1.000 53.17 |
| ATOM | 3099 | CG | ASN | B | 108 | 37.444 | 27.012 | 53.664 | 1.000 60.31 |
| ATOM | 3100 | OD1 | ASN | B | 108 | 36.332 | 26.632 | 53.279 | 1.000 45.80 |
| ATOM | 3101 | ND2 | ASN | B | 108 | 37.724 | 27.248 | 54.945 | 1.000 39.45 |
| ATOM | 3102 | C | ASN | B | 108 | 40.545 | 26.159 | 51.574 | 1.000 41.89 |
| ATOM | 3103 | O | ASN | B | 108 | 40.633 | 26.284 | 50.347 | 1.000 48.34 |
| ATOM | 3104 | N | PHE | B | 109 | 41.607 | 26.266 | 52.373 | 1.000 32.76 |
| ATOM | 3105 | CA | PHE | B | 109 | 42.947 | 26.513 | 51.844 | 1.000 22.32 |
| ATOM | 3106 | CB | PHE | B | 109 | 43.245 | 28.009 | 51.738 | 1.000 27.58 |
| ATOM | 3107 | CG | PHE | B | 109 | 42.837 | 28.902 | 52.878 | 1.000 36.26 |
| ATOM | 3108 | CD1 | PHE | B | 109 | 43.785 | 29.482 | 53.709 | 1.000 36.93 |
| ATOM | 3109 | CE1 | PHE | B | 109 | 43.434 | 30.318 | 54.748 | 1.000 43.65 |
| ATOM | 3110 | CZ | PHE | B | 109 | 42.102 | 30.599 | 54.991 | 1.000 46.87 |
| ATOM | 3111 | CE2 | PHE | B | 109 | 41.144 | 30.029 | 54.175 | 1.000 48.29 |
| ATOM | 3112 | CD2 | PHE | B | 109 | 41.509 | 29.191 | 53.140 | 1.000 38.59 |
| ATOM | 3113 | C | PHE | B | 109 | 44.009 | 25.809 | 52.681 | 1.000 26.82 |
| ATOM | 3114 | O | PHE | B | 109 | 43.745 | 25.302 | 53.775 | 1.000 33.42 |
| ATOM | 3115 | N | ARG | B | 110 | 45.231 | 25.760 | 52.163 | 1.000 21.41 |
| ATOM | 3116 | CA | ARG | B | 110 | 46.293 | 24.976 | 52.783 | 1.000 29.86 |
| ATOM | 3117 | CB | ARG | B | 110 | 47.331 | 24.635 | 51.691 | 1.000 23.08 |
| ATOM | 3118 | CG | ARG | B | 110 | 46.678 | 23.836 | 50.567 | 1.000 24.73 |
| ATOM | 3119 | CD | ARG | B | 110 | 47.700 | 23.142 | 49.690 | 1.000 35.94 |

FIGURE 66

| ATOM | 3120 | NE  | ARG | B | 110 | 48.602 | 22.284 | 50.447 | 1.000 | 54.44 |
| ATOM | 3121 | CZ  | ARG | B | 110 | 48.689 | 20.963 | 50.337 | 1.000 | 65.83 |
| ATOM | 3122 | NH1 | ARG | B | 110 | 47.907 | 20.318 | 49.480 | 1.000 | 62.56 |
| ATOM | 3123 | NH2 | ARG | B | 110 | 49.562 | 20.304 | 51.095 | 1.000 | 60.21 |
| ATOM | 3124 | C   | ARG | B | 110 | 46.975 | 25.640 | 53.960 | 1.000 | 33.08 |
| ATOM | 3125 | O   | ARG | B | 110 | 47.566 | 24.963 | 54.817 | 1.000 | 25.95 |
| ATOM | 3126 | N   | ARG | B | 111 | 46.949 | 26.968 | 54.073 | 1.000 | 29.38 |
| ATOM | 3127 | CA  | ARG | B | 111 | 47.600 | 27.571 | 55.248 | 1.000 | 25.02 |
| ATOM | 3128 | CB  | ARG | B | 111 | 48.716 | 28.513 | 54.839 | 1.000 | 22.60 |
| ATOM | 3129 | CG  | ARG | B | 111 | 49.940 | 27.889 | 54.187 | 1.000 | 25.96 |
| ATOM | 3130 | CD  | ARG | B | 111 | 51.044 | 28.951 | 54.077 | 1.000 | 25.11 |
| ATOM | 3131 | NE  | ARG | B | 111 | 52.352 | 28.321 | 54.010 | 1.000 | 31.63 |
| ATOM | 3132 | CZ  | ARG | B | 111 | 53.527 | 28.919 | 53.942 | 1.000 | 26.99 |
| ATOM | 3133 | NH1 | ARG | B | 111 | 53.614 | 30.238 | 53.935 | 1.000 | 28.95 |
| ATOM | 3134 | NH2 | ARG | B | 111 | 54.622 | 28.173 | 53.884 | 1.000 | 31.47 |
| ATOM | 3135 | C   | ARG | B | 111 | 46.556 | 28.306 | 56.085 | 1.000 | 24.94 |
| ATOM | 3136 | O   | ARG | B | 111 | 46.687 | 29.475 | 56.447 | 1.000 | 29.91 |
| ATOM | 3137 | N   | GLU | B | 112 | 45.493 | 27.571 | 56.391 | 1.000 | 23.64 |
| ATOM | 3138 | CA  | GLU | B | 112 | 44.323 | 28.134 | 57.049 | 1.000 | 17.42 |
| ATOM | 3139 | CB  | GLU | B | 112 | 43.130 | 27.204 | 56.817 | 1.000 | 18.28 |
| ATOM | 3140 | CG  | GLU | B | 112 | 41.790 | 27.862 | 57.105 | 1.000 | 24.48 |
| ATOM | 3141 | CD  | GLU | B | 112 | 40.654 | 27.199 | 56.351 | 1.000 | 26.29 |
| ATOM | 3142 | OE1 | GLU | B | 112 | 39.501 | 27.461 | 56.751 | 1.000 | 26.21 |
| ATOM | 3143 | OE2 | GLU | B | 112 | 40.909 | 26.434 | 55.398 | 1.000 | 31.20 |
| ATOM | 3144 | C   | GLU | B | 112 | 44.592 | 28.379 | 58.528 | 1.000 | 17.73 |
| ATOM | 3145 | O   | GLU | B | 112 | 44.083 | 29.339 | 59.110 | 1.000 | 22.88 |
| ATOM | 3146 | N   | TYR | B | 113 | 45.416 | 27.518 | 59.101 | 1.000 | 16.08 |
| ATOM | 3147 | CA  | TYR | B | 113 | 45.780 | 27.574 | 60.502 | 1.000 | 21.42 |
| ATOM | 3148 | CB  | TYR | B | 113 | 45.177 | 26.393 | 61.277 | 1.000 | 23.13 |
| ATOM | 3149 | CG  | TYR | B | 113 | 43.707 | 26.143 | 61.023 | 1.000 | 21.61 |
| ATOM | 3150 | CD1 | TYR | B | 113 | 43.282 | 25.255 | 60.046 | 1.000 | 20.99 |
| ATOM | 3151 | CE1 | TYR | B | 113 | 41.933 | 25.027 | 59.815 | 1.000 | 20.86 |
| ATOM | 3152 | CZ  | TYR | B | 113 | 40.987 | 25.692 | 60.567 | 1.000 | 21.97 |
| ATOM | 3153 | OH  | TYR | B | 113 | 39.644 | 25.476 | 60.352 | 1.000 | 20.75 |
| ATOM | 3154 | CE2 | TYR | B | 113 | 41.385 | 26.582 | 61.546 | 1.000 | 21.97 |
| ATOM | 3155 | CD2 | TYR | B | 113 | 42.735 | 26.804 | 61.770 | 1.000 | 21.68 |
| ATOM | 3156 | C   | TYR | B | 113 | 47.295 | 27.552 | 60.685 | 1.000 | 27.43 |
| ATOM | 3157 | O   | TYR | B | 113 | 48.024 | 26.950 | 59.899 | 1.000 | 18.10 |
| ATOM | 3158 | N   | ILE | B | 114 | 47.733 | 28.214 | 61.752 | 1.000 | 19.17 |
| ATOM | 3159 | CA  | ILE | B | 114 | 49.024 | 27.953 | 62.338 | 1.000 | 17.32 |
| ATOM | 3160 | CB  | ILE | B | 114 | 49.919 | 29.192 | 62.464 | 1.000 | 22.32 |
| ATOM | 3161 | CG1 | ILE | B | 114 | 50.399 | 29.756 | 61.124 | 1.000 | 15.29 |
| ATOM | 3162 | CD1 | ILE | B | 114 | 50.784 | 31.212 | 61.142 | 1.000 | 18.68 |
| ATOM | 3163 | CG2 | ILE | B | 114 | 51.079 | 28.849 | 63.390 | 1.000 | 21.25 |
| ATOM | 3164 | C   | ILE | B | 114 | 48.786 | 27.336 | 63.725 | 1.000 | 21.28 |
| ATOM | 3165 | O   | ILE | B | 114 | 48.140 | 27.927 | 64.594 | 1.000 | 17.78 |
| ATOM | 3166 | N   | VAL | B | 115 | 49.305 | 26.125 | 63.911 | 1.000 | 17.69 |
| ATOM | 3167 | CA  | VAL | B | 115 | 49.196 | 25.470 | 65.217 | 1.000 | 24.09 |
| ATOM | 3168 | CB  | VAL | B | 115 | 48.867 | 23.969 | 65.081 | 1.000 | 25.84 |
| ATOM | 3169 | CG1 | VAL | B | 115 | 49.290 | 23.223 | 66.338 | 1.000 | 28.88 |
| ATOM | 3170 | CG2 | VAL | B | 115 | 47.385 | 23.774 | 64.788 | 1.000 | 23.07 |
| ATOM | 3171 | C   | VAL | B | 115 | 50.500 | 25.641 | 65.985 | 1.000 | 22.51 |

FIGURE 67

| ATOM | 3172 | O   | VAL | B | 115 | 51.594 | 25.418 | 65.450 | 1.000 | 14.78 |
| ATOM | 3173 | N   | THR | B | 116 | 50.429 | 26.049 | 67.251 | 1.000 | 21.02 |
| ATOM | 3174 | CA  | THR | B | 116 | 51.704 | 26.242 | 67.962 | 1.000 | 19.77 |
| ATOM | 3175 | CB  | THR | B | 116 | 52.149 | 27.711 | 67.869 | 1.000 | 23.82 |
| ATOM | 3176 | OG1 | THR | B | 116 | 53.495 | 27.907 | 68.350 | 1.000 | 16.84 |
| ATOM | 3177 | CG2 | THR | B | 116 | 51.242 | 28.587 | 68.722 | 1.000 | 19.85 |
| ATOM | 3178 | C   | THR | B | 116 | 51.552 | 25.744 | 69.390 | 1.000 | 22.67 |
| ATOM | 3179 | O   | THR | B | 116 | 50.467 | 25.376 | 69.849 | 1.000 | 17.14 |
| ATOM | 3180 | N   | GLN | B | 117 | 52.654 | 25.693 | 70.119 | 1.000 | 23.60 |
| ATOM | 3181 | CA  | GLN | B | 117 | 52.679 | 25.319 | 71.514 | 1.000 | 23.36 |
| ATOM | 3182 | CB  | GLN | B | 117 | 54.080 | 24.807 | 71.898 | 1.000 | 24.62 |
| ATOM | 3183 | CG  | GLN | B | 117 | 55.034 | 25.933 | 72.239 | 1.000 | 18.72 |
| ATOM | 3184 | CD  | GLN | B | 117 | 56.479 | 25.515 | 72.375 | 1.000 | 26.17 |
| ATOM | 3185 | OE1 | GLN | B | 117 | 56.812 | 24.331 | 72.431 | 1.000 | 27.92 |
| ATOM | 3186 | NE2 | GLN | B | 117 | 57.357 | 26.520 | 72.419 | 1.000 | 23.64 |
| ATOM | 3187 | C   | GLN | B | 117 | 52.327 | 26.512 | 72.391 | 1.000 | 23.75 |
| ATOM | 3188 | O   | GLN | B | 117 | 52.440 | 27.656 | 71.939 | 1.000 | 18.82 |
| ATOM | 3189 | N   | GLY | B | 118 | 51.927 | 26.261 | 73.638 | 1.000 | 21.15 |
| ATOM | 3190 | CA  | GLY | B | 118 | 51.716 | 27.416 | 74.523 | 1.000 | 21.52 |
| ATOM | 3191 | C   | GLY | B | 118 | 53.050 | 28.104 | 74.761 | 1.000 | 17.96 |
| ATOM | 3192 | O   | GLY | B | 118 | 54.002 | 27.456 | 75.207 | 1.000 | 23.95 |
| ATOM | 3193 | N   | PRO | B | 119 | 53.131 | 29.390 | 74.454 | 1.000 | 18.88 |
| ATOM | 3194 | CA  | PRO | B | 119 | 54.401 | 30.117 | 74.548 | 1.000 | 23.38 |
| ATOM | 3195 | CB  | PRO | B | 119 | 53.993 | 31.581 | 74.327 | 1.000 | 19.87 |
| ATOM | 3196 | CG  | PRO | B | 119 | 52.757 | 31.486 | 73.500 | 1.000 | 19.60 |
| ATOM | 3197 | CD  | PRO | B | 119 | 52.031 | 30.260 | 74.000 | 1.000 | 17.07 |
| ATOM | 3198 | C   | PRO | B | 119 | 55.064 | 29.980 | 75.917 | 1.000 | 25.74 |
| ATOM | 3199 | O   | PRO | B | 119 | 54.414 | 29.867 | 76.952 | 1.000 | 21.95 |
| ATOM | 3200 | N   | LEU | B | 120 | 56.384 | 29.996 | 75.884 | 1.000 | 24.68 |
| ATOM | 3201 | CA  | LEU | B | 120 | 57.259 | 29.997 | 77.034 | 1.000 | 28.37 |
| ATOM | 3202 | CB  | LEU | B | 120 | 58.542 | 29.210 | 76.755 | 1.000 | 21.91 |
| ATOM | 3203 | CG  | LEU | B | 120 | 58.366 | 27.711 | 76.511 | 1.000 | 23.23 |
| ATOM | 3204 | CD1 | LEU | B | 120 | 59.490 | 27.175 | 75.642 | 1.000 | 25.39 |
| ATOM | 3205 | CD2 | LEU | B | 120 | 58.314 | 26.965 | 77.837 | 1.000 | 31.44 |
| ATOM | 3206 | C   | LEU | B | 120 | 57.615 | 31.439 | 77.377 | 1.000 | 22.77 |
| ATOM | 3207 | O   | LEU | B | 120 | 57.514 | 32.304 | 76.499 | 1.000 | 23.03 |
| ATOM | 3208 | N   | PRO | B | 121 | 58.016 | 31.692 | 78.615 | 1.000 | 26.35 |
| ATOM | 3209 | CA  | PRO | B | 121 | 58.561 | 33.014 | 78.945 | 1.000 | 22.57 |
| ATOM | 3210 | CB  | PRO | B | 121 | 59.171 | 32.787 | 80.326 | 1.000 | 27.81 |
| ATOM | 3211 | CG  | PRO | B | 121 | 58.375 | 31.675 | 80.918 | 1.000 | 32.45 |
| ATOM | 3212 | CD  | PRO | B | 121 | 57.975 | 30.783 | 79.773 | 1.000 | 28.73 |
| ATOM | 3213 | C   | PRO | B | 121 | 59.641 | 33.414 | 77.943 | 1.000 | 28.24 |
| ATOM | 3214 | O   | PRO | B | 121 | 59.741 | 34.555 | 77.489 | 1.000 | 30.29 |
| ATOM | 3215 | N   | GLY | B | 122 | 60.489 | 32.450 | 77.562 | 1.000 | 22.78 |
| ATOM | 3216 | CA  | GLY | B | 122 | 61.573 | 32.788 | 76.653 | 1.000 | 20.37 |
| ATOM | 3217 | C   | GLY | B | 122 | 61.178 | 32.799 | 75.191 | 1.000 | 28.02 |
| ATOM | 3218 | O   | GLY | B | 122 | 61.990 | 33.229 | 74.365 | 1.000 | 28.41 |
| ATOM | 3219 | N   | THR | B | 123 | 59.980 | 32.360 | 74.810 | 1.000 | 27.99 |
| ATOM | 3220 | CA  | THR | B | 123 | 59.604 | 32.385 | 73.401 | 1.000 | 33.24 |
| ATOM | 3221 | CB  | THR | B | 123 | 59.259 | 30.981 | 72.854 | 1.000 | 33.57 |
| ATOM | 3222 | OG1 | THR | B | 123 | 58.039 | 30.554 | 73.480 | 1.000 | 25.65 |
| ATOM | 3223 | CG2 | THR | B | 123 | 60.341 | 29.968 | 73.169 | 1.000 | 20.05 |

FIGURE 68

| | | | | | | | | | |
|---|---|---|---|---|---|---|---|---|---|
| ATOM | 3224 | C | THR | B | 123 | 58.385 | 33.260 | 73.106 | 1.000 29.44 |
| ATOM | 3225 | O | THR | B | 123 | 57.931 | 33.303 | 71.961 | 1.000 25.91 |
| ATOM | 3226 | N | LYS | B | 124 | 57.853 | 33.950 | 74.105 | 1.000 26.51 |
| ATOM | 3227 | CA | LYS | B | 124 | 56.691 | 34.807 | 73.893 | 1.000 28.23 |
| ATOM | 3228 | CB | LYS | B | 124 | 56.273 | 35.483 | 75.199 | 1.000 32.16 |
| ATOM | 3229 | CG | LYS | B | 124 | 57.460 | 35.814 | 76.097 | 1.000 43.91 |
| ATOM | 3230 | CD | LYS | B | 124 | 57.144 | 37.009 | 76.981 | 1.000 56.45 |
| ATOM | 3231 | CE | LYS | B | 124 | 57.277 | 36.684 | 78.458 | 1.000 47.68 |
| ATOM | 3232 | NZ | LYS | B | 124 | 56.082 | 37.130 | 79.224 | 1.000 47.04 |
| ATOM | 3233 | C | LYS | B | 124 | 56.961 | 35.882 | 72.845 | 1.000 31.27 |
| ATOM | 3234 | O | LYS | B | 124 | 56.010 | 36.336 | 72.203 | 1.000 20.04 |
| ATOM | 3235 | N | ASP | B | 125 | 58.221 | 36.273 | 72.690 | 1.000 27.24 |
| ATOM | 3236 | CA | ASP | B | 125 | 58.589 | 37.344 | 71.759 | 1.000 30.97 |
| ATOM | 3237 | CB | ASP | B | 125 | 59.998 | 37.856 | 72.044 | 1.000 30.13 |
| ATOM | 3238 | CG | ASP | B | 125 | 60.063 | 38.882 | 73.163 | 1.000 37.62 |
| ATOM | 3239 | OD1 | ASP | B | 125 | 59.010 | 39.337 | 73.647 | 1.000 29.79 |
| ATOM | 3240 | OD2 | ASP | B | 125 | 61.180 | 39.261 | 73.577 | 1.000 55.37 |
| ATOM | 3241 | C | ASP | B | 125 | 58.486 | 36.861 | 70.313 | 1.000 29.10 |
| ATOM | 3242 | O | ASP | B | 125 | 58.053 | 37.590 | 69.423 | 1.000 23.13 |
| ATOM | 3243 | N | ASP | B | 126 | 58.894 | 35.619 | 70.119 | 1.000 29.81 |
| ATOM | 3244 | CA | ASP | B | 126 | 58.855 | 34.917 | 68.846 | 1.000 29.93 |
| ATOM | 3245 | CB | ASP | B | 126 | 59.612 | 33.590 | 68.923 | 1.000 33.34 |
| ATOM | 3246 | CG | ASP | B | 126 | 61.095 | 33.725 | 69.208 | 1.000 42.49 |
| ATOM | 3247 | OD1 | ASP | B | 126 | 61.684 | 34.754 | 68.799 | 1.000 33.29 |
| ATOM | 3248 | OD2 | ASP | B | 126 | 61.666 | 32.798 | 69.837 | 1.000 36.63 |
| ATOM | 3249 | C | ASP | B | 126 | 57.410 | 34.663 | 68.425 | 1.000 29.50 |
| ATOM | 3250 | O | ASP | B | 126 | 57.077 | 34.759 | 67.243 | 1.000 23.31 |
| ATOM | 3251 | N | PHE | B | 127 | 56.556 | 34.333 | 69.391 | 1.000 27.35 |
| ATOM | 3252 | CA | PHE | B | 127 | 55.135 | 34.135 | 69.089 | 1.000 28.78 |
| ATOM | 3253 | CB | PHE | B | 127 | 54.360 | 33.783 | 70.363 | 1.000 25.58 |
| ATOM | 3254 | CG | PHE | B | 127 | 52.860 | 33.698 | 70.240 | 1.000 22.20 |
| ATOM | 3255 | CD1 | PHE | B | 127 | 52.255 | 32.500 | 69.878 | 1.000 21.35 |
| ATOM | 3256 | CE1 | PHE | B | 127 | 50.881 | 32.398 | 69.750 | 1.000 20.50 |
| ATOM | 3257 | CZ | PHE | B | 127 | 50.087 | 33.500 | 70.006 | 1.000 26.34 |
| ATOM | 3258 | CE2 | PHE | B | 127 | 50.667 | 34.705 | 70.361 | 1.000 17.31 |
| ATOM | 3259 | CD2 | PHE | B | 127 | 52.039 | 34.789 | 70.487 | 1.000 15.23 |
| ATOM | 3260 | C | PHE | B | 127 | 54.535 | 35.373 | 68.426 | 1.000 22.38 |
| ATOM | 3261 | O | PHE | B | 127 | 53.905 | 35.276 | 67.377 | 1.000 24.96 |
| ATOM | 3262 | N | TRP | B | 128 | 54.685 | 36.549 | 69.032 | 1.000 24.70 |
| ATOM | 3263 | CA | TRP | B | 128 | 54.065 | 37.773 | 68.523 | 1.000 19.09 |
| ATOM | 3264 | CB | TRP | B | 128 | 54.104 | 38.859 | 69.604 | 1.000 17.25 |
| ATOM | 3265 | CG | TRP | B | 128 | 53.145 | 38.614 | 70.734 | 1.000 17.80 |
| ATOM | 3266 | CD1 | TRP | B | 128 | 53.470 | 38.390 | 72.040 | 1.000 22.53 |
| ATOM | 3267 | NE1 | TRP | B | 128 | 52.331 | 38.203 | 72.789 | 1.000 21.74 |
| ATOM | 3268 | CE2 | TRP | B | 128 | 51.240 | 38.303 | 71.966 | 1.000 19.23 |
| ATOM | 3269 | CD2 | TRP | B | 128 | 51.714 | 38.558 | 70.668 | 1.000 19.24 |
| ATOM | 3270 | CE3 | TRP | B | 128 | 50.778 | 38.703 | 69.637 | 1.000 28.93 |
| ATOM | 3271 | CZ3 | TRP | B | 128 | 49.429 | 38.592 | 69.915 | 1.000 22.05 |
| ATOM | 3272 | CH2 | TRP | B | 128 | 48.991 | 38.335 | 71.226 | 1.000 17.91 |
| ATOM | 3273 | CZ2 | TRP | B | 128 | 49.878 | 38.187 | 72.259 | 1.000 22.46 |
| ATOM | 3274 | C | TRP | B | 128 | 54.735 | 38.234 | 67.237 | 1.000 18.56 |
| ATOM | 3275 | O | TRP | B | 128 | 54.116 | 38.775 | 66.322 | 1.000 21.01 |

FIGURE 69

| | | | | | | | | | |
|---|---|---|---|---|---|---|---|---|---|
| ATOM | 3276 | N | LYS | B | 129 | 56.042 | 38.016 | 67.133 | 1.000 13.97 |
| ATOM | 3277 | CA | LYS | B | 129 | 56.723 | 38.282 | 65.866 | 1.000 15.64 |
| ATOM | 3278 | CB | LYS | B | 129 | 58.217 | 37.994 | 65.979 | 1.000 22.55 |
| ATOM | 3279 | CG | LYS | B | 129 | 58.950 | 37.985 | 64.651 | 1.000 39.82 |
| ATOM | 3280 | CD | LYS | B | 129 | 60.460 | 38.047 | 64.814 | 1.000 48.10 |
| ATOM | 3281 | CE | LYS | B | 129 | 61.160 | 37.738 | 63.491 | 1.000 52.05 |
| ATOM | 3282 | NZ | LYS | B | 129 | 62.627 | 37.573 | 63.678 | 1.000 61.20 |
| ATOM | 3283 | C | LYS | B | 129 | 56.113 | 37.409 | 64.776 | 1.000 27.27 |
| ATOM | 3284 | O | LYS | B | 129 | 55.893 | 37.876 | 63.661 | 1.000 29.01 |
| ATOM | 3285 | N | MET | B | 130 | 55.848 | 36.148 | 65.124 | 1.000 29.80 |
| ATOM | 3286 | CA | MET | B | 130 | 55.154 | 35.233 | 64.230 | 1.000 27.17 |
| ATOM | 3287 | CB | MET | B | 130 | 54.979 | 33.827 | 64.845 | 1.000 19.02 |
| ATOM | 3288 | CG | MET | B | 130 | 54.169 | 32.925 | 63.904 | 1.000 19.86 |
| ATOM | 3289 | SD | MET | B | 130 | 54.092 | 31.205 | 64.479 | 1.000 25.65 |
| ATOM | 3290 | CE | MET | B | 130 | 52.919 | 31.427 | 65.833 | 1.000 14.58 |
| ATOM | 3291 | C | MET | B | 130 | 53.777 | 35.775 | 63.863 | 1.000 17.87 |
| ATOM | 3292 | O | MET | B | 130 | 53.351 | 35.838 | 62.715 | 1.000 21.77 |
| ATOM | 3293 | N | VAL | B | 131 | 53.029 | 36.170 | 64.886 | 1.000 12.63 |
| ATOM | 3294 | CA | VAL | B | 131 | 51.706 | 36.739 | 64.639 | 1.000 19.47 |
| ATOM | 3295 | CB | VAL | B | 131 | 51.028 | 37.081 | 65.977 | 1.000 24.44 |
| ATOM | 3296 | CG1 | VAL | B | 131 | 49.870 | 38.035 | 65.754 | 1.000 20.24 |
| ATOM | 3297 | CG2 | VAL | B | 131 | 50.586 | 35.801 | 66.687 | 1.000 20.58 |
| ATOM | 3298 | C | VAL | B | 131 | 51.794 | 37.977 | 63.748 | 1.000 29.32 |
| ATOM | 3299 | O | VAL | B | 131 | 50.974 | 38.203 | 62.851 | 1.000 27.58 |
| ATOM | 3300 | N | TRP | B | 132 | 52.810 | 38.804 | 63.985 | 1.000 24.33 |
| ATOM | 3301 | CA | TRP | B | 132 | 52.980 | 40.015 | 63.177 | 1.000 25.60 |
| ATOM | 3302 | CB | TRP | B | 132 | 54.037 | 40.918 | 63.807 | 1.000 21.12 |
| ATOM | 3303 | CG | TRP | B | 132 | 54.280 | 42.211 | 63.101 | 1.000 30.16 |
| ATOM | 3304 | CD1 | TRP | B | 132 | 55.382 | 42.547 | 62.364 | 1.000 34.45 |
| ATOM | 3305 | NE1 | TRP | B | 132 | 55.258 | 43.822 | 61.863 | 1.000 35.96 |
| ATOM | 3306 | CE2 | TRP | B | 132 | 54.059 | 44.338 | 62.273 | 1.000 34.79 |
| ATOM | 3307 | CD2 | TRP | B | 132 | 53.417 | 43.354 | 63.054 | 1.000 29.88 |
| ATOM | 3308 | CE3 | TRP | B | 132 | 52.159 | 43.629 | 63.598 | 1.000 23.47 |
| ATOM | 3309 | CZ3 | TRP | B | 132 | 51.604 | 44.866 | 63.343 | 1.000 29.19 |
| ATOM | 3310 | CH2 | TRP | B | 132 | 52.271 | 45.821 | 62.564 | 1.000 30.89 |
| ATOM | 3311 | CZ2 | TRP | B | 132 | 53.499 | 45.590 | 62.016 | 1.000 31.90 |
| ATOM | 3312 | C | TRP | B | 132 | 53.348 | 39.679 | 61.736 | 1.000 27.64 |
| ATOM | 3313 | O | TRP | B | 132 | 52.732 | 40.210 | 60.809 | 1.000 25.13 |
| ATOM | 3314 | N | GLU | B | 133 | 54.336 | 38.817 | 61.516 | 1.000 19.97 |
| ATOM | 3315 | CA | GLU | B | 133 | 54.803 | 38.528 | 60.167 | 1.000 21.72 |
| ATOM | 3316 | CB | GLU | B | 133 | 56.122 | 37.762 | 60.268 | 1.000 25.50 |
| ATOM | 3317 | CG | GLU | B | 133 | 57.215 | 38.565 | 60.953 | 1.000 21.80 |
| ATOM | 3318 | CD | GLU | B | 133 | 58.525 | 37.797 | 60.960 | 1.000 30.30 |
| ATOM | 3319 | OE1 | GLU | B | 133 | 58.479 | 36.560 | 60.767 | 1.000 25.13 |
| ATOM | 3320 | OE2 | GLU | B | 133 | 59.568 | 38.461 | 61.151 | 1.000 35.58 |
| ATOM | 3321 | C | GLU | B | 133 | 53.810 | 37.732 | 59.339 | 1.000 28.77 |
| ATOM | 3322 | O | GLU | B | 133 | 53.729 | 37.935 | 58.127 | 1.000 26.53 |
| ATOM | 3323 | N | GLN | B | 134 | 53.050 | 36.828 | 59.957 | 1.000 25.47 |
| ATOM | 3324 | CA | GLN | B | 134 | 52.103 | 36.010 | 59.204 | 1.000 24.21 |
| ATOM | 3325 | CB | GLN | B | 134 | 51.962 | 34.639 | 59.875 | 1.000 30.73 |
| ATOM | 3326 | CG | GLN | B | 134 | 53.313 | 33.951 | 60.093 | 1.000 29.62 |
| ATOM | 3327 | CD | GLN | B | 134 | 53.852 | 33.400 | 58.783 | 1.000 30.05 |

FIGURE 70

| | | | | | | | | | |
|---|---|---|---|---|---|---|---|---|---|
| ATOM | 3328 | OE1 | GLN | B | 134 | 53.182 | 32.656 | 58.068 | 1.000 33.53 |
| ATOM | 3329 | NE2 | GLN | B | 134 | 55.080 | 33.772 | 58.460 | 1.000 33.18 |
| ATOM | 3330 | C | GLN | B | 134 | 50.739 | 36.668 | 59.092 | 1.000 26.45 |
| ATOM | 3331 | O | GLN | B | 134 | 49.769 | 36.050 | 58.640 | 1.000 25.94 |
| ATOM | 3332 | N | ASN | B | 135 | 50.646 | 37.924 | 59.510 | 1.000 24.63 |
| ATOM | 3333 | CA | ASN | B | 135 | 49.405 | 38.687 | 59.374 | 1.000 25.47 |
| ATOM | 3334 | CB | ASN | B | 135 | 49.089 | 38.902 | 57.885 | 1.000 27.21 |
| ATOM | 3335 | CG | ASN | B | 135 | 49.300 | 40.369 | 57.529 | 1.000 46.77 |
| ATOM | 3336 | OD1 | ASN | B | 135 | 48.353 | 41.121 | 57.307 | 1.000 69.94 |
| ATOM | 3337 | ND2 | ASN | B | 135 | 50.565 | 40.770 | 57.500 | 1.000 36.37 |
| ATOM | 3338 | C | ASN | B | 135 | 48.223 | 38.027 | 60.069 | 1.000 31.62 |
| ATOM | 3339 | O | ASN | B | 135 | 47.088 | 38.019 | 59.589 | 1.000 28.84 |
| ATOM | 3340 | N | VAL | B | 136 | 48.484 | 37.467 | 61.246 | 1.000 27.43 |
| ATOM | 3341 | CA | VAL | B | 136 | 47.416 | 36.859 | 62.032 | 1.000 24.98 |
| ATOM | 3342 | CB | VAL | B | 136 | 48.035 | 36.029 | 63.179 | 1.000 20.72 |
| ATOM | 3343 | CG1 | VAL | B | 136 | 46.958 | 35.491 | 64.102 | 1.000 26.47 |
| ATOM | 3344 | CG2 | VAL | B | 136 | 48.887 | 34.909 | 62.599 | 1.000 13.70 |
| ATOM | 3345 | C | VAL | B | 136 | 46.469 | 37.891 | 62.619 | 1.000 23.98 |
| ATOM | 3346 | O | VAL | B | 136 | 46.875 | 38.904 | 63.196 | 1.000 19.31 |
| ATOM | 3347 | N | HIS | B | 137 | 45.165 | 37.662 | 62.502 | 1.000 24.96 |
| ATOM | 3348 | CA | HIS | B | 137 | 44.208 | 38.529 | 63.180 | 1.000 24.73 |
| ATOM | 3349 | CB | HIS | B | 137 | 43.215 | 39.124 | 62.170 | 1.000 30.08 |
| ATOM | 3350 | CG | HIS | B | 137 | 43.872 | 40.090 | 61.240 | 1.000 35.97 |
| ATOM | 3351 | ND1 | HIS | B | 137 | 43.604 | 41.435 | 61.247 | 1.000 47.37 |
| ATOM | 3352 | CE1 | HIS | B | 137 | 44.338 | 42.022 | 60.314 | 1.000 50.81 |
| ATOM | 3353 | NE2 | HIS | B | 137 | 45.073 | 41.107 | 59.706 | 1.000 44.95 |
| ATOM | 3354 | CD2 | HIS | B | 137 | 44.799 | 39.891 | 60.275 | 1.000 40.02 |
| ATOM | 3355 | C | HIS | B | 137 | 43.407 | 37.801 | 64.253 | 1.000 21.29 |
| ATOM | 3356 | O | HIS | B | 137 | 42.727 | 38.467 | 65.026 | 1.000 27.23 |
| ATOM | 3357 | N | ASN | B | 138 | 43.469 | 36.470 | 64.274 | 1.000 22.17 |
| ATOM | 3358 | CA | ASN | B | 138 | 42.685 | 35.702 | 65.233 | 1.000 20.26 |
| ATOM | 3359 | CB | ASN | B | 138 | 41.491 | 35.030 | 64.534 | 1.000 26.81 |
| ATOM | 3360 | CG | ASN | B | 138 | 40.525 | 36.056 | 63.968 | 1.000 33.07 |
| ATOM | 3361 | OD1 | ASN | B | 138 | 40.383 | 36.164 | 62.750 | 1.000 31.33 |
| ATOM | 3362 | ND2 | ASN | B | 138 | 39.869 | 36.819 | 64.842 | 1.000 20.76 |
| ATOM | 3363 | C | ASN | B | 138 | 43.540 | 34.655 | 65.938 | 1.000 23.24 |
| ATOM | 3364 | O | ASN | B | 138 | 44.238 | 33.895 | 65.262 | 1.000 18.61 |
| ATOM | 3365 | N | ILE | B | 139 | 43.462 | 34.638 | 67.266 | 1.000 19.79 |
| ATOM | 3366 | CA | ILE | B | 139 | 44.122 | 33.625 | 68.077 | 1.000 25.68 |
| ATOM | 3367 | CB | ILE | B | 139 | 45.258 | 34.217 | 68.934 | 1.000 29.82 |
| ATOM | 3368 | CG1 | ILE | B | 139 | 46.318 | 34.945 | 68.101 | 1.000 41.20 |
| ATOM | 3369 | CD1 | ILE | B | 139 | 47.149 | 35.964 | 68.850 | 1.000 20.87 |
| ATOM | 3370 | CG2 | ILE | B | 139 | 45.900 | 33.146 | 69.806 | 1.000 14.95 |
| ATOM | 3371 | C | ILE | B | 139 | 43.126 | 32.902 | 68.985 | 1.000 24.46 |
| ATOM | 3372 | O | ILE | B | 139 | 42.278 | 33.526 | 69.624 | 1.000 24.46 |
| ATOM | 3373 | N | VAL | B | 140 | 43.264 | 31.585 | 69.008 | 1.000 19.79 |
| ATOM | 3374 | CA | VAL | B | 140 | 42.449 | 30.644 | 69.744 | 1.000 20.63 |
| ATOM | 3375 | CB | VAL | B | 140 | 41.747 | 29.622 | 68.832 | 1.000 28.33 |
| ATOM | 3376 | CG1 | VAL | B | 140 | 41.044 | 28.585 | 69.698 | 1.000 19.08 |
| ATOM | 3377 | CG2 | VAL | B | 140 | 40.773 | 30.296 | 67.875 | 1.000 24.28 |
| ATOM | 3378 | C | VAL | B | 140 | 43.320 | 29.857 | 70.731 | 1.000 24.37 |
| ATOM | 3379 | O | VAL | B | 140 | 44.279 | 29.223 | 70.306 | 1.000 18.12 |

FIGURE 71

| | | | | | | | | | |
|---|---|---|---|---|---|---|---|---|---|
| ATOM | 3380 | N | MET | B | 141 | 42.990 | 29.911 | 72.007 | 1.000 26.02 |
| ATOM | 3381 | CA | MET | B | 141 | 43.681 | 29.264 | 73.114 | 1.000 26.63 |
| ATOM | 3382 | CB | MET | B | 141 | 44.180 | 30.349 | 74.076 | 1.000 21.56 |
| ATOM | 3383 | CG | MET | B | 141 | 44.895 | 29.837 | 75.314 | 1.000 23.47 |
| ATOM | 3384 | SD | MET | B | 141 | 45.830 | 31.148 | 76.140 | 1.000 25.00 |
| ATOM | 3385 | CE | MET | B | 141 | 46.435 | 30.216 | 77.558 | 1.000 23.28 |
| ATOM | 3386 | C | MET | B | 141 | 42.749 | 28.270 | 73.801 | 1.000 21.18 |
| ATOM | 3387 | O | MET | B | 141 | 41.699 | 28.664 | 74.320 | 1.000 21.43 |
| ATOM | 3388 | N | VAL | B | 142 | 43.079 | 26.991 | 73.799 | 1.000 20.95 |
| ATOM | 3389 | CA | VAL | B | 142 | 42.221 | 25.959 | 74.364 | 1.000 24.30 |
| ATOM | 3390 | CB | VAL | B | 142 | 41.813 | 24.856 | 73.371 | 1.000 21.57 |
| ATOM | 3391 | CG1 | VAL | B | 142 | 40.925 | 25.432 | 72.277 | 1.000 44.18 |
| ATOM | 3392 | CG2 | VAL | B | 142 | 43.039 | 24.197 | 72.760 | 1.000 32.97 |
| ATOM | 3393 | C | VAL | B | 142 | 42.918 | 25.273 | 75.538 | 1.000 24.63 |
| ATOM | 3394 | O | VAL | B | 142 | 42.870 | 24.057 | 75.706 | 1.000 36.20 |
| ATOM | 3395 | N | THR | B | 143 | 43.566 | 26.104 | 76.333 | 1.000 27.52 |
| ATOM | 3396 | CA | THR | B | 143 | 44.179 | 25.667 | 77.575 | 1.000 32.61 |
| ATOM | 3397 | CB | THR | B | 143 | 45.641 | 25.224 | 77.402 | 1.000 33.85 |
| ATOM | 3398 | OG1 | THR | B | 143 | 46.111 | 24.687 | 78.647 | 1.000 32.96 |
| ATOM | 3399 | CG2 | THR | B | 143 | 46.518 | 26.417 | 77.065 | 1.000 21.18 |
| ATOM | 3400 | C | THR | B | 143 | 44.152 | 26.815 | 78.577 | 1.000 28.98 |
| ATOM | 3401 | O | THR | B | 143 | 44.172 | 27.975 | 78.178 | 1.000 26.70 |
| ATOM | 3402 | N | GLN | B | 144 | 44.115 | 26.478 | 79.855 | 1.000 26.36 |
| ATOM | 3403 | CA | GLN | B | 144 | 44.388 | 27.496 | 80.868 | 1.000 31.26 |
| ATOM | 3404 | CB | GLN | B | 144 | 43.644 | 27.201 | 82.158 | 1.000 36.91 |
| ATOM | 3405 | CG | GLN | B | 144 | 42.161 | 27.541 | 82.146 | 1.000 45.71 |
| ATOM | 3406 | CD | GLN | B | 144 | 41.465 | 27.010 | 83.387 | 1.000 58.10 |
| ATOM | 3407 | OE1 | GLN | B | 144 | 41.528 | 27.640 | 84.446 | 1.000 62.95 |
| ATOM | 3408 | NE2 | GLN | B | 144 | 40.807 | 25.859 | 83.268 | 1.000 68.48 |
| ATOM | 3409 | C | GLN | B | 144 | 45.899 | 27.536 | 81.085 | 1.000 30.16 |
| ATOM | 3410 | O | GLN | B | 144 | 46.586 | 26.558 | 80.764 | 1.000 23.48 |
| ATOM | 3411 | N | CYS | B | 145 | 46.426 | 28.637 | 81.607 | 1.000 23.70 |
| ATOM | 3412 | CA | CYS | B | 145 | 47.868 | 28.723 | 81.803 | 1.000 23.35 |
| ATOM | 3413 | CB | CYS | B | 145 | 48.244 | 30.127 | 82.276 | 1.000 17.96 |
| ATOM | 3414 | SG | CYS | B | 145 | 48.066 | 31.371 | 80.965 | 1.000 36.78 |
| ATOM | 3415 | C | CYS | B | 145 | 48.383 | 27.692 | 82.799 | 1.000 29.59 |
| ATOM | 3416 | O | CYS | B | 145 | 49.493 | 27.168 | 82.657 | 1.000 29.74 |
| ATOM | 3417 | N | VAL | B | 146 | 47.547 | 27.437 | 83.792 | 1.000 26.86 |
| ATOM | 3418 | CA | VAL | B | 146 | 47.809 | 26.499 | 84.877 | 1.000 25.79 |
| ATOM | 3419 | CB | VAL | B | 146 | 48.125 | 27.210 | 86.202 | 1.000 30.10 |
| ATOM | 3420 | CG1 | VAL | B | 146 | 48.824 | 26.274 | 87.179 | 1.000 28.99 |
| ATOM | 3421 | CG2 | VAL | B | 146 | 48.980 | 28.443 | 85.953 | 1.000 32.92 |
| ATOM | 3422 | C | VAL | B | 146 | 46.606 | 25.573 | 85.059 | 1.000 20.95 |
| ATOM | 3423 | O | VAL | B | 146 | 45.458 | 25.979 | 85.215 | 1.000 28.86 |
| ATOM | 3424 | N | GLU | B | 147 | 46.878 | 24.288 | 85.002 | 1.000 24.41 |
| ATOM | 3425 | CA | GLU | B | 147 | 45.881 | 23.235 | 85.161 | 1.000 40.57 |
| ATOM | 3426 | CB | GLU | B | 147 | 45.538 | 22.562 | 83.839 | 1.000 35.73 |
| ATOM | 3427 | CG | GLU | B | 147 | 44.603 | 23.349 | 82.943 | 1.000 41.76 |
| ATOM | 3428 | CD | GLU | B | 147 | 44.308 | 22.690 | 81.610 | 1.000 45.31 |
| ATOM | 3429 | OE1 | GLU | B | 147 | 44.722 | 21.531 | 81.403 | 1.000 43.78 |
| ATOM | 3430 | OE2 | GLU | B | 147 | 43.653 | 23.322 | 80.749 | 1.000 28.21 |
| ATOM | 3431 | C | GLU | B | 147 | 46.496 | 22.288 | 86.182 | 1.000 45.18 |

FIGURE 72

| | | | | | | | | | |
|---|---|---|---|---|---|---|---|---|---|
| ATOM | 3432 | O | GLU | B | 147 | 47.457 | 21.558 | 85.926 | 1.000 48.42 |
| ATOM | 3433 | N | LYS | B | 148 | 45.992 | 22.325 | 87.419 | 1.000 49.18 |
| ATOM | 3434 | CA | LYS | B | 148 | 46.881 | 21.658 | 88.390 | 1.000 54.02 |
| ATOM | 3435 | CB | LYS | B | 148 | 46.836 | 22.434 | 89.703 | 1.000 46.43 |
| ATOM | 3436 | CG | LYS | B | 148 | 48.184 | 23.017 | 90.088 | 1.000 42.28 |
| ATOM | 3437 | CD | LYS | B | 148 | 49.019 | 23.482 | 88.921 | 1.000 48.15 |
| ATOM | 3438 | CE | LYS | B | 148 | 50.503 | 23.260 | 89.180 | 1.000 46.56 |
| ATOM | 3439 | NZ | LYS | B | 148 | 51.361 | 24.153 | 88.358 | 1.000 39.33 |
| ATOM | 3440 | C | LYS | B | 148 | 46.554 | 20.182 | 88.515 | 1.000 54.15 |
| ATOM | 3441 | O | LYS | B | 148 | 45.415 | 19.737 | 88.387 | 1.000 67.03 |
| ATOM | 3442 | N | GLY | B | 149 | 47.628 | 19.428 | 88.760 | 1.000 52.37 |
| ATOM | 3443 | CA | GLY | B | 149 | 48.941 | 20.037 | 88.892 | 1.000 55.56 |
| ATOM | 3444 | C | GLY | B | 149 | 49.697 | 20.137 | 87.583 | 1.000 63.58 |
| ATOM | 3445 | O | GLY | B | 149 | 50.182 | 19.100 | 87.123 | 1.000 62.06 |
| ATOM | 3446 | N | ARG | B | 150 | 49.813 | 21.330 | 86.999 | 1.000 67.43 |
| ATOM | 3447 | CA | ARG | B | 150 | 50.589 | 21.516 | 85.780 | 1.000 68.36 |
| ATOM | 3448 | CB | ARG | B | 150 | 50.037 | 20.536 | 84.725 | 1.000 77.22 |
| ATOM | 3449 | CG | ARG | B | 150 | 50.929 | 19.341 | 84.438 | 1.000 76.56 |
| ATOM | 3450 | CD | ARG | B | 150 | 52.223 | 19.406 | 85.233 | 1.000 73.15 |
| ATOM | 3451 | NE | ARG | B | 150 | 53.346 | 19.893 | 84.431 | 1.000 71.83 |
| ATOM | 3452 | CZ | ARG | B | 150 | 54.098 | 19.105 | 83.668 | 1.000 75.97 |
| ATOM | 3453 | NH1 | ARG | B | 150 | 53.840 | 17.803 | 83.608 | 1.000 77.01 |
| ATOM | 3454 | NH2 | ARG | B | 150 | 55.103 | 19.611 | 82.967 | 1.000 68.43 |
| ATOM | 3455 | C | ARG | B | 150 | 50.600 | 22.925 | 85.204 | 1.000 53.31 |
| ATOM | 3456 | O | ARG | B | 150 | 49.604 | 23.442 | 84.687 | 1.000 35.27 |
| ATOM | 3457 | N | VAL | B | 151 | 51.750 | 23.608 | 85.234 | 1.000 34.49 |
| ATOM | 3458 | CA | VAL | B | 151 | 51.924 | 24.799 | 84.411 | 1.000 38.16 |
| ATOM | 3459 | CB | VAL | B | 151 | 53.297 | 25.469 | 84.557 | 1.000 41.62 |
| ATOM | 3460 | CG1 | VAL | B | 151 | 53.498 | 26.491 | 83.437 | 1.000 40.64 |
| ATOM | 3461 | CG2 | VAL | B | 151 | 53.471 | 26.163 | 85.899 | 1.000 39.00 |
| ATOM | 3462 | C | VAL | B | 151 | 51.760 | 24.387 | 82.945 | 1.000 41.12 |
| ATOM | 3463 | O | VAL | B | 151 | 52.372 | 23.400 | 82.525 | 1.000 39.66 |
| ATOM | 3464 | N | LYS | B | 152 | 50.959 | 25.079 | 82.142 | 1.000 33.45 |
| ATOM | 3465 | CA | LYS | B | 152 | 50.754 | 24.596 | 80.776 | 1.000 28.24 |
| ATOM | 3466 | CB | LYS | B | 152 | 49.302 | 24.144 | 80.591 | 1.000 34.13 |
| ATOM | 3467 | CG | LYS | B | 152 | 48.830 | 23.155 | 81.645 | 1.000 34.20 |
| ATOM | 3468 | CD | LYS | B | 152 | 49.804 | 22.001 | 81.780 | 1.000 38.68 |
| ATOM | 3469 | CE | LYS | B | 152 | 49.120 | 20.664 | 81.549 | 1.000 48.80 |
| ATOM | 3470 | NZ | LYS | B | 152 | 50.119 | 19.577 | 81.342 | 1.000 72.66 |
| ATOM | 3471 | C | LYS | B | 152 | 51.098 | 25.644 | 79.729 | 1.000 31.18 |
| ATOM | 3472 | O | LYS | B | 152 | 51.407 | 25.310 | 78.584 | 1.000 33.64 |
| ATOM | 3473 | N | CYS | B | 153 | 51.049 | 26.923 | 80.090 | 1.000 27.35 |
| ATOM | 3474 | CA | CYS | B | 153 | 51.346 | 27.960 | 79.093 | 1.000 22.51 |
| ATOM | 3475 | CB | CYS | B | 153 | 50.165 | 28.100 | 78.150 | 1.000 16.46 |
| ATOM | 3476 | SG | CYS | B | 153 | 50.211 | 29.416 | 76.916 | 1.000 26.45 |
| ATOM | 3477 | C | CYS | B | 153 | 51.678 | 29.265 | 79.801 | 1.000 31.82 |
| ATOM | 3478 | O | CYS | B | 153 | 51.084 | 29.606 | 80.822 | 1.000 28.53 |
| ATOM | 3479 | N | ASP | B | 154 | 52.637 | 30.023 | 79.279 | 1.000 33.07 |
| ATOM | 3480 | CA | ASP | B | 154 | 52.907 | 31.332 | 79.858 | 1.000 35.38 |
| ATOM | 3481 | CB | ASP | B | 154 | 54.191 | 31.929 | 79.261 | 1.000 35.82 |
| ATOM | 3482 | CG | ASP | B | 154 | 54.817 | 32.947 | 80.200 | 1.000 41.73 |
| ATOM | 3483 | OD1 | ASP | B | 154 | 56.002 | 33.296 | 80.044 | 1.000 63.43 |

FIGURE 73

| | | | | | | | | | |
|---|---|---|---|---|---|---|---|---|---|
| ATOM | 3484 | OD2 | ASP | B | 154 | 54.104 | 33.398 | 81.117 | 1.000 50.87 |
| ATOM | 3485 | C | ASP | B | 154 | 51.735 | 32.287 | 79.642 | 1.000 41.87 |
| ATOM | 3486 | O | ASP | B | 154 | 50.951 | 32.111 | 78.703 | 1.000 33.32 |
| ATOM | 3487 | N | HIS | B | 155 | 51.623 | 33.296 | 80.509 | 1.000 35.60 |
| ATOM | 3488 | CA | HIS | B | 155 | 50.654 | 34.375 | 80.304 | 1.000 37.44 |
| ATOM | 3489 | CB | HIS | B | 155 | 50.312 | 35.059 | 81.628 | 1.000 36.58 |
| ATOM | 3490 | CG | HIS | B | 155 | 49.205 | 36.062 | 81.526 | 1.000 32.90 |
| ATOM | 3491 | ND1 | HIS | B | 155 | 47.930 | 35.814 | 82.000 | 1.000 29.00 |
| ATOM | 3492 | CE1 | HIS | B | 155 | 47.168 | 36.872 | 81.774 | 1.000 30.32 |
| ATOM | 3493 | NE2 | HIS | B | 155 | 47.903 | 37.796 | 81.172 | 1.000 34.71 |
| ATOM | 3494 | CD2 | HIS | B | 155 | 49.182 | 37.312 | 81.009 | 1.000 27.70 |
| ATOM | 3495 | C | HIS | B | 155 | 51.236 | 35.374 | 79.311 | 1.000 36.71 |
| ATOM | 3496 | O | HIS | B | 155 | 51.750 | 36.422 | 79.691 | 1.000 42.00 |
| ATOM | 3497 | N | TYR | B | 156 | 51.192 | 35.068 | 78.016 | 1.000 29.11 |
| ATOM | 3498 | CA | TYR | B | 156 | 52.011 | 35.820 | 77.081 | 1.000 24.84 |
| ATOM | 3499 | CB | TYR | B | 156 | 52.303 | 34.932 | 75.855 | 1.000 27.19 |
| ATOM | 3500 | CG | TYR | B | 156 | 51.050 | 34.394 | 75.208 | 1.000 24.09 |
| ATOM | 3501 | CD1 | TYR | B | 156 | 50.488 | 35.051 | 74.120 | 1.000 16.98 |
| ATOM | 3502 | CE1 | TYR | B | 156 | 49.344 | 34.554 | 73.528 | 1.000 17.14 |
| ATOM | 3503 | CZ | TYR | B | 156 | 48.745 | 33.407 | 73.996 | 1.000 25.77 |
| ATOM | 3504 | OH | TYR | B | 156 | 47.596 | 32.928 | 73.387 | 1.000 23.27 |
| ATOM | 3505 | CE2 | TYR | B | 156 | 49.294 | 32.745 | 75.074 | 1.000 27.41 |
| ATOM | 3506 | CD2 | TYR | B | 156 | 50.439 | 33.238 | 75.672 | 1.000 27.13 |
| ATOM | 3507 | C | TYR | B | 156 | 51.409 | 37.129 | 76.615 | 1.000 23.96 |
| ATOM | 3508 | O | TYR | B | 156 | 51.948 | 37.722 | 75.673 | 1.000 30.34 |
| ATOM | 3509 | N | TRP | B | 157 | 50.332 | 37.596 | 77.228 | 1.000 29.38 |
| ATOM | 3510 | CA | TRP | B | 157 | 49.801 | 38.920 | 76.885 | 1.000 30.99 |
| ATOM | 3511 | CB | TRP | B | 157 | 48.389 | 38.798 | 76.324 | 1.000 35.30 |
| ATOM | 3512 | CG | TRP | B | 157 | 47.436 | 38.178 | 77.304 | 1.000 37.36 |
| ATOM | 3513 | CD1 | TRP | B | 157 | 46.608 | 38.819 | 78.180 | 1.000 32.25 |
| ATOM | 3514 | NE1 | TRP | B | 157 | 45.897 | 37.886 | 78.896 | 1.000 33.37 |
| ATOM | 3515 | CE2 | TRP | B | 157 | 46.257 | 36.626 | 78.495 | 1.000 24.24 |
| ATOM | 3516 | CD2 | TRP | B | 157 | 47.227 | 36.772 | 77.488 | 1.000 31.89 |
| ATOM | 3517 | CE3 | TRP | B | 157 | 47.774 | 35.630 | 76.894 | 1.000 32.73 |
| ATOM | 3518 | CZ3 | TRP | B | 157 | 47.334 | 34.394 | 77.324 | 1.000 31.61 |
| ATOM | 3519 | CH2 | TRP | B | 157 | 46.366 | 34.269 | 78.328 | 1.000 31.07 |
| ATOM | 3520 | CZ2 | TRP | B | 157 | 45.819 | 35.378 | 78.923 | 1.000 30.59 |
| ATOM | 3521 | C | TRP | B | 157 | 49.806 | 39.815 | 78.116 | 1.000 33.23 |
| ATOM | 3522 | O | TRP | B | 157 | 50.003 | 39.308 | 79.229 | 1.000 47.58 |
| ATOM | 3523 | N | PRO | B | 158 | 49.613 | 41.119 | 77.999 | 1.000 35.32 |
| ATOM | 3524 | CA | PRO | B | 158 | 49.665 | 41.957 | 79.206 | 1.000 42.97 |
| ATOM | 3525 | CB | PRO | B | 158 | 49.605 | 43.384 | 78.670 | 1.000 36.94 |
| ATOM | 3526 | CG | PRO | B | 158 | 49.779 | 43.296 | 77.200 | 1.000 32.51 |
| ATOM | 3527 | CD | PRO | B | 158 | 49.347 | 41.916 | 76.793 | 1.000 36.20 |
| ATOM | 3528 | C | PRO | B | 158 | 48.468 | 41.701 | 80.128 | 1.000 58.41 |
| ATOM | 3529 | O | PRO | B | 158 | 47.343 | 41.559 | 79.645 | 1.000 65.51 |
| ATOM | 3530 | N | ALA | B | 159 | 48.739 | 41.658 | 81.422 | 1.000 68.74 |
| ATOM | 3531 | CA | ALA | B | 159 | 47.823 | 41.404 | 82.518 | 1.000 64.94 |
| ATOM | 3532 | CB | ALA | B | 159 | 48.387 | 41.972 | 83.819 | 1.000 34.74 |
| ATOM | 3533 | C | ALA | B | 159 | 46.428 | 41.975 | 82.282 | 1.000 65.31 |
| ATOM | 3534 | O | ALA | B | 159 | 45.468 | 41.222 | 82.121 | 1.000 68.71 |
| ATOM | 3535 | N | ASP | B | 160 | 46.330 | 43.297 | 82.278 | 1.000 66.84 |

FIGURE 74

| ATOM | 3536 | CA | ASP | B | 160 | 45.079 | 44.010 | 82.063 | 1.000 | 69.30 |
| ATOM | 3537 | CB | ASP | B | 160 | 44.668 | 44.824 | 83.286 | 1.000 | 73.78 |
| ATOM | 3538 | CG | ASP | B | 160 | 45.671 | 44.813 | 84.417 | 1.000 | 78.54 |
| ATOM | 3539 | OD1 | ASP | B | 160 | 46.696 | 45.535 | 84.324 | 1.000 | 85.06 |
| ATOM | 3540 | OD2 | ASP | B | 160 | 45.449 | 44.083 | 85.410 | 1.000 | 82.66 |
| ATOM | 3541 | C | ASP | B | 160 | 45.199 | 44.934 | 80.850 | 1.000 | 70.60 |
| ATOM | 3542 | O | ASP | B | 160 | 45.922 | 44.612 | 79.904 | 1.000 | 80.81 |
| ATOM | 3543 | N | GLN | B | 161 | 44.503 | 46.063 | 80.897 | 1.000 | 65.68 |
| ATOM | 3544 | CA | GLN | B | 161 | 44.460 | 47.034 | 79.813 | 1.000 | 60.98 |
| ATOM | 3545 | CB | GLN | B | 161 | 43.341 | 48.054 | 80.079 | 1.000 | 66.64 |
| ATOM | 3546 | CG | GLN | B | 161 | 41.977 | 47.435 | 80.326 | 1.000 | 70.82 |
| ATOM | 3547 | CD | GLN | B | 161 | 41.431 | 46.682 | 79.129 | 1.000 | 73.10 |
| ATOM | 3548 | OE1 | GLN | B | 161 | 41.858 | 46.906 | 77.995 | 1.000 | 91.18 |
| ATOM | 3549 | NE2 | GLN | B | 161 | 40.481 | 45.781 | 79.367 | 1.000 | 51.42 |
| ATOM | 3550 | C | GLN | B | 161 | 45.774 | 47.770 | 79.607 | 1.000 | 52.94 |
| ATOM | 3551 | O | GLN | B | 161 | 45.860 | 48.713 | 78.819 | 1.000 | 46.56 |
| ATOM | 3552 | N | ASP | B | 162 | 46.841 | 47.376 | 80.294 | 1.000 | 57.53 |
| ATOM | 3553 | CA | ASP | B | 162 | 48.126 | 48.048 | 80.111 | 1.000 | 53.21 |
| ATOM | 3554 | CB | ASP | B | 162 | 49.080 | 47.691 | 81.251 | 1.000 | 60.81 |
| ATOM | 3555 | CG | ASP | B | 162 | 49.331 | 46.204 | 81.393 | 1.000 | 64.03 |
| ATOM | 3556 | OD1 | ASP | B | 162 | 48.588 | 45.415 | 80.770 | 1.000 | 73.29 |
| ATOM | 3557 | OD2 | ASP | B | 162 | 50.272 | 45.829 | 82.129 | 1.000 | 52.70 |
| ATOM | 3558 | C | ASP | B | 162 | 48.742 | 47.700 | 78.759 | 1.000 | 46.46 |
| ATOM | 3559 | O | ASP | B | 162 | 48.083 | 47.149 | 77.874 | 1.000 | 52.43 |
| ATOM | 3560 | N | SER | B | 163 | 50.014 | 48.039 | 78.604 | 1.000 | 36.08 |
| ATOM | 3561 | CA | SER | B | 163 | 50.763 | 47.761 | 77.385 | 1.000 | 30.11 |
| ATOM | 3562 | CB | SER | B | 163 | 50.905 | 49.014 | 76.523 | 1.000 | 37.96 |
| ATOM | 3563 | OG | SER | B | 163 | 51.383 | 50.101 | 77.295 | 1.000 | 38.12 |
| ATOM | 3564 | C | SER | B | 163 | 52.141 | 47.223 | 77.724 | 1.000 | 31.57 |
| ATOM | 3565 | O | SER | B | 163 | 52.646 | 47.355 | 78.838 | 1.000 | 35.55 |
| ATOM | 3566 | N | LEU | B | 164 | 52.776 | 46.591 | 76.741 | 1.000 | 30.19 |
| ATOM | 3567 | CA | LEU | B | 164 | 54.081 | 46.002 | 77.023 | 1.000 | 21.86 |
| ATOM | 3568 | CB | LEU | B | 164 | 53.918 | 44.691 | 77.779 | 1.000 | 37.42 |
| ATOM | 3569 | CG | LEU | B | 164 | 53.641 | 44.732 | 79.281 | 1.000 | 38.91 |
| ATOM | 3570 | CD1 | LEU | B | 164 | 53.495 | 43.319 | 79.843 | 1.000 | 28.89 |
| ATOM | 3571 | CD2 | LEU | B | 164 | 54.736 | 45.470 | 80.031 | 1.000 | 42.72 |
| ATOM | 3572 | C | LEU | B | 164 | 54.822 | 45.780 | 75.715 | 1.000 | 27.76 |
| ATOM | 3573 | O | LEU | B | 164 | 54.201 | 45.635 | 74.660 | 1.000 | 28.16 |
| ATOM | 3574 | N | TYR | B | 165 | 56.150 | 45.767 | 75.799 | 1.000 | 29.39 |
| ATOM | 3575 | CA | TYR | B | 165 | 56.959 | 45.469 | 74.631 | 1.000 | 27.11 |
| ATOM | 3576 | CB | TYR | B | 165 | 58.338 | 46.113 | 74.728 | 1.000 | 24.50 |
| ATOM | 3577 | CG | TYR | B | 165 | 58.373 | 47.576 | 74.362 | 1.000 | 33.29 |
| ATOM | 3578 | CD1 | TYR | B | 165 | 58.505 | 47.926 | 73.022 | 1.000 | 27.89 |
| ATOM | 3579 | CE1 | TYR | B | 165 | 58.538 | 49.248 | 72.635 | 1.000 | 31.36 |
| ATOM | 3580 | CZ | TYR | B | 165 | 58.443 | 50.244 | 73.581 | 1.000 | 24.85 |
| ATOM | 3581 | OH | TYR | B | 165 | 58.487 | 51.546 | 73.139 | 1.000 | 26.61 |
| ATOM | 3582 | CE2 | TYR | B | 165 | 58.309 | 49.930 | 74.915 | 1.000 | 28.53 |
| ATOM | 3583 | CD2 | TYR | B | 165 | 58.271 | 48.594 | 75.307 | 1.000 | 28.19 |
| ATOM | 3584 | C | TYR | B | 165 | 57.109 | 43.955 | 74.503 | 1.000 | 32.17 |
| ATOM | 3585 | O | TYR | B | 165 | 57.195 | 43.254 | 75.511 | 1.000 | 29.95 |
| ATOM | 3586 | N | TYR | B | 166 | 57.152 | 43.472 | 73.271 | 1.000 | 28.70 |
| ATOM | 3587 | CA | TYR | B | 166 | 57.498 | 42.072 | 73.035 | 1.000 | 27.96 |

FIGURE 75

| ATOM | 3588 | CB | TYR | B | 166 | 56.268 | 41.232 | 72.710 | 1.000 | 29.27 |
| --- | --- | --- | --- | --- | --- | --- | --- | --- | --- | --- |
| ATOM | 3589 | CG | TYR | B | 166 | 55.350 | 41.031 | 73.899 | 1.000 | 32.16 |
| ATOM | 3590 | CD1 | TYR | B | 166 | 55.542 | 39.987 | 74.805 | 1.000 | 27.15 |
| ATOM | 3591 | CE1 | TYR | B | 166 | 54.689 | 39.821 | 75.884 | 1.000 | 26.48 |
| ATOM | 3592 | CZ | TYR | B | 166 | 53.637 | 40.699 | 76.065 | 1.000 | 31.42 |
| ATOM | 3593 | OH | TYR | B | 166 | 52.780 | 40.552 | 77.133 | 1.000 | 26.92 |
| ATOM | 3594 | CE2 | TYR | B | 166 | 53.427 | 41.738 | 75.182 | 1.000 | 25.16 |
| ATOM | 3595 | CD2 | TYR | B | 166 | 54.282 | 41.897 | 74.107 | 1.000 | 30.85 |
| ATOM | 3596 | C | TYR | B | 166 | 58.533 | 42.065 | 71.926 | 1.000 | 23.40 |
| ATOM | 3597 | O | TYR | B | 166 | 58.221 | 42.038 | 70.746 | 1.000 | 29.44 |
| ATOM | 3598 | N | GLY | B | 167 | 59.815 | 42.124 | 72.303 | 1.000 | 30.73 |
| ATOM | 3599 | CA | GLY | B | 167 | 60.795 | 42.293 | 71.225 | 1.000 | 31.29 |
| ATOM | 3600 | C | GLY | B | 167 | 60.629 | 43.677 | 70.620 | 1.000 | 34.66 |
| ATOM | 3601 | O | GLY | B | 167 | 60.636 | 44.683 | 71.340 | 1.000 | 26.60 |
| ATOM | 3602 | N | ASP | B | 168 | 60.475 | 43.757 | 69.302 | 1.000 | 29.65 |
| ATOM | 3603 | CA | ASP | B | 168 | 60.388 | 45.070 | 68.660 | 1.000 | 31.97 |
| ATOM | 3604 | CB | ASP | B | 168 | 61.050 | 45.062 | 67.282 | 1.000 | 30.77 |
| ATOM | 3605 | CG | ASP | B | 168 | 62.559 | 44.932 | 67.417 | 1.000 | 44.29 |
| ATOM | 3606 | OD1 | ASP | B | 168 | 63.059 | 45.103 | 68.550 | 1.000 | 70.44 |
| ATOM | 3607 | OD2 | ASP | B | 168 | 63.238 | 44.655 | 66.411 | 1.000 | 63.44 |
| ATOM | 3608 | C | ASP | B | 168 | 58.935 | 45.510 | 68.551 | 1.000 | 32.07 |
| ATOM | 3609 | O | ASP | B | 168 | 58.619 | 46.594 | 68.076 | 1.000 | 32.90 |
| ATOM | 3610 | N | LEU | B | 169 | 58.073 | 44.613 | 69.025 | 1.000 | 29.35 |
| ATOM | 3611 | CA | LEU | B | 169 | 56.648 | 44.870 | 68.984 | 1.000 | 33.24 |
| ATOM | 3612 | CB | LEU | B | 169 | 55.877 | 43.576 | 68.686 | 1.000 | 30.90 |
| ATOM | 3613 | CG | LEU | B | 169 | 56.205 | 42.932 | 67.336 | 1.000 | 32.40 |
| ATOM | 3614 | CD1 | LEU | B | 169 | 55.292 | 41.738 | 67.129 | 1.000 | 26.83 |
| ATOM | 3615 | CD2 | LEU | B | 169 | 56.082 | 43.955 | 66.219 | 1.000 | 27.58 |
| ATOM | 3616 | C | LEU | B | 169 | 56.111 | 45.433 | 70.294 | 1.000 | 32.00 |
| ATOM | 3617 | O | LEU | B | 169 | 56.642 | 45.147 | 71.365 | 1.000 | 27.18 |
| ATOM | 3618 | N | ILE | B | 170 | 55.042 | 46.205 | 70.127 | 1.000 | 23.43 |
| ATOM | 3619 | CA | ILE | B | 170 | 54.297 | 46.711 | 71.263 | 1.000 | 37.97 |
| ATOM | 3620 | CB | ILE | B | 170 | 54.333 | 48.242 | 71.369 | 1.000 | 44.96 |
| ATOM | 3621 | CG1 | ILE | B | 170 | 53.206 | 48.832 | 72.219 | 1.000 | 51.13 |
| ATOM | 3622 | CD1 | ILE | B | 170 | 53.662 | 49.989 | 73.089 | 1.000 | 79.46 |
| ATOM | 3623 | CG2 | ILE | B | 170 | 54.345 | 48.876 | 69.991 | 1.000 | 56.59 |
| ATOM | 3624 | C | ILE | B | 170 | 52.851 | 46.228 | 71.147 | 1.000 | 36.98 |
| ATOM | 3625 | O | ILE | B | 170 | 52.247 | 46.337 | 70.083 | 1.000 | 29.48 |
| ATOM | 3626 | N | LEU | B | 171 | 52.367 | 45.700 | 72.258 | 1.000 | 37.92 |
| ATOM | 3627 | CA | LEU | B | 171 | 51.015 | 45.200 | 72.405 | 1.000 | 39.12 |
| ATOM | 3628 | CB | LEU | B | 171 | 51.037 | 43.709 | 72.767 | 1.000 | 46.39 |
| ATOM | 3629 | CG | LEU | B | 171 | 50.043 | 42.860 | 71.971 | 1.000 | 52.95 |
| ATOM | 3630 | CD1 | LEU | B | 171 | 50.694 | 41.558 | 71.563 | 1.000 | 42.82 |
| ATOM | 3631 | CD2 | LEU | B | 171 | 48.783 | 42.619 | 72.784 | 1.000 | 80.84 |
| ATOM | 3632 | C | LEU | B | 171 | 50.235 | 45.939 | 73.482 | 1.000 | 37.92 |
| ATOM | 3633 | O | LEU | B | 171 | 50.744 | 46.261 | 74.556 | 1.000 | 41.84 |
| ATOM | 3634 | N | GLN | B | 172 | 48.962 | 46.207 | 73.191 | 1.000 | 33.26 |
| ATOM | 3635 | CA | GLN | B | 172 | 48.132 | 46.767 | 74.257 | 1.000 | 42.90 |
| ATOM | 3636 | CB | GLN | B | 172 | 47.929 | 48.272 | 74.095 | 1.000 | 43.81 |
| ATOM | 3637 | CG | GLN | B | 172 | 46.841 | 48.669 | 73.123 | 1.000 | 44.65 |
| ATOM | 3638 | CD | GLN | B | 172 | 46.760 | 50.170 | 72.905 | 1.000 | 41.71 |
| ATOM | 3639 | OE1 | GLN | B | 172 | 47.004 | 50.675 | 71.809 | 1.000 | 39.38 |

FIGURE 76

| ATOM | 3640 | NE2 | GLN | B | 172 | 46.410 | 50.886 | 73.963 | 1.000 | 51.04 |
|------|------|-----|-----|---|-----|--------|--------|--------|-------|-------|
| ATOM | 3641 | C   | GLN | B | 172 | 46.800 | 46.028 | 74.274 | 1.000 | 36.46 |
| ATOM | 3642 | O   | GLN | B | 172 | 46.205 | 45.820 | 73.214 | 1.000 | 30.33 |
| ATOM | 3643 | N   | MET | B | 173 | 46.349 | 45.629 | 75.460 | 1.000 | 34.57 |
| ATOM | 3644 | CA  | MET | B | 173 | 45.024 | 45.020 | 75.526 | 1.000 | 37.82 |
| ATOM | 3645 | CB  | MET | B | 173 | 44.827 | 44.177 | 76.786 | 1.000 | 44.70 |
| ATOM | 3646 | CG  | MET | B | 173 | 43.371 | 44.165 | 77.243 | 1.000 | 48.88 |
| ATOM | 3647 | SD  | MET | B | 173 | 43.091 | 43.051 | 78.637 | 1.000 | 61.82 |
| ATOM | 3648 | CE  | MET | B | 173 | 43.023 | 41.490 | 77.765 | 1.000 | 30.24 |
| ATOM | 3649 | C   | MET | B | 173 | 43.960 | 46.115 | 75.496 | 1.000 | 37.98 |
| ATOM | 3650 | O   | MET | B | 173 | 43.913 | 46.968 | 76.387 | 1.000 | 50.74 |
| ATOM | 3651 | N   | LEU | B | 174 | 43.116 | 46.087 | 74.476 | 1.000 | 39.28 |
| ATOM | 3652 | CA  | LEU | B | 174 | 42.041 | 47.069 | 74.379 | 1.000 | 40.72 |
| ATOM | 3653 | CB  | LEU | B | 174 | 41.705 | 47.353 | 72.911 | 1.000 | 40.97 |
| ATOM | 3654 | CG  | LEU | B | 174 | 42.894 | 47.860 | 72.084 | 1.000 | 48.67 |
| ATOM | 3655 | CD1 | LEU | B | 174 | 42.466 | 48.190 | 70.666 | 1.000 | 63.07 |
| ATOM | 3656 | CD2 | LEU | B | 174 | 43.524 | 49.058 | 72.778 | 1.000 | 40.09 |
| ATOM | 3657 | C   | LEU | B | 174 | 40.794 | 46.608 | 75.113 | 1.000 | 37.13 |
| ATOM | 3658 | O   | LEU | B | 174 | 39.994 | 47.450 | 75.515 | 1.000 | 41.98 |
| ATOM | 3659 | N   | SER | B | 175 | 40.613 | 45.295 | 75.288 | 1.000 | 36.81 |
| ATOM | 3660 | CA  | SER | B | 175 | 39.379 | 44.856 | 75.936 | 1.000 | 37.02 |
| ATOM | 3661 | CB  | SER | B | 175 | 38.204 | 45.077 | 74.978 | 1.000 | 39.53 |
| ATOM | 3662 | OG  | SER | B | 175 | 38.164 | 44.075 | 73.975 | 1.000 | 60.16 |
| ATOM | 3663 | C   | SER | B | 175 | 39.419 | 43.397 | 76.372 | 1.000 | 43.07 |
| ATOM | 3664 | O   | SER | B | 175 | 40.144 | 42.583 | 75.801 | 1.000 | 35.52 |
| ATOM | 3665 | N   | GLU | B | 176 | 38.616 | 43.077 | 77.387 | 1.000 | 36.53 |
| ATOM | 3666 | CA  | GLU | B | 176 | 38.525 | 41.721 | 77.899 | 1.000 | 37.42 |
| ATOM | 3667 | CB  | GLU | B | 176 | 39.524 | 41.528 | 79.050 | 1.000 | 29.90 |
| ATOM | 3668 | CG  | GLU | B | 176 | 39.524 | 40.101 | 79.570 | 1.000 | 36.55 |
| ATOM | 3669 | CD  | GLU | B | 176 | 40.377 | 39.924 | 80.806 | 1.000 | 41.20 |
| ATOM | 3670 | OE1 | GLU | B | 176 | 39.808 | 39.980 | 81.913 | 1.000 | 65.49 |
| ATOM | 3671 | OE2 | GLU | B | 176 | 41.602 | 39.726 | 80.667 | 1.000 | 51.95 |
| ATOM | 3672 | C   | GLU | B | 176 | 37.120 | 41.366 | 78.371 | 1.000 | 42.69 |
| ATOM | 3673 | O   | GLU | B | 176 | 36.658 | 41.868 | 79.400 | 1.000 | 44.27 |
| ATOM | 3674 | N   | SER | B | 177 | 36.434 | 40.496 | 77.627 | 1.000 | 39.90 |
| ATOM | 3675 | CA  | SER | B | 177 | 35.073 | 40.107 | 77.983 | 1.000 | 35.04 |
| ATOM | 3676 | CB  | SER | B | 177 | 34.101 | 40.295 | 76.816 | 1.000 | 36.67 |
| ATOM | 3677 | OG  | SER | B | 177 | 34.475 | 41.395 | 76.007 | 1.000 | 52.82 |
| ATOM | 3678 | C   | SER | B | 177 | 35.030 | 38.658 | 78.448 | 1.000 | 41.90 |
| ATOM | 3679 | O   | SER | B | 177 | 35.160 | 37.715 | 77.669 | 1.000 | 42.75 |
| ATOM | 3680 | N   | VAL | B | 178 | 34.840 | 38.482 | 79.750 | 1.000 | 40.45 |
| ATOM | 3681 | CA  | VAL | B | 178 | 34.819 | 37.128 | 80.295 | 1.000 | 49.91 |
| ATOM | 3682 | CB  | VAL | B | 178 | 35.272 | 37.144 | 81.768 | 1.000 | 56.06 |
| ATOM | 3683 | CG1 | VAL | B | 178 | 35.518 | 35.735 | 82.276 | 1.000 | 36.78 |
| ATOM | 3684 | CG2 | VAL | B | 178 | 36.520 | 38.006 | 81.909 | 1.000 | 58.94 |
| ATOM | 3685 | C   | VAL | B | 178 | 33.439 | 36.509 | 80.163 | 1.000 | 50.01 |
| ATOM | 3686 | O   | VAL | B | 178 | 32.445 | 37.037 | 80.659 | 1.000 | 63.04 |
| ATOM | 3687 | N   | LEU | B | 179 | 33.372 | 35.372 | 79.478 | 1.000 | 45.68 |
| ATOM | 3688 | CA  | LEU | B | 179 | 32.098 | 34.653 | 79.362 | 1.000 | 38.65 |
| ATOM | 3689 | CB  | LEU | B | 179 | 31.753 | 34.401 | 77.900 | 1.000 | 37.56 |
| ATOM | 3690 | CG  | LEU | B | 179 | 30.892 | 35.472 | 77.222 | 1.000 | 42.61 |
| ATOM | 3691 | CD1 | LEU | B | 179 | 30.991 | 36.805 | 77.946 | 1.000 | 33.74 |

FIGURE 77

| ATOM | 3692 | CD2 | LEU | B | 179 | 31.286 | 35.631 | 75.766 | 1.000 | 47.05 |
|------|------|-----|-----|---|-----|--------|--------|--------|-------|-------|
| ATOM | 3693 | C   | LEU | B | 179 | 32.206 | 33.383 | 80.189 | 1.000 | 30.01 |
| ATOM | 3694 | O   | LEU | B | 179 | 33.317 | 33.035 | 80.611 | 1.000 | 33.11 |
| ATOM | 3695 | N   | PRO | B | 180 | 31.108 | 32.694 | 80.467 | 1.000 | 44.43 |
| ATOM | 3696 | CA  | PRO | B | 180 | 31.210 | 31.516 | 81.345 | 1.000 | 49.89 |
| ATOM | 3697 | CB  | PRO | B | 180 | 29.766 | 31.004 | 81.441 | 1.000 | 47.48 |
| ATOM | 3698 | CG  | PRO | B | 180 | 28.932 | 32.194 | 81.096 | 1.000 | 47.96 |
| ATOM | 3699 | CD  | PRO | B | 180 | 29.720 | 32.929 | 80.038 | 1.000 | 48.96 |
| ATOM | 3700 | C   | PRO | B | 180 | 32.130 | 30.439 | 80.793 | 1.000 | 43.82 |
| ATOM | 3701 | O   | PRO | B | 180 | 32.877 | 29.834 | 81.569 | 1.000 | 44.36 |
| ATOM | 3702 | N   | GLU | B | 181 | 32.144 | 30.139 | 79.492 | 1.000 | 42.02 |
| ATOM | 3703 | CA  | GLU | B | 181 | 33.041 | 29.044 | 79.095 | 1.000 | 41.65 |
| ATOM | 3704 | CB  | GLU | B | 181 | 32.305 | 28.017 | 78.245 | 1.000 | 42.17 |
| ATOM | 3705 | CG  | GLU | B | 181 | 31.191 | 27.274 | 78.964 | 1.000 | 46.96 |
| ATOM | 3706 | CD  | GLU | B | 181 | 30.000 | 27.055 | 78.047 | 1.000 | 47.94 |
| ATOM | 3707 | OE1 | GLU | B | 181 | 29.114 | 27.932 | 78.017 | 1.000 | 66.99 |
| ATOM | 3708 | OE2 | GLU | B | 181 | 29.958 | 26.017 | 77.358 | 1.000 | 66.16 |
| ATOM | 3709 | C   | GLU | B | 181 | 34.270 | 29.552 | 78.353 | 1.000 | 42.89 |
| ATOM | 3710 | O   | GLU | B | 181 | 35.211 | 28.790 | 78.114 | 1.000 | 45.33 |
| ATOM | 3711 | N   | TRP | B | 182 | 34.287 | 30.831 | 77.987 | 1.000 | 38.96 |
| ATOM | 3712 | CA  | TRP | B | 182 | 35.473 | 31.378 | 77.343 | 1.000 | 34.57 |
| ATOM | 3713 | CB  | TRP | B | 182 | 35.493 | 31.021 | 75.853 | 1.000 | 34.24 |
| ATOM | 3714 | CG  | TRP | B | 182 | 34.289 | 31.453 | 75.078 | 1.000 | 31.49 |
| ATOM | 3715 | CD1 | TRP | B | 182 | 34.055 | 32.679 | 74.531 | 1.000 | 33.21 |
| ATOM | 3716 | NE1 | TRP | B | 182 | 32.839 | 32.683 | 73.891 | 1.000 | 30.07 |
| ATOM | 3717 | CE2 | TRP | B | 182 | 32.258 | 31.451 | 74.014 | 1.000 | 24.47 |
| ATOM | 3718 | CD2 | TRP | B | 182 | 33.145 | 30.644 | 74.755 | 1.000 | 36.54 |
| ATOM | 3719 | CE3 | TRP | B | 182 | 32.793 | 29.317 | 75.030 | 1.000 | 38.44 |
| ATOM | 3720 | CZ3 | TRP | B | 182 | 31.582 | 28.837 | 74.562 | 1.000 | 36.86 |
| ATOM | 3721 | CH2 | TRP | B | 182 | 30.725 | 29.670 | 73.827 | 1.000 | 32.83 |
| ATOM | 3722 | CZ2 | TRP | B | 182 | 31.038 | 30.971 | 73.543 | 1.000 | 25.32 |
| ATOM | 3723 | C   | TRP | B | 182 | 35.581 | 32.890 | 77.481 | 1.000 | 29.73 |
| ATOM | 3724 | O   | TRP | B | 182 | 34.637 | 33.609 | 77.802 | 1.000 | 34.04 |
| ATOM | 3725 | N   | THR | B | 183 | 36.786 | 33.370 | 77.203 | 1.000 | 19.61 |
| ATOM | 3726 | CA  | THR | B | 183 | 37.043 | 34.808 | 77.245 | 1.000 | 24.25 |
| ATOM | 3727 | CB  | THR | B | 183 | 38.106 | 35.096 | 78.329 | 1.000 | 27.46 |
| ATOM | 3728 | OG1 | THR | B | 183 | 37.562 | 34.709 | 79.589 | 1.000 | 35.93 |
| ATOM | 3729 | CG2 | THR | B | 183 | 38.446 | 36.570 | 78.408 | 1.000 | 27.17 |
| ATOM | 3730 | C   | THR | B | 183 | 37.539 | 35.333 | 75.910 | 1.000 | 20.91 |
| ATOM | 3731 | O   | THR | B | 183 | 38.454 | 34.749 | 75.312 | 1.000 | 28.00 |
| ATOM | 3732 | N   | ILE | B | 184 | 36.966 | 36.423 | 75.422 | 1.000 | 26.34 |
| ATOM | 3733 | CA  | ILE | B | 184 | 37.472 | 37.068 | 74.208 | 1.000 | 26.11 |
| ATOM | 3734 | CB  | ILE | B | 184 | 36.341 | 37.420 | 73.235 | 1.000 | 29.02 |
| ATOM | 3735 | CG1 | ILE | B | 184 | 35.592 | 36.198 | 72.681 | 1.000 | 36.60 |
| ATOM | 3736 | CD1 | ILE | B | 184 | 34.154 | 36.545 | 72.341 | 1.000 | 36.57 |
| ATOM | 3737 | CG2 | ILE | B | 184 | 36.819 | 38.293 | 72.087 | 1.000 | 18.36 |
| ATOM | 3738 | C   | ILE | B | 184 | 38.232 | 38.333 | 74.580 | 1.000 | 31.53 |
| ATOM | 3739 | O   | ILE | B | 184 | 37.781 | 39.186 | 75.345 | 1.000 | 38.29 |
| ATOM | 3740 | N   | ARG | B | 185 | 39.437 | 38.501 | 74.043 | 1.000 | 34.57 |
| ATOM | 3741 | CA  | ARG | B | 185 | 40.147 | 39.754 | 74.292 | 1.000 | 25.10 |
| ATOM | 3742 | CB  | ARG | B | 185 | 41.417 | 39.538 | 75.100 | 1.000 | 28.99 |
| ATOM | 3743 | CG  | ARG | B | 185 | 41.209 | 39.034 | 76.522 | 1.000 | 31.53 |

FIGURE 78

```
ATOM   3744  CD   ARG B 185      42.403  38.222  76.976  1.000  25.65
ATOM   3745  NE   ARG B 185      42.343  37.791  78.364  1.000  21.83
ATOM   3746  CZ   ARG B 185      42.092  36.551  78.753  1.000  23.41
ATOM   3747  NH1  ARG B 185      41.864  35.591  77.867  1.000  20.48
ATOM   3748  NH2  ARG B 185      42.064  36.264  80.047  1.000  23.08
ATOM   3749  C    ARG B 185      40.474  40.399  72.952  1.000  34.69
ATOM   3750  O    ARG B 185      40.557  39.744  71.909  1.000  35.97
ATOM   3751  N    GLU B 186      40.657  41.714  72.993  1.000  27.86
ATOM   3752  CA   GLU B 186      41.104  42.376  71.771  1.000  30.56
ATOM   3753  CB   GLU B 186      40.003  43.261  71.200  1.000  27.97
ATOM   3754  CG   GLU B 186      38.651  42.555  71.232  1.000  39.02
ATOM   3755  CD   GLU B 186      37.530  43.456  70.746  1.000  52.48
ATOM   3756  OE1  GLU B 186      37.819  44.357  69.928  1.000  68.25
ATOM   3757  OE2  GLU B 186      36.378  43.243  71.180  1.000  77.37
ATOM   3758  C    GLU B 186      42.373  43.152  72.110  1.000  32.85
ATOM   3759  O    GLU B 186      42.405  43.798  73.154  1.000  31.08
ATOM   3760  N    PHE B 187      43.349  43.031  71.236  1.000  30.67
ATOM   3761  CA   PHE B 187      44.651  43.643  71.332  1.000  28.22
ATOM   3762  CB   PHE B 187      45.761  42.599  71.472  1.000  23.26
ATOM   3763  CG   PHE B 187      45.580  41.563  72.546  1.000  30.99
ATOM   3764  CD1  PHE B 187      45.238  40.260  72.244  1.000  27.35
ATOM   3765  CE1  PHE B 187      45.074  39.304  73.230  1.000  20.96
ATOM   3766  CZ   PHE B 187      45.244  39.654  74.558  1.000  27.74
ATOM   3767  CE2  PHE B 187      45.589  40.951  74.882  1.000  33.31
ATOM   3768  CD2  PHE B 187      45.760  41.891  73.884  1.000  33.33
ATOM   3769  C    PHE B 187      44.937  44.474  70.079  1.000  32.36
ATOM   3770  O    PHE B 187      44.466  44.149  68.989  1.000  24.82
ATOM   3771  N    LYS B 188      45.731  45.502  70.304  1.000  33.51
ATOM   3772  CA   LYS B 188      46.366  46.294  69.265  1.000  39.34
ATOM   3773  CB   LYS B 188      46.107  47.786  69.445  1.000  52.27
ATOM   3774  CG   LYS B 188      47.360  48.631  69.623  1.000  65.67
ATOM   3775  CD   LYS B 188      47.208  49.980  68.916  1.000  71.88
ATOM   3776  CE   LYS B 188      48.299  50.947  69.345  1.000  76.68
ATOM   3777  NZ   LYS B 188      48.492  52.055  68.375  1.000  77.91
ATOM   3778  C    LYS B 188      47.867  46.005  69.285  1.000  31.64
ATOM   3779  O    LYS B 188      48.496  46.016  70.345  1.000  31.25
ATOM   3780  N    ILE B 189      48.432  45.740  68.110  1.000  25.97
ATOM   3781  CA   ILE B 189      49.869  45.521  68.045  1.000  32.80
ATOM   3782  CB   ILE B 189      50.247  44.098  67.612  1.000  38.71
ATOM   3783  CG1  ILE B 189      49.093  43.327  66.974  1.000  46.51
ATOM   3784  CD1  ILE B 189      48.715  43.822  65.594  1.000  39.76
ATOM   3785  CG2  ILE B 189      50.838  43.337  68.787  1.000  53.93
ATOM   3786  C    ILE B 189      50.485  46.515  67.066  1.000  33.72
ATOM   3787  O    ILE B 189      49.888  46.777  66.022  1.000  37.58
ATOM   3788  N    CYS B 190      51.648  47.022  67.450  1.000  30.23
ATOM   3789  CA   CYS B 190      52.400  47.934  66.602  1.000  40.89
ATOM   3790  CB   CYS B 190      52.596  49.307  67.233  1.000  42.64
ATOM   3791  SG   CYS B 190      51.150  50.118  67.926  1.000  58.03
ATOM   3792  C    CYS B 190      53.775  47.334  66.282  1.000  44.57
ATOM   3793  O    CYS B 190      54.446  46.804  67.173  1.000  40.52
ATOM   3794  N    GLY B 191      54.140  47.444  65.011  1.000  36.59
ATOM   3795  CA   GLY B 191      55.407  46.950  64.504  1.000  43.85
```

FIGURE 79

| | | | | | | | | | |
|---|---|---|---|---|---|---|---|---|---|
| ATOM | 3796 | C | GLY | B | 191 | 56.063 | 48.026 | 63.654 | 1.000 51.14 |
| ATOM | 3797 | O | GLY | B | 191 | 55.515 | 49.122 | 63.561 | 1.000 44.72 |
| ATOM | 3798 | N | GLU | B | 192 | 57.206 | 47.732 | 63.051 | 1.000 65.39 |
| ATOM | 3799 | CA | GLU | B | 192 | 57.917 | 48.729 | 62.251 | 1.000 74.92 |
| ATOM | 3800 | CB | GLU | B | 192 | 59.164 | 48.118 | 61.620 | 1.000 80.08 |
| ATOM | 3801 | CG | GLU | B | 192 | 59.486 | 46.705 | 62.068 | 1.000 89.69 |
| ATOM | 3802 | CD | GLU | B | 192 | 60.187 | 46.619 | 63.406 | 1.000 99.45 |
| ATOM | 3803 | OE1 | GLU | B | 192 | 59.909 | 45.653 | 64.155 | 1.000109.46 |
| ATOM | 3804 | OE2 | GLU | B | 192 | 61.017 | 47.500 | 63.734 | 1.000105.75 |
| ATOM | 3805 | C | GLU | B | 192 | 56.982 | 49.325 | 61.190 | 1.000 77.53 |
| ATOM | 3806 | O | GLU | B | 192 | 57.093 | 50.520 | 60.921 | 1.000 71.90 |
| ATOM | 3807 | N | GLU | B | 193 | 56.119 | 48.468 | 60.689 | 1.000 80.23 |
| ATOM | 3808 | CA | GLU | B | 193 | 55.037 | 48.642 | 59.748 | 1.000 85.66 |
| ATOM | 3809 | CB | GLU | B | 193 | 54.717 | 50.116 | 59.508 | 1.000 94.37 |
| ATOM | 3810 | CG | GLU | B | 193 | 53.928 | 50.436 | 58.253 | 1.000106.40 |
| ATOM | 3811 | CD | GLU | B | 193 | 52.595 | 49.734 | 58.174 | 1.000115.65 |
| ATOM | 3812 | OE1 | GLU | B | 193 | 51.537 | 50.403 | 58.158 | 1.000130.32 |
| ATOM | 3813 | OE2 | GLU | B | 193 | 52.613 | 48.478 | 58.138 | 1.000120.48 |
| ATOM | 3814 | C | GLU | B | 193 | 55.364 | 47.949 | 58.424 | 1.000 90.24 |
| ATOM | 3815 | O | GLU | B | 193 | 56.248 | 48.389 | 57.684 | 1.000 99.18 |
| ATOM | 3816 | N | GLN | B | 194 | 54.652 | 46.858 | 58.146 | 1.000 94.55 |
| ATOM | 3817 | CA | GLN | B | 194 | 54.801 | 46.130 | 56.892 | 1.000 99.07 |
| ATOM | 3818 | CB | GLN | B | 194 | 55.799 | 44.984 | 57.030 | 1.000 99.47 |
| ATOM | 3819 | CG | GLN | B | 194 | 56.655 | 45.014 | 58.284 | 1.000 99.46 |
| ATOM | 3820 | CD | GLN | B | 194 | 58.097 | 44.616 | 58.010 | 1.000 96.93 |
| ATOM | 3821 | OE1 | GLN | B | 194 | 58.678 | 44.953 | 56.977 | 1.000 92.58 |
| ATOM | 3822 | NE2 | GLN | B | 194 | 58.682 | 43.863 | 58.944 | 1.000 90.47 |
| ATOM | 3823 | C | GLN | B | 194 | 53.449 | 45.595 | 56.413 | 1.000102.41 |
| ATOM | 3824 | O | GLN | B | 194 | 53.158 | 44.410 | 56.574 | 1.000106.43 |
| ATOM | 3825 | N | LEU | B | 195 | 52.649 | 46.481 | 55.833 | 1.000102.43 |
| ATOM | 3826 | CA | LEU | B | 195 | 51.322 | 46.214 | 55.301 | 1.000100.78 |
| ATOM | 3827 | CB | LEU | B | 195 | 51.291 | 44.888 | 54.539 | 1.000 96.19 |
| ATOM | 3828 | CG | LEU | B | 195 | 51.096 | 44.962 | 53.021 | 1.000 88.64 |
| ATOM | 3829 | CD1 | LEU | B | 195 | 51.473 | 46.333 | 52.484 | 1.000 68.61 |
| ATOM | 3830 | CD2 | LEU | B | 195 | 51.917 | 43.868 | 52.320 | 1.000 77.73 |
| ATOM | 3831 | C | LEU | B | 195 | 50.270 | 46.236 | 56.412 | 1.000101.84 |
| ATOM | 3832 | O | LEU | B | 195 | 49.132 | 45.812 | 56.210 | 1.000107.43 |
| ATOM | 3833 | N | ASP | B | 196 | 50.667 | 46.740 | 57.570 | 1.000100.14 |
| ATOM | 3834 | CA | ASP | B | 196 | 49.834 | 46.918 | 58.754 | 1.000 95.50 |
| ATOM | 3835 | CB | ASP | B | 196 | 49.258 | 45.605 | 59.253 | 1.000 93.87 |
| ATOM | 3836 | CG | ASP | B | 196 | 50.159 | 44.699 | 60.049 | 1.000 86.73 |
| ATOM | 3837 | OD1 | ASP | B | 196 | 51.251 | 44.300 | 59.589 | 1.000 56.18 |
| ATOM | 3838 | OD2 | ASP | B | 196 | 49.770 | 44.325 | 61.183 | 1.000 68.86 |
| ATOM | 3839 | C | ASP | B | 196 | 50.665 | 47.613 | 59.833 | 1.000 91.65 |
| ATOM | 3840 | O | ASP | B | 196 | 51.757 | 47.144 | 60.157 | 1.000 97.39 |
| ATOM | 3841 | N | ALA | B | 197 | 50.175 | 48.732 | 60.358 | 1.000 87.23 |
| ATOM | 3842 | CA | ALA | B | 197 | 50.971 | 49.522 | 61.291 | 1.000 84.73 |
| ATOM | 3843 | CB | ALA | B | 197 | 51.043 | 50.971 | 60.832 | 1.000 82.95 |
| ATOM | 3844 | C | ALA | B | 197 | 50.426 | 49.456 | 62.716 | 1.000 82.50 |
| ATOM | 3845 | O | ALA | B | 197 | 51.192 | 49.650 | 63.662 | 1.000 66.61 |
| ATOM | 3846 | N | HIS | B | 198 | 49.132 | 49.213 | 62.833 | 1.000 82.67 |
| ATOM | 3847 | CA | HIS | B | 198 | 48.373 | 49.029 | 64.057 | 1.000 77.93 |

FIGURE 80

```
ATOM   3848  CB   HIS B 198      47.927  50.338  64.697  1.000  77.67
ATOM   3849  CG   HIS B 198      48.200  51.573  63.899  1.000  84.79
ATOM   3850  ND1  HIS B 198      47.669  51.785  62.645  1.000  86.88
ATOM   3851  CE1  HIS B 198      48.085  52.952  62.182  1.000  88.81
ATOM   3852  NE2  HIS B 198      48.869  53.503  63.089  1.000  87.71
ATOM   3853  CD2  HIS B 198      48.959  52.659  64.170  1.000  85.49
ATOM   3854  C    HIS B 198      47.141  48.164  63.752  1.000  75.55
ATOM   3855  O    HIS B 198      46.055  48.678  63.493  1.000  83.33
ATOM   3856  N    ARG B 199      47.365  46.860  63.783  1.000  63.26
ATOM   3857  CA   ARG B 199      46.380  45.839  63.475  1.000  55.42
ATOM   3858  CB   ARG B 199      47.074  44.642  62.808  1.000  56.72
ATOM   3859  CG   ARG B 199      46.181  43.423  62.663  1.000  47.99
ATOM   3860  CD   ARG B 199      46.961  42.174  62.308  1.000  37.39
ATOM   3861  NE   ARG B 199      48.216  42.423  61.614  1.000  35.84
ATOM   3862  CZ   ARG B 199      49.253  41.591  61.677  1.000  43.79
ATOM   3863  NH1  ARG B 199      49.171  40.475  62.398  1.000  20.33
ATOM   3864  NH2  ARG B 199      50.368  41.875  61.018  1.000  25.11
ATOM   3865  C    ARG B 199      45.629  45.376  64.717  1.000  43.83
ATOM   3866  O    ARG B 199      46.181  45.353  65.817  1.000  40.98
ATOM   3867  N    LEU B 200      44.361  45.010  64.551  1.000  35.65
ATOM   3868  CA   LEU B 200      43.571  44.511  65.672  1.000  34.82
ATOM   3869  CB   LEU B 200      42.096  44.866  65.560  1.000  37.89
ATOM   3870  CG   LEU B 200      41.296  45.146  66.831  1.000  47.74
ATOM   3871  CD1  LEU B 200      41.329  43.974  67.800  1.000  44.43
ATOM   3872  CD2  LEU B 200      41.794  46.411  67.514  1.000  55.08
ATOM   3873  C    LEU B 200      43.707  42.991  65.738  1.000  36.55
ATOM   3874  O    LEU B 200      43.563  42.331  64.706  1.000  39.15
ATOM   3875  N    ILE B 201      43.977  42.484  66.938  1.000  29.95
ATOM   3876  CA   ILE B 201      44.033  41.033  67.101  1.000  25.47
ATOM   3877  CB   ILE B 201      45.314  40.531  67.770  1.000  25.78
ATOM   3878  CG1  ILE B 201      46.630  40.929  67.102  1.000  24.11
ATOM   3879  CD1  ILE B 201      46.743  40.486  65.660  1.000  22.88
ATOM   3880  CG2  ILE B 201      45.271  39.009  67.912  1.000  28.86
ATOM   3881  C    ILE B 201      42.824  40.609  67.935  1.000  25.30
ATOM   3882  O    ILE B 201      42.468  41.326  68.864  1.000  36.64
ATOM   3883  N    ARG B 202      42.229  39.478  67.597  1.000  29.04
ATOM   3884  CA   ARG B 202      41.111  38.919  68.353  1.000  28.15
ATOM   3885  CB   ARG B 202      39.928  38.698  67.421  1.000  32.44
ATOM   3886  CG   ARG B 202      38.587  39.177  67.941  1.000  38.49
ATOM   3887  CD   ARG B 202      38.061  40.347  67.121  1.000  51.50
ATOM   3888  NE   ARG B 202      36.996  41.057  67.815  1.000  62.80
ATOM   3889  CZ   ARG B 202      36.709  42.345  67.754  1.000  72.90
ATOM   3890  NH1  ARG B 202      37.410  43.184  67.004  1.000  64.58
ATOM   3891  NH2  ARG B 202      35.690  42.818  68.467  1.000  95.35
ATOM   3892  C    ARG B 202      41.552  37.621  69.013  1.000  24.66
ATOM   3893  O    ARG B 202      41.976  36.706  68.299  1.000  31.26
ATOM   3894  N    HIS B 203      41.479  37.532  70.330  1.000  19.54
ATOM   3895  CA   HIS B 203      41.943  36.336  71.046  1.000  27.13
ATOM   3896  CB   HIS B 203      43.011  36.754  72.047  1.000  23.50
ATOM   3897  CG   HIS B 203      43.762  35.711  72.798  1.000  26.59
ATOM   3898  ND1  HIS B 203      43.264  35.062  73.902  1.000  33.06
ATOM   3899  CE1  HIS B 203      44.154  34.200  74.365  1.000  29.95
```

FIGURE 81

```
ATOM   3900  NE2 HIS B 203      45.231  34.264  73.603 1.000 28.32
ATOM   3901  CD2 HIS B 203      45.012  35.203  72.620 1.000 29.08
ATOM   3902  C   HIS B 203      40.790  35.608  71.729 1.000 29.92
ATOM   3903  O   HIS B 203      40.060  36.152  72.557 1.000 25.16
ATOM   3904  N   PHE B 204      40.599  34.337  71.385 1.000 23.26
ATOM   3905  CA  PHE B 204      39.474  33.561  71.878 1.000 17.30
ATOM   3906  CB  PHE B 204      38.735  32.923  70.702 1.000 21.59
ATOM   3907  CG  PHE B 204      38.310  33.929  69.657 1.000 29.41
ATOM   3908  CD1 PHE B 204      39.097  34.183  68.548 1.000 28.21
ATOM   3909  CE1 PHE B 204      38.720  35.091  67.585 1.000 29.05
ATOM   3910  CZ  PHE B 204      37.537  35.792  67.732 1.000 29.20
ATOM   3911  CE2 PHE B 204      36.737  35.544  68.829 1.000 29.69
ATOM   3912  CD2 PHE B 204      37.114  34.616  69.779 1.000 29.48
ATOM   3913  C   PHE B 204      39.947  32.481  72.844 1.000 28.09
ATOM   3914  O   PHE B 204      40.557  31.502  72.406 1.000 31.26
ATOM   3915  N   HIS B 205      39.676  32.681  74.133 1.000 18.80
ATOM   3916  CA  HIS B 205      40.188  31.784  75.156 1.000 21.65
ATOM   3917  CB  HIS B 205      40.883  32.621  76.249 1.000 23.81
ATOM   3918  CG  HIS B 205      41.692  31.816  77.216 1.000 24.84
ATOM   3919  ND1 HIS B 205      42.280  32.371  78.328 1.000 29.84
ATOM   3920  CE1 HIS B 205      42.931  31.440  78.997 1.000 32.02
ATOM   3921  NE2 HIS B 205      42.793  30.285  78.364 1.000 25.82
ATOM   3922  CD2 HIS B 205      42.029  30.502  77.251 1.000 28.58
ATOM   3923  C   HIS B 205      39.114  30.895  75.778 1.000 28.42
ATOM   3924  O   HIS B 205      38.277  31.351  76.564 1.000 24.92
ATOM   3925  N   TYR B 206      39.190  29.613  75.438 1.000 26.78
ATOM   3926  CA  TYR B 206      38.347  28.572  76.005 1.000 25.27
ATOM   3927  CB  TYR B 206      38.308  27.361  75.091 1.000 25.32
ATOM   3928  CG  TYR B 206      37.302  26.289  75.429 1.000 21.60
ATOM   3929  CD1 TYR B 206      35.946  26.502  75.229 1.000 21.30
ATOM   3930  CE1 TYR B 206      35.027  25.519  75.537 1.000 22.97
ATOM   3931  CZ  TYR B 206      35.457  24.313  76.039 1.000 26.67
ATOM   3932  OH  TYR B 206      34.536  23.336  76.341 1.000 53.16
ATOM   3933  CE2 TYR B 206      36.799  24.073  76.248 1.000 25.66
ATOM   3934  CD2 TYR B 206      37.708  25.067  75.939 1.000 23.88
ATOM   3935  C   TYR B 206      38.850  28.115  77.369 1.000 23.63
ATOM   3936  O   TYR B 206      39.927  27.531  77.442 1.000 22.75
ATOM   3937  N   THR B 207      38.078  28.362  78.419 1.000 28.47
ATOM   3938  CA  THR B 207      38.594  28.239  79.781 1.000 34.58
ATOM   3939  CB  THR B 207      38.251  29.523  80.579 1.000 29.68
ATOM   3940  OG1 THR B 207      36.868  29.844  80.409 1.000 32.12
ATOM   3941  CG2 THR B 207      39.025  30.717  80.039 1.000 27.42
ATOM   3942  C   THR B 207      38.079  27.031  80.540 1.000 38.19
ATOM   3943  O   THR B 207      38.351  26.891  81.740 1.000 46.50
ATOM   3944  N   VAL B 208      37.333  26.118  79.912 1.000 36.23
ATOM   3945  CA  VAL B 208      36.752  25.066  80.760 1.000 32.80
ATOM   3946  CB  VAL B 208      35.226  25.275  80.831 1.000 28.19
ATOM   3947  CG1 VAL B 208      34.942  26.537  81.638 1.000 27.38
ATOM   3948  CG2 VAL B 208      34.601  25.387  79.454 1.000 32.82
ATOM   3949  C   VAL B 208      37.089  23.660  80.314 1.000 39.69
ATOM   3950  O   VAL B 208      36.491  22.707  80.825 1.000 41.93
ATOM   3951  N   TRP B 209      38.039  23.467  79.397 1.000 40.70
```

FIGURE 82

```
ATOM   3952  CA   TRP B 209      38.445  22.102  79.049  1.000  36.47
ATOM   3953  CB   TRP B 209      39.577  22.083  78.032  1.000  31.02
ATOM   3954  CG   TRP B 209      39.652  20.846  77.194  1.000  28.16
ATOM   3955  CD1  TRP B 209      39.949  19.583  77.597  1.000  27.98
ATOM   3956  NE1  TRP B 209      39.921  18.716  76.527  1.000  33.60
ATOM   3957  CE2  TRP B 209      39.600  19.427  75.396  1.000  27.75
ATOM   3958  CD2  TRP B 209      39.426  20.768  75.775  1.000  24.17
ATOM   3959  CE3  TRP B 209      39.092  21.719  74.805  1.000  28.32
ATOM   3960  CZ3  TRP B 209      38.941  21.300  73.496  1.000  34.71
ATOM   3961  CH2  TRP B 209      39.121  19.954  73.151  1.000  31.19
ATOM   3962  CZ2  TRP B 209      39.450  18.999  74.078  1.000  21.94
ATOM   3963  C    TRP B 209      38.888  21.358  80.309  1.000  39.28
ATOM   3964  O    TRP B 209      39.737  21.872  81.039  1.000  33.04
ATOM   3965  N    PRO B 210      38.325  20.185  80.563  1.000  38.49
ATOM   3966  CA   PRO B 210      38.574  19.480  81.825  1.000  33.55
ATOM   3967  CB   PRO B 210      37.657  18.251  81.742  1.000  33.67
ATOM   3968  CG   PRO B 210      36.654  18.591  80.688  1.000  33.65
ATOM   3969  CD   PRO B 210      37.408  19.429  79.689  1.000  31.99
ATOM   3970  C    PRO B 210      40.020  19.024  81.943  1.000  39.20
ATOM   3971  O    PRO B 210      40.737  18.955  80.943  1.000  45.02
ATOM   3972  N    ASP B 211      40.425  18.710  83.167  1.000  42.94
ATOM   3973  CA   ASP B 211      41.772  18.214  83.426  1.000  48.87
ATOM   3974  CB   ASP B 211      42.010  18.080  84.934  1.000  57.39
ATOM   3975  CG   ASP B 211      42.375  19.402  85.586  1.000  66.45
ATOM   3976  OD1  ASP B 211      42.136  20.463  84.966  1.000  52.25
ATOM   3977  OD2  ASP B 211      42.903  19.369  86.721  1.000  87.29
ATOM   3978  C    ASP B 211      42.020  16.872  82.747  1.000  39.83
ATOM   3979  O    ASP B 211      43.122  16.559  82.300  1.000  47.17
ATOM   3980  N    HIS B 212      40.987  16.044  82.672  1.000  40.86
ATOM   3981  CA   HIS B 212      41.117  14.730  82.050  1.000  47.36
ATOM   3982  CB   HIS B 212      41.076  13.599  83.066  1.000  59.57
ATOM   3983  CG   HIS B 212      42.146  13.536  84.102  1.000  71.70
ATOM   3984  ND1  HIS B 212      42.060  14.183  85.313  1.000  74.03
ATOM   3985  CE1  HIS B 212      43.144  13.953  86.032  1.000  77.44
ATOM   3986  NE2  HIS B 212      43.938  13.155  85.336  1.000  79.18
ATOM   3987  CD2  HIS B 212      43.332  12.879  84.131  1.000  78.65
ATOM   3988  C    HIS B 212      39.976  14.556  81.049  1.000  44.25
ATOM   3989  O    HIS B 212      38.865  14.996  81.354  1.000  50.41
ATOM   3990  N    GLY B 213      40.237  13.936  79.906  1.000  43.28
ATOM   3991  CA   GLY B 213      39.210  13.707  78.905  1.000  34.05
ATOM   3992  C    GLY B 213      38.716  14.968  78.223  1.000  36.21
ATOM   3993  O    GLY B 213      39.361  16.015  78.258  1.000  46.36
ATOM   3994  N    VAL B 214      37.550  14.875  77.595  1.000  38.56
ATOM   3995  CA   VAL B 214      36.931  15.933  76.818  1.000  39.41
ATOM   3996  CB   VAL B 214      36.356  15.345  75.510  1.000  40.18
ATOM   3997  CG1  VAL B 214      37.467  14.671  74.725  1.000  35.68
ATOM   3998  CG2  VAL B 214      35.226  14.382  75.831  1.000  48.90
ATOM   3999  C    VAL B 214      35.809  16.620  77.575  1.000  43.12
ATOM   4000  O    VAL B 214      35.366  16.105  78.602  1.000  64.15
ATOM   4001  N    PRO B 215      35.344  17.763  77.089  1.000  42.93
ATOM   4002  CA   PRO B 215      34.151  18.378  77.679  1.000  40.14
ATOM   4003  CB   PRO B 215      33.784  19.448  76.653  1.000  42.40
```

FIGURE 83

```
ATOM   4004  CG   PRO B 215      35.090  19.835  76.040  1.000 41.27
ATOM   4005  CD   PRO B 215      35.888  18.567  75.982  1.000 37.96
ATOM   4006  C    PRO B 215      33.008  17.374  77.800  1.000 45.59
ATOM   4007  O    PRO B 215      32.766  16.617  76.859  1.000 40.94
ATOM   4008  N    GLU B 216      32.333  17.381  78.942  1.000 50.95
ATOM   4009  CA   GLU B 216      31.204  16.498  79.215  1.000 53.03
ATOM   4010  CB   GLU B 216      30.693  16.699  80.643  1.000 59.73
ATOM   4011  CG   GLU B 216      29.489  15.856  81.030  1.000 65.18
ATOM   4012  CD   GLU B 216      28.745  16.402  82.236  1.000 71.96
ATOM   4013  OE1  GLU B 216      29.388  16.616  83.292  1.000 79.59
ATOM   4014  OE2  GLU B 216      27.515  16.622  82.138  1.000 56.48
ATOM   4015  C    GLU B 216      30.083  16.748  78.217  1.000 50.99
ATOM   4016  O    GLU B 216      29.274  15.873  77.907  1.000 49.11
ATOM   4017  N    THR B 217      30.038  17.981  77.699  1.000 46.20
ATOM   4018  CA   THR B 217      29.017  18.266  76.693  1.000 46.03
ATOM   4019  CB   THR B 217      28.092  19.430  77.079  1.000 38.73
ATOM   4020  OG1  THR B 217      26.778  19.154  76.564  1.000 61.70
ATOM   4021  CG2  THR B 217      28.539  20.738  76.440  1.000 30.35
ATOM   4022  C    THR B 217      29.666  18.582  75.347  1.000 49.34
ATOM   4023  O    THR B 217      30.797  19.060  75.290  1.000 48.39
ATOM   4024  N    THR B 218      28.918  18.307  74.287  1.000 45.15
ATOM   4025  CA   THR B 218      29.328  18.657  72.938  1.000 38.83
ATOM   4026  CB   THR B 218      28.599  17.780  71.908  1.000 40.05
ATOM   4027  OG1  THR B 218      27.195  18.052  72.006  1.000 47.92
ATOM   4028  CG2  THR B 218      28.789  16.302  72.204  1.000 37.44
ATOM   4029  C    THR B 218      29.025  20.122  72.648  1.000 40.85
ATOM   4030  O    THR B 218      29.781  20.830  71.985  1.000 49.43
ATOM   4031  N    GLN B 219      27.886  20.590  73.149  1.000 39.19
ATOM   4032  CA   GLN B 219      27.423  21.943  72.863  1.000 40.36
ATOM   4033  CB   GLN B 219      26.112  22.238  73.599  1.000 47.97
ATOM   4034  CG   GLN B 219      25.063  22.954  72.773  1.000 57.22
ATOM   4035  CD   GLN B 219      24.636  24.294  73.334  1.000 65.42
ATOM   4036  OE1  GLN B 219      24.948  24.653  74.471  1.000 76.84
ATOM   4037  NE2  GLN B 219      23.901  25.061  72.531  1.000 73.40
ATOM   4038  C    GLN B 219      28.486  22.976  73.229  1.000 40.36
ATOM   4039  O    GLN B 219      28.610  23.987  72.535  1.000 40.22
ATOM   4040  N    SER B 220      29.229  22.716  74.293  1.000 38.53
ATOM   4041  CA   SER B 220      30.296  23.588  74.774  1.000 40.28
ATOM   4042  CB   SER B 220      31.039  22.897  75.927  1.000 36.16
ATOM   4043  OG   SER B 220      31.787  23.830  76.681  1.000 43.68
ATOM   4044  C    SER B 220      31.282  23.969  73.678  1.000 39.40
ATOM   4045  O    SER B 220      31.451  25.138  73.322  1.000 40.25
ATOM   4046  N    LEU B 221      31.977  22.990  73.102  1.000 42.59
ATOM   4047  CA   LEU B 221      32.991  23.314  72.093  1.000 37.94
ATOM   4048  CB   LEU B 221      33.912  22.118  71.864  1.000 36.81
ATOM   4049  CG   LEU B 221      35.282  22.419  71.247  1.000 44.42
ATOM   4050  CD1  LEU B 221      36.044  23.445  72.073  1.000 31.31
ATOM   4051  CD2  LEU B 221      36.111  21.152  71.101  1.000 39.34
ATOM   4052  C    LEU B 221      32.323  23.778  70.805  1.000 37.27
ATOM   4053  O    LEU B 221      32.776  24.708  70.136  1.000 50.72
ATOM   4054  N    ILE B 222      31.217  23.135  70.456  1.000 35.78
ATOM   4055  CA   ILE B 222      30.451  23.526  69.277  1.000 40.80
```

FIGURE 84

```
ATOM   4056  CB   ILE B 222      29.169  22.678  69.172  1.000  36.72
ATOM   4057  CG1  ILE B 222      29.431  21.240  68.707  1.000  28.35
ATOM   4058  CD1  ILE B 222      28.159  20.425  68.645  1.000  27.69
ATOM   4059  CG2  ILE B 222      28.131  23.351  68.293  1.000  33.22
ATOM   4060  C    ILE B 222      30.103  25.005  69.293  1.000  36.01
ATOM   4061  O    ILE B 222      30.270  25.723  68.300  1.000  32.03
ATOM   4062  N    GLN B 223      29.607  25.516  70.425  1.000  29.32
ATOM   4063  CA   GLN B 223      29.310  26.951  70.415  1.000  35.50
ATOM   4064  CB   GLN B 223      28.535  27.378  71.662  1.000  46.37
ATOM   4065  CG   GLN B 223      27.155  27.943  71.365  1.000  60.65
ATOM   4066  CD   GLN B 223      26.869  29.302  71.968  1.000  64.54
ATOM   4067  OE1  GLN B 223      27.164  30.353  71.390  1.000  52.88
ATOM   4068  NE2  GLN B 223      26.268  29.309  73.157  1.000  64.34
ATOM   4069  C    GLN B 223      30.601  27.759  70.275  1.000  32.82
ATOM   4070  O    GLN B 223      30.633  28.704  69.482  1.000  40.85
ATOM   4071  N    PHE B 224      31.643  27.396  71.019  1.000  25.74
ATOM   4072  CA   PHE B 224      32.907  28.131  70.963  1.000  27.71
ATOM   4073  CB   PHE B 224      33.949  27.479  71.869  1.000  24.79
ATOM   4074  CG   PHE B 224      35.314  28.117  71.858  1.000  25.53
ATOM   4075  CD1  PHE B 224      35.532  29.343  72.466  1.000  23.05
ATOM   4076  CE1  PHE B 224      36.785  29.925  72.476  1.000  27.91
ATOM   4077  CZ   PHE B 224      37.861  29.306  71.869  1.000  21.81
ATOM   4078  CE2  PHE B 224      37.654  28.086  71.253  1.000  21.78
ATOM   4079  CD2  PHE B 224      36.400  27.506  71.255  1.000  21.56
ATOM   4080  C    PHE B 224      33.441  28.175  69.535  1.000  25.15
ATOM   4081  O    PHE B 224      33.832  29.206  68.999  1.000  25.80
ATOM   4082  N    VAL B 225      33.454  27.006  68.903  1.000  26.67
ATOM   4083  CA   VAL B 225      33.933  26.919  67.532  1.000  29.86
ATOM   4084  CB   VAL B 225      33.999  25.467  67.029  1.000  20.12
ATOM   4085  CG1  VAL B 225      34.080  25.457  65.499  1.000  25.23
ATOM   4086  CG2  VAL B 225      35.171  24.740  67.654  1.000  26.39
ATOM   4087  C    VAL B 225      33.042  27.709  66.581  1.000  34.74
ATOM   4088  O    VAL B 225      33.545  28.329  65.644  1.000  35.87
ATOM   4089  N    ARG B 226      31.732  27.673  66.823  1.000  30.68
ATOM   4090  CA   ARG B 226      30.851  28.464  65.957  1.000  28.68
ATOM   4091  CB   ARG B 226      29.398  28.070  66.220  1.000  35.23
ATOM   4092  CG   ARG B 226      29.089  26.678  65.666  1.000  37.49
ATOM   4093  CD   ARG B 226      27.609  26.495  65.389  1.000  45.19
ATOM   4094  NE   ARG B 226      27.284  25.237  64.718  1.000  47.88
ATOM   4095  CZ   ARG B 226      26.232  24.481  65.025  1.000  52.72
ATOM   4096  NH1  ARG B 226      25.394  24.845  65.994  1.000  43.21
ATOM   4097  NH2  ARG B 226      26.003  23.348  64.369  1.000  42.49
ATOM   4098  C    ARG B 226      31.120  29.943  66.166  1.000  34.17
ATOM   4099  O    ARG B 226      31.166  30.741  65.228  1.000  36.74
ATOM   4100  N    THR B 227      31.340  30.366  67.409  1.000  28.96
ATOM   4101  CA   THR B 227      31.672  31.767  67.647  1.000  24.50
ATOM   4102  CB   THR B 227      31.786  32.029  69.165  1.000  34.83
ATOM   4103  OG1  THR B 227      30.553  31.661  69.790  1.000  51.39
ATOM   4104  CG2  THR B 227      32.011  33.502  69.440  1.000  28.79
ATOM   4105  C    THR B 227      32.980  32.179  66.987  1.000  26.81
ATOM   4106  O    THR B 227      33.096  33.245  66.375  1.000  44.96
ATOM   4107  N    VAL B 228      34.011  31.345  67.106  1.000  28.59
```

FIGURE 85

| | | | | | | | | | |
|---|---|---|---|---|---|---|---|---|---|
| ATOM | 4108 | CA | VAL | B | 228 | 35.306 | 31.681 | 66.512 | 1.000 31.86 |
| ATOM | 4109 | CB | VAL | B | 228 | 36.413 | 30.705 | 66.949 | 1.000 36.11 |
| ATOM | 4110 | CG1 | VAL | B | 228 | 37.648 | 30.824 | 66.068 | 1.000 29.10 |
| ATOM | 4111 | CG2 | VAL | B | 228 | 36.821 | 30.927 | 68.408 | 1.000 24.69 |
| ATOM | 4112 | C | VAL | B | 228 | 35.169 | 31.706 | 64.996 | 1.000 31.35 |
| ATOM | 4113 | O | VAL | B | 228 | 35.760 | 32.543 | 64.321 | 1.000 23.32 |
| ATOM | 4114 | N | ARG | B | 229 | 34.386 | 30.796 | 64.422 | 1.000 32.50 |
| ATOM | 4115 | CA | ARG | B | 229 | 34.313 | 30.758 | 62.950 | 1.000 35.15 |
| ATOM | 4116 | CB | ARG | B | 229 | 33.635 | 29.463 | 62.517 | 1.000 29.29 |
| ATOM | 4117 | CG | ARG | B | 229 | 33.187 | 29.363 | 61.077 | 1.000 32.09 |
| ATOM | 4118 | CD | ARG | B | 229 | 34.246 | 29.762 | 60.075 | 1.000 36.20 |
| ATOM | 4119 | NE | ARG | B | 229 | 35.498 | 29.024 | 60.225 | 1.000 34.10 |
| ATOM | 4120 | CZ | ARG | B | 229 | 36.530 | 29.145 | 59.398 | 1.000 31.12 |
| ATOM | 4121 | NH1 | ARG | B | 229 | 36.458 | 29.976 | 58.364 | 1.000 29.99 |
| ATOM | 4122 | NH2 | ARG | B | 229 | 37.637 | 28.440 | 59.603 | 1.000 25.49 |
| ATOM | 4123 | C | ARG | B | 229 | 33.634 | 32.009 | 62.407 | 1.000 37.12 |
| ATOM | 4124 | O | ARG | B | 229 | 34.041 | 32.534 | 61.363 | 1.000 38.65 |
| ATOM | 4125 | N | ASP | B | 230 | 32.621 | 32.517 | 63.102 | 1.000 33.49 |
| ATOM | 4126 | CA | ASP | B | 230 | 31.983 | 33.770 | 62.716 | 1.000 34.08 |
| ATOM | 4127 | CB | ASP | B | 230 | 30.892 | 34.161 | 63.717 | 1.000 43.05 |
| ATOM | 4128 | CG | ASP | B | 230 | 29.629 | 33.328 | 63.559 | 1.000 58.43 |
| ATOM | 4129 | OD1 | ASP | B | 230 | 29.284 | 32.975 | 62.409 | 1.000 90.62 |
| ATOM | 4130 | OD2 | ASP | B | 230 | 28.986 | 33.029 | 64.589 | 1.000 59.92 |
| ATOM | 4131 | C | ASP | B | 230 | 32.996 | 34.899 | 62.621 | 1.000 32.94 |
| ATOM | 4132 | O | ASP | B | 230 | 32.925 | 35.752 | 61.737 | 1.000 48.01 |
| ATOM | 4133 | N | TYR | B | 231 | 33.967 | 34.941 | 63.537 | 1.000 28.38 |
| ATOM | 4134 | CA | TYR | B | 231 | 34.903 | 36.062 | 63.457 | 1.000 31.35 |
| ATOM | 4135 | CB | TYR | B | 231 | 35.624 | 36.312 | 64.779 | 1.000 33.15 |
| ATOM | 4136 | CG | TYR | B | 231 | 34.805 | 37.080 | 65.791 | 1.000 35.44 |
| ATOM | 4137 | CD1 | TYR | B | 231 | 33.863 | 36.439 | 66.582 | 1.000 39.03 |
| ATOM | 4138 | CE1 | TYR | B | 231 | 33.119 | 37.148 | 67.508 | 1.000 45.49 |
| ATOM | 4139 | CZ | TYR | B | 231 | 33.311 | 38.506 | 67.647 | 1.000 43.26 |
| ATOM | 4140 | OH | TYR | B | 231 | 32.572 | 39.217 | 68.563 | 1.000 57.83 |
| ATOM | 4141 | CE2 | TYR | B | 231 | 34.240 | 39.164 | 66.874 | 1.000 37.85 |
| ATOM | 4142 | CD2 | TYR | B | 231 | 34.981 | 38.448 | 65.951 | 1.000 38.89 |
| ATOM | 4143 | C | TYR | B | 231 | 35.937 | 35.836 | 62.358 | 1.000 32.28 |
| ATOM | 4144 | O | TYR | B | 231 | 36.404 | 36.825 | 61.794 | 1.000 29.21 |
| ATOM | 4145 | N | ILE | B | 232 | 36.288 | 34.583 | 62.079 | 1.000 29.70 |
| ATOM | 4146 | CA | ILE | B | 232 | 37.274 | 34.317 | 61.032 | 1.000 26.08 |
| ATOM | 4147 | CB | ILE | B | 232 | 37.731 | 32.855 | 60.956 | 1.000 26.12 |
| ATOM | 4148 | CG1 | ILE | B | 232 | 38.610 | 32.387 | 62.123 | 1.000 28.07 |
| ATOM | 4149 | CD1 | ILE | B | 232 | 38.492 | 30.888 | 62.342 | 1.000 30.24 |
| ATOM | 4150 | CG2 | ILE | B | 232 | 38.435 | 32.591 | 59.628 | 1.000 13.37 |
| ATOM | 4151 | C | ILE | B | 232 | 36.664 | 34.713 | 59.686 | 1.000 24.35 |
| ATOM | 4152 | O | ILE | B | 232 | 37.327 | 35.289 | 58.829 | 1.000 42.38 |
| ATOM | 4153 | N | ASN | B | 233 | 35.384 | 34.401 | 59.536 | 1.000 24.49 |
| ATOM | 4154 | CA | ASN | B | 233 | 34.678 | 34.774 | 58.310 | 1.000 35.31 |
| ATOM | 4155 | CB | ASN | B | 233 | 33.288 | 34.125 | 58.331 | 1.000 33.92 |
| ATOM | 4156 | CG | ASN | B | 233 | 33.411 | 32.644 | 58.011 | 1.000 35.63 |
| ATOM | 4157 | OD1 | ASN | B | 233 | 34.456 | 32.194 | 57.542 | 1.000 30.58 |
| ATOM | 4158 | ND2 | ASN | B | 233 | 32.353 | 31.889 | 58.275 | 1.000 39.02 |
| ATOM | 4159 | C | ASN | B | 233 | 34.602 | 36.285 | 58.135 | 1.000 39.52 |

FIGURE 86

| | | | | | | | | | |
|---|---|---|---|---|---|---|---|---|---|
| ATOM | 4160 | O | ASN | B | 233 | 34.526 | 36.785 | 57.012 | 1.000 35.15 |
| ATOM | 4161 | N | ARG | B | 234 | 34.636 | 37.051 | 59.217 | 1.000 38.25 |
| ATOM | 4162 | CA | ARG | B | 234 | 34.605 | 38.501 | 59.186 | 1.000 36.43 |
| ATOM | 4163 | CB | ARG | B | 234 | 33.826 | 39.055 | 60.391 | 1.000 49.91 |
| ATOM | 4164 | CG | ARG | B | 234 | 32.397 | 38.562 | 60.514 | 1.000 60.74 |
| ATOM | 4165 | CD | ARG | B | 234 | 31.528 | 39.486 | 61.349 | 1.000 58.98 |
| ATOM | 4166 | NE | ARG | B | 234 | 30.847 | 38.790 | 62.440 | 1.000 54.26 |
| ATOM | 4167 | CZ | ARG | B | 234 | 31.260 | 38.870 | 63.702 | 1.000 52.64 |
| ATOM | 4168 | NH1 | ARG | B | 234 | 32.325 | 39.608 | 63.990 | 1.000 52.91 |
| ATOM | 4169 | NH2 | ARG | B | 234 | 30.626 | 38.228 | 64.671 | 1.000 46.68 |
| ATOM | 4170 | C | ARG | B | 234 | 35.998 | 39.117 | 59.211 | 1.000 33.22 |
| ATOM | 4171 | O | ARG | B | 234 | 36.115 | 40.331 | 59.418 | 1.000 48.40 |
| ATOM | 4172 | N | SER | B | 235 | 37.061 | 38.347 | 59.020 | 1.000 28.34 |
| ATOM | 4173 | CA | SER | B | 235 | 38.421 | 38.885 | 59.043 | 1.000 32.54 |
| ATOM | 4174 | CB | SER | B | 235 | 39.279 | 38.104 | 60.042 | 1.000 34.07 |
| ATOM | 4175 | OG | SER | B | 235 | 38.666 | 38.004 | 61.314 | 1.000 34.54 |
| ATOM | 4176 | C | SER | B | 235 | 39.076 | 38.841 | 57.671 | 1.000 40.54 |
| ATOM | 4177 | O | SER | B | 235 | 40.079 | 38.152 | 57.421 | 1.000 36.22 |
| ATOM | 4178 | N | PRO | B | 236 | 38.561 | 39.592 | 56.707 | 1.000 42.54 |
| ATOM | 4179 | CA | PRO | B | 236 | 39.064 | 39.383 | 55.341 | 1.000 46.53 |
| ATOM | 4180 | CB | PRO | B | 236 | 38.093 | 40.193 | 54.494 | 1.000 50.52 |
| ATOM | 4181 | CG | PRO | B | 236 | 37.658 | 41.297 | 55.406 | 1.000 55.25 |
| ATOM | 4182 | CD | PRO | B | 236 | 37.577 | 40.675 | 56.775 | 1.000 50.10 |
| ATOM | 4183 | C | PRO | B | 236 | 40.491 | 39.914 | 55.278 | 1.000 45.59 |
| ATOM | 4184 | O | PRO | B | 236 | 40.815 | 40.861 | 56.008 | 1.000 34.18 |
| ATOM | 4185 | N | GLY | B | 237 | 41.304 | 39.292 | 54.422 | 1.000 33.61 |
| ATOM | 4186 | CA | GLY | B | 237 | 42.692 | 39.734 | 54.313 | 1.000 30.68 |
| ATOM | 4187 | C | GLY | B | 237 | 43.533 | 39.226 | 55.468 | 1.000 27.98 |
| ATOM | 4188 | O | GLY | B | 237 | 44.720 | 39.537 | 55.554 | 1.000 36.96 |
| ATOM | 4189 | N | ALA | B | 238 | 42.940 | 38.440 | 56.365 | 1.000 31.80 |
| ATOM | 4190 | CA | ALA | B | 238 | 43.680 | 37.890 | 57.499 | 1.000 29.23 |
| ATOM | 4191 | CB | ALA | B | 238 | 42.706 | 37.471 | 58.590 | 1.000 24.93 |
| ATOM | 4192 | C | ALA | B | 238 | 44.543 | 36.705 | 57.090 | 1.000 29.82 |
| ATOM | 4193 | O | ALA | B | 238 | 44.178 | 35.916 | 56.220 | 1.000 23.87 |
| ATOM | 4194 | N | GLY | B | 239 | 45.703 | 36.544 | 57.722 | 1.000 26.54 |
| ATOM | 4195 | CA | GLY | B | 239 | 46.486 | 35.346 | 57.425 | 1.000 26.69 |
| ATOM | 4196 | C | GLY | B | 239 | 45.930 | 34.157 | 58.191 | 1.000 26.81 |
| ATOM | 4197 | O | GLY | B | 239 | 44.747 | 34.100 | 58.534 | 1.000 29.92 |
| ATOM | 4198 | N | PRO | B | 240 | 46.775 | 33.188 | 58.496 | 1.000 20.79 |
| ATOM | 4199 | CA | PRO | B | 240 | 46.306 | 31.999 | 59.199 | 1.000 22.49 |
| ATOM | 4200 | CB | PRO | B | 240 | 47.566 | 31.135 | 59.350 | 1.000 22.87 |
| ATOM | 4201 | CG | PRO | B | 240 | 48.509 | 31.669 | 58.321 | 1.000 27.01 |
| ATOM | 4202 | CD | PRO | B | 240 | 48.223 | 33.140 | 58.223 | 1.000 26.31 |
| ATOM | 4203 | C | PRO | B | 240 | 45.763 | 32.328 | 60.583 | 1.000 25.93 |
| ATOM | 4204 | O | PRO | B | 240 | 46.235 | 33.194 | 61.314 | 1.000 24.16 |
| ATOM | 4205 | N | THR | B | 241 | 44.723 | 31.581 | 60.949 | 1.000 27.93 |
| ATOM | 4206 | CA | THR | B | 241 | 44.224 | 31.620 | 62.317 | 1.000 18.48 |
| ATOM | 4207 | CB | THR | B | 241 | 42.791 | 31.078 | 62.389 | 1.000 20.63 |
| ATOM | 4208 | OG1 | THR | B | 241 | 41.906 | 31.922 | 61.633 | 1.000 18.88 |
| ATOM | 4209 | CG2 | THR | B | 241 | 42.286 | 31.088 | 63.823 | 1.000 21.94 |
| ATOM | 4210 | C | THR | B | 241 | 45.177 | 30.793 | 63.182 | 1.000 26.66 |
| ATOM | 4211 | O | THR | B | 241 | 45.459 | 29.624 | 62.873 | 1.000 23.21 |

FIGURE 87

```
ATOM   4212  N    VAL B 242      45.693  31.386  64.249  1.000  26.37
ATOM   4213  CA   VAL B 242      46.571  30.686  65.183  1.000  20.09
ATOM   4214  CB   VAL B 242      47.476  31.650  65.969  1.000  17.77
ATOM   4215  CG1  VAL B 242      47.993  30.997  67.245  1.000  24.64
ATOM   4216  CG2  VAL B 242      48.652  32.105  65.118  1.000  18.35
ATOM   4217  C    VAL B 242      45.745  29.871  66.171  1.000  21.82
ATOM   4218  O    VAL B 242      44.763  30.387  66.707  1.000  22.41
ATOM   4219  N    VAL B 243      46.124  28.618  66.415  1.000  24.38
ATOM   4220  CA   VAL B 243      45.444  27.807  67.426  1.000  16.94
ATOM   4221  CB   VAL B 243      44.512  26.759  66.797  1.000  22.95
ATOM   4222  CG1  VAL B 243      43.664  26.072  67.863  1.000  26.25
ATOM   4223  CG2  VAL B 243      43.612  27.396  65.744  1.000  15.21
ATOM   4224  C    VAL B 243      46.477  27.132  68.314  1.000  19.30
ATOM   4225  O    VAL B 243      47.444  26.568  67.807  1.000  19.80
ATOM   4226  N    HIS B 244      46.315  27.189  69.642  1.000  17.73
ATOM   4227  CA   HIS B 244      47.275  26.507  70.500  1.000  23.12
ATOM   4228  CB   HIS B 244      48.487  27.365  70.842  1.000  20.11
ATOM   4229  CG   HIS B 244      48.250  28.450  71.842  1.000  20.40
ATOM   4230  ND1  HIS B 244      48.315  28.263  73.200  1.000  23.45
ATOM   4231  CE1  HIS B 244      48.067  29.396  73.828  1.000  22.23
ATOM   4232  NE2  HIS B 244      47.850  30.330  72.921  1.000  22.87
ATOM   4233  CD2  HIS B 244      47.962  29.762  71.675  1.000  18.95
ATOM   4234  C    HIS B 244      46.582  26.046  71.783  1.000  26.22
ATOM   4235  O    HIS B 244      45.501  26.501  72.131  1.000  23.10
ATOM   4236  N    CYS B 245      47.252  25.119  72.440  1.000  22.02
ATOM   4237  CA   CYS B 245      46.907  24.642  73.777  1.000  19.58
ATOM   4238  CB   CYS B 245      46.233  23.282  73.751  1.000  24.57
ATOM   4239  SG   CYS B 245      47.070  21.959  72.834  1.000  28.98
ATOM   4240  C    CYS B 245      48.229  24.655  74.539  1.000  28.34
ATOM   4241  O    CYS B 245      48.948  25.667  74.457  1.000  29.70
ATOM   4242  N    SER B 246      48.559  23.571  75.231  1.000  25.71
ATOM   4243  CA   SER B 246      49.846  23.537  75.921  1.000  18.89
ATOM   4244  CB   SER B 246      49.839  22.627  77.146  1.000  23.17
ATOM   4245  OG   SER B 246      51.066  22.797  77.853  1.000  25.65
ATOM   4246  C    SER B 246      50.934  23.087  74.951  1.000  24.25
ATOM   4247  O    SER B 246      51.940  23.789  74.856  1.000  33.31
ATOM   4248  N    ALA B 247      50.731  21.962  74.259  1.000  18.83
ATOM   4249  CA   ALA B 247      51.743  21.518  73.314  1.000  15.18
ATOM   4250  CB   ALA B 247      52.036  20.041  73.514  1.000  17.96
ATOM   4251  C    ALA B 247      51.363  21.733  71.851  1.000  26.35
ATOM   4252  O    ALA B 247      52.187  21.474  70.959  1.000  31.41
ATOM   4253  N    GLY B 248      50.146  22.178  71.569  1.000  21.25
ATOM   4254  CA   GLY B 248      49.642  22.228  70.206  1.000  20.49
ATOM   4255  C    GLY B 248      49.312  20.840  69.659  1.000  30.46
ATOM   4256  O    GLY B 248      49.670  20.541  68.517  1.000  41.55
ATOM   4257  N    VAL B 249      48.635  19.983  70.414  1.000  28.50
ATOM   4258  CA   VAL B 249      48.393  18.586  70.073  1.000  34.64
ATOM   4259  CB   VAL B 249      49.048  17.670  71.137  1.000  36.74
ATOM   4260  CG1  VAL B 249      50.523  17.496  70.828  1.000  29.63
ATOM   4261  CG2  VAL B 249      48.858  18.238  72.545  1.000  30.44
ATOM   4262  C    VAL B 249      46.931  18.172  69.964  1.000  33.93
ATOM   4263  O    VAL B 249      46.301  18.395  68.930  1.000  40.05
```

FIGURE 88

| | | | | | | | | | |
|---|---|---|---|---|---|---|---|---|---|
| ATOM | 4264 | N | GLY | B | 250 | 46.392 | 17.537 | 71.003 | 1.000 28.29 |
| ATOM | 4265 | CA | GLY | B | 250 | 45.069 | 16.957 | 71.039 | 1.000 22.14 |
| ATOM | 4266 | C | GLY | B | 250 | 43.943 | 17.966 | 70.997 | 1.000 24.67 |
| ATOM | 4267 | O | GLY | B | 250 | 43.137 | 17.979 | 70.063 | 1.000 30.05 |
| ATOM | 4268 | N | ARG | B | 251 | 43.872 | 18.828 | 72.003 | 1.000 16.63 |
| ATOM | 4269 | CA | ARG | B | 251 | 42.869 | 19.882 | 72.038 | 1.000 19.31 |
| ATOM | 4270 | CB | ARG | B | 251 | 43.124 | 20.810 | 73.240 | 1.000 16.91 |
| ATOM | 4271 | CG | ARG | B | 251 | 43.429 | 20.052 | 74.521 | 1.000 25.85 |
| ATOM | 4272 | CD | ARG | B | 251 | 43.443 | 21.003 | 75.708 | 1.000 27.38 |
| ATOM | 4273 | NE | ARG | B | 251 | 43.437 | 20.283 | 76.974 | 1.000 25.25 |
| ATOM | 4274 | CZ | ARG | B | 251 | 43.500 | 20.852 | 78.167 | 1.000 28.05 |
| ATOM | 4275 | NH1 | ARG | B | 251 | 43.577 | 22.171 | 78.279 | 1.000 20.04 |
| ATOM | 4276 | NH2 | ARG | B | 251 | 43.485 | 20.081 | 79.246 | 1.000 33.27 |
| ATOM | 4277 | C | ARG | B | 251 | 42.857 | 20.719 | 70.764 | 1.000 22.20 |
| ATOM | 4278 | O | ARG | B | 251 | 41.814 | 20.925 | 70.142 | 1.000 37.10 |
| ATOM | 4279 | N | THR | B | 252 | 44.023 | 21.228 | 70.372 | 1.000 25.42 |
| ATOM | 4280 | CA | THR | B | 252 | 44.120 | 22.091 | 69.200 | 1.000 22.56 |
| ATOM | 4281 | CB | THR | B | 252 | 45.571 | 22.546 | 68.965 | 1.000 23.97 |
| ATOM | 4282 | OG1 | THR | B | 252 | 45.903 | 23.531 | 69.956 | 1.000 25.35 |
| ATOM | 4283 | CG2 | THR | B | 252 | 45.734 | 23.196 | 67.600 | 1.000 15.93 |
| ATOM | 4284 | C | THR | B | 252 | 43.631 | 21.357 | 67.965 | 1.000 20.90 |
| ATOM | 4285 | O | THR | B | 252 | 42.825 | 21.833 | 67.170 | 1.000 27.79 |
| ATOM | 4286 | N | GLY | B | 253 | 44.161 | 20.145 | 67.819 | 1.000 23.41 |
| ATOM | 4287 | CA | GLY | B | 253 | 43.796 | 19.353 | 66.642 | 1.000 23.12 |
| ATOM | 4288 | C | GLY | B | 253 | 42.313 | 19.031 | 66.705 | 1.000 28.00 |
| ATOM | 4289 | O | GLY | B | 253 | 41.682 | 18.906 | 65.663 | 1.000 25.61 |
| ATOM | 4290 | N | THR | B | 254 | 41.803 | 18.914 | 67.932 | 1.000 30.82 |
| ATOM | 4291 | CA | THR | B | 254 | 40.382 | 18.631 | 68.136 | 1.000 28.89 |
| ATOM | 4292 | CB | THR | B | 254 | 40.052 | 18.236 | 69.589 | 1.000 30.33 |
| ATOM | 4293 | OG1 | THR | B | 254 | 40.646 | 16.971 | 69.891 | 1.000 17.84 |
| ATOM | 4294 | CG2 | THR | B | 254 | 38.553 | 18.043 | 69.764 | 1.000 23.85 |
| ATOM | 4295 | C | THR | B | 254 | 39.560 | 19.849 | 67.750 | 1.000 24.95 |
| ATOM | 4296 | O | THR | B | 254 | 38.534 | 19.750 | 67.093 | 1.000 25.70 |
| ATOM | 4297 | N | PHE | B | 255 | 40.023 | 21.033 | 68.168 | 1.000 20.14 |
| ATOM | 4298 | CA | PHE | B | 255 | 39.330 | 22.238 | 67.761 | 1.000 18.66 |
| ATOM | 4299 | CB | PHE | B | 255 | 40.055 | 23.472 | 68.309 | 1.000 20.98 |
| ATOM | 4300 | CG | PHE | B | 255 | 39.468 | 24.795 | 67.891 | 1.000 25.32 |
| ATOM | 4301 | CD1 | PHE | B | 255 | 38.462 | 25.342 | 68.685 | 1.000 21.68 |
| ATOM | 4302 | CE1 | PHE | B | 255 | 37.893 | 26.550 | 68.349 | 1.000 20.94 |
| ATOM | 4303 | CZ | PHE | B | 255 | 38.291 | 27.240 | 67.224 | 1.000 24.52 |
| ATOM | 4304 | CE2 | PHE | B | 255 | 39.287 | 26.713 | 66.419 | 1.000 22.92 |
| ATOM | 4305 | CD2 | PHE | B | 255 | 39.877 | 25.519 | 66.779 | 1.000 24.05 |
| ATOM | 4306 | C | PHE | B | 255 | 39.255 | 22.352 | 66.239 | 1.000 20.18 |
| ATOM | 4307 | O | PHE | B | 255 | 38.229 | 22.668 | 65.647 | 1.000 23.46 |
| ATOM | 4308 | N | ILE | B | 256 | 40.401 | 22.192 | 65.592 | 1.000 14.95 |
| ATOM | 4309 | CA | ILE | B | 256 | 40.468 | 22.444 | 64.155 | 1.000 19.23 |
| ATOM | 4310 | CB | ILE | B | 256 | 41.923 | 22.480 | 63.668 | 1.000 24.98 |
| ATOM | 4311 | CG1 | ILE | B | 256 | 42.735 | 23.658 | 64.220 | 1.000 27.51 |
| ATOM | 4312 | CD1 | ILE | B | 256 | 44.198 | 23.613 | 63.833 | 1.000 28.76 |
| ATOM | 4313 | CG2 | ILE | B | 256 | 41.988 | 22.469 | 62.146 | 1.000 19.65 |
| ATOM | 4314 | C | ILE | B | 256 | 39.642 | 21.413 | 63.395 | 1.000 21.66 |
| ATOM | 4315 | O | ILE | B | 256 | 38.931 | 21.770 | 62.448 | 1.000 28.91 |

FIGURE 89

| | | | | | | | | | |
|---|---|---|---|---|---|---|---|---|---|
| ATOM | 4316 | N | ALA | B | 257 | 39.699 | 20.142 | 63.782 | 1.000 18.05 |
| ATOM | 4317 | CA | ALA | B | 257 | 38.802 | 19.169 | 63.158 | 1.000 19.47 |
| ATOM | 4318 | CB | ALA | B | 257 | 38.987 | 17.798 | 63.775 | 1.000 21.30 |
| ATOM | 4319 | C | ALA | B | 257 | 37.346 | 19.600 | 63.303 | 1.000 24.28 |
| ATOM | 4320 | O | ALA | B | 257 | 36.588 | 19.578 | 62.335 | 1.000 29.52 |
| ATOM | 4321 | N | LEU | B | 258 | 36.913 | 19.998 | 64.506 | 1.000 19.55 |
| ATOM | 4322 | CA | LEU | B | 258 | 35.511 | 20.383 | 64.656 | 1.000 23.44 |
| ATOM | 4323 | CB | LEU | B | 258 | 35.187 | 20.725 | 66.109 | 1.000 26.54 |
| ATOM | 4324 | CG | LEU | B | 258 | 33.718 | 21.043 | 66.402 | 1.000 26.93 |
| ATOM | 4325 | CD1 | LEU | B | 258 | 32.830 | 19.879 | 65.989 | 1.000 33.89 |
| ATOM | 4326 | CD2 | LEU | B | 258 | 33.523 | 21.383 | 67.874 | 1.000 26.13 |
| ATOM | 4327 | C | LEU | B | 258 | 35.162 | 21.561 | 63.747 | 1.000 26.19 |
| ATOM | 4328 | O | LEU | B | 258 | 34.104 | 21.555 | 63.113 | 1.000 34.02 |
| ATOM | 4329 | N | ASP | B | 259 | 36.047 | 22.546 | 63.699 | 1.000 24.40 |
| ATOM | 4330 | CA | ASP | B | 259 | 35.925 | 23.714 | 62.834 | 1.000 27.44 |
| ATOM | 4331 | CB | ASP | B | 259 | 37.184 | 24.585 | 62.907 | 1.000 26.51 |
| ATOM | 4332 | CG | ASP | B | 259 | 37.015 | 25.907 | 62.185 | 1.000 31.73 |
| ATOM | 4333 | OD1 | ASP | B | 259 | 35.871 | 26.400 | 62.144 | 1.000 33.45 |
| ATOM | 4334 | OD2 | ASP | B | 259 | 38.013 | 26.448 | 61.664 | 1.000 25.69 |
| ATOM | 4335 | C | ASP | B | 259 | 35.678 | 23.286 | 61.392 | 1.000 22.95 |
| ATOM | 4336 | O | ASP | B | 259 | 34.813 | 23.822 | 60.702 | 1.000 30.45 |
| ATOM | 4337 | N | ARG | B | 260 | 36.446 | 22.302 | 60.950 | 1.000 26.62 |
| ATOM | 4338 | CA | ARG | B | 260 | 36.361 | 21.798 | 59.585 | 1.000 33.18 |
| ATOM | 4339 | CB | ARG | B | 260 | 37.519 | 20.835 | 59.319 | 1.000 31.29 |
| ATOM | 4340 | CG | ARG | B | 260 | 38.785 | 21.473 | 58.778 | 1.000 30.70 |
| ATOM | 4341 | CD | ARG | B | 260 | 39.239 | 20.700 | 57.536 | 1.000 37.95 |
| ATOM | 4342 | NE | ARG | B | 260 | 40.673 | 20.498 | 57.556 | 1.000 41.13 |
| ATOM | 4343 | CZ | ARG | B | 260 | 41.391 | 19.709 | 56.782 | 1.000 33.80 |
| ATOM | 4344 | NH1 | ARG | B | 260 | 40.798 | 18.979 | 55.856 | 1.000 42.79 |
| ATOM | 4345 | NH2 | ARG | B | 260 | 42.705 | 19.660 | 56.957 | 1.000 37.06 |
| ATOM | 4346 | C | ARG | B | 260 | 35.055 | 21.066 | 59.301 | 1.000 38.95 |
| ATOM | 4347 | O | ARG | B | 260 | 34.398 | 21.344 | 58.296 | 1.000 34.89 |
| ATOM | 4348 | N | ILE | B | 261 | 34.673 | 20.123 | 60.157 | 1.000 40.78 |
| ATOM | 4349 | CA | ILE | B | 261 | 33.506 | 19.282 | 59.888 | 1.000 36.65 |
| ATOM | 4350 | CB | ILE | B | 261 | 33.512 | 18.013 | 60.759 | 1.000 36.83 |
| ATOM | 4351 | CG1 | ILE | B | 261 | 33.172 | 18.232 | 62.236 | 1.000 36.37 |
| ATOM | 4352 | CD1 | ILE | B | 261 | 33.788 | 17.170 | 63.128 | 1.000 27.30 |
| ATOM | 4353 | CG2 | ILE | B | 261 | 34.851 | 17.297 | 60.648 | 1.000 30.19 |
| ATOM | 4354 | C | ILE | B | 261 | 32.193 | 20.033 | 60.076 | 1.000 37.68 |
| ATOM | 4355 | O | ILE | B | 261 | 31.233 | 19.779 | 59.332 | 1.000 29.23 |
| ATOM | 4356 | N | LEU | B | 262 | 32.121 | 20.960 | 61.032 | 1.000 29.30 |
| ATOM | 4357 | CA | LEU | B | 262 | 30.910 | 21.778 | 61.134 | 1.000 34.05 |
| ATOM | 4358 | CB | LEU | B | 262 | 30.909 | 22.676 | 62.372 | 1.000 34.84 |
| ATOM | 4359 | CG | LEU | B | 262 | 30.865 | 21.951 | 63.722 | 1.000 33.81 |
| ATOM | 4360 | CD1 | LEU | B | 262 | 30.907 | 22.931 | 64.886 | 1.000 29.40 |
| ATOM | 4361 | CD2 | LEU | B | 262 | 29.628 | 21.067 | 63.813 | 1.000 31.05 |
| ATOM | 4362 | C | LEU | B | 262 | 30.763 | 22.639 | 59.882 | 1.000 49.12 |
| ATOM | 4363 | O | LEU | B | 262 | 29.667 | 23.081 | 59.538 | 1.000 56.67 |
| ATOM | 4364 | N | GLN | B | 263 | 31.888 | 22.887 | 59.204 | 1.000 44.18 |
| ATOM | 4365 | CA | GLN | B | 263 | 31.808 | 23.682 | 57.982 | 1.000 46.28 |
| ATOM | 4366 | CB | GLN | B | 263 | 33.169 | 24.218 | 57.542 | 1.000 42.43 |
| ATOM | 4367 | CG | GLN | B | 263 | 33.463 | 25.604 | 58.110 | 1.000 37.21 |

FIGURE 90

```
ATOM   4368  CD   GLN B 263      34.905  25.991  57.847 1.000 38.82
ATOM   4369  OE1  GLN B 263      35.200  26.564  56.803 1.000 42.28
ATOM   4370  NE2  GLN B 263      35.789  25.670  58.782 1.000 38.53
ATOM   4371  C    GLN B 263      31.207  22.830  56.870 1.000 43.95
ATOM   4372  O    GLN B 263      30.412  23.325  56.083 1.000 46.04
ATOM   4373  N    GLN B 264      31.609  21.563  56.843 1.000 40.32
ATOM   4374  CA   GLN B 264      31.058  20.637  55.859 1.000 43.58
ATOM   4375  CB   GLN B 264      31.776  19.291  55.904 1.000 41.24
ATOM   4376  CG   GLN B 264      33.299  19.353  55.893 1.000 32.42
ATOM   4377  CD   GLN B 264      33.885  17.975  56.138 1.000 34.83
ATOM   4378  OE1  GLN B 264      33.154  16.982  56.114 1.000 49.05
ATOM   4379  NE2  GLN B 264      35.181  17.880  56.386 1.000 36.65
ATOM   4380  C    GLN B 264      29.557  20.453  56.088 1.000 46.84
ATOM   4381  O    GLN B 264      28.787  20.463  55.125 1.000 60.95
ATOM   4382  N    LEU B 265      29.143  20.293  57.339 1.000 44.06
ATOM   4383  CA   LEU B 265      27.744  20.092  57.689 1.000 48.45
ATOM   4384  CB   LEU B 265      27.541  20.198  59.204 1.000 48.90
ATOM   4385  CG   LEU B 265      28.027  19.015  60.044 1.000 49.51
ATOM   4386  CD1  LEU B 265      27.374  19.048  61.416 1.000 39.17
ATOM   4387  CD2  LEU B 265      27.761  17.702  59.326 1.000 46.39
ATOM   4388  C    LEU B 265      26.816  21.098  57.009 1.000 55.29
ATOM   4389  O    LEU B 265      25.738  20.747  56.529 1.000 61.57
ATOM   4390  N    ASP B 266      27.242  22.353  56.989 1.000 56.37
ATOM   4391  CA   ASP B 266      26.489  23.438  56.374 1.000 56.13
ATOM   4392  CB   ASP B 266      26.708  24.734  57.154 1.000 62.09
ATOM   4393  CG   ASP B 266      26.306  24.619  58.612 1.000 68.79
ATOM   4394  OD1  ASP B 266      25.108  24.405  58.894 1.000 79.54
ATOM   4395  OD2  ASP B 266      27.190  24.742  59.489 1.000 81.01
ATOM   4396  C    ASP B 266      26.905  23.610  54.917 1.000 50.88
ATOM   4397  O    ASP B 266      26.597  24.607  54.265 1.000 58.84
ATOM   4398  N    SER B 267      27.632  22.622  54.407 1.000 53.13
ATOM   4399  CA   SER B 267      28.177  22.699  53.056 1.000 64.34
ATOM   4400  CB   SER B 267      29.708  22.798  53.101 1.000 56.46
ATOM   4401  OG   SER B 267      30.143  24.108  52.784 1.000 60.08
ATOM   4402  C    SER B 267      27.759  21.499  52.214 1.000 75.07
ATOM   4403  O    SER B 267      26.653  21.444  51.677 1.000 79.48
ATOM   4404  N    LYS B 268      28.656  20.523  52.092 1.000 83.42
ATOM   4405  CA   LYS B 268      28.385  19.358  51.257 1.000 86.00
ATOM   4406  CB   LYS B 268      29.664  18.545  51.050 1.000 90.22
ATOM   4407  CG   LYS B 268      30.899  19.402  50.804 1.000 90.85
ATOM   4408  CD   LYS B 268      31.608  19.724  52.110 1.000 87.44
ATOM   4409  CE   LYS B 268      32.908  20.484  51.868 1.000 87.50
ATOM   4410  NZ   LYS B 268      33.982  19.590  51.340 1.000 90.86
ATOM   4411  C    LYS B 268      27.279  18.493  51.854 1.000 79.53
ATOM   4412  O    LYS B 268      26.697  18.840  52.883 1.000 65.16
ATOM   4413  N    ASP B 269      27.000  17.380  51.183 1.000 75.19
ATOM   4414  CA   ASP B 269      25.948  16.453  51.576 1.000 74.46
ATOM   4415  CB   ASP B 269      25.390  15.742  50.342 1.000 83.40
ATOM   4416  CG   ASP B 269      25.381  16.633  49.114 1.000 92.95
ATOM   4417  OD1  ASP B 269      24.301  16.816  48.509 1.000 99.02
ATOM   4418  OD2  ASP B 269      26.460  17.153  48.752 1.000105.13
ATOM   4419  C    ASP B 269      26.475  15.440  52.584 1.000 69.56
```

FIGURE 91

| ATOM | 4420 | O   | ASP | B | 269 | 25.755 | 14.571 | 53.071 | 1.000 | 66.15 |
| ATOM | 4421 | N   | SER | B | 270 | 27.763 | 15.573 | 52.883 | 1.000 | 63.01 |
| ATOM | 4422 | CA  | SER | B | 270 | 28.449 | 14.658 | 53.782 | 1.000 | 53.77 |
| ATOM | 4423 | CB  | SER | B | 270 | 29.261 | 13.633 | 52.991 | 1.000 | 58.45 |
| ATOM | 4424 | OG  | SER | B | 270 | 30.230 | 12.983 | 53.797 | 1.000 | 73.26 |
| ATOM | 4425 | C   | SER | B | 270 | 29.357 | 15.436 | 54.734 | 1.000 | 46.99 |
| ATOM | 4426 | O   | SER | B | 270 | 29.393 | 16.664 | 54.654 | 1.000 | 42.15 |
| ATOM | 4427 | N   | VAL | B | 271 | 30.035 | 14.690 | 55.588 | 1.000 | 48.78 |
| ATOM | 4428 | CA  | VAL | B | 271 | 31.029 | 15.141 | 56.544 | 1.000 | 48.00 |
| ATOM | 4429 | CB  | VAL | B | 271 | 30.446 | 15.379 | 57.946 | 1.000 | 49.59 |
| ATOM | 4430 | CG1 | VAL | B | 271 | 29.390 | 14.335 | 58.283 | 1.000 | 49.18 |
| ATOM | 4431 | CG2 | VAL | B | 271 | 31.569 | 15.369 | 58.980 | 1.000 | 36.94 |
| ATOM | 4432 | C   | VAL | B | 271 | 32.145 | 14.100 | 56.637 | 1.000 | 42.78 |
| ATOM | 4433 | O   | VAL | B | 271 | 31.864 | 12.911 | 56.794 | 1.000 | 49.77 |
| ATOM | 4434 | N   | ASP | B | 272 | 33.390 | 14.532 | 56.524 | 1.000 | 38.85 |
| ATOM | 4435 | CA  | ASP | B | 272 | 34.530 | 13.630 | 56.527 | 1.000 | 35.40 |
| ATOM | 4436 | CB  | ASP | B | 272 | 35.438 | 13.862 | 55.314 | 1.000 | 27.29 |
| ATOM | 4437 | CG  | ASP | B | 272 | 36.212 | 12.617 | 54.924 | 1.000 | 35.62 |
| ATOM | 4438 | OD1 | ASP | B | 272 | 36.101 | 11.583 | 55.615 | 1.000 | 37.07 |
| ATOM | 4439 | OD2 | ASP | B | 272 | 36.947 | 12.666 | 53.915 | 1.000 | 50.42 |
| ATOM | 4440 | C   | ASP | B | 272 | 35.359 | 13.795 | 57.792 | 1.000 | 40.21 |
| ATOM | 4441 | O   | ASP | B | 272 | 36.364 | 14.503 | 57.797 | 1.000 | 41.63 |
| ATOM | 4442 | N   | ILE | B | 273 | 34.929 | 13.131 | 58.862 | 1.000 | 40.79 |
| ATOM | 4443 | CA  | ILE | B | 273 | 35.679 | 13.285 | 60.108 | 1.000 | 34.29 |
| ATOM | 4444 | CB  | ILE | B | 273 | 34.909 | 12.721 | 61.310 | 1.000 | 30.34 |
| ATOM | 4445 | CG1 | ILE | B | 273 | 33.565 | 13.409 | 61.576 | 1.000 | 31.83 |
| ATOM | 4446 | CD1 | ILE | B | 273 | 32.766 | 12.740 | 62.679 | 1.000 | 27.01 |
| ATOM | 4447 | CG2 | ILE | B | 273 | 35.768 | 12.761 | 62.563 | 1.000 | 28.54 |
| ATOM | 4448 | C   | ILE | B | 273 | 37.053 | 12.639 | 59.968 | 1.000 | 39.35 |
| ATOM | 4449 | O   | ILE | B | 273 | 38.060 | 13.284 | 60.295 | 1.000 | 37.96 |
| ATOM | 4450 | N   | TYR | B | 274 | 37.080 | 11.404 | 59.482 | 1.000 | 40.06 |
| ATOM | 4451 | CA  | TYR | B | 274 | 38.320 | 10.692 | 59.209 | 1.000 | 36.37 |
| ATOM | 4452 | CB  | TYR | B | 274 | 38.083 |  9.343 | 58.534 | 1.000 | 34.20 |
| ATOM | 4453 | CG  | TYR | B | 274 | 39.288 |  8.485 | 58.221 | 1.000 | 26.44 |
| ATOM | 4454 | CD1 | TYR | B | 274 | 39.691 |  7.499 | 59.115 | 1.000 | 29.38 |
| ATOM | 4455 | CE1 | TYR | B | 274 | 40.787 |  6.698 | 58.847 | 1.000 | 34.20 |
| ATOM | 4456 | CZ  | TYR | B | 274 | 41.501 |  6.863 | 57.683 | 1.000 | 32.34 |
| ATOM | 4457 | OH  | TYR | B | 274 | 42.595 |  6.077 | 57.401 | 1.000 | 45.24 |
| ATOM | 4458 | CE2 | TYR | B | 274 | 41.126 |  7.829 | 56.774 | 1.000 | 32.36 |
| ATOM | 4459 | CD2 | TYR | B | 274 | 40.033 |  8.609 | 57.056 | 1.000 | 26.39 |
| ATOM | 4460 | C   | TYR | B | 274 | 39.228 | 11.528 | 58.299 | 1.000 | 32.63 |
| ATOM | 4461 | O   | TYR | B | 274 | 40.436 | 11.567 | 58.534 | 1.000 | 31.00 |
| ATOM | 4462 | N   | GLY | B | 275 | 38.634 | 12.102 | 57.266 | 1.000 | 39.31 |
| ATOM | 4463 | CA  | GLY | B | 275 | 39.375 | 12.824 | 56.239 | 1.000 | 35.88 |
| ATOM | 4464 | C   | GLY | B | 275 | 40.102 | 14.006 | 56.865 | 1.000 | 40.67 |
| ATOM | 4465 | O   | GLY | B | 275 | 41.263 | 14.270 | 56.555 | 1.000 | 33.84 |
| ATOM | 4466 | N   | ALA | B | 276 | 39.376 | 14.679 | 57.751 | 1.000 | 36.51 |
| ATOM | 4467 | CA  | ALA | B | 276 | 39.906 | 15.849 | 58.442 | 1.000 | 37.26 |
| ATOM | 4468 | CB  | ALA | B | 276 | 38.791 | 16.511 | 59.244 | 1.000 | 29.45 |
| ATOM | 4469 | C   | ALA | B | 276 | 41.097 | 15.502 | 59.323 | 1.000 | 31.12 |
| ATOM | 4470 | O   | ALA | B | 276 | 42.147 | 16.150 | 59.234 | 1.000 | 27.41 |
| ATOM | 4471 | N   | VAL | B | 277 | 40.972 | 14.480 | 60.169 | 1.000 | 28.39 |

FIGURE 92

```
ATOM   4472  CA   VAL B 277      42.049  14.164  61.101  1.000  26.25
ATOM   4473  CB   VAL B 277      41.639  13.101  62.138  1.000  27.10
ATOM   4474  CG1  VAL B 277      42.882  12.558  62.827  1.000  24.03
ATOM   4475  CG2  VAL B 277      40.671  13.681  63.159  1.000  28.27
ATOM   4476  C    VAL B 277      43.306  13.654  60.402  1.000  31.14
ATOM   4477  O    VAL B 277      44.411  13.880  60.897  1.000  29.79
ATOM   4478  N    HIS B 278      43.121  12.975  59.277  1.000  27.18
ATOM   4479  CA   HIS B 278      44.202  12.495  58.431  1.000  25.97
ATOM   4480  CB   HIS B 278      43.601  11.645  57.309  1.000  33.39
ATOM   4481  CG   HIS B 278      44.609  11.055  56.378  1.000  34.11
ATOM   4482  ND1  HIS B 278      45.201  11.773  55.367  1.000  25.09
ATOM   4483  CE1  HIS B 278      46.048  11.002  54.708  1.000  28.44
ATOM   4484  NE2  HIS B 278      46.026   9.801  55.267  1.000  31.16
ATOM   4485  CD2  HIS B 278      45.138   9.806  56.307  1.000  31.49
ATOM   4486  C    HIS B 278      45.001  13.660  57.859  1.000  24.46
ATOM   4487  O    HIS B 278      46.225  13.753  57.928  1.000  25.14
ATOM   4488  N    ASP B 279      44.283  14.603  57.260  1.000  23.15
ATOM   4489  CA   ASP B 279      44.887  15.817  56.715  1.000  24.67
ATOM   4490  CB   ASP B 279      43.776  16.718  56.178  1.000  29.92
ATOM   4491  CG   ASP B 279      44.160  17.578  55.001  1.000  37.07
ATOM   4492  OD1  ASP B 279      45.077  17.212  54.235  1.000  38.06
ATOM   4493  OD2  ASP B 279      43.537  18.648  54.835  1.000  30.88
ATOM   4494  C    ASP B 279      45.706  16.530  57.784  1.000  25.54
ATOM   4495  O    ASP B 279      46.843  16.941  57.550  1.000  21.93
ATOM   4496  N    LEU B 280      45.150  16.673  58.991  1.000  18.66
ATOM   4497  CA   LEU B 280      45.867  17.373  60.061  1.000  27.59
ATOM   4498  CB   LEU B 280      45.025  17.491  61.331  1.000  23.76
ATOM   4499  CG   LEU B 280      43.732  18.302  61.281  1.000  29.33
ATOM   4500  CD1  LEU B 280      43.374  18.821  62.668  1.000  34.75
ATOM   4501  CD2  LEU B 280      43.836  19.450  60.293  1.000  30.06
ATOM   4502  C    LEU B 280      47.181  16.678  60.432  1.000  33.16
ATOM   4503  O    LEU B 280      48.218  17.326  60.576  1.000  22.56
ATOM   4504  N    ARG B 281      47.077  15.363  60.589  1.000  29.37
ATOM   4505  CA   ARG B 281      48.168  14.491  60.979  1.000  31.07
ATOM   4506  CB   ARG B 281      47.675  13.042  61.092  1.000  28.63
ATOM   4507  CG   ARG B 281      46.655  12.833  62.199  1.000  26.35
ATOM   4508  CD   ARG B 281      47.328  12.460  63.506  1.000  27.07
ATOM   4509  NE   ARG B 281      46.350  12.116  64.535  1.000  30.18
ATOM   4510  CZ   ARG B 281      46.041  10.880  64.893  1.000  27.85
ATOM   4511  NH1  ARG B 281      46.628   9.852  64.310  1.000  31.06
ATOM   4512  NH2  ARG B 281      45.138  10.667  65.838  1.000  39.11
ATOM   4513  C    ARG B 281      49.318  14.561  59.985  1.000  29.17
ATOM   4514  O    ARG B 281      50.478  14.363  60.347  1.000  28.56
ATOM   4515  N    LEU B 282      48.986  14.842  58.727  1.000  30.67
ATOM   4516  CA   LEU B 282      50.041  15.001  57.727  1.000  30.29
ATOM   4517  CB   LEU B 282      49.455  15.139  56.327  1.000  24.52
ATOM   4518  CG   LEU B 282      48.830  13.899  55.689  1.000  27.65
ATOM   4519  CD1  LEU B 282      48.201  14.290  54.357  1.000  22.99
ATOM   4520  CD2  LEU B 282      49.859  12.792  55.511  1.000  27.48
ATOM   4521  C    LEU B 282      50.913  16.222  58.014  1.000  27.27
ATOM   4522  O    LEU B 282      52.030  16.277  57.506  1.000  26.46
ATOM   4523  N    HIS B 283      50.418  17.178  58.794  1.000  26.63
```

FIGURE 93

| | | | | | | | | | |
|---|---|---|---|---|---|---|---|---|---|
| ATOM | 4524 | CA | HIS | B | 283 | 51.104 | 18.459 | 58.962 | 1.000 28.55 |
| ATOM | 4525 | CB | HIS | B | 283 | 50.157 | 19.615 | 58.551 | 1.000 26.78 |
| ATOM | 4526 | CG | HIS | B | 283 | 49.852 | 19.437 | 57.083 | 1.000 31.38 |
| ATOM | 4527 | ND1 | HIS | B | 283 | 50.669 | 19.906 | 56.078 | 1.000 29.31 |
| ATOM | 4528 | CE1 | HIS | B | 283 | 50.164 | 19.584 | 54.901 | 1.000 26.22 |
| ATOM | 4529 | NE2 | HIS | B | 283 | 49.048 | 18.905 | 55.114 | 1.000 26.82 |
| ATOM | 4530 | CD2 | HIS | B | 283 | 48.838 | 18.792 | 56.461 | 1.000 28.69 |
| ATOM | 4531 | C | HIS | B | 283 | 51.658 | 18.636 | 60.359 | 1.000 26.35 |
| ATOM | 4532 | O | HIS | B | 283 | 52.552 | 19.465 | 60.565 | 1.000 24.96 |
| ATOM | 4533 | N | ARG | B | 284 | 51.186 | 17.858 | 61.335 | 1.000 20.29 |
| ATOM | 4534 | CA | ARG | B | 284 | 51.798 | 17.980 | 62.664 | 1.000 21.12 |
| ATOM | 4535 | CB | ARG | B | 284 | 51.322 | 19.245 | 63.391 | 1.000 20.38 |
| ATOM | 4536 | CG | ARG | B | 284 | 52.150 | 19.588 | 64.639 | 1.000 22.36 |
| ATOM | 4537 | CD | ARG | B | 284 | 51.699 | 20.875 | 65.292 | 1.000 21.53 |
| ATOM | 4538 | NE | ARG | B | 284 | 52.054 | 21.061 | 66.698 | 1.000 19.46 |
| ATOM | 4539 | CZ | ARG | B | 284 | 53.142 | 21.705 | 67.107 | 1.000 25.24 |
| ATOM | 4540 | NH1 | ARG | B | 284 | 54.004 | 22.225 | 66.238 | 1.000 24.69 |
| ATOM | 4541 | NH2 | ARG | B | 284 | 53.412 | 21.850 | 68.402 | 1.000 27.97 |
| ATOM | 4542 | C | ARG | B | 284 | 51.493 | 16.731 | 63.482 | 1.000 16.74 |
| ATOM | 4543 | O | ARG | B | 284 | 50.383 | 16.207 | 63.410 | 1.000 20.61 |
| ATOM | 4544 | N | VAL | B | 285 | 52.454 | 16.252 | 64.253 | 1.000 21.81 |
| ATOM | 4545 | CA | VAL | B | 285 | 52.238 | 15.089 | 65.112 | 1.000 29.13 |
| ATOM | 4546 | CB | VAL | B | 285 | 53.540 | 14.760 | 65.869 | 1.000 29.57 |
| ATOM | 4547 | CG1 | VAL | B | 285 | 53.834 | 15.855 | 66.888 | 1.000 24.27 |
| ATOM | 4548 | CG2 | VAL | B | 285 | 53.448 | 13.399 | 66.536 | 1.000 22.96 |
| ATOM | 4549 | C | VAL | B | 285 | 51.105 | 15.309 | 66.112 | 1.000 27.63 |
| ATOM | 4550 | O | VAL | B | 285 | 50.869 | 16.442 | 66.513 | 1.000 21.60 |
| ATOM | 4551 | N | HIS | B | 286 | 50.396 | 14.271 | 66.516 | 1.000 32.06 |
| ATOM | 4552 | CA | HIS | B | 286 | 49.336 | 14.195 | 67.498 | 1.000 25.21 |
| ATOM | 4553 | CB | HIS | B | 286 | 49.885 | 14.551 | 68.892 | 1.000 28.70 |
| ATOM | 4554 | CG | HIS | B | 286 | 51.021 | 13.664 | 69.305 | 1.000 32.98 |
| ATOM | 4555 | ND1 | HIS | B | 286 | 51.067 | 12.319 | 69.031 | 1.000 39.17 |
| ATOM | 4556 | CE1 | HIS | B | 286 | 52.186 | 11.799 | 69.506 | 1.000 36.14 |
| ATOM | 4557 | NE2 | HIS | B | 286 | 52.871 | 12.769 | 70.082 | 1.000 30.56 |
| ATOM | 4558 | CD2 | HIS | B | 286 | 52.169 | 13.944 | 69.969 | 1.000 33.55 |
| ATOM | 4559 | C | HIS | B | 286 | 48.127 | 15.077 | 67.218 | 1.000 30.46 |
| ATOM | 4560 | O | HIS | B | 286 | 47.387 | 15.403 | 68.154 | 1.000 40.44 |
| ATOM | 4561 | N | MET | B | 287 | 47.881 | 15.467 | 65.973 | 1.000 22.86 |
| ATOM | 4562 | CA | MET | B | 287 | 46.691 | 16.259 | 65.664 | 1.000 22.17 |
| ATOM | 4563 | CB | MET | B | 287 | 46.756 | 16.854 | 64.270 | 1.000 18.80 |
| ATOM | 4564 | CG | MET | B | 287 | 47.775 | 17.949 | 64.042 | 1.000 29.11 |
| ATOM | 4565 | SD | MET | B | 287 | 47.516 | 19.438 | 65.055 | 1.000 32.43 |
| ATOM | 4566 | CE | MET | B | 287 | 48.661 | 19.026 | 66.372 | 1.000 13.54 |
| ATOM | 4567 | C | MET | B | 287 | 45.457 | 15.368 | 65.848 | 1.000 29.49 |
| ATOM | 4568 | O | MET | B | 287 | 45.182 | 14.511 | 65.013 | 1.000 22.99 |
| ATOM | 4569 | N | VAL | B | 288 | 44.774 | 15.611 | 66.952 | 1.000 34.12 |
| ATOM | 4570 | CA | VAL | B | 288 | 43.740 | 14.820 | 67.589 | 1.000 28.81 |
| ATOM | 4571 | CB | VAL | B | 288 | 42.560 | 14.478 | 66.675 | 1.000 27.58 |
| ATOM | 4572 | CG1 | VAL | B | 288 | 41.636 | 13.502 | 67.385 | 1.000 26.91 |
| ATOM | 4573 | CG2 | VAL | B | 288 | 41.797 | 15.726 | 66.275 | 1.000 19.05 |
| ATOM | 4574 | C | VAL | B | 288 | 44.390 | 13.535 | 68.093 | 1.000 30.95 |
| ATOM | 4575 | O | VAL | B | 288 | 44.556 | 12.583 | 67.334 | 1.000 40.72 |

FIGURE 94

| ATOM | 4576 | N   | GLN | B | 289 | 44.783 | 13.526 | 69.362 | 1.000 | 42.21 |
|------|------|-----|-----|---|-----|--------|--------|--------|-------|-------|
| ATOM | 4577 | CA  | GLN | B | 289 | 45.728 | 12.504 | 69.827 | 1.000 | 40.64 |
| ATOM | 4578 | CB  | GLN | B | 289 | 46.907 | 13.254 | 70.450 | 1.000 | 38.74 |
| ATOM | 4579 | CG  | GLN | B | 289 | 47.311 | 12.901 | 71.865 | 1.000 | 38.30 |
| ATOM | 4580 | CD  | GLN | B | 289 | 48.223 | 13.989 | 72.413 | 1.000 | 37.90 |
| ATOM | 4581 | OE1 | GLN | B | 289 | 47.738 | 15.038 | 72.837 | 1.000 | 34.96 |
| ATOM | 4582 | NE2 | GLN | B | 289 | 49.525 | 13.736 | 72.392 | 1.000 | 42.59 |
| ATOM | 4583 | C   | GLN | B | 289 | 45.156 | 11.454 | 70.756 | 1.000 | 35.16 |
| ATOM | 4584 | O   | GLN | B | 289 | 45.899 | 10.560 | 71.181 | 1.000 | 34.51 |
| ATOM | 4585 | N   | THR | B | 290 | 43.869 | 11.469 | 71.086 | 1.000 | 27.99 |
| ATOM | 4586 | CA  | THR | B | 290 | 43.294 | 10.342 | 71.819 | 1.000 | 34.56 |
| ATOM | 4587 | CB  | THR | B | 290 | 42.922 | 10.643 | 73.277 | 1.000 | 36.69 |
| ATOM | 4588 | OG1 | THR | B | 290 | 41.958 | 11.699 | 73.369 | 1.000 | 39.54 |
| ATOM | 4589 | CG2 | THR | B | 290 | 44.140 | 11.134 | 74.049 | 1.000 | 28.24 |
| ATOM | 4590 | C   | THR | B | 290 | 42.053 |  9.858 | 71.067 | 1.000 | 45.19 |
| ATOM | 4591 | O   | THR | B | 290 | 41.423 | 10.630 | 70.344 | 1.000 | 37.85 |
| ATOM | 4592 | N   | GLU | B | 291 | 41.708 |  8.583 | 71.228 | 1.000 | 40.04 |
| ATOM | 4593 | CA  | GLU | B | 291 | 40.514 |  8.060 | 70.569 | 1.000 | 31.40 |
| ATOM | 4594 | CB  | GLU | B | 291 | 40.426 |  6.549 | 70.769 | 1.000 | 33.20 |
| ATOM | 4595 | CG  | GLU | B | 291 | 38.992 |  6.033 | 70.734 | 1.000 | 54.35 |
| ATOM | 4596 | CD  | GLU | B | 291 | 38.936 |  4.515 | 70.792 | 1.000 | 61.38 |
| ATOM | 4597 | OE1 | GLU | B | 291 | 37.831 |  3.978 | 71.011 | 1.000 | 56.63 |
| ATOM | 4598 | OE2 | GLU | B | 291 | 40.009 |  3.898 | 70.610 | 1.000 | 65.55 |
| ATOM | 4599 | C   | GLU | B | 291 | 39.274 |  8.756 | 71.108 | 1.000 | 27.13 |
| ATOM | 4600 | O   | GLU | B | 291 | 38.289 |  9.026 | 70.424 | 1.000 | 39.02 |
| ATOM | 4601 | N   | CYS | B | 292 | 39.330 |  9.074 | 72.393 | 1.000 | 30.92 |
| ATOM | 4602 | CA  | CYS | B | 292 | 38.290 |  9.823 | 73.085 | 1.000 | 28.64 |
| ATOM | 4603 | CB  | CYS | B | 292 | 38.815 | 10.131 | 74.493 | 1.000 | 36.66 |
| ATOM | 4604 | SG  | CYS | B | 292 | 37.722 | 11.163 | 75.490 | 1.000 | 55.37 |
| ATOM | 4605 | C   | CYS | B | 292 | 37.903 | 11.103 | 72.351 | 1.000 | 31.79 |
| ATOM | 4606 | O   | CYS | B | 292 | 36.723 | 11.332 | 72.070 | 1.000 | 36.92 |
| ATOM | 4607 | N   | GLN | B | 293 | 38.892 | 11.940 | 72.039 | 1.000 | 33.19 |
| ATOM | 4608 | CA  | GLN | B | 293 | 38.724 | 13.169 | 71.267 | 1.000 | 28.60 |
| ATOM | 4609 | CB  | GLN | B | 293 | 40.056 | 13.880 | 71.039 | 1.000 | 27.95 |
| ATOM | 4610 | CG  | GLN | B | 293 | 40.532 | 14.744 | 72.194 | 1.000 | 27.18 |
| ATOM | 4611 | CD  | GLN | B | 293 | 42.023 | 15.015 | 72.172 | 1.000 | 33.21 |
| ATOM | 4612 | OE1 | GLN | B | 293 | 42.730 | 14.694 | 71.211 | 1.000 | 26.74 |
| ATOM | 4613 | NE2 | GLN | B | 293 | 42.533 | 15.611 | 73.245 | 1.000 | 24.69 |
| ATOM | 4614 | C   | GLN | B | 293 | 38.076 | 12.811 | 69.931 | 1.000 | 28.40 |
| ATOM | 4615 | O   | GLN | B | 293 | 37.089 | 13.407 | 69.513 | 1.000 | 41.52 |
| ATOM | 4616 | N   | TYR | B | 294 | 38.647 | 11.795 | 69.281 | 1.000 | 24.64 |
| ATOM | 4617 | CA  | TYR | B | 294 | 38.065 | 11.284 | 68.041 | 1.000 | 29.87 |
| ATOM | 4618 | CB  | TYR | B | 294 | 38.826 | 10.059 | 67.528 | 1.000 | 35.21 |
| ATOM | 4619 | CG  | TYR | B | 294 | 38.549 |  9.719 | 66.079 | 1.000 | 39.63 |
| ATOM | 4620 | CD1 | TYR | B | 294 | 38.696 | 10.672 | 65.081 | 1.000 | 28.61 |
| ATOM | 4621 | CE1 | TYR | B | 294 | 38.451 | 10.386 | 63.754 | 1.000 | 28.44 |
| ATOM | 4622 | CZ  | TYR | B | 294 | 38.047 |  9.119 | 63.401 | 1.000 | 38.28 |
| ATOM | 4623 | OH  | TYR | B | 294 | 37.803 |  8.837 | 62.078 | 1.000 | 41.13 |
| ATOM | 4624 | CE2 | TYR | B | 294 | 37.891 |  8.151 | 64.368 | 1.000 | 40.14 |
| ATOM | 4625 | CD2 | TYR | B | 294 | 38.141 |  8.446 | 65.695 | 1.000 | 38.49 |
| ATOM | 4626 | C   | TYR | B | 294 | 36.603 | 10.923 | 68.261 | 1.000 | 28.62 |
| ATOM | 4627 | O   | TYR | B | 294 | 35.741 | 11.211 | 67.434 | 1.000 | 36.24 |

FIGURE 95

| ATOM | 4628 | N | VAL | B | 295 | 36.302 | 10.285 | 69.396 | 1.000 | 34.52 |
| --- | --- | --- | --- | --- | --- | --- | --- | --- | --- | --- |
| ATOM | 4629 | CA | VAL | B | 295 | 34.910 | 9.921 | 69.662 | 1.000 | 31.51 |
| ATOM | 4630 | CB | VAL | B | 295 | 34.752 | 9.065 | 70.932 | 1.000 | 35.21 |
| ATOM | 4631 | CG1 | VAL | B | 295 | 33.272 | 8.911 | 71.238 | 1.000 | 40.28 |
| ATOM | 4632 | CG2 | VAL | B | 295 | 35.432 | 7.720 | 70.755 | 1.000 | 35.85 |
| ATOM | 4633 | C | VAL | B | 295 | 34.043 | 11.161 | 69.834 | 1.000 | 27.72 |
| ATOM | 4634 | O | VAL | B | 295 | 32.911 | 11.223 | 69.360 | 1.000 | 36.42 |
| ATOM | 4635 | N | TYR | B | 296 | 34.613 | 12.139 | 70.527 | 1.000 | 37.43 |
| ATOM | 4636 | CA | TYR | B | 296 | 33.941 | 13.417 | 70.761 | 1.000 | 36.42 |
| ATOM | 4637 | CB | TYR | B | 296 | 34.866 | 14.321 | 71.578 | 1.000 | 43.28 |
| ATOM | 4638 | CG | TYR | B | 296 | 34.259 | 15.599 | 72.102 | 1.000 | 42.68 |
| ATOM | 4639 | CD1 | TYR | B | 296 | 33.533 | 15.620 | 73.285 | 1.000 | 41.40 |
| ATOM | 4640 | CE1 | TYR | B | 296 | 32.979 | 16.794 | 73.765 | 1.000 | 39.34 |
| ATOM | 4641 | CZ | TYR | B | 296 | 33.146 | 17.964 | 73.062 | 1.000 | 34.82 |
| ATOM | 4642 | OH | TYR | B | 296 | 32.597 | 19.132 | 73.530 | 1.000 | 27.53 |
| ATOM | 4643 | CE2 | TYR | B | 296 | 33.865 | 17.973 | 71.884 | 1.000 | 41.20 |
| ATOM | 4644 | CD2 | TYR | B | 296 | 34.415 | 16.796 | 71.415 | 1.000 | 43.82 |
| ATOM | 4645 | C | TYR | B | 296 | 33.527 | 14.083 | 69.458 | 1.000 | 28.58 |
| ATOM | 4646 | O | TYR | B | 296 | 32.421 | 14.622 | 69.341 | 1.000 | 31.47 |
| ATOM | 4647 | N | LEU | B | 297 | 34.403 | 14.066 | 68.453 | 1.000 | 30.22 |
| ATOM | 4648 | CA | LEU | B | 297 | 34.076 | 14.745 | 67.196 | 1.000 | 30.67 |
| ATOM | 4649 | CB | LEU | B | 297 | 35.195 | 14.583 | 66.180 | 1.000 | 30.58 |
| ATOM | 4650 | CG | LEU | B | 297 | 36.483 | 15.373 | 66.375 | 1.000 | 32.73 |
| ATOM | 4651 | CD1 | LEU | B | 297 | 37.535 | 14.919 | 65.367 | 1.000 | 29.68 |
| ATOM | 4652 | CD2 | LEU | B | 297 | 36.220 | 16.866 | 66.250 | 1.000 | 27.24 |
| ATOM | 4653 | C | LEU | B | 297 | 32.782 | 14.187 | 66.605 | 1.000 | 33.83 |
| ATOM | 4654 | O | LEU | B | 297 | 31.891 | 14.932 | 66.215 | 1.000 | 31.16 |
| ATOM | 4655 | N | HIS | B | 298 | 32.737 | 12.860 | 66.570 | 1.000 | 41.22 |
| ATOM | 4656 | CA | HIS | B | 298 | 31.562 | 12.114 | 66.138 | 1.000 | 38.95 |
| ATOM | 4657 | CB | HIS | B | 298 | 31.818 | 10.612 | 66.255 | 1.000 | 34.71 |
| ATOM | 4658 | CG | HIS | B | 298 | 32.822 | 10.070 | 65.285 | 1.000 | 34.66 |
| ATOM | 4659 | ND1 | HIS | B | 298 | 34.177 | 10.070 | 65.531 | 1.000 | 40.08 |
| ATOM | 4660 | CE1 | HIS | B | 298 | 34.825 | 9.528 | 64.511 | 1.000 | 38.60 |
| ATOM | 4661 | NE2 | HIS | B | 298 | 33.935 | 9.166 | 63.602 | 1.000 | 36.65 |
| ATOM | 4662 | CD2 | HIS | B | 298 | 32.679 | 9.494 | 64.071 | 1.000 | 35.52 |
| ATOM | 4663 | C | HIS | B | 298 | 30.340 | 12.523 | 66.951 | 1.000 | 36.47 |
| ATOM | 4664 | O | HIS | B | 298 | 29.314 | 12.914 | 66.389 | 1.000 | 36.46 |
| ATOM | 4665 | N | GLN | B | 299 | 30.420 | 12.464 | 68.280 | 1.000 | 33.50 |
| ATOM | 4666 | CA | GLN | B | 299 | 29.250 | 12.855 | 69.073 | 1.000 | 36.05 |
| ATOM | 4667 | CB | GLN | B | 299 | 29.525 | 12.674 | 70.563 | 1.000 | 39.72 |
| ATOM | 4668 | CG | GLN | B | 299 | 30.053 | 11.279 | 70.887 | 1.000 | 48.51 |
| ATOM | 4669 | CD | GLN | B | 299 | 30.367 | 11.132 | 72.362 | 1.000 | 53.01 |
| ATOM | 4670 | OE1 | GLN | B | 299 | 30.932 | 12.045 | 72.967 | 1.000 | 50.76 |
| ATOM | 4671 | NE2 | GLN | B | 299 | 29.999 | 9.994 | 72.931 | 1.000 | 51.27 |
| ATOM | 4672 | C | GLN | B | 299 | 28.841 | 14.289 | 68.782 | 1.000 | 38.19 |
| ATOM | 4673 | O | GLN | B | 299 | 27.660 | 14.644 | 68.781 | 1.000 | 36.44 |
| ATOM | 4674 | N | CYS | B | 300 | 29.837 | 15.136 | 68.520 | 1.000 | 36.51 |
| ATOM | 4675 | CA | CYS | B | 300 | 29.496 | 16.519 | 68.201 | 1.000 | 31.01 |
| ATOM | 4676 | CB | CYS | B | 300 | 30.752 | 17.368 | 68.017 | 1.000 | 32.05 |
| ATOM | 4677 | SG | CYS | B | 300 | 31.545 | 17.931 | 69.542 | 1.000 | 33.82 |
| ATOM | 4678 | C | CYS | B | 300 | 28.665 | 16.568 | 66.925 | 1.000 | 30.84 |
| ATOM | 4679 | O | CYS | B | 300 | 27.706 | 17.327 | 66.828 | 1.000 | 37.19 |

FIGURE 96

```
ATOM   4680  N    VAL B 301      29.042  15.767  65.927  1.000  30.57
ATOM   4681  CA   VAL B 301      28.357  15.877  64.636  1.000  35.77
ATOM   4682  CB   VAL B 301      29.131  15.124  63.542  1.000  37.54
ATOM   4683  CG1  VAL B 301      28.252  14.886  62.327  1.000  28.37
ATOM   4684  CG2  VAL B 301      30.380  15.915  63.165  1.000  38.14
ATOM   4685  C    VAL B 301      26.925  15.369  64.735  1.000  39.26
ATOM   4686  O    VAL B 301      25.977  16.025  64.295  1.000  52.69
ATOM   4687  N    ARG B 302      26.736  14.201  65.327  1.000  38.31
ATOM   4688  CA   ARG B 302      25.403  13.654  65.555  1.000  45.66
ATOM   4689  CB   ARG B 302      25.506  12.385  66.410  1.000  42.74
ATOM   4690  CG   ARG B 302      24.268  12.102  67.240  1.000  46.88
ATOM   4691  CD   ARG B 302      24.579  11.103  68.354  1.000  45.04
ATOM   4692  NE   ARG B 302      25.118  11.799  69.513  1.000  48.32
ATOM   4693  CZ   ARG B 302      25.697  11.252  70.567  1.000  45.65
ATOM   4694  NH1  ARG B 302      25.838   9.937  70.659  1.000  43.04
ATOM   4695  NH2  ARG B 302      26.131  12.057  71.531  1.000  48.35
ATOM   4696  C    ARG B 302      24.480  14.642  66.256  1.000  54.36
ATOM   4697  O    ARG B 302      23.339  14.882  65.856  1.000  40.59
ATOM   4698  N    ASP B 303      24.975  15.234  67.348  1.000  56.40
ATOM   4699  CA   ASP B 303      24.142  16.171  68.100  1.000  55.70
ATOM   4700  CB   ASP B 303      24.898  16.662  69.342  1.000  57.02
ATOM   4701  CG   ASP B 303      25.181  15.521  70.303  1.000  59.83
ATOM   4702  OD1  ASP B 303      24.651  14.412  70.073  1.000  59.82
ATOM   4703  OD2  ASP B 303      25.930  15.724  71.281  1.000  60.83
ATOM   4704  C    ASP B 303      23.688  17.342  67.236  1.000  50.72
ATOM   4705  O    ASP B 303      22.538  17.775  67.357  1.000  47.41
ATOM   4706  N    VAL B 304      24.571  17.839  66.374  1.000  44.96
ATOM   4707  CA   VAL B 304      24.268  18.980  65.512  1.000  47.93
ATOM   4708  CB   VAL B 304      25.515  19.435  64.739  1.000  46.69
ATOM   4709  CG1  VAL B 304      25.147  20.348  63.575  1.000  43.96
ATOM   4710  CG2  VAL B 304      26.484  20.141  65.677  1.000  44.01
ATOM   4711  C    VAL B 304      23.137  18.626  64.546  1.000  53.73
ATOM   4712  O    VAL B 304      22.178  19.375  64.347  1.000  37.08
ATOM   4713  N    LEU B 305      23.286  17.442  63.958  1.000  51.48
ATOM   4714  CA   LEU B 305      22.264  16.852  63.108  1.000  52.53
ATOM   4715  CB   LEU B 305      22.789  15.569  62.455  1.000  39.00
ATOM   4716  CG   LEU B 305      24.083  15.749  61.649  1.000  37.23
ATOM   4717  CD1  LEU B 305      24.587  14.409  61.143  1.000  51.92
ATOM   4718  CD2  LEU B 305      23.868  16.711  60.496  1.000  36.51
ATOM   4719  C    LEU B 305      20.979  16.583  63.901  1.000  53.75
ATOM   4720  O    LEU B 305      19.939  17.100  63.476  1.000  35.65
ATOM   4721  N    ARG B 306      21.076  15.820  64.980  1.000  57.84
ATOM   4722  CA   ARG B 306      20.003  15.505  65.913  1.000  58.04
ATOM   4723  CB   ARG B 306      20.540  15.067  67.268  1.000  54.34
ATOM   4724  CG   ARG B 306      20.660  13.573  67.496  1.000  55.97
ATOM   4725  CD   ARG B 306      21.035  13.272  68.943  1.000  61.19
ATOM   4726  NE   ARG B 306      21.719  11.995  69.097  1.000  68.99
ATOM   4727  CZ   ARG B 306      21.752  11.249  70.190  1.000  74.79
ATOM   4728  NH1  ARG B 306      21.132  11.608  71.304  1.000  69.23
ATOM   4729  NH2  ARG B 306      22.421  10.100  70.183  1.000  80.87
ATOM   4730  C    ARG B 306      19.118  16.738  66.111  1.000  62.20
ATOM   4731  O    ARG B 306      17.971  16.763  65.681  1.000  63.69
```

FIGURE 97

| | | | | | | | | | |
|---|---|---|---|---|---|---|---|---|---|
| ATOM | 4732 | N | ALA | B | 307 | 19.734 | 17.737 | 66.728 | 1.000 65.49 |
| ATOM | 4733 | CA | ALA | B | 307 | 19.143 | 19.057 | 66.891 | 1.000 64.51 |
| ATOM | 4734 | CB | ALA | B | 307 | 20.143 | 19.994 | 67.558 | 1.000 51.87 |
| ATOM | 4735 | C | ALA | B | 307 | 18.680 | 19.605 | 65.548 | 1.000 64.66 |
| ATOM | 4736 | O | ALA | B | 307 | 17.611 | 20.209 | 65.423 | 1.000 65.97 |
| ATOM | 4737 | N | ARG | B | 308 | 19.468 | 19.412 | 64.491 | 1.000 61.42 |
| ATOM | 4738 | CA | ARG | B | 308 | 19.012 | 19.929 | 63.193 | 1.000 70.94 |
| ATOM | 4739 | CB | ARG | B | 308 | 20.088 | 19.697 | 62.137 | 1.000 76.27 |
| ATOM | 4740 | CG | ARG | B | 308 | 19.741 | 20.209 | 60.748 | 1.000 86.23 |
| ATOM | 4741 | CD | ARG | B | 308 | 20.397 | 21.547 | 60.456 | 1.000 95.24 |
| ATOM | 4742 | NE | ARG | B | 308 | 21.821 | 21.417 | 60.163 | 1.000101.38 |
| ATOM | 4743 | CZ | ARG | B | 308 | 22.786 | 21.666 | 61.049 | 1.000107.77 |
| ATOM | 4744 | NH1 | ARG | B | 308 | 22.485 | 22.054 | 62.288 | 1.000110.29 |
| ATOM | 4745 | NH2 | ARG | B | 308 | 24.056 | 21.519 | 60.695 | 1.000113.92 |
| ATOM | 4746 | C | ARG | B | 308 | 17.685 | 19.293 | 62.787 | 1.000 73.80 |
| ATOM | 4747 | O | ARG | B | 308 | 16.827 | 19.955 | 62.197 | 1.000 73.18 |
| ATOM | 4748 | N | LYS | B | 309 | 17.486 | 18.015 | 63.102 | 1.000 73.43 |
| ATOM | 4749 | CA | LYS | B | 309 | 16.283 | 17.286 | 62.718 | 1.000 76.77 |
| ATOM | 4750 | CB | LYS | B | 309 | 16.472 | 15.788 | 62.979 | 1.000 79.31 |
| ATOM | 4751 | CG | LYS | B | 309 | 17.591 | 15.149 | 62.164 | 1.000 80.69 |
| ATOM | 4752 | CD | LYS | B | 309 | 17.436 | 13.637 | 62.104 | 1.000 82.88 |
| ATOM | 4753 | CE | LYS | B | 309 | 18.186 | 13.050 | 60.925 | 1.000 82.69 |
| ATOM | 4754 | NZ | LYS | B | 309 | 19.523 | 12.501 | 61.319 | 1.000 75.87 |
| ATOM | 4755 | C | LYS | B | 309 | 15.033 | 17.778 | 63.442 | 1.000 74.89 |
| ATOM | 4756 | O | LYS | B | 309 | 14.006 | 18.014 | 62.802 | 1.000 70.03 |
| ATOM | 4757 | N | LEU | B | 310 | 15.106 | 17.915 | 64.760 | 1.000 66.81 |
| ATOM | 4758 | CA | LEU | B | 310 | 13.993 | 18.391 | 65.566 | 1.000 57.56 |
| ATOM | 4759 | CB | LEU | B | 310 | 14.439 | 18.679 | 67.003 | 1.000 58.43 |
| ATOM | 4760 | CG | LEU | B | 310 | 14.439 | 17.504 | 67.980 | 1.000 59.58 |
| ATOM | 4761 | CD1 | LEU | B | 310 | 15.451 | 17.728 | 69.090 | 1.000 37.85 |
| ATOM | 4762 | CD2 | LEU | B | 310 | 13.055 | 17.278 | 68.570 | 1.000 65.92 |
| ATOM | 4763 | C | LEU | B | 310 | 13.371 | 19.657 | 64.978 | 1.000 57.95 |
| ATOM | 4764 | O | LEU | B | 310 | 12.371 | 20.157 | 65.507 | 1.000 56.97 |
| ATOM | 4765 | O1 | HOH | W | 1 | -3.530 | -2.470 | 27.550 | 1.000 17.96 |
| ATOM | 4766 | O1 | HOH | W | 2 | 60.077 | 26.796 | 63.038 | 1.000 15.33 |
| ATOM | 4767 | O1 | HOH | W | 3 | 55.045 | 17.613 | 63.918 | 1.000 20.66 |
| ATOM | 4768 | O1 | HOH | W | 4 | 10.035 | -6.431 | 48.617 | 1.000 19.03 |
| ATOM | 4769 | O1 | HOH | W | 5 | -2.541 | 7.405 | 22.573 | 1.000 24.15 |
| ATOM | 4770 | O1 | HOH | W | 6 | -1.465 | 3.010 | 37.742 | 1.000 20.37 |
| ATOM | 4771 | O1 | HOH | W | 7 | 1.064 | 6.887 | 29.228 | 1.000 21.37 |
| ATOM | 4772 | O1 | HOH | W | 8 | 12.797 | -10.463 | 28.170 | 1.000 21.33 |
| ATOM | 4773 | O1 | HOH | W | 9 | 44.023 | 30.928 | 82.230 | 1.000 23.35 |
| ATOM | 4774 | O1 | HOH | W | 10 | 15.262 | -6.127 | 25.706 | 1.000 20.03 |
| ATOM | 4775 | O1 | HOH | W | 11 | 41.135 | 13.077 | 75.806 | 1.000 24.83 |
| ATOM | 4776 | O1 | HOH | W | 12 | 44.160 | 35.266 | 61.596 | 1.000 21.20 |
| ATOM | 4777 | O1 | HOH | W | 13 | -2.293 | 13.135 | 27.030 | 1.000 29.16 |
| ATOM | 4778 | O1 | HOH | W | 14 | -1.152 | -4.851 | 36.331 | 1.000 18.92 |
| ATOM | 4779 | O1 | HOH | W | 15 | 12.494 | -9.297 | 20.888 | 1.000 32.44 |
| ATOM | 4780 | O1 | HOH | W | 16 | 10.561 | -4.413 | 17.800 | 1.000 27.50 |
| ATOM | 4781 | O1 | HOH | W | 17 | 12.953 | -1.978 | 15.793 | 1.000 23.51 |
| ATOM | 4782 | O1 | HOH | W | 18 | 54.169 | 29.526 | 70.613 | 1.000 20.32 |
| ATOM | 4783 | O1 | HOH | W | 19 | 13.709 | 11.416 | 42.827 | 1.000 18.88 |

FIGURE 98

| | | | | | | | | | | |
|---|---|---|---|---|---|---|---|---|---|---|
| ATOM | 4784 | O1 | HOH | W | 20 | 55.731 | 28.213 | 80.604 | 1.000 | 26.83 |
| ATOM | 4785 | O1 | HOH | W | 21 | 4.760 | 11.444 | 27.886 | 1.000 | 20.66 |
| ATOM | 4786 | O1 | HOH | W | 22 | 56.913 | 29.110 | 71.387 | 1.000 | 17.72 |
| ATOM | 4787 | O1 | HOH | W | 23 | 18.440 | -8.145 | 47.574 | 1.000 | 28.67 |
| ATOM | 4788 | O1 | HOH | W | 24 | 51.613 | 13.126 | 62.266 | 1.000 | 25.40 |
| ATOM | 4789 | O1 | HOH | W | 25 | 56.785 | 21.500 | 72.666 | 1.000 | 22.09 |
| ATOM | 4790 | O1 | HOH | W | 26 | 46.913 | 32.045 | 55.417 | 1.000 | 36.86 |
| ATOM | 4791 | O1 | HOH | W | 27 | 10.490 | -7.264 | 21.479 | 1.000 | 24.68 |
| ATOM | 4792 | O1 | HOH | W | 28 | -4.811 | -5.788 | 33.716 | 1.000 | 23.37 |
| ATOM | 4793 | O1 | HOH | W | 29 | 58.662 | 11.046 | 62.178 | 1.000 | 28.32 |
| ATOM | 4794 | O1 | HOH | W | 30 | 40.935 | 36.024 | 75.388 | 1.000 | 36.78 |
| ATOM | 4795 | O1 | HOH | W | 31 | 56.949 | 30.099 | 57.221 | 1.000 | 20.47 |
| ATOM | 4796 | O1 | HOH | W | 32 | 45.404 | 15.934 | 74.179 | 1.000 | 31.95 |
| ATOM | 4797 | O1 | HOH | W | 33 | -6.695 | -5.778 | 43.032 | 1.000 | 31.77 |
| ATOM | 4798 | O1 | HOH | W | 34 | 46.397 | 21.045 | 76.403 | 1.000 | 35.06 |
| ATOM | 4799 | O1 | HOH | W | 35 | 60.957 | 30.231 | 69.118 | 1.000 | 21.63 |
| ATOM | 4800 | O1 | HOH | W | 36 | -3.350 | -17.246 | 31.808 | 1.000 | 41.60 |
| ATOM | 4801 | O1 | HOH | W | 37 | 55.555 | 12.895 | 71.190 | 1.000 | 29.48 |
| ATOM | 4802 | O1 | HOH | W | 38 | 1.468 | -5.097 | 35.986 | 1.000 | 22.35 |
| ATOM | 4803 | O1 | HOH | W | 39 | 15.156 | -9.650 | 27.646 | 1.000 | 20.92 |
| ATOM | 4804 | O1 | HOH | W | 40 | 38.773 | 25.200 | 57.849 | 1.000 | 23.39 |
| ATOM | 4805 | O1 | HOH | W | 41 | 10.348 | 17.067 | 32.030 | 1.000 | 41.46 |
| ATOM | 4806 | O1 | HOH | W | 42 | 1.648 | -14.559 | 44.147 | 1.000 | 28.83 |
| ATOM | 4807 | O1 | HOH | W | 43 | 61.596 | 20.901 | 62.903 | 1.000 | 28.38 |
| ATOM | 4808 | O1 | HOH | W | 44 | 14.144 | -11.298 | 42.153 | 1.000 | 36.30 |
| ATOM | 4809 | O1 | HOH | W | 45 | 59.647 | 17.031 | 57.868 | 1.000 | 23.78 |
| ATOM | 4810 | O1 | HOH | W | 46 | 53.695 | 23.952 | 54.917 | 1.000 | 39.83 |
| ATOM | 4811 | O1 | HOH | W | 47 | 27.056 | 31.327 | 66.272 | 1.000 | 55.85 |
| ATOM | 4812 | O1 | HOH | W | 48 | 37.053 | 41.920 | 74.032 | 1.000 | 46.26 |
| ATOM | 4813 | O1 | HOH | W | 49 | -2.397 | 0.653 | 20.483 | 1.000 | 37.18 |
| ATOM | 4814 | O1 | HOH | W | 50 | 41.473 | 15.741 | 75.531 | 1.000 | 43.52 |
| ATOM | 4815 | O1 | HOH | W | 51 | -2.370 | -15.863 | 33.885 | 1.000 | 30.41 |
| ATOM | 4816 | O1 | HOH | W | 52 | -12.538 | 6.131 | 27.682 | 1.000 | 29.52 |
| ATOM | 4817 | O1 | HOH | W | 53 | 53.221 | 16.883 | 55.102 | 1.000 | 33.14 |
| ATOM | 4818 | O1 | HOH | W | 54 | 14.966 | -8.503 | 24.747 | 1.000 | 25.12 |
| ATOM | 4819 | O1 | HOH | W | 55 | 8.494 | -4.831 | 50.889 | 1.000 | 30.18 |
| ATOM | 4820 | O1 | HOH | W | 56 | 24.585 | -9.942 | 22.611 | 1.000 | 54.01 |
| ATOM | 4821 | O1 | HOH | W | 57 | 18.441 | -20.771 | 46.004 | 1.000 | 39.24 |
| ATOM | 4822 | O1 | HOH | W | 58 | 51.873 | 22.607 | 56.086 | 1.000 | 29.82 |
| ATOM | 4823 | O1 | HOH | W | 59 | 1.396 | -6.152 | 18.909 | 1.000 | 47.00 |
| ATOM | 4824 | O1 | HOH | W | 60 | 44.607 | 38.534 | 81.740 | 1.000 | 40.03 |
| ATOM | 4825 | O1 | HOH | W | 61 | 18.322 | -0.373 | 24.933 | 1.000 | 28.92 |
| ATOM | 4826 | O1 | HOH | W | 62 | 39.406 | 39.382 | 64.024 | 1.000 | 36.75 |
| ATOM | 4827 | O1 | HOH | W | 63 | 71.786 | 42.646 | 67.354 | 1.000 | 38.18 |
| ATOM | 4828 | O1 | HOH | W | 64 | 41.387 | 20.207 | 52.496 | 1.000 | 61.66 |
| ATOM | 4829 | O1 | HOH | W | 65 | 58.599 | 39.944 | 69.257 | 1.000 | 22.54 |
| ATOM | 4830 | O1 | HOH | W | 66 | 7.902 | 0.663 | 20.612 | 1.000 | 25.67 |
| ATOM | 4831 | O1 | HOH | W | 67 | 49.818 | 23.739 | 54.522 | 1.000 | 26.64 |
| ATOM | 4832 | O1 | HOH | W | 68 | 0.323 | -5.848 | 22.222 | 1.000 | 21.16 |
| ATOM | 4833 | O1 | HOH | W | 69 | 8.339 | -2.798 | 16.062 | 1.000 | 35.15 |
| ATOM | 4834 | O1 | HOH | W | 70 | 10.628 | -6.726 | 18.494 | 1.000 | 23.48 |
| ATOM | 4835 | O1 | HOH | W | 71 | 34.368 | 9.766 | 58.834 | 1.000 | 46.05 |

FIGURE 99

```
ATOM   4836  O1  HOH W   72     0.104   -9.966  24.934 1.000 31.25
ATOM   4837  O1  HOH W   73    -3.205   -3.781  34.722 1.000 24.34
ATOM   4838  O1  HOH W   74    40.443   25.217  78.384 1.000 21.19
ATOM   4839  O1  HOH W   75    60.161   17.919  77.858 1.000 43.49
ATOM   4840  O1  HOH W   76    57.383   25.403  56.423 1.000 28.69
ATOM   4841  O1  HOH W   77    -0.918   -4.290  45.708 1.000 23.94
ATOM   4842  O1  HOH W   78    39.671   29.793  57.818 1.000 28.43
ATOM   4843  O1  HOH W   79    -0.151   -0.962  21.277 1.000 31.95
ATOM   4844  O1  HOH W   80     7.936   -8.337  20.044 1.000 31.62
ATOM   4845  O1  HOH W   81    41.764   30.809  59.091 1.000 32.37
ATOM   4846  O1  HOH W   82    16.518   -9.547  23.062 1.000 37.01
ATOM   4847  O1  HOH W   83    30.713   30.994  77.311 1.000 33.53
ATOM   4848  O1  HOH W   84    28.454   -2.369  72.054 1.000 47.39
ATOM   4849  O1  HOH W   85    -5.917   -8.292  22.002 1.000 37.83
ATOM   4850  O1  HOH W   86     7.580  -10.565  21.487 1.000 31.50
ATOM   4851  O1  HOH W   87    13.747    8.631  42.204 1.000 29.91
ATOM   4852  O1  HOH W   88    34.378    8.211  61.163 1.000 35.02
ATOM   4853  O1  HOH W   89    55.698   21.340  61.326 1.000 34.48
ATOM   4854  O1  HOH W   90    -0.448   -6.040  47.787 1.000 38.54
ATOM   4855  O1  HOH W   91    -0.537   -4.018  20.186 1.000 52.78
ATOM   4856  O1  HOH W   92    58.171   28.185  55.468 1.000 35.33
ATOM   4857  O1  HOH W   93    -1.835  -17.836  29.482 1.000 43.68
ATOM   4858  O1  HOH W   94    19.387  -17.439  48.725 1.000 53.98
ATOM   4859  O1  HOH W   95    60.252   41.304  67.862 1.000 40.39
ATOM   4860  O1  HOH W   96    33.297   25.666  61.866 1.000 30.40
ATOM   4861  O1  HOH W   97    -0.856   -8.441  21.984 1.000 40.05
ATOM   4862  O1  HOH W   98     1.309    3.127  26.649 1.000 32.55
ATOM   4863  O1  HOH W   99    -1.694  -18.493  42.845 1.000 43.76
ATOM   4864  O1  HOH W  100    24.060   -6.419  45.384 1.000 40.45
ATOM   4865  O1  HOH W  101   -16.201    0.201  30.012 1.000 60.21
ATOM   4866  O1  HOH W  102    26.465   -8.482  43.564 1.000 39.40
ATOM   4867  O1  HOH W  103    26.382   -4.680  30.946 1.000 37.07
ATOM   4868  O1  HOH W  104    14.152   -0.770  45.187 1.000 31.90
ATOM   4869  O1  HOH W  105    45.353    7.442  65.377 1.000 41.13
ATOM   4870  O1  HOH W  106    61.574   29.765  78.858 1.000 30.33
ATOM   4871  O1  HOH W  107     7.240   13.732  33.506 1.000 51.68
ATOM   4872  O1  HOH W  108    63.827   31.328  67.142 1.000 34.68
ATOM   4873  O1  HOH W  109    27.765    8.197  72.253 1.000 40.60
ATOM   4874  O1  HOH W  110    26.746   31.022  63.432 1.000 78.25
ATOM   4875  O1  HOH W  111     5.779   12.491  31.119 1.000 40.18
ATOM   4876  O1  HOH W  112     0.254   17.249  30.260 1.000 37.62
ATOM   4877  O1  HOH W  113    12.595   10.239  20.359 1.000 35.26
ATOM   4878  O1  HOH W  114   -12.231    8.847  27.346 1.000 34.71
ATOM   4879  O1  HOH W  115     6.080   14.549  28.922 1.000 38.97
ATOM   4880  O1  HOH W  116    42.291   33.445  57.940 1.000 22.41
ATOM   4881  O1  HOH W  117    59.009   28.099  70.085 1.000 25.15
ATOM   4882  O1  HOH W  118    21.222    2.455  47.444 1.000 48.38
ATOM   4883  O1  HOH W  119    15.608  -16.455  31.001 1.000 42.95
ATOM   4884  O1  HOH W  120    -0.125   11.690  36.476 1.000 30.48
ATOM   4885  O1  HOH W  121     1.726   11.454  38.848 1.000 32.74
ATOM   4886  O1  HOH W  122    28.290   -0.445  30.933 1.000 38.16
ATOM   4887  O1  HOH W  123     6.212  -24.378  36.045 1.000 44.15
```

FIGURE 100

```
ATOM   4888  O1   HOH W  124     1.177 -29.065  27.544 1.000  45.02
ATOM   4889  O1   HOH W  125    56.979  34.259  60.005 1.000  48.14
ATOM   4890  O1   HOH W  126    58.730  33.237  57.099 1.000  45.63
ATOM   4891  O1   HOH W  127    15.046  11.322  20.955 1.000  40.69
ATOM   4892  O1   HOH W  128    17.468  -4.910  24.971 1.000  27.77
ATOM   4893  O1   HOH W  129    -7.587  -7.450  31.742 1.000  42.13
ATOM   4894  O1   HOH W  130    62.587  23.632  57.526 1.000  35.90
ATOM   4895  O1   HOH W  131    -1.756   3.962  17.316 1.000  54.25
ATOM   4896  O1   HOH W  132    -7.965  -8.197  36.101 1.000  44.77
ATOM   4897  O1   HOH W  133    24.522 -12.151  40.839 1.000  47.60
ATOM   4898  O1   HOH W  134    41.871  34.231  60.791 1.000  28.90
ATOM   4899  O1   HOH W  135     0.084   1.514  45.812 1.000  36.86
ATOM   4900  O1   HOH W  136    -8.408   3.637  36.615 1.000  38.14
ATOM   4901  O1   HOH W  137    40.900  41.156  64.403 1.000  36.63
ATOM   4902  O1   HOH W  138   -11.020 -17.691  22.512 1.000  75.97
ATOM   4903  O1   HOH W  139     7.850   3.732  42.421 1.000  36.40
ATOM   4904  O1   HOH W  140    26.443 -10.866  28.599 1.000  51.16
ATOM   4905  O1   HOH W  141    23.109   4.111  20.091 1.000  51.94
ATOM   4906  O1   HOH W  142    38.297  16.036  84.787 1.000  45.01
ATOM   4907  O1   HOH W  143    21.913  17.019  28.707 1.000  43.32
ATOM   4908  O1   HOH W  144    59.964  41.572  65.028 1.000  58.77
ATOM   4909  O1   HOH W  145    46.873  21.994  79.174 1.000  40.67
ATOM   4910  O1   HOH W  146    19.058 -16.861  40.797 1.000  48.41
ATOM   4911  O1   HOH W  147    50.103  11.202  73.004 1.000  41.20
ATOM   4912  O1   HOH W  148    -3.801   9.680  21.040 1.000  40.17
ATOM   4913  O1   HOH W  149     0.486   8.561  18.811 1.000  40.75
ATOM   4914  O1   HOH W  150    19.935   8.387  60.381 1.000  53.72
ATOM   4915  O1   HOH W  151    23.477  -0.731  29.783 1.000  32.64
ATOM   4916  O1   HOH W  152    43.876  43.513  55.758 1.000  69.30
ATOM   4917  O1   HOH W  153    -5.161   3.525  27.477 1.000  32.16
ATOM   4918  O1   HOH W  154    41.525  16.199  52.939 1.000  81.81
ATOM   4919  O1   HOH W  155    -4.928 -12.335  20.354 1.000  61.63
ATOM   4920  O1   HOH W  156    13.058   0.354  47.602 1.000  30.77
ATOM   4921  O1   HOH W  157    43.059  17.423  76.789 1.000  45.11
ATOM   4922  O1   HOH W  158    62.494  11.714  59.113 1.000 108.46
ATOM   4923  O1   HOH W  159    48.631  10.662  67.791 1.000  38.71
ATOM   4924  O1   HOH W  160    36.309  22.824  83.433 1.000  53.78
ATOM   4925  O1   HOH W  161    34.255  41.203  81.271 1.000  58.61
ATOM   4926  O1   HOH W  162    41.197  23.937  80.959 1.000  34.06
ATOM   4927  O1   HOH W  163    41.828  13.385  50.732 1.000  77.14
ATOM   4928  O1   HOH W  164    31.641  33.672  55.019 1.000  59.40
ATOM   4929  O1   HOH W  165    15.868  14.555  66.209 1.000  65.90
ATOM   4930  O1   HOH W  166    57.742  42.116  78.337 1.000  65.62
ATOM   4931  O1   HOH W  167     4.617 -25.082  27.972 1.000  47.28
ATOM   4932  O1   HOH W  168     2.787  17.721  23.213 1.000  98.79
ATOM   4933  O1   HOH W  169    59.715  23.680  80.391 1.000  59.77
ATOM   4934  O1   HOH W  170    37.169  14.176  35.477 1.000  57.67
ATOM   4935  O1   HOH W  171    15.841 -25.349  41.958 1.000  68.09
ATOM   4936  O1   HOH W  172    69.007  25.633  74.020 1.000  68.84
ATOM   4937  O1   HOH W  173    63.270  32.699  57.782 1.000  41.40
ATOM   4938  O1   HOH W  174    38.069  44.790  79.133 1.000  74.12
ATOM   4939  O1   HOH W  175    74.296  43.345  65.746 1.000  58.77
```

FIGURE 101

```
ATOM   4940  O1  HOH W 176      29.671  29.752  62.465 1.000 48.75
ATOM   4941  O1  HOH W 177      27.349  16.661  41.834 1.000 64.12
ATOM   4942  O1  HOH W 178      68.864  18.200  64.263 1.000 44.37
ATOM   4943  O1  HOH W 179      51.540  25.428  52.448 1.000 52.06
ATOM   4944  O1  HOH W 180      28.343  -0.494  74.952 1.000 90.20
ATOM   4945  O1  HOH W 181     -12.972  -6.360  31.919 1.000 61.07
ATOM   4946  O1  HOH W 182      29.627  16.979  37.935 1.000 63.71
ATOM   4947  O1  HOH W 183      30.147  -2.678  28.953 1.000 52.59
ATOM   4948  O1  HOH W 184      55.934  13.116  53.037 1.000 49.11
ATOM   4949  O1  HOH W 185      -4.863 -11.799  39.588 1.000 42.83
ATOM   4950  O1  HOH W 186      52.756  41.765  58.587 1.000 57.97
ATOM   4951  O1  HOH W 187      27.188  -2.332  27.244 1.000 43.06
ATOM   4952  O1  HOH W 188      30.473   7.380  75.791 1.000 81.10
ATOM   4953  O1  HOH W 189      -7.908 -19.633  34.839 1.000 59.42
ATOM   4954  O1  HOH W 190      28.733  14.583  42.278 1.000 54.80
ATOM   4955  O1  HOH W 191     -13.906  -5.879  34.683 1.000 54.42
ATOM   4956  O1  HOH W 192      60.646  30.561  54.430 1.000103.36
ATOM   4957  O1  HOH W 193      35.855  14.670  80.980 1.000 52.28
ATOM   4958  O1  HOH W 194      19.267  -7.719  50.684 1.000 99.38
ATOM   4959  O1  HOH W 195      17.702 -14.597  31.579 1.000 48.72
ATOM   4960  O1  HOH W 196      25.127   1.357  21.179 1.000 86.89
ATOM   4961  O1  HOH W 197       7.136  23.308  30.331 1.000 67.50
ATOM   4962  O1  HOH W 198      66.979  28.356  73.926 1.000 73.15
ATOM   4963  O1  HOH W 199      58.649  27.550  81.422 1.000 51.44
ATOM   4964  O1  HOH W 200      26.717  16.527  75.237 1.000 49.85
ATOM   4965  O1  HOH W 201      50.540  18.935  78.454 1.000 49.28
END
```

FIGURE 102

```
CRYST1    62.186    71.797    70.448  90.00  93.56  90.00
ATOM      1  N   THR A  20      13.220  15.647  19.635  1.00 51.11
ATOM      2  CA  THR A  20      14.046  16.499  20.485  1.00 49.11
ATOM      3  CB  THR A  20      13.219  17.270  21.525  1.00 56.84
ATOM      4  OG1 THR A  20      11.822  17.025  21.318  1.00 82.00
ATOM      5  CG2 THR A  20      13.411  18.771  21.351  1.00 62.78
ATOM      6  C   THR A  20      15.126  15.682  21.189  1.00 47.28
ATOM      7  O   THR A  20      14.920  14.601  21.731  1.00 36.27
ATOM      8  N   SER A  21      16.332  16.238  21.145  1.00 41.80
ATOM      9  CA  SER A  21      17.525  15.585  21.640  1.00 38.45
ATOM     10  CB  SER A  21      18.027  14.556  20.623  1.00 50.01
ATOM     11  OG  SER A  21      18.114  15.125  19.328  1.00 57.39
ATOM     12  C   SER A  21      18.628  16.597  21.924  1.00 40.97
ATOM     13  O   SER A  21      18.818  17.552  21.172  1.00 54.77
ATOM     14  N   CYS A  22      19.351  16.377  23.013  1.00 38.55
ATOM     15  CA  CYS A  22      20.465  17.251  23.365  1.00 41.82
ATOM     16  CB  CYS A  22      20.194  17.972  24.677  1.00 49.07
ATOM     17  SG  CYS A  22      21.184  19.448  24.992  1.00157.91
ATOM     18  C   CYS A  22      21.737  16.416  23.433  1.00 40.34
ATOM     19  O   CYS A  22      22.215  16.085  24.518  1.00 48.60
ATOM     20  N   PRO A  23      22.270  16.062  22.271  1.00 32.99
ATOM     21  CA  PRO A  23      23.464  15.210  22.261  1.00 38.72
ATOM     22  CB  PRO A  23      23.710  14.926  20.790  1.00 42.84
ATOM     23  CG  PRO A  23      22.474  15.348  20.073  1.00 43.60
ATOM     24  CD  PRO A  23      21.836  16.415  20.914  1.00 38.82
ATOM     25  C   PRO A  23      24.615  15.995  22.881  1.00 48.13
ATOM     26  O   PRO A  23      24.711  17.211  22.701  1.00 47.03
ATOM     27  N   ILE A  24      25.460  15.298  23.625  1.00 44.75
ATOM     28  CA  ILE A  24      26.566  15.975  24.297  1.00 44.40
ATOM     29  CB  ILE A  24      26.272  16.206  25.788  1.00 42.81
ATOM     30  CG1 ILE A  24      25.075  17.122  26.057  1.00 46.37
ATOM     31  CD1 ILE A  24      24.076  16.565  27.047  1.00 66.22
ATOM     32  CG2 ILE A  24      27.512  16.726  26.502  1.00 39.08
ATOM     33  C   ILE A  24      27.832  15.154  24.125  1.00 40.83
ATOM     34  O   ILE A  24      27.907  13.977  24.460  1.00 37.86
ATOM     35  N   LYS A  25      28.852  15.794  23.569  1.00 44.53
ATOM     36  CA  LYS A  25      30.123  15.105  23.390  1.00 43.13
ATOM     37  CB  LYS A  25      31.053  15.966  22.534  1.00 53.45
ATOM     38  CG  LYS A  25      30.471  16.274  21.159  1.00 54.09
ATOM     39  CD  LYS A  25      31.401  15.816  20.047  1.00 53.48
ATOM     40  CE  LYS A  25      30.749  14.744  19.184  1.00 52.46
ATOM     41  NZ  LYS A  25      31.611  13.534  19.051  1.00 56.82
ATOM     42  C   LYS A  25      30.742  14.777  24.743  1.00 35.84
ATOM     43  O   LYS A  25      30.676  15.549  25.699  1.00 35.11
ATOM     44  N   ILE A  26      31.342  13.599  24.805  1.00 30.07
ATOM     45  CA  ILE A  26      31.956  13.072  26.009  1.00 44.79
ATOM     46  CB  ILE A  26      32.828  11.842  25.666  1.00 53.22
ATOM     47  CG1 ILE A  26      32.077  10.710  24.967  1.00 52.52
ATOM     48  CD1 ILE A  26      30.646  10.520  25.409  1.00 30.26
ATOM     49  CG2 ILE A  26      33.540  11.331  26.909  1.00 64.21
ATOM     50  C   ILE A  26      32.827  14.089  26.738  1.00 48.16
ATOM     51  O   ILE A  26      32.683  14.275  27.948  1.00 50.00
```

FIGURE 103

| | | | | | | | | | |
|---|---|---|---|---|---|---|---|---|---|
| ATOM | 52 | N | ASN | A | 27 | 33.731 | 14.732 | 26.005 | 1.00 46.06 |
| ATOM | 53 | CA | ASN | A | 27 | 34.745 | 15.593 | 26.605 | 1.00 48.63 |
| ATOM | 54 | CB | ASN | A | 27 | 35.900 | 15.802 | 25.627 | 1.00 60.83 |
| ATOM | 55 | CG | ASN | A | 27 | 35.840 | 16.989 | 24.701 | 1.00 62.73 |
| ATOM | 56 | OD1 | ASN | A | 27 | 34.812 | 17.621 | 24.451 | 1.00 61.11 |
| ATOM | 57 | ND2 | ASN | A | 27 | 37.003 | 17.330 | 24.140 | 1.00 50.07 |
| ATOM | 58 | C | ASN | A | 27 | 34.158 | 16.914 | 27.075 | 1.00 49.04 |
| ATOM | 59 | O | ASN | A | 27 | 34.843 | 17.726 | 27.705 | 1.00 47.37 |
| ATOM | 60 | N | GLN | A | 28 | 32.878 | 17.141 | 26.778 | 1.00 46.15 |
| ATOM | 61 | CA | GLN | A | 28 | 32.271 | 18.381 | 27.266 | 1.00 49.97 |
| ATOM | 62 | CB | GLN | A | 28 | 31.655 | 19.163 | 26.101 | 1.00 56.77 |
| ATOM | 63 | CG | GLN | A | 28 | 32.595 | 19.346 | 24.918 | 1.00 66.10 |
| ATOM | 64 | CD | GLN | A | 28 | 32.102 | 20.390 | 23.934 | 1.00 71.73 |
| ATOM | 65 | OE1 | GLN | A | 28 | 31.403 | 21.326 | 24.320 | 1.00 72.33 |
| ATOM | 66 | NE2 | GLN | A | 28 | 32.453 | 20.244 | 22.661 | 1.00 76.09 |
| ATOM | 67 | C | GLN | A | 28 | 31.227 | 18.109 | 28.337 | 1.00 40.82 |
| ATOM | 68 | O | GLN | A | 28 | 30.634 | 19.039 | 28.895 | 1.00 38.64 |
| ATOM | 69 | N | PHE | A | 29 | 30.965 | 16.838 | 28.647 | 1.00 40.55 |
| ATOM | 70 | CA | PHE | A | 29 | 29.821 | 16.576 | 29.522 | 1.00 33.60 |
| ATOM | 71 | CB | PHE | A | 29 | 29.591 | 15.064 | 29.660 | 1.00 39.21 |
| ATOM | 72 | CG | PHE | A | 29 | 28.380 | 14.777 | 30.544 | 1.00 32.38 |
| ATOM | 73 | CD1 | PHE | A | 29 | 27.109 | 14.865 | 30.005 | 1.00 33.31 |
| ATOM | 74 | CE1 | PHE | A | 29 | 25.985 | 14.624 | 30.772 | 1.00 33.30 |
| ATOM | 75 | CZ | PHE | A | 29 | 26.136 | 14.282 | 32.103 | 1.00 38.62 |
| ATOM | 76 | CE2 | PHE | A | 29 | 27.402 | 14.192 | 32.648 | 1.00 37.08 |
| ATOM | 77 | CD2 | PHE | A | 29 | 28.520 | 14.426 | 31.874 | 1.00 28.51 |
| ATOM | 78 | C | PHE | A | 29 | 29.981 | 17.210 | 30.898 | 1.00 25.63 |
| ATOM | 79 | O | PHE | A | 29 | 29.074 | 17.856 | 31.430 | 1.00 40.09 |
| ATOM | 80 | N | GLU | A | 30 | 31.161 | 17.013 | 31.469 | 1.00 36.23 |
| ATOM | 81 | CA | GLU | A | 30 | 31.510 | 17.549 | 32.778 | 1.00 43.91 |
| ATOM | 82 | CB | GLU | A | 30 | 33.004 | 17.328 | 33.045 | 1.00 55.32 |
| ATOM | 83 | CG | GLU | A | 30 | 33.738 | 16.650 | 31.903 | 1.00 66.32 |
| ATOM | 84 | CD | GLU | A | 30 | 33.492 | 15.158 | 31.798 | 1.00 75.29 |
| ATOM | 85 | OE1 | GLU | A | 30 | 33.517 | 14.458 | 32.833 | 1.00 81.66 |
| ATOM | 86 | OE2 | GLU | A | 30 | 33.270 | 14.685 | 30.659 | 1.00 78.35 |
| ATOM | 87 | C | GLU | A | 30 | 31.153 | 19.024 | 32.895 | 1.00 33.72 |
| ATOM | 88 | O | GLU | A | 30 | 30.421 | 19.428 | 33.800 | 1.00 34.69 |
| ATOM | 89 | N | GLY | A | 31 | 31.659 | 19.845 | 31.973 | 1.00 36.69 |
| ATOM | 90 | CA | GLY | A | 31 | 31.407 | 21.279 | 32.045 | 1.00 29.29 |
| ATOM | 91 | C | GLY | A | 31 | 29.939 | 21.581 | 31.824 | 1.00 40.96 |
| ATOM | 92 | O | GLY | A | 31 | 29.333 | 22.407 | 32.512 | 1.00 37.93 |
| ATOM | 93 | N | HIS | A | 32 | 29.401 | 20.867 | 30.835 | 1.00 51.96 |
| ATOM | 94 | CA | HIS | A | 32 | 27.980 | 20.958 | 30.502 | 1.00 44.37 |
| ATOM | 95 | CB | HIS | A | 32 | 27.638 | 19.919 | 29.443 | 1.00 58.95 |
| ATOM | 96 | CG | HIS | A | 32 | 26.265 | 19.339 | 29.512 | 1.00 69.53 |
| ATOM | 97 | ND1 | HIS | A | 32 | 25.190 | 19.878 | 28.841 | 1.00 71.46 |
| ATOM | 98 | CE1 | HIS | A | 32 | 24.109 | 19.159 | 29.083 | 1.00 73.05 |
| ATOM | 99 | NE2 | HIS | A | 32 | 24.441 | 18.167 | 29.890 | 1.00 73.89 |
| ATOM | 100 | CD2 | HIS | A | 32 | 25.783 | 18.259 | 30.170 | 1.00 73.95 |
| ATOM | 101 | C | HIS | A | 32 | 27.176 | 20.784 | 31.777 | 1.00 40.30 |
| ATOM | 102 | O | HIS | A | 32 | 26.380 | 21.635 | 32.177 | 1.00 35.23 |
| ATOM | 103 | N | PHE | A | 33 | 27.414 | 19.655 | 32.448 | 1.00 37.93 |

FIGURE 104

| | | | | | | | | | |
|---|---|---|---|---|---|---|---|---|---|
| ATOM | 104 | CA  | PHE | A | 33 | 26.660 | 19.416 | 33.684 | 1.00 35.86 |
| ATOM | 105 | CB  | PHE | A | 33 | 27.026 | 18.033 | 34.233 | 1.00 30.87 |
| ATOM | 106 | CG  | PHE | A | 33 | 26.146 | 17.593 | 35.390 | 1.00 31.86 |
| ATOM | 107 | CD1 | PHE | A | 33 | 24.793 | 17.870 | 35.387 | 1.00 30.87 |
| ATOM | 108 | CE1 | PHE | A | 33 | 23.998 | 17.487 | 36.449 | 1.00 39.07 |
| ATOM | 109 | CZ  | PHE | A | 33 | 24.556 | 16.815 | 37.521 | 1.00 40.71 |
| ATOM | 110 | CE2 | PHE | A | 33 | 25.911 | 16.528 | 37.534 | 1.00 33.73 |
| ATOM | 111 | CD2 | PHE | A | 33 | 26.694 | 16.911 | 36.464 | 1.00 32.41 |
| ATOM | 112 | C   | PHE | A | 33 | 26.888 | 20.531 | 34.694 | 1.00 33.77 |
| ATOM | 113 | O   | PHE | A | 33 | 25.952 | 20.961 | 35.381 | 1.00 36.95 |
| ATOM | 114 | N   | MET | A | 34 | 28.109 | 21.054 | 34.812 | 1.00 40.28 |
| ATOM | 115 | CA  | MET | A | 34 | 28.365 | 22.163 | 35.733 | 1.00 36.53 |
| ATOM | 116 | CB  | MET | A | 34 | 29.840 | 22.550 | 35.715 | 1.00 37.70 |
| ATOM | 117 | CG  | MET | A | 34 | 30.725 | 21.619 | 36.533 | 1.00 44.64 |
| ATOM | 118 | SD  | MET | A | 34 | 32.467 | 21.981 | 36.237 | 1.00 57.03 |
| ATOM | 119 | CE  | MET | A | 34 | 32.639 | 23.515 | 37.150 | 1.00 38.10 |
| ATOM | 120 | C   | MET | A | 34 | 27.538 | 23.393 | 35.382 | 1.00 32.51 |
| ATOM | 121 | O   | MET | A | 34 | 26.955 | 24.065 | 36.235 | 1.00 52.72 |
| ATOM | 122 | N   | LYS | A | 35 | 27.508 | 23.672 | 34.081 | 1.00 35.94 |
| ATOM | 123 | CA  | LYS | A | 35 | 26.695 | 24.776 | 33.583 | 1.00 42.22 |
| ATOM | 124 | CB  | LYS | A | 35 | 26.769 | 24.818 | 32.059 | 1.00 53.72 |
| ATOM | 125 | CG  | LYS | A | 35 | 27.490 | 26.026 | 31.488 | 1.00 64.13 |
| ATOM | 126 | CD  | LYS | A | 35 | 26.830 | 26.522 | 30.211 | 1.00 73.45 |
| ATOM | 127 | CE  | LYS | A | 35 | 25.799 | 27.603 | 30.481 | 1.00 79.66 |
| ATOM | 128 | NZ  | LYS | A | 35 | 25.397 | 28.334 | 29.244 | 1.00 65.59 |
| ATOM | 129 | C   | LYS | A | 35 | 25.261 | 24.606 | 34.072 | 1.00 42.89 |
| ATOM | 130 | O   | LYS | A | 35 | 24.679 | 25.467 | 34.733 | 1.00 40.73 |
| ATOM | 131 | N   | LEU | A | 36 | 24.707 | 23.441 | 33.733 | 1.00 35.38 |
| ATOM | 132 | CA  | LEU | A | 36 | 23.356 | 23.091 | 34.131 | 1.00 26.66 |
| ATOM | 133 | CB  | LEU | A | 36 | 23.027 | 21.631 | 33.793 | 1.00 34.71 |
| ATOM | 134 | CG  | LEU | A | 36 | 22.556 | 21.329 | 32.373 | 1.00 35.84 |
| ATOM | 135 | CD1 | LEU | A | 36 | 23.700 | 21.485 | 31.388 | 1.00 40.98 |
| ATOM | 136 | CD2 | LEU | A | 36 | 21.974 | 19.922 | 32.277 | 1.00 32.82 |
| ATOM | 137 | C   | LEU | A | 36 | 23.172 | 23.283 | 35.629 | 1.00 24.20 |
| ATOM | 138 | O   | LEU | A | 36 | 22.123 | 23.748 | 36.062 | 1.00 28.20 |
| ATOM | 139 | N   | GLN | A | 37 | 24.207 | 22.901 | 36.378 | 1.00 25.36 |
| ATOM | 140 | CA  | GLN | A | 37 | 24.143 | 22.963 | 37.831 | 1.00 31.18 |
| ATOM | 141 | CB  | GLN | A | 37 | 25.189 | 22.007 | 38.420 | 1.00 38.07 |
| ATOM | 142 | CG  | GLN | A | 37 | 24.588 | 20.611 | 38.573 | 1.00 46.59 |
| ATOM | 143 | CD  | GLN | A | 37 | 25.546 | 19.648 | 39.244 | 1.00 51.11 |
| ATOM | 144 | OE1 | GLN | A | 37 | 26.637 | 19.410 | 38.728 | 1.00 44.66 |
| ATOM | 145 | NE2 | GLN | A | 37 | 25.114 | 19.115 | 40.378 | 1.00 36.68 |
| ATOM | 146 | C   | GLN | A | 37 | 24.337 | 24.373 | 38.379 | 1.00 40.44 |
| ATOM | 147 | O   | GLN | A | 37 | 23.814 | 24.666 | 39.455 | 1.00 35.38 |
| ATOM | 148 | N   | ALA | A | 38 | 25.050 | 25.199 | 37.630 | 1.00 45.31 |
| ATOM | 149 | CA  | ALA | A | 38 | 25.238 | 26.608 | 37.933 | 1.00 58.11 |
| ATOM | 150 | CB  | ALA | A | 38 | 25.738 | 27.359 | 36.705 | 1.00 66.03 |
| ATOM | 151 | C   | ALA | A | 38 | 23.953 | 27.264 | 38.431 | 1.00 66.10 |
| ATOM | 152 | O   | ALA | A | 38 | 22.853 | 26.812 | 38.114 | 1.00 78.27 |
| ATOM | 153 | N   | ASP | A | 39 | 24.121 | 28.331 | 39.199 | 1.00 68.10 |
| ATOM | 154 | CA  | ASP | A | 39 | 23.041 | 29.104 | 39.794 | 1.00 71.28 |
| ATOM | 155 | CB  | ASP | A | 39 | 22.423 | 30.060 | 38.774 | 1.00 77.06 |

FIGURE 105

| ATOM | 156 | CG | ASP | A | 39 | 23.365 | 30.405 | 37.638 | 1.00 | 86.83 |
| --- | --- | --- | --- | --- | --- | --- | --- | --- | --- | --- |
| ATOM | 157 | OD1 | ASP | A | 39 | 23.544 | 29.551 | 36.742 | 1.00 | 105.52 |
| ATOM | 158 | OD2 | ASP | A | 39 | 23.932 | 31.516 | 37.639 | 1.00 | 105.04 |
| ATOM | 159 | C | ASP | A | 39 | 21.969 | 28.188 | 40.383 | 1.00 | 69.59 |
| ATOM | 160 | O | ASP | A | 39 | 20.770 | 28.436 | 40.271 | 1.00 | 51.64 |
| ATOM | 161 | N | SER | A | 40 | 22.436 | 27.116 | 41.014 | 1.00 | 72.47 |
| ATOM | 162 | CA | SER | A | 40 | 21.569 | 26.129 | 41.639 | 1.00 | 73.99 |
| ATOM | 163 | CB | SER | A | 40 | 20.695 | 26.792 | 42.708 | 1.00 | 78.30 |
| ATOM | 164 | OG | SER | A | 40 | 20.340 | 25.862 | 43.718 | 1.00 | 96.66 |
| ATOM | 165 | C | SER | A | 40 | 20.698 | 25.414 | 40.612 | 1.00 | 69.44 |
| ATOM | 166 | O | SER | A | 40 | 19.473 | 25.380 | 40.738 | 1.00 | 68.61 |
| ATOM | 167 | N | ASN | A | 41 | 21.324 | 24.836 | 39.588 | 1.00 | 67.73 |
| ATOM | 168 | CA | ASN | A | 41 | 20.564 | 24.038 | 38.628 | 1.00 | 64.81 |
| ATOM | 169 | CB | ASN | A | 41 | 19.846 | 22.901 | 39.367 | 1.00 | 61.79 |
| ATOM | 170 | CG | ASN | A | 41 | 20.795 | 21.929 | 40.031 | 1.00 | 61.73 |
| ATOM | 171 | OD1 | ASN | A | 41 | 22.000 | 21.958 | 39.789 | 1.00 | 69.43 |
| ATOM | 172 | ND2 | ASN | A | 41 | 20.260 | 21.055 | 40.876 | 1.00 | 77.55 |
| ATOM | 173 | C | ASN | A | 41 | 19.542 | 24.870 | 37.871 | 1.00 | 61.80 |
| ATOM | 174 | O | ASN | A | 41 | 18.448 | 24.397 | 37.545 | 1.00 | 46.20 |
| ATOM | 175 | N | TYR | A | 42 | 19.871 | 26.131 | 37.586 | 1.00 | 55.50 |
| ATOM | 176 | CA | TYR | A | 42 | 18.879 | 26.965 | 36.907 | 1.00 | 53.77 |
| ATOM | 177 | CB | TYR | A | 42 | 19.293 | 28.437 | 36.963 | 1.00 | 58.34 |
| ATOM | 178 | CG | TYR | A | 42 | 18.328 | 29.359 | 36.248 | 1.00 | 57.25 |
| ATOM | 179 | CD1 | TYR | A | 42 | 17.106 | 29.704 | 36.812 | 1.00 | 53.13 |
| ATOM | 180 | CE1 | TYR | A | 42 | 16.237 | 30.547 | 36.143 | 1.00 | 55.57 |
| ATOM | 181 | CZ | TYR | A | 42 | 16.586 | 31.048 | 34.908 | 1.00 | 57.51 |
| ATOM | 182 | OH | TYR | A | 42 | 15.728 | 31.888 | 34.236 | 1.00 | 77.05 |
| ATOM | 183 | CE2 | TYR | A | 42 | 17.792 | 30.720 | 34.327 | 1.00 | 53.44 |
| ATOM | 184 | CD2 | TYR | A | 42 | 18.652 | 29.878 | 35.001 | 1.00 | 54.42 |
| ATOM | 185 | C | TYR | A | 42 | 18.676 | 26.523 | 35.463 | 1.00 | 46.65 |
| ATOM | 186 | O | TYR | A | 42 | 17.565 | 26.523 | 34.925 | 1.00 | 42.26 |
| ATOM | 187 | N | LEU | A | 43 | 19.772 | 26.135 | 34.813 | 1.00 | 33.69 |
| ATOM | 188 | CA | LEU | A | 43 | 19.638 | 25.715 | 33.419 | 1.00 | 35.76 |
| ATOM | 189 | CB | LEU | A | 43 | 20.980 | 25.835 | 32.706 | 1.00 | 39.54 |
| ATOM | 190 | CG | LEU | A | 43 | 21.238 | 27.199 | 32.047 | 1.00 | 40.56 |
| ATOM | 191 | CD1 | LEU | A | 43 | 20.408 | 28.282 | 32.714 | 1.00 | 40.30 |
| ATOM | 192 | CD2 | LEU | A | 43 | 22.709 | 27.555 | 32.093 | 1.00 | 29.81 |
| ATOM | 193 | C | LEU | A | 43 | 19.077 | 24.300 | 33.348 | 1.00 | 48.21 |
| ATOM | 194 | O | LEU | A | 43 | 18.421 | 23.937 | 32.371 | 1.00 | 40.48 |
| ATOM | 195 | N | LEU | A | 44 | 19.326 | 23.509 | 34.394 | 1.00 | 46.35 |
| ATOM | 196 | CA | LEU | A | 44 | 18.762 | 22.160 | 34.438 | 1.00 | 44.23 |
| ATOM | 197 | CB | LEU | A | 44 | 19.440 | 21.300 | 35.503 | 1.00 | 45.17 |
| ATOM | 198 | CG | LEU | A | 44 | 19.102 | 19.805 | 35.499 | 1.00 | 45.62 |
| ATOM | 199 | CD1 | LEU | A | 44 | 20.365 | 18.965 | 35.586 | 1.00 | 31.11 |
| ATOM | 200 | CD2 | LEU | A | 44 | 18.148 | 19.475 | 36.638 | 1.00 | 39.34 |
| ATOM | 201 | C | LEU | A | 44 | 17.257 | 22.238 | 34.682 | 1.00 | 40.48 |
| ATOM | 202 | O | LEU | A | 44 | 16.490 | 21.546 | 34.017 | 1.00 | 46.20 |
| ATOM | 203 | N | SER | A | 45 | 16.833 | 23.079 | 35.624 | 1.00 | 37.28 |
| ATOM | 204 | CA | SER | A | 45 | 15.412 | 23.227 | 35.909 | 1.00 | 41.63 |
| ATOM | 205 | CB | SER | A | 45 | 15.183 | 24.298 | 36.971 | 1.00 | 49.13 |
| ATOM | 206 | OG | SER | A | 45 | 15.258 | 23.742 | 38.273 | 1.00 | 45.34 |
| ATOM | 207 | C | SER | A | 45 | 14.644 | 23.557 | 34.635 | 1.00 | 47.28 |

FIGURE 106

| | | | | | | | | | |
|---|---|---|---|---|---|---|---|---|---|
| ATOM | 208 | O | SER | A | 45 | 13.532 | 23.071 | 34.420 | 1.00 56.54 |
| ATOM | 209 | N | LYS | A | 46 | 15.239 | 24.377 | 33.775 | 1.00 48.99 |
| ATOM | 210 | CA | LYS | A | 46 | 14.588 | 24.708 | 32.508 | 1.00 53.30 |
| ATOM | 211 | CB | LYS | A | 46 | 15.228 | 25.954 | 31.890 | 1.00 59.16 |
| ATOM | 212 | CG | LYS | A | 46 | 15.006 | 27.210 | 32.725 | 1.00 63.86 |
| ATOM | 213 | CD | LYS | A | 46 | 15.835 | 28.379 | 32.220 | 1.00 64.48 |
| ATOM | 214 | CE | LYS | A | 46 | 15.039 | 29.675 | 32.252 | 1.00 64.98 |
| ATOM | 215 | NZ | LYS | A | 46 | 15.675 | 30.745 | 31.433 | 1.00 56.04 |
| ATOM | 216 | C | LYS | A | 46 | 14.622 | 23.533 | 31.535 | 1.00 47.85 |
| ATOM | 217 | O | LYS | A | 46 | 13.603 | 23.266 | 30.890 | 1.00 55.12 |
| ATOM | 218 | N | GLU | A | 47 | 15.746 | 22.834 | 31.420 | 1.00 36.87 |
| ATOM | 219 | CA | GLU | A | 47 | 15.840 | 21.669 | 30.546 | 1.00 45.16 |
| ATOM | 220 | CB | GLU | A | 47 | 17.247 | 21.060 | 30.588 | 1.00 47.65 |
| ATOM | 221 | CG | GLU | A | 47 | 17.495 | 20.034 | 29.498 | 1.00 48.46 |
| ATOM | 222 | CD | GLU | A | 47 | 18.919 | 19.534 | 29.410 | 1.00 55.44 |
| ATOM | 223 | OE1 | GLU | A | 47 | 19.665 | 19.977 | 28.510 | 1.00 68.33 |
| ATOM | 224 | OE2 | GLU | A | 47 | 19.316 | 18.675 | 30.229 | 1.00 55.44 |
| ATOM | 225 | C | GLU | A | 47 | 14.799 | 20.615 | 30.918 | 1.00 39.97 |
| ATOM | 226 | O | GLU | A | 47 | 14.010 | 20.178 | 30.080 | 1.00 39.03 |
| ATOM | 227 | N | TYR | A | 48 | 14.770 | 20.191 | 32.177 | 1.00 35.97 |
| ATOM | 228 | CA | TYR | A | 48 | 13.770 | 19.221 | 32.614 | 1.00 40.19 |
| ATOM | 229 | CB | TYR | A | 48 | 13.910 | 18.925 | 34.105 | 1.00 35.08 |
| ATOM | 230 | CG | TYR | A | 48 | 13.004 | 17.856 | 34.671 | 1.00 32.74 |
| ATOM | 231 | CD1 | TYR | A | 48 | 13.165 | 16.505 | 34.361 | 1.00 28.30 |
| ATOM | 232 | CE1 | TYR | A | 48 | 12.316 | 15.553 | 34.903 | 1.00 22.32 |
| ATOM | 233 | CZ | TYR | A | 48 | 11.301 | 15.922 | 35.753 | 1.00 30.86 |
| ATOM | 234 | OH | TYR | A | 48 | 10.450 | 14.983 | 36.292 | 1.00 30.54 |
| ATOM | 235 | CE2 | TYR | A | 48 | 11.115 | 17.253 | 36.080 | 1.00 26.20 |
| ATOM | 236 | CD2 | TYR | A | 48 | 11.970 | 18.194 | 35.534 | 1.00 28.57 |
| ATOM | 237 | C | TYR | A | 48 | 12.369 | 19.729 | 32.302 | 1.00 49.53 |
| ATOM | 238 | O | TYR | A | 48 | 11.526 | 19.006 | 31.769 | 1.00 51.41 |
| ATOM | 239 | N | GLU | A | 49 | 12.105 | 20.994 | 32.637 | 1.00 46.93 |
| ATOM | 240 | CA | GLU | A | 49 | 10.772 | 21.536 | 32.378 | 1.00 42.89 |
| ATOM | 241 | CB | GLU | A | 49 | 10.655 | 22.963 | 32.912 | 1.00 52.01 |
| ATOM | 242 | CG | GLU | A | 49 | 9.269 | 23.330 | 33.420 | 1.00 65.78 |
| ATOM | 243 | CD | GLU | A | 49 | 8.788 | 22.347 | 34.472 | 1.00 79.04 |
| ATOM | 244 | OE1 | GLU | A | 49 | 9.560 | 22.068 | 35.413 | 1.00 96.40 |
| ATOM | 245 | OE2 | GLU | A | 49 | 7.646 | 21.856 | 34.354 | 1.00 91.96 |
| ATOM | 246 | C | GLU | A | 49 | 10.462 | 21.493 | 30.883 | 1.00 29.38 |
| ATOM | 247 | O | GLU | A | 49 | 9.309 | 21.423 | 30.462 | 1.00 38.63 |
| ATOM | 248 | N | GLU | A | 50 | 11.510 | 21.544 | 30.075 | 1.00 34.87 |
| ATOM | 249 | CA | GLU | A | 50 | 11.357 | 21.477 | 28.626 | 1.00 46.84 |
| ATOM | 250 | CB | GLU | A | 50 | 12.745 | 21.550 | 27.998 | 1.00 52.28 |
| ATOM | 251 | CG | GLU | A | 50 | 12.782 | 21.554 | 26.483 | 1.00 62.44 |
| ATOM | 252 | CD | GLU | A | 50 | 13.712 | 22.655 | 25.996 | 1.00 72.44 |
| ATOM | 253 | OE1 | GLU | A | 50 | 14.373 | 22.454 | 24.958 | 1.00 92.62 |
| ATOM | 254 | OE2 | GLU | A | 50 | 13.753 | 23.697 | 26.686 | 1.00 72.72 |
| ATOM | 255 | C | GLU | A | 50 | 10.644 | 20.199 | 28.208 | 1.00 52.30 |
| ATOM | 256 | O | GLU | A | 50 | 9.964 | 20.114 | 27.186 | 1.00 54.37 |
| ATOM | 257 | N | LEU | A | 51 | 10.816 | 19.164 | 29.028 | 1.00 44.46 |
| ATOM | 258 | CA | LEU | A | 51 | 10.319 | 17.841 | 28.691 | 1.00 34.94 |
| ATOM | 259 | CB | LEU | A | 51 | 11.233 | 16.772 | 29.304 | 1.00 24.94 |

FIGURE 107

| ATOM | 260 | CG | LEU | A | 51 | 12.654 | 16.734 | 28.754 | 1.00 | 21.39 |
| --- | --- | --- | --- | --- | --- | --- | --- | --- | --- | --- |
| ATOM | 261 | CD1 | LEU | A | 51 | 13.621 | 16.312 | 29.850 | 1.00 | 34.46 |
| ATOM | 262 | CD2 | LEU | A | 51 | 12.731 | 15.811 | 27.550 | 1.00 | 25.27 |
| ATOM | 263 | C | LEU | A | 51 | 8.912 | 17.588 | 29.202 | 1.00 | 42.88 |
| ATOM | 264 | O | LEU | A | 51 | 8.350 | 16.541 | 28.883 | 1.00 | 29.33 |
| ATOM | 265 | N | LYS | A | 52 | 8.399 | 18.530 | 29.983 | 1.00 | 44.99 |
| ATOM | 266 | CA | LYS | A | 52 | 7.115 | 18.337 | 30.643 | 1.00 | 49.66 |
| ATOM | 267 | CB | LYS | A | 52 | 6.789 | 19.557 | 31.513 | 1.00 | 57.53 |
| ATOM | 268 | CG | LYS | A | 52 | 6.095 | 20.683 | 30.765 | 1.00 | 69.23 |
| ATOM | 269 | CD | LYS | A | 52 | 6.543 | 22.048 | 31.263 | 1.00 | 75.40 |
| ATOM | 270 | CE | LYS | A | 52 | 5.563 | 23.135 | 30.850 | 1.00 | 81.49 |
| ATOM | 271 | NZ | LYS | A | 52 | 4.161 | 22.796 | 31.229 | 1.00 | 87.53 |
| ATOM | 272 | C | LYS | A | 52 | 5.973 | 18.083 | 29.671 | 1.00 | 38.67 |
| ATOM | 273 | O | LYS | A | 52 | 5.052 | 17.334 | 29.988 | 1.00 | 35.81 |
| ATOM | 274 | N | ASP | A | 53 | 5.984 | 18.692 | 28.489 | 1.00 | 36.11 |
| ATOM | 275 | CA | ASP | A | 53 | 4.829 | 18.567 | 27.605 | 1.00 | 40.07 |
| ATOM | 276 | CB | ASP | A | 53 | 4.529 | 19.928 | 26.954 | 1.00 | 49.22 |
| ATOM | 277 | CG | ASP | A | 53 | 4.334 | 21.018 | 27.995 | 1.00 | 54.49 |
| ATOM | 278 | OD1 | ASP | A | 53 | 5.153 | 21.961 | 28.039 | 1.00 | 73.06 |
| ATOM | 279 | OD2 | ASP | A | 53 | 3.367 | 20.942 | 28.782 | 1.00 | 35.35 |
| ATOM | 280 | C | ASP | A | 53 | 5.012 | 17.503 | 26.537 | 1.00 | 32.08 |
| ATOM | 281 | O | ASP | A | 53 | 4.126 | 17.303 | 25.702 | 1.00 | 27.30 |
| ATOM | 282 | N | VAL | A | 54 | 6.138 | 16.789 | 26.531 | 1.00 | 23.82 |
| ATOM | 283 | CA | VAL | A | 54 | 6.275 | 15.745 | 25.515 | 1.00 | 26.43 |
| ATOM | 284 | CB | VAL | A | 54 | 7.644 | 15.063 | 25.611 | 1.00 | 23.01 |
| ATOM | 285 | CG1 | VAL | A | 54 | 7.804 | 13.986 | 24.545 | 1.00 | 19.26 |
| ATOM | 286 | CG2 | VAL | A | 54 | 8.762 | 16.096 | 25.487 | 1.00 | 34.53 |
| ATOM | 287 | C | VAL | A | 54 | 5.166 | 14.704 | 25.659 | 1.00 | 26.62 |
| ATOM | 288 | O | VAL | A | 54 | 4.905 | 14.234 | 26.761 | 1.00 | 17.16 |
| ATOM | 289 | N | GLY | A | 55 | 4.527 | 14.349 | 24.554 | 1.00 | 21.88 |
| ATOM | 290 | CA | GLY | A | 55 | 3.558 | 13.282 | 24.475 | 1.00 | 23.39 |
| ATOM | 291 | C | GLY | A | 55 | 2.195 | 13.617 | 25.024 | 1.00 | 30.22 |
| ATOM | 292 | O | GLY | A | 55 | 1.314 | 12.758 | 25.104 | 1.00 | 23.51 |
| ATOM | 293 | N | ARG | A | 56 | 1.989 | 14.875 | 25.405 | 1.00 | 31.50 |
| ATOM | 294 | CA | ARG | A | 56 | 0.782 | 15.271 | 26.119 | 1.00 | 28.44 |
| ATOM | 295 | CB | ARG | A | 56 | 0.984 | 16.662 | 26.743 | 1.00 | 36.73 |
| ATOM | 296 | CG | ARG | A | 56 | 1.082 | 17.789 | 25.719 | 1.00 | 31.99 |
| ATOM | 297 | CD | ARG | A | 56 | 1.004 | 19.156 | 26.390 | 1.00 | 37.18 |
| ATOM | 298 | NE | ARG | A | 56 | -0.281 | 19.323 | 27.056 | 1.00 | 43.75 |
| ATOM | 299 | CZ | ARG | A | 56 | -0.556 | 19.932 | 28.193 | 1.00 | 45.89 |
| ATOM | 300 | NH1 | ARG | A | 56 | 0.380 | 20.516 | 28.923 | 1.00 | 38.18 |
| ATOM | 301 | NH2 | ARG | A | 56 | -1.817 | 19.962 | 28.623 | 1.00 | 39.43 |
| ATOM | 302 | C | ARG | A | 56 | -0.450 | 15.279 | 25.227 | 1.00 | 29.67 |
| ATOM | 303 | O | ARG | A | 56 | -1.567 | 15.445 | 25.732 | 1.00 | 27.62 |
| ATOM | 304 | N | ASN | A | 57 | -0.237 | 15.110 | 23.922 | 1.00 | 26.65 |
| ATOM | 305 | CA | ASN | A | 57 | -1.345 | 15.090 | 22.982 | 1.00 | 27.28 |
| ATOM | 306 | CB | ASN | A | 57 | -0.843 | 15.400 | 21.560 | 1.00 | 38.20 |
| ATOM | 307 | CG | ASN | A | 57 | 0.466 | 14.695 | 21.254 | 1.00 | 54.73 |
| ATOM | 308 | OD1 | ASN | A | 57 | 1.420 | 14.764 | 22.038 | 1.00 | 55.09 |
| ATOM | 309 | ND2 | ASN | A | 57 | 0.530 | 14.011 | 20.113 | 1.00 | 53.28 |
| ATOM | 310 | C | ASN | A | 57 | -2.063 | 13.752 | 22.942 | 1.00 | 24.18 |
| ATOM | 311 | O | ASN | A | 57 | -3.083 | 13.668 | 22.252 | 1.00 | 23.88 |

FIGURE 108

| | | | | | | | | | |
|---|---|---|---|---|---|---|---|---|---|
| ATOM | 312 | N | GLN | A | 58 | -1.579 | 12.719 | 23.623 | 1.00 27.84 |
| ATOM | 313 | CA | GLN | A | 58 | -2.119 | 11.366 | 23.492 | 1.00 20.86 |
| ATOM | 314 | CB | GLN | A | 58 | -0.963 | 10.339 | 23.556 | 1.00 16.18 |
| ATOM | 315 | CG | GLN | A | 58 | -0.004 | 10.576 | 22.386 | 1.00 19.18 |
| ATOM | 316 | CD | GLN | A | 58 | 1.282 | 9.797 | 22.440 | 1.00 17.89 |
| ATOM | 317 | OE1 | GLN | A | 58 | 1.430 | 8.818 | 21.702 | 1.00 27.40 |
| ATOM | 318 | NE2 | GLN | A | 58 | 2.226 | 10.196 | 23.293 | 1.00 22.07 |
| ATOM | 319 | C | GLN | A | 58 | -3.169 | 11.060 | 24.540 | 1.00 24.60 |
| ATOM | 320 | O | GLN | A | 58 | -3.146 | 11.517 | 25.685 | 1.00 28.29 |
| ATOM | 321 | N | SER | A | 59 | -4.147 | 10.253 | 24.129 | 1.00 19.50 |
| ATOM | 322 | CA | SER | A | 59 | -5.255 | 9.909 | 25.012 | 1.00 17.23 |
| ATOM | 323 | CB | SER | A | 59 | -6.538 | 9.850 | 24.170 | 1.00 25.69 |
| ATOM | 324 | OG | SER | A | 59 | -6.970 | 11.173 | 23.891 | 1.00 42.05 |
| ATOM | 325 | C | SER | A | 59 | -5.039 | 8.570 | 25.710 | 1.00 19.80 |
| ATOM | 326 | O | SER | A | 59 | -4.224 | 7.784 | 25.210 | 1.00 16.72 |
| ATOM | 327 | N | CYS | A | 60 | -5.766 | 8.346 | 26.789 | 1.00 18.16 |
| ATOM | 328 | CA | CYS | A | 60 | -5.784 | 7.104 | 27.553 | 1.00 24.60 |
| ATOM | 329 | CB | CYS | A | 60 | -5.166 | 7.309 | 28.946 | 1.00 22.29 |
| ATOM | 330 | SG | CYS | A | 60 | -3.478 | 7.963 | 28.894 | 1.00 32.87 |
| ATOM | 331 | C | CYS | A | 60 | -7.200 | 6.568 | 27.701 | 1.00 24.69 |
| ATOM | 332 | O | CYS | A | 60 | -7.633 | 6.163 | 28.783 | 1.00 15.41 |
| ATOM | 333 | N | ASP | A | 61 | -7.989 | 6.554 | 26.627 | 1.00 21.29 |
| ATOM | 334 | CA | ASP | A | 61 | -9.399 | 6.222 | 26.803 | 1.00 17.62 |
| ATOM | 335 | CB | ASP | A | 61 | -10.193 | 6.519 | 25.524 | 1.00 24.76 |
| ATOM | 336 | CG | ASP | A | 61 | -10.158 | 7.992 | 25.163 | 1.00 30.04 |
| ATOM | 337 | OD1 | ASP | A | 61 | -9.946 | 8.844 | 26.050 | 1.00 27.96 |
| ATOM | 338 | OD2 | ASP | A | 61 | -10.334 | 8.286 | 23.966 | 1.00 30.86 |
| ATOM | 339 | C | ASP | A | 61 | -9.618 | 4.764 | 27.165 | 1.00 22.87 |
| ATOM | 340 | O | ASP | A | 61 | -10.577 | 4.424 | 27.849 | 1.00 23.80 |
| ATOM | 341 | N | ILE | A | 62 | -8.760 | 3.857 | 26.693 | 1.00 17.20 |
| ATOM | 342 | CA | ILE | A | 62 | -9.073 | 2.454 | 27.018 | 1.00 17.76 |
| ATOM | 343 | CB | ILE | A | 62 | -8.198 | 1.491 | 26.203 | 1.00 19.59 |
| ATOM | 344 | CG1 | ILE | A | 62 | -8.434 | 1.614 | 24.694 | 1.00 30.45 |
| ATOM | 345 | CD1 | ILE | A | 62 | -9.906 | 1.542 | 24.325 | 1.00 29.59 |
| ATOM | 346 | CG2 | ILE | A | 62 | -8.389 | 0.061 | 26.685 | 1.00 19.52 |
| ATOM | 347 | C | ILE | A | 62 | -8.891 | 2.209 | 28.509 | 1.00 24.81 |
| ATOM | 348 | O | ILE | A | 62 | -9.671 | 1.523 | 29.170 | 1.00 20.96 |
| ATOM | 349 | N | ALA | A | 63 | -7.831 | 2.828 | 29.030 | 1.00 18.90 |
| ATOM | 350 | CA | ALA | A | 63 | -7.515 | 2.680 | 30.442 | 1.00 17.49 |
| ATOM | 351 | CB | ALA | A | 63 | -6.214 | 3.420 | 30.729 | 1.00 14.17 |
| ATOM | 352 | C | ALA | A | 63 | -8.646 | 3.193 | 31.321 | 1.00 22.60 |
| ATOM | 353 | O | ALA | A | 63 | -8.776 | 2.756 | 32.467 | 1.00 21.69 |
| ATOM | 354 | N | LEU | A | 64 | -9.433 | 4.106 | 30.768 | 1.00 22.09 |
| ATOM | 355 | CA | LEU | A | 64 | -10.531 | 4.780 | 31.447 | 1.00 24.05 |
| ATOM | 356 | CB | LEU | A | 64 | -10.635 | 6.212 | 30.898 | 1.00 20.03 |
| ATOM | 357 | CG | LEU | A | 64 | -9.562 | 7.184 | 31.388 | 1.00 17.09 |
| ATOM | 358 | CD1 | LEU | A | 64 | -9.621 | 8.500 | 30.633 | 1.00 23.40 |
| ATOM | 359 | CD2 | LEU | A | 64 | -9.722 | 7.431 | 32.885 | 1.00 18.46 |
| ATOM | 360 | C | LEU | A | 64 | -11.867 | 4.072 | 31.310 | 1.00 28.67 |
| ATOM | 361 | O | LEU | A | 64 | -12.878 | 4.468 | 31.898 | 1.00 24.74 |
| ATOM | 362 | N | LEU | A | 65 | -11.959 | 2.988 | 30.544 | 1.00 23.30 |
| ATOM | 363 | CA | LEU | A | 65 | -13.262 | 2.317 | 30.495 | 1.00 26.61 |

FIGURE 109

| | | | | | | | | | |
|---|---|---|---|---|---|---|---|---|---|
| ATOM | 364 | CB | LEU | A | 65 | -13.254 | 1.209 | 29.436 | 1.00 27.54 |
| ATOM | 365 | CG | LEU | A | 65 | -12.864 | 1.722 | 28.042 | 1.00 27.54 |
| ATOM | 366 | CD1 | LEU | A | 65 | -12.668 | 0.573 | 27.069 | 1.00 25.94 |
| ATOM | 367 | CD2 | LEU | A | 65 | -13.911 | 2.707 | 27.542 | 1.00 31.37 |
| ATOM | 368 | C | LEU | A | 65 | -13.622 | 1.772 | 31.869 | 1.00 24.88 |
| ATOM | 369 | O | LEU | A | 65 | -12.743 | 1.361 | 32.617 | 1.00 27.17 |
| ATOM | 370 | N | PRO | A | 66 | -14.907 | 1.798 | 32.204 | 1.00 28.42 |
| ATOM | 371 | CA | PRO | A | 66 | -15.378 | 1.350 | 33.511 | 1.00 32.94 |
| ATOM | 372 | CB | PRO | A | 66 | -16.909 | 1.316 | 33.342 | 1.00 34.08 |
| ATOM | 373 | CG | PRO | A | 66 | -17.188 | 2.301 | 32.262 | 1.00 39.92 |
| ATOM | 374 | CD | PRO | A | 66 | -16.002 | 2.281 | 31.339 | 1.00 35.79 |
| ATOM | 375 | C | PRO | A | 66 | -14.879 | -0.038 | 33.884 | 1.00 25.20 |
| ATOM | 376 | O | PRO | A | 66 | -14.577 | -0.329 | 35.039 | 1.00 30.25 |
| ATOM | 377 | N | GLU | A | 67 | -14.784 | -0.948 | 32.916 | 1.00 26.85 |
| ATOM | 378 | CA | GLU | A | 67 | -14.418 | -2.299 | 33.346 | 1.00 35.73 |
| ATOM | 379 | CB | GLU | A | 67 | -14.879 | -3.321 | 32.308 | 1.00 39.08 |
| ATOM | 380 | CG | GLU | A | 67 | -15.067 | -2.754 | 30.914 | 1.00 48.88 |
| ATOM | 381 | CD | GLU | A | 67 | -14.264 | -3.501 | 29.864 | 1.00 57.56 |
| ATOM | 382 | OE1 | GLU | A | 67 | -14.251 | -4.752 | 29.884 | 1.00 77.10 |
| ATOM | 383 | OE2 | GLU | A | 67 | -13.642 | -2.832 | 29.012 | 1.00 41.80 |
| ATOM | 384 | C | GLU | A | 67 | -12.923 | -2.398 | 33.622 | 1.00 36.25 |
| ATOM | 385 | O | GLU | A | 67 | -12.447 | -3.441 | 34.078 | 1.00 32.32 |
| ATOM | 386 | N | ASN | A | 68 | -12.167 | -1.333 | 33.359 | 1.00 31.47 |
| ATOM | 387 | CA | ASN | A | 68 | -10.724 | -1.380 | 33.588 | 1.00 21.87 |
| ATOM | 388 | CB | ASN | A | 68 | -9.950 | -0.794 | 32.395 | 1.00 22.35 |
| ATOM | 389 | CG | ASN | A | 68 | -10.008 | -1.714 | 31.195 | 1.00 19.79 |
| ATOM | 390 | OD1 | ASN | A | 68 | -10.127 | -2.930 | 31.350 | 1.00 23.52 |
| ATOM | 391 | ND2 | ASN | A | 68 | -9.927 | -1.147 | 29.997 | 1.00 19.33 |
| ATOM | 392 | C | ASN | A | 68 | -10.329 | -0.618 | 34.841 | 1.00 20.30 |
| ATOM | 393 | O | ASN | A | 68 | -9.154 | -0.604 | 35.215 | 1.00 22.70 |
| ATOM | 394 | N | ARG | A | 69 | -11.286 | 0.026 | 35.508 | 1.00 26.70 |
| ATOM | 395 | CA | ARG | A | 69 | -10.894 | 0.889 | 36.623 | 1.00 33.64 |
| ATOM | 396 | CB | ARG | A | 69 | -12.116 | 1.607 | 37.211 | 1.00 44.80 |
| ATOM | 397 | CG | ARG | A | 69 | -11.775 | 2.959 | 37.824 | 1.00 54.18 |
| ATOM | 398 | CD | ARG | A | 69 | -12.982 | 3.581 | 38.508 | 1.00 63.01 |
| ATOM | 399 | NE | ARG | A | 69 | -12.717 | 3.903 | 39.904 | 1.00 71.32 |
| ATOM | 400 | CZ | ARG | A | 69 | -13.573 | 3.781 | 40.910 | 1.00 77.50 |
| ATOM | 401 | NH1 | ARG | A | 69 | -14.801 | 3.330 | 40.694 | 1.00 86.91 |
| ATOM | 402 | NH2 | ARG | A | 69 | -13.203 | 4.108 | 42.144 | 1.00 73.55 |
| ATOM | 403 | C | ARG | A | 69 | -10.153 | 0.129 | 37.715 | 1.00 29.65 |
| ATOM | 404 | O | ARG | A | 69 | -9.113 | 0.604 | 38.189 | 1.00 40.10 |
| ATOM | 405 | N | GLY | A | 70 | -10.644 | -1.040 | 38.113 | 1.00 23.99 |
| ATOM | 406 | CA | GLY | A | 70 | -9.961 | -1.818 | 39.143 | 1.00 19.86 |
| ATOM | 407 | C | GLY | A | 70 | -8.590 | -2.288 | 38.689 | 1.00 24.39 |
| ATOM | 408 | O | GLY | A | 70 | -7.784 | -2.734 | 39.521 | 1.00 22.56 |
| ATOM | 409 | N | LYS | A | 71 | -8.301 | -2.205 | 37.379 | 1.00 19.98 |
| ATOM | 410 | CA | LYS | A | 71 | -7.003 | -2.702 | 36.908 | 1.00 15.60 |
| ATOM | 411 | CB | LYS | A | 71 | -7.123 | -3.252 | 35.480 | 1.00 18.68 |
| ATOM | 412 | CG | LYS | A | 71 | -8.200 | -4.318 | 35.326 | 1.00 15.28 |
| ATOM | 413 | CD | LYS | A | 71 | -8.403 | -4.675 | 33.855 | 1.00 15.32 |
| ATOM | 414 | CE | LYS | A | 71 | -9.713 | -5.448 | 33.703 | 1.00 27.04 |
| ATOM | 415 | NZ | LYS | A | 71 | -10.141 | -5.554 | 32.281 | 1.00 31.96 |

FIGURE 110

| | | | | | | | | | |
|---|---|---|---|---|---|---|---|---|---|
| ATOM | 416 | C | LYS | A | 71 | -5.890 | -1.672 | 36.944 | 1.00 14.54 |
| ATOM | 417 | O | LYS | A | 71 | -4.752 | -1.993 | 36.578 | 1.00 17.52 |
| ATOM | 418 | N | ASN | A | 72 | -6.149 | -0.439 | 37.371 | 1.00 11.96 |
| ATOM | 419 | CA | ASN | A | 72 | -5.101 | 0.568 | 37.479 | 1.00 11.74 |
| ATOM | 420 | CB | ASN | A | 72 | -5.545 | 1.876 | 36.813 | 1.00 14.82 |
| ATOM | 421 | CG | ASN | A | 72 | -5.837 | 1.654 | 35.339 | 1.00 23.46 |
| ATOM | 422 | OD1 | ASN | A | 72 | -5.007 | 1.128 | 34.599 | 1.00 16.09 |
| ATOM | 423 | ND2 | ASN | A | 72 | -7.025 | 2.057 | 34.903 | 1.00 21.08 |
| ATOM | 424 | C | ASN | A | 72 | -4.753 | 0.835 | 38.937 | 1.00 16.08 |
| ATOM | 425 | O | ASN | A | 72 | -5.647 | 1.079 | 39.741 | 1.00 18.28 |
| ATOM | 426 | N | ARG | A | 73 | -3.471 | 0.788 | 39.258 | 1.00 12.51 |
| ATOM | 427 | CA | ARG | A | 73 | -3.013 | 1.010 | 40.621 | 1.00 20.92 |
| ATOM | 428 | CB | ARG | A | 73 | -1.525 | 0.666 | 40.738 | 1.00 13.10 |
| ATOM | 429 | CG | ARG | A | 73 | -0.989 | 0.829 | 42.148 | 1.00 9.31 |
| ATOM | 430 | CD | ARG | A | 73 | 0.454 | 0.359 | 42.272 | 1.00 11.98 |
| ATOM | 431 | NE | ARG | A | 73 | 0.510 | -1.117 | 42.294 | 1.00 9.41 |
| ATOM | 432 | CZ | ARG | A | 73 | 0.265 | -1.768 | 43.428 | 1.00 17.50 |
| ATOM | 433 | NH1 | ARG | A | 73 | -0.024 | -1.096 | 44.549 | 1.00 14.11 |
| ATOM | 434 | NH2 | ARG | A | 73 | 0.330 | -3.094 | 43.391 | 1.00 16.87 |
| ATOM | 435 | C | ARG | A | 73 | -3.255 | 2.460 | 41.041 | 1.00 25.16 |
| ATOM | 436 | O | ARG | A | 73 | -3.658 | 2.737 | 42.170 | 1.00 14.89 |
| ATOM | 437 | N | TYR | A | 74 | -2.991 | 3.373 | 40.114 | 1.00 17.87 |
| ATOM | 438 | CA | TYR | A | 74 | -3.209 | 4.806 | 40.336 | 1.00 15.26 |
| ATOM | 439 | CB | TYR | A | 74 | -1.887 | 5.539 | 40.348 | 1.00 18.93 |
| ATOM | 440 | CG | TYR | A | 74 | -0.898 | 5.054 | 41.388 | 1.00 19.16 |
| ATOM | 441 | CD1 | TYR | A | 74 | -1.081 | 5.313 | 42.735 | 1.00 22.07 |
| ATOM | 442 | CE1 | TYR | A | 74 | -0.174 | 4.871 | 43.684 | 1.00 17.71 |
| ATOM | 443 | CZ | TYR | A | 74 | 0.932 | 4.160 | 43.289 | 1.00 16.94 |
| ATOM | 444 | OH | TYR | A | 74 | 1.851 | 3.713 | 44.213 | 1.00 16.65 |
| ATOM | 445 | CE2 | TYR | A | 74 | 1.139 | 3.891 | 41.947 | 1.00 20.51 |
| ATOM | 446 | CD2 | TYR | A | 74 | 0.225 | 4.337 | 41.009 | 1.00 14.89 |
| ATOM | 447 | C | TYR | A | 74 | -4.150 | 5.322 | 39.263 | 1.00 23.96 |
| ATOM | 448 | O | TYR | A | 74 | -3.994 | 5.065 | 38.065 | 1.00 19.22 |
| ATOM | 449 | N | ASN | A | 75 | -5.202 | 6.053 | 39.641 | 1.00 18.99 |
| ATOM | 450 | CA | ASN | A | 75 | -6.220 | 6.288 | 38.610 | 1.00 23.42 |
| ATOM | 451 | CB | ASN | A | 75 | -7.557 | 6.585 | 39.296 | 1.00 34.45 |
| ATOM | 452 | CG | ASN | A | 75 | -8.137 | 5.350 | 39.975 | 1.00 51.03 |
| ATOM | 453 | OD1 | ASN | A | 75 | -8.673 | 5.414 | 41.085 | 1.00 50.00 |
| ATOM | 454 | ND2 | ASN | A | 75 | -8.051 | 4.180 | 39.342 | 1.00 38.85 |
| ATOM | 455 | C | ASN | A | 75 | -5.736 | 7.353 | 37.640 | 1.00 18.82 |
| ATOM | 456 | O | ASN | A | 75 | -6.317 | 7.585 | 36.580 | 1.00 20.63 |
| ATOM | 457 | N | ASN | A | 76 | -4.615 | 7.991 | 37.977 | 1.00 16.28 |
| ATOM | 458 | CA | ASN | A | 76 | -4.105 | 9.045 | 37.110 | 1.00 19.45 |
| ATOM | 459 | CB | ASN | A | 76 | -3.997 | 10.339 | 37.926 | 1.00 22.45 |
| ATOM | 460 | CG | ASN | A | 76 | -2.980 | 10.295 | 39.044 | 1.00 33.59 |
| ATOM | 461 | OD1 | ASN | A | 76 | -2.679 | 9.257 | 39.636 | 1.00 26.17 |
| ATOM | 462 | ND2 | ASN | A | 76 | -2.431 | 11.474 | 39.344 | 1.00 29.60 |
| ATOM | 463 | C | ASN | A | 76 | -2.781 | 8.692 | 36.465 | 1.00 17.17 |
| ATOM | 464 | O | ASN | A | 76 | -2.066 | 9.532 | 35.917 | 1.00 17.91 |
| ATOM | 465 | N | ILE | A | 77 | -2.389 | 7.423 | 36.475 | 1.00 20.00 |
| ATOM | 466 | CA | ILE | A | 77 | -1.171 | 6.992 | 35.791 | 1.00 14.81 |
| ATOM | 467 | CB | ILE | A | 77 | -0.049 | 6.504 | 36.702 | 1.00 11.59 |

FIGURE 111

| | | | | | | | | | |
|---|---|---|---|---|---|---|---|---|---|
| ATOM | 468 | CG1 | ILE | A | 77 | 0.336 | 7.468 | 37.832 | 1.00 17.04 |
| ATOM | 469 | CD1 | ILE | A | 77 | 0.986 | 8.713 | 37.282 | 1.00 17.56 |
| ATOM | 470 | CG2 | ILE | A | 77 | 1.227 | 6.165 | 35.924 | 1.00 15.42 |
| ATOM | 471 | C | ILE | A | 77 | -1.617 | 5.835 | 34.878 | 1.00 16.96 |
| ATOM | 472 | O | ILE | A | 77 | -1.733 | 4.718 | 35.381 | 1.00 15.55 |
| ATOM | 473 | N | LEU | A | 78 | -1.897 | 6.184 | 33.632 | 1.00 12.76 |
| ATOM | 474 | CA | LEU | A | 78 | -2.530 | 5.255 | 32.689 | 1.00 10.94 |
| ATOM | 475 | CB | LEU | A | 78 | -3.984 | 5.623 | 32.413 | 1.00 12.51 |
| ATOM | 476 | CG | LEU | A | 78 | -4.880 | 5.963 | 33.601 | 1.00 19.43 |
| ATOM | 477 | CD1 | LEU | A | 78 | -6.237 | 6.497 | 33.151 | 1.00 22.19 |
| ATOM | 478 | CD2 | LEU | A | 78 | -5.082 | 4.744 | 34.486 | 1.00 24.35 |
| ATOM | 479 | C | LEU | A | 78 | -1.723 | 5.244 | 31.398 | 1.00 17.94 |
| ATOM | 480 | O | LEU | A | 78 | -1.093 | 6.248 | 31.056 | 1.00 16.73 |
| ATOM | 481 | N | PRO | A | 79 | -1.711 | 4.123 | 30.692 | 1.00 19.09 |
| ATOM | 482 | CA | PRO | A | 79 | -0.920 | 4.050 | 29.450 | 1.00 16.12 |
| ATOM | 483 | CB | PRO | A | 79 | -0.870 | 2.539 | 29.199 | 1.00 9.23 |
| ATOM | 484 | CG | PRO | A | 79 | -2.204 | 2.074 | 29.718 | 1.00 11.75 |
| ATOM | 485 | CD | PRO | A | 79 | -2.411 | 2.860 | 30.988 | 1.00 15.77 |
| ATOM | 486 | C | PRO | A | 79 | -1.655 | 4.794 | 28.339 | 1.00 15.99 |
| ATOM | 487 | O | PRO | A | 79 | -2.893 | 4.828 | 28.388 | 1.00 15.25 |
| ATOM | 488 | N | TYR | A | 80 | -0.926 | 5.362 | 27.389 | 1.00 10.13 |
| ATOM | 489 | CA | TYR | A | 80 | -1.502 | 5.993 | 26.206 | 1.00 11.18 |
| ATOM | 490 | CB | TYR | A | 80 | -0.451 | 6.764 | 25.423 | 1.00 13.27 |
| ATOM | 491 | CG | TYR | A | 80 | 0.146 | 7.959 | 26.117 | 1.00 12.63 |
| ATOM | 492 | CD1 | TYR | A | 80 | -0.697 | 8.902 | 26.685 | 1.00 18.08 |
| ATOM | 493 | CE1 | TYR | A | 80 | -0.173 | 10.005 | 27.321 | 1.00 20.03 |
| ATOM | 494 | CZ | TYR | A | 80 | 1.186 | 10.172 | 27.391 | 1.00 16.07 |
| ATOM | 495 | OH | TYR | A | 80 | 1.682 | 11.281 | 28.032 | 1.00 21.65 |
| ATOM | 496 | CE2 | TYR | A | 80 | 2.054 | 9.257 | 26.837 | 1.00 13.46 |
| ATOM | 497 | CD2 | TYR | A | 80 | 1.507 | 8.150 | 26.198 | 1.00 14.05 |
| ATOM | 498 | C | TYR | A | 80 | -2.104 | 4.930 | 25.286 | 1.00 18.00 |
| ATOM | 499 | O | TYR | A | 80 | -1.568 | 3.823 | 25.165 | 1.00 15.44 |
| ATOM | 500 | N | ASP | A | 81 | -3.222 | 5.206 | 24.625 | 1.00 15.66 |
| ATOM | 501 | CA | ASP | A | 81 | -3.849 | 4.129 | 23.846 | 1.00 18.95 |
| ATOM | 502 | CB | ASP | A | 81 | -5.184 | 4.541 | 23.239 | 1.00 21.06 |
| ATOM | 503 | CG | ASP | A | 81 | -6.217 | 5.004 | 24.239 | 1.00 23.24 |
| ATOM | 504 | OD1 | ASP | A | 81 | -6.322 | 4.394 | 25.318 | 1.00 20.28 |
| ATOM | 505 | OD2 | ASP | A | 81 | -6.944 | 5.971 | 23.937 | 1.00 21.10 |
| ATOM | 506 | C | ASP | A | 81 | -2.919 | 3.699 | 22.717 | 1.00 19.22 |
| ATOM | 507 | O | ASP | A | 81 | -2.884 | 2.543 | 22.314 | 1.00 24.23 |
| ATOM | 508 | N | ALA | A | 82 | -2.171 | 4.664 | 22.193 | 1.00 20.83 |
| ATOM | 509 | CA | ALA | A | 82 | -1.326 | 4.375 | 21.033 | 1.00 21.56 |
| ATOM | 510 | CB | ALA | A | 82 | -0.802 | 5.697 | 20.471 | 1.00 18.25 |
| ATOM | 511 | C | ALA | A | 82 | -0.179 | 3.424 | 21.333 | 1.00 17.70 |
| ATOM | 512 | O | ALA | A | 82 | 0.344 | 2.784 | 20.412 | 1.00 24.59 |
| ATOM | 513 | N | THR | A | 83 | 0.291 | 3.282 | 22.570 | 1.00 14.11 |
| ATOM | 514 | CA | THR | A | 83 | 1.482 | 2.482 | 22.831 | 1.00 15.16 |
| ATOM | 515 | CB | THR | A | 83 | 2.667 | 3.349 | 23.283 | 1.00 26.72 |
| ATOM | 516 | OG1 | THR | A | 83 | 2.291 | 4.126 | 24.431 | 1.00 20.70 |
| ATOM | 517 | CG2 | THR | A | 83 | 3.076 | 4.358 | 22.213 | 1.00 24.85 |
| ATOM | 518 | C | THR | A | 83 | 1.223 | 1.437 | 23.918 | 1.00 17.17 |
| ATOM | 519 | O | THR | A | 83 | 2.168 | 0.825 | 24.412 | 1.00 17.29 |

FIGURE 112

| ATOM | 520 | N   | ARG A | 84 | -0.030  | 1.226   | 24.310 | 1.00 | 14.78  |
|------|-----|-----|-------|----|---------|---------|--------|------|--------|
| ATOM | 521 | CA  | ARG A | 84 | -0.304  | 0.265   | 25.377 | 1.00 | 14.16  |
| ATOM | 522 | CB  | ARG A | 84 | -1.752  | 0.389   | 25.832 | 1.00 | 16.16  |
| ATOM | 523 | CG  | ARG A | 84 | -2.824  | -0.021  | 24.841 | 1.00 | 12.30  |
| ATOM | 524 | CD  | ARG A | 84 | -4.206  | 0.035   | 25.483 | 1.00 | 18.81  |
| ATOM | 525 | NE  | ARG A | 84 | -5.231  | -0.504  | 24.587 | 1.00 | 18.67  |
| ATOM | 526 | CZ  | ARG A | 84 | -5.856  | -1.657  | 24.745 | 1.00 | 25.65  |
| ATOM | 527 | NH1 | ARG A | 84 | -5.570  | -2.421  | 25.794 | 1.00 | 18.24  |
| ATOM | 528 | NH2 | ARG A | 84 | -6.769  | -2.038  | 23.856 | 1.00 | 23.18  |
| ATOM | 529 | C   | ARG A | 84 | 0.002   | -1.164  | 24.926 | 1.00 | 19.54  |
| ATOM | 530 | O   | ARG A | 84 | -0.053  | -1.498  | 23.748 | 1.00 | 16.47  |
| ATOM | 531 | N   | VAL A | 85 | 0.340   | -2.027  | 25.871 | 1.00 | 14.56  |
| ATOM | 532 | CA  | VAL A | 85 | 0.511   | -3.453  | 25.593 | 1.00 | 15.91  |
| ATOM | 533 | CB  | VAL A | 85 | 1.516   | -4.099  | 26.552 | 1.00 | 9.66   |
| ATOM | 534 | CG1 | VAL A | 85 | 1.595   | -5.605  | 26.279 | 1.00 | 26.22  |
| ATOM | 535 | CG2 | VAL A | 85 | 2.900   | -3.489  | 26.419 | 1.00 | 8.35   |
| ATOM | 536 | C   | VAL A | 85 | -0.824  | -4.164  | 25.708 | 1.00 | 18.09  |
| ATOM | 537 | O   | VAL A | 85 | -1.596  | -4.001  | 26.664 | 1.00 | 17.84  |
| ATOM | 538 | N   | LYS A | 86 | -1.170  | -4.991  | 24.713 | 1.00 | 17.85  |
| ATOM | 539 | CA  | LYS A | 86 | -2.481  | -5.634  | 24.797 | 1.00 | 16.55  |
| ATOM | 540 | CB  | LYS A | 86 | -3.270  | -5.448  | 23.499 | 1.00 | 22.98  |
| ATOM | 541 | CG  | LYS A | 86 | -3.353  | -4.027  | 22.972 | 1.00 | 25.37  |
| ATOM | 542 | CD  | LYS A | 86 | -4.093  | -3.996  | 21.641 | 1.00 | 35.98  |
| ATOM | 543 | CE  | LYS A | 86 | -4.302  | -2.569  | 21.152 | 1.00 | 41.61  |
| ATOM | 544 | NZ  | LYS A | 86 | -5.067  | -2.535  | 19.870 | 1.00 | 41.47  |
| ATOM | 545 | C   | LYS A | 86 | -2.354  | -7.130  | 25.073 | 1.00 | 17.71  |
| ATOM | 546 | O   | LYS A | 86 | -1.473  | -7.780  | 24.495 | 1.00 | 26.73  |
| ATOM | 547 | N   | LEU A | 87 | -3.238  | -7.641  | 25.909 | 1.00 | 16.65  |
| ATOM | 548 | CA  | LEU A | 87 | -3.386  | -9.070  | 26.157 | 1.00 | 21.87  |
| ATOM | 549 | CB  | LEU A | 87 | -4.108  | -9.340  | 27.477 | 1.00 | 22.56  |
| ATOM | 550 | CG  | LEU A | 87 | -3.573  | -8.679  | 28.751 | 1.00 | 19.45  |
| ATOM | 551 | CD1 | LEU A | 87 | -4.502  | -8.981  | 29.920 | 1.00 | 33.41  |
| ATOM | 552 | CD2 | LEU A | 87 | -2.155  | -9.123  | 29.057 | 1.00 | 19.25  |
| ATOM | 553 | C   | LEU A | 87 | -4.194  | -9.716  | 25.033 | 1.00 | 34.42  |
| ATOM | 554 | O   | LEU A | 87 | -5.103  | -9.087  | 24.480 | 1.00 | 29.92  |
| ATOM | 555 | N   | SER A | 88 | -3.906  | -10.961 | 24.684 | 1.00 | 39.81  |
| ATOM | 556 | CA  | SER A | 88 | -4.712  | -11.686 | 23.715 | 1.00 | 42.02  |
| ATOM | 557 | CB  | SER A | 88 | -4.153  | -13.103 | 23.509 | 1.00 | 45.96  |
| ATOM | 558 | OG  | SER A | 88 | -4.499  | -13.843 | 24.684 | 1.00 | 44.96  |
| ATOM | 559 | C   | SER A | 88 | -6.154  | -11.853 | 24.182 | 1.00 | 39.54  |
| ATOM | 560 | O   | SER A | 88 | -6.425  | -11.712 | 25.374 | 1.00 | 35.93  |
| ATOM | 561 | N   | ASN A | 89 | -7.041  | -12.175 | 23.251 | 1.00 | 58.52  |
| ATOM | 562 | CA  | ASN A | 89 | -8.435  | -12.501 | 23.518 | 1.00 | 76.46  |
| ATOM | 563 | CB  | ASN A | 89 | -9.366  | -11.396 | 23.017 | 1.00 | 82.65  |
| ATOM | 564 | CG  | ASN A | 89 | -9.457  | -11.372 | 21.501 | 1.00 | 93.50  |
| ATOM | 565 | OD1 | ASN A | 89 | -10.512 | -11.100 | 20.929 | 1.00 | 104.34 |
| ATOM | 566 | ND2 | ASN A | 89 | -8.337  | -11.659 | 20.847 | 1.00 | 109.77 |
| ATOM | 567 | C   | ASN A | 89 | -8.807  | -13.831 | 22.860 | 1.00 | 88.77  |
| ATOM | 568 | O   | ASN A | 89 | -8.533  | -14.011 | 21.671 | 1.00 | 92.19  |
| ATOM | 569 | N   | VAL A | 90 | -9.407  | -14.736 | 23.621 | 1.00 | 99.23  |
| ATOM | 570 | CA  | VAL A | 90 | -9.793  | -16.059 | 23.144 | 1.00 | 106.42 |
| ATOM | 571 | CB  | VAL A | 90 | -8.923  | -17.172 | 23.760 | 1.00 | 106.95 |

FIGURE 113

| | | | | | | | | | |
|---|---|---|---|---|---|---|---|---|---|
| ATOM | 572 | CG1 | VAL | A | 90 | -9.298 | -18.525 | 23.172 | 1.00 112.12 |
| ATOM | 573 | CG2 | VAL | A | 90 | -7.444 | -16.892 | 23.548 | 1.00 105.34 |
| ATOM | 574 | C | VAL | A | 90 | -11.258 | -16.369 | 23.451 | 1.00 111.33 |
| ATOM | 575 | O | VAL | A | 90 | -12.138 | -16.117 | 22.628 | 1.00 105.84 |
| ATOM | 576 | N | ASP | A | 91 | -11.510 | -16.921 | 24.632 | 1.00 119.26 |
| ATOM | 577 | CA | ASP | A | 91 | -12.855 | -17.239 | 25.095 | 1.00 128.16 |
| ATOM | 578 | CB | ASP | A | 91 | -12.828 | -18.448 | 26.031 | 1.00 125.07 |
| ATOM | 579 | CG | ASP | A | 91 | -14.191 | -18.774 | 26.609 | 1.00 121.16 |
| ATOM | 580 | OD1 | ASP | A | 91 | -15.007 | -19.377 | 25.880 | 1.00 104.75 |
| ATOM | 581 | OD2 | ASP | A | 91 | -14.447 | -18.433 | 27.785 | 1.00 117.18 |
| ATOM | 582 | C | ASP | A | 91 | -13.482 | -16.042 | 25.807 | 1.00 139.13 |
| ATOM | 583 | O | ASP | A | 91 | -13.028 | -15.676 | 26.894 | 1.00 148.32 |
| ATOM | 584 | N | ASP | A | 92 | -14.503 | -15.447 | 25.202 | 1.00 145.93 |
| ATOM | 585 | CA | ASP | A | 92 | -15.147 | -14.241 | 25.726 | 1.00 149.70 |
| ATOM | 586 | CB | ASP | A | 92 | -15.415 | -14.375 | 27.225 | 1.00 149.57 |
| ATOM | 587 | CG | ASP | A | 92 | -16.361 | -15.502 | 27.584 | 1.00 147.36 |
| ATOM | 588 | OD1 | ASP | A | 92 | -17.567 | -15.233 | 27.781 | 1.00 137.75 |
| ATOM | 589 | OD2 | ASP | A | 92 | -15.912 | -16.665 | 27.677 | 1.00 148.40 |
| ATOM | 590 | C | ASP | A | 92 | -14.286 | -13.021 | 25.419 | 1.00 150.50 |
| ATOM | 591 | O | ASP | A | 92 | -13.148 | -12.934 | 25.892 | 1.00 155.89 |
| ATOM | 592 | N | ASP | A | 93 | -14.778 | -12.068 | 24.620 | 1.00 148.19 |
| ATOM | 593 | CA | ASP | A | 93 | -13.886 | -10.998 | 24.173 | 1.00 145.42 |
| ATOM | 594 | CB | ASP | A | 93 | -13.545 | -11.222 | 22.687 | 1.00 146.89 |
| ATOM | 595 | CG | ASP | A | 93 | -14.744 | -11.594 | 21.844 | 1.00 147.24 |
| ATOM | 596 | OD1 | ASP | A | 93 | -15.278 | -12.710 | 22.011 | 1.00 141.98 |
| ATOM | 597 | OD2 | ASP | A | 93 | -15.159 | -10.772 | 21.001 | 1.00 148.93 |
| ATOM | 598 | C | ASP | A | 93 | -14.404 | -9.578 | 24.346 | 1.00 140.50 |
| ATOM | 599 | O | ASP | A | 93 | -14.742 | -8.922 | 23.357 | 1.00 135.04 |
| ATOM | 600 | N | PRO | A | 94 | -14.451 | -9.070 | 25.570 | 1.00 137.75 |
| ATOM | 601 | CA | PRO | A | 94 | -14.684 | -7.638 | 25.812 | 1.00 134.16 |
| ATOM | 602 | CB | PRO | A | 94 | -15.340 | -7.646 | 27.190 | 1.00 136.91 |
| ATOM | 603 | CG | PRO | A | 94 | -14.801 | -8.848 | 27.882 | 1.00 138.06 |
| ATOM | 604 | CD | PRO | A | 94 | -14.305 | -9.803 | 26.837 | 1.00 139.01 |
| ATOM | 605 | C | PRO | A | 94 | -13.363 | -6.879 | 25.830 | 1.00 126.58 |
| ATOM | 606 | O | PRO | A | 94 | -12.437 | -7.253 | 25.099 | 1.00 132.66 |
| ATOM | 607 | N | CYS | A | 95 | -13.220 | -5.827 | 26.639 | 1.00 114.33 |
| ATOM | 608 | CA | CYS | A | 95 | -11.898 | -5.198 | 26.765 | 1.00 95.06 |
| ATOM | 609 | CB | CYS | A | 95 | -11.947 | -3.690 | 26.961 | 1.00 97.01 |
| ATOM | 610 | SG | CYS | A | 95 | -10.323 | -2.901 | 27.121 | 1.00 74.50 |
| ATOM | 611 | C | CYS | A | 95 | -11.146 | -5.872 | 27.913 | 1.00 71.83 |
| ATOM | 612 | O | CYS | A | 95 | -10.629 | -5.311 | 28.870 | 1.00 58.75 |
| ATOM | 613 | N | SER | A | 96 | -11.089 | -7.193 | 27.759 | 1.00 54.83 |
| ATOM | 614 | CA | SER | A | 96 | -10.254 | -8.038 | 28.595 | 1.00 46.09 |
| ATOM | 615 | CB | SER | A | 96 | -10.848 | -9.437 | 28.720 | 1.00 49.86 |
| ATOM | 616 | OG | SER | A | 96 | -10.801 | -10.147 | 27.491 | 1.00 47.97 |
| ATOM | 617 | C | SER | A | 96 | -8.854 | -8.076 | 27.988 | 1.00 31.56 |
| ATOM | 618 | O | SER | A | 96 | -8.045 | -8.933 | 28.321 | 1.00 30.50 |
| ATOM | 619 | N | ASP | A | 97 | -8.562 | -7.129 | 27.085 | 1.00 25.83 |
| ATOM | 620 | CA | ASP | A | 97 | -7.233 | -7.050 | 26.495 | 1.00 17.26 |
| ATOM | 621 | CB | ASP | A | 97 | -7.317 | -6.646 | 25.029 | 1.00 22.22 |
| ATOM | 622 | CG | ASP | A | 97 | -7.590 | -5.179 | 24.772 | 1.00 32.54 |
| ATOM | 623 | OD1 | ASP | A | 97 | -7.945 | -4.404 | 25.681 | 1.00 25.44 |

FIGURE 114

| | | | | | | | | | |
|---|---|---|---|---|---|---|---|---|---|
| ATOM | 624 | OD2 | ASP | A | 97 | -7.444 | -4.765 | 23.600 | 1.00 44.31 |
| ATOM | 625 | C | ASP | A | 97 | -6.357 | -6.065 | 27.271 | 1.00 18.88 |
| ATOM | 626 | O | ASP | A | 97 | -5.194 | -5.883 | 26.902 | 1.00 18.89 |
| ATOM | 627 | N | TYR | A | 98 | -6.947 | -5.456 | 28.296 | 1.00 20.04 |
| ATOM | 628 | CA | TYR | A | 98 | -6.313 | -4.338 | 28.976 | 1.00 18.41 |
| ATOM | 629 | CB | TYR | A | 98 | -7.366 | -3.378 | 29.609 | 1.00 18.59 |
| ATOM | 630 | CG | TYR | A | 98 | -6.631 | -2.221 | 30.288 | 1.00 20.03 |
| ATOM | 631 | CD1 | TYR | A | 98 | -6.043 | -1.216 | 29.522 | 1.00 16.83 |
| ATOM | 632 | CE1 | TYR | A | 98 | -5.361 | -0.144 | 30.090 | 1.00 13.49 |
| ATOM | 633 | CZ | TYR | A | 98 | -5.276 | -0.116 | 31.471 | 1.00 19.51 |
| ATOM | 634 | OH | TYR | A | 98 | -4.624 | 0.908 | 32.106 | 1.00 14.09 |
| ATOM | 635 | CE2 | TYR | A | 98 | -5.846 | -1.095 | 32.255 | 1.00 13.64 |
| ATOM | 636 | CD2 | TYR | A | 98 | -6.528 | -2.145 | 31.673 | 1.00 17.45 |
| ATOM | 637 | C | TYR | A | 98 | -5.343 | -4.746 | 30.066 | 1.00 18.17 |
| ATOM | 638 | O | TYR | A | 98 | -5.664 | -5.449 | 31.020 | 1.00 22.86 |
| ATOM | 639 | N | ILE | A | 99 | -4.130 | -4.218 | 29.989 | 1.00 14.66 |
| ATOM | 640 | CA | ILE | A | 99 | -3.274 | -4.175 | 31.172 | 1.00 17.87 |
| ATOM | 641 | CB | ILE | A | 99 | -2.221 | -5.290 | 31.223 | 1.00 17.34 |
| ATOM | 642 | CG1 | ILE | A | 99 | -1.274 | -5.190 | 32.428 | 1.00 13.76 |
| ATOM | 643 | CD1 | ILE | A | 99 | -0.492 | -6.481 | 32.633 | 1.00 14.80 |
| ATOM | 644 | CG2 | ILE | A | 99 | -1.443 | -5.348 | 29.924 | 1.00 15.59 |
| ATOM | 645 | C | ILE | A | 99 | -2.594 | -2.807 | 31.227 | 1.00 14.26 |
| ATOM | 646 | O | ILE | A | 99 | -2.353 | -2.191 | 30.183 | 1.00 16.44 |
| ATOM | 647 | N | ASN | A | 100 | -2.315 | -2.334 | 32.435 | 1.00 14.80 |
| ATOM | 648 | CA | ASN | A | 100 | -1.609 | -1.054 | 32.562 | 1.00 12.64 |
| ATOM | 649 | CB | ASN | A | 100 | -1.818 | -0.440 | 33.951 | 1.00 11.26 |
| ATOM | 650 | CG | ASN | A | 100 | -1.326 | 0.997 | 33.976 | 1.00 13.09 |
| ATOM | 651 | OD1 | ASN | A | 100 | -0.260 | 1.278 | 33.456 | 1.00 13.19 |
| ATOM | 652 | ND2 | ASN | A | 100 | -2.099 | 1.903 | 34.579 | 1.00 15.88 |
| ATOM | 653 | C | ASN | A | 100 | -0.134 | -1.242 | 32.244 | 1.00 10.03 |
| ATOM | 654 | O | ASN | A | 100 | 0.698 | -1.477 | 33.119 | 1.00 12.85 |
| ATOM | 655 | N | ALA | A | 101 | 0.193 | -1.152 | 30.946 | 1.00 10.66 |
| ATOM | 656 | CA | ALA | A | 101 | 1.550 | -1.361 | 30.488 | 1.00 9.30 |
| ATOM | 657 | CB | ALA | A | 101 | 1.839 | -2.863 | 30.397 | 1.00 13.80 |
| ATOM | 658 | C | ALA | A | 101 | 1.777 | -0.712 | 29.125 | 1.00 6.85 |
| ATOM | 659 | O | ALA | A | 101 | 0.809 | -0.539 | 28.394 | 1.00 12.08 |
| ATOM | 660 | N | SER | A | 102 | 3.026 | -0.393 | 28.829 | 1.00 9.92 |
| ATOM | 661 | CA | SER | A | 102 | 3.389 | 0.362 | 27.641 | 1.00 14.73 |
| ATOM | 662 | CB | SER | A | 102 | 3.650 | 1.831 | 28.010 | 1.00 11.60 |
| ATOM | 663 | OG | SER | A | 102 | 2.561 | 2.407 | 28.691 | 1.00 11.12 |
| ATOM | 664 | C | SER | A | 102 | 4.644 | -0.211 | 26.986 | 1.00 15.69 |
| ATOM | 665 | O | SER | A | 102 | 5.563 | -0.654 | 27.686 | 1.00 12.17 |
| ATOM | 666 | N | TYR | A | 103 | 4.680 | -0.176 | 25.652 | 1.00 9.06 |
| ATOM | 667 | CA | TYR | A | 103 | 5.889 | -0.530 | 24.933 | 1.00 9.07 |
| ATOM | 668 | CB | TYR | A | 103 | 5.549 | -0.917 | 23.486 | 1.00 9.50 |
| ATOM | 669 | CG | TYR | A | 103 | 4.870 | -2.239 | 23.265 | 1.00 12.57 |
| ATOM | 670 | CD1 | TYR | A | 103 | 5.544 | -3.435 | 23.487 | 1.00 12.90 |
| ATOM | 671 | CE1 | TYR | A | 103 | 4.895 | -4.640 | 23.272 | 1.00 20.46 |
| ATOM | 672 | CZ | TYR | A | 103 | 3.592 | -4.680 | 22.839 | 1.00 22.70 |
| ATOM | 673 | OH | TYR | A | 103 | 2.962 | -5.894 | 22.627 | 1.00 18.14 |
| ATOM | 674 | CE2 | TYR | A | 103 | 2.903 | -3.500 | 22.608 | 1.00 18.79 |
| ATOM | 675 | CD2 | TYR | A | 103 | 3.551 | -2.304 | 22.825 | 1.00 15.94 |

FIGURE 115

| ATOM | 676 | C | TYR | A | 103 | 6.867 | 0.630 | 24.891 | 1.00 | 18.09 |
| ATOM | 677 | O | TYR | A | 103 | 6.457 | 1.768 | 24.641 | 1.00 | 20.48 |
| ATOM | 678 | N | ILE | A | 104 | 8.155 | 0.358 | 25.111 | 1.00 | 15.21 |
| ATOM | 679 | CA | ILE | A | 104 | 9.108 | 1.466 | 25.121 | 1.00 | 15.90 |
| ATOM | 680 | CB | ILE | A | 104 | 9.608 | 1.785 | 26.545 | 1.00 | 22.38 |
| ATOM | 681 | CG1 | ILE | A | 104 | 8.496 | 1.941 | 27.585 | 1.00 | 20.69 |
| ATOM | 682 | CD1 | ILE | A | 104 | 7.599 | 3.126 | 27.276 | 1.00 | 17.88 |
| ATOM | 683 | CG2 | ILE | A | 104 | 10.476 | 3.034 | 26.538 | 1.00 | 22.81 |
| ATOM | 684 | C | ILE | A | 104 | 10.309 | 1.146 | 24.243 | 1.00 | 17.74 |
| ATOM | 685 | O | ILE | A | 104 | 10.911 | 0.086 | 24.357 | 1.00 | 16.43 |
| ATOM | 686 | N | PRO | A | 105 | 10.677 | 2.062 | 23.352 | 1.00 | 17.30 |
| ATOM | 687 | CA | PRO | A | 105 | 11.894 | 1.894 | 22.563 | 1.00 | 16.76 |
| ATOM | 688 | CB | PRO | A | 105 | 11.837 | 3.088 | 21.592 | 1.00 | 24.69 |
| ATOM | 689 | CG | PRO | A | 105 | 10.418 | 3.563 | 21.626 | 1.00 | 25.93 |
| ATOM | 690 | CD | PRO | A | 105 | 9.941 | 3.295 | 23.030 | 1.00 | 21.65 |
| ATOM | 691 | C | PRO | A | 105 | 13.174 | 2.007 | 23.372 | 1.00 | 21.81 |
| ATOM | 692 | O | PRO | A | 105 | 13.286 | 2.726 | 24.368 | 1.00 | 21.23 |
| ATOM | 693 | N | GLY | A | 106 | 14.205 | 1.282 | 22.935 | 1.00 | 17.97 |
| ATOM | 694 | CA | GLY | A | 106 | 15.504 | 1.436 | 23.569 | 1.00 | 16.53 |
| ATOM | 695 | C | GLY | A | 106 | 16.557 | 1.885 | 22.578 | 1.00 | 24.48 |
| ATOM | 696 | O | GLY | A | 106 | 16.248 | 2.474 | 21.543 | 1.00 | 24.56 |
| ATOM | 697 | N | ASN | A | 107 | 17.824 | 1.595 | 22.858 | 1.00 | 24.62 |
| ATOM | 698 | CA | ASN | A | 107 | 18.889 | 2.049 | 21.971 | 1.00 | 31.26 |
| ATOM | 699 | CB | ASN | A | 107 | 20.249 | 1.899 | 22.661 | 1.00 | 38.05 |
| ATOM | 700 | CG | ASN | A | 107 | 20.775 | 3.221 | 23.184 | 1.00 | 50.06 |
| ATOM | 701 | OD1 | ASN | A | 107 | 20.008 | 4.143 | 23.476 | 1.00 | 66.78 |
| ATOM | 702 | ND2 | ASN | A | 107 | 22.094 | 3.313 | 23.301 | 1.00 | 52.90 |
| ATOM | 703 | C | ASN | A | 107 | 18.917 | 1.269 | 20.663 | 1.00 | 30.81 |
| ATOM | 704 | O | ASN | A | 107 | 19.482 | 1.767 | 19.693 | 1.00 | 28.48 |
| ATOM | 705 | N | ASN | A | 108 | 18.329 | 0.080 | 20.679 | 1.00 | 32.22 |
| ATOM | 706 | CA | ASN | A | 108 | 18.512 | -0.922 | 19.640 | 1.00 | 32.10 |
| ATOM | 707 | CB | ASN | A | 108 | 19.098 | -2.184 | 20.305 | 1.00 | 37.07 |
| ATOM | 708 | CG | ASN | A | 108 | 20.233 | -1.830 | 21.251 | 1.00 | 46.06 |
| ATOM | 709 | OD1 | ASN | A | 108 | 21.309 | -1.443 | 20.780 | 1.00 | 27.30 |
| ATOM | 710 | ND2 | ASN | A | 108 | 20.005 | -1.966 | 22.559 | 1.00 | 28.03 |
| ATOM | 711 | C | ASN | A | 108 | 17.262 | -1.291 | 18.863 | 1.00 | 34.62 |
| ATOM | 712 | O | ASN | A | 108 | 17.392 | -1.721 | 17.708 | 1.00 | 34.88 |
| ATOM | 713 | N | PHE | A | 109 | 16.060 | -1.168 | 19.423 | 1.00 | 25.20 |
| ATOM | 714 | CA | PHE | A | 109 | 14.840 | -1.500 | 18.690 | 1.00 | 22.97 |
| ATOM | 715 | CB | PHE | A | 109 | 14.603 | -2.993 | 18.522 | 1.00 | 22.47 |
| ATOM | 716 | CG | PHE | A | 109 | 14.885 | -3.951 | 19.661 | 1.00 | 28.29 |
| ATOM | 717 | CD1 | PHE | A | 109 | 13.849 | -4.560 | 20.357 | 1.00 | 24.27 |
| ATOM | 718 | CE1 | PHE | A | 109 | 14.113 | -5.455 | 21.391 | 1.00 | 22.67 |
| ATOM | 719 | CZ | PHE | A | 109 | 15.414 | -5.748 | 21.750 | 1.00 | 19.40 |
| ATOM | 720 | CE2 | PHE | A | 109 | 16.451 | -5.143 | 21.061 | 1.00 | 34.44 |
| ATOM | 721 | CD2 | PHE | A | 109 | 16.183 | -4.259 | 20.033 | 1.00 | 33.01 |
| ATOM | 722 | C | PHE | A | 109 | 13.620 | -0.886 | 19.383 | 1.00 | 19.13 |
| ATOM | 723 | O | PHE | A | 109 | 13.686 | -0.531 | 20.559 | 1.00 | 20.41 |
| ATOM | 724 | N | ARG | A | 110 | 12.538 | -0.787 | 18.641 | 1.00 | 16.32 |
| ATOM | 725 | CA | ARG | A | 110 | 11.318 | -0.110 | 19.048 | 1.00 | 23.52 |
| ATOM | 726 | CB | ARG | A | 110 | 10.342 | -0.036 | 17.853 | 1.00 | 22.40 |
| ATOM | 727 | CG | ARG | A | 110 | 10.918 | 0.753 | 16.688 | 1.00 | 29.99 |

FIGURE 116

```
ATOM    728  CD   ARG A 110       9.987   1.901  16.317  1.00 44.00
ATOM    729  NE   ARG A 110      10.461   3.122  16.971  1.00 64.93
ATOM    730  CZ   ARG A 110      10.694   4.269  16.352  1.00 72.68
ATOM    731  NH1  ARG A 110      10.494   4.368  15.044  1.00 62.39
ATOM    732  NH2  ARG A 110      11.125   5.318  17.045  1.00 82.09
ATOM    733  C    ARG A 110      10.607  -0.783  20.197  1.00 28.20
ATOM    734  O    ARG A 110       9.959  -0.177  21.052  1.00 29.57
ATOM    735  N    ARG A 111      10.665  -2.120  20.269  1.00 19.46
ATOM    736  CA   ARG A 111       9.868  -2.607  21.432  1.00 19.03
ATOM    737  CB   ARG A 111       8.795  -3.563  20.962  1.00 15.07
ATOM    738  CG   ARG A 111       7.581  -2.905  20.332  1.00 22.11
ATOM    739  CD   ARG A 111       6.553  -3.962  19.940  1.00 34.64
ATOM    740  NE   ARG A 111       5.295  -3.339  19.524  1.00 33.18
ATOM    741  CZ   ARG A 111       4.166  -4.022  19.393  1.00 25.21
ATOM    742  NH1  ARG A 111       4.172  -5.327  19.654  1.00 22.23
ATOM    743  NH2  ARG A 111       3.074  -3.380  19.012  1.00 32.75
ATOM    744  C    ARG A 111      10.831  -3.241  22.417  1.00 17.42
ATOM    745  O    ARG A 111      10.720  -4.425  22.726  1.00 18.84
ATOM    746  N    GLU A 112      11.800  -2.432  22.855  1.00 12.49
ATOM    747  CA   GLU A 112      12.900  -2.998  23.629  1.00 13.99
ATOM    748  CB   GLU A 112      14.070  -2.005  23.581  1.00 15.59
ATOM    749  CG   GLU A 112      15.378  -2.703  23.860  1.00 21.33
ATOM    750  CD   GLU A 112      16.623  -2.023  23.352  1.00 27.40
ATOM    751  OE1  GLU A 112      17.658  -2.284  23.998  1.00 26.38
ATOM    752  OE2  GLU A 112      16.619  -1.264  22.363  1.00 25.78
ATOM    753  C    GLU A 112      12.516  -3.334  25.062  1.00 18.95
ATOM    754  O    GLU A 112      13.022  -4.273  25.693  1.00 14.06
ATOM    755  N    TYR A 113      11.576  -2.551  25.570  1.00 17.52
ATOM    756  CA   TYR A 113      11.060  -2.731  26.911  1.00 15.61
ATOM    757  CB   TYR A 113      11.542  -1.629  27.858  1.00 17.96
ATOM    758  CG   TYR A 113      12.990  -1.237  27.756  1.00 14.87
ATOM    759  CD1  TYR A 113      13.405  -0.255  26.878  1.00 17.71
ATOM    760  CE1  TYR A 113      14.734   0.114  26.781  1.00 16.32
ATOM    761  CZ   TYR A 113      15.671  -0.495  27.574  1.00 15.65
ATOM    762  OH   TYR A 113      17.002  -0.145  27.493  1.00 18.69
ATOM    763  CE2  TYR A 113      15.289  -1.484  28.467  1.00 14.44
ATOM    764  CD2  TYR A 113      13.959  -1.844  28.553  1.00 14.04
ATOM    765  C    TYR A 113       9.551  -2.702  26.926  1.00  9.51
ATOM    766  O    TYR A 113       8.855  -2.122  26.096  1.00 11.17
ATOM    767  N    ILE A 114       9.031  -3.382  27.957  1.00 12.36
ATOM    768  CA   ILE A 114       7.655  -3.187  28.333  1.00  9.29
ATOM    769  CB   ILE A 114       6.831  -4.487  28.322  1.00 13.67
ATOM    770  CG1  ILE A 114       6.425  -4.912  26.904  1.00 14.89
ATOM    771  CD1  ILE A 114       5.910  -6.337  26.844  1.00 15.51
ATOM    772  CG2  ILE A 114       5.623  -4.377  29.232  1.00  8.31
ATOM    773  C    ILE A 114       7.674  -2.598  29.746  1.00 16.23
ATOM    774  O    ILE A 114       8.249  -3.182  30.662  1.00 15.28
ATOM    775  N    VAL A 115       7.060  -1.438  29.910  1.00 14.17
ATOM    776  CA   VAL A 115       7.015  -0.801  31.225  1.00 15.15
ATOM    777  CB   VAL A 115       7.294   0.710  31.084  1.00 20.35
ATOM    778  CG1  VAL A 115       6.761   1.465  32.288  1.00 29.43
ATOM    779  CG2  VAL A 115       8.792   0.932  30.901  1.00 19.15
```

FIGURE 117

| ATOM | 780 | C | VAL | A | 115 | 5.645 | -1.011 | 31.821 | 1.00 | 13.67 |
| ATOM | 781 | O | VAL | A | 115 | 4.631 | -0.945 | 31.114 | 1.00 | 12.23 |
| ATOM | 782 | N | THR | A | 116 | 5.556 | -1.291 | 33.122 | 1.00 | 13.19 |
| ATOM | 783 | CA | THR | A | 116 | 4.208 | -1.553 | 33.635 | 1.00 | 12.05 |
| ATOM | 784 | CB | THR | A | 116 | 3.828 | -3.042 | 33.478 | 1.00 | 14.77 |
| ATOM | 785 | OG1 | THR | A | 116 | 2.432 | -3.257 | 33.750 | 1.00 | 13.69 |
| ATOM | 786 | CG2 | THR | A | 116 | 4.589 | -3.936 | 34.458 | 1.00 | 17.06 |
| ATOM | 787 | C | THR | A | 116 | 4.173 | -1.057 | 35.072 | 1.00 | 9.33 |
| ATOM | 788 | O | THR | A | 116 | 5.221 | -0.780 | 35.652 | 1.00 | 8.64 |
| ATOM | 789 | N | GLN | A | 117 | 2.982 | -0.942 | 35.626 | 1.00 | 10.66 |
| ATOM | 790 | CA | GLN | A | 117 | 2.843 | -0.618 | 37.039 | 1.00 | 8.65 |
| ATOM | 791 | CB | GLN | A | 117 | 1.384 | -0.239 | 37.297 | 1.00 | 9.54 |
| ATOM | 792 | CG | GLN | A | 117 | 0.384 | -1.351 | 37.114 | 1.00 | 12.18 |
| ATOM | 793 | CD | GLN | A | 117 | -1.071 | -1.010 | 37.307 | 1.00 | 19.05 |
| ATOM | 794 | OE1 | GLN | A | 117 | -1.506 | 0.143 | 37.314 | 1.00 | 13.39 |
| ATOM | 795 | NE2 | GLN | A | 117 | -1.918 | -2.025 | 37.476 | 1.00 | 9.71 |
| ATOM | 796 | C | GLN | A | 117 | 3.215 | -1.826 | 37.895 | 1.00 | 11.64 |
| ATOM | 797 | O | GLN | A | 117 | 3.347 | -2.918 | 37.345 | 1.00 | 15.93 |
| ATOM | 798 | N | GLY | A | 118 | 3.356 | -1.703 | 39.207 | 1.00 | 11.16 |
| ATOM | 799 | CA | GLY | A | 118 | 3.499 | -2.903 | 40.060 | 1.00 | 10.85 |
| ATOM | 800 | C | GLY | A | 118 | 2.157 | -3.620 | 40.096 | 1.00 | 13.55 |
| ATOM | 801 | O | GLY | A | 118 | 1.119 | -3.034 | 40.400 | 1.00 | 15.26 |
| ATOM | 802 | N | PRO | A | 119 | 2.148 | -4.916 | 39.758 | 1.00 | 12.96 |
| ATOM | 803 | CA | PRO | A | 119 | 0.901 | -5.678 | 39.674 | 1.00 | 9.13 |
| ATOM | 804 | CB | PRO | A | 119 | 1.408 | -7.119 | 39.531 | 1.00 | 18.59 |
| ATOM | 805 | CG | PRO | A | 119 | 2.720 | -6.964 | 38.824 | 1.00 | 19.31 |
| ATOM | 806 | CD | PRO | A | 119 | 3.341 | -5.706 | 39.396 | 1.00 | 15.37 |
| ATOM | 807 | C | PRO | A | 119 | 0.079 | -5.567 | 40.953 | 1.00 | 8.91 |
| ATOM | 808 | O | PRO | A | 119 | 0.680 | -5.487 | 42.027 | 1.00 | 19.14 |
| ATOM | 809 | N | LEU | A | 120 | -1.228 | -5.555 | 40.787 | 1.00 | 13.32 |
| ATOM | 810 | CA | LEU | A | 120 | -2.126 | -5.581 | 41.935 | 1.00 | 15.54 |
| ATOM | 811 | CB | LEU | A | 120 | -3.388 | -4.787 | 41.631 | 1.00 | 19.85 |
| ATOM | 812 | CG | LEU | A | 120 | -3.158 | -3.297 | 41.331 | 1.00 | 20.01 |
| ATOM | 813 | CD1 | LEU | A | 120 | -4.225 | -2.766 | 40.392 | 1.00 | 17.81 |
| ATOM | 814 | CD2 | LEU | A | 120 | -3.135 | -2.537 | 42.646 | 1.00 | 24.41 |
| ATOM | 815 | C | LEU | A | 120 | -2.481 | -7.038 | 42.220 | 1.00 | 19.68 |
| ATOM | 816 | O | LEU | A | 120 | -2.257 | -7.863 | 41.327 | 1.00 | 18.35 |
| ATOM | 817 | N | PRO | A | 121 | -3.030 | -7.304 | 43.390 | 1.00 | 24.41 |
| ATOM | 818 | CA | PRO | A | 121 | -3.516 | -8.674 | 43.666 | 1.00 | 25.78 |
| ATOM | 819 | CB | PRO | A | 121 | -4.280 | -8.500 | 44.981 | 1.00 | 26.53 |
| ATOM | 820 | CG | PRO | A | 121 | -3.702 | -7.283 | 45.633 | 1.00 | 23.83 |
| ATOM | 821 | CD | PRO | A | 121 | -3.243 | -6.377 | 44.519 | 1.00 | 22.44 |
| ATOM | 822 | C | PRO | A | 121 | -4.419 | -9.154 | 42.533 | 1.00 | 25.28 |
| ATOM | 823 | O | PRO | A | 121 | -4.338 | -10.302 | 42.074 | 1.00 | 26.89 |
| ATOM | 824 | N | GLY | A | 122 | -5.292 | -8.281 | 42.027 | 1.00 | 28.95 |
| ATOM | 825 | CA | GLY | A | 122 | -6.226 | -8.601 | 40.969 | 1.00 | 25.36 |
| ATOM | 826 | C | GLY | A | 122 | -5.706 | -8.512 | 39.557 | 1.00 | 27.04 |
| ATOM | 827 | O | GLY | A | 122 | -6.422 | -8.858 | 38.606 | 1.00 | 25.16 |
| ATOM | 828 | N | THR | A | 123 | -4.472 | -8.062 | 39.322 | 1.00 | 18.42 |
| ATOM | 829 | CA | THR | A | 123 | -3.944 | -8.084 | 37.954 | 1.00 | 17.40 |
| ATOM | 830 | CB | THR | A | 123 | -3.607 | -6.662 | 37.448 | 1.00 | 16.82 |
| ATOM | 831 | OG1 | THR | A | 123 | -2.539 | -6.104 | 38.220 | 1.00 | 16.41 |

FIGURE 118

| ATOM | 832 | CG2 | THR | A | 123 | -4.828 | -5.762 | 37.609 | 1.00 | 13.52 |
| ATOM | 833 | C | THR | A | 123 | -2.691 | -8.924 | 37.831 | 1.00 | 15.59 |
| ATOM | 834 | O | THR | A | 123 | -2.040 | -8.987 | 36.787 | 1.00 | 20.37 |
| ATOM | 835 | N | LYS | A | 124 | -2.242 | -9.614 | 38.888 | 1.00 | 15.84 |
| ATOM | 836 | CA | LYS | A | 124 | -0.996 | -10.357 | 38.635 | 1.00 | 17.87 |
| ATOM | 837 | CB | LYS | A | 124 | -0.395 | -10.888 | 39.928 | 1.00 | 14.86 |
| ATOM | 838 | CG | LYS | A | 124 | -1.274 | -11.701 | 40.840 | 1.00 | 15.78 |
| ATOM | 839 | CD | LYS | A | 124 | -0.510 | -11.950 | 42.138 | 1.00 | 23.39 |
| ATOM | 840 | CE | LYS | A | 124 | -1.394 | -12.535 | 43.232 | 1.00 | 25.01 |
| ATOM | 841 | NZ | LYS | A | 124 | -0.522 | -12.822 | 44.422 | 1.00 | 30.58 |
| ATOM | 842 | C | LYS | A | 124 | -1.169 | -11.500 | 37.639 | 1.00 | 13.08 |
| ATOM | 843 | O | LYS | A | 124 | -0.190 | -11.858 | 36.969 | 1.00 | 18.52 |
| ATOM | 844 | N | ASP | A | 125 | -2.359 | -12.084 | 37.537 | 1.00 | 16.39 |
| ATOM | 845 | CA | ASP | A | 125 | -2.521 | -13.172 | 36.561 | 1.00 | 18.39 |
| ATOM | 846 | CB | ASP | A | 125 | -3.854 | -13.887 | 36.710 | 1.00 | 25.32 |
| ATOM | 847 | CG | ASP | A | 125 | -3.975 | -14.629 | 38.028 | 1.00 | 28.44 |
| ATOM | 848 | OD1 | ASP | A | 125 | -2.925 | -14.835 | 38.666 | 1.00 | 26.58 |
| ATOM | 849 | OD2 | ASP | A | 125 | -5.108 | -14.987 | 38.393 | 1.00 | 36.95 |
| ATOM | 850 | C | ASP | A | 125 | -2.397 | -12.588 | 35.160 | 1.00 | 17.43 |
| ATOM | 851 | O | ASP | A | 125 | -1.848 | -13.215 | 34.260 | 1.00 | 22.46 |
| ATOM | 852 | N | ASP | A | 126 | -2.906 | -11.376 | 35.006 | 1.00 | 18.42 |
| ATOM | 853 | CA | ASP | A | 126 | -2.740 | -10.637 | 33.754 | 1.00 | 17.99 |
| ATOM | 854 | CB | ASP | A | 126 | -3.494 | -9.310 | 33.841 | 1.00 | 20.62 |
| ATOM | 855 | CG | ASP | A | 126 | -4.982 | -9.448 | 34.061 | 1.00 | 38.88 |
| ATOM | 856 | OD1 | ASP | A | 126 | -5.618 | -10.322 | 33.434 | 1.00 | 37.14 |
| ATOM | 857 | OD2 | ASP | A | 126 | -5.512 | -8.656 | 34.867 | 1.00 | 50.50 |
| ATOM | 858 | C | ASP | A | 126 | -1.278 | -10.346 | 33.451 | 1.00 | 19.58 |
| ATOM | 859 | O | ASP | A | 126 | -0.763 | -10.451 | 32.338 | 1.00 | 19.76 |
| ATOM | 860 | N | PHE | A | 127 | -0.558 | -9.916 | 34.485 | 1.00 | 20.86 |
| ATOM | 861 | CA | PHE | A | 127 | 0.860 | -9.628 | 34.340 | 1.00 | 14.49 |
| ATOM | 862 | CB | PHE | A | 127 | 1.450 | -9.238 | 35.698 | 1.00 | 12.42 |
| ATOM | 863 | CG | PHE | A | 127 | 2.959 | -9.103 | 35.725 | 1.00 | 16.56 |
| ATOM | 864 | CD1 | PHE | A | 127 | 3.522 | -7.877 | 35.359 | 1.00 | 14.21 |
| ATOM | 865 | CE1 | PHE | A | 127 | 4.879 | -7.705 | 35.354 | 1.00 | 16.34 |
| ATOM | 866 | CZ | PHE | A | 127 | 5.727 | -8.740 | 35.709 | 1.00 | 23.61 |
| ATOM | 867 | CE2 | PHE | A | 127 | 5.187 | -9.955 | 36.082 | 1.00 | 17.94 |
| ATOM | 868 | CD2 | PHE | A | 127 | 3.820 | -10.126 | 36.094 | 1.00 | 10.35 |
| ATOM | 869 | C | PHE | A | 127 | 1.581 | -10.861 | 33.812 | 1.00 | 17.74 |
| ATOM | 870 | O | PHE | A | 127 | 2.410 | -10.836 | 32.917 | 1.00 | 13.35 |
| ATOM | 871 | N | TRP | A | 128 | 1.311 | -12.025 | 34.435 | 1.00 | 11.40 |
| ATOM | 872 | CA | TRP | A | 128 | 2.102 | -13.181 | 33.987 | 1.00 | 15.21 |
| ATOM | 873 | CB | TRP | A | 128 | 1.989 | -14.340 | 34.993 | 1.00 | 10.56 |
| ATOM | 874 | CG | TRP | A | 128 | 2.845 | -14.116 | 36.205 | 1.00 | 8.09 |
| ATOM | 875 | CD1 | TRP | A | 128 | 2.376 | -13.938 | 37.463 | 1.00 | 11.21 |
| ATOM | 876 | NE1 | TRP | A | 128 | 3.421 | -13.764 | 38.325 | 1.00 | 8.52 |
| ATOM | 877 | CE2 | TRP | A | 128 | 4.594 | -13.825 | 37.643 | 1.00 | 13.75 |
| ATOM | 878 | CD2 | TRP | A | 128 | 4.266 | -14.046 | 36.298 | 1.00 | 12.80 |
| ATOM | 879 | CE3 | TRP | A | 128 | 5.315 | -14.155 | 35.373 | 1.00 | 11.11 |
| ATOM | 880 | CZ3 | TRP | A | 128 | 6.605 | -14.034 | 35.821 | 1.00 | 11.38 |
| ATOM | 881 | CH2 | TRP | A | 128 | 6.893 | -13.810 | 37.181 | 1.00 | 16.48 |
| ATOM | 882 | CZ2 | TRP | A | 128 | 5.902 | -13.701 | 38.112 | 1.00 | 15.53 |
| ATOM | 883 | C | TRP | A | 128 | 1.654 | -13.612 | 32.601 | 1.00 | 12.30 |

FIGURE 119

```
ATOM    884  O    TRP A 128       2.460 -14.098  31.798  1.00 20.27
ATOM    885  N    LYS A 129       0.386 -13.432  32.287  1.00 14.47
ATOM    886  CA   LYS A 129      -0.123 -13.666  30.937  1.00 19.61
ATOM    887  CB   LYS A 129      -1.619 -13.344  30.895  1.00 17.71
ATOM    888  CG   LYS A 129      -2.234 -13.587  29.519  1.00 25.76
ATOM    889  CD   LYS A 129      -3.746 -13.768  29.659  1.00 30.81
ATOM    890  CE   LYS A 129      -4.330 -14.309  28.366  1.00 42.38
ATOM    891  NZ   LYS A 129      -5.236 -13.325  27.707  1.00 64.19
ATOM    892  C    LYS A 129       0.600 -12.834  29.884  1.00 20.15
ATOM    893  O    LYS A 129       0.974 -13.321  28.816  1.00 19.90
ATOM    894  N    MET A 130       0.803 -11.553  30.185  1.00 15.51
ATOM    895  CA   MET A 130       1.625 -10.693  29.342  1.00 12.30
ATOM    896  CB   MET A 130       1.651  -9.264  29.941  1.00 13.90
ATOM    897  CG   MET A 130       2.496  -8.310  29.089  1.00 21.15
ATOM    898  SD   MET A 130       2.449  -6.632  29.804  1.00 18.25
ATOM    899  CE   MET A 130       3.476  -6.963  31.261  1.00  9.99
ATOM    900  C    MET A 130       3.032 -11.212  29.173  1.00 12.39
ATOM    901  O    MET A 130       3.562 -11.277  28.043  1.00 16.98
ATOM    902  N    VAL A 131       3.694 -11.586  30.273  1.00 12.09
ATOM    903  CA   VAL A 131       5.070 -12.076  30.234  1.00 11.97
ATOM    904  CB   VAL A 131       5.538 -12.430  31.659  1.00 16.20
ATOM    905  CG1  VAL A 131       6.799 -13.282  31.685  1.00 15.59
ATOM    906  CG2  VAL A 131       5.769 -11.144  32.455  1.00 15.38
ATOM    907  C    VAL A 131       5.163 -13.304  29.317  1.00 15.84
ATOM    908  O    VAL A 131       6.079 -13.467  28.514  1.00 16.14
ATOM    909  N    TRP A 132       4.164 -14.167  29.469  1.00 14.48
ATOM    910  CA   TRP A 132       4.080 -15.371  28.632  1.00 22.42
ATOM    911  CB   TRP A 132       2.932 -16.265  29.104  1.00 21.06
ATOM    912  CG   TRP A 132       2.745 -17.494  28.255  1.00 22.35
ATOM    913  CD1  TRP A 132       1.874 -17.689  27.232  1.00 23.78
ATOM    914  NE1  TRP A 132       2.025 -18.958  26.719  1.00 33.60
ATOM    915  CE2  TRP A 132       3.010 -19.603  27.414  1.00 33.31
ATOM    916  CD2  TRP A 132       3.490 -18.709  28.393  1.00 28.48
ATOM    917  CE3  TRP A 132       4.512 -19.117  29.253  1.00 28.47
ATOM    918  CZ3  TRP A 132       5.026 -20.393  29.117  1.00 36.09
ATOM    919  CH2  TRP A 132       4.526 -21.255  28.134  1.00 36.28
ATOM    920  CZ2  TRP A 132       3.528 -20.889  27.277  1.00 36.96
ATOM    921  C    TRP A 132       3.856 -15.027  27.164  1.00 20.60
ATOM    922  O    TRP A 132       4.646 -15.362  26.287  1.00 21.95
ATOM    923  N    GLU A 133       2.758 -14.324  26.879  1.00 25.53
ATOM    924  CA   GLU A 133       2.457 -13.988  25.485  1.00 19.74
ATOM    925  CB   GLU A 133       1.135 -13.223  25.431  1.00 18.87
ATOM    926  CG   GLU A 133      -0.060 -14.082  25.806  1.00 25.68
ATOM    927  CD   GLU A 133      -1.358 -13.302  25.838  1.00 29.70
ATOM    928  OE1  GLU A 133      -1.312 -12.052  25.763  1.00 30.46
ATOM    929  OE2  GLU A 133      -2.414 -13.968  25.938  1.00 36.60
ATOM    930  C    GLU A 133       3.539 -13.175  24.804  1.00 28.51
ATOM    931  O    GLU A 133       3.674 -13.293  23.581  1.00 21.96
ATOM    932  N    GLN A 134       4.290 -12.351  25.538  1.00 19.31
ATOM    933  CA   GLN A 134       5.274 -11.491  24.889  1.00 19.87
ATOM    934  CB   GLN A 134       5.351 -10.130  25.608  1.00 17.70
ATOM    935  CG   GLN A 134       4.018  -9.384  25.508  1.00 16.42
```

FIGURE 120

| | | | | | | | | | |
|---|---|---|---|---|---|---|---|---|---|
| ATOM | 936 | CD | GLN | A | 134 | 3.914 | −8.755 | 24.122 | 1.00 23.73 |
| ATOM | 937 | OE1 | GLN | A | 134 | 4.912 | −8.253 | 23.602 | 1.00 28.15 |
| ATOM | 938 | NE2 | GLN | A | 134 | 2.717 | −8.831 | 23.569 | 1.00 32.92 |
| ATOM | 939 | C | GLN | A | 134 | 6.657 | −12.107 | 24.865 | 1.00 20.31 |
| ATOM | 940 | O | GLN | A | 134 | 7.638 | −11.458 | 24.496 | 1.00 17.95 |
| ATOM | 941 | N | ASN | A | 135 | 6.778 | −13.370 | 25.276 | 1.00 19.01 |
| ATOM | 942 | CA | ASN | A | 135 | 8.098 | −13.993 | 25.193 | 1.00 21.67 |
| ATOM | 943 | CB | ASN | A | 135 | 8.553 | −13.988 | 23.723 | 1.00 21.93 |
| ATOM | 944 | CG | ASN | A | 135 | 7.716 | −14.985 | 22.931 | 1.00 35.97 |
| ATOM | 945 | OD1 | ASN | A | 135 | 7.987 | −16.184 | 23.006 | 1.00 58.93 |
| ATOM | 946 | ND2 | ASN | A | 135 | 6.729 | −14.503 | 22.186 | 1.00 42.17 |
| ATOM | 947 | C | ASN | A | 135 | 9.119 | −13.307 | 26.077 | 1.00 19.81 |
| ATOM | 948 | O | ASN | A | 135 | 10.309 | −13.220 | 25.769 | 1.00 16.12 |
| ATOM | 949 | N | VAL | A | 136 | 8.655 | −12.799 | 27.229 | 1.00 20.36 |
| ATOM | 950 | CA | VAL | A | 136 | 9.581 | −12.111 | 28.122 | 1.00 15.08 |
| ATOM | 951 | CB | VAL | A | 136 | 8.778 | −11.340 | 29.200 | 1.00 15.13 |
| ATOM | 952 | CG1 | VAL | A | 136 | 9.745 | −10.779 | 30.232 | 1.00 12.04 |
| ATOM | 953 | CG2 | VAL | A | 136 | 7.926 | −10.264 | 28.538 | 1.00 15.49 |
| ATOM | 954 | C | VAL | A | 136 | 10.502 | −13.092 | 28.836 | 1.00 14.70 |
| ATOM | 955 | O | VAL | A | 136 | 9.982 | −14.072 | 29.366 | 1.00 16.57 |
| ATOM | 956 | N | HIS | A | 137 | 11.802 | −12.874 | 28.906 | 1.00 14.74 |
| ATOM | 957 | CA | HIS | A | 137 | 12.674 | −13.744 | 29.696 | 1.00 21.99 |
| ATOM | 958 | CB | HIS | A | 137 | 13.779 | −14.320 | 28.813 | 1.00 29.85 |
| ATOM | 959 | CG | HIS | A | 137 | 13.243 | −15.085 | 27.643 | 1.00 41.77 |
| ATOM | 960 | ND1 | HIS | A | 137 | 12.224 | −14.609 | 26.847 | 1.00 47.82 |
| ATOM | 961 | CE1 | HIS | A | 137 | 11.951 | −15.483 | 25.894 | 1.00 50.67 |
| ATOM | 962 | NE2 | HIS | A | 137 | 12.762 | −16.515 | 26.043 | 1.00 51.38 |
| ATOM | 963 | CD2 | HIS | A | 137 | 13.575 | −16.290 | 27.131 | 1.00 52.47 |
| ATOM | 964 | C | HIS | A | 137 | 13.278 | −12.993 | 30.881 | 1.00 19.04 |
| ATOM | 965 | O | HIS | A | 137 | 13.809 | −13.584 | 31.822 | 1.00 20.60 |
| ATOM | 966 | N | ASN | A | 138 | 13.193 | −11.663 | 30.864 | 1.00 14.47 |
| ATOM | 967 | CA | ASN | A | 138 | 13.841 | −10.854 | 31.884 | 1.00 13.33 |
| ATOM | 968 | CB | ASN | A | 138 | 15.068 | −10.147 | 31.291 | 1.00 17.70 |
| ATOM | 969 | CG | ASN | A | 138 | 16.167 | −11.101 | 30.874 | 1.00 22.71 |
| ATOM | 970 | OD1 | ASN | A | 138 | 16.544 | −11.199 | 29.699 | 1.00 22.97 |
| ATOM | 971 | ND2 | ASN | A | 138 | 16.701 | −11.826 | 31.845 | 1.00 11.98 |
| ATOM | 972 | C | ASN | A | 138 | 12.881 | −9.806 | 32.455 | 1.00 19.07 |
| ATOM | 973 | O | ASN | A | 138 | 12.306 | −9.048 | 31.668 | 1.00 14.29 |
| ATOM | 974 | N | ILE | A | 139 | 12.750 | −9.775 | 33.771 | 1.00 13.58 |
| ATOM | 975 | CA | ILE | A | 139 | 11.914 | −8.814 | 34.474 | 1.00 17.38 |
| ATOM | 976 | CB | ILE | A | 139 | 10.769 | −9.506 | 35.247 | 1.00 14.95 |
| ATOM | 977 | CG1 | ILE | A | 139 | 9.801 | −10.303 | 34.371 | 1.00 16.27 |
| ATOM | 978 | CD1 | ILE | A | 139 | 8.895 | −11.256 | 35.154 | 1.00 11.30 |
| ATOM | 979 | CG2 | ILE | A | 139 | 10.015 | −8.481 | 36.087 | 1.00 10.83 |
| ATOM | 980 | C | ILE | A | 139 | 12.749 | −7.985 | 35.446 | 1.00 22.75 |
| ATOM | 981 | O | ILE | A | 139 | 13.512 | −8.536 | 36.247 | 1.00 19.39 |
| ATOM | 982 | N | VAL | A | 140 | 12.624 | −6.663 | 35.401 | 1.00 11.65 |
| ATOM | 983 | CA | VAL | A | 140 | 13.383 | −5.800 | 36.301 | 1.00 8.08 |
| ATOM | 984 | CB | VAL | A | 140 | 14.205 | −4.745 | 35.542 | 1.00 17.09 |
| ATOM | 985 | CG1 | VAL | A | 140 | 14.949 | −3.802 | 36.480 | 1.00 11.40 |
| ATOM | 986 | CG2 | VAL | A | 140 | 15.188 | −5.436 | 34.593 | 1.00 15.24 |
| ATOM | 987 | C | VAL | A | 140 | 12.387 | −5.094 | 37.211 | 1.00 15.07 |

FIGURE 121

| ATOM | 988 | O | VAL | A | 140 | 11.457 | -4.455 | 36.710 | 1.00 | 14.02 |
|------|------|-----|-----|---|-----|--------|--------|--------|------|-------|
| ATOM | 989 | N | MET | A | 141 | 12.575 | -5.238 | 38.515 | 1.00 | 14.68 |
| ATOM | 990 | CA | MET | A | 141 | 11.685 | -4.587 | 39.483 | 1.00 | 13.84 |
| ATOM | 991 | CB | MET | A | 141 | 11.042 | -5.664 | 40.363 | 1.00 | 10.75 |
| ATOM | 992 | CG | MET | A | 141 | 10.187 | -5.130 | 41.494 | 1.00 | 13.65 |
| ATOM | 993 | SD | MET | A | 141 | 9.374 | -6.486 | 42.348 | 1.00 | 17.62 |
| ATOM | 994 | CE | MET | A | 141 | 8.443 | -5.608 | 43.606 | 1.00 | 16.36 |
| ATOM | 995 | C | MET | A | 141 | 12.481 | -3.580 | 40.309 | 1.00 | 15.95 |
| ATOM | 996 | O | MET | A | 141 | 13.483 | -3.948 | 40.946 | 1.00 | 13.08 |
| ATOM | 997 | N | VAL | A | 142 | 12.088 | -2.304 | 40.318 | 1.00 | 11.30 |
| ATOM | 998 | CA | VAL | A | 142 | 12.946 | -1.331 | 41.013 | 1.00 | 9.46 |
| ATOM | 999 | CB | VAL | A | 142 | 13.600 | -0.291 | 40.092 | 1.00 | 13.94 |
| ATOM | 1000 | CG1 | VAL | A | 142 | 14.741 | -0.924 | 39.288 | 1.00 | 13.37 |
| ATOM | 1001 | CG2 | VAL | A | 142 | 12.590 | 0.342 | 39.149 | 1.00 | 17.83 |
| ATOM | 1002 | C | VAL | A | 142 | 12.140 | -0.611 | 42.099 | 1.00 | 17.41 |
| ATOM | 1003 | O | VAL | A | 142 | 12.299 | 0.591 | 42.303 | 1.00 | 23.87 |
| ATOM | 1004 | N | THR | A | 143 | 11.299 | -1.355 | 42.791 | 1.00 | 14.35 |
| ATOM | 1005 | CA | THR | A | 143 | 10.552 | -0.929 | 43.977 | 1.00 | 16.41 |
| ATOM | 1006 | CB | THR | A | 143 | 9.117 | -0.509 | 43.638 | 1.00 | 23.66 |
| ATOM | 1007 | OG1 | THR | A | 143 | 8.452 | 0.041 | 44.789 | 1.00 | 20.68 |
| ATOM | 1008 | CG2 | THR | A | 143 | 8.267 | -1.698 | 43.207 | 1.00 | 9.56 |
| ATOM | 1009 | C | THR | A | 143 | 10.561 | -2.079 | 44.982 | 1.00 | 22.05 |
| ATOM | 1010 | O | THR | A | 143 | 10.851 | -3.218 | 44.614 | 1.00 | 15.75 |
| ATOM | 1011 | N | GLN | A | 144 | 10.262 | -1.792 | 46.241 | 1.00 | 15.62 |
| ATOM | 1012 | CA | GLN | A | 144 | 9.910 | -2.851 | 47.187 | 1.00 | 19.93 |
| ATOM | 1013 | CB | GLN | A | 144 | 10.410 | -2.626 | 48.609 | 1.00 | 17.14 |
| ATOM | 1014 | CG | GLN | A | 144 | 11.927 | -2.605 | 48.704 | 1.00 | 20.52 |
| ATOM | 1015 | CD | GLN | A | 144 | 12.348 | -2.080 | 50.072 | 1.00 | 35.53 |
| ATOM | 1016 | OE1 | GLN | A | 144 | 12.254 | -2.790 | 51.068 | 1.00 | 40.58 |
| ATOM | 1017 | NE2 | GLN | A | 144 | 12.801 | -0.835 | 50.111 | 1.00 | 40.58 |
| ATOM | 1018 | C | GLN | A | 144 | 8.384 | -2.911 | 47.180 | 1.00 | 22.04 |
| ATOM | 1019 | O | GLN | A | 144 | 7.791 | -1.911 | 46.762 | 1.00 | 16.80 |
| ATOM | 1020 | N | CYS | A | 145 | 7.844 | -4.039 | 47.614 | 1.00 | 15.58 |
| ATOM | 1021 | CA | CYS | A | 145 | 6.417 | -4.249 | 47.637 | 1.00 | 12.91 |
| ATOM | 1022 | CB | CYS | A | 145 | 6.103 | -5.685 | 48.076 | 1.00 | 16.62 |
| ATOM | 1023 | SG | CYS | A | 145 | 6.632 | -6.849 | 46.778 | 1.00 | 21.90 |
| ATOM | 1024 | C | CYS | A | 145 | 5.740 | -3.273 | 48.598 | 1.00 | 16.44 |
| ATOM | 1025 | O | CYS | A | 145 | 4.638 | -2.796 | 48.381 | 1.00 | 16.10 |
| ATOM | 1026 | N | VAL | A | 146 | 6.468 | -3.025 | 49.680 | 1.00 | 17.59 |
| ATOM | 1027 | CA | VAL | A | 146 | 5.917 | -2.095 | 50.680 | 1.00 | 20.28 |
| ATOM | 1028 | CB | VAL | A | 146 | 5.285 | -2.784 | 51.889 | 1.00 | 22.74 |
| ATOM | 1029 | CG1 | VAL | A | 146 | 4.932 | -1.757 | 52.972 | 1.00 | 22.42 |
| ATOM | 1030 | CG2 | VAL | A | 146 | 4.037 | -3.548 | 51.478 | 1.00 | 22.17 |
| ATOM | 1031 | C | VAL | A | 146 | 7.070 | -1.198 | 51.104 | 1.00 | 16.66 |
| ATOM | 1032 | O | VAL | A | 146 | 8.171 | -1.704 | 51.357 | 1.00 | 18.81 |
| ATOM | 1033 | N | GLU | A | 147 | 6.824 | 0.111 | 51.141 | 1.00 | 13.43 |
| ATOM | 1034 | CA | GLU | A | 147 | 7.898 | 0.995 | 51.588 | 1.00 | 16.86 |
| ATOM | 1035 | CB | GLU | A | 147 | 8.417 | 1.873 | 50.447 | 1.00 | 21.49 |
| ATOM | 1036 | CG | GLU | A | 147 | 9.145 | 1.028 | 49.405 | 1.00 | 26.38 |
| ATOM | 1037 | CD | GLU | A | 147 | 9.550 | 1.808 | 48.172 | 1.00 | 37.10 |
| ATOM | 1038 | OE1 | GLU | A | 147 | 9.453 | 3.051 | 48.188 | 1.00 | 32.89 |
| ATOM | 1039 | OE2 | GLU | A | 147 | 9.980 | 1.139 | 47.206 | 1.00 | 27.53 |

FIGURE 122

| | | | | | | | | | |
|---|---|---|---|---|---|---|---|---|---|
| ATOM | 1040 | C | GLU | A | 147 | 7.403 | 1.850 | 52.761 | 1.00 19.26 |
| ATOM | 1041 | O | GLU | A | 147 | 6.402 | 2.535 | 52.577 | 1.00 27.69 |
| ATOM | 1042 | N | LYS | A | 148 | 8.115 | 1.732 | 53.874 | 1.00 26.96 |
| ATOM | 1043 | CA | LYS | A | 148 | 7.743 | 2.395 | 55.125 | 1.00 26.67 |
| ATOM | 1044 | CB | LYS | A | 148 | 8.105 | 3.878 | 55.092 | 1.00 33.37 |
| ATOM | 1045 | CG | LYS | A | 148 | 9.582 | 4.143 | 55.371 | 1.00 42.34 |
| ATOM | 1046 | CD | LYS | A | 148 | 10.220 | 4.913 | 54.226 | 1.00 49.37 |
| ATOM | 1047 | CE | LYS | A | 148 | 11.467 | 5.651 | 54.685 | 1.00 56.84 |
| ATOM | 1048 | NZ | LYS | A | 148 | 11.213 | 7.114 | 54.810 | 1.00 51.81 |
| ATOM | 1049 | C | LYS | A | 148 | 6.261 | 2.210 | 55.380 | 1.00 29.22 |
| ATOM | 1050 | O | LYS | A | 148 | 5.510 | 3.102 | 55.771 | 1.00 34.85 |
| ATOM | 1051 | N | GLY | A | 149 | 5.788 | 0.979 | 55.133 | 1.00 21.30 |
| ATOM | 1052 | CA | GLY | A | 149 | 4.379 | 0.765 | 55.390 | 1.00 23.12 |
| ATOM | 1053 | C | GLY | A | 149 | 3.451 | 1.142 | 54.264 | 1.00 28.88 |
| ATOM | 1054 | O | GLY | A | 149 | 2.288 | 0.724 | 54.322 | 1.00 23.12 |
| ATOM | 1055 | N | ARG | A | 150 | 3.892 | 1.910 | 53.264 | 1.00 23.43 |
| ATOM | 1056 | CA | ARG | A | 150 | 2.967 | 2.235 | 52.172 | 1.00 19.35 |
| ATOM | 1057 | CB | ARG | A | 150 | 3.237 | 3.651 | 51.657 | 1.00 27.51 |
| ATOM | 1058 | CG | ARG | A | 150 | 3.022 | 4.689 | 52.755 | 1.00 36.85 |
| ATOM | 1059 | CD | ARG | A | 150 | 3.433 | 6.085 | 52.332 | 1.00 46.96 |
| ATOM | 1060 | NE | ARG | A | 150 | 4.879 | 6.252 | 52.377 | 1.00 54.45 |
| ATOM | 1061 | CZ | ARG | A | 150 | 5.541 | 7.218 | 52.990 | 1.00 55.25 |
| ATOM | 1062 | NH1 | ARG | A | 150 | 4.899 | 8.166 | 53.652 | 1.00 47.81 |
| ATOM | 1063 | NH2 | ARG | A | 150 | 6.868 | 7.238 | 52.944 | 1.00 64.89 |
| ATOM | 1064 | C | ARG | A | 150 | 3.097 | 1.201 | 51.060 | 1.00 17.74 |
| ATOM | 1065 | O | ARG | A | 150 | 4.206 | 0.894 | 50.604 | 1.00 20.32 |
| ATOM | 1066 | N | VAL | A | 151 | 1.980 | 0.628 | 50.655 | 1.00 18.03 |
| ATOM | 1067 | CA | VAL | A | 151 | 1.948 | -0.432 | 49.654 | 1.00 23.37 |
| ATOM | 1068 | CB | VAL | A | 151 | 0.528 | -1.030 | 49.571 | 1.00 28.77 |
| ATOM | 1069 | CG1 | VAL | A | 151 | 0.412 | -2.015 | 48.412 | 1.00 18.49 |
| ATOM | 1070 | CG2 | VAL | A | 151 | 0.162 | -1.691 | 50.895 | 1.00 20.07 |
| ATOM | 1071 | C | VAL | A | 151 | 2.351 | 0.114 | 48.294 | 1.00 20.37 |
| ATOM | 1072 | O | VAL | A | 151 | 1.847 | 1.164 | 47.899 | 1.00 19.29 |
| ATOM | 1073 | N | LYS | A | 152 | 3.209 | -0.566 | 47.557 | 1.00 18.81 |
| ATOM | 1074 | CA | LYS | A | 152 | 3.673 | -0.055 | 46.270 | 1.00 16.66 |
| ATOM | 1075 | CB | LYS | A | 152 | 5.157 | 0.303 | 46.308 | 1.00 10.31 |
| ATOM | 1076 | CG | LYS | A | 152 | 5.629 | 1.240 | 47.419 | 1.00 16.94 |
| ATOM | 1077 | CD | LYS | A | 152 | 5.089 | 2.652 | 47.170 | 1.00 19.08 |
| ATOM | 1078 | CE | LYS | A | 152 | 5.831 | 3.663 | 48.050 | 1.00 16.36 |
| ATOM | 1079 | NZ | LYS | A | 152 | 5.565 | 5.051 | 47.592 | 1.00 31.76 |
| ATOM | 1080 | C | LYS | A | 152 | 3.460 | -1.111 | 45.189 | 1.00 18.63 |
| ATOM | 1081 | O | LYS | A | 152 | 3.313 | -0.808 | 44.006 | 1.00 14.72 |
| ATOM | 1082 | N | CYS | A | 153 | 3.472 | -2.381 | 45.605 | 1.00 10.99 |
| ATOM | 1083 | CA | CYS | A | 153 | 3.426 | -3.447 | 44.599 | 1.00 14.85 |
| ATOM | 1084 | CB | CYS | A | 153 | 4.777 | -3.577 | 43.886 | 1.00 10.33 |
| ATOM | 1085 | SG | CYS | A | 153 | 4.784 | -4.845 | 42.573 | 1.00 15.08 |
| ATOM | 1086 | C | CYS | A | 153 | 3.025 | -4.752 | 45.279 | 1.00 19.72 |
| ATOM | 1087 | O | CYS | A | 153 | 3.429 | -5.011 | 46.409 | 1.00 17.06 |
| ATOM | 1088 | N | ASP | A | 154 | 2.207 | -5.564 | 44.633 | 1.00 14.81 |
| ATOM | 1089 | CA | ASP | A | 154 | 1.872 | -6.852 | 45.241 | 1.00 15.17 |
| ATOM | 1090 | CB | ASP | A | 154 | 0.662 | -7.429 | 44.514 | 1.00 12.59 |
| ATOM | 1091 | CG | ASP | A | 154 | 0.186 | -8.745 | 45.101 | 1.00 24.42 |

FIGURE 123

| | | | | | | | | | |
|---|---|---|---|---|---|---|---|---|---|
| ATOM | 1092 | OD1 | ASP | A | 154 | 0.232 | -9.777 | 44.397 | 1.00 33.37 |
| ATOM | 1093 | OD2 | ASP | A | 154 | -0.223 | -8.736 | 46.278 | 1.00 26.94 |
| ATOM | 1094 | C | ASP | A | 154 | 3.083 | -7.782 | 45.165 | 1.00 21.36 |
| ATOM | 1095 | O | ASP | A | 154 | 3.914 | -7.662 | 44.252 | 1.00 23.22 |
| ATOM | 1096 | N | HIS | A | 155 | 3.228 | -8.717 | 46.091 | 1.00 15.03 |
| ATOM | 1097 | CA | HIS | A | 155 | 4.241 | -9.766 | 46.046 | 1.00 19.74 |
| ATOM | 1098 | CB | HIS | A | 155 | 4.479 | -10.390 | 47.434 | 1.00 18.44 |
| ATOM | 1099 | CG | HIS | A | 155 | 5.718 | -11.249 | 47.473 | 1.00 16.91 |
| ATOM | 1100 | ND1 | HIS | A | 155 | 5.772 | -12.503 | 46.910 | 1.00 21.58 |
| ATOM | 1101 | CE1 | HIS | A | 155 | 6.975 | -13.028 | 47.088 | 1.00 15.22 |
| ATOM | 1102 | NE2 | HIS | A | 155 | 7.719 | -12.158 | 47.752 | 1.00 21.40 |
| ATOM | 1103 | CD2 | HIS | A | 155 | 6.946 | -11.046 | 47.997 | 1.00 13.16 |
| ATOM | 1104 | C | HIS | A | 155 | 3.765 | -10.828 | 45.054 | 1.00 25.16 |
| ATOM | 1105 | O | HIS | A | 155 | 3.222 | -11.863 | 45.434 | 1.00 22.33 |
| ATOM | 1106 | N | TYR | A | 156 | 3.935 | -10.543 | 43.764 | 1.00 14.86 |
| ATOM | 1107 | CA | TYR | A | 156 | 3.238 | -11.265 | 42.715 | 1.00 14.13 |
| ATOM | 1108 | CB | TYR | A | 156 | 3.055 | -10.354 | 41.479 | 1.00 13.04 |
| ATOM | 1109 | CG | TYR | A | 156 | 4.342 | -9.814 | 40.905 | 1.00 13.16 |
| ATOM | 1110 | CD1 | TYR | A | 156 | 5.071 | -10.496 | 39.932 | 1.00 10.49 |
| ATOM | 1111 | CE1 | TYR | A | 156 | 6.239 | -10.006 | 39.407 | 1.00 17.75 |
| ATOM | 1112 | CZ | TYR | A | 156 | 6.718 | -8.786 | 39.842 | 1.00 15.46 |
| ATOM | 1113 | OH | TYR | A | 156 | 7.895 | -8.286 | 39.320 | 1.00 14.59 |
| ATOM | 1114 | CE2 | TYR | A | 156 | 6.021 | -8.087 | 40.801 | 1.00 14.68 |
| ATOM | 1115 | CD2 | TYR | A | 156 | 4.843 | -8.585 | 41.331 | 1.00 12.40 |
| ATOM | 1116 | C | TYR | A | 156 | 3.959 | -12.526 | 42.265 | 1.00 17.42 |
| ATOM | 1117 | O | TYR | A | 156 | 3.533 | -13.067 | 41.242 | 1.00 15.62 |
| ATOM | 1118 | N | TRP | A | 157 | 4.994 | -12.933 | 42.972 | 1.00 21.73 |
| ATOM | 1119 | CA | TRP | A | 157 | 5.722 | -14.154 | 42.677 | 1.00 16.38 |
| ATOM | 1120 | CB | TRP | A | 157 | 7.152 | -13.878 | 42.223 | 1.00 14.65 |
| ATOM | 1121 | CG | TRP | A | 157 | 7.993 | -13.290 | 43.317 | 1.00 20.93 |
| ATOM | 1122 | CD1 | TRP | A | 157 | 8.817 | -13.924 | 44.200 | 1.00 19.30 |
| ATOM | 1123 | NE1 | TRP | A | 157 | 9.401 | -13.009 | 45.041 | 1.00 18.29 |
| ATOM | 1124 | CE2 | TRP | A | 157 | 8.956 | -11.758 | 44.703 | 1.00 20.37 |
| ATOM | 1125 | CD2 | TRP | A | 157 | 8.070 | -11.895 | 43.622 | 1.00 12.37 |
| ATOM | 1126 | CE3 | TRP | A | 157 | 7.469 | -10.759 | 43.083 | 1.00 15.46 |
| ATOM | 1127 | CZ3 | TRP | A | 157 | 7.772 | -9.522 | 43.635 | 1.00 13.34 |
| ATOM | 1128 | CH2 | TRP | A | 157 | 8.657 | -9.418 | 44.709 | 1.00 18.59 |
| ATOM | 1129 | CZ2 | TRP | A | 157 | 9.262 | -10.519 | 45.259 | 1.00 21.33 |
| ATOM | 1130 | C | TRP | A | 157 | 5.728 | -15.029 | 43.926 | 1.00 30.00 |
| ATOM | 1131 | O | TRP | A | 157 | 5.456 | -14.475 | 44.994 | 1.00 24.21 |
| ATOM | 1132 | N | PRO | A | 158 | 6.007 | -16.316 | 43.798 | 1.00 29.81 |
| ATOM | 1133 | CA | PRO | A | 158 | 6.016 | -17.206 | 44.965 | 1.00 32.16 |
| ATOM | 1134 | CB | PRO | A | 158 | 6.531 | -18.527 | 44.371 | 1.00 30.44 |
| ATOM | 1135 | CG | PRO | A | 158 | 6.069 | -18.476 | 42.946 | 1.00 26.74 |
| ATOM | 1136 | CD | PRO | A | 158 | 6.307 | -17.040 | 42.542 | 1.00 22.30 |
| ATOM | 1137 | C | PRO | A | 158 | 6.961 | -16.803 | 46.089 | 1.00 29.52 |
| ATOM | 1138 | O | PRO | A | 158 | 8.088 | -16.362 | 45.866 | 1.00 43.48 |
| ATOM | 1139 | N | ALA | A | 159 | 6.502 | -16.986 | 47.322 | 1.00 34.03 |
| ATOM | 1140 | CA | ALA | A | 159 | 7.303 | -16.748 | 48.519 | 1.00 33.58 |
| ATOM | 1141 | CB | ALA | A | 159 | 6.444 | -16.986 | 49.760 | 1.00 34.30 |
| ATOM | 1142 | C | ALA | A | 159 | 8.547 | -17.621 | 48.576 | 1.00 32.85 |
| ATOM | 1143 | O | ALA | A | 159 | 9.602 | -17.201 | 49.045 | 1.00 40.76 |

FIGURE 124

| ATOM | 1144 | N   | ASP | A | 160 | 8.427  | -18.858 | 48.101 | 1.00 | 29.96 |
|------|------|-----|-----|---|-----|--------|---------|--------|------|-------|
| ATOM | 1145 | CA  | ASP | A | 160 | 9.520  | -19.826 | 48.164 | 1.00 | 28.99 |
| ATOM | 1146 | CB  | ASP | A | 160 | 9.468  | -20.587 | 49.485 | 1.00 | 27.85 |
| ATOM | 1147 | CG  | ASP | A | 160 | 8.150  | -21.298 | 49.727 | 1.00 | 33.73 |
| ATOM | 1148 | OD1 | ASP | A | 160 | 7.767  | -21.452 | 50.910 | 1.00 | 36.35 |
| ATOM | 1149 | OD2 | ASP | A | 160 | 7.486  | -21.709 | 48.750 | 1.00 | 38.51 |
| ATOM | 1150 | C   | ASP | A | 160 | 9.449  | -20.784 | 46.983 | 1.00 | 24.92 |
| ATOM | 1151 | O   | ASP | A | 160 | 8.857  | -20.443 | 45.951 | 1.00 | 29.16 |
| ATOM | 1152 | N   | GLN | A | 161 | 10.025 | -21.975 | 47.125 | 1.00 | 19.70 |
| ATOM | 1153 | CA  | GLN | A | 161 | 10.089 | -22.904 | 46.006 | 1.00 | 29.75 |
| ATOM | 1154 | CB  | GLN | A | 161 | 11.241 | -23.901 | 46.254 | 1.00 | 33.52 |
| ATOM | 1155 | CG  | GLN | A | 161 | 12.575 | -23.383 | 45.720 | 1.00 | 41.43 |
| ATOM | 1156 | CD  | GLN | A | 161 | 13.754 | -23.856 | 46.547 | 1.00 | 53.65 |
| ATOM | 1157 | OE1 | GLN | A | 161 | 14.390 | -24.865 | 46.229 | 1.00 | 54.16 |
| ATOM | 1158 | NE2 | GLN | A | 161 | 14.053 | -23.128 | 47.619 | 1.00 | 75.55 |
| ATOM | 1159 | C   | GLN | A | 161 | 8.798  | -23.664 | 45.760 | 1.00 | 32.87 |
| ATOM | 1160 | O   | GLN | A | 161 | 8.730  | -24.481 | 44.833 | 1.00 | 27.15 |
| ATOM | 1161 | N   | ASP | A | 162 | 7.759  | -23.443 | 46.559 | 1.00 | 32.19 |
| ATOM | 1162 | CA  | ASP | A | 162 | 6.508  | -24.162 | 46.313 | 1.00 | 25.87 |
| ATOM | 1163 | CB  | ASP | A | 162 | 5.547  | -24.078 | 47.488 | 1.00 | 27.76 |
| ATOM | 1164 | CG  | ASP | A | 162 | 5.916  | -24.971 | 48.652 | 1.00 | 40.60 |
| ATOM | 1165 | OD1 | ASP | A | 162 | 7.006  | -25.582 | 48.628 | 1.00 | 39.74 |
| ATOM | 1166 | OD2 | ASP | A | 162 | 5.099  | -25.049 | 49.598 | 1.00 | 66.88 |
| ATOM | 1167 | C   | ASP | A | 162 | 5.855  | -23.557 | 45.072 | 1.00 | 29.94 |
| ATOM | 1168 | O   | ASP | A | 162 | 5.977  | -22.348 | 44.880 | 1.00 | 36.10 |
| ATOM | 1169 | N   | SER | A | 163 | 5.201  | -24.359 | 44.249 | 1.00 | 23.42 |
| ATOM | 1170 | CA  | SER | A | 163 | 4.656  | -23.839 | 42.997 | 1.00 | 21.05 |
| ATOM | 1171 | CB  | SER | A | 163 | 4.556  | -24.994 | 41.988 | 1.00 | 26.60 |
| ATOM | 1172 | OG  | SER | A | 163 | 3.896  | -26.074 | 42.630 | 1.00 | 25.84 |
| ATOM | 1173 | C   | SER | A | 163 | 3.306  | -23.190 | 43.194 | 1.00 | 17.83 |
| ATOM | 1174 | O   | SER | A | 163 | 2.600  | -23.381 | 44.183 | 1.00 | 21.12 |
| ATOM | 1175 | N   | LEU | A | 164 | 2.909  | -22.379 | 42.208 | 1.00 | 22.53 |
| ATOM | 1176 | CA  | LEU | A | 164 | 1.618  | -21.708 | 42.296 | 1.00 | 17.81 |
| ATOM | 1177 | CB  | LEU | A | 164 | 1.770  | -20.333 | 42.942 | 1.00 | 22.42 |
| ATOM | 1178 | CG  | LEU | A | 164 | 1.717  | -20.210 | 44.457 | 1.00 | 30.71 |
| ATOM | 1179 | CD1 | LEU | A | 164 | 1.783  | -18.736 | 44.854 | 1.00 | 38.32 |
| ATOM | 1180 | CD2 | LEU | A | 164 | 0.464  | -20.862 | 45.021 | 1.00 | 31.30 |
| ATOM | 1181 | C   | LEU | A | 164 | 1.042  | -21.526 | 40.897 | 1.00 | 16.82 |
| ATOM | 1182 | O   | LEU | A | 164 | 1.843  | -21.285 | 39.990 | 1.00 | 20.87 |
| ATOM | 1183 | N   | TYR | A | 165 | -0.269 | -21.616 | 40.758 | 1.00 | 15.24 |
| ATOM | 1184 | CA  | TYR | A | 165 | -0.942 | -21.169 | 39.550 | 1.00 | 22.53 |
| ATOM | 1185 | CB  | TYR | A | 165 | -2.365 | -21.741 | 39.489 | 1.00 | 16.95 |
| ATOM | 1186 | CG  | TYR | A | 165 | -2.417 | -23.194 | 39.073 | 1.00 | 20.26 |
| ATOM | 1187 | CD1 | TYR | A | 165 | -2.541 | -24.180 | 40.038 | 1.00 | 15.27 |
| ATOM | 1188 | CE1 | TYR | A | 165 | -2.593 | -25.515 | 39.711 | 1.00 | 15.03 |
| ATOM | 1189 | CZ  | TYR | A | 165 | -2.522 | -25.882 | 38.390 | 1.00 | 19.11 |
| ATOM | 1190 | OH  | TYR | A | 165 | -2.579 | -27.227 | 38.066 | 1.00 | 25.32 |
| ATOM | 1191 | CE2 | TYR | A | 165 | -2.402 | -24.928 | 37.410 | 1.00 | 19.58 |
| ATOM | 1192 | CD2 | TYR | A | 165 | -2.348 | -23.582 | 37.740 | 1.00 | 25.42 |
| ATOM | 1193 | C   | TYR | A | 165 | -1.076 | -19.646 | 39.464 | 1.00 | 25.11 |
| ATOM | 1194 | O   | TYR | A | 165 | -1.337 | -18.969 | 40.459 | 1.00 | 19.81 |
| ATOM | 1195 | N   | TYR | A | 166 | -0.938 | -19.095 | 38.264 | 1.00 | 18.82 |

FIGURE 125

| | | | | | | | | | |
|---|---|---|---|---|---|---|---|---|---|
| ATOM | 1196 | CA | TYR | A | 166 | -1.373 | -17.719 | 38.014 | 1.00 23.86 |
| ATOM | 1197 | CB | TYR | A | 166 | -0.202 | -16.754 | 37.949 | 1.00 25.11 |
| ATOM | 1198 | CG | TYR | A | 166 | 0.652 | -16.636 | 39.182 | 1.00 17.66 |
| ATOM | 1199 | CD1 | TYR | A | 166 | 0.365 | -15.669 | 40.134 | 1.00 17.33 |
| ATOM | 1200 | CE1 | TYR | A | 166 | 1.133 | -15.541 | 41.265 | 1.00 20.35 |
| ATOM | 1201 | CZ | TYR | A | 166 | 2.205 | -16.369 | 41.485 | 1.00 26.41 |
| ATOM | 1202 | OH | TYR | A | 166 | 2.943 | -16.198 | 42.636 | 1.00 24.80 |
| ATOM | 1203 | CE2 | TYR | A | 166 | 2.521 | -17.338 | 40.561 | 1.00 24.56 |
| ATOM | 1204 | CD2 | TYR | A | 166 | 1.738 | -17.457 | 39.421 | 1.00 19.47 |
| ATOM | 1205 | C | TYR | A | 166 | -2.168 | -17.720 | 36.706 | 1.00 15.43 |
| ATOM | 1206 | O | TYR | A | 166 | -1.541 | -17.809 | 35.655 | 1.00 16.56 |
| ATOM | 1207 | N | GLY | A | 167 | -3.474 | -17.641 | 36.810 | 1.00 17.70 |
| ATOM | 1208 | CA | GLY | A | 167 | -4.449 | -17.953 | 35.792 | 1.00 24.28 |
| ATOM | 1209 | C | GLY | A | 167 | -4.211 | -19.347 | 35.220 | 1.00 31.57 |
| ATOM | 1210 | O | GLY | A | 167 | -4.329 | -20.338 | 35.943 | 1.00 28.31 |
| ATOM | 1211 | N | ASP | A | 168 | -3.856 | -19.435 | 33.943 | 1.00 24.61 |
| ATOM | 1212 | CA | ASP | A | 168 | -3.616 | -20.695 | 33.265 | 1.00 28.49 |
| ATOM | 1213 | CB | ASP | A | 168 | -4.089 | -20.622 | 31.802 | 1.00 29.53 |
| ATOM | 1214 | CG | ASP | A | 168 | -5.587 | -20.382 | 31.765 | 1.00 33.69 |
| ATOM | 1215 | OD1 | ASP | A | 168 | -6.283 | -21.001 | 32.589 | 1.00 33.30 |
| ATOM | 1216 | OD2 | ASP | A | 168 | -6.063 | -19.582 | 30.947 | 1.00 43.14 |
| ATOM | 1217 | C | ASP | A | 168 | -2.152 | -21.097 | 33.273 | 1.00 28.68 |
| ATOM | 1218 | O | ASP | A | 168 | -1.802 | -22.113 | 32.667 | 1.00 34.81 |
| ATOM | 1219 | N | LEU | A | 169 | -1.310 | -20.309 | 33.937 | 1.00 22.13 |
| ATOM | 1220 | CA | LEU | A | 169 | 0.109 | -20.623 | 33.989 | 1.00 18.47 |
| ATOM | 1221 | CB | LEU | A | 169 | 0.958 | -19.356 | 33.795 | 1.00 21.38 |
| ATOM | 1222 | CG | LEU | A | 169 | 0.732 | -18.594 | 32.489 | 1.00 25.30 |
| ATOM | 1223 | CD1 | LEU | A | 169 | 1.565 | -17.313 | 32.456 | 1.00 21.42 |
| ATOM | 1224 | CD2 | LEU | A | 169 | 1.043 | -19.474 | 31.290 | 1.00 27.51 |
| ATOM | 1225 | C | LEU | A | 169 | 0.470 | -21.268 | 35.322 | 1.00 19.04 |
| ATOM | 1226 | O | LEU | A | 169 | -0.213 | -21.003 | 36.309 | 1.00 21.82 |
| ATOM | 1227 | N | ILE | A | 170 | 1.516 | -22.084 | 35.337 | 1.00 20.12 |
| ATOM | 1228 | CA | ILE | A | 170 | 2.068 | -22.592 | 36.587 | 1.00 21.11 |
| ATOM | 1229 | CB | ILE | A | 170 | 2.138 | -24.120 | 36.675 | 1.00 20.24 |
| ATOM | 1230 | CG1 | ILE | A | 170 | 0.783 | -24.795 | 36.514 | 1.00 27.42 |
| ATOM | 1231 | CD1 | ILE | A | 170 | 0.840 | -26.292 | 36.777 | 1.00 29.31 |
| ATOM | 1232 | CG2 | ILE | A | 170 | 2.804 | -24.547 | 37.980 | 1.00 23.61 |
| ATOM | 1233 | C | ILE | A | 170 | 3.478 | -22.031 | 36.736 | 1.00 20.55 |
| ATOM | 1234 | O | ILE | A | 170 | 4.251 | -22.062 | 35.786 | 1.00 28.78 |
| ATOM | 1235 | N | LEU | A | 171 | 3.763 | -21.531 | 37.926 | 1.00 22.31 |
| ATOM | 1236 | CA | LEU | A | 171 | 5.044 | -20.881 | 38.181 | 1.00 24.43 |
| ATOM | 1237 | CB | LEU | A | 171 | 4.758 | -19.393 | 38.433 | 1.00 27.91 |
| ATOM | 1238 | CG | LEU | A | 171 | 5.910 | -18.408 | 38.278 | 1.00 37.79 |
| ATOM | 1239 | CD1 | LEU | A | 171 | 5.400 | -17.017 | 37.942 | 1.00 44.63 |
| ATOM | 1240 | CD2 | LEU | A | 171 | 6.747 | -18.374 | 39.551 | 1.00 34.65 |
| ATOM | 1241 | C | LEU | A | 171 | 5.774 | -21.519 | 39.352 | 1.00 19.86 |
| ATOM | 1242 | O | LEU | A | 171 | 5.179 | -21.847 | 40.382 | 1.00 20.05 |
| ATOM | 1243 | N | GLN | A | 172 | 7.077 | -21.692 | 39.203 | 1.00 21.32 |
| ATOM | 1244 | CA | GLN | A | 172 | 7.936 | -22.247 | 40.234 | 1.00 29.54 |
| ATOM | 1245 | CB | GLN | A | 172 | 8.315 | -23.689 | 39.862 | 1.00 43.33 |
| ATOM | 1246 | CG | GLN | A | 172 | 7.514 | -24.770 | 40.555 | 1.00 53.47 |
| ATOM | 1247 | CD | GLN | A | 172 | 8.301 | -26.042 | 40.814 | 1.00 63.05 |

FIGURE 126

```
ATOM   1248  OE1 GLN A 172       9.068 -26.503  39.964  1.00 39.02
ATOM   1249  NE2 GLN A 172       8.114 -26.624  41.998  1.00 64.69
ATOM   1250  C   GLN A 172       9.211 -21.440  40.411  1.00 19.61
ATOM   1251  O   GLN A 172       9.974 -21.265  39.457  1.00 19.10
ATOM   1252  N   MET A 173       9.497 -20.971  41.628  1.00 16.88
ATOM   1253  CA  MET A 173      10.792 -20.353  41.863  1.00 19.35
ATOM   1254  CB  MET A 173      10.808 -19.485  43.130  1.00 24.60
ATOM   1255  CG  MET A 173      12.118 -18.710  43.277  1.00 27.16
ATOM   1256  SD  MET A 173      11.885 -17.267  44.349  1.00 39.15
ATOM   1257  CE  MET A 173      11.807 -18.102  45.934  1.00 35.39
ATOM   1258  C   MET A 173      11.914 -21.384  42.027  1.00 24.07
ATOM   1259  O   MET A 173      11.953 -22.072  43.043  1.00 31.47
ATOM   1260  N   LEU A 174      12.782 -21.438  41.036  1.00 23.52
ATOM   1261  CA  LEU A 174      13.945 -22.311  40.998  1.00 33.03
ATOM   1262  CB  LEU A 174      14.403 -22.478  39.543  1.00 27.30
ATOM   1263  CG  LEU A 174      13.369 -23.075  38.590  1.00 32.33
ATOM   1264  CD1 LEU A 174      14.023 -23.477  37.276  1.00 44.31
ATOM   1265  CD2 LEU A 174      12.665 -24.270  39.214  1.00 40.73
ATOM   1266  C   LEU A 174      15.096 -21.796  41.841  1.00 33.13
ATOM   1267  O   LEU A 174      15.857 -22.565  42.431  1.00 36.31
ATOM   1268  N   SER A 175      15.271 -20.475  41.923  1.00 32.25
ATOM   1269  CA  SER A 175      16.386 -19.961  42.712  1.00 28.55
ATOM   1270  CB  SER A 175      17.696 -20.148  41.952  1.00 36.29
ATOM   1271  OG  SER A 175      17.775 -19.299  40.825  1.00 30.88
ATOM   1272  C   SER A 175      16.199 -18.488  43.069  1.00 34.24
ATOM   1273  O   SER A 175      15.445 -17.778  42.404  1.00 23.93
ATOM   1274  N   GLU A 176      16.909 -18.101  44.118  1.00 24.79
ATOM   1275  CA  GLU A 176      16.841 -16.777  44.717  1.00 24.84
ATOM   1276  CB  GLU A 176      15.678 -16.730  45.704  1.00 29.85
ATOM   1277  CG  GLU A 176      15.447 -15.387  46.377  1.00 32.22
ATOM   1278  CD  GLU A 176      14.223 -15.390  47.270  1.00 34.82
ATOM   1279  OE1 GLU A 176      14.358 -15.795  48.447  1.00 50.78
ATOM   1280  OE2 GLU A 176      13.135 -14.988  46.806  1.00 39.74
ATOM   1281  C   GLU A 176      18.166 -16.441  45.398  1.00 35.34
ATOM   1282  O   GLU A 176      18.519 -17.072  46.397  1.00 33.01
ATOM   1283  N   SER A 177      18.884 -15.477  44.837  1.00 29.77
ATOM   1284  CA  SER A 177      20.151 -14.997  45.367  1.00 25.28
ATOM   1285  CB  SER A 177      21.299 -15.094  44.377  1.00 27.96
ATOM   1286  OG  SER A 177      21.253 -16.278  43.606  1.00 51.47
ATOM   1287  C   SER A 177      20.003 -13.547  45.831  1.00 30.74
ATOM   1288  O   SER A 177      19.856 -12.591  45.070  1.00 23.11
ATOM   1289  N   VAL A 178      20.042 -13.454  47.153  1.00 31.26
ATOM   1290  CA  VAL A 178      19.964 -12.168  47.825  1.00 31.69
ATOM   1291  CB  VAL A 178      19.343 -12.317  49.218  1.00 34.41
ATOM   1292  CG1 VAL A 178      19.192 -10.964  49.903  1.00 48.17
ATOM   1293  CG2 VAL A 178      17.989 -13.008  49.117  1.00 26.99
ATOM   1294  C   VAL A 178      21.367 -11.579  47.885  1.00 39.05
ATOM   1295  O   VAL A 178      22.306 -12.239  48.333  1.00 45.15
ATOM   1296  N   LEU A 179      21.484 -10.351  47.400  1.00 29.28
ATOM   1297  CA  LEU A 179      22.713  -9.567  47.511  1.00 24.54
ATOM   1298  CB  LEU A 179      23.278  -9.294  46.122  1.00 27.13
ATOM   1299  CG  LEU A 179      23.427 -10.559  45.262  1.00 39.41
```

FIGURE 127

| | | | | | | | | | |
|---|---|---|---|---|---|---|---|---|---|
| ATOM | 1300 | CD1 | LEU | A | 179 | 23.571 | -10.210 | 43.793 | 1.00 56.70 |
| ATOM | 1301 | CD2 | LEU | A | 179 | 24.604 | -11.381 | 45.760 | 1.00 42.38 |
| ATOM | 1302 | C | LEU | A | 179 | 22.370 | -8.317 | 48.298 | 1.00 32.59 |
| ATOM | 1303 | O | LEU | A | 179 | 21.180 | -8.081 | 48.548 | 1.00 37.75 |
| ATOM | 1304 | N | PRO | A | 180 | 23.330 | -7.522 | 48.737 | 1.00 39.11 |
| ATOM | 1305 | CA | PRO | A | 180 | 22.960 | -6.390 | 49.597 | 1.00 42.52 |
| ATOM | 1306 | CB | PRO | A | 180 | 24.299 | -5.699 | 49.872 | 1.00 48.91 |
| ATOM | 1307 | CG | PRO | A | 180 | 25.323 | -6.759 | 49.636 | 1.00 51.16 |
| ATOM | 1308 | CD | PRO | A | 180 | 24.778 | -7.596 | 48.511 | 1.00 44.82 |
| ATOM | 1309 | C | PRO | A | 180 | 22.012 | -5.425 | 48.910 | 1.00 35.13 |
| ATOM | 1310 | O | PRO | A | 180 | 21.144 | -4.829 | 49.553 | 1.00 43.71 |
| ATOM | 1311 | N | GLU | A | 181 | 22.138 | -5.225 | 47.594 | 1.00 25.87 |
| ATOM | 1312 | CA | GLU | A | 181 | 21.282 | -4.161 | 47.054 | 1.00 26.32 |
| ATOM | 1313 | CB | GLU | A | 181 | 22.162 | -3.079 | 46.420 | 1.00 29.01 |
| ATOM | 1314 | CG | GLU | A | 181 | 22.810 | -2.178 | 47.465 | 1.00 30.02 |
| ATOM | 1315 | CD | GLU | A | 181 | 24.001 | -1.472 | 46.840 | 1.00 32.75 |
| ATOM | 1316 | OE1 | GLU | A | 181 | 24.714 | -2.135 | 46.060 | 1.00 55.04 |
| ATOM | 1317 | OE2 | GLU | A | 181 | 24.190 | -0.279 | 47.144 | 1.00 78.18 |
| ATOM | 1318 | C | GLU | A | 181 | 20.279 | -4.658 | 46.035 | 1.00 19.68 |
| ATOM | 1319 | O | GLU | A | 181 | 19.432 | -3.890 | 45.579 | 1.00 22.96 |
| ATOM | 1320 | N | TRP | A | 182 | 20.393 | -5.937 | 45.683 | 1.00 23.62 |
| ATOM | 1321 | CA | TRP | A | 182 | 19.378 | -6.504 | 44.799 | 1.00 20.73 |
| ATOM | 1322 | CB | TRP | A | 182 | 19.626 | -6.134 | 43.344 | 1.00 22.35 |
| ATOM | 1323 | CG | TRP | A | 182 | 21.019 | -6.447 | 42.864 | 1.00 21.68 |
| ATOM | 1324 | CD1 | TRP | A | 182 | 21.493 | -7.660 | 42.455 | 1.00 20.02 |
| ATOM | 1325 | NE1 | TRP | A | 182 | 22.813 | -7.552 | 42.089 | 1.00 24.79 |
| ATOM | 1326 | CE2 | TRP | A | 182 | 23.214 | -6.252 | 42.256 | 1.00 33.15 |
| ATOM | 1327 | CD2 | TRP | A | 182 | 22.107 | -5.528 | 42.743 | 1.00 28.28 |
| ATOM | 1328 | CE3 | TRP | A | 182 | 22.241 | -4.160 | 43.006 | 1.00 26.77 |
| ATOM | 1329 | CZ3 | TRP | A | 182 | 23.476 | -3.579 | 42.767 | 1.00 34.39 |
| ATOM | 1330 | CH2 | TRP | A | 182 | 24.560 | -4.324 | 42.281 | 1.00 31.42 |
| ATOM | 1331 | CZ2 | TRP | A | 182 | 24.460 | -5.664 | 42.018 | 1.00 30.61 |
| ATOM | 1332 | C | TRP | A | 182 | 19.349 | -8.017 | 44.977 | 1.00 23.48 |
| ATOM | 1333 | O | TRP | A | 182 | 20.281 | -8.619 | 45.513 | 1.00 24.37 |
| ATOM | 1334 | N | THR | A | 183 | 18.240 | -8.569 | 44.517 | 1.00 20.84 |
| ATOM | 1335 | CA | THR | A | 183 | 17.987 | -10.000 | 44.561 | 1.00 22.33 |
| ATOM | 1336 | CB | THR | A | 183 | 16.773 | -10.266 | 45.471 | 1.00 20.04 |
| ATOM | 1337 | OG1 | THR | A | 183 | 17.130 | -9.789 | 46.776 | 1.00 26.68 |
| ATOM | 1338 | CG2 | THR | A | 183 | 16.466 | -11.751 | 45.577 | 1.00 20.82 |
| ATOM | 1339 | C | THR | A | 183 | 17.725 | -10.538 | 43.168 | 1.00 26.38 |
| ATOM | 1340 | O | THR | A | 183 | 16.949 | -9.925 | 42.429 | 1.00 23.46 |
| ATOM | 1341 | N | ILE | A | 184 | 18.351 | -11.655 | 42.819 | 1.00 16.60 |
| ATOM | 1342 | CA | ILE | A | 184 | 18.094 | -12.248 | 41.505 | 1.00 14.97 |
| ATOM | 1343 | CB | ILE | A | 184 | 19.399 | -12.402 | 40.716 | 1.00 20.49 |
| ATOM | 1344 | CG1 | ILE | A | 184 | 20.113 | -11.053 | 40.565 | 1.00 22.48 |
| ATOM | 1345 | CD1 | ILE | A | 184 | 21.400 | -11.102 | 39.778 | 1.00 24.88 |
| ATOM | 1346 | CG2 | ILE | A | 184 | 19.181 | -13.048 | 39.360 | 1.00 15.87 |
| ATOM | 1347 | C | ILE | A | 184 | 17.374 | -13.570 | 41.711 | 1.00 19.06 |
| ATOM | 1348 | O | ILE | A | 184 | 17.874 | -14.392 | 42.481 | 1.00 22.71 |
| ATOM | 1349 | N | ARG | A | 185 | 16.228 | -13.724 | 41.066 | 1.00 17.97 |
| ATOM | 1350 | CA | ARG | A | 185 | 15.419 | -14.931 | 41.157 | 1.00 18.52 |
| ATOM | 1351 | CB | ARG | A | 185 | 14.031 | -14.667 | 41.733 | 1.00 15.90 |

FIGURE 128

| | | | | | | | | | |
|---|---|---|---|---|---|---|---|---|---|
| ATOM | 1352 | CG | ARG | A | 185 | 14.102 | -14.003 | 43.105 | 1.00 20.67 |
| ATOM | 1353 | CD | ARG | A | 185 | 12.739 | -13.580 | 43.574 | 1.00 23.49 |
| ATOM | 1354 | NE | ARG | A | 185 | 12.620 | -13.167 | 44.962 | 1.00 21.66 |
| ATOM | 1355 | CZ | ARG | A | 185 | 12.709 | -11.898 | 45.350 | 1.00 25.33 |
| ATOM | 1356 | NH1 | ARG | A | 185 | 12.934 | -10.945 | 44.455 | 1.00 22.07 |
| ATOM | 1357 | NH2 | ARG | A | 185 | 12.581 | -11.547 | 46.624 | 1.00 27.50 |
| ATOM | 1358 | C | ARG | A | 185 | 15.285 | -15.562 | 39.776 | 1.00 22.74 |
| ATOM | 1359 | O | ARG | A | 185 | 15.369 | -14.866 | 38.768 | 1.00 20.98 |
| ATOM | 1360 | N | GLU | A | 186 | 15.113 | -16.874 | 39.766 | 1.00 23.54 |
| ATOM | 1361 | CA | GLU | A | 186 | 14.810 | -17.562 | 38.512 | 1.00 27.25 |
| ATOM | 1362 | CB | GLU | A | 186 | 15.910 | -18.545 | 38.151 | 1.00 26.23 |
| ATOM | 1363 | CG | GLU | A | 186 | 16.337 | -18.573 | 36.696 | 1.00 29.12 |
| ATOM | 1364 | CD | GLU | A | 186 | 17.731 | -19.181 | 36.591 | 1.00 39.66 |
| ATOM | 1365 | OE1 | GLU | A | 186 | 18.272 | -19.548 | 37.660 | 1.00 56.70 |
| ATOM | 1366 | OE2 | GLU | A | 186 | 18.262 | -19.282 | 35.470 | 1.00 48.51 |
| ATOM | 1367 | C | GLU | A | 186 | 13.463 | -18.273 | 38.668 | 1.00 22.29 |
| ATOM | 1368 | O | GLU | A | 186 | 13.280 | -18.945 | 39.685 | 1.00 18.10 |
| ATOM | 1369 | N | PHE | A | 187 | 12.578 | -18.097 | 37.695 | 1.00 18.63 |
| ATOM | 1370 | CA | PHE | A | 187 | 11.303 | -18.785 | 37.643 | 1.00 16.57 |
| ATOM | 1371 | CB | PHE | A | 187 | 10.106 | -17.835 | 37.663 | 1.00 17.31 |
| ATOM | 1372 | CG | PHE | A | 187 | 10.225 | -16.820 | 38.799 | 1.00 28.29 |
| ATOM | 1373 | CD1 | PHE | A | 187 | 10.561 | -15.507 | 38.521 | 1.00 35.36 |
| ATOM | 1374 | CE1 | PHE | A | 187 | 10.660 | -14.575 | 39.550 | 1.00 25.40 |
| ATOM | 1375 | CZ | PHE | A | 187 | 10.448 | -14.987 | 40.849 | 1.00 21.30 |
| ATOM | 1376 | CE2 | PHE | A | 187 | 10.104 | -16.285 | 41.143 | 1.00 18.72 |
| ATOM | 1377 | CD2 | PHE | A | 187 | 9.991 | -17.207 | 40.113 | 1.00 25.67 |
| ATOM | 1378 | C | PHE | A | 187 | 11.210 | -19.663 | 36.381 | 1.00 26.48 |
| ATOM | 1379 | O | PHE | A | 187 | 11.754 | -19.296 | 35.347 | 1.00 22.46 |
| ATOM | 1380 | N | LYS | A | 188 | 10.530 | -20.777 | 36.559 | 1.00 27.77 |
| ATOM | 1381 | CA | LYS | A | 188 | 10.122 | -21.741 | 35.559 | 1.00 29.70 |
| ATOM | 1382 | CB | LYS | A | 188 | 10.530 | -23.158 | 35.948 | 1.00 39.93 |
| ATOM | 1383 | CG | LYS | A | 188 | 9.420 | -24.194 | 35.867 | 1.00 49.03 |
| ATOM | 1384 | CD | LYS | A | 188 | 9.938 | -25.587 | 36.210 | 1.00 53.96 |
| ATOM | 1385 | CE | LYS | A | 188 | 8.835 | -26.451 | 36.802 | 1.00 55.37 |
| ATOM | 1386 | NZ | LYS | A | 188 | 8.767 | -27.803 | 36.178 | 1.00 45.26 |
| ATOM | 1387 | C | LYS | A | 188 | 8.603 | -21.640 | 35.400 | 1.00 23.00 |
| ATOM | 1388 | O | LYS | A | 188 | 7.888 | -21.828 | 36.378 | 1.00 26.46 |
| ATOM | 1389 | N | ILE | A | 189 | 8.132 | -21.324 | 34.203 | 1.00 23.28 |
| ATOM | 1390 | CA | ILE | A | 189 | 6.734 | -21.106 | 33.898 | 1.00 25.13 |
| ATOM | 1391 | CB | ILE | A | 189 | 6.489 | -19.717 | 33.278 | 1.00 37.23 |
| ATOM | 1392 | CG1 | ILE | A | 189 | 6.899 | -18.538 | 34.159 | 1.00 42.70 |
| ATOM | 1393 | CD1 | ILE | A | 189 | 6.097 | -17.286 | 33.840 | 1.00 58.33 |
| ATOM | 1394 | CG2 | ILE | A | 189 | 5.029 | -19.569 | 32.866 | 1.00 42.16 |
| ATOM | 1395 | C | ILE | A | 189 | 6.228 | -22.144 | 32.895 | 1.00 28.65 |
| ATOM | 1396 | O | ILE | A | 189 | 6.897 | -22.279 | 31.869 | 1.00 28.97 |
| ATOM | 1397 | N | CYS | A | 190 | 5.129 | -22.799 | 33.219 | 1.00 28.96 |
| ATOM | 1398 | CA | CYS | A | 190 | 4.509 | -23.828 | 32.396 | 1.00 35.44 |
| ATOM | 1399 | CB | CYS | A | 190 | 4.306 | -25.127 | 33.185 | 1.00 38.00 |
| ATOM | 1400 | SG | CYS | A | 190 | 5.768 | -25.627 | 34.128 | 1.00 68.71 |
| ATOM | 1401 | C | CYS | A | 190 | 3.178 | -23.331 | 31.836 | 1.00 40.13 |
| ATOM | 1402 | O | CYS | A | 190 | 2.263 | -22.985 | 32.586 | 1.00 32.30 |
| ATOM | 1403 | N | GLY | A | 191 | 3.122 | -23.308 | 30.510 | 1.00 37.25 |

FIGURE 129

```
ATOM   1404  CA   GLY A 191       2.017 -22.800  29.737  1.00 41.56
ATOM   1405  C    GLY A 191       1.357 -23.872  28.890  1.00 48.56
ATOM   1406  O    GLY A 191       1.577 -25.066  29.095  1.00 45.07
ATOM   1407  N    GLU A 192       0.549 -23.428  27.936  1.00 54.18
ATOM   1408  CA   GLU A 192      -0.200 -24.305  27.048  1.00 69.22
ATOM   1409  CB   GLU A 192      -1.434 -23.566  26.522  1.00 74.04
ATOM   1410  CG   GLU A 192      -2.761 -24.220  26.866  1.00 80.18
ATOM   1411  CD   GLU A 192      -3.579 -23.505  27.916  1.00 81.21
ATOM   1412  OE1  GLU A 192      -3.733 -24.045  29.033  1.00 64.52
ATOM   1413  OE2  GLU A 192      -4.092 -22.396  27.649  1.00 98.21
ATOM   1414  C    GLU A 192       0.670 -24.817  25.901  1.00 77.66
ATOM   1415  O    GLU A 192       0.153 -25.106  24.821  1.00 91.62
ATOM   1416  N    GLU A 193       1.963 -24.929  26.155  1.00 83.58
ATOM   1417  CA   GLU A 193       3.011 -25.361  25.250  1.00 93.54
ATOM   1418  CB   GLU A 193       2.953 -26.877  25.035  1.00 96.89
ATOM   1419  CG   GLU A 193       4.249 -27.604  25.348  1.00 98.33
ATOM   1420  CD   GLU A 193       4.432 -28.893  24.572  1.00 96.49
ATOM   1421  OE1  GLU A 193       3.518 -29.278  23.811  1.00 93.16
ATOM   1422  OE2  GLU A 193       5.494 -29.536  24.722  1.00 88.57
ATOM   1423  C    GLU A 193       2.918 -24.636  23.910  1.00 99.98
ATOM   1424  O    GLU A 193       2.701 -25.271  22.877  1.00108.24
ATOM   1425  N    GLN A 194       3.077 -23.317  23.931  1.00102.55
ATOM   1426  CA   GLN A 194       2.938 -22.499  22.728  1.00105.80
ATOM   1427  CB   GLN A 194       2.358 -21.129  23.088  1.00108.21
ATOM   1428  CG   GLN A 194       0.857 -21.133  23.330  1.00106.39
ATOM   1429  CD   GLN A 194       0.501 -21.310  24.793  1.00103.56
ATOM   1430  OE1  GLN A 194       1.330 -21.724  25.602  1.00 98.95
ATOM   1431  NE2  GLN A 194      -0.741 -20.994  25.143  1.00 99.79
ATOM   1432  C    GLN A 194       4.267 -22.341  21.999  1.00105.62
ATOM   1433  O    GLN A 194       4.998 -23.324  21.847  1.00116.12
ATOM   1434  N    LEU A 195       4.582 -21.125  21.553  1.00101.17
ATOM   1435  CA   LEU A 195       5.860 -20.881  20.883  1.00 95.89
ATOM   1436  CB   LEU A 195       6.034 -19.411  20.507  1.00 88.27
ATOM   1437  CG   LEU A 195       6.093 -19.063  19.016  1.00 76.59
ATOM   1438  CD1  LEU A 195       6.613 -17.648  18.786  1.00 35.43
ATOM   1439  CD2  LEU A 195       6.948 -20.068  18.254  1.00 62.06
ATOM   1440  C    LEU A 195       7.001 -21.372  21.776  1.00 95.74
ATOM   1441  O    LEU A 195       8.005 -21.890  21.287  1.00104.53
ATOM   1442  N    ASP A 196       6.831 -21.227  23.085  1.00 93.29
ATOM   1443  CA   ASP A 196       7.763 -21.771  24.069  1.00 89.45
ATOM   1444  CB   ASP A 196       8.450 -20.660  24.857  1.00 83.52
ATOM   1445  CG   ASP A 196       7.556 -19.912  25.817  1.00 71.43
ATOM   1446  OD1  ASP A 196       6.442 -19.474  25.450  1.00 46.66
ATOM   1447  OD2  ASP A 196       7.964 -19.724  26.984  1.00 45.20
ATOM   1448  C    ASP A 196       7.029 -22.731  25.002  1.00 89.72
ATOM   1449  O    ASP A 196       5.897 -22.456  25.409  1.00 82.68
ATOM   1450  N    ALA A 197       7.657 -23.857  25.335  1.00 93.55
ATOM   1451  CA   ALA A 197       7.020 -24.842  26.208  1.00 94.35
ATOM   1452  CB   ALA A 197       7.240 -26.255  25.691  1.00 80.84
ATOM   1453  C    ALA A 197       7.520 -24.718  27.644  1.00 94.80
ATOM   1454  O    ALA A 197       6.712 -24.641  28.574  1.00 92.09
ATOM   1455  N    HIS A 198       8.839 -24.700  27.838  1.00 92.53
```

FIGURE 130

```
ATOM   1456  CA   HIS A 198       9.370 -24.519  29.182  1.00 88.28
ATOM   1457  CB   HIS A 198      10.131 -25.748  29.703  1.00 89.87
ATOM   1458  CG   HIS A 198      10.859 -25.377  30.967  1.00 91.21
ATOM   1459  ND1  HIS A 198      10.190 -24.902  32.073  1.00 94.03
ATOM   1460  CE1  HIS A 198      11.057 -24.649  33.038  1.00 94.08
ATOM   1461  NE2  HIS A 198      12.268 -24.939  32.593  1.00 94.64
ATOM   1462  CD2  HIS A 198      12.167 -25.392  31.299  1.00 92.48
ATOM   1463  C    HIS A 198      10.316 -23.322  29.267  1.00 77.76
ATOM   1464  O    HIS A 198      11.500 -23.417  28.954  1.00 88.55
ATOM   1465  N    ARG A 199       9.769 -22.197  29.709  1.00 65.70
ATOM   1466  CA   ARG A 199      10.523 -20.957  29.782  1.00 47.47
ATOM   1467  CB   ARG A 199       9.612 -19.780  29.400  1.00 44.67
ATOM   1468  CG   ARG A 199      10.165 -18.453  29.889  1.00 53.42
ATOM   1469  CD   ARG A 199       9.994 -17.331  28.879  1.00 46.83
ATOM   1470  NE   ARG A 199       8.914 -17.624  27.941  1.00 46.19
ATOM   1471  CZ   ARG A 199       7.852 -16.844  27.777  1.00 51.98
ATOM   1472  NH1  ARG A 199       7.744 -15.728  28.495  1.00 21.30
ATOM   1473  NH2  ARG A 199       6.920 -17.196  26.901  1.00 32.81
ATOM   1474  C    ARG A 199      11.133 -20.718  31.161  1.00 32.26
ATOM   1475  O    ARG A 199      10.541 -21.045  32.190  1.00 25.30
ATOM   1476  N    LEU A 200      12.327 -20.133  31.142  1.00 25.66
ATOM   1477  CA   LEU A 200      13.010 -19.678  32.340  1.00 25.37
ATOM   1478  CB   LEU A 200      14.414 -20.256  32.468  1.00 37.98
ATOM   1479  CG   LEU A 200      14.511 -21.782  32.585  1.00 50.45
ATOM   1480  CD1  LEU A 200      15.956 -22.239  32.447  1.00 66.02
ATOM   1481  CD2  LEU A 200      13.911 -22.270  33.899  1.00 46.72
ATOM   1482  C    LEU A 200      13.058 -18.146  32.323  1.00 26.91
ATOM   1483  O    LEU A 200      13.521 -17.544  31.358  1.00 22.85
ATOM   1484  N    ILE A 201      12.549 -17.552  33.391  1.00 23.54
ATOM   1485  CA   ILE A 201      12.463 -16.102  33.528  1.00 16.69
ATOM   1486  CB   ILE A 201      11.023 -15.688  33.897  1.00 18.39
ATOM   1487  CG1  ILE A 201       9.983 -16.468  33.096  1.00 32.11
ATOM   1488  CD1  ILE A 201       9.613 -15.818  31.788  1.00 38.11
ATOM   1489  CG2  ILE A 201      10.814 -14.183  33.790  1.00 26.56
ATOM   1490  C    ILE A 201      13.394 -15.625  34.626  1.00 17.67
ATOM   1491  O    ILE A 201      13.380 -16.158  35.732  1.00 23.89
ATOM   1492  N    ARG A 202      14.218 -14.617  34.353  1.00 16.91
ATOM   1493  CA   ARG A 202      15.020 -14.076  35.443  1.00 13.64
ATOM   1494  CB   ARG A 202      16.465 -13.807  35.065  1.00 20.15
ATOM   1495  CG   ARG A 202      17.322 -15.053  34.928  1.00 33.93
ATOM   1496  CD   ARG A 202      18.698 -14.896  35.558  1.00 44.89
ATOM   1497  NE   ARG A 202      19.494 -16.112  35.342  1.00 57.70
ATOM   1498  CZ   ARG A 202      19.879 -16.510  34.134  1.00 61.66
ATOM   1499  NH1  ARG A 202      19.549 -15.798  33.063  1.00 39.90
ATOM   1500  NH2  ARG A 202      20.596 -17.615  33.984  1.00 69.32
ATOM   1501  C    ARG A 202      14.351 -12.781  35.905  1.00 20.61
ATOM   1502  O    ARG A 202      13.802 -12.033  35.094  1.00 14.26
ATOM   1503  N    HIS A 203      14.431 -12.604  37.207  1.00 18.91
ATOM   1504  CA   HIS A 203      13.836 -11.436  37.870  1.00 18.64
ATOM   1505  CB   HIS A 203      12.711 -11.896  38.765  1.00 13.88
ATOM   1506  CG   HIS A 203      11.813 -10.917  39.426  1.00 22.44
ATOM   1507  ND1  HIS A 203      12.104 -10.321  40.633  1.00 23.99
```

FIGURE 131

```
ATOM   1508  CE1 HIS A 203      11.127  -9.510  40.981  1.00 23.53
ATOM   1509  NE2 HIS A 203      10.189  -9.558  40.046  1.00 17.09
ATOM   1510  CD2 HIS A 203      10.604 -10.429  39.065  1.00 18.86
ATOM   1511  C   HIS A 203      14.961 -10.731  38.626  1.00 17.56
ATOM   1512  O   HIS A 203      15.649 -11.341  39.451  1.00 18.34
ATOM   1513  N   PHE A 204      15.146  -9.457  38.314  1.00 15.90
ATOM   1514  CA  PHE A 204      16.181  -8.621  38.906  1.00 15.46
ATOM   1515  CB  PHE A 204      17.037  -7.984  37.819  1.00 15.83
ATOM   1516  CG  PHE A 204      17.538  -8.995  36.783  1.00 15.57
ATOM   1517  CD1 PHE A 204      16.751  -9.377  35.717  1.00 12.76
ATOM   1518  CE1 PHE A 204      17.208 -10.292  34.785  1.00 23.10
ATOM   1519  CZ  PHE A 204      18.474 -10.839  34.923  1.00 22.35
ATOM   1520  CE2 PHE A 204      19.277 -10.461  35.989  1.00 21.53
ATOM   1521  CD2 PHE A 204      18.807  -9.538  36.904  1.00 20.18
ATOM   1522  C   PHE A 204      15.527  -7.556  39.785  1.00 20.25
ATOM   1523  O   PHE A 204      14.885  -6.620  39.312  1.00 17.21
ATOM   1524  N   HIS A 205      15.672  -7.713  41.097  1.00 17.28
ATOM   1525  CA  HIS A 205      14.949  -6.855  42.035  1.00 14.35
ATOM   1526  CB  HIS A 205      14.203  -7.745  43.021  1.00 20.27
ATOM   1527  CG  HIS A 205      13.221  -7.056  43.900  1.00 17.93
ATOM   1528  ND1 HIS A 205      12.549  -7.729  44.905  1.00 19.18
ATOM   1529  CE1 HIS A 205      11.738  -6.874  45.516  1.00 22.04
ATOM   1530  NE2 HIS A 205      11.866  -5.681  44.947  1.00 17.85
ATOM   1531  CD2 HIS A 205      12.788  -5.771  43.928  1.00 12.88
ATOM   1532  C   HIS A 205      15.896  -5.931  42.782  1.00 17.06
ATOM   1533  O   HIS A 205      16.635  -6.400  43.658  1.00 21.06
ATOM   1534  N   TYR A 206      15.883  -4.660  42.429  1.00 13.61
ATOM   1535  CA  TYR A 206      16.715  -3.648  43.082  1.00 11.14
ATOM   1536  CB  TYR A 206      17.008  -2.490  42.141  1.00 12.43
ATOM   1537  CG  TYR A 206      18.011  -1.486  42.668  1.00 17.70
ATOM   1538  CD1 TYR A 206      19.376  -1.745  42.568  1.00 14.03
ATOM   1539  CE1 TYR A 206      20.334  -0.866  43.027  1.00 20.29
ATOM   1540  CZ  TYR A 206      19.892   0.318  43.602  1.00 22.75
ATOM   1541  OH  TYR A 206      20.839   1.200  44.070  1.00 25.15
ATOM   1542  CE2 TYR A 206      18.553   0.609  43.718  1.00 19.11
ATOM   1543  CD2 TYR A 206      17.596  -0.287  43.249  1.00 18.90
ATOM   1544  C   TYR A 206      15.953  -3.189  44.315  1.00 15.80
ATOM   1545  O   TYR A 206      14.828  -2.701  44.188  1.00 19.33
ATOM   1546  N   THR A 207      16.503  -3.371  45.520  1.00 16.37
ATOM   1547  CA  THR A 207      15.652  -3.191  46.691  1.00 18.59
ATOM   1548  CB  THR A 207      15.789  -4.385  47.669  1.00 18.47
ATOM   1549  OG1 THR A 207      17.175  -4.639  47.895  1.00 23.23
ATOM   1550  CG2 THR A 207      15.217  -5.655  47.056  1.00 23.19
ATOM   1551  C   THR A 207      15.955  -1.923  47.481  1.00 23.83
ATOM   1552  O   THR A 207      15.371  -1.745  48.556  1.00 24.21
ATOM   1553  N   VAL A 208      16.848  -1.060  47.004  1.00 22.88
ATOM   1554  CA  VAL A 208      17.156   0.123  47.814  1.00 23.02
ATOM   1555  CB  VAL A 208      18.604   0.059  48.325  1.00 22.02
ATOM   1556  CG1 VAL A 208      18.747  -1.128  49.276  1.00 31.63
ATOM   1557  CG2 VAL A 208      19.599  -0.045  47.185  1.00 23.30
ATOM   1558  C   VAL A 208      16.951   1.425  47.059  1.00 16.29
ATOM   1559  O   VAL A 208      17.782   2.331  47.160  1.00 26.60
```

FIGURE 132

| | | | | | | | | |
|---|---|---|---|---|---|---|---|---|
| ATOM | 1560 | N | TRP | A 209 | 15.861 | 1.525 | 46.321 | 1.00 14.67 |
| ATOM | 1561 | CA | TRP | A 209 | 15.522 | 2.734 | 45.570 | 1.00 21.23 |
| ATOM | 1562 | CB | TRP | A 209 | 15.364 | 2.460 | 44.075 | 1.00 23.37 |
| ATOM | 1563 | CG | TRP | A 209 | 15.364 | 3.656 | 43.171 | 1.00 17.61 |
| ATOM | 1564 | CD1 | TRP | A 209 | 15.121 | 4.978 | 43.419 | 1.00 16.97 |
| ATOM | 1565 | NE1 | TRP | A 209 | 15.236 | 5.726 | 42.271 | 1.00 24.39 |
| ATOM | 1566 | CE2 | TRP | A 209 | 15.560 | 4.876 | 41.238 | 1.00 22.16 |
| ATOM | 1567 | CD2 | TRP | A 209 | 15.649 | 3.568 | 41.766 | 1.00 16.31 |
| ATOM | 1568 | CE3 | TRP | A 209 | 15.969 | 2.508 | 40.918 | 1.00 20.86 |
| ATOM | 1569 | CZ3 | TRP | A 209 | 16.190 | 2.771 | 39.578 | 1.00 24.91 |
| ATOM | 1570 | CH2 | TRP | A 209 | 16.095 | 4.077 | 39.075 | 1.00 20.45 |
| ATOM | 1571 | CZ2 | TRP | A 209 | 15.785 | 5.131 | 39.888 | 1.00 19.42 |
| ATOM | 1572 | C | TRP | A 209 | 14.212 | 3.314 | 46.101 | 1.00 23.30 |
| ATOM | 1573 | O | TRP | A 209 | 13.164 | 2.827 | 45.672 | 1.00 25.49 |
| ATOM | 1574 | N | PRO | A 210 | 14.299 | 4.324 | 46.963 | 1.00 23.84 |
| ATOM | 1575 | CA | PRO | A 210 | 13.107 | 4.901 | 47.582 | 1.00 18.86 |
| ATOM | 1576 | CB | PRO | A 210 | 13.655 | 5.980 | 48.508 | 1.00 26.38 |
| ATOM | 1577 | CG | PRO | A 210 | 15.115 | 5.736 | 48.620 | 1.00 29.41 |
| ATOM | 1578 | CD | PRO | A 210 | 15.540 | 4.996 | 47.383 | 1.00 23.17 |
| ATOM | 1579 | C | PRO | A 210 | 12.199 | 5.553 | 46.536 | 1.00 24.85 |
| ATOM | 1580 | O | PRO | A 210 | 12.696 | 6.304 | 45.689 | 1.00 25.87 |
| ATOM | 1581 | N | ASP | A 211 | 10.901 | 5.271 | 46.601 | 1.00 19.16 |
| ATOM | 1582 | CA | ASP | A 211 | 9.942 | 5.886 | 45.698 | 1.00 23.36 |
| ATOM | 1583 | CB | ASP | A 211 | 8.499 | 5.590 | 46.126 | 1.00 25.37 |
| ATOM | 1584 | CG | ASP | A 211 | 7.576 | 5.865 | 44.943 | 1.00 24.78 |
| ATOM | 1585 | OD1 | ASP | A 211 | 6.379 | 5.571 | 45.094 | 1.00 26.65 |
| ATOM | 1586 | OD2 | ASP | A 211 | 8.078 | 6.348 | 43.899 | 1.00 23.48 |
| ATOM | 1587 | C | ASP | A 211 | 10.124 | 7.395 | 45.610 | 1.00 29.53 |
| ATOM | 1588 | O | ASP | A 211 | 10.525 | 8.061 | 46.573 | 1.00 32.57 |
| ATOM | 1589 | N | HIS | A 212 | 9.888 | 7.977 | 44.442 | 1.00 28.91 |
| ATOM | 1590 | CA | HIS | A 212 | 10.051 | 9.398 | 44.175 | 1.00 28.03 |
| ATOM | 1591 | CB | HIS | A 212 | 9.080 | 10.227 | 45.032 | 1.00 21.33 |
| ATOM | 1592 | CG | HIS | A 212 | 7.681 | 9.700 | 44.958 | 1.00 26.06 |
| ATOM | 1593 | ND1 | HIS | A 212 | 6.939 | 9.760 | 43.801 | 1.00 23.57 |
| ATOM | 1594 | CE1 | HIS | A 212 | 5.754 | 9.219 | 44.023 | 1.00 25.96 |
| ATOM | 1595 | NE2 | HIS | A 212 | 5.703 | 8.814 | 45.279 | 1.00 26.25 |
| ATOM | 1596 | CD2 | HIS | A 212 | 6.902 | 9.100 | 45.884 | 1.00 27.02 |
| ATOM | 1597 | C | HIS | A 212 | 11.460 | 9.932 | 44.425 | 1.00 34.91 |
| ATOM | 1598 | O | HIS | A 212 | 11.653 | 11.152 | 44.346 | 1.00 42.93 |
| ATOM | 1599 | N | GLY | A 213 | 12.418 | 9.071 | 44.709 | 1.00 25.41 |
| ATOM | 1600 | CA | GLY | A 213 | 13.772 | 9.392 | 45.079 | 1.00 25.24 |
| ATOM | 1601 | C | GLY | A 213 | 14.771 | 8.747 | 44.143 | 1.00 27.01 |
| ATOM | 1602 | O | GLY | A 213 | 14.471 | 8.336 | 43.027 | 1.00 22.02 |
| ATOM | 1603 | N | VAL | A 214 | 16.012 | 8.697 | 44.602 | 1.00 26.65 |
| ATOM | 1604 | CA | VAL | A 214 | 17.102 | 8.144 | 43.810 | 1.00 31.35 |
| ATOM | 1605 | CB | VAL | A 214 | 17.945 | 9.250 | 43.163 | 1.00 35.53 |
| ATOM | 1606 | CG1 | VAL | A 214 | 17.091 | 10.182 | 42.307 | 1.00 27.84 |
| ATOM | 1607 | CG2 | VAL | A 214 | 18.668 | 10.055 | 44.234 | 1.00 40.38 |
| ATOM | 1608 | C | VAL | A 214 | 17.953 | 7.295 | 44.742 | 1.00 28.56 |
| ATOM | 1609 | O | VAL | A 214 | 17.887 | 7.492 | 45.959 | 1.00 28.51 |
| ATOM | 1610 | N | PRO | A 215 | 18.720 | 6.349 | 44.228 | 1.00 23.57 |
| ATOM | 1611 | CA | PRO | A 215 | 19.542 | 5.511 | 45.116 | 1.00 29.45 |

FIGURE 133

| | | | | | | | | |
|---|---|---|---|---|---|---|---|---|
| ATOM | 1612 | CB | PRO | A | 215 | 20.192 | 4.526 | 44.146 | 1.00 | 29.52 |
| ATOM | 1613 | CG | PRO | A | 215 | 19.235 | 4.515 | 42.984 | 1.00 | 28.93 |
| ATOM | 1614 | CD | PRO | A | 215 | 18.865 | 5.974 | 42.820 | 1.00 | 23.13 |
| ATOM | 1615 | C | PRO | A | 215 | 20.601 | 6.338 | 45.842 | 1.00 | 35.63 |
| ATOM | 1616 | O | PRO | A | 215 | 20.990 | 7.415 | 45.396 | 1.00 | 30.87 |
| ATOM | 1617 | N | GLU | A | 216 | 21.073 | 5.828 | 46.972 | 1.00 | 35.49 |
| ATOM | 1618 | CA | GLU | A | 216 | 22.063 | 6.538 | 47.780 | 1.00 | 35.03 |
| ATOM | 1619 | CB | GLU | A | 216 | 22.254 | 5.768 | 49.090 | 1.00 | 36.48 |
| ATOM | 1620 | CG | GLU | A | 216 | 23.661 | 5.715 | 49.649 | 1.00 | 52.93 |
| ATOM | 1621 | CD | GLU | A | 216 | 23.844 | 4.606 | 50.672 | 1.00 | 63.63 |
| ATOM | 1622 | OE1 | GLU | A | 216 | 24.879 | 3.902 | 50.618 | 1.00 | 59.31 |
| ATOM | 1623 | OE2 | GLU | A | 216 | 22.952 | 4.437 | 51.532 | 1.00 | 69.52 |
| ATOM | 1624 | C | GLU | A | 216 | 23.368 | 6.751 | 47.032 | 1.00 | 33.10 |
| ATOM | 1625 | O | GLU | A | 216 | 24.121 | 7.675 | 47.370 | 1.00 | 39.10 |
| ATOM | 1626 | N | THR | A | 217 | 23.711 | 5.964 | 46.014 | 1.00 | 32.88 |
| ATOM | 1627 | CA | THR | A | 217 | 24.924 | 6.230 | 45.242 | 1.00 | 34.43 |
| ATOM | 1628 | CB | THR | A | 217 | 26.135 | 5.360 | 45.635 | 1.00 | 41.56 |
| ATOM | 1629 | OG1 | THR | A | 217 | 25.910 | 4.010 | 45.183 | 1.00 | 31.22 |
| ATOM | 1630 | CG2 | THR | A | 217 | 26.341 | 5.329 | 47.138 | 1.00 | 44.45 |
| ATOM | 1631 | C | THR | A | 217 | 24.711 | 5.979 | 43.748 | 1.00 | 30.56 |
| ATOM | 1632 | O | THR | A | 217 | 23.787 | 5.258 | 43.382 | 1.00 | 25.88 |
| ATOM | 1633 | N | THR | A | 218 | 25.578 | 6.530 | 42.901 | 1.00 | 26.73 |
| ATOM | 1634 | CA | THR | A | 218 | 25.494 | 6.239 | 41.469 | 1.00 | 30.02 |
| ATOM | 1635 | CB | THR | A | 218 | 26.251 | 7.270 | 40.615 | 1.00 | 29.46 |
| ATOM | 1636 | OG1 | THR | A | 218 | 27.594 | 7.382 | 41.105 | 1.00 | 27.79 |
| ATOM | 1637 | CG2 | THR | A | 218 | 25.616 | 8.644 | 40.740 | 1.00 | 30.31 |
| ATOM | 1638 | C | THR | A | 218 | 26.045 | 4.846 | 41.171 | 1.00 | 27.66 |
| ATOM | 1639 | O | THR | A | 218 | 25.499 | 4.105 | 40.348 | 1.00 | 23.92 |
| ATOM | 1640 | N | GLN | A | 219 | 27.123 | 4.478 | 41.848 | 1.00 | 26.54 |
| ATOM | 1641 | CA | GLN | A | 219 | 27.764 | 3.182 | 41.661 | 1.00 | 25.35 |
| ATOM | 1642 | CB | GLN | A | 219 | 28.845 | 2.982 | 42.729 | 1.00 | 35.12 |
| ATOM | 1643 | CG | GLN | A | 219 | 30.230 | 3.445 | 42.313 | 1.00 | 50.76 |
| ATOM | 1644 | CD | GLN | A | 219 | 31.311 | 2.472 | 42.754 | 1.00 | 70.22 |
| ATOM | 1645 | OE1 | GLN | A | 219 | 31.350 | 1.331 | 42.286 | 1.00 | 92.23 |
| ATOM | 1646 | NE2 | GLN | A | 219 | 32.187 | 2.921 | 43.650 | 1.00 | 63.32 |
| ATOM | 1647 | C | GLN | A | 219 | 26.783 | 2.013 | 41.730 | 1.00 | 26.20 |
| ATOM | 1648 | O | GLN | A | 219 | 26.802 | 1.112 | 40.897 | 1.00 | 29.61 |
| ATOM | 1649 | N | SER | A | 220 | 25.929 | 2.027 | 42.746 | 1.00 | 26.43 |
| ATOM | 1650 | CA | SER | A | 220 | 24.978 | 0.956 | 42.997 | 1.00 | 31.59 |
| ATOM | 1651 | CB | SER | A | 220 | 24.116 | 1.337 | 44.205 | 1.00 | 38.90 |
| ATOM | 1652 | OG | SER | A | 220 | 23.043 | 0.429 | 44.379 | 1.00 | 33.12 |
| ATOM | 1653 | C | SER | A | 220 | 24.097 | 0.682 | 41.788 | 1.00 | 31.15 |
| ATOM | 1654 | O | SER | A | 220 | 23.995 | -0.428 | 41.264 | 1.00 | 22.82 |
| ATOM | 1655 | N | LEU | A | 221 | 23.421 | 1.736 | 41.316 | 1.00 | 26.37 |
| ATOM | 1656 | CA | LEU | A | 221 | 22.527 | 1.511 | 40.181 | 1.00 | 22.50 |
| ATOM | 1657 | CB | LEU | A | 221 | 21.564 | 2.696 | 40.002 | 1.00 | 25.48 |
| ATOM | 1658 | CG | LEU | A | 221 | 20.346 | 2.374 | 39.125 | 1.00 | 27.75 |
| ATOM | 1659 | CD1 | LEU | A | 221 | 19.596 | 1.169 | 39.683 | 1.00 | 24.04 |
| ATOM | 1660 | CD2 | LEU | A | 221 | 19.428 | 3.572 | 39.007 | 1.00 | 26.75 |
| ATOM | 1661 | C | LEU | A | 221 | 23.311 | 1.255 | 38.907 | 1.00 | 16.37 |
| ATOM | 1662 | O | LEU | A | 221 | 22.870 | 0.452 | 38.078 | 1.00 | 25.76 |
| ATOM | 1663 | N | ILE | A | 222 | 24.462 | 1.917 | 38.728 | 1.00 | 17.23 |

FIGURE 134

```
ATOM   1664  CA   ILE A 222      25.230   1.662  37.507  1.00 21.02
ATOM   1665  CB   ILE A 222      26.510   2.506  37.436  1.00 23.08
ATOM   1666  CG1  ILE A 222      26.245   3.966  37.060  1.00 23.12
ATOM   1667  CD1  ILE A 222      27.289   4.943  37.546  1.00 25.12
ATOM   1668  CG2  ILE A 222      27.498   1.864  36.473  1.00 26.15
ATOM   1669  C    ILE A 222      25.573   0.179  37.422  1.00 20.38
ATOM   1670  O    ILE A 222      25.462  -0.473  36.385  1.00 18.34
ATOM   1671  N    GLN A 223      26.005  -0.362  38.558  1.00 24.24
ATOM   1672  CA   GLN A 223      26.401  -1.763  38.598  1.00 23.96
ATOM   1673  CB   GLN A 223      27.058  -2.162  39.919  1.00 26.95
ATOM   1674  CG   GLN A 223      28.327  -1.426  40.293  1.00 37.08
ATOM   1675  CD   GLN A 223      29.119  -0.836  39.150  1.00 56.97
ATOM   1676  OE1  GLN A 223      29.337  -1.473  38.116  1.00 84.38
ATOM   1677  NE2  GLN A 223      29.581   0.404  39.315  1.00 54.63
ATOM   1678  C    GLN A 223      25.163  -2.627  38.391  1.00 24.09
ATOM   1679  O    GLN A 223      25.262  -3.654  37.737  1.00 19.87
ATOM   1680  N    PHE A 224      24.017  -2.212  38.943  1.00 20.92
ATOM   1681  CA   PHE A 224      22.831  -3.055  38.717  1.00 22.52
ATOM   1682  CB   PHE A 224      21.658  -2.527  39.529  1.00 21.20
ATOM   1683  CG   PHE A 224      20.330  -3.222  39.302  1.00 23.79
ATOM   1684  CD1  PHE A 224      20.105  -4.505  39.792  1.00 21.63
ATOM   1685  CE1  PHE A 224      18.881  -5.123  39.606  1.00 15.71
ATOM   1686  CZ   PHE A 224      17.867  -4.481  38.919  1.00 16.76
ATOM   1687  CE2  PHE A 224      18.074  -3.204  38.415  1.00 13.56
ATOM   1688  CD2  PHE A 224      19.306  -2.589  38.609  1.00 16.88
ATOM   1689  C    PHE A 224      22.477  -3.104  37.240  1.00 26.00
ATOM   1690  O    PHE A 224      22.266  -4.142  36.617  1.00 17.57
ATOM   1691  N    VAL A 225      22.406  -1.916  36.636  1.00 17.86
ATOM   1692  CA   VAL A 225      22.097  -1.855  35.214  1.00 14.81
ATOM   1693  CB   VAL A 225      22.100  -0.383  34.764  1.00 15.04
ATOM   1694  CG1  VAL A 225      22.090  -0.273  33.250  1.00 17.94
ATOM   1695  CG2  VAL A 225      20.903   0.328  35.391  1.00 19.94
ATOM   1696  C    VAL A 225      23.068  -2.668  34.378  1.00 17.19
ATOM   1697  O    VAL A 225      22.674  -3.427  33.481  1.00 19.92
ATOM   1698  N    ARG A 226      24.371  -2.550  34.632  1.00 18.63
ATOM   1699  CA   ARG A 226      25.295  -3.342  33.809  1.00 24.02
ATOM   1700  CB   ARG A 226      26.735  -2.935  34.122  1.00 26.46
ATOM   1701  CG   ARG A 226      27.107  -1.562  33.582  1.00 23.91
ATOM   1702  CD   ARG A 226      28.568  -1.275  33.905  1.00 30.68
ATOM   1703  NE   ARG A 226      28.977   0.040  33.425  1.00 37.38
ATOM   1704  CZ   ARG A 226      29.848   0.828  34.046  1.00 45.40
ATOM   1705  NH1  ARG A 226      30.416   0.454  35.185  1.00 41.82
ATOM   1706  NH2  ARG A 226      30.154   2.009  33.522  1.00 45.68
ATOM   1707  C    ARG A 226      25.094  -4.836  34.022  1.00 22.36
ATOM   1708  O    ARG A 226      25.220  -5.649  33.106  1.00 24.97
ATOM   1709  N    THR A 227      24.762  -5.258  35.243  1.00 21.54
ATOM   1710  CA   THR A 227      24.427  -6.660  35.455  1.00 21.82
ATOM   1711  CB   THR A 227      24.206  -6.945  36.957  1.00 29.96
ATOM   1712  OG1  THR A 227      25.358  -6.463  37.648  1.00 28.79
ATOM   1713  CG2  THR A 227      24.081  -8.437  37.182  1.00 29.12
ATOM   1714  C    THR A 227      23.182  -7.107  34.713  1.00 19.03
ATOM   1715  O    THR A 227      23.188  -8.158  34.074  1.00 26.29
```

FIGURE 135

| ATOM | 1716 | N   | VAL | A | 228 | 22.097 | -6.336  | 34.778 | 1.00 | 17.49 |
|------|------|-----|-----|---|-----|--------|---------|--------|------|-------|
| ATOM | 1717 | CA  | VAL | A | 228 | 20.926 | -6.679  | 33.967 | 1.00 | 17.38 |
| ATOM | 1718 | CB  | VAL | A | 228 | 19.784 | -5.686  | 34.259 | 1.00 | 18.18 |
| ATOM | 1719 | CG1 | VAL | A | 228 | 18.550 | -5.978  | 33.411 | 1.00 | 19.51 |
| ATOM | 1720 | CG2 | VAL | A | 228 | 19.437 | -5.770  | 35.741 | 1.00 | 15.24 |
| ATOM | 1721 | C   | VAL | A | 228 | 21.238 | -6.711  | 32.477 | 1.00 | 17.43 |
| ATOM | 1722 | O   | VAL | A | 228 | 20.849 | -7.647  | 31.766 | 1.00 | 19.11 |
| ATOM | 1723 | N   | ARG | A | 229 | 21.943 | -5.703  | 31.972 | 1.00 | 17.01 |
| ATOM | 1724 | CA  | ARG | A | 229 | 22.204 | -5.651  | 30.527 | 1.00 | 21.03 |
| ATOM | 1725 | CB  | ARG | A | 229 | 22.833 | -4.291  | 30.221 | 1.00 | 17.71 |
| ATOM | 1726 | CG  | ARG | A | 229 | 23.465 | -4.129  | 28.873 | 1.00 | 18.28 |
| ATOM | 1727 | CD  | ARG | A | 229 | 22.589 | -3.886  | 27.687 | 1.00 | 26.78 |
| ATOM | 1728 | NE  | ARG | A | 229 | 21.245 | -3.355  | 27.849 | 1.00 | 22.41 |
| ATOM | 1729 | CZ  | ARG | A | 229 | 20.263 | -3.671  | 27.008 | 1.00 | 26.65 |
| ATOM | 1730 | NH1 | ARG | A | 229 | 20.514 | -4.494  | 25.992 | 1.00 | 28.43 |
| ATOM | 1731 | NH2 | ARG | A | 229 | 19.031 | -3.197  | 27.144 | 1.00 | 22.64 |
| ATOM | 1732 | C   | ARG | A | 229 | 23.052 | -6.833  | 30.076 | 1.00 | 26.78 |
| ATOM | 1733 | O   | ARG | A | 229 | 22.914 | -7.389  | 28.974 | 1.00 | 22.93 |
| ATOM | 1734 | N   | ASP | A | 230 | 23.970 | -7.282  | 30.931 | 1.00 | 22.22 |
| ATOM | 1735 | CA  | ASP | A | 230 | 24.761 | -8.474  | 30.615 | 1.00 | 19.37 |
| ATOM | 1736 | CB  | ASP | A | 230 | 25.720 | -8.746  | 31.770 | 1.00 | 26.22 |
| ATOM | 1737 | CG  | ASP | A | 230 | 26.764 | -9.808  | 31.496 | 1.00 | 37.14 |
| ATOM | 1738 | OD1 | ASP | A | 230 | 27.772 | -9.830  | 32.234 | 1.00 | 43.30 |
| ATOM | 1739 | OD2 | ASP | A | 230 | 26.579 | -10.609 | 30.558 | 1.00 | 48.34 |
| ATOM | 1740 | C   | ASP | A | 230 | 23.856 | -9.667  | 30.369 | 1.00 | 24.85 |
| ATOM | 1741 | O   | ASP | A | 230 | 24.007 | -10.389 | 29.383 | 1.00 | 27.24 |
| ATOM | 1742 | N   | TYR | A | 231 | 22.897 | -9.868  | 31.276 | 1.00 | 24.39 |
| ATOM | 1743 | CA  | TYR | A | 231 | 21.924 | -10.943 | 31.156 | 1.00 | 17.89 |
| ATOM | 1744 | CB  | TYR | A | 231 | 21.011 | -10.999 | 32.384 | 1.00 | 18.72 |
| ATOM | 1745 | CG  | TYR | A | 231 | 21.604 | -11.752 | 33.540 | 1.00 | 21.03 |
| ATOM | 1746 | CD1 | TYR | A | 231 | 22.218 | -11.040 | 34.559 | 1.00 | 27.60 |
| ATOM | 1747 | CE1 | TYR | A | 231 | 22.770 | -11.713 | 35.627 | 1.00 | 32.43 |
| ATOM | 1748 | CZ  | TYR | A | 231 | 22.716 | -13.085 | 35.692 | 1.00 | 25.45 |
| ATOM | 1749 | OH  | TYR | A | 231 | 23.283 | -13.694 | 36.789 | 1.00 | 36.71 |
| ATOM | 1750 | CE2 | TYR | A | 231 | 22.116 | -13.815 | 34.698 | 1.00 | 23.54 |
| ATOM | 1751 | CD2 | TYR | A | 231 | 21.561 | -13.136 | 33.622 | 1.00 | 30.94 |
| ATOM | 1752 | C   | TYR | A | 231 | 21.006 | -10.771 | 29.954 | 1.00 | 21.66 |
| ATOM | 1753 | O   | TYR | A | 231 | 20.659 | -11.726 | 29.269 | 1.00 | 23.21 |
| ATOM | 1754 | N   | ILE | A | 232 | 20.581 | -9.527  | 29.718 | 1.00 | 16.63 |
| ATOM | 1755 | CA  | ILE | A | 232 | 19.785 | -9.280  | 28.517 | 1.00 | 19.85 |
| ATOM | 1756 | CB  | ILE | A | 232 | 19.349 | -7.808  | 28.395 | 1.00 | 18.50 |
| ATOM | 1757 | CG1 | ILE | A | 232 | 18.391 | -7.370  | 29.499 | 1.00 | 22.29 |
| ATOM | 1758 | CD1 | ILE | A | 232 | 18.084 | -5.901  | 29.616 | 1.00 | 17.14 |
| ATOM | 1759 | CG2 | ILE | A | 232 | 18.773 | -7.570  | 26.999 | 1.00 | 22.60 |
| ATOM | 1760 | C   | ILE | A | 232 | 20.574 | -9.652  | 27.262 | 1.00 | 21.88 |
| ATOM | 1761 | O   | ILE | A | 232 | 20.066 | -10.308 | 26.358 | 1.00 | 24.41 |
| ATOM | 1762 | N   | ASN | A | 233 | 21.840 | -9.242  | 27.197 | 1.00 | 23.34 |
| ATOM | 1763 | CA  | ASN | A | 233 | 22.592 | -9.555  | 25.975 | 1.00 | 30.61 |
| ATOM | 1764 | CB  | ASN | A | 233 | 23.963 | -8.883  | 25.996 | 1.00 | 27.03 |
| ATOM | 1765 | CG  | ASN | A | 233 | 23.869 | -7.379  | 25.800 | 1.00 | 29.17 |
| ATOM | 1766 | OD1 | ASN | A | 233 | 22.902 | -6.849  | 25.248 | 1.00 | 36.95 |
| ATOM | 1767 | ND2 | ASN | A | 233 | 24.882 | -6.648  | 26.251 | 1.00 | 36.00 |

FIGURE 136

| ATOM | 1768 | C | ASN | A | 233 | 22.705 | -11.062 | 25.808 | 1.00 | 31.90 |
|------|------|------|------|---|-----|--------|---------|--------|------|-------|
| ATOM | 1769 | O | ASN | A | 233 | 22.823 | -11.595 | 24.711 | 1.00 | 37.58 |
| ATOM | 1770 | N | ARG | A | 234 | 22.659 | -11.778 | 26.927 | 1.00 | 29.26 |
| ATOM | 1771 | CA | ARG | A | 234 | 22.766 | -13.225 | 26.874 | 1.00 | 31.78 |
| ATOM | 1772 | CB | ARG | A | 234 | 23.465 | -13.746 | 28.129 | 1.00 | 38.80 |
| ATOM | 1773 | CG | ARG | A | 234 | 24.878 | -13.216 | 28.320 | 1.00 | 43.23 |
| ATOM | 1774 | CD | ARG | A | 234 | 25.391 | -13.632 | 29.692 | 1.00 | 51.48 |
| ATOM | 1775 | NE | ARG | A | 234 | 26.840 | -13.511 | 29.800 | 1.00 | 58.62 |
| ATOM | 1776 | CZ | ARG | A | 234 | 27.670 | -14.516 | 30.055 | 1.00 | 57.56 |
| ATOM | 1777 | NH1 | ARG | A | 234 | 27.201 | -15.746 | 30.232 | 1.00 | 60.00 |
| ATOM | 1778 | NH2 | ARG | A | 234 | 28.975 | -14.277 | 30.128 | 1.00 | 30.80 |
| ATOM | 1779 | C | ARG | A | 234 | 21.407 | -13.890 | 26.747 | 1.00 | 34.88 |
| ATOM | 1780 | O | ARG | A | 234 | 21.304 | -15.085 | 27.031 | 1.00 | 32.66 |
| ATOM | 1781 | N | SER | A | 235 | 20.351 | -13.186 | 26.337 | 1.00 | 24.05 |
| ATOM | 1782 | CA | SER | A | 235 | 19.065 | -13.884 | 26.273 | 1.00 | 27.03 |
| ATOM | 1783 | CB | SER | A | 235 | 17.992 | -13.249 | 27.156 | 1.00 | 26.67 |
| ATOM | 1784 | OG | SER | A | 235 | 18.396 | -13.237 | 28.520 | 1.00 | 34.69 |
| ATOM | 1785 | C | SER | A | 235 | 18.578 | -13.933 | 24.827 | 1.00 | 31.92 |
| ATOM | 1786 | O | SER | A | 235 | 17.770 | -13.103 | 24.425 | 1.00 | 28.81 |
| ATOM | 1787 | N | PRO | A | 236 | 19.099 | -14.914 | 24.105 | 1.00 | 37.48 |
| ATOM | 1788 | CA | PRO | A | 236 | 18.765 | -15.087 | 22.693 | 1.00 | 39.12 |
| ATOM | 1789 | CB | PRO | A | 236 | 19.584 | -16.312 | 22.269 | 1.00 | 46.32 |
| ATOM | 1790 | CG | PRO | A | 236 | 19.866 | -17.038 | 23.546 | 1.00 | 44.02 |
| ATOM | 1791 | CD | PRO | A | 236 | 20.033 | -15.957 | 24.580 | 1.00 | 42.48 |
| ATOM | 1792 | C | PRO | A | 236 | 17.279 | -15.378 | 22.517 | 1.00 | 34.00 |
| ATOM | 1793 | O | PRO | A | 236 | 16.696 | -16.221 | 23.207 | 1.00 | 43.89 |
| ATOM | 1794 | N | GLY | A | 237 | 16.668 | -14.660 | 21.577 | 1.00 | 27.25 |
| ATOM | 1795 | CA | GLY | A | 237 | 15.280 | -14.912 | 21.249 | 1.00 | 25.75 |
| ATOM | 1796 | C | GLY | A | 237 | 14.296 | -14.183 | 22.132 | 1.00 | 21.94 |
| ATOM | 1797 | O | GLY | A | 237 | 13.109 | -14.257 | 21.848 | 1.00 | 21.04 |
| ATOM | 1798 | N | ALA | A | 238 | 14.739 | -13.494 | 23.181 | 1.00 | 22.86 |
| ATOM | 1799 | CA | ALA | A | 238 | 13.836 | -12.838 | 24.112 | 1.00 | 20.89 |
| ATOM | 1800 | CB | ALA | A | 238 | 14.669 | -12.130 | 25.194 | 1.00 | 22.60 |
| ATOM | 1801 | C | ALA | A | 238 | 12.923 | -11.807 | 23.470 | 1.00 | 20.68 |
| ATOM | 1802 | O | ALA | A | 238 | 13.361 | -11.132 | 22.539 | 1.00 | 27.83 |
| ATOM | 1803 | N | GLY | A | 239 | 11.712 | -11.670 | 23.986 | 1.00 | 18.60 |
| ATOM | 1804 | CA | GLY | A | 239 | 10.829 | -10.549 | 23.700 | 1.00 | 18.19 |
| ATOM | 1805 | C | GLY | A | 239 | 11.346 | -9.351 | 24.497 | 1.00 | 15.46 |
| ATOM | 1806 | O | GLY | A | 239 | 12.521 | -9.353 | 24.887 | 1.00 | 18.43 |
| ATOM | 1807 | N | PRO | A | 240 | 10.484 | -8.378 | 24.743 | 1.00 | 17.13 |
| ATOM | 1808 | CA | PRO | A | 240 | 10.889 | -7.184 | 25.496 | 1.00 | 15.73 |
| ATOM | 1809 | CB | PRO | A | 240 | 9.626 | -6.323 | 25.550 | 1.00 | 18.54 |
| ATOM | 1810 | CG | PRO | A | 240 | 8.740 | -6.868 | 24.479 | 1.00 | 25.69 |
| ATOM | 1811 | CD | PRO | A | 240 | 9.073 | -8.329 | 24.350 | 1.00 | 13.87 |
| ATOM | 1812 | C | PRO | A | 240 | 11.306 | -7.518 | 26.923 | 1.00 | 14.71 |
| ATOM | 1813 | O | PRO | A | 240 | 10.867 | -8.502 | 27.508 | 1.00 | 14.52 |
| ATOM | 1814 | N | THR | A | 241 | 12.179 | -6.683 | 27.461 | 1.00 | 13.92 |
| ATOM | 1815 | CA | THR | A | 241 | 12.533 | -6.674 | 28.869 | 1.00 | 14.60 |
| ATOM | 1816 | CB | THR | A | 241 | 13.890 | -5.989 | 29.061 | 1.00 | 14.17 |
| ATOM | 1817 | OG1 | THR | A | 241 | 14.893 | -6.769 | 28.389 | 1.00 | 18.17 |
| ATOM | 1818 | CG2 | THR | A | 241 | 14.291 | -5.941 | 30.536 | 1.00 | 17.28 |
| ATOM | 1819 | C | THR | A | 241 | 11.441 | -5.931 | 29.639 | 1.00 | 16.58 |

FIGURE 137

| ATOM | 1820 | O   | THR A 241 | 11.124 | -4.784 | 29.305 | 1.00 | 13.03 |
| ATOM | 1821 | N   | VAL A 242 | 10.856 | -6.571 | 30.646 | 1.00 | 12.88 |
| ATOM | 1822 | CA  | VAL A 242 |  9.842 | -5.913 | 31.464 | 1.00 |  9.81 |
| ATOM | 1823 | CB  | VAL A 242 |  8.866 | -6.900 | 32.116 | 1.00 | 14.04 |
| ATOM | 1824 | CG1 | VAL A 242 |  8.019 | -6.223 | 33.179 | 1.00 | 16.00 |
| ATOM | 1825 | CG2 | VAL A 242 |  7.942 | -7.536 | 31.081 | 1.00 | 15.42 |
| ATOM | 1826 | C   | VAL A 242 | 10.564 | -5.128 | 32.554 | 1.00 | 12.01 |
| ATOM | 1827 | O   | VAL A 242 | 11.501 | -5.623 | 33.171 | 1.00 | 15.03 |
| ATOM | 1828 | N   | VAL A 243 | 10.107 | -3.893 | 32.785 | 1.00 | 11.17 |
| ATOM | 1829 | CA  | VAL A 243 | 10.668 | -3.065 | 33.838 | 1.00 |  9.13 |
| ATOM | 1830 | CB  | VAL A 243 | 11.575 | -1.931 | 33.352 | 1.00 | 15.38 |
| ATOM | 1831 | CG1 | VAL A 243 | 12.196 | -1.213 | 34.555 | 1.00 | 10.88 |
| ATOM | 1832 | CG2 | VAL A 243 | 12.666 | -2.463 | 32.442 | 1.00 | 12.02 |
| ATOM | 1833 | C   | VAL A 243 |  9.482 | -2.452 | 34.574 | 1.00 | 12.00 |
| ATOM | 1834 | O   | VAL A 243 |  8.576 | -1.930 | 33.932 | 1.00 |  9.88 |
| ATOM | 1835 | N   | HIS A 244 |  9.484 | -2.539 | 35.899 | 1.00 | 11.09 |
| ATOM | 1836 | CA  | HIS A 244 |  8.412 | -1.896 | 36.618 | 1.00 |  8.29 |
| ATOM | 1837 | CB  | HIS A 244 |  7.205 | -2.846 | 36.762 | 1.00 |  7.72 |
| ATOM | 1838 | CG  | HIS A 244 |  7.327 | -3.897 | 37.824 | 1.00 | 15.86 |
| ATOM | 1839 | ND1 | HIS A 244 |  7.058 | -3.666 | 39.160 | 1.00 | 14.99 |
| ATOM | 1840 | CE1 | HIS A 244 |  7.236 | -4.775 | 39.871 | 1.00 | 13.71 |
| ATOM | 1841 | NE2 | HIS A 244 |  7.617 | -5.753 | 39.039 | 1.00 | 16.24 |
| ATOM | 1842 | CD2 | HIS A 244 |  7.666 | -5.215 | 37.766 | 1.00 | 15.19 |
| ATOM | 1843 | C   | HIS A 244 |  8.890 | -1.434 | 37.999 | 1.00 | 11.45 |
| ATOM | 1844 | O   | HIS A 244 |  9.917 | -1.896 | 38.509 | 1.00 | 12.61 |
| ATOM | 1845 | N   | CYS A 245 |  8.085 | -0.528 | 38.539 | 1.00 | 18.46 |
| ATOM | 1846 | CA  | CYS A 245 |  8.250 | -0.016 | 39.911 | 1.00 | 14.56 |
| ATOM | 1847 | CB  | CYS A 245 |  9.019 |  1.304 | 39.865 | 1.00 | 10.22 |
| ATOM | 1848 | SG  | CYS A 245 |  8.326 |  2.556 | 38.746 | 1.00 | 14.87 |
| ATOM | 1849 | C   | CYS A 245 |  6.876 |  0.022 | 40.549 | 1.00 | 15.86 |
| ATOM | 1850 | O   | CYS A 245 |  6.192 | -1.015 | 40.537 | 1.00 | 13.86 |
| ATOM | 1851 | N   | SER A 246 |  6.376 |  1.128 | 41.113 | 1.00 |  9.56 |
| ATOM | 1852 | CA  | SER A 246 |  4.987 |  1.073 | 41.577 | 1.00 |  9.76 |
| ATOM | 1853 | CB  | SER A 246 |  4.844 |  1.783 | 42.926 | 1.00 |  7.75 |
| ATOM | 1854 | OG  | SER A 246 |  3.495 |  1.651 | 43.398 | 1.00 |  9.89 |
| ATOM | 1855 | C   | SER A 246 |  4.052 |  1.626 | 40.505 | 1.00 |  9.69 |
| ATOM | 1856 | O   | SER A 246 |  3.099 |  0.947 | 40.088 | 1.00 | 10.94 |
| ATOM | 1857 | N   | ALA A 247 |  4.265 |  2.853 | 40.014 | 1.00 | 15.37 |
| ATOM | 1858 | CA  | ALA A 247 |  3.443 |  3.430 | 38.976 | 1.00 | 12.59 |
| ATOM | 1859 | CB  | ALA A 247 |  3.411 |  4.964 | 38.966 | 1.00 | 11.87 |
| ATOM | 1860 | C   | ALA A 247 |  3.960 |  3.046 | 37.583 | 1.00 | 10.49 |
| ATOM | 1861 | O   | ALA A 247 |  3.242 |  3.172 | 36.600 | 1.00 | 15.72 |
| ATOM | 1862 | N   | GLY A 248 |  5.216 |  2.627 | 37.542 | 1.00 |  9.25 |
| ATOM | 1863 | CA  | GLY A 248 |  5.870 |  2.318 | 36.284 | 1.00 | 13.53 |
| ATOM | 1864 | C   | GLY A 248 |  6.210 |  3.615 | 35.570 | 1.00 | 20.73 |
| ATOM | 1865 | O   | GLY A 248 |  6.104 |  3.656 | 34.349 | 1.00 | 15.35 |
| ATOM | 1866 | N   | VAL A 249 |  6.616 |  4.653 | 36.301 | 1.00 | 14.47 |
| ATOM | 1867 | CA  | VAL A 249 |  7.031 |  5.853 | 35.561 | 1.00 | 23.41 |
| ATOM | 1868 | CB  | VAL A 249 |  5.942 |  6.948 | 35.534 | 1.00 | 27.80 |
| ATOM | 1869 | CG1 | VAL A 249 |  4.675 |  6.441 | 34.850 | 1.00 | 10.99 |
| ATOM | 1870 | CG2 | VAL A 249 |  5.615 |  7.470 | 36.930 | 1.00 | 21.36 |
| ATOM | 1871 | C   | VAL A 249 |  8.342 |  6.437 | 36.071 | 1.00 | 18.78 |

FIGURE 138

| | | | | | | | | |
|---|---|---|---|---|---|---|---|---|
| ATOM | 1872 | O | VAL | A | 249 | 9.252 | 6.752 | 35.288 | 1.00 | 16.76 |
| ATOM | 1873 | N | GLY | A | 250 | 8.505 | 6.625 | 37.372 | 1.00 | 17.57 |
| ATOM | 1874 | CA | GLY | A | 250 | 9.695 | 7.363 | 37.801 | 1.00 | 15.55 |
| ATOM | 1875 | C | GLY | A | 250 | 10.939 | 6.526 | 37.860 | 1.00 | 11.84 |
| ATOM | 1876 | O | GLY | A | 250 | 11.945 | 6.720 | 37.165 | 1.00 | 17.28 |
| ATOM | 1877 | N | ARG | A | 251 | 10.945 | 5.519 | 38.740 | 1.00 | 11.43 |
| ATOM | 1878 | CA | ARG | A | 251 | 12.141 | 4.687 | 38.866 | 1.00 | 10.27 |
| ATOM | 1879 | CB | ARG | A | 251 | 12.050 | 3.844 | 40.148 | 1.00 | 14.41 |
| ATOM | 1880 | CG | ARG | A | 251 | 12.082 | 4.786 | 41.366 | 1.00 | 15.59 |
| ATOM | 1881 | CD | ARG | A | 251 | 11.706 | 4.068 | 42.647 | 1.00 | 10.84 |
| ATOM | 1882 | NE | ARG | A | 251 | 10.278 | 3.795 | 42.721 | 1.00 | 15.91 |
| ATOM | 1883 | CZ | ARG | A | 251 | 9.729 | 3.085 | 43.709 | 1.00 | 22.05 |
| ATOM | 1884 | NH1 | ARG | A | 251 | 10.528 | 2.610 | 44.665 | 1.00 | 12.86 |
| ATOM | 1885 | NH2 | ARG | A | 251 | 8.413 | 2.887 | 43.697 | 1.00 | 19.96 |
| ATOM | 1886 | C | ARG | A | 251 | 12.319 | 3.826 | 37.620 | 1.00 | 7.84 |
| ATOM | 1887 | O | ARG | A | 251 | 13.444 | 3.643 | 37.141 | 1.00 | 13.49 |
| ATOM | 1888 | N | THR | A | 252 | 11.189 | 3.332 | 37.112 | 1.00 | 10.86 |
| ATOM | 1889 | CA | THR | A | 252 | 11.278 | 2.605 | 35.826 | 1.00 | 8.96 |
| ATOM | 1890 | CB | THR | A | 252 | 9.877 | 2.125 | 35.429 | 1.00 | 16.98 |
| ATOM | 1891 | OG1 | THR | A | 252 | 9.509 | 1.052 | 36.311 | 1.00 | 15.33 |
| ATOM | 1892 | CG2 | THR | A | 252 | 9.847 | 1.560 | 34.015 | 1.00 | 18.22 |
| ATOM | 1893 | C | THR | A | 252 | 11.901 | 3.464 | 34.745 | 1.00 | 13.54 |
| ATOM | 1894 | O | THR | A | 252 | 12.828 | 3.103 | 34.003 | 1.00 | 14.11 |
| ATOM | 1895 | N | GLY | A | 253 | 11.410 | 4.690 | 34.594 | 1.00 | 14.04 |
| ATOM | 1896 | CA | GLY | A | 253 | 11.976 | 5.531 | 33.532 | 1.00 | 16.89 |
| ATOM | 1897 | C | GLY | A | 253 | 13.426 | 5.881 | 33.711 | 1.00 | 11.18 |
| ATOM | 1898 | O | GLY | A | 253 | 14.233 | 5.937 | 32.777 | 1.00 | 14.06 |
| ATOM | 1899 | N | THR | A | 254 | 13.831 | 6.138 | 34.965 | 1.00 | 12.53 |
| ATOM | 1900 | CA | THR | A | 254 | 15.235 | 6.408 | 35.233 | 1.00 | 13.37 |
| ATOM | 1901 | CB | THR | A | 254 | 15.455 | 6.837 | 36.695 | 1.00 | 16.96 |
| ATOM | 1902 | OG1 | THR | A | 254 | 14.606 | 7.960 | 36.960 | 1.00 | 17.14 |
| ATOM | 1903 | CG2 | THR | A | 254 | 16.884 | 7.294 | 36.923 | 1.00 | 17.26 |
| ATOM | 1904 | C | THR | A | 254 | 16.108 | 5.200 | 34.937 | 1.00 | 18.94 |
| ATOM | 1905 | O | THR | A | 254 | 17.217 | 5.344 | 34.409 | 1.00 | 17.66 |
| ATOM | 1906 | N | PHE | A | 255 | 15.602 | 4.014 | 35.263 | 1.00 | 11.19 |
| ATOM | 1907 | CA | PHE | A | 255 | 16.362 | 2.796 | 34.987 | 1.00 | 10.10 |
| ATOM | 1908 | CB | PHE | A | 255 | 15.617 | 1.534 | 35.479 | 1.00 | 12.68 |
| ATOM | 1909 | CG | PHE | A | 255 | 16.273 | 0.217 | 35.051 | 1.00 | 13.42 |
| ATOM | 1910 | CD1 | PHE | A | 255 | 17.258 | -0.329 | 35.873 | 1.00 | 14.10 |
| ATOM | 1911 | CE1 | PHE | A | 255 | 17.901 | -1.509 | 35.535 | 1.00 | 15.64 |
| ATOM | 1912 | CZ | PHE | A | 255 | 17.592 | -2.156 | 34.345 | 1.00 | 14.48 |
| ATOM | 1913 | CE2 | PHE | A | 255 | 16.600 | -1.645 | 33.523 | 1.00 | 15.99 |
| ATOM | 1914 | CD2 | PHE | A | 255 | 15.937 | -0.487 | 33.898 | 1.00 | 19.84 |
| ATOM | 1915 | C | PHE | A | 255 | 16.626 | 2.687 | 33.493 | 1.00 | 11.10 |
| ATOM | 1916 | O | PHE | A | 255 | 17.732 | 2.397 | 33.060 | 1.00 | 14.84 |
| ATOM | 1917 | N | ILE | A | 256 | 15.561 | 2.863 | 32.704 | 1.00 | 14.82 |
| ATOM | 1918 | CA | ILE | A | 256 | 15.726 | 2.641 | 31.264 | 1.00 | 10.00 |
| ATOM | 1919 | CB | ILE | A | 256 | 14.352 | 2.607 | 30.589 | 1.00 | 12.80 |
| ATOM | 1920 | CG1 | ILE | A | 256 | 13.558 | 1.345 | 30.943 | 1.00 | 11.66 |
| ATOM | 1921 | CD1 | ILE | A | 256 | 12.084 | 1.457 | 30.602 | 1.00 | 12.54 |
| ATOM | 1922 | CG2 | ILE | A | 256 | 14.463 | 2.826 | 29.091 | 1.00 | 14.64 |
| ATOM | 1923 | C | ILE | A | 256 | 16.584 | 3.736 | 30.662 | 1.00 | 14.37 |

FIGURE 139

```
ATOM   1924  O    ILE A 256      17.387   3.496  29.766  1.00 20.73
ATOM   1925  N    ALA A 257      16.399   4.970  31.154  1.00 16.70
ATOM   1926  CA   ALA A 257      17.236   6.040  30.612  1.00 12.87
ATOM   1927  CB   ALA A 257      16.865   7.389  31.209  1.00 18.47
ATOM   1928  C    ALA A 257      18.699   5.703  30.858  1.00 19.90
ATOM   1929  O    ALA A 257      19.567   5.851  29.993  1.00 19.76
ATOM   1930  N    LEU A 258      18.967   5.203  32.071  1.00 15.65
ATOM   1931  CA   LEU A 258      20.358   4.894  32.395  1.00 16.29
ATOM   1932  CB   LEU A 258      20.501   4.631  33.901  1.00 18.82
ATOM   1933  CG   LEU A 258      21.938   4.343  34.350  1.00 18.09
ATOM   1934  CD1  LEU A 258      22.864   5.426  33.809  1.00 16.26
ATOM   1935  CD2  LEU A 258      22.000   4.251  35.864  1.00 19.56
ATOM   1936  C    LEU A 258      20.840   3.708  31.580  1.00 21.01
ATOM   1937  O    LEU A 258      21.974   3.651  31.110  1.00 23.61
ATOM   1938  N    ASP A 259      19.972   2.715  31.377  1.00 14.03
ATOM   1939  CA   ASP A 259      20.372   1.573  30.549  1.00 19.00
ATOM   1940  CB   ASP A 259      19.247   0.544  30.512  1.00 16.27
ATOM   1941  CG   ASP A 259      19.491  -0.692  29.670  1.00 16.85
ATOM   1942  OD1  ASP A 259      20.621  -1.227  29.689  1.00 22.41
ATOM   1943  OD2  ASP A 259      18.564  -1.164  28.976  1.00 22.35
ATOM   1944  C    ASP A 259      20.732   2.051  29.142  1.00 24.46
ATOM   1945  O    ASP A 259      21.715   1.611  28.532  1.00 22.50
ATOM   1946  N    ARG A 260      19.915   2.967  28.624  1.00 18.68
ATOM   1947  CA   ARG A 260      20.166   3.492  27.277  1.00 21.73
ATOM   1948  CB   ARG A 260      18.965   4.302  26.759  1.00 19.52
ATOM   1949  CG   ARG A 260      17.772   3.420  26.379  1.00 21.69
ATOM   1950  CD   ARG A 260      16.687   4.238  25.678  1.00 27.46
ATOM   1951  NE   ARG A 260      17.207   4.867  24.479  1.00 35.48
ATOM   1952  CZ   ARG A 260      16.651   5.618  23.551  1.00 36.55
ATOM   1953  NH1  ARG A 260      15.372   5.944  23.580  1.00 47.22
ATOM   1954  NH2  ARG A 260      17.404   6.063  22.548  1.00 36.27
ATOM   1955  C    ARG A 260      21.432   4.331  27.217  1.00 26.15
ATOM   1956  O    ARG A 260      22.192   4.165  26.256  1.00 23.92
ATOM   1957  N    ILE A 261      21.688   5.215  28.182  1.00 26.20
ATOM   1958  CA   ILE A 261      22.842   6.103  28.059  1.00 22.09
ATOM   1959  CB   ILE A 261      22.764   7.376  28.922  1.00 23.64
ATOM   1960  CG1  ILE A 261      23.001   7.148  30.418  1.00 30.05
ATOM   1961  CD1  ILE A 261      22.191   8.055  31.328  1.00 30.61
ATOM   1962  CG2  ILE A 261      21.452   8.105  28.674  1.00 18.34
ATOM   1963  C    ILE A 261      24.146   5.381  28.394  1.00 28.75
ATOM   1964  O    ILE A 261      25.206   5.722  27.854  1.00 36.26
ATOM   1965  N    LEU A 262      24.110   4.384  29.276  1.00 25.96
ATOM   1966  CA   LEU A 262      25.364   3.663  29.544  1.00 24.13
ATOM   1967  CB   LEU A 262      25.207   2.686  30.699  1.00 24.26
ATOM   1968  CG   LEU A 262      25.112   3.236  32.123  1.00 20.71
ATOM   1969  CD1  LEU A 262      25.079   2.071  33.101  1.00 24.55
ATOM   1970  CD2  LEU A 262      26.257   4.176  32.453  1.00 23.31
ATOM   1971  C    LEU A 262      25.812   2.958  28.271  1.00 29.49
ATOM   1972  O    LEU A 262      27.004   2.863  27.968  1.00 38.42
ATOM   1973  N    GLN A 263      24.851   2.454  27.494  1.00 29.52
ATOM   1974  CA   GLN A 263      25.225   1.863  26.204  1.00 35.18
ATOM   1975  CB   GLN A 263      24.015   1.216  25.545  1.00 34.97
```

FIGURE 140

| | | | | | | | | | |
|---|---|---|---|---|---|---|---|---|---|
| ATOM | 1976 | CG | GLN | A | 263 | 23.632 | -0.140 | 26.125 | 1.00 36.78 |
| ATOM | 1977 | CD | GLN | A | 263 | 22.277 | -0.630 | 25.661 | 1.00 34.45 |
| ATOM | 1978 | OE1 | GLN | A | 263 | 22.167 | -1.327 | 24.653 | 1.00 32.02 |
| ATOM | 1979 | NE2 | GLN | A | 263 | 21.219 | -0.276 | 26.388 | 1.00 29.68 |
| ATOM | 1980 | C | GLN | A | 263 | 25.867 | 2.912 | 25.300 | 1.00 38.62 |
| ATOM | 1981 | O | GLN | A | 263 | 26.927 | 2.694 | 24.702 | 1.00 44.23 |
| ATOM | 1982 | N | GLN | A | 264 | 25.255 | 4.084 | 25.187 | 1.00 40.04 |
| ATOM | 1983 | CA | GLN | A | 264 | 25.848 | 5.189 | 24.439 | 1.00 37.35 |
| ATOM | 1984 | CB | GLN | A | 264 | 25.018 | 6.461 | 24.597 | 1.00 30.80 |
| ATOM | 1985 | CG | GLN | A | 264 | 23.739 | 6.499 | 23.777 | 1.00 28.49 |
| ATOM | 1986 | CD | GLN | A | 264 | 22.842 | 7.650 | 24.195 | 1.00 36.13 |
| ATOM | 1987 | OE1 | GLN | A | 264 | 23.318 | 8.630 | 24.778 | 1.00 35.61 |
| ATOM | 1988 | NE2 | GLN | A | 264 | 21.552 | 7.519 | 23.905 | 1.00 30.19 |
| ATOM | 1989 | C | GLN | A | 264 | 27.280 | 5.460 | 24.900 | 1.00 46.87 |
| ATOM | 1990 | O | GLN | A | 264 | 28.192 | 5.539 | 24.076 | 1.00 59.11 |
| ATOM | 1991 | N | LEU | A | 265 | 27.474 | 5.599 | 26.210 | 1.00 44.30 |
| ATOM | 1992 | CA | LEU | A | 265 | 28.805 | 5.808 | 26.774 | 1.00 44.22 |
| ATOM | 1993 | CB | LEU | A | 265 | 28.794 | 5.779 | 28.295 | 1.00 47.83 |
| ATOM | 1994 | CG | LEU | A | 265 | 28.082 | 6.900 | 29.043 | 1.00 50.56 |
| ATOM | 1995 | CD1 | LEU | A | 265 | 28.140 | 6.641 | 30.544 | 1.00 39.48 |
| ATOM | 1996 | CD2 | LEU | A | 265 | 28.678 | 8.255 | 28.696 | 1.00 54.16 |
| ATOM | 1997 | C | LEU | A | 265 | 29.763 | 4.736 | 26.265 | 1.00 45.05 |
| ATOM | 1998 | O | LEU | A | 265 | 30.912 | 5.011 | 25.925 | 1.00 54.65 |
| ATOM | 1999 | N | ASP | A | 266 | 29.280 | 3.495 | 26.209 | 1.00 40.79 |
| ATOM | 2000 | CA | ASP | A | 266 | 30.137 | 2.440 | 25.670 | 1.00 47.27 |
| ATOM | 2001 | CB | ASP | A | 266 | 29.739 | 1.083 | 26.257 | 1.00 43.47 |
| ATOM | 2002 | CG | ASP | A | 266 | 30.102 | 0.960 | 27.721 | 1.00 44.36 |
| ATOM | 2003 | OD1 | ASP | A | 266 | 31.196 | 1.428 | 28.101 | 1.00 58.24 |
| ATOM | 2004 | OD2 | ASP | A | 266 | 29.297 | 0.391 | 28.488 | 1.00 53.34 |
| ATOM | 2005 | C | ASP | A | 266 | 30.066 | 2.396 | 24.154 | 1.00 58.50 |
| ATOM | 2006 | O | ASP | A | 266 | 30.476 | 1.429 | 23.506 | 1.00 56.64 |
| ATOM | 2007 | N | SER | A | 267 | 29.538 | 3.434 | 23.497 | 1.00 67.18 |
| ATOM | 2008 | CA | SER | A | 267 | 29.465 | 3.282 | 22.038 | 1.00 73.64 |
| ATOM | 2009 | CB | SER | A | 267 | 28.110 | 2.671 | 21.667 | 1.00 75.02 |
| ATOM | 2010 | OG | SER | A | 267 | 28.161 | 1.258 | 21.786 | 1.00 72.08 |
| ATOM | 2011 | C | SER | A | 267 | 29.693 | 4.592 | 21.301 | 1.00 81.56 |
| ATOM | 2012 | O | SER | A | 267 | 30.504 | 4.666 | 20.376 | 1.00 96.45 |
| ATOM | 2013 | N | LYS | A | 268 | 28.971 | 5.630 | 21.705 | 1.00 82.73 |
| ATOM | 2014 | CA | LYS | A | 268 | 29.039 | 6.931 | 21.064 | 1.00 81.39 |
| ATOM | 2015 | CB | LYS | A | 268 | 27.736 | 7.709 | 21.286 | 1.00 92.60 |
| ATOM | 2016 | CG | LYS | A | 268 | 26.518 | 7.115 | 20.597 | 1.00 98.30 |
| ATOM | 2017 | CD | LYS | A | 268 | 25.516 | 8.187 | 20.194 | 1.00 99.41 |
| ATOM | 2018 | CE | LYS | A | 268 | 25.288 | 9.191 | 21.312 | 1.00 97.43 |
| ATOM | 2019 | NZ | LYS | A | 268 | 23.896 | 9.151 | 21.836 | 1.00 86.39 |
| ATOM | 2020 | C | LYS | A | 268 | 30.209 | 7.766 | 21.583 | 1.00 67.12 |
| ATOM | 2021 | O | LYS | A | 268 | 30.930 | 7.340 | 22.478 | 1.00 61.30 |
| ATOM | 2022 | N | ASP | A | 269 | 30.340 | 8.941 | 20.995 | 1.00 57.55 |
| ATOM | 2023 | CA | ASP | A | 269 | 31.277 | 9.986 | 21.380 | 1.00 61.48 |
| ATOM | 2024 | CB | ASP | A | 269 | 31.994 | 10.514 | 20.137 | 1.00 71.27 |
| ATOM | 2025 | CG | ASP | A | 269 | 31.482 | 9.789 | 18.899 | 1.00 80.60 |
| ATOM | 2026 | OD1 | ASP | A | 269 | 32.270 | 9.060 | 18.261 | 1.00 87.05 |
| ATOM | 2027 | OD2 | ASP | A | 269 | 30.283 | 9.954 | 18.585 | 1.00 82.09 |

FIGURE 141

```
ATOM   2028  C    ASP A 269      30.498  11.081  22.096  1.00 54.39
ATOM   2029  O    ASP A 269      30.997  12.070  22.621  1.00 37.16
ATOM   2030  N    SER A 270      29.183  10.843  22.108  1.00 44.05
ATOM   2031  CA   SER A 270      28.290  11.754  22.805  1.00 48.15
ATOM   2032  CB   SER A 270      27.593  12.687  21.814  1.00 54.66
ATOM   2033  OG   SER A 270      27.367  12.009  20.588  1.00 61.37
ATOM   2034  C    SER A 270      27.261  10.971  23.609  1.00 44.27
ATOM   2035  O    SER A 270      27.045   9.781  23.410  1.00 33.61
ATOM   2036  N    VAL A 271      26.613  11.652  24.544  1.00 41.56
ATOM   2037  CA   VAL A 271      25.550  10.966  25.288  1.00 44.74
ATOM   2038  CB   VAL A 271      25.984  10.636  26.722  1.00 43.78
ATOM   2039  CG1  VAL A 271      26.585  11.844  27.428  1.00 22.16
ATOM   2040  CG2  VAL A 271      24.822  10.084  27.544  1.00 24.65
ATOM   2041  C    VAL A 271      24.316  11.852  25.185  1.00 43.38
ATOM   2042  O    VAL A 271      24.418  13.084  25.177  1.00 32.23
ATOM   2043  N    ASP A 272      23.146  11.232  25.058  1.00 35.09
ATOM   2044  CA   ASP A 272      21.929  12.022  24.874  1.00 36.34
ATOM   2045  CB   ASP A 272      21.317  11.723  23.500  1.00 28.68
ATOM   2046  CG   ASP A 272      20.345  12.806  23.075  1.00 25.29
ATOM   2047  OD1  ASP A 272      20.363  13.875  23.726  1.00 33.02
ATOM   2048  OD2  ASP A 272      19.581  12.595  22.112  1.00 37.57
ATOM   2049  C    ASP A 272      20.936  11.754  25.993  1.00 33.69
ATOM   2050  O    ASP A 272      19.969  11.023  25.818  1.00 35.34
ATOM   2051  N    ILE A 273      21.171  12.338  27.166  1.00 29.39
ATOM   2052  CA   ILE A 273      20.262  12.106  28.281  1.00 31.17
ATOM   2053  CB   ILE A 273      20.840  12.632  29.611  1.00 33.58
ATOM   2054  CG1  ILE A 273      22.112  11.900  30.045  1.00 34.59
ATOM   2055  CD1  ILE A 273      22.785  12.475  31.270  1.00 32.68
ATOM   2056  CG2  ILE A 273      19.793  12.604  30.714  1.00 21.45
ATOM   2057  C    ILE A 273      18.909  12.754  28.018  1.00 36.45
ATOM   2058  O    ILE A 273      17.873  12.152  28.319  1.00 29.72
ATOM   2059  N    TYR A 274      18.921  13.967  27.465  1.00 23.18
ATOM   2060  CA   TYR A 274      17.658  14.663  27.204  1.00 23.24
ATOM   2061  CB   TYR A 274      17.927  16.065  26.659  1.00 21.30
ATOM   2062  CG   TYR A 274      16.720  16.885  26.286  1.00 28.11
ATOM   2063  CD1  TYR A 274      16.099  17.722  27.205  1.00 30.12
ATOM   2064  CE1  TYR A 274      14.991  18.475  26.855  1.00 36.51
ATOM   2065  CZ   TYR A 274      14.486  18.401  25.576  1.00 39.07
ATOM   2066  OH   TYR A 274      13.384  19.137  25.206  1.00 39.75
ATOM   2067  CE2  TYR A 274      15.082  17.578  24.641  1.00 33.12
ATOM   2068  CD2  TYR A 274      16.183  16.837  25.003  1.00 30.11
ATOM   2069  C    TYR A 274      16.810  13.851  26.229  1.00 23.51
ATOM   2070  O    TYR A 274      15.604  13.715  26.425  1.00 26.03
ATOM   2071  N    GLY A 275      17.435  13.350  25.181  1.00 21.12
ATOM   2072  CA   GLY A 275      16.774  12.633  24.100  1.00 24.69
ATOM   2073  C    GLY A 275      16.230  11.296  24.575  1.00 30.05
ATOM   2074  O    GLY A 275      15.206  10.793  24.115  1.00 26.82
ATOM   2075  N    ALA A 276      16.950  10.705  25.531  1.00 28.67
ATOM   2076  CA   ALA A 276      16.477   9.436  26.087  1.00 28.22
ATOM   2077  CB   ALA A 276      17.538   8.828  26.980  1.00 23.79
ATOM   2078  C    ALA A 276      15.165   9.685  26.816  1.00 25.48
ATOM   2079  O    ALA A 276      14.174   8.993  26.612  1.00 21.68
```

FIGURE 142

| ATOM | 2080 | N | VAL | A | 277 | 15.134 | 10.709 | 27.669 | 1.00 | 19.63 |
|------|------|------|------|---|-----|--------|--------|--------|------|-------|
| ATOM | 2081 | CA | VAL | A | 277 | 13.928 | 10.960 | 28.450 | 1.00 | 18.94 |
| ATOM | 2082 | CB | VAL | A | 277 | 14.184 | 11.957 | 29.592 | 1.00 | 18.63 |
| ATOM | 2083 | CG1 | VAL | A | 277 | 12.919 | 12.193 | 30.417 | 1.00 | 19.37 |
| ATOM | 2084 | CG2 | VAL | A | 277 | 15.308 | 11.457 | 30.497 | 1.00 | 23.87 |
| ATOM | 2085 | C | VAL | A | 277 | 12.820 | 11.458 | 27.538 | 1.00 | 22.49 |
| ATOM | 2086 | O | VAL | A | 277 | 11.642 | 11.184 | 27.731 | 1.00 | 18.77 |
| ATOM | 2087 | N | HIS | A | 278 | 13.225 | 12.224 | 26.522 | 1.00 | 20.21 |
| ATOM | 2088 | CA | HIS | A | 278 | 12.220 | 12.729 | 25.587 | 1.00 | 20.77 |
| ATOM | 2089 | CB | HIS | A | 278 | 12.888 | 13.637 | 24.538 | 1.00 | 19.46 |
| ATOM | 2090 | CG | HIS | A | 278 | 11.915 | 14.109 | 23.501 | 1.00 | 27.73 |
| ATOM | 2091 | ND1 | HIS | A | 278 | 11.599 | 13.361 | 22.387 | 1.00 | 25.43 |
| ATOM | 2092 | CE1 | HIS | A | 278 | 10.714 | 14.023 | 21.661 | 1.00 | 26.78 |
| ATOM | 2093 | NE2 | HIS | A | 278 | 10.441 | 15.169 | 22.258 | 1.00 | 30.40 |
| ATOM | 2094 | CD2 | HIS | A | 278 | 11.180 | 15.243 | 23.412 | 1.00 | 29.32 |
| ATOM | 2095 | C | HIS | A | 278 | 11.505 | 11.529 | 24.958 | 1.00 | 17.28 |
| ATOM | 2096 | O | HIS | A | 278 | 10.282 | 11.474 | 24.934 | 1.00 | 19.03 |
| ATOM | 2097 | N | ASP | A | 279 | 12.283 | 10.576 | 24.448 | 1.00 | 19.78 |
| ATOM | 2098 | CA | ASP | A | 279 | 11.736 | 9.408 | 23.766 | 1.00 | 23.11 |
| ATOM | 2099 | CB | ASP | A | 279 | 12.830 | 8.508 | 23.192 | 1.00 | 31.32 |
| ATOM | 2100 | CG | ASP | A | 279 | 12.445 | 7.760 | 21.931 | 1.00 | 41.53 |
| ATOM | 2101 | OD1 | ASP | A | 279 | 11.649 | 8.288 | 21.124 | 1.00 | 44.27 |
| ATOM | 2102 | OD2 | ASP | A | 279 | 12.924 | 6.627 | 21.689 | 1.00 | 31.21 |
| ATOM | 2103 | C | ASP | A | 279 | 10.860 | 8.613 | 24.733 | 1.00 | 16.22 |
| ATOM | 2104 | O | ASP | A | 279 | 9.794 | 8.139 | 24.359 | 1.00 | 17.27 |
| ATOM | 2105 | N | LEU | A | 280 | 11.327 | 8.486 | 25.974 | 1.00 | 18.29 |
| ATOM | 2106 | CA | LEU | A | 280 | 10.517 | 7.786 | 26.974 | 1.00 | 19.74 |
| ATOM | 2107 | CB | LEU | A | 280 | 11.270 | 7.751 | 28.301 | 1.00 | 15.55 |
| ATOM | 2108 | CG | LEU | A | 280 | 12.388 | 6.723 | 28.463 | 1.00 | 26.78 |
| ATOM | 2109 | CD1 | LEU | A | 280 | 13.190 | 6.944 | 29.734 | 1.00 | 23.32 |
| ATOM | 2110 | CD2 | LEU | A | 280 | 11.836 | 5.303 | 28.501 | 1.00 | 32.51 |
| ATOM | 2111 | C | LEU | A | 280 | 9.162 | 8.456 | 27.109 | 1.00 | 19.74 |
| ATOM | 2112 | O | LEU | A | 280 | 8.100 | 7.831 | 27.099 | 1.00 | 15.47 |
| ATOM | 2113 | N | ARG | A | 281 | 9.152 | 9.785 | 27.240 | 1.00 | 17.32 |
| ATOM | 2114 | CA | ARG | A | 281 | 7.931 | 10.535 | 27.402 | 1.00 | 18.47 |
| ATOM | 2115 | CB | ARG | A | 281 | 8.195 | 12.047 | 27.522 | 1.00 | 21.28 |
| ATOM | 2116 | CG | ARG | A | 281 | 9.115 | 12.436 | 28.661 | 1.00 | 29.75 |
| ATOM | 2117 | CD | ARG | A | 281 | 8.318 | 12.580 | 29.951 | 1.00 | 34.02 |
| ATOM | 2118 | NE | ARG | A | 281 | 9.199 | 13.015 | 31.026 | 1.00 | 37.36 |
| ATOM | 2119 | CZ | ARG | A | 281 | 8.851 | 13.737 | 32.071 | 1.00 | 39.23 |
| ATOM | 2120 | NH1 | ARG | A | 281 | 7.595 | 14.129 | 32.206 | 1.00 | 60.17 |
| ATOM | 2121 | NH2 | ARG | A | 281 | 9.769 | 14.055 | 32.972 | 1.00 | 36.32 |
| ATOM | 2122 | C | ARG | A | 281 | 6.987 | 10.381 | 26.220 | 1.00 | 16.87 |
| ATOM | 2123 | O | ARG | A | 281 | 5.785 | 10.568 | 26.424 | 1.00 | 18.99 |
| ATOM | 2124 | N | LEU | A | 282 | 7.549 | 10.111 | 25.034 | 1.00 | 15.85 |
| ATOM | 2125 | CA | LEU | A | 282 | 6.620 | 9.977 | 23.899 | 1.00 | 17.78 |
| ATOM | 2126 | CB | LEU | A | 282 | 7.338 | 9.907 | 22.559 | 1.00 | 21.15 |
| ATOM | 2127 | CG | LEU | A | 282 | 8.060 | 11.126 | 21.997 | 1.00 | 32.88 |
| ATOM | 2128 | CD1 | LEU | A | 282 | 8.732 | 10.767 | 20.673 | 1.00 | 28.74 |
| ATOM | 2129 | CD2 | LEU | A | 282 | 7.133 | 12.311 | 21.783 | 1.00 | 24.88 |
| ATOM | 2130 | C | LEU | A | 282 | 5.763 | 8.721 | 24.078 | 1.00 | 18.42 |
| ATOM | 2131 | O | LEU | A | 282 | 4.658 | 8.631 | 23.532 | 1.00 | 21.04 |

FIGURE 143

| | | | | | | | | | |
|---|---|---|---|---|---|---|---|---|---|
| ATOM | 2132 | N   | HIS | A | 283 | 6.263  | 7.739  | 24.823 | 1.00 16.75 |
| ATOM | 2133 | CA  | HIS | A | 283 | 5.574  | 6.450  | 24.905 | 1.00 17.03 |
| ATOM | 2134 | CB  | HIS | A | 283 | 6.621  | 5.350  | 24.644 | 1.00 17.45 |
| ATOM | 2135 | CG  | HIS | A | 283 | 7.133  | 5.464  | 23.234 | 1.00 19.75 |
| ATOM | 2136 | ND1 | HIS | A | 283 | 6.502  | 4.868  | 22.169 | 1.00 24.70 |
| ATOM | 2137 | CE1 | HIS | A | 283 | 7.156  | 5.149  | 21.056 | 1.00 24.61 |
| ATOM | 2138 | NE2 | HIS | A | 283 | 8.191  | 5.913  | 21.353 | 1.00 23.33 |
| ATOM | 2139 | CD2 | HIS | A | 283 | 8.186  | 6.126  | 22.714 | 1.00 25.41 |
| ATOM | 2140 | C   | HIS | A | 283 | 4.831  | 6.199  | 26.209 | 1.00 17.38 |
| ATOM | 2141 | O   | HIS | A | 283 | 3.932  | 5.336  | 26.249 | 1.00 12.95 |
| ATOM | 2142 | N   | ARG | A | 284 | 5.125  | 6.923  | 27.282 | 1.00 12.46 |
| ATOM | 2143 | CA  | ARG | A | 284 | 4.367  | 6.792  | 28.527 | 1.00 12.55 |
| ATOM | 2144 | CB  | ARG | A | 284 | 4.869  | 5.622  | 29.366 | 1.00 13.17 |
| ATOM | 2145 | CG  | ARG | A | 284 | 4.072  | 5.322  | 30.633 | 1.00 10.87 |
| ATOM | 2146 | CD  | ARG | A | 284 | 4.464  | 3.909  | 31.097 | 1.00 17.92 |
| ATOM | 2147 | NE  | ARG | A | 284 | 3.933  | 3.546  | 32.404 | 1.00 11.92 |
| ATOM | 2148 | CZ  | ARG | A | 284 | 2.752  | 2.965  | 32.601 | 1.00 15.19 |
| ATOM | 2149 | NH1 | ARG | A | 284 | 1.953  | 2.675  | 31.577 | 1.00 12.14 |
| ATOM | 2150 | NH2 | ARG | A | 284 | 2.348  | 2.666  | 33.837 | 1.00 11.55 |
| ATOM | 2151 | C   | ARG | A | 284 | 4.496  | 8.059  | 29.372 | 1.00 12.80 |
| ATOM | 2152 | O   | ARG | A | 284 | 5.555  | 8.665  | 29.370 | 1.00 13.52 |
| ATOM | 2153 | N   | VAL | A | 285 | 3.435  | 8.425  | 30.059 | 1.00 17.40 |
| ATOM | 2154 | CA  | VAL | A | 285 | 3.419  | 9.665  | 30.847 | 1.00 15.70 |
| ATOM | 2155 | CB  | VAL | A | 285 | 1.998  | 9.930  | 31.379 | 1.00 18.07 |
| ATOM | 2156 | CG1 | VAL | A | 285 | 1.657  | 8.972  | 32.521 | 1.00 14.53 |
| ATOM | 2157 | CG2 | VAL | A | 285 | 1.848  | 11.380 | 31.837 | 1.00 21.60 |
| ATOM | 2158 | C   | VAL | A | 285 | 4.429  | 9.640  | 31.982 | 1.00 24.82 |
| ATOM | 2159 | O   | VAL | A | 285 | 4.767  | 8.581  | 32.511 | 1.00 18.02 |
| ATOM | 2160 | N   | HIS | A | 286 | 4.926  | 10.823 | 32.336 | 1.00 22.81 |
| ATOM | 2161 | CA  | HIS | A | 286 | 5.818  | 11.084 | 33.440 | 1.00 20.84 |
| ATOM | 2162 | CB  | HIS | A | 286 | 5.069  | 10.872 | 34.768 | 1.00 24.11 |
| ATOM | 2163 | CG  | HIS | A | 286 | 3.818  | 11.663 | 34.965 | 1.00 28.34 |
| ATOM | 2164 | ND1 | HIS | A | 286 | 3.763  | 13.039 | 34.936 | 1.00 28.84 |
| ATOM | 2165 | CE1 | HIS | A | 286 | 2.526  | 13.448 | 35.147 | 1.00 28.83 |
| ATOM | 2166 | NE2 | HIS | A | 286 | 1.766  | 12.380 | 35.317 | 1.00 32.75 |
| ATOM | 2167 | CD2 | HIS | A | 286 | 2.548  | 11.255 | 35.216 | 1.00 26.94 |
| ATOM | 2168 | C   | HIS | A | 286 | 7.084  | 10.232 | 33.510 | 1.00 21.64 |
| ATOM | 2169 | O   | HIS | A | 286 | 7.661  | 10.218 | 34.615 | 1.00 26.93 |
| ATOM | 2170 | N   | MET | A | 287 | 7.550  | 9.548  | 32.468 | 1.00 13.96 |
| ATOM | 2171 | CA  | MET | A | 287 | 8.792  | 8.783  | 32.560 | 1.00 13.56 |
| ATOM | 2172 | CB  | MET | A | 287 | 9.223  | 8.171  | 31.264 | 1.00 16.67 |
| ATOM | 2173 | CG  | MET | A | 287 | 8.741  | 6.954  | 30.564 | 1.00 32.18 |
| ATOM | 2174 | SD  | MET | A | 287 | 8.371  | 5.520  | 31.623 | 1.00 31.45 |
| ATOM | 2175 | CE  | MET | A | 287 | 6.873  | 6.119  | 32.287 | 1.00 12.41 |
| ATOM | 2176 | C   | MET | A | 287 | 9.919  | 9.708  | 33.070 | 1.00 31.47 |
| ATOM | 2177 | O   | MET | A | 287 | 10.136 | 10.813 | 32.556 | 1.00 27.35 |
| ATOM | 2178 | N   | VAL | A | 288 | 10.581 | 9.213  | 34.107 | 1.00 19.43 |
| ATOM | 2179 | CA  | VAL | A | 288 | 11.539 | 9.968  | 34.906 | 1.00 20.51 |
| ATOM | 2180 | CB  | VAL | A | 288 | 12.719 | 10.500 | 34.089 | 1.00 18.73 |
| ATOM | 2181 | CG1 | VAL | A | 288 | 13.598 | 11.361 | 34.989 | 1.00 27.60 |
| ATOM | 2182 | CG2 | VAL | A | 288 | 13.506 | 9.344  | 33.475 | 1.00 16.71 |
| ATOM | 2183 | C   | VAL | A | 288 | 10.780 | 11.107 | 35.584 | 1.00 24.09 |

FIGURE 144

| ATOM | 2184 | O   | VAL | A | 288 | 10.586 | 12.174 | 35.013 | 1.00 | 30.01 |
|------|------|-----|-----|---|-----|--------|--------|--------|------|-------|
| ATOM | 2185 | N   | GLN | A | 289 | 10.325 | 10.820 | 36.799 | 1.00 | 20.54 |
| ATOM | 2186 | CA  | GLN | A | 289 | 9.237  | 11.559 | 37.407 | 1.00 | 28.07 |
| ATOM | 2187 | CB  | GLN | A | 289 | 8.381  | 10.595 | 38.239 | 1.00 | 31.79 |
| ATOM | 2188 | CG  | GLN | A | 289 | 7.078  | 11.185 | 38.754 | 1.00 | 34.58 |
| ATOM | 2189 | CD  | GLN | A | 289 | 7.101  | 11.363 | 40.266 | 1.00 | 35.98 |
| ATOM | 2190 | OE1 | GLN | A | 289 | 7.791  | 10.623 | 40.972 | 1.00 | 26.51 |
| ATOM | 2191 | NE2 | GLN | A | 289 | 6.346  | 12.347 | 40.753 | 1.00 | 36.09 |
| ATOM | 2192 | C   | GLN | A | 289 | 9.689  | 12.720 | 38.278 | 1.00 | 33.05 |
| ATOM | 2193 | O   | GLN | A | 289 | 8.858  | 13.599 | 38.525 | 1.00 | 35.10 |
| ATOM | 2194 | N   | THR | A | 290 | 10.936 | 12.736 | 38.736 | 1.00 | 30.88 |
| ATOM | 2195 | CA  | THR | A | 290 | 11.372 | 13.920 | 39.491 | 1.00 | 28.02 |
| ATOM | 2196 | CB  | THR | A | 290 | 11.590 | 13.611 | 40.984 | 1.00 | 29.29 |
| ATOM | 2197 | OG1 | THR | A | 290 | 12.661 | 12.677 | 41.160 | 1.00 | 35.40 |
| ATOM | 2198 | CG2 | THR | A | 290 | 10.331 | 12.980 | 41.563 | 1.00 | 24.35 |
| ATOM | 2199 | C   | THR | A | 290 | 12.639 | 14.518 | 38.909 | 1.00 | 23.50 |
| ATOM | 2200 | O   | THR | A | 290 | 13.496 | 13.903 | 38.287 | 1.00 | 21.72 |
| ATOM | 2201 | N   | GLU | A | 291 | 12.806 | 15.830 | 39.108 | 1.00 | 33.06 |
| ATOM | 2202 | CA  | GLU | A | 291 | 13.996 | 16.481 | 38.534 | 1.00 | 26.38 |
| ATOM | 2203 | CB  | GLU | A | 291 | 13.849 | 17.986 | 38.728 | 1.00 | 36.13 |
| ATOM | 2204 | CG  | GLU | A | 291 | 14.794 | 18.656 | 39.697 | 1.00 | 47.55 |
| ATOM | 2205 | CD  | GLU | A | 291 | 15.133 | 20.079 | 39.279 | 1.00 | 50.62 |
| ATOM | 2206 | OE1 | GLU | A | 291 | 16.237 | 20.541 | 39.645 | 1.00 | 58.58 |
| ATOM | 2207 | OE2 | GLU | A | 291 | 14.306 | 20.719 | 38.593 | 1.00 | 33.56 |
| ATOM | 2208 | C   | GLU | A | 291 | 15.255 | 15.901 | 39.151 | 1.00 | 20.43 |
| ATOM | 2209 | O   | GLU | A | 291 | 16.325 | 15.881 | 38.543 | 1.00 | 24.26 |
| ATOM | 2210 | N   | CYS | A | 292 | 15.139 | 15.407 | 40.386 | 1.00 | 20.50 |
| ATOM | 2211 | CA  | CYS | A | 292 | 16.308 | 14.825 | 41.039 | 1.00 | 19.18 |
| ATOM | 2212 | CB  | CYS | A | 292 | 16.040 | 14.535 | 42.517 | 1.00 | 31.41 |
| ATOM | 2213 | SG  | CYS | A | 292 | 17.552 | 14.159 | 43.444 | 1.00 |101.20 |
| ATOM | 2214 | C   | CYS | A | 292 | 16.721 | 13.542 | 40.335 | 1.00 | 20.87 |
| ATOM | 2215 | O   | CYS | A | 292 | 17.899 | 13.219 | 40.202 | 1.00 | 24.99 |
| ATOM | 2216 | N   | GLN | A | 293 | 15.718 | 12.795 | 39.862 | 1.00 | 26.29 |
| ATOM | 2217 | CA  | GLN | A | 293 | 16.062 | 11.613 | 39.055 | 1.00 | 22.01 |
| ATOM | 2218 | CB  | GLN | A | 293 | 14.785 | 10.827 | 38.720 | 1.00 | 22.44 |
| ATOM | 2219 | CG  | GLN | A | 293 | 14.242 | 10.156 | 39.972 | 1.00 | 21.37 |
| ATOM | 2220 | CD  | GLN | A | 293 | 12.831 | 9.628  | 39.838 | 1.00 | 24.27 |
| ATOM | 2221 | OE1 | GLN | A | 293 | 12.134 | 9.855  | 38.848 | 1.00 | 23.20 |
| ATOM | 2222 | NE2 | GLN | A | 293 | 12.439 | 8.904  | 40.884 | 1.00 | 18.53 |
| ATOM | 2223 | C   | GLN | A | 293 | 16.816 | 12.029 | 37.805 | 1.00 | 18.20 |
| ATOM | 2224 | O   | GLN | A | 293 | 17.797 | 11.408 | 37.389 | 1.00 | 21.10 |
| ATOM | 2225 | N   | TYR | A | 294 | 16.355 | 13.121 | 37.196 | 1.00 | 20.29 |
| ATOM | 2226 | CA  | TYR | A | 294 | 17.034 | 13.649 | 36.006 | 1.00 | 17.93 |
| ATOM | 2227 | CB  | TYR | A | 294 | 16.239 | 14.824 | 35.456 | 1.00 | 20.72 |
| ATOM | 2228 | CG  | TYR | A | 294 | 16.600 | 15.299 | 34.066 | 1.00 | 22.13 |
| ATOM | 2229 | CD1 | TYR | A | 294 | 16.441 | 14.487 | 32.949 | 1.00 | 22.03 |
| ATOM | 2230 | CE1 | TYR | A | 294 | 16.767 | 14.926 | 31.680 | 1.00 | 27.01 |
| ATOM | 2231 | CZ  | TYR | A | 294 | 17.259 | 16.212 | 31.527 | 1.00 | 31.26 |
| ATOM | 2232 | OH  | TYR | A | 294 | 17.590 | 16.669 | 30.275 | 1.00 | 31.95 |
| ATOM | 2233 | CE2 | TYR | A | 294 | 17.426 | 17.043 | 32.614 | 1.00 | 24.60 |
| ATOM | 2234 | CD2 | TYR | A | 294 | 17.093 | 16.581 | 33.871 | 1.00 | 24.21 |
| ATOM | 2235 | C   | TYR | A | 294 | 18.457 | 14.063 | 36.353 | 1.00 | 26.00 |

FIGURE 145

| | | | | | | | | | |
|---|---|---|---|---|---|---|---|---|---|
| ATOM | 2236 | O | TYR | A | 294 | 19.401 | 13.726 | 35.643 | 1.00 24.45 |
| ATOM | 2237 | N | VAL | A | 295 | 18.626 | 14.790 | 37.467 | 1.00 27.38 |
| ATOM | 2238 | CA | VAL | A | 295 | 19.981 | 15.130 | 37.908 | 1.00 26.38 |
| ATOM | 2239 | CB | VAL | A | 295 | 19.989 | 15.931 | 39.225 | 1.00 21.43 |
| ATOM | 2240 | CG1 | VAL | A | 295 | 21.402 | 15.984 | 39.784 | 1.00 28.13 |
| ATOM | 2241 | CG2 | VAL | A | 295 | 19.428 | 17.326 | 39.000 | 1.00 34.94 |
| ATOM | 2242 | C | VAL | A | 295 | 20.839 | 13.888 | 38.136 | 1.00 21.34 |
| ATOM | 2243 | O | VAL | A | 295 | 21.991 | 13.837 | 37.730 | 1.00 23.60 |
| ATOM | 2244 | N | TYR | A | 296 | 20.296 | 12.876 | 38.792 | 1.00 22.55 |
| ATOM | 2245 | CA | TYR | A | 296 | 20.976 | 11.609 | 39.039 | 1.00 27.13 |
| ATOM | 2246 | CB | TYR | A | 296 | 20.011 | 10.665 | 39.773 | 1.00 19.15 |
| ATOM | 2247 | CG | TYR | A | 296 | 20.587 | 9.329 | 40.167 | 1.00 22.85 |
| ATOM | 2248 | CD1 | TYR | A | 296 | 21.493 | 9.191 | 41.211 | 1.00 21.56 |
| ATOM | 2249 | CE1 | TYR | A | 296 | 22.022 | 7.967 | 41.576 | 1.00 20.08 |
| ATOM | 2250 | CZ | TYR | A | 296 | 21.628 | 6.841 | 40.876 | 1.00 22.87 |
| ATOM | 2251 | OH | TYR | A | 296 | 22.136 | 5.601 | 41.213 | 1.00 22.11 |
| ATOM | 2252 | CE2 | TYR | A | 296 | 20.734 | 6.954 | 39.842 | 1.00 23.68 |
| ATOM | 2253 | CD2 | TYR | A | 296 | 20.211 | 8.179 | 39.483 | 1.00 25.13 |
| ATOM | 2254 | C | TYR | A | 296 | 21.495 | 10.947 | 37.771 | 1.00 22.49 |
| ATOM | 2255 | O | TYR | A | 296 | 22.607 | 10.406 | 37.752 | 1.00 24.52 |
| ATOM | 2256 | N | LEU | A | 297 | 20.734 | 10.960 | 36.675 | 1.00 24.50 |
| ATOM | 2257 | CA | LEU | A | 297 | 21.265 | 10.390 | 35.437 | 1.00 19.36 |
| ATOM | 2258 | CB | LEU | A | 297 | 20.278 | 10.510 | 34.275 | 1.00 22.49 |
| ATOM | 2259 | CG | LEU | A | 297 | 18.987 | 9.697 | 34.406 | 1.00 21.19 |
| ATOM | 2260 | CD1 | LEU | A | 297 | 17.931 | 10.172 | 33.424 | 1.00 18.99 |
| ATOM | 2261 | CD2 | LEU | A | 297 | 19.330 | 8.224 | 34.235 | 1.00 22.58 |
| ATOM | 2262 | C | LEU | A | 297 | 22.563 | 11.092 | 35.039 | 1.00 22.83 |
| ATOM | 2263 | O | LEU | A | 297 | 23.545 | 10.455 | 34.672 | 1.00 26.28 |
| ATOM | 2264 | N | HIS | A | 298 | 22.539 | 12.432 | 35.118 | 1.00 27.23 |
| ATOM | 2265 | CA | HIS | A | 298 | 23.760 | 13.165 | 34.773 | 1.00 26.75 |
| ATOM | 2266 | CB | HIS | A | 298 | 23.526 | 14.672 | 34.793 | 1.00 25.81 |
| ATOM | 2267 | CG | HIS | A | 298 | 22.724 | 15.186 | 33.644 | 1.00 24.47 |
| ATOM | 2268 | ND1 | HIS | A | 298 | 21.358 | 15.061 | 33.562 | 1.00 26.77 |
| ATOM | 2269 | CE1 | HIS | A | 298 | 20.938 | 15.617 | 32.434 | 1.00 31.41 |
| ATOM | 2270 | NE2 | HIS | A | 298 | 21.982 | 16.099 | 31.780 | 1.00 22.95 |
| ATOM | 2271 | CD2 | HIS | A | 298 | 23.105 | 15.841 | 32.519 | 1.00 26.28 |
| ATOM | 2272 | C | HIS | A | 298 | 24.877 | 12.814 | 35.749 | 1.00 24.86 |
| ATOM | 2273 | O | HIS | A | 298 | 26.009 | 12.584 | 35.342 | 1.00 32.20 |
| ATOM | 2274 | N | GLN | A | 299 | 24.555 | 12.775 | 37.044 | 1.00 20.61 |
| ATOM | 2275 | CA | GLN | A | 299 | 25.600 | 12.405 | 38.005 | 1.00 27.30 |
| ATOM | 2276 | CB | GLN | A | 299 | 25.077 | 12.420 | 39.440 | 1.00 29.89 |
| ATOM | 2277 | CG | GLN | A | 299 | 24.644 | 13.789 | 39.945 | 1.00 29.83 |
| ATOM | 2278 | CD | GLN | A | 299 | 24.030 | 13.768 | 41.327 | 1.00 39.67 |
| ATOM | 2279 | OE1 | GLN | A | 299 | 23.233 | 12.894 | 41.678 | 1.00 50.54 |
| ATOM | 2280 | NE2 | GLN | A | 299 | 24.382 | 14.755 | 42.148 | 1.00 42.66 |
| ATOM | 2281 | C | GLN | A | 299 | 26.174 | 11.033 | 37.665 | 1.00 30.62 |
| ATOM | 2282 | O | GLN | A | 299 | 27.380 | 10.808 | 37.781 | 1.00 24.65 |
| ATOM | 2283 | N | CYS | A | 300 | 25.311 | 10.110 | 37.244 | 1.00 32.98 |
| ATOM | 2284 | CA | CYS | A | 300 | 25.750 | 8.773 | 36.865 | 1.00 31.19 |
| ATOM | 2285 | CB | CYS | A | 300 | 24.539 | 7.921 | 36.453 | 1.00 27.79 |
| ATOM | 2286 | SG | CYS | A | 300 | 23.647 | 7.209 | 37.864 | 1.00 24.58 |
| ATOM | 2287 | C | CYS | A | 300 | 26.765 | 8.828 | 35.727 | 1.00 34.76 |

FIGURE 146

```
ATOM   2288  O    CYS A 300      27.822    8.196   35.729  1.00 23.29
ATOM   2289  N    VAL A 301      26.420    9.615   34.708  1.00 32.86
ATOM   2290  CA   VAL A 301      27.302    9.758   33.561  1.00 33.82
ATOM   2291  CB   VAL A 301      26.630   10.582   32.444  1.00 31.77
ATOM   2292  CG1  VAL A 301      27.618   10.894   31.330  1.00 32.91
ATOM   2293  CG2  VAL A 301      25.418    9.821   31.923  1.00 36.31
ATOM   2294  C    VAL A 301      28.618   10.429   33.941  1.00 30.73
ATOM   2295  O    VAL A 301      29.692   10.022   33.501  1.00 35.82
ATOM   2296  N    ARG A 302      28.541   11.468   34.763  1.00 31.17
ATOM   2297  CA   ARG A 302      29.790   12.172   35.086  1.00 30.26
ATOM   2298  CB   ARG A 302      29.484   13.422   35.894  1.00 32.62
ATOM   2299  CG   ARG A 302      30.689   14.073   36.564  1.00 30.76
ATOM   2300  CD   ARG A 302      30.203   14.793   37.826  1.00 35.56
ATOM   2301  NE   ARG A 302      29.679   13.851   38.796  1.00 36.12
ATOM   2302  CZ   ARG A 302      28.999   14.106   39.898  1.00 43.20
ATOM   2303  NH1  ARG A 302      28.702   15.351   40.255  1.00 58.84
ATOM   2304  NH2  ARG A 302      28.601   13.098   40.671  1.00 37.42
ATOM   2305  C    ARG A 302      30.720   11.213   35.811  1.00 38.00
ATOM   2306  O    ARG A 302      31.934   11.187   35.602  1.00 46.79
ATOM   2307  N    ASP A 303      30.137   10.376   36.668  1.00 34.78
ATOM   2308  CA   ASP A 303      30.980    9.431   37.404  1.00 31.64
ATOM   2309  CB   ASP A 303      30.186    8.844   38.579  1.00 32.29
ATOM   2310  CG   ASP A 303      29.766    9.934   39.553  1.00 41.64
ATOM   2311  OD1  ASP A 303      30.143   11.104   39.315  1.00 48.79
ATOM   2312  OD2  ASP A 303      29.060    9.645   40.542  1.00 39.40
ATOM   2313  C    ASP A 303      31.529    8.359   36.484  1.00 33.95
ATOM   2314  O    ASP A 303      32.681    7.925   36.612  1.00 41.56
ATOM   2315  N    VAL A 304      30.755    7.875   35.510  1.00 31.21
ATOM   2316  CA   VAL A 304      31.349    6.840   34.658  1.00 39.08
ATOM   2317  CB   VAL A 304      30.371    6.167   33.685  1.00 44.47
ATOM   2318  CG1  VAL A 304      31.089    5.084   32.889  1.00 27.60
ATOM   2319  CG2  VAL A 304      29.173    5.541   34.381  1.00 27.78
ATOM   2320  C    VAL A 304      32.485    7.483   33.859  1.00 39.60
ATOM   2321  O    VAL A 304      33.515    6.865   33.615  1.00 37.42
ATOM   2322  N    LEU A 305      32.257    8.736   33.484  1.00 36.24
ATOM   2323  CA   LEU A 305      33.241    9.491   32.714  1.00 42.98
ATOM   2324  CB   LEU A 305      32.620   10.746   32.093  1.00 39.34
ATOM   2325  CG   LEU A 305      31.658   10.512   30.929  1.00 34.01
ATOM   2326  CD1  LEU A 305      31.183   11.828   30.327  1.00 28.76
ATOM   2327  CD2  LEU A 305      32.315    9.625   29.876  1.00 34.10
ATOM   2328  C    LEU A 305      34.425    9.863   33.598  1.00 42.82
ATOM   2329  O    LEU A 305      35.578    9.705   33.198  1.00 54.32
ATOM   2330  N    ARG A 306      34.150   10.353   34.805  1.00 41.87
ATOM   2331  CA   ARG A 306      35.253   10.741   35.681  1.00 51.42
ATOM   2332  CB   ARG A 306      34.725   11.361   36.979  1.00 50.76
ATOM   2333  CG   ARG A 306      34.163   12.761   36.809  1.00 57.18
ATOM   2334  CD   ARG A 306      33.547   13.297   38.093  1.00 63.89
ATOM   2335  NE   ARG A 306      33.871   14.701   38.302  1.00 65.68
ATOM   2336  CZ   ARG A 306      33.491   15.494   39.287  1.00 66.42
ATOM   2337  NH1  ARG A 306      32.710   15.080   40.276  1.00 39.94
ATOM   2338  NH2  ARG A 306      33.906   16.759   39.290  1.00 95.50
ATOM   2339  C    ARG A 306      36.161    9.553   35.988  1.00 65.39
```

FIGURE 147

| ATOM | 2340 | O | ARG | A | 306 | 37.371 | 9.710 | 36.183 | 1.00 | 79.48 |
| --- | --- | --- | --- | --- | --- | --- | --- | --- | --- | --- |
| ATOM | 2341 | N | ALA | A | 307 | 35.593 | 8.350 | 36.039 | 1.00 | 63.13 |
| ATOM | 2342 | CA | ALA | A | 307 | 36.358 | 7.181 | 36.463 | 1.00 | 59.88 |
| ATOM | 2343 | CB | ALA | A | 307 | 35.424 | 6.123 | 37.032 | 1.00 | 62.57 |
| ATOM | 2344 | C | ALA | A | 307 | 37.190 | 6.603 | 35.327 | 1.00 | 63.48 |
| ATOM | 2345 | O | ALA | A | 307 | 38.185 | 5.922 | 35.576 | 1.00 | 71.07 |
| ATOM | 2346 | N | ARG | A | 308 | 36.778 | 6.878 | 34.095 | 1.00 | 66.80 |
| ATOM | 2347 | CA | ARG | A | 308 | 37.460 | 6.357 | 32.916 | 1.00 | 63.53 |
| ATOM | 2348 | CB | ARG | A | 308 | 36.431 | 5.843 | 31.910 | 1.00 | 64.58 |
| ATOM | 2349 | CG | ARG | A | 308 | 35.909 | 6.905 | 30.956 | 1.00 | 73.99 |
| ATOM | 2350 | CD | ARG | A | 308 | 34.390 | 6.946 | 30.959 | 1.00 | 81.85 |
| ATOM | 2351 | NE | ARG | A | 308 | 33.814 | 5.939 | 30.070 | 1.00 | 85.42 |
| ATOM | 2352 | CZ | ARG | A | 308 | 33.523 | 6.167 | 28.794 | 1.00 | 82.34 |
| ATOM | 2353 | NH1 | ARG | A | 308 | 33.757 | 7.365 | 28.275 | 1.00 | 72.00 |
| ATOM | 2354 | NH2 | ARG | A | 308 | 33.001 | 5.198 | 28.053 | 1.00 | 74.84 |
| ATOM | 2355 | C | ARG | A | 308 | 38.356 | 7.408 | 32.272 | 1.00 | 66.32 |
| ATOM | 2356 | O | ARG | A | 308 | 39.461 | 7.117 | 31.813 | 1.00 | 55.04 |
| ATOM | 2357 | N | THR | B | 20 | 44.023 | 9.553 | 52.894 | 1.00 | 44.19 |
| ATOM | 2358 | CA | THR | B | 20 | 43.083 | 8.735 | 53.658 | 1.00 | 52.64 |
| ATOM | 2359 | CB | THR | B | 20 | 43.790 | 7.980 | 54.795 | 1.00 | 59.51 |
| ATOM | 2360 | OG1 | THR | B | 20 | 45.173 | 7.808 | 54.450 | 1.00 | 74.31 |
| ATOM | 2361 | CG2 | THR | B | 20 | 43.208 | 6.590 | 54.985 | 1.00 | 67.07 |
| ATOM | 2362 | C | THR | B | 20 | 41.947 | 9.580 | 54.229 | 1.00 | 46.00 |
| ATOM | 2363 | O | THR | B | 20 | 42.162 | 10.580 | 54.911 | 1.00 | 47.42 |
| ATOM | 2364 | N | SER | B | 21 | 40.725 | 9.158 | 53.926 | 1.00 | 41.46 |
| ATOM | 2365 | CA | SER | B | 21 | 39.496 | 9.819 | 54.320 | 1.00 | 39.05 |
| ATOM | 2366 | CB | SER | B | 21 | 39.040 | 10.796 | 53.232 | 1.00 | 49.38 |
| ATOM | 2367 | OG | SER | B | 21 | 37.654 | 10.651 | 52.968 | 1.00 | 64.42 |
| ATOM | 2368 | C | SER | B | 21 | 38.381 | 8.816 | 54.580 | 1.00 | 45.97 |
| ATOM | 2369 | O | SER | B | 21 | 38.392 | 7.690 | 54.078 | 1.00 | 58.15 |
| ATOM | 2370 | N | CYS | B | 22 | 37.384 | 9.218 | 55.363 | 1.00 | 49.85 |
| ATOM | 2371 | CA | CYS | B | 22 | 36.237 | 8.334 | 55.572 | 1.00 | 50.77 |
| ATOM | 2372 | CB | CYS | B | 22 | 36.423 | 7.465 | 56.816 | 1.00 | 55.65 |
| ATOM | 2373 | SG | CYS | B | 22 | 35.067 | 6.307 | 57.123 | 1.00 | 88.47 |
| ATOM | 2374 | C | CYS | B | 22 | 34.951 | 9.143 | 55.677 | 1.00 | 45.29 |
| ATOM | 2375 | O | CYS | B | 22 | 34.411 | 9.331 | 56.767 | 1.00 | 58.34 |
| ATOM | 2376 | N | PRO | B | 23 | 34.467 | 9.632 | 54.543 | 1.00 | 39.55 |
| ATOM | 2377 | CA | PRO | B | 23 | 33.212 | 10.389 | 54.528 | 1.00 | 41.51 |
| ATOM | 2378 | CB | PRO | B | 23 | 33.049 | 10.758 | 53.050 | 1.00 | 40.09 |
| ATOM | 2379 | CG | PRO | B | 23 | 34.441 | 10.713 | 52.503 | 1.00 | 41.78 |
| ATOM | 2380 | CD | PRO | B | 23 | 35.072 | 9.531 | 53.203 | 1.00 | 44.99 |
| ATOM | 2381 | C | PRO | B | 23 | 32.027 | 9.552 | 55.000 | 1.00 | 44.21 |
| ATOM | 2382 | O | PRO | B | 23 | 31.963 | 8.335 | 54.814 | 1.00 | 52.40 |
| ATOM | 2383 | N | ILE | B | 24 | 31.065 | 10.223 | 55.624 | 1.00 | 44.34 |
| ATOM | 2384 | CA | ILE | B | 24 | 29.827 | 9.587 | 56.044 | 1.00 | 48.20 |
| ATOM | 2385 | CB | ILE | B | 24 | 29.721 | 9.319 | 57.555 | 1.00 | 45.03 |
| ATOM | 2386 | CG1 | ILE | B | 24 | 31.043 | 9.095 | 58.282 | 1.00 | 44.77 |
| ATOM | 2387 | CD1 | ILE | B | 24 | 31.305 | 10.113 | 59.373 | 1.00 | 61.25 |
| ATOM | 2388 | CG2 | ILE | B | 24 | 28.778 | 8.151 | 57.813 | 1.00 | 56.04 |
| ATOM | 2389 | C | ILE | B | 24 | 28.646 | 10.483 | 55.663 | 1.00 | 48.34 |
| ATOM | 2390 | O | ILE | B | 24 | 28.590 | 11.626 | 56.128 | 1.00 | 36.96 |
| ATOM | 2391 | N | LYS | B | 25 | 27.747 | 9.948 | 54.848 | 1.00 | 44.27 |

FIGURE 148

| ATOM | 2392 | CA | LYS | B | 25 | 26.540 | 10.698 | 54.492 | 1.00 | 52.98 |
|------|------|-----|-----|---|----|--------|--------|--------|------|-------|
| ATOM | 2393 | CB | LYS | B | 25 | 25.594 | 9.846 | 53.655 | 1.00 | 62.63 |
| ATOM | 2394 | CG | LYS | B | 25 | 25.908 | 9.737 | 52.176 | 1.00 | 62.43 |
| ATOM | 2395 | CD | LYS | B | 25 | 27.378 | 9.486 | 51.908 | 1.00 | 63.27 |
| ATOM | 2396 | CE | LYS | B | 25 | 27.772 | 8.047 | 52.197 | 1.00 | 62.30 |
| ATOM | 2397 | NZ | LYS | B | 25 | 29.243 | 7.842 | 52.072 | 1.00 | 60.67 |
| ATOM | 2398 | C | LYS | B | 25 | 25.859 | 11.181 | 55.772 | 1.00 | 48.94 |
| ATOM | 2399 | O | LYS | B | 25 | 25.679 | 10.387 | 56.698 | 1.00 | 46.18 |
| ATOM | 2400 | N | ILE | B | 26 | 25.523 | 12.466 | 55.828 | 1.00 | 51.90 |
| ATOM | 2401 | CA | ILE | B | 26 | 24.977 | 13.025 | 57.066 | 1.00 | 54.24 |
| ATOM | 2402 | CB | ILE | B | 26 | 24.660 | 14.523 | 56.951 | 1.00 | 63.05 |
| ATOM | 2403 | CG1 | ILE | B | 26 | 23.589 | 14.879 | 55.916 | 1.00 | 68.15 |
| ATOM | 2404 | CD1 | ILE | B | 26 | 22.545 | 15.837 | 56.460 | 1.00 | 71.59 |
| ATOM | 2405 | CG2 | ILE | B | 26 | 25.929 | 15.325 | 56.685 | 1.00 | 65.12 |
| ATOM | 2406 | C | ILE | B | 26 | 23.733 | 12.241 | 57.465 | 1.00 | 51.02 |
| ATOM | 2407 | O | ILE | B | 26 | 23.573 | 11.830 | 58.614 | 1.00 | 47.65 |
| ATOM | 2408 | N | ASN | B | 27 | 22.870 | 12.003 | 56.483 | 1.00 | 51.44 |
| ATOM | 2409 | CA | ASN | B | 27 | 21.666 | 11.219 | 56.721 | 1.00 | 61.45 |
| ATOM | 2410 | CB | ASN | B | 27 | 20.899 | 10.993 | 55.415 | 1.00 | 75.84 |
| ATOM | 2411 | CG | ASN | B | 27 | 20.870 | 12.209 | 54.511 | 1.00 | 85.31 |
| ATOM | 2412 | OD1 | ASN | B | 27 | 21.910 | 12.672 | 54.041 | 1.00 | 99.97 |
| ATOM | 2413 | ND2 | ASN | B | 27 | 19.672 | 12.729 | 54.262 | 1.00 | 93.77 |
| ATOM | 2414 | C | ASN | B | 27 | 21.985 | 9.885 | 57.379 | 1.00 | 55.35 |
| ATOM | 2415 | O | ASN | B | 27 | 21.135 | 9.336 | 58.089 | 1.00 | 88.25 |
| ATOM | 2416 | N | GLN | B | 28 | 23.176 | 9.311 | 57.195 | 1.00 | 48.45 |
| ATOM | 2417 | CA | GLN | B | 28 | 23.415 | 8.047 | 57.894 | 1.00 | 52.09 |
| ATOM | 2418 | CB | GLN | B | 28 | 24.024 | 6.974 | 56.990 | 1.00 | 57.63 |
| ATOM | 2419 | CG | GLN | B | 28 | 24.654 | 7.430 | 55.694 | 1.00 | 63.93 |
| ATOM | 2420 | CD | GLN | B | 28 | 24.174 | 6.638 | 54.490 | 1.00 | 71.84 |
| ATOM | 2421 | OE1 | GLN | B | 28 | 24.797 | 5.657 | 54.074 | 1.00 | 79.09 |
| ATOM | 2422 | NE2 | GLN | B | 28 | 23.051 | 7.067 | 53.920 | 1.00 | 63.99 |
| ATOM | 2423 | C | GLN | B | 28 | 24.321 | 8.227 | 59.103 | 1.00 | 48.62 |
| ATOM | 2424 | O | GLN | B | 28 | 24.763 | 7.214 | 59.654 | 1.00 | 48.29 |
| ATOM | 2425 | N | PHE | B | 29 | 24.617 | 9.452 | 59.529 | 1.00 | 55.12 |
| ATOM | 2426 | CA | PHE | B | 29 | 25.569 | 9.586 | 60.626 | 1.00 | 55.39 |
| ATOM | 2427 | CB | PHE | B | 29 | 25.852 | 11.055 | 61.000 | 1.00 | 55.09 |
| ATOM | 2428 | CG | PHE | B | 29 | 27.126 | 11.084 | 61.852 | 1.00 | 51.70 |
| ATOM | 2429 | CD1 | PHE | B | 29 | 28.363 | 11.038 | 61.233 | 1.00 | 54.80 |
| ATOM | 2430 | CE1 | PHE | B | 29 | 29.521 | 11.046 | 61.984 | 1.00 | 57.30 |
| ATOM | 2431 | CZ | PHE | B | 29 | 29.458 | 11.100 | 63.365 | 1.00 | 54.61 |
| ATOM | 2432 | CE2 | PHE | B | 29 | 28.227 | 11.150 | 63.988 | 1.00 | 44.82 |
| ATOM | 2433 | CD2 | PHE | B | 29 | 27.071 | 11.145 | 63.230 | 1.00 | 41.09 |
| ATOM | 2434 | C | PHE | B | 29 | 25.123 | 8.850 | 61.890 | 1.00 | 57.59 |
| ATOM | 2435 | O | PHE | B | 29 | 25.964 | 8.281 | 62.594 | 1.00 | 47.92 |
| ATOM | 2436 | N | GLU | B | 30 | 23.828 | 8.867 | 62.167 | 1.00 | 63.38 |
| ATOM | 2437 | CA | GLU | B | 30 | 23.280 | 8.207 | 63.344 | 1.00 | 62.77 |
| ATOM | 2438 | CB | GLU | B | 30 | 21.748 | 8.203 | 63.264 | 1.00 | 73.02 |
| ATOM | 2439 | CG | GLU | B | 30 | 21.122 | 9.397 | 63.971 | 1.00 | 77.36 |
| ATOM | 2440 | CD | GLU | B | 30 | 21.462 | 9.438 | 65.448 | 1.00 | 78.77 |
| ATOM | 2441 | OE1 | GLU | B | 30 | 20.929 | 10.329 | 66.141 | 1.00 | 79.79 |
| ATOM | 2442 | OE2 | GLU | B | 30 | 22.251 | 8.592 | 65.918 | 1.00 | 84.00 |
| ATOM | 2443 | C | GLU | B | 30 | 23.793 | 6.783 | 63.519 | 1.00 | 54.87 |

FIGURE 149

| | | | | | | | | | |
|---|---|---|---|---|---|---|---|---|---|
| ATOM | 2444 | O | GLU | B | 30 | 24.369 | 6.475 | 64.563 | 1.00 35.09 |
| ATOM | 2445 | N | GLY | B | 31 | 23.595 | 5.938 | 62.517 | 1.00 59.10 |
| ATOM | 2446 | CA | GLY | B | 31 | 23.994 | 4.545 | 62.525 | 1.00 56.95 |
| ATOM | 2447 | C | GLY | B | 31 | 25.493 | 4.331 | 62.443 | 1.00 59.39 |
| ATOM | 2448 | O | GLY | B | 31 | 26.019 | 3.379 | 63.037 | 1.00 42.38 |
| ATOM | 2449 | N | HIS | B | 32 | 26.167 | 5.215 | 61.710 | 1.00 59.10 |
| ATOM | 2450 | CA | HIS | B | 32 | 27.629 | 5.216 | 61.649 | 1.00 51.48 |
| ATOM | 2451 | CB | HIS | B | 32 | 28.127 | 6.437 | 60.888 | 1.00 51.68 |
| ATOM | 2452 | CG | HIS | B | 32 | 29.593 | 6.534 | 60.618 | 1.00 64.14 |
| ATOM | 2453 | ND1 | HIS | B | 32 | 30.445 | 7.321 | 61.368 | 1.00 66.96 |
| ATOM | 2454 | CE1 | HIS | B | 32 | 31.680 | 7.223 | 60.917 | 1.00 64.66 |
| ATOM | 2455 | NE2 | HIS | B | 32 | 31.669 | 6.399 | 59.884 | 1.00 69.62 |
| ATOM | 2456 | CD2 | HIS | B | 32 | 30.382 | 5.959 | 59.681 | 1.00 69.44 |
| ATOM | 2457 | C | HIS | B | 32 | 28.174 | 5.164 | 63.071 | 1.00 48.27 |
| ATOM | 2458 | O | HIS | B | 32 | 28.812 | 4.198 | 63.493 | 1.00 43.02 |
| ATOM | 2459 | N | PHE | B | 33 | 27.893 | 6.215 | 63.836 | 1.00 52.78 |
| ATOM | 2460 | CA | PHE | B | 33 | 28.398 | 6.300 | 65.205 | 1.00 56.25 |
| ATOM | 2461 | CB | PHE | B | 33 | 27.898 | 7.596 | 65.853 | 1.00 58.42 |
| ATOM | 2462 | CG | PHE | B | 33 | 28.693 | 8.008 | 67.083 | 1.00 52.11 |
| ATOM | 2463 | CD1 | PHE | B | 33 | 30.015 | 7.634 | 67.229 | 1.00 40.98 |
| ATOM | 2464 | CE1 | PHE | B | 33 | 30.727 | 8.001 | 68.354 | 1.00 46.43 |
| ATOM | 2465 | CZ | PHE | B | 33 | 30.127 | 8.753 | 69.348 | 1.00 46.14 |
| ATOM | 2466 | CE2 | PHE | B | 33 | 28.806 | 9.135 | 69.208 | 1.00 46.50 |
| ATOM | 2467 | CD2 | PHE | B | 33 | 28.101 | 8.767 | 68.079 | 1.00 53.38 |
| ATOM | 2468 | C | PHE | B | 33 | 28.022 | 5.075 | 66.032 | 1.00 55.13 |
| ATOM | 2469 | O | PHE | B | 33 | 28.890 | 4.473 | 66.675 | 1.00 37.79 |
| ATOM | 2470 | N | MET | B | 34 | 26.755 | 4.681 | 66.032 | 1.00 65.84 |
| ATOM | 2471 | CA | MET | B | 34 | 26.316 | 3.484 | 66.751 | 1.00 75.38 |
| ATOM | 2472 | CB | MET | B | 34 | 24.841 | 3.195 | 66.464 | 1.00 80.09 |
| ATOM | 2473 | CG | MET | B | 34 | 23.886 | 3.798 | 67.480 | 1.00 84.30 |
| ATOM | 2474 | SD | MET | B | 34 | 22.339 | 4.405 | 66.779 | 1.00 87.53 |
| ATOM | 2475 | CE | MET | B | 34 | 21.767 | 2.952 | 65.905 | 1.00 52.16 |
| ATOM | 2476 | C | MET | B | 34 | 27.188 | 2.284 | 66.383 | 1.00 75.48 |
| ATOM | 2477 | O | MET | B | 34 | 27.588 | 1.495 | 67.238 | 1.00 66.38 |
| ATOM | 2478 | N | LYS | B | 35 | 27.503 | 2.192 | 65.096 | 1.00 75.62 |
| ATOM | 2479 | CA | LYS | B | 35 | 28.410 | 1.192 | 64.561 | 1.00 70.36 |
| ATOM | 2480 | CB | LYS | B | 35 | 28.646 | 1.437 | 63.066 | 1.00 73.89 |
| ATOM | 2481 | CG | LYS | B | 35 | 27.460 | 1.150 | 62.169 | 1.00 77.64 |
| ATOM | 2482 | CD | LYS | B | 35 | 27.860 | 0.247 | 61.008 | 1.00 79.39 |
| ATOM | 2483 | CE | LYS | B | 35 | 27.676 | -1.218 | 61.371 | 1.00 81.96 |
| ATOM | 2484 | NZ | LYS | B | 35 | 28.542 | -1.629 | 62.510 | 1.00 89.41 |
| ATOM | 2485 | C | LYS | B | 35 | 29.760 | 1.199 | 65.265 | 1.00 64.44 |
| ATOM | 2486 | O | LYS | B | 35 | 30.185 | 0.235 | 65.901 | 1.00 37.91 |
| ATOM | 2487 | N | LEU | B | 36 | 30.485 | 2.316 | 65.147 | 1.00 63.16 |
| ATOM | 2488 | CA | LEU | B | 36 | 31.841 | 2.334 | 65.693 | 1.00 63.09 |
| ATOM | 2489 | CB | LEU | B | 36 | 32.573 | 3.624 | 65.324 | 1.00 65.24 |
| ATOM | 2490 | CG | LEU | B | 36 | 32.842 | 3.848 | 63.836 | 1.00 68.40 |
| ATOM | 2491 | CD1 | LEU | B | 36 | 31.931 | 4.933 | 63.279 | 1.00 66.79 |
| ATOM | 2492 | CD2 | LEU | B | 36 | 34.303 | 4.199 | 63.599 | 1.00 81.44 |
| ATOM | 2493 | C | LEU | B | 36 | 31.826 | 2.156 | 67.209 | 1.00 56.96 |
| ATOM | 2494 | O | LEU | B | 36 | 32.833 | 1.728 | 67.774 | 1.00 56.27 |
| ATOM | 2495 | N | GLN | B | 37 | 30.691 | 2.487 | 67.805 | 1.00 53.43 |

FIGURE 150

```
ATOM   2496  CA   GLN B  37      30.459   2.414  69.236  1.00 69.43
ATOM   2497  CB   GLN B  37      29.331   3.386  69.619  1.00 68.76
ATOM   2498  CG   GLN B  37      29.831   4.826  69.657  1.00 75.93
ATOM   2499  CD   GLN B  37      28.722   5.824  69.917  1.00 77.13
ATOM   2500  OE1  GLN B  37      27.936   6.137  69.020  1.00 87.89
ATOM   2501  NE2  GLN B  37      28.671   6.319  71.147  1.00 60.96
ATOM   2502  C    GLN B  37      30.117   1.006  69.706  1.00 79.22
ATOM   2503  O    GLN B  37      30.388   0.635  70.850  1.00 73.11
ATOM   2504  N    ALA B  38      29.518   0.228  68.808  1.00 83.91
ATOM   2505  CA   ALA B  38      29.154  -1.148  69.119  1.00 85.90
ATOM   2506  CB   ALA B  38      28.533  -1.809  67.896  1.00 73.44
ATOM   2507  C    ALA B  38      30.354  -1.952  69.612  1.00 87.80
ATOM   2508  O    ALA B  38      31.504  -1.707  69.247  1.00 77.48
ATOM   2509  N    ASP B  39      30.073  -2.936  70.462  1.00 88.62
ATOM   2510  CA   ASP B  39      31.113  -3.821  70.969  1.00 85.89
ATOM   2511  CB   ASP B  39      31.626  -4.719  69.837  1.00 87.42
ATOM   2512  CG   ASP B  39      30.689  -5.885  69.586  1.00 90.49
ATOM   2513  OD1  ASP B  39      30.455  -6.223  68.408  1.00 97.09
ATOM   2514  OD2  ASP B  39      30.188  -6.455  70.579  1.00 93.16
ATOM   2515  C    ASP B  39      32.267  -3.044  71.587  1.00 82.50
ATOM   2516  O    ASP B  39      33.429  -3.298  71.271  1.00 76.36
ATOM   2517  N    SER B  40      31.940  -2.102  72.465  1.00 82.73
ATOM   2518  CA   SER B  40      32.957  -1.326  73.165  1.00 79.40
ATOM   2519  CB   SER B  40      33.839  -2.246  74.009  1.00 75.80
ATOM   2520  OG   SER B  40      34.651  -3.081  73.205  1.00 54.94
ATOM   2521  C    SER B  40      33.807  -0.518  72.180  1.00 76.46
ATOM   2522  O    SER B  40      35.024  -0.714  72.131  1.00 64.01
ATOM   2523  N    ASN B  41      33.121   0.352  71.454  1.00 73.19
ATOM   2524  CA   ASN B  41      33.647   1.191  70.394  1.00 71.55
ATOM   2525  CB   ASN B  41      34.253   2.492  70.912  1.00 67.00
ATOM   2526  CG   ASN B  41      33.360   3.337  71.784  1.00 65.98
ATOM   2527  OD1  ASN B  41      32.134   3.225  71.788  1.00 77.13
ATOM   2528  ND2  ASN B  41      33.976   4.224  72.563  1.00 62.14
ATOM   2529  C    ASN B  41      34.710   0.429  69.603  1.00 74.40
ATOM   2530  O    ASN B  41      35.806   0.941  69.376  1.00 81.24
ATOM   2531  N    TYR B  42      34.393  -0.804  69.212  1.00 74.86
ATOM   2532  CA   TYR B  42      35.405  -1.610  68.534  1.00 74.76
ATOM   2533  CB   TYR B  42      34.880  -3.002  68.168  1.00 75.15
ATOM   2534  CG   TYR B  42      35.907  -3.795  67.386  1.00 75.66
ATOM   2535  CD1  TYR B  42      37.017  -4.332  68.023  1.00 78.98
ATOM   2536  CE1  TYR B  42      37.961  -5.054  67.316  1.00 81.79
ATOM   2537  CZ   TYR B  42      37.804  -5.243  65.959  1.00 81.37
ATOM   2538  OH   TYR B  42      38.747  -5.962  65.258  1.00 80.99
ATOM   2539  CE2  TYR B  42      36.713  -4.717  65.304  1.00 76.53
ATOM   2540  CD2  TYR B  42      35.775  -3.996  66.019  1.00 75.88
ATOM   2541  C    TYR B  42      35.914  -0.906  67.277  1.00 72.94
ATOM   2542  O    TYR B  42      37.119  -0.676  67.155  1.00 61.94
ATOM   2543  N    LEU B  43      35.004  -0.570  66.366  1.00 68.88
ATOM   2544  CA   LEU B  43      35.396   0.092  65.128  1.00 70.56
ATOM   2545  CB   LEU B  43      34.188   0.493  64.286  1.00 72.58
ATOM   2546  CG   LEU B  43      33.017  -0.487  64.224  1.00 76.87
ATOM   2547  CD1  LEU B  43      31.993  -0.053  63.184  1.00 62.51
```

FIGURE 151

```
ATOM   2548  CD2 LEU B  43      33.520   -1.895   63.937  1.00 77.97
ATOM   2549  C   LEU B  43      36.248    1.336   65.417  1.00 67.14
ATOM   2550  O   LEU B  43      37.449    1.316   65.140  1.00 50.41
ATOM   2551  N   LEU B  44      35.580    2.345   65.951  1.00 66.03
ATOM   2552  CA  LEU B  44      36.109    3.651   66.304  1.00 61.62
ATOM   2553  CB  LEU B  44      35.238    4.313   67.375  1.00 62.58
ATOM   2554  CG  LEU B  44      35.741    5.640   67.946  1.00 58.19
ATOM   2555  CD1 LEU B  44      34.587    6.622   68.088  1.00 55.67
ATOM   2556  CD2 LEU B  44      36.446    5.433   69.276  1.00 48.14
ATOM   2557  C   LEU B  44      37.551    3.568   66.793  1.00 59.86
ATOM   2558  O   LEU B  44      38.446    4.143   66.175  1.00 48.99
ATOM   2559  N   SER B  45      37.750    2.840   67.887  1.00 64.48
ATOM   2560  CA  SER B  45      39.072    2.646   68.456  1.00 71.61
ATOM   2561  CB  SER B  45      39.047    1.584   69.560  1.00 73.68
ATOM   2562  OG  SER B  45      40.284    0.883   69.574  1.00 76.78
ATOM   2563  C   SER B  45      40.089    2.224   67.396  1.00 71.36
ATOM   2564  O   SER B  45      41.209    2.728   67.377  1.00 52.39
ATOM   2565  N   LYS B  46      39.662    1.295   66.549  1.00 78.57
ATOM   2566  CA  LYS B  46      40.501    0.742   65.494  1.00 84.31
ATOM   2567  CB  LYS B  46      39.848   -0.499   64.885  1.00 89.10
ATOM   2568  CG  LYS B  46      40.772   -1.693   64.707  1.00 85.70
ATOM   2569  CD  LYS B  46      40.699   -2.236   63.288  1.00 83.59
ATOM   2570  CE  LYS B  46      41.199   -3.666   63.201  1.00 84.74
ATOM   2571  NZ  LYS B  46      40.192   -4.641   63.706  1.00 92.84
ATOM   2572  C   LYS B  46      40.773    1.795   64.420  1.00 81.13
ATOM   2573  O   LYS B  46      41.920    1.966   64.005  1.00 84.85
ATOM   2574  N   GLU B  47      39.718    2.485   64.012  1.00 74.35
ATOM   2575  CA  GLU B  47      39.755    3.570   63.041  1.00 70.19
ATOM   2576  CB  GLU B  47      38.323    3.963   62.661  1.00 66.52
ATOM   2577  CG  GLU B  47      38.025    5.446   62.668  1.00 62.55
ATOM   2578  CD  GLU B  47      36.885    5.861   61.763  1.00 59.88
ATOM   2579  OE1 GLU B  47      36.350    5.017   61.015  1.00 48.61
ATOM   2580  OE2 GLU B  47      36.514    7.057   61.794  1.00 47.49
ATOM   2581  C   GLU B  47      40.536    4.777   63.555  1.00 65.98
ATOM   2582  O   GLU B  47      40.806    5.729   62.818  1.00 61.94
ATOM   2583  N   TYR B  48      40.929    4.759   64.822  1.00 59.02
ATOM   2584  CA  TYR B  48      41.740    5.813   65.412  1.00 54.32
ATOM   2585  CB  TYR B  48      41.164    6.221   66.766  1.00 47.04
ATOM   2586  CG  TYR B  48      41.966    7.305   67.448  1.00 43.40
ATOM   2587  CD1 TYR B  48      41.837    8.629   67.048  1.00 39.64
ATOM   2588  CE1 TYR B  48      42.565    9.622   67.667  1.00 35.48
ATOM   2589  CZ  TYR B  48      43.426    9.313   68.688  1.00 33.02
ATOM   2590  OH  TYR B  48      44.149   10.314   69.302  1.00 49.28
ATOM   2591  CE2 TYR B  48      43.570    8.007   69.103  1.00 43.77
ATOM   2592  CD2 TYR B  48      42.842    7.011   68.481  1.00 38.80
ATOM   2593  C   TYR B  48      43.182    5.374   65.585  1.00 59.37
ATOM   2594  O   TYR B  48      44.124    6.169   65.563  1.00 53.93
ATOM   2595  N   GLU B  49      43.427    4.067   65.759  1.00 56.83
ATOM   2596  CA  GLU B  49      44.857    3.719   65.788  1.00 52.72
ATOM   2597  CB  GLU B  49      45.118    2.439   66.568  1.00 61.99
ATOM   2598  CG  GLU B  49      46.098    2.586   67.723  1.00 66.59
ATOM   2599  CD  GLU B  49      45.724    3.661   68.723  1.00 68.99
```

FIGURE 152

| ATOM | 2600 | OE1 | GLU | B | 49 | 44.737 | 3.486 | 69.468 | 1.00 | 71.09 |
| ATOM | 2601 | OE2 | GLU | B | 49 | 46.424 | 4.699 | 68.778 | 1.00 | 64.67 |
| ATOM | 2602 | C | GLU | B | 49 | 45.353 | 3.635 | 64.349 | 1.00 | 43.12 |
| ATOM | 2603 | O | GLU | B | 49 | 46.539 | 3.492 | 64.069 | 1.00 | 46.58 |
| ATOM | 2604 | N | GLU | B | 50 | 44.424 | 3.733 | 63.404 | 1.00 | 35.51 |
| ATOM | 2605 | CA | GLU | B | 50 | 44.790 | 3.731 | 61.992 | 1.00 | 48.92 |
| ATOM | 2606 | CB | GLU | B | 50 | 43.546 | 3.509 | 61.132 | 1.00 | 55.98 |
| ATOM | 2607 | CG | GLU | B | 50 | 43.820 | 2.894 | 59.769 | 1.00 | 62.45 |
| ATOM | 2608 | CD | GLU | B | 50 | 42.672 | 3.111 | 58.802 | 1.00 | 72.64 |
| ATOM | 2609 | OE1 | GLU | B | 50 | 42.932 | 3.465 | 57.632 | 1.00 | 97.10 |
| ATOM | 2610 | OE2 | GLU | B | 50 | 41.505 | 2.932 | 59.214 | 1.00 | 90.89 |
| ATOM | 2611 | C | GLU | B | 50 | 45.484 | 5.036 | 61.609 | 1.00 | 51.81 |
| ATOM | 2612 | O | GLU | B | 50 | 46.447 | 5.031 | 60.840 | 1.00 | 60.14 |
| ATOM | 2613 | N | LEU | B | 51 | 44.993 | 6.142 | 62.157 | 1.00 | 45.17 |
| ATOM | 2614 | CA | LEU | B | 51 | 45.544 | 7.474 | 61.921 | 1.00 | 36.37 |
| ATOM | 2615 | CB | LEU | B | 51 | 44.599 | 8.527 | 62.511 | 1.00 | 31.85 |
| ATOM | 2616 | CG | LEU | B | 51 | 43.381 | 8.867 | 61.656 | 1.00 | 28.95 |
| ATOM | 2617 | CD1 | LEU | B | 51 | 42.269 | 9.488 | 62.490 | 1.00 | 29.93 |
| ATOM | 2618 | CD2 | LEU | B | 51 | 43.770 | 9.789 | 60.507 | 1.00 | 38.39 |
| ATOM | 2619 | C | LEU | B | 51 | 46.931 | 7.623 | 62.529 | 1.00 | 40.25 |
| ATOM | 2620 | O | LEU | B | 51 | 47.666 | 8.567 | 62.254 | 1.00 | 43.39 |
| ATOM | 2621 | N | LYS | B | 52 | 47.288 | 6.661 | 63.367 | 1.00 | 39.11 |
| ATOM | 2622 | CA | LYS | B | 52 | 48.486 | 6.628 | 64.172 | 1.00 | 41.30 |
| ATOM | 2623 | CB | LYS | B | 52 | 48.607 | 5.228 | 64.795 | 1.00 | 38.29 |
| ATOM | 2624 | CG | LYS | B | 52 | 49.077 | 5.211 | 66.234 | 1.00 | 41.48 |
| ATOM | 2625 | CD | LYS | B | 52 | 49.745 | 3.871 | 66.543 | 1.00 | 42.51 |
| ATOM | 2626 | CE | LYS | B | 52 | 49.996 | 3.752 | 68.036 | 1.00 | 44.45 |
| ATOM | 2627 | NZ | LYS | B | 52 | 48.720 | 3.710 | 68.803 | 1.00 | 54.34 |
| ATOM | 2628 | C | LYS | B | 52 | 49.776 | 6.939 | 63.433 | 1.00 | 43.04 |
| ATOM | 2629 | O | LYS | B | 52 | 50.637 | 7.651 | 63.963 | 1.00 | 51.42 |
| ATOM | 2630 | N | ASP | B | 53 | 49.981 | 6.421 | 62.225 | 1.00 | 35.92 |
| ATOM | 2631 | CA | ASP | B | 53 | 51.272 | 6.646 | 61.580 | 1.00 | 36.34 |
| ATOM | 2632 | CB | ASP | B | 53 | 51.714 | 5.388 | 60.823 | 1.00 | 46.86 |
| ATOM | 2633 | CG | ASP | B | 53 | 51.520 | 4.136 | 61.665 | 1.00 | 60.28 |
| ATOM | 2634 | OD1 | ASP | B | 53 | 50.750 | 3.258 | 61.221 | 1.00 | 74.44 |
| ATOM | 2635 | OD2 | ASP | B | 53 | 52.132 | 4.051 | 62.753 | 1.00 | 57.58 |
| ATOM | 2636 | C | ASP | B | 53 | 51.267 | 7.819 | 60.606 | 1.00 | 25.54 |
| ATOM | 2637 | O | ASP | B | 53 | 52.315 | 8.092 | 60.019 | 1.00 | 31.31 |
| ATOM | 2638 | N | VAL | B | 54 | 50.126 | 8.459 | 60.444 | 1.00 | 25.37 |
| ATOM | 2639 | CA | VAL | B | 54 | 50.004 | 9.549 | 59.477 | 1.00 | 28.87 |
| ATOM | 2640 | CB | VAL | B | 54 | 48.603 | 10.168 | 59.522 | 1.00 | 32.29 |
| ATOM | 2641 | CG1 | VAL | B | 54 | 48.397 | 11.175 | 58.399 | 1.00 | 27.43 |
| ATOM | 2642 | CG2 | VAL | B | 54 | 47.541 | 9.073 | 59.433 | 1.00 | 35.45 |
| ATOM | 2643 | C | VAL | B | 54 | 51.089 | 10.587 | 59.747 | 1.00 | 35.40 |
| ATOM | 2644 | O | VAL | B | 54 | 51.266 | 11.007 | 60.887 | 1.00 | 28.36 |
| ATOM | 2645 | N | GLY | B | 55 | 51.818 | 10.950 | 58.704 | 1.00 | 30.35 |
| ATOM | 2646 | CA | GLY | B | 55 | 52.888 | 11.904 | 58.678 | 1.00 | 26.77 |
| ATOM | 2647 | C | GLY | B | 55 | 54.129 | 11.566 | 59.459 | 1.00 | 31.10 |
| ATOM | 2648 | O | GLY | B | 55 | 54.988 | 12.440 | 59.618 | 1.00 | 28.63 |
| ATOM | 2649 | N | ARG | B | 56 | 54.281 | 10.344 | 59.959 | 1.00 | 31.74 |
| ATOM | 2650 | CA | ARG | B | 56 | 55.404 | 9.997 | 60.827 | 1.00 | 37.30 |
| ATOM | 2651 | CB | ARG | B | 56 | 55.077 | 8.697 | 61.573 | 1.00 | 46.87 |

FIGURE 153

| | | | | | | | | | |
|---|---|---|---|---|---|---|---|---|---|
| ATOM | 2652 | CG | ARG | B | 56 | 55.107 | 7.449 | 60.705 | 1.00 56.15 |
| ATOM | 2653 | CD | ARG | B | 56 | 55.129 | 6.169 | 61.530 | 1.00 51.35 |
| ATOM | 2654 | NE | ARG | B | 56 | 56.387 | 5.999 | 62.253 | 1.00 46.32 |
| ATOM | 2655 | CZ | ARG | B | 56 | 56.583 | 5.142 | 63.245 | 1.00 43.24 |
| ATOM | 2656 | NH1 | ARG | B | 56 | 55.595 | 4.357 | 63.646 | 1.00 38.49 |
| ATOM | 2657 | NH2 | ARG | B | 56 | 57.771 | 5.074 | 63.831 | 1.00 37.94 |
| ATOM | 2658 | C | ARG | B | 56 | 56.729 | 9.869 | 60.089 | 1.00 44.81 |
| ATOM | 2659 | O | ARG | B | 56 | 57.782 | 9.586 | 60.675 | 1.00 33.22 |
| ATOM | 2660 | N | ASN | B | 57 | 56.702 | 10.084 | 58.779 | 1.00 40.44 |
| ATOM | 2661 | CA | ASN | B | 57 | 57.876 | 10.023 | 57.931 | 1.00 33.30 |
| ATOM | 2662 | CB | ASN | B | 57 | 57.436 | 9.773 | 56.482 | 1.00 44.90 |
| ATOM | 2663 | CG | ASN | B | 57 | 56.483 | 10.848 | 55.987 | 1.00 53.38 |
| ATOM | 2664 | OD1 | ASN | B | 57 | 56.798 | 11.576 | 55.040 | 1.00 73.52 |
| ATOM | 2665 | ND2 | ASN | B | 57 | 55.311 | 10.971 | 56.602 | 1.00 38.90 |
| ATOM | 2666 | C | ASN | B | 57 | 58.691 | 11.308 | 57.972 | 1.00 31.80 |
| ATOM | 2667 | O | ASN | B | 57 | 59.810 | 11.344 | 57.465 | 1.00 31.72 |
| ATOM | 2668 | N | GLN | B | 58 | 58.129 | 12.357 | 58.569 | 1.00 28.77 |
| ATOM | 2669 | CA | GLN | B | 58 | 58.736 | 13.681 | 58.549 | 1.00 24.41 |
| ATOM | 2670 | CB | GLN | B | 58 | 57.611 | 14.729 | 58.466 | 1.00 27.17 |
| ATOM | 2671 | CG | GLN | B | 58 | 56.688 | 14.411 | 57.292 | 1.00 28.52 |
| ATOM | 2672 | CD | GLN | B | 58 | 55.494 | 15.335 | 57.233 | 1.00 31.70 |
| ATOM | 2673 | OE1 | GLN | B | 58 | 55.513 | 16.340 | 56.520 | 1.00 30.23 |
| ATOM | 2674 | NE2 | GLN | B | 58 | 54.460 | 14.991 | 57.992 | 1.00 28.20 |
| ATOM | 2675 | C | GLN | B | 58 | 59.621 | 13.965 | 59.743 | 1.00 26.40 |
| ATOM | 2676 | O | GLN | B | 58 | 59.307 | 13.588 | 60.865 | 1.00 32.07 |
| ATOM | 2677 | N | SER | B | 59 | 60.750 | 14.633 | 59.494 | 1.00 21.54 |
| ATOM | 2678 | CA | SER | B | 59 | 61.713 | 14.878 | 60.552 | 1.00 25.17 |
| ATOM | 2679 | CB | SER | B | 59 | 63.136 | 14.784 | 60.000 | 1.00 31.63 |
| ATOM | 2680 | OG | SER | B | 59 | 63.435 | 15.925 | 59.212 | 1.00 43.09 |
| ATOM | 2681 | C | SER | B | 59 | 61.470 | 16.250 | 61.193 | 1.00 29.30 |
| ATOM | 2682 | O | SER | B | 59 | 60.674 | 17.010 | 60.635 | 1.00 24.20 |
| ATOM | 2683 | N | CYS | B | 60 | 62.166 | 16.479 | 62.290 | 1.00 25.59 |
| ATOM | 2684 | CA | CYS | B | 60 | 62.116 | 17.647 | 63.149 | 1.00 30.08 |
| ATOM | 2685 | CB | CYS | B | 60 | 61.390 | 17.257 | 64.451 | 1.00 26.43 |
| ATOM | 2686 | SG | CYS | B | 60 | 59.647 | 16.884 | 64.130 | 1.00 33.04 |
| ATOM | 2687 | C | CYS | B | 60 | 63.489 | 18.201 | 63.472 | 1.00 33.64 |
| ATOM | 2688 | O | CYS | B | 60 | 63.790 | 18.632 | 64.592 | 1.00 25.31 |
| ATOM | 2689 | N | ASP | B | 61 | 64.361 | 18.193 | 62.463 | 1.00 23.90 |
| ATOM | 2690 | CA | ASP | B | 61 | 65.744 | 18.559 | 62.696 | 1.00 19.83 |
| ATOM | 2691 | CB | ASP | B | 61 | 66.538 | 18.374 | 61.392 | 1.00 28.21 |
| ATOM | 2692 | CG | ASP | B | 61 | 66.602 | 16.912 | 60.974 | 1.00 37.45 |
| ATOM | 2693 | OD1 | ASP | B | 61 | 66.668 | 16.033 | 61.857 | 1.00 46.92 |
| ATOM | 2694 | OD2 | ASP | B | 61 | 66.585 | 16.633 | 59.756 | 1.00 39.28 |
| ATOM | 2695 | C | ASP | B | 61 | 65.931 | 19.978 | 63.202 | 1.00 18.89 |
| ATOM | 2696 | O | ASP | B | 61 | 66.742 | 20.234 | 64.100 | 1.00 26.23 |
| ATOM | 2697 | N | ILE | B | 62 | 65.208 | 20.944 | 62.642 | 1.00 17.76 |
| ATOM | 2698 | CA | ILE | B | 62 | 65.463 | 22.312 | 63.098 | 1.00 16.77 |
| ATOM | 2699 | CB | ILE | B | 62 | 64.737 | 23.351 | 62.222 | 1.00 26.79 |
| ATOM | 2700 | CG1 | ILE | B | 62 | 65.028 | 23.219 | 60.729 | 1.00 30.78 |
| ATOM | 2701 | CD1 | ILE | B | 62 | 66.350 | 22.561 | 60.400 | 1.00 49.88 |
| ATOM | 2702 | CG2 | ILE | B | 62 | 65.029 | 24.761 | 62.731 | 1.00 20.53 |
| ATOM | 2703 | C | ILE | B | 62 | 65.015 | 22.503 | 64.540 | 1.00 21.81 |

FIGURE 154

| | | | | | | | | | |
|---|---|---|---|---|---|---|---|---|---|
| ATOM | 2704 | O   | ILE | B | 62 | 65.635 | 23.218 | 65.328 | 1.00 26.45 |
| ATOM | 2705 | N   | ALA | B | 63 | 63.903 | 21.860 | 64.890 | 1.00 22.22 |
| ATOM | 2706 | CA  | ALA | B | 63 | 63.421 | 22.042 | 66.267 | 1.00 23.49 |
| ATOM | 2707 | CB  | ALA | B | 63 | 62.039 | 21.427 | 66.404 | 1.00 13.73 |
| ATOM | 2708 | C   | ALA | B | 63 | 64.438 | 21.456 | 67.235 | 1.00 32.72 |
| ATOM | 2709 | O   | ALA | B | 63 | 64.621 | 21.898 | 68.366 | 1.00 29.49 |
| ATOM | 2710 | N   | LEU | B | 64 | 65.142 | 20.427 | 66.770 | 1.00 26.75 |
| ATOM | 2711 | CA  | LEU | B | 64 | 66.097 | 19.704 | 67.590 | 1.00 24.87 |
| ATOM | 2712 | CB  | LEU | B | 64 | 66.248 | 18.272 | 67.035 | 1.00 30.01 |
| ATOM | 2713 | CG  | LEU | B | 64 | 65.032 | 17.393 | 67.356 | 1.00 30.13 |
| ATOM | 2714 | CD1 | LEU | B | 64 | 65.068 | 16.082 | 66.591 | 1.00 23.61 |
| ATOM | 2715 | CD2 | LEU | B | 64 | 64.982 | 17.171 | 68.862 | 1.00 35.44 |
| ATOM | 2716 | C   | LEU | B | 64 | 67.454 | 20.371 | 67.657 | 1.00 28.99 |
| ATOM | 2717 | O   | LEU | B | 64 | 68.343 | 19.889 | 68.367 | 1.00 41.07 |
| ATOM | 2718 | N   | LEU | B | 65 | 67.636 | 21.470 | 66.927 | 1.00 26.97 |
| ATOM | 2719 | CA  | LEU | B | 65 | 68.925 | 22.152 | 66.964 | 1.00 25.83 |
| ATOM | 2720 | CB  | LEU | B | 65 | 68.955 | 23.340 | 66.001 | 1.00 29.04 |
| ATOM | 2721 | CG  | LEU | B | 65 | 69.017 | 23.002 | 64.513 | 1.00 33.55 |
| ATOM | 2722 | CD1 | LEU | B | 65 | 68.843 | 24.264 | 63.679 | 1.00 36.14 |
| ATOM | 2723 | CD2 | LEU | B | 65 | 70.327 | 22.301 | 64.180 | 1.00 39.25 |
| ATOM | 2724 | C   | LEU | B | 65 | 69.234 | 22.654 | 68.373 | 1.00 30.40 |
| ATOM | 2725 | O   | LEU | B | 65 | 68.329 | 23.174 | 69.021 | 1.00 31.08 |
| ATOM | 2726 | N   | PRO | B | 66 | 70.470 | 22.487 | 68.809 | 1.00 33.09 |
| ATOM | 2727 | CA  | PRO | B | 66 | 70.935 | 22.972 | 70.112 | 1.00 41.49 |
| ATOM | 2728 | CB  | PRO | B | 66 | 72.456 | 23.052 | 69.889 | 1.00 43.28 |
| ATOM | 2729 | CG  | PRO | B | 66 | 72.722 | 21.860 | 69.020 | 1.00 38.43 |
| ATOM | 2730 | CD  | PRO | B | 66 | 71.543 | 21.766 | 68.091 | 1.00 35.99 |
| ATOM | 2731 | C   | PRO | B | 66 | 70.390 | 24.336 | 70.511 | 1.00 44.08 |
| ATOM | 2732 | O   | PRO | B | 66 | 69.735 | 24.440 | 71.557 | 1.00 50.98 |
| ATOM | 2733 | N   | GLU | B | 67 | 70.636 | 25.375 | 69.722 | 1.00 35.08 |
| ATOM | 2734 | CA  | GLU | B | 67 | 70.246 | 26.724 | 70.105 | 1.00 39.35 |
| ATOM | 2735 | CB  | GLU | B | 67 | 70.775 | 27.730 | 69.068 | 1.00 38.98 |
| ATOM | 2736 | CG  | GLU | B | 67 | 71.059 | 27.062 | 67.732 | 1.00 52.87 |
| ATOM | 2737 | CD  | GLU | B | 67 | 70.712 | 27.954 | 66.555 | 1.00 59.99 |
| ATOM | 2738 | OE1 | GLU | B | 67 | 71.040 | 29.158 | 66.611 | 1.00 78.27 |
| ATOM | 2739 | OE2 | GLU | B | 67 | 70.119 | 27.433 | 65.586 | 1.00 46.11 |
| ATOM | 2740 | C   | GLU | B | 67 | 68.744 | 26.916 | 70.246 | 1.00 38.16 |
| ATOM | 2741 | O   | GLU | B | 67 | 68.327 | 27.971 | 70.736 | 1.00 36.75 |
| ATOM | 2742 | N   | ASN | B | 68 | 67.935 | 25.950 | 69.821 | 1.00 29.98 |
| ATOM | 2743 | CA  | ASN | B | 68 | 66.493 | 26.069 | 69.927 | 1.00 24.34 |
| ATOM | 2744 | CB  | ASN | B | 68 | 65.775 | 25.589 | 68.662 | 1.00 22.49 |
| ATOM | 2745 | CG  | ASN | B | 68 | 66.037 | 26.469 | 67.459 | 1.00 23.36 |
| ATOM | 2746 | OD1 | ASN | B | 68 | 66.205 | 27.674 | 67.613 | 1.00 24.40 |
| ATOM | 2747 | ND2 | ASN | B | 68 | 66.092 | 25.871 | 66.273 | 1.00 19.47 |
| ATOM | 2748 | C   | ASN | B | 68 | 65.957 | 25.255 | 71.100 | 1.00 28.35 |
| ATOM | 2749 | O   | ASN | B | 68 | 64.733 | 25.161 | 71.233 | 1.00 31.84 |
| ATOM | 2750 | N   | ARG | B | 69 | 66.821 | 24.667 | 71.924 | 1.00 28.07 |
| ATOM | 2751 | CA  | ARG | B | 69 | 66.284 | 23.759 | 72.950 | 1.00 39.17 |
| ATOM | 2752 | CB  | ARG | B | 69 | 67.429 | 23.142 | 73.757 | 1.00 53.87 |
| ATOM | 2753 | CG  | ARG | B | 69 | 66.997 | 22.065 | 74.739 | 1.00 67.65 |
| ATOM | 2754 | CD  | ARG | B | 69 | 68.095 | 21.761 | 75.748 | 1.00 84.00 |
| ATOM | 2755 | NE  | ARG | B | 69 | 67.751 | 22.204 | 77.096 | 1.00 97.13 |

FIGURE 155

| | | | | | | | | | |
|---|---|---|---|---|---|---|---|---|---|
| ATOM | 2756 | CZ | ARG | B | 69 | 68.057 | 21.573 | 78.220 | 1.00 102.06 |
| ATOM | 2757 | NH1 | ARG | B | 69 | 68.733 | 20.432 | 78.192 | 1.00 107.87 |
| ATOM | 2758 | NH2 | ARG | B | 69 | 67.686 | 22.083 | 79.390 | 1.00 97.89 |
| ATOM | 2759 | C | ARG | B | 69 | 65.290 | 24.445 | 73.877 | 1.00 34.20 |
| ATOM | 2760 | O | ARG | B | 69 | 64.217 | 23.908 | 74.184 | 1.00 35.41 |
| ATOM | 2761 | N | GLY | B | 70 | 65.616 | 25.659 | 74.328 | 1.00 21.83 |
| ATOM | 2762 | CA | GLY | B | 70 | 64.720 | 26.300 | 75.284 | 1.00 24.46 |
| ATOM | 2763 | C | GLY | B | 70 | 63.455 | 26.843 | 74.655 | 1.00 27.71 |
| ATOM | 2764 | O | GLY | B | 70 | 62.569 | 27.348 | 75.354 | 1.00 27.30 |
| ATOM | 2765 | N | LYS | B | 71 | 63.327 | 26.770 | 73.329 | 1.00 24.69 |
| ATOM | 2766 | CA | LYS | B | 71 | 62.166 | 27.353 | 72.655 | 1.00 22.38 |
| ATOM | 2767 | CB | LYS | B | 71 | 62.587 | 27.893 | 71.274 | 1.00 24.49 |
| ATOM | 2768 | CG | LYS | B | 71 | 63.764 | 28.870 | 71.323 | 1.00 19.45 |
| ATOM | 2769 | CD | LYS | B | 71 | 64.184 | 29.275 | 69.921 | 1.00 23.88 |
| ATOM | 2770 | CE | LYS | B | 71 | 65.345 | 30.261 | 69.951 | 1.00 28.97 |
| ATOM | 2771 | NZ | LYS | B | 71 | 66.081 | 30.241 | 68.653 | 1.00 31.46 |
| ATOM | 2772 | C | LYS | B | 71 | 61.010 | 26.379 | 72.521 | 1.00 17.66 |
| ATOM | 2773 | O | LYS | B | 71 | 59.934 | 26.726 | 72.014 | 1.00 18.84 |
| ATOM | 2774 | N | ASN | B | 72 | 61.211 | 25.140 | 72.984 | 1.00 15.08 |
| ATOM | 2775 | CA | ASN | B | 72 | 60.162 | 24.136 | 72.990 | 1.00 14.64 |
| ATOM | 2776 | CB | ASN | B | 72 | 60.706 | 22.823 | 72.400 | 1.00 18.63 |
| ATOM | 2777 | CG | ASN | B | 72 | 61.196 | 23.022 | 70.977 | 1.00 21.72 |
| ATOM | 2778 | OD1 | ASN | B | 72 | 60.464 | 23.572 | 70.157 | 1.00 19.84 |
| ATOM | 2779 | ND2 | ASN | B | 72 | 62.409 | 22.607 | 70.663 | 1.00 16.01 |
| ATOM | 2780 | C | ASN | B | 72 | 59.640 | 23.891 | 74.408 | 1.00 14.08 |
| ATOM | 2781 | O | ASN | B | 72 | 60.429 | 23.667 | 75.324 | 1.00 19.73 |
| ATOM | 2782 | N | ARG | B | 73 | 58.334 | 23.951 | 74.601 | 1.00 15.40 |
| ATOM | 2783 | CA | ARG | B | 73 | 57.720 | 23.714 | 75.893 | 1.00 23.30 |
| ATOM | 2784 | CB | ARG | B | 73 | 56.221 | 23.993 | 75.832 | 1.00 17.66 |
| ATOM | 2785 | CG | ARG | B | 73 | 55.551 | 23.888 | 77.187 | 1.00 14.92 |
| ATOM | 2786 | CD | ARG | B | 73 | 54.140 | 24.412 | 77.108 | 1.00 14.81 |
| ATOM | 2787 | NE | ARG | B | 73 | 54.131 | 25.882 | 77.110 | 1.00 17.20 |
| ATOM | 2788 | CZ | ARG | B | 73 | 54.259 | 26.568 | 78.241 | 1.00 22.34 |
| ATOM | 2789 | NH1 | ARG | B | 73 | 54.403 | 25.967 | 79.421 | 1.00 13.10 |
| ATOM | 2790 | NH2 | ARG | B | 73 | 54.229 | 27.883 | 78.127 | 1.00 19.63 |
| ATOM | 2791 | C | ARG | B | 73 | 57.917 | 22.253 | 76.319 | 1.00 28.40 |
| ATOM | 2792 | O | ARG | B | 73 | 58.144 | 21.962 | 77.484 | 1.00 19.38 |
| ATOM | 2793 | N | TYR | B | 74 | 57.810 | 21.373 | 75.335 | 1.00 22.53 |
| ATOM | 2794 | CA | TYR | B | 74 | 57.930 | 19.925 | 75.513 | 1.00 16.28 |
| ATOM | 2795 | CB | TYR | B | 74 | 56.580 | 19.271 | 75.323 | 1.00 19.24 |
| ATOM | 2796 | CG | TYR | B | 74 | 55.438 | 19.771 | 76.176 | 1.00 19.80 |
| ATOM | 2797 | CD1 | TYR | B | 74 | 55.345 | 19.402 | 77.515 | 1.00 21.42 |
| ATOM | 2798 | CE1 | TYR | B | 74 | 54.301 | 19.844 | 78.304 | 1.00 21.50 |
| ATOM | 2799 | CZ | TYR | B | 74 | 53.324 | 20.663 | 77.785 | 1.00 18.77 |
| ATOM | 2800 | OH | TYR | B | 74 | 52.288 | 21.098 | 78.587 | 1.00 23.74 |
| ATOM | 2801 | CE2 | TYR | B | 74 | 53.379 | 21.045 | 76.460 | 1.00 12.51 |
| ATOM | 2802 | CD2 | TYR | B | 74 | 54.439 | 20.586 | 75.681 | 1.00 13.12 |
| ATOM | 2803 | C | TYR | B | 74 | 58.958 | 19.399 | 74.521 | 1.00 22.96 |
| ATOM | 2804 | O | TYR | B | 74 | 58.901 | 19.662 | 73.319 | 1.00 22.52 |
| ATOM | 2805 | N | ASN | B | 75 | 59.951 | 18.640 | 74.966 | 1.00 26.45 |
| ATOM | 2806 | CA | ASN | B | 75 | 61.042 | 18.268 | 74.058 | 1.00 23.82 |
| ATOM | 2807 | CB | ASN | B | 75 | 62.205 | 17.736 | 74.904 | 1.00 32.86 |

FIGURE 156

| ATOM | 2808 | CG  | ASN | B | 75 | 62.817 | 18.860 | 75.726 | 1.00 | 45.64 |
|------|------|-----|-----|---|----|--------|--------|--------|------|-------|
| ATOM | 2809 | OD1 | ASN | B | 75 | 63.098 | 18.687 | 76.911 | 1.00 | 76.89 |
| ATOM | 2810 | ND2 | ASN | B | 75 | 63.024 | 20.023 | 75.113 | 1.00 | 56.37 |
| ATOM | 2811 | C   | ASN | B | 75 | 60.615 | 17.280 | 72.990 | 1.00 | 17.41 |
| ATOM | 2812 | O   | ASN | B | 75 | 61.316 | 17.091 | 71.993 | 1.00 | 28.78 |
| ATOM | 2813 | N   | ASN | B | 76 | 59.458 | 16.656 | 73.144 | 1.00 | 23.38 |
| ATOM | 2814 | CA  | ASN | B | 76 | 58.985 | 15.644 | 72.207 | 1.00 | 29.72 |
| ATOM | 2815 | CB  | ASN | B | 76 | 58.807 | 14.310 | 72.941 | 1.00 | 30.87 |
| ATOM | 2816 | CG  | ASN | B | 76 | 57.687 | 14.316 | 73.956 | 1.00 | 32.40 |
| ATOM | 2817 | OD1 | ASN | B | 76 | 57.263 | 15.350 | 74.472 | 1.00 | 30.85 |
| ATOM | 2818 | ND2 | ASN | B | 76 | 57.182 | 13.123 | 74.264 | 1.00 | 26.52 |
| ATOM | 2819 | C   | ASN | B | 76 | 57.695 | 16.072 | 71.529 | 1.00 | 27.58 |
| ATOM | 2820 | O   | ASN | B | 76 | 56.906 | 15.286 | 71.002 | 1.00 | 20.64 |
| ATOM | 2821 | N   | ILE | B | 77 | 57.457 | 17.394 | 71.539 | 1.00 | 21.12 |
| ATOM | 2822 | CA  | ILE | B | 77 | 56.355 | 17.899 | 70.728 | 1.00 | 21.78 |
| ATOM | 2823 | CB  | ILE | B | 77 | 55.141 | 18.381 | 71.519 | 1.00 | 18.13 |
| ATOM | 2824 | CG1 | ILE | B | 77 | 54.513 | 17.334 | 72.446 | 1.00 | 20.08 |
| ATOM | 2825 | CD1 | ILE | B | 77 | 53.650 | 16.337 | 71.722 | 1.00 | 23.88 |
| ATOM | 2826 | CG2 | ILE | B | 77 | 54.103 | 18.928 | 70.552 | 1.00 | 17.41 |
| ATOM | 2827 | C   | ILE | B | 77 | 56.919 | 19.048 | 69.880 | 1.00 | 21.40 |
| ATOM | 2828 | O   | ILE | B | 77 | 56.994 | 20.175 | 70.348 | 1.00 | 16.51 |
| ATOM | 2829 | N   | LEU | B | 78 | 57.354 | 18.703 | 68.682 | 1.00 | 17.91 |
| ATOM | 2830 | CA  | LEU | B | 78 | 58.074 | 19.610 | 67.792 | 1.00 | 14.62 |
| ATOM | 2831 | CB  | LEU | B | 78 | 59.558 | 19.235 | 67.683 | 1.00 | 19.22 |
| ATOM | 2832 | CG  | LEU | B | 78 | 60.190 | 18.709 | 68.980 | 1.00 | 24.19 |
| ATOM | 2833 | CD1 | LEU | B | 78 | 61.387 | 17.832 | 68.669 | 1.00 | 25.60 |
| ATOM | 2834 | CD2 | LEU | B | 78 | 60.571 | 19.861 | 69.903 | 1.00 | 24.35 |
| ATOM | 2835 | C   | LEU | B | 78 | 57.435 | 19.608 | 66.409 | 1.00 | 18.54 |
| ATOM | 2836 | O   | LEU | B | 78 | 56.815 | 18.637 | 65.968 | 1.00 | 20.82 |
| ATOM | 2837 | N   | PRO | B | 79 | 57.571 | 20.731 | 65.709 | 1.00 | 20.55 |
| ATOM | 2838 | CA  | PRO | B | 79 | 56.989 | 20.844 | 64.367 | 1.00 | 19.22 |
| ATOM | 2839 | CB  | PRO | B | 79 | 57.039 | 22.345 | 64.119 | 1.00 | 13.66 |
| ATOM | 2840 | CG  | PRO | B | 79 | 58.250 | 22.790 | 64.870 | 1.00 | 15.94 |
| ATOM | 2841 | CD  | PRO | B | 79 | 58.277 | 21.944 | 66.121 | 1.00 | 16.86 |
| ATOM | 2842 | C   | PRO | B | 79 | 57.883 | 20.131 | 63.351 | 1.00 | 11.53 |
| ATOM | 2843 | O   | PRO | B | 79 | 59.095 | 20.108 | 63.519 | 1.00 | 19.21 |
| ATOM | 2844 | N   | TYR | B | 80 | 57.241 | 19.570 | 62.352 | 1.00 | 16.10 |
| ATOM | 2845 | CA  | TYR | B | 80 | 57.888 | 18.998 | 61.189 | 1.00 | 18.42 |
| ATOM | 2846 | CB  | TYR | B | 80 | 56.838 | 18.332 | 60.309 | 1.00 | 19.59 |
| ATOM | 2847 | CG  | TYR | B | 80 | 56.182 | 17.120 | 60.923 | 1.00 | 16.10 |
| ATOM | 2848 | CD1 | TYR | B | 80 | 56.947 | 16.162 | 61.577 | 1.00 | 18.02 |
| ATOM | 2849 | CE1 | TYR | B | 80 | 56.303 | 15.060 | 62.124 | 1.00 | 17.97 |
| ATOM | 2850 | CZ  | TYR | B | 80 | 54.947 | 14.908 | 62.021 | 1.00 | 19.16 |
| ATOM | 2851 | OH  | TYR | B | 80 | 54.319 | 13.807 | 62.575 | 1.00 | 29.70 |
| ATOM | 2852 | CE2 | TYR | B | 80 | 54.174 | 15.848 | 61.375 | 1.00 | 23.11 |
| ATOM | 2853 | CD2 | TYR | B | 80 | 54.816 | 16.945 | 60.831 | 1.00 | 16.60 |
| ATOM | 2854 | C   | TYR | B | 80 | 58.596 | 20.101 | 60.399 | 1.00 | 23.17 |
| ATOM | 2855 | O   | TYR | B | 80 | 58.013 | 21.187 | 60.227 | 1.00 | 20.07 |
| ATOM | 2856 | N   | ASP | B | 81 | 59.813 | 19.801 | 59.961 | 1.00 | 18.92 |
| ATOM | 2857 | CA  | ASP | B | 81 | 60.613 | 20.748 | 59.186 | 1.00 | 25.46 |
| ATOM | 2858 | CB  | ASP | B | 81 | 61.883 | 20.083 | 58.649 | 1.00 | 35.12 |
| ATOM | 2859 | CG  | ASP | B | 81 | 62.912 | 19.827 | 59.726 | 1.00 | 34.96 |

FIGURE 157

| | | | | | | | | | |
|---|---|---|---|---|---|---|---|---|---|
| ATOM | 2860 | OD1 | ASP | B | 81 | 62.916 | 20.589 | 60.714 | 1.00 26.58 |
| ATOM | 2861 | OD2 | ASP | B | 81 | 63.711 | 18.878 | 59.602 | 1.00 34.17 |
| ATOM | 2862 | C | ASP | B | 81 | 59.815 | 21.292 | 58.006 | 1.00 24.68 |
| ATOM | 2863 | O | ASP | B | 81 | 59.877 | 22.476 | 57.667 | 1.00 30.63 |
| ATOM | 2864 | N | ALA | B | 82 | 59.076 | 20.393 | 57.377 | 1.00 21.31 |
| ATOM | 2865 | CA | ALA | B | 82 | 58.381 | 20.689 | 56.123 | 1.00 26.95 |
| ATOM | 2866 | CB | ALA | B | 82 | 57.912 | 19.386 | 55.477 | 1.00 20.31 |
| ATOM | 2867 | C | ALA | B | 82 | 57.202 | 21.637 | 56.283 | 1.00 33.87 |
| ATOM | 2868 | O | ALA | B | 82 | 56.749 | 22.267 | 55.323 | 1.00 20.97 |
| ATOM | 2869 | N | THR | B | 83 | 56.636 | 21.770 | 57.486 | 1.00 28.89 |
| ATOM | 2870 | CA | THR | B | 83 | 55.445 | 22.602 | 57.616 | 1.00 17.68 |
| ATOM | 2871 | CB | THR | B | 83 | 54.208 | 21.738 | 57.906 | 1.00 21.79 |
| ATOM | 2872 | OG1 | THR | B | 83 | 54.406 | 21.013 | 59.135 | 1.00 23.91 |
| ATOM | 2873 | CG2 | THR | B | 83 | 54.006 | 20.709 | 56.804 | 1.00 19.27 |
| ATOM | 2874 | C | THR | B | 83 | 55.581 | 23.645 | 58.723 | 1.00 17.70 |
| ATOM | 2875 | O | THR | B | 83 | 54.598 | 24.307 | 59.062 | 1.00 19.85 |
| ATOM | 2876 | N | ARG | B | 84 | 56.768 | 23.799 | 59.299 | 1.00 17.15 |
| ATOM | 2877 | CA | ARG | B | 84 | 56.880 | 24.747 | 60.406 | 1.00 21.26 |
| ATOM | 2878 | CB | ARG | B | 84 | 58.224 | 24.629 | 61.116 | 1.00 18.18 |
| ATOM | 2879 | CG | ARG | B | 84 | 59.419 | 25.008 | 60.264 | 1.00 19.29 |
| ATOM | 2880 | CD | ARG | B | 84 | 60.737 | 24.812 | 60.999 | 1.00 26.01 |
| ATOM | 2881 | NE | ARG | B | 84 | 61.852 | 25.270 | 60.167 | 1.00 27.31 |
| ATOM | 2882 | CZ | ARG | B | 84 | 62.526 | 26.386 | 60.390 | 1.00 21.69 |
| ATOM | 2883 | NH1 | ARG | B | 84 | 62.193 | 27.161 | 61.422 | 1.00 22.24 |
| ATOM | 2884 | NH2 | ARG | B | 84 | 63.521 | 26.738 | 59.595 | 1.00 19.19 |
| ATOM | 2885 | C | ARG | B | 84 | 56.677 | 26.175 | 59.897 | 1.00 24.93 |
| ATOM | 2886 | O | ARG | B | 84 | 56.868 | 26.452 | 58.713 | 1.00 16.17 |
| ATOM | 2887 | N | VAL | B | 85 | 56.283 | 27.055 | 60.809 | 1.00 19.84 |
| ATOM | 2888 | CA | VAL | B | 85 | 56.219 | 28.487 | 60.544 | 1.00 18.69 |
| ATOM | 2889 | CB | VAL | B | 85 | 55.146 | 29.192 | 61.386 | 1.00 16.28 |
| ATOM | 2890 | CG1 | VAL | B | 85 | 55.102 | 30.685 | 61.039 | 1.00 23.59 |
| ATOM | 2891 | CG2 | VAL | B | 85 | 53.777 | 28.590 | 61.148 | 1.00 12.01 |
| ATOM | 2892 | C | VAL | B | 85 | 57.571 | 29.131 | 60.815 | 1.00 17.55 |
| ATOM | 2893 | O | VAL | B | 85 | 58.203 | 28.908 | 61.852 | 1.00 25.85 |
| ATOM | 2894 | N | LYS | B | 86 | 58.044 | 29.941 | 59.868 | 1.00 18.16 |
| ATOM | 2895 | CA | LYS | B | 86 | 59.348 | 30.575 | 60.022 | 1.00 22.13 |
| ATOM | 2896 | CB | LYS | B | 86 | 60.149 | 30.469 | 58.717 | 1.00 23.96 |
| ATOM | 2897 | CG | LYS | B | 86 | 60.650 | 29.070 | 58.416 | 1.00 23.28 |
| ATOM | 2898 | CD | LYS | B | 86 | 60.864 | 28.859 | 56.929 | 1.00 35.17 |
| ATOM | 2899 | CE | LYS | B | 86 | 61.343 | 27.446 | 56.630 | 1.00 42.63 |
| ATOM | 2900 | NZ | LYS | B | 86 | 62.795 | 27.284 | 56.931 | 1.00 62.83 |
| ATOM | 2901 | C | LYS | B | 86 | 59.240 | 32.051 | 60.400 | 1.00 25.13 |
| ATOM | 2902 | O | LYS | B | 86 | 58.381 | 32.768 | 59.867 | 1.00 22.58 |
| ATOM | 2903 | N | LEU | B | 87 | 60.112 | 32.497 | 61.294 | 1.00 23.50 |
| ATOM | 2904 | CA | LEU | B | 87 | 60.204 | 33.921 | 61.604 | 1.00 27.10 |
| ATOM | 2905 | CB | LEU | B | 87 | 60.653 | 34.189 | 63.033 | 1.00 25.75 |
| ATOM | 2906 | CG | LEU | B | 87 | 59.927 | 33.453 | 64.164 | 1.00 30.29 |
| ATOM | 2907 | CD1 | LEU | B | 87 | 60.620 | 33.695 | 65.499 | 1.00 34.70 |
| ATOM | 2908 | CD2 | LEU | B | 87 | 58.467 | 33.866 | 64.258 | 1.00 17.70 |
| ATOM | 2909 | C | LEU | B | 87 | 61.205 | 34.550 | 60.631 | 1.00 35.83 |
| ATOM | 2910 | O | LEU | B | 87 | 62.080 | 33.839 | 60.127 | 1.00 31.73 |
| ATOM | 2911 | N | SER | B | 88 | 61.082 | 35.842 | 60.383 | 1.00 37.78 |

FIGURE 158

| | | | | | | | | | |
|---|---|---|---|---|---|---|---|---|---|
| ATOM | 2912 | CA | SER | B | 88 | 62.022 | 36.595 | 59.565 | 1.00 39.22 |
| ATOM | 2913 | CB | SER | B | 88 | 61.501 | 38.024 | 59.360 | 1.00 37.70 |
| ATOM | 2914 | OG | SER | B | 88 | 62.058 | 38.842 | 60.384 | 1.00 56.30 |
| ATOM | 2915 | C | SER | B | 88 | 63.405 | 36.685 | 60.202 | 1.00 54.75 |
| ATOM | 2916 | O | SER | B | 88 | 63.540 | 36.552 | 61.419 | 1.00 56.41 |
| ATOM | 2917 | N | ASN | B | 89 | 64.420 | 36.927 | 59.382 | 1.00 75.33 |
| ATOM | 2918 | CA | ASN | B | 89 | 65.802 | 37.090 | 59.812 | 1.00 89.87 |
| ATOM | 2919 | CB | ASN | B | 89 | 66.720 | 37.253 | 58.599 | 1.00 90.11 |
| ATOM | 2920 | CG | ASN | B | 89 | 66.156 | 38.159 | 57.525 | 1.00 90.26 |
| ATOM | 2921 | OD1 | ASN | B | 89 | 65.038 | 38.666 | 57.636 | 1.00 84.88 |
| ATOM | 2922 | ND2 | ASN | B | 89 | 66.932 | 38.372 | 56.466 | 1.00 89.32 |
| ATOM | 2923 | C | ASN | B | 89 | 65.966 | 38.281 | 60.749 | 1.00 104.61 |
| ATOM | 2924 | O | ASN | B | 89 | 65.046 | 39.100 | 60.888 | 1.00 106.28 |
| ATOM | 2925 | N | VAL | B | 90 | 67.134 | 38.404 | 61.376 | 1.00 117.38 |
| ATOM | 2926 | CA | VAL | B | 90 | 67.381 | 39.480 | 62.324 | 1.00 128.11 |
| ATOM | 2927 | CB | VAL | B | 90 | 66.614 | 39.227 | 63.643 | 1.00 131.44 |
| ATOM | 2928 | CG1 | VAL | B | 90 | 65.182 | 39.743 | 63.544 | 1.00 127.66 |
| ATOM | 2929 | CG2 | VAL | B | 90 | 66.623 | 37.744 | 64.000 | 1.00 133.27 |
| ATOM | 2930 | C | VAL | B | 90 | 68.865 | 39.654 | 62.644 | 1.00 131.59 |
| ATOM | 2931 | O | VAL | B | 90 | 69.731 | 39.301 | 61.846 | 1.00 124.37 |
| ATOM | 2932 | N | ASP | B | 91 | 69.146 | 40.207 | 63.826 | 1.00 135.31 |
| ATOM | 2933 | CA | ASP | B | 91 | 70.502 | 40.379 | 64.339 | 1.00 137.26 |
| ATOM | 2934 | CB | ASP | B | 91 | 70.482 | 40.895 | 65.775 | 1.00 133.67 |
| ATOM | 2935 | CG | ASP | B | 91 | 71.529 | 41.944 | 66.104 | 1.00 129.34 |
| ATOM | 2936 | OD1 | ASP | B | 91 | 72.177 | 42.475 | 65.180 | 1.00 133.28 |
| ATOM | 2937 | OD2 | ASP | B | 91 | 71.709 | 42.256 | 67.303 | 1.00 105.69 |
| ATOM | 2938 | C | ASP | B | 91 | 71.250 | 39.050 | 64.250 | 1.00 141.41 |
| ATOM | 2939 | O | ASP | B | 91 | 70.663 | 38.007 | 64.553 | 1.00 146.90 |
| ATOM | 2940 | N | ASP | B | 92 | 72.513 | 39.087 | 63.838 | 1.00 141.54 |
| ATOM | 2941 | CA | ASP | B | 92 | 73.278 | 37.858 | 63.613 | 1.00 138.38 |
| ATOM | 2942 | CB | ASP | B | 92 | 73.621 | 37.167 | 64.928 | 1.00 136.13 |
| ATOM | 2943 | CG | ASP | B | 92 | 75.034 | 37.428 | 65.408 | 1.00 132.67 |
| ATOM | 2944 | OD1 | ASP | B | 92 | 75.913 | 37.722 | 64.570 | 1.00 132.34 |
| ATOM | 2945 | OD2 | ASP | B | 92 | 75.280 | 37.340 | 66.632 | 1.00 122.69 |
| ATOM | 2946 | C | ASP | B | 92 | 72.468 | 36.947 | 62.696 | 1.00 135.79 |
| ATOM | 2947 | O | ASP | B | 92 | 71.582 | 37.442 | 61.988 | 1.00 127.98 |
| ATOM | 2948 | N | ASP | B | 93 | 72.728 | 35.641 | 62.690 | 1.00 134.71 |
| ATOM | 2949 | CA | ASP | B | 93 | 71.890 | 34.782 | 61.848 | 1.00 133.27 |
| ATOM | 2950 | CB | ASP | B | 93 | 72.308 | 34.930 | 60.381 | 1.00 139.50 |
| ATOM | 2951 | CG | ASP | B | 93 | 71.490 | 35.955 | 59.623 | 1.00 143.40 |
| ATOM | 2952 | OD1 | ASP | B | 93 | 70.243 | 35.893 | 59.679 | 1.00 148.49 |
| ATOM | 2953 | OD2 | ASP | B | 93 | 72.087 | 36.837 | 58.963 | 1.00 144.76 |
| ATOM | 2954 | C | ASP | B | 93 | 71.922 | 33.319 | 62.260 | 1.00 125.52 |
| ATOM | 2955 | O | ASP | B | 93 | 72.239 | 32.451 | 61.438 | 1.00 114.55 |
| ATOM | 2956 | N | PRO | B | 94 | 71.590 | 32.989 | 63.500 | 1.00 122.86 |
| ATOM | 2957 | CA | PRO | B | 94 | 71.432 | 31.573 | 63.874 | 1.00 118.08 |
| ATOM | 2958 | CB | PRO | B | 94 | 71.775 | 31.592 | 65.361 | 1.00 119.79 |
| ATOM | 2959 | CG | PRO | B | 94 | 71.314 | 32.928 | 65.833 | 1.00 121.96 |
| ATOM | 2960 | CD | PRO | B | 94 | 71.339 | 33.859 | 64.657 | 1.00 123.38 |
| ATOM | 2961 | C | PRO | B | 94 | 69.991 | 31.145 | 63.644 | 1.00 109.34 |
| ATOM | 2962 | O | PRO | B | 94 | 69.324 | 31.674 | 62.746 | 1.00 96.86 |
| ATOM | 2963 | N | CYS | B | 95 | 69.466 | 30.208 | 64.436 | 1.00 101.66 |

FIGURE 159

```
ATOM   2964  CA   CYS B  95       68.051  29.878  64.254  1.00 88.82
ATOM   2965  CB   CYS B  95       67.674  28.484  64.735  1.00 90.50
ATOM   2966  SG   CYS B  95       66.393  27.656  63.760  1.00135.13
ATOM   2967  C    CYS B  95       67.191  30.918  64.979  1.00 70.52
ATOM   2968  O    CYS B  95       66.476  30.585  65.919  1.00 43.58
ATOM   2969  N    SER B  96       67.296  32.147  64.494  1.00 60.87
ATOM   2970  CA   SER B  96       66.446  33.248  64.919  1.00 51.63
ATOM   2971  CB   SER B  96       67.101  34.608  64.689  1.00 54.58
ATOM   2972  OG   SER B  96       67.550  34.751  63.352  1.00 59.05
ATOM   2973  C    SER B  96       65.124  33.166  64.152  1.00 37.78
ATOM   2974  O    SER B  96       64.267  34.025  64.352  1.00 49.18
ATOM   2975  N    ASP B  97       65.021  32.137  63.309  1.00 31.64
ATOM   2976  CA   ASP B  97       63.824  31.873  62.516  1.00 27.57
ATOM   2977  CB   ASP B  97       64.227  31.446  61.103  1.00 23.15
ATOM   2978  CG   ASP B  97       64.442  29.970  60.866  1.00 34.09
ATOM   2979  OD1  ASP B  97       64.645  29.151  61.783  1.00 28.80
ATOM   2980  OD2  ASP B  97       64.413  29.585  59.675  1.00 47.02
ATOM   2981  C    ASP B  97       62.890  30.840  63.150  1.00 18.50
ATOM   2982  O    ASP B  97       61.800  30.601  62.619  1.00 19.32
ATOM   2983  N    TYR B  98       63.315  30.229  64.254  1.00 22.52
ATOM   2984  CA   TYR B  98       62.577  29.112  64.817  1.00 19.25
ATOM   2985  CB   TYR B  98       63.509  28.066  65.493  1.00 21.90
ATOM   2986  CG   TYR B  98       62.669  26.947  66.087  1.00 23.21
ATOM   2987  CD1  TYR B  98       62.108  26.015  65.211  1.00 18.81
ATOM   2988  CE1  TYR B  98       61.328  24.979  65.683  1.00 18.20
ATOM   2989  CZ   TYR B  98       61.098  24.872  67.048  1.00 27.42
ATOM   2990  OH   TYR B  98       60.311  23.833  67.506  1.00 16.71
ATOM   2991  CE2  TYR B  98       61.630  25.785  67.929  1.00 16.10
ATOM   2992  CD2  TYR B  98       62.415  26.819  67.453  1.00 15.44
ATOM   2993  C    TYR B  98       61.524  29.537  65.833  1.00 21.92
ATOM   2994  O    TYR B  98       61.779  30.233  66.820  1.00 22.98
ATOM   2995  N    ILE B  99       60.320  29.031  65.582  1.00 16.17
ATOM   2996  CA   ILE B  99       59.284  29.019  66.598  1.00 17.96
ATOM   2997  CB   ILE B  99       58.282  30.173  66.466  1.00 18.22
ATOM   2998  CG1  ILE B  99       57.208  30.134  67.564  1.00 17.54
ATOM   2999  CD1  ILE B  99       56.327  31.368  67.580  1.00 25.26
ATOM   3000  CG2  ILE B  99       57.629  30.221  65.094  1.00 17.90
ATOM   3001  C    ILE B  99       58.551  27.679  66.534  1.00 23.11
ATOM   3002  O    ILE B  99       58.319  27.138  65.454  1.00 19.27
ATOM   3003  N    ASN B 100       58.185  27.139  67.694  1.00 23.62
ATOM   3004  CA   ASN B 100       57.381  25.908  67.687  1.00 17.64
ATOM   3005  CB   ASN B 100       57.354  25.270  69.079  1.00 18.48
ATOM   3006  CG   ASN B 100       56.794  23.863  69.078  1.00 13.37
ATOM   3007  OD1  ASN B 100       55.775  23.626  68.446  1.00 18.56
ATOM   3008  ND2  ASN B 100       57.453  22.935  69.780  1.00 17.03
ATOM   3009  C    ASN B 100       55.995  26.223  67.175  1.00 17.36
ATOM   3010  O    ASN B 100       55.058  26.498  67.938  1.00 16.80
ATOM   3011  N    ALA B 101       55.867  26.172  65.839  1.00 13.82
ATOM   3012  CA   ALA B 101       54.584  26.447  65.209  1.00  8.38
ATOM   3013  CB   ALA B 101       54.344  27.949  65.090  1.00 14.14
ATOM   3014  C    ALA B 101       54.488  25.803  63.815  1.00 10.67
ATOM   3015  O    ALA B 101       55.532  25.598  63.187  1.00 17.26
```

FIGURE 160

| | | | | | | | | | |
|---|---|---|---|---|---|---|---|---|---|
| ATOM | 3016 | N | SER | B | 102 | 53.268 | 25.514 | 63.375 | 1.00 10.49 |
| ATOM | 3017 | CA | SER | B | 102 | 53.065 | 24.791 | 62.119 | 1.00 15.63 |
| ATOM | 3018 | CB | SER | B | 102 | 52.782 | 23.308 | 62.372 | 1.00 17.37 |
| ATOM | 3019 | OG | SER | B | 102 | 53.658 | 22.704 | 63.287 | 1.00 15.04 |
| ATOM | 3020 | C | SER | B | 102 | 51.879 | 25.328 | 61.337 | 1.00 17.17 |
| ATOM | 3021 | O | SER | B | 102 | 50.844 | 25.684 | 61.902 | 1.00 18.22 |
| ATOM | 3022 | N | TYR | B | 103 | 51.990 | 25.368 | 60.011 | 1.00 16.28 |
| ATOM | 3023 | CA | TYR | B | 103 | 50.851 | 25.708 | 59.172 | 1.00 17.81 |
| ATOM | 3024 | CB | TYR | B | 103 | 51.321 | 26.133 | 57.778 | 1.00 18.72 |
| ATOM | 3025 | CG | TYR | B | 103 | 52.139 | 27.398 | 57.701 | 1.00 12.87 |
| ATOM | 3026 | CD1 | TYR | B | 103 | 51.547 | 28.633 | 57.956 | 1.00 23.49 |
| ATOM | 3027 | CE1 | TYR | B | 103 | 52.288 | 29.795 | 57.886 | 1.00 21.55 |
| ATOM | 3028 | CZ | TYR | B | 103 | 53.619 | 29.769 | 57.564 | 1.00 22.19 |
| ATOM | 3029 | OH | TYR | B | 103 | 54.334 | 30.948 | 57.499 | 1.00 32.87 |
| ATOM | 3030 | CE2 | TYR | B | 103 | 54.238 | 28.562 | 57.303 | 1.00 23.02 |
| ATOM | 3031 | CD2 | TYR | B | 103 | 53.483 | 27.400 | 57.377 | 1.00 19.58 |
| ATOM | 3032 | C | TYR | B | 103 | 49.915 | 24.504 | 59.015 | 1.00 24.37 |
| ATOM | 3033 | O | TYR | B | 103 | 50.388 | 23.378 | 58.803 | 1.00 20.89 |
| ATOM | 3034 | N | ILE | B | 104 | 48.612 | 24.720 | 59.106 | 1.00 17.36 |
| ATOM | 3035 | CA | ILE | B | 104 | 47.596 | 23.693 | 58.951 | 1.00 20.36 |
| ATOM | 3036 | CB | ILE | B | 104 | 46.894 | 23.397 | 60.301 | 1.00 24.05 |
| ATOM | 3037 | CG1 | ILE | B | 104 | 47.859 | 23.206 | 61.472 | 1.00 23.04 |
| ATOM | 3038 | CD1 | ILE | B | 104 | 48.755 | 21.992 | 61.352 | 1.00 23.46 |
| ATOM | 3039 | CG2 | ILE | B | 104 | 45.961 | 22.211 | 60.187 | 1.00 28.18 |
| ATOM | 3040 | C | ILE | B | 104 | 46.532 | 24.093 | 57.945 | 1.00 23.59 |
| ATOM | 3041 | O | ILE | B | 104 | 45.944 | 25.175 | 58.016 | 1.00 20.30 |
| ATOM | 3042 | N | PRO | B | 105 | 46.247 | 23.225 | 56.979 | 1.00 20.21 |
| ATOM | 3043 | CA | PRO | B | 105 | 45.145 | 23.455 | 56.051 | 1.00 17.40 |
| ATOM | 3044 | CB | PRO | B | 105 | 45.259 | 22.284 | 55.052 | 1.00 20.56 |
| ATOM | 3045 | CG | PRO | B | 105 | 46.684 | 21.880 | 55.173 | 1.00 22.00 |
| ATOM | 3046 | CD | PRO | B | 105 | 46.978 | 21.979 | 56.663 | 1.00 22.12 |
| ATOM | 3047 | C | PRO | B | 105 | 43.779 | 23.370 | 56.704 | 1.00 23.93 |
| ATOM | 3048 | O | PRO | B | 105 | 43.584 | 22.625 | 57.664 | 1.00 32.98 |
| ATOM | 3049 | N | GLY | B | 106 | 42.850 | 24.133 | 56.156 | 1.00 21.83 |
| ATOM | 3050 | CA | GLY | B | 106 | 41.473 | 24.095 | 56.614 | 1.00 27.14 |
| ATOM | 3051 | C | GLY | B | 106 | 40.541 | 23.642 | 55.502 | 1.00 26.84 |
| ATOM | 3052 | O | GLY | B | 106 | 40.994 | 23.136 | 54.472 | 1.00 26.33 |
| ATOM | 3053 | N | ASN | B | 107 | 39.234 | 23.821 | 55.689 | 1.00 23.33 |
| ATOM | 3054 | CA | ASN | B | 107 | 38.309 | 23.403 | 54.648 | 1.00 33.39 |
| ATOM | 3055 | CB | ASN | B | 107 | 36.859 | 23.587 | 55.104 | 1.00 40.50 |
| ATOM | 3056 | CG | ASN | B | 107 | 36.393 | 22.414 | 55.950 | 1.00 42.30 |
| ATOM | 3057 | OD1 | ASN | B | 107 | 37.022 | 21.357 | 55.975 | 1.00 50.74 |
| ATOM | 3058 | ND2 | ASN | B | 107 | 35.282 | 22.645 | 56.633 | 1.00 52.70 |
| ATOM | 3059 | C | ASN | B | 107 | 38.485 | 24.195 | 53.354 | 1.00 41.23 |
| ATOM | 3060 | O | ASN | B | 107 | 38.042 | 23.711 | 52.312 | 1.00 34.23 |
| ATOM | 3061 | N | ASN | B | 108 | 39.085 | 25.371 | 53.459 | 1.00 40.92 |
| ATOM | 3062 | CA | ASN | B | 108 | 39.051 | 26.395 | 52.426 | 1.00 31.26 |
| ATOM | 3063 | CB | ASN | B | 108 | 38.527 | 27.684 | 53.085 | 1.00 41.62 |
| ATOM | 3064 | CG | ASN | B | 108 | 37.199 | 27.416 | 53.777 | 1.00 52.11 |
| ATOM | 3065 | OD1 | ASN | B | 108 | 36.227 | 27.042 | 53.112 | 1.00 34.83 |
| ATOM | 3066 | ND2 | ASN | B | 108 | 37.163 | 27.598 | 55.094 | 1.00 31.17 |
| ATOM | 3067 | C | ASN | B | 108 | 40.386 | 26.637 | 51.756 | 1.00 31.83 |

FIGURE 161

| ATOM | 3068 | O   | ASN | B | 108 | 40.482 | 26.772 | 50.534 | 1.00 | 39.22 |
| ATOM | 3069 | N   | PHE | B | 109 | 41.468 | 26.703 | 52.531 | 1.00 | 30.33 |
| ATOM | 3070 | CA  | PHE | B | 109 | 42.774 | 26.919 | 51.911 | 1.00 | 21.96 |
| ATOM | 3071 | CB  | PHE | B | 109 | 43.085 | 28.400 | 51.749 | 1.00 | 20.80 |
| ATOM | 3072 | CG  | PHE | B | 109 | 42.708 | 29.329 | 52.890 | 1.00 | 28.79 |
| ATOM | 3073 | CD1 | PHE | B | 109 | 43.692 | 29.911 | 53.674 | 1.00 | 25.92 |
| ATOM | 3074 | CE1 | PHE | B | 109 | 43.376 | 30.759 | 54.718 | 1.00 | 31.45 |
| ATOM | 3075 | CZ  | PHE | B | 109 | 42.054 | 31.055 | 54.993 | 1.00 | 37.19 |
| ATOM | 3076 | CE2 | PHE | B | 109 | 41.064 | 30.476 | 54.218 | 1.00 | 41.01 |
| ATOM | 3077 | CD2 | PHE | B | 109 | 41.386 | 29.628 | 53.175 | 1.00 | 32.74 |
| ATOM | 3078 | C   | PHE | B | 109 | 43.860 | 26.236 | 52.741 | 1.00 | 20.75 |
| ATOM | 3079 | O   | PHE | B | 109 | 43.593 | 25.834 | 53.871 | 1.00 | 23.61 |
| ATOM | 3080 | N   | ARG | B | 110 | 45.045 | 26.137 | 52.178 | 1.00 | 19.49 |
| ATOM | 3081 | CA  | ARG | B | 110 | 46.176 | 25.416 | 52.710 | 1.00 | 22.84 |
| ATOM | 3082 | CB  | ARG | B | 110 | 47.210 | 25.227 | 51.575 | 1.00 | 21.99 |
| ATOM | 3083 | CG  | ARG | B | 110 | 46.634 | 24.284 | 50.511 | 1.00 | 30.90 |
| ATOM | 3084 | CD  | ARG | B | 110 | 47.726 | 23.349 | 50.019 | 1.00 | 39.83 |
| ATOM | 3085 | NE  | ARG | B | 110 | 47.226 | 22.405 | 49.014 | 1.00 | 54.08 |
| ATOM | 3086 | CZ  | ARG | B | 110 | 47.347 | 21.087 | 49.185 | 1.00 | 72.63 |
| ATOM | 3087 | NH1 | ARG | B | 110 | 47.930 | 20.619 | 50.282 | 1.00 | 79.88 |
| ATOM | 3088 | NH2 | ARG | B | 110 | 46.889 | 20.253 | 48.262 | 1.00 | 87.83 |
| ATOM | 3089 | C   | ARG | B | 110 | 46.863 | 26.073 | 53.890 | 1.00 | 29.52 |
| ATOM | 3090 | O   | ARG | B | 110 | 47.454 | 25.377 | 54.728 | 1.00 | 28.77 |
| ATOM | 3091 | N   | ARG | B | 111 | 46.847 | 27.402 | 53.997 | 1.00 | 20.01 |
| ATOM | 3092 | CA  | ARG | B | 111 | 47.476 | 27.910 | 55.233 | 1.00 | 24.11 |
| ATOM | 3093 | CB  | ARG | B | 111 | 48.635 | 28.837 | 54.943 | 1.00 | 22.68 |
| ATOM | 3094 | CG  | ARG | B | 111 | 49.880 | 28.255 | 54.313 | 1.00 | 19.86 |
| ATOM | 3095 | CD  | ARG | B | 111 | 50.961 | 29.325 | 54.127 | 1.00 | 25.94 |
| ATOM | 3096 | NE  | ARG | B | 111 | 52.272 | 28.701 | 53.923 | 1.00 | 30.60 |
| ATOM | 3097 | CZ  | ARG | B | 111 | 53.449 | 29.295 | 54.017 | 1.00 | 21.38 |
| ATOM | 3098 | NH1 | ARG | B | 111 | 53.524 | 30.583 | 54.324 | 1.00 | 42.58 |
| ATOM | 3099 | NH2 | ARG | B | 111 | 54.570 | 28.620 | 53.808 | 1.00 | 29.00 |
| ATOM | 3100 | C   | ARG | B | 111 | 46.398 | 28.613 | 56.060 | 1.00 | 21.97 |
| ATOM | 3101 | O   | ARG | B | 111 | 46.481 | 29.791 | 56.388 | 1.00 | 19.77 |
| ATOM | 3102 | N   | GLU | B | 112 | 45.354 | 27.865 | 56.383 | 1.00 | 16.17 |
| ATOM | 3103 | CA  | GLU | B | 112 | 44.185 | 28.417 | 57.045 | 1.00 | 16.65 |
| ATOM | 3104 | CB  | GLU | B | 112 | 42.994 | 27.458 | 56.911 | 1.00 | 17.98 |
| ATOM | 3105 | CG  | GLU | B | 112 | 41.678 | 28.188 | 57.126 | 1.00 | 27.35 |
| ATOM | 3106 | CD  | GLU | B | 112 | 40.479 | 27.519 | 56.495 | 1.00 | 27.95 |
| ATOM | 3107 | OE1 | GLU | B | 112 | 39.370 | 27.881 | 56.934 | 1.00 | 28.26 |
| ATOM | 3108 | OE2 | GLU | B | 112 | 40.609 | 26.665 | 55.596 | 1.00 | 25.50 |
| ATOM | 3109 | C   | GLU | B | 112 | 44.461 | 28.700 | 58.518 | 1.00 | 23.99 |
| ATOM | 3110 | O   | GLU | B | 112 | 43.974 | 29.662 | 59.122 | 1.00 | 19.68 |
| ATOM | 3111 | N   | TYR | B | 113 | 45.280 | 27.832 | 59.107 | 1.00 | 19.82 |
| ATOM | 3112 | CA  | TYR | B | 113 | 45.597 | 28.015 | 60.522 | 1.00 | 17.80 |
| ATOM | 3113 | CB  | TYR | B | 113 | 44.940 | 26.997 | 61.450 | 1.00 | 25.68 |
| ATOM | 3114 | CG  | TYR | B | 113 | 43.505 | 26.647 | 61.175 | 1.00 | 20.88 |
| ATOM | 3115 | CD1 | TYR | B | 113 | 43.208 | 25.633 | 60.274 | 1.00 | 19.21 |
| ATOM | 3116 | CE1 | TYR | B | 113 | 41.902 | 25.283 | 60.002 | 1.00 | 20.32 |
| ATOM | 3117 | CZ  | TYR | B | 113 | 40.871 | 25.942 | 60.626 | 1.00 | 20.68 |
| ATOM | 3118 | OH  | TYR | B | 113 | 39.572 | 25.584 | 60.345 | 1.00 | 24.62 |
| ATOM | 3119 | CE2 | TYR | B | 113 | 41.133 | 26.956 | 61.534 | 1.00 | 14.80 |

FIGURE 162

| ATOM | 3120 | CD2 | TYR | B | 113 | 42.450 | 27.300 | 61.802 | 1.00 | 15.14 |
| ATOM | 3121 | C | TYR | B | 113 | 47.090 | 27.916 | 60.726 | 1.00 | 11.85 |
| ATOM | 3122 | O | TYR | B | 113 | 47.865 | 27.314 | 59.989 | 1.00 | 18.08 |
| ATOM | 3123 | N | ILE | B | 114 | 47.491 | 28.590 | 61.805 | 1.00 | 17.37 |
| ATOM | 3124 | CA | ILE | B | 114 | 48.801 | 28.423 | 62.389 | 1.00 | 12.30 |
| ATOM | 3125 | CB | ILE | B | 114 | 49.576 | 29.751 | 62.490 | 1.00 | 19.28 |
| ATOM | 3126 | CG1 | ILE | B | 114 | 50.011 | 30.240 | 61.102 | 1.00 | 19.55 |
| ATOM | 3127 | CD1 | ILE | B | 114 | 51.019 | 31.347 | 61.037 | 1.00 | 18.32 |
| ATOM | 3128 | CG2 | ILE | B | 114 | 50.722 | 29.619 | 63.473 | 1.00 | 10.43 |
| ATOM | 3129 | C | ILE | B | 114 | 48.607 | 27.809 | 63.771 | 1.00 | 13.65 |
| ATOM | 3130 | O | ILE | B | 114 | 47.920 | 28.374 | 64.607 | 1.00 | 20.47 |
| ATOM | 3131 | N | VAL | B | 115 | 49.207 | 26.630 | 63.960 | 1.00 | 18.21 |
| ATOM | 3132 | CA | VAL | B | 115 | 49.068 | 25.982 | 65.260 | 1.00 | 21.54 |
| ATOM | 3133 | CB | VAL | B | 115 | 48.724 | 24.487 | 65.134 | 1.00 | 26.76 |
| ATOM | 3134 | CG1 | VAL | B | 115 | 49.151 | 23.747 | 66.394 | 1.00 | 21.17 |
| ATOM | 3135 | CG2 | VAL | B | 115 | 47.236 | 24.353 | 64.859 | 1.00 | 23.83 |
| ATOM | 3136 | C | VAL | B | 115 | 50.366 | 26.144 | 66.018 | 1.00 | 15.13 |
| ATOM | 3137 | O | VAL | B | 115 | 51.470 | 26.092 | 65.484 | 1.00 | 15.47 |
| ATOM | 3138 | N | THR | B | 116 | 50.255 | 26.378 | 67.328 | 1.00 | 14.92 |
| ATOM | 3139 | CA | THR | B | 116 | 51.530 | 26.594 | 68.022 | 1.00 | 12.65 |
| ATOM | 3140 | CB | THR | B | 116 | 51.927 | 28.078 | 67.913 | 1.00 | 16.69 |
| ATOM | 3141 | OG1 | THR | B | 116 | 53.253 | 28.333 | 68.385 | 1.00 | 15.71 |
| ATOM | 3142 | CG2 | THR | B | 116 | 50.956 | 28.910 | 68.764 | 1.00 | 17.43 |
| ATOM | 3143 | C | THR | B | 116 | 51.360 | 26.112 | 69.463 | 1.00 | 11.03 |
| ATOM | 3144 | O | THR | B | 116 | 50.246 | 25.848 | 69.902 | 1.00 | 11.09 |
| ATOM | 3145 | N | GLN | B | 117 | 52.459 | 25.961 | 70.161 | 1.00 | 12.28 |
| ATOM | 3146 | CA | GLN | B | 117 | 52.444 | 25.635 | 71.579 | 1.00 | 13.83 |
| ATOM | 3147 | CB | GLN | B | 117 | 53.863 | 25.230 | 71.985 | 1.00 | 14.30 |
| ATOM | 3148 | CG | GLN | B | 117 | 54.898 | 26.324 | 71.994 | 1.00 | 10.96 |
| ATOM | 3149 | CD | GLN | B | 117 | 56.300 | 25.936 | 72.377 | 1.00 | 19.11 |
| ATOM | 3150 | OE1 | GLN | B | 117 | 56.676 | 24.759 | 72.435 | 1.00 | 18.55 |
| ATOM | 3151 | NE2 | GLN | B | 117 | 57.164 | 26.915 | 72.649 | 1.00 | 17.68 |
| ATOM | 3152 | C | GLN | B | 117 | 51.991 | 26.834 | 72.400 | 1.00 | 20.95 |
| ATOM | 3153 | O | GLN | B | 117 | 52.025 | 27.946 | 71.859 | 1.00 | 14.87 |
| ATOM | 3154 | N | GLY | B | 118 | 51.630 | 26.648 | 73.666 | 1.00 | 14.16 |
| ATOM | 3155 | CA | GLY | B | 118 | 51.461 | 27.815 | 74.553 | 1.00 | 11.25 |
| ATOM | 3156 | C | GLY | B | 118 | 52.809 | 28.483 | 74.732 | 1.00 | 11.67 |
| ATOM | 3157 | O | GLY | B | 118 | 53.804 | 27.871 | 75.122 | 1.00 | 18.12 |
| ATOM | 3158 | N | PRO | B | 119 | 52.897 | 29.771 | 74.383 | 1.00 | 15.72 |
| ATOM | 3159 | CA | PRO | B | 119 | 54.165 | 30.499 | 74.473 | 1.00 | 17.34 |
| ATOM | 3160 | CB | PRO | B | 119 | 53.761 | 31.941 | 74.150 | 1.00 | 18.05 |
| ATOM | 3161 | CG | PRO | B | 119 | 52.540 | 31.802 | 73.307 | 1.00 | 16.94 |
| ATOM | 3162 | CD | PRO | B | 119 | 51.802 | 30.606 | 73.862 | 1.00 | 18.02 |
| ATOM | 3163 | C | PRO | B | 119 | 54.767 | 30.441 | 75.878 | 1.00 | 12.82 |
| ATOM | 3164 | O | PRO | B | 119 | 54.020 | 30.432 | 76.865 | 1.00 | 17.29 |
| ATOM | 3165 | N | LEU | B | 120 | 56.088 | 30.366 | 75.889 | 1.00 | 22.15 |
| ATOM | 3166 | CA | LEU | B | 120 | 56.900 | 30.382 | 77.094 | 1.00 | 25.66 |
| ATOM | 3167 | CB | LEU | B | 120 | 58.171 | 29.551 | 76.952 | 1.00 | 21.93 |
| ATOM | 3168 | CG | LEU | B | 120 | 57.984 | 28.079 | 76.585 | 1.00 | 26.05 |
| ATOM | 3169 | CD1 | LEU | B | 120 | 59.239 | 27.508 | 75.941 | 1.00 | 24.09 |
| ATOM | 3170 | CD2 | LEU | B | 120 | 57.592 | 27.308 | 77.828 | 1.00 | 25.20 |
| ATOM | 3171 | C | LEU | B | 120 | 57.275 | 31.832 | 77.417 | 1.00 | 23.76 |

FIGURE 163

```
ATOM   3172  O    LEU B 120      57.201  32.682  76.533  1.00  21.98
ATOM   3173  N    PRO B 121      57.659  32.087  78.659  1.00  19.89
ATOM   3174  CA   PRO B 121      58.151  33.418  79.028  1.00  22.32
ATOM   3175  CB   PRO B 121      58.751  33.181  80.415  1.00  25.42
ATOM   3176  CG   PRO B 121      57.957  32.033  80.964  1.00  28.77
ATOM   3177  CD   PRO B 121      57.648  31.145  79.793  1.00  23.68
ATOM   3178  C    PRO B 121      59.228  33.871  78.048  1.00  24.84
ATOM   3179  O    PRO B 121      59.278  35.032  77.646  1.00  28.28
ATOM   3180  N    GLY B 122      60.083  32.929  77.647  1.00  24.79
ATOM   3181  CA   GLY B 122      61.164  33.214  76.738  1.00  26.40
ATOM   3182  C    GLY B 122      60.850  33.227  75.260  1.00  19.61
ATOM   3183  O    GLY B 122      61.744  33.609  74.493  1.00  26.22
ATOM   3184  N    THR B 123      59.660  32.849  74.813  1.00  19.28
ATOM   3185  CA   THR B 123      59.353  32.851  73.388  1.00  21.38
ATOM   3186  CB   THR B 123      59.009  31.450  72.839  1.00  17.49
ATOM   3187  OG1  THR B 123      57.825  30.952  73.499  1.00  18.47
ATOM   3188  CG2  THR B 123      60.136  30.465  73.099  1.00  21.69
ATOM   3189  C    THR B 123      58.182  33.770  73.092  1.00  18.63
ATOM   3190  O    THR B 123      57.760  33.895  71.942  1.00  21.10
ATOM   3191  N    LYS B 124      57.616  34.408  74.128  1.00  17.85
ATOM   3192  CA   LYS B 124      56.401  35.150  73.790  1.00  19.83
ATOM   3193  CB   LYS B 124      55.659  35.684  74.999  1.00  20.67
ATOM   3194  CG   LYS B 124      56.454  36.481  76.010  1.00  22.46
ATOM   3195  CD   LYS B 124      55.540  36.754  77.204  1.00  32.02
ATOM   3196  CE   LYS B 124      56.234  37.523  78.317  1.00  34.93
ATOM   3197  NZ   LYS B 124      55.312  37.592  79.499  1.00  34.71
ATOM   3198  C    LYS B 124      56.716  36.320  72.843  1.00  17.31
ATOM   3199  O    LYS B 124      55.797  36.775  72.162  1.00  18.88
ATOM   3200  N    ASP B 125      57.972  36.753  72.843  1.00  22.11
ATOM   3201  CA   ASP B 125      58.311  37.850  71.919  1.00  32.47
ATOM   3202  CB   ASP B 125      59.648  38.486  72.278  1.00  25.76
ATOM   3203  CG   ASP B 125      59.590  39.330  73.544  1.00  26.93
ATOM   3204  OD1  ASP B 125      58.487  39.534  74.093  1.00  23.69
ATOM   3205  OD2  ASP B 125      60.656  39.797  73.994  1.00  34.33
ATOM   3206  C    ASP B 125      58.275  37.287  70.500  1.00  25.35
ATOM   3207  O    ASP B 125      57.755  37.900  69.568  1.00  20.65
ATOM   3208  N    ASP B 126      58.823  36.085  70.361  1.00  23.45
ATOM   3209  CA   ASP B 126      58.740  35.345  69.103  1.00  28.27
ATOM   3210  CB   ASP B 126      59.416  33.982  69.251  1.00  31.70
ATOM   3211  CG   ASP B 126      60.912  34.025  69.453  1.00  37.78
ATOM   3212  OD1  ASP B 126      61.567  34.998  69.021  1.00  35.70
ATOM   3213  OD2  ASP B 126      61.452  33.065  70.055  1.00  41.12
ATOM   3214  C    ASP B 126      57.297  35.155  68.655  1.00  24.03
ATOM   3215  O    ASP B 126      56.928  35.305  67.484  1.00  21.60
ATOM   3216  N    PHE B 127      56.418  34.780  69.586  1.00  19.45
ATOM   3217  CA   PHE B 127      55.017  34.576  69.246  1.00  18.59
ATOM   3218  CB   PHE B 127      54.220  34.196  70.505  1.00  15.64
ATOM   3219  CG   PHE B 127      52.714  34.146  70.345  1.00  18.56
ATOM   3220  CD1  PHE B 127      52.137  32.939  69.936  1.00  16.99
ATOM   3221  CE1  PHE B 127      50.771  32.846  69.790  1.00  15.74
ATOM   3222  CZ   PHE B 127      49.941  33.925  70.023  1.00  21.60
ATOM   3223  CE2  PHE B 127      50.506  35.127  70.433  1.00  14.92
```

FIGURE 164

| ATOM | 3224 | CD2 | PHE | B | 127 | 51.865 | 35.219 | 70.593 | 1.00 | 11.80 |
| --- | --- | --- | --- | --- | --- | --- | --- | --- | --- | --- |
| ATOM | 3225 | C | PHE | B | 127 | 54.417 | 35.835 | 68.628 | 1.00 | 15.63 |
| ATOM | 3226 | O | PHE | B | 127 | 53.711 | 35.819 | 67.627 | 1.00 | 14.92 |
| ATOM | 3227 | N | TRP | B | 128 | 54.630 | 36.977 | 69.295 | 1.00 | 14.67 |
| ATOM | 3228 | CA | TRP | B | 128 | 53.959 | 38.186 | 68.805 | 1.00 | 16.59 |
| ATOM | 3229 | CB | TRP | B | 128 | 53.990 | 39.330 | 69.835 | 1.00 | 14.86 |
| ATOM | 3230 | CG | TRP | B | 128 | 52.966 | 39.089 | 70.927 | 1.00 | 13.08 |
| ATOM | 3231 | CD1 | TRP | B | 128 | 53.298 | 38.867 | 72.240 | 1.00 | 14.73 |
| ATOM | 3232 | NE1 | TRP | B | 128 | 52.169 | 38.677 | 72.995 | 1.00 | 12.11 |
| ATOM | 3233 | CE2 | TRP | B | 128 | 51.074 | 38.775 | 72.179 | 1.00 | 13.55 |
| ATOM | 3234 | CD2 | TRP | B | 128 | 51.542 | 39.029 | 70.874 | 1.00 | 12.42 |
| ATOM | 3235 | CE3 | TRP | B | 128 | 50.575 | 39.166 | 69.868 | 1.00 | 13.65 |
| ATOM | 3236 | CZ3 | TRP | B | 128 | 49.246 | 39.052 | 70.168 | 1.00 | 19.72 |
| ATOM | 3237 | CH2 | TRP | B | 128 | 48.814 | 38.796 | 71.482 | 1.00 | 22.04 |
| ATOM | 3238 | CZ2 | TRP | B | 128 | 49.725 | 38.655 | 72.495 | 1.00 | 19.42 |
| ATOM | 3239 | C | TRP | B | 128 | 54.577 | 38.581 | 67.460 | 1.00 | 13.73 |
| ATOM | 3240 | O | TRP | B | 128 | 53.849 | 39.046 | 66.583 | 1.00 | 22.69 |
| ATOM | 3241 | N | LYS | B | 129 | 55.877 | 38.373 | 67.292 | 1.00 | 16.55 |
| ATOM | 3242 | CA | LYS | B | 129 | 56.523 | 38.666 | 66.013 | 1.00 | 19.71 |
| ATOM | 3243 | CB | LYS | B | 129 | 58.015 | 38.363 | 66.108 | 1.00 | 22.40 |
| ATOM | 3244 | CG | LYS | B | 129 | 58.811 | 38.769 | 64.883 | 1.00 | 25.13 |
| ATOM | 3245 | CD | LYS | B | 129 | 60.267 | 38.316 | 64.882 | 1.00 | 28.99 |
| ATOM | 3246 | CE | LYS | B | 129 | 60.695 | 38.135 | 63.426 | 1.00 | 37.78 |
| ATOM | 3247 | NZ | LYS | B | 129 | 62.137 | 37.915 | 63.203 | 1.00 | 37.99 |
| ATOM | 3248 | C | LYS | B | 129 | 55.856 | 37.871 | 64.893 | 1.00 | 32.26 |
| ATOM | 3249 | O | LYS | B | 129 | 55.560 | 38.383 | 63.811 | 1.00 | 23.65 |
| ATOM | 3250 | N | MET | B | 130 | 55.586 | 36.593 | 65.147 | 1.00 | 23.24 |
| ATOM | 3251 | CA | MET | B | 130 | 54.908 | 35.732 | 64.180 | 1.00 | 23.01 |
| ATOM | 3252 | CB | MET | B | 130 | 54.804 | 34.277 | 64.673 | 1.00 | 20.78 |
| ATOM | 3253 | CG | MET | B | 130 | 53.968 | 33.376 | 63.751 | 1.00 | 16.92 |
| ATOM | 3254 | SD | MET | B | 130 | 53.852 | 31.724 | 64.483 | 1.00 | 24.92 |
| ATOM | 3255 | CE | MET | B | 130 | 52.612 | 31.968 | 65.746 | 1.00 | 15.70 |
| ATOM | 3256 | C | MET | B | 130 | 53.516 | 36.249 | 63.878 | 1.00 | 16.75 |
| ATOM | 3257 | O | MET | B | 130 | 53.068 | 36.268 | 62.733 | 1.00 | 21.38 |
| ATOM | 3258 | N | VAL | B | 131 | 52.799 | 36.648 | 64.923 | 1.00 | 14.58 |
| ATOM | 3259 | CA | VAL | B | 131 | 51.451 | 37.179 | 64.697 | 1.00 | 11.14 |
| ATOM | 3260 | CB | VAL | B | 131 | 50.818 | 37.503 | 66.056 | 1.00 | 24.53 |
| ATOM | 3261 | CG1 | VAL | B | 131 | 49.602 | 38.413 | 65.954 | 1.00 | 18.70 |
| ATOM | 3262 | CG2 | VAL | B | 131 | 50.452 | 36.195 | 66.761 | 1.00 | 13.43 |
| ATOM | 3263 | C | VAL | B | 131 | 51.546 | 38.398 | 63.773 | 1.00 | 16.31 |
| ATOM | 3264 | O | VAL | B | 131 | 50.746 | 38.556 | 62.845 | 1.00 | 23.18 |
| ATOM | 3265 | N | TRP | B | 132 | 52.527 | 39.248 | 64.033 | 1.00 | 21.92 |
| ATOM | 3266 | CA | TRP | B | 132 | 52.707 | 40.480 | 63.256 | 1.00 | 28.19 |
| ATOM | 3267 | CB | TRP | B | 132 | 53.735 | 41.385 | 63.925 | 1.00 | 16.64 |
| ATOM | 3268 | CG | TRP | B | 132 | 54.047 | 42.651 | 63.178 | 1.00 | 32.79 |
| ATOM | 3269 | CD1 | TRP | B | 132 | 55.127 | 42.862 | 62.368 | 1.00 | 31.98 |
| ATOM | 3270 | NE1 | TRP | B | 132 | 55.094 | 44.132 | 61.851 | 1.00 | 28.50 |
| ATOM | 3271 | CE2 | TRP | B | 132 | 53.983 | 44.776 | 62.318 | 1.00 | 33.94 |
| ATOM | 3272 | CD2 | TRP | B | 132 | 53.299 | 43.876 | 63.159 | 1.00 | 30.28 |
| ATOM | 3273 | CE3 | TRP | B | 132 | 52.112 | 44.298 | 63.769 | 1.00 | 34.50 |
| ATOM | 3274 | CZ3 | TRP | B | 132 | 51.663 | 45.586 | 63.522 | 1.00 | 38.33 |
| ATOM | 3275 | CH2 | TRP | B | 132 | 52.373 | 46.450 | 62.681 | 1.00 | 35.73 |

FIGURE 165

| | | | | | | | | | |
|---|---|---|---|---|---|---|---|---|---|
| ATOM | 3276 | CZ2 | TRP | B | 132 | 53.535 | 46.073 | 62.065 | 1.00 39.63 |
| ATOM | 3277 | C | TRP | B | 132 | 53.126 | 40.162 | 61.823 | 1.00 30.15 |
| ATOM | 3278 | O | TRP | B | 132 | 52.480 | 40.618 | 60.883 | 1.00 22.50 |
| ATOM | 3279 | N | GLU | B | 133 | 54.185 | 39.377 | 61.636 | 1.00 27.59 |
| ATOM | 3280 | CA | GLU | B | 133 | 54.620 | 39.019 | 60.289 | 1.00 24.71 |
| ATOM | 3281 | CB | GLU | B | 133 | 55.914 | 38.198 | 60.359 | 1.00 21.40 |
| ATOM | 3282 | CG | GLU | B | 133 | 56.932 | 38.826 | 61.304 | 1.00 27.89 |
| ATOM | 3283 | CD | GLU | B | 133 | 58.303 | 38.200 | 61.158 | 1.00 32.83 |
| ATOM | 3284 | OE1 | GLU | B | 133 | 58.377 | 36.959 | 61.046 | 1.00 36.49 |
| ATOM | 3285 | OE2 | GLU | B | 133 | 59.287 | 38.963 | 61.157 | 1.00 38.19 |
| ATOM | 3286 | C | GLU | B | 133 | 53.583 | 38.245 | 59.492 | 1.00 28.74 |
| ATOM | 3287 | O | GLU | B | 133 | 53.540 | 38.416 | 58.266 | 1.00 22.81 |
| ATOM | 3288 | N | GLN | B | 134 | 52.763 | 37.406 | 60.128 | 1.00 20.49 |
| ATOM | 3289 | CA | GLN | B | 134 | 51.817 | 36.563 | 59.392 | 1.00 16.15 |
| ATOM | 3290 | CB | GLN | B | 134 | 51.619 | 35.216 | 60.088 | 1.00 20.39 |
| ATOM | 3291 | CG | GLN | B | 134 | 52.869 | 34.348 | 60.135 | 1.00 23.00 |
| ATOM | 3292 | CD | GLN | B | 134 | 53.168 | 33.663 | 58.815 | 1.00 29.61 |
| ATOM | 3293 | OE1 | GLN | B | 134 | 52.258 | 33.147 | 58.166 | 1.00 37.61 |
| ATOM | 3294 | NE2 | GLN | B | 134 | 54.437 | 33.658 | 58.425 | 1.00 26.32 |
| ATOM | 3295 | C | GLN | B | 134 | 50.466 | 37.236 | 59.220 | 1.00 19.93 |
| ATOM | 3296 | O | GLN | B | 134 | 49.519 | 36.586 | 58.783 | 1.00 24.92 |
| ATOM | 3297 | N | ASN | B | 135 | 50.372 | 38.515 | 59.575 | 1.00 20.36 |
| ATOM | 3298 | CA | ASN | B | 135 | 49.118 | 39.244 | 59.402 | 1.00 18.42 |
| ATOM | 3299 | CB | ASN | B | 135 | 48.860 | 39.385 | 57.893 | 1.00 28.65 |
| ATOM | 3300 | CG | ASN | B | 135 | 50.072 | 40.027 | 57.229 | 1.00 39.16 |
| ATOM | 3301 | OD1 | ASN | B | 135 | 50.454 | 41.140 | 57.596 | 1.00 35.15 |
| ATOM | 3302 | ND2 | ASN | B | 135 | 50.693 | 39.350 | 56.271 | 1.00 39.15 |
| ATOM | 3303 | C | ASN | B | 135 | 47.956 | 38.565 | 60.092 | 1.00 21.37 |
| ATOM | 3304 | O | ASN | B | 135 | 46.828 | 38.506 | 59.609 | 1.00 20.97 |
| ATOM | 3305 | N | VAL | B | 136 | 48.226 | 38.024 | 61.282 | 1.00 23.56 |
| ATOM | 3306 | CA | VAL | B | 136 | 47.159 | 37.346 | 62.021 | 1.00 22.94 |
| ATOM | 3307 | CB | VAL | B | 136 | 47.773 | 36.475 | 63.134 | 1.00 19.22 |
| ATOM | 3308 | CG1 | VAL | B | 136 | 46.690 | 35.933 | 64.043 | 1.00 20.50 |
| ATOM | 3309 | CG2 | VAL | B | 136 | 48.621 | 35.365 | 62.511 | 1.00 13.95 |
| ATOM | 3310 | C | VAL | B | 136 | 46.210 | 38.363 | 62.640 | 1.00 19.65 |
| ATOM | 3311 | O | VAL | B | 136 | 46.679 | 39.369 | 63.195 | 1.00 23.44 |
| ATOM | 3312 | N | HIS | B | 137 | 44.914 | 38.117 | 62.542 | 1.00 15.94 |
| ATOM | 3313 | CA | HIS | B | 137 | 43.919 | 38.956 | 63.175 | 1.00 22.68 |
| ATOM | 3314 | CB | HIS | B | 137 | 42.921 | 39.537 | 62.162 | 1.00 32.34 |
| ATOM | 3315 | CG | HIS | B | 137 | 43.539 | 40.472 | 61.174 | 1.00 50.91 |
| ATOM | 3316 | ND1 | HIS | B | 137 | 42.795 | 41.144 | 60.227 | 1.00 62.67 |
| ATOM | 3317 | CE1 | HIS | B | 137 | 43.597 | 41.891 | 59.487 | 1.00 61.13 |
| ATOM | 3318 | NE2 | HIS | B | 137 | 44.835 | 41.728 | 59.922 | 1.00 55.36 |
| ATOM | 3319 | CD2 | HIS | B | 137 | 44.823 | 40.845 | 60.971 | 1.00 46.21 |
| ATOM | 3320 | C | HIS | B | 137 | 43.129 | 38.192 | 64.237 | 1.00 21.18 |
| ATOM | 3321 | O | HIS | B | 137 | 42.446 | 38.847 | 65.029 | 1.00 25.91 |
| ATOM | 3322 | N | ASN | B | 138 | 43.200 | 36.861 | 64.239 | 1.00 20.71 |
| ATOM | 3323 | CA | ASN | B | 138 | 42.435 | 36.117 | 65.251 | 1.00 20.35 |
| ATOM | 3324 | CB | ASN | B | 138 | 41.167 | 35.466 | 64.683 | 1.00 19.57 |
| ATOM | 3325 | CG | ASN | B | 138 | 40.246 | 36.482 | 64.038 | 1.00 25.55 |
| ATOM | 3326 | OD1 | ASN | B | 138 | 40.149 | 36.530 | 62.809 | 1.00 32.78 |
| ATOM | 3327 | ND2 | ASN | B | 138 | 39.593 | 37.321 | 64.827 | 1.00 15.27 |

FIGURE 166

| | | | | | | | | | |
|---|---|---|---|---|---|---|---|---|---|
| ATOM | 3328 | C | ASN | B | 138 | 43.316 | 35.057 | 65.905 | 1.00 16.32 |
| ATOM | 3329 | O | ASN | B | 138 | 44.016 | 34.315 | 65.217 | 1.00 22.33 |
| ATOM | 3330 | N | ILE | B | 139 | 43.256 | 35.021 | 67.224 | 1.00 12.38 |
| ATOM | 3331 | CA | ILE | B | 139 | 43.981 | 34.065 | 68.039 | 1.00 13.90 |
| ATOM | 3332 | CB | ILE | B | 139 | 45.010 | 34.736 | 68.966 | 1.00 17.37 |
| ATOM | 3333 | CG1 | ILE | B | 139 | 46.050 | 35.606 | 68.246 | 1.00 18.49 |
| ATOM | 3334 | CD1 | ILE | B | 139 | 47.007 | 36.323 | 69.166 | 1.00 12.78 |
| ATOM | 3335 | CG2 | ILE | B | 139 | 45.702 | 33.693 | 69.832 | 1.00 17.74 |
| ATOM | 3336 | C | ILE | B | 139 | 43.005 | 33.252 | 68.883 | 1.00 21.32 |
| ATOM | 3337 | O | ILE | B | 139 | 42.141 | 33.824 | 69.551 | 1.00 17.35 |
| ATOM | 3338 | N | VAL | B | 140 | 43.161 | 31.923 | 68.805 | 1.00 13.24 |
| ATOM | 3339 | CA | VAL | B | 140 | 42.268 | 31.051 | 69.568 | 1.00 16.27 |
| ATOM | 3340 | CB | VAL | B | 140 | 41.494 | 30.072 | 68.677 | 1.00 27.64 |
| ATOM | 3341 | CG1 | VAL | B | 140 | 40.663 | 29.111 | 69.518 | 1.00 15.58 |
| ATOM | 3342 | CG2 | VAL | B | 140 | 40.592 | 30.819 | 67.697 | 1.00 23.20 |
| ATOM | 3343 | C | VAL | B | 140 | 43.114 | 30.311 | 70.610 | 1.00 18.13 |
| ATOM | 3344 | O | VAL | B | 140 | 44.176 | 29.761 | 70.291 | 1.00 14.05 |
| ATOM | 3345 | N | MET | B | 141 | 42.658 | 30.324 | 71.870 | 1.00 13.85 |
| ATOM | 3346 | CA | MET | B | 141 | 43.424 | 29.744 | 72.969 | 1.00 17.23 |
| ATOM | 3347 | CB | MET | B | 141 | 43.894 | 30.844 | 73.939 | 1.00 16.81 |
| ATOM | 3348 | CG | MET | B | 141 | 44.730 | 30.340 | 75.094 | 1.00 16.69 |
| ATOM | 3349 | SD | MET | B | 141 | 45.484 | 31.660 | 76.071 | 1.00 18.21 |
| ATOM | 3350 | CE | MET | B | 141 | 46.209 | 30.676 | 77.403 | 1.00 22.43 |
| ATOM | 3351 | C | MET | B | 141 | 42.539 | 28.740 | 73.681 | 1.00 18.04 |
| ATOM | 3352 | O | MET | B | 141 | 41.502 | 29.159 | 74.204 | 1.00 23.03 |
| ATOM | 3353 | N | VAL | B | 142 | 42.894 | 27.450 | 73.708 | 1.00 13.36 |
| ATOM | 3354 | CA | VAL | B | 142 | 41.913 | 26.540 | 74.325 | 1.00 13.57 |
| ATOM | 3355 | CB | VAL | B | 142 | 41.368 | 25.488 | 73.342 | 1.00 16.78 |
| ATOM | 3356 | CG1 | VAL | B | 142 | 40.352 | 26.126 | 72.403 | 1.00 25.66 |
| ATOM | 3357 | CG2 | VAL | B | 142 | 42.526 | 24.857 | 72.591 | 1.00 22.06 |
| ATOM | 3358 | C | VAL | B | 142 | 42.536 | 25.823 | 75.513 | 1.00 15.54 |
| ATOM | 3359 | O | VAL | B | 142 | 42.224 | 24.690 | 75.854 | 1.00 36.13 |
| ATOM | 3360 | N | THR | B | 143 | 43.443 | 26.538 | 76.161 | 1.00 19.81 |
| ATOM | 3361 | CA | THR | B | 143 | 44.013 | 26.054 | 77.415 | 1.00 23.30 |
| ATOM | 3362 | CB | THR | B | 143 | 45.474 | 25.625 | 77.268 | 1.00 20.98 |
| ATOM | 3363 | OG1 | THR | B | 143 | 45.916 | 24.941 | 78.455 | 1.00 20.64 |
| ATOM | 3364 | CG2 | THR | B | 143 | 46.363 | 26.856 | 77.104 | 1.00 18.59 |
| ATOM | 3365 | C | THR | B | 143 | 43.915 | 27.174 | 78.445 | 1.00 27.90 |
| ATOM | 3366 | O | THR | B | 143 | 43.801 | 28.343 | 78.083 | 1.00 18.82 |
| ATOM | 3367 | N | GLN | B | 144 | 43.972 | 26.814 | 79.720 | 1.00 24.18 |
| ATOM | 3368 | CA | GLN | B | 144 | 44.194 | 27.849 | 80.726 | 1.00 26.49 |
| ATOM | 3369 | CB | GLN | B | 144 | 43.490 | 27.554 | 82.038 | 1.00 25.93 |
| ATOM | 3370 | CG | GLN | B | 144 | 41.973 | 27.692 | 81.972 | 1.00 31.81 |
| ATOM | 3371 | CD | GLN | B | 144 | 41.409 | 27.232 | 83.315 | 1.00 43.70 |
| ATOM | 3372 | OE1 | GLN | B | 144 | 41.157 | 28.059 | 84.185 | 1.00 50.17 |
| ATOM | 3373 | NE2 | GLN | B | 144 | 41.251 | 25.923 | 83.447 | 1.00 42.17 |
| ATOM | 3374 | C | GLN | B | 144 | 45.701 | 27.911 | 80.950 | 1.00 21.88 |
| ATOM | 3375 | O | GLN | B | 144 | 46.371 | 26.926 | 80.618 | 1.00 18.20 |
| ATOM | 3376 | N | CYS | B | 145 | 46.176 | 29.017 | 81.502 | 1.00 17.45 |
| ATOM | 3377 | CA | CYS | B | 145 | 47.594 | 29.207 | 81.718 | 1.00 13.43 |
| ATOM | 3378 | CB | CYS | B | 145 | 47.853 | 30.629 | 82.221 | 1.00 20.41 |
| ATOM | 3379 | SG | CYS | B | 145 | 47.629 | 31.851 | 80.891 | 1.00 23.38 |

FIGURE 167

| ATOM | 3380 | C | CYS | B | 145 | 48.151 | 28.198 | 82.726 | 1.00 | 13.94 |
|------|------|-----|-----|---|-----|--------|--------|--------|------|-------|
| ATOM | 3381 | O | CYS | B | 145 | 49.278 | 27.738 | 82.611 | 1.00 | 14.73 |
| ATOM | 3382 | N | VAL | B | 146 | 47.320 | 27.912 | 83.716 | 1.00 | 19.10 |
| ATOM | 3383 | CA | VAL | B | 146 | 47.674 | 26.994 | 84.798 | 1.00 | 21.25 |
| ATOM | 3384 | CB | VAL | B | 146 | 48.116 | 27.718 | 86.081 | 1.00 | 23.42 |
| ATOM | 3385 | CG1 | VAL | B | 146 | 48.515 | 26.713 | 87.163 | 1.00 | 17.61 |
| ATOM | 3386 | CG2 | VAL | B | 146 | 49.270 | 28.661 | 85.793 | 1.00 | 20.80 |
| ATOM | 3387 | C | VAL | B | 146 | 46.449 | 26.145 | 85.081 | 1.00 | 19.88 |
| ATOM | 3388 | O | VAL | B | 146 | 45.355 | 26.702 | 85.219 | 1.00 | 21.18 |
| ATOM | 3389 | N | GLU | B | 147 | 46.590 | 24.824 | 85.132 | 1.00 | 18.68 |
| ATOM | 3390 | CA | GLU | B | 147 | 45.398 | 24.012 | 85.422 | 1.00 | 18.49 |
| ATOM | 3391 | CB | GLU | B | 147 | 45.048 | 23.119 | 84.225 | 1.00 | 21.59 |
| ATOM | 3392 | CG | GLU | B | 147 | 44.374 | 23.905 | 83.116 | 1.00 | 23.43 |
| ATOM | 3393 | CD | GLU | B | 147 | 44.162 | 23.234 | 81.785 | 1.00 | 38.61 |
| ATOM | 3394 | OE1 | GLU | B | 147 | 44.493 | 22.040 | 81.618 | 1.00 | 34.89 |
| ATOM | 3395 | OE2 | GLU | B | 147 | 43.636 | 23.926 | 80.870 | 1.00 | 30.39 |
| ATOM | 3396 | C | GLU | B | 147 | 45.675 | 23.194 | 86.675 | 1.00 | 22.32 |
| ATOM | 3397 | O | GLU | B | 147 | 46.589 | 22.361 | 86.632 | 1.00 | 27.28 |
| ATOM | 3398 | N | LYS | B | 148 | 44.956 | 23.423 | 87.767 | 1.00 | 30.22 |
| ATOM | 3399 | CA | LYS | B | 148 | 45.226 | 22.630 | 88.976 | 1.00 | 32.97 |
| ATOM | 3400 | CB | LYS | B | 148 | 44.850 | 21.169 | 88.720 | 1.00 | 39.67 |
| ATOM | 3401 | CG | LYS | B | 148 | 43.346 | 20.947 | 88.598 | 1.00 | 44.29 |
| ATOM | 3402 | CD | LYS | B | 148 | 43.029 | 19.958 | 87.489 | 1.00 | 44.33 |
| ATOM | 3403 | CE | LYS | B | 148 | 41.527 | 19.780 | 87.325 | 1.00 | 49.46 |
| ATOM | 3404 | NZ | LYS | B | 148 | 41.028 | 20.351 | 86.043 | 1.00 | 61.43 |
| ATOM | 3405 | C | LYS | B | 148 | 46.681 | 22.757 | 89.395 | 1.00 | 28.17 |
| ATOM | 3406 | O | LYS | B | 148 | 47.401 | 21.830 | 89.761 | 1.00 | 28.44 |
| ATOM | 3407 | N | GLY | B | 149 | 47.163 | 24.001 | 89.303 | 1.00 | 19.82 |
| ATOM | 3408 | CA | GLY | B | 149 | 48.533 | 24.259 | 89.642 | 1.00 | 14.78 |
| ATOM | 3409 | C | GLY | B | 149 | 49.550 | 23.826 | 88.611 | 1.00 | 25.79 |
| ATOM | 3410 | O | GLY | B | 149 | 50.723 | 24.180 | 88.775 | 1.00 | 24.43 |
| ATOM | 3411 | N | ARG | B | 150 | 49.192 | 23.090 | 87.559 | 1.00 | 24.49 |
| ATOM | 3412 | CA | ARG | B | 150 | 50.193 | 22.668 | 86.579 | 1.00 | 21.93 |
| ATOM | 3413 | CB | ARG | B | 150 | 49.803 | 21.317 | 85.965 | 1.00 | 24.07 |
| ATOM | 3414 | CG | ARG | B | 150 | 49.775 | 20.179 | 86.980 | 1.00 | 28.42 |
| ATOM | 3415 | CD | ARG | B | 150 | 49.328 | 18.870 | 86.341 | 1.00 | 38.83 |
| ATOM | 3416 | NE | ARG | B | 150 | 48.126 | 18.371 | 87.014 | 1.00 | 49.80 |
| ATOM | 3417 | CZ | ARG | B | 150 | 46.904 | 18.817 | 86.738 | 1.00 | 54.11 |
| ATOM | 3418 | NH1 | ARG | B | 150 | 46.718 | 19.752 | 85.811 | 1.00 | 48.84 |
| ATOM | 3419 | NH2 | ARG | B | 150 | 45.865 | 18.319 | 87.394 | 1.00 | 45.18 |
| ATOM | 3420 | C | ARG | B | 150 | 50.346 | 23.708 | 85.467 | 1.00 | 15.49 |
| ATOM | 3421 | O | ARG | B | 150 | 49.325 | 24.039 | 84.872 | 1.00 | 23.49 |
| ATOM | 3422 | N | VAL | B | 151 | 51.543 | 24.202 | 85.215 | 1.00 | 18.22 |
| ATOM | 3423 | CA | VAL | B | 151 | 51.760 | 25.224 | 84.188 | 1.00 | 20.43 |
| ATOM | 3424 | CB | VAL | B | 151 | 53.188 | 25.789 | 84.283 | 1.00 | 27.81 |
| ATOM | 3425 | CG1 | VAL | B | 151 | 53.440 | 26.853 | 83.216 | 1.00 | 35.66 |
| ATOM | 3426 | CG2 | VAL | B | 151 | 53.439 | 26.378 | 85.667 | 1.00 | 24.07 |
| ATOM | 3427 | C | VAL | B | 151 | 51.513 | 24.667 | 82.790 | 1.00 | 23.20 |
| ATOM | 3428 | O | VAL | B | 151 | 52.059 | 23.622 | 82.440 | 1.00 | 19.63 |
| ATOM | 3429 | N | LYS | B | 152 | 50.707 | 25.370 | 82.006 | 1.00 | 24.64 |
| ATOM | 3430 | CA | LYS | B | 152 | 50.357 | 24.963 | 80.651 | 1.00 | 14.29 |
| ATOM | 3431 | CB | LYS | B | 152 | 48.860 | 24.691 | 80.517 | 1.00 | 10.40 |

FIGURE 168

| | | | | | | | | | |
|---|---|---|---|---|---|---|---|---|---|
| ATOM | 3432 | CG | LYS | B | 152 | 48.253 | 23.776 | 81.578 | 1.00 17.03 |
| ATOM | 3433 | CD | LYS | B | 152 | 48.788 | 22.349 | 81.417 | 1.00 21.83 |
| ATOM | 3434 | CE | LYS | B | 152 | 47.958 | 21.386 | 82.264 | 1.00 22.06 |
| ATOM | 3435 | NZ | LYS | B | 152 | 48.298 | 19.972 | 81.959 | 1.00 36.68 |
| ATOM | 3436 | C | LYS | B | 152 | 50.754 | 26.040 | 79.644 | 1.00 24.64 |
| ATOM | 3437 | O | LYS | B | 152 | 51.009 | 25.763 | 78.468 | 1.00 18.65 |
| ATOM | 3438 | N | CYS | B | 153 | 50.803 | 27.314 | 80.047 | 1.00 11.48 |
| ATOM | 3439 | CA | CYS | B | 153 | 51.051 | 28.334 | 79.016 | 1.00 12.40 |
| ATOM | 3440 | CB | CYS | B | 153 | 49.804 | 28.484 | 78.135 | 1.00 12.34 |
| ATOM | 3441 | SG | CYS | B | 153 | 49.930 | 29.808 | 76.878 | 1.00 18.57 |
| ATOM | 3442 | C | CYS | B | 153 | 51.402 | 29.647 | 79.697 | 1.00 21.82 |
| ATOM | 3443 | O | CYS | B | 153 | 50.893 | 29.972 | 80.777 | 1.00 18.60 |
| ATOM | 3444 | N | ASP | B | 154 | 52.295 | 30.439 | 79.135 | 1.00 16.73 |
| ATOM | 3445 | CA | ASP | B | 154 | 52.588 | 31.722 | 79.807 | 1.00 16.66 |
| ATOM | 3446 | CB | ASP | B | 154 | 53.893 | 32.268 | 79.253 | 1.00 17.86 |
| ATOM | 3447 | CG | ASP | B | 154 | 54.346 | 33.504 | 80.006 | 1.00 28.26 |
| ATOM | 3448 | OD1 | ASP | B | 154 | 54.311 | 34.561 | 79.347 | 1.00 32.47 |
| ATOM | 3449 | OD2 | ASP | B | 154 | 54.693 | 33.396 | 81.199 | 1.00 26.75 |
| ATOM | 3450 | C | ASP | B | 154 | 51.417 | 32.676 | 79.644 | 1.00 19.16 |
| ATOM | 3451 | O | ASP | B | 154 | 50.633 | 32.566 | 78.696 | 1.00 19.76 |
| ATOM | 3452 | N | HIS | B | 155 | 51.254 | 33.609 | 80.583 | 1.00 18.37 |
| ATOM | 3453 | CA | HIS | B | 155 | 50.258 | 34.666 | 80.434 | 1.00 19.93 |
| ATOM | 3454 | CB | HIS | B | 155 | 49.911 | 35.303 | 81.787 | 1.00 13.95 |
| ATOM | 3455 | CG | HIS | B | 155 | 48.744 | 36.236 | 81.679 | 1.00 17.38 |
| ATOM | 3456 | ND1 | HIS | B | 155 | 47.470 | 35.952 | 82.137 | 1.00 21.90 |
| ATOM | 3457 | CE1 | HIS | B | 155 | 46.665 | 36.975 | 81.889 | 1.00 23.51 |
| ATOM | 3458 | NE2 | HIS | B | 155 | 47.376 | 37.912 | 81.278 | 1.00 25.28 |
| ATOM | 3459 | CD2 | HIS | B | 155 | 48.669 | 37.476 | 81.135 | 1.00 15.32 |
| ATOM | 3460 | C | HIS | B | 155 | 50.871 | 35.672 | 79.468 | 1.00 23.82 |
| ATOM | 3461 | O | HIS | B | 155 | 51.437 | 36.664 | 79.913 | 1.00 26.73 |
| ATOM | 3462 | N | TYR | B | 156 | 50.820 | 35.411 | 78.158 | 1.00 12.99 |
| ATOM | 3463 | CA | TYR | B | 156 | 51.669 | 36.173 | 77.258 | 1.00 17.64 |
| ATOM | 3464 | CB | TYR | B | 156 | 51.996 | 35.306 | 76.025 | 1.00 17.34 |
| ATOM | 3465 | CG | TYR | B | 156 | 50.780 | 34.829 | 75.270 | 1.00 14.33 |
| ATOM | 3466 | CD1 | TYR | B | 156 | 50.206 | 35.541 | 74.233 | 1.00 9.88 |
| ATOM | 3467 | CE1 | TYR | B | 156 | 49.095 | 35.057 | 73.566 | 1.00 17.37 |
| ATOM | 3468 | CZ | TYR | B | 156 | 48.537 | 33.843 | 73.912 | 1.00 16.91 |
| ATOM | 3469 | OH | TYR | B | 156 | 47.427 | 33.352 | 73.252 | 1.00 16.15 |
| ATOM | 3470 | CE2 | TYR | B | 156 | 49.095 | 33.107 | 74.941 | 1.00 16.17 |
| ATOM | 3471 | CD2 | TYR | B | 156 | 50.202 | 33.597 | 75.603 | 1.00 19.17 |
| ATOM | 3472 | C | TYR | B | 156 | 51.099 | 37.488 | 76.740 | 1.00 15.11 |
| ATOM | 3473 | O | TYR | B | 156 | 51.731 | 38.066 | 75.839 | 1.00 17.69 |
| ATOM | 3474 | N | TRP | B | 157 | 49.973 | 37.913 | 77.257 | 1.00 20.44 |
| ATOM | 3475 | CA | TRP | B | 157 | 49.317 | 39.185 | 76.948 | 1.00 22.51 |
| ATOM | 3476 | CB | TRP | B | 157 | 47.941 | 38.916 | 76.355 | 1.00 19.87 |
| ATOM | 3477 | CG | TRP | B | 157 | 46.985 | 38.298 | 77.330 | 1.00 19.72 |
| ATOM | 3478 | CD1 | TRP | B | 157 | 46.114 | 38.986 | 78.133 | 1.00 21.12 |
| ATOM | 3479 | NE1 | TRP | B | 157 | 45.393 | 38.102 | 78.898 | 1.00 21.03 |
| ATOM | 3480 | CE2 | TRP | B | 157 | 45.787 | 36.823 | 78.596 | 1.00 22.01 |
| ATOM | 3481 | CD2 | TRP | B | 157 | 46.788 | 36.910 | 77.612 | 1.00 21.27 |
| ATOM | 3482 | CE3 | TRP | B | 157 | 47.353 | 35.722 | 77.140 | 1.00 15.87 |
| ATOM | 3483 | CZ3 | TRP | B | 157 | 46.911 | 34.519 | 77.650 | 1.00 21.70 |

FIGURE 169

| | | | | | | | | | |
|---|---|---|---|---|---|---|---|---|---|
| ATOM | 3484 | CH2 | TRP | B | 157 | 45.909 | 34.468 | 78.629 | 1.00 22.88 |
| ATOM | 3485 | CZ2 | TRP | B | 157 | 45.339 | 35.614 | 79.114 | 1.00 25.47 |
| ATOM | 3486 | C | TRP | B | 157 | 49.245 | 40.010 | 78.227 | 1.00 31.95 |
| ATOM | 3487 | O | TRP | B | 157 | 49.455 | 39.413 | 79.292 | 1.00 26.71 |
| ATOM | 3488 | N | PRO | B | 158 | 48.992 | 41.310 | 78.208 | 1.00 31.73 |
| ATOM | 3489 | CA | PRO | B | 158 | 49.055 | 42.131 | 79.423 | 1.00 27.67 |
| ATOM | 3490 | CB | PRO | B | 158 | 48.882 | 43.564 | 78.893 | 1.00 33.72 |
| ATOM | 3491 | CG | PRO | B | 158 | 49.181 | 43.472 | 77.432 | 1.00 33.76 |
| ATOM | 3492 | CD | PRO | B | 158 | 48.645 | 42.119 | 77.021 | 1.00 35.38 |
| ATOM | 3493 | C | PRO | B | 158 | 47.944 | 41.845 | 80.427 | 1.00 34.39 |
| ATOM | 3494 | O | PRO | B | 158 | 46.852 | 41.408 | 80.064 | 1.00 43.08 |
| ATOM | 3495 | N | ALA | B | 159 | 48.213 | 42.100 | 81.706 | 1.00 42.13 |
| ATOM | 3496 | CA | ALA | B | 159 | 47.276 | 41.840 | 82.796 | 1.00 36.27 |
| ATOM | 3497 | CB | ALA | B | 159 | 47.929 | 42.175 | 84.134 | 1.00 24.16 |
| ATOM | 3498 | C | ALA | B | 159 | 45.986 | 42.624 | 82.659 | 1.00 36.43 |
| ATOM | 3499 | O | ALA | B | 159 | 44.871 | 42.160 | 82.889 | 1.00 36.44 |
| ATOM | 3500 | N | ASP | B | 160 | 46.124 | 43.889 | 82.264 | 1.00 30.03 |
| ATOM | 3501 | CA | ASP | B | 160 | 44.940 | 44.748 | 82.237 | 1.00 35.84 |
| ATOM | 3502 | CB | ASP | B | 160 | 44.838 | 45.506 | 83.566 | 1.00 38.86 |
| ATOM | 3503 | CG | ASP | B | 160 | 46.127 | 46.268 | 83.835 | 1.00 40.84 |
| ATOM | 3504 | OD1 | ASP | B | 160 | 46.496 | 47.091 | 82.969 | 1.00 44.84 |
| ATOM | 3505 | OD2 | ASP | B | 160 | 46.760 | 46.038 | 84.883 | 1.00 45.44 |
| ATOM | 3506 | C | ASP | B | 160 | 45.033 | 45.682 | 81.045 | 1.00 34.03 |
| ATOM | 3507 | O | ASP | B | 160 | 45.484 | 45.251 | 79.981 | 1.00 35.16 |
| ATOM | 3508 | N | GLN | B | 161 | 44.646 | 46.947 | 81.174 | 1.00 31.44 |
| ATOM | 3509 | CA | GLN | B | 161 | 44.665 | 47.795 | 79.971 | 1.00 37.31 |
| ATOM | 3510 | CB | GLN | B | 161 | 43.443 | 48.713 | 79.958 | 1.00 48.77 |
| ATOM | 3511 | CG | GLN | B | 161 | 42.113 | 48.002 | 80.141 | 1.00 63.63 |
| ATOM | 3512 | CD | GLN | B | 161 | 41.545 | 47.351 | 78.898 | 1.00 66.46 |
| ATOM | 3513 | OE1 | GLN | B | 161 | 41.702 | 47.819 | 77.769 | 1.00 73.28 |
| ATOM | 3514 | NE2 | GLN | B | 161 | 40.851 | 46.230 | 79.085 | 1.00 44.47 |
| ATOM | 3515 | C | GLN | B | 161 | 45.959 | 48.574 | 79.868 | 1.00 30.80 |
| ATOM | 3516 | O | GLN | B | 161 | 46.164 | 49.414 | 78.991 | 1.00 30.61 |
| ATOM | 3517 | N | ASP | B | 162 | 46.927 | 48.325 | 80.752 | 1.00 31.03 |
| ATOM | 3518 | CA | ASP | B | 162 | 48.201 | 49.018 | 80.507 | 1.00 39.93 |
| ATOM | 3519 | CB | ASP | B | 162 | 49.077 | 49.016 | 81.756 | 1.00 50.93 |
| ATOM | 3520 | CG | ASP | B | 162 | 49.441 | 47.616 | 82.213 | 1.00 68.18 |
| ATOM | 3521 | OD1 | ASP | B | 162 | 48.998 | 46.637 | 81.574 | 1.00 86.94 |
| ATOM | 3522 | OD2 | ASP | B | 162 | 50.176 | 47.492 | 83.218 | 1.00 99.89 |
| ATOM | 3523 | C | ASP | B | 162 | 48.904 | 48.357 | 79.324 | 1.00 39.36 |
| ATOM | 3524 | O | ASP | B | 162 | 48.627 | 47.197 | 79.014 | 1.00 54.50 |
| ATOM | 3525 | N | SER | B | 163 | 49.796 | 49.081 | 78.659 | 1.00 29.38 |
| ATOM | 3526 | CA | SER | B | 163 | 50.522 | 48.555 | 77.510 | 1.00 24.30 |
| ATOM | 3527 | CB | SER | B | 163 | 50.671 | 49.686 | 76.476 | 1.00 24.27 |
| ATOM | 3528 | OG | SER | B | 163 | 51.323 | 50.772 | 77.118 | 1.00 33.50 |
| ATOM | 3529 | C | SER | B | 163 | 51.887 | 47.999 | 77.867 | 1.00 27.40 |
| ATOM | 3530 | O | SER | B | 163 | 52.500 | 48.320 | 78.886 | 1.00 30.35 |
| ATOM | 3531 | N | LEU | B | 164 | 52.412 | 47.131 | 77.004 | 1.00 22.69 |
| ATOM | 3532 | CA | LEU | B | 164 | 53.721 | 46.549 | 77.197 | 1.00 23.41 |
| ATOM | 3533 | CB | LEU | B | 164 | 53.666 | 45.205 | 77.926 | 1.00 32.71 |
| ATOM | 3534 | CG | LEU | B | 164 | 53.276 | 45.168 | 79.401 | 1.00 41.07 |
| ATOM | 3535 | CD1 | LEU | B | 164 | 52.777 | 43.780 | 79.796 | 1.00 39.52 |

FIGURE 170

| | | | | | | | | | |
|---|---|---|---|---|---|---|---|---|---|
| ATOM | 3536 | CD2 | LEU | B | 164 | 54.432 | 45.565 | 80.311 | 1.00 34.59 |
| ATOM | 3537 | C | LEU | B | 164 | 54.400 | 46.334 | 75.839 | 1.00 19.77 |
| ATOM | 3538 | O | LEU | B | 164 | 53.727 | 46.182 | 74.820 | 1.00 25.31 |
| ATOM | 3539 | N | TYR | B | 165 | 55.717 | 46.327 | 75.881 | 1.00 22.94 |
| ATOM | 3540 | CA | TYR | B | 165 | 56.537 | 45.961 | 74.752 | 1.00 22.36 |
| ATOM | 3541 | CB | TYR | B | 165 | 57.888 | 46.643 | 74.765 | 1.00 18.40 |
| ATOM | 3542 | CG | TYR | B | 165 | 57.974 | 48.100 | 74.409 | 1.00 29.19 |
| ATOM | 3543 | CD1 | TYR | B | 165 | 57.965 | 49.067 | 75.410 | 1.00 33.88 |
| ATOM | 3544 | CE1 | TYR | B | 165 | 58.049 | 50.410 | 75.103 | 1.00 30.20 |
| ATOM | 3545 | CZ | TYR | B | 165 | 58.150 | 50.803 | 73.792 | 1.00 29.95 |
| ATOM | 3546 | OH | TYR | B | 165 | 58.232 | 52.144 | 73.492 | 1.00 23.81 |
| ATOM | 3547 | CE2 | TYR | B | 165 | 58.167 | 49.866 | 72.780 | 1.00 32.37 |
| ATOM | 3548 | CD2 | TYR | B | 165 | 58.082 | 48.525 | 73.091 | 1.00 29.59 |
| ATOM | 3549 | C | TYR | B | 165 | 56.812 | 44.448 | 74.759 | 1.00 28.65 |
| ATOM | 3550 | O | TYR | B | 165 | 57.094 | 43.855 | 75.793 | 1.00 27.24 |
| ATOM | 3551 | N | TYR | B | 166 | 56.752 | 43.893 | 73.562 | 1.00 26.38 |
| ATOM | 3552 | CA | TYR | B | 166 | 57.169 | 42.527 | 73.276 | 1.00 23.90 |
| ATOM | 3553 | CB | TYR | B | 166 | 55.962 | 41.650 | 73.008 | 1.00 20.88 |
| ATOM | 3554 | CG | TYR | B | 166 | 54.973 | 41.508 | 74.140 | 1.00 22.61 |
| ATOM | 3555 | CD1 | TYR | B | 166 | 55.113 | 40.482 | 75.076 | 1.00 21.82 |
| ATOM | 3556 | CE1 | TYR | B | 166 | 54.199 | 40.362 | 76.101 | 1.00 17.08 |
| ATOM | 3557 | CZ | TYR | B | 166 | 53.148 | 41.235 | 76.224 | 1.00 19.26 |
| ATOM | 3558 | OH | TYR | B | 166 | 52.255 | 41.100 | 77.248 | 1.00 19.82 |
| ATOM | 3559 | CE2 | TYR | B | 166 | 52.976 | 42.262 | 75.313 | 1.00 22.80 |
| ATOM | 3560 | CD2 | TYR | B | 166 | 53.901 | 42.367 | 74.291 | 1.00 23.91 |
| ATOM | 3561 | C | TYR | B | 166 | 58.105 | 42.598 | 72.069 | 1.00 15.01 |
| ATOM | 3562 | O | TYR | B | 166 | 57.616 | 42.676 | 70.943 | 1.00 23.20 |
| ATOM | 3563 | N | GLY | B | 167 | 59.399 | 42.596 | 72.328 | 1.00 23.31 |
| ATOM | 3564 | CA | GLY | B | 167 | 60.399 | 42.819 | 71.301 | 1.00 30.99 |
| ATOM | 3565 | C | GLY | B | 167 | 60.278 | 44.237 | 70.754 | 1.00 32.92 |
| ATOM | 3566 | O | GLY | B | 167 | 60.252 | 45.223 | 71.498 | 1.00 31.28 |
| ATOM | 3567 | N | ASP | B | 168 | 60.195 | 44.348 | 69.432 | 1.00 24.47 |
| ATOM | 3568 | CA | ASP | B | 168 | 60.036 | 45.656 | 68.810 | 1.00 30.37 |
| ATOM | 3569 | CB | ASP | B | 168 | 60.661 | 45.694 | 67.414 | 1.00 35.10 |
| ATOM | 3570 | CG | ASP | B | 168 | 62.142 | 45.378 | 67.460 | 1.00 42.09 |
| ATOM | 3571 | OD1 | ASP | B | 168 | 62.723 | 45.550 | 68.550 | 1.00 47.47 |
| ATOM | 3572 | OD2 | ASP | B | 168 | 62.684 | 44.966 | 66.414 | 1.00 47.31 |
| ATOM | 3573 | C | ASP | B | 168 | 58.570 | 46.022 | 68.666 | 1.00 29.02 |
| ATOM | 3574 | O | ASP | B | 168 | 58.240 | 46.976 | 67.967 | 1.00 37.58 |
| ATOM | 3575 | N | LEU | B | 169 | 57.674 | 45.259 | 69.296 | 1.00 24.88 |
| ATOM | 3576 | CA | LEU | B | 169 | 56.265 | 45.583 | 69.132 | 1.00 19.15 |
| ATOM | 3577 | CB | LEU | B | 169 | 55.436 | 44.377 | 68.702 | 1.00 29.37 |
| ATOM | 3578 | CG | LEU | B | 169 | 55.736 | 43.693 | 67.375 | 1.00 33.58 |
| ATOM | 3579 | CD1 | LEU | B | 169 | 55.206 | 42.262 | 67.367 | 1.00 22.11 |
| ATOM | 3580 | CD2 | LEU | B | 169 | 55.145 | 44.492 | 66.220 | 1.00 40.24 |
| ATOM | 3581 | C | LEU | B | 169 | 55.705 | 46.081 | 70.461 | 1.00 18.08 |
| ATOM | 3582 | O | LEU | B | 169 | 56.260 | 45.744 | 71.498 | 1.00 30.36 |
| ATOM | 3583 | N | ILE | B | 170 | 54.625 | 46.828 | 70.374 | 1.00 23.85 |
| ATOM | 3584 | CA | ILE | B | 170 | 53.900 | 47.229 | 71.571 | 1.00 29.93 |
| ATOM | 3585 | CB | ILE | B | 170 | 53.947 | 48.744 | 71.817 | 1.00 31.71 |
| ATOM | 3586 | CG1 | ILE | B | 170 | 53.316 | 49.167 | 73.144 | 1.00 36.34 |
| ATOM | 3587 | CD1 | ILE | B | 170 | 54.269 | 49.867 | 74.084 | 1.00 48.77 |

FIGURE 171

| ATOM | 3588 | CG2 | ILE | B | 170 | 53.304 | 49.482 | 70.662 | 1.00 | 37.89 |
| --- | --- | --- | --- | --- | --- | --- | --- | --- | --- | --- |
| ATOM | 3589 | C | ILE | B | 170 | 52.460 | 46.757 | 71.433 | 1.00 | 30.07 |
| ATOM | 3590 | O | ILE | B | 170 | 51.841 | 46.853 | 70.374 | 1.00 | 29.12 |
| ATOM | 3591 | N | LEU | B | 171 | 51.955 | 46.223 | 72.535 | 1.00 | 25.46 |
| ATOM | 3592 | CA | LEU | B | 171 | 50.604 | 45.701 | 72.589 | 1.00 | 21.46 |
| ATOM | 3593 | CB | LEU | B | 171 | 50.612 | 44.200 | 72.895 | 1.00 | 29.41 |
| ATOM | 3594 | CG | LEU | B | 171 | 50.226 | 43.287 | 71.727 | 1.00 | 39.01 |
| ATOM | 3595 | CD1 | LEU | B | 171 | 51.391 | 43.140 | 70.758 | 1.00 | 43.97 |
| ATOM | 3596 | CD2 | LEU | B | 171 | 49.774 | 41.940 | 72.246 | 1.00 | 47.22 |
| ATOM | 3597 | C | LEU | B | 171 | 49.805 | 46.423 | 73.668 | 1.00 | 25.20 |
| ATOM | 3598 | O | LEU | B | 171 | 50.337 | 46.746 | 74.734 | 1.00 | 26.76 |
| ATOM | 3599 | N | GLN | B | 172 | 48.536 | 46.660 | 73.377 | 1.00 | 22.79 |
| ATOM | 3600 | CA | GLN | B | 172 | 47.630 | 47.237 | 74.358 | 1.00 | 37.17 |
| ATOM | 3601 | CB | GLN | B | 172 | 47.376 | 48.734 | 74.126 | 1.00 | 40.40 |
| ATOM | 3602 | CG | GLN | B | 172 | 46.844 | 49.424 | 75.378 | 1.00 | 50.87 |
| ATOM | 3603 | CD | GLN | B | 172 | 46.684 | 50.924 | 75.272 | 1.00 | 51.56 |
| ATOM | 3604 | OE1 | GLN | B | 172 | 46.258 | 51.440 | 74.240 | 1.00 | 46.34 |
| ATOM | 3605 | NE2 | GLN | B | 172 | 47.013 | 51.651 | 76.339 | 1.00 | 33.78 |
| ATOM | 3606 | C | GLN | B | 172 | 46.300 | 46.486 | 74.342 | 1.00 | 38.38 |
| ATOM | 3607 | O | GLN | B | 172 | 45.611 | 46.417 | 73.322 | 1.00 | 24.25 |
| ATOM | 3608 | N | MET | B | 173 | 45.967 | 45.927 | 75.511 | 1.00 | 30.63 |
| ATOM | 3609 | CA | MET | B | 173 | 44.650 | 45.325 | 75.643 | 1.00 | 25.80 |
| ATOM | 3610 | CB | MET | B | 173 | 44.534 | 44.392 | 76.853 | 1.00 | 20.42 |
| ATOM | 3611 | CG | MET | B | 173 | 43.257 | 43.557 | 76.754 | 1.00 | 26.50 |
| ATOM | 3612 | SD | MET | B | 173 | 43.176 | 42.237 | 77.997 | 1.00 | 36.50 |
| ATOM | 3613 | CE | MET | B | 173 | 42.811 | 43.236 | 79.442 | 1.00 | 44.10 |
| ATOM | 3614 | C | MET | B | 173 | 43.598 | 46.437 | 75.729 | 1.00 | 38.57 |
| ATOM | 3615 | O | MET | B | 173 | 43.630 | 47.252 | 76.654 | 1.00 | 49.37 |
| ATOM | 3616 | N | LEU | B | 174 | 42.707 | 46.443 | 74.754 | 1.00 | 32.34 |
| ATOM | 3617 | CA | LEU | B | 174 | 41.663 | 47.434 | 74.587 | 1.00 | 32.40 |
| ATOM | 3618 | CB | LEU | B | 174 | 41.355 | 47.609 | 73.093 | 1.00 | 27.63 |
| ATOM | 3619 | CG | LEU | B | 174 | 41.749 | 48.955 | 72.490 | 1.00 | 42.29 |
| ATOM | 3620 | CD1 | LEU | B | 174 | 42.587 | 48.766 | 71.239 | 1.00 | 52.03 |
| ATOM | 3621 | CD2 | LEU | B | 174 | 40.490 | 49.769 | 72.215 | 1.00 | 46.08 |
| ATOM | 3622 | C | LEU | B | 174 | 40.384 | 47.037 | 75.305 | 1.00 | 41.65 |
| ATOM | 3623 | O | LEU | B | 174 | 39.616 | 47.862 | 75.795 | 1.00 | 43.69 |
| ATOM | 3624 | N | SER | B | 175 | 40.165 | 45.721 | 75.328 | 1.00 | 28.31 |
| ATOM | 3625 | CA | SER | B | 175 | 38.911 | 45.204 | 75.845 | 1.00 | 21.60 |
| ATOM | 3626 | CB | SER | B | 175 | 37.807 | 45.343 | 74.801 | 1.00 | 21.97 |
| ATOM | 3627 | OG | SER | B | 175 | 37.672 | 44.133 | 74.073 | 1.00 | 61.12 |
| ATOM | 3628 | C | SER | B | 175 | 39.059 | 43.732 | 76.238 | 1.00 | 31.76 |
| ATOM | 3629 | O | SER | B | 175 | 39.831 | 43.018 | 75.598 | 1.00 | 21.28 |
| ATOM | 3630 | N | GLU | B | 176 | 38.305 | 43.370 | 77.266 | 1.00 | 32.04 |
| ATOM | 3631 | CA | GLU | B | 176 | 38.286 | 42.031 | 77.838 | 1.00 | 33.85 |
| ATOM | 3632 | CB | GLU | B | 176 | 39.330 | 41.927 | 78.969 | 1.00 | 27.59 |
| ATOM | 3633 | CG | GLU | B | 176 | 39.308 | 40.570 | 79.654 | 1.00 | 29.03 |
| ATOM | 3634 | CD | GLU | B | 176 | 40.283 | 40.373 | 80.782 | 1.00 | 40.65 |
| ATOM | 3635 | OE1 | GLU | B | 176 | 39.972 | 40.727 | 81.940 | 1.00 | 49.86 |
| ATOM | 3636 | OE2 | GLU | B | 176 | 41.389 | 39.838 | 80.534 | 1.00 | 40.12 |
| ATOM | 3637 | C | GLU | B | 176 | 36.889 | 41.675 | 78.328 | 1.00 | 39.65 |
| ATOM | 3638 | O | GLU | B | 176 | 36.400 | 42.226 | 79.318 | 1.00 | 44.09 |
| ATOM | 3639 | N | SER | B | 177 | 36.195 | 40.757 | 77.654 | 1.00 | 38.39 |

FIGURE 172

| | | | | | | | | | |
|---|---|---|---|---|---|---|---|---|---|
| ATOM | 3640 | CA | SER | B | 177 | 34.858 | 40.361 | 78.111 | 1.00 40.70 |
| ATOM | 3641 | CB | SER | B | 177 | 33.787 | 40.649 | 77.069 | 1.00 44.75 |
| ATOM | 3642 | OG | SER | B | 177 | 33.979 | 39.939 | 75.863 | 1.00 61.24 |
| ATOM | 3643 | C | SER | B | 177 | 34.856 | 38.884 | 78.518 | 1.00 38.46 |
| ATOM | 3644 | O | SER | B | 177 | 35.006 | 37.984 | 77.695 | 1.00 25.34 |
| ATOM | 3645 | N | VAL | B | 178 | 34.692 | 38.696 | 79.815 | 1.00 35.33 |
| ATOM | 3646 | CA | VAL | B | 178 | 34.780 | 37.440 | 80.534 | 1.00 44.36 |
| ATOM | 3647 | CB | VAL | B | 178 | 35.355 | 37.668 | 81.947 | 1.00 47.13 |
| ATOM | 3648 | CG1 | VAL | B | 178 | 35.862 | 36.376 | 82.570 | 1.00 47.45 |
| ATOM | 3649 | CG2 | VAL | B | 178 | 36.477 | 38.698 | 81.898 | 1.00 51.70 |
| ATOM | 3650 | C | VAL | B | 178 | 33.419 | 36.763 | 80.621 | 1.00 45.86 |
| ATOM | 3651 | O | VAL | B | 178 | 32.512 | 37.204 | 81.327 | 1.00 51.44 |
| ATOM | 3652 | N | LEU | B | 179 | 33.283 | 35.674 | 79.872 | 1.00 37.27 |
| ATOM | 3653 | CA | LEU | B | 179 | 32.036 | 34.908 | 79.851 | 1.00 34.97 |
| ATOM | 3654 | CB | LEU | B | 179 | 31.628 | 34.661 | 78.400 | 1.00 37.51 |
| ATOM | 3655 | CG | LEU | B | 179 | 30.834 | 35.785 | 77.730 | 1.00 43.44 |
| ATOM | 3656 | CD1 | LEU | B | 179 | 31.470 | 37.140 | 77.989 | 1.00 54.18 |
| ATOM | 3657 | CD2 | LEU | B | 179 | 30.704 | 35.528 | 76.237 | 1.00 54.36 |
| ATOM | 3658 | C | LEU | B | 179 | 32.193 | 33.620 | 80.645 | 1.00 34.28 |
| ATOM | 3659 | O | LEU | B | 179 | 33.309 | 33.220 | 81.010 | 1.00 36.89 |
| ATOM | 3660 | N | PRO | B | 180 | 31.101 | 32.937 | 80.970 | 1.00 45.49 |
| ATOM | 3661 | CA | PRO | B | 180 | 31.209 | 31.705 | 81.756 | 1.00 42.82 |
| ATOM | 3662 | CB | PRO | B | 180 | 29.774 | 31.148 | 81.733 | 1.00 47.75 |
| ATOM | 3663 | CG | PRO | B | 180 | 28.932 | 32.376 | 81.617 | 1.00 51.41 |
| ATOM | 3664 | CD | PRO | B | 180 | 29.695 | 33.258 | 80.665 | 1.00 53.24 |
| ATOM | 3665 | C | PRO | B | 180 | 32.153 | 30.666 | 81.176 | 1.00 31.68 |
| ATOM | 3666 | O | PRO | B | 180 | 32.821 | 29.985 | 81.963 | 1.00 42.99 |
| ATOM | 3667 | N | GLU | B | 181 | 32.242 | 30.482 | 79.858 | 1.00 28.10 |
| ATOM | 3668 | CA | GLU | B | 181 | 33.166 | 29.435 | 79.396 | 1.00 30.70 |
| ATOM | 3669 | CB | GLU | B | 181 | 32.420 | 28.305 | 78.697 | 1.00 24.19 |
| ATOM | 3670 | CG | GLU | B | 181 | 31.130 | 27.923 | 79.409 | 1.00 35.82 |
| ATOM | 3671 | CD | GLU | B | 181 | 30.054 | 27.533 | 78.413 | 1.00 40.31 |
| ATOM | 3672 | OE1 | GLU | B | 181 | 29.358 | 28.440 | 77.912 | 1.00 49.12 |
| ATOM | 3673 | OE2 | GLU | B | 181 | 29.924 | 26.323 | 78.142 | 1.00 45.80 |
| ATOM | 3674 | C | GLU | B | 181 | 34.229 | 29.976 | 78.447 | 1.00 33.02 |
| ATOM | 3675 | O | GLU | B | 181 | 35.127 | 29.240 | 78.043 | 1.00 34.02 |
| ATOM | 3676 | N | TRP | B | 182 | 34.139 | 31.254 | 78.085 | 1.00 26.28 |
| ATOM | 3677 | CA | TRP | B | 182 | 35.215 | 31.807 | 77.263 | 1.00 25.54 |
| ATOM | 3678 | CB | TRP | B | 182 | 35.049 | 31.542 | 75.780 | 1.00 25.17 |
| ATOM | 3679 | CG | TRP | B | 182 | 33.799 | 31.961 | 75.090 | 1.00 23.98 |
| ATOM | 3680 | CD1 | TRP | B | 182 | 33.495 | 33.162 | 74.507 | 1.00 27.11 |
| ATOM | 3681 | NE1 | TRP | B | 182 | 32.228 | 33.126 | 73.975 | 1.00 26.38 |
| ATOM | 3682 | CE2 | TRP | B | 182 | 31.689 | 31.888 | 74.210 | 1.00 29.12 |
| ATOM | 3683 | CD2 | TRP | B | 182 | 32.649 | 31.127 | 74.905 | 1.00 25.63 |
| ATOM | 3684 | CE3 | TRP | B | 182 | 32.372 | 29.806 | 75.280 | 1.00 26.46 |
| ATOM | 3685 | CZ3 | TRP | B | 182 | 31.130 | 29.299 | 74.938 | 1.00 31.22 |
| ATOM | 3686 | CH2 | TRP | B | 182 | 30.191 | 30.079 | 74.244 | 1.00 33.39 |
| ATOM | 3687 | CZ2 | TRP | B | 182 | 30.441 | 31.371 | 73.869 | 1.00 31.20 |
| ATOM | 3688 | C | TRP | B | 182 | 35.337 | 33.308 | 77.529 | 1.00 27.72 |
| ATOM | 3689 | O | TRP | B | 182 | 34.418 | 33.935 | 78.055 | 1.00 30.24 |
| ATOM | 3690 | N | THR | B | 183 | 36.493 | 33.818 | 77.150 | 1.00 24.75 |
| ATOM | 3691 | CA | THR | B | 183 | 36.809 | 35.234 | 77.261 | 1.00 29.67 |

FIGURE 173

| | | | | | | | | | |
|---|---|---|---|---|---|---|---|---|---|
| ATOM | 3692 | CB | THR | B | 183 | 37.897 | 35.481 | 78.320 | 1.00 36.72 |
| ATOM | 3693 | OG1 | THR | B | 183 | 37.419 | 35.055 | 79.606 | 1.00 30.73 |
| ATOM | 3694 | CG2 | THR | B | 183 | 38.218 | 36.961 | 78.455 | 1.00 25.96 |
| ATOM | 3695 | C | THR | B | 183 | 37.263 | 35.756 | 75.903 | 1.00 23.78 |
| ATOM | 3696 | O | THR | B | 183 | 38.157 | 35.191 | 75.276 | 1.00 16.05 |
| ATOM | 3697 | N | ILE | B | 184 | 36.649 | 36.838 | 75.455 | 1.00 21.97 |
| ATOM | 3698 | CA | ILE | B | 184 | 37.110 | 37.497 | 74.227 | 1.00 26.63 |
| ATOM | 3699 | CB | ILE | B | 184 | 35.918 | 37.735 | 73.288 | 1.00 30.23 |
| ATOM | 3700 | CG1 | ILE | B | 184 | 35.305 | 36.415 | 72.797 | 1.00 29.99 |
| ATOM | 3701 | CD1 | ILE | B | 184 | 33.881 | 36.539 | 72.305 | 1.00 36.01 |
| ATOM | 3702 | CG2 | ILE | B | 184 | 36.293 | 38.648 | 72.133 | 1.00 24.86 |
| ATOM | 3703 | C | ILE | B | 184 | 37.843 | 38.782 | 74.573 | 1.00 26.33 |
| ATOM | 3704 | O | ILE | B | 184 | 37.296 | 39.625 | 75.285 | 1.00 27.53 |
| ATOM | 3705 | N | ARG | B | 185 | 39.072 | 38.936 | 74.095 | 1.00 21.56 |
| ATOM | 3706 | CA | ARG | B | 185 | 39.876 | 40.127 | 74.341 | 1.00 21.72 |
| ATOM | 3707 | CB | ARG | B | 185 | 41.151 | 39.785 | 75.111 | 1.00 18.90 |
| ATOM | 3708 | CG | ARG | B | 185 | 40.884 | 39.061 | 76.431 | 1.00 20.33 |
| ATOM | 3709 | CD | ARG | B | 185 | 42.207 | 38.540 | 76.980 | 1.00 31.19 |
| ATOM | 3710 | NE | ARG | B | 185 | 42.119 | 38.235 | 78.404 | 1.00 29.95 |
| ATOM | 3711 | CZ | ARG | B | 185 | 41.905 | 37.012 | 78.867 | 1.00 30.90 |
| ATOM | 3712 | NH1 | ARG | B | 185 | 41.770 | 36.026 | 77.993 | 1.00 28.15 |
| ATOM | 3713 | NH2 | ARG | B | 185 | 41.831 | 36.768 | 80.165 | 1.00 26.93 |
| ATOM | 3714 | C | ARG | B | 185 | 40.246 | 40.824 | 73.038 | 1.00 24.49 |
| ATOM | 3715 | O | ARG | B | 185 | 40.342 | 40.197 | 71.990 | 1.00 22.11 |
| ATOM | 3716 | N | GLU | B | 186 | 40.440 | 42.137 | 73.098 | 1.00 23.85 |
| ATOM | 3717 | CA | GLU | B | 186 | 40.858 | 42.852 | 71.895 | 1.00 23.99 |
| ATOM | 3718 | CB | GLU | B | 186 | 39.831 | 43.906 | 71.499 | 1.00 32.77 |
| ATOM | 3719 | CG | GLU | B | 186 | 38.961 | 43.556 | 70.303 | 1.00 49.41 |
| ATOM | 3720 | CD | GLU | B | 186 | 38.376 | 44.815 | 69.677 | 1.00 57.85 |
| ATOM | 3721 | OE1 | GLU | B | 186 | 38.831 | 45.212 | 68.585 | 1.00 58.65 |
| ATOM | 3722 | OE2 | GLU | B | 186 | 37.465 | 45.405 | 70.295 | 1.00 46.66 |
| ATOM | 3723 | C | GLU | B | 186 | 42.215 | 43.486 | 72.141 | 1.00 20.03 |
| ATOM | 3724 | O | GLU | B | 186 | 42.426 | 44.138 | 73.165 | 1.00 28.24 |
| ATOM | 3725 | N | PHE | B | 187 | 43.151 | 43.295 | 71.214 | 1.00 19.91 |
| ATOM | 3726 | CA | PHE | B | 187 | 44.452 | 43.922 | 71.357 | 1.00 17.69 |
| ATOM | 3727 | CB | PHE | B | 187 | 45.562 | 42.872 | 71.461 | 1.00 24.10 |
| ATOM | 3728 | CG | PHE | B | 187 | 45.394 | 41.859 | 72.581 | 1.00 26.73 |
| ATOM | 3729 | CD1 | PHE | B | 187 | 45.114 | 40.535 | 72.294 | 1.00 32.91 |
| ATOM | 3730 | CE1 | PHE | B | 187 | 44.967 | 39.593 | 73.304 | 1.00 27.10 |
| ATOM | 3731 | CZ | PHE | B | 187 | 45.089 | 39.989 | 74.620 | 1.00 21.98 |
| ATOM | 3732 | CE2 | PHE | B | 187 | 45.369 | 41.308 | 74.928 | 1.00 27.08 |
| ATOM | 3733 | CD2 | PHE | B | 187 | 45.539 | 42.233 | 73.907 | 1.00 28.39 |
| ATOM | 3734 | C | PHE | B | 187 | 44.809 | 44.842 | 70.189 | 1.00 27.70 |
| ATOM | 3735 | O | PHE | B | 187 | 44.560 | 44.562 | 69.019 | 1.00 24.34 |
| ATOM | 3736 | N | LYS | B | 188 | 45.446 | 45.953 | 70.538 | 1.00 29.92 |
| ATOM | 3737 | CA | LYS | B | 188 | 46.049 | 46.816 | 69.521 | 1.00 36.57 |
| ATOM | 3738 | CB | LYS | B | 188 | 45.678 | 48.276 | 69.774 | 1.00 42.75 |
| ATOM | 3739 | CG | LYS | B | 188 | 46.817 | 49.269 | 69.641 | 1.00 52.83 |
| ATOM | 3740 | CD | LYS | B | 188 | 46.349 | 50.713 | 69.711 | 1.00 58.55 |
| ATOM | 3741 | CE | LYS | B | 188 | 46.124 | 51.181 | 71.139 | 1.00 59.40 |
| ATOM | 3742 | NZ | LYS | B | 188 | 47.298 | 50.947 | 72.026 | 1.00 34.15 |
| ATOM | 3743 | C | LYS | B | 188 | 47.553 | 46.584 | 69.518 | 1.00 30.49 |

FIGURE 174

| | | | | | | | | | |
|---|---|---|---|---|---|---|---|---|---|
| ATOM | 3744 | O | LYS | B | 188 | 48.240 | 46.624 | 70.539 | 1.00 22.92 |
| ATOM | 3745 | N | ILE | B | 189 | 48.136 | 46.304 | 68.350 | 1.00 24.79 |
| ATOM | 3746 | CA | ILE | B | 189 | 49.581 | 46.144 | 68.310 | 1.00 26.54 |
| ATOM | 3747 | CB | ILE | B | 189 | 49.992 | 44.714 | 67.933 | 1.00 29.28 |
| ATOM | 3748 | CG1 | ILE | B | 189 | 51.461 | 44.597 | 67.523 | 1.00 33.98 |
| ATOM | 3749 | CD1 | ILE | B | 189 | 51.848 | 43.205 | 67.067 | 1.00 52.63 |
| ATOM | 3750 | CG2 | ILE | B | 189 | 49.079 | 44.160 | 66.853 | 1.00 36.95 |
| ATOM | 3751 | C | ILE | B | 189 | 50.175 | 47.152 | 67.321 | 1.00 26.97 |
| ATOM | 3752 | O | ILE | B | 189 | 49.539 | 47.447 | 66.312 | 1.00 25.84 |
| ATOM | 3753 | N | CYS | B | 190 | 51.344 | 47.657 | 67.659 | 1.00 32.86 |
| ATOM | 3754 | CA | CYS | B | 190 | 52.103 | 48.607 | 66.874 | 1.00 31.79 |
| ATOM | 3755 | CB | CYS | B | 190 | 52.243 | 49.961 | 67.577 | 1.00 35.55 |
| ATOM | 3756 | SG | CYS | B | 190 | 50.732 | 50.549 | 68.369 | 1.00 48.07 |
| ATOM | 3757 | C | CYS | B | 190 | 53.492 | 48.052 | 66.576 | 1.00 32.84 |
| ATOM | 3758 | O | CYS | B | 190 | 54.208 | 47.629 | 67.478 | 1.00 29.87 |
| ATOM | 3759 | N | GLY | B | 191 | 53.858 | 48.065 | 65.295 | 1.00 35.69 |
| ATOM | 3760 | CA | GLY | B | 191 | 55.151 | 47.519 | 64.910 | 1.00 46.05 |
| ATOM | 3761 | C | GLY | B | 191 | 55.917 | 48.502 | 64.045 | 1.00 51.49 |
| ATOM | 3762 | O | GLY | B | 191 | 55.540 | 49.677 | 64.025 | 1.00 57.04 |
| ATOM | 3763 | N | GLU | B | 192 | 56.944 | 48.025 | 63.353 | 1.00 53.82 |
| ATOM | 3764 | CA | GLU | B | 192 | 57.794 | 48.872 | 62.522 | 1.00 71.96 |
| ATOM | 3765 | CB | GLU | B | 192 | 58.741 | 48.013 | 61.681 | 1.00 79.49 |
| ATOM | 3766 | CG | GLU | B | 192 | 60.088 | 48.655 | 61.399 | 1.00 83.42 |
| ATOM | 3767 | CD | GLU | B | 192 | 61.126 | 48.395 | 62.472 | 1.00 90.04 |
| ATOM | 3768 | OE1 | GLU | B | 192 | 60.759 | 48.211 | 63.654 | 1.00 98.44 |
| ATOM | 3769 | OE2 | GLU | B | 192 | 62.329 | 48.371 | 62.130 | 1.00 89.90 |
| ATOM | 3770 | C | GLU | B | 192 | 56.969 | 49.797 | 61.622 | 1.00 79.73 |
| ATOM | 3771 | O | GLU | B | 192 | 57.359 | 50.943 | 61.396 | 1.00 81.84 |
| ATOM | 3772 | N | GLU | B | 193 | 55.861 | 49.274 | 61.154 | 1.00 88.39 |
| ATOM | 3773 | CA | GLU | B | 193 | 54.815 | 49.806 | 60.317 | 1.00 96.64 |
| ATOM | 3774 | CB | GLU | B | 193 | 54.932 | 51.307 | 60.055 | 1.00 98.26 |
| ATOM | 3775 | CG | GLU | B | 193 | 53.693 | 51.905 | 59.401 | 1.00 98.54 |
| ATOM | 3776 | CD | GLU | B | 193 | 53.567 | 53.404 | 59.562 | 1.00 97.01 |
| ATOM | 3777 | OE1 | GLU | B | 193 | 52.688 | 53.853 | 60.336 | 1.00 83.43 |
| ATOM | 3778 | OE2 | GLU | B | 193 | 54.330 | 54.154 | 58.911 | 1.00 98.66 |
| ATOM | 3779 | C | GLU | B | 193 | 54.823 | 49.030 | 58.991 | 1.00102.76 |
| ATOM | 3780 | O | GLU | B | 193 | 54.656 | 49.612 | 57.926 | 1.00116.30 |
| ATOM | 3781 | N | GLN | B | 194 | 55.029 | 47.726 | 59.137 | 1.00102.86 |
| ATOM | 3782 | CA | GLN | B | 194 | 55.067 | 46.786 | 58.022 | 1.00100.17 |
| ATOM | 3783 | CB | GLN | B | 194 | 55.150 | 45.351 | 58.544 | 1.00 94.78 |
| ATOM | 3784 | CG | GLN | B | 194 | 56.548 | 44.913 | 58.944 | 1.00 90.58 |
| ATOM | 3785 | CD | GLN | B | 194 | 57.076 | 45.627 | 60.173 | 1.00 89.36 |
| ATOM | 3786 | OE1 | GLN | B | 194 | 56.393 | 46.444 | 60.792 | 1.00 75.86 |
| ATOM | 3787 | NE2 | GLN | B | 194 | 58.314 | 45.317 | 60.547 | 1.00 97.42 |
| ATOM | 3788 | C | GLN | B | 194 | 53.848 | 46.979 | 57.135 | 1.00100.06 |
| ATOM | 3789 | O | GLN | B | 194 | 53.618 | 48.060 | 56.588 | 1.00106.59 |
| ATOM | 3790 | N | LEU | B | 195 | 53.019 | 45.946 | 56.971 | 1.00 96.75 |
| ATOM | 3791 | CA | LEU | B | 195 | 51.800 | 46.199 | 56.191 | 1.00 92.05 |
| ATOM | 3792 | CB | LEU | B | 195 | 51.420 | 44.991 | 55.342 | 1.00 85.63 |
| ATOM | 3793 | CG | LEU | B | 195 | 51.792 | 45.085 | 53.856 | 1.00 78.28 |
| ATOM | 3794 | CD1 | LEU | B | 195 | 53.216 | 44.593 | 53.634 | 1.00 84.54 |
| ATOM | 3795 | CD2 | LEU | B | 195 | 50.811 | 44.310 | 52.989 | 1.00 43.11 |

FIGURE 175

```
ATOM   3796  C    LEU B 195      50.684  46.623  57.141  1.00 93.25
ATOM   3797  O    LEU B 195      49.499  46.559  56.823  1.00106.23
ATOM   3798  N    ASP B 196      51.100  47.071  58.323  1.00 88.54
ATOM   3799  CA   ASP B 196      50.208  47.654  59.311  1.00 85.36
ATOM   3800  CB   ASP B 196      49.937  46.706  60.472  1.00 77.13
ATOM   3801  CG   ASP B 196      50.263  45.256  60.196  1.00 69.71
ATOM   3802  OD1  ASP B 196      51.435  44.924  59.922  1.00 56.81
ATOM   3803  OD2  ASP B 196      49.318  44.442  60.267  1.00 49.34
ATOM   3804  C    ASP B 196      50.795  48.962  59.853  1.00 86.61
ATOM   3805  O    ASP B 196      52.000  49.194  59.771  1.00 72.64
ATOM   3806  N    ALA B 197      49.924  49.797  60.398  1.00 87.67
ATOM   3807  CA   ALA B 197      50.287  51.051  61.042  1.00 89.69
ATOM   3808  CB   ALA B 197      50.135  52.222  60.096  1.00 83.48
ATOM   3809  C    ALA B 197      49.426  51.223  62.302  1.00 94.67
ATOM   3810  O    ALA B 197      49.317  52.318  62.843  1.00100.04
ATOM   3811  N    HIS B 198      48.864  50.096  62.692  1.00 93.88
ATOM   3812  CA   HIS B 198      47.955  49.838  63.785  1.00 88.36
ATOM   3813  CB   HIS B 198      47.173  51.099  64.161  1.00 92.99
ATOM   3814  CG   HIS B 198      45.965  50.823  64.998  1.00104.14
ATOM   3815  ND1  HIS B 198      46.045  50.478  66.329  1.00108.50
ATOM   3816  CE1  HIS B 198      44.830  50.292  66.813  1.00111.40
ATOM   3817  NE2  HIS B 198      43.960  50.506  65.840  1.00112.45
ATOM   3818  CD2  HIS B 198      44.647  50.839  64.696  1.00109.03
ATOM   3819  C    HIS B 198      46.988  48.711  63.416  1.00 81.60
ATOM   3820  O    HIS B 198      46.100  48.902  62.581  1.00 85.74
ATOM   3821  N    ARG B 199      47.151  47.537  64.020  1.00 68.93
ATOM   3822  CA   ARG B 199      46.278  46.398  63.754  1.00 51.46
ATOM   3823  CB   ARG B 199      47.089  45.192  63.265  1.00 49.03
ATOM   3824  CG   ARG B 199      46.204  44.080  62.716  1.00 46.46
ATOM   3825  CD   ARG B 199      46.953  42.775  62.585  1.00 51.43
ATOM   3826  NE   ARG B 199      48.202  42.873  61.850  1.00 58.26
ATOM   3827  CZ   ARG B 199      49.185  41.980  61.891  1.00 57.04
ATOM   3828  NH1  ARG B 199      49.068  40.896  62.649  1.00 28.91
ATOM   3829  NH2  ARG B 199      50.288  42.168  61.174  1.00 39.20
ATOM   3830  C    ARG B 199      45.464  46.004  64.987  1.00 33.01
ATOM   3831  O    ARG B 199      45.928  46.200  66.112  1.00 29.63
ATOM   3832  N    LEU B 200      44.268  45.459  64.781  1.00 24.89
ATOM   3833  CA   LEU B 200      43.422  45.004  65.880  1.00 27.88
ATOM   3834  CB   LEU B 200      42.010  45.570  65.783  1.00 34.27
ATOM   3835  CG   LEU B 200      41.523  46.288  67.047  1.00 42.11
ATOM   3836  CD1  LEU B 200      41.605  45.366  68.249  1.00 45.77
ATOM   3837  CD2  LEU B 200      42.333  47.553  67.292  1.00 51.38
ATOM   3838  C    LEU B 200      43.353  43.477  65.913  1.00 30.00
ATOM   3839  O    LEU B 200      42.871  42.868  64.959  1.00 32.82
ATOM   3840  N    ILE B 201      43.834  42.882  67.003  1.00 28.87
ATOM   3841  CA   ILE B 201      43.821  41.425  67.118  1.00 24.18
ATOM   3842  CB   ILE B 201      45.174  40.900  67.623  1.00 24.29
ATOM   3843  CG1  ILE B 201      46.350  41.222  66.696  1.00 28.49
ATOM   3844  CD1  ILE B 201      45.941  41.124  65.247  1.00 39.78
ATOM   3845  CG2  ILE B 201      45.105  39.401  67.873  1.00 25.71
ATOM   3846  C    ILE B 201      42.717  40.972  68.059  1.00 22.16
ATOM   3847  O    ILE B 201      42.640  41.494  69.168  1.00 23.92
```

FIGURE 176

| | | | | | | | | |
|---|---|---|---|---|---|---|---|---|
| ATOM | 3848 | N   | ARG | B | 202 | 41.883 | 40.037 | 67.647 | 1.00 | 18.44 |
| ATOM | 3849 | CA  | ARG | B | 202 | 40.849 | 39.447 | 68.478 | 1.00 | 22.50 |
| ATOM | 3850 | CB  | ARG | B | 202 | 39.585 | 39.119 | 67.693 | 1.00 | 33.06 |
| ATOM | 3851 | CG  | ARG | B | 202 | 38.305 | 39.726 | 68.233 | 1.00 | 52.62 |
| ATOM | 3852 | CD  | ARG | B | 202 | 37.344 | 40.048 | 67.098 | 1.00 | 66.81 |
| ATOM | 3853 | NE  | ARG | B | 202 | 36.728 | 41.358 | 67.260 | 1.00 | 75.75 |
| ATOM | 3854 | CZ  | ARG | B | 202 | 37.372 | 42.512 | 67.362 | 1.00 | 85.03 |
| ATOM | 3855 | NH1 | ARG | B | 202 | 38.698 | 42.553 | 67.322 | 1.00 | 98.51 |
| ATOM | 3856 | NH2 | ARG | B | 202 | 36.677 | 43.635 | 67.506 | 1.00 | 92.03 |
| ATOM | 3857 | C   | ARG | B | 202 | 41.359 | 38.141 | 69.099 | 1.00 | 26.96 |
| ATOM | 3858 | O   | ARG | B | 202 | 41.955 | 37.319 | 68.410 | 1.00 | 18.58 |
| ATOM | 3859 | N   | HIS | B | 203 | 41.120 | 37.977 | 70.384 | 1.00 | 28.22 |
| ATOM | 3860 | CA  | HIS | B | 203 | 41.595 | 36.823 | 71.148 | 1.00 | 23.47 |
| ATOM | 3861 | CB  | HIS | B | 203 | 42.637 | 37.287 | 72.150 | 1.00 | 18.39 |
| ATOM | 3862 | CG  | HIS | B | 203 | 43.392 | 36.213 | 72.850 | 1.00 | 20.01 |
| ATOM | 3863 | ND1 | HIS | B | 203 | 42.935 | 35.618 | 73.999 | 1.00 | 22.68 |
| ATOM | 3864 | CE1 | HIS | B | 203 | 43.797 | 34.707 | 74.400 | 1.00 | 22.72 |
| ATOM | 3865 | NE2 | HIS | B | 203 | 44.809 | 34.694 | 73.548 | 1.00 | 18.58 |
| ATOM | 3866 | CD2 | HIS | B | 203 | 44.580 | 35.624 | 72.563 | 1.00 | 22.68 |
| ATOM | 3867 | C   | HIS | B | 203 | 40.398 | 36.148 | 71.813 | 1.00 | 23.95 |
| ATOM | 3868 | O   | HIS | B | 203 | 39.651 | 36.785 | 72.562 | 1.00 | 18.73 |
| ATOM | 3869 | N   | PHE | B | 204 | 40.248 | 34.876 | 71.479 | 1.00 | 17.03 |
| ATOM | 3870 | CA  | PHE | B | 204 | 39.161 | 33.994 | 71.840 | 1.00 | 16.70 |
| ATOM | 3871 | CB  | PHE | B | 204 | 38.534 | 33.311 | 70.614 | 1.00 | 22.28 |
| ATOM | 3872 | CG  | PHE | B | 204 | 38.026 | 34.329 | 69.604 | 1.00 | 24.33 |
| ATOM | 3873 | CD1 | PHE | B | 204 | 38.876 | 34.813 | 68.622 | 1.00 | 22.40 |
| ATOM | 3874 | CE1 | PHE | B | 204 | 38.411 | 35.764 | 67.735 | 1.00 | 18.80 |
| ATOM | 3875 | CZ  | PHE | B | 204 | 37.103 | 36.205 | 67.847 | 1.00 | 19.32 |
| ATOM | 3876 | CE2 | PHE | B | 204 | 36.244 | 35.727 | 68.811 | 1.00 | 25.22 |
| ATOM | 3877 | CD2 | PHE | B | 204 | 36.716 | 34.768 | 69.694 | 1.00 | 26.02 |
| ATOM | 3878 | C   | PHE | B | 204 | 39.702 | 32.924 | 72.788 | 1.00 | 22.01 |
| ATOM | 3879 | O   | PHE | B | 204 | 40.366 | 31.995 | 72.324 | 1.00 | 24.15 |
| ATOM | 3880 | N   | HIS | B | 205 | 39.416 | 33.083 | 74.068 | 1.00 | 17.87 |
| ATOM | 3881 | CA  | HIS | B | 205 | 40.000 | 32.212 | 75.077 | 1.00 | 18.30 |
| ATOM | 3882 | CB  | HIS | B | 205 | 40.620 | 33.068 | 76.193 | 1.00 | 17.58 |
| ATOM | 3883 | CG  | HIS | B | 205 | 41.469 | 32.282 | 77.137 | 1.00 | 20.30 |
| ATOM | 3884 | ND1 | HIS | B | 205 | 41.954 | 32.812 | 78.310 | 1.00 | 22.02 |
| ATOM | 3885 | CE1 | HIS | B | 205 | 42.670 | 31.902 | 78.946 | 1.00 | 21.93 |
| ATOM | 3886 | NE2 | HIS | B | 205 | 42.663 | 30.786 | 78.227 | 1.00 | 22.68 |
| ATOM | 3887 | CD2 | HIS | B | 205 | 41.915 | 31.001 | 77.092 | 1.00 | 15.40 |
| ATOM | 3888 | C   | HIS | B | 205 | 38.958 | 31.270 | 75.658 | 1.00 | 23.56 |
| ATOM | 3889 | O   | HIS | B | 205 | 38.102 | 31.697 | 76.438 | 1.00 | 19.47 |
| ATOM | 3890 | N   | TYR | B | 206 | 39.032 | 29.996 | 75.287 | 1.00 | 18.88 |
| ATOM | 3891 | CA  | TYR | B | 206 | 38.073 | 29.022 | 75.836 | 1.00 | 22.05 |
| ATOM | 3892 | CB  | TYR | B | 206 | 37.855 | 27.895 | 74.846 | 1.00 | 20.72 |
| ATOM | 3893 | CG  | TYR | B | 206 | 36.757 | 26.923 | 75.209 | 1.00 | 18.73 |
| ATOM | 3894 | CD1 | TYR | B | 206 | 35.420 | 27.266 | 75.039 | 1.00 | 20.87 |
| ATOM | 3895 | CE1 | TYR | B | 206 | 34.413 | 26.376 | 75.372 | 1.00 | 26.51 |
| ATOM | 3896 | CZ  | TYR | B | 206 | 34.752 | 25.135 | 75.870 | 1.00 | 28.96 |
| ATOM | 3897 | OH  | TYR | B | 206 | 33.753 | 24.244 | 76.205 | 1.00 | 33.83 |
| ATOM | 3898 | CE2 | TYR | B | 206 | 36.067 | 24.773 | 76.049 | 1.00 | 30.27 |
| ATOM | 3899 | CD2 | TYR | B | 206 | 37.073 | 25.671 | 75.719 | 1.00 | 28.39 |

FIGURE 177

```
ATOM   3900  C    TYR B 206      38.613  28.499  77.156  1.00 24.76
ATOM   3901  O    TYR B 206      39.717  27.943  77.181  1.00 19.80
ATOM   3902  N    THR B 207      37.887  28.679  78.261  1.00 20.66
ATOM   3903  CA   THR B 207      38.554  28.426  79.533  1.00 20.59
ATOM   3904  CB   THR B 207      38.343  29.630  80.477  1.00 23.62
ATOM   3905  OG1  THR B 207      36.964  30.008  80.399  1.00 20.08
ATOM   3906  CG2  THR B 207      39.198  30.803  80.014  1.00 30.98
ATOM   3907  C    THR B 207      38.084  27.179  80.263  1.00 23.84
ATOM   3908  O    THR B 207      38.498  26.972  81.414  1.00 22.22
ATOM   3909  N    VAL B 208      37.254  26.345  79.643  1.00 23.82
ATOM   3910  CA   VAL B 208      36.825  25.167  80.402  1.00 28.06
ATOM   3911  CB   VAL B 208      35.322  25.266  80.749  1.00 27.30
ATOM   3912  CG1  VAL B 208      35.074  26.517  81.590  1.00 32.43
ATOM   3913  CG2  VAL B 208      34.465  25.241  79.494  1.00 27.40
ATOM   3914  C    VAL B 208      37.116  23.851  79.698  1.00 30.84
ATOM   3915  O    VAL B 208      36.320  22.909  79.773  1.00 35.95
ATOM   3916  N    TRP B 209      38.255  23.743  79.031  1.00 26.26
ATOM   3917  CA   TRP B 209      38.657  22.486  78.391  1.00 24.69
ATOM   3918  CB   TRP B 209      38.976  22.685  76.918  1.00 30.19
ATOM   3919  CG   TRP B 209      39.163  21.465  76.068  1.00 24.30
ATOM   3920  CD1  TRP B 209      39.449  20.169  76.361  1.00 26.73
ATOM   3921  NE1  TRP B 209      39.526  19.394  75.229  1.00 27.16
ATOM   3922  CE2  TRP B 209      39.278  20.210  74.148  1.00 34.57
ATOM   3923  CD2  TRP B 209      39.048  21.513  74.632  1.00 23.58
ATOM   3924  CE3  TRP B 209      38.768  22.558  73.746  1.00 24.70
ATOM   3925  CZ3  TRP B 209      38.731  22.256  72.395  1.00 35.51
ATOM   3926  CH2  TRP B 209      38.964  20.951  71.930  1.00 33.08
ATOM   3927  CZ2  TRP B 209      39.236  19.917  72.782  1.00 32.65
ATOM   3928  C    TRP B 209      39.889  21.934  79.099  1.00 26.90
ATOM   3929  O    TRP B 209      40.981  22.462  78.880  1.00 24.25
ATOM   3930  N    PRO B 210      39.733  20.881  79.886  1.00 30.43
ATOM   3931  CA   PRO B 210      40.872  20.308  80.611  1.00 22.74
ATOM   3932  CB   PRO B 210      40.241  19.228  81.492  1.00 26.14
ATOM   3933  CG   PRO B 210      38.776  19.517  81.488  1.00 31.27
ATOM   3934  CD   PRO B 210      38.486  20.136  80.147  1.00 27.01
ATOM   3935  C    PRO B 210      41.871  19.648  79.668  1.00 22.10
ATOM   3936  O    PRO B 210      41.475  19.064  78.662  1.00 34.64
ATOM   3937  N    ASP B 211      43.153  19.724  80.001  1.00 15.18
ATOM   3938  CA   ASP B 211      44.183  19.090  79.209  1.00 21.45
ATOM   3939  CB   ASP B 211      45.565  19.247  79.849  1.00 28.68
ATOM   3940  CG   ASP B 211      46.648  19.134  78.790  1.00 26.69
ATOM   3941  OD1  ASP B 211      47.820  19.370  79.138  1.00 34.33
ATOM   3942  OD2  ASP B 211      46.281  18.819  77.638  1.00 25.77
ATOM   3943  C    ASP B 211      43.901  17.600  79.038  1.00 40.98
ATOM   3944  O    ASP B 211      43.349  16.940  79.926  1.00 28.43
ATOM   3945  N    HIS B 212      44.254  17.081  77.868  1.00 34.69
ATOM   3946  CA   HIS B 212      44.020  15.705  77.459  1.00 29.07
ATOM   3947  CB   HIS B 212      44.864  14.770  78.328  1.00 22.05
ATOM   3948  CG   HIS B 212      46.266  15.247  78.527  1.00 23.98
ATOM   3949  ND1  HIS B 212      47.183  15.323  77.504  1.00 29.39
ATOM   3950  CE1  HIS B 212      48.329  15.777  77.969  1.00 33.66
ATOM   3951  NE2  HIS B 212      48.187  15.996  79.268  1.00 32.42
```

FIGURE 178

| | | | | | | | | | |
|---|---|---|---|---|---|---|---|---|---|
| ATOM | 3952 | CD2 | HIS | B | 212 | 46.906 | 15.670 | 79.637 | 1.00 23.94 |
| ATOM | 3953 | C | HIS | B | 212 | 42.564 | 15.267 | 77.538 | 1.00 39.31 |
| ATOM | 3954 | O | HIS | B | 212 | 42.251 | 14.074 | 77.466 | 1.00 50.27 |
| ATOM | 3955 | N | GLY | B | 213 | 41.642 | 16.207 | 77.683 | 1.00 40.41 |
| ATOM | 3956 | CA | GLY | B | 213 | 40.245 | 15.925 | 77.912 | 1.00 30.96 |
| ATOM | 3957 | C | GLY | B | 213 | 39.401 | 16.580 | 76.835 | 1.00 33.95 |
| ATOM | 3958 | O | GLY | B | 213 | 39.938 | 17.004 | 75.817 | 1.00 33.78 |
| ATOM | 3959 | N | VAL | B | 214 | 38.120 | 16.610 | 77.144 | 1.00 31.79 |
| ATOM | 3960 | CA | VAL | B | 214 | 37.081 | 17.170 | 76.303 | 1.00 31.65 |
| ATOM | 3961 | CB | VAL | B | 214 | 36.238 | 16.035 | 75.701 | 1.00 35.28 |
| ATOM | 3962 | CG1 | VAL | B | 214 | 37.120 | 15.151 | 74.832 | 1.00 45.38 |
| ATOM | 3963 | CG2 | VAL | B | 214 | 35.582 | 15.230 | 76.815 | 1.00 24.44 |
| ATOM | 3964 | C | VAL | B | 214 | 36.205 | 18.070 | 77.150 | 1.00 36.18 |
| ATOM | 3965 | O | VAL | B | 214 | 36.097 | 17.826 | 78.358 | 1.00 35.44 |
| ATOM | 3966 | N | PRO | B | 215 | 35.582 | 19.094 | 76.597 | 1.00 32.79 |
| ATOM | 3967 | CA | PRO | B | 215 | 34.679 | 19.888 | 77.449 | 1.00 35.01 |
| ATOM | 3968 | CB | PRO | B | 215 | 34.113 | 20.923 | 76.488 | 1.00 32.92 |
| ATOM | 3969 | CG | PRO | B | 215 | 35.146 | 21.018 | 75.406 | 1.00 39.93 |
| ATOM | 3970 | CD | PRO | B | 215 | 35.654 | 19.604 | 75.225 | 1.00 33.73 |
| ATOM | 3971 | C | PRO | B | 215 | 33.574 | 18.999 | 78.031 | 1.00 40.15 |
| ATOM | 3972 | O | PRO | B | 215 | 33.366 | 17.872 | 77.581 | 1.00 31.33 |
| ATOM | 3973 | N | GLU | B | 216 | 32.896 | 19.532 | 79.028 | 1.00 39.88 |
| ATOM | 3974 | CA | GLU | B | 216 | 31.810 | 18.913 | 79.763 | 1.00 43.51 |
| ATOM | 3975 | CB | GLU | B | 216 | 31.406 | 19.850 | 80.906 | 1.00 52.27 |
| ATOM | 3976 | CG | GLU | B | 216 | 31.040 | 19.159 | 82.203 | 1.00 67.80 |
| ATOM | 3977 | CD | GLU | B | 216 | 31.677 | 19.781 | 83.429 | 1.00 77.24 |
| ATOM | 3978 | OE1 | GLU | B | 216 | 31.550 | 19.193 | 84.527 | 1.00 81.69 |
| ATOM | 3979 | OE2 | GLU | B | 216 | 32.302 | 20.857 | 83.300 | 1.00 89.24 |
| ATOM | 3980 | C | GLU | B | 216 | 30.617 | 18.606 | 78.864 | 1.00 40.84 |
| ATOM | 3981 | O | GLU | B | 216 | 30.010 | 17.536 | 78.967 | 1.00 53.80 |
| ATOM | 3982 | N | THR | B | 217 | 30.269 | 19.531 | 77.983 | 1.00 38.95 |
| ATOM | 3983 | CA | THR | B | 217 | 29.204 | 19.383 | 77.008 | 1.00 42.02 |
| ATOM | 3984 | CB | THR | B | 217 | 28.040 | 20.379 | 77.205 | 1.00 45.29 |
| ATOM | 3985 | OG1 | THR | B | 217 | 28.483 | 21.708 | 76.887 | 1.00 35.12 |
| ATOM | 3986 | CG2 | THR | B | 217 | 27.573 | 20.406 | 78.649 | 1.00 41.50 |
| ATOM | 3987 | C | THR | B | 217 | 29.708 | 19.600 | 75.580 | 1.00 41.46 |
| ATOM | 3988 | O | THR | B | 217 | 30.806 | 20.088 | 75.328 | 1.00 31.75 |
| ATOM | 3989 | N | THR | B | 218 | 28.852 | 19.241 | 74.631 | 1.00 44.21 |
| ATOM | 3990 | CA | THR | B | 218 | 29.157 | 19.469 | 73.222 | 1.00 46.58 |
| ATOM | 3991 | CB | THR | B | 218 | 28.428 | 18.436 | 72.347 | 1.00 50.20 |
| ATOM | 3992 | OG1 | THR | B | 218 | 27.030 | 18.755 | 72.322 | 1.00 60.14 |
| ATOM | 3993 | CG2 | THR | B | 218 | 28.539 | 17.047 | 72.953 | 1.00 48.45 |
| ATOM | 3994 | C | THR | B | 218 | 28.751 | 20.877 | 72.807 | 1.00 39.87 |
| ATOM | 3995 | O | THR | B | 218 | 29.472 | 21.575 | 72.100 | 1.00 33.12 |
| ATOM | 3996 | N | GLN | B | 219 | 27.581 | 21.301 | 73.262 | 1.00 42.47 |
| ATOM | 3997 | CA | GLN | B | 219 | 27.023 | 22.603 | 72.942 | 1.00 48.42 |
| ATOM | 3998 | CB | GLN | B | 219 | 25.735 | 22.859 | 73.734 | 1.00 61.04 |
| ATOM | 3999 | CG | GLN | B | 219 | 24.465 | 22.396 | 73.043 | 1.00 75.20 |
| ATOM | 4000 | CD | GLN | B | 219 | 23.709 | 21.356 | 73.846 | 1.00 86.54 |
| ATOM | 4001 | OE1 | GLN | B | 219 | 24.156 | 20.217 | 73.990 | 1.00100.39 |
| ATOM | 4002 | NE2 | GLN | B | 219 | 22.552 | 21.750 | 74.373 | 1.00 96.05 |
| ATOM | 4003 | C | GLN | B | 219 | 27.988 | 23.745 | 73.241 | 1.00 42.13 |

FIGURE 179

```
ATOM   4004  O    GLN B 219      27.912  24.784  72.588  1.00 38.02
ATOM   4005  N    SER B 220      28.856  23.557  74.230  1.00 41.58
ATOM   4006  CA   SER B 220      29.702  24.652  74.687  1.00 41.47
ATOM   4007  CB   SER B 220      30.377  24.324  76.022  1.00 40.77
ATOM   4008  OG   SER B 220      31.170  25.425  76.432  1.00 52.01
ATOM   4009  C    SER B 220      30.781  24.985  73.661  1.00 32.19
ATOM   4010  O    SER B 220      30.948  26.137  73.270  1.00 34.50
ATOM   4011  N    LEU B 221      31.491  23.939  73.262  1.00 32.63
ATOM   4012  CA   LEU B 221      32.578  24.130  72.312  1.00 30.11
ATOM   4013  CB   LEU B 221      33.532  22.934  72.268  1.00 31.66
ATOM   4014  CG   LEU B 221      34.848  23.244  71.525  1.00 33.07
ATOM   4015  CD1  LEU B 221      35.653  24.288  72.290  1.00 29.11
ATOM   4016  CD2  LEU B 221      35.641  21.978  71.284  1.00 29.80
ATOM   4017  C    LEU B 221      31.970  24.416  70.944  1.00 30.52
ATOM   4018  O    LEU B 221      32.479  25.263  70.210  1.00 31.28
ATOM   4019  N    ILE B 222      30.879  23.712  70.649  1.00 30.64
ATOM   4020  CA   ILE B 222      30.208  23.955  69.364  1.00 35.39
ATOM   4021  CB   ILE B 222      28.961  23.069  69.244  1.00 28.31
ATOM   4022  CG1  ILE B 222      29.280  21.656  68.733  1.00 23.30
ATOM   4023  CD1  ILE B 222      28.138  20.695  68.988  1.00 31.06
ATOM   4024  CG2  ILE B 222      27.871  23.684  68.394  1.00 30.00
ATOM   4025  C    ILE B 222      29.871  25.433  69.215  1.00 31.09
ATOM   4026  O    ILE B 222      30.088  26.049  68.169  1.00 30.29
ATOM   4027  N    GLN B 223      29.352  26.009  70.296  1.00 31.17
ATOM   4028  CA   GLN B 223      28.973  27.416  70.289  1.00 33.58
ATOM   4029  CB   GLN B 223      28.201  27.804  71.554  1.00 39.47
ATOM   4030  CG   GLN B 223      27.198  28.916  71.237  1.00 56.44
ATOM   4031  CD   GLN B 223      26.886  28.937  69.747  1.00 72.62
ATOM   4032  OE1  GLN B 223      26.007  28.216  69.269  1.00 73.13
ATOM   4033  NE2  GLN B 223      27.618  29.765  69.008  1.00 86.88
ATOM   4034  C    GLN B 223      30.210  28.300  70.151  1.00 27.54
ATOM   4035  O    GLN B 223      30.195  29.217  69.338  1.00 28.05
ATOM   4036  N    PHE B 224      31.238  27.991  70.934  1.00 26.93
ATOM   4037  CA   PHE B 224      32.529  28.675  70.816  1.00 21.53
ATOM   4038  CB   PHE B 224      33.554  28.029  71.726  1.00 22.20
ATOM   4039  CG   PHE B 224      34.930  28.683  71.736  1.00 25.50
ATOM   4040  CD1  PHE B 224      35.141  29.892  72.381  1.00 24.49
ATOM   4041  CE1  PHE B 224      36.398  30.465  72.413  1.00 22.79
ATOM   4042  CZ   PHE B 224      37.451  29.853  71.766  1.00 14.40
ATOM   4043  CE2  PHE B 224      37.260  28.650  71.125  1.00 22.52
ATOM   4044  CD2  PHE B 224      36.000  28.071  71.113  1.00 23.70
ATOM   4045  C    PHE B 224      33.033  28.659  69.372  1.00 25.07
ATOM   4046  O    PHE B 224      33.291  29.707  68.770  1.00 33.29
ATOM   4047  N    VAL B 225      33.166  27.464  68.800  1.00 21.05
ATOM   4048  CA   VAL B 225      33.655  27.335  67.431  1.00 21.13
ATOM   4049  CB   VAL B 225      33.656  25.868  66.962  1.00 20.06
ATOM   4050  CG1  VAL B 225      33.778  25.769  65.448  1.00 21.52
ATOM   4051  CG2  VAL B 225      34.796  25.101  67.607  1.00 23.47
ATOM   4052  C    VAL B 225      32.826  28.179  66.470  1.00 34.08
ATOM   4053  O    VAL B 225      33.395  28.901  65.641  1.00 30.78
ATOM   4054  N    ARG B 226      31.498  28.088  66.584  1.00 33.79
ATOM   4055  CA   ARG B 226      30.663  28.875  65.670  1.00 32.97
```

FIGURE 180

| | | | | | | | | |
|---|---|---|---|---|---|---|---|---|
| ATOM | 4056 | CB | ARG | B | 226 | 29.185 | 28.551 | 65.852 | 1.00 | 36.13 |
| ATOM | 4057 | CG | ARG | B | 226 | 28.846 | 27.076 | 65.682 | 1.00 | 38.26 |
| ATOM | 4058 | CD | ARG | B | 226 | 27.340 | 26.867 | 65.634 | 1.00 | 43.64 |
| ATOM | 4059 | NE | ARG | B | 226 | 26.967 | 25.743 | 64.773 | 1.00 | 52.04 |
| ATOM | 4060 | CZ | ARG | B | 226 | 25.960 | 24.913 | 65.031 | 1.00 | 56.46 |
| ATOM | 4061 | NH1 | ARG | B | 226 | 25.229 | 25.084 | 66.127 | 1.00 | 38.23 |
| ATOM | 4062 | NH2 | ARG | B | 226 | 25.688 | 23.917 | 64.197 | 1.00 | 53.92 |
| ATOM | 4063 | C | ARG | B | 226 | 30.933 | 30.356 | 65.886 | 1.00 | 38.04 |
| ATOM | 4064 | O | ARG | B | 226 | 31.031 | 31.144 | 64.947 | 1.00 | 40.50 |
| ATOM | 4065 | N | THR | B | 227 | 31.077 | 30.745 | 67.151 | 1.00 | 32.88 |
| ATOM | 4066 | CA | THR | B | 227 | 31.406 | 32.146 | 67.425 | 1.00 | 34.79 |
| ATOM | 4067 | CB | THR | B | 227 | 31.474 | 32.430 | 68.937 | 1.00 | 37.87 |
| ATOM | 4068 | OG1 | THR | B | 227 | 30.160 | 32.368 | 69.504 | 1.00 | 44.90 |
| ATOM | 4069 | CG2 | THR | B | 227 | 31.977 | 33.840 | 69.194 | 1.00 | 37.73 |
| ATOM | 4070 | C | THR | B | 227 | 32.728 | 32.514 | 66.772 | 1.00 | 33.01 |
| ATOM | 4071 | O | THR | B | 227 | 32.879 | 33.558 | 66.136 | 1.00 | 29.02 |
| ATOM | 4072 | N | VAL | B | 228 | 33.737 | 31.645 | 66.903 | 1.00 | 29.04 |
| ATOM | 4073 | CA | VAL | B | 228 | 35.022 | 32.021 | 66.300 | 1.00 | 25.89 |
| ATOM | 4074 | CB | VAL | B | 228 | 36.125 | 31.038 | 66.728 | 1.00 | 27.50 |
| ATOM | 4075 | CG1 | VAL | B | 228 | 37.419 | 31.376 | 66.005 | 1.00 | 25.74 |
| ATOM | 4076 | CG2 | VAL | B | 228 | 36.316 | 31.066 | 68.244 | 1.00 | 22.05 |
| ATOM | 4077 | C | VAL | B | 228 | 34.929 | 32.108 | 64.779 | 1.00 | 25.85 |
| ATOM | 4078 | O | VAL | B | 228 | 35.454 | 33.028 | 64.145 | 1.00 | 26.36 |
| ATOM | 4079 | N | ARG | B | 229 | 34.253 | 31.163 | 64.145 | 1.00 | 30.24 |
| ATOM | 4080 | CA | ARG | B | 229 | 34.172 | 31.158 | 62.678 | 1.00 | 30.97 |
| ATOM | 4081 | CB | ARG | B | 229 | 33.486 | 29.872 | 62.232 | 1.00 | 35.10 |
| ATOM | 4082 | CG | ARG | B | 229 | 33.083 | 29.811 | 60.772 | 1.00 | 37.64 |
| ATOM | 4083 | CD | ARG | B | 229 | 34.250 | 30.014 | 59.828 | 1.00 | 31.83 |
| ATOM | 4084 | NE | ARG | B | 229 | 35.361 | 29.082 | 60.089 | 1.00 | 32.88 |
| ATOM | 4085 | CZ | ARG | B | 229 | 36.512 | 29.276 | 59.439 | 1.00 | 32.94 |
| ATOM | 4086 | NH1 | ARG | B | 229 | 36.535 | 30.304 | 58.602 | 1.00 | 27.58 |
| ATOM | 4087 | NH2 | ARG | B | 229 | 37.576 | 28.513 | 59.590 | 1.00 | 33.74 |
| ATOM | 4088 | C | ARG | B | 229 | 33.459 | 32.398 | 62.160 | 1.00 | 38.61 |
| ATOM | 4089 | O | ARG | B | 229 | 33.809 | 32.946 | 61.105 | 1.00 | 36.42 |
| ATOM | 4090 | N | ASP | B | 230 | 32.458 | 32.876 | 62.897 | 1.00 | 30.67 |
| ATOM | 4091 | CA | ASP | B | 230 | 31.792 | 34.128 | 62.548 | 1.00 | 40.26 |
| ATOM | 4092 | CB | ASP | B | 230 | 30.693 | 34.455 | 63.561 | 1.00 | 50.06 |
| ATOM | 4093 | CG | ASP | B | 230 | 29.903 | 35.704 | 63.234 | 1.00 | 61.05 |
| ATOM | 4094 | OD1 | ASP | B | 230 | 30.234 | 36.779 | 63.781 | 1.00 | 62.97 |
| ATOM | 4095 | OD2 | ASP | B | 230 | 28.939 | 35.635 | 62.438 | 1.00 | 74.52 |
| ATOM | 4096 | C | ASP | B | 230 | 32.777 | 35.287 | 62.469 | 1.00 | 38.62 |
| ATOM | 4097 | O | ASP | B | 230 | 32.680 | 36.128 | 61.574 | 1.00 | 42.73 |
| ATOM | 4098 | N | TYR | B | 231 | 33.732 | 35.352 | 63.398 | 1.00 | 33.95 |
| ATOM | 4099 | CA | TYR | B | 231 | 34.680 | 36.464 | 63.395 | 1.00 | 30.28 |
| ATOM | 4100 | CB | TYR | B | 231 | 35.391 | 36.596 | 64.743 | 1.00 | 28.40 |
| ATOM | 4101 | CG | TYR | B | 231 | 34.545 | 37.304 | 65.783 | 1.00 | 31.94 |
| ATOM | 4102 | CD1 | TYR | B | 231 | 33.721 | 36.575 | 66.632 | 1.00 | 31.04 |
| ATOM | 4103 | CE1 | TYR | B | 231 | 32.953 | 37.221 | 67.582 | 1.00 | 39.71 |
| ATOM | 4104 | CZ | TYR | B | 231 | 33.006 | 38.593 | 67.685 | 1.00 | 44.93 |
| ATOM | 4105 | OH | TYR | B | 231 | 32.237 | 39.231 | 68.633 | 1.00 | 67.37 |
| ATOM | 4106 | CE2 | TYR | B | 231 | 33.819 | 39.333 | 66.854 | 1.00 | 41.23 |
| ATOM | 4107 | CD2 | TYR | B | 231 | 34.587 | 38.684 | 65.905 | 1.00 | 39.54 |

FIGURE 181

| | | | | | | | | | |
|---|---|---|---|---|---|---|---|---|---|
| ATOM | 4108 | C | TYR | B | 231 | 35.726 | 36.297 | 62.305 | 1.00 28.70 |
| ATOM | 4109 | O | TYR | B | 231 | 36.213 | 37.238 | 61.692 | 1.00 29.85 |
| ATOM | 4110 | N | ILE | B | 232 | 36.093 | 35.038 | 62.062 | 1.00 24.82 |
| ATOM | 4111 | CA | ILE | B | 232 | 37.053 | 34.819 | 60.989 | 1.00 25.65 |
| ATOM | 4112 | CB | ILE | B | 232 | 37.473 | 33.341 | 60.961 | 1.00 22.20 |
| ATOM | 4113 | CG1 | ILE | B | 232 | 38.346 | 32.951 | 62.164 | 1.00 25.46 |
| ATOM | 4114 | CD1 | ILE | B | 232 | 38.402 | 31.452 | 62.401 | 1.00 22.19 |
| ATOM | 4115 | CG2 | ILE | B | 232 | 38.159 | 32.987 | 59.653 | 1.00 26.03 |
| ATOM | 4116 | C | ILE | B | 232 | 36.450 | 35.262 | 59.657 | 1.00 29.68 |
| ATOM | 4117 | O | ILE | B | 232 | 37.061 | 35.995 | 58.876 | 1.00 29.18 |
| ATOM | 4118 | N | ASN | B | 233 | 35.229 | 34.806 | 59.410 | 1.00 29.88 |
| ATOM | 4119 | CA | ASN | B | 233 | 34.545 | 35.100 | 58.151 | 1.00 43.60 |
| ATOM | 4120 | CB | ASN | B | 233 | 33.148 | 34.472 | 58.179 | 1.00 35.22 |
| ATOM | 4121 | CG | ASN | B | 233 | 33.220 | 32.979 | 57.909 | 1.00 32.42 |
| ATOM | 4122 | OD1 | ASN | B | 233 | 34.221 | 32.501 | 57.366 | 1.00 44.01 |
| ATOM | 4123 | ND2 | ASN | B | 233 | 32.188 | 32.220 | 58.277 | 1.00 29.47 |
| ATOM | 4124 | C | ASN | B | 233 | 34.512 | 36.604 | 57.892 | 1.00 43.88 |
| ATOM | 4125 | O | ASN | B | 233 | 34.637 | 37.078 | 56.762 | 1.00 42.08 |
| ATOM | 4126 | N | ARG | B | 234 | 34.368 | 37.357 | 58.967 | 1.00 40.25 |
| ATOM | 4127 | CA | ARG | B | 234 | 34.313 | 38.803 | 58.982 | 1.00 36.71 |
| ATOM | 4128 | CB | ARG | B | 234 | 33.385 | 39.259 | 60.130 | 1.00 40.64 |
| ATOM | 4129 | CG | ARG | B | 234 | 31.918 | 39.153 | 59.733 | 1.00 50.04 |
| ATOM | 4130 | CD | ARG | B | 234 | 30.963 | 39.234 | 60.907 | 1.00 52.66 |
| ATOM | 4131 | NE | ARG | B | 234 | 31.267 | 40.346 | 61.795 | 1.00 61.93 |
| ATOM | 4132 | CZ | ARG | B | 234 | 31.331 | 40.270 | 63.116 | 1.00 64.33 |
| ATOM | 4133 | NH1 | ARG | B | 234 | 31.107 | 39.119 | 63.732 | 1.00 53.92 |
| ATOM | 4134 | NH2 | ARG | B | 234 | 31.619 | 41.352 | 63.825 | 1.00 74.42 |
| ATOM | 4135 | C | ARG | B | 234 | 35.685 | 39.434 | 59.137 | 1.00 37.82 |
| ATOM | 4136 | O | ARG | B | 234 | 35.784 | 40.545 | 59.659 | 1.00 49.54 |
| ATOM | 4137 | N | SER | B | 235 | 36.743 | 38.756 | 58.701 | 1.00 31.78 |
| ATOM | 4138 | CA | SER | B | 235 | 38.087 | 39.304 | 58.815 | 1.00 29.31 |
| ATOM | 4139 | CB | SER | B | 235 | 38.901 | 38.548 | 59.875 | 1.00 32.90 |
| ATOM | 4140 | OG | SER | B | 235 | 38.135 | 38.323 | 61.045 | 1.00 44.62 |
| ATOM | 4141 | C | SER | B | 235 | 38.846 | 39.252 | 57.494 | 1.00 35.75 |
| ATOM | 4142 | O | SER | B | 235 | 39.935 | 38.678 | 57.421 | 1.00 35.41 |
| ATOM | 4143 | N | PRO | B | 236 | 38.319 | 39.848 | 56.436 | 1.00 47.17 |
| ATOM | 4144 | CA | PRO | B | 236 | 38.933 | 39.718 | 55.109 | 1.00 44.13 |
| ATOM | 4145 | CB | PRO | B | 236 | 38.008 | 40.545 | 54.210 | 1.00 50.97 |
| ATOM | 4146 | CG | PRO | B | 236 | 37.355 | 41.506 | 55.150 | 1.00 56.25 |
| ATOM | 4147 | CD | PRO | B | 236 | 37.121 | 40.705 | 56.408 | 1.00 56.24 |
| ATOM | 4148 | C | PRO | B | 236 | 40.345 | 40.289 | 55.070 | 1.00 37.49 |
| ATOM | 4149 | O | PRO | B | 236 | 40.660 | 41.313 | 55.678 | 1.00 43.03 |
| ATOM | 4150 | N | GLY | B | 237 | 41.209 | 39.586 | 54.341 | 1.00 33.65 |
| ATOM | 4151 | CA | GLY | B | 237 | 42.601 | 39.994 | 54.248 | 1.00 33.46 |
| ATOM | 4152 | C | GLY | B | 237 | 43.421 | 39.477 | 55.407 | 1.00 26.07 |
| ATOM | 4153 | O | GLY | B | 237 | 44.630 | 39.670 | 55.500 | 1.00 25.20 |
| ATOM | 4154 | N | ALA | B | 238 | 42.775 | 38.780 | 56.352 | 1.00 26.17 |
| ATOM | 4155 | CA | ALA | B | 238 | 43.611 | 38.252 | 57.430 | 1.00 26.70 |
| ATOM | 4156 | CB | ALA | B | 238 | 42.759 | 37.864 | 58.628 | 1.00 26.33 |
| ATOM | 4157 | C | ALA | B | 238 | 44.430 | 37.058 | 56.946 | 1.00 32.60 |
| ATOM | 4158 | O | ALA | B | 238 | 44.004 | 36.279 | 56.094 | 1.00 20.91 |
| ATOM | 4159 | N | GLY | B | 239 | 45.618 | 36.924 | 57.534 | 1.00 28.56 |

FIGURE 182

| | | | | | | | | | |
|---|---|---|---|---|---|---|---|---|---|
| ATOM | 4160 | CA | GLY | B | 239 | 46.374 | 35.691 | 57.339 | 1.00 28.75 |
| ATOM | 4161 | C | GLY | B | 239 | 45.729 | 34.583 | 58.179 | 1.00 23.57 |
| ATOM | 4162 | O | GLY | B | 239 | 44.556 | 34.686 | 58.553 | 1.00 18.99 |
| ATOM | 4163 | N | PRO | B | 240 | 46.550 | 33.575 | 58.437 | 1.00 19.16 |
| ATOM | 4164 | CA | PRO | B | 240 | 46.088 | 32.396 | 59.170 | 1.00 19.17 |
| ATOM | 4165 | CB | PRO | B | 240 | 47.379 | 31.599 | 59.391 | 1.00 21.18 |
| ATOM | 4166 | CG | PRO | B | 240 | 48.234 | 32.001 | 58.234 | 1.00 25.38 |
| ATOM | 4167 | CD | PRO | B | 240 | 47.974 | 33.480 | 58.072 | 1.00 25.67 |
| ATOM | 4168 | C | PRO | B | 240 | 45.451 | 32.781 | 60.494 | 1.00 19.52 |
| ATOM | 4169 | O | PRO | B | 240 | 45.740 | 33.818 | 61.093 | 1.00 24.13 |
| ATOM | 4170 | N | THR | B | 241 | 44.550 | 31.928 | 60.942 | 1.00 18.39 |
| ATOM | 4171 | CA | THR | B | 241 | 43.980 | 32.007 | 62.281 | 1.00 20.07 |
| ATOM | 4172 | CB | THR | B | 241 | 42.583 | 31.387 | 62.332 | 1.00 20.89 |
| ATOM | 4173 | OG1 | THR | B | 241 | 41.622 | 32.194 | 61.631 | 1.00 19.78 |
| ATOM | 4174 | CG2 | THR | B | 241 | 42.096 | 31.306 | 63.780 | 1.00 20.55 |
| ATOM | 4175 | C | THR | B | 241 | 44.926 | 31.258 | 63.221 | 1.00 23.29 |
| ATOM | 4176 | O | THR | B | 241 | 45.272 | 30.103 | 62.927 | 1.00 13.70 |
| ATOM | 4177 | N | VAL | B | 242 | 45.381 | 31.875 | 64.316 | 1.00 18.05 |
| ATOM | 4178 | CA | VAL | B | 242 | 46.289 | 31.126 | 65.197 | 1.00 19.59 |
| ATOM | 4179 | CB | VAL | B | 242 | 47.234 | 32.049 | 65.978 | 1.00 19.99 |
| ATOM | 4180 | CG1 | VAL | B | 242 | 47.973 | 31.281 | 67.071 | 1.00 22.26 |
| ATOM | 4181 | CG2 | VAL | B | 242 | 48.256 | 32.701 | 65.060 | 1.00 15.38 |
| ATOM | 4182 | C | VAL | B | 242 | 45.478 | 30.266 | 66.157 | 1.00 17.32 |
| ATOM | 4183 | O | VAL | B | 242 | 44.453 | 30.702 | 66.663 | 1.00 14.54 |
| ATOM | 4184 | N | VAL | B | 243 | 45.897 | 29.019 | 66.424 | 1.00 16.24 |
| ATOM | 4185 | CA | VAL | B | 243 | 45.166 | 28.247 | 67.444 | 1.00 13.16 |
| ATOM | 4186 | CB | VAL | B | 243 | 44.275 | 27.150 | 66.860 | 1.00 15.05 |
| ATOM | 4187 | CG1 | VAL | B | 243 | 43.399 | 26.461 | 67.922 | 1.00 13.07 |
| ATOM | 4188 | CG2 | VAL | B | 243 | 43.389 | 27.729 | 65.760 | 1.00 10.83 |
| ATOM | 4189 | C | VAL | B | 243 | 46.218 | 27.641 | 68.355 | 1.00 12.85 |
| ATOM | 4190 | O | VAL | B | 243 | 47.232 | 27.116 | 67.875 | 1.00 13.00 |
| ATOM | 4191 | N | HIS | B | 244 | 46.034 | 27.683 | 69.667 | 1.00 17.27 |
| ATOM | 4192 | CA | HIS | B | 244 | 47.023 | 27.037 | 70.522 | 1.00 14.69 |
| ATOM | 4193 | CB | HIS | B | 244 | 48.209 | 27.931 | 70.868 | 1.00 17.49 |
| ATOM | 4194 | CG | HIS | B | 244 | 47.942 | 28.983 | 71.909 | 1.00 22.46 |
| ATOM | 4195 | ND1 | HIS | B | 244 | 48.065 | 28.773 | 73.260 | 1.00 18.81 |
| ATOM | 4196 | CE1 | HIS | B | 244 | 47.778 | 29.877 | 73.925 | 1.00 16.49 |
| ATOM | 4197 | NE2 | HIS | B | 244 | 47.471 | 30.820 | 73.044 | 1.00 20.57 |
| ATOM | 4198 | CD2 | HIS | B | 244 | 47.576 | 30.286 | 71.781 | 1.00 22.25 |
| ATOM | 4199 | C | HIS | B | 244 | 46.349 | 26.574 | 71.821 | 1.00 12.09 |
| ATOM | 4200 | O | HIS | B | 244 | 45.286 | 27.061 | 72.168 | 1.00 14.03 |
| ATOM | 4201 | N | CYS | B | 245 | 47.029 | 25.631 | 72.434 | 1.00 16.27 |
| ATOM | 4202 | CA | CYS | B | 245 | 46.655 | 25.083 | 73.747 | 1.00 15.96 |
| ATOM | 4203 | CB | CYS | B | 245 | 45.929 | 23.756 | 73.577 | 1.00 24.17 |
| ATOM | 4204 | SG | CYS | B | 245 | 46.767 | 22.530 | 72.540 | 1.00 19.97 1 |
| ATOM | 4205 | C | CYS | B | 245 | 47.952 | 25.010 | 74.536 | 1.00 23.79 |
| ATOM | 4206 | O | CYS | B | 245 | 48.651 | 26.039 | 74.621 | 1.00 17.71 |
| ATOM | 4207 | N | SER | B | 246 | 48.357 | 23.869 | 75.088 | 1.00 15.26 |
| ATOM | 4208 | CA | SER | B | 246 | 49.645 | 23.864 | 75.785 | 1.00 15.41 |
| ATOM | 4209 | CB | SER | B | 246 | 49.587 | 23.047 | 77.091 | 1.00 8.58 |
| ATOM | 4210 | OG | SER | B | 246 | 50.839 | 23.185 | 77.745 | 1.00 14.15 |
| ATOM | 4211 | C | SER | B | 246 | 50.725 | 23.332 | 74.858 | 1.00 19.97 |

FIGURE 183

| ATOM | 4212 | O   | SER | B | 246 | 51.746 | 23.963 | 74.592 | 1.00 | 14.07 |
| ATOM | 4213 | N   | ALA | B | 247 | 50.505 | 22.130 | 74.328 | 1.00 | 17.84 |
| ATOM | 4214 | CA  | ALA | B | 247 | 51.486 | 21.562 | 73.428 | 1.00 | 12.20 |
| ATOM | 4215 | CB  | ALA | B | 247 | 51.563 | 20.047 | 73.532 | 1.00 | 18.43 |
| ATOM | 4216 | C   | ALA | B | 247 | 51.157 | 21.898 | 71.970 | 1.00 | 13.39 |
| ATOM | 4217 | O   | ALA | B | 247 | 52.039 | 21.689 | 71.133 | 1.00 | 21.82 |
| ATOM | 4218 | N   | GLY | B | 248 | 49.949 | 22.376 | 71.712 | 1.00 | 11.10 |
| ATOM | 4219 | CA  | GLY | B | 248 | 49.513 | 22.677 | 70.361 | 1.00 | 14.48 |
| ATOM | 4220 | C   | GLY | B | 248 | 49.114 | 21.449 | 69.571 | 1.00 | 26.17 |
| ATOM | 4221 | O   | GLY | B | 248 | 49.288 | 21.419 | 68.350 | 1.00 | 26.33 |
| ATOM | 4222 | N   | VAL | B | 249 | 48.574 | 20.398 | 70.200 | 1.00 | 19.25 |
| ATOM | 4223 | CA  | VAL | B | 249 | 48.239 | 19.232 | 69.365 | 1.00 | 19.23 |
| ATOM | 4224 | CB  | VAL | B | 249 | 49.293 | 18.114 | 69.401 | 1.00 | 18.92 |
| ATOM | 4225 | CG1 | VAL | B | 249 | 50.682 | 18.568 | 68.977 | 1.00 | 15.44 |
| ATOM | 4226 | CG2 | VAL | B | 249 | 49.432 | 17.478 | 70.794 | 1.00 | 20.80 |
| ATOM | 4227 | C   | VAL | B | 249 | 46.884 | 18.672 | 69.748 | 1.00 | 16.22 |
| ATOM | 4228 | O   | VAL | B | 249 | 46.010 | 18.434 | 68.890 | 1.00 | 22.29 |
| ATOM | 4229 | N   | GLY | B | 250 | 46.602 | 18.422 | 71.030 | 1.00 | 21.24 |
| ATOM | 4230 | CA  | GLY | B | 250 | 45.334 | 17.751 | 71.313 | 1.00 | 23.25 |
| ATOM | 4231 | C   | GLY | B | 250 | 44.109 | 18.612 | 71.266 | 1.00 | 24.10 |
| ATOM | 4232 | O   | GLY | B | 250 | 43.159 | 18.477 | 70.484 | 1.00 | 21.30 |
| ATOM | 4233 | N   | ARG | B | 251 | 44.071 | 19.606 | 72.170 | 1.00 | 12.60 |
| ATOM | 4234 | CA  | ARG | B | 251 | 42.891 | 20.459 | 72.174 | 1.00 | 14.08 |
| ATOM | 4235 | CB  | ARG | B | 251 | 42.941 | 21.317 | 73.449 | 1.00 | 17.84 |
| ATOM | 4236 | CG  | ARG | B | 251 | 42.681 | 20.419 | 74.664 | 1.00 | 18.30 |
| ATOM | 4237 | CD  | ARG | B | 251 | 42.862 | 21.184 | 75.963 | 1.00 | 15.33 |
| ATOM | 4238 | NE  | ARG | B | 251 | 44.280 | 21.335 | 76.262 | 1.00 | 21.24 |
| ATOM | 4239 | CZ  | ARG | B | 251 | 44.713 | 22.030 | 77.317 | 1.00 | 22.30 |
| ATOM | 4240 | NH1 | ARG | B | 251 | 43.820 | 22.588 | 78.124 | 1.00 | 18.21 |
| ATOM | 4241 | NH2 | ARG | B | 251 | 46.013 | 22.129 | 77.516 | 1.00 | 17.67 |
| ATOM | 4242 | C   | ARG | B | 251 | 42.869 | 21.322 | 70.928 | 1.00 | 18.05 |
| ATOM | 4243 | O   | ARG | B | 251 | 41.815 | 21.598 | 70.358 | 1.00 | 21.59 |
| ATOM | 4244 | N   | THR | B | 252 | 44.086 | 21.740 | 70.545 | 1.00 | 14.56 |
| ATOM | 4245 | CA  | THR | B | 252 | 44.135 | 22.560 | 69.328 | 1.00 | 21.90 |
| ATOM | 4246 | CB  | THR | B | 252 | 45.580 | 23.025 | 69.081 | 1.00 | 21.05 |
| ATOM | 4247 | OG1 | THR | B | 252 | 45.872 | 24.089 | 70.001 | 1.00 | 21.60 |
| ATOM | 4248 | CG2 | THR | B | 252 | 45.705 | 23.561 | 67.670 | 1.00 | 19.25 |
| ATOM | 4249 | C   | THR | B | 252 | 43.600 | 21.794 | 68.120 | 1.00 | 21.20 |
| ATOM | 4250 | O   | THR | B | 252 | 42.811 | 22.292 | 67.312 | 1.00 | 19.48 |
| ATOM | 4251 | N   | GLY | B | 253 | 44.043 | 20.545 | 68.002 | 1.00 | 22.67 |
| ATOM | 4252 | CA  | GLY | B | 253 | 43.671 | 19.713 | 66.862 | 1.00 | 16.29 |
| ATOM | 4253 | C   | GLY | B | 253 | 42.198 | 19.395 | 66.821 | 1.00 | 22.35 |
| ATOM | 4254 | O   | GLY | B | 253 | 41.587 | 19.330 | 65.747 | 1.00 | 19.39 |
| ATOM | 4255 | N   | THR | B | 254 | 41.634 | 19.191 | 68.022 | 1.00 | 25.18 |
| ATOM | 4256 | CA  | THR | B | 254 | 40.194 | 18.939 | 68.106 | 1.00 | 15.84 |
| ATOM | 4257 | CB  | THR | B | 254 | 39.805 | 18.402 | 69.499 | 1.00 | 21.21 |
| ATOM | 4258 | OG1 | THR | B | 254 | 40.624 | 17.266 | 69.796 | 1.00 | 19.04 |
| ATOM | 4259 | CG2 | THR | B | 254 | 38.361 | 17.943 | 69.525 | 1.00 | 24.29 |
| ATOM | 4260 | C   | THR | B | 254 | 39.422 | 20.198 | 67.781 | 1.00 | 19.07 |
| ATOM | 4261 | O   | THR | B | 254 | 38.352 | 20.162 | 67.182 | 1.00 | 21.18 |
| ATOM | 4262 | N   | PHE | B | 255 | 39.931 | 21.367 | 68.178 | 1.00 | 21.95 |
| ATOM | 4263 | CA  | PHE | B | 255 | 39.225 | 22.595 | 67.821 | 1.00 | 22.07 |

FIGURE 184

```
ATOM   4264  CB   PHE B 255      39.910  23.855  68.368  1.00 20.64
ATOM   4265  CG   PHE B 255      39.280  25.177  67.939  1.00 16.94
ATOM   4266  CD1  PHE B 255      38.222  25.716  68.650  1.00 17.36
ATOM   4267  CE1  PHE B 255      37.628  26.901  68.272  1.00 16.83
ATOM   4268  CZ   PHE B 255      38.079  27.576  67.156  1.00 20.63
ATOM   4269  CE2  PHE B 255      39.141  27.067  66.427  1.00 15.59
ATOM   4270  CD2  PHE B 255      39.730  25.892  66.841  1.00 26.52
ATOM   4271  C    PHE B 255      39.148  22.712  66.298  1.00 16.89
ATOM   4272  O    PHE B 255      38.114  23.045  65.727  1.00 22.55
ATOM   4273  N    ILE B 256      40.305  22.497  65.682  1.00 22.37
ATOM   4274  CA   ILE B 256      40.393  22.694  64.232  1.00 26.45
ATOM   4275  CB   ILE B 256      41.841  22.644  63.742  1.00 22.17
ATOM   4276  CG1  ILE B 256      42.717  23.802  64.245  1.00 19.09
ATOM   4277  CD1  ILE B 256      44.182  23.636  63.845  1.00 17.45
ATOM   4278  CG2  ILE B 256      41.861  22.570  62.218  1.00 25.40
ATOM   4279  C    ILE B 256      39.556  21.645  63.513  1.00 25.61
ATOM   4280  O    ILE B 256      38.871  21.935  62.537  1.00 32.43
ATOM   4281  N    ALA B 257      39.588  20.418  64.006  1.00 22.52
ATOM   4282  CA   ALA B 257      38.740  19.395  63.390  1.00 28.35
ATOM   4283  CB   ALA B 257      39.011  18.049  64.057  1.00 23.53
ATOM   4284  C    ALA B 257      37.271  19.768  63.462  1.00 31.55
ATOM   4285  O    ALA B 257      36.495  19.520  62.536  1.00 36.42
ATOM   4286  N    LEU B 258      36.833  20.366  64.568  1.00 27.78
ATOM   4287  CA   LEU B 258      35.425  20.714  64.735  1.00 25.99
ATOM   4288  CB   LEU B 258      35.101  21.046  66.201  1.00 29.85
ATOM   4289  CG   LEU B 258      33.612  21.160  66.530  1.00 31.93
ATOM   4290  CD1  LEU B 258      32.852  19.931  66.050  1.00 21.42
ATOM   4291  CD2  LEU B 258      33.381  21.372  68.020  1.00 29.92
ATOM   4292  C    LEU B 258      35.049  21.898  63.862  1.00 28.98
ATOM   4293  O    LEU B 258      33.955  21.967  63.306  1.00 33.28
ATOM   4294  N    ASP B 259      35.976  22.850  63.743  1.00 25.38
ATOM   4295  CA   ASP B 259      35.725  23.991  62.856  1.00 26.70
ATOM   4296  CB   ASP B 259      36.911  24.943  62.895  1.00 25.83
ATOM   4297  CG   ASP B 259      36.704  26.266  62.193  1.00 34.39
ATOM   4298  OD1  ASP B 259      35.615  26.855  62.335  1.00 28.39
ATOM   4299  OD2  ASP B 259      37.650  26.717  61.505  1.00 32.58
ATOM   4300  C    ASP B 259      35.466  23.504  61.433  1.00 19.95
ATOM   4301  O    ASP B 259      34.559  23.983  60.753  1.00 32.03
ATOM   4302  N    ARG B 260      36.261  22.532  60.984  1.00 24.53
ATOM   4303  CA   ARG B 260      36.087  22.057  59.603  1.00 25.87
ATOM   4304  CB   ARG B 260      37.297  21.239  59.169  1.00 26.24
ATOM   4305  CG   ARG B 260      38.591  22.045  59.058  1.00 28.14
ATOM   4306  CD   ARG B 260      39.709  21.131  58.569  1.00 24.62
ATOM   4307  NE   ARG B 260      39.311  20.472  57.320  1.00 31.53
ATOM   4308  CZ   ARG B 260      40.177  20.214  56.345  1.00 39.36
ATOM   4309  NH1  ARG B 260      41.447  20.563  56.493  1.00 41.26
ATOM   4310  NH2  ARG B 260      39.778  19.617  55.231  1.00 56.76
ATOM   4311  C    ARG B 260      34.822  21.239  59.447  1.00 31.74
ATOM   4312  O    ARG B 260      34.189  21.251  58.392  1.00 39.13
ATOM   4313  N    ILE B 261      34.381  20.492  60.468  1.00 30.98
ATOM   4314  CA   ILE B 261      33.208  19.657  60.165  1.00 35.76
ATOM   4315  CB   ILE B 261      33.146  18.381  61.023  1.00 33.31
```

FIGURE 185

| | | | | | | | | | |
|---|---|---|---|---|---|---|---|---|---|
| ATOM | 4316 | CG1 | ILE | B | 261 | 32.912 | 18.576 | 62.521 | 1.00 27.49 |
| ATOM | 4317 | CD1 | ILE | B | 261 | 33.493 | 17.459 | 63.368 | 1.00 32.91 |
| ATOM | 4318 | CG2 | ILE | B | 261 | 34.414 | 17.561 | 60.796 | 1.00 33.85 |
| ATOM | 4319 | C | ILE | B | 261 | 31.938 | 20.476 | 60.307 | 1.00 41.61 |
| ATOM | 4320 | O | ILE | B | 261 | 30.932 | 20.212 | 59.641 | 1.00 42.61 |
| ATOM | 4321 | N | LEU | B | 262 | 31.977 | 21.494 | 61.170 | 1.00 36.25 |
| ATOM | 4322 | CA | LEU | B | 262 | 30.747 | 22.281 | 61.321 | 1.00 37.79 |
| ATOM | 4323 | CB | LEU | B | 262 | 30.868 | 23.297 | 62.448 | 1.00 33.16 |
| ATOM | 4324 | CG | LEU | B | 262 | 30.867 | 22.707 | 63.865 | 1.00 34.98 |
| ATOM | 4325 | CD1 | LEU | B | 262 | 30.730 | 23.791 | 64.918 | 1.00 35.24 |
| ATOM | 4326 | CD2 | LEU | B | 262 | 29.751 | 21.680 | 64.011 | 1.00 39.50 |
| ATOM | 4327 | C | LEU | B | 262 | 30.444 | 22.945 | 59.982 | 1.00 48.10 |
| ATOM | 4328 | O | LEU | B | 262 | 29.297 | 23.137 | 59.592 | 1.00 54.41 |
| ATOM | 4329 | N | GLN | B | 263 | 31.536 | 23.268 | 59.294 | 1.00 42.55 |
| ATOM | 4330 | CA | GLN | B | 263 | 31.446 | 23.852 | 57.963 | 1.00 45.39 |
| ATOM | 4331 | CB | GLN | B | 263 | 32.819 | 24.403 | 57.562 | 1.00 47.06 |
| ATOM | 4332 | CG | GLN | B | 263 | 33.160 | 25.695 | 58.293 | 1.00 52.92 |
| ATOM | 4333 | CD | GLN | B | 263 | 34.546 | 26.217 | 57.972 | 1.00 51.62 |
| ATOM | 4334 | OE1 | GLN | B | 263 | 34.689 | 27.171 | 57.208 | 1.00 48.47 |
| ATOM | 4335 | NE2 | GLN | B | 263 | 35.575 | 25.609 | 58.552 | 1.00 34.73 |
| ATOM | 4336 | C | GLN | B | 263 | 30.935 | 22.825 | 56.961 | 1.00 37.20 |
| ATOM | 4337 | O | GLN | B | 263 | 29.987 | 23.076 | 56.223 | 1.00 36.52 |
| ATOM | 4338 | N | GLN | B | 264 | 31.551 | 21.651 | 56.930 | 1.00 48.77 |
| ATOM | 4339 | CA | GLN | B | 264 | 31.089 | 20.583 | 56.052 | 1.00 54.55 |
| ATOM | 4340 | CB | GLN | B | 264 | 31.890 | 19.305 | 56.289 | 1.00 51.39 |
| ATOM | 4341 | CG | GLN | B | 264 | 33.377 | 19.395 | 55.996 | 1.00 45.82 |
| ATOM | 4342 | CD | GLN | B | 264 | 34.080 | 18.072 | 56.248 | 1.00 49.30 |
| ATOM | 4343 | OE1 | GLN | B | 264 | 33.426 | 17.046 | 56.440 | 1.00 54.85 |
| ATOM | 4344 | NE2 | GLN | B | 264 | 35.410 | 18.093 | 56.256 | 1.00 42.52 |
| ATOM | 4345 | C | GLN | B | 264 | 29.602 | 20.309 | 56.268 | 1.00 65.82 |
| ATOM | 4346 | O | GLN | B | 264 | 28.854 | 20.101 | 55.312 | 1.00 71.36 |
| ATOM | 4347 | N | LEU | B | 265 | 29.169 | 20.311 | 57.529 | 1.00 66.58 |
| ATOM | 4348 | CA | LEU | B | 265 | 27.766 | 20.033 | 57.816 | 1.00 67.06 |
| ATOM | 4349 | CB | LEU | B | 265 | 27.465 | 20.150 | 59.309 | 1.00 67.27 |
| ATOM | 4350 | CG | LEU | B | 265 | 27.604 | 18.870 | 60.130 | 1.00 71.80 |
| ATOM | 4351 | CD1 | LEU | B | 265 | 27.000 | 19.066 | 61.515 | 1.00 69.10 |
| ATOM | 4352 | CD2 | LEU | B | 265 | 26.955 | 17.695 | 59.409 | 1.00 78.85 |
| ATOM | 4353 | C | LEU | B | 265 | 26.858 | 20.996 | 57.055 | 1.00 65.79 |
| ATOM | 4354 | O | LEU | B | 265 | 25.951 | 20.581 | 56.340 | 1.00 62.34 |
| ATOM | 4355 | N | ASP | B | 266 | 27.140 | 22.278 | 57.242 | 1.00 61.77 |
| ATOM | 4356 | CA | ASP | B | 266 | 26.333 | 23.341 | 56.663 | 1.00 64.82 |
| ATOM | 4357 | CB | ASP | B | 266 | 26.740 | 24.673 | 57.312 | 1.00 71.48 |
| ATOM | 4358 | CG | ASP | B | 266 | 26.589 | 24.603 | 58.822 | 1.00 82.79 |
| ATOM | 4359 | OD1 | ASP | B | 266 | 26.033 | 23.597 | 59.312 | 1.00 89.00 |
| ATOM | 4360 | OD2 | ASP | B | 266 | 27.021 | 25.562 | 59.500 | 1.00104.58 |
| ATOM | 4361 | C | ASP | B | 266 | 26.454 | 23.433 | 55.152 | 1.00 62.69 |
| ATOM | 4362 | O | ASP | B | 266 | 25.779 | 24.251 | 54.519 | 1.00 61.16 |
| ATOM | 4363 | N | SER | B | 267 | 27.294 | 22.612 | 54.520 | 1.00 56.01 |
| ATOM | 4364 | CA | SER | B | 267 | 27.375 | 22.733 | 53.063 | 1.00 54.60 |
| ATOM | 4365 | CB | SER | B | 267 | 28.557 | 23.647 | 52.720 | 1.00 53.27 |
| ATOM | 4366 | OG | SER | B | 267 | 29.698 | 23.231 | 53.454 | 1.00 48.03 |
| ATOM | 4367 | C | SER | B | 267 | 27.529 | 21.401 | 52.353 | 1.00 61.19 |

FIGURE 186

| | | | | | | | | | |
|---|---|---|---|---|---|---|---|---|---|
| ATOM | 4368 | O | SER | B | 267 | 27.489 | 21.325 | 51.121 | 1.00 78.99 |
| ATOM | 4369 | N | LYS | B | 268 | 27.711 | 20.321 | 53.101 | 1.00 66.12 |
| ATOM | 4370 | CA | LYS | B | 268 | 27.946 | 19.017 | 52.481 | 1.00 67.60 |
| ATOM | 4371 | CB | LYS | B | 268 | 29.387 | 18.583 | 52.742 | 1.00 73.63 |
| ATOM | 4372 | CG | LYS | B | 268 | 29.798 | 17.277 | 52.087 | 1.00 76.35 |
| ATOM | 4373 | CD | LYS | B | 268 | 31.310 | 17.139 | 52.000 | 1.00 69.59 |
| ATOM | 4374 | CE | LYS | B | 268 | 31.983 | 17.228 | 53.356 | 1.00 57.88 |
| ATOM | 4375 | NZ | LYS | B | 268 | 32.516 | 15.916 | 53.815 | 1.00 46.13 |
| ATOM | 4376 | C | LYS | B | 268 | 26.957 | 17.982 | 52.997 | 1.00 59.94 |
| ATOM | 4377 | O | LYS | B | 268 | 26.428 | 18.102 | 54.100 | 1.00 64.53 |
| ATOM | 4378 | N | ASP | B | 269 | 26.692 | 16.955 | 52.201 | 1.00 56.14 |
| ATOM | 4379 | CA | ASP | B | 269 | 25.749 | 15.913 | 52.591 | 1.00 60.87 |
| ATOM | 4380 | CB | ASP | B | 269 | 24.980 | 15.392 | 51.377 | 1.00 71.26 |
| ATOM | 4381 | CG | ASP | B | 269 | 25.670 | 15.678 | 50.060 | 1.00 82.48 |
| ATOM | 4382 | OD1 | ASP | B | 269 | 26.027 | 16.846 | 49.797 | 1.00 101.89 |
| ATOM | 4383 | OD2 | ASP | B | 269 | 25.856 | 14.725 | 49.273 | 1.00 103.90 |
| ATOM | 4384 | C | ASP | B | 269 | 26.479 | 14.771 | 53.294 | 1.00 57.30 |
| ATOM | 4385 | O | ASP | B | 269 | 25.869 | 13.797 | 53.732 | 1.00 54.94 |
| ATOM | 4386 | N | SER | B | 270 | 27.797 | 14.922 | 53.393 | 1.00 44.67 |
| ATOM | 4387 | CA | SER | B | 270 | 28.633 | 13.990 | 54.132 | 1.00 41.73 |
| ATOM | 4388 | CB | SER | B | 270 | 29.526 | 13.168 | 53.206 | 1.00 43.00 |
| ATOM | 4389 | OG | SER | B | 270 | 28.790 | 12.556 | 52.162 | 1.00 51.47 |
| ATOM | 4390 | C | SER | B | 270 | 29.487 | 14.760 | 55.142 | 1.00 42.93 |
| ATOM | 4391 | O | SER | B | 270 | 29.563 | 15.988 | 55.100 | 1.00 44.44 |
| ATOM | 4392 | N | VAL | B | 271 | 30.122 | 14.024 | 56.045 | 1.00 39.47 |
| ATOM | 4393 | CA | VAL | B | 271 | 31.033 | 14.606 | 57.020 | 1.00 42.42 |
| ATOM | 4394 | CB | VAL | B | 271 | 30.399 | 14.754 | 58.412 | 1.00 43.26 |
| ATOM | 4395 | CG1 | VAL | B | 271 | 29.733 | 13.460 | 58.864 | 1.00 32.79 |
| ATOM | 4396 | CG2 | VAL | B | 271 | 31.460 | 15.183 | 59.417 | 1.00 35.29 |
| ATOM | 4397 | C | VAL | B | 271 | 32.282 | 13.735 | 57.095 | 1.00 48.99 |
| ATOM | 4398 | O | VAL | B | 271 | 32.184 | 12.509 | 57.041 | 1.00 58.21 |
| ATOM | 4399 | N | ASP | B | 272 | 33.444 | 14.367 | 57.209 | 1.00 45.99 |
| ATOM | 4400 | CA | ASP | B | 272 | 34.707 | 13.648 | 57.135 | 1.00 35.10 |
| ATOM | 4401 | CB | ASP | B | 272 | 35.417 | 14.055 | 55.832 | 1.00 36.44 |
| ATOM | 4402 | CG | ASP | B | 272 | 36.191 | 12.901 | 55.232 | 1.00 35.96 |
| ATOM | 4403 | OD1 | ASP | B | 272 | 36.367 | 11.892 | 55.943 | 1.00 46.07 |
| ATOM | 4404 | OD2 | ASP | B | 272 | 36.621 | 13.010 | 54.067 | 1.00 60.29 |
| ATOM | 4405 | C | ASP | B | 272 | 35.605 | 13.897 | 58.334 | 1.00 38.48 |
| ATOM | 4406 | O | ASP | B | 272 | 36.631 | 14.567 | 58.238 | 1.00 37.38 |
| ATOM | 4407 | N | ILE | B | 273 | 35.225 | 13.349 | 59.485 | 1.00 44.55 |
| ATOM | 4408 | CA | ILE | B | 273 | 36.018 | 13.484 | 60.706 | 1.00 42.80 |
| ATOM | 4409 | CB | ILE | B | 273 | 35.239 | 12.986 | 61.941 | 1.00 44.89 |
| ATOM | 4410 | CG1 | ILE | B | 273 | 34.010 | 13.836 | 62.283 | 1.00 43.95 |
| ATOM | 4411 | CD1 | ILE | B | 273 | 32.873 | 13.080 | 62.950 | 1.00 28.68 |
| ATOM | 4412 | CG2 | ILE | B | 273 | 36.135 | 12.859 | 63.164 | 1.00 35.00 |
| ATOM | 4413 | C | ILE | B | 273 | 37.341 | 12.749 | 60.554 | 1.00 43.03 |
| ATOM | 4414 | O | ILE | B | 273 | 38.397 | 13.283 | 60.903 | 1.00 47.22 |
| ATOM | 4415 | N | TYR | B | 274 | 37.333 | 11.528 | 60.019 | 1.00 33.68 |
| ATOM | 4416 | CA | TYR | B | 274 | 38.587 | 10.824 | 59.758 | 1.00 33.83 |
| ATOM | 4417 | CB | TYR | B | 274 | 38.323 | 9.463 | 59.101 | 1.00 31.32 |
| ATOM | 4418 | CG | TYR | B | 274 | 39.536 | 8.615 | 58.815 | 1.00 34.21 |
| ATOM | 4419 | CD1 | TYR | B | 274 | 40.011 | 7.706 | 59.752 | 1.00 27.81 |

FIGURE 187

| | | | | | | | | | |
|---|---|---|---|---|---|---|---|---|---|
| ATOM | 4420 | CE1 | TYR | B | 274 | 41.124 | 6.936 | 59.481 | 1.00 33.31 |
| ATOM | 4421 | CZ | TYR | B | 274 | 41.783 | 7.051 | 58.280 | 1.00 38.03 |
| ATOM | 4422 | OH | TYR | B | 274 | 42.894 | 6.287 | 57.994 | 1.00 74.99 |
| ATOM | 4423 | CE2 | TYR | B | 274 | 41.334 | 7.942 | 57.338 | 1.00 34.20 |
| ATOM | 4424 | CD2 | TYR | B | 274 | 40.227 | 8.704 | 57.615 | 1.00 30.48 |
| ATOM | 4425 | C | TYR | B | 274 | 39.499 | 11.654 | 58.857 | 1.00 30.77 |
| ATOM | 4426 | O | TYR | B | 274 | 40.699 | 11.762 | 59.091 | 1.00 42.32 |
| ATOM | 4427 | N | GLY | B | 275 | 38.914 | 12.201 | 57.796 | 1.00 33.93 |
| ATOM | 4428 | CA | GLY | B | 275 | 39.661 | 12.924 | 56.786 | 1.00 34.96 |
| ATOM | 4429 | C | GLY | B | 275 | 40.242 | 14.213 | 57.340 | 1.00 28.44 |
| ATOM | 4430 | O | GLY | B | 275 | 41.328 | 14.628 | 56.928 | 1.00 26.09 |
| ATOM | 4431 | N | ALA | B | 276 | 39.508 | 14.838 | 58.264 | 1.00 30.51 |
| ATOM | 4432 | CA | ALA | B | 276 | 40.037 | 16.083 | 58.849 | 1.00 32.53 |
| ATOM | 4433 | CB | ALA | B | 276 | 38.977 | 16.819 | 59.633 | 1.00 28.84 |
| ATOM | 4434 | C | ALA | B | 276 | 41.233 | 15.754 | 59.724 | 1.00 28.27 |
| ATOM | 4435 | O | ALA | B | 276 | 42.298 | 16.355 | 59.634 | 1.00 27.29 |
| ATOM | 4436 | N | VAL | B | 277 | 41.052 | 14.745 | 60.587 | 1.00 22.62 |
| ATOM | 4437 | CA | VAL | B | 277 | 42.157 | 14.409 | 61.478 | 1.00 22.13 |
| ATOM | 4438 | CB | VAL | B | 277 | 41.713 | 13.420 | 62.569 | 1.00 25.76 |
| ATOM | 4439 | CG1 | VAL | B | 277 | 42.931 | 12.861 | 63.293 | 1.00 33.74 |
| ATOM | 4440 | CG2 | VAL | B | 277 | 40.769 | 14.087 | 63.561 | 1.00 22.07 |
| ATOM | 4441 | C | VAL | B | 277 | 43.342 | 13.846 | 60.712 | 1.00 31.87 |
| ATOM | 4442 | O | VAL | B | 277 | 44.512 | 14.018 | 61.076 | 1.00 30.97 |
| ATOM | 4443 | N | HIS | B | 278 | 43.053 | 13.141 | 59.616 | 1.00 26.49 |
| ATOM | 4444 | CA | HIS | B | 278 | 44.180 | 12.632 | 58.831 | 1.00 24.97 |
| ATOM | 4445 | CB | HIS | B | 278 | 43.663 | 11.735 | 57.699 | 1.00 26.29 |
| ATOM | 4446 | CG | HIS | B | 278 | 44.716 | 11.393 | 56.689 | 1.00 35.64 |
| ATOM | 4447 | ND1 | HIS | B | 278 | 45.145 | 12.273 | 55.723 | 1.00 32.18 |
| ATOM | 4448 | CE1 | HIS | B | 278 | 46.077 | 11.699 | 54.986 | 1.00 36.91 |
| ATOM | 4449 | NE2 | HIS | B | 278 | 46.280 | 10.473 | 55.443 | 1.00 39.75 |
| ATOM | 4450 | CD2 | HIS | B | 278 | 45.440 | 10.261 | 56.509 | 1.00 40.27 |
| ATOM | 4451 | C | HIS | B | 278 | 44.988 | 13.809 | 58.294 | 1.00 17.49 |
| ATOM | 4452 | O | HIS | B | 278 | 46.212 | 13.862 | 58.377 | 1.00 21.10 |
| ATOM | 4453 | N | ASP | B | 279 | 44.262 | 14.777 | 57.736 | 1.00 23.86 |
| ATOM | 4454 | CA | ASP | B | 279 | 44.908 | 15.964 | 57.171 | 1.00 33.69 |
| ATOM | 4455 | CB | ASP | B | 279 | 43.864 | 16.870 | 56.522 | 1.00 34.31 |
| ATOM | 4456 | CG | ASP | B | 279 | 44.369 | 17.652 | 55.325 | 1.00 49.90 |
| ATOM | 4457 | OD1 | ASP | B | 279 | 45.255 | 17.163 | 54.584 | 1.00 38.05 |
| ATOM | 4458 | OD2 | ASP | B | 279 | 43.867 | 18.782 | 55.115 | 1.00 40.80 |
| ATOM | 4459 | C | ASP | B | 279 | 45.697 | 16.716 | 58.238 | 1.00 26.60 |
| ATOM | 4460 | O | ASP | B | 279 | 46.841 | 17.124 | 58.034 | 1.00 28.11 |
| ATOM | 4461 | N | LEU | B | 280 | 45.088 | 16.895 | 59.408 | 1.00 25.81 |
| ATOM | 4462 | CA | LEU | B | 280 | 45.801 | 17.538 | 60.510 | 1.00 28.08 |
| ATOM | 4463 | CB | LEU | B | 280 | 44.955 | 17.535 | 61.782 | 1.00 24.40 |
| ATOM | 4464 | CG | LEU | B | 280 | 43.689 | 18.389 | 61.749 | 1.00 26.95 |
| ATOM | 4465 | CD1 | LEU | B | 280 | 43.088 | 18.489 | 63.138 | 1.00 30.65 |
| ATOM | 4466 | CD2 | LEU | B | 280 | 43.987 | 19.757 | 61.164 | 1.00 49.17 |
| ATOM | 4467 | C | LEU | B | 280 | 47.117 | 16.834 | 60.804 | 1.00 32.98 |
| ATOM | 4468 | O | LEU | B | 280 | 48.141 | 17.483 | 61.022 | 1.00 28.16 |
| ATOM | 4469 | N | ARG | B | 281 | 47.078 | 15.503 | 60.816 | 1.00 21.92 |
| ATOM | 4470 | CA | ARG | B | 281 | 48.252 | 14.703 | 61.134 | 1.00 14.30 |
| ATOM | 4471 | CB | ARG | B | 281 | 47.854 | 13.212 | 61.199 | 1.00 15.59 |

FIGURE 188

| | | | | | | | | | |
|---|---|---|---|---|---|---|---|---|---|
| ATOM | 4472 | CG | ARG | B | 281 | 46.856 | 12.946 | 62.326 | 1.00 30.08 |
| ATOM | 4473 | CD | ARG | B | 281 | 47.580 | 12.419 | 63.554 | 1.00 35.07 |
| ATOM | 4474 | NE | ARG | B | 281 | 46.665 | 12.288 | 64.685 | 1.00 41.36 |
| ATOM | 4475 | CZ | ARG | B | 281 | 46.356 | 11.125 | 65.243 | 1.00 44.73 |
| ATOM | 4476 | NH1 | ARG | B | 281 | 46.894 | 10.010 | 64.769 | 1.00 39.14 |
| ATOM | 4477 | NH2 | ARG | B | 281 | 45.515 | 11.092 | 66.268 | 1.00 40.94 |
| ATOM | 4478 | C | ARG | B | 281 | 49.378 | 14.834 | 60.141 | 1.00 16.56 |
| ATOM | 4479 | O | ARG | B | 281 | 50.574 | 14.692 | 60.430 | 1.00 23.41 |
| ATOM | 4480 | N | LEU | B | 282 | 49.000 | 15.098 | 58.885 | 1.00 21.94 |
| ATOM | 4481 | CA | LEU | B | 282 | 50.085 | 15.295 | 57.919 | 1.00 22.08 |
| ATOM | 4482 | CB | LEU | B | 282 | 49.505 | 15.415 | 56.508 | 1.00 30.24 |
| ATOM | 4483 | CG | LEU | B | 282 | 48.946 | 14.129 | 55.895 | 1.00 38.66 |
| ATOM | 4484 | CD1 | LEU | B | 282 | 48.260 | 14.402 | 54.563 | 1.00 35.05 |
| ATOM | 4485 | CD2 | LEU | B | 282 | 50.055 | 13.099 | 55.724 | 1.00 35.97 |
| ATOM | 4486 | C | LEU | B | 282 | 50.921 | 16.528 | 58.246 | 1.00 22.11 |
| ATOM | 4487 | O | LEU | B | 282 | 52.089 | 16.605 | 57.854 | 1.00 27.03 |
| ATOM | 4488 | N | HIS | B | 283 | 50.359 | 17.509 | 58.949 | 1.00 19.17 |
| ATOM | 4489 | CA | HIS | B | 283 | 51.085 | 18.767 | 59.129 | 1.00 22.40 |
| ATOM | 4490 | CB | HIS | B | 283 | 50.140 | 19.931 | 58.762 | 1.00 28.15 |
| ATOM | 4491 | CG | HIS | B | 283 | 49.775 | 19.824 | 57.305 | 1.00 27.86 |
| ATOM | 4492 | ND1 | HIS | B | 283 | 48.636 | 19.183 | 56.872 | 1.00 29.65 |
| ATOM | 4493 | CE1 | HIS | B | 283 | 48.585 | 19.229 | 55.549 | 1.00 28.25 |
| ATOM | 4494 | NE2 | HIS | B | 283 | 49.648 | 19.884 | 55.115 | 1.00 28.83 |
| ATOM | 4495 | CD2 | HIS | B | 283 | 50.417 | 20.257 | 56.193 | 1.00 25.31 |
| ATOM | 4496 | C | HIS | B | 283 | 51.683 | 18.946 | 60.513 | 1.00 16.39 |
| ATOM | 4497 | O | HIS | B | 283 | 52.619 | 19.732 | 60.696 | 1.00 19.23 |
| ATOM | 4498 | N | ARG | B | 284 | 51.215 | 18.186 | 61.499 | 1.00 14.42 |
| ATOM | 4499 | CA | ARG | B | 284 | 51.851 | 18.254 | 62.811 | 1.00 16.63 |
| ATOM | 4500 | CB | ARG | B | 284 | 51.353 | 19.503 | 63.539 | 1.00 17.04 |
| ATOM | 4501 | CG | ARG | B | 284 | 51.990 | 19.779 | 64.894 | 1.00 20.73 |
| ATOM | 4502 | CD | ARG | B | 284 | 51.670 | 21.227 | 65.288 | 1.00 19.31 |
| ATOM | 4503 | NE | ARG | B | 284 | 51.932 | 21.473 | 66.705 | 1.00 16.50 |
| ATOM | 4504 | CZ | ARG | B | 284 | 53.027 | 22.065 | 67.155 | 1.00 18.89 |
| ATOM | 4505 | NH1 | ARG | B | 284 | 53.961 | 22.471 | 66.295 | 1.00 16.50 |
| ATOM | 4506 | NH2 | ARG | B | 284 | 53.184 | 22.249 | 68.464 | 1.00 12.75 |
| ATOM | 4507 | C | ARG | B | 284 | 51.515 | 17.002 | 63.621 | 1.00 15.24 |
| ATOM | 4508 | O | ARG | B | 284 | 50.395 | 16.503 | 63.515 | 1.00 21.78 |
| ATOM | 4509 | N | VAL | B | 285 | 52.472 | 16.553 | 64.400 | 1.00 22.07 |
| ATOM | 4510 | CA | VAL | B | 285 | 52.309 | 15.357 | 65.228 | 1.00 18.47 |
| ATOM | 4511 | CB | VAL | B | 285 | 53.643 | 15.032 | 65.919 | 1.00 22.85 |
| ATOM | 4512 | CG1 | VAL | B | 285 | 53.931 | 15.996 | 67.065 | 1.00 21.98 |
| ATOM | 4513 | CG2 | VAL | B | 285 | 53.647 | 13.591 | 66.415 | 1.00 31.56 |
| ATOM | 4514 | C | VAL | B | 285 | 51.181 | 15.513 | 66.237 | 1.00 31.62 |
| ATOM | 4515 | O | VAL | B | 285 | 50.887 | 16.594 | 66.739 | 1.00 20.75 |
| ATOM | 4516 | N | HIS | B | 286 | 50.511 | 14.404 | 66.519 | 1.00 35.82 |
| ATOM | 4517 | CA | HIS | B | 286 | 49.576 | 14.183 | 67.598 | 1.00 24.99 |
| ATOM | 4518 | CB | HIS | B | 286 | 50.264 | 14.498 | 68.941 | 1.00 23.90 |
| ATOM | 4519 | CG | HIS | B | 286 | 51.337 | 13.511 | 69.289 | 1.00 30.81 |
| ATOM | 4520 | ND1 | HIS | B | 286 | 51.236 | 12.162 | 69.015 | 1.00 39.23 |
| ATOM | 4521 | CE1 | HIS | B | 286 | 52.326 | 11.537 | 69.425 | 1.00 40.25 |
| ATOM | 4522 | NE2 | HIS | B | 286 | 53.144 | 12.431 | 69.963 | 1.00 40.87 |
| ATOM | 4523 | CD2 | HIS | B | 286 | 52.543 | 13.669 | 69.883 | 1.00 30.11 |

FIGURE 189

| | | | | | | | | | |
|---|---|---|---|---|---|---|---|---|---|
| ATOM | 4524 | C | HIS | B 286 | 48.282 | 14.973 | 67.520 | 1.00 | 28.12 |
| ATOM | 4525 | O | HIS | B 286 | 47.543 | 15.026 | 68.515 | 1.00 | 34.48 |
| ATOM | 4526 | N | MET | B 287 | 47.981 | 15.578 | 66.382 | 1.00 | 19.24 |
| ATOM | 4527 | CA | MET | B 287 | 46.741 | 16.320 | 66.214 | 1.00 | 22.67 |
| ATOM | 4528 | CB | MET | B 287 | 46.545 | 16.759 | 64.771 | 1.00 | 29.06 |
| ATOM | 4529 | CG | MET | B 287 | 47.551 | 17.692 | 64.153 | 1.00 | 26.09 |
| ATOM | 4530 | SD | MET | B 287 | 47.319 | 19.403 | 64.727 | 1.00 | 57.61 | 1 |
| ATOM | 4531 | CE | MET | B 287 | 48.486 | 19.307 | 66.054 | 1.00 | 8.09 |
| ATOM | 4532 | C | MET | B 287 | 45.535 | 15.468 | 66.623 | 1.00 | 35.86 |
| ATOM | 4533 | O | MET | B 287 | 45.367 | 14.357 | 66.108 | 1.00 | 33.56 |
| ATOM | 4534 | N | VAL | B 288 | 44.728 | 16.000 | 67.527 | 1.00 | 31.94 |
| ATOM | 4535 | CA | VAL | B 288 | 43.671 | 15.249 | 68.206 | 1.00 | 29.58 |
| ATOM | 4536 | CB | VAL | B 288 | 42.591 | 14.724 | 67.262 | 1.00 | 25.44 |
| ATOM | 4537 | CG1 | VAL | B 288 | 41.504 | 13.994 | 68.051 | 1.00 | 27.03 |
| ATOM | 4538 | CG2 | VAL | B 288 | 41.978 | 15.870 | 66.483 | 1.00 | 25.23 |
| ATOM | 4539 | C | VAL | B 288 | 44.331 | 14.102 | 68.975 | 1.00 | 28.49 |
| ATOM | 4540 | O | VAL | B 288 | 44.486 | 12.998 | 68.463 | 1.00 | 31.96 |
| ATOM | 4541 | N | GLN | B 289 | 44.734 | 14.434 | 70.194 | 1.00 | 22.07 |
| ATOM | 4542 | CA | GLN | B 289 | 45.722 | 13.703 | 70.953 | 1.00 | 30.99 |
| ATOM | 4543 | CB | GLN | B 289 | 46.399 | 14.641 | 71.955 | 1.00 | 32.52 |
| ATOM | 4544 | CG | GLN | B 289 | 47.584 | 14.032 | 72.686 | 1.00 | 31.56 |
| ATOM | 4545 | CD | GLN | B 289 | 47.342 | 13.990 | 74.187 | 1.00 | 46.43 |
| ATOM | 4546 | OE1 | GLN | B 289 | 46.897 | 14.972 | 74.782 | 1.00 | 45.11 |
| ATOM | 4547 | NE2 | GLN | B 289 | 47.639 | 12.848 | 74.795 | 1.00 | 56.32 |
| ATOM | 4548 | C | GLN | B 289 | 45.165 | 12.495 | 71.695 | 1.00 | 34.06 |
| ATOM | 4549 | O | GLN | B 289 | 45.949 | 11.582 | 71.976 | 1.00 | 37.74 |
| ATOM | 4550 | N | THR | B 290 | 43.874 | 12.473 | 71.997 | 1.00 | 34.47 |
| ATOM | 4551 | CA | THR | B 290 | 43.323 | 11.278 | 72.636 | 1.00 | 38.23 |
| ATOM | 4552 | CB | THR | B 290 | 42.869 | 11.533 | 74.089 | 1.00 | 29.88 |
| ATOM | 4553 | OG1 | THR | B 290 | 41.723 | 12.396 | 74.064 | 1.00 | 32.43 |
| ATOM | 4554 | CG2 | THR | B 290 | 43.954 | 12.209 | 74.903 | 1.00 | 30.96 |
| ATOM | 4555 | C | THR | B 290 | 42.131 | 10.704 | 71.879 | 1.00 | 38.89 |
| ATOM | 4556 | O | THR | B 290 | 41.394 | 11.381 | 71.170 | 1.00 | 37.95 |
| ATOM | 4557 | N | GLU | B 291 | 41.927 | 9.397 | 72.062 | 1.00 | 40.68 |
| ATOM | 4558 | CA | GLU | B 291 | 40.760 | 8.735 | 71.494 | 1.00 | 35.35 |
| ATOM | 4559 | CB | GLU | B 291 | 40.764 | 7.261 | 71.915 | 1.00 | 46.96 |
| ATOM | 4560 | CG | GLU | B 291 | 39.750 | 6.391 | 71.186 | 1.00 | 52.82 |
| ATOM | 4561 | CD | GLU | B 291 | 39.890 | 4.935 | 71.603 | 1.00 | 55.59 |
| ATOM | 4562 | OE1 | GLU | B 291 | 38.878 | 4.210 | 71.644 | 1.00 | 67.94 |
| ATOM | 4563 | OE2 | GLU | B 291 | 41.035 | 4.536 | 71.899 | 1.00 | 48.99 |
| ATOM | 4564 | C | GLU | B 291 | 39.465 | 9.394 | 71.939 | 1.00 | 29.83 |
| ATOM | 4565 | O | GLU | B 291 | 38.487 | 9.486 | 71.192 | 1.00 | 34.01 |
| ATOM | 4566 | N | CYS | B 292 | 39.421 | 9.874 | 73.194 | 1.00 | 31.22 |
| ATOM | 4567 | CA | CYS | B 292 | 38.144 | 10.429 | 73.647 | 1.00 | 30.43 |
| ATOM | 4568 | CB | CYS | B 292 | 38.112 | 10.562 | 75.169 | 1.00 | 36.01 |
| ATOM | 4569 | SG | CYS | B 292 | 39.681 | 11.083 | 75.904 | 1.00 | 131.76 | 1 |
| ATOM | 4570 | C | CYS | B 292 | 37.862 | 11.764 | 72.979 | 1.00 | 24.32 |
| ATOM | 4571 | O | CYS | B 292 | 36.720 | 12.200 | 72.903 | 1.00 | 28.29 |
| ATOM | 4572 | N | GLN | B 293 | 38.915 | 12.415 | 72.489 | 1.00 | 33.10 |
| ATOM | 4573 | CA | GLN | B 293 | 38.751 | 13.630 | 71.694 | 1.00 | 30.62 |
| ATOM | 4574 | CB | GLN | B 293 | 40.117 | 14.322 | 71.527 | 1.00 | 28.49 |
| ATOM | 4575 | CG | GLN | B 293 | 40.470 | 15.209 | 72.711 | 1.00 | 27.02 |

FIGURE 190

| ATOM | 4576 | CD  | GLN | B | 293 | 41.904 | 15.666 | 72.787 | 1.00 | 29.40 |
| ATOM | 4577 | OE1 | GLN | B | 293 | 42.722 | 15.395 | 71.907 | 1.00 | 31.27 |
| ATOM | 4578 | NE2 | GLN | B | 293 | 42.261 | 16.375 | 73.858 | 1.00 | 29.27 |
| ATOM | 4579 | C   | GLN | B | 293 | 38.132 | 13.286 | 70.347 | 1.00 | 26.72 |
| ATOM | 4580 | O   | GLN | B | 293 | 37.224 | 13.930 | 69.828 | 1.00 | 39.00 |
| ATOM | 4581 | N   | TYR | B | 294 | 38.662 | 12.203 | 69.763 | 1.00 | 28.45 |
| ATOM | 4582 | CA  | TYR | B | 294 | 38.117 | 11.677 | 68.512 | 1.00 | 24.87 |
| ATOM | 4583 | CB  | TYR | B | 294 | 38.861 | 10.398 | 68.098 | 1.00 | 32.22 |
| ATOM | 4584 | CG  | TYR | B | 294 | 38.628 | 10.021 | 66.650 | 1.00 | 42.38 |
| ATOM | 4585 | CD1 | TYR | B | 294 | 39.072 | 10.848 | 65.621 | 1.00 | 43.00 |
| ATOM | 4586 | CE1 | TYR | B | 294 | 38.867 | 10.520 | 64.294 | 1.00 | 47.37 |
| ATOM | 4587 | CZ  | TYR | B | 294 | 38.207 |  9.350 | 63.975 | 1.00 | 48.16 |
| ATOM | 4588 | OH  | TYR | B | 294 | 38.001 |  9.025 | 62.651 | 1.00 | 34.98 |
| ATOM | 4589 | CE2 | TYR | B | 294 | 37.756 |  8.516 | 64.976 | 1.00 | 41.30 |
| ATOM | 4590 | CD2 | TYR | B | 294 | 37.966 |  8.851 | 66.302 | 1.00 | 40.38 |
| ATOM | 4591 | C   | TYR | B | 294 | 36.628 | 11.405 | 68.664 | 1.00 | 32.24 |
| ATOM | 4592 | O   | TYR | B | 294 | 35.800 | 11.862 | 67.885 | 1.00 | 38.08 |
| ATOM | 4593 | N   | VAL | B | 295 | 36.302 | 10.647 | 69.711 | 1.00 | 45.53 |
| ATOM | 4594 | CA  | VAL | B | 295 | 34.926 | 10.315 | 70.045 | 1.00 | 44.59 |
| ATOM | 4595 | CB  | VAL | B | 295 | 34.844 |  9.467 | 71.331 | 1.00 | 40.45 |
| ATOM | 4596 | CG1 | VAL | B | 295 | 33.478 |  9.640 | 71.975 | 1.00 | 39.76 |
| ATOM | 4597 | CG2 | VAL | B | 295 | 35.134 |  8.009 | 71.030 | 1.00 | 42.13 |
| ATOM | 4598 | C   | VAL | B | 295 | 34.096 | 11.573 | 70.258 | 1.00 | 43.22 |
| ATOM | 4599 | O   | VAL | B | 295 | 32.963 | 11.696 | 69.798 | 1.00 | 39.21 |
| ATOM | 4600 | N   | TYR | B | 296 | 34.680 | 12.529 | 70.983 | 1.00 | 39.28 |
| ATOM | 4601 | CA  | TYR | B | 296 | 33.973 | 13.791 | 71.204 | 1.00 | 38.11 |
| ATOM | 4602 | CB  | TYR | B | 296 | 34.866 | 14.740 | 72.004 | 1.00 | 36.49 |
| ATOM | 4603 | CG  | TYR | B | 296 | 34.235 | 16.065 | 72.341 | 1.00 | 29.43 |
| ATOM | 4604 | CD1 | TYR | B | 296 | 33.274 | 16.182 | 73.337 | 1.00 | 26.96 |
| ATOM | 4605 | CE1 | TYR | B | 296 | 32.688 | 17.392 | 73.655 | 1.00 | 26.29 |
| ATOM | 4606 | CZ  | TYR | B | 296 | 33.072 | 18.524 | 72.963 | 1.00 | 36.48 |
| ATOM | 4607 | OH  | TYR | B | 296 | 32.503 | 19.739 | 73.267 | 1.00 | 28.44 |
| ATOM | 4608 | CE2 | TYR | B | 296 | 34.023 | 18.443 | 71.970 | 1.00 | 34.08 |
| ATOM | 4609 | CD2 | TYR | B | 296 | 34.602 | 17.224 | 71.661 | 1.00 | 38.40 |
| ATOM | 4610 | C   | TYR | B | 296 | 33.582 | 14.431 | 69.883 | 1.00 | 30.28 |
| ATOM | 4611 | O   | TYR | B | 296 | 32.516 | 15.027 | 69.739 | 1.00 | 28.21 |
| ATOM | 4612 | N   | LEU | B | 297 | 34.477 | 14.309 | 68.896 | 1.00 | 32.45 |
| ATOM | 4613 | CA  | LEU | B | 297 | 34.172 | 14.905 | 67.592 | 1.00 | 29.13 |
| ATOM | 4614 | CB  | LEU | B | 297 | 35.329 | 14.627 | 66.633 | 1.00 | 28.47 |
| ATOM | 4615 | CG  | LEU | B | 297 | 36.560 | 15.523 | 66.842 | 1.00 | 31.47 |
| ATOM | 4616 | CD1 | LEU | B | 297 | 37.742 | 14.998 | 66.052 | 1.00 | 24.45 |
| ATOM | 4617 | CD2 | LEU | B | 297 | 36.235 | 16.958 | 66.462 | 1.00 | 26.38 |
| ATOM | 4618 | C   | LEU | B | 297 | 32.852 | 14.378 | 67.039 | 1.00 | 34.78 |
| ATOM | 4619 | O   | LEU | B | 297 | 31.967 | 15.133 | 66.639 | 1.00 | 26.92 |
| ATOM | 4620 | N   | HIS | B | 298 | 32.719 | 13.055 | 67.036 | 1.00 | 42.39 |
| ATOM | 4621 | CA  | HIS | B | 298 | 31.505 | 12.405 | 66.536 | 1.00 | 42.94 |
| ATOM | 4622 | CB  | HIS | B | 298 | 31.714 | 10.888 | 66.528 | 1.00 | 40.75 |
| ATOM | 4623 | CG  | HIS | B | 298 | 32.747 | 10.427 | 65.545 | 1.00 | 42.36 |
| ATOM | 4624 | ND1 | HIS | B | 298 | 34.085 | 10.309 | 65.850 | 1.00 | 43.84 |
| ATOM | 4625 | CE1 | HIS | B | 298 | 34.758 |  9.881 | 64.795 | 1.00 | 39.31 |
| ATOM | 4626 | NE2 | HIS | B | 298 | 33.901 |  9.708 | 63.804 | 1.00 | 42.05 |
| ATOM | 4627 | CD2 | HIS | B | 298 | 32.640 | 10.043 | 64.249 | 1.00 | 43.47 |

FIGURE 191

| | | | | | | | | | |
|---|---|---|---|---|---|---|---|---|---|
| ATOM | 4628 | C | HIS | B | 298 | 30.278 | 12.791 | 67.348 | 1.00 35.51 |
| ATOM | 4629 | O | HIS | B | 298 | 29.192 | 12.997 | 66.800 | 1.00 32.51 |
| ATOM | 4630 | N | GLN | B | 299 | 30.409 | 12.916 | 68.669 | 1.00 33.21 |
| ATOM | 4631 | CA | GLN | B | 299 | 29.266 | 13.336 | 69.483 | 1.00 33.23 |
| ATOM | 4632 | CB | GLN | B | 299 | 29.581 | 13.264 | 70.982 | 1.00 40.20 |
| ATOM | 4633 | CG | GLN | B | 299 | 30.119 | 11.919 | 71.443 | 1.00 49.41 |
| ATOM | 4634 | CD | GLN | B | 299 | 30.348 | 11.829 | 72.937 | 1.00 54.91 |
| ATOM | 4635 | OE1 | GLN | B | 299 | 31.345 | 12.313 | 73.477 | 1.00 54.96 |
| ATOM | 4636 | NE2 | GLN | B | 299 | 29.412 | 11.192 | 73.633 | 1.00 62.12 |
| ATOM | 4637 | C | GLN | B | 299 | 28.826 | 14.743 | 69.114 | 1.00 32.95 |
| ATOM | 4638 | O | GLN | B | 299 | 27.638 | 15.068 | 69.089 | 1.00 41.61 |
| ATOM | 4639 | N | CYS | B | 300 | 29.787 | 15.623 | 68.810 | 1.00 32.51 |
| ATOM | 4640 | CA | CYS | B | 300 | 29.370 | 16.967 | 68.419 | 1.00 25.41 |
| ATOM | 4641 | CB | CYS | B | 300 | 30.603 | 17.848 | 68.163 | 1.00 23.71 |
| ATOM | 4642 | SG | CYS | B | 300 | 31.486 | 18.320 | 69.679 | 1.00 41.45   1 |
| ATOM | 4643 | C | CYS | B | 300 | 28.493 | 16.946 | 67.175 | 1.00 29.79 |
| ATOM | 4644 | O | CYS | B | 300 | 27.472 | 17.628 | 67.074 | 1.00 30.90 |
| ATOM | 4645 | N | VAL | B | 301 | 28.920 | 16.157 | 66.190 | 1.00 37.78 |
| ATOM | 4646 | CA | VAL | B | 301 | 28.176 | 16.043 | 64.943 | 1.00 31.92 |
| ATOM | 4647 | CB | VAL | B | 301 | 28.938 | 15.212 | 63.899 | 1.00 35.00 |
| ATOM | 4648 | CG1 | VAL | B | 301 | 28.024 | 14.868 | 62.728 | 1.00 40.94 |
| ATOM | 4649 | CG2 | VAL | B | 301 | 30.179 | 15.957 | 63.430 | 1.00 37.17 |
| ATOM | 4650 | C | VAL | B | 301 | 26.819 | 15.404 | 65.220 | 1.00 27.85 |
| ATOM | 4651 | O | VAL | B | 301 | 25.795 | 15.854 | 64.720 | 1.00 36.79 |
| ATOM | 4652 | N | ARG | B | 302 | 26.825 | 14.349 | 66.036 | 1.00 42.30 |
| ATOM | 4653 | CA | ARG | B | 302 | 25.557 | 13.697 | 66.370 | 1.00 48.19 |
| ATOM | 4654 | CB | ARG | B | 302 | 25.771 | 12.523 | 67.322 | 1.00 48.82 |
| ATOM | 4655 | CG | ARG | B | 302 | 24.477 | 11.943 | 67.886 | 1.00 51.72 |
| ATOM | 4656 | CD | ARG | B | 302 | 24.723 | 11.322 | 69.253 | 1.00 57.09 |
| ATOM | 4657 | NE | ARG | B | 302 | 24.895 | 12.340 | 70.291 | 1.00 63.02 |
| ATOM | 4658 | CZ | ARG | B | 302 | 25.940 | 12.384 | 71.110 | 1.00 68.57 |
| ATOM | 4659 | NH1 | ARG | B | 302 | 26.895 | 11.472 | 71.013 | 1.00 88.06 |
| ATOM | 4660 | NH2 | ARG | B | 302 | 26.046 | 13.329 | 72.036 | 1.00 62.92 |
| ATOM | 4661 | C | ARG | B | 302 | 24.599 | 14.715 | 66.979 | 1.00 52.02 |
| ATOM | 4662 | O | ARG | B | 302 | 23.481 | 14.911 | 66.506 | 1.00 55.97 |
| ATOM | 4663 | N | ASP | B | 303 | 25.064 | 15.381 | 68.036 | 1.00 43.78 |
| ATOM | 4664 | CA | ASP | B | 303 | 24.206 | 16.380 | 68.673 | 1.00 41.33 |
| ATOM | 4665 | CB | ASP | B | 303 | 24.923 | 16.943 | 69.911 | 1.00 45.65 |
| ATOM | 4666 | CG | ASP | B | 303 | 25.039 | 15.864 | 70.980 | 1.00 50.16 |
| ATOM | 4667 | OD1 | ASP | B | 303 | 24.298 | 14.861 | 70.855 | 1.00 45.98 |
| ATOM | 4668 | OD2 | ASP | B | 303 | 25.846 | 15.982 | 71.927 | 1.00 34.68 |
| ATOM | 4669 | C | ASP | B | 303 | 23.795 | 17.459 | 67.691 | 1.00 40.46 |
| ATOM | 4670 | O | ASP | B | 303 | 22.662 | 17.955 | 67.734 | 1.00 56.09 |
| ATOM | 4671 | N | VAL | B | 304 | 24.662 | 17.874 | 66.763 | 1.00 34.45 |
| ATOM | 4672 | CA | VAL | B | 304 | 24.201 | 18.942 | 65.868 | 1.00 48.95 |
| ATOM | 4673 | CB | VAL | B | 304 | 25.351 | 19.587 | 65.075 | 1.00 49.79 |
| ATOM | 4674 | CG1 | VAL | B | 304 | 24.862 | 20.185 | 63.765 | 1.00 28.51 |
| ATOM | 4675 | CG2 | VAL | B | 304 | 26.027 | 20.662 | 65.919 | 1.00 59.44 |
| ATOM | 4676 | C | VAL | B | 304 | 23.143 | 18.410 | 64.907 | 1.00 54.85 |
| ATOM | 4677 | O | VAL | B | 304 | 22.147 | 19.072 | 64.611 | 1.00 47.47 |
| ATOM | 4678 | N | LEU | B | 305 | 23.356 | 17.194 | 64.408 | 1.00 51.63 |
| ATOM | 4679 | CA | LEU | B | 305 | 22.375 | 16.636 | 63.478 | 1.00 51.67 |

FIGURE 192

| | | | | | | | | | |
|---|---|---|---|---|---|---|---|---|---|
| ATOM | 4680 | CB | LEU | B | 305 | 22.844 | 15.260 | 62.996 | 1.00 41.22 |
| ATOM | 4681 | CG | LEU | B | 305 | 24.018 | 15.265 | 62.015 | 1.00 34.32 |
| ATOM | 4682 | CD1 | LEU | B | 305 | 24.215 | 13.904 | 61.375 | 1.00 47.80 |
| ATOM | 4683 | CD2 | LEU | B | 305 | 23.809 | 16.325 | 60.944 | 1.00 28.65 |
| ATOM | 4684 | C | LEU | B | 305 | 21.001 | 16.567 | 64.128 | 1.00 56.67 |
| ATOM | 4685 | O | LEU | B | 305 | 20.041 | 17.177 | 63.650 | 1.00 54.42 |
| ATOM | 4686 | N | ARG | B | 306 | 20.874 | 15.835 | 65.235 | 1.00 57.52 |
| ATOM | 4687 | CA | ARG | B | 306 | 19.539 | 15.658 | 65.806 | 1.00 66.45 |
| ATOM | 4688 | CB | ARG | B | 306 | 19.575 | 14.723 | 67.019 | 1.00 67.88 |
| ATOM | 4689 | CG | ARG | B | 306 | 20.951 | 14.533 | 67.625 | 1.00 72.91 |
| ATOM | 4690 | CD | ARG | B | 306 | 20.877 | 14.354 | 69.133 | 1.00 75.55 |
| ATOM | 4691 | NE | ARG | B | 306 | 21.300 | 13.007 | 69.521 | 1.00 78.32 |
| ATOM | 4692 | CZ | ARG | B | 306 | 21.914 | 12.752 | 70.670 | 1.00 79.74 |
| ATOM | 4693 | NH1 | ARG | B | 306 | 22.161 | 13.748 | 71.509 | 1.00 73.02 |
| ATOM | 4694 | NH2 | ARG | B | 306 | 22.275 | 11.514 | 70.971 | 1.00 90.52 |
| ATOM | 4695 | C | ARG | B | 306 | 18.884 | 16.972 | 66.211 | 1.00 65.71 |
| ATOM | 4696 | O | ARG | B | 306 | 17.651 | 17.050 | 66.270 | 1.00 60.57 |
| ATOM | 4697 | N | ALA | B | 307 | 19.674 | 18.000 | 66.503 | 1.00 63.41 |
| ATOM | 4698 | CA | ALA | B | 307 | 19.082 | 19.268 | 66.929 | 1.00 60.95 |
| ATOM | 4699 | CB | ALA | B | 307 | 20.137 | 20.143 | 67.585 | 1.00 47.72 |
| ATOM | 4700 | C | ALA | B | 307 | 18.413 | 19.987 | 65.760 | 1.00 65.50 |
| ATOM | 4701 | O | ALA | B | 307 | 17.285 | 20.470 | 65.877 | 1.00 57.65 |
| ATOM | 4702 | N | ARG | B | 308 | 19.113 | 20.054 | 64.634 | 1.00 73.88 |
| ATOM | 4703 | CA | ARG | B | 308 | 18.601 | 20.681 | 63.421 | 1.00 83.95 |
| ATOM | 4704 | CB | ARG | B | 308 | 19.685 | 20.718 | 62.342 | 1.00 82.20 |
| ATOM | 4705 | CG | ARG | B | 308 | 21.069 | 21.087 | 62.860 | 1.00 81.07 |
| ATOM | 4706 | CD | ARG | B | 308 | 22.138 | 20.840 | 61.803 | 1.00 76.97 |
| ATOM | 4707 | NE | ARG | B | 308 | 21.546 | 20.677 | 60.482 | 1.00 76.87 |
| ATOM | 4708 | CZ | ARG | B | 308 | 22.159 | 20.442 | 59.337 | 1.00 74.18 |
| ATOM | 4709 | NH1 | ARG | B | 308 | 23.476 | 20.316 | 59.248 | 1.00 57.78 |
| ATOM | 4710 | NH2 | ARG | B | 308 | 21.427 | 20.324 | 58.233 | 1.00 64.71 |
| ATOM | 4711 | C | ARG | B | 308 | 17.365 | 19.943 | 62.917 | 1.00 92.86 |
| ATOM | 4712 | O | ARG | B | 308 | 16.278 | 20.515 | 62.815 | 1.00 85.75 |
| ATOM | 4713 | N | LYS | B | 309 | 17.535 | 18.658 | 62.606 | 1.00 97.18 |
| ATOM | 4714 | CA | LYS | B | 309 | 16.407 | 17.851 | 62.152 | 1.00101.48 |
| ATOM | 4715 | CB | LYS | B | 309 | 16.828 | 16.414 | 61.850 | 1.00103.32 |
| ATOM | 4716 | CG | LYS | B | 309 | 15.687 | 15.410 | 61.805 | 1.00104.02 |
| ATOM | 4717 | CD | LYS | B | 309 | 15.273 | 15.077 | 60.382 | 1.00104.29 |
| ATOM | 4718 | CE | LYS | B | 309 | 13.920 | 14.382 | 60.342 | 1.00101.24 |
| ATOM | 4719 | NZ | LYS | B | 309 | 13.811 | 13.409 | 59.216 | 1.00 84.67 |
| ATOM | 4720 | C | LYS | B | 309 | 15.292 | 17.866 | 63.202 | 1.00101.41 |
| ATOM | 4721 | O | LYS | B | 309 | 15.282 | 16.996 | 64.071 | 1.00109.20 |
| ATOM | 4722 | N | LEU | B | 310 | 14.415 | 18.846 | 63.079 | 1.00 97.60 |
| ATOM | 4723 | CA | LEU | B | 310 | 13.251 | 19.077 | 63.916 | 1.00 95.62 |
| ATOM | 4724 | CB | LEU | B | 310 | 13.533 | 18.739 | 65.380 | 1.00 95.83 |
| ATOM | 4725 | CG | LEU | B | 310 | 13.082 | 17.359 | 65.866 | 1.00 98.74 |
| ATOM | 4726 | CD1 | LEU | B | 310 | 12.607 | 16.487 | 64.713 | 1.00 84.93 |
| ATOM | 4727 | CD2 | LEU | B | 310 | 14.202 | 16.667 | 66.632 | 1.00113.56 |
| ATOM | 4728 | C | LEU | B | 310 | 12.786 | 20.528 | 63.789 | 1.00 92.71 |
| ATOM | 4729 | O | LEU | B | 310 | 12.515 | 21.222 | 64.765 | 1.00 74.63 |
| ATOM | 4730 | O14 | INH | Z | 2 | 55.288 | 16.173 | 78.572 | 1.00 68.22 |
| ATOM | 4731 | O4 | INH | Z | 2 | 48.070 | 20.932 | 75.258 | 1.00 24.37 |

FIGURE 193

| | | | | | | | | | | |
|---|---|---|---|---|---|---|---|---|---|---|
| ATOM | 4732 | S1 | INH | Z | 2 | 47.385 | 19.830 | 74.500 | 1.00 29.84 | 1 |
| ATOM | 4733 | O2 | INH | Z | 2 | 48.097 | 19.600 | 73.249 | 1.00 23.28 | |
| ATOM | 4734 | O3 | INH | Z | 2 | 45.976 | 19.785 | 74.420 | 1.00 19.75 | |
| ATOM | 4735 | N1 | INH | Z | 2 | 47.628 | 18.601 | 75.423 | 1.00 29.61 | |
| ATOM | 4736 | C2 | INH | Z | 2 | 48.913 | 18.097 | 75.576 | 1.00 22.41 | |
| ATOM | 4737 | C1 | INH | Z | 2 | 49.706 | 18.569 | 76.616 | 1.00 17.58 | |
| ATOM | 4738 | C3 | INH | Z | 2 | 49.439 | 17.157 | 74.694 | 1.00 25.75 | |
| ATOM | 4739 | C4 | INH | Z | 2 | 50.726 | 16.698 | 74.879 | 1.00 21.37 | |
| ATOM | 4740 | C5 | INH | Z | 2 | 51.537 | 17.205 | 75.894 | 1.00 28.97 | |
| ATOM | 4741 | C6 | INH | Z | 2 | 50.996 | 18.159 | 76.786 | 1.00 18.78 | |
| ATOM | 4742 | C8 | INH | Z | 2 | 52.976 | 16.759 | 76.061 | 1.00 30.10 | |
| ATOM | 4743 | C7 | INH | Z | 2 | 53.147 | 15.585 | 77.076 | 1.00 38.47 | |
| ATOM | 4744 | C9 | INH | Z | 2 | 52.112 | 14.479 | 76.942 | 1.00 50.15 | |
| ATOM | 4745 | N2 | INH | Z | 2 | 52.210 | 13.593 | 75.955 | 1.00 46.78 | |
| ATOM | 4746 | C10 | INH | Z | 2 | 51.114 | 12.942 | 75.276 | 1.00 48.01 | |
| ATOM | 4747 | O1 | INH | Z | 2 | 51.204 | 14.431 | 77.757 | 1.00 53.75 | |
| ATOM | 4748 | N11 | INH | Z | 2 | 53.037 | 16.040 | 78.545 | 1.00 43.33 | |
| ATOM | 4749 | C12 | INH | Z | 2 | 54.320 | 16.516 | 79.194 | 1.00 55.88 | |
| ATOM | 4750 | O6 | INH | Z | 2 | 54.055 | 17.245 | 80.374 | 1.00 62.18 | |
| ATOM | 4751 | C13 | INH | Z | 2 | 55.182 | 17.437 | 81.254 | 1.00 68.88 | |
| ATOM | 4752 | C14 | INH | Z | 2 | 55.890 | 18.762 | 81.044 | 1.00 69.79 | |
| ATOM | 4753 | C15 | INH | Z | 2 | 57.051 | 18.833 | 80.275 | 1.00 67.74 | |
| ATOM | 4754 | C16 | INH | Z | 2 | 57.681 | 20.064 | 80.042 | 1.00 70.03 | |
| ATOM | 4755 | C17 | INH | Z | 2 | 57.152 | 21.249 | 80.558 | 1.00 70.11 | |
| ATOM | 4756 | C18 | INH | Z | 2 | 55.999 | 21.166 | 81.352 | 1.00 69.36 | |
| ATOM | 4757 | C19 | INH | Z | 2 | 55.377 | 19.934 | 81.606 | 1.00 69.79 | |
| ATOM | 4758 | O14 | INH | Z | 1 | -1.113 | 8.871 | 44.215 | 1.00 38.80 | |
| ATOM | 4759 | O4 | INH | Z | 1 | 6.622 | 4.171 | 41.248 | 1.00 25.08 | |
| ATOM | 4760 | S1 | INH | Z | 1 | 7.335 | 5.325 | 40.618 | 1.00 22.22 | 1 |
| ATOM | 4761 | O2 | INH | Z | 1 | 6.828 | 5.548 | 39.260 | 1.00 16.51 | |
| ATOM | 4762 | O3 | INH | Z | 1 | 8.747 | 5.431 | 40.711 | 1.00 19.75 | |
| ATOM | 4763 | N1 | INH | Z | 1 | 6.835 | 6.493 | 41.497 | 1.00 20.76 | |
| ATOM | 4764 | C2 | INH | Z | 1 | 5.527 | 6.957 | 41.421 | 1.00 21.28 | |
| ATOM | 4765 | C1 | INH | Z | 1 | 4.584 | 6.427 | 42.291 | 1.00 13.44 | |
| ATOM | 4766 | C3 | INH | Z | 1 | 5.132 | 7.960 | 40.530 | 1.00 21.95 | |
| ATOM | 4767 | C4 | INH | Z | 1 | 3.817 | 8.382 | 40.524 | 1.00 18.36 | |
| ATOM | 4768 | C5 | INH | Z | 1 | 2.870 | 7.861 | 41.415 | 1.00 23.03 | |
| ATOM | 4769 | C6 | INH | Z | 1 | 3.283 | 6.862 | 42.323 | 1.00 16.81 | |
| ATOM | 4770 | C8 | INH | Z | 1 | 1.429 | 8.323 | 41.430 | 1.00 24.83 | |
| ATOM | 4771 | C7 | INH | Z | 1 | 1.120 | 9.380 | 42.549 | 1.00 39.39 | |
| ATOM | 4772 | C9 | INH | Z | 1 | 2.120 | 10.521 | 42.630 | 1.00 40.58 | |
| ATOM | 4773 | N2 | INH | Z | 1 | 2.202 | 11.436 | 41.667 | 1.00 41.79 | |
| ATOM | 4774 | C10 | INH | Z | 1 | 3.287 | 12.393 | 41.566 | 1.00 43.35 | |
| ATOM | 4775 | O1 | INH | Z | 1 | 2.868 | 10.605 | 43.592 | 1.00 44.71 | |
| ATOM | 4776 | N11 | INH | Z | 1 | 1.157 | 8.742 | 43.948 | 1.00 50.75 | |
| ATOM | 4777 | C12 | INH | Z | 1 | -0.086 | 8.670 | 44.797 | 1.00 50.71 | |
| ATOM | 4778 | O6 | INH | Z | 1 | 0.284 | 8.365 | 46.128 | 1.00 57.94 | |
| ATOM | 4779 | C13 | INH | Z | 1 | -0.788 | 8.005 | 47.016 | 1.00 62.79 | |
| ATOM | 4780 | C14 | INH | Z | 1 | -1.038 | 6.513 | 47.116 | 1.00 58.14 | |
| ATOM | 4781 | C15 | INH | Z | 1 | -2.097 | 5.926 | 46.420 | 1.00 57.59 | |
| ATOM | 4782 | C16 | INH | Z | 1 | -2.357 | 4.551 | 46.525 | 1.00 58.75 | |
| ATOM | 4783 | C17 | INH | Z | 1 | -1.560 | 3.742 | 47.338 | 1.00 55.57 | |

FIGURE 194

```
ATOM   4784  C18  INH Z    1     -0.493    4.337   48.028  1.00  55.37
ATOM   4785  C19  INH Z    1     -0.220    5.707   47.913  1.00  55.41
ATOM   4786  O1   HOH W    1     10.045   -6.206   48.501  1.00   9.70
ATOM   4787  O1   HOH W    2     44.009   31.332   82.099  1.00  12.76
ATOM   4788  O1   HOH W    3     -1.504    3.025   37.601  1.00  14.12
ATOM   4789  O1   HOH W    4     56.634   21.887   72.619  1.00  18.84
ATOM   4790  O1   HOH W    5     -3.336   -2.466   27.653  1.00  16.96
ATOM   4791  O1   HOH W    6     59.893   27.230   63.111  1.00  20.75
ATOM   4792  O1   HOH W    7      0.940    7.097   29.426  1.00  15.51
ATOM   4793  O1   HOH W    8     56.585   29.393   71.563  1.00  17.34
ATOM   4794  O1   HOH W    9     -3.244   -3.725   34.798  1.00  13.56
ATOM   4795  O1   HOH W   10      1.553   -4.822   35.953  1.00  13.15
ATOM   4796  O1   HOH W   11     -4.895   -5.747   33.816  1.00  16.00
ATOM   4797  O1   HOH W   12     55.065   17.796   64.150  1.00  18.78
ATOM   4798  O1   HOH W   13     -2.710    7.632   22.526  1.00  25.85
ATOM   4799  O1   HOH W   14     -1.058   -4.632   36.416  1.00  16.59
ATOM   4800  O1   HOH W   15     58.883   28.512   70.102  1.00  17.41
ATOM   4801  O1   HOH W   16     14.129  -11.346   42.224  1.00  25.25
ATOM   4802  O1   HOH W   17     15.198   -5.722   25.861  1.00  17.95
ATOM   4803  O1   HOH W   18     -5.309    3.570   27.477  1.00  17.89
ATOM   4804  O1   HOH W   19     59.756   17.517   57.776  1.00  24.77
ATOM   4805  O1   HOH W   20     -6.619   -5.980   43.124  1.00  18.09
ATOM   4806  O1   HOH W   21     54.142   29.809   70.726  1.00  17.84
ATOM   4807  O1   HOH W   22      0.201   -5.367   22.242  1.00  20.61
ATOM   4808  O1   HOH W   23      4.276   11.648   28.034  1.00  21.90
ATOM   4809  O1   HOH W   24     51.995   13.231   62.486  1.00  21.98
ATOM   4810  O1   HOH W   25     -2.328   13.484   27.320  1.00  20.24
ATOM   4811  O1   HOH W   26     41.283   24.669   80.924  1.00  23.47
ATOM   4812  O1   HOH W   27     13.869   -0.367   45.406  1.00  23.14
ATOM   4813  O1   HOH W   28     15.304   -9.348   27.802  1.00  21.59
ATOM   4814  O1   HOH W   29     12.631  -10.292   28.093  1.00  20.50
ATOM   4815  O1   HOH W   30     44.431   39.247   81.240  1.00  25.13
ATOM   4816  O1   HOH W   31     -0.865   -4.102   45.807  1.00  17.03
ATOM   4817  O1   HOH W   32     56.944   30.639   57.225  1.00  27.48
ATOM   4818  O1   HOH W   33     44.974   29.800   84.482  1.00  24.66
ATOM   4819  O1   HOH W   34     40.344   25.679   78.385  1.00  25.40
ATOM   4820  O1   HOH W   35     -0.817   11.896   36.268  1.00  27.05
ATOM   4821  O1   HOH W   36     45.813   26.347   88.982  1.00  29.74
ATOM   4822  O1   HOH W   37     61.459   21.495   62.950  1.00  24.86
ATOM   4823  O1   HOH W   38     61.161   30.493   78.889  1.00  24.20
ATOM   4824  O1   HOH W   39     18.380   -0.097   25.182  1.00  20.65
ATOM   4825  O1   HOH W   40     51.721   30.553   83.500  1.00  23.95
ATOM   4826  O1   HOH W   41     44.911   34.060   54.571  1.00  25.17
ATOM   4827  O1   HOH W   42     55.088   28.823   80.613  1.00  20.78
ATOM   4828  O1   HOH W   43     38.439   25.424   57.676  1.00  24.32
ATOM   4829  O1   HOH W   44     17.651   -4.708   24.960  1.00  23.35
ATOM   4830  O1   HOH W   45     60.668   30.480   69.410  1.00  20.33
ATOM   4831  O1   HOH W   46     10.176  -14.189   47.531  1.00  30.12
ATOM   4832  O1   HOH W   47     -0.430   -5.789   47.698  1.00  31.64
ATOM   4833  O1   HOH W   48     49.454   24.259   54.551  1.00  24.40
ATOM   4834  O1   HOH W   49      8.659   -4.775   50.631  1.00  26.30
ATOM   4835  O1   HOH W   50      8.016  -21.216   43.873  1.00  28.15
```

FIGURE 195

```
ATOM   4836  O1  HOH  W   51    41.695   31.267   59.043  1.00  30.73
ATOM   4837  O1  HOH  W   52     0.050    1.522   45.671  1.00  24.08
ATOM   4838  O1  HOH  W   53     9.328    8.423   41.215  1.00  24.60
ATOM   4839  O1  HOH  W   54    18.246   -7.424   47.752  1.00  27.95
ATOM   4840  O1  HOH  W   55    17.680  -18.968   48.425  1.00  49.05
ATOM   4841  O1  HOH  W   56    63.663   32.033   67.334  1.00  33.07
ATOM   4842  O1  HOH  W   57    12.879   -8.580   21.032  1.00  30.73
ATOM   4843  O1  HOH  W   58    43.952   35.751   61.678  1.00  24.11
ATOM   4844  O1  HOH  W   59     5.457    2.609   21.937  1.00  33.95
ATOM   4845  O1  HOH  W   60    41.656   34.732   60.883  1.00  26.67
ATOM   4846  O1  HOH  W   61    10.826   -7.011   21.512  1.00  26.24
ATOM   4847  O1  HOH  W   62    46.866   32.271   55.142  1.00  28.91
ATOM   4848  O1  HOH  W   63    -4.848  -11.748   39.346  1.00  22.84
ATOM   4849  O1  HOH  W   64    -1.807  -15.828   33.871  1.00  27.34
ATOM   4850  O1  HOH  W   65    15.309   -8.364   24.800  1.00  25.02
ATOM   4851  O1  HOH  W   66    10.589   -3.957   17.825  1.00  26.51
ATOM   4852  O1  HOH  W   67    53.967   24.496   54.681  1.00  44.06
ATOM   4853  O1  HOH  W   68    24.990  -11.936   38.629  1.00  28.80
ATOM   4854  O1  HOH  W   69     7.664    0.885   20.675  1.00  28.07
ATOM   4855  O1  HOH  W   70    59.900   18.836   77.896  1.00  40.35
ATOM   4856  O1  HOH  W   71    45.172   16.962   74.854  1.00  28.34
ATOM   4857  O1  HOH  W   72    -7.743   -7.173   31.484  1.00  26.07
ATOM   4858  O1  HOH  W   73    62.769   33.034   57.586  1.00  26.41
ATOM   4859  O1  HOH  W   74     1.944  -14.302   44.406  1.00  26.86
ATOM   4860  O1  HOH  W   75    23.222   -0.340   29.959  1.00  22.19
ATOM   4861  O1  HOH  W   76    -0.197   -0.646   21.222  1.00  27.09
ATOM   4862  O1  HOH  W   77    42.078   33.736   57.956  1.00  26.98
ATOM   4863  O1  HOH  W   78    57.402   25.819   56.138  1.00  32.63
ATOM   4864  O1  HOH  W   79    55.439   12.986   71.228  1.00  29.87
ATOM   4865  O1  HOH  W   80    34.396    8.529   61.576  1.00  43.51
ATOM   4866  O1  HOH  W   81    47.286   29.177   51.681  1.00  31.35
ATOM   4867  O1  HOH  W   82    30.677   31.060   77.998  1.00  47.26
ATOM   4868  O1  HOH  W   83    41.588   15.444   81.328  1.00  41.21
ATOM   4869  O1  HOH  W   84     2.486    5.248   46.367  1.00  34.85
ATOM   4870  O1  HOH  W   85    63.709   21.021   72.928  1.00  28.76
ATOM   4871  O1  HOH  W   86    27.619    8.328   44.050  1.00  31.73
ATOM   4872  O1  HOH  W   87    -5.332  -10.734   36.523  1.00  25.53
ATOM   4873  O1  HOH  W   88    62.256   24.240   57.795  1.00  27.98
ATOM   4874  O1  HOH  W   89     7.339   -1.362   55.174  1.00  27.75
ATOM   4875  O1  HOH  W   90    -3.541   -2.818   46.374  1.00  29.31
ATOM   4876  O1  HOH  W   91    12.753    0.559   47.705  1.00  25.52
ATOM   4877  O1  HOH  W   92    52.949   39.174   79.040  1.00  31.30
ATOM   4878  O1  HOH  W   93    36.070   32.961   80.601  1.00  30.93
ATOM   4879  O1  HOH  W   94    59.810   36.762   74.769  1.00  30.79
ATOM   4880  O1  HOH  W   95   -12.875    5.864   27.849  1.00  26.59
ATOM   4881  O1  HOH  W   96    53.121   29.855   85.728  1.00  31.07
ATOM   4882  O1  HOH  W   97    51.540   25.787   52.492  1.00  31.52
ATOM   4883  O1  HOH  W   98    18.594  -19.849   45.929  1.00  43.83
ATOM   4884  O1  HOH  W   99    -1.532  -18.000   43.060  1.00  30.93
ATOM   4885  O1  HOH  W  100    42.535   36.857   53.627  1.00  38.22
ATOM   4886  O1  HOH  W  101    56.933   34.861   60.367  1.00  32.82
ATOM   4887  O1  HOH  W  102    25.851   -1.470   29.859  1.00  36.64
```

FIGURE 196

```
ATOM   4888  O1  HOH W 103    0.077 -10.003  25.584  1.00 32.46
ATOM   4889  O1  HOH W 104    6.037  -0.243  18.292  1.00 42.47
ATOM   4890  O1  HOH W 105   -5.627  -8.277  21.845  1.00 34.15
ATOM   4891  O1  HOH W 106    4.857  13.360  30.883  1.00 31.69
ATOM   4892  O1  HOH W 107    5.308  15.537  21.988  1.00 25.42
ATOM   4893  O1  HOH W 108    6.752  -6.565  51.673  1.00 33.36
ATOM   4894  O1  HOH W 109   58.057  40.591  69.174  1.00 29.89
ATOM   4895  O1  HOH W 110   58.754   7.470  62.072  1.00 35.42
ATOM   4896  O1  HOH W 111    3.972   1.588  20.509  1.00 37.26
ATOM   4897  O1  HOH W 112   53.197  17.249  55.411  1.00 35.13
ATOM   4898  O1  HOH W 113   36.243  21.471  51.543  1.00 48.69
ATOM   4899  O1  HOH W 114   -0.096  -4.011  20.309  1.00 39.42
ATOM   4900  O1  HOH W 115   49.696  32.306  84.528  1.00 35.44
ATOM   4901  O1  HOH W 116   16.010 -16.452  31.337  1.00 44.52
ATOM   4902  O1  HOH W 117   54.391  30.745  82.842  1.00 30.52
ATOM   4903  O1  HOH W 118   69.018  18.815  64.039  1.00 33.34
ATOM   4904  O1  HOH W 119   39.522  30.110  57.759  1.00 23.80
ATOM   4905  O1  HOH W 120  -10.594   2.764  34.249  1.00 29.91
ATOM   4906  O1  HOH W 121    3.787  -7.512  50.278  1.00 24.62
ATOM   4907  O1  HOH W 122   53.957  23.288  80.378  1.00 30.02
ATOM   4908  O1  HOH W 123   18.987 -16.652  40.990  1.00 30.01
ATOM   4909  O1  HOH W 124    3.080   7.934  45.807  1.00 36.85
ATOM   4910  O1  HOH W 125   55.436   7.031  65.054  1.00 41.50
ATOM   4911  O1  HOH W 126   12.352   9.382  48.476  1.00 33.99
ATOM   4912  O1  HOH W 127   14.471   6.265  26.018  1.00 42.81
ATOM   4913  O1  HOH W 128   43.330  38.653  51.761  1.00 46.93
ATOM   4914  O1  HOH W 129   -5.913 -20.550  38.143  1.00 33.89
ATOM   4915  O1  HOH W 130   20.250   3.300  47.738  1.00 34.00
ATOM   4916  O1  HOH W 131    7.970  -2.668  16.219  1.00 35.55
ATOM   4917  O1  HOH W 132   61.696  45.509  74.227  1.00 35.13
ATOM   4918  O1  HOH W 133   53.846  13.143  73.631  1.00 39.37
ATOM   4919  O1  HOH W 134   29.945  17.996  36.926  1.00 46.09
ATOM   4920  O1  HOH W 135   58.559  11.600  62.402  1.00 26.91
ATOM   4921  O1  HOH W 136   -7.418  -5.438  40.009  1.00 30.49
ATOM   4922  O1  HOH W 137   40.559  41.165  64.176  1.00 45.19
ATOM   4923  O1  HOH W 138   49.766  27.636  50.150  1.00 29.35
ATOM   4924  O1  HOH W 139   65.075  22.379  57.198  1.00 35.09
ATOM   4925  O1  HOH W 140   -8.508   3.715  36.930  1.00 34.08
ATOM   4926  O1  HOH W 141   58.237  33.281  56.920  1.00 33.91
ATOM   4927  O1  HOH W 142   59.723  42.167  67.906  1.00 31.58
ATOM   4928  O1  HOH W 143   62.056  30.740  54.701  1.00 46.78
ATOM   4929  O1  HOH W 144    1.919   3.683  26.777  1.00 58.65
ATOM   4930  O1  HOH W 145    0.229   8.607  19.127  1.00 28.35
ATOM   4931  O1  HOH W 146   12.101  11.343  20.627  1.00 49.67
ATOM   4932  O1  HOH W 147   23.889  -5.655  45.864  1.00 40.68
ATOM   4933  O1  HOH W 148   41.109  26.972  47.802  1.00 38.59
ATOM   4934  O1  HOH W 149   61.067  15.824  56.464  1.00 36.37
ATOM   4935  O1  HOH W 150   53.684  36.619  56.025  1.00 38.94
ATOM   4936  O1  HOH W 151    9.718   4.642  49.998  1.00 29.80
ATOM   4937  O1  HOH W 152   15.016 -11.381  20.564  1.00 35.94
ATOM   4938  O1  HOH W 153   -8.503   6.204  36.690  1.00 33.15
ATOM   4939  O1  HOH W 154   52.945  32.067  87.165  1.00 38.96
```

FIGURE 197

```
ATOM   4940  O1  HOH W 155    -3.303 -17.298  32.155  1.00 30.64
ATOM   4941  O1  HOH W 156    43.328  22.392  52.292  1.00 47.87
ATOM   4942  O1  HOH W 157    28.970   3.140  30.250  1.00 36.23
ATOM   4943  O1  HOH W 158    26.533  -4.056  30.628  1.00 35.32
ATOM   4944  O1  HOH W 159     3.437   3.324  18.731  1.00 37.41
ATOM   4945  O1  HOH W 160    12.257   5.668  24.272  1.00 33.12
ATOM   4946  O1  HOH W 161    28.150   0.298  30.479  1.00 34.00
ATOM   4947  O1  HOH W 162   -17.348 -19.031  28.122  1.00 36.82
ATOM   4948  O1  HOH W 163    -0.825  -8.283  21.905  1.00 38.81
ATOM   4949  O1  HOH W 164    33.831  22.123  80.266  1.00 41.38
ATOM   4950  O1  HOH W 165    49.420  49.137  70.663  1.00 48.62
ATOM   4951  O1  HOH W 166    50.346  11.884  65.231  1.00 44.32
ATOM   4952  O1  HOH W 167     6.773  13.068  43.904  1.00 50.36
ATOM   4953  O1  HOH W 168    56.962  16.533  53.665  1.00 38.99
ATOM   4954  O1  HOH W 169    19.408   8.728  24.340  1.00 35.51
ATOM   4955  O1  HOH W 170    -5.185   6.989  42.383  1.00 48.15
ATOM   4956  O1  HOH W 171    33.871   8.380  22.002  1.00 42.56
ATOM   4957  O1  HOH W 172    32.356  27.890  84.104  1.00 38.54
ATOM   4958  O1  HOH W 173    -1.961   0.606  20.306  1.00 37.03
ATOM   4959  O1  HOH W 174    62.208  29.832  76.581  1.00 55.22
ATOM   4960  O1  HOH W 175    33.040  26.033  62.143  1.00 33.40
ATOM   4961  O1  HOH W 176    17.532 -14.378  31.456  1.00 33.99
ATOM   4962  O1  HOH W 177    37.206   7.422  74.312  1.00 38.76
ATOM   4963  O1  HOH W 178    29.817  29.620  62.244  1.00 43.78
ATOM   4964  O1  HOH W 179     2.238  -5.806  48.797  1.00 24.11
ATOM   4965  O1  HOH W 180    50.166  25.503  48.673  1.00 31.60
ATOM   4966  O1  HOH W 181    58.506  42.575  64.866  1.00 35.82
ATOM   4967  O1  HOH W 182    66.265  21.921  70.420  1.00 39.64
ATOM   4968  O1  HOH W 183     0.671  -9.941  18.215  1.00 52.37
ATOM   4969  O1  HOH W 184     5.293  12.702  45.868  1.00 64.96
ATOM   4970  O1  HOH W 185    26.178  16.910  42.036  1.00 39.26
ATOM   4971  O1  HOH W 186     1.316  -1.635  54.945  1.00 32.69
ATOM   4972  O1  HOH W 187    15.079  11.723  21.275  1.00 48.90
ATOM   4973  O1  HOH W 188    58.780   8.778  52.598  1.00 55.31
ATOM   4974  O1  HOH W 189    -1.566 -17.744  29.231  1.00 40.69
ATOM   4975  O1  HOH W 190    -1.443 -20.552  29.054  1.00 36.00
ATOM   4976  O1  HOH W 191    40.753  36.433  75.429  1.00 40.90
ATOM   4977  O1  HOH W 192    43.705  20.194  83.394  1.00 38.59
ATOM   4978  O1  HOH W 193    13.952   8.216  50.830  1.00 55.41
ATOM   4979  O1  HOH W 194    17.477  -1.718  14.946  1.00 30.24
ATOM   4980  O1  HOH W 195    32.069   3.048  36.009  1.00 37.45
ATOM   4981  O1  HOH W 196    49.867  21.149  90.949  1.00 40.22
ATOM   4982  O1  HOH W 197    31.011  39.913  82.015  1.00 44.40
ATOM   4983  O1  HOH W 198     3.768   7.854  20.763  1.00 37.31
ATOM   4984  O1  HOH W 199    36.080  45.674  78.448  1.00 51.48
ATOM   4985  O1  HOH W 200    41.126   8.733  35.756  1.00 45.43
ATOM   4986  O1  HOH W 201    -3.605   9.194  21.065  1.00 42.26
ATOM   4987  O1  HOH W 202    45.411  20.667  52.071  1.00 47.75
ATOM   4988  O1  HOH W 203    22.572  -2.433  51.460  1.00 51.25
ATOM   4989  O1  HOH W 204    -2.340  18.437  23.217  1.00 35.94
ATOM   4990  O1  HOH W 205     4.213   5.779  19.058  1.00 42.01
ATOM   4991  O1  HOH W 206    -0.746   1.998  51.309  1.00 32.75
```

FIGURE 198

| | | | | | | | | | |
|---|---|---|---|---|---|---|---|---|---|
| ATOM | 4992 | O1 | HOH | W | 207 | 28.139 | 33.211 | 71.066 | 1.00 52.64 |
| ATOM | 4993 | O1 | HOH | W | 208 | 45.744 | 7.612 | 66.653 | 1.00 41.29 |
| ATOM | 4994 | O1 | HOH | W | 209 | 36.066 | 48.240 | 71.868 | 1.00 37.65 |
| ATOM | 4995 | O1 | HOH | W | 210 | 27.068 | 31.927 | 66.243 | 1.00 45.28 |
| ATOM | 4996 | O1 | HOH | W | 211 | 6.224 | 6.872 | 49.187 | 1.00 28.10 |
| ATOM | 4997 | O1 | HOH | W | 212 | -4.674 | 3.941 | 19.505 | 1.00 49.63 |
| ATOM | 4998 | O1 | HOH | W | 213 | 36.180 | 26.038 | 50.897 | 1.00 39.62 |
| ATOM | 4999 | O1 | HOH | W | 214 | 43.768 | 26.501 | 91.776 | 1.00 47.54 |
| ATOM | 5000 | O1 | HOH | W | 215 | 23.227 | -12.725 | 42.616 | 1.00 47.18 |
| ATOM | 5001 | O1 | HOH | W | 216 | -5.818 | -21.605 | 40.616 | 1.00 37.05 |
| ATOM | 5002 | O1 | HOH | W | 217 | 31.418 | -0.721 | 30.887 | 1.00 50.68 |
| ATOM | 5003 | O1 | HOH | W | 218 | 30.636 | 27.485 | 62.006 | 1.00 46.74 |
| ATOM | 5004 | O1 | HOH | W | 219 | 26.116 | 18.310 | 75.358 | 1.00 48.38 |
| ATOM | 5005 | O1 | HOH | W | 220 | 1.345 | -9.074 | 48.599 | 1.00 38.50 |
| ATOM | 5006 | O1 | HOH | W | 221 | 0.416 | -1.086 | 17.311 | 1.00 48.92 |
| ATOM | 5007 | O1 | HOH | W | 222 | 54.434 | 21.262 | 61.419 | 1.00 42.93 |
| ATOM | 5008 | O1 | HOH | W | 223 | 51.386 | 9.817 | 55.916 | 1.00 33.89 |
| ATOM | 5009 | O1 | HOH | W | 224 | 47.376 | 31.902 | 85.186 | 1.00 47.01 |
| ATOM | 5010 | O1 | HOH | W | 225 | 14.573 | 9.677 | 49.224 | 1.00 33.72 |
| ATOM | 5011 | O1 | HOH | W | 226 | 53.818 | 34.420 | 83.299 | 1.00 40.34 |
| ATOM | 5012 | O1 | HOH | W | 227 | 11.775 | 4.191 | 51.814 | 1.00 46.81 |
| ATOM | 5013 | O1 | HOH | W | 228 | 36.320 | 19.863 | 21.440 | 1.00 41.37 |
| ATOM | 5014 | O1 | HOH | W | 229 | 15.790 | 10.248 | 47.362 | 1.00 37.82 |
| ATOM | 5015 | O1 | HOH | W | 230 | 1.272 | 11.705 | 38.927 | 1.00 32.13 |
| ATOM | 5016 | O1 | HOH | W | 231 | -7.721 | 2.573 | 21.097 | 1.00 38.10 |
| ATOM | 5017 | O1 | HOH | W | 232 | 53.283 | 19.471 | 53.553 | 1.00 38.71 |
| ATOM | 5018 | O1 | HOH | W | 233 | 51.950 | 32.548 | 55.051 | 1.00 30.33 |
| ATOM | 5019 | O1 | HOH | W | 234 | 58.877 | 41.394 | 62.179 | 1.00 45.27 |
| ATOM | 5020 | O1 | HOH | W | 235 | -8.538 | -1.081 | 21.839 | 1.00 39.11 |
| ATOM | 5021 | O1 | HOH | W | 236 | -0.733 | 4.812 | 51.216 | 1.00 41.83 |
| ATOM | 5022 | O1 | HOH | W | 237 | 60.623 | 35.681 | 72.217 | 1.00 39.90 |
| ATOM | 5023 | O1 | HOH | W | 238 | 57.744 | 28.339 | 55.220 | 1.00 37.07 |
| ATOM | 5024 | O1 | HOH | W | 239 | 59.092 | 12.614 | 50.910 | 1.00 48.79 |
| ATOM | 5025 | O1 | HOH | W | 240 | 68.091 | 31.724 | 68.601 | 1.00 34.66 |
| ATOM | 5026 | O1 | HOH | W | 241 | 63.691 | 18.438 | 72.638 | 1.00 33.62 |
| ATOM | 5027 | O1 | HOH | W | 242 | 53.127 | 41.929 | 58.612 | 1.00 47.21 |
| ATOM | 5028 | O1 | HOH | W | 243 | 1.457 | -17.227 | 23.707 | 1.00 48.59 |
| ATOM | 5029 | O1 | HOH | W | 244 | 44.599 | 4.374 | 53.989 | 1.00 55.66 |
| ATOM | 5030 | O1 | HOH | W | 245 | -2.827 | 19.837 | 25.584 | 1.00 44.10 |
| ATOM | 5031 | O1 | HOH | W | 246 | 22.401 | -9.408 | 51.289 | 1.00 46.21 |
| ATOM | 5032 | O1 | HOH | W | 247 | -7.242 | -11.447 | 30.436 | 1.00 45.75 |
| ATOM | 5033 | O1 | HOH | W | 248 | 35.419 | 11.112 | 74.634 | 1.00 40.36 |
| ATOM | 5034 | O1 | HOH | W | 249 | 49.132 | 5.615 | 57.803 | 1.00 41.51 |
| ATOM | 5035 | O1 | HOH | W | 250 | -12.594 | 4.646 | 35.004 | 1.00 44.27 |
| ATOM | 5036 | O1 | HOH | W | 251 | -12.226 | 3.502 | 24.096 | 1.00 53.57 |
| ATOM | 5037 | O1 | HOH | W | 252 | 49.280 | 12.394 | 79.591 | 1.00 54.74 |
| ATOM | 5038 | O1 | HOH | W | 253 | 44.128 | 17.693 | 48.227 | 1.00 50.05 |
| ATOM | 5039 | O1 | HOH | W | 254 | 2.013 | -8.971 | 51.042 | 1.00 34.88 |
| ATOM | 5040 | O1 | HOH | W | 255 | 29.402 | -6.675 | 32.345 | 1.00 54.78 |
| ATOM | 5041 | O1 | HOH | W | 256 | 43.680 | 17.273 | 82.570 | 1.00 36.27 |
| ATOM | 5042 | O1 | HOH | W | 257 | 31.835 | -0.971 | 66.953 | 1.00 53.67 |
| ATOM | 5043 | O1 | HOH | W | 258 | 34.738 | 9.985 | 59.599 | 1.00 38.24 |

FIGURE 199

| | | | | | | | | | |
|---|---|---|---|---|---|---|---|---|---|
| ATOM | 5044 | O1 | HOH | W | 259 | 52.495 | 11.009 | 53.739 | 1.00 47.65 |
| ATOM | 5045 | O1 | HOH | W | 260 | 0.140 | -7.165 | 52.324 | 1.00 48.04 |
| ATOM | 5046 | O1 | HOH | W | 261 | 64.908 | 25.810 | 56.847 | 1.00 47.20 |
| ATOM | 5047 | O1 | HOH | W | 262 | 54.501 | 32.978 | 55.500 | 1.00 42.65 |
| ATOM | 5048 | O1 | HOH | W | 263 | 38.723 | 39.573 | 64.125 | 1.00 44.25 |
| ATOM | 5049 | O1 | HOH | W | 264 | 60.016 | 5.683 | 60.372 | 1.00 39.48 |
| ATOM | 5050 | O1 | HOH | W | 265 | 41.596 | 40.187 | 50.813 | 1.00 39.03 |
| ATOM | 5051 | O1 | HOH | W | 266 | 9.560 | 17.462 | 32.534 | 1.00 35.34 |
| ATOM | 5052 | O1 | HOH | W | 267 | 3.163 | -20.952 | 48.609 | 1.00 33.97 |
| ATOM | 5053 | O1 | HOH | W | 268 | 16.265 | 18.009 | 17.553 | 1.00 51.71 |
| ATOM | 5054 | O1 | HOH | W | 269 | 22.132 | 26.469 | 35.632 | 1.00 49.25 |
| ATOM | 5055 | O1 | HOH | W | 270 | 0.202 | 17.702 | 30.444 | 1.00 39.18 |
| ATOM | 5056 | O1 | HOH | W | 271 | 28.128 | 10.379 | 42.510 | 1.00 41.98 |
| ATOM | 5057 | O1 | HOH | W | 272 | 19.729 | -16.688 | 38.739 | 1.00 29.83 |
| ATOM | 5058 | O1 | HOH | W | 273 | 37.288 | 16.310 | 56.333 | 1.00 54.08 |
| ATOM | 5059 | O1 | HOH | W | 274 | 26.953 | 23.484 | 61.752 | 1.00 50.25 |
| ATOM | 5060 | O1 | HOH | W | 275 | 44.052 | 42.974 | 56.507 | 1.00 45.06 |
| ATOM | 5061 | O1 | HOH | W | 276 | 25.652 | 3.648 | 70.742 | 1.00 42.16 |
| ATOM | 5062 | O1 | HOH | W | 277 | 1.252 | 3.132 | 54.632 | 1.00 46.31 |
| ATOM | 5063 | O1 | HOH | W | 278 | 52.770 | 49.829 | 63.294 | 1.00 42.77 |
| ATOM | 5064 | O1 | HOH | W | 279 | -2.597 | 8.623 | 42.111 | 1.00 42.65 |
| ATOM | 5065 | O1 | HOH | W | 280 | 2.122 | -5.441 | 52.479 | 1.00 50.02 |
| ATOM | 5066 | O1 | HOH | W | 281 | 51.073 | 19.397 | 80.420 | 1.00 48.41 |
| ATOM | 5067 | O1 | HOH | W | 282 | 22.162 | 16.861 | 29.165 | 1.00 44.50 |
| ATOM | 5068 | O1 | HOH | W | 283 | 11.469 | 25.200 | 29.589 | 1.00 50.84 |
| ATOM | 5069 | O1 | HOH | W | 284 | 23.699 | 3.262 | 46.867 | 1.00 46.89 |
| ATOM | 5070 | O1 | HOH | W | 285 | 45.993 | 9.491 | 73.544 | 1.00 47.59 |
| ATOM | 5071 | O1 | HOH | W | 286 | 34.089 | 35.336 | 54.479 | 1.00 49.25 |
| ATOM | 5072 | O1 | HOH | W | 287 | 27.009 | -10.733 | 37.488 | 1.00 33.68 |
| ATOM | 5073 | O1 | HOH | W | 288 | 52.692 | 21.442 | 83.608 | 1.00 42.65 |
| ATOM | 5074 | O1 | HOH | W | 289 | 31.129 | 22.350 | 28.703 | 1.00 42.85 |
| ATOM | 5075 | O1 | HOH | W | 290 | 36.979 | 25.478 | 48.592 | 1.00 35.15 |
| ATOM | 5076 | O1 | HOH | W | 291 | 59.056 | 24.357 | 55.498 | 1.00 42.95 |
| ATOM | 5077 | O1 | HOH | W | 292 | 45.058 | 19.677 | 57.915 | 1.00 35.81 |
| ATOM | 5078 | O1 | HOH | W | 293 | 27.531 | 31.666 | 63.768 | 1.00 55.59 |
| ATOM | 5079 | O1 | HOH | W | 294 | 15.733 | 8.228 | 20.545 | 1.00 55.53 |
| ATOM | 5080 | O1 | HOH | W | 295 | 21.402 | 1.241 | 51.437 | 1.00 51.66 |
| ATOM | 5081 | O1 | HOH | W | 296 | 24.337 | -2.308 | 23.410 | 1.00 40.84 |
| ATOM | 5082 | O1 | HOH | W | 297 | 45.597 | 49.644 | 86.607 | 1.00 60.74 |
| ATOM | 5083 | O1 | HOH | W | 298 | 48.392 | 7.844 | 54.894 | 1.00 40.30 |
| ATOM | 5084 | O1 | HOH | W | 299 | 10.706 | -0.247 | 53.887 | 1.00 36.83 |
| ATOM | 5085 | O1 | HOH | W | 300 | 30.841 | 6.772 | 42.114 | 1.00 46.90 |
| ATOM | 5086 | O1 | HOH | W | 301 | 56.984 | 31.594 | 84.598 | 1.00 64.61 |
| ATOM | 5087 | O1 | HOH | W | 302 | 23.975 | 0.753 | 21.900 | 1.00 58.72 |
| ATOM | 5088 | O1 | HOH | W | 303 | 25.943 | -3.970 | 26.011 | 1.00 34.27 |
| ATOM | 5089 | O1 | HOH | W | 304 | 57.745 | 27.571 | 81.771 | 1.00 39.39 |
| ATOM | 5090 | O1 | HOH | W | 305 | 8.725 | 13.816 | 46.139 | 1.00 62.61 |
| ATOM | 5091 | O1 | HOH | W | 306 | 9.642 | -2.831 | 53.313 | 1.00 48.15 |
| ATOM | 5092 | O1 | HOH | W | 307 | -12.355 | -6.712 | 32.342 | 1.00 40.12 |
| ATOM | 5093 | O1 | HOH | W | 308 | 10.024 | 7.396 | 49.256 | 1.00 37.70 |
| ATOM | 5094 | O1 | HOH | W | 309 | 41.071 | 3.104 | 32.909 | 1.00 61.81 |
| ATOM | 5095 | O1 | HOH | W | 310 | 60.474 | 28.281 | 80.505 | 1.00 58.55 |

FIGURE 200

```
ATOM  5096  O1  HOH W 311   -0.719    1.660   54.184  1.00 46.99
ATOM  5097  O1  HOH W 312   42.157    0.641   32.043  1.00 61.15
ATOM  5098  O1  HOH W 313   26.844   31.094   74.091  1.00 57.31
ATOM  5099  O1  HOH W 314    7.696   11.428   47.893  1.00 49.96
ATOM  5100  O1  HOH W 315   54.048   21.906   53.414  1.00 50.41
ATOM  5101  O1  HOH W 316   47.093    3.308   57.181  1.00 49.89
ATOM  5102  O1  HOH W 317    0.538   11.547   46.107  1.00 65.71
ATOM  5103  O1  HOH W 318    8.860   16.730   39.751  1.00 67.14
ATOM  5104  O1  HOH W 319   17.788  -19.138   29.587  1.00 65.65
ATOM  5105  O1  HOH W 320   19.712   14.524   17.149  1.00 66.48
ATOM  5106  O1  HOH W 321   -1.219  -11.550   22.358  1.00 64.74
ATOM  5107  O1  HOH W 322    6.040   14.352   34.149  1.00 62.82
ATOM  5108  O1  HOH W 323   65.030   28.876   55.181  1.00 54.52
ATOM  5109  O1  HOH W 324   41.175    4.830   36.570  1.00 59.29
ATOM  5110  O1  HOH W 325   15.916   -2.843   51.316  1.00 58.50
ATOM  5111  O1  HOH W 326   21.478   17.683   70.720  1.00 50.48
END
```

FIGURE 201

```
CRYST1   39.250    71.126  119.912  90.00  90.00  90.00
ATOM    1    N    LYS A  19    -12.134  41.491  10.114 1.000 47.16
ATOM    2    CA   LYS A  19    -12.088  40.464   9.085 1.000 46.31
ATOM    3    CB   LYS A  19    -11.200  40.822   7.902 1.000 46.34
ATOM    4    CG   LYS A  19     -9.707  40.790   8.149 1.000 42.97
ATOM    5    CD   LYS A  19     -8.945  40.965   6.847 1.000 43.94
ATOM    6    CE   LYS A  19     -7.609  41.670   7.059 1.000 39.13
ATOM    7    NZ   LYS A  19     -6.732  41.562   5.856 1.000 48.25
ATOM    8    C    LYS A  19    -11.602  39.144   9.702 1.000 47.15
ATOM    9    O    LYS A  19    -10.921  39.174  10.723 1.000 50.63
ATOM   10    N    THR A  20    -11.999  38.090   9.024 1.000 38.61
ATOM   11    CA   THR A  20    -11.875  36.698   9.401 1.000 42.80
ATOM   12    CB   THR A  20    -13.310  36.133   9.502 1.000 46.49
ATOM   13    OG1  THR A  20    -13.660  36.080  10.896 1.000 54.76
ATOM   14    CG2  THR A  20    -13.393  34.742   8.933 1.000 40.58
ATOM   15    C    THR A  20    -11.069  35.879   8.414 1.000 38.96
ATOM   16    O    THR A  20    -10.606  34.774   8.695 1.000 26.83
ATOM   17    N    SER A  21    -10.899  36.432   7.211 1.000 27.43
ATOM   18    CA   SER A  21    -10.213  35.731   6.137 1.000 21.10
ATOM   19    CB   SER A  21    -11.193  34.767   5.449 1.000 34.39
ATOM   20    OG   SER A  21    -10.929  34.678   4.055 1.000 44.20
ATOM   21    C    SER A  21     -9.647  36.730   5.144 1.000 25.82
ATOM   22    O    SER A  21    -10.151  37.858   5.158 1.000 39.09
ATOM   23    N    CYS A  22     -8.669  36.373   4.325 1.000 26.63
ATOM   24    CA   CYS A  22     -8.080  37.358   3.404 1.000 29.32
ATOM   25    CB   CYS A  22     -7.041  38.266   4.056 1.000 29.54
ATOM   26    SG   CYS A  22     -6.599  39.770   3.116 1.000 40.23
ATOM   27    C    CYS A  22     -7.445  36.575   2.264 1.000 28.58
ATOM   28    O    CYS A  22     -6.219  36.546   2.161 1.000 36.15
ATOM   29    N    PRO A  23     -8.315  35.942   1.482 1.000 31.23
ATOM   30    CA   PRO A  23     -7.853  35.032   0.450 1.000 28.72
ATOM   31    CB   PRO A  23     -9.120  34.324  -0.025 1.000 32.50
ATOM   32    CG   PRO A  23    -10.228  35.253   0.317 1.000 32.13
ATOM   33    CD   PRO A  23     -9.784  36.062   1.490 1.000 33.79
ATOM   34    C    PRO A  23     -7.229  35.869  -0.664 1.000 27.64
ATOM   35    O    PRO A  23     -7.703  36.980  -0.890 1.000 28.84
ATOM   36    N    ILE A  24     -6.205  35.309  -1.275 1.000 25.07
ATOM   37    CA   ILE A  24     -5.480  35.988  -2.347 1.000 26.87
ATOM   38    CB   ILE A  24     -4.118  36.521  -1.880 1.000 23.03
ATOM   39    CG1  ILE A  24     -4.194  37.387  -0.616 1.000 32.69
ATOM   40    CD1  ILE A  24     -4.803  38.749  -0.870 1.000 36.67
ATOM   41    CG2  ILE A  24     -3.411  37.301  -2.982 1.000 35.11
ATOM   42    C    ILE A  24     -5.297  35.003  -3.489 1.000 23.25
ATOM   43    O    ILE A  24     -4.816  33.891  -3.288 1.000 28.71
ATOM   44    N    LYS A  25     -5.703  35.414  -4.692 1.000 28.16
ATOM   45    CA   LYS A  25     -5.530  34.603  -5.877 1.000 28.40
ATOM   46    CB   LYS A  25     -6.067  35.296  -7.130 1.000 34.65
ATOM   47    CG   LYS A  25     -7.546  35.653  -7.058 1.000 38.17
ATOM   48    CD   LYS A  25     -7.944  36.538  -8.227 1.000 48.55
ATOM   49    CE   LYS A  25     -9.420  36.915  -8.158 1.000 55.62
ATOM   50    NZ   LYS A  25     -9.640  38.251  -7.532 1.000 59.24
ATOM   51    C    LYS A  25     -4.034  34.363  -6.051 1.000 26.23
```

FIGURE 202

| | | | | | | | | | |
|---|---|---|---|---|---|---|---|---|---|
| ATOM | 52 | O | LYS | A | 25 | -3.283 | 35.312 | -5.797 | 1.000 35.63 |
| ATOM | 53 | N | ILE | A | 26 | -3.655 | 33.153 | -6.449 | 1.000 26.51 |
| ATOM | 54 | CA | ILE | A | 26 | -2.202 | 32.943 | -6.476 | 1.000 39.40 |
| ATOM | 55 | CB | ILE | A | 26 | -1.848 | 31.483 | -6.769 | 1.000 41.92 |
| ATOM | 56 | CG1 | ILE | A | 26 | -2.538 | 30.872 | -7.986 | 1.000 55.69 |
| ATOM | 57 | CD1 | ILE | A | 26 | -1.953 | 29.527 | -8.398 | 1.000 43.15 |
| ATOM | 58 | CG2 | ILE | A | 26 | -2.092 | 30.645 | -5.505 | 1.000 30.44 |
| ATOM | 59 | C | ILE | A | 26 | -1.545 | 33.891 | -7.468 | 1.000 49.89 |
| ATOM | 60 | O | ILE | A | 26 | -0.403 | 34.315 | -7.258 | 1.000 61.92 |
| ATOM | 61 | N | ASN | A | 27 | -2.257 | 34.261 | -8.535 | 1.000 47.63 |
| ATOM | 62 | CA | ASN | A | 27 | -1.622 | 35.182 | -9.489 | 1.000 48.85 |
| ATOM | 63 | CB | ASN | A | 27 | -2.409 | 35.259 | -10.789 | 1.000 58.29 |
| ATOM | 64 | CG | ASN | A | 27 | -3.867 | 35.634 | -10.702 | 1.000 64.78 |
| ATOM | 65 | OD1 | ASN | A | 27 | -4.735 | 34.952 | -11.257 | 1.000 66.47 |
| ATOM | 66 | ND2 | ASN | A | 27 | -4.181 | 36.732 | -10.026 | 1.000 76.39 |
| ATOM | 67 | C | ASN | A | 27 | -1.419 | 36.560 | -8.875 | 1.000 42.84 |
| ATOM | 68 | O | ASN | A | 27 | -0.555 | 37.314 | -9.323 | 1.000 45.62 |
| ATOM | 69 | N | GLN | A | 28 | -2.197 | 36.926 | -7.856 | 1.000 38.86 |
| ATOM | 70 | CA | GLN | A | 28 | -1.986 | 38.188 | -7.174 | 1.000 39.38 |
| ATOM | 71 | CB | GLN | A | 28 | -3.330 | 38.731 | -6.666 | 1.000 44.68 |
| ATOM | 72 | CG | GLN | A | 28 | -3.622 | 40.150 | -7.123 | 1.000 69.70 |
| ATOM | 73 | CD | GLN | A | 28 | -3.103 | 40.420 | -8.526 | 1.000 86.93 |
| ATOM | 74 | OE1 | GLN | A | 28 | -3.225 | 39.566 | -9.412 | 1.000117.05 |
| ATOM | 75 | NE2 | GLN | A | 28 | -2.527 | 41.600 | -8.735 | 1.000 74.84 |
| ATOM | 76 | C | GLN | A | 28 | -1.024 | 38.107 | -5.992 | 1.000 38.67 |
| ATOM | 77 | O | GLN | A | 28 | -0.763 | 39.173 | -5.416 | 1.000 27.96 |
| ATOM | 78 | N | PHE | A | 29 | -0.525 | 36.933 | -5.609 | 1.000 36.04 |
| ATOM | 79 | CA | PHE | A | 29 | 0.171 | 36.807 | -4.326 | 1.000 34.34 |
| ATOM | 80 | CB | PHE | A | 29 | 0.531 | 35.339 | -3.998 | 1.000 30.22 |
| ATOM | 81 | CG | PHE | A | 29 | 0.922 | 35.274 | -2.520 | 1.000 26.86 |
| ATOM | 82 | CD1 | PHE | A | 29 | -0.074 | 35.297 | -1.554 | 1.000 29.29 |
| ATOM | 83 | CE1 | PHE | A | 29 | 0.225 | 35.248 | -0.203 | 1.000 28.67 |
| ATOM | 84 | CZ | PHE | A | 29 | 1.560 | 35.208 | 0.168 | 1.000 38.22 |
| ATOM | 85 | CE2 | PHE | A | 29 | 2.567 | 35.166 | -0.786 | 1.000 38.42 |
| ATOM | 86 | CD2 | PHE | A | 29 | 2.249 | 35.197 | -2.134 | 1.000 32.07 |
| ATOM | 87 | C | PHE | A | 29 | 1.448 | 37.636 | -4.193 | 1.000 33.30 |
| ATOM | 88 | O | PHE | A | 29 | 1.580 | 38.350 | -3.187 | 1.000 34.15 |
| ATOM | 89 | N | GLU | A | 30 | 2.352 | 37.531 | -5.149 | 1.000 41.14 |
| ATOM | 90 | CA | GLU | A | 30 | 3.603 | 38.271 | -5.221 | 1.000 38.75 |
| ATOM | 91 | CB | GLU | A | 30 | 4.200 | 38.126 | -6.629 | 1.000 41.90 |
| ATOM | 92 | CG | GLU | A | 30 | 5.619 | 38.657 | -6.739 | 1.000 50.56 |
| ATOM | 93 | CD | GLU | A | 30 | 6.619 | 37.768 | -6.022 | 1.000 60.13 |
| ATOM | 94 | OE1 | GLU | A | 30 | 6.912 | 36.658 | -6.515 | 1.000 51.89 |
| ATOM | 95 | OE2 | GLU | A | 30 | 7.109 | 38.196 | -4.954 | 1.000 80.65 |
| ATOM | 96 | C | GLU | A | 30 | 3.456 | 39.755 | -4.931 | 1.000 38.26 |
| ATOM | 97 | O | GLU | A | 30 | 4.217 | 40.361 | -4.169 | 1.000 39.06 |
| ATOM | 98 | N | GLY | A | 31 | 2.463 | 40.378 | -5.572 | 1.000 33.74 |
| ATOM | 99 | CA | GLY | A | 31 | 2.321 | 41.815 | -5.409 | 1.000 29.48 |
| ATOM | 100 | C | GLY | A | 31 | 1.552 | 42.106 | -4.143 | 1.000 35.24 |
| ATOM | 101 | O | GLY | A | 31 | 1.757 | 43.141 | -3.521 | 1.000 37.25 |
| ATOM | 102 | N | HIS | A | 32 | 0.678 | 41.149 | -3.786 | 1.000 36.89 |
| ATOM | 103 | CA | HIS | A | 32 | 0.025 | 41.293 | -2.488 | 1.000 33.45 |

FIGURE 203

| ATOM | 104 | CB  | HIS | A | 32 | -0.863 | 40.102 | -2.149 | 1.000 | 30.08 |
| ATOM | 105 | CG  | HIS | A | 32 | -1.356 | 40.057 | -0.738 | 1.000 | 25.45 |
| ATOM | 106 | ND1 | HIS | A | 32 | -2.309 | 40.907 | -0.234 | 1.000 | 36.70 |
| ATOM | 107 | CE1 | HIS | A | 32 | -2.555 | 40.630 |  1.038 | 1.000 | 39.89 |
| ATOM | 108 | NE2 | HIS | A | 32 | -1.786 | 39.603 |  1.379 | 1.000 | 36.80 |
| ATOM | 109 | CD2 | HIS | A | 32 | -1.032 | 39.232 |  0.292 | 1.000 | 26.97 |
| ATOM | 110 | C   | HIS | A | 32 |  1.101 | 41.431 | -1.410 | 1.000 | 35.73 |
| ATOM | 111 | O   | HIS | A | 32 |  1.007 | 42.277 | -0.516 | 1.000 | 32.27 |
| ATOM | 112 | N   | PHE | A | 33 |  2.090 | 40.543 | -1.556 | 1.000 | 34.68 |
| ATOM | 113 | CA  | PHE | A | 33 |  3.120 | 40.431 | -0.515 | 1.000 | 32.48 |
| ATOM | 114 | CB  | PHE | A | 33 |  3.828 | 39.071 | -0.591 | 1.000 | 36.84 |
| ATOM | 115 | CG  | PHE | A | 33 |  4.751 | 38.835 |  0.595 | 1.000 | 37.98 |
| ATOM | 116 | CD1 | PHE | A | 33 |  4.471 | 39.433 |  1.812 | 1.000 | 40.95 |
| ATOM | 117 | CE1 | PHE | A | 33 |  5.308 | 39.272 |  2.895 | 1.000 | 43.07 |
| ATOM | 118 | CZ  | PHE | A | 33 |  6.440 | 38.479 |  2.754 | 1.000 | 34.64 |
| ATOM | 119 | CE2 | PHE | A | 33 |  6.724 | 37.866 |  1.554 | 1.000 | 26.60 |
| ATOM | 120 | CD2 | PHE | A | 33 |  5.875 | 38.039 |  0.472 | 1.000 | 32.44 |
| ATOM | 121 | C   | PHE | A | 33 |  4.050 | 41.630 | -0.607 | 1.000 | 36.33 |
| ATOM | 122 | O   | PHE | A | 33 |  4.526 | 42.116 |  0.428 | 1.000 | 41.59 |
| ATOM | 123 | N   | MET | A | 34 |  4.284 | 42.170 | -1.802 | 1.000 | 45.92 |
| ATOM | 124 | CA  | MET | A | 34 |  5.094 | 43.397 | -1.876 | 1.000 | 40.90 |
| ATOM | 125 | CB  | MET | A | 34 |  5.460 | 43.656 | -3.336 | 1.000 | 48.61 |
| ATOM | 126 | CG  | MET | A | 34 |  6.895 | 43.260 | -3.662 | 1.000 | 40.86 |
| ATOM | 127 | SD  | MET | A | 34 |  6.983 | 41.845 | -4.774 | 1.000 | 86.63 |
| ATOM | 128 | CE  | MET | A | 34 |  8.572 | 41.170 | -4.254 | 1.000 | 72.85 |
| ATOM | 129 | C   | MET | A | 34 |  4.383 | 44.588 | -1.259 | 1.000 | 42.23 |
| ATOM | 130 | O   | MET | A | 34 |  4.968 | 45.443 | -0.568 | 1.000 | 50.41 |
| ATOM | 131 | N   | LYS | A | 35 |  3.065 | 44.686 | -1.458 | 1.000 | 34.55 |
| ATOM | 132 | CA  | LYS | A | 35 |  2.351 | 45.788 | -0.795 | 1.000 | 45.08 |
| ATOM | 133 | CB  | LYS | A | 35 |  0.889 | 45.809 | -1.279 | 1.000 | 48.74 |
| ATOM | 134 | CG  | LYS | A | 35 |  0.793 | 46.296 | -2.720 | 1.000 | 51.47 |
| ATOM | 135 | CD  | LYS | A | 35 | -0.509 | 45.889 | -3.382 | 1.000 | 56.83 |
| ATOM | 136 | CE  | LYS | A | 35 | -0.788 | 46.795 | -4.577 | 1.000 | 55.04 |
| ATOM | 137 | NZ  | LYS | A | 35 | -0.993 | 46.020 | -5.830 | 1.000 | 61.49 |
| ATOM | 138 | C   | LYS | A | 35 |  2.417 | 45.703 |  0.717 | 1.000 | 38.13 |
| ATOM | 139 | O   | LYS | A | 35 |  2.575 | 46.713 |  1.419 | 1.000 | 38.53 |
| ATOM | 140 | N   | LEU | A | 36 |  2.293 | 44.483 |  1.267 | 1.000 | 37.05 |
| ATOM | 141 | CA  | LEU | A | 36 |  2.281 | 44.337 |  2.720 | 1.000 | 33.35 |
| ATOM | 142 | CB  | LEU | A | 36 |  1.904 | 42.922 |  3.179 | 1.000 | 29.64 |
| ATOM | 143 | CG  | LEU | A | 36 |  0.453 | 42.474 |  3.024 | 1.000 | 30.10 |
| ATOM | 144 | CD1 | LEU | A | 36 |  0.259 | 41.052 |  3.567 | 1.000 | 35.30 |
| ATOM | 145 | CD2 | LEU | A | 36 | -0.516 | 43.409 |  3.723 | 1.000 | 31.56 |
| ATOM | 146 | C   | LEU | A | 36 |  3.641 | 44.718 |  3.311 | 1.000 | 26.53 |
| ATOM | 147 | O   | LEU | A | 36 |  3.664 | 45.268 |  4.415 | 1.000 | 45.90 |
| ATOM | 148 | N   | GLN | A | 37 |  4.713 | 44.426 |  2.591 | 1.000 | 30.34 |
| ATOM | 149 | CA  | GLN | A | 37 |  6.073 | 44.682 |  3.038 | 1.000 | 46.11 |
| ATOM | 150 | CB  | GLN | A | 37 |  7.038 | 43.727 |  2.321 | 1.000 | 45.16 |
| ATOM | 151 | CG  | GLN | A | 37 |  7.047 | 42.323 |  2.925 | 1.000 | 46.46 |
| ATOM | 152 | CD  | GLN | A | 37 |  7.963 | 41.397 |  2.146 | 1.000 | 41.79 |
| ATOM | 153 | OE1 | GLN | A | 37 |  8.895 | 40.818 |  2.701 | 1.000 | 53.12 |
| ATOM | 154 | NE2 | GLN | A | 37 |  7.682 | 41.253 |  0.854 | 1.000 | 59.23 |
| ATOM | 155 | C   | GLN | A | 37 |  6.554 | 46.116 |  2.816 | 1.000 | 58.12 |

FIGURE 204

| | | | | | | | | | |
|---|---|---|---|---|---|---|---|---|---|
| ATOM | 156 | O | GLN | A | 37 | 7.585 | 46.535 | 3.366 | 1.000 44.71 |
| ATOM | 157 | N | ALA | A | 38 | 5.820 | 46.878 | 2.014 | 1.000 51.00 |
| ATOM | 158 | CA | ALA | A | 38 | 6.214 | 48.252 | 1.734 | 1.000 51.95 |
| ATOM | 159 | CB | ALA | A | 38 | 5.334 | 48.856 | 0.638 | 1.000 33.90 |
| ATOM | 160 | C | ALA | A | 38 | 6.155 | 49.144 | 2.971 | 1.000 53.47 |
| ATOM | 161 | O | ALA | A | 38 | 5.408 | 48.911 | 3.916 | 1.000 39.54 |
| ATOM | 162 | N | ASP | A | 39 | 6.967 | 50.198 | 2.923 | 1.000 54.79 |
| ATOM | 163 | CA | ASP | A | 39 | 7.037 | 51.192 | 3.990 | 1.000 41.76 |
| ATOM | 164 | CB | ASP | A | 39 | 5.738 | 51.973 | 4.114 | 1.000 38.24 |
| ATOM | 165 | CG | ASP | A | 39 | 5.127 | 52.287 | 2.757 | 1.000 53.89 |
| ATOM | 166 | OD1 | ASP | A | 39 | 4.001 | 52.837 | 2.732 | 1.000 61.68 |
| ATOM | 167 | OD2 | ASP | A | 39 | 5.750 | 52.000 | 1.707 | 1.000 55.37 |
| ATOM | 168 | C | ASP | A | 39 | 7.401 | 50.477 | 5.289 | 1.000 41.78 |
| ATOM | 169 | O | ASP | A | 39 | 6.886 | 50.753 | 6.369 | 1.000 42.20 |
| ATOM | 170 | N | SER | A | 40 | 8.339 | 49.547 | 5.104 | 1.000 41.63 |
| ATOM | 171 | CA | SER | A | 40 | 8.819 | 48.736 | 6.213 | 1.000 39.11 |
| ATOM | 172 | CB | SER | A | 40 | 9.331 | 49.627 | 7.344 | 1.000 45.54 |
| ATOM | 173 | OG | SER | A | 40 | 10.507 | 50.325 | 6.967 | 1.000 63.33 |
| ATOM | 174 | C | SER | A | 40 | 7.701 | 47.838 | 6.726 | 1.000 33.78 |
| ATOM | 175 | O | SER | A | 40 | 7.500 | 47.791 | 7.939 | 1.000 44.33 |
| ATOM | 176 | N | ASN | A | 41 | 6.979 | 47.158 | 5.831 | 1.000 36.63 |
| ATOM | 177 | CA | ASN | A | 41 | 5.911 | 46.290 | 6.314 | 1.000 46.11 |
| ATOM | 178 | CB | ASN | A | 41 | 6.386 | 45.245 | 7.332 | 1.000 39.56 |
| ATOM | 179 | CG | ASN | A | 41 | 7.336 | 44.240 | 6.734 | 1.000 39.34 |
| ATOM | 180 | OD1 | ASN | A | 41 | 7.679 | 43.246 | 7.379 | 1.000 66.37 |
| ATOM | 181 | ND2 | ASN | A | 41 | 7.760 | 44.503 | 5.505 | 1.000 47.43 |
| ATOM | 182 | C | ASN | A | 41 | 4.833 | 47.097 | 7.034 | 1.000 52.00 |
| ATOM | 183 | O | ASN | A | 41 | 4.484 | 46.727 | 8.159 | 1.000 45.88 |
| ATOM | 184 | N | TYR | A | 42 | 4.366 | 48.150 | 6.376 | 1.000 47.78 |
| ATOM | 185 | CA | TYR | A | 42 | 3.394 | 49.022 | 7.014 | 1.000 48.64 |
| ATOM | 186 | CB | TYR | A | 42 | 3.181 | 50.305 | 6.197 | 1.000 50.57 |
| ATOM | 187 | CG | TYR | A | 42 | 2.110 | 51.181 | 6.818 | 1.000 60.30 |
| ATOM | 188 | CD1 | TYR | A | 42 | 2.315 | 51.798 | 8.049 | 1.000 73.71 |
| ATOM | 189 | CE1 | TYR | A | 42 | 1.345 | 52.597 | 8.619 | 1.000 79.76 |
| ATOM | 190 | CZ | TYR | A | 42 | 0.148 | 52.779 | 7.947 | 1.000 83.87 |
| ATOM | 191 | OH | TYR | A | 42 | -0.829 | 53.570 | 8.494 | 1.000 96.86 |
| ATOM | 192 | CE2 | TYR | A | 42 | -0.084 | 52.176 | 6.728 | 1.000 77.87 |
| ATOM | 193 | CD2 | TYR | A | 42 | 0.899 | 51.382 | 6.173 | 1.000 69.62 |
| ATOM | 194 | C | TYR | A | 42 | 2.080 | 48.272 | 7.202 | 1.000 40.91 |
| ATOM | 195 | O | TYR | A | 42 | 1.518 | 48.233 | 8.297 | 1.000 38.94 |
| ATOM | 196 | N | LEU | A | 43 | 1.628 | 47.688 | 6.094 | 1.000 39.86 |
| ATOM | 197 | CA | LEU | A | 43 | 0.324 | 47.037 | 6.065 | 1.000 38.25 |
| ATOM | 198 | CB | LEU | A | 43 | -0.240 | 46.976 | 4.648 | 1.000 34.42 |
| ATOM | 199 | CG | LEU | A | 43 | -0.625 | 48.329 | 4.021 | 1.000 39.05 |
| ATOM | 200 | CD1 | LEU | A | 43 | -0.840 | 48.146 | 2.529 | 1.000 35.82 |
| ATOM | 201 | CD2 | LEU | A | 43 | -1.869 | 48.904 | 4.671 | 1.000 38.28 |
| ATOM | 202 | C | LEU | A | 43 | 0.401 | 45.628 | 6.658 | 1.000 40.26 |
| ATOM | 203 | O | LEU | A | 43 | -0.571 | 45.204 | 7.288 | 1.000 41.80 |
| ATOM | 204 | N | LEU | A | 44 | 1.531 | 44.954 | 6.473 | 1.000 40.52 |
| ATOM | 205 | CA | LEU | A | 44 | 1.755 | 43.658 | 7.118 | 1.000 40.17 |
| ATOM | 206 | CB | LEU | A | 44 | 3.181 | 43.148 | 6.903 | 1.000 40.11 |
| ATOM | 207 | CG | LEU | A | 44 | 3.410 | 41.689 | 7.327 | 1.000 39.64 |

FIGURE 205

| | | | | | | | | | | |
|---|---|---|---|---|---|---|---|---|---|---|
| ATOM | 208 | CD1 | LEU | A | 44 | 4.236 | 40.957 | 6.288 | 1.000 | 46.27 |
| ATOM | 209 | CD2 | LEU | A | 44 | 4.073 | 41.640 | 8.693 | 1.000 | 36.71 |
| ATOM | 210 | C | LEU | A | 44 | 1.490 | 43.724 | 8.616 | 1.000 | 40.53 |
| ATOM | 211 | O | LEU | A | 44 | 0.821 | 42.859 | 9.180 | 1.000 | 35.07 |
| ATOM | 212 | N | SER | A | 45 | 2.019 | 44.759 | 9.269 | 1.000 | 33.52 |
| ATOM | 213 | CA | SER | A | 45 | 1.856 | 44.909 | 10.710 | 1.000 | 33.03 |
| ATOM | 214 | CB | SER | A | 45 | 2.871 | 45.946 | 11.228 | 1.000 | 29.94 |
| ATOM | 215 | OG | SER | A | 45 | 4.137 | 45.710 | 10.612 | 1.000 | 33.78 |
| ATOM | 216 | C | SER | A | 45 | 0.433 | 45.275 | 11.087 | 1.000 | 36.97 |
| ATOM | 217 | O | SER | A | 45 | -0.131 | 44.758 | 12.058 | 1.000 | 34.42 |
| ATOM | 218 | N | LYS | A | 46 | -0.211 | 46.176 | 10.345 | 1.000 | 34.85 |
| ATOM | 219 | CA | LYS | A | 46 | -1.630 | 46.418 | 10.604 | 1.000 | 31.36 |
| ATOM | 220 | CB | LYS | A | 46 | -2.199 | 47.461 | 9.636 | 1.000 | 36.80 |
| ATOM | 221 | CG | LYS | A | 46 | -1.400 | 48.758 | 9.630 | 1.000 | 46.16 |
| ATOM | 222 | CD | LYS | A | 46 | -2.286 | 49.966 | 9.884 | 1.000 | 50.59 |
| ATOM | 223 | CE | LYS | A | 46 | -1.915 | 50.631 | 11.197 | 1.000 | 58.31 |
| ATOM | 224 | NZ | LYS | A | 46 | -0.513 | 51.127 | 11.179 | 1.000 | 66.09 |
| ATOM | 225 | C | LYS | A | 46 | -2.425 | 45.116 | 10.503 | 1.000 | 31.41 |
| ATOM | 226 | O | LYS | A | 46 | -3.340 | 44.917 | 11.304 | 1.000 | 42.72 |
| ATOM | 227 | N | GLU | A | 47 | -2.082 | 44.251 | 9.555 | 1.000 | 27.42 |
| ATOM | 228 | CA | GLU | A | 47 | -2.810 | 43.006 | 9.332 | 1.000 | 33.85 |
| ATOM | 229 | CB | GLU | A | 47 | -2.437 | 42.314 | 8.018 | 1.000 | 35.99 |
| ATOM | 230 | CG | GLU | A | 47 | -3.311 | 41.079 | 7.802 | 1.000 | 36.26 |
| ATOM | 231 | CD | GLU | A | 47 | -3.301 | 40.603 | 6.369 | 1.000 | 33.51 |
| ATOM | 232 | OE1 | GLU | A | 47 | -4.136 | 41.068 | 5.559 | 1.000 | 34.52 |
| ATOM | 233 | OE2 | GLU | A | 47 | -2.433 | 39.753 | 6.076 | 1.000 | 31.53 |
| ATOM | 234 | C | GLU | A | 47 | -2.560 | 41.985 | 10.443 | 1.000 | 30.28 |
| ATOM | 235 | O | GLU | A | 47 | -3.506 | 41.345 | 10.901 | 1.000 | 37.61 |
| ATOM | 236 | N | TYR | A | 48 | -1.298 | 41.883 | 10.836 | 1.000 | 30.47 |
| ATOM | 237 | CA | TYR | A | 48 | -0.931 | 41.057 | 11.983 | 1.000 | 29.64 |
| ATOM | 238 | CB | TYR | A | 48 | 0.590 | 41.107 | 12.208 | 1.000 | 34.11 |
| ATOM | 239 | CG | TYR | A | 48 | 1.016 | 40.197 | 13.336 | 1.000 | 31.94 |
| ATOM | 240 | CD1 | TYR | A | 48 | 0.866 | 38.821 | 13.183 | 1.000 | 33.96 |
| ATOM | 241 | CE1 | TYR | A | 48 | 1.231 | 37.938 | 14.175 | 1.000 | 32.68 |
| ATOM | 242 | CZ | TYR | A | 48 | 1.754 | 38.404 | 15.360 | 1.000 | 35.81 |
| ATOM | 243 | OH | TYR | A | 48 | 2.101 | 37.491 | 16.330 | 1.000 | 39.47 |
| ATOM | 244 | CE2 | TYR | A | 48 | 1.911 | 39.760 | 15.548 | 1.000 | 38.83 |
| ATOM | 245 | CD2 | TYR | A | 48 | 1.542 | 40.648 | 14.540 | 1.000 | 36.26 |
| ATOM | 246 | C | TYR | A | 48 | -1.712 | 41.530 | 13.202 | 1.000 | 39.70 |
| ATOM | 247 | O | TYR | A | 48 | -2.201 | 40.748 | 14.015 | 1.000 | 34.67 |
| ATOM | 248 | N | GLU | A | 49 | -1.839 | 42.852 | 13.334 | 1.000 | 34.55 |
| ATOM | 249 | CA | GLU | A | 49 | -2.480 | 43.503 | 14.469 | 1.000 | 26.84 |
| ATOM | 250 | CB | GLU | A | 49 | -2.226 | 45.029 | 14.435 | 1.000 | 31.26 |
| ATOM | 251 | CG | GLU | A | 49 | -0.796 | 45.295 | 14.919 | 1.000 | 41.28 |
| ATOM | 252 | CD | GLU | A | 49 | -0.707 | 44.824 | 16.368 | 1.000 | 46.36 |
| ATOM | 253 | OE1 | GLU | A | 49 | 0.167 | 44.004 | 16.694 | 1.000 | 49.76 |
| ATOM | 254 | OE2 | GLU | A | 49 | -1.540 | 45.294 | 17.171 | 1.000 | 64.46 |
| ATOM | 255 | C | GLU | A | 49 | -3.968 | 43.243 | 14.489 | 1.000 | 17.64 |
| ATOM | 256 | O | GLU | A | 49 | -4.611 | 43.212 | 15.530 | 1.000 | 31.99 |
| ATOM | 257 | N | GLU | A | 50 | -4.527 | 43.054 | 13.298 | 1.000 | 24.66 |
| ATOM | 258 | CA | GLU | A | 50 | -5.942 | 42.729 | 13.220 | 1.000 | 33.35 |
| ATOM | 259 | CB | GLU | A | 50 | -6.441 | 42.674 | 11.768 | 1.000 | 34.57 |

FIGURE 206

| ATOM | 260 | CG | GLU | A | 50 | -6.190 | 43.933 | 10.956 | 1.000 | 42.22 |
| --- | --- | --- | --- | --- | --- | --- | --- | --- | --- | --- |
| ATOM | 261 | CD | GLU | A | 50 | -7.128 | 43.945 | 9.750 | 1.000 | 52.34 |
| ATOM | 262 | OE1 | GLU | A | 50 | -8.357 | 43.957 | 9.988 | 1.000 | 46.50 |
| ATOM | 263 | OE2 | GLU | A | 50 | -6.639 | 43.930 | 8.604 | 1.000 | 70.90 |
| ATOM | 264 | C | GLU | A | 50 | -6.238 | 41.369 | 13.861 | 1.000 | 25.23 |
| ATOM | 265 | O | GLU | A | 50 | -7.375 | 41.121 | 14.248 | 1.000 | 30.99 |
| ATOM | 266 | N | LEU | A | 51 | -5.239 | 40.508 | 13.957 | 1.000 | 26.01 |
| ATOM | 267 | CA | LEU | A | 51 | -5.447 | 39.194 | 14.580 | 1.000 | 21.27 |
| ATOM | 268 | CB | LEU | A | 51 | -4.470 | 38.237 | 13.898 | 1.000 | 22.16 |
| ATOM | 269 | CG | LEU | A | 51 | -4.752 | 38.015 | 12.411 | 1.000 | 26.33 |
| ATOM | 270 | CD1 | LEU | A | 51 | -3.531 | 37.428 | 11.721 | 1.000 | 24.42 |
| ATOM | 271 | CD2 | LEU | A | 51 | -5.938 | 37.091 | 12.208 | 1.000 | 28.60 |
| ATOM | 272 | C | LEU | A | 51 | -5.186 | 39.188 | 16.068 | 1.000 | 28.00 |
| ATOM | 273 | O | LEU | A | 51 | -5.315 | 38.171 | 16.742 | 1.000 | 26.46 |
| ATOM | 274 | N | LYS | A | 52 | -4.767 | 40.325 | 16.620 | 1.000 | 26.04 |
| ATOM | 275 | CA | LYS | A | 52 | -4.297 | 40.372 | 18.002 | 1.000 | 27.42 |
| ATOM | 276 | CB | LYS | A | 52 | -3.950 | 41.832 | 18.319 | 1.000 | 30.97 |
| ATOM | 277 | CG | LYS | A | 52 | -3.602 | 42.133 | 19.765 | 1.000 | 36.67 |
| ATOM | 278 | CD | LYS | A | 52 | -2.878 | 43.478 | 19.823 | 1.000 | 47.93 |
| ATOM | 279 | CE | LYS | A | 52 | -3.089 | 44.186 | 21.148 | 1.000 | 54.43 |
| ATOM | 280 | NZ | LYS | A | 52 | -3.831 | 45.481 | 20.963 | 1.000 | 76.91 |
| ATOM | 281 | C | LYS | A | 52 | -5.281 | 39.803 | 19.009 | 1.000 | 30.56 |
| ATOM | 282 | O | LYS | A | 52 | -4.866 | 38.997 | 19.848 | 1.000 | 31.78 |
| ATOM | 283 | N | ASP | A | 53 | -6.560 | 40.166 | 18.951 | 1.000 | 22.00 |
| ATOM | 284 | CA | ASP | A | 53 | -7.502 | 39.716 | 19.960 | 1.000 | 27.33 |
| ATOM | 285 | CB | ASP | A | 53 | -8.442 | 40.858 | 20.385 | 1.000 | 30.10 |
| ATOM | 286 | CG | ASP | A | 53 | -7.622 | 42.098 | 20.721 | 1.000 | 47.01 |
| ATOM | 287 | OD1 | ASP | A | 53 | -6.798 | 42.004 | 21.657 | 1.000 | 67.96 |
| ATOM | 288 | OD2 | ASP | A | 53 | -7.810 | 43.119 | 20.027 | 1.000 | 65.18 |
| ATOM | 289 | C | ASP | A | 53 | -8.370 | 38.541 | 19.536 | 1.000 | 25.20 |
| ATOM | 290 | O | ASP | A | 53 | -9.268 | 38.189 | 20.304 | 1.000 | 25.98 |
| ATOM | 291 | N | VAL | A | 54 | -8.123 | 37.957 | 18.372 | 1.000 | 23.81 |
| ATOM | 292 | CA | VAL | A | 54 | -8.897 | 36.770 | 17.995 | 1.000 | 20.94 |
| ATOM | 293 | CB | VAL | A | 54 | -8.477 | 36.258 | 16.616 | 1.000 | 22.31 |
| ATOM | 294 | CG1 | VAL | A | 54 | -9.232 | 34.978 | 16.241 | 1.000 | 29.30 |
| ATOM | 295 | CG2 | VAL | A | 54 | -8.710 | 37.323 | 15.543 | 1.000 | 21.16 |
| ATOM | 296 | C | VAL | A | 54 | -8.722 | 35.657 | 19.047 | 1.000 | 22.79 |
| ATOM | 297 | O | VAL | A | 54 | -7.595 | 35.307 | 19.395 | 1.000 | 24.33 |
| ATOM | 298 | N | GLY | A | 55 | -9.835 | 35.135 | 19.514 | 1.000 | 19.38 |
| ATOM | 299 | CA | GLY | A | 55 | -10.013 | 34.105 | 20.496 | 1.000 | 21.67 |
| ATOM | 300 | C | GLY | A | 55 | -9.849 | 34.607 | 21.923 | 1.000 | 26.11 |
| ATOM | 301 | O | GLY | A | 55 | -10.150 | 33.822 | 22.828 | 1.000 | 24.18 |
| ATOM | 302 | N | ARG | A | 56 | -9.400 | 35.842 | 22.115 | 1.000 | 28.14 |
| ATOM | 303 | CA | ARG | A | 56 | -8.976 | 36.366 | 23.416 | 1.000 | 31.63 |
| ATOM | 304 | CB | ARG | A | 56 | -8.162 | 37.661 | 23.262 | 1.000 | 32.19 |
| ATOM | 305 | CG | ARG | A | 56 | -6.762 | 37.493 | 22.699 | 1.000 | 31.76 |
| ATOM | 306 | CD | ARG | A | 56 | -5.957 | 36.532 | 23.528 | 1.000 | 29.57 |
| ATOM | 307 | NE | ARG | A | 56 | -4.544 | 36.431 | 23.220 | 1.000 | 30.87 |
| ATOM | 308 | CZ | ARG | A | 56 | -3.526 | 37.074 | 23.757 | 1.000 | 30.34 |
| ATOM | 309 | NH1 | ARG | A | 56 | -3.681 | 37.983 | 24.710 | 1.000 | 22.02 |
| ATOM | 310 | NH2 | ARG | A | 56 | -2.280 | 36.828 | 23.339 | 1.000 | 31.11 |
| ATOM | 311 | C | ARG | A | 56 | -10.110 | 36.645 | 24.386 | 1.000 | 27.29 |

FIGURE 207

| | | | | | | | | | |
|---|---|---|---|---|---|---|---|---|---|
| ATOM | 312 | O | ARG | A | 56 | -9.904 | 37.126 | 25.512 | 1.000 30.11 |
| ATOM | 313 | N | ASN | A | 57 | -11.352 | 36.365 | 24.023 | 1.000 19.89 |
| ATOM | 314 | CA | ASN | A | 57 | -12.429 | 36.544 | 24.990 | 1.000 21.90 |
| ATOM | 315 | CB | ASN | A | 57 | -13.713 | 36.926 | 24.246 | 1.000 27.73 |
| ATOM | 316 | CG | ASN | A | 57 | -14.041 | 35.852 | 23.214 | 1.000 36.94 |
| ATOM | 317 | OD1 | ASN | A | 57 | -13.158 | 35.389 | 22.486 | 1.000 42.61 |
| ATOM | 318 | ND2 | ASN | A | 57 | -15.303 | 35.449 | 23.148 | 1.000 39.27 |
| ATOM | 319 | C | ASN | A | 57 | -12.594 | 35.274 | 25.807 | 1.000 27.58 |
| ATOM | 320 | O | ASN | A | 57 | -13.336 | 35.218 | 26.785 | 1.000 32.05 |
| ATOM | 321 | N | GLN | A | 58 | -11.917 | 34.193 | 25.434 | 1.000 25.93 |
| ATOM | 322 | CA | GLN | A | 58 | -12.213 | 32.925 | 26.103 | 1.000 23.11 |
| ATOM | 323 | CB | GLN | A | 58 | -11.975 | 31.773 | 25.109 | 1.000 24.51 |
| ATOM | 324 | CG | GLN | A | 58 | -12.758 | 31.911 | 23.809 | 1.000 19.93 |
| ATOM | 325 | CD | GLN | A | 58 | -12.245 | 30.977 | 22.712 | 1.000 21.00 |
| ATOM | 326 | OE1 | GLN | A | 58 | -11.224 | 31.206 | 22.055 | 1.000 21.51 |
| ATOM | 327 | NE2 | GLN | A | 58 | -12.953 | 29.879 | 22.484 | 1.000 21.23 |
| ATOM | 328 | C | GLN | A | 58 | -11.396 | 32.695 | 27.366 | 1.000 23.30 |
| ATOM | 329 | O | GLN | A | 58 | -10.242 | 33.132 | 27.462 | 1.000 24.27 |
| ATOM | 330 | N | SER | A | 59 | -11.981 | 31.996 | 28.335 | 1.000 19.68 |
| ATOM | 331 | CA | SER | A | 59 | -11.377 | 31.719 | 29.620 | 1.000 20.00 |
| ATOM | 332 | CB | SER | A | 59 | -12.481 | 31.570 | 30.673 | 1.000 29.01 |
| ATOM | 333 | OG | SER | A | 59 | -13.222 | 30.375 | 30.394 | 1.000 51.65 |
| ATOM | 334 | C | SER | A | 59 | -10.565 | 30.423 | 29.617 | 1.000 32.69 |
| ATOM | 335 | O | SER | A | 59 | -10.792 | 29.571 | 28.754 | 1.000 24.40 |
| ATOM | 336 | N | CYS | A | 60 | -9.682 | 30.285 | 30.596 | 1.000 21.63 |
| ATOM | 337 | CA | CYS | A | 60 | -8.872 | 29.128 | 30.861 | 1.000 19.92 |
| ATOM | 338 | CB | CYS | A | 60 | -7.392 | 29.346 | 30.568 | 1.000 20.33 |
| ATOM | 339 | SG | CYS | A | 60 | -7.068 | 30.023 | 28.934 | 1.000 23.64 |
| ATOM | 340 | C | CYS | A | 60 | -8.980 | 28.736 | 32.344 | 1.000 21.45 |
| ATOM | 341 | O | CYS | A | 60 | -7.941 | 28.497 | 32.959 | 1.000 20.03 |
| ATOM | 342 | N | ASP | A | 61 | -10.220 | 28.697 | 32.804 | 1.000 22.24 |
| ATOM | 343 | CA | ASP | A | 61 | -10.439 | 28.455 | 34.236 | 1.000 22.76 |
| ATOM | 344 | CB | ASP | A | 61 | -11.912 | 28.676 | 34.545 | 1.000 26.65 |
| ATOM | 345 | CG | ASP | A | 61 | -12.408 | 30.099 | 34.398 | 1.000 27.80 |
| ATOM | 346 | OD1 | ASP | A | 61 | -11.617 | 31.062 | 34.345 | 1.000 25.45 |
| ATOM | 347 | OD2 | ASP | A | 61 | -13.650 | 30.248 | 34.356 | 1.000 28.50 |
| ATOM | 348 | C | ASP | A | 61 | -9.962 | 27.065 | 34.629 | 1.000 27.73 |
| ATOM | 349 | O | ASP | A | 61 | -9.345 | 26.878 | 35.690 | 1.000 25.51 |
| ATOM | 350 | N | ILE | A | 62 | -10.221 | 26.052 | 33.792 | 1.000 24.65 |
| ATOM | 351 | CA | ILE | A | 62 | -9.809 | 24.698 | 34.223 | 1.000 21.14 |
| ATOM | 352 | CB | ILE | A | 62 | -10.325 | 23.659 | 33.214 | 1.000 21.34 |
| ATOM | 353 | CG1 | ILE | A | 62 | -11.838 | 23.755 | 33.010 | 1.000 22.01 |
| ATOM | 354 | CD1 | ILE | A | 62 | -12.609 | 23.524 | 34.306 | 1.000 33.06 |
| ATOM | 355 | CG2 | ILE | A | 62 | -9.903 | 22.258 | 33.624 | 1.000 31.17 |
| ATOM | 356 | C | ILE | A | 62 | -8.309 | 24.617 | 34.399 | 1.000 22.92 |
| ATOM | 357 | O | ILE | A | 62 | -7.792 | 24.134 | 35.422 | 1.000 26.58 |
| ATOM | 358 | N | ALA | A | 63 | -7.566 | 25.123 | 33.412 | 1.000 19.57 |
| ATOM | 359 | CA | ALA | A | 63 | -6.122 | 25.164 | 33.470 | 1.000 19.70 |
| ATOM | 360 | CB | ALA | A | 63 | -5.549 | 25.916 | 32.285 | 1.000 22.66 |
| ATOM | 361 | C | ALA | A | 63 | -5.604 | 25.864 | 34.733 | 1.000 27.00 |
| ATOM | 362 | O | ALA | A | 63 | -4.516 | 25.553 | 35.212 | 1.000 21.30 |
| ATOM | 363 | N | LEU | A | 64 | -6.404 | 26.799 | 35.235 | 1.000 23.07 |

FIGURE 208

| | | | | | | | | | |
|---|---|---|---|---|---|---|---|---|---|
| ATOM | 364 | CA | LEU | A | 64 | -6.027 | 27.582 | 36.400 | 1.000 24.35 |
| ATOM | 365 | CB | LEU | A | 64 | -6.749 | 28.929 | 36.297 | 1.000 23.45 |
| ATOM | 366 | CG | LEU | A | 64 | -6.102 | 29.880 | 35.306 | 1.000 23.45 |
| ATOM | 367 | CD1 | LEU | A | 64 | -6.952 | 31.144 | 35.230 | 1.000 26.55 |
| ATOM | 368 | CD2 | LEU | A | 64 | -4.677 | 30.179 | 35.723 | 1.000 24.94 |
| ATOM | 369 | C | LEU | A | 64 | -6.381 | 26.919 | 37.713 | 1.000 31.23 |
| ATOM | 370 | O | LEU | A | 64 | -6.097 | 27.521 | 38.750 | 1.000 30.60 |
| ATOM | 371 | N | LEU | A | 65 | -6.982 | 25.733 | 37.690 | 1.000 25.47 |
| ATOM | 372 | CA | LEU | A | 65 | -7.306 | 25.047 | 38.937 | 1.000 27.75 |
| ATOM | 373 | CB | LEU | A | 65 | -8.162 | 23.817 | 38.624 | 1.000 29.69 |
| ATOM | 374 | CG | LEU | A | 65 | -9.587 | 24.168 | 38.169 | 1.000 29.27 |
| ATOM | 375 | CD1 | LEU | A | 65 | -10.317 | 22.915 | 37.710 | 1.000 22.91 |
| ATOM | 376 | CD2 | LEU | A | 65 | -10.326 | 24.875 | 39.294 | 1.000 45.21 |
| ATOM | 377 | C | LEU | A | 65 | -6.045 | 24.666 | 39.697 | 1.000 32.88 |
| ATOM | 378 | O | LEU | A | 65 | -5.049 | 24.217 | 39.140 | 1.000 35.70 |
| ATOM | 379 | N | PRO | A | 66 | -6.075 | 24.876 | 41.014 | 1.000 36.18 |
| ATOM | 380 | CA | PRO | A | 66 | -4.904 | 24.635 | 41.858 | 1.000 36.18 |
| ATOM | 381 | CB | PRO | A | 66 | -5.488 | 24.754 | 43.275 | 1.000 47.92 |
| ATOM | 382 | CG | PRO | A | 66 | -6.648 | 25.684 | 43.117 | 1.000 42.33 |
| ATOM | 383 | CD | PRO | A | 66 | -7.235 | 25.378 | 41.764 | 1.000 30.77 |
| ATOM | 384 | C | PRO | A | 66 | -4.302 | 23.248 | 41.658 | 1.000 26.18 |
| ATOM | 385 | O | PRO | A | 66 | -3.084 | 23.122 | 41.569 | 1.000 37.38 |
| ATOM | 386 | N | GLU | A | 67 | -5.151 | 22.242 | 41.580 | 1.000 33.07 |
| ATOM | 387 | CA | GLU | A | 67 | -4.828 | 20.867 | 41.244 | 1.000 38.66 |
| ATOM | 388 | CB | GLU | A | 67 | -6.138 | 20.071 | 41.150 | 1.000 40.47 |
| ATOM | 389 | CG | GLU | A | 67 | -7.142 | 20.605 | 40.154 | 1.000 58.25 |
| ATOM | 390 | CD | GLU | A | 67 | -8.530 | 20.002 | 40.228 | 1.000 70.71 |
| ATOM | 391 | OE1 | GLU | A | 67 | -8.874 | 19.134 | 39.390 | 1.000 47.20 |
| ATOM | 392 | OE2 | GLU | A | 67 | -9.311 | 20.406 | 41.123 | 1.000 81.59 |
| ATOM | 393 | C | GLU | A | 67 | -4.033 | 20.762 | 39.946 | 1.000 40.21 |
| ATOM | 394 | O | GLU | A | 67 | -3.232 | 19.837 | 39.768 | 1.000 33.36 |
| ATOM | 395 | N | ASN | A | 68 | -4.202 | 21.695 | 39.001 | 1.000 27.60 |
| ATOM | 396 | CA | ASN | A | 68 | -3.494 | 21.553 | 37.729 | 1.000 27.03 |
| ATOM | 397 | CB | ASN | A | 68 | -4.471 | 21.891 | 36.584 | 1.000 25.75 |
| ATOM | 398 | CG | ASN | A | 68 | -5.638 | 20.924 | 36.530 | 1.000 27.63 |
| ATOM | 399 | OD1 | ASN | A | 68 | -5.417 | 19.725 | 36.763 | 1.000 27.03 |
| ATOM | 400 | ND2 | ASN | A | 68 | -6.837 | 21.424 | 36.223 | 1.000 20.87 |
| ATOM | 401 | C | ASN | A | 68 | -2.244 | 22.400 | 37.582 | 1.000 29.26 |
| ATOM | 402 | O | ASN | A | 68 | -1.561 | 22.322 | 36.543 | 1.000 32.09 |
| ATOM | 403 | N | ARG | A | 69 | -1.877 | 23.230 | 38.550 | 1.000 39.29 |
| ATOM | 404 | CA | ARG | A | 69 | -0.765 | 24.169 | 38.333 | 1.000 36.83 |
| ATOM | 405 | CB | ARG | A | 69 | -0.581 | 25.036 | 39.587 | 1.000 41.69 |
| ATOM | 406 | CG | ARG | A | 69 | 0.072 | 26.376 | 39.290 | 1.000 44.04 |
| ATOM | 407 | CD | ARG | A | 69 | -0.117 | 27.331 | 40.461 | 1.000 60.35 |
| ATOM | 408 | NE | ARG | A | 69 | -1.481 | 27.376 | 40.972 | 1.000 61.46 |
| ATOM | 409 | CZ | ARG | A | 69 | -1.832 | 27.284 | 42.248 | 1.000 67.83 |
| ATOM | 410 | NH1 | ARG | A | 69 | -3.113 | 27.336 | 42.599 | 1.000 61.15 |
| ATOM | 411 | NH2 | ARG | A | 69 | -0.920 | 27.136 | 43.202 | 1.000 84.01 |
| ATOM | 412 | C | ARG | A | 69 | 0.541 | 23.491 | 37.948 | 1.000 31.02 |
| ATOM | 413 | O | ARG | A | 69 | 1.225 | 23.924 | 37.009 | 1.000 34.71 |
| ATOM | 414 | N | GLY | A | 70 | 0.895 | 22.385 | 38.603 | 1.000 27.71 |
| ATOM | 415 | CA | GLY | A | 70 | 2.103 | 21.679 | 38.203 | 1.000 25.00 |

FIGURE 209

| ATOM | 416 | C | GLY | A | 70 | 2.044 | 21.041 | 36.822 | 1.000 | 24.89 |
|------|-----|------|-----|---|----|-------|--------|--------|-------|-------|
| ATOM | 417 | O | GLY | A | 70 | 3.083 | 20.564 | 36.376 | 1.000 | 31.72 |
| ATOM | 418 | N | LYS | A | 71 | 0.903 | 21.014 | 36.147 | 1.000 | 27.08 |
| ATOM | 419 | CA | LYS | A | 71 | 0.763 | 20.318 | 34.866 | 1.000 | 24.21 |
| ATOM | 420 | CB | LYS | A | 71 | -0.653 | 19.731 | 34.781 | 1.000 | 21.70 |
| ATOM | 421 | CG | LYS | A | 71 | -0.943 | 18.621 | 35.788 | 1.000 | 25.95 |
| ATOM | 422 | CD | LYS | A | 71 | -2.404 | 18.202 | 35.750 | 1.000 | 27.35 |
| ATOM | 423 | CE | LYS | A | 71 | -2.743 | 17.164 | 36.834 | 1.000 | 26.32 |
| ATOM | 424 | NZ | LYS | A | 71 | -4.227 | 17.045 | 36.994 | 1.000 | 29.99 |
| ATOM | 425 | C | LYS | A | 71 | 1.003 | 21.230 | 33.678 | 1.000 | 26.31 |
| ATOM | 426 | O | LYS | A | 71 | 0.999 | 20.826 | 32.508 | 1.000 | 21.01 |
| ATOM | 427 | N | ASN | A | 72 | 1.209 | 22.517 | 33.974 | 1.000 | 24.08 |
| ATOM | 428 | CA | ASN | A | 72 | 1.520 | 23.503 | 32.951 | 1.000 | 24.06 |
| ATOM | 429 | CB | ASN | A | 72 | 0.700 | 24.782 | 33.236 | 1.000 | 23.98 |
| ATOM | 430 | CG | ASN | A | 72 | -0.782 | 24.508 | 33.170 | 1.000 | 24.00 |
| ATOM | 431 | OD1 | ASN | A | 72 | -1.229 | 23.905 | 32.180 | 1.000 | 27.29 |
| ATOM | 432 | ND2 | ASN | A | 72 | -1.564 | 24.932 | 34.139 | 1.000 | 21.52 |
| ATOM | 433 | C | ASN | A | 72 | 2.999 | 23.855 | 32.902 | 1.000 | 24.14 |
| ATOM | 434 | O | ASN | A | 72 | 3.539 | 24.242 | 33.952 | 1.000 | 32.17 |
| ATOM | 435 | N | ARG | A | 73 | 3.669 | 23.767 | 31.763 | 1.000 | 18.37 |
| ATOM | 436 | CA | ARG | A | 73 | 5.068 | 24.153 | 31.624 | 1.000 | 20.26 |
| ATOM | 437 | CB | ARG | A | 73 | 5.606 | 23.824 | 30.236 | 1.000 | 27.07 |
| ATOM | 438 | CG | ARG | A | 73 | 7.082 | 24.137 | 30.020 | 1.000 | 24.27 |
| ATOM | 439 | CD | ARG | A | 73 | 7.645 | 23.603 | 28.712 | 1.000 | 22.01 |
| ATOM | 440 | NE | ARG | A | 73 | 7.794 | 22.144 | 28.739 | 1.000 | 23.84 |
| ATOM | 441 | CZ | ARG | A | 73 | 8.809 | 21.516 | 29.321 | 1.000 | 33.27 |
| ATOM | 442 | NH1 | ARG | A | 73 | 9.757 | 22.240 | 29.913 | 1.000 | 21.92 |
| ATOM | 443 | NH2 | ARG | A | 73 | 8.909 | 20.191 | 29.335 | 1.000 | 23.01 |
| ATOM | 444 | C | ARG | A | 73 | 5.231 | 25.648 | 31.916 | 1.000 | 30.65 |
| ATOM | 445 | O | ARG | A | 73 | 6.184 | 26.110 | 32.549 | 1.000 | 32.85 |
| ATOM | 446 | N | TYR | A | 74 | 4.279 | 26.440 | 31.452 | 1.000 | 27.96 |
| ATOM | 447 | CA | TYR | A | 74 | 4.329 | 27.903 | 31.619 | 1.000 | 22.72 |
| ATOM | 448 | CB | TYR | A | 74 | 4.778 | 28.577 | 30.343 | 1.000 | 24.68 |
| ATOM | 449 | CG | TYR | A | 74 | 6.008 | 28.085 | 29.620 | 1.000 | 40.81 |
| ATOM | 450 | CD1 | TYR | A | 74 | 7.302 | 28.339 | 30.080 | 1.000 | 42.06 |
| ATOM | 451 | CE1 | TYR | A | 74 | 8.424 | 27.881 | 29.404 | 1.000 | 30.31 |
| ATOM | 452 | CZ | TYR | A | 74 | 8.304 | 27.155 | 28.238 | 1.000 | 36.98 |
| ATOM | 453 | OH | TYR | A | 74 | 9.426 | 26.707 | 27.567 | 1.000 | 31.11 |
| ATOM | 454 | CE2 | TYR | A | 74 | 7.038 | 26.881 | 27.739 | 1.000 | 33.48 |
| ATOM | 455 | CD2 | TYR | A | 74 | 5.932 | 27.349 | 28.434 | 1.000 | 32.64 |
| ATOM | 456 | C | TYR | A | 74 | 2.932 | 28.320 | 32.074 | 1.000 | 35.24 |
| ATOM | 457 | O | TYR | A | 74 | 1.980 | 28.127 | 31.311 | 1.000 | 28.99 |
| ATOM | 458 | N | ASN | A | 75 | 2.831 | 28.838 | 33.293 | 1.000 | 34.47 |
| ATOM | 459 | CA | ASN | A | 75 | 1.587 | 29.142 | 33.973 | 1.000 | 26.33 |
| ATOM | 460 | CB | ASN | A | 75 | 1.844 | 29.654 | 35.396 | 1.000 | 28.02 |
| ATOM | 461 | CG | ASN | A | 75 | 2.541 | 28.595 | 36.230 | 1.000 | 47.27 |
| ATOM | 462 | OD1 | ASN | A | 75 | 2.639 | 27.427 | 35.838 | 1.000 | 38.13 |
| ATOM | 463 | ND2 | ASN | A | 75 | 3.009 | 29.045 | 37.388 | 1.000 | 58.84 |
| ATOM | 464 | C | ASN | A | 75 | 0.752 | 30.193 | 33.247 | 1.000 | 19.13 |
| ATOM | 465 | O | ASN | A | 75 | -0.423 | 30.394 | 33.561 | 1.000 | 27.32 |
| ATOM | 466 | N | ASN | A | 76 | 1.348 | 30.876 | 32.289 | 1.000 | 18.49 |
| ATOM | 467 | CA | ASN | A | 76 | 0.562 | 31.826 | 31.510 | 1.000 | 26.54 |

FIGURE 210

| | | | | | | | | | |
|---|---|---|---|---|---|---|---|---|---|
| ATOM | 468 | CB | ASN | A | 76 | 1.244 | 33.195 | 31.432 | 1.000 26.00 |
| ATOM | 469 | CG | ASN | A | 76 | 2.628 | 33.130 | 30.821 | 1.000 27.59 |
| ATOM | 470 | OD1 | ASN | A | 76 | 3.295 | 32.100 | 30.926 | 1.000 28.39 |
| ATOM | 471 | ND2 | ASN | A | 76 | 3.131 | 34.186 | 30.182 | 1.000 26.81 |
| ATOM | 472 | C | ASN | A | 76 | 0.331 | 31.297 | 30.101 | 1.000 26.92 |
| ATOM | 473 | O | ASN | A | 76 | -0.145 | 32.065 | 29.263 | 1.000 24.80 |
| ATOM | 474 | N | ILE | A | 77 | 0.659 | 30.023 | 29.813 | 1.000 21.21 |
| ATOM | 475 | CA | ILE | A | 77 | 0.313 | 29.527 | 28.477 | 1.000 20.79 |
| ATOM | 476 | CB | ILE | A | 77 | 1.534 | 29.187 | 27.632 | 1.000 25.15 |
| ATOM | 477 | CG1 | ILE | A | 77 | 2.596 | 30.315 | 27.595 | 1.000 31.48 |
| ATOM | 478 | CD1 | ILE | A | 77 | 2.862 | 30.817 | 26.195 | 1.000 49.78 |
| ATOM | 479 | CG2 | ILE | A | 77 | 1.116 | 28.793 | 26.229 | 1.000 23.01 |
| ATOM | 480 | C | ILE | A | 77 | -0.604 | 28.313 | 28.648 | 1.000 23.40 |
| ATOM | 481 | O | ILE | A | 77 | -0.121 | 27.210 | 28.877 | 1.000 24.16 |
| ATOM | 482 | N | LEU | A | 78 | -1.899 | 28.584 | 28.583 | 1.000 20.25 |
| ATOM | 483 | CA | LEU | A | 78 | -2.931 | 27.667 | 29.035 | 1.000 19.58 |
| ATOM | 484 | CB | LEU | A | 78 | -3.621 | 28.170 | 30.307 | 1.000 18.02 |
| ATOM | 485 | CG | LEU | A | 78 | -2.711 | 28.581 | 31.476 | 1.000 22.60 |
| ATOM | 486 | CD1 | LEU | A | 78 | -3.510 | 29.136 | 32.647 | 1.000 18.50 |
| ATOM | 487 | CD2 | LEU | A | 78 | -1.854 | 27.424 | 31.993 | 1.000 19.12 |
| ATOM | 488 | C | LEU | A | 78 | -3.946 | 27.471 | 27.912 | 1.000 18.12 |
| ATOM | 489 | O | LEU | A | 78 | -4.186 | 28.398 | 27.142 | 1.000 19.00 |
| ATOM | 490 | N | PRO | A | 79 | -4.511 | 26.269 | 27.863 | 1.000 18.26 |
| ATOM | 491 | CA | PRO | A | 79 | -5.546 | 26.003 | 26.858 | 1.000 16.50 |
| ATOM | 492 | CB | PRO | A | 79 | -5.707 | 24.485 | 26.984 | 1.000 21.55 |
| ATOM | 493 | CG | PRO | A | 79 | -5.462 | 24.228 | 28.452 | 1.000 13.29 |
| ATOM | 494 | CD | PRO | A | 79 | -4.246 | 25.103 | 28.705 | 1.000 14.71 |
| ATOM | 495 | C | PRO | A | 79 | -6.844 | 26.703 | 27.235 | 1.000 17.47 |
| ATOM | 496 | O | PRO | A | 79 | -7.176 | 26.850 | 28.420 | 1.000 20.15 |
| ATOM | 497 | N | TYR | A | 80 | -7.613 | 27.139 | 26.237 | 1.000 15.99 |
| ATOM | 498 | CA | TYR | A | 80 | -8.958 | 27.654 | 26.481 | 1.000 17.04 |
| ATOM | 499 | CB | TYR | A | 80 | -9.454 | 28.253 | 25.165 | 1.000 16.02 |
| ATOM | 500 | CG | TYR | A | 80 | -8.756 | 29.502 | 24.697 | 1.000 17.83 |
| ATOM | 501 | CD1 | TYR | A | 80 | -8.514 | 30.562 | 25.574 | 1.000 17.44 |
| ATOM | 502 | CE1 | TYR | A | 80 | -7.879 | 31.711 | 25.143 | 1.000 18.38 |
| ATOM | 503 | CZ | TYR | A | 80 | -7.474 | 31.828 | 23.837 | 1.000 17.97 |
| ATOM | 504 | OH | TYR | A | 80 | -6.845 | 32.976 | 23.415 | 1.000 20.65 |
| ATOM | 505 | CE2 | TYR | A | 80 | -7.700 | 30.802 | 22.930 | 1.000 19.84 |
| ATOM | 506 | CD2 | TYR | A | 80 | -8.338 | 29.655 | 23.381 | 1.000 17.33 |
| ATOM | 507 | C | TYR | A | 80 | -9.884 | 26.547 | 26.977 | 1.000 18.38 |
| ATOM | 508 | O | TYR | A | 80 | -9.791 | 25.404 | 26.525 | 1.000 19.85 |
| ATOM | 509 | N | ASP | A | 81 | -10.785 | 26.816 | 27.908 | 1.000 18.35 |
| ATOM | 510 | CA | ASP | A | 81 | -11.772 | 25.824 | 28.336 | 1.000 23.15 |
| ATOM | 511 | CB | ASP | A | 81 | -12.734 | 26.485 | 29.337 | 1.000 20.21 |
| ATOM | 512 | CG | ASP | A | 81 | -12.050 | 26.883 | 30.626 | 1.000 19.62 |
| ATOM | 513 | OD1 | ASP | A | 81 | -11.107 | 26.212 | 31.082 | 1.000 20.36 |
| ATOM | 514 | OD2 | ASP | A | 81 | -12.437 | 27.911 | 31.225 | 1.000 24.76 |
| ATOM | 515 | C | ASP | A | 81 | -12.539 | 25.250 | 27.153 | 1.000 19.52 |
| ATOM | 516 | O | ASP | A | 81 | -12.771 | 24.029 | 27.079 | 1.000 21.17 |
| ATOM | 517 | N | ALA | A | 82 | -12.910 | 26.116 | 26.218 | 1.000 19.35 |
| ATOM | 518 | CA | ALA | A | 82 | -13.787 | 25.780 | 25.106 | 1.000 20.79 |
| ATOM | 519 | CB | ALA | A | 82 | -14.147 | 27.041 | 24.318 | 1.000 21.73 |

FIGURE 211

| ATOM | 520 | C   | ALA | A | 82 | -13.218 | 24.780 | 24.117 | 1.000 | 24.48 |
| ATOM | 521 | O   | ALA | A | 82 | -14.017 | 24.152 | 23.409 | 1.000 | 24.01 |
| ATOM | 522 | N   | THR | A | 83 | -11.910 | 24.613 | 24.002 | 1.000 | 19.51 |
| ATOM | 523 | CA  | THR | A | 83 | -11.324 | 23.717 | 22.995 | 1.000 | 17.80 |
| ATOM | 524 | CB  | THR | A | 83 | -10.631 | 24.588 | 21.940 | 1.000 | 16.46 |
| ATOM | 525 | OG1 | THR | A | 83 | -9.691  | 25.412 | 22.665 | 1.000 | 18.46 |
| ATOM | 526 | CG2 | THR | A | 83 | -11.616 | 25.512 | 21.246 | 1.000 | 23.15 |
| ATOM | 527 | C   | THR | A | 83 | -10.302 | 22.753 | 23.586 | 1.000 | 19.19 |
| ATOM | 528 | O   | THR | A | 83 | -9.519  | 22.101 | 22.875 | 1.000 | 18.99 |
| ATOM | 529 | N   | ARG | A | 84 | -10.239 | 22.638 | 24.919 | 1.000 | 15.87 |
| ATOM | 530 | CA  | ARG | A | 84 | -9.214  | 21.790 | 25.521 | 1.000 | 13.38 |
| ATOM | 531 | CB  | ARG | A | 84 | -9.125  | 22.053 | 27.033 | 1.000 | 17.35 |
| ATOM | 532 | CG  | ARG | A | 84 | -10.272 | 21.451 | 27.842 | 1.000 | 15.57 |
| ATOM | 533 | CD  | ARG | A | 84 | -10.161 | 21.906 | 29.303 | 1.000 | 23.22 |
| ATOM | 534 | NE  | ARG | A | 84 | -11.142 | 21.257 | 30.168 | 1.000 | 23.41 |
| ATOM | 535 | CZ  | ARG | A | 84 | -10.962 | 20.204 | 30.948 | 1.000 | 20.47 |
| ATOM | 536 | NH1 | ARG | A | 84 | -9.809  | 19.561 | 31.054 | 1.000 | 19.35 |
| ATOM | 537 | NH2 | ARG | A | 84 | -11.994 | 19.773 | 31.664 | 1.000 | 22.12 |
| ATOM | 538 | C   | ARG | A | 84 | -9.470  | 20.299 | 25.308 | 1.000 | 18.88 |
| ATOM | 539 | O   | ARG | A | 84 | -10.635 | 19.874 | 25.268 | 1.000 | 22.06 |
| ATOM | 540 | N   | VAL | A | 85 | -8.375  | 19.551 | 25.196 | 1.000 | 16.89 |
| ATOM | 541 | CA  | VAL | A | 85 | -8.423  | 18.097 | 25.114 | 1.000 | 16.58 |
| ATOM | 542 | CB  | VAL | A | 85 | -7.184  | 17.483 | 24.455 | 1.000 | 22.94 |
| ATOM | 543 | CG1 | VAL | A | 85 | -7.356  | 15.966 | 24.274 | 1.000 | 23.40 |
| ATOM | 544 | CG2 | VAL | A | 85 | -6.893  | 18.086 | 23.091 | 1.000 | 17.65 |
| ATOM | 545 | C   | VAL | A | 85 | -8.595  | 17.535 | 26.523 | 1.000 | 19.64 |
| ATOM | 546 | O   | VAL | A | 85 | -7.844  | 17.914 | 27.424 | 1.000 | 19.96 |
| ATOM | 547 | N   | LYS | A | 86 | -9.550  | 16.650 | 26.756 | 1.000 | 17.33 |
| ATOM | 548 | CA  | LYS | A | 86 | -9.719  | 16.095 | 28.096 | 1.000 | 23.43 |
| ATOM | 549 | CB  | LYS | A | 86 | -11.191 | 16.082 | 28.526 | 1.000 | 27.56 |
| ATOM | 550 | CG  | LYS | A | 86 | -11.884 | 17.432 | 28.490 | 1.000 | 32.74 |
| ATOM | 551 | CD  | LYS | A | 86 | -13.319 | 17.288 | 28.987 | 1.000 | 42.78 |
| ATOM | 552 | CE  | LYS | A | 86 | -14.275 | 18.120 | 28.145 | 1.000 | 53.05 |
| ATOM | 553 | NZ  | LYS | A | 86 | -14.205 | 19.569 | 28.476 | 1.000 | 47.90 |
| ATOM | 554 | C   | LYS | A | 86 | -9.213  | 14.660 | 28.171 | 1.000 | 23.69 |
| ATOM | 555 | O   | LYS | A | 86 | -9.417  | 13.887 | 27.241 | 1.000 | 24.18 |
| ATOM | 556 | N   | LEU | A | 87 | -8.580  | 14.294 | 29.273 | 1.000 | 21.05 |
| ATOM | 557 | CA  | LEU | A | 87 | -8.225  | 12.906 | 29.504 | 1.000 | 18.28 |
| ATOM | 558 | CB  | LEU | A | 87 | -7.106  | 12.861 | 30.540 | 1.000 | 19.01 |
| ATOM | 559 | CG  | LEU | A | 87 | -5.824  | 13.608 | 30.146 | 1.000 | 24.48 |
| ATOM | 560 | CD1 | LEU | A | 87 | -4.865  | 13.612 | 31.326 | 1.000 | 21.86 |
| ATOM | 561 | CD2 | LEU | A | 87 | -5.175  | 12.994 | 28.916 | 1.000 | 21.83 |
| ATOM | 562 | C   | LEU | A | 87 | -9.433  | 12.132 | 30.001 | 1.000 | 30.80 |
| ATOM | 563 | O   | LEU | A | 87 | -10.293 | 12.739 | 30.652 | 1.000 | 27.84 |
| ATOM | 564 | N   | SER | A | 88 | -9.561  | 10.832 | 29.745 | 1.000 | 25.76 |
| ATOM | 565 | CA  | SER | A | 88 | -10.662 | 10.132 | 30.429 | 1.000 | 30.68 |
| ATOM | 566 | CB  | SER | A | 88 | -10.751 | 8.668  | 29.990 | 1.000 | 25.39 |
| ATOM | 567 | OG  | SER | A | 88 | -9.581  | 7.992  | 30.416 | 1.000 | 28.79 |
| ATOM | 568 | C   | SER | A | 88 | -10.554 | 10.163 | 31.955 | 1.000 | 34.04 |
| ATOM | 569 | O   | SER | A | 88 | -9.497  | 10.278 | 32.577 | 1.000 | 30.33 |
| ATOM | 570 | N   | ASN | A | 89 | -11.728 | 10.055 | 32.566 | 1.000 | 43.34 |
| ATOM | 571 | CA  | ASN | A | 89 | -11.976 | 10.144 | 33.991 | 1.000 | 56.50 |

FIGURE 212

| | | | | | | | | | |
|---|---|---|---|---|---|---|---|---|---|
| ATOM | 572 | CB | ASN | A | 89 | -13.369 | 9.595 | 34.329 | 1.000 60.50 |
| ATOM | 573 | CG | ASN | A | 89 | -13.557 | 8.127 | 34.024 | 1.000 66.77 |
| ATOM | 574 | OD1 | ASN | A | 89 | -12.606 | 7.351 | 33.952 | 1.000 60.44 |
| ATOM | 575 | ND2 | ASN | A | 89 | -14.807 | 7.703 | 33.844 | 1.000 70.97 |
| ATOM | 576 | C | ASN | A | 89 | -10.926 | 9.410 | 34.821 | 1.000 65.63 |
| ATOM | 577 | O | ASN | A | 89 | -10.996 | 9.390 | 36.052 | 1.000 72.13 |
| ATOM | 578 | N | SER | A | 96 | -8.513 | 15.291 | 37.171 | 1.000 39.19 |
| ATOM | 579 | CA | SER | A | 96 | -7.743 | 14.211 | 36.560 | 1.000 29.84 |
| ATOM | 580 | CB | SER | A | 96 | -8.043 | 12.853 | 37.183 | 1.000 29.33 |
| ATOM | 581 | OG | SER | A | 96 | -9.336 | 12.376 | 36.866 | 1.000 31.86 |
| ATOM | 582 | C | SER | A | 96 | -7.971 | 14.200 | 35.049 | 1.000 25.03 |
| ATOM | 583 | O | SER | A | 96 | -7.285 | 13.420 | 34.378 | 1.000 30.76 |
| ATOM | 584 | N | ASP | A | 97 | -8.874 | 15.033 | 34.527 | 1.000 26.35 |
| ATOM | 585 | CA | ASP | A | 97 | -9.072 | 15.047 | 33.069 | 1.000 23.38 |
| ATOM | 586 | CB | ASP | A | 97 | -10.495 | 15.418 | 32.661 | 1.000 21.60 |
| ATOM | 587 | CG | ASP | A | 97 | -10.928 | 16.834 | 32.933 | 1.000 26.73 |
| ATOM | 588 | OD1 | ASP | A | 97 | -10.115 | 17.686 | 33.354 | 1.000 26.07 |
| ATOM | 589 | OD2 | ASP | A | 97 | -12.136 | 17.107 | 32.701 | 1.000 29.59 |
| ATOM | 590 | C | ASP | A | 97 | -8.112 | 16.015 | 32.379 | 1.000 28.59 |
| ATOM | 591 | O | ASP | A | 97 | -8.144 | 16.087 | 31.149 | 1.000 22.81 |
| ATOM | 592 | N | TYR | A | 98 | -7.316 | 16.753 | 33.150 | 1.000 24.51 |
| ATOM | 593 | CA | TYR | A | 98 | -6.573 | 17.864 | 32.576 | 1.000 18.45 |
| ATOM | 594 | CB | TYR | A | 98 | -6.287 | 18.947 | 33.663 | 1.000 21.47 |
| ATOM | 595 | CG | TYR | A | 98 | -5.566 | 20.114 | 33.013 | 1.000 18.45 |
| ATOM | 596 | CD1 | TYR | A | 98 | -6.288 | 21.015 | 32.223 | 1.000 20.80 |
| ATOM | 597 | CE1 | TYR | A | 98 | -5.651 | 22.093 | 31.617 | 1.000 19.85 |
| ATOM | 598 | CZ | TYR | A | 98 | -4.300 | 22.277 | 31.775 | 1.000 20.41 |
| ATOM | 599 | OH | TYR | A | 98 | -3.617 | 23.313 | 31.194 | 1.000 18.24 |
| ATOM | 600 | CE2 | TYR | A | 98 | -3.554 | 21.399 | 32.546 | 1.000 19.23 |
| ATOM | 601 | CD2 | TYR | A | 98 | -4.206 | 20.342 | 33.147 | 1.000 19.12 |
| ATOM | 602 | C | TYR | A | 98 | -5.263 | 17.498 | 31.918 | 1.000 19.64 |
| ATOM | 603 | O | TYR | A | 98 | -4.369 | 16.840 | 32.439 | 1.000 20.66 |
| ATOM | 604 | N | ILE | A | 99 | -5.119 | 18.053 | 30.711 | 1.000 16.91 |
| ATOM | 605 | CA | ILE | A | 99 | -3.822 | 18.176 | 30.062 | 1.000 16.84 |
| ATOM | 606 | CB | ILE | A | 99 | -3.536 | 17.002 | 29.113 | 1.000 17.82 |
| ATOM | 607 | CG1 | ILE | A | 99 | -2.137 | 16.977 | 28.518 | 1.000 15.01 |
| ATOM | 608 | CD1 | ILE | A | 99 | -1.789 | 15.688 | 27.785 | 1.000 15.78 |
| ATOM | 609 | CG2 | ILE | A | 99 | -4.615 | 16.953 | 28.023 | 1.000 17.57 |
| ATOM | 610 | C | ILE | A | 99 | -3.766 | 19.520 | 29.325 | 1.000 15.16 |
| ATOM | 611 | O | ILE | A | 99 | -4.767 | 20.020 | 28.812 | 1.000 17.38 |
| ATOM | 612 | N | ASN | A | 100 | -2.587 | 20.120 | 29.308 | 1.000 17.52 |
| ATOM | 613 | CA | ASN | A | 100 | -2.392 | 21.383 | 28.584 | 1.000 13.18 |
| ATOM | 614 | CB | ASN | A | 100 | -1.125 | 22.085 | 29.028 | 1.000 14.04 |
| ATOM | 615 | CG | ASN | A | 100 | -1.059 | 23.494 | 28.450 | 1.000 15.18 |
| ATOM | 616 | OD1 | ASN | A | 100 | -1.331 | 23.713 | 27.280 | 1.000 18.72 |
| ATOM | 617 | ND2 | ASN | A | 100 | -0.702 | 24.455 | 29.274 | 1.000 16.16 |
| ATOM | 618 | C | ASN | A | 100 | -2.333 | 21.054 | 27.090 | 1.000 12.55 |
| ATOM | 619 | O | ASN | A | 100 | -1.244 | 20.809 | 26.544 | 1.000 15.92 |
| ATOM | 620 | N | ALA | A | 101 | -3.521 | 21.008 | 26.492 | 1.000 15.34 |
| ATOM | 621 | CA | ALA | A | 101 | -3.655 | 20.605 | 25.088 | 1.000 18.55 |
| ATOM | 622 | CB | ALA | A | 101 | -3.556 | 19.090 | 24.924 | 1.000 16.55 |
| ATOM | 623 | C | ALA | A | 101 | -4.971 | 21.137 | 24.527 | 1.000 13.59 |

FIGURE 213

| | | | | | | | | |
|---|---|---|---|---|---|---|---|---|
| ATOM | 624 | O | ALA | A | 101 | -5.924 | 21.365 | 25.274 1.000 16.49 |
| ATOM | 625 | N | SER | A | 102 | -5.001 | 21.341 | 23.211 1.000 13.49 |
| ATOM | 626 | CA | SER | A | 102 | -6.108 | 21.993 | 22.553 1.000 16.27 |
| ATOM | 627 | CB | SER | A | 102 | -5.855 | 23.491 | 22.338 1.000 21.21 |
| ATOM | 628 | OG | SER | A | 102 | -5.352 | 24.131 | 23.503 1.000 17.32 |
| ATOM | 629 | C | SER | A | 102 | -6.356 | 21.367 | 21.169 1.000 14.55 |
| ATOM | 630 | O | SER | A | 102 | -5.410 | 21.018 | 20.464 1.000 15.20 |
| ATOM | 631 | N | TYR | A | 103 | -7.636 | 21.254 | 20.835 1.000 16.64 |
| ATOM | 632 | CA | TYR | A | 103 | -8.048 | 20.802 | 19.512 1.000 14.77 |
| ATOM | 633 | CB | TYR | A | 103 | -9.467 | 20.239 | 19.531 1.000 18.66 |
| ATOM | 634 | CG | TYR | A | 103 | -9.703 | 18.944 | 20.270 1.000 18.68 |
| ATOM | 635 | CD1 | TYR | A | 103 | -9.140 | 17.745 | 19.852 1.000 16.61 |
| ATOM | 636 | CE1 | TYR | A | 103 | -9.358 | 16.546 | 20.528 1.000 17.11 |
| ATOM | 637 | CZ | TYR | A | 103 | -10.159 | 16.548 | 21.648 1.000 20.45 |
| ATOM | 638 | OH | TYR | A | 103 | -10.386 | 15.378 | 22.329 1.000 23.33 |
| ATOM | 639 | CE2 | TYR | A | 103 | -10.730 | 17.732 | 22.079 1.000 22.73 |
| ATOM | 640 | CD2 | TYR | A | 103 | -10.517 | 18.922 | 21.410 1.000 19.22 |
| ATOM | 641 | C | TYR | A | 103 | -7.987 | 21.941 | 18.505 1.000 13.95 |
| ATOM | 642 | O | TYR | A | 103 | -8.391 | 23.073 | 18.745 1.000 19.80 |
| ATOM | 643 | N | ILE | A | 104 | -7.482 | 21.618 | 17.316 1.000 18.42 |
| ATOM | 644 | CA | ILE | A | 104 | -7.360 | 22.569 | 16.229 1.000 18.12 |
| ATOM | 645 | CB | ILE | A | 104 | -5.872 | 22.884 | 15.979 1.000 23.14 |
| ATOM | 646 | CG1 | ILE | A | 104 | -5.070 | 23.233 | 17.226 1.000 28.92 |
| ATOM | 647 | CD1 | ILE | A | 104 | -5.524 | 24.493 | 17.940 1.000 29.26 |
| ATOM | 648 | CG2 | ILE | A | 104 | -5.741 | 24.005 | 14.967 1.000 26.42 |
| ATOM | 649 | C | ILE | A | 104 | -7.946 | 22.001 | 14.952 1.000 23.75 |
| ATOM | 650 | O | ILE | A | 104 | -7.672 | 20.852 | 14.601 1.000 21.79 |
| ATOM | 651 | N | PRO | A | 105 | -8.754 | 22.779 | 14.241 1.000 28.20 |
| ATOM | 652 | CA | PRO | A | 105 | -9.258 | 22.365 | 12.917 1.000 23.95 |
| ATOM | 653 | CB | PRO | A | 105 | -10.391 | 23.355 | 12.645 1.000 31.38 |
| ATOM | 654 | CG | PRO | A | 105 | -10.630 | 24.049 | 13.941 1.000 40.77 |
| ATOM | 655 | CD | PRO | A | 105 | -9.285 | 24.093 | 14.643 1.000 28.64 |
| ATOM | 656 | C | PRO | A | 105 | -8.174 | 22.464 | 11.860 1.000 28.29 |
| ATOM | 657 | O | PRO | A | 105 | -7.183 | 23.199 | 11.926 1.000 24.10 |
| ATOM | 658 | N | GLY | A | 106 | -8.320 | 21.674 | 10.798 1.000 25.13 |
| ATOM | 659 | CA | GLY | A | 106 | -7.343 | 21.757 | 9.710 1.000 22.26 |
| ATOM | 660 | C | GLY | A | 106 | -8.127 | 21.803 | 8.403 1.000 28.91 |
| ATOM | 661 | O | GLY | A | 106 | -9.318 | 22.118 | 8.467 1.000 26.90 |
| ATOM | 662 | N | ASN | A | 107 | -7.481 | 21.487 | 7.285 1.000 25.90 |
| ATOM | 663 | CA | ASN | A | 107 | -8.184 | 21.653 | 6.010 1.000 35.70 |
| ATOM | 664 | CB | ASN | A | 107 | -7.264 | 21.551 | 4.794 1.000 32.05 |
| ATOM | 665 | CG | ASN | A | 107 | -6.326 | 22.729 | 4.615 1.000 27.43 |
| ATOM | 666 | OD1 | ASN | A | 107 | -5.615 | 22.864 | 3.606 1.000 22.24 |
| ATOM | 667 | ND2 | ASN | A | 107 | -6.328 | 23.567 | 5.634 1.000 26.27 |
| ATOM | 668 | C | ASN | A | 107 | -9.273 | 20.581 | 5.877 1.000 38.65 |
| ATOM | 669 | O | ASN | A | 107 | -10.274 | 20.887 | 5.236 1.000 46.02 |
| ATOM | 670 | N | ASN | A | 108 | -9.002 | 19.431 | 6.465 1.000 30.37 |
| ATOM | 671 | CA | ASN | A | 108 | -9.700 | 18.170 | 6.282 1.000 36.09 |
| ATOM | 672 | CB | ASN | A | 108 | -8.676 | 17.017 | 6.195 1.000 40.88 |
| ATOM | 673 | CG | ASN | A | 108 | -7.647 | 17.276 | 5.099 1.000 44.34 |
| ATOM | 674 | OD1 | ASN | A | 108 | -7.988 | 17.259 | 3.914 1.000 26.73 |
| ATOM | 675 | ND2 | ASN | A | 108 | -6.392 | 17.525 | 5.466 1.000 23.01 |

FIGURE 214

| ATOM | 676 | C | ASN A 108 | -10.712 | 17.862 | 7.369 | 1.000 | 27.84 |
|---|---|---|---|---|---|---|---|---|
| ATOM | 677 | O | ASN A 108 | -11.746 | 17.240 | 7.087 | 1.000 | 45.47 |
| ATOM | 678 | N | PHE A 109 | -10.515 | 18.262 | 8.614 | 1.000 | 28.68 |
| ATOM | 679 | CA | PHE A 109 | -11.601 | 17.986 | 9.569 | 1.000 | 29.14 |
| ATOM | 680 | CB | PHE A 109 | -11.727 | 16.503 | 9.837 | 1.000 | 33.67 |
| ATOM | 681 | CG | PHE A 109 | -10.501 | 15.678 | 10.128 | 1.000 | 32.21 |
| ATOM | 682 | CD1 | PHE A 109 | -9.720 | 15.199 | 9.088 | 1.000 | 36.73 |
| ATOM | 683 | CE1 | PHE A 109 | -8.604 | 14.419 | 9.325 | 1.000 | 33.86 |
| ATOM | 684 | CZ | PHE A 109 | -8.275 | 14.120 | 10.633 | 1.000 | 42.76 |
| ATOM | 685 | CE2 | PHE A 109 | -9.036 | 14.590 | 11.683 | 1.000 | 37.98 |
| ATOM | 686 | CD2 | PHE A 109 | -10.143 | 15.376 | 11.430 | 1.000 | 37.01 |
| ATOM | 687 | C | PHE A 109 | -11.450 | 18.785 | 10.856 | 1.000 | 28.59 |
| ATOM | 688 | O | PHE A 109 | -10.493 | 19.529 | 11.101 | 1.000 | 25.57 |
| ATOM | 689 | N | ARG A 110 | -12.457 | 18.692 | 11.728 | 1.000 | 29.57 |
| ATOM | 690 | CA | ARG A 110 | -12.560 | 19.633 | 12.835 | 1.000 | 29.56 |
| ATOM | 691 | CB | ARG A 110 | -13.912 | 19.447 | 13.560 | 1.000 | 39.08 |
| ATOM | 692 | CG | ARG A 110 | -15.115 | 19.581 | 12.647 | 1.000 | 51.99 |
| ATOM | 693 | CD | ARG A 110 | -15.714 | 20.978 | 12.671 | 1.000 | 60.61 |
| ATOM | 694 | NE | ARG A 110 | -16.438 | 21.295 | 11.439 | 1.000 | 56.28 |
| ATOM | 695 | CZ | ARG A 110 | -17.049 | 22.446 | 11.187 | 1.000 | 59.30 |
| ATOM | 696 | NH1 | ARG A 110 | -17.685 | 22.657 | 10.040 | 1.000 | 45.23 |
| ATOM | 697 | NH2 | ARG A 110 | -17.032 | 23.413 | 12.100 | 1.000 | 84.92 |
| ATOM | 698 | C | ARG A 110 | -11.462 | 19.550 | 13.898 | 1.000 | 32.92 |
| ATOM | 699 | O | ARG A 110 | -10.952 | 20.588 | 14.359 | 1.000 | 36.08 |
| ATOM | 700 | N | ARG A 111 | -11.163 | 18.325 | 14.281 | 1.000 | 28.03 |
| ATOM | 701 | CA | ARG A 111 | -10.152 | 17.978 | 15.275 | 1.000 | 26.59 |
| ATOM | 702 | CB | ARG A 111 | -10.714 | 17.032 | 16.339 | 1.000 | 33.75 |
| ATOM | 703 | CG | ARG A 111 | -11.497 | 17.792 | 17.422 | 1.000 | 39.79 |
| ATOM | 704 | CD | ARG A 111 | -12.543 | 16.891 | 18.038 | 1.000 | 40.61 |
| ATOM | 705 | NE | ARG A 111 | -13.133 | 17.383 | 19.283 | 1.000 | 34.63 |
| ATOM | 706 | CZ | ARG A 111 | -13.380 | 16.499 | 20.268 | 1.000 | 44.09 |
| ATOM | 707 | NH1 | ARG A 111 | -13.087 | 15.209 | 20.117 | 1.000 | 40.26 |
| ATOM | 708 | NH2 | ARG A 111 | -13.915 | 16.924 | 21.402 | 1.000 | 48.99 |
| ATOM | 709 | C | ARG A 111 | -8.977 | 17.326 | 14.564 | 1.000 | 26.23 |
| ATOM | 710 | O | ARG A 111 | -8.583 | 16.195 | 14.813 | 1.000 | 22.76 |
| ATOM | 711 | N | GLU A 112 | -8.437 | 18.086 | 13.603 | 1.000 | 18.42 |
| ATOM | 712 | CA | GLU A 112 | -7.400 | 17.493 | 12.752 | 1.000 | 19.07 |
| ATOM | 713 | CB | GLU A 112 | -7.339 | 18.364 | 11.470 | 1.000 | 13.71 |
| ATOM | 714 | CG | GLU A 112 | -6.317 | 17.831 | 10.484 | 1.000 | 14.61 |
| ATOM | 715 | CD | GLU A 112 | -6.654 | 18.208 | 9.049 | 1.000 | 20.17 |
| ATOM | 716 | OE1 | GLU A 112 | -7.701 | 18.836 | 8.814 | 1.000 | 23.80 |
| ATOM | 717 | OE2 | GLU A 112 | -5.819 | 17.872 | 8.184 | 1.000 | 20.53 |
| ATOM | 718 | C | GLU A 112 | -6.059 | 17.425 | 13.457 | 1.000 | 13.05 |
| ATOM | 719 | O | GLU A 112 | -5.177 | 16.583 | 13.179 | 1.000 | 16.04 |
| ATOM | 720 | N | TYR A 113 | -5.888 | 18.365 | 14.392 | 1.000 | 14.44 |
| ATOM | 721 | CA | TYR A 113 | -4.660 | 18.455 | 15.170 | 1.000 | 14.56 |
| ATOM | 722 | CB | TYR A 113 | -3.783 | 19.667 | 14.843 | 1.000 | 13.32 |
| ATOM | 723 | CG | TYR A 113 | -3.500 | 19.908 | 13.376 | 1.000 | 17.76 |
| ATOM | 724 | CD1 | TYR A 113 | -2.393 | 19.395 | 12.721 | 1.000 | 18.07 |
| ATOM | 725 | CE1 | TYR A 113 | -2.151 | 19.630 | 11.364 | 1.000 | 14.90 |
| ATOM | 726 | CZ | TYR A 113 | -3.049 | 20.406 | 10.658 | 1.000 | 18.66 |
| ATOM | 727 | OH | TYR A 113 | -2.860 | 20.666 | 9.306 | 1.000 | 17.72 |

FIGURE 215

```
ATOM    728  CE2 TYR A 113      -4.162  20.925  11.293 1.000 20.77
ATOM    729  CD2 TYR A 113      -4.392  20.683  12.633 1.000 15.75
ATOM    730  C   TYR A 113      -4.980  18.563  16.668 1.000 15.81
ATOM    731  O   TYR A 113      -5.993  19.136  17.046 1.000 16.02
ATOM    732  N   ILE A 114      -4.051  18.047  17.461 1.000 12.86
ATOM    733  CA  ILE A 114      -4.004  18.364  18.882 1.000 12.93
ATOM    734  CB  ILE A 114      -4.060  17.088  19.740 1.000 17.81
ATOM    735  CG1 ILE A 114      -5.461  16.478  19.730 1.000 20.46
ATOM    736  CD1 ILE A 114      -5.604  15.068  20.250 1.000 18.86
ATOM    737  CG2 ILE A 114      -3.565  17.380  21.156 1.000 18.53
ATOM    738  C   ILE A 114      -2.712  19.118  19.104 1.000 14.86
ATOM    739  O   ILE A 114      -1.650  18.594  18.750 1.000 17.75
ATOM    740  N   VAL A 115      -2.797  20.311  19.631 1.000 16.67
ATOM    741  CA  VAL A 115      -1.600  21.072  19.972 1.000 13.98
ATOM    742  CB  VAL A 115      -1.749  22.543  19.584 1.000 14.73
ATOM    743  CG1 VAL A 115      -0.680  23.353  20.303 1.000 27.44
ATOM    744  CG2 VAL A 115      -1.659  22.643  18.059 1.000 22.61
ATOM    745  C   VAL A 115      -1.360  20.975  21.472 1.000 13.84
ATOM    746  O   VAL A 115      -2.303  21.113  22.246 1.000 17.38
ATOM    747  N   THR A 116      -0.116  20.748  21.863 1.000 13.55
ATOM    748  CA  THR A 116       0.108  20.593  23.304 1.000 17.85
ATOM    749  CB  THR A 116      -0.042  19.101  23.682 1.000 16.90
ATOM    750  OG1 THR A 116      -0.019  18.974  25.104 1.000 16.67
ATOM    751  CG2 THR A 116       1.092  18.252  23.118 1.000 18.44
ATOM    752  C   THR A 116       1.462  21.186  23.681 1.000 14.01
ATOM    753  O   THR A 116       2.258  21.452  22.775 1.000 13.95
ATOM    754  N   GLN A 117       1.702  21.380  24.961 1.000 15.16
ATOM    755  CA  GLN A 117       3.032  21.825  25.403 1.000 20.32
ATOM    756  CB  GLN A 117       2.866  22.383  26.829 1.000 17.18
ATOM    757  CG  GLN A 117       2.751  21.245  27.841 1.000 23.10
ATOM    758  CD  GLN A 117       2.459  21.700  29.254 1.000 22.85
ATOM    759  OE1 GLN A 117       2.255  22.879  29.560 1.000 19.09
ATOM    760  NE2 GLN A 117       2.428  20.740  30.181 1.000 25.28
ATOM    761  C   GLN A 117       4.051  20.714  25.344 1.000 22.35
ATOM    762  O   GLN A 117       3.743  19.524  25.186 1.000 21.90
ATOM    763  N   GLY A 118       5.348  20.995  25.467 1.000 20.42
ATOM    764  CA  GLY A 118       6.280  19.856  25.478 1.000 16.32
ATOM    765  C   GLY A 118       6.111  19.186  26.830 1.000 14.48
ATOM    766  O   GLY A 118       6.206  19.869  27.834 1.000 20.82
ATOM    767  N   PRO A 119       5.850  17.888  26.898 1.000 19.04
ATOM    768  CA  PRO A 119       5.598  17.210  28.158 1.000 17.15
ATOM    769  CB  PRO A 119       5.626  15.716  27.778 1.000 17.56
ATOM    770  CG  PRO A 119       5.109  15.747  26.360 1.000 16.78
ATOM    771  CD  PRO A 119       5.766  16.966  25.749 1.000 16.98
ATOM    772  C   PRO A 119       6.686  17.470  29.215 1.000 14.53
ATOM    773  O   PRO A 119       7.852  17.580  28.857 1.000 20.14
ATOM    774  N   LEU A 120       6.193  17.562  30.436 1.000 20.34
ATOM    775  CA  LEU A 120       7.014  17.632  31.639 1.000 26.17
ATOM    776  CB  LEU A 120       6.259  18.379  32.752 1.000 18.48
ATOM    777  CG  LEU A 120       6.077  19.879  32.495 1.000 23.01
ATOM    778  CD1 LEU A 120       4.937  20.427  33.332 1.000 23.31
ATOM    779  CD2 LEU A 120       7.399  20.586  32.764 1.000 24.84
```

FIGURE 216

| | | | | | | | | | |
|---|---|---|---|---|---|---|---|---|---|
| ATOM | 780 | C | LEU | A | 120 | 7.358 | 16.227 | 32.124 | 1.000 25.96 |
| ATOM | 781 | O | LEU | A | 120 | 6.667 | 15.274 | 31.750 | 1.000 21.42 |
| ATOM | 782 | N | PRO | A | 121 | 8.381 | 16.072 | 32.957 | 1.000 29.05 |
| ATOM | 783 | CA | PRO | A | 121 | 8.595 | 14.786 | 33.629 | 1.000 25.75 |
| ATOM | 784 | CB | PRO | A | 121 | 9.597 | 15.156 | 34.739 | 1.000 25.40 |
| ATOM | 785 | CG | PRO | A | 121 | 10.409 | 16.244 | 34.108 | 1.000 27.02 |
| ATOM | 786 | CD | PRO | A | 121 | 9.405 | 17.064 | 33.325 | 1.000 27.21 |
| ATOM | 787 | C | PRO | A | 121 | 7.317 | 14.251 | 34.258 | 1.000 22.30 |
| ATOM | 788 | O | PRO | A | 121 | 7.004 | 13.056 | 34.125 | 1.000 25.28 |
| ATOM | 789 | N | GLY | A | 122 | 6.557 | 15.136 | 34.914 | 1.000 18.79 |
| ATOM | 790 | CA | GLY | A | 122 | 5.347 | 14.719 | 35.583 | 1.000 16.68 |
| ATOM | 791 | C | GLY | A | 122 | 4.075 | 14.740 | 34.751 | 1.000 28.03 |
| ATOM | 792 | O | GLY | A | 122 | 3.020 | 14.526 | 35.376 | 1.000 24.04 |
| ATOM | 793 | N | THR | A | 123 | 4.110 | 14.977 | 33.436 | 1.000 20.34 |
| ATOM | 794 | CA | THR | A | 123 | 2.930 | 14.937 | 32.578 | 1.000 14.07 |
| ATOM | 795 | CB | THR | A | 123 | 2.534 | 16.297 | 31.970 | 1.000 14.80 |
| ATOM | 796 | OG1 | THR | A | 123 | 3.597 | 16.765 | 31.130 | 1.000 20.06 |
| ATOM | 797 | CG2 | THR | A | 123 | 2.290 | 17.355 | 33.043 | 1.000 21.03 |
| ATOM | 798 | C | THR | A | 123 | 3.121 | 13.982 | 31.401 | 1.000 17.25 |
| ATOM | 799 | O | THR | A | 123 | 2.189 | 13.769 | 30.625 | 1.000 19.21 |
| ATOM | 800 | N | LYS | A | 124 | 4.290 | 13.385 | 31.258 | 1.000 17.35 |
| ATOM | 801 | CA | LYS | A | 124 | 4.591 | 12.474 | 30.157 | 1.000 20.84 |
| ATOM | 802 | CB | LYS | A | 124 | 6.056 | 12.057 | 30.163 | 1.000 23.80 |
| ATOM | 803 | CG | LYS | A | 124 | 6.574 | 11.185 | 31.268 | 1.000 22.00 |
| ATOM | 804 | CD | LYS | A | 124 | 8.053 | 10.832 | 31.082 | 1.000 30.29 |
| ATOM | 805 | CE | LYS | A | 124 | 8.441 | 9.720 | 32.044 | 1.000 45.34 |
| ATOM | 806 | NZ | LYS | A | 124 | 9.868 | 9.696 | 32.452 | 1.000 41.63 |
| ATOM | 807 | C | LYS | A | 124 | 3.636 | 11.275 | 30.163 | 1.000 19.38 |
| ATOM | 808 | O | LYS | A | 124 | 3.239 | 10.855 | 29.071 | 1.000 19.48 |
| ATOM | 809 | N | ASP | A | 125 | 3.233 | 10.748 | 31.314 | 1.000 20.33 |
| ATOM | 810 | CA | ASP | A | 125 | 2.250 | 9.666 | 31.286 | 1.000 20.85 |
| ATOM | 811 | CB | ASP | A | 125 | 2.042 | 9.048 | 32.667 | 1.000 21.24 |
| ATOM | 812 | CG | ASP | A | 125 | 3.216 | 8.294 | 33.256 | 1.000 23.35 |
| ATOM | 813 | OD1 | ASP | A | 125 | 4.196 | 8.028 | 32.528 | 1.000 20.34 |
| ATOM | 814 | OD2 | ASP | A | 125 | 3.124 | 7.972 | 34.488 | 1.000 20.58 |
| ATOM | 815 | C | ASP | A | 125 | 0.903 | 10.155 | 30.758 | 1.000 18.95 |
| ATOM | 816 | O | ASP | A | 125 | 0.264 | 9.434 | 29.979 | 1.000 17.28 |
| ATOM | 817 | N | ASP | A | 126 | 0.462 | 11.327 | 31.199 | 1.000 20.58 |
| ATOM | 818 | CA | ASP | A | 126 | -0.740 | 11.974 | 30.672 | 1.000 16.25 |
| ATOM | 819 | CB | ASP | A | 126 | -0.971 | 13.331 | 31.325 | 1.000 22.07 |
| ATOM | 820 | CG | ASP | A | 126 | -1.198 | 13.393 | 32.813 | 1.000 35.20 |
| ATOM | 821 | OD1 | ASP | A | 126 | -1.760 | 12.424 | 33.363 | 1.000 28.11 |
| ATOM | 822 | OD2 | ASP | A | 126 | -0.833 | 14.421 | 33.448 | 1.000 29.77 |
| ATOM | 823 | C | ASP | A | 126 | -0.636 | 12.184 | 29.153 | 1.000 14.70 |
| ATOM | 824 | O | ASP | A | 126 | -1.589 | 11.970 | 28.403 | 1.000 17.56 |
| ATOM | 825 | N | PHE | A | 127 | 0.509 | 12.629 | 28.658 | 1.000 16.52 |
| ATOM | 826 | CA | PHE | A | 127 | 0.641 | 12.855 | 27.203 | 1.000 16.00 |
| ATOM | 827 | CB | PHE | A | 127 | 2.039 | 13.358 | 26.853 | 1.000 16.31 |
| ATOM | 828 | CG | PHE | A | 127 | 2.432 | 13.364 | 25.376 | 1.000 15.99 |
| ATOM | 829 | CD1 | PHE | A | 127 | 2.178 | 14.498 | 24.615 | 1.000 18.51 |
| ATOM | 830 | CE1 | PHE | A | 127 | 2.518 | 14.549 | 23.273 | 1.000 10.71 |
| ATOM | 831 | CZ | PHE | A | 127 | 3.108 | 13.449 | 22.681 | 1.000 15.27 |

FIGURE 217

```
ATOM    832  CE2 PHE A 127       3.382  12.289  23.403  1.000  19.04
ATOM    833  CD2 PHE A 127       3.061  12.299  24.747  1.000  16.38
ATOM    834  C   PHE A 127       0.385  11.547  26.468  1.000  22.45
ATOM    835  O   PHE A 127      -0.332  11.482  25.478  1.000  16.59
ATOM    836  N   TRP A 128       1.052  10.479  26.939  1.000  15.18
ATOM    837  CA  TRP A 128       0.896   9.221  26.182  1.000  16.47
ATOM    838  CB  TRP A 128       1.938   8.201  26.653  1.000  14.81
ATOM    839  CG  TRP A 128       3.329   8.492  26.170  1.000  17.83
ATOM    840  CD1 TRP A 128       4.444   8.788  26.892  1.000  15.04
ATOM    841  NE1 TRP A 128       5.526   8.987  26.043  1.000  16.38
ATOM    842  CE2 TRP A 128       5.110   8.818  24.749  1.000  15.72
ATOM    843  CD2 TRP A 128       3.738   8.509  24.787  1.000  15.19
ATOM    844  CE3 TRP A 128       3.062   8.282  23.587  1.000  16.34
ATOM    845  CZ3 TRP A 128       3.760   8.373  22.395  1.000  18.84
ATOM    846  CH2 TRP A 128       5.126   8.684  22.375  1.000  18.88
ATOM    847  CZ2 TRP A 128       5.797   8.906  23.544  1.000  19.59
ATOM    848  C   TRP A 128      -0.516   8.680  26.335  1.000  18.33
ATOM    849  O   TRP A 128      -1.095   8.039  25.441  1.000  17.84
ATOM    850  N   LYS A 129      -1.136   8.925  27.490  1.000  16.01
ATOM    851  CA  LYS A 129      -2.552   8.577  27.669  1.000  15.83
ATOM    852  CB  LYS A 129      -2.959   8.905  29.107  1.000  16.11
ATOM    853  CG  LYS A 129      -4.428   8.639  29.383  1.000  22.20
ATOM    854  CD  LYS A 129      -4.734   8.820  30.866  1.000  21.45
ATOM    855  CE  LYS A 129      -6.258   8.852  31.065  1.000  26.32
ATOM    856  NZ  LYS A 129      -6.584   9.011  32.510  1.000  34.60
ATOM    857  C   LYS A 129      -3.418   9.305  26.655  1.000  22.77
ATOM    858  O   LYS A 129      -4.278   8.695  26.000  1.000  18.99
ATOM    859  N   MET A 130      -3.188  10.621  26.479  1.000  15.75
ATOM    860  CA  MET A 130      -3.893  11.366  25.434  1.000  13.41
ATOM    861  CB  MET A 130      -3.416  12.840  25.476  1.000  16.79
ATOM    862  CG  MET A 130      -4.077  13.682  24.379  1.000  18.60
ATOM    863  SD  MET A 130      -3.548  15.406  24.457  1.000  18.90
ATOM    864  CE  MET A 130      -1.867  15.262  23.906  1.000  14.57
ATOM    865  C   MET A 130      -3.662  10.816  24.035  1.000  16.03
ATOM    866  O   MET A 130      -4.577  10.636  23.228  1.000  21.60
ATOM    867  N   VAL A 131      -2.421  10.513  23.688  1.000  16.52
ATOM    868  CA  VAL A 131      -2.096   9.907  22.395  1.000  17.62
ATOM    869  CB  VAL A 131      -0.576   9.659  22.293  1.000  15.16
ATOM    870  CG1 VAL A 131      -0.228   8.757  21.118  1.000  16.01
ATOM    871  CG2 VAL A 131       0.162  10.996  22.200  1.000  14.77
ATOM    872  C   VAL A 131      -2.891   8.614  22.198  1.000  14.71
ATOM    873  O   VAL A 131      -3.480   8.392  21.126  1.000  17.34
ATOM    874  N   TRP A 132      -2.952   7.787  23.223  1.000  14.88
ATOM    875  CA  TRP A 132      -3.697   6.516  23.124  1.000  22.11
ATOM    876  CB  TRP A 132      -3.433   5.620  24.339  1.000  22.48
ATOM    877  CG  TRP A 132      -4.168   4.301  24.280  1.000  27.32
ATOM    878  CD1 TRP A 132      -5.262   3.909  25.019  1.000  25.14
ATOM    879  NE1 TRP A 132      -5.611   2.623  24.645  1.000  23.87
ATOM    880  CE2 TRP A 132      -4.763   2.172  23.681  1.000  18.18
ATOM    881  CD2 TRP A 132      -3.834   3.198  23.418  1.000  18.05
ATOM    882  CE3 TRP A 132      -2.840   2.999  22.460  1.000  22.17
ATOM    883  CZ3 TRP A 132      -2.774   1.795  21.772  1.000  28.54
```

FIGURE 218

```
ATOM    884  CH2 TRP A 132      -3.721   0.806  22.066 1.000 23.87
ATOM    885  CZ2 TRP A 132      -4.696   0.966  22.993 1.000 20.35
ATOM    886  C   TRP A 132      -5.193   6.750  22.947 1.000 17.05
ATOM    887  O   TRP A 132      -5.818   6.256  21.987 1.000 20.64
ATOM    888  N   GLU A 133      -5.791   7.519  23.839 1.000 14.90
ATOM    889  CA  GLU A 133      -7.219   7.778  23.820 1.000 17.45
ATOM    890  CB  GLU A 133      -7.610   8.589  25.078 1.000 18.05
ATOM    891  CG  GLU A 133      -7.397   7.760  26.341 1.000 19.08
ATOM    892  CD  GLU A 133      -7.868   8.505  27.588 1.000 27.21
ATOM    893  OE1 GLU A 133      -8.176   9.707  27.515 1.000 24.17
ATOM    894  OE2 GLU A 133      -7.926   7.874  28.661 1.000 32.77
ATOM    895  C   GLU A 133      -7.680   8.510  22.579 1.000 20.80
ATOM    896  O   GLU A 133      -8.825   8.300  22.156 1.000 22.88
ATOM    897  N   GLN A 134      -6.829   9.358  22.026 1.000 17.73
ATOM    898  CA  GLN A 134      -7.237  10.221  20.900 1.000 16.57
ATOM    899  CB  GLN A 134      -6.549  11.579  21.008 1.000 14.29
ATOM    900  CG  GLN A 134      -6.990  12.288  22.299 1.000 16.77
ATOM    901  CD  GLN A 134      -8.452  12.650  22.274 1.000 21.52
ATOM    902  OE1 GLN A 134      -9.006  13.127  21.277 1.000 27.29
ATOM    903  NE2 GLN A 134      -9.111  12.430  23.414 1.000 22.22
ATOM    904  C   GLN A 134      -6.950   9.599  19.542 1.000 19.42
ATOM    905  O   GLN A 134      -7.196  10.269  18.542 1.000 18.38
ATOM    906  N   ASN A 135      -6.467   8.362  19.537 1.000 19.05
ATOM    907  CA  ASN A 135      -6.213   7.579  18.343 1.000 19.16
ATOM    908  CB  ASN A 135      -7.480   7.376  17.494 1.000 20.31
ATOM    909  CG  ASN A 135      -8.541   6.596  18.257 1.000 31.86
ATOM    910  OD1 ASN A 135      -8.283   5.493  18.725 1.000 33.23
ATOM    911  ND2 ASN A 135      -9.742   7.149  18.391 1.000 30.19
ATOM    912  C   ASN A 135      -5.155   8.263  17.482 1.000 17.39
ATOM    913  O   ASN A 135      -5.206   8.264  16.256 1.000 22.39
ATOM    914  N   VAL A 136      -4.196   8.866  18.167 1.000 14.13
ATOM    915  CA  VAL A 136      -3.123   9.563  17.457 1.000 16.02
ATOM    916  CB  VAL A 136      -2.417  10.541  18.433 1.000 18.99
ATOM    917  CG1 VAL A 136      -1.100  11.000  17.793 1.000 20.47
ATOM    918  CG2 VAL A 136      -3.330  11.692  18.794 1.000 13.05
ATOM    919  C   VAL A 136      -2.120   8.585  16.871 1.000 18.76
ATOM    920  O   VAL A 136      -1.653   7.669  17.563 1.000 17.38
ATOM    921  N   HIS A 137      -1.756   8.745  15.591 1.000 15.53
ATOM    922  CA  HIS A 137      -0.715   7.888  15.035 1.000 18.61
ATOM    923  CB  HIS A 137      -1.197   7.109  13.799 1.000 19.72
ATOM    924  CG  HIS A 137      -2.274   6.119  14.090 1.000 22.80
ATOM    925  ND1 HIS A 137      -3.478   6.436  14.669 1.000 26.95
ATOM    926  CE1 HIS A 137      -4.209   5.343  14.795 1.000 30.61
ATOM    927  NE2 HIS A 137      -3.516   4.331  14.319 1.000 27.83
ATOM    928  CD2 HIS A 137      -2.301   4.778  13.869 1.000 31.20
ATOM    929  C   HIS A 137       0.523   8.677  14.620 1.000 19.42
ATOM    930  O   HIS A 137       1.534   8.071  14.287 1.000 19.32
ATOM    931  N   ASN A 138       0.469  10.009  14.624 1.000 18.64
ATOM    932  CA  ASN A 138       1.609  10.809  14.197 1.000 16.59
ATOM    933  CB  ASN A 138       1.368  11.460  12.823 1.000 14.79
ATOM    934  CG  ASN A 138       1.182  10.388  11.774 1.000 14.32
ATOM    935  OD1 ASN A 138       0.070  10.154  11.277 1.000 23.35
```

FIGURE 219

| | | | | | | | | | |
|---|---|---|---|---|---|---|---|---|---|
| ATOM | 936 | ND2 | ASN | A | 138 | 2.272 | 9.719 | 11.442 | 1.000 15.72 |
| ATOM | 937 | C | ASN | A | 138 | 1.882 | 11.894 | 15.224 | 1.000 17.49 |
| ATOM | 938 | O | ASN | A | 138 | 0.923 | 12.540 | 15.639 | 1.000 16.64 |
| ATOM | 939 | N | ILE | A | 139 | 3.138 | 12.081 | 15.595 | 1.000 13.57 |
| ATOM | 940 | CA | ILE | A | 139 | 3.492 | 13.222 | 16.443 | 1.000 13.49 |
| ATOM | 941 | CB | ILE | A | 139 | 4.046 | 12.705 | 17.788 | 1.000 15.96 |
| ATOM | 942 | CG1 | ILE | A | 139 | 3.032 | 11.892 | 18.597 | 1.000 17.56 |
| ATOM | 943 | CD1 | ILE | A | 139 | 3.647 | 11.054 | 19.710 | 1.000 16.60 |
| ATOM | 944 | CG2 | ILE | A | 139 | 4.641 | 13.849 | 18.601 | 1.000 17.93 |
| ATOM | 945 | C | ILE | A | 139 | 4.545 | 14.100 | 15.776 | 1.000 16.72 |
| ATOM | 946 | O | ILE | A | 139 | 5.507 | 13.555 | 15.211 | 1.000 18.97 |
| ATOM | 947 | N | VAL | A | 140 | 4.378 | 15.416 | 15.843 | 1.000 15.29 |
| ATOM | 948 | CA | VAL | A | 140 | 5.330 | 16.361 | 15.282 | 1.000 15.83 |
| ATOM | 949 | CB | VAL | A | 140 | 4.672 | 17.254 | 14.202 | 1.000 17.91 |
| ATOM | 950 | CG1 | VAL | A | 140 | 5.691 | 18.249 | 13.647 | 1.000 18.30 |
| ATOM | 951 | CG2 | VAL | A | 140 | 4.073 | 16.418 | 13.086 | 1.000 14.97 |
| ATOM | 952 | C | VAL | A | 140 | 5.892 | 17.200 | 16.427 | 1.000 15.79 |
| ATOM | 953 | O | VAL | A | 140 | 5.144 | 17.816 | 17.200 | 1.000 16.44 |
| ATOM | 954 | N | MET | A | 141 | 7.208 | 17.203 | 16.579 | 1.000 16.25 |
| ATOM | 955 | CA | MET | A | 141 | 7.900 | 17.899 | 17.660 | 1.000 21.24 |
| ATOM | 956 | CB | MET | A | 141 | 8.745 | 16.916 | 18.480 | 1.000 18.76 |
| ATOM | 957 | CG | MET | A | 141 | 9.555 | 17.528 | 19.619 | 1.000 15.74 |
| ATOM | 958 | SD | MET | A | 141 | 10.162 | 16.187 | 20.709 | 1.000 19.42 |
| ATOM | 959 | CE | MET | A | 141 | 11.299 | 17.174 | 21.703 | 1.000 22.74 |
| ATOM | 960 | C | MET | A | 141 | 8.795 | 18.989 | 17.072 | 1.000 14.50 |
| ATOM | 961 | O | MET | A | 141 | 9.715 | 18.659 | 16.332 | 1.000 19.95 |
| ATOM | 962 | N | VAL | A | 142 | 8.551 | 20.246 | 17.347 | 1.000 18.34 |
| ATOM | 963 | CA | VAL | A | 142 | 9.296 | 21.313 | 16.698 | 1.000 19.48 |
| ATOM | 964 | CB | VAL | A | 142 | 8.396 | 22.310 | 15.933 | 1.000 22.88 |
| ATOM | 965 | CG1 | VAL | A | 142 | 9.226 | 22.965 | 14.836 | 1.000 28.48 |
| ATOM | 966 | CG2 | VAL | A | 142 | 7.180 | 21.668 | 15.294 | 1.000 30.53 |
| ATOM | 967 | C | VAL | A | 142 | 10.112 | 22.075 | 17.732 | 1.000 23.04 |
| ATOM | 968 | O | VAL | A | 142 | 9.990 | 23.280 | 17.923 | 1.000 23.56 |
| ATOM | 969 | N | THR | A | 143 | 10.952 | 21.298 | 18.417 | 1.000 29.09 |
| ATOM | 970 | CA | THR | A | 143 | 11.788 | 21.805 | 19.501 | 1.000 28.45 |
| ATOM | 971 | CB | THR | A | 143 | 10.984 | 22.204 | 20.751 | 1.000 26.09 |
| ATOM | 972 | OG1 | THR | A | 143 | 11.837 | 22.963 | 21.620 | 1.000 30.17 |
| ATOM | 973 | CG2 | THR | A | 143 | 10.487 | 21.021 | 21.586 | 1.000 17.97 |
| ATOM | 974 | C | THR | A | 143 | 12.829 | 20.744 | 19.826 | 1.000 29.90 |
| ATOM | 975 | O | THR | A | 143 | 12.598 | 19.553 | 19.664 | 1.000 23.69 |
| ATOM | 976 | N | GLN | A | 144 | 14.008 | 21.163 | 20.257 | 1.000 35.84 |
| ATOM | 977 | CA | GLN | A | 144 | 14.993 | 20.221 | 20.781 | 1.000 28.60 |
| ATOM | 978 | CB | GLN | A | 144 | 16.415 | 20.692 | 20.494 | 1.000 27.98 |
| ATOM | 979 | CG | GLN | A | 144 | 16.871 | 20.426 | 19.061 | 1.000 31.33 |
| ATOM | 980 | CD | GLN | A | 144 | 18.293 | 20.929 | 18.844 | 1.000 44.78 |
| ATOM | 981 | OE1 | GLN | A | 144 | 19.270 | 20.199 | 19.004 | 1.000 50.77 |
| ATOM | 982 | NE2 | GLN | A | 144 | 18.424 | 22.197 | 18.474 | 1.000 34.02 |
| ATOM | 983 | C | GLN | A | 144 | 14.724 | 20.124 | 22.271 | 1.000 28.09 |
| ATOM | 984 | O | GLN | A | 144 | 14.141 | 21.024 | 22.878 | 1.000 24.45 |
| ATOM | 985 | N | CYS | A | 145 | 15.115 | 19.032 | 22.927 | 1.000 30.90 |
| ATOM | 986 | CA | CYS | A | 145 | 14.856 | 18.998 | 24.365 | 1.000 21.87 |
| ATOM | 987 | CB | CYS | A | 145 | 15.313 | 17.631 | 24.897 | 1.000 20.92 |

FIGURE 220

| ATOM | 988 | SG | CYS | A | 145 | 14.184 | 16.278 | 24.463 | 1.000 | 30.08 |
|------|------|-----|-----|---|-----|--------|--------|--------|-------|-------|
| ATOM | 989 | C | CYS | A | 145 | 15.601 | 20.109 | 25.083 | 1.000 | 26.27 |
| ATOM | 990 | O | CYS | A | 145 | 15.152 | 20.691 | 26.056 | 1.000 | 25.34 |
| ATOM | 991 | N | VAL | A | 146 | 16.795 | 20.375 | 24.555 | 1.000 | 27.66 |
| ATOM | 992 | CA | VAL | A | 146 | 17.696 | 21.367 | 25.097 | 1.000 | 30.29 |
| ATOM | 993 | CB | VAL | A | 146 | 18.963 | 20.721 | 25.711 | 1.000 | 36.55 |
| ATOM | 994 | CG1 | VAL | A | 146 | 19.918 | 21.827 | 26.139 | 1.000 | 34.60 |
| ATOM | 995 | CG2 | VAL | A | 146 | 18.601 | 19.795 | 26.859 | 1.000 | 44.23 |
| ATOM | 996 | C | VAL | A | 146 | 18.213 | 22.307 | 24.014 | 1.000 | 28.45 |
| ATOM | 997 | O | VAL | A | 146 | 18.841 | 21.790 | 23.076 | 1.000 | 40.86 |
| ATOM | 998 | N | GLU | A | 147 | 17.971 | 23.586 | 24.167 | 1.000 | 28.57 |
| ATOM | 999 | CA | GLU | A | 147 | 18.452 | 24.625 | 23.258 | 1.000 | 37.00 |
| ATOM | 1000 | CB | GLU | A | 147 | 17.283 | 25.228 | 22.467 | 1.000 | 37.35 |
| ATOM | 1001 | CG | GLU | A | 147 | 16.357 | 24.218 | 21.821 | 1.000 | 32.42 |
| ATOM | 1002 | CD | GLU | A | 147 | 15.173 | 24.836 | 21.097 | 1.000 | 36.64 |
| ATOM | 1003 | OE1 | GLU | A | 147 | 14.684 | 25.926 | 21.465 | 1.000 | 28.99 |
| ATOM | 1004 | OE2 | GLU | A | 147 | 14.708 | 24.197 | 20.129 | 1.000 | 29.46 |
| ATOM | 1005 | C | GLU | A | 147 | 19.191 | 25.727 | 24.028 | 1.000 | 41.02 |
| ATOM | 1006 | O | GLU | A | 147 | 18.682 | 26.143 | 25.080 | 1.000 | 35.27 |
| ATOM | 1007 | N | LYS | A | 148 | 20.338 | 26.211 | 23.559 | 1.000 | 49.35 |
| ATOM | 1008 | CA | LYS | A | 148 | 21.141 | 27.170 | 24.317 | 1.000 | 50.64 |
| ATOM | 1009 | CB | LYS | A | 148 | 20.525 | 28.547 | 24.520 | 1.000 | 54.31 |
| ATOM | 1010 | CG | LYS | A | 148 | 21.448 | 29.714 | 24.766 | 1.000 | 56.11 |
| ATOM | 1011 | CD | LYS | A | 148 | 22.091 | 29.906 | 26.107 | 1.000 | 51.55 |
| ATOM | 1012 | CE | LYS | A | 148 | 23.607 | 30.019 | 26.124 | 1.000 | 45.10 |
| ATOM | 1013 | NZ | LYS | A | 148 | 24.142 | 30.959 | 27.163 | 1.000 | 37.78 |
| ATOM | 1014 | C | LYS | A | 148 | 21.369 | 26.580 | 25.712 | 1.000 | 33.28 |
| ATOM | 1015 | O | LYS | A | 148 | 21.186 | 27.326 | 26.676 | 1.000 | 40.06 |
| ATOM | 1016 | N | GLY | A | 149 | 21.686 | 25.282 | 25.751 | 1.000 | 23.87 |
| ATOM | 1017 | CA | GLY | A | 149 | 21.915 | 24.686 | 27.061 | 1.000 | 33.16 |
| ATOM | 1018 | C | GLY | A | 149 | 20.778 | 24.925 | 28.034 | 1.000 | 34.12 |
| ATOM | 1019 | O | GLY | A | 149 | 20.966 | 24.992 | 29.241 | 1.000 | 33.20 |
| ATOM | 1020 | N | ARG | A | 150 | 19.544 | 25.082 | 27.560 | 1.000 | 43.51 |
| ATOM | 1021 | CA | ARG | A | 150 | 18.420 | 25.138 | 28.502 | 1.000 | 47.78 |
| ATOM | 1022 | CB | ARG | A | 150 | 17.913 | 26.553 | 28.703 | 1.000 | 56.08 |
| ATOM | 1023 | CG | ARG | A | 150 | 16.416 | 26.706 | 28.896 | 1.000 | 63.73 |
| ATOM | 1024 | CD | ARG | A | 150 | 16.066 | 28.176 | 29.132 | 1.000 | 69.11 |
| ATOM | 1025 | NE | ARG | A | 150 | 16.737 | 28.703 | 30.311 | 1.000 | 74.23 |
| ATOM | 1026 | CZ | ARG | A | 150 | 16.496 | 29.840 | 30.951 | 1.000 | 82.40 |
| ATOM | 1027 | NH1 | ARG | A | 150 | 15.544 | 30.672 | 30.553 | 1.000 | 94.75 |
| ATOM | 1028 | NH2 | ARG | A | 150 | 17.228 | 30.148 | 32.023 | 1.000 | 84.24 |
| ATOM | 1029 | C | ARG | A | 150 | 17.319 | 24.195 | 28.020 | 1.000 | 40.29 |
| ATOM | 1030 | O | ARG | A | 150 | 17.214 | 23.897 | 26.826 | 1.000 | 44.43 |
| ATOM | 1031 | N | VAL | A | 151 | 16.553 | 23.714 | 28.991 | 1.000 | 42.19 |
| ATOM | 1032 | CA | VAL | A | 151 | 15.612 | 22.624 | 28.731 | 1.000 | 40.59 |
| ATOM | 1033 | CB | VAL | A | 151 | 15.397 | 21.764 | 29.991 | 1.000 | 39.25 |
| ATOM | 1034 | CG1 | VAL | A | 151 | 16.743 | 21.494 | 30.643 | 1.000 | 35.31 |
| ATOM | 1035 | CG2 | VAL | A | 151 | 14.448 | 22.442 | 30.961 | 1.000 | 47.15 |
| ATOM | 1036 | C | VAL | A | 151 | 14.286 | 23.143 | 28.204 | 1.000 | 34.87 |
| ATOM | 1037 | O | VAL | A | 151 | 13.588 | 23.974 | 28.783 | 1.000 | 42.34 |
| ATOM | 1038 | N | LYS | A | 152 | 13.921 | 22.633 | 27.028 | 1.000 | 34.21 |
| ATOM | 1039 | CA | LYS | A | 152 | 12.658 | 23.089 | 26.435 | 1.000 | 32.45 |

FIGURE 221

```
ATOM   1040  CB   LYS A 152      12.936  23.469  24.983 1.000 29.05
ATOM   1041  CG   LYS A 152      13.723  24.774  24.884 1.000 40.50
ATOM   1042  CD   LYS A 152      13.161  25.824  25.832 1.000 34.61
ATOM   1043  CE   LYS A 152      12.890  27.143  25.135 1.000 41.44
ATOM   1044  NZ   LYS A 152      12.672  28.247  26.118 1.000 47.72
ATOM   1045  C    LYS A 152      11.580  22.023  26.534 1.000 32.08
ATOM   1046  O    LYS A 152      10.386  22.284  26.459 1.000 26.51
ATOM   1047  N    CYS A 153      11.986  20.771  26.708 1.000 26.76
ATOM   1048  CA   CYS A 153      11.021  19.668  26.654 1.000 25.46
ATOM   1049  CB   CYS A 153      10.682  19.380  25.189 1.000 21.77
ATOM   1050  SG   CYS A 153       9.398  18.138  24.927 1.000 22.14
ATOM   1051  C    CYS A 153      11.618  18.432  27.306 1.000 26.32
ATOM   1052  O    CYS A 153      12.824  18.201  27.158 1.000 25.23
ATOM   1053  N    ASP A 154      10.807  17.640  27.999 1.000 23.11
ATOM   1054  CA   ASP A 154      11.355  16.378  28.515 1.000 21.66
ATOM   1055  CB   ASP A 154      10.361  15.731  29.473 1.000 21.13
ATOM   1056  CG   ASP A 154      10.962  14.589  30.267 1.000 28.12
ATOM   1057  OD1  ASP A 154      11.961  14.786  30.981 1.000 33.22
ATOM   1058  OD2  ASP A 154      10.428  13.470  30.165 1.000 29.23
ATOM   1059  C    ASP A 154      11.654  15.413  27.380 1.000 25.41
ATOM   1060  O    ASP A 154      10.996  15.507  26.341 1.000 20.63
ATOM   1061  N    HIS A 155      12.599  14.484  27.555 1.000 22.40
ATOM   1062  CA   HIS A 155      12.785  13.364  26.630 1.000 23.74
ATOM   1063  CB   HIS A 155      14.212  12.842  26.726 1.000 20.26
ATOM   1064  CG   HIS A 155      14.625  11.929  25.619 1.000 22.14
ATOM   1065  ND1  HIS A 155      14.138  10.655  25.468 1.000 22.08
ATOM   1066  CE1  HIS A 155      14.671  10.085  24.412 1.000 22.58
ATOM   1067  NE2  HIS A 155      15.510  10.940  23.845 1.000 19.53
ATOM   1068  CD2  HIS A 155      15.484  12.098  24.594 1.000 24.73
ATOM   1069  C    HIS A 155      11.740  12.307  26.966 1.000 21.85
ATOM   1070  O    HIS A 155      11.993  11.292  27.629 1.000 26.15
ATOM   1071  N    TYR A 156      10.500  12.546  26.561 1.000 21.24
ATOM   1072  CA   TYR A 156       9.346  11.821  27.075 1.000 18.68
ATOM   1073  CB   TYR A 156       8.041  12.643  26.958 1.000 17.87
ATOM   1074  CG   TYR A 156       7.765  13.067  25.525 1.000 18.81
ATOM   1075  CD1  TYR A 156       7.032  12.280  24.647 1.000 23.10
ATOM   1076  CE1  TYR A 156       6.778  12.662  23.333 1.000 19.51
ATOM   1077  CZ   TYR A 156       7.267  13.880  22.886 1.000 17.53
ATOM   1078  OH   TYR A 156       7.003  14.236  21.579 1.000 16.54
ATOM   1079  CE2  TYR A 156       7.997  14.689  23.725 1.000 17.15
ATOM   1080  CD2  TYR A 156       8.247  14.285  25.047 1.000 15.43
ATOM   1081  C    TYR A 156       9.152  10.478  26.379 1.000 17.16
ATOM   1082  O    TYR A 156       8.180   9.801  26.732 1.000 17.59
ATOM   1083  N    TRP A 157      10.005  10.148  25.427 1.000 20.71
ATOM   1084  CA   TRP A 157       9.956   8.852  24.736 1.000 21.44
ATOM   1085  CB   TRP A 157       9.852   9.047  23.221 1.000 17.84
ATOM   1086  CG   TRP A 157      11.092   9.674  22.655 1.000 22.69
ATOM   1087  CD1  TRP A 157      12.153   9.009  22.094 1.000 24.11
ATOM   1088  NE1  TRP A 157      13.100   9.922  21.690 1.000 23.85
ATOM   1089  CE2  TRP A 157      12.655  11.191  21.991 1.000 20.42
ATOM   1090  CD2  TRP A 157      11.390  11.072  22.597 1.000 18.79
ATOM   1091  CE3  TRP A 157      10.724  12.233  22.996 1.000 18.30
```

FIGURE 222

| ATOM | 1092 | CZ3 | TRP | A | 157 | 11.325 | 13.459 | 22.787 | 1.000 | 18.73 |
|------|------|-----|-----|---|-----|--------|--------|--------|-------|-------|
| ATOM | 1093 | CH2 | TRP | A | 157 | 12.582 | 13.548 | 22.179 | 1.000 | 19.11 |
| ATOM | 1094 | CZ2 | TRP | A | 157 | 13.254 | 12.423 | 21.783 | 1.000 | 16.74 |
| ATOM | 1095 | C   | TRP | A | 157 | 11.180 | 8.027  | 25.116 | 1.000 | 21.33 |
| ATOM | 1096 | O   | TRP | A | 157 | 12.146 | 8.606  | 25.626 | 1.000 | 22.55 |
| ATOM | 1097 | N   | PRO | A | 158 | 11.211 | 6.722  | 24.940 | 1.000 | 25.25 |
| ATOM | 1098 | CA  | PRO | A | 158 | 12.363 | 5.904  | 25.331 | 1.000 | 23.55 |
| ATOM | 1099 | CB  | PRO | A | 158 | 11.959 | 4.495  | 24.848 | 1.000 | 23.59 |
| ATOM | 1100 | CG  | PRO | A | 158 | 10.459 | 4.540  | 25.001 | 1.000 | 24.03 |
| ATOM | 1101 | CD  | PRO | A | 158 | 10.115 | 5.887  | 24.391 | 1.000 | 24.42 |
| ATOM | 1102 | C   | PRO | A | 158 | 13.675 | 6.254  | 24.671 | 1.000 | 22.71 |
| ATOM | 1103 | O   | PRO | A | 158 | 13.804 | 6.665  | 23.522 | 1.000 | 24.60 |
| ATOM | 1104 | N   | ALA | A | 159 | 14.735 | 6.052  | 25.470 | 1.000 | 25.38 |
| ATOM | 1105 | CA  | ALA | A | 159 | 16.057 | 6.433  | 24.978 | 1.000 | 26.79 |
| ATOM | 1106 | CB  | ALA | A | 159 | 16.933 | 6.787  | 26.175 | 1.000 | 30.60 |
| ATOM | 1107 | C   | ALA | A | 159 | 16.686 | 5.340  | 24.141 | 1.000 | 31.84 |
| ATOM | 1108 | O   | ALA | A | 159 | 17.702 | 5.599  | 23.481 | 1.000 | 37.52 |
| ATOM | 1109 | N   | ASP | A | 160 | 16.119 | 4.135  | 24.142 | 1.000 | 24.95 |
| ATOM | 1110 | CA  | ASP | A | 160 | 16.648 | 3.021  | 23.361 | 1.000 | 29.97 |
| ATOM | 1111 | CB  | ASP | A | 160 | 17.725 | 2.249  | 24.119 | 1.000 | 33.98 |
| ATOM | 1112 | CG  | ASP | A | 160 | 17.259 | 1.971  | 25.541 | 1.000 | 35.26 |
| ATOM | 1113 | OD1 | ASP | A | 160 | 16.102 | 1.530  | 25.682 | 1.000 | 31.88 |
| ATOM | 1114 | OD2 | ASP | A | 160 | 18.045 | 2.209  | 26.482 | 1.000 | 37.41 |
| ATOM | 1115 | C   | ASP | A | 160 | 15.522 | 2.053  | 23.016 | 1.000 | 28.09 |
| ATOM | 1116 | O   | ASP | A | 160 | 14.364 | 2.428  | 23.164 | 1.000 | 25.87 |
| ATOM | 1117 | N   | GLN | A | 161 | 15.855 | 0.834  | 22.622 | 1.000 | 24.92 |
| ATOM | 1118 | CA  | GLN | A | 161 | 14.765 | -0.040 | 22.162 | 1.000 | 23.89 |
| ATOM | 1119 | CB  | GLN | A | 161 | 15.223 | -0.925 | 20.993 | 1.000 | 30.92 |
| ATOM | 1120 | CG  | GLN | A | 161 | 15.788 | -0.089 | 19.845 | 1.000 | 45.69 |
| ATOM | 1121 | CD  | GLN | A | 161 | 15.671 | -0.678 | 18.458 | 1.000 | 48.73 |
| ATOM | 1122 | OE1 | GLN | A | 161 | 15.341 | -1.845 | 18.249 | 1.000 | 48.46 |
| ATOM | 1123 | NE2 | GLN | A | 161 | 15.952 | 0.136  | 17.441 | 1.000 | 68.57 |
| ATOM | 1124 | C   | GLN | A | 161 | 14.187 | -0.899 | 23.271 | 1.000 | 24.30 |
| ATOM | 1125 | O   | GLN | A | 161 | 13.413 | -1.806 | 22.956 | 1.000 | 25.26 |
| ATOM | 1126 | N   | ASP | A | 162 | 14.518 | -0.604 | 24.521 | 1.000 | 25.88 |
| ATOM | 1127 | CA  | ASP | A | 162 | 13.974 | -1.361 | 25.644 | 1.000 | 27.98 |
| ATOM | 1128 | CB  | ASP | A | 162 | 14.876 | -1.203 | 26.872 | 1.000 | 26.59 |
| ATOM | 1129 | CG  | ASP | A | 162 | 16.207 | -1.921 | 26.713 | 1.000 | 28.66 |
| ATOM | 1130 | OD1 | ASP | A | 162 | 16.491 | -2.448 | 25.628 | 1.000 | 31.96 |
| ATOM | 1131 | OD2 | ASP | A | 162 | 16.968 | -1.953 | 27.694 | 1.000 | 34.72 |
| ATOM | 1132 | C   | ASP | A | 162 | 12.569 | -0.891 | 25.982 | 1.000 | 26.99 |
| ATOM | 1133 | O   | ASP | A | 162 | 12.382 | 0.304  | 26.182 | 1.000 | 27.57 |
| ATOM | 1134 | N   | SER | A | 163 | 11.587 | -1.785 | 26.071 | 1.000 | 22.21 |
| ATOM | 1135 | CA  | SER | A | 163 | 10.208 | -1.323 | 26.297 | 1.000 | 18.32 |
| ATOM | 1136 | CB  | SER | A | 163 | 9.239  | -2.491 | 26.111 | 1.000 | 19.11 |
| ATOM | 1137 | OG  | SER | A | 163 | 9.616  | -3.639 | 26.863 | 1.000 | 24.74 |
| ATOM | 1138 | C   | SER | A | 163 | 10.065 | -0.701 | 27.671 | 1.000 | 19.89 |
| ATOM | 1139 | O   | SER | A | 163 | 10.822 | -1.039 | 28.596 | 1.000 | 23.48 |
| ATOM | 1140 | N   | LEU | A | 164 | 9.115  | 0.215  | 27.839 | 1.000 | 22.10 |
| ATOM | 1141 | CA  | LEU | A | 164 | 8.902  | 0.835  | 29.142 | 1.000 | 25.88 |
| ATOM | 1142 | CB  | LEU | A | 164 | 9.650  | 2.160  | 29.279 | 1.000 | 23.32 |
| ATOM | 1143 | CG  | LEU | A | 164 | 11.081 | 2.263  | 29.771 | 1.000 | 32.69 |

FIGURE 223

| | | | | | | | | | |
|---|---|---|---|---|---|---|---|---|---|
| ATOM | 1144 | CD1 | LEU | A | 164 | 11.536 | 3.726 | 29.711 | 1.000 28.59 |
| ATOM | 1145 | CD2 | LEU | A | 164 | 11.280 | 1.731 | 31.183 | 1.000 31.11 |
| ATOM | 1146 | C | LEU | A | 164 | 7.421 | 1.126 | 29.396 | 1.000 27.10 |
| ATOM | 1147 | O | LEU | A | 164 | 6.712 | 1.554 | 28.476 | 1.000 18.26 |
| ATOM | 1148 | N | TYR | A | 165 | 6.948 | 0.930 | 30.633 | 1.000 16.81 |
| ATOM | 1149 | CA | TYR | A | 165 | 5.610 | 1.374 | 30.989 | 1.000 15.66 |
| ATOM | 1150 | CB | TYR | A | 165 | 5.152 | 0.803 | 32.324 | 1.000 17.16 |
| ATOM | 1151 | CG | TYR | A | 165 | 4.704 | -0.642 | 32.238 | 1.000 22.22 |
| ATOM | 1152 | CD1 | TYR | A | 165 | 3.479 | -0.947 | 31.670 | 1.000 22.09 |
| ATOM | 1153 | CE1 | TYR | A | 165 | 3.008 | -2.244 | 31.568 | 1.000 21.78 |
| ATOM | 1154 | CZ | TYR | A | 165 | 3.812 | -3.256 | 32.062 | 1.000 20.60 |
| ATOM | 1155 | OH | TYR | A | 165 | 3.338 | -4.550 | 31.950 | 1.000 25.51 |
| ATOM | 1156 | CE2 | TYR | A | 165 | 5.032 | -2.978 | 32.631 | 1.000 18.30 |
| ATOM | 1157 | CD2 | TYR | A | 165 | 5.506 | -1.670 | 32.740 | 1.000 18.57 |
| ATOM | 1158 | C | TYR | A | 165 | 5.563 | 2.905 | 31.134 | 1.000 20.90 |
| ATOM | 1159 | O | TYR | A | 165 | 6.525 | 3.443 | 31.688 | 1.000 19.46 |
| ATOM | 1160 | N | TYR | A | 166 | 4.495 | 3.530 | 30.690 | 1.000 17.57 |
| ATOM | 1161 | CA | TYR | A | 166 | 4.172 | 4.933 | 30.964 | 1.000 16.74 |
| ATOM | 1162 | CB | TYR | A | 166 | 4.262 | 5.809 | 29.718 | 1.000 17.74 |
| ATOM | 1163 | CG | TYR | A | 166 | 5.648 | 6.083 | 29.202 | 1.000 18.55 |
| ATOM | 1164 | CD1 | TYR | A | 166 | 6.318 | 7.284 | 29.472 | 1.000 15.85 |
| ATOM | 1165 | CE1 | TYR | A | 166 | 7.589 | 7.509 | 28.990 | 1.000 15.83 |
| ATOM | 1166 | CZ | TYR | A | 166 | 8.236 | 6.569 | 28.235 | 1.000 17.11 |
| ATOM | 1167 | OH | TYR | A | 166 | 9.498 | 6.772 | 27.739 | 1.000 21.34 |
| ATOM | 1168 | CE2 | TYR | A | 166 | 7.597 | 5.380 | 27.954 | 1.000 20.45 |
| ATOM | 1169 | CD2 | TYR | A | 166 | 6.324 | 5.153 | 28.434 | 1.000 19.30 |
| ATOM | 1170 | C | TYR | A | 166 | 2.755 | 4.969 | 31.521 | 1.000 17.54 |
| ATOM | 1171 | O | TYR | A | 166 | 1.784 | 4.874 | 30.773 | 1.000 18.04 |
| ATOM | 1172 | N | GLY | A | 167 | 2.582 | 5.076 | 32.829 | 1.000 18.81 |
| ATOM | 1173 | CA | GLY | A | 167 | 1.205 | 4.954 | 33.330 | 1.000 22.60 |
| ATOM | 1174 | C | GLY | A | 167 | 0.691 | 3.555 | 33.040 | 1.000 22.40 |
| ATOM | 1175 | O | GLY | A | 167 | 1.404 | 2.570 | 33.233 | 1.000 24.80 |
| ATOM | 1176 | N | ASP | A | 168 | -0.529 | 3.434 | 32.527 | 1.000 21.14 |
| ATOM | 1177 | CA | ASP | A | 168 | -1.052 | 2.125 | 32.187 | 1.000 19.46 |
| ATOM | 1178 | CB | ASP | A | 168 | -2.583 | 2.105 | 32.330 | 1.000 19.01 |
| ATOM | 1179 | CG | ASP | A | 168 | -2.972 | 2.233 | 33.792 | 1.000 29.38 |
| ATOM | 1180 | OD1 | ASP | A | 168 | -2.199 | 1.795 | 34.675 | 1.000 31.79 |
| ATOM | 1181 | OD2 | ASP | A | 168 | -4.064 | 2.776 | 34.047 | 1.000 41.21 |
| ATOM | 1182 | C | ASP | A | 168 | -0.707 | 1.690 | 30.779 | 1.000 22.83 |
| ATOM | 1183 | O | ASP | A | 168 | -1.223 | 0.665 | 30.330 | 1.000 32.53 |
| ATOM | 1184 | N | LEU | A | 169 | 0.113 | 2.428 | 30.059 | 1.000 22.05 |
| ATOM | 1185 | CA | LEU | A | 169 | 0.439 | 2.054 | 28.685 | 1.000 20.08 |
| ATOM | 1186 | CB | LEU | A | 169 | 0.372 | 3.268 | 27.736 | 1.000 19.68 |
| ATOM | 1187 | CG | LEU | A | 169 | -0.925 | 4.075 | 27.798 | 1.000 38.06 |
| ATOM | 1188 | CD1 | LEU | A | 169 | -0.792 | 5.463 | 27.170 | 1.000 25.80 |
| ATOM | 1189 | CD2 | LEU | A | 169 | -2.049 | 3.304 | 27.119 | 1.000 37.43 |
| ATOM | 1190 | C | LEU | A | 169 | 1.840 | 1.480 | 28.619 | 1.000 21.18 |
| ATOM | 1191 | O | LEU | A | 169 | 2.677 | 1.776 | 29.476 | 1.000 22.88 |
| ATOM | 1192 | N | ILE | A | 170 | 2.110 | 0.675 | 27.585 | 1.000 15.34 |
| ATOM | 1193 | CA | ILE | A | 170 | 3.498 | 0.257 | 27.438 | 1.000 16.78 |
| ATOM | 1194 | CB | ILE | A | 170 | 3.759 | -1.248 | 27.605 | 1.000 23.77 |
| ATOM | 1195 | CG1 | ILE | A | 170 | 5.235 | -1.602 | 27.342 | 1.000 28.45 |

FIGURE 224

| | | | | | | | | | |
|---|---|---|---|---|---|---|---|---|---|
| ATOM | 1196 | CD1 | ILE | A | 170 | 5.709 | -2.782 | 28.165 | 1.000 28.18 |
| ATOM | 1197 | CG2 | ILE | A | 170 | 2.849 | -2.102 | 26.746 | 1.000 23.17 |
| ATOM | 1198 | C | ILE | A | 170 | 3.966 | 0.706 | 26.047 | 1.000 19.57 |
| ATOM | 1199 | O | ILE | A | 170 | 3.177 | 0.625 | 25.107 | 1.000 18.10 |
| ATOM | 1200 | N | LEU | A | 171 | 5.196 | 1.186 | 26.013 | 1.000 19.57 |
| ATOM | 1201 | CA | LEU | A | 171 | 5.709 | 1.829 | 24.789 | 1.000 23.46 |
| ATOM | 1202 | CB | LEU | A | 171 | 5.723 | 3.318 | 25.102 | 1.000 24.58 |
| ATOM | 1203 | CG | LEU | A | 171 | 6.059 | 4.395 | 24.098 | 1.000 38.61 |
| ATOM | 1204 | CD1 | LEU | A | 171 | 4.995 | 4.543 | 23.027 | 1.000 29.72 |
| ATOM | 1205 | CD2 | LEU | A | 171 | 6.247 | 5.726 | 24.826 | 1.000 32.91 |
| ATOM | 1206 | C | LEU | A | 171 | 7.042 | 1.210 | 24.442 | 1.000 25.87 |
| ATOM | 1207 | O | LEU | A | 171 | 7.863 | 0.848 | 25.294 | 1.000 22.43 |
| ATOM | 1208 | N | GLN | A | 172 | 7.320 | 1.018 | 23.159 | 1.000 18.94 |
| ATOM | 1209 | CA | GLN | A | 172 | 8.609 | 0.485 | 22.749 | 1.000 18.74 |
| ATOM | 1210 | CB | GLN | A | 172 | 8.516 | -1.033 | 22.548 | 1.000 25.07 |
| ATOM | 1211 | CG | GLN | A | 172 | 9.801 | -1.733 | 22.146 | 1.000 23.89 |
| ATOM | 1212 | CD | GLN | A | 172 | 9.639 | -3.222 | 21.918 | 1.000 32.82 |
| ATOM | 1213 | OE1 | GLN | A | 172 | 8.737 | -3.720 | 21.242 | 1.000 36.92 |
| ATOM | 1214 | NE2 | GLN | A | 172 | 10.552 | -3.981 | 22.530 | 1.000 34.84 |
| ATOM | 1215 | C | GLN | A | 172 | 9.049 | 1.190 | 21.475 | 1.000 20.94 |
| ATOM | 1216 | O | GLN | A | 172 | 8.271 | 1.224 | 20.521 | 1.000 27.01 |
| ATOM | 1217 | N | MET | A | 173 | 10.265 | 1.709 | 21.448 | 1.000 21.76 |
| ATOM | 1218 | CA | MET | A | 173 | 10.771 | 2.361 | 20.246 | 1.000 19.32 |
| ATOM | 1219 | CB | MET | A | 173 | 11.848 | 3.393 | 20.622 | 1.000 20.29 |
| ATOM | 1220 | CG | MET | A | 173 | 12.395 | 4.082 | 19.350 | 1.000 23.01 |
| ATOM | 1221 | SD | MET | A | 173 | 13.333 | 5.573 | 19.752 | 1.000 23.47 |
| ATOM | 1222 | CE | MET | A | 173 | 14.788 | 4.835 | 20.498 | 1.000 34.32 |
| ATOM | 1223 | C | MET | A | 173 | 11.331 | 1.325 | 19.286 | 1.000 21.94 |
| ATOM | 1224 | O | MET | A | 173 | 12.211 | 0.554 | 19.678 | 1.000 25.02 |
| ATOM | 1225 | N | LEU | A | 174 | 10.824 | 1.300 | 18.058 | 1.000 21.94 |
| ATOM | 1226 | CA | LEU | A | 174 | 11.188 | 0.272 | 17.086 | 1.000 26.84 |
| ATOM | 1227 | CB | LEU | A | 174 | 9.993 | -0.104 | 16.224 | 1.000 29.19 |
| ATOM | 1228 | CG | LEU | A | 174 | 8.732 | -0.590 | 16.934 | 1.000 33.01 |
| ATOM | 1229 | CD1 | LEU | A | 174 | 7.688 | -0.964 | 15.897 | 1.000 29.01 |
| ATOM | 1230 | CD2 | LEU | A | 174 | 9.062 | -1.757 | 17.857 | 1.000 38.21 |
| ATOM | 1231 | C | LEU | A | 174 | 12.299 | 0.737 | 16.159 | 1.000 27.31 |
| ATOM | 1232 | O | LEU | A | 174 | 13.081 | -0.049 | 15.641 | 1.000 28.22 |
| ATOM | 1233 | N | SER | A | 175 | 12.364 | 2.050 | 15.956 | 1.000 28.86 |
| ATOM | 1234 | CA | SER | A | 175 | 13.420 | 2.612 | 15.111 | 1.000 30.23 |
| ATOM | 1235 | CB | SER | A | 175 | 13.135 | 2.372 | 13.626 | 1.000 29.79 |
| ATOM | 1236 | OG | SER | A | 175 | 12.320 | 3.403 | 13.111 | 1.000 28.04 |
| ATOM | 1237 | C | SER | A | 175 | 13.595 | 4.101 | 15.397 | 1.000 22.48 |
| ATOM | 1238 | O | SER | A | 175 | 12.690 | 4.787 | 15.885 | 1.000 22.47 |
| ATOM | 1239 | N | GLU | A | 176 | 14.798 | 4.562 | 15.104 | 1.000 20.99 |
| ATOM | 1240 | CA | GLU | A | 176 | 15.204 | 5.939 | 15.322 | 1.000 21.52 |
| ATOM | 1241 | CB | GLU | A | 176 | 15.885 | 6.109 | 16.674 | 1.000 18.41 |
| ATOM | 1242 | CG | GLU | A | 176 | 16.366 | 7.514 | 16.976 | 1.000 22.49 |
| ATOM | 1243 | CD | GLU | A | 176 | 16.890 | 7.563 | 18.413 | 1.000 39.47 |
| ATOM | 1244 | OE1 | GLU | A | 176 | 18.041 | 7.104 | 18.596 | 1.000 35.29 |
| ATOM | 1245 | OE2 | GLU | A | 176 | 16.182 | 8.023 | 19.331 | 1.000 26.84 |
| ATOM | 1246 | C | GLU | A | 176 | 16.158 | 6.334 | 14.203 | 1.000 35.39 |
| ATOM | 1247 | O | GLU | A | 176 | 17.237 | 5.756 | 14.149 | 1.000 26.11 |

FIGURE 225

```
ATOM   1248  N    SER A 177      15.754    7.260   13.341  1.000  26.10
ATOM   1249  CA   SER A 177      16.562    7.596   12.175  1.000  22.13
ATOM   1250  CB   SER A 177      15.850    7.215   10.880  1.000  24.63
ATOM   1251  OG   SER A 177      15.442    5.858   10.852  1.000  32.57
ATOM   1252  C    SER A 177      16.888    9.079   12.211  1.000  19.74
ATOM   1253  O    SER A 177      16.041    9.955   12.003  1.000  24.72
ATOM   1254  N    VAL A 178      18.142    9.387   12.521  1.000  21.76
ATOM   1255  CA   VAL A 178      18.577   10.766   12.651  1.000  20.70
ATOM   1256  CB   VAL A 178      19.777   10.890   13.604  1.000  30.20
ATOM   1257  CG1  VAL A 178      20.138   12.353   13.823  1.000  22.39
ATOM   1258  CG2  VAL A 178      19.478   10.224   14.943  1.000  30.74
ATOM   1259  C    VAL A 178      18.959   11.311   11.280  1.000  27.01
ATOM   1260  O    VAL A 178      19.885   10.794   10.652  1.000  26.60
ATOM   1261  N    LEU A 179      18.244   12.333   10.828  1.000  23.24
ATOM   1262  CA   LEU A 179      18.550   12.947    9.541  1.000  17.95
ATOM   1263  CB   LEU A 179      17.292   12.950    8.668  1.000  19.90
ATOM   1264  CG   LEU A 179      16.414   11.712    8.694  1.000  19.48
ATOM   1265  CD1  LEU A 179      15.201   11.861    7.765  1.000  20.09
ATOM   1266  CD2  LEU A 179      17.209   10.467    8.304  1.000  23.69
ATOM   1267  C    LEU A 179      19.119   14.337    9.791  1.000  22.68
ATOM   1268  O    LEU A 179      19.079   14.824   10.939  1.000  23.34
ATOM   1269  N    PRO A 180      19.677   15.022    8.798  1.000  26.71
ATOM   1270  CA   PRO A 180      20.320   16.317    9.086  1.000  23.99
ATOM   1271  CB   PRO A 180      20.700   16.849    7.686  1.000  24.76
ATOM   1272  CG   PRO A 180      20.859   15.612    6.863  1.000  30.87
ATOM   1273  CD   PRO A 180      19.801   14.649    7.378  1.000  29.95
ATOM   1274  C    PRO A 180      19.439   17.339    9.771  1.000  23.60
ATOM   1275  O    PRO A 180      19.901   18.080   10.636  1.000  22.88
ATOM   1276  N    GLU A 181      18.151   17.441    9.439  1.000  21.19
ATOM   1277  CA   GLU A 181      17.363   18.480   10.078  1.000  21.28
ATOM   1278  CB   GLU A 181      16.858   19.455    8.991  1.000  24.45
ATOM   1279  CG   GLU A 181      18.003   20.315    8.476  1.000  34.87
ATOM   1280  CD   GLU A 181      17.596   21.325    7.421  1.000  37.86
ATOM   1281  OE1  GLU A 181      16.746   21.008    6.567  1.000  32.02
ATOM   1282  OE2  GLU A 181      18.154   22.440    7.452  1.000  44.17
ATOM   1283  C    GLU A 181      16.178   17.945   10.870  1.000  17.99
ATOM   1284  O    GLU A 181      15.507   18.740   11.537  1.000  19.13
ATOM   1285  N    TRP A 182      15.906   16.648   10.817  1.000  23.72
ATOM   1286  CA   TRP A 182      14.848   16.095   11.672  1.000  20.93
ATOM   1287  CB   TRP A 182      13.432   16.217   11.113  1.000  15.09
ATOM   1288  CG   TRP A 182      13.192   15.913    9.681  1.000  16.03
ATOM   1289  CD1  TRP A 182      12.852   14.727    9.123  1.000  20.35
ATOM   1290  NE1  TRP A 182      12.715   14.821    7.763  1.000  23.86
ATOM   1291  CE2  TRP A 182      12.971   16.112    7.407  1.000  15.42
ATOM   1292  CD2  TRP A 182      13.275   16.826    8.568  1.000  18.32
ATOM   1293  CE3  TRP A 182      13.583   18.197    8.484  1.000  18.38
ATOM   1294  CZ3  TRP A 182      13.571   18.785    7.229  1.000  19.84
ATOM   1295  CH2  TRP A 182      13.261   18.032    6.085  1.000  21.10
ATOM   1296  CZ2  TRP A 182      12.956   16.698    6.134  1.000  18.37
ATOM   1297  C    TRP A 182      15.188   14.629   11.929  1.000  21.61
ATOM   1298  O    TRP A 182      15.996   14.011   11.228  1.000  21.72
ATOM   1299  N    THR A 183      14.549   14.085   12.961  1.000  18.39
```

FIGURE 226

| | | | | | | | | | |
|---|---|---|---|---|---|---|---|---|---|
| ATOM | 1300 | CA | THR | A | 183 | 14.699 | 12.677 | 13.292 | 1.000 20.50 |
| ATOM | 1301 | CB | THR | A | 183 | 15.328 | 12.553 | 14.701 | 1.000 23.44 |
| ATOM | 1302 | OG1 | THR | A | 183 | 16.636 | 13.143 | 14.619 | 1.000 24.00 |
| ATOM | 1303 | CG2 | THR | A | 183 | 15.453 | 11.104 | 15.137 | 1.000 21.54 |
| ATOM | 1304 | C | THR | A | 183 | 13.349 | 11.988 | 13.226 | 1.000 16.48 |
| ATOM | 1305 | O | THR | A | 183 | 12.354 | 12.543 | 13.710 | 1.000 18.87 |
| ATOM | 1306 | N | ILE | A | 184 | 13.301 | 10.809 | 12.641 | 1.000 15.19 |
| ATOM | 1307 | CA | ILE | A | 184 | 12.051 | 10.059 | 12.556 | 1.000 15.66 |
| ATOM | 1308 | CB | ILE | A | 184 | 11.775 | 9.676 | 11.096 | 1.000 19.83 |
| ATOM | 1309 | CG1 | ILE | A | 184 | 11.821 | 10.921 | 10.196 | 1.000 20.74 |
| ATOM | 1310 | CD1 | ILE | A | 184 | 11.379 | 10.717 | 8.765 | 1.000 23.01 |
| ATOM | 1311 | CG2 | ILE | A | 184 | 10.481 | 8.900 | 10.978 | 1.000 19.48 |
| ATOM | 1312 | C | ILE | A | 184 | 12.134 | 8.828 | 13.450 | 1.000 25.32 |
| ATOM | 1313 | O | ILE | A | 184 | 13.056 | 8.018 | 13.311 | 1.000 28.73 |
| ATOM | 1314 | N | ARG | A | 185 | 11.189 | 8.678 | 14.370 | 1.000 21.95 |
| ATOM | 1315 | CA | ARG | A | 185 | 11.171 | 7.501 | 15.231 | 1.000 19.00 |
| ATOM | 1316 | CB | ARG | A | 185 | 11.381 | 7.882 | 16.693 | 1.000 17.64 |
| ATOM | 1317 | CG | ARG | A | 185 | 12.739 | 8.478 | 17.011 | 1.000 22.12 |
| ATOM | 1318 | CD | ARG | A | 185 | 12.764 | 9.060 | 18.407 | 1.000 22.23 |
| ATOM | 1319 | NE | ARG | A | 185 | 13.977 | 9.765 | 18.768 | 1.000 27.88 |
| ATOM | 1320 | CZ | ARG | A | 185 | 14.318 | 11.031 | 18.624 | 1.000 22.96 |
| ATOM | 1321 | NH1 | ARG | A | 185 | 13.515 | 11.930 | 18.062 | 1.000 21.31 |
| ATOM | 1322 | NH2 | ARG | A | 185 | 15.513 | 11.426 | 19.056 | 1.000 28.28 |
| ATOM | 1323 | C | ARG | A | 185 | 9.836 | 6.796 | 15.067 | 1.000 20.34 |
| ATOM | 1324 | O | ARG | A | 185 | 8.827 | 7.415 | 14.740 | 1.000 19.60 |
| ATOM | 1325 | N | GLU | A | 186 | 9.842 | 5.499 | 15.318 | 1.000 21.83 |
| ATOM | 1326 | CA | GLU | A | 186 | 8.590 | 4.756 | 15.330 | 1.000 19.84 |
| ATOM | 1327 | CB | GLU | A | 186 | 8.495 | 3.779 | 14.165 | 1.000 27.08 |
| ATOM | 1328 | CG | GLU | A | 186 | 7.086 | 3.286 | 13.877 | 1.000 38.65 |
| ATOM | 1329 | CD | GLU | A | 186 | 6.961 | 2.255 | 12.778 | 1.000 49.85 |
| ATOM | 1330 | OE1 | GLU | A | 186 | 7.958 | 1.554 | 12.481 | 1.000 59.07 |
| ATOM | 1331 | OE2 | GLU | A | 186 | 5.874 | 2.119 | 12.169 | 1.000 41.81 |
| ATOM | 1332 | C | GLU | A | 186 | 8.507 | 4.004 | 16.664 | 1.000 24.47 |
| ATOM | 1333 | O | GLU | A | 186 | 9.494 | 3.391 | 17.085 | 1.000 28.68 |
| ATOM | 1334 | N | PHE | A | 187 | 7.342 | 4.092 | 17.281 | 1.000 21.26 |
| ATOM | 1335 | CA | PHE | A | 187 | 7.016 | 3.401 | 18.513 | 1.000 17.58 |
| ATOM | 1336 | CB | PHE | A | 187 | 6.609 | 4.390 | 19.609 | 1.000 19.02 |
| ATOM | 1337 | CG | PHE | A | 187 | 7.601 | 5.542 | 19.741 | 1.000 26.16 |
| ATOM | 1338 | CD1 | PHE | A | 187 | 7.288 | 6.798 | 19.268 | 1.000 22.44 |
| ATOM | 1339 | CE1 | PHE | A | 187 | 8.192 | 7.832 | 19.409 | 1.000 30.77 |
| ATOM | 1340 | CZ | PHE | A | 187 | 9.428 | 7.634 | 19.993 | 1.000 26.12 |
| ATOM | 1341 | CE2 | PHE | A | 187 | 9.746 | 6.376 | 20.477 | 1.000 27.12 |
| ATOM | 1342 | CD2 | PHE | A | 187 | 8.832 | 5.341 | 20.350 | 1.000 25.25 |
| ATOM | 1343 | C | PHE | A | 187 | 5.836 | 2.453 | 18.339 | 1.000 20.12 |
| ATOM | 1344 | O | PHE | A | 187 | 4.844 | 2.733 | 17.687 | 1.000 23.02 |
| ATOM | 1345 | N | LYS | A | 188 | 5.969 | 1.320 | 19.015 | 1.000 29.00 |
| ATOM | 1346 | CA | LYS | A | 188 | 4.814 | 0.486 | 19.315 | 1.000 23.44 |
| ATOM | 1347 | CB | LYS | A | 188 | 5.229 | -0.986 | 19.280 | 1.000 29.53 |
| ATOM | 1348 | CG | LYS | A | 188 | 4.064 | -1.959 | 19.180 | 1.000 41.78 |
| ATOM | 1349 | CD | LYS | A | 188 | 4.560 | -3.360 | 18.830 | 1.000 46.50 |
| ATOM | 1350 | CE | LYS | A | 188 | 5.255 | -3.976 | 20.036 | 1.000 45.29 |
| ATOM | 1351 | NZ | LYS | A | 188 | 5.958 | -5.246 | 19.707 | 1.000 51.18 |

FIGURE 227

| | | | | | | | | | |
|---|---|---|---|---|---|---|---|---|---|
| ATOM | 1352 | C   | LYS | A | 188 | 4.247   | 0.908  | 20.669 | 1.000 21.37 |
| ATOM | 1353 | O   | LYS | A | 188 | 4.984   | 1.012  | 21.650 | 1.000 20.70 |
| ATOM | 1354 | N   | ILE | A | 189 | 2.942   | 1.151  | 20.722 | 1.000 19.68 |
| ATOM | 1355 | CA  | ILE | A | 189 | 2.280   | 1.419  | 21.990 | 1.000 20.68 |
| ATOM | 1356 | CB  | ILE | A | 189 | 1.712   | 2.853  | 22.019 | 1.000 26.52 |
| ATOM | 1357 | CG1 | ILE | A | 189 | 1.092   | 3.235  | 23.363 | 1.000 22.26 |
| ATOM | 1358 | CD1 | ILE | A | 189 | 0.940   | 4.748  | 23.485 | 1.000 39.28 |
| ATOM | 1359 | CG2 | ILE | A | 189 | 0.721   | 3.104  | 20.879 | 1.000 26.76 |
| ATOM | 1360 | C   | ILE | A | 189 | 1.160   | 0.429  | 22.259 | 1.000 25.87 |
| ATOM | 1361 | O   | ILE | A | 189 | 0.397   | 0.070  | 21.351 | 1.000 23.56 |
| ATOM | 1362 | N   | CYS | A | 190 | 1.032   | -0.021 | 23.514 | 1.000 24.27 |
| ATOM | 1363 | CA  | CYS | A | 190 | -0.078  | -0.912 | 23.859 | 1.000 21.00 |
| ATOM | 1364 | CB  | CYS | A | 190 | 0.402   | -2.336 | 24.179 | 1.000 28.92 |
| ATOM | 1365 | SG  | CYS | A | 190 | 1.318   | -3.174 | 22.867 | 1.000 32.32 |
| ATOM | 1366 | C   | CYS | A | 190 | -0.838  | -0.365 | 25.055 | 1.000 26.90 |
| ATOM | 1367 | O   | CYS | A | 190 | -0.279  | -0.024 | 26.098 | 1.000 22.81 |
| ATOM | 1368 | N   | GLY | A | 191 | -2.159  | -0.270 | 24.946 | 1.000 28.18 |
| ATOM | 1369 | CA  | GLY | A | 191 | -2.883  | 0.291  | 26.094 | 1.000 35.73 |
| ATOM | 1370 | C   | GLY | A | 191 | -4.150  | -0.485 | 26.348 | 1.000 42.74 |
| ATOM | 1371 | O   | GLY | A | 191 | -4.326  | -1.578 | 25.793 | 1.000 32.85 |
| ATOM | 1372 | N   | GLU | A | 192 | -5.093  | -0.003 | 27.180 | 1.000 51.55 |
| ATOM | 1373 | CA  | GLU | A | 192 | -6.223  | -0.938 | 27.283 | 1.000 66.18 |
| ATOM | 1374 | CB  | GLU | A | 192 | -7.133  | -0.742 | 28.489 | 1.000 76.10 |
| ATOM | 1375 | CG  | GLU | A | 192 | -7.860  | -2.067 | 28.785 | 1.000 85.72 |
| ATOM | 1376 | CD  | GLU | A | 192 | -7.026  | -3.266 | 28.356 | 1.000 87.86 |
| ATOM | 1377 | OE1 | GLU | A | 192 | -6.184  | -3.687 | 29.190 | 1.000106.89 |
| ATOM | 1378 | OE2 | GLU | A | 192 | -7.174  | -3.794 | 27.229 | 1.000 63.79 |
| ATOM | 1379 | C   | GLU | A | 192 | -7.019  | -0.844 | 25.974 | 1.000 60.51 |
| ATOM | 1380 | O   | GLU | A | 192 | -7.455  | 0.251  | 25.638 | 1.000 49.89 |
| ATOM | 1381 | N   | GLU | A | 193 | -7.112  | -1.996 | 25.326 | 1.000 57.69 |
| ATOM | 1382 | CA  | GLU | A | 193 | -7.600  | -2.127 | 23.973 | 1.000 58.03 |
| ATOM | 1383 | CB  | GLU | A | 193 | -7.726  | -3.604 | 23.546 | 1.000 59.99 |
| ATOM | 1384 | CG  | GLU | A | 193 | -8.209  | -3.661 | 22.102 | 1.000 70.62 |
| ATOM | 1385 | CD  | GLU | A | 193 | -8.606  | -5.058 | 21.671 | 1.000 69.93 |
| ATOM | 1386 | OE1 | GLU | A | 193 | -9.439  | -5.674 | 22.369 | 1.000 80.76 |
| ATOM | 1387 | OE2 | GLU | A | 193 | -8.081  | -5.511 | 20.636 | 1.000 63.90 |
| ATOM | 1388 | C   | GLU | A | 193 | -8.963  | -1.475 | 23.781 | 1.000 64.42 |
| ATOM | 1389 | O   | GLU | A | 193 | -9.945  | -1.868 | 24.403 | 1.000100.70 |
| ATOM | 1390 | N   | GLN | A | 194 | -9.008  | -0.492 | 22.895 | 1.000 65.44 |
| ATOM | 1391 | CA  | GLN | A | 194 | -10.257 | 0.128  | 22.460 | 1.000 65.33 |
| ATOM | 1392 | CB  | GLN | A | 194 | -10.256 | 1.622  | 22.773 | 1.000 59.27 |
| ATOM | 1393 | CG  | GLN | A | 194 | -8.915  | 2.066  | 23.359 | 1.000 64.93 |
| ATOM | 1394 | CD  | GLN | A | 194 | -8.739  | 3.571  | 23.383 | 1.000 63.48 |
| ATOM | 1395 | OE1 | GLN | A | 194 | -8.193  | 4.160  | 22.449 | 1.000 39.84 |
| ATOM | 1396 | NE2 | GLN | A | 194 | -9.206  | 4.183  | 24.467 | 1.000 72.21 |
| ATOM | 1397 | C   | GLN | A | 194 | -10.409 | -0.139 | 20.964 | 1.000 65.87 |
| ATOM | 1398 | O   | GLN | A | 194 | -10.725 | -1.270 | 20.581 | 1.000 56.74 |
| ATOM | 1399 | N   | LEU | A | 195 | -10.151 | 0.891  | 20.161 | 1.000 58.59 |
| ATOM | 1400 | CA  | LEU | A | 195 | -10.167 | 0.734  | 18.707 | 1.000 53.57 |
| ATOM | 1401 | CB  | LEU | A | 195 | -10.095 | 2.103  | 18.027 | 1.000 34.01 |
| ATOM | 1402 | CG  | LEU | A | 195 | -11.473 | 2.711  | 17.749 | 1.000 52.84 |
| ATOM | 1403 | CD1 | LEU | A | 195 | -11.369 | 4.144  | 17.248 | 1.000 64.31 |

FIGURE 228

| | | | | | | | | | |
|---|---|---|---|---|---|---|---|---|---|
| ATOM | 1404 | CD2 | LEU | A | 195 | -12.213 | 1.828 | 16.745 | 1.000 77.61 |
| ATOM | 1405 | C | LEU | A | 195 | -9.029 | -0.175 | 18.251 | 1.000 62.19 |
| ATOM | 1406 | O | LEU | A | 195 | -9.207 | -0.990 | 17.345 | 1.000 74.97 |
| ATOM | 1407 | N | ASP | A | 196 | -7.874 | -0.040 | 18.893 | 1.000 64.63 |
| ATOM | 1408 | CA | ASP | A | 196 | -6.730 | -0.907 | 18.651 | 1.000 71.88 |
| ATOM | 1409 | CB | ASP | A | 196 | -5.616 | -0.149 | 17.929 | 1.000 69.22 |
| ATOM | 1410 | CG | ASP | A | 196 | -5.589 | 1.331 | 18.254 | 1.000 68.85 |
| ATOM | 1411 | OD1 | ASP | A | 196 | -5.984 | 1.716 | 19.374 | 1.000 46.56 |
| ATOM | 1412 | OD2 | ASP | A | 196 | -5.168 | 2.105 | 17.363 | 1.000 68.77 |
| ATOM | 1413 | C | ASP | A | 196 | -6.197 | -1.496 | 19.959 | 1.000 75.55 |
| ATOM | 1414 | O | ASP | A | 196 | -6.396 | -0.908 | 21.026 | 1.000 52.97 |
| ATOM | 1415 | N | ALA | A | 197 | -5.530 | -2.643 | 19.864 | 1.000 77.66 |
| ATOM | 1416 | CA | ALA | A | 197 | -4.895 | -3.267 | 21.020 | 1.000 76.86 |
| ATOM | 1417 | CB | ALA | A | 197 | -5.256 | -4.738 | 21.113 | 1.000 89.29 |
| ATOM | 1418 | C | ALA | A | 197 | -3.376 | -3.077 | 20.976 | 1.000 70.52 |
| ATOM | 1419 | O | ALA | A | 197 | -2.709 | -3.074 | 22.013 | 1.000 40.24 |
| ATOM | 1420 | N | HIS | A | 198 | -2.852 | -2.910 | 19.772 | 1.000 66.05 |
| ATOM | 1421 | CA | HIS | A | 198 | -1.497 | -2.444 | 19.510 | 1.000 70.91 |
| ATOM | 1422 | CB | HIS | A | 198 | -0.565 | -3.597 | 19.162 | 1.000 75.50 |
| ATOM | 1423 | CG | HIS | A | 198 | -1.090 | -4.481 | 18.069 | 1.000 88.48 |
| ATOM | 1424 | ND1 | HIS | A | 198 | -1.492 | -5.779 | 18.290 | 1.000 94.26 |
| ATOM | 1425 | CE1 | HIS | A | 198 | -1.906 | -6.315 | 17.155 | 1.000 93.97 |
| ATOM | 1426 | NE2 | HIS | A | 198 | -1.788 | -5.411 | 16.199 | 1.000 94.98 |
| ATOM | 1427 | CD2 | HIS | A | 198 | -1.280 | -4.259 | 16.747 | 1.000 92.03 |
| ATOM | 1428 | C | HIS | A | 198 | -1.534 | -1.404 | 18.383 | 1.000 71.60 |
| ATOM | 1429 | O | HIS | A | 198 | -2.374 | -1.488 | 17.480 | 1.000 79.54 |
| ATOM | 1430 | N | ARG | A | 199 | -0.649 | -0.416 | 18.408 | 1.000 59.29 |
| ATOM | 1431 | CA | ARG | A | 199 | -0.625 | 0.649 | 17.409 | 1.000 35.48 |
| ATOM | 1432 | CB | ARG | A | 199 | -1.445 | 1.854 | 17.881 | 1.000 27.18 |
| ATOM | 1433 | CG | ARG | A | 199 | -1.499 | 2.997 | 16.876 | 1.000 28.09 |
| ATOM | 1434 | CD | ARG | A | 199 | -2.136 | 4.248 | 17.473 | 1.000 30.52 |
| ATOM | 1435 | NE | ARG | A | 199 | -3.326 | 3.985 | 18.281 | 1.000 24.15 |
| ATOM | 1436 | CZ | ARG | A | 199 | -3.802 | 4.809 | 19.209 | 1.000 28.77 |
| ATOM | 1437 | NH1 | ARG | A | 199 | -3.159 | 5.961 | 19.433 | 1.000 21.27 |
| ATOM | 1438 | NH2 | ARG | A | 199 | -4.894 | 4.481 | 19.891 | 1.000 20.72 |
| ATOM | 1439 | C | ARG | A | 199 | 0.811 | 1.091 | 17.148 | 1.000 34.48 |
| ATOM | 1440 | O | ARG | A | 199 | 1.652 | 1.004 | 18.041 | 1.000 33.43 |
| ATOM | 1441 | N | LEU | A | 200 | 1.073 | 1.574 | 15.945 | 1.000 25.06 |
| ATOM | 1442 | CA | LEU | A | 200 | 2.347 | 2.162 | 15.564 | 1.000 24.44 |
| ATOM | 1443 | CB | LEU | A | 200 | 2.763 | 1.609 | 14.186 | 1.000 33.41 |
| ATOM | 1444 | CG | LEU | A | 200 | 2.956 | 0.076 | 14.187 | 1.000 38.30 |
| ATOM | 1445 | CD1 | LEU | A | 200 | 3.183 | -0.457 | 12.783 | 1.000 34.53 |
| ATOM | 1446 | CD2 | LEU | A | 200 | 4.085 | -0.324 | 15.136 | 1.000 24.70 |
| ATOM | 1447 | C | LEU | A | 200 | 2.247 | 3.680 | 15.530 | 1.000 27.60 |
| ATOM | 1448 | O | LEU | A | 200 | 1.329 | 4.254 | 14.940 | 1.000 27.27 |
| ATOM | 1449 | N | ILE | A | 201 | 3.190 | 4.352 | 16.167 | 1.000 21.65 |
| ATOM | 1450 | CA | ILE | A | 201 | 3.223 | 5.805 | 16.195 | 1.000 19.45 |
| ATOM | 1451 | CB | ILE | A | 201 | 3.243 | 6.350 | 17.634 | 1.000 23.93 |
| ATOM | 1452 | CG1 | ILE | A | 201 | 2.224 | 5.707 | 18.555 | 1.000 27.08 |
| ATOM | 1453 | CD1 | ILE | A | 201 | 0.840 | 6.267 | 18.547 | 1.000 32.15 |
| ATOM | 1454 | CG2 | ILE | A | 201 | 3.105 | 7.874 | 17.627 | 1.000 22.88 |
| ATOM | 1455 | C | ILE | A | 201 | 4.494 | 6.275 | 15.498 | 1.000 16.73 |

FIGURE 229

| | | | | | | | | | |
|---|---|---|---|---|---|---|---|---|---|
| ATOM | 1456 | O | ILE | A | 201 | 5.543 | 5.697 | 15.797 | 1.000 21.43 |
| ATOM | 1457 | N | ARG | A | 202 | 4.395 | 7.244 | 14.609 | 1.000 15.34 |
| ATOM | 1458 | CA | ARG | A | 202 | 5.529 | 7.874 | 13.952 | 1.000 13.92 |
| ATOM | 1459 | CB | ARG | A | 202 | 5.344 | 8.052 | 12.442 | 1.000 21.70 |
| ATOM | 1460 | CG | ARG | A | 202 | 4.824 | 6.798 | 11.747 | 1.000 37.52 |
| ATOM | 1461 | CD | ARG | A | 202 | 5.397 | 6.648 | 10.346 | 1.000 48.86 |
| ATOM | 1462 | NE | ARG | A | 202 | 6.613 | 5.885 | 10.269 | 1.000 46.03 |
| ATOM | 1463 | CZ | ARG | A | 202 | 7.751 | 6.058 | 9.632 | 1.000 45.70 |
| ATOM | 1464 | NH1 | ARG | A | 202 | 8.037 | 7.082 | 8.834 | 1.000 37.98 |
| ATOM | 1465 | NH2 | ARG | A | 202 | 8.673 | 5.112 | 9.812 | 1.000 32.36 |
| ATOM | 1466 | C | ARG | A | 202 | 5.730 | 9.248 | 14.587 | 1.000 16.51 |
| ATOM | 1467 | O | ARG | A | 202 | 4.762 | 9.959 | 14.863 | 1.000 18.08 |
| ATOM | 1468 | N | HIS | A | 203 | 6.987 | 9.543 | 14.854 | 1.000 17.20 |
| ATOM | 1469 | CA | HIS | A | 203 | 7.433 | 10.725 | 15.560 | 1.000 16.92 |
| ATOM | 1470 | CB | HIS | A | 203 | 8.142 | 10.336 | 16.854 | 1.000 20.76 |
| ATOM | 1471 | CG | HIS | A | 203 | 8.421 | 11.450 | 17.803 | 1.000 16.82 |
| ATOM | 1472 | ND1 | HIS | A | 203 | 9.626 | 12.125 | 17.837 | 1.000 21.78 |
| ATOM | 1473 | CE1 | HIS | A | 203 | 9.592 | 13.064 | 18.762 | 1.000 18.85 |
| ATOM | 1474 | NE2 | HIS | A | 203 | 8.404 | 13.021 | 19.331 | 1.000 19.59 |
| ATOM | 1475 | CD2 | HIS | A | 203 | 7.654 | 12.037 | 18.755 | 1.000 16.71 |
| ATOM | 1476 | C | HIS | A | 203 | 8.357 | 11.516 | 14.629 | 1.000 15.29 |
| ATOM | 1477 | O | HIS | A | 203 | 9.374 | 10.977 | 14.206 | 1.000 20.50 |
| ATOM | 1478 | N | PHE | A | 204 | 7.949 | 12.737 | 14.315 | 1.000 19.40 |
| ATOM | 1479 | CA | PHE | A | 204 | 8.668 | 13.627 | 13.398 | 1.000 22.59 |
| ATOM | 1480 | CB | PHE | A | 204 | 7.750 | 14.112 | 12.280 | 1.000 16.25 |
| ATOM | 1481 | CG | PHE | A | 204 | 7.133 | 12.949 | 11.535 | 1.000 19.17 |
| ATOM | 1482 | CD1 | PHE | A | 204 | 5.859 | 12.519 | 11.888 | 1.000 20.80 |
| ATOM | 1483 | CE1 | PHE | A | 204 | 5.296 | 11.466 | 11.195 | 1.000 18.80 |
| ATOM | 1484 | CZ | PHE | A | 204 | 5.976 | 10.843 | 10.173 | 1.000 24.56 |
| ATOM | 1485 | CE2 | PHE | A | 204 | 7.246 | 11.266 | 9.820 | 1.000 23.53 |
| ATOM | 1486 | CD2 | PHE | A | 204 | 7.825 | 12.307 | 10.529 | 1.000 21.57 |
| ATOM | 1487 | C | PHE | A | 204 | 9.237 | 14.789 | 14.191 | 1.000 15.29 |
| ATOM | 1488 | O | PHE | A | 204 | 8.545 | 15.706 | 14.632 | 1.000 18.02 |
| ATOM | 1489 | N | HIS | A | 205 | 10.552 | 14.693 | 14.407 | 1.000 17.57 |
| ATOM | 1490 | CA | HIS | A | 205 | 11.231 | 15.586 | 15.336 | 1.000 20.77 |
| ATOM | 1491 | CB | HIS | A | 205 | 12.017 | 14.705 | 16.297 | 1.000 22.15 |
| ATOM | 1492 | CG | HIS | A | 205 | 12.733 | 15.407 | 17.404 | 1.000 23.38 |
| ATOM | 1493 | ND1 | HIS | A | 205 | 12.618 | 16.749 | 17.686 | 1.000 28.56 |
| ATOM | 1494 | CE1 | HIS | A | 205 | 13.372 | 17.053 | 18.726 | 1.000 22.17 |
| ATOM | 1495 | NE2 | HIS | A | 205 | 13.982 | 15.963 | 19.129 | 1.000 23.37 |
| ATOM | 1496 | CD2 | HIS | A | 205 | 13.598 | 14.913 | 18.326 | 1.000 19.72 |
| ATOM | 1497 | C | HIS | A | 205 | 12.140 | 16.556 | 14.583 | 1.000 20.64 |
| ATOM | 1498 | O | HIS | A | 205 | 13.207 | 16.157 | 14.120 | 1.000 20.31 |
| ATOM | 1499 | N | TYR | A | 206 | 11.736 | 17.808 | 14.448 | 1.000 20.99 |
| ATOM | 1500 | CA | TYR | A | 206 | 12.552 | 18.816 | 13.771 | 1.000 18.48 |
| ATOM | 1501 | CB | TYR | A | 206 | 11.683 | 19.944 | 13.305 | 1.000 21.09 |
| ATOM | 1502 | CG | TYR | A | 206 | 12.270 | 20.944 | 12.340 | 1.000 17.56 |
| ATOM | 1503 | CD1 | TYR | A | 206 | 12.517 | 20.592 | 11.011 | 1.000 16.37 |
| ATOM | 1504 | CE1 | TYR | A | 206 | 13.048 | 21.568 | 10.167 | 1.000 22.62 |
| ATOM | 1505 | CZ | TYR | A | 206 | 13.294 | 22.833 | 10.665 | 1.000 23.75 |
| ATOM | 1506 | OH | TYR | A | 206 | 13.820 | 23.786 | 9.833 | 1.000 24.85 |
| ATOM | 1507 | CE2 | TYR | A | 206 | 13.044 | 23.195 | 11.972 | 1.000 25.09 |

FIGURE 230

| ATOM | 1508 | CD2 | TYR | A | 206 | 12.518 | 22.219 | 12.812 | 1.000 | 22.77 |
| ATOM | 1509 | C | TYR | A | 206 | 13.580 | 19.341 | 14.783 | 1.000 | 16.12 |
| ATOM | 1510 | O | TYR | A | 206 | 13.165 | 19.799 | 15.824 | 1.000 | 21.03 |
| ATOM | 1511 | N | THR | A | 207 | 14.855 | 19.255 | 14.458 | 1.000 | 20.95 |
| ATOM | 1512 | CA | THR | A | 207 | 15.937 | 19.446 | 15.406 | 1.000 | 25.39 |
| ATOM | 1513 | CB | THR | A | 207 | 16.825 | 18.181 | 15.436 | 1.000 | 21.21 |
| ATOM | 1514 | OG1 | THR | A | 207 | 17.300 | 17.892 | 14.110 | 1.000 | 24.55 |
| ATOM | 1515 | CG2 | THR | A | 207 | 16.034 | 16.975 | 15.913 | 1.000 | 20.79 |
| ATOM | 1516 | C | THR | A | 207 | 16.791 | 20.668 | 15.090 | 1.000 | 29.49 |
| ATOM | 1517 | O | THR | A | 207 | 17.837 | 20.877 | 15.720 | 1.000 | 27.61 |
| ATOM | 1518 | N | VAL | A | 208 | 16.366 | 21.501 | 14.140 | 1.000 | 24.45 |
| ATOM | 1519 | CA | VAL | A | 208 | 17.216 | 22.662 | 13.859 | 1.000 | 21.06 |
| ATOM | 1520 | CB | VAL | A | 208 | 17.883 | 22.496 | 12.481 | 1.000 | 28.39 |
| ATOM | 1521 | CG1 | VAL | A | 208 | 18.791 | 21.272 | 12.532 | 1.000 | 23.56 |
| ATOM | 1522 | CG2 | VAL | A | 208 | 16.849 | 22.387 | 11.368 | 1.000 | 20.57 |
| ATOM | 1523 | C | VAL | A | 208 | 16.523 | 23.999 | 13.935 | 1.000 | 31.86 |
| ATOM | 1524 | O | VAL | A | 208 | 17.084 | 24.981 | 13.417 | 1.000 | 27.99 |
| ATOM | 1525 | N | TRP | A | 209 | 15.359 | 24.144 | 14.567 | 1.000 | 26.72 |
| ATOM | 1526 | CA | TRP | A | 209 | 14.797 | 25.499 | 14.665 | 1.000 | 30.27 |
| ATOM | 1527 | CB | TRP | A | 209 | 13.424 | 25.461 | 15.322 | 1.000 | 28.47 |
| ATOM | 1528 | CG | TRP | A | 209 | 12.553 | 26.652 | 15.078 | 1.000 | 31.11 |
| ATOM | 1529 | CD1 | TRP | A | 209 | 12.747 | 27.933 | 15.523 | 1.000 | 31.15 |
| ATOM | 1530 | NE1 | TRP | A | 209 | 11.725 | 28.752 | 15.093 | 1.000 | 28.46 |
| ATOM | 1531 | CE2 | TRP | A | 209 | 10.845 | 28.000 | 14.356 | 1.000 | 28.45 |
| ATOM | 1532 | CD2 | TRP | A | 209 | 11.331 | 26.678 | 14.325 | 1.000 | 27.55 |
| ATOM | 1533 | CE3 | TRP | A | 209 | 10.611 | 25.704 | 13.629 | 1.000 | 22.81 |
| ATOM | 1534 | CZ3 | TRP | A | 209 | 9.445 | 26.095 | 13.005 | 1.000 | 25.86 |
| ATOM | 1535 | CH2 | TRP | A | 209 | 8.973 | 27.410 | 13.044 | 1.000 | 21.32 |
| ATOM | 1536 | CZ2 | TRP | A | 209 | 9.666 | 28.388 | 13.720 | 1.000 | 25.69 |
| ATOM | 1537 | C | TRP | A | 209 | 15.756 | 26.384 | 15.452 | 1.000 | 27.61 |
| ATOM | 1538 | O | TRP | A | 209 | 16.199 | 25.947 | 16.515 | 1.000 | 25.68 |
| ATOM | 1539 | N | PRO | A | 210 | 16.119 | 27.575 | 15.000 | 1.000 | 24.36 |
| ATOM | 1540 | CA | PRO | A | 210 | 17.083 | 28.369 | 15.787 | 1.000 | 26.72 |
| ATOM | 1541 | CB | PRO | A | 210 | 17.398 | 29.537 | 14.854 | 1.000 | 23.52 |
| ATOM | 1542 | CG | PRO | A | 210 | 16.330 | 29.568 | 13.828 | 1.000 | 30.83 |
| ATOM | 1543 | CD | PRO | A | 210 | 15.721 | 28.197 | 13.735 | 1.000 | 24.56 |
| ATOM | 1544 | C | PRO | A | 210 | 16.551 | 28.877 | 17.112 | 1.000 | 29.12 |
| ATOM | 1545 | O | PRO | A | 210 | 15.359 | 29.056 | 17.335 | 1.000 | 26.48 |
| ATOM | 1546 | N | ASP | A | 211 | 17.443 | 29.158 | 18.079 | 1.000 | 39.44 |
| ATOM | 1547 | CA | ASP | A | 211 | 17.006 | 29.720 | 19.366 | 1.000 | 34.21 |
| ATOM | 1548 | CB | ASP | A | 211 | 18.098 | 29.809 | 20.429 | 1.000 | 42.94 |
| ATOM | 1549 | CG | ASP | A | 211 | 19.528 | 29.592 | 20.007 | 1.000 | 62.84 |
| ATOM | 1550 | OD1 | ASP | A | 211 | 20.028 | 30.231 | 19.044 | 1.000 | 74.38 |
| ATOM | 1551 | OD2 | ASP | A | 211 | 20.212 | 28.773 | 20.663 | 1.000 | 76.33 |
| ATOM | 1552 | C | ASP | A | 211 | 16.433 | 31.124 | 19.187 | 1.000 | 35.17 |
| ATOM | 1553 | O | ASP | A | 211 | 15.656 | 31.640 | 19.987 | 1.000 | 38.20 |
| ATOM | 1554 | N | HIS | A | 212 | 16.818 | 31.816 | 18.113 | 1.000 | 39.51 |
| ATOM | 1555 | CA | HIS | A | 212 | 16.184 | 33.125 | 17.909 | 1.000 | 42.28 |
| ATOM | 1556 | CB | HIS | A | 212 | 17.197 | 34.250 | 18.143 | 1.000 | 51.96 |
| ATOM | 1557 | CG | HIS | A | 212 | 17.690 | 34.249 | 19.563 | 1.000 | 70.14 |
| ATOM | 1558 | ND1 | HIS | A | 212 | 18.969 | 33.878 | 19.916 | 1.000 | 72.27 |
| ATOM | 1559 | CE1 | HIS | A | 212 | 19.109 | 33.968 | 21.227 | 1.000 | 71.31 |

FIGURE 231

| ATOM | 1560 | NE2 | HIS | A | 212 | 17.962 | 34.385 | 21.735 | 1.000 | 73.22 |
| ATOM | 1561 | CD2 | HIS | A | 212 | 17.056 | 34.563 | 20.718 | 1.000 | 71.91 |
| ATOM | 1562 | C | HIS | A | 212 | 15.568 | 33.188 | 16.521 | 1.000 | 35.23 |
| ATOM | 1563 | O | HIS | A | 212 | 16.155 | 32.711 | 15.551 | 1.000 | 36.51 |
| ATOM | 1564 | N | GLY | A | 213 | 14.380 | 33.777 | 16.425 | 1.000 | 39.89 |
| ATOM | 1565 | CA | GLY | A | 213 | 13.712 | 33.934 | 15.149 | 1.000 | 35.59 |
| ATOM | 1566 | C | GLY | A | 213 | 13.306 | 32.607 | 14.530 | 1.000 | 40.76 |
| ATOM | 1567 | O | GLY | A | 213 | 13.230 | 31.604 | 15.240 | 1.000 | 29.83 |
| ATOM | 1568 | N | VAL | A | 214 | 13.073 | 32.661 | 13.224 | 1.000 | 26.99 |
| ATOM | 1569 | CA | VAL | A | 214 | 12.556 | 31.542 | 12.457 | 1.000 | 23.88 |
| ATOM | 1570 | CB | VAL | A | 214 | 11.489 | 32.069 | 11.477 | 1.000 | 27.24 |
| ATOM | 1571 | CG1 | VAL | A | 214 | 10.282 | 32.612 | 12.225 | 1.000 | 25.46 |
| ATOM | 1572 | CG2 | VAL | A | 214 | 12.081 | 33.158 | 10.585 | 1.000 | 32.07 |
| ATOM | 1573 | C | VAL | A | 214 | 13.672 | 30.841 | 11.701 | 1.000 | 33.49 |
| ATOM | 1574 | O | VAL | A | 214 | 14.782 | 31.393 | 11.653 | 1.000 | 41.50 |
| ATOM | 1575 | N | PRO | A | 215 | 13.433 | 29.666 | 11.132 | 1.000 | 33.79 |
| ATOM | 1576 | CA | PRO | A | 215 | 14.416 | 29.011 | 10.262 | 1.000 | 32.45 |
| ATOM | 1577 | CB | PRO | A | 215 | 13.625 | 27.863 | 9.628 | 1.000 | 27.07 |
| ATOM | 1578 | CG | PRO | A | 215 | 12.646 | 27.518 | 10.693 | 1.000 | 25.47 |
| ATOM | 1579 | CD | PRO | A | 215 | 12.228 | 28.835 | 11.297 | 1.000 | 29.25 |
| ATOM | 1580 | C | PRO | A | 215 | 14.948 | 29.950 | 9.185 | 1.000 | 39.16 |
| ATOM | 1581 | O | PRO | A | 215 | 14.249 | 30.839 | 8.704 | 1.000 | 42.31 |
| ATOM | 1582 | N | GLU | A | 216 | 16.215 | 29.755 | 8.813 | 1.000 | 33.87 |
| ATOM | 1583 | CA | GLU | A | 216 | 16.877 | 30.778 | 8.004 | 1.000 | 44.43 |
| ATOM | 1584 | CB | GLU | A | 216 | 18.392 | 30.715 | 8.244 | 1.000 | 52.43 |
| ATOM | 1585 | CG | GLU | A | 216 | 18.841 | 31.700 | 9.324 | 1.000 | 56.31 |
| ATOM | 1586 | CD | GLU | A | 216 | 20.119 | 32.423 | 8.940 | 1.000 | 68.80 |
| ATOM | 1587 | OE1 | GLU | A | 216 | 20.015 | 33.454 | 8.242 | 1.000 | 80.56 |
| ATOM | 1588 | OE2 | GLU | A | 216 | 21.208 | 31.946 | 9.333 | 1.000 | 68.46 |
| ATOM | 1589 | C | GLU | A | 216 | 16.531 | 30.688 | 6.522 | 1.000 | 40.23 |
| ATOM | 1590 | O | GLU | A | 216 | 16.633 | 31.700 | 5.823 | 1.000 | 37.48 |
| ATOM | 1591 | N | THR | A | 217 | 16.112 | 29.522 | 6.063 | 1.000 | 29.61 |
| ATOM | 1592 | CA | THR | A | 217 | 15.492 | 29.314 | 4.778 | 1.000 | 32.71 |
| ATOM | 1593 | CB | THR | A | 217 | 16.185 | 28.187 | 3.991 | 1.000 | 30.46 |
| ATOM | 1594 | OG1 | THR | A | 217 | 16.030 | 26.987 | 4.770 | 1.000 | 35.61 |
| ATOM | 1595 | CG2 | THR | A | 217 | 17.669 | 28.469 | 3.835 | 1.000 | 34.53 |
| ATOM | 1596 | C | THR | A | 217 | 14.031 | 28.881 | 4.915 | 1.000 | 36.27 |
| ATOM | 1597 | O | THR | A | 217 | 13.686 | 28.153 | 5.839 | 1.000 | 30.65 |
| ATOM | 1598 | N | THR | A | 218 | 13.176 | 29.290 | 3.990 | 1.000 | 31.97 |
| ATOM | 1599 | CA | THR | A | 218 | 11.842 | 28.692 | 3.901 | 1.000 | 22.66 |
| ATOM | 1600 | CB | THR | A | 218 | 10.987 | 29.433 | 2.861 | 1.000 | 20.62 |
| ATOM | 1601 | OG1 | THR | A | 218 | 11.671 | 29.423 | 1.600 | 1.000 | 24.39 |
| ATOM | 1602 | CG2 | THR | A | 218 | 10.804 | 30.879 | 3.294 | 1.000 | 23.42 |
| ATOM | 1603 | C | THR | A | 218 | 11.951 | 27.225 | 3.518 | 1.000 | 28.74 |
| ATOM | 1604 | O | THR | A | 218 | 11.142 | 26.377 | 3.905 | 1.000 | 32.65 |
| ATOM | 1605 | N | GLN | A | 219 | 12.969 | 26.889 | 2.721 | 1.000 | 25.74 |
| ATOM | 1606 | CA | GLN | A | 219 | 13.056 | 25.550 | 2.173 | 1.000 | 20.41 |
| ATOM | 1607 | CB | GLN | A | 219 | 14.365 | 25.386 | 1.388 | 1.000 | 28.06 |
| ATOM | 1608 | CG | GLN | A | 219 | 14.167 | 24.541 | 0.137 | 1.000 | 47.72 |
| ATOM | 1609 | CD | GLN | A | 219 | 14.872 | 23.201 | 0.253 | 1.000 | 57.11 |
| ATOM | 1610 | OE1 | GLN | A | 219 | 14.297 | 22.182 | -0.133 | 1.000 | 42.74 |
| ATOM | 1611 | NE2 | GLN | A | 219 | 16.096 | 23.246 | 0.779 | 1.000 | 56.71 |

FIGURE 232

| | | | | | | | | | |
|---|---|---|---|---|---|---|---|---|---|
|ATOM|1612|C|GLN|A|219|13.010|24.421|3.211|1.000 22.65|
|ATOM|1613|O|GLN|A|219|12.351|23.416|3.001|1.000 26.69|
|ATOM|1614|N|SER|A|220|13.741|24.594|4.294|1.000 26.94|
|ATOM|1615|CA|SER|A|220|13.846|23.658|5.400|1.000 30.86|
|ATOM|1616|CB|SER|A|220|14.660|24.279|6.537|1.000 29.59|
|ATOM|1617|OG|SER|A|220|14.662|23.505|7.717|1.000 28.43|
|ATOM|1618|C|SER|A|220|12.463|23.280|5.946|1.000 20.04|
|ATOM|1619|O|SER|A|220|12.135|22.096|5.958|1.000 27.37|
|ATOM|1620|N|LEU|A|221|11.711|24.297|6.378|1.000 21.52|
|ATOM|1621|CA|LEU|A|221|10.414|23.978|6.996|1.000 19.60|
|ATOM|1622|CB|LEU|A|221|9.875|25.107|7.874|1.000 18.57|
|ATOM|1623|CG|LEU|A|221|8.762|24.639|8.827|1.000 20.88|
|ATOM|1624|CD1|LEU|A|221|9.333|23.645|9.830|1.000 24.60|
|ATOM|1625|CD2|LEU|A|221|8.061|25.779|9.537|1.000 16.09|
|ATOM|1626|C|LEU|A|221|9.436|23.546|5.914|1.000 21.46|
|ATOM|1627|O|LEU|A|221|8.613|22.659|6.182|1.000 22.12|
|ATOM|1628|N|ILE|A|222|9.507|24.112|4.703|1.000 21.43|
|ATOM|1629|CA|ILE|A|222|8.594|23.627|3.661|1.000 19.51|
|ATOM|1630|CB|ILE|A|222|8.782|24.425|2.352|1.000 17.06|
|ATOM|1631|CG1|ILE|A|222|8.267|25.866|2.483|1.000 22.29|
|ATOM|1632|CD1|ILE|A|222|8.545|26.686|1.227|1.000 25.18|
|ATOM|1633|CG2|ILE|A|222|8.150|23.690|1.193|1.000 22.06|
|ATOM|1634|C|ILE|A|222|8.788|22.150|3.399|1.000 23.90|
|ATOM|1635|O|ILE|A|222|7.832|21.361|3.253|1.000 19.79|
|ATOM|1636|N|GLN|A|223|10.049|21.706|3.348|1.000 23.36|
|ATOM|1637|CA|GLN|A|223|10.361|20.297|3.096|1.000 22.31|
|ATOM|1638|CB|GLN|A|223|11.867|20.094|2.866|1.000 27.99|
|ATOM|1639|CG|GLN|A|223|12.297|18.683|2.510|1.000 27.69|
|ATOM|1640|CD|GLN|A|223|11.727|18.170|1.203|1.000 36.04|
|ATOM|1641|OE1|GLN|A|223|11.311|18.929|0.325|1.000 38.77|
|ATOM|1642|NE2|GLN|A|223|11.677|16.854|1.025|1.000 34.81|
|ATOM|1643|C|GLN|A|223|9.921|19.383|4.245|1.000 22.46|
|ATOM|1644|O|GLN|A|223|9.447|18.263|3.994|1.000 19.87|
|ATOM|1645|N|PHE|A|224|10.087|19.878|5.470|1.000 20.95|
|ATOM|1646|CA|PHE|A|224|9.694|19.074|6.635|1.000 20.11|
|ATOM|1647|CB|PHE|A|224|10.163|19.747|7.918|1.000 18.59|
|ATOM|1648|CG|PHE|A|224|9.767|19.057|9.228|1.000 14.91|
|ATOM|1649|CD1|PHE|A|224|10.211|17.795|9.547|1.000 18.83|
|ATOM|1650|CE1|PHE|A|224|9.852|17.187|10.760|1.000 16.08|
|ATOM|1651|CZ|PHE|A|224|9.030|17.866|11.638|1.000 14.76|
|ATOM|1652|CE2|PHE|A|224|8.568|19.140|11.351|1.000 18.06|
|ATOM|1653|CD2|PHE|A|224|8.947|19.716|10.141|1.000 19.42|
|ATOM|1654|C|PHE|A|224|8.172|18.890|6.630|1.000 16.39|
|ATOM|1655|O|PHE|A|224|7.689|17.764|6.787|1.000 18.08|
|ATOM|1656|N|VAL|A|225|7.464|20.012|6.459|1.000 20.25|
|ATOM|1657|CA|VAL|A|225|5.992|19.996|6.408|1.000 17.55|
|ATOM|1658|CB|VAL|A|225|5.419|21.411|6.253|1.000 21.00|
|ATOM|1659|CG1|VAL|A|225|3.947|21.344|5.850|1.000 16.31|
|ATOM|1660|CG2|VAL|A|225|5.626|22.177|7.560|1.000 13.40|
|ATOM|1661|C|VAL|A|225|5.512|19.084|5.298|1.000 17.64|
|ATOM|1662|O|VAL|A|225|4.671|18.200|5.484|1.000 18.82|
|ATOM|1663|N|ARG|A|226|6.062|19.192|4.088|1.000 19.58|

FIGURE 233

| | | | | | | | | | |
|---|---|---|---|---|---|---|---|---|---|
| ATOM | 1664 | CA | ARG | A | 226 | 5.619 | 18.308 | 3.009 | 1.000 20.05 |
| ATOM | 1665 | CB | ARG | A | 226 | 6.285 | 18.775 | 1.705 | 1.000 20.92 |
| ATOM | 1666 | CG | ARG | A | 226 | 5.686 | 20.090 | 1.204 | 1.000 21.90 |
| ATOM | 1667 | CD | ARG | A | 226 | 6.324 | 20.446 | -0.145 | 1.000 22.66 |
| ATOM | 1668 | NE | ARG | A | 226 | 5.564 | 21.504 | -0.798 | 1.000 24.99 |
| ATOM | 1669 | CZ | ARG | A | 226 | 6.095 | 22.322 | -1.697 | 1.000 40.94 |
| ATOM | 1670 | NH1 | ARG | A | 226 | 7.381 | 22.153 | -1.994 | 1.000 28.79 |
| ATOM | 1671 | NH2 | ARG | A | 226 | 5.371 | 23.272 | -2.281 | 1.000 30.57 |
| ATOM | 1672 | C | ARG | A | 226 | 5.923 | 16.848 | 3.263 | 1.000 17.75 |
| ATOM | 1673 | O | ARG | A | 226 | 5.172 | 15.933 | 2.955 | 1.000 19.58 |
| ATOM | 1674 | N | THR | A | 227 | 7.055 | 16.531 | 3.881 | 1.000 19.90 |
| ATOM | 1675 | CA | THR | A | 227 | 7.391 | 15.168 | 4.247 | 1.000 15.51 |
| ATOM | 1676 | CB | THR | A | 227 | 8.835 | 15.143 | 4.821 | 1.000 21.32 |
| ATOM | 1677 | OG1 | THR | A | 227 | 9.764 | 15.609 | 3.823 | 1.000 22.05 |
| ATOM | 1678 | CG2 | THR | A | 227 | 9.217 | 13.723 | 5.189 | 1.000 20.98 |
| ATOM | 1679 | C | THR | A | 227 | 6.413 | 14.588 | 5.271 | 1.000 15.49 |
| ATOM | 1680 | O | THR | A | 227 | 5.919 | 13.477 | 5.141 | 1.000 19.20 |
| ATOM | 1681 | N | VAL | A | 228 | 6.109 | 15.318 | 6.325 | 1.000 16.11 |
| ATOM | 1682 | CA | VAL | A | 228 | 5.143 | 14.927 | 7.341 | 1.000 18.46 |
| ATOM | 1683 | CB | VAL | A | 228 | 5.031 | 15.957 | 8.477 | 1.000 17.87 |
| ATOM | 1684 | CG1 | VAL | A | 228 | 3.887 | 15.568 | 9.414 | 1.000 18.37 |
| ATOM | 1685 | CG2 | VAL | A | 228 | 6.318 | 16.108 | 9.270 | 1.000 27.25 |
| ATOM | 1686 | C | VAL | A | 228 | 3.751 | 14.744 | 6.713 | 1.000 17.43 |
| ATOM | 1687 | O | VAL | A | 228 | 3.112 | 13.723 | 6.983 | 1.000 17.33 |
| ATOM | 1688 | N | ARG | A | 229 | 3.338 | 15.721 | 5.898 | 1.000 18.35 |
| ATOM | 1689 | CA | ARG | A | 229 | 2.003 | 15.683 | 5.292 | 1.000 20.21 |
| ATOM | 1690 | CB | ARG | A | 229 | 1.710 | 16.982 | 4.560 | 1.000 20.48 |
| ATOM | 1691 | CG | ARG | A | 229 | 0.475 | 16.989 | 3.670 | 1.000 22.85 |
| ATOM | 1692 | CD | ARG | A | 229 | -0.750 | 16.409 | 4.384 | 1.000 19.41 |
| ATOM | 1693 | NE | ARG | A | 229 | -1.031 | 17.165 | 5.615 | 1.000 19.35 |
| ATOM | 1694 | CZ | ARG | A | 229 | -2.026 | 16.831 | 6.444 | 1.000 19.18 |
| ATOM | 1695 | NH1 | ARG | A | 229 | -2.773 | 15.784 | 6.097 | 1.000 19.75 |
| ATOM | 1696 | NH2 | ARG | A | 229 | -2.266 | 17.508 | 7.550 | 1.000 14.67 |
| ATOM | 1697 | C | ARG | A | 229 | 1.917 | 14.434 | 4.421 | 1.000 25.70 |
| ATOM | 1698 | O | ARG | A | 229 | 0.933 | 13.683 | 4.482 | 1.000 28.00 |
| ATOM | 1699 | N | ASP | A | 230 | 2.949 | 14.152 | 3.627 | 1.000 23.44 |
| ATOM | 1700 | CA | ASP | A | 230 | 3.008 | 12.884 | 2.886 | 1.000 26.19 |
| ATOM | 1701 | CB | ASP | A | 230 | 4.322 | 12.757 | 2.098 | 1.000 25.54 |
| ATOM | 1702 | CG | ASP | A | 230 | 4.325 | 13.611 | 0.845 | 1.000 39.61 |
| ATOM | 1703 | OD1 | ASP | A | 230 | 3.251 | 14.111 | 0.450 | 1.000 29.77 |
| ATOM | 1704 | OD2 | ASP | A | 230 | 5.398 | 13.806 | 0.233 | 1.000 42.44 |
| ATOM | 1705 | C | ASP | A | 230 | 2.880 | 11.659 | 3.771 | 1.000 30.77 |
| ATOM | 1706 | O | ASP | A | 230 | 2.146 | 10.713 | 3.455 | 1.000 27.25 |
| ATOM | 1707 | N | TYR | A | 231 | 3.596 | 11.597 | 4.906 | 1.000 26.11 |
| ATOM | 1708 | CA | TYR | A | 231 | 3.418 | 10.399 | 5.737 | 1.000 21.69 |
| ATOM | 1709 | CB | TYR | A | 231 | 4.351 | 10.385 | 6.946 | 1.000 30.21 |
| ATOM | 1710 | CG | TYR | A | 231 | 5.747 | 9.892 | 6.649 | 1.000 33.51 |
| ATOM | 1711 | CD1 | TYR | A | 231 | 5.992 | 8.543 | 6.409 | 1.000 34.93 |
| ATOM | 1712 | CE1 | TYR | A | 231 | 7.275 | 8.109 | 6.131 | 1.000 37.60 |
| ATOM | 1713 | CZ | TYR | A | 231 | 8.331 | 8.999 | 6.092 | 1.000 28.01 |
| ATOM | 1714 | OH | TYR | A | 231 | 9.604 | 8.546 | 5.820 | 1.000 29.93 |
| ATOM | 1715 | CE2 | TYR | A | 231 | 8.100 | 10.334 | 6.323 | 1.000 19.51 |

FIGURE 234

| | | | | | | | | |
|---|---|---|---|---|---|---|---|---|
| ATOM | 1716 | CD2 | TYR A 231 | 6.819 | 10.771 | 6.592 | 1.000 | 19.51 |
| ATOM | 1717 | C | TYR A 231 | 1.994 | 10.314 | 6.274 | 1.000 | 26.15 |
| ATOM | 1718 | O | TYR A 231 | 1.372 | 9.255 | 6.320 | 1.000 | 30.72 |
| ATOM | 1719 | N | ILE A 232 | 1.503 | 11.467 | 6.729 | 1.000 | 22.90 |
| ATOM | 1720 | CA | ILE A 232 | 0.167 | 11.452 | 7.319 | 1.000 | 24.42 |
| ATOM | 1721 | CB | ILE A 232 | -0.271 | 12.843 | 7.788 | 1.000 | 28.90 |
| ATOM | 1722 | CG1 | ILE A 232 | 0.566 | 13.416 | 8.935 | 1.000 | 17.25 |
| ATOM | 1723 | CD1 | ILE A 232 | 0.205 | 14.859 | 9.204 | 1.000 | 22.29 |
| ATOM | 1724 | CG2 | ILE A 232 | -1.764 | 12.825 | 8.134 | 1.000 | 28.46 |
| ATOM | 1725 | C | ILE A 232 | -0.881 | 10.941 | 6.329 | 1.000 | 26.86 |
| ATOM | 1726 | O | ILE A 232 | -1.758 | 10.140 | 6.669 | 1.000 | 32.19 |
| ATOM | 1727 | N | ASN A 233 | -0.764 | 11.429 | 5.106 | 1.000 | 25.93 |
| ATOM | 1728 | CA | ASN A 233 | -1.751 | 11.166 | 4.070 | 1.000 | 30.21 |
| ATOM | 1729 | CB | ASN A 233 | -1.549 | 12.124 | 2.900 | 1.000 | 24.13 |
| ATOM | 1730 | CG | ASN A 233 | -2.266 | 13.446 | 3.088 | 1.000 | 31.27 |
| ATOM | 1731 | OD1 | ASN A 233 | -2.889 | 13.743 | 4.112 | 1.000 | 29.17 |
| ATOM | 1732 | ND2 | ASN A 233 | -2.134 | 14.239 | 2.035 | 1.000 | 30.92 |
| ATOM | 1733 | C | ASN A 233 | -1.671 | 9.730 | 3.568 | 1.000 | 41.91 |
| ATOM | 1734 | O | ASN A 233 | -2.603 | 9.199 | 2.958 | 1.000 | 41.91 |
| ATOM | 1735 | N | ARG A 234 | -0.536 | 9.078 | 3.791 | 1.000 | 45.86 |
| ATOM | 1736 | CA | ARG A 234 | -0.326 | 7.804 | 3.086 | 1.000 | 50.95 |
| ATOM | 1737 | CB | ARG A 234 | 1.109 | 7.725 | 2.547 | 1.000 | 40.12 |
| ATOM | 1738 | CG | ARG A 234 | 1.343 | 8.844 | 1.545 | 1.000 | 46.93 |
| ATOM | 1739 | CD | ARG A 234 | 2.117 | 8.452 | 0.310 | 1.000 | 57.95 |
| ATOM | 1740 | NE | ARG A 234 | 2.532 | 9.653 | -0.429 | 1.000 | 68.35 |
| ATOM | 1741 | CZ | ARG A 234 | 3.780 | 10.094 | -0.506 | 1.000 | 67.12 |
| ATOM | 1742 | NH1 | ARG A 234 | 4.774 | 9.450 | 0.100 | 1.000 | 63.01 |
| ATOM | 1743 | NH2 | ARG A 234 | 4.041 | 11.192 | -1.199 | 1.000 | 61.94 |
| ATOM | 1744 | C | ARG A 234 | -0.696 | 6.676 | 4.029 | 1.000 | 60.20 |
| ATOM | 1745 | O | ARG A 234 | -0.601 | 5.491 | 3.730 | 1.000 | 87.41 |
| ATOM | 1746 | N | SER A 235 | -1.146 | 7.142 | 5.194 | 1.000 | 44.81 |
| ATOM | 1747 | CA | SER A 235 | -1.664 | 6.224 | 6.191 | 1.000 | 50.50 |
| ATOM | 1748 | CB | SER A 235 | -1.332 | 6.720 | 7.596 | 1.000 | 40.08 |
| ATOM | 1749 | OG | SER A 235 | -2.550 | 7.165 | 8.201 | 1.000 | 64.20 |
| ATOM | 1750 | C | SER A 235 | -3.184 | 6.066 | 6.042 | 1.000 | 58.76 |
| ATOM | 1751 | O | SER A 235 | -3.835 | 6.996 | 5.553 | 1.000 | 38.45 |
| ATOM | 1752 | N | PRO A 236 | -3.665 | 4.905 | 6.477 | 1.000 | 62.13 |
| ATOM | 1753 | CA | PRO A 236 | -5.059 | 4.491 | 6.327 | 1.000 | 58.65 |
| ATOM | 1754 | CB | PRO A 236 | -5.065 | 3.010 | 6.716 | 1.000 | 53.85 |
| ATOM | 1755 | CG | PRO A 236 | -3.634 | 2.599 | 6.792 | 1.000 | 49.45 |
| ATOM | 1756 | CD | PRO A 236 | -2.898 | 3.851 | 7.185 | 1.000 | 58.01 |
| ATOM | 1757 | C | PRO A 236 | -5.975 | 5.258 | 7.275 | 1.000 | 58.23 |
| ATOM | 1758 | O | PRO A 236 | -7.033 | 5.742 | 6.887 | 1.000 | 62.93 |
| ATOM | 1759 | N | GLY A 237 | -5.535 | 5.351 | 8.526 | 1.000 | 50.71 |
| ATOM | 1760 | CA | GLY A 237 | -6.297 | 6.108 | 9.514 | 1.000 | 46.90 |
| ATOM | 1761 | C | GLY A 237 | -5.292 | 6.580 | 10.552 | 1.000 | 55.40 |
| ATOM | 1762 | O | GLY A 237 | -4.274 | 5.894 | 10.681 | 1.000 | 60.29 |
| ATOM | 1763 | N | ALA A 238 | -5.566 | 7.689 | 11.229 | 1.000 | 61.94 |
| ATOM | 1764 | CA | ALA A 238 | -4.552 | 8.203 | 12.150 | 1.000 | 56.95 |
| ATOM | 1765 | CB | ALA A 238 | -3.434 | 8.854 | 11.328 | 1.000 | 52.44 |
| ATOM | 1766 | C | ALA A 238 | -5.070 | 9.174 | 13.195 | 1.000 | 50.99 |
| ATOM | 1767 | O | ALA A 238 | -4.242 | 9.571 | 14.033 | 1.000 | 57.56 |

FIGURE 235

| | | | | | | | | | |
|---|---|---|---|---|---|---|---|---|---|
| ATOM | 1768 | N | GLY | A | 239 | -6.349 | 9.552 | 13.199 | 1.000 34.51 |
| ATOM | 1769 | CA | GLY | A | 239 | -6.845 | 10.375 | 14.310 | 1.000 33.83 |
| ATOM | 1770 | C | GLY | A | 239 | -6.120 | 11.715 | 14.312 | 1.000 20.85 |
| ATOM | 1771 | O | GLY | A | 239 | -5.394 | 11.963 | 13.335 | 1.000 30.52 |
| ATOM | 1772 | N | PRO | A | 240 | -6.258 | 12.599 | 15.276 | 1.000 28.46 |
| ATOM | 1773 | CA | PRO | A | 240 | -5.589 | 13.905 | 15.105 | 1.000 23.74 |
| ATOM | 1774 | CB | PRO | A | 240 | -6.004 | 14.716 | 16.315 | 1.000 31.69 |
| ATOM | 1775 | CG | PRO | A | 240 | -7.078 | 13.958 | 16.996 | 1.000 36.41 |
| ATOM | 1776 | CD | PRO | A | 240 | -6.964 | 12.527 | 16.559 | 1.000 28.90 |
| ATOM | 1777 | C | PRO | A | 240 | -4.072 | 13.702 | 15.099 | 1.000 25.52 |
| ATOM | 1778 | O | PRO | A | 240 | -3.538 | 12.739 | 15.647 | 1.000 25.98 |
| ATOM | 1779 | N | THR | A | 241 | -3.404 | 14.642 | 14.458 | 1.000 19.16 |
| ATOM | 1780 | CA | THR | A | 241 | -1.954 | 14.695 | 14.504 | 1.000 17.79 |
| ATOM | 1781 | CB | THR | A | 241 | -1.388 | 15.324 | 13.206 | 1.000 16.44 |
| ATOM | 1782 | OG1 | THR | A | 241 | -1.782 | 14.534 | 12.091 | 1.000 18.37 |
| ATOM | 1783 | CG2 | THR | A | 241 | 0.130 | 15.352 | 13.322 | 1.000 18.85 |
| ATOM | 1784 | C | THR | A | 241 | -1.547 | 15.547 | 15.690 | 1.000 16.03 |
| ATOM | 1785 | O | THR | A | 241 | -2.027 | 16.671 | 15.783 | 1.000 14.26 |
| ATOM | 1786 | N | VAL | A | 242 | -0.710 | 15.081 | 16.604 | 1.000 14.89 |
| ATOM | 1787 | CA | VAL | A | 242 | -0.276 | 15.964 | 17.707 | 1.000 12.20 |
| ATOM | 1788 | CB | VAL | A | 242 | 0.120 | 15.076 | 18.909 | 1.000 15.21 |
| ATOM | 1789 | CG1 | VAL | A | 242 | 0.983 | 15.784 | 19.937 | 1.000 15.58 |
| ATOM | 1790 | CG2 | VAL | A | 242 | -1.132 | 14.525 | 19.592 | 1.000 15.20 |
| ATOM | 1791 | C | VAL | A | 242 | 0.896 | 16.806 | 17.253 | 1.000 15.62 |
| ATOM | 1792 | O | VAL | A | 242 | 1.838 | 16.295 | 16.614 | 1.000 16.25 |
| ATOM | 1793 | N | VAL | A | 243 | 0.877 | 18.091 | 17.577 | 1.000 13.63 |
| ATOM | 1794 | CA | VAL | A | 243 | 1.995 | 18.961 | 17.231 | 1.000 14.54 |
| ATOM | 1795 | CB | VAL | A | 243 | 1.707 | 19.938 | 16.086 | 1.000 18.21 |
| ATOM | 1796 | CG1 | VAL | A | 243 | 2.970 | 20.692 | 15.648 | 1.000 15.88 |
| ATOM | 1797 | CG2 | VAL | A | 243 | 1.120 | 19.216 | 14.869 | 1.000 17.94 |
| ATOM | 1798 | C | VAL | A | 243 | 2.377 | 19.709 | 18.502 | 1.000 14.26 |
| ATOM | 1799 | O | VAL | A | 243 | 1.559 | 20.250 | 19.248 | 1.000 16.04 |
| ATOM | 1800 | N | HIS | A | 244 | 3.686 | 19.752 | 18.781 | 1.000 17.37 |
| ATOM | 1801 | CA | HIS | A | 244 | 4.097 | 20.519 | 19.951 | 1.000 14.10 |
| ATOM | 1802 | CB | HIS | A | 244 | 4.022 | 19.648 | 21.202 | 1.000 15.84 |
| ATOM | 1803 | CG | HIS | A | 244 | 5.142 | 18.657 | 21.367 | 1.000 17.02 |
| ATOM | 1804 | ND1 | HIS | A | 244 | 6.351 | 19.001 | 21.955 | 1.000 21.61 |
| ATOM | 1805 | CE1 | HIS | A | 244 | 7.130 | 17.936 | 21.988 | 1.000 17.38 |
| ATOM | 1806 | NE2 | HIS | A | 244 | 6.471 | 16.897 | 21.474 | 1.000 16.96 |
| ATOM | 1807 | CD2 | HIS | A | 244 | 5.226 | 17.346 | 21.099 | 1.000 12.72 |
| ATOM | 1808 | C | HIS | A | 244 | 5.511 | 21.073 | 19.792 | 1.000 15.92 |
| ATOM | 1809 | O | HIS | A | 244 | 6.302 | 20.556 | 18.999 | 1.000 15.50 |
| ATOM | 1810 | N | CYS | A | 245 | 5.762 | 22.123 | 20.572 | 1.000 19.65 |
| ATOM | 1811 | CA | CYS | A | 245 | 7.129 | 22.659 | 20.697 | 1.000 23.91 |
| ATOM | 1812 | CB | CYS | A | 245 | 7.258 | 24.015 | 19.998 | 1.000 21.22 |
| ATOM | 1813 | SG | CYS | A | 245 | 5.939 | 25.207 | 20.299 | 1.000 27.54 |
| ATOM | 1814 | C | CYS | A | 245 | 7.436 | 22.703 | 22.181 | 1.000 25.09 |
| ATOM | 1815 | O | CYS | A | 245 | 7.226 | 21.699 | 22.894 | 1.000 22.16 |
| ATOM | 1816 | N | SER | A | 246 | 7.888 | 23.809 | 22.751 | 1.000 19.84 |
| ATOM | 1817 | CA | SER | A | 246 | 7.969 | 23.838 | 24.223 | 1.000 16.95 |
| ATOM | 1818 | CB | SER | A | 246 | 9.152 | 24.728 | 24.635 | 1.000 22.80 |
| ATOM | 1819 | OG | SER | A | 246 | 9.277 | 24.846 | 26.034 | 1.000 23.37 |

FIGURE 236

```
ATOM   1820  C    SER A 246       6.660  24.303  24.834  1.000  18.58
ATOM   1821  O    SER A 246       6.097  23.705  25.756  1.000  23.44
ATOM   1822  N    ALA A 247       6.105  25.428  24.344  1.000  21.38
ATOM   1823  CA   ALA A 247       4.834  25.878  24.909  1.000  26.84
ATOM   1824  CB   ALA A 247       4.815  27.397  25.044  1.000  30.94
ATOM   1825  C    ALA A 247       3.627  25.429  24.082  1.000  18.61
ATOM   1826  O    ALA A 247       2.500  25.492  24.563  1.000  23.09
ATOM   1827  N    GLY A 248       3.876  24.984  22.867  1.000  20.85
ATOM   1828  CA   GLY A 248       2.846  24.579  21.933  1.000  24.45
ATOM   1829  C    GLY A 248       2.113  25.731  21.278  1.000  30.38
ATOM   1830  O    GLY A 248       0.928  25.550  20.948  1.000  32.96
ATOM   1831  N    VAL A 249       2.794  26.852  21.091  1.000  21.75
ATOM   1832  CA   VAL A 249       2.214  28.061  20.510  1.000  26.90
ATOM   1833  CB   VAL A 249       2.293  29.257  21.504  1.000  35.49
ATOM   1834  CG1  VAL A 249       1.266  29.099  22.616  1.000  56.26
ATOM   1835  CG2  VAL A 249       3.654  29.410  22.145  1.000  24.47
ATOM   1836  C    VAL A 249       2.839  28.525  19.210  1.000  22.79
ATOM   1837  O    VAL A 249       2.200  28.508  18.151  1.000  26.47
ATOM   1838  N    GLY A 250       4.064  29.056  19.197  1.000  24.61
ATOM   1839  CA   GLY A 250       4.490  29.816  18.032  1.000  16.91
ATOM   1840  C    GLY A 250       4.953  28.914  16.917  1.000  21.72
ATOM   1841  O    GLY A 250       4.438  28.910  15.787  1.000  20.15
ATOM   1842  N    ARG A 251       5.967  28.114  17.253  1.000  19.78
ATOM   1843  CA   ARG A 251       6.512  27.182  16.284  1.000  21.28
ATOM   1844  CB   ARG A 251       7.717  26.381  16.767  1.000  26.04
ATOM   1845  CG   ARG A 251       8.878  27.181  17.346  1.000  34.41
ATOM   1846  CD   ARG A 251      10.132  26.322  17.479  1.000  26.22
ATOM   1847  NE   ARG A 251      11.199  27.043  18.161  1.000  30.53
ATOM   1848  CZ   ARG A 251      12.191  26.523  18.874  1.000  32.54
ATOM   1849  NH1  ARG A 251      12.297  25.212  19.033  1.000  22.98
ATOM   1850  NH2  ARG A 251      13.080  27.349  19.428  1.000  27.69
ATOM   1851  C    ARG A 251       5.417  26.194  15.829  1.000  22.23
ATOM   1852  O    ARG A 251       5.358  25.859  14.651  1.000  15.33
ATOM   1853  N    THR A 252       4.631  25.769  16.810  1.000  19.69
ATOM   1854  CA   THR A 252       3.579  24.773  16.547  1.000  20.16
ATOM   1855  CB   THR A 252       2.960  24.322  17.888  1.000  22.57
ATOM   1856  OG1  THR A 252       3.926  23.485  18.569  1.000  20.75
ATOM   1857  CG2  THR A 252       1.709  23.474  17.699  1.000  17.40
ATOM   1858  C    THR A 252       2.554  25.401  15.618  1.000  18.08
ATOM   1859  O    THR A 252       2.136  24.800  14.632  1.000  19.10
ATOM   1860  N    GLY A 253       2.134  26.639  15.924  1.000  17.29
ATOM   1861  CA   GLY A 253       1.142  27.297  15.074  1.000  14.74
ATOM   1862  C    GLY A 253       1.662  27.585  13.675  1.000  23.43
ATOM   1863  O    GLY A 253       0.946  27.483  12.672  1.000  14.99
ATOM   1864  N    THR A 254       2.940  27.949  13.575  1.000  18.08
ATOM   1865  CA   THR A 254       3.601  28.145  12.289  1.000  17.61
ATOM   1866  CB   THR A 254       5.014  28.741  12.533  1.000  16.64
ATOM   1867  OG1  THR A 254       4.873  29.982  13.251  1.000  20.15
ATOM   1868  CG2  THR A 254       5.694  29.043  11.221  1.000  17.02
ATOM   1869  C    THR A 254       3.643  26.845  11.511  1.000  16.81
ATOM   1870  O    THR A 254       3.355  26.769  10.313  1.000  17.03
ATOM   1871  N    PHE A 255       3.981  25.701  12.162  1.000  17.85
```

FIGURE 237

| ATOM | 1872 | CA  | PHE | A | 255 | 3.963  | 24.414 | 11.477 | 1.000 | 13.47 |
| ATOM | 1873 | CB  | PHE | A | 255 | 4.343  | 23.241 | 12.408 | 1.000 | 13.89 |
| ATOM | 1874 | CG  | PHE | A | 255 | 4.219  | 21.881 | 11.732 | 1.000 | 14.73 |
| ATOM | 1875 | CD1 | PHE | A | 255 | 5.240  | 21.372 | 10.954 | 1.000 | 12.62 |
| ATOM | 1876 | CE1 | PHE | A | 255 | 5.203  | 20.153 | 10.292 | 1.000 | 16.48 |
| ATOM | 1877 | CZ  | PHE | A | 255 | 4.042  | 19.390 | 10.390 | 1.000 | 17.68 |
| ATOM | 1878 | CE2 | PHE | A | 255 | 3.012  | 19.881 | 11.182 | 1.000 | 13.26 |
| ATOM | 1879 | CD2 | PHE | A | 255 | 3.081  | 21.074 | 11.855 | 1.000 | 16.37 |
| ATOM | 1880 | C   | PHE | A | 255 | 2.554  | 24.154 | 10.899 | 1.000 | 10.19 |
| ATOM | 1881 | O   | PHE | A | 255 | 2.385  | 23.771 | 9.748  | 1.000 | 15.90 |
| ATOM | 1882 | N   | ILE | A | 256 | 1.557  | 24.332 | 11.785 | 1.000 | 12.97 |
| ATOM | 1883 | CA  | ILE | A | 256 | 0.188  | 23.972 | 11.333 | 1.000 | 13.95 |
| ATOM | 1884 | CB  | ILE | A | 256 | -0.779 | 23.954 | 12.523 | 1.000 | 13.52 |
| ATOM | 1885 | CG1 | ILE | A | 256 | -0.475 | 22.759 | 13.451 | 1.000 | 15.18 |
| ATOM | 1886 | CD1 | ILE | A | 256 | -1.294 | 22.825 | 14.733 | 1.000 | 19.48 |
| ATOM | 1887 | CG2 | ILE | A | 256 | -2.238 | 23.941 | 12.124 | 1.000 | 19.86 |
| ATOM | 1888 | C   | ILE | A | 256 | -0.290 | 24.885 | 10.223 | 1.000 | 12.32 |
| ATOM | 1889 | O   | ILE | A | 256 | -0.822 | 24.432 | 9.205  | 1.000 | 16.82 |
| ATOM | 1890 | N   | ALA | A | 257 | -0.075 | 26.179 | 10.375 | 1.000 | 13.56 |
| ATOM | 1891 | CA  | ALA | A | 257 | -0.526 | 27.108 | 9.330  | 1.000 | 13.60 |
| ATOM | 1892 | CB  | ALA | A | 257 | -0.232 | 28.522 | 9.818  | 1.000 | 18.20 |
| ATOM | 1893 | C   | ALA | A | 257 | 0.148  | 26.789 | 8.011  | 1.000 | 17.01 |
| ATOM | 1894 | O   | ALA | A | 257 | -0.446 | 26.751 | 6.923  | 1.000 | 16.67 |
| ATOM | 1895 | N   | LEU | A | 258 | 1.461  | 26.519 | 8.059  | 1.000 | 17.25 |
| ATOM | 1896 | CA  | LEU | A | 258 | 2.147  | 26.158 | 6.822  | 1.000 | 17.53 |
| ATOM | 1897 | CB  | LEU | A | 258 | 3.654  | 26.013 | 7.044  | 1.000 | 17.08 |
| ATOM | 1898 | CG  | LEU | A | 258 | 4.507  | 25.868 | 5.780  | 1.000 | 20.80 |
| ATOM | 1899 | CD1 | LEU | A | 258 | 4.222  | 27.003 | 4.793  | 1.000 | 15.05 |
| ATOM | 1900 | CD2 | LEU | A | 258 | 5.992  | 25.859 | 6.121  | 1.000 | 18.82 |
| ATOM | 1901 | C   | LEU | A | 258 | 1.622  | 24.850 | 6.248  | 1.000 | 18.92 |
| ATOM | 1902 | O   | LEU | A | 258 | 1.448  | 24.706 | 5.036  | 1.000 | 18.97 |
| ATOM | 1903 | N   | ASP | A | 259 | 1.363  | 23.837 | 7.090  | 1.000 | 16.07 |
| ATOM | 1904 | CA  | ASP | A | 259 | 0.754  | 22.618 | 6.578  | 1.000 | 10.97 |
| ATOM | 1905 | CB  | ASP | A | 259 | 0.551  | 21.650 | 7.742  | 1.000 | 13.81 |
| ATOM | 1906 | CG  | ASP | A | 259 | -0.025 | 20.310 | 7.371  | 1.000 | 17.58 |
| ATOM | 1907 | OD1 | ASP | A | 259 | 0.282  | 19.727 | 6.307  | 1.000 | 16.06 |
| ATOM | 1908 | OD2 | ASP | A | 259 | -0.800 | 19.817 | 8.233  | 1.000 | 19.09 |
| ATOM | 1909 | C   | ASP | A | 259 | -0.574 | 22.893 | 5.858  | 1.000 | 13.42 |
| ATOM | 1910 | O   | ASP | A | 259 | -0.784 | 22.386 | 4.764  | 1.000 | 18.06 |
| ATOM | 1911 | N   | ARG | A | 260 | -1.456 | 23.673 | 6.457  | 1.000 | 15.30 |
| ATOM | 1912 | CA  | ARG | A | 260 | -2.741 | 24.034 | 5.845  | 1.000 | 17.67 |
| ATOM | 1913 | CB  | ARG | A | 260 | -3.567 | 24.849 | 6.842  | 1.000 | 14.27 |
| ATOM | 1914 | CG  | ARG | A | 260 | -3.970 | 24.009 | 8.067  | 1.000 | 12.81 |
| ATOM | 1915 | CD  | ARG | A | 260 | -4.923 | 24.884 | 8.885  | 1.000 | 20.83 |
| ATOM | 1916 | NE  | ARG | A | 260 | -6.158 | 25.124 | 8.125  | 1.000 | 27.40 |
| ATOM | 1917 | CZ  | ARG | A | 260 | -7.185 | 25.786 | 8.663  | 1.000 | 40.82 |
| ATOM | 1918 | NH1 | ARG | A | 260 | -7.082 | 26.236 | 9.907  | 1.000 | 36.06 |
| ATOM | 1919 | NH2 | ARG | A | 260 | -8.288 | 25.988 | 7.962  | 1.000 | 39.48 |
| ATOM | 1920 | C   | ARG | A | 260 | -2.523 | 24.808 | 4.549  | 1.000 | 19.93 |
| ATOM | 1921 | O   | ARG | A | 260 | -3.148 | 24.535 | 3.519  | 1.000 | 17.22 |
| ATOM | 1922 | N   | ILE | A | 261 | -1.618 | 25.791 | 4.553  | 1.000 | 16.11 |
| ATOM | 1923 | CA  | ILE | A | 261 | -1.516 | 26.628 | 3.338  | 1.000 | 17.32 |

FIGURE 238

| | | | | | | | | | |
|---|---|---|---|---|---|---|---|---|---|
| ATOM | 1924 | CB | ILE | A | 261 | -0.841 | 27.994 | 3.615 | 1.000 21.93 |
| ATOM | 1925 | CG1 | ILE | A | 261 | 0.658 | 27.969 | 3.875 | 1.000 27.34 |
| ATOM | 1926 | CD1 | ILE | A | 261 | 1.186 | 29.227 | 4.546 | 1.000 33.86 |
| ATOM | 1927 | CG2 | ILE | A | 261 | -1.581 | 28.703 | 4.758 | 1.000 18.92 |
| ATOM | 1928 | C | ILE | A | 261 | -0.851 | 25.876 | 2.216 | 1.000 20.48 |
| ATOM | 1929 | O | ILE | A | 261 | -1.226 | 26.009 | 1.034 | 1.000 22.32 |
| ATOM | 1930 | N | LEU | A | 262 | 0.143 | 25.028 | 2.509 | 1.000 16.93 |
| ATOM | 1931 | CA | LEU | A | 262 | 0.737 | 24.302 | 1.387 | 1.000 17.22 |
| ATOM | 1932 | CB | LEU | A | 262 | 1.975 | 23.501 | 1.820 | 1.000 16.74 |
| ATOM | 1933 | CG | LEU | A | 262 | 3.194 | 24.340 | 2.240 | 1.000 20.68 |
| ATOM | 1934 | CD1 | LEU | A | 262 | 4.319 | 23.422 | 2.693 | 1.000 18.57 |
| ATOM | 1935 | CD2 | LEU | A | 262 | 3.634 | 25.246 | 1.085 | 1.000 18.30 |
| ATOM | 1936 | C | LEU | A | 262 | -0.280 | 23.362 | 0.776 | 1.000 19.77 |
| ATOM | 1937 | O | LEU | A | 262 | -0.261 | 23.155 | -0.436 | 1.000 20.56 |
| ATOM | 1938 | N | GLN | A | 263 | -1.139 | 22.759 | 1.613 | 1.000 19.67 |
| ATOM | 1939 | CA | GLN | A | 263 | -2.241 | 21.952 | 1.056 | 1.000 19.49 |
| ATOM | 1940 | CB | GLN | A | 263 | -3.050 | 21.287 | 2.170 | 1.000 17.39 |
| ATOM | 1941 | CG | GLN | A | 263 | -2.289 | 20.167 | 2.891 | 1.000 15.52 |
| ATOM | 1942 | CD | GLN | A | 263 | -3.138 | 19.572 | 4.012 | 1.000 20.67 |
| ATOM | 1943 | OE1 | GLN | A | 263 | -3.928 | 18.638 | 3.850 | 1.000 20.81 |
| ATOM | 1944 | NE2 | GLN | A | 263 | -2.956 | 20.185 | 5.176 | 1.000 17.87 |
| ATOM | 1945 | C | GLN | A | 263 | -3.138 | 22.833 | 0.183 | 1.000 13.70 |
| ATOM | 1946 | O | GLN | A | 263 | -3.554 | 22.415 | -0.904 | 1.000 24.55 |
| ATOM | 1947 | N | GLN | A | 264 | -3.444 | 24.043 | 0.641 | 1.000 15.00 |
| ATOM | 1948 | CA | GLN | A | 264 | -4.260 | 24.907 | -0.217 | 1.000 22.95 |
| ATOM | 1949 | CB | GLN | A | 264 | -4.553 | 26.223 | 0.485 | 1.000 26.53 |
| ATOM | 1950 | CG | GLN | A | 264 | -5.586 | 26.136 | 1.595 | 1.000 29.68 |
| ATOM | 1951 | CD | GLN | A | 264 | -5.638 | 27.472 | 2.328 | 1.000 32.15 |
| ATOM | 1952 | OE1 | GLN | A | 264 | -5.197 | 28.482 | 1.781 | 1.000 29.91 |
| ATOM | 1953 | NE2 | GLN | A | 264 | -6.154 | 27.458 | 3.550 | 1.000 38.37 |
| ATOM | 1954 | C | GLN | A | 264 | -3.583 | 25.159 | -1.559 | 1.000 21.95 |
| ATOM | 1955 | O | GLN | A | 264 | -4.225 | 25.050 | -2.610 | 1.000 24.60 |
| ATOM | 1956 | N | LEU | A | 265 | -2.293 | 25.490 | -1.552 | 1.000 16.75 |
| ATOM | 1957 | CA | LEU | A | 265 | -1.536 | 25.721 | -2.771 | 1.000 19.81 |
| ATOM | 1958 | CB | LEU | A | 265 | -0.067 | 26.053 | -2.420 | 1.000 23.63 |
| ATOM | 1959 | CG | LEU | A | 265 | 0.195 | 27.420 | -1.807 | 1.000 29.98 |
| ATOM | 1960 | CD1 | LEU | A | 265 | 1.682 | 27.725 | -1.734 | 1.000 26.97 |
| ATOM | 1961 | CD2 | LEU | A | 265 | -0.519 | 28.505 | -2.613 | 1.000 33.62 |
| ATOM | 1962 | C | LEU | A | 265 | -1.541 | 24.553 | -3.735 | 1.000 19.01 |
| ATOM | 1963 | O | LEU | A | 265 | -1.324 | 24.723 | -4.947 | 1.000 22.58 |
| ATOM | 1964 | N | ASP | A | 266 | -1.767 | 23.324 | -3.273 | 1.000 19.07 |
| ATOM | 1965 | CA | ASP | A | 266 | -1.801 | 22.167 | -4.139 | 1.000 16.52 |
| ATOM | 1966 | CB | ASP | A | 266 | -1.173 | 20.917 | -3.509 | 1.000 22.85 |
| ATOM | 1967 | CG | ASP | A | 266 | 0.336 | 21.022 | -3.334 | 1.000 25.04 |
| ATOM | 1968 | OD1 | ASP | A | 266 | 0.957 | 21.963 | -3.836 | 1.000 21.32 |
| ATOM | 1969 | OD2 | ASP | A | 266 | 0.899 | 20.138 | -2.658 | 1.000 26.79 |
| ATOM | 1970 | C | ASP | A | 266 | -3.227 | 21.776 | -4.570 | 1.000 17.40 |
| ATOM | 1971 | O | ASP | A | 266 | -3.354 | 20.825 | -5.337 | 1.000 24.62 |
| ATOM | 1972 | N | SER | A | 267 | -4.231 | 22.487 | -4.092 | 1.000 22.55 |
| ATOM | 1973 | CA | SER | A | 267 | -5.619 | 22.129 | -4.359 | 1.000 24.11 |
| ATOM | 1974 | CB | SER | A | 267 | -6.289 | 21.776 | -3.019 | 1.000 23.25 |
| ATOM | 1975 | OG | SER | A | 267 | -6.418 | 20.374 | -2.892 | 1.000 34.75 |

FIGURE 239

| | | | | | | | | |
|---|---|---|---|---|---|---|---|---|
| ATOM | 1976 | C | SER | A | 267 | -6.419 | 23.235 | -5.033 1.000 19.22 |
| ATOM | 1977 | O | SER | A | 267 | -7.300 | 22.941 | -5.859 1.000 20.89 |
| ATOM | 1978 | N | LYS | A | 268 | -6.137 | 24.463 | -4.684 1.000 21.22 |
| ATOM | 1979 | CA | LYS | A | 268 | -6.907 | 25.624 | -5.091 1.000 30.13 |
| ATOM | 1980 | CB | LYS | A | 268 | -7.595 | 26.250 | -3.869 1.000 24.53 |
| ATOM | 1981 | CG | LYS | A | 268 | -8.563 | 25.304 | -3.175 1.000 30.56 |
| ATOM | 1982 | CD | LYS | A | 268 | -8.969 | 25.910 | -1.838 1.000 28.63 |
| ATOM | 1983 | CE | LYS | A | 268 | -10.158 | 26.834 | -1.992 1.000 29.96 |
| ATOM | 1984 | NZ | LYS | A | 268 | -10.686 | 27.208 | -0.641 1.000 30.06 |
| ATOM | 1985 | C | LYS | A | 268 | -6.095 | 26.737 | -5.735 1.000 30.67 |
| ATOM | 1986 | O | LYS | A | 268 | -4.872 | 26.833 | -5.660 1.000 23.21 |
| ATOM | 1987 | N | ASP | A | 269 | -6.834 | 27.650 | -6.387 1.000 26.00 |
| ATOM | 1988 | CA | ASP | A | 269 | -6.096 | 28.750 | -7.019 1.000 24.51 |
| ATOM | 1989 | CB | ASP | A | 269 | -6.616 | 28.978 | -8.444 1.000 36.81 |
| ATOM | 1990 | CG | ASP | A | 269 | -8.072 | 29.337 | -8.608 1.000 32.33 |
| ATOM | 1991 | OD1 | ASP | A | 269 | -8.854 | 29.152 | -7.660 1.000 26.79 |
| ATOM | 1992 | OD2 | ASP | A | 269 | -8.465 | 29.822 | -9.701 1.000 28.81 |
| ATOM | 1993 | C | ASP | A | 269 | -6.126 | 30.000 | -6.165 1.000 21.36 |
| ATOM | 1994 | O | ASP | A | 269 | -5.857 | 31.124 | -6.623 1.000 25.20 |
| ATOM | 1995 | N | SER | A | 270 | -6.434 | 29.846 | -4.867 1.000 19.08 |
| ATOM | 1996 | CA | SER | A | 270 | -6.204 | 30.978 | -3.973 1.000 22.27 |
| ATOM | 1997 | CB | SER | A | 270 | -7.455 | 31.809 | -3.722 1.000 31.53 |
| ATOM | 1998 | OG | SER | A | 270 | -8.466 | 31.045 | -3.109 1.000 46.83 |
| ATOM | 1999 | C | SER | A | 270 | -5.632 | 30.493 | -2.626 1.000 17.38 |
| ATOM | 2000 | O | SER | A | 270 | -5.828 | 29.315 | -2.334 1.000 22.28 |
| ATOM | 2001 | N | VAL | A | 271 | -5.000 | 31.394 | -1.910 1.000 20.10 |
| ATOM | 2002 | CA | VAL | A | 271 | -4.413 | 31.067 | -0.596 1.000 21.99 |
| ATOM | 2003 | CB | VAL | A | 271 | -2.876 | 31.020 | -0.706 1.000 36.16 |
| ATOM | 2004 | CG1 | VAL | A | 271 | -2.305 | 32.413 | -0.921 1.000 35.70 |
| ATOM | 2005 | CG2 | VAL | A | 271 | -2.233 | 30.370 | 0.514 1.000 31.05 |
| ATOM | 2006 | C | VAL | A | 271 | -4.845 | 32.054 | 0.464 1.000 23.10 |
| ATOM | 2007 | O | VAL | A | 271 | -5.012 | 33.251 | 0.241 1.000 21.67 |
| ATOM | 2008 | N | ASP | A | 272 | -5.046 | 31.547 | 1.689 1.000 22.69 |
| ATOM | 2009 | CA | ASP | A | 272 | -5.591 | 32.427 | 2.728 1.000 29.48 |
| ATOM | 2010 | CB | ASP | A | 272 | -7.070 | 32.095 | 2.910 1.000 26.70 |
| ATOM | 2011 | CG | ASP | A | 272 | -7.813 | 32.991 | 3.869 1.000 27.37 |
| ATOM | 2012 | OD1 | ASP | A | 272 | -7.274 | 34.038 | 4.288 1.000 23.01 |
| ATOM | 2013 | OD2 | ASP | A | 272 | -8.973 | 32.599 | 4.175 1.000 25.43 |
| ATOM | 2014 | C | ASP | A | 272 | -4.807 | 32.259 | 4.021 1.000 22.94 |
| ATOM | 2015 | O | ASP | A | 272 | -5.200 | 31.536 | 4.930 1.000 19.80 |
| ATOM | 2016 | N | ILE | A | 273 | -3.661 | 32.934 | 4.069 1.000 24.25 |
| ATOM | 2017 | CA | ILE | A | 273 | -2.806 | 32.829 | 5.255 1.000 22.39 |
| ATOM | 2018 | CB | ILE | A | 273 | -1.436 | 33.465 | 4.962 1.000 25.49 |
| ATOM | 2019 | CG1 | ILE | A | 273 | -0.747 | 32.812 | 3.755 1.000 18.59 |
| ATOM | 2020 | CD1 | ILE | A | 273 | 0.498 | 33.584 | 3.329 1.000 24.40 |
| ATOM | 2021 | CG2 | ILE | A | 273 | -0.532 | 33.454 | 6.177 1.000 18.07 |
| ATOM | 2022 | C | ILE | A | 273 | -3.472 | 33.457 | 6.452 1.000 20.71 |
| ATOM | 2023 | O | ILE | A | 273 | -3.470 | 32.853 | 7.530 1.000 17.55 |
| ATOM | 2024 | N | TYR | A | 274 | -4.038 | 34.646 | 6.266 1.000 21.57 |
| ATOM | 2025 | CA | TYR | A | 274 | -4.765 | 35.332 | 7.338 1.000 27.63 |
| ATOM | 2026 | CB | TYR | A | 274 | -5.414 | 36.646 | 6.864 1.000 23.61 |
| ATOM | 2027 | CG | TYR | A | 274 | -6.110 | 37.456 | 7.937 1.000 24.88 |

FIGURE 240

```
ATOM   2028  CD1 TYR A 274      -7.427  37.236   8.347 1.000 25.22
ATOM   2029  CE1 TYR A 274      -8.040  37.979   9.328 1.000 24.84
ATOM   2030  CZ  TYR A 274      -7.346  39.009   9.937 1.000 24.82
ATOM   2031  OH  TYR A 274      -7.979  39.740  10.919 1.000 31.02
ATOM   2032  CE2 TYR A 274      -6.040  39.266   9.571 1.000 24.34
ATOM   2033  CD2 TYR A 274      -5.435  38.503   8.582 1.000 21.36
ATOM   2034  C   TYR A 274      -5.834  34.413   7.922 1.000 22.02
ATOM   2035  O   TYR A 274      -5.962  34.308   9.150 1.000 23.59
ATOM   2036  N   GLY A 275      -6.642  33.818   7.042 1.000 19.06
ATOM   2037  CA  GLY A 275      -7.741  32.997   7.563 1.000 18.44
ATOM   2038  C   GLY A 275      -7.221  31.755   8.284 1.000 18.35
ATOM   2039  O   GLY A 275      -7.789  31.310   9.278 1.000 20.87
ATOM   2040  N   ALA A 276      -6.123  31.168   7.823 1.000 19.89
ATOM   2041  CA  ALA A 276      -5.591  30.008   8.560 1.000 22.21
ATOM   2042  CB  ALA A 276      -4.480  29.371   7.758 1.000 17.74
ATOM   2043  C   ALA A 276      -5.091  30.429   9.932 1.000 24.08
ATOM   2044  O   ALA A 276      -5.321  29.770  10.938 1.000 19.77
ATOM   2045  N   VAL A 277      -4.390  31.569  10.019 1.000 18.02
ATOM   2046  CA  VAL A 277      -3.912  31.978  11.353 1.000 17.46
ATOM   2047  CB  VAL A 277      -2.831  33.079  11.246 1.000 21.08
ATOM   2048  CG1 VAL A 277      -2.405  33.553  12.631 1.000 21.06
ATOM   2049  CG2 VAL A 277      -1.645  32.548  10.467 1.000 16.97
ATOM   2050  C   VAL A 277      -5.084  32.426  12.205 1.000 20.56
ATOM   2051  O   VAL A 277      -5.142  32.112  13.390 1.000 18.55
ATOM   2052  N   HIS A 278      -6.044  33.156  11.644 1.000 18.91
ATOM   2053  CA  HIS A 278      -7.281  33.470  12.314 1.000 16.67
ATOM   2054  CB  HIS A 278      -8.297  34.063  11.303 1.000 18.69
ATOM   2055  CG  HIS A 278      -9.520  34.540  12.036 1.000 22.21
ATOM   2056  ND1 HIS A 278     -10.626  33.756  12.252 1.000 21.90
ATOM   2057  CE1 HIS A 278     -11.535  34.445  12.925 1.000 23.09
ATOM   2058  NE2 HIS A 278     -11.055  35.656  13.150 1.000 23.99
ATOM   2059  CD2 HIS A 278      -9.801  35.745  12.602 1.000 20.21
ATOM   2060  C   HIS A 278      -7.924  32.254  12.971 1.000 19.90
ATOM   2061  O   HIS A 278      -8.255  32.244  14.165 1.000 22.96
ATOM   2062  N   ASP A 279      -8.105  31.202  12.180 1.000 18.82
ATOM   2063  CA  ASP A 279      -8.742  30.004  12.711 1.000 23.67
ATOM   2064  CB  ASP A 279      -8.995  29.015  11.565 1.000 25.00
ATOM   2065  CG  ASP A 279     -10.100  29.571  10.669 1.000 50.27
ATOM   2066  OD1 ASP A 279     -10.713  30.592  11.074 1.000 51.54
ATOM   2067  OD2 ASP A 279     -10.315  28.989   9.582 1.000 44.55
ATOM   2068  C   ASP A 279      -7.914  29.352  13.811 1.000 21.55
ATOM   2069  O   ASP A 279      -8.488  28.905  14.806 1.000 24.05
ATOM   2070  N   LEU A 280      -6.595  29.300  13.681 1.000 17.02
ATOM   2071  CA  LEU A 280      -5.777  28.736  14.760 1.000 15.09
ATOM   2072  CB  LEU A 280      -4.307  28.672  14.339 1.000 16.04
ATOM   2073  CG  LEU A 280      -3.998  27.877  13.066 1.000 25.79
ATOM   2074  CD1 LEU A 280      -2.505  27.860  12.743 1.000 19.03
ATOM   2075  CD2 LEU A 280      -4.512  26.448  13.134 1.000 25.95
ATOM   2076  C   LEU A 280      -5.928  29.541  16.041 1.000 17.95
ATOM   2077  O   LEU A 280      -6.048  28.991  17.142 1.000 16.96
ATOM   2078  N   ARG A 281      -5.940  30.867  15.909 1.000 17.70
ATOM   2079  CA  ARG A 281      -6.048  31.750  17.064 1.000 20.80
```

FIGURE 241

```
ATOM   2080  CB   ARG A 281      -5.937  33.220  16.611  1.000  16.23
ATOM   2081  CG   ARG A 281      -4.518  33.577  16.185  1.000  21.03
ATOM   2082  CD   ARG A 281      -3.551  33.775  17.350  1.000  20.13
ATOM   2083  NE   ARG A 281      -2.333  34.410  16.826  1.000  22.94
ATOM   2084  CZ   ARG A 281      -2.155  35.711  16.631  1.000  25.63
ATOM   2085  NH1  ARG A 281      -3.096  36.606  16.909  1.000  26.26
ATOM   2086  NH2  ARG A 281      -0.990  36.116  16.136  1.000  24.35
ATOM   2087  C    ARG A 281      -7.348  31.512  17.810  1.000  18.17
ATOM   2088  O    ARG A 281      -7.399  31.612  19.040  1.000  16.51
ATOM   2089  N    LEU A 282      -8.411  31.197  17.055  1.000  14.33
ATOM   2090  CA   LEU A 282      -9.670  30.904  17.725  1.000  19.27
ATOM   2091  CB   LEU A 282     -10.750  30.565  16.690  1.000  19.77
ATOM   2092  CG   LEU A 282     -11.369  31.764  15.966  1.000  29.93
ATOM   2093  CD1  LEU A 282     -12.445  31.274  15.006  1.000  21.91
ATOM   2094  CD2  LEU A 282     -11.916  32.785  16.951  1.000  25.11
ATOM   2095  C    LEU A 282      -9.567  29.715  18.673  1.000  15.90
ATOM   2096  O    LEU A 282     -10.343  29.644  19.622  1.000  19.86
ATOM   2097  N    HIS A 283      -8.652  28.771  18.444  1.000  13.25
ATOM   2098  CA   HIS A 283      -8.655  27.556  19.262  1.000  15.14
ATOM   2099  CB   HIS A 283      -8.585  26.315  18.339  1.000  17.23
ATOM   2100  CG   HIS A 283      -9.761  26.332  17.393  1.000  20.06
ATOM   2101  ND1  HIS A 283     -10.931  25.651  17.625  1.000  31.88
ATOM   2102  CE1  HIS A 283     -11.785  25.866  16.626  1.000  22.40
ATOM   2103  NE2  HIS A 283     -11.210  26.665  15.743  1.000  22.21
ATOM   2104  CD2  HIS A 283      -9.959  26.969  16.216  1.000  21.15
ATOM   2105  C    HIS A 283      -7.541  27.484  20.301  1.000  17.70
ATOM   2106  O    HIS A 283      -7.668  26.724  21.286  1.000  18.21
ATOM   2107  N    ARG A 284      -6.460  28.254  20.155  1.000  18.34
ATOM   2108  CA   ARG A 284      -5.462  28.288  21.252  1.000  17.74
ATOM   2109  CB   ARG A 284      -4.494  27.114  21.172  1.000  19.63
ATOM   2110  CG   ARG A 284      -3.445  26.954  22.275  1.000  18.29
ATOM   2111  CD   ARG A 284      -2.651  25.656  22.082  1.000  20.72
ATOM   2112  NE   ARG A 284      -1.458  25.545  22.957  1.000  15.01
ATOM   2113  CZ   ARG A 284      -1.489  25.046  24.189  1.000  14.81
ATOM   2114  NH1  ARG A 284      -2.637  24.611  24.697  1.000  14.36
ATOM   2115  NH2  ARG A 284      -0.419  24.947  24.977  1.000  17.97
ATOM   2116  C    ARG A 284      -4.746  29.631  21.220  1.000  19.40
ATOM   2117  O    ARG A 284      -4.570  30.222  20.158  1.000  18.68
ATOM   2118  N    VAL A 285      -4.331  30.137  22.382  1.000  20.56
ATOM   2119  CA   VAL A 285      -3.577  31.396  22.467  1.000  19.97
ATOM   2120  CB   VAL A 285      -3.329  31.773  23.942  1.000  20.57
ATOM   2121  CG1  VAL A 285      -2.329  30.829  24.584  1.000  17.50
ATOM   2122  CG2  VAL A 285      -2.811  33.203  24.085  1.000  29.47
ATOM   2123  C    VAL A 285      -2.259  31.298  21.714  1.000  17.66
ATOM   2124  O    VAL A 285      -1.641  30.232  21.618  1.000  17.67
ATOM   2125  N    HIS A 286      -1.814  32.423  21.166  1.000  19.91
ATOM   2126  CA   HIS A 286      -0.537  32.572  20.510  1.000  25.50
ATOM   2127  CB   HIS A 286       0.610  32.334  21.518  1.000  24.01
ATOM   2128  CG   HIS A 286       0.534  33.321  22.640  1.000  27.47
ATOM   2129  ND1  HIS A 286       0.673  32.943  23.966  1.000  36.12
ATOM   2130  CE1  HIS A 286       0.544  34.024  24.711  1.000  31.77
ATOM   2131  NE2  HIS A 286       0.333  35.065  23.927  1.000  32.36
```

FIGURE 242

| | | | | | | | | |
|---|---|---|---|---|---|---|---|---|
| ATOM | 2132 | CD2 | HIS | A | 286 | 0.312 | 34.647 | 22.624 1.000 25.03 |
| ATOM | 2133 | C | HIS | A | 286 | -0.272 | 31.626 | 19.358 1.000 21.57 |
| ATOM | 2134 | O | HIS | A | 286 | 0.915 | 31.389 | 19.095 1.000 27.54 |
| ATOM | 2135 | N | MET | A | 287 | -1.298 | 31.074 | 18.700 1.000 20.51 |
| ATOM | 2136 | CA | MET | A | 287 | -1.005 | 30.215 | 17.540 1.000 17.32 |
| ATOM | 2137 | CB | MET | A | 287 | -2.248 | 29.446 | 17.099 1.000 15.20 |
| ATOM | 2138 | CG | MET | A | 287 | -2.726 | 28.475 | 18.174 1.000 18.71 |
| ATOM | 2139 | SD | MET | A | 287 | -1.588 | 27.070 | 18.339 1.000 23.88 |
| ATOM | 2140 | CE | MET | A | 287 | -2.087 | 26.118 | 16.902 1.000 40.45 |
| ATOM | 2141 | C | MET | A | 287 | -0.449 | 31.093 | 16.419 1.000 19.40 |
| ATOM | 2142 | O | MET | A | 287 | -1.200 | 31.865 | 15.805 1.000 23.59 |
| ATOM | 2143 | N | VAL | A | 288 | 0.842 | 30.986 | 16.169 1.000 18.22 |
| ATOM | 2144 | CA | VAL | A | 288 | 1.568 | 31.941 | 15.322 1.000 22.64 |
| ATOM | 2145 | CB | VAL | A | 288 | 0.926 | 32.326 | 13.986 1.000 17.14 |
| ATOM | 2146 | CG1 | VAL | A | 288 | 1.879 | 33.209 | 13.183 1.000 23.13 |
| ATOM | 2147 | CG2 | VAL | A | 288 | 0.607 | 31.099 | 13.159 1.000 21.03 |
| ATOM | 2148 | C | VAL | A | 288 | 1.718 | 33.186 | 16.211 1.000 25.94 |
| ATOM | 2149 | O | VAL | A | 288 | 0.851 | 34.046 | 16.243 1.000 27.22 |
| ATOM | 2150 | N | GLN | A | 289 | 2.824 | 33.161 | 16.945 1.000 27.43 |
| ATOM | 2151 | CA | GLN | A | 289 | 3.003 | 34.056 | 18.091 1.000 24.77 |
| ATOM | 2152 | CB | GLN | A | 289 | 3.839 | 33.286 | 19.112 1.000 23.16 |
| ATOM | 2153 | CG | GLN | A | 289 | 4.041 | 33.984 | 20.443 1.000 22.98 |
| ATOM | 2154 | CD | GLN | A | 289 | 4.639 | 33.050 | 21.469 1.000 24.02 |
| ATOM | 2155 | OE1 | GLN | A | 289 | 5.224 | 32.012 | 21.115 1.000 27.34 |
| ATOM | 2156 | NE2 | GLN | A | 289 | 4.479 | 33.454 | 22.716 1.000 30.58 |
| ATOM | 2157 | C | GLN | A | 289 | 3.664 | 35.376 | 17.751 1.000 28.02 |
| ATOM | 2158 | O | GLN | A | 289 | 3.430 | 36.375 | 18.436 1.000 35.00 |
| ATOM | 2159 | N | THR | A | 290 | 4.492 | 35.409 | 16.717 1.000 22.20 |
| ATOM | 2160 | CA | THR | A | 290 | 5.169 | 36.667 | 16.419 1.000 24.68 |
| ATOM | 2161 | CB | THR | A | 290 | 6.682 | 36.492 | 16.619 1.000 25.80 |
| ATOM | 2162 | OG1 | THR | A | 290 | 7.133 | 35.616 | 15.579 1.000 22.41 |
| ATOM | 2163 | CG2 | THR | A | 290 | 7.012 | 35.803 | 17.932 1.000 28.39 |
| ATOM | 2164 | C | THR | A | 290 | 4.964 | 37.120 | 14.984 1.000 35.97 |
| ATOM | 2165 | O | THR | A | 290 | 4.668 | 36.327 | 14.090 1.000 25.80 |
| ATOM | 2166 | N | GLU | A | 291 | 5.148 | 38.416 | 14.746 1.000 29.48 |
| ATOM | 2167 | CA | GLU | A | 291 | 5.038 | 38.965 | 13.403 1.000 28.57 |
| ATOM | 2168 | CB | GLU | A | 291 | 5.285 | 40.473 | 13.478 1.000 29.75 |
| ATOM | 2169 | CG | GLU | A | 291 | 5.073 | 41.210 | 12.184 1.000 39.81 |
| ATOM | 2170 | CD | GLU | A | 291 | 4.812 | 42.699 | 12.387 1.000 39.37 |
| ATOM | 2171 | OE1 | GLU | A | 291 | 4.858 | 43.418 | 11.371 1.000 42.29 |
| ATOM | 2172 | OE2 | GLU | A | 291 | 4.556 | 43.148 | 13.519 1.000 40.22 |
| ATOM | 2173 | C | GLU | A | 291 | 6.029 | 38.283 | 12.484 1.000 23.04 |
| ATOM | 2174 | O | GLU | A | 291 | 5.824 | 37.994 | 11.304 1.000 23.87 |
| ATOM | 2175 | N | CYS | A | 292 | 7.200 | 37.987 | 13.054 1.000 24.91 |
| ATOM | 2176 | CA | CYS | A | 292 | 8.230 | 37.313 | 12.255 1.000 20.83 |
| ATOM | 2177 | CB | CYS | A | 292 | 9.434 | 37.106 | 13.178 1.000 33.84 |
| ATOM | 2178 | SG | CYS | A | 292 | 10.875 | 36.380 | 12.364 1.000 50.67 |
| ATOM | 2179 | C | CYS | A | 292 | 7.777 | 35.977 | 11.679 1.000 25.36 |
| ATOM | 2180 | O | CYS | A | 292 | 8.056 | 35.544 | 10.549 1.000 26.36 |
| ATOM | 2181 | N | GLN | A | 293 | 7.024 | 35.250 | 12.515 1.000 23.19 |
| ATOM | 2182 | CA | GLN | A | 293 | 6.425 | 33.998 | 12.069 1.000 22.92 |
| ATOM | 2183 | CB | GLN | A | 293 | 5.779 | 33.269 | 13.256 1.000 20.65 |

FIGURE 243

| | | | | | | | | | |
|---|---|---|---|---|---|---|---|---|---|
| ATOM | 2184 | CG | GLN | A | 293 | 6.783 | 32.437 | 14.036 | 1.000 20.24 |
| ATOM | 2185 | CD | GLN | A | 293 | 6.355 | 32.071 | 15.433 | 1.000 17.59 |
| ATOM | 2186 | OE1 | GLN | A | 293 | 5.282 | 32.450 | 15.901 | 1.000 18.69 |
| ATOM | 2187 | NE2 | GLN | A | 293 | 7.203 | 31.336 | 16.150 | 1.000 25.13 |
| ATOM | 2188 | C | GLN | A | 293 | 5.400 | 34.266 | 10.967 | 1.000 17.64 |
| ATOM | 2189 | O | GLN | A | 293 | 5.398 | 33.582 | 9.954 | 1.000 20.18 |
| ATOM | 2190 | N | TYR | A | 294 | 4.522 | 35.253 | 11.178 | 1.000 20.42 |
| ATOM | 2191 | CA | TYR | A | 294 | 3.526 | 35.600 | 10.153 | 1.000 19.65 |
| ATOM | 2192 | CB | TYR | A | 294 | 2.680 | 36.758 | 10.698 | 1.000 19.00 |
| ATOM | 2193 | CG | TYR | A | 294 | 1.392 | 36.980 | 9.943 | 1.000 21.07 |
| ATOM | 2194 | CD1 | TYR | A | 294 | 0.438 | 35.986 | 9.843 | 1.000 19.94 |
| ATOM | 2195 | CE1 | TYR | A | 294 | -0.747 | 36.155 | 9.158 | 1.000 25.08 |
| ATOM | 2196 | CZ | TYR | A | 294 | -0.978 | 37.374 | 8.547 | 1.000 34.68 |
| ATOM | 2197 | OH | TYR | A | 294 | -2.148 | 37.565 | 7.856 | 1.000 23.20 |
| ATOM | 2198 | CE2 | TYR | A | 294 | -0.047 | 38.385 | 8.622 | 1.000 26.61 |
| ATOM | 2199 | CD2 | TYR | A | 294 | 1.129 | 38.197 | 9.316 | 1.000 23.82 |
| ATOM | 2200 | C | TYR | A | 294 | 4.202 | 35.931 | 8.834 | 1.000 24.14 |
| ATOM | 2201 | O | TYR | A | 294 | 3.860 | 35.493 | 7.737 | 1.000 23.97 |
| ATOM | 2202 | N | VAL | A | 295 | 5.254 | 36.744 | 8.919 | 1.000 25.60 |
| ATOM | 2203 | CA | VAL | A | 295 | 6.065 | 37.085 | 7.762 | 1.000 26.06 |
| ATOM | 2204 | CB | VAL | A | 295 | 7.222 | 38.039 | 8.161 | 1.000 22.22 |
| ATOM | 2205 | CG1 | VAL | A | 295 | 8.189 | 38.107 | 6.995 | 1.000 24.48 |
| ATOM | 2206 | CG2 | VAL | A | 295 | 6.668 | 39.400 | 8.553 | 1.000 22.52 |
| ATOM | 2207 | C | VAL | A | 295 | 6.648 | 35.853 | 7.111 | 1.000 20.01 |
| ATOM | 2208 | O | VAL | A | 295 | 6.582 | 35.637 | 5.897 | 1.000 23.07 |
| ATOM | 2209 | N | TYR | A | 296 | 7.233 | 34.941 | 7.888 | 1.000 29.06 |
| ATOM | 2210 | CA | TYR | A | 296 | 7.779 | 33.698 | 7.342 | 1.000 20.10 |
| ATOM | 2211 | CB | TYR | A | 296 | 8.307 | 32.873 | 8.528 | 1.000 20.14 |
| ATOM | 2212 | CG | TYR | A | 296 | 9.099 | 31.652 | 8.140 | 1.000 22.62 |
| ATOM | 2213 | CD1 | TYR | A | 296 | 10.343 | 31.723 | 7.536 | 1.000 24.11 |
| ATOM | 2214 | CE1 | TYR | A | 296 | 11.044 | 30.582 | 7.188 | 1.000 24.78 |
| ATOM | 2215 | CZ | TYR | A | 296 | 10.500 | 29.338 | 7.451 | 1.000 30.65 |
| ATOM | 2216 | OH | TYR | A | 296 | 11.171 | 28.185 | 7.115 | 1.000 25.95 |
| ATOM | 2217 | CE2 | TYR | A | 296 | 9.263 | 29.241 | 8.048 | 1.000 21.75 |
| ATOM | 2218 | CD2 | TYR | A | 296 | 8.570 | 30.384 | 8.389 | 1.000 22.93 |
| ATOM | 2219 | C | TYR | A | 296 | 6.802 | 32.832 | 6.546 | 1.000 19.59 |
| ATOM | 2220 | O | TYR | A | 296 | 7.163 | 32.193 | 5.540 | 1.000 20.16 |
| ATOM | 2221 | N | LEU | A | 297 | 5.555 | 32.742 | 6.984 | 1.000 21.48 |
| ATOM | 2222 | CA | LEU | A | 297 | 4.501 | 32.003 | 6.276 | 1.000 16.66 |
| ATOM | 2223 | CB | LEU | A | 297 | 3.186 | 31.985 | 7.052 | 1.000 17.75 |
| ATOM | 2224 | CG | LEU | A | 297 | 3.215 | 31.148 | 8.360 | 1.000 16.83 |
| ATOM | 2225 | CD1 | LEU | A | 297 | 2.035 | 31.495 | 9.235 | 1.000 17.79 |
| ATOM | 2226 | CD2 | LEU | A | 297 | 3.299 | 29.668 | 8.014 | 1.000 17.48 |
| ATOM | 2227 | C | LEU | A | 297 | 4.276 | 32.654 | 4.904 | 1.000 17.96 |
| ATOM | 2228 | O | LEU | A | 297 | 4.156 | 31.967 | 3.898 | 1.000 20.64 |
| ATOM | 2229 | N | HIS | A | 298 | 4.256 | 33.978 | 4.931 | 1.000 22.58 |
| ATOM | 2230 | CA | HIS | A | 298 | 4.152 | 34.678 | 3.633 | 1.000 23.47 |
| ATOM | 2231 | CB | HIS | A | 298 | 3.950 | 36.157 | 3.901 | 1.000 25.50 |
| ATOM | 2232 | CG | HIS | A | 298 | 2.562 | 36.496 | 4.341 | 1.000 26.24 |
| ATOM | 2233 | ND1 | HIS | A | 298 | 2.118 | 36.313 | 5.625 | 1.000 22.98 |
| ATOM | 2234 | CE1 | HIS | A | 298 | 0.865 | 36.709 | 5.744 | 1.000 24.82 |
| ATOM | 2235 | NE2 | HIS | A | 298 | 0.470 | 37.141 | 4.565 | 1.000 27.56 |

FIGURE 244

| | | | | | | | | | |
|---|---|---|---|---|---|---|---|---|---|
| ATOM | 2236 | CD2 | HIS | A | 298 | 1.512 | 37.022 | 3.673 | 1.000 23.83 |
| ATOM | 2237 | C | HIS | A | 298 | 5.379 | 34.412 | 2.785 | 1.000 20.56 |
| ATOM | 2238 | O | HIS | A | 298 | 5.260 | 34.132 | 1.597 | 1.000 21.25 |
| ATOM | 2239 | N | GLN | A | 299 | 6.602 | 34.457 | 3.323 | 1.000 24.45 |
| ATOM | 2240 | CA | GLN | A | 299 | 7.767 | 34.186 | 2.484 | 1.000 23.57 |
| ATOM | 2241 | CB | GLN | A | 299 | 9.094 | 34.286 | 3.248 | 1.000 24.20 |
| ATOM | 2242 | CG | GLN | A | 299 | 9.618 | 35.701 | 3.344 | 1.000 38.95 |
| ATOM | 2243 | CD | GLN | A | 299 | 10.513 | 35.927 | 4.544 | 1.000 41.27 |
| ATOM | 2244 | OE1 | GLN | A | 299 | 10.525 | 35.111 | 5.469 | 1.000 47.05 |
| ATOM | 2245 | NE2 | GLN | A | 299 | 11.230 | 37.044 | 4.501 | 1.000 36.99 |
| ATOM | 2246 | C | GLN | A | 299 | 7.706 | 32.790 | 1.911 | 1.000 17.62 |
| ATOM | 2247 | O | GLN | A | 299 | 8.136 | 32.450 | 0.809 | 1.000 25.21 |
| ATOM | 2248 | N | CYS | A | 300 | 7.152 | 31.871 | 2.733 | 1.000 23.78 |
| ATOM | 2249 | CA | CYS | A | 300 | 7.113 | 30.506 | 2.245 | 1.000 15.17 |
| ATOM | 2250 | CB | CYS | A | 300 | 6.555 | 29.579 | 3.330 | 1.000 26.74 |
| ATOM | 2251 | SG | CYS | A | 300 | 7.710 | 29.138 | 4.647 | 1.000 25.71 |
| ATOM | 2252 | C | CYS | A | 300 | 6.212 | 30.350 | 1.023 | 1.000 21.29 |
| ATOM | 2253 | O | CYS | A | 300 | 6.539 | 29.695 | 0.050 | 1.000 24.33 |
| ATOM | 2254 | N | VAL | A | 301 | 5.033 | 30.956 | 1.118 | 1.000 22.72 |
| ATOM | 2255 | CA | VAL | A | 301 | 4.112 | 30.918 | -0.014 | 1.000 22.06 |
| ATOM | 2256 | CB | VAL | A | 301 | 2.771 | 31.522 | 0.407 | 1.000 23.59 |
| ATOM | 2257 | CG1 | VAL | A | 301 | 1.869 | 31.780 | -0.793 | 1.000 27.41 |
| ATOM | 2258 | CG2 | VAL | A | 301 | 2.103 | 30.549 | 1.385 | 1.000 22.39 |
| ATOM | 2259 | C | VAL | A | 301 | 4.739 | 31.650 | -1.213 | 1.000 26.22 |
| ATOM | 2260 | O | VAL | A | 301 | 4.684 | 31.075 | -2.300 | 1.000 25.21 |
| ATOM | 2261 | N | ARG | A | 302 | 5.299 | 32.832 | -0.941 | 1.000 30.33 |
| ATOM | 2262 | CA | ARG | A | 302 | 5.937 | 33.614 | -2.013 | 1.000 27.54 |
| ATOM | 2263 | CB | ARG | A | 302 | 6.701 | 34.808 | -1.462 | 1.000 26.63 |
| ATOM | 2264 | CG | ARG | A | 302 | 7.324 | 35.658 | -2.568 | 1.000 39.21 |
| ATOM | 2265 | CD | ARG | A | 302 | 8.529 | 36.449 | -2.082 | 1.000 43.43 |
| ATOM | 2266 | NE | ARG | A | 302 | 9.554 | 35.568 | -1.510 | 1.000 37.14 |
| ATOM | 2267 | CZ | ARG | A | 302 | 10.329 | 35.931 | -0.494 | 1.000 41.54 |
| ATOM | 2268 | NH1 | ARG | A | 302 | 10.197 | 37.132 | 0.049 | 1.000 63.42 |
| ATOM | 2269 | NH2 | ARG | A | 302 | 11.233 | 35.083 | -0.027 | 1.000 50.68 |
| ATOM | 2270 | C | ARG | A | 302 | 6.895 | 32.701 | -2.764 | 1.000 32.29 |
| ATOM | 2271 | O | ARG | A | 302 | 6.982 | 32.557 | -3.972 | 1.000 31.68 |
| ATOM | 2272 | N | ASP | A | 303 | 7.670 | 31.982 | -1.931 | 1.000 27.62 |
| ATOM | 2273 | CA | ASP | A | 303 | 8.736 | 31.200 | -2.547 | 1.000 23.05 |
| ATOM | 2274 | CB | ASP | A | 303 | 9.749 | 30.722 | -1.496 | 1.000 29.94 |
| ATOM | 2275 | CG | ASP | A | 303 | 10.561 | 31.886 | -0.934 | 1.000 44.96 |
| ATOM | 2276 | OD1 | ASP | A | 303 | 10.575 | 33.000 | -1.513 | 1.000 37.48 |
| ATOM | 2277 | OD2 | ASP | A | 303 | 11.207 | 31.698 | 0.125 | 1.000 27.41 |
| ATOM | 2278 | C | ASP | A | 303 | 8.159 | 30.064 | -3.366 | 1.000 32.89 |
| ATOM | 2279 | O | ASP | A | 303 | 8.647 | 29.887 | -4.490 | 1.000 34.89 |
| ATOM | 2280 | N | VAL | A | 304 | 7.167 | 29.345 | -2.844 | 1.000 30.50 |
| ATOM | 2281 | CA | VAL | A | 304 | 6.548 | 28.260 | -3.598 | 1.000 23.94 |
| ATOM | 2282 | CB | VAL | A | 304 | 5.491 | 27.493 | -2.783 | 1.000 27.62 |
| ATOM | 2283 | CG1 | VAL | A | 304 | 4.652 | 26.589 | -3.669 | 1.000 23.38 |
| ATOM | 2284 | CG2 | VAL | A | 304 | 6.165 | 26.665 | -1.692 | 1.000 24.59 |
| ATOM | 2285 | C | VAL | A | 304 | 5.884 | 28.774 | -4.877 | 1.000 22.14 |
| ATOM | 2286 | O | VAL | A | 304 | 6.042 | 28.169 | -5.933 | 1.000 25.47 |
| ATOM | 2287 | N | LEU | A | 305 | 5.140 | 29.874 | -4.827 | 1.000 27.71 |

FIGURE 245

```
ATOM   2288  CA   LEU A 305       4.558  30.400  -6.073 1.000 29.38
ATOM   2289  CB   LEU A 305       3.555  31.506  -5.706 1.000 38.16
ATOM   2290  CG   LEU A 305       2.392  31.001  -4.830 1.000 35.13
ATOM   2291  CD1  LEU A 305       1.344  32.082  -4.643 1.000 31.50
ATOM   2292  CD2  LEU A 305       1.810  29.740  -5.458 1.000 27.65
ATOM   2293  C    LEU A 305       5.606  30.942  -7.043 1.000 39.73
ATOM   2294  O    LEU A 305       5.477  30.795  -8.267 1.000 34.97
ATOM   2295  N    ARG A 306       6.644  31.587  -6.500 1.000 30.15
ATOM   2296  CA   ARG A 306       7.696  32.191  -7.303 1.000 41.94
ATOM   2297  CB   ARG A 306       8.843  32.715  -6.443 1.000 44.09
ATOM   2298  CG   ARG A 306       9.589  33.889  -7.052 1.000 39.22
ATOM   2299  CD   ARG A 306      10.448  34.547  -5.980 1.000 42.72
ATOM   2300  NE   ARG A 306       9.979  35.884  -5.635 1.000 52.78
ATOM   2301  CZ   ARG A 306      10.606  36.671  -4.767 1.000 54.00
ATOM   2302  NH1  ARG A 306      11.714  36.247  -4.169 1.000 67.12
ATOM   2303  NH2  ARG A 306      10.130  37.875  -4.496 1.000 46.01
ATOM   2304  C    ARG A 306       8.287  31.172  -8.271 1.000 29.94
ATOM   2305  O    ARG A 306       8.462  31.437  -9.450 1.000 37.35
ATOM   2306  N    ALA A 307       8.569  30.025  -7.699 1.000 31.66
ATOM   2307  CA   ALA A 307       9.158  28.861  -8.317 1.000 23.60
ATOM   2308  CB   ALA A 307       9.447  27.819  -7.233 1.000 26.10
ATOM   2309  C    ALA A 307       8.306  28.189  -9.381 1.000 47.11
ATOM   2310  O    ALA A 307       8.799  28.044 -10.499 1.000 44.35
ATOM   2311  N    ARG A 308       7.102  27.762  -9.042 1.000 52.74
ATOM   2312  CA   ARG A 308       6.308  26.829  -9.829 1.000 54.48
ATOM   2313  CB   ARG A 308       4.971  26.558  -9.115 1.000 57.15
ATOM   2314  CG   ARG A 308       5.194  25.951  -7.736 1.000 58.94
ATOM   2315  CD   ARG A 308       4.116  24.969  -7.323 1.000 55.91
ATOM   2316  NE   ARG A 308       2.804  25.598  -7.229 1.000 48.91
ATOM   2317  CZ   ARG A 308       1.773  25.117  -6.536 1.000 51.64
ATOM   2318  NH1  ARG A 308       1.868  23.990  -5.844 1.000 35.99
ATOM   2319  NH2  ARG A 308       0.639  25.806  -6.558 1.000 44.89
ATOM   2320  C    ARG A 308       6.063  27.269 -11.267 1.000 53.61
ATOM   2321  O    ARG A 308       5.807  26.391 -12.115 1.000 48.27
ATOM   2322  N    LYS A 309       6.155  28.565 -11.523 1.000 43.56
ATOM   2323  CA   LYS A 309       6.129  29.126 -12.866 1.000 55.87
ATOM   2324  CB   LYS A 309       6.515  30.617 -12.836 1.000 53.73
ATOM   2325  CG   LYS A 309       5.322  31.519 -12.555 1.000 50.14
ATOM   2326  CD   LYS A 309       5.733  32.861 -11.988 1.000 51.79
ATOM   2327  CE   LYS A 309       5.194  33.994 -12.859 1.000 58.07
ATOM   2328  NZ   LYS A 309       5.302  35.321 -12.188 1.000 68.64
ATOM   2329  C    LYS A 309       7.071  28.394 -13.819 1.000 49.69
ATOM   2330  O    LYS A 309       6.769  28.146 -14.991 1.000 49.16
ATOM   2331  N    LEU A 310       8.259  28.052 -13.326 1.000 28.26
ATOM   2332  CA   LEU A 310       9.179  27.229 -14.104 1.000 38.83
ATOM   2333  CB   LEU A 310      10.617  27.612 -13.747 1.000 55.29
ATOM   2334  CG   LEU A 310      10.793  29.062 -13.278 1.000 62.65
ATOM   2335  CD1  LEU A 310      12.262  29.360 -12.996 1.000 82.48
ATOM   2336  CD2  LEU A 310      10.245  30.039 -14.295 1.000 58.72
ATOM   2337  C    LEU A 310       8.920  25.745 -13.861 1.000 34.79
ATOM   2338  O1   HOH W   1       2.014  17.687  26.597 1.000 14.70
ATOM   2339  O1   HOH W   2      -5.416  28.864  24.748 1.000 14.82
```

FIGURE 246

```
ATOM   2340  O1  HOH W   3     9.941  34.403  15.794  1.000  20.77
ATOM   2341  O1  HOH W   4     1.150  20.544   3.861  1.000  16.32
ATOM   2342  O1  HOH W   5    11.855   1.496  23.723  1.000  20.79
ATOM   2343  O1  HOH W   6    11.026  19.440  31.061  1.000  22.81
ATOM   2344  O1  HOH W   7    -4.100  15.347  34.619  1.000  20.35
ATOM   2345  O1  HOH W   8    -8.502  35.220  27.278  1.000  20.31
ATOM   2346  O1  HOH W   9    10.956   8.876  28.629  1.000  24.20
ATOM   2347  O1  HOH W  10    13.818  22.433  16.330  1.000  21.57
ATOM   2348  O1  HOH W  11    -4.748  20.337   7.520  1.000  18.34
ATOM   2349  O1  HOH W  12     7.144  17.757  36.248  1.000  23.39
ATOM   2350  O1  HOH W  13    -8.500  25.553  30.582  1.000  21.46
ATOM   2351  O1  HOH W  14     1.872  18.169  29.324  1.000  19.74
ATOM   2352  O1  HOH W  15   -12.583  28.920  26.833  1.000  23.46
ATOM   2353  O1  HOH W  16    17.845  15.230  13.268  1.000  25.48
ATOM   2354  O1  HOH W  17     2.522  25.792  29.444  1.000  21.14
ATOM   2355  O1  HOH W  18   -12.414  36.213  18.671  1.000  35.42
ATOM   2356  O1  HOH W  19    -0.308  19.015  30.907  1.000  20.05
ATOM   2357  O1  HOH W  20    -4.507  15.507   8.656  1.000  26.56
ATOM   2358  O1  HOH W  21    -1.463  16.804  32.355  1.000  19.87
ATOM   2359  O1  HOH W  22    -7.774  24.896  24.411  1.000  25.30
ATOM   2360  O1  HOH W  23     2.487  23.390  -2.046  1.000  21.28
ATOM   2361  O1  HOH W  24    -5.084  36.399  19.340  1.000  24.16
ATOM   2362  O1  HOH W  25    11.554  11.480  16.357  1.000  25.31
ATOM   2363  O1  HOH W  26    12.946   5.581  11.917  1.000  24.23
ATOM   2364  O1  HOH W  27   -12.980  20.577  24.368  1.000  27.97
ATOM   2365  O1  HOH W  28    10.212  31.138  15.942  1.000  33.79
ATOM   2366  O1  HOH W  29    14.372   4.995  27.900  1.000  26.39
ATOM   2367  O1  HOH W  30    -2.960  34.484   1.831  1.000  27.40
ATOM   2368  O1  HOH W  31    10.824  30.078  18.289  1.000  25.67
ATOM   2369  O1  HOH W  32    13.982   2.205  27.167  1.000  25.41
ATOM   2370  O1  HOH W  33     1.575  12.107  33.860  1.000  34.16
ATOM   2371  O1  HOH W  34    -3.137  19.220  -7.395  1.000  25.27
ATOM   2372  O1  HOH W  35    -6.170  33.272  20.828  1.000  21.49
ATOM   2373  O1  HOH W  36    -1.632  39.007  16.222  1.000  27.21
ATOM   2374  O1  HOH W  37     7.347  31.206  19.263  1.000  26.77
ATOM   2375  O1  HOH W  38     9.444  26.520  21.341  1.000  29.37
ATOM   2376  O1  HOH W  39    -8.237   9.947  35.385  1.000  47.49
ATOM   2377  O1  HOH W  40    -2.103  38.773  20.445  1.000  27.92
ATOM   2378  O1  HOH W  41    -9.820  28.498  38.052  1.000  26.65
ATOM   2379  O1  HOH W  42    10.051  20.936  -0.828  1.000  26.93
ATOM   2380  O1  HOH W  43   -14.963  17.351  10.401  1.000  37.99
ATOM   2381  O1  HOH W  44    15.436   8.322  21.787  1.000  29.21
ATOM   2382  O1  HOH W  45     1.871  19.354   1.571  1.000  22.03
ATOM   2383  O1  HOH W  46    -7.599  19.535  29.453  1.000  22.96
ATOM   2384  O1  HOH W  47     3.330  17.045   1.103  1.000  26.08
ATOM   2385  O1  HOH W  48    14.921  28.549   0.827  1.000  30.69
ATOM   2386  O1  HOH W  49     4.221  11.439  33.921  1.000  28.27
ATOM   2387  O1  HOH W  50     6.471   7.214  33.313  1.000  30.73
ATOM   2388  O1  HOH W  51     6.997  11.081   3.016  1.000  29.06
ATOM   2389  O1  HOH W  52     9.828  14.413   1.356  1.000  36.16
ATOM   2390  O1  HOH W  53    -2.049   5.578  31.420  1.000  34.40
ATOM   2391  O1  HOH W  54     7.546  28.605  19.653  1.000  38.00
```

FIGURE 247

```
ATOM   2392  O1  HOH W   55   -11.689  15.787  24.708 1.000 27.99
ATOM   2393  O1  HOH W   56    -1.930  38.222   3.832 1.000 26.57
ATOM   2394  O1  HOH W   57     3.629   5.858  35.758 1.000 33.41
ATOM   2395  O1  HOH W   58     2.994  20.770  -0.697 1.000 26.75
ATOM   2396  O1  HOH W   59   -13.363  22.643  29.523 1.000 32.53
ATOM   2397  O1  HOH W   60    -3.967  36.098   3.552 1.000 24.24
ATOM   2398  O1  HOH W   61   -13.003  28.717  20.098 1.000 30.30
ATOM   2399  O1  HOH W   62    -3.571  34.737  21.021 1.000 24.77
ATOM   2400  O1  HOH W   63    -3.353  25.782  37.784 1.000 31.16
ATOM   2401  O1  HOH W   64    -4.181  15.085  11.174 1.000 23.09
ATOM   2402  O1  HOH W   65    14.882   1.430  29.740 1.000 32.36
ATOM   2403  O1  HOH W   66    -2.385  10.919  14.099 1.000 31.04
ATOM   2404  O1  HOH W   67    -2.022  11.997  12.100 1.000 34.23
ATOM   2405  O1  HOH W   68    -0.074   6.701  29.852 1.000 28.84
ATOM   2406  O1  HOH W   69    13.012  17.319  31.049 1.000 34.35
ATOM   2407  O1  HOH W   70    -0.945  -1.322  32.490 1.000 27.87
ATOM   2408  O1  HOH W   71   -14.687  16.999   7.638 1.000 39.15
ATOM   2409  O1  HOH W   72     5.621  40.002  16.979 1.000 36.19
ATOM   2410  O1  HOH W   73     5.019  34.934  -5.124 1.000 30.14
ATOM   2411  O1  HOH W   74   -13.469  20.866  21.275 1.000 35.79
ATOM   2412  O1  HOH W   75    -6.587  38.439  -4.937 1.000 34.64
ATOM   2413  O1  HOH W   76    -6.586  20.943   1.389 1.000 34.28
ATOM   2414  O1  HOH W   77    16.678   2.326  14.116 1.000 34.62
ATOM   2415  O1  HOH W   78    -0.115   2.845  36.291 1.000 30.53
ATOM   2416  O1  HOH W   79    -0.221  19.000  -0.242 1.000 25.17
ATOM   2417  O1  HOH W   80    18.011  13.617  17.062 1.000 28.47
ATOM   2418  O1  HOH W   81     8.378   5.752  31.945 1.000 25.91
ATOM   2419  O1  HOH W   82    -1.655  40.288  22.680 1.000 32.53
ATOM   2420  O1  HOH W   83     6.545  30.062  22.582 1.000 41.03
ATOM   2421  O1  HOH W   84     8.148  39.805  15.692 1.000 35.25
ATOM   2422  O1  HOH W   85   -14.461  20.880  32.244 1.000 35.66
ATOM   2423  O1  HOH W   86     5.851   3.752  34.055 1.000 36.71
ATOM   2424  O1  HOH W   87    -0.955   1.090  13.636 1.000 39.92
ATOM   2425  O1  HOH W   88     8.422  39.414  -0.957 1.000 48.27
ATOM   2426  O1  HOH W   89    10.954  39.318   2.465 1.000 44.33
ATOM   2427  O1  HOH W   90     2.579  50.503   2.300 1.000 54.86
ATOM   2428  O1  HOH W   91     3.085  48.432   3.786 1.000 37.84
ATOM   2429  O1  HOH W   92     6.015  47.673  10.758 1.000 46.93
ATOM   2430  O1  HOH W   93    -4.388  -7.612  19.050 1.000 45.59
ATOM   2431  O1  HOH W   94     0.214  18.775  39.716 1.000 51.95
ATOM   2432  O1  HOH W   95   -12.966  13.296  30.655 1.000 33.33
ATOM   2433  O1  HOH W   96     0.538  14.855  35.881 1.000 40.77
ATOM   2434  O1  HOH W   97    17.070  25.109   3.747 1.000 45.67
ATOM   2435  O1  HOH W   98    11.830  27.957  -0.458 1.000 43.72
ATOM   2436  O1  HOH W   99    -4.616  12.312  11.217 1.000 40.90
ATOM   2437  O1  HOH W  100    11.872  35.092   7.761 1.000 55.45
ATOM   2438  O1  HOH W  101    10.663  36.578   9.005 1.000 38.01
ATOM   2439  O1  HOH W  102    14.787  30.925   2.347 1.000 38.58
ATOM   2440  O1  HOH W  103    -7.639  22.432  -0.126 1.000 30.65
ATOM   2441  O1  HOH W  104    -0.768  39.758  18.325 1.000 32.85
ATOM   2442  O1  HOH W  105    11.805  25.356  22.168 1.000 40.43
ATOM   2443  O1  HOH W  106    20.422  18.338  13.902 1.000 45.59
```

FIGURE 248

| | | | | | | | | | |
|---|---|---|---|---|---|---|---|---|---|
| ATOM | 2444 | O1 | HOH | W | 107 | 10.183 | 24.874 | 30.453 | 1.000 38.68 |
| ATOM | 2445 | O1 | HOH | W | 108 | 16.785 | 32.728 | 12.612 | 1.000 31.96 |
| ATOM | 2446 | O1 | HOH | W | 109 | 13.492 | 30.752 | 17.655 | 1.000 39.37 |
| ATOM | 2447 | O1 | HOH | W | 110 | -3.931 | 16.862 | 2.029 | 1.000 30.36 |
| ATOM | 2448 | O1 | HOH | W | 111 | -7.045 | 29.232 | 5.340 | 1.000 28.48 |
| ATOM | 2449 | O1 | HOH | W | 112 | -7.762 | 11.786 | 25.923 | 1.000 28.04 |
| ATOM | 2450 | O1 | HOH | W | 113 | -13.605 | 33.677 | 20.128 | 1.000 32.20 |
| ATOM | 2451 | O1 | HOH | W | 114 | 10.065 | 39.638 | 9.803 | 1.000 38.13 |
| ATOM | 2452 | O1 | HOH | W | 115 | -8.934 | 24.435 | 1.974 | 1.000 31.50 |
| ATOM | 2453 | O1 | HOH | W | 116 | 17.216 | 10.741 | 21.573 | 1.000 34.76 |
| ATOM | 2454 | O1 | HOH | W | 117 | -11.923 | 22.839 | 19.220 | 1.000 39.73 |
| ATOM | 2455 | O1 | HOH | W | 118 | 7.473 | 12.705 | 1.120 | 1.000 36.05 |
| ATOM | 2456 | O1 | HOH | W | 119 | 5.483 | 8.873 | 2.549 | 1.000 43.08 |
| ATOM | 2457 | O1 | HOH | W | 120 | -14.010 | 13.235 | 28.254 | 1.000 43.67 |
| ATOM | 2458 | O1 | HOH | W | 121 | -6.810 | 4.829 | 28.513 | 1.000 38.61 |
| ATOM | 2459 | O1 | HOH | W | 122 | -14.132 | 10.542 | 31.339 | 1.000 58.03 |
| ATOM | 2460 | O1 | HOH | W | 123 | 5.390 | 21.831 | 37.038 | 1.000 43.01 |
| ATOM | 2461 | O1 | HOH | W | 124 | -14.479 | 21.966 | 26.038 | 1.000 35.30 |
| ATOM | 2462 | O1 | HOH | W | 125 | 4.264 | 17.945 | -1.288 | 1.000 36.29 |
| ATOM | 2463 | O1 | HOH | W | 126 | 23.828 | 24.174 | 30.873 | 1.000 49.73 |
| ATOM | 2464 | O1 | HOH | W | 127 | -6.176 | 26.450 | 5.939 | 1.000 65.00 |
| ATOM | 2465 | O1 | HOH | W | 128 | 3.350 | 34.622 | 26.589 | 1.000 39.90 |
| ATOM | 2466 | O1 | HOH | W | 129 | 16.916 | 27.171 | 7.485 | 1.000 41.94 |
| ATOM | 2467 | O1 | HOH | W | 130 | -11.189 | 32.210 | 8.814 | 1.000 35.24 |
| ATOM | 2468 | O1 | HOH | W | 131 | -4.460 | 2.050 | 29.021 | 1.000 40.95 |
| ATOM | 2469 | O1 | HOH | W | 132 | -15.621 | 16.785 | 16.397 | 1.000 51.14 |
| ATOM | 2470 | O1 | HOH | W | 133 | 13.141 | -0.750 | 30.285 | 1.000 35.50 |
| ATOM | 2471 | O1 | HOH | W | 134 | 16.391 | 14.131 | 18.996 | 1.000 33.72 |
| ATOM | 2472 | O1 | HOH | W | 135 | 15.720 | 23.607 | 18.037 | 1.000 36.32 |
| ATOM | 2473 | O1 | HOH | W | 136 | -9.180 | 28.989 | 7.435 | 1.000 51.57 |
| ATOM | 2474 | O1 | HOH | W | 137 | -13.398 | 18.098 | 35.125 | 1.000 52.51 |
| ATOM | 2475 | O1 | HOH | W | 138 | -14.347 | 26.998 | 19.051 | 1.000 43.88 |
| ATOM | 2476 | O1 | HOH | W | 139 | 17.167 | 1.215 | 28.662 | 1.000 40.00 |
| ATOM | 2477 | O1 | HOH | W | 140 | -5.468 | 13.807 | 7.111 | 1.000 45.45 |
| ATOM | 2478 | O1 | HOH | W | 141 | -4.475 | 4.635 | 29.841 | 1.000 36.10 |
| ATOM | 2479 | O1 | HOH | W | 142 | -12.828 | 27.385 | 13.802 | 1.000 33.50 |
| ATOM | 2480 | O1 | HOH | W | 143 | -13.938 | 17.712 | 24.521 | 1.000 31.09 |
| ATOM | 2481 | O1 | HOH | W | 144 | 16.503 | 26.254 | 10.447 | 1.000 46.13 |
| ATOM | 2482 | O1 | HOH | W | 145 | 20.599 | 20.875 | 15.821 | 1.000 41.98 |
| ATOM | 2483 | O1 | HOH | W | 146 | 20.503 | 19.870 | 22.082 | 1.000 51.04 |
| ATOM | 2484 | O1 | HOH | W | 147 | 4.262 | 18.175 | 36.175 | 1.000 33.32 |
| ATOM | 2485 | O1 | HOH | W | 148 | -0.297 | 26.441 | 36.081 | 1.000 52.28 |
| ATOM | 2486 | O1 | HOH | W | 149 | 20.297 | 28.737 | 16.671 | 1.000 44.74 |
| ATOM | 2487 | O1 | HOH | W | 150 | 7.203 | 23.388 | 35.762 | 1.000 66.45 |
| ATOM | 2488 | O1 | HOH | W | 151 | 10.549 | 7.398 | 31.284 | 1.000 38.68 |
| ATOM | 2489 | O1 | HOH | W | 152 | 6.081 | 38.872 | -2.812 | 1.000 40.08 |
| ATOM | 2490 | O1 | HOH | W | 153 | 13.265 | 33.000 | 1.040 | 1.000 36.24 |
| ATOM | 2491 | O1 | HOH | W | 154 | -12.530 | 39.835 | 27.125 | 1.000105.41 |
| ATOM | 2492 | O1 | HOH | W | 155 | 11.420 | 11.430 | 30.533 | 1.000 47.78 |
| ATOM | 2493 | O1 | HOH | W | 156 | 0.901 | 8.244 | 35.852 | 1.000 33.14 |
| ATOM | 2494 | O1 | HOH | W | 157 | -7.963 | 29.336 | -0.295 | 1.000 50.61 |
| ATOM | 2495 | O1 | HOH | W | 158 | 20.035 | 12.009 | 18.471 | 1.000 34.37 |

FIGURE 249

```
ATOM   2496  O1  HOH W 159    -4.350    3.543   10.491 1.000 84.51
ATOM   2497  O1  HOH W 160     4.286    9.674   36.102 1.000 40.87
ATOM   2498  O1  HOH W 161    -8.003   41.353   17.020 1.000 48.97
ATOM   2499  O1  HOH W 162    15.195   17.562   28.763 1.000 43.23
ATOM   2500  O1  HOH W 163   -10.778    5.540   28.103 1.000 47.36
ATOM   2501  O1  HOH W 164    19.303   31.924   16.796 1.000 51.07
ATOM   2502  O1  HOH W 165    -4.383   19.665   -0.828 1.000 32.47
ATOM   2503  O1  HOH W 166     8.839   24.816   -3.783 1.000 41.71
ATOM   2504  O1  HOH W 167     6.219   15.861   -1.300 1.000 43.10
ATOM   2505  O1  HOH W 168    10.025   33.624   18.562 1.000 40.32
ATOM   2506  O1  HOH W 169     7.836   30.797   27.712 1.000 56.16
ATOM   2507  O1  HOH W 170    -9.946   19.362   35.362 1.000 41.05
ATOM   2508  O1  HOH W 171    22.397   23.179   24.094 1.000 37.17
ATOM   2509  O1  HOH W 172     6.196   31.438   24.998 1.000 39.04
ATOM   2510  O1  HOH W 173     2.656   29.647  -11.398 1.000 69.02
ATOM   2511  O1  HOH W 174    -7.993   19.195    2.017 1.000 51.50
ATOM   2512  O1  HOH W 175    -7.725    9.838   10.116 1.000 41.23
ATOM   2513  O1  HOH W 176    10.217    8.209   35.322 1.000 52.55
ATOM   2514  O1  HOH W 177    22.886   18.048    5.069 1.000 50.22
ATOM   2515  O1  HOH W 178    13.259    6.843   29.204 1.000 37.28
ATOM   2516  O1  HOH W 179   -11.344   39.086   20.797 1.000 63.58
ATOM   2517  O1  HOH W 180    13.661   33.712    7.349 1.000 48.08
ATOM   2518  O1  HOH W 181    -3.554    0.841   36.601 1.000 44.25
ATOM   2519  O1  HOH W 182     2.483   16.905   37.338 1.000 45.30
ATOM   2520  O1  HOH W 183    20.094    7.002   12.783 1.000 44.53
ATOM   2521  O1  HOH W 184    13.549   19.866   -1.559 1.000 51.39
ATOM   2522  O1  HOH W 185    11.649   -2.468   19.869 1.000 58.70
ATOM   2523  O1  HOH W 186   -11.387    9.057   20.869 1.000 50.26
ATOM   2524  O1  HOH W 187     2.270   53.746    3.948 1.000 77.69
ATOM   2525  O1  HOH W 188     7.272   43.089   10.416 1.000 40.06
ATOM   2526  O1  HOH W 189   -10.704   43.630   20.531 1.000 67.96
ATOM   2527  O1  HOH W 190   -10.161   31.212   -6.317 1.000 49.46
ATOM   2528  O1  HOH W 191     9.522    6.064    4.334 1.000 40.34
ATOM   2529  O1  HOH W 192    16.516   16.717   21.174 1.000 20.43
ATOM   2530  O1  HOH W 193    -0.857   36.253   20.284 1.000 32.45
ATOM   2531  O1  HOH W 194    18.504   18.275   22.970 1.000 34.08
ATOM   2532  O1  HOH W 195     5.801   29.116  -17.383 1.000 43.44
ATOM   2533  O1  HOH W 196    -7.990   22.703   42.079 1.000 44.28
ATOM   2534  O1  HOH W 197    -6.632   16.747   36.401 1.000 37.74
ATOM   2535  O1  HOH W 198   -11.815   21.607   16.468 1.000 30.66
ATOM   2536  O1  HOH W 199    -2.843   32.478  -11.634 1.000 33.04
ATOM   2537  O1  HOH W 200   -10.429   21.931    2.610 1.000 43.58
ATOM   2538  O1  HOH W 201   -12.782   11.466   36.315 1.000 64.73
ATOM   2539  O1  HOH W 202    -1.120    8.730    9.515 1.000 39.25
ATOM   2540  O1  HOH W 203     7.752   27.565   23.146 1.000 40.81
ATOM   2541  O1  HOH W 204    -4.173   17.946   -3.218 1.000 40.93
ATOM   2542  O1  HOH W 205   -12.084    5.496   19.653 1.000 41.61
ATOM   2543  O1  HOH W 206     1.514    0.000   33.985 1.000 47.99
ATOM   2544  O1  HOH W 207    -4.358   32.825   -9.953 1.000 43.82
ATOM   2545  O1  HOH W 208    14.414   14.005   29.829 1.000 45.03
ATOM   2546  O1  HOH W 209    22.352   27.139   21.459 1.000 63.00
ATOM   2547  O1  HOH W 210   -12.128   21.274    9.705 1.000 39.35
```

FIGURE 250

| | | | | | | | | | |
|---|---|---|---|---|---|---|---|---|---|
| ATOM | 2548 | O1 | HOH | W | 211 | -15.431 | 29.589 | 23.297 | 1.000 42.10 |
| ATOM | 2549 | O1 | HOH | W | 212 | 15.717 | 21.134 | 2.051 | 1.000 44.92 |
| ATOM | 2550 | O1 | HOH | W | 213 | 22.149 | 19.371 | 9.989 | 1.000 42.03 |
| ATOM | 2551 | O1 | HOH | W | 214 | -12.478 | 28.555 | 38.340 | 1.000 49.23 |
| ATOM | 2552 | O1 | HOH | W | 215 | -10.373 | 26.583 | 11.557 | 1.000 78.42 |
| ATOM | 2553 | O1 | HOH | W | 216 | 5.904 | 28.076 | 21.168 | 1.000 47.47 |
| ATOM | 2554 | O1 | HOH | W | 217 | 18.063 | 28.353 | 10.622 | 1.000 39.47 |
| ATOM | 2555 | O1 | HOH | W | 218 | 5.741 | 29.596 | 34.757 | 1.000 50.24 |
| ATOM | 2556 | O1 | HOH | W | 219 | 23.482 | 28.211 | 28.256 | 1.000 35.92 |
| ATOM | 2557 | O1 | HOH | W | 220 | 20.729 | 22.839 | 22.289 | 1.000 47.92 |
| ATOM | 2558 | O1 | HOH | W | 221 | -13.743 | 23.631 | 15.768 | 1.000 56.18 |
| ATOM | 2559 | O1 | HOH | W | 222 | 0.808 | 4.763 | 11.965 | 1.000 52.58 |
| ATOM | 2560 | O1 | HOH | W | 223 | 19.695 | 26.083 | 30.808 | 1.000 48.34 |
| ATOM | 2561 | O1 | HOH | W | 224 | -10.086 | 39.766 | 26.571 | 1.000 37.07 |
| ATOM | 2562 | O1 | HOH | W | 225 | -8.185 | 26.002 | 12.785 | 1.000 43.04 |
| ATOM | 2563 | O1 | HOH | W | 226 | -15.767 | 14.896 | 27.476 | 1.000 47.84 |
| ATOM | 2564 | O1 | HOH | W | 227 | -8.943 | 41.210 | 23.852 | 1.000 51.44 |
| ATOM | 2565 | O1 | HOH | W | 228 | -13.243 | 38.293 | 6.326 | 1.000 46.48 |
| ATOM | 2566 | O1 | HOH | W | 229 | 18.663 | 0.325 | 20.946 | 1.000 45.85 |
| ATOM | 2567 | O1 | HOH | W | 230 | 12.773 | 6.887 | 31.536 | 1.000 35.71 |
| ATOM | 2568 | O1 | HOH | W | 231 | -7.081 | 32.709 | -9.020 | 1.000 54.13 |
| ATOM | 2569 | O1 | HOH | W | 232 | -14.685 | 24.271 | 19.574 | 1.000 44.68 |
| ATOM | 2570 | O1 | HOH | W | 233 | 1.541 | 7.037 | 10.861 | 1.000 42.37 |
| ATOM | 2571 | O1 | HOH | W | 234 | 17.407 | 14.624 | 24.034 | 1.000 49.34 |
| ATOM | 2572 | O1 | HOH | W | 235 | -8.898 | 25.154 | 4.255 | 1.000 55.39 |
| ATOM | 2573 | O1 | HOH | W | 236 | 9.061 | 28.544 | 24.947 | 1.000 39.46 |
| ATOM | 2574 | O1 | HOH | W | 237 | -13.663 | 15.439 | 32.214 | 1.000 45.65 |
| ATOM | 2575 | O1 | HOH | W | 238 | 13.791 | 17.581 | 34.085 | 1.000 46.31 |
| ATOM | 2576 | O1 | HOH | W | 239 | -11.961 | 16.055 | 13.445 | 1.000 40.48 |
| ATOM | 2577 | O1 | HOH | W | 240 | 15.223 | 9.544 | 28.176 | 1.000 44.69 |
| ATOM | 2578 | O1 | HOH | W | 241 | -13.353 | 32.529 | 7.227 | 1.000 57.27 |
| ATOM | 2579 | O1 | HOH | W | 242 | 8.996 | 26.371 | -16.754 | 1.000 48.64 |
| ATOM | 2580 | O1 | HOH | W | 243 | 6.092 | 23.068 | -5.367 | 1.000 48.87 |
| ATOM | 2581 | O1 | HOH | W | 244 | 22.747 | 32.593 | 25.452 | 1.000 44.40 |
| ATOM | 2582 | O1 | HOH | W | 245 | -0.304 | 32.548 | -11.298 | 1.000 48.96 |
| ATOM | 2583 | O1 | HOH | W | 246 | -4.988 | -3.152 | 23.809 | 1.000 62.34 |
| ATOM | 2584 | O1 | HOH | W | 247 | 1.129 | 39.597 | -7.798 | 1.000 53.14 |
| ATOM | 2585 | O1 | HOH | W | 248 | -6.772 | 14.727 | 4.405 | 1.000 81.57 |
| ATOM | 2586 | O1 | HOH | W | 249 | 17.223 | 10.068 | 27.178 | 1.000 40.37 |
| ATOM | 2587 | O1 | HOH | W | 250 | 17.655 | 12.530 | 28.719 | 1.000 50.20 |
| ATOM | 2588 | O1 | HOH | W | 251 | 4.037 | 7.351 | 8.012 | 1.000 58.42 |
| ATOM | 2589 | O1 | HOH | W | 252 | -1.828 | 7.240 | 33.526 | 1.000 45.82 |
| ATOM | 2590 | O1 | HOH | W | 253 | -12.257 | 12.014 | 23.313 | 1.000 42.52 |
| ATOM | 2591 | O1 | HOH | W | 254 | 18.878 | 30.723 | 23.928 | 1.000 81.96 |
| ATOM | 2592 | O1 | HOH | W | 255 | -2.406 | 13.001 | 35.608 | 1.000 49.36 |
| ATOM | 2593 | O1 | HOH | W | 256 | 0.100 | 42.639 | 18.634 | 1.000 42.69 |
| ATOM | 2594 | O1 | HOH | W | 257 | 8.781 | 15.841 | -0.776 | 1.000 42.10 |
| ATOM | 2595 | O1 | HOH | W | 258 | 8.836 | 41.627 | 14.232 | 1.000 37.51 |
| ATOM | 2596 | O1 | HOH | W | 259 | 10.082 | 41.227 | 7.652 | 1.000 51.86 |
| ATOM | 2597 | O1 | HOH | W | 260 | 16.536 | 4.886 | 29.969 | 1.000 46.99 |
| ATOM | 2598 | O1 | HOH | W | 261 | 8.904 | 2.996 | 11.102 | 1.000 59.35 |
| ATOM | 2599 | O1 | HOH | W | 262 | 17.169 | 18.558 | 5.383 | 1.000 42.46 |

FIGURE 251

```
ATOM   2600  O1  HOH W 263      22.449  12.846   9.882 1.000 39.10
ATOM   2601  O1  HOH W 264      11.441  22.960  -0.297 1.000 46.40
ATOM   2602  O1  HOH W 265      12.891  35.186  -7.958 1.000 59.81
ATOM   2603  O1  HOH W 266     -13.897  24.909  13.026 1.000 45.86
ATOM   2604  O1  HOH W 267      19.060   9.563  25.380 1.000 45.48
ATOM   2605  O1  HOH W 268       3.802  25.392 -14.805 1.000 50.59
ATOM   2606  O1  HOH W 269      16.184  28.549  22.110 1.000 43.02
ATOM   2607  O1  HOH W 270      -1.154  37.399 -12.192 1.000 53.68
ATOM   2608  O1  HOH W 271      -4.123  -5.269  18.602 1.000 79.29
ATOM   2609  O1  HOH W 272      -7.384   2.425  21.048 1.000 57.48
ATOM   2610  O1  HOH W 273      18.456  25.557  18.479 1.000 44.20
ATOM   2611  O1  HOH W 274       6.328   1.205   9.458 1.000 59.21
ATOM   2612  O1  HOH W 275     -14.117   5.491  34.696 1.000 60.85
ATOM   2613  O1  HOH W 276     -10.629  13.583  38.737 1.000 45.87
ATOM   2614  O1  HOH W 277     -11.913  20.085  36.715 1.000 51.46
ATOM   2615  O1  HOH W 278      -8.375  43.387   4.147 1.000 45.52
ATOM   2616  O1  HOH W 279      -9.702  -4.797  28.731 1.000 54.85
ATOM   2617  O1  HOH W 280     -12.340  25.454  10.801 1.000 58.08
ATOM   2618  O1  HOH W 281      -4.825  10.727   8.928 1.000 55.18
ATOM   2619  O1  HOH W 282      -0.469  27.271  21.450 1.000143.86
ATOM   2620  O1  HOH W 283       1.342   6.223  -2.164 1.000 59.20
ATOM   2621  O1  HOH W 284     -13.187   3.566  20.610 1.000 59.09
ATOM   2622  O1  HOH W 285     -10.963  -4.464  24.556 1.000 70.44
ATOM   2623  O1  HOH W 286       2.082   7.263   5.127 1.000 59.07
ATOM   2624  O1  HOH W 287     -14.375  31.030  19.349 1.000 42.90
ATOM   2625  O1  HOH W 288     -13.932  23.344  10.653 1.000 42.75
ATOM   2626  O1  HOH W 289     -10.496  31.449   2.357 1.000 37.15
ATOM   2627  O1  HOH W 290      -5.935  42.393   1.278 1.000 48.92
ATOM   2628  O1  HOH W 291      -2.417  29.064  38.937 1.000 98.13
ATOM   2629  O1  HOH W 292       4.370   7.161   3.591 1.000 54.78
ATOM   2630  O1  HOH W 293     -12.101  29.567  -1.765 1.000 45.21
ATOM   2631  O1  HOH W 294      -2.974  52.167   6.924 1.000 54.46
ATOM   2632  O1  HOH W 295       6.373  24.732 -15.736 1.000 55.54
ATOM   2633  O1  HOH W 296       5.144   2.212  15.505 1.000132.19
ATOM   2634  O1  HOH W 297       4.119  25.540 -18.043 1.000 63.04
ATOM   2635  O1  HOH W 298      -6.584  46.120   5.004 1.000 61.91
ATOM   2636  O1  HOH W 299      17.182  15.542  27.047 1.000 45.04
ATOM   2637  O1  HOH W 300      12.276  33.194  -3.953 1.000 50.26
ATOM   2638  O1  HOH W 301       4.057  25.805  36.737 1.000 51.03
ATOM   2639  O1  HOH W 302      17.210  27.508  26.182 1.000 43.16
ATOM   2640  O1  HOH W 303     -13.383  20.836   7.055 1.000 53.40
ATOM   2641  O1  HOH W 304      19.482  17.276  28.478 1.000 60.44
ATOM   2642  O1  HOH W 305      -6.950  41.249  -1.159 1.000 53.64
ATOM   2643  O1  HOH W 306     -10.165   8.508  39.743 1.000 61.15
ATOM   2644  O1  HOH W 307       4.134  19.769  -3.502 1.000 52.25
ATOM   2645  O1  HOH W 308       3.101  15.563  -2.031 1.000 45.06
ATOM   2646  O1  HOH W 309       8.724  40.739  11.753 1.000 47.08
ATOM   2647  O1  HOH W 310     -10.535   2.414  25.587 1.000 88.70
END
```

FIGURE 252

```
CRYST1   38.852   69.610  117.777  90.00  90.00  90.00 P 21 21 21
ATOM      1  N   LYS A  19     -13.362  32.383  10.240  1.00 48.36
ATOM      2  CA  LYS A  19     -13.935  33.412   9.318  1.00 47.56
ATOM      3  CB  LYS A  19     -14.789  34.414  10.102  1.00 48.40
ATOM      4  CG  LYS A  19     -16.107  34.813   9.444  1.00 50.42
ATOM      5  CD  LYS A  19     -16.509  36.212   9.896  1.00 51.36
ATOM      6  CE  LYS A  19     -17.815  36.655   9.263  1.00 52.93
ATOM      7  NZ  LYS A  19     -18.963  36.009   9.969  1.00 50.02
ATOM      8  C   LYS A  19     -12.885  34.153   8.487  1.00 45.61
ATOM      9  O   LYS A  19     -12.823  33.994   7.265  1.00 46.13
ATOM     10  N   THR A  20     -12.070  34.966   9.153  1.00 43.56
ATOM     11  CA  THR A  20     -11.312  35.995   8.460  1.00 40.00
ATOM     12  CB  THR A  20     -11.081  37.248   9.348  1.00 41.25
ATOM     13  OG1 THR A  20     -11.320  38.444   8.598  1.00 41.63
ATOM     14  CG2 THR A  20      -9.647  37.393   9.810  1.00 43.82
ATOM     15  C   THR A  20     -10.091  35.385   7.764  1.00 36.65
ATOM     16  O   THR A  20      -9.557  34.349   8.149  1.00 34.08
ATOM     17  N   SER A  21      -9.707  36.004   6.662  1.00 33.82
ATOM     18  CA  SER A  21      -9.158  35.238   5.553  1.00 31.39
ATOM     19  CB  SER A  21     -10.279  34.427   4.900  1.00 32.67
ATOM     20  OG  SER A  21      -9.913  33.919   3.630  1.00 34.27
ATOM     21  C   SER A  21      -8.654  36.302   4.606  1.00 31.16
ATOM     22  O   SER A  21      -9.312  37.328   4.434  1.00 30.44
ATOM     23  N   CYS A  22      -7.494  36.064   4.005  1.00 28.46
ATOM     24  CA  CYS A  22      -6.989  36.913   2.927  1.00 28.63
ATOM     25  CB  CYS A  22      -5.891  37.819   3.465  1.00 28.57
ATOM     26  SG ACYS A  22      -6.413  38.961   4.757  0.50 34.99
ATOM     27  SG BCYS A  22      -5.652  39.300   2.462  0.50 30.02
ATOM     28  C   CYS A  22      -6.377  36.077   1.801  1.00 26.91
ATOM     29  O   CYS A  22      -5.154  35.976   1.717  1.00 26.74
ATOM     30  N   PRO A  23      -7.204  35.459   0.965  1.00 27.39
ATOM     31  CA  PRO A  23      -6.683  34.571  -0.080  1.00 27.48
ATOM     32  CB  PRO A  23      -7.934  33.853  -0.574  1.00 28.38
ATOM     33  CG  PRO A  23      -8.993  34.875  -0.368  1.00 30.20
ATOM     34  CD  PRO A  23      -8.674  35.517   0.952  1.00 27.17
ATOM     35  C   PRO A  23      -6.036  35.395  -1.185  1.00 27.85
ATOM     36  O   PRO A  23      -6.513  36.495  -1.487  1.00 28.68
ATOM     37  N   ILE A  24      -4.929  34.890  -1.723  1.00 25.89
ATOM     38  CA  ILE A  24      -4.148  35.595  -2.723  1.00 24.61
ATOM     39  CB  ILE A  24      -2.747  35.890  -2.154  1.00 25.01
ATOM     40  CG1 ILE A  24      -2.821  36.742  -0.873  1.00 23.94
ATOM     41  CD1 ILE A  24      -3.654  38.013  -1.033  1.00 28.76
ATOM     42  CG2 ILE A  24      -1.845  36.467  -3.229  1.00 24.43
ATOM     43  C   ILE A  24      -4.044  34.641  -3.898  1.00 24.73
ATOM     44  O   ILE A  24      -3.774  33.445  -3.719  1.00 24.14
ATOM     45  N   LYS A  25      -4.262  35.138  -5.112  1.00 23.63
ATOM     46  CA  LYS A  25      -4.158  34.245  -6.261  1.00 23.86
ATOM     47  CB  LYS A  25      -4.639  34.948  -7.538  1.00 25.41
ATOM     48  CG  LYS A  25      -6.138  35.188  -7.552  1.00 29.05
ATOM     49  CD  LYS A  25      -6.540  35.965  -8.799  1.00 35.15
ATOM     50  CE  LYS A  25      -8.054  36.059  -8.951  1.00 40.89
ATOM     51  NZ  LYS A  25      -8.390  36.581 -10.313  1.00 45.05
```

FIGURE 253

| | | | | | | | | | |
|---|---|---|---|---|---|---|---|---|---|
| ATOM | 52 | C | LYS | A | 25 | -2.688 | 33.885 | -6.407 | 1.00 22.99 |
| ATOM | 53 | O | LYS | A | 25 | -1.823 | 34.725 | -6.195 | 1.00 23.91 |
| ATOM | 54 | N | ILE | A | 26 | -2.374 | 32.643 | -6.762 | 1.00 24.14 |
| ATOM | 55 | CA | ILE | A | 26 | -0.961 | 32.283 | -6.723 | 1.00 26.45 |
| ATOM | 56 | CB | ILE | A | 26 | -0.718 | 30.774 | -6.781 | 1.00 26.63 |
| ATOM | 57 | CG1 | ILE | A | 26 | -1.088 | 30.233 | -8.158 | 1.00 25.40 |
| ATOM | 58 | CD1 | ILE | A | 26 | -0.405 | 28.926 | -8.497 | 1.00 33.92 |
| ATOM | 59 | CG2 | ILE | A | 26 | -1.424 | 30.068 | -5.616 | 1.00 25.53 |
| ATOM | 60 | C | ILE | A | 26 | -0.148 | 33.072 | -7.745 | 1.00 28.11 |
| ATOM | 61 | O | ILE | A | 26 | 1.003 | 33.402 | -7.493 | 1.00 30.02 |
| ATOM | 62 | N | ASN | A | 27 | -0.770 | 33.454 | -8.855 | 1.00 30.78 |
| ATOM | 63 | CA | ASN | A | 27 | -0.033 | 34.223 | -9.862 | 1.00 35.08 |
| ATOM | 64 | CB | ASN | A | 27 | -0.710 | 34.094 | -11.236 | 1.00 34.95 |
| ATOM | 65 | CG | ASN | A | 27 | -1.552 | 32.824 | -11.347 | 1.00 40.82 |
| ATOM | 66 | OD1 | ASN | A | 27 | -1.093 | 31.822 | -11.915 | 1.00 44.00 |
| ATOM | 67 | ND2 | ASN | A | 27 | -2.770 | 32.844 | -10.778 | 1.00 42.15 |
| ATOM | 68 | C | ASN | A | 27 | 0.174 | 35.683 | -9.455 | 1.00 34.87 |
| ATOM | 69 | O | ASN | A | 27 | 0.938 | 36.415 | -10.098 | 1.00 38.32 |
| ATOM | 70 | N | GLN | A | 28 | -0.491 | 36.100 | -8.379 | 1.00 33.79 |
| ATOM | 71 | CA | GLN | A | 28 | -0.283 | 37.411 | -7.776 | 1.00 33.05 |
| ATOM | 72 | CB | GLN | A | 28 | -1.633 | 38.093 | -7.546 | 1.00 34.54 |
| ATOM | 73 | CG | GLN | A | 28 | -2.004 | 39.014 | -8.699 | 1.00 40.43 |
| ATOM | 74 | CD | GLN | A | 28 | -3.422 | 38.827 | -9.172 | 1.00 46.19 |
| ATOM | 75 | OE1 | GLN | A | 28 | -4.339 | 38.673 | -8.362 | 1.00 49.62 |
| ATOM | 76 | NE2 | GLN | A | 28 | -3.612 | 38.845 | -10.491 | 1.00 49.01 |
| ATOM | 77 | C | GLN | A | 28 | 0.520 | 37.409 | -6.478 | 1.00 31.93 |
| ATOM | 78 | O | GLN | A | 28 | 0.823 | 38.469 | -5.920 | 1.00 30.78 |
| ATOM | 79 | N | PHE | A | 29 | 0.863 | 36.216 | -5.996 | 1.00 31.01 |
| ATOM | 80 | CA | PHE | A | 29 | 1.573 | 36.132 | -4.720 | 1.00 29.71 |
| ATOM | 81 | CB | PHE | A | 29 | 1.805 | 34.688 | -4.249 | 1.00 29.10 |
| ATOM | 82 | CG | PHE | A | 29 | 2.257 | 34.608 | -2.809 | 1.00 25.53 |
| ATOM | 83 | CD1 | PHE | A | 29 | 1.331 | 34.519 | -1.790 | 1.00 25.89 |
| ATOM | 84 | CE1 | PHE | A | 29 | 1.749 | 34.470 | -0.465 | 1.00 25.38 |
| ATOM | 85 | CZ | PHE | A | 29 | 3.101 | 34.545 | -0.156 | 1.00 23.03 |
| ATOM | 86 | CE2 | PHE | A | 29 | 4.024 | 34.658 | -1.171 | 1.00 22.38 |
| ATOM | 87 | CD2 | PHE | A | 29 | 3.608 | 34.678 | -2.481 | 1.00 22.17 |
| ATOM | 88 | C | PHE | A | 29 | 2.872 | 36.930 | -4.662 | 1.00 31.08 |
| ATOM | 89 | O | PHE | A | 29 | 3.104 | 37.662 | -3.690 | 1.00 30.41 |
| ATOM | 90 | N | GLU | A | 30 | 3.719 | 36.779 | -5.680 | 1.00 30.60 |
| ATOM | 91 | CA | GLU | A | 30 | 5.044 | 37.388 | -5.633 | 1.00 32.65 |
| ATOM | 92 | CB | GLU | A | 30 | 5.766 | 37.120 | -6.953 | 1.00 33.47 |
| ATOM | 93 | CG | GLU | A | 30 | 7.107 | 37.828 | -7.096 | 1.00 38.26 |
| ATOM | 94 | CD | GLU | A | 30 | 8.210 | 37.192 | -6.273 | 1.00 41.01 |
| ATOM | 95 | OE1 | GLU | A | 30 | 8.324 | 35.942 | -6.263 | 1.00 41.31 |
| ATOM | 96 | OE2 | GLU | A | 30 | 8.972 | 37.954 | -5.638 | 1.00 43.55 |
| ATOM | 97 | C | GLU | A | 30 | 4.913 | 38.890 | -5.391 | 1.00 32.57 |
| ATOM | 98 | O | GLU | A | 30 | 5.570 | 39.475 | -4.523 | 1.00 31.57 |
| ATOM | 99 | N | GLY | A | 31 | 4.031 | 39.504 | -6.171 | 1.00 34.44 |
| ATOM | 100 | CA | GLY | A | 31 | 3.688 | 40.905 | -5.986 | 1.00 35.40 |
| ATOM | 101 | C | GLY | A | 31 | 2.984 | 41.274 | -4.697 | 1.00 35.45 |
| ATOM | 102 | O | GLY | A | 31 | 3.285 | 42.311 | -4.102 | 1.00 36.66 |
| ATOM | 103 | N | HIS | A | 32 | 2.040 | 40.449 | -4.250 | 1.00 35.17 |

FIGURE 254

| | | | | | | | | | |
|---|---|---|---|---|---|---|---|---|---|
| ATOM | 104 | CA | HIS | A | 32 | 1.406 | 40.666 | -2.953 | 1.00 34.19 |
| ATOM | 105 | CB | HIS | A | 32 | 0.377 | 39.571 | -2.650 | 1.00 33.45 |
| ATOM | 106 | CG | HIS | A | 32 | -0.137 | 39.576 | -1.239 | 1.00 35.35 |
| ATOM | 107 | ND1 | HIS | A | 32 | -1.005 | 40.533 | -0.759 | 1.00 34.86 |
| ATOM | 108 | CE1 | HIS | A | 32 | -1.294 | 40.275 | 0.504 | 1.00 38.34 |
| ATOM | 109 | NE2 | HIS | A | 32 | -0.667 | 39.165 | 0.856 | 1.00 39.21 |
| ATOM | 110 | CD2 | HIS | A | 32 | 0.072 | 38.714 | -0.212 | 1.00 36.26 |
| ATOM | 111 | C | HIS | A | 32 | 2.471 | 40.749 | -1.861 | 1.00 33.35 |
| ATOM | 112 | O | HIS | A | 32 | 2.461 | 41.663 | -1.037 | 1.00 31.23 |
| ATOM | 113 | N | PHE | A | 33 | 3.409 | 39.806 | -1.884 | 1.00 32.01 |
| ATOM | 114 | CA | PHE | A | 33 | 4.435 | 39.728 | -0.852 | 1.00 31.66 |
| ATOM | 115 | CB | PHE | A | 33 | 5.168 | 38.384 | -0.942 | 1.00 32.90 |
| ATOM | 116 | CG | PHE | A | 33 | 6.024 | 38.057 | 0.254 | 1.00 30.75 |
| ATOM | 117 | CD1 | PHE | A | 33 | 5.708 | 38.529 | 1.524 | 1.00 34.33 |
| ATOM | 118 | CE1 | PHE | A | 33 | 6.507 | 38.213 | 2.616 | 1.00 34.24 |
| ATOM | 119 | CZ | PHE | A | 33 | 7.643 | 37.424 | 2.450 | 1.00 35.46 |
| ATOM | 120 | CE2 | PHE | A | 33 | 7.961 | 36.943 | 1.186 | 1.00 32.02 |
| ATOM | 121 | CD2 | PHE | A | 33 | 7.145 | 37.255 | 0.106 | 1.00 27.29 |
| ATOM | 122 | C | PHE | A | 33 | 5.395 | 40.917 | -0.953 | 1.00 31.91 |
| ATOM | 123 | O | PHE | A | 33 | 5.757 | 41.484 | 0.077 | 1.00 30.81 |
| ATOM | 124 | N | MET | A | 34 | 5.784 | 41.309 | -2.170 | 1.00 31.13 |
| ATOM | 125 | CA | MET | A | 34 | 6.599 | 42.512 | -2.328 | 1.00 34.10 |
| ATOM | 126 | CB | MET | A | 34 | 6.951 | 42.790 | -3.797 | 1.00 33.71 |
| ATOM | 127 | CG | MET | A | 34 | 7.918 | 41.787 | -4.410 | 1.00 36.64 |
| ATOM | 128 | SD | MET | A | 34 | 9.456 | 41.519 | -3.504 | 1.00 45.35 |
| ATOM | 129 | CE | MET | A | 34 | 10.582 | 40.969 | -4.820 | 1.00 46.02 |
| ATOM | 130 | C | MET | A | 34 | 5.903 | 43.709 | -1.674 | 1.00 33.09 |
| ATOM | 131 | O | MET | A | 34 | 6.504 | 44.406 | -0.866 | 1.00 34.24 |
| ATOM | 132 | N | LYS | A | 35 | 4.629 | 43.919 | -1.996 | 1.00 35.14 |
| ATOM | 133 | CA | LYS | A | 35 | 3.835 | 44.999 | -1.411 | 1.00 35.12 |
| ATOM | 134 | CB | LYS | A | 35 | 2.416 | 44.986 | -1.990 | 1.00 36.58 |
| ATOM | 135 | CG | LYS | A | 35 | 2.372 | 45.164 | -3.500 | 1.00 39.86 |
| ATOM | 136 | CD | LYS | A | 35 | 1.013 | 45.684 | -3.944 | 1.00 44.78 |
| ATOM | 137 | CE | LYS | A | 35 | 1.181 | 46.751 | -5.007 | 1.00 46.40 |
| ATOM | 138 | NZ | LYS | A | 35 | 1.355 | 46.127 | -6.352 | 1.00 48.36 |
| ATOM | 139 | C | LYS | A | 35 | 3.808 | 44.960 | 0.122 | 1.00 35.83 |
| ATOM | 140 | O | LYS | A | 35 | 4.075 | 45.958 | 0.793 | 1.00 34.45 |
| ATOM | 141 | N | LEU | A | 36 | 3.505 | 43.799 | 0.695 | 1.00 34.49 |
| ATOM | 142 | CA | LEU | A | 36 | 3.546 | 43.658 | 2.144 | 1.00 33.34 |
| ATOM | 143 | CB | LEU | A | 36 | 3.238 | 42.218 | 2.534 | 1.00 33.70 |
| ATOM | 144 | CG | LEU | A | 36 | 1.800 | 41.748 | 2.349 | 1.00 34.08 |
| ATOM | 145 | CD1 | LEU | A | 36 | 1.759 | 40.272 | 2.714 | 1.00 39.25 |
| ATOM | 146 | CD2 | LEU | A | 36 | 0.827 | 42.549 | 3.202 | 1.00 35.36 |
| ATOM | 147 | C | LEU | A | 36 | 4.908 | 44.006 | 2.720 | 1.00 34.23 |
| ATOM | 148 | O | LEU | A | 36 | 5.017 | 44.469 | 3.855 | 1.00 32.77 |
| ATOM | 149 | N | GLN | A | 37 | 5.952 | 43.758 | 1.934 | 1.00 36.11 |
| ATOM | 150 | CA | GLN | A | 37 | 7.315 | 43.871 | 2.434 | 1.00 38.15 |
| ATOM | 151 | CB | GLN | A | 37 | 8.226 | 42.852 | 1.746 | 1.00 39.69 |
| ATOM | 152 | CG | GLN | A | 37 | 8.393 | 41.537 | 2.507 | 1.00 41.08 |
| ATOM | 153 | CD | GLN | A | 37 | 9.248 | 40.543 | 1.750 | 1.00 42.50 |
| ATOM | 154 | OE1 | GLN | A | 37 | 10.228 | 40.029 | 2.281 | 1.00 46.33 |
| ATOM | 155 | NE2 | GLN | A | 37 | 8.882 | 40.274 | 0.505 | 1.00 46.39 |

FIGURE 255

| ATOM | 156 | C   | GLN | A | 37 | 7.888  | 45.280 | 2.283 | 1.00 | 39.26 |
|------|-----|-----|-----|---|----|--------|--------|-------|------|-------|
| ATOM | 157 | O   | GLN | A | 37 | 8.913  | 45.600 | 2.881 | 1.00 | 38.73 |
| ATOM | 158 | N   | ALA | A | 38 | 7.219  | 46.099 | 1.481 | 1.00 | 39.85 |
| ATOM | 159 | CA  | ALA | A | 38 | 7.634  | 47.480 | 1.237 | 1.00 | 41.68 |
| ATOM | 160 | CB  | ALA | A | 38 | 6.717  | 48.129 | 0.200 | 1.00 | 40.33 |
| ATOM | 161 | C   | ALA | A | 38 | 7.638  | 48.288 | 2.538 | 1.00 | 42.41 |
| ATOM | 162 | O   | ALA | A | 38 | 7.000  | 47.898 | 3.515 | 1.00 | 42.66 |
| ATOM | 163 | N   | ASP | A | 39 | 8.358  | 49.408 | 2.545 | 1.00 | 43.16 |
| ATOM | 164 | CA  | ASP | A | 39 | 8.490  | 50.253 | 3.731 | 1.00 | 43.58 |
| ATOM | 165 | CB  | ASP | A | 39 | 7.222  | 51.066 | 3.995 | 1.00 | 43.94 |
| ATOM | 166 | CG  | ASP | A | 39 | 6.539  | 51.521 | 2.733 | 1.00 | 46.50 |
| ATOM | 167 | OD1 | ASP | A | 39 | 5.474  | 52.165 | 2.853 | 1.00 | 53.13 |
| ATOM | 168 | OD2 | ASP | A | 39 | 6.982  | 51.279 | 1.592 | 1.00 | 51.25 |
| ATOM | 169 | C   | ASP | A | 39 | 8.782  | 49.487 | 5.011 | 1.00 | 43.69 |
| ATOM | 170 | O   | ASP | A | 39 | 8.062  | 49.653 | 5.991 | 1.00 | 44.78 |
| ATOM | 171 | N   | SER | A | 40 | 9.823  | 48.663 | 5.025 | 1.00 | 44.51 |
| ATOM | 172 | CA  | SER | A | 40 | 10.177 | 47.964 | 6.256 | 1.00 | 44.47 |
| ATOM | 173 | CB  | SER | A | 40 | 10.697 | 48.954 | 7.308 | 1.00 | 45.60 |
| ATOM | 174 | OG  | SER | A | 40 | 11.858 | 49.640 | 6.852 | 1.00 | 45.70 |
| ATOM | 175 | C   | SER | A | 40 | 8.934  | 47.224 | 6.770 | 1.00 | 44.23 |
| ATOM | 176 | O   | SER | A | 40 | 8.450  | 47.477 | 7.879 | 1.00 | 43.64 |
| ATOM | 177 | N   | ASN | A | 41 | 8.410  | 46.338 | 5.927 | 1.00 | 42.57 |
| ATOM | 178 | CA  | ASN | A | 41 | 7.313  | 45.448 | 6.293 | 1.00 | 41.50 |
| ATOM | 179 | CB  | ASN | A | 41 | 7.802  | 44.364 | 7.264 | 1.00 | 42.19 |
| ATOM | 180 | CG  | ASN | A | 41 | 8.525  | 43.225 | 6.559 | 1.00 | 43.25 |
| ATOM | 181 | OD1 | ASN | A | 41 | 8.753  | 43.268 | 5.350 | 1.00 | 47.07 |
| ATOM | 182 | ND2 | ASN | A | 41 | 8.897  | 42.200 | 7.317 | 1.00 | 44.15 |
| ATOM | 183 | C   | ASN | A | 41 | 6.051  | 46.146 | 6.805 | 1.00 | 40.97 |
| ATOM | 184 | O   | ASN | A | 41 | 5.262  | 45.570 | 7.559 | 1.00 | 40.09 |
| ATOM | 185 | N   | TYR | A | 42 | 5.842  | 47.383 | 6.370 | 1.00 | 39.82 |
| ATOM | 186 | CA  | TYR | A | 42 | 4.723  | 48.184 | 6.859 | 1.00 | 40.35 |
| ATOM | 187 | CB  | TYR | A | 42 | 4.655  | 49.528 | 6.125 | 1.00 | 41.74 |
| ATOM | 188 | CG  | TYR | A | 42 | 3.461  | 50.359 | 6.527 | 1.00 | 45.15 |
| ATOM | 189 | CD1 | TYR | A | 42 | 3.431  | 51.021 | 7.753 | 1.00 | 48.34 |
| ATOM | 190 | CE1 | TYR | A | 42 | 2.333  | 51.778 | 8.137 | 1.00 | 51.74 |
| ATOM | 191 | CZ  | TYR | A | 42 | 1.246  | 51.877 | 7.287 | 1.00 | 54.21 |
| ATOM | 192 | OH  | TYR | A | 42 | 0.154  | 52.632 | 7.659 | 1.00 | 55.81 |
| ATOM | 193 | CE2 | TYR | A | 42 | 1.250  | 51.227 | 6.065 | 1.00 | 52.92 |
| ATOM | 194 | CD2 | TYR | A | 42 | 2.358  | 50.472 | 5.690 | 1.00 | 49.40 |
| ATOM | 195 | C   | TYR | A | 42 | 3.369  | 47.472 | 6.809 | 1.00 | 38.41 |
| ATOM | 196 | O   | TYR | A | 42 | 2.685  | 47.355 | 7.826 | 1.00 | 37.47 |
| ATOM | 197 | N   | LEU | A | 43 | 2.985  | 46.978 | 5.635 | 1.00 | 37.22 |
| ATOM | 198 | CA  | LEU | A | 43 | 1.667  | 46.380 | 5.480 | 1.00 | 34.65 |
| ATOM | 199 | CB  | LEU | A | 43 | 1.205  | 46.392 | 4.021 | 1.00 | 36.77 |
| ATOM | 200 | CG  | LEU | A | 43 | 0.731  | 47.739 | 3.455 | 1.00 | 34.94 |
| ATOM | 201 | CD1 | LEU | A | 43 | 0.530  | 47.603 | 1.962 | 1.00 | 38.85 |
| ATOM | 202 | CD2 | LEU | A | 43 | -0.567 | 48.164 | 4.139 | 1.00 | 37.34 |
| ATOM | 203 | C   | LEU | A | 43 | 1.660  | 44.953 | 6.016 | 1.00 | 34.58 |
| ATOM | 204 | O   | LEU | A | 43 | 0.613  | 44.459 | 6.441 | 1.00 | 33.18 |
| ATOM | 205 | N   | LEU | A | 44 | 2.812  | 44.290 | 5.972 | 1.00 | 32.70 |
| ATOM | 206 | CA  | LEU | A | 44 | 2.917  | 42.976 | 6.606 | 1.00 | 32.37 |
| ATOM | 207 | CB  | LEU | A | 44 | 4.316  | 42.376 | 6.458 | 1.00 | 32.08 |

FIGURE 256

| | | | | | | | | | |
|---|---|---|---|---|---|---|---|---|---|
| ATOM | 208 | CG | LEU | A | 44 | 4.293 | 40.922 | 6.948 | 1.00 30.67 |
| ATOM | 209 | CD1 | LEU | A | 44 | 4.884 | 39.953 | 5.934 | 1.00 35.30 |
| ATOM | 210 | CD2 | LEU | A | 44 | 4.877 | 40.746 | 8.342 | 1.00 30.73 |
| ATOM | 211 | C | LEU | A | 44 | 2.574 | 43.078 | 8.092 | 1.00 33.04 |
| ATOM | 212 | O | LEU | A | 44 | 1.743 | 42.326 | 8.603 | 1.00 31.84 |
| ATOM | 213 | N | SER | A | 45 | 3.248 | 43.992 | 8.784 | 1.00 32.72 |
| ATOM | 214 | CA | SER | A | 45 | 3.023 | 44.200 | 10.211 | 1.00 32.14 |
| ATOM | 215 | CB | SER | A | 45 | 3.937 | 45.297 | 10.761 | 1.00 32.86 |
| ATOM | 216 | OG | SER | A | 45 | 5.298 | 44.946 | 10.616 | 1.00 33.52 |
| ATOM | 217 | C | SER | A | 45 | 1.579 | 44.543 | 10.543 | 1.00 31.96 |
| ATOM | 218 | O | SER | A | 45 | 1.063 | 44.085 | 11.562 | 1.00 31.93 |
| ATOM | 219 | N | LYS | A | 46 | 0.937 | 45.378 | 9.730 | 1.00 31.67 |
| ATOM | 220 | CA | LYS | A | 46 | -0.452 | 45.743 | 9.983 | 1.00 32.52 |
| ATOM | 221 | CB | LYS | A | 46 | -0.907 | 46.880 | 9.058 | 1.00 33.10 |
| ATOM | 222 | CG | LYS | A | 46 | -0.320 | 48.247 | 9.408 | 1.00 37.46 |
| ATOM | 223 | CD | LYS | A | 46 | -1.206 | 49.024 | 10.362 | 1.00 43.28 |
| ATOM | 224 | CE | LYS | A | 46 | -0.660 | 48.938 | 11.785 | 1.00 46.45 |
| ATOM | 225 | NZ | LYS | A | 46 | -1.645 | 48.309 | 12.714 | 1.00 43.98 |
| ATOM | 226 | C | LYS | A | 46 | -1.361 | 44.534 | 9.819 | 1.00 31.81 |
| ATOM | 227 | O | LYS | A | 46 | -2.279 | 44.313 | 10.608 | 1.00 33.52 |
| ATOM | 228 | N | GLU | A | 47 | -1.108 | 43.735 | 8.788 | 1.00 30.77 |
| ATOM | 229 | CA | GLU | A | 47 | -1.921 | 42.546 | 8.607 | 1.00 29.42 |
| ATOM | 230 | CB | GLU | A | 47 | -1.527 | 41.852 | 7.317 | 1.00 29.31 |
| ATOM | 231 | CG | GLU | A | 47 | -2.261 | 40.540 | 7.157 | 1.00 30.91 |
| ATOM | 232 | CD | GLU | A | 47 | -2.032 | 39.991 | 5.770 | 1.00 33.04 |
| ATOM | 233 | OE1 | GLU | A | 47 | -2.462 | 40.656 | 4.790 | 1.00 31.27 |
| ATOM | 234 | OE2 | GLU | A | 47 | -1.387 | 38.923 | 5.697 | 1.00 30.22 |
| ATOM | 235 | C | GLU | A | 47 | -1.745 | 41.573 | 9.764 | 1.00 27.29 |
| ATOM | 236 | O | GLU | A | 47 | -2.729 | 41.065 | 10.317 | 1.00 28.88 |
| ATOM | 237 | N | TYR | A | 48 | -0.488 | 41.316 | 10.110 | 1.00 27.52 |
| ATOM | 238 | CA | TYR | A | 48 | -0.170 | 40.444 | 11.234 | 1.00 28.53 |
| ATOM | 239 | CB | TYR | A | 48 | 1.337 | 40.327 | 11.426 | 1.00 26.41 |
| ATOM | 240 | CG | TYR | A | 48 | 1.697 | 39.418 | 12.574 | 1.00 30.88 |
| ATOM | 241 | CD1 | TYR | A | 48 | 1.508 | 38.039 | 12.489 | 1.00 27.50 |
| ATOM | 242 | CE1 | TYR | A | 48 | 1.854 | 37.212 | 13.547 | 1.00 26.46 |
| ATOM | 243 | CZ | TYR | A | 48 | 2.341 | 37.759 | 14.713 | 1.00 31.48 |
| ATOM | 244 | OH | TYR | A | 48 | 2.683 | 36.975 | 15.797 | 1.00 33.16 |
| ATOM | 245 | CE2 | TYR | A | 48 | 2.539 | 39.118 | 14.814 | 1.00 33.37 |
| ATOM | 246 | CD2 | TYR | A | 48 | 2.198 | 39.937 | 13.760 | 1.00 31.15 |
| ATOM | 247 | C | TYR | A | 48 | -0.807 | 40.876 | 12.555 | 1.00 30.00 |
| ATOM | 248 | O | TYR | A | 48 | -1.212 | 40.047 | 13.374 | 1.00 29.71 |
| ATOM | 249 | N | GLU | A | 49 | -0.867 | 42.179 | 12.800 | 1.00 29.94 |
| ATOM | 250 | CA | GLU | A | 49 | -1.423 | 42.607 | 14.082 | 1.00 29.29 |
| ATOM | 251 | CB | GLU | A | 49 | -0.863 | 43.970 | 14.510 | 1.00 31.83 |
| ATOM | 252 | CG | GLU | A | 49 | 0.648 | 43.941 | 14.759 | 1.00 34.43 |
| ATOM | 253 | CD | GLU | A | 49 | 1.103 | 43.090 | 15.942 | 1.00 41.82 |
| ATOM | 254 | OE1 | GLU | A | 49 | 2.329 | 42.964 | 16.146 | 1.00 45.44 |
| ATOM | 255 | OE2 | GLU | A | 49 | 0.267 | 42.555 | 16.705 | 1.00 49.14 |
| ATOM | 256 | C | GLU | A | 49 | -2.948 | 42.494 | 14.156 | 1.00 28.43 |
| ATOM | 257 | O | GLU | A | 49 | -3.519 | 42.445 | 15.243 | 1.00 28.47 |
| ATOM | 258 | N | GLU | A | 50 | -3.597 | 42.362 | 13.002 | 1.00 26.77 |
| ATOM | 259 | CA | GLU | A | 50 | -5.026 | 42.129 | 12.939 | 1.00 28.42 |

FIGURE 257

```
ATOM    260  CB   GLU A  50      -5.501  42.167  11.493  1.00 29.72
ATOM    261  CG   GLU A  50      -5.695  43.555  10.902  1.00 37.08
ATOM    262  CD   GLU A  50      -6.521  43.494   9.635  1.00 48.22
ATOM    263  OE1  GLU A  50      -7.094  44.536   9.235  1.00 53.56
ATOM    264  OE2  GLU A  50      -6.588  42.394   9.038  1.00 51.31
ATOM    265  C    GLU A  50      -5.369  40.744  13.487  1.00 26.59
ATOM    266  O    GLU A  50      -6.498  40.514  13.903  1.00 28.10
ATOM    267  N    LEU A  51      -4.385  39.855  13.481  1.00 26.25
ATOM    268  CA   LEU A  51      -4.561  38.486  13.994  1.00 23.60
ATOM    269  CB   LEU A  51      -3.585  37.538  13.284  1.00 22.99
ATOM    270  CG   LEU A  51      -3.829  37.234  11.798  1.00 22.34
ATOM    271  CD1  LEU A  51      -2.549  36.611  11.228  1.00 18.21
ATOM    272  CD2  LEU A  51      -5.087  36.385  11.612  1.00 24.13
ATOM    273  C    LEU A  51      -4.370  38.363  15.509  1.00 24.96
ATOM    274  O    LEU A  51      -4.677  37.326  16.111  1.00 22.08
ATOM    275  N    LYS A  52      -3.855  39.417  16.144  1.00 26.20
ATOM    276  CA   LYS A  52      -3.365  39.323  17.514  1.00 26.71
ATOM    277  CB   LYS A  52      -2.860  40.693  17.980  1.00 26.43
ATOM    278  CG   LYS A  52      -2.737  40.861  19.471  1.00 33.28
ATOM    279  CD   LYS A  52      -2.346  42.297  19.849  1.00 36.15
ATOM    280  CE   LYS A  52      -2.370  42.442  21.371  1.00 39.71
ATOM    281  NZ   LYS A  52      -3.746  42.725  21.891  1.00 41.67
ATOM    282  C    LYS A  52      -4.401  38.751  18.487  1.00 25.95
ATOM    283  O    LYS A  52      -4.071  37.922  19.335  1.00 28.87
ATOM    284  N    ASP A  53      -5.647  39.193  18.369  1.00 25.82
ATOM    285  CA   ASP A  53      -6.665  38.840  19.352  1.00 27.69
ATOM    286  CB   ASP A  53      -7.547  40.052  19.677  1.00 29.82
ATOM    287  CG   ASP A  53      -6.811  41.109  20.492  1.00 35.24
ATOM    288  OD1  ASP A  53      -7.138  42.300  20.303  1.00 41.07
ATOM    289  OD2  ASP A  53      -5.893  40.851  21.306  1.00 38.05
ATOM    290  C    ASP A  53      -7.569  37.670  18.980  1.00 25.40
ATOM    291  O    ASP A  53      -8.525  37.364  19.698  1.00 26.92
ATOM    292  N    VAL A  54      -7.297  37.026  17.853  1.00 21.25
ATOM    293  CA   VAL A  54      -8.181  35.958  17.403  1.00 20.37
ATOM    294  CB   VAL A  54      -7.674  35.400  16.059  1.00 20.28
ATOM    295  CG1  VAL A  54      -8.452  34.176  15.627  1.00 20.13
ATOM    296  CG2  VAL A  54      -7.640  36.526  14.988  1.00 20.70
ATOM    297  C    VAL A  54      -8.155  34.888  18.496  1.00 21.34
ATOM    298  O    VAL A  54      -7.068  34.539  18.969  1.00 21.56
ATOM    299  N    GLY A  55      -9.345  34.408  18.857  1.00 19.73
ATOM    300  CA   GLY A  55      -9.501  33.351  19.830  1.00 21.36
ATOM    301  C    GLY A  55      -9.516  33.779  21.284  1.00 25.60
ATOM    302  O    GLY A  55      -9.779  32.934  22.137  1.00 25.18
ATOM    303  N    ARG A  56      -9.243  35.041  21.597  1.00 28.66
ATOM    304  CA   ARG A  56      -8.825  35.351  22.967  1.00 33.28
ATOM    305  CB   ARG A  56      -7.723  36.420  23.019  1.00 34.38
ATOM    306  CG   ARG A  56      -6.566  36.172  22.048  1.00 38.44
ATOM    307  CD   ARG A  56      -5.400  35.366  22.594  1.00 41.11
ATOM    308  NE   ARG A  56      -4.139  35.991  22.211  1.00 47.68
ATOM    309  CZ   ARG A  56      -3.441  36.808  22.989  1.00 51.01
ATOM    310  NH1  ARG A  56      -3.880  37.097  24.206  1.00 50.37
ATOM    311  NH2  ARG A  56      -2.308  37.346  22.551  1.00 48.68
```

FIGURE 258

| ATOM | 312 | C   | ARG | A | 56 | -10.003 | 35.704 | 23.870 | 1.00 | 34.09 |
|------|-----|-----|-----|---|----|---------|--------|--------|------|-------|
| ATOM | 313 | O   | ARG | A | 56 | -9.826  | 36.081 | 25.030 | 1.00 | 37.38 |
| ATOM | 314 | N   | ASN | A | 57 | -11.198 | 35.540 | 23.319 | 1.00 | 34.85 |
| ATOM | 315 | CA  | ASN | A | 57 | -12.448 | 35.609 | 24.046 | 1.00 | 34.43 |
| ATOM | 316 | CB  | ASN | A | 57 | -13.561 | 35.897 | 23.039 | 1.00 | 35.95 |
| ATOM | 317 | CG  | ASN | A | 57 | -13.661 | 34.836 | 21.944 | 1.00 | 40.08 |
| ATOM | 318 | OD1 | ASN | A | 57 | -12.748 | 34.655 | 21.124 | 1.00 | 42.89 |
| ATOM | 319 | ND2 | ASN | A | 57 | -14.799 | 34.144 | 21.912 | 1.00 | 40.39 |
| ATOM | 320 | C   | ASN | A | 57 | -12.760 | 34.309 | 24.799 | 1.00 | 31.67 |
| ATOM | 321 | O   | ASN | A | 57 | -13.767 | 34.232 | 25.487 | 1.00 | 33.78 |
| ATOM | 322 | N   | GLN | A | 58 | -11.920 | 33.286 | 24.653 | 1.00 | 27.75 |
| ATOM | 323 | CA  | GLN | A | 58 | -12.243 | 31.931 | 25.119 | 1.00 | 24.28 |
| ATOM | 324 | CB  | GLN | A | 58 | -11.843 | 30.903 | 24.058 | 1.00 | 23.90 |
| ATOM | 325 | CG  | GLN | A | 58 | -12.595 | 31.051 | 22.743 | 1.00 | 25.65 |
| ATOM | 326 | CD  | GLN | A | 58 | -12.102 | 30.074 | 21.714 | 1.00 | 26.89 |
| ATOM | 327 | OE1 | GLN | A | 58 | -10.971 | 30.202 | 21.238 | 1.00 | 28.76 |
| ATOM | 328 | NE2 | GLN | A | 58 | -12.933 | 29.084 | 21.381 | 1.00 | 28.16 |
| ATOM | 329 | C   | GLN | A | 58 | -11.584 | 31.583 | 26.458 | 1.00 | 23.11 |
| ATOM | 330 | O   | GLN | A | 58 | -10.450 | 32.001 | 26.725 | 1.00 | 21.96 |
| ATOM | 331 | N   | SER | A | 59 | -12.285 | 30.801 | 27.284 | 1.00 | 21.91 |
| ATOM | 332 | CA  | SER | A | 59 | -11.880 | 30.520 | 28.667 | 1.00 | 21.56 |
| ATOM | 333 | CB  | SER | A | 59 | -13.120 | 30.331 | 29.548 | 1.00 | 25.89 |
| ATOM | 334 | OG  | SER | A | 59 | -13.853 | 29.160 | 29.159 | 1.00 | 30.06 |
| ATOM | 335 | C   | SER | A | 59 | -10.966 | 29.293 | 28.744 | 1.00 | 20.75 |
| ATOM | 336 | O   | SER | A | 59 | -11.067 | 28.413 | 27.879 | 1.00 | 21.59 |
| ATOM | 337 | N   | CYS | A | 60 | -10.045 | 29.281 | 29.717 | 1.00 | 17.44 |
| ATOM | 338 | CA  | CYS | A | 60 | -9.241  | 28.110 | 30.066 | 1.00 | 16.53 |
| ATOM | 339 | CB  | CYS | A | 60 | -7.727  | 28.401 | 29.837 | 1.00 | 16.03 |
| ATOM | 340 | SG  | CYS | A | 60 | -7.335  | 28.999 | 28.191 | 1.00 | 20.55 |
| ATOM | 341 | C   | CYS | A | 60 | -9.464  | 27.783 | 31.540 | 1.00 | 15.89 |
| ATOM | 342 | O   | CYS | A | 60 | -8.518  | 27.605 | 32.301 | 1.00 | 16.90 |
| ATOM | 343 | N   | ASP | A | 61 | -10.724 | 27.666 | 31.948 | 1.00 | 16.95 |
| ATOM | 344 | CA  | ASP | A | 61 | -11.008 | 27.467 | 33.364 | 1.00 | 18.02 |
| ATOM | 345 | CB  | ASP | A | 61 | -12.496 | 27.660 | 33.610 | 1.00 | 19.47 |
| ATOM | 346 | CG  | ASP | A | 61 | -12.954 | 29.082 | 33.379 | 1.00 | 24.64 |
| ATOM | 347 | OD1 | ASP | A | 61 | -12.160 | 30.049 | 33.365 | 1.00 | 20.11 |
| ATOM | 348 | OD2 | ASP | A | 61 | -14.155 | 29.306 | 33.171 | 1.00 | 24.81 |
| ATOM | 349 | C   | ASP | A | 61 | -10.574 | 26.102 | 33.887 | 1.00 | 20.07 |
| ATOM | 350 | O   | ASP | A | 61 | -10.102 | 25.997 | 35.017 | 1.00 | 21.40 |
| ATOM | 351 | N   | ILE | A | 62 | -10.679 | 25.062 | 33.064 | 1.00 | 17.97 |
| ATOM | 352 | CA  | ILE | A | 62 | -10.298 | 23.747 | 33.574 | 1.00 | 16.98 |
| ATOM | 353 | CB  | ILE | A | 62 | -10.723 | 22.652 | 32.564 | 1.00 | 14.99 |
| ATOM | 354 | CG1 | ILE | A | 62 | -12.247 | 22.609 | 32.414 | 1.00 | 19.52 |
| ATOM | 355 | CD1 | ILE | A | 62 | -12.918 | 22.254 | 33.696 | 1.00 | 24.86 |
| ATOM | 356 | CG2 | ILE | A | 62 | -10.213 | 21.266 | 32.987 | 1.00 | 18.74 |
| ATOM | 357 | C   | ILE | A | 62 | -8.779  | 23.712 | 33.804 | 1.00 | 17.57 |
| ATOM | 358 | O   | ILE | A | 62 | -8.295  | 23.179 | 34.802 | 1.00 | 18.69 |
| ATOM | 359 | N   | ALA | A | 63 | -8.036  | 24.245 | 32.841 | 1.00 | 16.86 |
| ATOM | 360 | CA  | ALA | A | 63 | -6.570  | 24.285 | 32.923 | 1.00 | 18.52 |
| ATOM | 361 | CB  | ALA | A | 63 | -5.999  | 24.905 | 31.623 | 1.00 | 18.66 |
| ATOM | 362 | C   | ALA | A | 63 | -6.075  | 25.067 | 34.155 | 1.00 | 19.62 |
| ATOM | 363 | O   | ALA | A | 63 | -4.972  | 24.842 | 34.653 | 1.00 | 20.46 |

FIGURE 259

| | | | | | | | | | |
|---|---|---|---|---|---|---|---|---|---|
| ATOM | 364 | N | LEU | A | 64 | -6.919 | 25.972 | 34.632 | 1.00 20.64 |
| ATOM | 365 | CA | LEU | A | 64 | -6.605 | 26.811 | 35.779 | 1.00 21.59 |
| ATOM | 366 | CB | LEU | A | 64 | -7.316 | 28.157 | 35.640 | 1.00 21.74 |
| ATOM | 367 | CG | LEU | A | 64 | -6.603 | 29.150 | 34.735 | 1.00 22.91 |
| ATOM | 368 | CD1 | LEU | A | 64 | -7.504 | 30.360 | 34.530 | 1.00 26.23 |
| ATOM | 369 | CD2 | LEU | A | 64 | -5.274 | 29.607 | 35.346 | 1.00 20.97 |
| ATOM | 370 | C | LEU | A | 64 | -6.988 | 26.205 | 37.128 | 1.00 23.83 |
| ATOM | 371 | O | LEU | A | 64 | -6.666 | 26.792 | 38.168 | 1.00 24.37 |
| ATOM | 372 | N | LEU | A | 65 | -7.690 | 25.071 | 37.144 | 1.00 23.26 |
| ATOM | 373 | CA | LEU | A | 65 | -8.009 | 24.427 | 38.418 | 1.00 25.30 |
| ATOM | 374 | CB | LEU | A | 65 | -8.892 | 23.199 | 38.218 | 1.00 23.61 |
| ATOM | 375 | CG | LEU | A | 65 | -10.281 | 23.423 | 37.623 | 1.00 25.74 |
| ATOM | 376 | CD1 | LEU | A | 65 | -10.875 | 22.077 | 37.228 | 1.00 27.81 |
| ATOM | 377 | CD2 | LEU | A | 65 | -11.154 | 24.183 | 38.616 | 1.00 27.81 |
| ATOM | 378 | C | LEU | A | 65 | -6.739 | 24.069 | 39.184 | 1.00 25.22 |
| ATOM | 379 | O | LEU | A | 65 | -5.741 | 23.654 | 38.606 | 1.00 23.18 |
| ATOM | 380 | N | PRO | A | 66 | -6.716 | 24.280 | 40.498 | 1.00 26.80 |
| ATOM | 381 | CA | PRO | A | 66 | -5.463 | 24.105 | 41.234 | 1.00 26.96 |
| ATOM | 382 | CB | PRO | A | 66 | -5.830 | 24.483 | 42.678 | 1.00 28.00 |
| ATOM | 383 | CG | PRO | A | 66 | -7.289 | 24.642 | 42.717 | 1.00 27.81 |
| ATOM | 384 | CD | PRO | A | 66 | -7.827 | 24.762 | 41.333 | 1.00 29.27 |
| ATOM | 385 | C | PRO | A | 66 | -4.917 | 22.683 | 41.121 | 1.00 27.13 |
| ATOM | 386 | O | PRO | A | 66 | -3.697 | 22.517 | 41.088 | 1.00 25.29 |
| ATOM | 387 | N | GLU | A | 67 | -5.819 | 21.707 | 41.019 | 1.00 27.81 |
| ATOM | 388 | CA | GLU | A | 67 | -5.504 | 20.294 | 40.825 | 1.00 28.93 |
| ATOM | 389 | CB | GLU | A | 67 | -6.818 | 19.510 | 40.733 | 1.00 30.51 |
| ATOM | 390 | CG | AGLU | A | 67 | -6.790 | 18.040 | 41.147 | 0.50 32.82 |
| ATOM | 391 | CG | BGLU | A | 67 | -7.575 | 19.363 | 42.052 | 0.50 29.81 |
| ATOM | 392 | CD | AGLU | A | 67 | -5.497 | 17.580 | 41.804 | 0.50 34.06 |
| ATOM | 393 | CD | BGLU | A | 67 | -8.575 | 20.471 | 42.362 | 0.50 32.38 |
| ATOM | 394 | OE1 | AGLU | A | 67 | -5.465 | 17.473 | 43.049 | 0.50 33.59 |
| ATOM | 395 | OE1 | BGLU | A | 67 | -8.580 | 21.554 | 41.729 | 0.50 28.29 |
| ATOM | 396 | OE2 | AGLU | A | 67 | -4.523 | 17.281 | 41.077 | 0.50 37.14 |
| ATOM | 397 | OE2 | BGLU | A | 67 | -9.376 | 20.260 | 43.298 | 0.50 33.73 |
| ATOM | 398 | C | GLU | A | 67 | -4.681 | 20.052 | 39.557 | 1.00 28.81 |
| ATOM | 399 | O | GLU | A | 67 | -3.896 | 19.100 | 39.474 | 1.00 28.70 |
| ATOM | 400 | N | ASN | A | 68 | -4.841 | 20.938 | 38.577 | 1.00 27.24 |
| ATOM | 401 | CA | ASN | A | 68 | -4.105 | 20.833 | 37.324 | 1.00 26.55 |
| ATOM | 402 | CB | ASN | A | 68 | -5.043 | 21.171 | 36.157 | 1.00 23.97 |
| ATOM | 403 | CG | ASN | A | 68 | -6.154 | 20.139 | 35.977 | 1.00 25.76 |
| ATOM | 404 | OD1 | ASN | A | 68 | -5.976 | 18.936 | 36.227 | 1.00 21.62 |
| ATOM | 405 | ND2 | ASN | A | 68 | -7.312 | 20.596 | 35.510 | 1.00 21.09 |
| ATOM | 406 | C | ASN | A | 68 | -2.780 | 21.602 | 37.228 | 1.00 25.64 |
| ATOM | 407 | O | ASN | A | 68 | -2.087 | 21.528 | 36.213 | 1.00 26.59 |
| ATOM | 408 | N | ARG | A | 69 | -2.397 | 22.344 | 38.269 | 1.00 27.31 |
| ATOM | 409 | CA | ARG | A | 69 | -1.330 | 23.336 | 38.101 | 1.00 26.13 |
| ATOM | 410 | CB | ARG | A | 69 | -1.137 | 24.132 | 39.402 | 1.00 28.24 |
| ATOM | 411 | CG | ARG | A | 69 | 0.208 | 24.842 | 39.456 | 1.00 33.49 |
| ATOM | 412 | CD | ARG | A | 69 | 0.727 | 25.045 | 40.870 | 1.00 45.09 |
| ATOM | 413 | NE | ARG | A | 69 | 2.100 | 24.568 | 41.036 | 1.00 48.71 |
| ATOM | 414 | CZ | ARG | A | 69 | 3.132 | 25.001 | 40.319 | 1.00 51.40 |
| ATOM | 415 | NH1 | ARG | A | 69 | 2.961 | 25.927 | 39.384 | 1.00 45.02 |

FIGURE 260

| | | | | | | | | |
|---|---|---|---|---|---|---|---|---|
| ATOM | 416 | NH2 | ARG A | 69 | 4.347 | 24.514 | 40.549 | 1.00 54.13 |
| ATOM | 417 | C | ARG A | 69 | 0.003 | 22.714 | 37.665 | 1.00 26.18 |
| ATOM | 418 | O | ARG A | 69 | 0.695 | 23.211 | 36.756 | 1.00 27.17 |
| ATOM | 419 | N | GLY A | 70 | 0.319 | 21.578 | 38.279 | 1.00 24.09 |
| ATOM | 420 | CA | GLY A | 70 | 1.568 | 20.888 | 37.993 | 1.00 22.34 |
| ATOM | 421 | C | GLY A | 70 | 1.556 | 20.175 | 36.648 | 1.00 22.09 |
| ATOM | 422 | O | GLY A | 70 | 2.579 | 19.634 | 36.252 | 1.00 22.14 |
| ATOM | 423 | N | LYS A | 71 | 0.417 | 20.179 | 35.962 | 1.00 18.88 |
| ATOM | 424 | CA | LYS A | 71 | 0.261 | 19.527 | 34.658 | 1.00 18.61 |
| ATOM | 425 | CB | LYS A | 71 | -1.192 | 19.057 | 34.499 | 1.00 18.52 |
| ATOM | 426 | CG | LYS A | 71 | -1.516 | 18.010 | 35.558 | 1.00 17.03 |
| ATOM | 427 | CD | LYS A | 71 | -2.862 | 17.421 | 35.371 | 1.00 16.16 |
| ATOM | 428 | CE | LYS A | 71 | -3.257 | 16.744 | 36.685 | 1.00 19.61 |
| ATOM | 429 | NZ | LYS A | 71 | -4.691 | 16.331 | 36.616 | 1.00 22.15 |
| ATOM | 430 | C | LYS A | 71 | 0.589 | 20.487 | 33.527 | 1.00 18.47 |
| ATOM | 431 | O | LYS A | 71 | 0.596 | 20.124 | 32.341 | 1.00 18.95 |
| ATOM | 432 | N | ASN A | 72 | 0.790 | 21.743 | 33.885 | 1.00 18.67 |
| ATOM | 433 | CA | ASN A | 72 | 1.126 | 22.757 | 32.879 | 1.00 19.34 |
| ATOM | 434 | CB | ASN A | 72 | 0.245 | 23.977 | 33.056 | 1.00 18.51 |
| ATOM | 435 | CG | ASN A | 72 | -1.206 | 23.648 | 32.847 | 1.00 17.81 |
| ATOM | 436 | OD1 | ASN A | 72 | -1.576 | 23.040 | 31.838 | 1.00 16.74 |
| ATOM | 437 | ND2 | ASN A | 72 | -2.035 | 24.037 | 33.801 | 1.00 18.58 |
| ATOM | 438 | C | ASN A | 72 | 2.591 | 23.158 | 32.922 | 1.00 18.69 |
| ATOM | 439 | O | ASN A | 72 | 3.075 | 23.556 | 33.981 | 1.00 19.55 |
| ATOM | 440 | N | ARG A | 73 | 3.298 | 22.983 | 31.806 | 1.00 19.19 |
| ATOM | 441 | CA | ARG A | 73 | 4.706 | 23.394 | 31.736 | 1.00 18.17 |
| ATOM | 442 | CB | ARG A | 73 | 5.277 | 23.098 | 30.351 | 1.00 18.40 |
| ATOM | 443 | CG | ARG A | 73 | 6.735 | 23.539 | 30.185 | 1.00 16.99 |
| ATOM | 444 | CD | ARG A | 73 | 7.388 | 23.053 | 28.874 | 1.00 16.70 |
| ATOM | 445 | NE | ARG A | 73 | 7.620 | 21.604 | 28.934 | 1.00 16.40 |
| ATOM | 446 | CZ | ARG A | 73 | 8.650 | 21.038 | 29.565 | 1.00 19.62 |
| ATOM | 447 | NH1 | ARG A | 73 | 9.534 | 21.783 | 30.213 | 1.00 21.72 |
| ATOM | 448 | NH2 | ARG A | 73 | 8.794 | 19.709 | 29.568 | 1.00 20.41 |
| ATOM | 449 | C | ARG A | 73 | 4.811 | 24.891 | 31.984 | 1.00 19.99 |
| ATOM | 450 | O | ARG A | 73 | 5.660 | 25.359 | 32.765 | 1.00 21.05 |
| ATOM | 451 | N | TYR A | 74 | 3.961 | 25.633 | 31.292 | 1.00 18.61 |
| ATOM | 452 | CA | TYR A | 74 | 3.919 | 27.081 | 31.449 | 1.00 18.09 |
| ATOM | 453 | CB | TYR A | 74 | 4.190 | 27.726 | 30.102 | 1.00 16.79 |
| ATOM | 454 | CG | TYR A | 74 | 5.560 | 27.365 | 29.541 | 1.00 16.34 |
| ATOM | 455 | CD1 | TYR A | 74 | 6.722 | 27.696 | 30.196 | 1.00 20.25 |
| ATOM | 456 | CE1 | TYR A | 74 | 7.971 | 27.371 | 29.649 | 1.00 21.10 |
| ATOM | 457 | CZ | TYR A | 74 | 8.034 | 26.643 | 28.469 | 1.00 18.00 |
| ATOM | 458 | OH | TYR A | 74 | 9.254 | 26.324 | 27.902 | 1.00 18.74 |
| ATOM | 459 | CE2 | TYR A | 74 | 6.879 | 26.318 | 27.803 | 1.00 20.42 |
| ATOM | 460 | CD2 | TYR A | 74 | 5.644 | 26.667 | 28.342 | 1.00 17.70 |
| ATOM | 461 | C | TYR A | 74 | 2.539 | 27.463 | 31.946 | 1.00 20.00 |
| ATOM | 462 | O | TYR A | 74 | 1.567 | 27.207 | 31.254 | 1.00 19.46 |
| ATOM | 463 | N | ASN A | 75 | 2.442 | 28.052 | 33.138 | 1.00 19.96 |
| ATOM | 464 | CA | ASN A | 75 | 1.125 | 28.228 | 33.729 | 1.00 18.71 |
| ATOM | 465 | CB | ASN A | 75 | 1.218 | 28.665 | 35.186 | 1.00 19.98 |
| ATOM | 466 | CG | ASN A | 75 | 1.531 | 27.534 | 36.144 | 1.00 28.50 |
| ATOM | 467 | OD1 | ASN A | 75 | 1.941 | 27.798 | 37.276 | 1.00 41.57 |

FIGURE 261

| ATOM | 468 | ND2 | ASN | A | 75 | 1.291 | 26.291 | 35.743 | 1.00 | 34.02 |
| ATOM | 469 | C | ASN | A | 75 | 0.300 | 29.254 | 32.975 | 1.00 | 19.22 |
| ATOM | 470 | O | ASN | A | 75 | -0.933 | 29.328 | 33.123 | 1.00 | 19.65 |
| ATOM | 471 | N | ASN | A | 76 | 0.970 | 30.016 | 32.122 | 1.00 | 17.60 |
| ATOM | 472 | CA | ASN | A | 76 | 0.307 | 30.963 | 31.250 | 1.00 | 17.67 |
| ATOM | 473 | CB | ASN | A | 76 | 1.089 | 32.267 | 31.179 | 1.00 | 19.18 |
| ATOM | 474 | CG | ASN | A | 76 | 2.392 | 32.127 | 30.427 | 1.00 | 19.09 |
| ATOM | 475 | OD1 | ASN | A | 76 | 3.099 | 31.147 | 30.602 | 1.00 | 19.41 |
| ATOM | 476 | ND2 | ASN | A | 76 | 2.677 | 33.069 | 29.545 | 1.00 | 18.60 |
| ATOM | 477 | C | ASN | A | 76 | -0.027 | 30.485 | 29.828 | 1.00 | 18.54 |
| ATOM | 478 | O | ASN | A | 76 | -0.587 | 31.266 | 29.046 | 1.00 | 20.42 |
| ATOM | 479 | N | ILE | A | 77 | 0.332 | 29.243 | 29.499 | 1.00 | 17.75 |
| ATOM | 480 | CA | ILE | A | 77 | 0.023 | 28.679 | 28.175 | 1.00 | 16.98 |
| ATOM | 481 | CB | ILE | A | 77 | 1.267 | 28.284 | 27.363 | 1.00 | 17.92 |
| ATOM | 482 | CG1 | ILE | A | 77 | 2.270 | 29.429 | 27.287 | 1.00 | 17.69 |
| ATOM | 483 | CD1 | ILE | A | 77 | 1.825 | 30.580 | 26.477 | 1.00 | 24.18 |
| ATOM | 484 | CG2 | ILE | A | 77 | 0.802 | 27.838 | 25.951 | 1.00 | 14.34 |
| ATOM | 485 | C | ILE | A | 77 | -0.875 | 27.472 | 28.359 | 1.00 | 16.69 |
| ATOM | 486 | O | ILE | A | 77 | -0.438 | 26.387 | 28.721 | 1.00 | 17.71 |
| ATOM | 487 | N | LEU | A | 78 | -2.171 | 27.703 | 28.171 | 1.00 | 16.17 |
| ATOM | 488 | CA | LEU | A | 78 | -3.177 | 26.760 | 28.614 | 1.00 | 15.63 |
| ATOM | 489 | CB | LEU | A | 78 | -3.970 | 27.378 | 29.782 | 1.00 | 17.02 |
| ATOM | 490 | CG | LEU | A | 78 | -3.103 | 27.826 | 30.952 | 1.00 | 14.20 |
| ATOM | 491 | CD1 | LEU | A | 78 | -3.971 | 28.492 | 32.013 | 1.00 | 18.34 |
| ATOM | 492 | CD2 | LEU | A | 78 | -2.351 | 26.592 | 31.530 | 1.00 | 15.97 |
| ATOM | 493 | C | LEU | A | 78 | -4.116 | 26.521 | 27.448 | 1.00 | 16.27 |
| ATOM | 494 | O | LEU | A | 78 | -4.338 | 27.415 | 26.640 | 1.00 | 16.45 |
| ATOM | 495 | N | PRO | A | 79 | -4.676 | 25.319 | 27.365 | 1.00 | 15.77 |
| ATOM | 496 | CA | PRO | A | 79 | -5.657 | 25.005 | 26.325 | 1.00 | 16.37 |
| ATOM | 497 | CB | PRO | A | 79 | -5.825 | 23.494 | 26.465 | 1.00 | 15.52 |
| ATOM | 498 | CG | PRO | A | 79 | -5.511 | 23.196 | 27.896 | 1.00 | 16.91 |
| ATOM | 499 | CD | PRO | A | 79 | -4.409 | 24.186 | 28.269 | 1.00 | 16.37 |
| ATOM | 500 | C | PRO | A | 79 | -7.001 | 25.658 | 26.657 | 1.00 | 15.83 |
| ATOM | 501 | O | PRO | A | 79 | -7.397 | 25.687 | 27.824 | 1.00 | 16.64 |
| ATOM | 502 | N | TYR | A | 80 | -7.668 | 26.191 | 25.639 | 1.00 | 17.68 |
| ATOM | 503 | CA | TYR | A | 80 | -9.073 | 26.594 | 25.776 | 1.00 | 16.66 |
| ATOM | 504 | CB | TYR | A | 80 | -9.571 | 27.131 | 24.426 | 1.00 | 17.47 |
| ATOM | 505 | CG | TYR | A | 80 | -8.862 | 28.405 | 23.974 | 1.00 | 18.71 |
| ATOM | 506 | CD1 | TYR | A | 80 | -8.661 | 29.469 | 24.864 | 1.00 | 21.72 |
| ATOM | 507 | CE1 | TYR | A | 80 | -8.008 | 30.612 | 24.458 | 1.00 | 18.65 |
| ATOM | 508 | CZ | TYR | A | 80 | -7.552 | 30.728 | 23.163 | 1.00 | 18.69 |
| ATOM | 509 | OH | TYR | A | 80 | -6.951 | 31.901 | 22.794 | 1.00 | 19.69 |
| ATOM | 510 | CE2 | TYR | A | 80 | -7.730 | 29.709 | 22.252 | 1.00 | 19.15 |
| ATOM | 511 | CD2 | TYR | A | 80 | -8.363 | 28.532 | 22.676 | 1.00 | 18.51 |
| ATOM | 512 | C | TYR | A | 80 | -9.944 | 25.419 | 26.190 | 1.00 | 17.71 |
| ATOM | 513 | O | TYR | A | 80 | -9.835 | 24.326 | 25.641 | 1.00 | 18.31 |
| ATOM | 514 | N | ASP | A | 81 | -10.884 | 25.656 | 27.098 | 1.00 | 17.08 |
| ATOM | 515 | CA | ASP | A | 81 | -11.881 | 24.660 | 27.444 | 1.00 | 17.40 |
| ATOM | 516 | CB | ASP | A | 81 | -12.929 | 25.314 | 28.332 | 1.00 | 18.47 |
| ATOM | 517 | CG | ASP | A | 81 | -12.361 | 25.790 | 29.649 | 1.00 | 22.96 |
| ATOM | 518 | OD1 | ASP | A | 81 | -11.447 | 25.148 | 30.229 | 1.00 | 20.84 |
| ATOM | 519 | OD2 | ASP | A | 81 | -12.841 | 26.794 | 30.205 | 1.00 | 19.85 |

FIGURE 262

| ATOM | 520 | C   | ASP | A | 81 | -12.568 | 24.065 | 26.215 | 1.00 | 16.40 |
| ATOM | 521 | O   | ASP | A | 81 | -12.790 | 22.845 | 26.175 | 1.00 | 18.31 |
| ATOM | 522 | N   | ALA | A | 82 | -12.901 | 24.923 | 25.248 | 1.00 | 18.79 |
| ATOM | 523 | CA  | ALA | A | 82 | -13.714 | 24.544 | 24.096 | 1.00 | 21.05 |
| ATOM | 524 | CB  | ALA | A | 82 | -14.082 | 25.787 | 23.284 | 1.00 | 22.15 |
| ATOM | 525 | C   | ALA | A | 82 | -13.065 | 23.500 | 23.194 | 1.00 | 20.96 |
| ATOM | 526 | O   | ALA | A | 82 | -13.763 | 22.798 | 22.459 | 1.00 | 19.35 |
| ATOM | 527 | N   | THR | A | 83 | -11.730 | 23.441 | 23.203 | 1.00 | 18.07 |
| ATOM | 528 | CA  | THR | A | 83 | -11.029 | 22.560 | 22.274 | 1.00 | 20.13 |
| ATOM | 529 | CB  | THR | A | 83 | -10.260 | 23.375 | 21.204 | 1.00 | 21.39 |
| ATOM | 530 | OG1 | THR | A | 83 | -9.399  | 24.306 | 21.888 | 1.00 | 20.87 |
| ATOM | 531 | CG2 | THR | A | 83 | -11.215 | 24.257 | 20.373 | 1.00 | 22.64 |
| ATOM | 532 | C   | THR | A | 83 | -10.015 | 21.647 | 22.962 | 1.00 | 19.11 |
| ATOM | 533 | O   | THR | A | 83 | -9.241  | 21.027 | 22.255 | 1.00 | 18.63 |
| ATOM | 534 | N   | ARG | A | 84 | -10.008 | 21.543 | 24.292 | 1.00 | 16.72 |
| ATOM | 535 | CA  | ARG | A | 84 | -8.994  | 20.752 | 24.973 | 1.00 | 18.30 |
| ATOM | 536 | CB  | ARG | A | 84 | -8.977  | 21.025 | 26.481 | 1.00 | 20.17 |
| ATOM | 537 | CG  | ARG | A | 84 | -10.132 | 20.412 | 27.255 | 1.00 | 21.69 |
| ATOM | 538 | CD  | ARG | A | 84 | -10.152 | 20.875 | 28.716 | 1.00 | 21.07 |
| ATOM | 539 | NE  | ARG | A | 84 | -11.233 | 20.227 | 29.455 | 1.00 | 18.74 |
| ATOM | 540 | CZ  | ARG | A | 84 | -11.068 | 19.171 | 30.257 | 1.00 | 17.05 |
| ATOM | 541 | NH1 | ARG | A | 84 | -9.857  | 18.640 | 30.407 | 1.00 | 17.98 |
| ATOM | 542 | NH2 | ARG | A | 84 | -12.125 | 18.639 | 30.884 | 1.00 | 17.21 |
| ATOM | 543 | C   | ARG | A | 84 | -9.207  | 19.276 | 24.702 | 1.00 | 18.78 |
| ATOM | 544 | O   | ARG | A | 84 | -10.348 | 18.839 | 24.517 | 1.00 | 19.49 |
| ATOM | 545 | N   | VAL | A | 85 | -8.108  | 18.538 | 24.710 | 1.00 | 17.44 |
| ATOM | 546 | CA  | VAL | A | 85 | -8.130  | 17.081 | 24.614 | 1.00 | 17.40 |
| ATOM | 547 | CB  | VAL | A | 85 | -6.799  | 16.539 | 24.064 | 1.00 | 18.13 |
| ATOM | 548 | CG1 | VAL | A | 85 | -6.897  | 15.001 | 23.926 | 1.00 | 17.98 |
| ATOM | 549 | CG2 | VAL | A | 85 | -6.493  | 17.177 | 22.686 | 1.00 | 19.36 |
| ATOM | 550 | C   | VAL | A | 85 | -8.371  | 16.488 | 26.003 | 1.00 | 18.79 |
| ATOM | 551 | O   | VAL | A | 85 | -7.719  | 16.869 | 26.976 | 1.00 | 19.65 |
| ATOM | 552 | N   | LYS | A | 86 | -9.315  | 15.555 | 26.094 | 1.00 | 18.68 |
| ATOM | 553 | CA  | LYS | A | 86 | -9.613  | 14.946 | 27.396 | 1.00 | 17.68 |
| ATOM | 554 | CB  | LYS | A | 86 | -11.137 | 14.942 | 27.623 | 1.00 | 18.74 |
| ATOM | 555 | CG  | LYS | A | 86 | -11.672 | 16.355 | 27.728 | 1.00 | 22.75 |
| ATOM | 556 | CD  | LYS | A | 86 | -13.167 | 16.435 | 27.837 | 1.00 | 27.00 |
| ATOM | 557 | CE  | LYS | A | 86 | -13.540 | 17.906 | 27.691 | 1.00 | 30.36 |
| ATOM | 558 | NZ  | LYS | A | 86 | -14.942 | 18.132 | 27.228 | 1.00 | 34.08 |
| ATOM | 559 | C   | LYS | A | 86 | -9.118  | 13.517 | 27.445 | 1.00 | 19.75 |
| ATOM | 560 | O   | LYS | A | 86 | -9.357  | 12.766 | 26.489 | 1.00 | 22.00 |
| ATOM | 561 | N   | LEU | A | 87 | -8.443  | 13.188 | 28.544 | 1.00 | 19.49 |
| ATOM | 562 | CA  | LEU | A | 87 | -8.007  | 11.819 | 28.836 | 1.00 | 21.14 |
| ATOM | 563 | CB  | LEU | A | 87 | -6.883  | 11.849 | 29.871 | 1.00 | 20.71 |
| ATOM | 564 | CG  | LEU | A | 87 | -5.611  | 12.606 | 29.453 | 1.00 | 24.00 |
| ATOM | 565 | CD1 | LEU | A | 87 | -4.671  | 12.651 | 30.634 | 1.00 | 23.82 |
| ATOM | 566 | CD2 | LEU | A | 87 | -4.924  | 11.964 | 28.229 | 1.00 | 22.65 |
| ATOM | 567 | C   | LEU | A | 87 | -9.214  | 11.092 | 29.426 | 1.00 | 21.83 |
| ATOM | 568 | O   | LEU | A | 87 | -10.077 | 11.716 | 30.069 | 1.00 | 21.33 |
| ATOM | 569 | N   | SER | A | 88 | -9.278  | 9.777  | 29.239 | 1.00 | 22.50 |
| ATOM | 570 | CA  | SER | A | 88 | -10.267 | 9.015  | 30.030 | 1.00 | 27.20 |
| ATOM | 571 | CB  | SER | A | 88 | -10.199 | 7.517  | 29.746 | 1.00 | 26.15 |

FIGURE 263

```
ATOM    572  OG   SER A  88      -8.930    6.992   30.099  1.00 27.44
ATOM    573  C    SER A  88     -10.120    9.264   31.527  1.00 29.45
ATOM    574  O    SER A  88      -9.021    9.477   32.035  1.00 28.78
ATOM    575  N    ASN A  89     -11.244    9.263   32.234  1.00 33.66
ATOM    576  CA   ASN A  89     -11.240    9.331   33.697  1.00 38.59
ATOM    577  CB   ASN A  89     -12.675    9.420   34.228  1.00 40.00
ATOM    578  CG   ASN A  89     -13.511   10.437   33.472  1.00 44.74
ATOM    579  OD1  ASN A  89     -13.097   10.948   32.425  1.00 50.87
ATOM    580  ND2  ASN A  89     -14.702   10.725   33.990  1.00 48.81
ATOM    581  C    ASN A  89     -10.510    8.180   34.383  1.00 39.26
ATOM    582  O    ASN A  89     -10.637    7.018   33.977  1.00 40.17
ATOM    583  N    VAL A  90      -9.750    8.521   35.420  1.00 39.03
ATOM    584  CA   VAL A  90      -9.059    7.551   36.267  1.00 39.07
ATOM    585  CB   VAL A  90      -7.579    7.933   36.450  1.00 39.43
ATOM    586  CG1  VAL A  90      -6.890    7.053   37.502  1.00 39.89
ATOM    587  CG2  VAL A  90      -6.848    7.840   35.114  1.00 39.94
ATOM    588  C    VAL A  90      -9.724    7.437   37.641  1.00 39.53
ATOM    589  O    VAL A  90     -10.029    8.446   38.277  1.00 39.69
ATOM    590  N    CYS A  95     -10.123   15.551   38.257  1.00 32.20
ATOM    591  CA   CYS A  95      -9.274   16.239   37.274  1.00 31.56
ATOM    592  CB   CYS A  95      -8.436   17.341   37.923  1.00 32.45
ATOM    593  SG   CYS A  95      -9.470   18.646   38.623  1.00 39.21
ATOM    594  C    CYS A  95      -8.351   15.296   36.529  1.00 29.09
ATOM    595  O    CYS A  95      -7.399   15.760   35.888  1.00 28.47
ATOM    596  N    SER A  96      -8.624   13.992   36.611  1.00 25.31
ATOM    597  CA   SER A  96      -7.816   13.009   35.891  1.00 26.34
ATOM    598  CB   SER A  96      -8.104   11.576   36.380  1.00 26.13
ATOM    599  OG   SER A  96      -9.450   11.210   36.131  1.00 28.38
ATOM    600  C    SER A  96      -7.857   13.149   34.365  1.00 24.83
ATOM    601  O    SER A  96      -6.970   12.661   33.640  1.00 25.70
ATOM    602  N    ASP A  97      -8.863   13.860   33.873  1.00 23.60
ATOM    603  CA   ASP A  97      -9.022   14.004   32.432  1.00 23.00
ATOM    604  CB   ASP A  97     -10.486   14.244   32.031  1.00 23.06
ATOM    605  CG   ASP A  97     -10.939   15.704   32.178  1.00 25.86
ATOM    606  OD1  ASP A  97     -10.131   16.559   32.575  1.00 23.58
ATOM    607  OD2  ASP A  97     -12.113   16.073   31.926  1.00 27.66
ATOM    608  C    ASP A  97      -8.085   15.005   31.779  1.00 20.67
ATOM    609  O    ASP A  97      -8.055   15.123   30.548  1.00 21.87
ATOM    610  N    TYR A  98      -7.333   15.746   32.581  1.00 19.60
ATOM    611  CA   TYR A  98      -6.691   16.926   32.030  1.00 18.52
ATOM    612  CB   TYR A  98      -6.520   18.003   33.104  1.00 18.03
ATOM    613  CG   TYR A  98      -5.822   19.205   32.517  1.00 19.58
ATOM    614  CD1  TYR A  98      -6.534   20.124   31.746  1.00 21.57
ATOM    615  CE1  TYR A  98      -5.904   21.216   31.192  1.00 16.87
ATOM    616  CZ   TYR A  98      -4.536   21.375   31.389  1.00 16.22
ATOM    617  OH   TYR A  98      -3.906   22.447   30.797  1.00 18.85
ATOM    618  CE2  TYR A  98      -3.803   20.475   32.138  1.00 17.86
ATOM    619  CD2  TYR A  98      -4.445   19.385   32.694  1.00 19.81
ATOM    620  C    TYR A  98      -5.338   16.650   31.410  1.00 16.72
ATOM    621  O    TYR A  98      -4.485   16.025   32.040  1.00 19.70
ATOM    622  N    ILE A  99      -5.137   17.179   30.199  1.00 15.99
ATOM    623  CA   ILE A  99      -3.773   17.307   29.653  1.00 15.12
```

FIGURE 264

| | | | | | | | | | |
|---|---|---|---|---|---|---|---|---|---|
| ATOM | 624 | CB | ILE | A | 99 | -3.485 | 16.142 | 28.679 | 1.00 16.27 |
| ATOM | 625 | CG1 | ILE | A | 99 | -2.013 | 16.171 | 28.227 | 1.00 13.41 |
| ATOM | 626 | CD1 | ILE | A | 99 | -1.501 | 14.952 | 27.413 | 1.00 15.15 |
| ATOM | 627 | CG2 | ILE | A | 99 | -4.516 | 16.099 | 27.536 | 1.00 18.41 |
| ATOM | 628 | C | ILE | A | 99 | -3.730 | 18.654 | 28.924 | 1.00 14.61 |
| ATOM | 629 | O | ILE | A | 99 | -4.754 | 19.134 | 28.452 | 1.00 14.64 |
| ATOM | 630 | N | ASN | A | 100 | -2.549 | 19.246 | 28.845 | 1.00 13.96 |
| ATOM | 631 | CA | ASN | A | 100 | -2.381 | 20.522 | 28.162 | 1.00 15.20 |
| ATOM | 632 | CB | ASN | A | 100 | -1.218 | 21.330 | 28.763 | 1.00 15.09 |
| ATOM | 633 | CG | ASN | A | 100 | -1.167 | 22.726 | 28.214 | 1.00 15.71 |
| ATOM | 634 | OD1 | ASN | A | 100 | -1.374 | 22.917 | 27.020 | 1.00 16.88 |
| ATOM | 635 | ND2 | ASN | A | 100 | -0.873 | 23.698 | 29.060 | 1.00 15.13 |
| ATOM | 636 | C | ASN | A | 100 | -2.184 | 20.228 | 26.679 | 1.00 14.05 |
| ATOM | 637 | O | ASN | A | 100 | -1.068 | 20.052 | 26.188 | 1.00 15.61 |
| ATOM | 638 | N | ALA | A | 101 | -3.321 | 20.129 | 26.011 | 1.00 14.18 |
| ATOM | 639 | CA | ALA | A | 101 | -3.342 | 19.806 | 24.587 | 1.00 14.86 |
| ATOM | 640 | CB | ALA | A | 101 | -3.238 | 18.306 | 24.435 | 1.00 14.35 |
| ATOM | 641 | C | ALA | A | 101 | -4.665 | 20.251 | 24.018 | 1.00 15.17 |
| ATOM | 642 | O | ALA | A | 101 | -5.669 | 20.248 | 24.743 | 1.00 14.69 |
| ATOM | 643 | N | SER | A | 102 | -4.679 | 20.523 | 22.708 | 1.00 15.50 |
| ATOM | 644 | CA | SER | A | 102 | -5.810 | 21.159 | 22.047 | 1.00 15.05 |
| ATOM | 645 | CB | SER | A | 102 | -5.471 | 22.629 | 21.759 | 1.00 15.31 |
| ATOM | 646 | OG | SER | A | 102 | -5.151 | 23.291 | 22.969 | 1.00 15.76 |
| ATOM | 647 | C | SER | A | 102 | -6.060 | 20.499 | 20.687 | 1.00 14.47 |
| ATOM | 648 | O | SER | A | 102 | -5.122 | 20.253 | 19.962 | 1.00 16.41 |
| ATOM | 649 | N | TYR | A | 103 | -7.315 | 20.273 | 20.310 | 1.00 14.11 |
| ATOM | 650 | CA | TYR | A | 103 | -7.625 | 19.700 | 18.994 | 1.00 16.15 |
| ATOM | 651 | CB | TYR | A | 103 | -9.064 | 19.128 | 18.983 | 1.00 15.58 |
| ATOM | 652 | CG | TYR | A | 103 | -9.226 | 17.837 | 19.738 | 1.00 17.69 |
| ATOM | 653 | CD1 | TYR | A | 103 | -8.530 | 16.696 | 19.331 | 1.00 21.85 |
| ATOM | 654 | CE1 | TYR | A | 103 | -8.681 | 15.485 | 20.004 | 1.00 18.09 |
| ATOM | 655 | CZ | TYR | A | 103 | -9.560 | 15.417 | 21.070 | 1.00 23.34 |
| ATOM | 656 | OH | TYR | A | 103 | -9.763 | 14.235 | 21.749 | 1.00 25.07 |
| ATOM | 657 | CE2 | TYR | A | 103 | -10.281 | 16.527 | 21.482 | 1.00 22.71 |
| ATOM | 658 | CD2 | TYR | A | 103 | -10.123 | 17.724 | 20.808 | 1.00 19.56 |
| ATOM | 659 | C | TYR | A | 103 | -7.606 | 20.816 | 17.968 | 1.00 17.25 |
| ATOM | 660 | O | TYR | A | 103 | -8.067 | 21.930 | 18.244 | 1.00 18.82 |
| ATOM | 661 | N | ILE | A | 104 | -7.125 | 20.470 | 16.779 | 1.00 16.96 |
| ATOM | 662 | CA | ILE | A | 104 | -7.227 | 21.292 | 15.577 | 1.00 17.89 |
| ATOM | 663 | CB | ILE | A | 104 | -5.810 | 21.550 | 15.040 | 1.00 18.29 |
| ATOM | 664 | CG1 | ILE | A | 104 | -4.887 | 21.993 | 16.154 | 1.00 19.03 |
| ATOM | 665 | CD1 | ILE | A | 104 | -5.247 | 23.333 | 16.819 | 1.00 21.70 |
| ATOM | 666 | CG2 | ILE | A | 104 | -5.845 | 22.465 | 13.784 | 1.00 22.08 |
| ATOM | 667 | C | ILE | A | 104 | -8.013 | 20.483 | 14.547 | 1.00 20.87 |
| ATOM | 668 | O | ILE | A | 104 | -7.582 | 19.407 | 14.121 | 1.00 20.90 |
| ATOM | 669 | N | PRO | A | 105 | -9.188 | 20.966 | 14.154 | 1.00 21.39 |
| ATOM | 670 | CA | PRO | A | 105 | -9.980 | 20.233 | 13.162 | 1.00 20.64 |
| ATOM | 671 | CB | PRO | A | 105 | -11.348 | 20.918 | 13.214 | 1.00 21.14 |
| ATOM | 672 | CG | PRO | A | 105 | -11.064 | 22.320 | 13.696 | 1.00 25.38 |
| ATOM | 673 | CD | PRO | A | 105 | -9.836 | 22.219 | 14.596 | 1.00 22.10 |
| ATOM | 674 | C | PRO | A | 105 | -9.346 | 20.426 | 11.786 | 1.00 20.86 |
| ATOM | 675 | O | PRO | A | 105 | -8.621 | 21.420 | 11.579 | 1.00 22.00 |

FIGURE 265

| | | | | | | | | |
|---|---|---|---|---|---|---|---|---|
| ATOM | 676 | N | GLY | A | 106 | -9.603 | 19.487 | 10.872 | 1.00 20.78 |
| ATOM | 677 | CA | GLY | A | 106 | -9.258 | 19.643 | 9.472 | 1.00 23.04 |
| ATOM | 678 | C | GLY | A | 106 | -10.329 | 20.332 | 8.646 | 1.00 25.39 |
| ATOM | 679 | O | GLY | A | 106 | -11.440 | 20.586 | 9.124 | 1.00 24.34 |
| ATOM | 680 | N | ASN | A | 107 | -10.001 | 20.603 | 7.386 | 1.00 27.36 |
| ATOM | 681 | CA | ASN | A | 107 | -10.986 | 21.163 | 6.458 | 1.00 29.29 |
| ATOM | 682 | CB | ASN | A | 107 | -10.336 | 21.579 | 5.142 | 1.00 31.82 |
| ATOM | 683 | CG | ASN | A | 107 | -9.436 | 22.795 | 5.291 | 1.00 34.51 |
| ATOM | 684 | OD1 | ASN | A | 107 | -8.306 | 22.792 | 4.798 | 1.00 43.42 |
| ATOM | 685 | ND2 | ASN | A | 107 | -9.917 | 23.824 | 5.984 | 1.00 40.29 |
| ATOM | 686 | C | ASN | A | 107 | -12.080 | 20.168 | 6.153 | 1.00 28.84 |
| ATOM | 687 | O | ASN | A | 107 | -13.182 | 20.560 | 5.772 | 1.00 29.29 |
| ATOM | 688 | N | ASN | A | 108 | -11.776 | 18.881 | 6.300 | 1.00 27.42 |
| ATOM | 689 | CA | ASN | A | 108 | -12.716 | 17.847 | 5.886 | 1.00 28.42 |
| ATOM | 690 | CB | ASN | A | 108 | -12.020 | 16.861 | 4.947 | 1.00 29.82 |
| ATOM | 691 | CG | ASN | A | 108 | -11.769 | 17.438 | 3.570 | 1.00 33.34 |
| ATOM | 692 | OD1 | ASN | A | 108 | -10.623 | 17.630 | 3.158 | 1.00 39.32 |
| ATOM | 693 | ND2 | ASN | A | 108 | -12.846 | 17.710 | 2.843 | 1.00 37.81 |
| ATOM | 694 | C | ASN | A | 108 | -13.325 | 17.065 | 7.052 | 1.00 27.69 |
| ATOM | 695 | O | ASN | A | 108 | -14.371 | 16.440 | 6.895 | 1.00 28.98 |
| ATOM | 696 | N | PHE | A | 109 | -12.665 | 17.078 | 8.206 | 1.00 24.03 |
| ATOM | 697 | CA | PHE | A | 109 | -13.114 | 16.259 | 9.339 | 1.00 21.78 |
| ATOM | 698 | CB | PHE | A | 109 | -12.718 | 14.795 | 9.081 | 1.00 20.51 |
| ATOM | 699 | CG | PHE | A | 109 | -13.564 | 13.780 | 9.830 | 1.00 21.38 |
| ATOM | 700 | CD1 | PHE | A | 109 | -13.061 | 13.110 | 10.936 | 1.00 21.50 |
| ATOM | 701 | CE1 | PHE | A | 109 | -13.823 | 12.180 | 11.626 | 1.00 24.12 |
| ATOM | 702 | CZ | PHE | A | 109 | -15.129 | 11.909 | 11.208 | 1.00 25.45 |
| ATOM | 703 | CE2 | PHE | A | 109 | -15.641 | 12.561 | 10.113 | 1.00 21.35 |
| ATOM | 704 | CD2 | PHE | A | 109 | -14.866 | 13.493 | 9.421 | 1.00 18.54 |
| ATOM | 705 | C | PHE | A | 109 | -12.452 | 16.764 | 10.612 | 1.00 22.13 |
| ATOM | 706 | O | PHE | A | 109 | -11.412 | 17.437 | 10.545 | 1.00 21.08 |
| ATOM | 707 | N | ARG | A | 110 | -13.013 | 16.358 | 11.752 | 1.00 19.50 |
| ATOM | 708 | CA | ARG | A | 110 | -12.523 | 16.785 | 13.054 | 1.00 21.56 |
| ATOM | 709 | CB | ARG | A | 110 | -13.472 | 16.347 | 14.168 | 1.00 22.46 |
| ATOM | 710 | CG | ARG | A | 110 | -13.476 | 14.851 | 14.413 | 1.00 24.80 |
| ATOM | 711 | CD | ARG | A | 110 | -14.802 | 14.225 | 14.822 | 1.00 32.72 |
| ATOM | 712 | NE | ARG | A | 110 | -15.236 | 14.643 | 16.150 | 1.00 39.42 |
| ATOM | 713 | CZ | ARG | A | 110 | -15.044 | 13.914 | 17.243 | 1.00 43.17 |
| ATOM | 714 | NH1 | ARG | A | 110 | -14.400 | 12.750 | 17.162 | 1.00 42.56 |
| ATOM | 715 | NH2 | ARG | A | 110 | -15.474 | 14.358 | 18.418 | 1.00 43.79 |
| ATOM | 716 | C | ARG | A | 110 | -11.118 | 16.239 | 13.310 | 1.00 20.39 |
| ATOM | 717 | O | ARG | A | 110 | -10.729 | 15.220 | 12.746 | 1.00 21.44 |
| ATOM | 718 | N | ARG | A | 111 | -10.436 | 16.843 | 14.273 | 1.00 20.63 |
| ATOM | 719 | CA | ARG | A | 111 | -9.259 | 16.240 | 14.885 | 1.00 21.26 |
| ATOM | 720 | CB | ARG | A | 111 | -9.651 | 15.008 | 15.728 | 1.00 20.41 |
| ATOM | 721 | CG | ARG | A | 111 | -10.650 | 15.324 | 16.827 | 1.00 21.47 |
| ATOM | 722 | CD | ARG | A | 111 | -10.936 | 14.151 | 17.754 | 1.00 21.72 |
| ATOM | 723 | NE | ARG | A | 111 | -11.920 | 14.585 | 18.729 | 1.00 22.21 |
| ATOM | 724 | CZ | ARG | A | 111 | -12.269 | 13.928 | 19.825 | 1.00 27.64 |
| ATOM | 725 | NH1 | ARG | A | 111 | -11.713 | 12.759 | 20.119 | 1.00 30.92 |
| ATOM | 726 | NH2 | ARG | A | 111 | -13.175 | 14.456 | 20.633 | 1.00 26.56 |
| ATOM | 727 | C | ARG | A | 111 | -8.161 | 15.872 | 13.914 | 1.00 20.16 |

FIGURE 266

```
ATOM    728  O   ARG A 111      -7.612  14.761  13.972  1.00 21.20
ATOM    729  N   GLU A 112      -7.777  16.801  13.043  1.00 18.71
ATOM    730  CA  GLU A 112      -6.651  16.499  12.179  1.00 17.48
ATOM    731  CB  GLU A 112      -6.632  17.426  10.954  1.00 18.75
ATOM    732  CG  GLU A 112      -5.441  17.169  10.049  1.00 16.97
ATOM    733  CD  GLU A 112      -5.437  18.043   8.809  1.00 27.96
ATOM    734  OE1 GLU A 112      -4.889  17.541   7.805  1.00 25.67
ATOM    735  OE2 GLU A 112      -5.919  19.209   8.860  1.00 25.41
ATOM    736  C   GLU A 112      -5.307  16.580  12.906  1.00 16.93
ATOM    737  O   GLU A 112      -4.421  15.771  12.615  1.00 17.02
ATOM    738  N   TYR A 113      -5.168  17.526  13.834  1.00 16.48
ATOM    739  CA  TYR A 113      -3.964  17.632  14.673  1.00 17.06
ATOM    740  CB  TYR A 113      -3.168  18.898  14.387  1.00 15.83
ATOM    741  CG  TYR A 113      -2.779  19.127  12.955  1.00 18.99
ATOM    742  CD1 TYR A 113      -3.606  19.884  12.148  1.00 22.98
ATOM    743  CE1 TYR A 113      -3.290  20.157  10.850  1.00 24.83
ATOM    744  CZ  TYR A 113      -2.089  19.709  10.356  1.00 22.77
ATOM    745  OH  TYR A 113      -1.838  20.017   9.035  1.00 28.70
ATOM    746  CE2 TYR A 113      -1.233  18.945  11.118  1.00 22.82
ATOM    747  CD2 TYR A 113      -1.570  18.678  12.457  1.00 24.11
ATOM    748  C   TYR A 113      -4.327  17.701  16.163  1.00 14.55
ATOM    749  O   TYR A 113      -5.445  18.039  16.533  1.00 16.23
ATOM    750  N   ILE A 114      -3.439  17.251  17.029  1.00 13.11
ATOM    751  CA  ILE A 114      -3.500  17.610  18.439  1.00 13.46
ATOM    752  CB  ILE A 114      -3.501  16.340  19.331  1.00 13.02
ATOM    753  CG1 ILE A 114      -4.859  15.643  19.231  1.00 15.50
ATOM    754  CD1 ILE A 114      -4.796  14.175  19.736  1.00 17.84
ATOM    755  CG2 ILE A 114      -3.233  16.721  20.803  1.00 15.76
ATOM    756  C   ILE A 114      -2.239  18.421  18.708  1.00 15.12
ATOM    757  O   ILE A 114      -1.146  17.951  18.448  1.00 16.55
ATOM    758  N   VAL A 115      -2.407  19.636  19.215  1.00 15.68
ATOM    759  CA  VAL A 115      -1.262  20.440  19.619  1.00 14.96
ATOM    760  CB  VAL A 115      -1.499  21.899  19.277  1.00 15.98
ATOM    761  CG1 VAL A 115      -0.446  22.789  19.895  1.00 18.83
ATOM    762  CG2 VAL A 115      -1.501  22.011  17.767  1.00 19.14
ATOM    763  C   VAL A 115      -1.078  20.282  21.114  1.00 15.79
ATOM    764  O   VAL A 115      -2.039  20.346  21.880  1.00 15.38
ATOM    765  N   THR A 116       0.163  20.062  21.541  1.00 14.14
ATOM    766  CA  THR A 116       0.399  19.938  22.966  1.00 15.23
ATOM    767  CB  THR A 116       0.267  18.421  23.362  1.00 15.94
ATOM    768  OG1 THR A 116       0.282  18.318  24.792  1.00 16.48
ATOM    769  CG2 THR A 116       1.492  17.619  22.906  1.00 20.42
ATOM    770  C   THR A 116       1.737  20.589  23.403  1.00 14.47
ATOM    771  O   THR A 116       2.563  20.939  22.583  1.00 17.79
ATOM    772  N   GLN A 117       1.924  20.762  24.706  1.00 16.11
ATOM    773  CA  GLN A 117       3.181  21.248  25.251  1.00 15.39
ATOM    774  CB  GLN A 117       2.975  21.710  26.716  1.00 14.51
ATOM    775  CG  GLN A 117       2.597  20.569  27.659  1.00 15.32
ATOM    776  CD  GLN A 117       2.327  21.017  29.072  1.00 16.29
ATOM    777  OE1 GLN A 117       2.162  22.202  29.329  1.00 17.89
ATOM    778  NE2 GLN A 117       2.265  20.073  29.987  1.00 15.78
ATOM    779  C   GLN A 117       4.208  20.143  25.228  1.00 16.18
```

FIGURE 267

| ATOM | 780 | O   | GLN | A | 117 | 3.895  | 18.970 | 25.110 | 1.00 | 16.55 |
| ---- | --- | --- | --- | - | --- | ------ | ------ | ------ | ---- | ----- |
| ATOM | 781 | N   | GLY | A | 118 | 5.469  | 20.517 | 25.375 | 1.00 | 16.92 |
| ATOM | 782 | CA  | GLY | A | 118 | 6.470  | 19.495 | 25.606 | 1.00 | 16.65 |
| ATOM | 783 | C   | GLY | A | 118 | 6.186  | 18.761 | 26.901 | 1.00 | 15.21 |
| ATOM | 784 | O   | GLY | A | 118 | 6.087  | 19.352 | 27.989 | 1.00 | 16.22 |
| ATOM | 785 | N   | PRO | A | 119 | 6.035  | 17.445 | 26.822 | 1.00 | 15.88 |
| ATOM | 786 | CA  | PRO | A | 119 | 5.791  | 16.689 | 28.055 | 1.00 | 15.90 |
| ATOM | 787 | CB  | PRO | A | 119 | 5.878  | 15.243 | 27.582 | 1.00 | 17.35 |
| ATOM | 788 | CG  | PRO | A | 119 | 5.520  | 15.281 | 26.147 | 1.00 | 16.27 |
| ATOM | 789 | CD  | PRO | A | 119 | 6.092  | 16.575 | 25.628 | 1.00 | 16.39 |
| ATOM | 790 | C   | PRO | A | 119 | 6.768  | 16.949 | 29.213 | 1.00 | 17.04 |
| ATOM | 791 | O   | PRO | A | 119 | 7.972  | 17.127 | 28.997 | 1.00 | 17.25 |
| ATOM | 792 | N   | LEU | A | 120 | 6.230  | 16.986 | 30.427 | 1.00 | 20.34 |
| ATOM | 793 | CA  | LEU | A | 120 | 7.006  | 17.119 | 31.660 | 1.00 | 20.38 |
| ATOM | 794 | CB  | LEU | A | 120 | 6.171  | 17.875 | 32.683 | 1.00 | 20.80 |
| ATOM | 795 | CG  | LEU | A | 120 | 5.899  | 19.355 | 32.400 | 1.00 | 20.40 |
| ATOM | 796 | CD1 | LEU | A | 120 | 4.670  | 19.772 | 33.207 | 1.00 | 20.65 |
| ATOM | 797 | CD2 | LEU | A | 120 | 7.087  | 20.257 | 32.655 | 1.00 | 22.46 |
| ATOM | 798 | C   | LEU | A | 120 | 7.324  | 15.718 | 32.190 | 1.00 | 22.07 |
| ATOM | 799 | O   | LEU | A | 120 | 6.642  | 14.762 | 31.824 | 1.00 | 19.88 |
| ATOM | 800 | N   | PRO | A | 121 | 8.343  | 15.566 | 33.032 | 1.00 | 22.56 |
| ATOM | 801 | CA  | PRO | A | 121 | 8.590  | 14.265 | 33.676 | 1.00 | 22.53 |
| ATOM | 802 | CB  | PRO | A | 121 | 9.586  | 14.599 | 34.790 | 1.00 | 22.51 |
| ATOM | 803 | CG  | PRO | A | 121 | 10.302 | 15.799 | 34.270 | 1.00 | 24.46 |
| ATOM | 804 | CD  | PRO | A | 121 | 9.302  | 16.594 | 33.481 | 1.00 | 23.40 |
| ATOM | 805 | C   | PRO | A | 121 | 7.295  | 13.766 | 34.308 | 1.00 | 20.90 |
| ATOM | 806 | O   | PRO | A | 121 | 7.019  | 12.575 | 34.178 | 1.00 | 22.13 |
| ATOM | 807 | N   | GLY | A | 122 | 6.529  | 14.643 | 34.946 | 1.00 | 18.52 |
| ATOM | 808 | CA  | GLY | A | 122 | 5.267  | 14.247 | 35.555 | 1.00 | 19.71 |
| ATOM | 809 | C   | GLY | A | 122 | 4.050  | 14.113 | 34.658 | 1.00 | 19.48 |
| ATOM | 810 | O   | GLY | A | 122 | 3.008  | 13.713 | 35.158 | 1.00 | 20.10 |
| ATOM | 811 | N   | THR | A | 123 | 4.152  | 14.463 | 33.376 | 1.00 | 19.70 |
| ATOM | 812 | CA  | THR | A | 123 | 3.013  | 14.300 | 32.467 | 1.00 | 20.05 |
| ATOM | 813 | CB  | THR | A | 123 | 2.470  | 15.643 | 31.910 | 1.00 | 19.02 |
| ATOM | 814 | OG1 | THR | A | 123 | 3.417  | 16.229 | 31.006 | 1.00 | 17.75 |
| ATOM | 815 | CG2 | THR | A | 123 | 2.286  | 16.724 | 33.011 | 1.00 | 21.52 |
| ATOM | 816 | C   | THR | A | 123 | 3.305  | 13.389 | 31.279 | 1.00 | 18.26 |
| ATOM | 817 | O   | THR | A | 123 | 2.428  | 13.238 | 30.410 | 1.00 | 19.28 |
| ATOM | 818 | N   | LYS | A | 124 | 4.498  | 12.810 | 31.219 | 1.00 | 18.95 |
| ATOM | 819 | CA  | LYS | A | 124 | 4.788  | 11.956 | 30.057 | 1.00 | 18.96 |
| ATOM | 820 | CB  | LYS | A | 124 | 6.283  | 11.641 | 29.950 | 1.00 | 20.13 |
| ATOM | 821 | CG  | LYS | A | 124 | 6.834  | 10.806 | 31.086 | 1.00 | 23.04 |
| ATOM | 822 | CD  | LYS | A | 124 | 8.336  | 10.603 | 30.898 | 1.00 | 29.73 |
| ATOM | 823 | CE  | LYS | A | 124 | 8.775  | 9.445  | 31.787 | 1.00 | 36.02 |
| ATOM | 824 | NZ  | LYS | A | 124 | 10.152 | 9.706  | 32.286 | 1.00 | 43.04 |
| ATOM | 825 | C   | LYS | A | 124 | 3.876  | 10.734 | 29.956 | 1.00 | 19.08 |
| ATOM | 826 | O   | LYS | A | 124 | 3.538  | 10.312 | 28.855 | 1.00 | 17.17 |
| ATOM | 827 | N   | ASP | A | 125 | 3.454  | 10.156 | 31.086 | 1.00 | 18.94 |
| ATOM | 828 | CA  | ASP | A | 125 | 2.497  | 9.066  | 31.016 | 1.00 | 19.18 |
| ATOM | 829 | CB  | ASP | A | 125 | 2.272  | 8.426  | 32.390 | 1.00 | 20.53 |
| ATOM | 830 | CG  | ASP | A | 125 | 3.531  | 7.858  | 32.991 | 1.00 | 22.30 |
| ATOM | 831 | OD1 | ASP | A | 125 | 4.545  | 7.684  | 32.280 | 1.00 | 23.89 |

FIGURE 268

| | | | | | | | | | |
|---|---|---|---|---|---|---|---|---|---|
| ATOM | 832 | OD2 | ASP | A | 125 | 3.577 | 7.580 | 34.216 | 1.00 25.30 |
| ATOM | 833 | C | ASP | A | 125 | 1.160 | 9.570 | 30.460 | 1.00 18.40 |
| ATOM | 834 | O | ASP | A | 125 | 0.519 | 8.877 | 29.670 | 1.00 19.13 |
| ATOM | 835 | N | ASP | A | 126 | 0.760 | 10.773 | 30.871 | 1.00 17.97 |
| ATOM | 836 | CA | ASP | A | 126 | -0.453 | 11.402 | 30.351 | 1.00 17.81 |
| ATOM | 837 | CB | ASP | A | 126 | -0.632 | 12.804 | 30.951 | 1.00 18.50 |
| ATOM | 838 | CG | ASP | A | 126 | -0.832 | 12.813 | 32.447 | 1.00 24.65 |
| ATOM | 839 | OD1 | ASP | A | 126 | -1.196 | 11.774 | 33.046 | 1.00 22.46 |
| ATOM | 840 | OD2 | ASP | A | 126 | -0.670 | 13.887 | 33.085 | 1.00 24.22 |
| ATOM | 841 | C | ASP | A | 126 | -0.314 | 11.606 | 28.837 | 1.00 16.85 |
| ATOM | 842 | O | ASP | A | 126 | -1.256 | 11.407 | 28.082 | 1.00 16.48 |
| ATOM | 843 | N | PHE | A | 127 | 0.868 | 12.008 | 28.380 | 1.00 17.92 |
| ATOM | 844 | CA | PHE | A | 127 | 1.068 | 12.282 | 26.958 | 1.00 16.02 |
| ATOM | 845 | CB | PHE | A | 127 | 2.459 | 12.901 | 26.744 | 1.00 15.67 |
| ATOM | 846 | CG | PHE | A | 127 | 2.886 | 12.934 | 25.300 | 1.00 15.63 |
| ATOM | 847 | CD1 | PHE | A | 127 | 2.614 | 14.040 | 24.513 | 1.00 15.34 |
| ATOM | 848 | CE1 | PHE | A | 127 | 3.015 | 14.065 | 23.170 | 1.00 18.23 |
| ATOM | 849 | CZ | PHE | A | 127 | 3.682 | 12.972 | 22.603 | 1.00 17.60 |
| ATOM | 850 | CE2 | PHE | A | 127 | 3.902 | 11.819 | 23.398 | 1.00 14.91 |
| ATOM | 851 | CD2 | PHE | A | 127 | 3.540 | 11.826 | 24.721 | 1.00 15.74 |
| ATOM | 852 | C | PHE | A | 127 | 0.913 | 10.967 | 26.199 | 1.00 15.37 |
| ATOM | 853 | O | PHE | A | 127 | 0.234 | 10.922 | 25.167 | 1.00 15.38 |
| ATOM | 854 | N | TRP | A | 128 | 1.486 | 9.880 | 26.710 | 1.00 15.77 |
| ATOM | 855 | CA | TRP | A | 128 | 1.412 | 8.643 | 25.951 | 1.00 15.30 |
| ATOM | 856 | CB | TRP | A | 128 | 2.416 | 7.618 | 26.452 | 1.00 14.62 |
| ATOM | 857 | CG | TRP | A | 128 | 3.800 | 7.961 | 26.004 | 1.00 15.64 |
| ATOM | 858 | CD1 | TRP | A | 128 | 4.848 | 8.266 | 26.796 | 1.00 16.32 |
| ATOM | 859 | NE1 | TRP | A | 128 | 5.978 | 8.498 | 26.047 | 1.00 16.04 |
| ATOM | 860 | CE2 | TRP | A | 128 | 5.658 | 8.340 | 24.721 | 1.00 17.00 |
| ATOM | 861 | CD2 | TRP | A | 128 | 4.275 | 8.037 | 24.656 | 1.00 14.14 |
| ATOM | 862 | CE3 | TRP | A | 128 | 3.697 | 7.798 | 23.401 | 1.00 18.83 |
| ATOM | 863 | CZ3 | TRP | A | 128 | 4.481 | 7.947 | 22.261 | 1.00 19.71 |
| ATOM | 864 | CH2 | TRP | A | 128 | 5.855 | 8.288 | 22.362 | 1.00 18.66 |
| ATOM | 865 | CZ2 | TRP | A | 128 | 6.446 | 8.494 | 23.583 | 1.00 17.54 |
| ATOM | 866 | C | TRP | A | 128 | 0.000 | 8.071 | 25.981 | 1.00 14.42 |
| ATOM | 867 | O | TRP | A | 128 | -0.410 | 7.416 | 25.021 | 1.00 15.80 |
| ATOM | 868 | N | LYS | A | 129 | -0.671 | 8.219 | 27.123 | 1.00 16.32 |
| ATOM | 869 | CA | LYS | A | 129 | -2.091 | 7.905 | 27.214 | 1.00 15.35 |
| ATOM | 870 | CB | LYS | A | 129 | -2.642 | 8.310 | 28.588 | 1.00 18.04 |
| ATOM | 871 | CG | LYS | A | 129 | -4.131 | 7.953 | 28.762 | 1.00 16.84 |
| ATOM | 872 | CD | LYS | A | 129 | -4.549 | 8.066 | 30.229 | 1.00 19.80 |
| ATOM | 873 | CE | LYS | A | 129 | -6.064 | 8.051 | 30.343 | 1.00 21.91 |
| ATOM | 874 | NZ | LYS | A | 129 | -6.439 | 8.260 | 31.807 | 1.00 25.23 |
| ATOM | 875 | C | LYS | A | 129 | -2.861 | 8.607 | 26.121 | 1.00 16.69 |
| ATOM | 876 | O | LYS | A | 129 | -3.713 | 8.011 | 25.465 | 1.00 16.75 |
| ATOM | 877 | N | MET | A | 130 | -2.618 | 9.909 | 25.990 | 1.00 15.72 |
| ATOM | 878 | CA | MET | A | 130 | -3.311 | 10.652 | 24.957 | 1.00 16.87 |
| ATOM | 879 | CB | MET | A | 130 | -3.026 | 12.145 | 25.080 | 1.00 14.45 |
| ATOM | 880 | CG | MET | A | 130 | -3.608 | 12.865 | 23.908 | 1.00 15.57 |
| ATOM | 881 | SD | MET | A | 130 | -3.131 | 14.614 | 23.936 | 1.00 17.91 |
| ATOM | 882 | CE | MET | A | 130 | -1.383 | 14.608 | 23.583 | 1.00 16.03 |
| ATOM | 883 | C | MET | A | 130 | -3.040 | 10.117 | 23.548 | 1.00 16.34 |

FIGURE 269

| | | | | | | | | | |
|---|---|---|---|---|---|---|---|---|---|
| ATOM | 884 | O | MET | A | 130 | -3.965 | 9.899 | 22.759 | 1.00 16.31 |
| ATOM | 885 | N | VAL | A | 131 | -1.783 | 9.837 | 23.226 | 1.00 15.65 |
| ATOM | 886 | CA | VAL | A | 131 | -1.402 | 9.283 | 21.924 | 1.00 13.92 |
| ATOM | 887 | CB | VAL | A | 131 | 0.120 | 9.049 | 21.956 | 1.00 14.34 |
| ATOM | 888 | CG1 | VAL | A | 131 | 0.588 | 8.212 | 20.797 | 1.00 18.45 |
| ATOM | 889 | CG2 | VAL | A | 131 | 0.877 | 10.386 | 21.984 | 1.00 18.04 |
| ATOM | 890 | C | VAL | A | 131 | -2.107 | 7.948 | 21.681 | 1.00 14.86 |
| ATOM | 891 | O | VAL | A | 131 | -2.609 | 7.668 | 20.579 | 1.00 15.81 |
| ATOM | 892 | N | TRP | A | 132 | -2.209 | 7.145 | 22.732 | 1.00 14.88 |
| ATOM | 893 | CA | TRP | A | 132 | -2.840 | 5.840 | 22.599 | 1.00 14.40 |
| ATOM | 894 | CB | TRP | A | 132 | -2.599 | 4.996 | 23.861 | 1.00 14.68 |
| ATOM | 895 | CG | TRP | A | 132 | -3.301 | 3.666 | 23.747 | 1.00 16.82 |
| ATOM | 896 | CD1 | TRP | A | 132 | -4.427 | 3.273 | 24.402 | 1.00 17.83 |
| ATOM | 897 | NE1 | TRP | A | 132 | -4.799 | 2.015 | 23.980 | 1.00 16.10 |
| ATOM | 898 | CE2 | TRP | A | 132 | -3.901 | 1.566 | 23.049 | 1.00 19.18 |
| ATOM | 899 | CD2 | TRP | A | 132 | -2.956 | 2.591 | 22.852 | 1.00 18.23 |
| ATOM | 900 | CE3 | TRP | A | 132 | -1.924 | 2.388 | 21.930 | 1.00 16.64 |
| ATOM | 901 | CZ3 | TRP | A | 132 | -1.857 | 1.165 | 21.233 | 1.00 18.77 |
| ATOM | 902 | CH2 | TRP | A | 132 | -2.841 | 0.177 | 21.450 | 1.00 19.47 |
| ATOM | 903 | CZ2 | TRP | A | 132 | -3.857 | 0.358 | 22.350 | 1.00 18.87 |
| ATOM | 904 | C | TRP | A | 132 | -4.346 | 6.021 | 22.375 | 1.00 14.57 |
| ATOM | 905 | O | TRP | A | 132 | -4.901 | 5.489 | 21.423 | 1.00 14.81 |
| ATOM | 906 | N | GLU | A | 133 | -4.977 | 6.784 | 23.257 | 1.00 17.42 |
| ATOM | 907 | CA | GLU | A | 133 | -6.450 | 6.895 | 23.277 | 1.00 15.50 |
| ATOM | 908 | CB | GLU | A | 133 | -6.924 | 7.614 | 24.526 | 1.00 15.78 |
| ATOM | 909 | CG | GLU | A | 133 | -6.669 | 6.814 | 25.790 | 1.00 17.18 |
| ATOM | 910 | CD | GLU | A | 133 | -7.390 | 7.374 | 26.988 | 1.00 25.51 |
| ATOM | 911 | OE1 | GLU | A | 133 | -7.721 | 8.585 | 26.977 | 1.00 22.92 |
| ATOM | 912 | OE2 | GLU | A | 133 | -7.539 | 6.592 | 27.957 | 1.00 21.86 |
| ATOM | 913 | C | GLU | A | 133 | -6.990 | 7.595 | 22.041 | 1.00 17.24 |
| ATOM | 914 | O | GLU | A | 133 | -8.144 | 7.335 | 21.609 | 1.00 16.93 |
| ATOM | 915 | N | GLN | A | 134 | -6.188 | 8.513 | 21.501 | 1.00 16.12 |
| ATOM | 916 | CA | GLN | A | 134 | -6.583 | 9.284 | 20.326 | 1.00 16.01 |
| ATOM | 917 | CB | GLN | A | 134 | -6.136 | 10.746 | 20.432 | 1.00 15.45 |
| ATOM | 918 | CG | GLN | A | 134 | -6.658 | 11.461 | 21.657 | 1.00 16.97 |
| ATOM | 919 | CD | GLN | A | 134 | -8.141 | 11.671 | 21.576 | 1.00 21.63 |
| ATOM | 920 | OE1 | GLN | A | 134 | -8.649 | 12.128 | 20.548 | 1.00 30.42 |
| ATOM | 921 | NE2 | GLN | A | 134 | -8.855 | 11.298 | 22.636 | 1.00 24.38 |
| ATOM | 922 | C | GLN | A | 134 | -6.211 | 8.681 | 18.987 | 1.00 16.29 |
| ATOM | 923 | O | GLN | A | 134 | -6.418 | 9.300 | 17.936 | 1.00 17.57 |
| ATOM | 924 | N | ASN | A | 135 | -5.721 | 7.438 | 19.007 | 1.00 16.26 |
| ATOM | 925 | CA | ASN | A | 135 | -5.338 | 6.741 | 17.788 | 1.00 16.42 |
| ATOM | 926 | CB | ASN | A | 135 | -6.562 | 6.516 | 16.901 | 1.00 18.03 |
| ATOM | 927 | CG | ASN | A | 135 | -7.602 | 5.656 | 17.580 | 1.00 22.43 |
| ATOM | 928 | OD1 | ASN | A | 135 | -7.358 | 4.475 | 17.849 | 1.00 28.78 |
| ATOM | 929 | ND2 | ASN | A | 135 | -8.757 | 6.232 | 17.865 | 1.00 27.37 |
| ATOM | 930 | C | ASN | A | 135 | -4.243 | 7.426 | 16.964 | 1.00 18.21 |
| ATOM | 931 | O | ASN | A | 135 | -4.199 | 7.287 | 15.749 | 1.00 17.34 |
| ATOM | 932 | N | VAL | A | 136 | -3.380 | 8.164 | 17.651 | 1.00 18.13 |
| ATOM | 933 | CA | VAL | A | 136 | -2.276 | 8.873 | 17.011 | 1.00 16.80 |
| ATOM | 934 | CB | VAL | A | 136 | -1.664 | 9.866 | 18.023 | 1.00 18.00 |
| ATOM | 935 | CG1 | VAL | A | 136 | -0.351 | 10.461 | 17.482 | 1.00 16.01 |

FIGURE 270

| ATOM | 936 | CG2 | VAL | A | 136 | -2.680 | 10.930 | 18.399 | 1.00 | 18.19 |
| ATOM | 937 | C   | VAL | A | 136 | -1.229 | 7.880  | 16.483 | 1.00 | 18.93 |
| ATOM | 938 | O   | VAL | A | 136 | -0.821 | 6.977  | 17.211 | 1.00 | 19.57 |
| ATOM | 939 | N   | HIS | A | 137 | -0.860 | 8.013  | 15.202 | 1.00 | 17.50 |
| ATOM | 940 | CA  | HIS | A | 137 | 0.264  | 7.277  | 14.623 | 1.00 | 16.22 |
| ATOM | 941 | CB  | HIS | A | 137 | -0.110 | 6.473  | 13.360 | 1.00 | 18.79 |
| ATOM | 942 | CG  | HIS | A | 137 | -1.152 | 5.414  | 13.571 | 1.00 | 19.38 |
| ATOM | 943 | ND1 | HIS | A | 137 | -2.419 | 5.691  | 14.034 | 1.00 | 20.18 |
| ATOM | 944 | CE1 | HIS | A | 137 | -3.116 | 4.572  | 14.115 | 1.00 | 22.60 |
| ATOM | 945 | NE2 | HIS | A | 137 | -2.358 | 3.579  | 13.680 | 1.00 | 22.19 |
| ATOM | 946 | CD2 | HIS | A | 137 | -1.121 | 4.078  | 13.344 | 1.00 | 20.32 |
| ATOM | 947 | C   | HIS | A | 137 | 1.494  | 8.093  | 14.295 | 1.00 | 17.23 |
| ATOM | 948 | O   | HIS | A | 137 | 2.513  | 7.496  | 13.947 | 1.00 | 17.71 |
| ATOM | 949 | N   | ASN | A | 138 | 1.428  | 9.423  | 14.394 | 1.00 | 16.24 |
| ATOM | 950 | CA  | ASN | A | 138 | 2.590  | 10.238 | 14.046 | 1.00 | 17.25 |
| ATOM | 951 | CB  | ASN | A | 138 | 2.470  | 10.816 | 12.632 | 1.00 | 17.99 |
| ATOM | 952 | CG  | ASN | A | 138 | 2.330  | 9.741  | 11.562 | 1.00 | 18.27 |
| ATOM | 953 | OD1 | ASN | A | 138 | 1.219  | 9.397  | 11.126 | 1.00 | 25.07 |
| ATOM | 954 | ND2 | ASN | A | 138 | 3.457  | 9.169  | 11.189 | 1.00 | 19.74 |
| ATOM | 955 | C   | ASN | A | 138 | 2.684  | 11.382 | 15.044 | 1.00 | 14.09 |
| ATOM | 956 | O   | ASN | A | 138 | 1.676  | 11.996 | 15.397 | 1.00 | 15.42 |
| ATOM | 957 | N   | ILE | A | 139 | 3.904  | 11.633 | 15.485 | 1.00 | 13.67 |
| ATOM | 958 | CA  | ILE | A | 139 | 4.204  | 12.739 | 16.391 | 1.00 | 13.12 |
| ATOM | 959 | CB  | ILE | A | 139 | 4.750  | 12.186 | 17.716 | 1.00 | 14.52 |
| ATOM | 960 | CG1 | ILE | A | 139 | 3.714  | 11.302 | 18.394 | 1.00 | 14.31 |
| ATOM | 961 | CD1 | ILE | A | 139 | 4.274  | 10.494 | 19.577 | 1.00 | 15.81 |
| ATOM | 962 | CG2 | ILE | A | 139 | 5.125  | 13.346 | 18.653 | 1.00 | 15.50 |
| ATOM | 963 | C   | ILE | A | 139 | 5.282  | 13.581 | 15.752 | 1.00 | 15.31 |
| ATOM | 964 | O   | ILE | A | 139 | 6.323  | 13.073 | 15.333 | 1.00 | 16.48 |
| ATOM | 965 | N   | VAL | A | 140 | 5.076  | 14.892 | 15.788 | 1.00 | 14.75 |
| ATOM | 966 | CA  | VAL | A | 140 | 6.049  | 15.831 | 15.231 | 1.00 | 15.93 |
| ATOM | 967 | CB  | VAL | A | 140 | 5.367  | 16.704 | 14.177 | 1.00 | 15.43 |
| ATOM | 968 | CG1 | VAL | A | 140 | 6.329  | 17.788 | 13.728 | 1.00 | 16.73 |
| ATOM | 969 | CG2 | VAL | A | 140 | 4.898  | 15.852 | 12.985 | 1.00 | 17.63 |
| ATOM | 970 | C   | VAL | A | 140 | 6.531  | 16.700 | 16.377 | 1.00 | 16.09 |
| ATOM | 971 | O   | VAL | A | 140 | 5.717  | 17.295 | 17.053 | 1.00 | 18.31 |
| ATOM | 972 | N   | MET | A | 141 | 7.839  | 16.702 | 16.645 | 1.00 | 16.31 |
| ATOM | 973 | CA  | MET | A | 141 | 8.421  | 17.472 | 17.741 | 1.00 | 17.39 |
| ATOM | 974 | CB  | MET | A | 141 | 9.226  | 16.515 | 18.632 | 1.00 | 16.11 |
| ATOM | 975 | CG  | MET | A | 141 | 10.082 | 17.201 | 19.670 | 1.00 | 16.87 |
| ATOM | 976 | SD  | MET | A | 141 | 10.679 | 15.960 | 20.837 | 1.00 | 18.61 |
| ATOM | 977 | CE  | MET | A | 141 | 11.650 | 16.998 | 21.959 | 1.00 | 19.51 |
| ATOM | 978 | C   | MET | A | 141 | 9.344  | 18.530 | 17.127 | 1.00 | 17.17 |
| ATOM | 979 | O   | MET | A | 141 | 10.303 | 18.177 | 16.439 | 1.00 | 17.62 |
| ATOM | 980 | N   | VAL | A | 142 | 9.081  | 19.805 | 17.364 | 1.00 | 16.69 |
| ATOM | 981 | CA  | VAL | A | 142 | 9.869  | 20.876 | 16.731 | 1.00 | 19.57 |
| ATOM | 982 | CB  | VAL | A | 142 | 9.050  | 21.674 | 15.715 | 1.00 | 17.61 |
| ATOM | 983 | CG1 | VAL | A | 142 | 8.808  | 20.820 | 14.463 | 1.00 | 20.20 |
| ATOM | 984 | CG2 | VAL | A | 142 | 7.675  | 22.009 | 16.283 | 1.00 | 19.28 |
| ATOM | 985 | C   | VAL | A | 142 | 10.477 | 21.756 | 17.829 | 1.00 | 21.83 |
| ATOM | 986 | O   | VAL | A | 142 | 10.473 | 22.986 | 17.763 | 1.00 | 24.11 |
| ATOM | 987 | N   | THR | A | 143 | 10.993 | 21.091 | 18.852 | 1.00 | 19.91 |

FIGURE 271

| ATOM | 988 | CA | THR | A | 143 | 11.845 | 21.727 | 19.857 | 1.00 | 20.81 |
| ATOM | 989 | CB | THR | A | 143 | 11.042 | 22.039 | 21.108 | 1.00 | 20.61 |
| ATOM | 990 | OG1 | THR | A | 143 | 11.835 | 22.818 | 22.014 | 1.00 | 20.47 |
| ATOM | 991 | CG2 | THR | A | 143 | 10.728 | 20.749 | 21.898 | 1.00 | 19.53 |
| ATOM | 992 | C | THR | A | 143 | 13.001 | 20.795 | 20.195 | 1.00 | 21.41 |
| ATOM | 993 | O | THR | A | 143 | 12.919 | 19.603 | 19.953 | 1.00 | 20.95 |
| ATOM | 994 | N | GLN | A | 144 | 14.096 | 21.337 | 20.719 | 1.00 | 21.06 |
| ATOM | 995 | CA | GLN | A | 144 | 15.047 | 20.523 | 21.456 | 1.00 | 21.41 |
| ATOM | 996 | CB | GLN | A | 144 | 16.453 | 21.107 | 21.274 | 1.00 | 20.22 |
| ATOM | 997 | CG | GLN | A | 144 | 16.883 | 21.003 | 19.815 | 1.00 | 24.39 |
| ATOM | 998 | CD | GLN | A | 144 | 18.359 | 21.298 | 19.583 | 1.00 | 35.02 |
| ATOM | 999 | OE1 | GLN | A | 144 | 19.223 | 20.456 | 19.834 | 1.00 | 39.33 |
| ATOM | 1000 | NE2 | GLN | A | 144 | 18.645 | 22.494 | 19.082 | 1.00 | 39.04 |
| ATOM | 1001 | C | GLN | A | 144 | 14.654 | 20.440 | 22.930 | 1.00 | 21.42 |
| ATOM | 1002 | O | GLN | A | 144 | 13.847 | 21.248 | 23.418 | 1.00 | 22.29 |
| ATOM | 1003 | N | CYS | A | 145 | 15.180 | 19.442 | 23.633 | 1.00 | 22.65 |
| ATOM | 1004 | CA | CYS | A | 145 | 14.894 | 19.289 | 25.055 | 1.00 | 21.56 |
| ATOM | 1005 | CB | CYS | A | 145 | 15.328 | 17.917 | 25.563 | 1.00 | 24.41 |
| ATOM | 1006 | SG | CYS | A | 145 | 14.340 | 16.594 | 24.859 | 1.00 | 25.88 |
| ATOM | 1007 | C | CYS | A | 145 | 15.512 | 20.364 | 25.934 | 1.00 | 22.77 |
| ATOM | 1008 | O | CYS | A | 145 | 14.891 | 20.755 | 26.915 | 1.00 | 24.26 |
| ATOM | 1009 | N | VAL | A | 146 | 16.719 | 20.828 | 25.592 | 1.00 | 23.87 |
| ATOM | 1010 | CA | VAL | A | 146 | 17.339 | 21.968 | 26.261 | 1.00 | 23.79 |
| ATOM | 1011 | CB | VAL | A | 146 | 18.563 | 21.575 | 27.130 | 1.00 | 24.52 |
| ATOM | 1012 | CG1 | VAL | A | 146 | 19.148 | 22.814 | 27.803 | 1.00 | 25.21 |
| ATOM | 1013 | CG2 | VAL | A | 146 | 18.189 | 20.488 | 28.141 | 1.00 | 23.81 |
| ATOM | 1014 | C | VAL | A | 146 | 17.767 | 22.977 | 25.204 | 1.00 | 24.71 |
| ATOM | 1015 | O | VAL | A | 146 | 18.313 | 22.613 | 24.157 | 1.00 | 25.61 |
| ATOM | 1016 | N | GLU | A | 147 | 17.443 | 24.238 | 25.459 | 1.00 | 25.28 |
| ATOM | 1017 | CA | GLU | A | 147 | 17.691 | 25.313 | 24.508 | 1.00 | 27.56 |
| ATOM | 1018 | CB | GLU | A | 147 | 16.406 | 25.661 | 23.747 | 1.00 | 26.39 |
| ATOM | 1019 | CG | GLU | A | 147 | 16.147 | 24.689 | 22.609 | 1.00 | 27.32 |
| ATOM | 1020 | CD | GLU | A | 147 | 14.780 | 24.858 | 21.965 | 1.00 | 30.78 |
| ATOM | 1021 | OE1 | GLU | A | 147 | 13.981 | 25.680 | 22.460 | 1.00 | 34.57 |
| ATOM | 1022 | OE2 | GLU | A | 147 | 14.494 | 24.143 | 20.984 | 1.00 | 29.08 |
| ATOM | 1023 | C | GLU | A | 147 | 18.200 | 26.521 | 25.286 | 1.00 | 29.05 |
| ATOM | 1024 | O | GLU | A | 147 | 17.526 | 27.046 | 26.173 | 1.00 | 29.89 |
| ATOM | 1025 | N | LYS | A | 148 | 19.419 | 26.935 | 24.961 | 1.00 | 32.08 |
| ATOM | 1026 | CA | LYS | A | 148 | 20.039 | 28.057 | 25.662 | 1.00 | 33.87 |
| ATOM | 1027 | CB | LYS | A | 148 | 19.459 | 29.383 | 25.157 | 1.00 | 34.11 |
| ATOM | 1028 | CG | LYS | A | 148 | 19.601 | 29.554 | 23.639 | 1.00 | 39.02 |
| ATOM | 1029 | CD | LYS | A | 148 | 19.140 | 30.923 | 23.161 | 1.00 | 46.18 |
| ATOM | 1030 | CE | LYS | A | 148 | 19.201 | 31.029 | 21.638 | 1.00 | 46.64 |
| ATOM | 1031 | NZ | LYS | A | 148 | 18.688 | 32.332 | 21.111 | 1.00 | 48.93 |
| ATOM | 1032 | C | LYS | A | 148 | 19.970 | 27.934 | 27.190 | 1.00 | 32.87 |
| ATOM | 1033 | O | LYS | A | 148 | 19.718 | 28.910 | 27.909 | 1.00 | 34.86 |
| ATOM | 1034 | N | GLY | A | 149 | 20.203 | 26.721 | 27.676 | 1.00 | 32.51 |
| ATOM | 1035 | CA | GLY | A | 149 | 20.364 | 26.475 | 29.100 | 1.00 | 31.75 |
| ATOM | 1036 | C | GLY | A | 149 | 19.065 | 26.281 | 29.850 | 1.00 | 32.98 |
| ATOM | 1037 | O | GLY | A | 149 | 19.060 | 26.224 | 31.078 | 1.00 | 34.77 |
| ATOM | 1038 | N | ARG | A | 150 | 17.960 | 26.198 | 29.113 | 1.00 | 28.60 |
| ATOM | 1039 | CA | ARG | A | 150 | 16.636 | 26.155 | 29.727 | 1.00 | 29.87 |

FIGURE 272

```
ATOM   1040  CB   ARG A 150      15.753  27.256  29.140  1.00 27.76
ATOM   1041  CG   ARG A 150      14.682  27.764  30.090  1.00 38.86
ATOM   1042  CD   ARG A 150      13.434  26.895  30.207  1.00 47.60
ATOM   1043  NE   ARG A 150      12.793  27.055  31.514  1.00 53.99
ATOM   1044  CZ   ARG A 150      11.684  27.754  31.725  1.00 57.80
ATOM   1045  NH1  ARG A 150      11.080  28.354  30.708  1.00 60.31
ATOM   1046  NH2  ARG A 150      11.170  27.851  32.947  1.00 59.21
ATOM   1047  C    ARG A 150      16.059  24.827  29.300  1.00 26.37
ATOM   1048  O    ARG A 150      16.204  24.456  28.136  1.00 26.29
ATOM   1049  N    VAL A 151      15.407  24.129  30.226  1.00 27.16
ATOM   1050  CA   VAL A 151      14.784  22.862  29.876  1.00 26.73
ATOM   1051  CB   VAL A 151      14.567  21.979  31.132  1.00 27.55
ATOM   1052  CG1  VAL A 151      13.608  20.849  30.835  1.00 25.30
ATOM   1053  CG2  VAL A 151      15.909  21.399  31.605  1.00 29.25
ATOM   1054  C    VAL A 151      13.486  23.199  29.136  1.00 24.76
ATOM   1055  O    VAL A 151      12.697  24.027  29.612  1.00 28.00
ATOM   1056  N    LYS A 152      13.285  22.595  27.964  1.00 23.05
ATOM   1057  CA   LYS A 152      12.147  22.954  27.114  1.00 23.12
ATOM   1058  CB   LYS A 152      12.622  23.481  25.741  1.00 24.16
ATOM   1059  CG   LYS A 152      13.479  24.753  25.812  1.00 26.71
ATOM   1060  CD   LYS A 152      12.677  26.053  25.966  1.00 31.53
ATOM   1061  CE   LYS A 152      13.274  27.189  25.109  1.00 31.75
ATOM   1062  NZ   LYS A 152      13.081  28.512  25.766  1.00 39.48
ATOM   1063  C    LYS A 152      11.170  21.809  26.923  1.00 22.29
ATOM   1064  O    LYS A 152       9.987  22.029  26.641  1.00 18.68
ATOM   1065  N    CYS A 153      11.677  20.599  27.139  1.00 22.37
ATOM   1066  CA   CYS A 153      10.914  19.385  26.901  1.00 20.12
ATOM   1067  CB   CYS A 153      10.752  19.107  25.412  1.00 19.37
ATOM   1068  SG   CYS A 153       9.611  17.737  25.063  1.00 18.76
ATOM   1069  C    CYS A 153      11.640  18.241  27.567  1.00 20.48
ATOM   1070  O    CYS A 153      12.868  18.148  27.498  1.00 21.39
ATOM   1071  N    ASP A 154      10.892  17.375  28.230  1.00 21.01
ATOM   1072  CA   ASP A 154      11.490  16.164  28.782  1.00 20.95
ATOM   1073  CB   ASP A 154      10.524  15.523  29.772  1.00 21.87
ATOM   1074  CG   ASP A 154      11.150  14.365  30.511  1.00 25.17
ATOM   1075  OD1  ASP A 154      12.202  14.589  31.155  1.00 24.97
ATOM   1076  OD2  ASP A 154      10.662  13.223  30.477  1.00 24.65
ATOM   1077  C    ASP A 154      11.831  15.185  27.650  1.00 20.85
ATOM   1078  O    ASP A 154      11.233  15.218  26.586  1.00 20.84
ATOM   1079  N    HIS A 155      12.838  14.337  27.860  1.00 20.25
ATOM   1080  CA   HIS A 155      13.113  13.265  26.916  1.00 20.35
ATOM   1081  CB   HIS A 155      14.579  12.839  27.069  1.00 21.06
ATOM   1082  CG   HIS A 155      15.056  11.901  26.007  1.00 22.85
ATOM   1083  ND1  HIS A 155      14.630  10.591  25.915  1.00 25.15
ATOM   1084  CE1  HIS A 155      15.237  10.003  24.900  1.00 24.10
ATOM   1085  NE2  HIS A 155      16.056  10.877  24.340  1.00 27.20
ATOM   1086  CD2  HIS A 155      15.975  12.067  25.026  1.00 27.39
ATOM   1087  C    HIS A 155      12.157  12.112  27.240  1.00 20.30
ATOM   1088  O    HIS A 155      12.458  11.225  28.053  1.00 19.64
ATOM   1089  N    TYR A 156      10.960  12.181  26.666  1.00 19.16
ATOM   1090  CA   TYR A 156       9.814  11.436  27.165  1.00 18.36
ATOM   1091  CB   TYR A 156       8.520  12.247  27.004  1.00 18.65
```

FIGURE 273

| ATOM | 1092 | CG | TYR A 156 | 8.250 | 12.664 | 25.569 | 1.00 | 17.99 |
| ATOM | 1093 | CD1 | TYR A 156 | 7.624 | 11.796 | 24.669 | 1.00 | 16.25 |
| ATOM | 1094 | CE1 | TYR A 156 | 7.427 | 12.171 | 23.328 | 1.00 | 16.10 |
| ATOM | 1095 | CZ | TYR A 156 | 7.776 | 13.457 | 22.936 | 1.00 | 15.17 |
| ATOM | 1096 | OH | TYR A 156 | 7.497 | 13.806 | 21.627 | 1.00 | 15.03 |
| ATOM | 1097 | CE2 | TYR A 156 | 8.397 | 14.321 | 23.810 | 1.00 | 21.32 |
| ATOM | 1098 | CD2 | TYR A 156 | 8.618 | 13.922 | 25.132 | 1.00 | 16.85 |
| ATOM | 1099 | C | TYR A 156 | 9.678 | 10.091 | 26.469 | 1.00 | 17.96 |
| ATOM | 1100 | O | TYR A 156 | 8.723 | 9.365 | 26.730 | 1.00 | 18.06 |
| ATOM | 1101 | N | TRP A 157 | 10.660 | 9.764 | 25.635 | 1.00 | 19.28 |
| ATOM | 1102 | CA | TRP A 157 | 10.722 | 8.482 | 24.933 | 1.00 | 20.13 |
| ATOM | 1103 | CB | TRP A 157 | 10.668 | 8.723 | 23.414 | 1.00 | 18.70 |
| ATOM | 1104 | CG | TRP A 157 | 11.885 | 9.431 | 22.911 | 1.00 | 18.38 |
| ATOM | 1105 | CD1 | TRP A 157 | 13.031 | 8.858 | 22.463 | 1.00 | 20.53 |
| ATOM | 1106 | NE1 | TRP A 157 | 13.924 | 9.827 | 22.075 | 1.00 | 19.49 |
| ATOM | 1107 | CE2 | TRP A 157 | 13.387 | 11.061 | 22.338 | 1.00 | 17.77 |
| ATOM | 1108 | CD2 | TRP A 157 | 12.085 | 10.848 | 22.833 | 1.00 | 18.54 |
| ATOM | 1109 | CE3 | TRP A 157 | 11.320 | 11.955 | 23.192 | 1.00 | 20.35 |
| ATOM | 1110 | CZ3 | TRP A 157 | 11.836 | 13.222 | 23.012 | 1.00 | 20.87 |
| ATOM | 1111 | CH2 | TRP A 157 | 13.145 | 13.404 | 22.500 | 1.00 | 22.03 |
| ATOM | 1112 | CZ2 | TRP A 157 | 13.920 | 12.335 | 22.150 | 1.00 | 20.41 |
| ATOM | 1113 | C | TRP A 157 | 11.993 | 7.755 | 25.370 | 1.00 | 22.07 |
| ATOM | 1114 | O | TRP A 157 | 12.912 | 8.357 | 25.928 | 1.00 | 21.87 |
| ATOM | 1115 | N | PRO A 158 | 12.042 | 6.446 | 25.173 | 1.00 | 23.81 |
| ATOM | 1116 | CA | PRO A 158 | 13.207 | 5.671 | 25.615 | 1.00 | 25.18 |
| ATOM | 1117 | CB | PRO A 158 | 12.854 | 4.227 | 25.238 | 1.00 | 25.31 |
| ATOM | 1118 | CG | PRO A 158 | 11.341 | 4.234 | 25.220 | 1.00 | 24.87 |
| ATOM | 1119 | CD | PRO A 158 | 10.976 | 5.594 | 24.619 | 1.00 | 25.87 |
| ATOM | 1120 | C | PRO A 158 | 14.515 | 6.105 | 24.973 | 1.00 | 24.62 |
| ATOM | 1121 | O | PRO A 158 | 14.568 | 6.599 | 23.836 | 1.00 | 24.33 |
| ATOM | 1122 | N | ALA A 159 | 15.567 | 5.872 | 25.742 | 1.00 | 25.95 |
| ATOM | 1123 | CA | ALA A 159 | 16.937 | 6.192 | 25.347 | 1.00 | 27.03 |
| ATOM | 1124 | CB | ALA A 159 | 17.775 | 6.378 | 26.592 | 1.00 | 26.95 |
| ATOM | 1125 | C | ALA A 159 | 17.529 | 5.113 | 24.441 | 1.00 | 28.60 |
| ATOM | 1126 | O | ALA A 159 | 18.512 | 5.345 | 23.723 | 1.00 | 31.08 |
| ATOM | 1127 | N | ASP A 160 | 16.921 | 3.932 | 24.461 | 1.00 | 26.27 |
| ATOM | 1128 | CA | ASP A 160 | 17.429 | 2.795 | 23.710 | 1.00 | 26.44 |
| ATOM | 1129 | CB | ASP A 160 | 18.488 | 2.056 | 24.529 | 1.00 | 27.67 |
| ATOM | 1130 | CG | ASP A 160 | 17.981 | 1.620 | 25.873 | 1.00 | 28.84 |
| ATOM | 1131 | OD1 | ASP A 160 | 16.776 | 1.290 | 26.014 | 1.00 | 26.79 |
| ATOM | 1132 | OD2 | ASP A 160 | 18.735 | 1.597 | 26.865 | 1.00 | 32.92 |
| ATOM | 1133 | C | ASP A 160 | 16.296 | 1.855 | 23.363 | 1.00 | 25.36 |
| ATOM | 1134 | O | ASP A 160 | 15.141 | 2.250 | 23.501 | 1.00 | 23.64 |
| ATOM | 1135 | N | GLN A 161 | 16.614 | 0.641 | 22.915 | 1.00 | 23.95 |
| ATOM | 1136 | CA | GLN A 161 | 15.585 | -0.240 | 22.365 | 1.00 | 24.83 |
| ATOM | 1137 | CB | GLN A 161 | 16.094 | -1.043 | 21.164 | 1.00 | 26.83 |
| ATOM | 1138 | CG | GLN A 161 | 16.563 | -0.146 | 20.012 | 1.00 | 32.67 |
| ATOM | 1139 | CD | GLN A 161 | 16.766 | -0.870 | 18.682 | 1.00 | 42.17 |
| ATOM | 1140 | OE1 | GLN A 161 | 16.550 | -2.078 | 18.566 | 1.00 | 44.45 |
| ATOM | 1141 | NE2 | GLN A 161 | 17.202 | -0.125 | 17.675 | 1.00 | 44.50 |
| ATOM | 1142 | C | GLN A 161 | 14.907 | -1.126 | 23.415 | 1.00 | 23.64 |
| ATOM | 1143 | O | GLN A 161 | 14.058 | -1.955 | 23.069 | 1.00 | 26.15 |

FIGURE 274

| | | | | | | | | | |
|---|---|---|---|---|---|---|---|---|---|
| ATOM | 1144 | N | ASP | A | 162 | 15.219 | -0.906 | 24.689 | 1.00 21.69 |
| ATOM | 1145 | CA | ASP | A | 162 | 14.621 | -1.750 | 25.724 | 1.00 22.06 |
| ATOM | 1146 | CB | ASP | A | 162 | 15.416 | -1.717 | 27.025 | 1.00 20.34 |
| ATOM | 1147 | CG | ASP | A | 162 | 16.797 | -2.326 | 26.891 | 1.00 29.79 |
| ATOM | 1148 | OD1 | ASP | A | 162 | 17.083 | -2.995 | 25.878 | 1.00 31.31 |
| ATOM | 1149 | OD2 | ASP | A | 162 | 17.657 | -2.177 | 27.779 | 1.00 39.34 |
| ATOM | 1150 | C | ASP | A | 162 | 13.240 | -1.174 | 26.011 | 1.00 20.10 |
| ATOM | 1151 | O | ASP | A | 162 | 13.149 | 0.028 | 26.267 | 1.00 21.67 |
| ATOM | 1152 | N | SER | A | 163 | 12.210 | -2.020 | 26.029 | 1.00 22.00 |
| ATOM | 1153 | CA | SER | A | 163 | 10.860 | -1.555 | 26.374 | 1.00 19.52 |
| ATOM | 1154 | CB | SER | A | 163 | 9.797 | -2.621 | 26.127 | 1.00 19.81 |
| ATOM | 1155 | OG | SER | A | 163 | 10.079 | -3.816 | 26.840 | 1.00 24.08 |
| ATOM | 1156 | C | SER | A | 163 | 10.742 | -0.998 | 27.791 | 1.00 20.81 |
| ATOM | 1157 | O | SER | A | 163 | 11.529 | -1.343 | 28.699 | 1.00 19.79 |
| ATOM | 1158 | N | LEU | A | 164 | 9.765 | -0.123 | 27.987 | 1.00 20.37 |
| ATOM | 1159 | CA | LEU | A | 164 | 9.525 | 0.494 | 29.298 | 1.00 20.27 |
| ATOM | 1160 | CB | LEU | A | 164 | 10.225 | 1.847 | 29.418 | 1.00 21.91 |
| ATOM | 1161 | CG | LEU | A | 164 | 11.716 | 2.029 | 29.730 | 1.00 28.59 |
| ATOM | 1162 | CD1 | LEU | A | 164 | 11.962 | 3.530 | 29.619 | 1.00 32.46 |
| ATOM | 1163 | CD2 | LEU | A | 164 | 11.994 | 1.587 | 31.160 | 1.00 29.88 |
| ATOM | 1164 | C | LEU | A | 164 | 8.031 | 0.814 | 29.392 | 1.00 17.64 |
| ATOM | 1165 | O | LEU | A | 164 | 7.400 | 1.129 | 28.385 | 1.00 19.87 |
| ATOM | 1166 | N | TYR | A | 165 | 7.511 | 0.782 | 30.613 | 1.00 18.28 |
| ATOM | 1167 | CA | TYR | A | 165 | 6.148 | 1.247 | 30.880 | 1.00 16.77 |
| ATOM | 1168 | CB | TYR | A | 165 | 5.625 | 0.605 | 32.160 | 1.00 17.12 |
| ATOM | 1169 | CG | TYR | A | 165 | 4.965 | -0.711 | 31.893 | 1.00 20.15 |
| ATOM | 1170 | CD1 | TYR | A | 165 | 3.698 | -0.753 | 31.322 | 1.00 21.67 |
| ATOM | 1171 | CE1 | TYR | A | 165 | 3.081 | -1.967 | 31.054 | 1.00 19.75 |
| ATOM | 1172 | CZ | TYR | A | 165 | 3.726 | -3.137 | 31.372 | 1.00 23.95 |
| ATOM | 1173 | OH | TYR | A | 165 | 3.113 | -4.342 | 31.095 | 1.00 28.45 |
| ATOM | 1174 | CE2 | TYR | A | 165 | 4.972 | -3.123 | 31.935 | 1.00 21.42 |
| ATOM | 1175 | CD2 | TYR | A | 165 | 5.587 | -1.906 | 32.230 | 1.00 21.96 |
| ATOM | 1176 | C | TYR | A | 165 | 6.107 | 2.749 | 31.085 | 1.00 19.28 |
| ATOM | 1177 | O | TYR | A | 165 | 6.948 | 3.318 | 31.778 | 1.00 22.32 |
| ATOM | 1178 | N | TYR | A | 166 | 5.105 | 3.372 | 30.480 | 1.00 19.16 |
| ATOM | 1179 | CA | TYR | A | 166 | 4.668 | 4.714 | 30.858 | 1.00 18.90 |
| ATOM | 1180 | CB | TYR | A | 166 | 4.762 | 5.650 | 29.639 | 1.00 19.56 |
| ATOM | 1181 | CG | TYR | A | 166 | 6.180 | 5.875 | 29.174 | 1.00 18.34 |
| ATOM | 1182 | CD1 | TYR | A | 166 | 6.896 | 6.985 | 29.601 | 1.00 16.76 |
| ATOM | 1183 | CE1 | TYR | A | 166 | 8.223 | 7.190 | 29.153 | 1.00 18.94 |
| ATOM | 1184 | CZ | TYR | A | 166 | 8.777 | 6.306 | 28.245 | 1.00 22.27 |
| ATOM | 1185 | OH | TYR | A | 166 | 10.067 | 6.497 | 27.780 | 1.00 24.37 |
| ATOM | 1186 | CE2 | TYR | A | 166 | 8.067 | 5.222 | 27.789 | 1.00 26.25 |
| ATOM | 1187 | CD2 | TYR | A | 166 | 6.768 | 5.016 | 28.245 | 1.00 22.49 |
| ATOM | 1188 | C | TYR | A | 166 | 3.235 | 4.628 | 31.372 | 1.00 19.75 |
| ATOM | 1189 | O | TYR | A | 166 | 2.297 | 4.549 | 30.586 | 1.00 20.21 |
| ATOM | 1190 | N | GLY | A | 167 | 3.032 | 4.609 | 32.694 | 1.00 20.43 |
| ATOM | 1191 | CA | GLY | A | 167 | 1.684 | 4.310 | 33.165 | 1.00 21.54 |
| ATOM | 1192 | C | GLY | A | 167 | 1.209 | 2.931 | 32.728 | 1.00 23.50 |
| ATOM | 1193 | O | GLY | A | 167 | 1.932 | 1.957 | 32.943 | 1.00 23.77 |
| ATOM | 1194 | N | ASP | A | 168 | 0.029 | 2.885 | 32.099 | 1.00 21.81 |
| ATOM | 1195 | CA | ASP | A | 168 | -0.673 | 1.718 | 31.567 | 1.00 26.70 |

FIGURE 275

| | | | | | | | | | |
|---|---|---|---|---|---|---|---|---|---|
| ATOM | 1196 | CB | ASP | A | 168 | -2.086 | 2.171 | 31.152 | 1.00 28.49 |
| ATOM | 1197 | CG | ASP | A | 168 | -3.021 | 2.345 | 32.289 | 1.00 35.95 |
| ATOM | 1198 | OD1 | ASP | A | 168 | -2.581 | 2.521 | 33.451 | 1.00 44.09 |
| ATOM | 1199 | OD2 | ASP | A | 168 | -4.248 | 2.352 | 32.078 | 1.00 36.92 |
| ATOM | 1200 | C | ASP | A | 168 | -0.150 | 1.270 | 30.206 | 1.00 24.58 |
| ATOM | 1201 | O | ASP | A | 168 | -0.717 | 0.345 | 29.619 | 1.00 26.11 |
| ATOM | 1202 | N | LEU | A | 169 | 0.840 | 1.971 | 29.657 | 1.00 21.74 |
| ATOM | 1203 | CA | LEU | A | 169 | 1.205 | 1.797 | 28.261 | 1.00 19.33 |
| ATOM | 1204 | CB | LEU | A | 169 | 1.174 | 3.152 | 27.567 | 1.00 19.99 |
| ATOM | 1205 | CG | LEU | A | 169 | 1.541 | 3.109 | 26.095 | 1.00 25.20 |
| ATOM | 1206 | CD1 | LEU | A | 169 | 0.471 | 3.894 | 25.397 | 1.00 26.72 |
| ATOM | 1207 | CD2 | LEU | A | 169 | 2.886 | 3.769 | 25.917 | 1.00 25.81 |
| ATOM | 1208 | C | LEU | A | 169 | 2.619 | 1.256 | 28.197 | 1.00 20.65 |
| ATOM | 1209 | O | LEU | A | 169 | 3.485 | 1.740 | 28.907 | 1.00 21.93 |
| ATOM | 1210 | N | ILE | A | 170 | 2.857 | 0.250 | 27.370 | 1.00 18.58 |
| ATOM | 1211 | CA | ILE | A | 170 | 4.239 | -0.182 | 27.197 | 1.00 19.82 |
| ATOM | 1212 | CB | ILE | A | 170 | 4.309 | -1.728 | 27.237 | 1.00 19.31 |
| ATOM | 1213 | CG1 | ILE | A | 170 | 5.746 | -2.220 | 26.983 | 1.00 22.75 |
| ATOM | 1214 | CD1 | ILE | A | 170 | 6.454 | -2.519 | 28.252 | 1.00 22.15 |
| ATOM | 1215 | CG2 | ILE | A | 170 | 3.367 | -2.344 | 26.238 | 1.00 22.33 |
| ATOM | 1216 | C | ILE | A | 170 | 4.745 | 0.359 | 25.870 | 1.00 19.44 |
| ATOM | 1217 | O | ILE | A | 170 | 4.000 | 0.382 | 24.898 | 1.00 19.22 |
| ATOM | 1218 | N | LEU | A | 171 | 6.009 | 0.775 | 25.817 | 1.00 18.90 |
| ATOM | 1219 | CA | LEU | A | 171 | 6.505 | 1.440 | 24.631 | 1.00 18.91 |
| ATOM | 1220 | CB | LEU | A | 171 | 6.697 | 2.923 | 24.954 | 1.00 19.73 |
| ATOM | 1221 | CG | LEU | A | 171 | 7.108 | 3.758 | 23.751 | 1.00 25.25 |
| ATOM | 1222 | CD1 | LEU | A | 171 | 6.670 | 5.162 | 24.054 | 1.00 28.25 |
| ATOM | 1223 | CD2 | LEU | A | 171 | 8.618 | 3.703 | 23.723 | 1.00 29.29 |
| ATOM | 1224 | C | LEU | A | 171 | 7.852 | 0.820 | 24.354 | 1.00 19.14 |
| ATOM | 1225 | O | LEU | A | 171 | 8.556 | 0.467 | 25.305 | 1.00 18.74 |
| ATOM | 1226 | N | GLN | A | 172 | 8.174 | 0.655 | 23.074 | 1.00 17.00 |
| ATOM | 1227 | CA | GLN | A | 172 | 9.485 | 0.117 | 22.713 | 1.00 18.63 |
| ATOM | 1228 | CB | GLN | A | 172 | 9.392 | -1.379 | 22.439 | 1.00 19.29 |
| ATOM | 1229 | CG | GLN | A | 172 | 10.724 | -2.109 | 22.277 | 1.00 25.23 |
| ATOM | 1230 | CD | GLN | A | 172 | 10.473 | -3.552 | 21.842 | 1.00 28.98 |
| ATOM | 1231 | OE1 | GLN | A | 172 | 9.779 | -3.776 | 20.859 | 1.00 30.54 |
| ATOM | 1232 | NE2 | GLN | A | 172 | 11.024 | -4.521 | 22.559 | 1.00 24.05 |
| ATOM | 1233 | C | GLN | A | 172 | 9.946 | 0.820 | 21.464 | 1.00 17.56 |
| ATOM | 1234 | O | GLN | A | 172 | 9.242 | 0.825 | 20.460 | 1.00 20.89 |
| ATOM | 1235 | N | MET | A | 173 | 11.166 | 1.337 | 21.506 | 1.00 18.09 |
| ATOM | 1236 | CA | MET | A | 173 | 11.703 | 2.006 | 20.315 | 1.00 19.64 |
| ATOM | 1237 | CB | MET | A | 173 | 12.860 | 2.934 | 20.713 | 1.00 15.61 |
| ATOM | 1238 | CG | MET | A | 173 | 13.415 | 3.696 | 19.493 | 1.00 20.90 |
| ATOM | 1239 | SD | MET | A | 173 | 14.248 | 5.251 | 19.921 | 1.00 22.90 |
| ATOM | 1240 | CE | MET | A | 173 | 15.666 | 4.695 | 20.787 | 1.00 24.34 |
| ATOM | 1241 | C | MET | A | 173 | 12.262 | 0.942 | 19.386 | 1.00 20.45 |
| ATOM | 1242 | O | MET | A | 173 | 13.189 | 0.219 | 19.790 | 1.00 23.02 |
| ATOM | 1243 | N | LEU | A | 174 | 11.783 | 0.916 | 18.144 | 1.00 19.05 |
| ATOM | 1244 | CA | LEU | A | 174 | 12.245 | -0.028 | 17.131 | 1.00 20.65 |
| ATOM | 1245 | CB | LEU | A | 174 | 11.102 | -0.481 | 16.243 | 1.00 22.05 |
| ATOM | 1246 | CG | LEU | A | 174 | 9.874 | -1.071 | 16.934 | 1.00 19.97 |
| ATOM | 1247 | CD1 | LEU | A | 174 | 8.825 | -1.459 | 15.899 | 1.00 25.97 |

FIGURE 276

```
ATOM   1248  CD2  LEU A 174     10.205   -2.246   17.825  1.00 24.09
ATOM   1249  C    LEU A 174     13.385    0.487   16.262  1.00 22.40
ATOM   1250  O    LEU A 174     14.226   -0.290   15.807  1.00 23.87
ATOM   1251  N    SER A 175     13.419    1.794   16.031  1.00 21.05
ATOM   1252  CA   SER A 175     14.501    2.374   15.250  1.00 20.96
ATOM   1253  CB   SER A 175     14.261    2.317   13.743  1.00 19.89
ATOM   1254  OG   SER A 175     13.038    2.900   13.345  1.00 21.43
ATOM   1255  C    SER A 175     14.670    3.819   15.645  1.00 18.88
ATOM   1256  O    SER A 175     13.739    4.466   16.097  1.00 19.35
ATOM   1257  N    GLU A 176     15.880    4.300   15.439  1.00 17.31
ATOM   1258  CA   GLU A 176     16.187    5.707   15.592  1.00 17.56
ATOM   1259  CB   GLU A 176     16.755    5.907   16.988  1.00 19.24
ATOM   1260  CG   GLU A 176     17.299    7.278   17.319  1.00 22.48
ATOM   1261  CD   GLU A 176     17.792    7.337   18.749  1.00 24.54
ATOM   1262  OE1  GLU A 176     18.951    6.933   19.003  1.00 35.75
ATOM   1263  OE2  GLU A 176     17.050    7.813   19.612  1.00 25.21
ATOM   1264  C    GLU A 176     17.141    6.067   14.463  1.00 17.07
ATOM   1265  O    GLU A 176     18.276    5.559   14.397  1.00 19.83
ATOM   1266  N    SER A 177     16.684    6.953   13.579  1.00 18.92
ATOM   1267  CA   SER A 177     17.484    7.339   12.419  1.00 20.17
ATOM   1268  CB   SER A 177     16.766    6.925   11.139  1.00 19.64
ATOM   1269  OG   SER A 177     16.378    5.553   11.196  1.00 26.41
ATOM   1270  C    SER A 177     17.786    8.844   12.477  1.00 18.07
ATOM   1271  O    SER A 177     16.922    9.671   12.295  1.00 16.18
ATOM   1272  N    VAL A 178     19.035    9.210   12.728  1.00 19.19
ATOM   1273  CA   VAL A 178     19.408   10.605   12.863  1.00 18.44
ATOM   1274  CB   VAL A 178     20.648   10.758   13.802  1.00 18.96
ATOM   1275  CG1  VAL A 178     21.063   12.211   13.900  1.00 19.33
ATOM   1276  CG2  VAL A 178     20.350   10.128   15.180  1.00 22.08
ATOM   1277  C    VAL A 178     19.814   11.098   11.472  1.00 17.78
ATOM   1278  O    VAL A 178     20.753   10.578   10.850  1.00 18.38
ATOM   1279  N    LEU A 179     19.070   12.075   10.970  1.00 18.02
ATOM   1280  CA   LEU A 179     19.347   12.663    9.663  1.00 16.64
ATOM   1281  CB   LEU A 179     18.074   12.673    8.777  1.00 17.91
ATOM   1282  CG   LEU A 179     17.193   11.405    8.899  1.00 18.10
ATOM   1283  CD1  LEU A 179     15.925   11.510    8.066  1.00 18.94
ATOM   1284  CD2  LEU A 179     17.912   10.091    8.610  1.00 15.53
ATOM   1285  C    LEU A 179     19.922   14.059    9.914  1.00 17.92
ATOM   1286  O    LEU A 179     20.078   14.486   11.066  1.00 18.05
ATOM   1287  N    PRO A 180     20.307   14.764    8.862  1.00 15.89
ATOM   1288  CA   PRO A 180     20.946   16.077    9.031  1.00 17.67
ATOM   1289  CB   PRO A 180     21.055   16.593    7.609  1.00 16.61
ATOM   1290  CG   PRO A 180     21.283   15.311    6.840  1.00 17.50
ATOM   1291  CD   PRO A 180     20.255   14.354    7.454  1.00 16.79
ATOM   1292  C    PRO A 180     20.190   17.085    9.863  1.00 17.87
ATOM   1293  O    PRO A 180     20.802   17.756   10.702  1.00 19.82
ATOM   1294  N    GLU A 181     18.878   17.189    9.656  1.00 17.72
ATOM   1295  CA   GLU A 181     18.130   18.231   10.335  1.00 19.40
ATOM   1296  CB   GLU A 181     17.737   19.349    9.366  1.00 20.16
ATOM   1297  CG   GLU A 181     18.973   20.058    8.833  1.00 24.30
ATOM   1298  CD   GLU A 181     18.615   21.064    7.765  1.00 30.86
ATOM   1299  OE1  GLU A 181     17.597   20.866    7.057  1.00 33.00
```

FIGURE 277

| | | | | | | | | | |
|---|---|---|---|---|---|---|---|---|---|
| ATOM | 1300 | OE2 | GLU | A | 181 | 19.384 | 22.040 | 7.641 | 1.00 39.73 |
| ATOM | 1301 | C | GLU | A | 181 | 16.890 | 17.704 | 11.048 | 1.00 19.38 |
| ATOM | 1302 | O | GLU | A | 181 | 16.209 | 18.470 | 11.692 | 1.00 19.21 |
| ATOM | 1303 | N | TRP | A | 182 | 16.619 | 16.405 | 10.942 | 1.00 16.49 |
| ATOM | 1304 | CA | TRP | A | 182 | 15.667 | 15.784 | 11.836 | 1.00 16.57 |
| ATOM | 1305 | CB | TRP | A | 182 | 14.242 | 15.924 | 11.286 | 1.00 15.22 |
| ATOM | 1306 | CG | TRP | A | 182 | 14.026 | 15.548 | 9.833 | 1.00 13.61 |
| ATOM | 1307 | CD1 | TRP | A | 182 | 13.615 | 14.342 | 9.354 | 1.00 15.76 |
| ATOM | 1308 | NE1 | TRP | A | 182 | 13.472 | 14.385 | 7.987 | 1.00 16.34 |
| ATOM | 1309 | CE2 | TRP | A | 182 | 13.726 | 15.663 | 7.565 | 1.00 13.66 |
| ATOM | 1310 | CD2 | TRP | A | 182 | 14.072 | 16.427 | 8.713 | 1.00 14.52 |
| ATOM | 1311 | CE3 | TRP | A | 182 | 14.416 | 17.767 | 8.547 | 1.00 16.17 |
| ATOM | 1312 | CZ3 | TRP | A | 182 | 14.369 | 18.307 | 7.265 | 1.00 17.28 |
| ATOM | 1313 | CH2 | TRP | A | 182 | 14.019 | 17.520 | 6.154 | 1.00 20.20 |
| ATOM | 1314 | CZ2 | TRP | A | 182 | 13.697 | 16.196 | 6.281 | 1.00 18.18 |
| ATOM | 1315 | C | TRP | A | 182 | 16.019 | 14.330 | 12.118 | 1.00 17.43 |
| ATOM | 1316 | O | TRP | A | 182 | 16.831 | 13.721 | 11.423 | 1.00 16.83 |
| ATOM | 1317 | N | THR | A | 183 | 15.372 | 13.776 | 13.135 | 1.00 17.91 |
| ATOM | 1318 | CA | THR | A | 183 | 15.570 | 12.391 | 13.524 | 1.00 17.41 |
| ATOM | 1319 | CB | THR | A | 183 | 16.158 | 12.387 | 14.941 | 1.00 17.91 |
| ATOM | 1320 | OG1 | THR | A | 183 | 17.508 | 12.889 | 14.867 | 1.00 19.93 |
| ATOM | 1321 | CG2 | THR | A | 183 | 16.379 | 10.952 | 15.444 | 1.00 19.10 |
| ATOM | 1322 | C | THR | A | 183 | 14.216 | 11.704 | 13.494 | 1.00 18.88 |
| ATOM | 1323 | O | THR | A | 183 | 13.253 | 12.259 | 14.020 | 1.00 17.96 |
| ATOM | 1324 | N | ILE | A | 184 | 14.159 | 10.521 | 12.884 | 1.00 14.76 |
| ATOM | 1325 | CA | ILE | A | 184 | 12.915 | 9.770 | 12.795 | 1.00 15.33 |
| ATOM | 1326 | CB | ILE | A | 184 | 12.636 | 9.313 | 11.362 | 1.00 15.60 |
| ATOM | 1327 | CG1 | ILE | A | 184 | 12.620 | 10.508 | 10.410 | 1.00 14.39 |
| ATOM | 1328 | CD1 | ILE | A | 184 | 12.371 | 10.133 | 8.960 | 1.00 16.80 |
| ATOM | 1329 | CG2 | ILE | A | 184 | 11.318 | 8.518 | 11.307 | 1.00 18.05 |
| ATOM | 1330 | C | ILE | A | 184 | 13.050 | 8.539 | 13.682 | 1.00 16.19 |
| ATOM | 1331 | O | ILE | A | 184 | 13.965 | 7.725 | 13.524 | 1.00 18.12 |
| ATOM | 1332 | N | ARG | A | 185 | 12.106 | 8.368 | 14.592 | 1.00 16.20 |
| ATOM | 1333 | CA | ARG | A | 185 | 12.083 | 7.159 | 15.425 | 1.00 15.84 |
| ATOM | 1334 | CB | ARG | A | 185 | 12.137 | 7.551 | 16.904 | 1.00 14.71 |
| ATOM | 1335 | CG | ARG | A | 185 | 13.505 | 8.055 | 17.326 | 1.00 14.82 |
| ATOM | 1336 | CD | ARG | A | 185 | 13.468 | 8.727 | 18.685 | 1.00 17.62 |
| ATOM | 1337 | NE | ARG | A | 185 | 14.822 | 9.174 | 19.013 | 1.00 21.26 |
| ATOM | 1338 | CZ | ARG | A | 185 | 15.195 | 10.448 | 18.973 | 1.00 21.83 |
| ATOM | 1339 | NH1 | ARG | A | 185 | 14.345 | 11.379 | 18.584 | 1.00 21.65 |
| ATOM | 1340 | NH2 | ARG | A | 185 | 16.422 | 10.807 | 19.323 | 1.00 26.56 |
| ATOM | 1341 | C | ARG | A | 185 | 10.808 | 6.386 | 15.181 | 1.00 16.96 |
| ATOM | 1342 | O | ARG | A | 185 | 9.775 | 6.967 | 14.866 | 1.00 18.49 |
| ATOM | 1343 | N | GLU | A | 186 | 10.876 | 5.063 | 15.330 | 1.00 18.06 |
| ATOM | 1344 | CA | GLU | A | 186 | 9.653 | 4.289 | 15.251 | 1.00 18.19 |
| ATOM | 1345 | CB | GLU | A | 186 | 9.729 | 3.232 | 14.126 | 1.00 18.51 |
| ATOM | 1346 | CG | GLU | A | 186 | 8.354 | 2.622 | 13.856 | 1.00 22.77 |
| ATOM | 1347 | CD | GLU | A | 186 | 8.367 | 1.477 | 12.851 | 1.00 31.07 |
| ATOM | 1348 | OE1 | GLU | A | 186 | 7.330 | 1.279 | 12.179 | 1.00 37.68 |
| ATOM | 1349 | OE2 | GLU | A | 186 | 9.388 | 0.775 | 12.730 | 1.00 33.77 |
| ATOM | 1350 | C | GLU | A | 186 | 9.452 | 3.600 | 16.597 | 1.00 18.63 |
| ATOM | 1351 | O | GLU | A | 186 | 10.411 | 3.051 | 17.142 | 1.00 19.33 |

FIGURE 278

| ATOM | 1352 | N | PHE | A | 187 | 8.223 | 3.614 | 17.108 | 1.00 | 18.68 |
|------|------|------|------|---|-----|--------|--------|--------|------|-------|
| ATOM | 1353 | CA | PHE | A | 187 | 7.927 | 2.978 | 18.399 | 1.00 | 18.08 |
| ATOM | 1354 | CB | PHE | A | 187 | 7.426 | 4.006 | 19.415 | 1.00 | 18.99 |
| ATOM | 1355 | CG | PHE | A | 187 | 8.400 | 5.092 | 19.715 | 1.00 | 19.80 |
| ATOM | 1356 | CD1 | PHE | A | 187 | 8.155 | 6.382 | 19.283 | 1.00 | 21.67 |
| ATOM | 1357 | CE1 | PHE | A | 187 | 9.066 | 7.403 | 19.559 | 1.00 | 23.38 |
| ATOM | 1358 | CZ | PHE | A | 187 | 10.242 | 7.106 | 20.223 | 1.00 | 20.03 |
| ATOM | 1359 | CE2 | PHE | A | 187 | 10.489 | 5.828 | 20.641 | 1.00 | 25.29 |
| ATOM | 1360 | CD2 | PHE | A | 187 | 9.595 | 4.819 | 20.369 | 1.00 | 22.12 |
| ATOM | 1361 | C | PHE | A | 187 | 6.815 | 1.954 | 18.257 | 1.00 | 19.06 |
| ATOM | 1362 | O | PHE | A | 187 | 5.881 | 2.161 | 17.472 | 1.00 | 18.23 |
| ATOM | 1363 | N | LYS | A | 188 | 6.898 | 0.863 | 19.018 | 1.00 | 18.39 |
| ATOM | 1364 | CA | LYS | A | 188 | 5.718 | 0.006 | 19.179 | 1.00 | 19.84 |
| ATOM | 1365 | CB | LYS | A | 188 | 6.146 | -1.466 | 19.179 | 1.00 | 21.30 |
| ATOM | 1366 | CG | LYS | A | 188 | 4.994 | -2.449 | 19.361 | 1.00 | 29.28 |
| ATOM | 1367 | CD | LYS | A | 188 | 5.549 | -3.835 | 19.650 | 1.00 | 39.42 |
| ATOM | 1368 | CE | LYS | A | 188 | 4.535 | -4.915 | 19.312 | 1.00 | 41.60 |
| ATOM | 1369 | NZ | LYS | A | 188 | 5.247 | -6.141 | 18.830 | 1.00 | 47.94 |
| ATOM | 1370 | C | LYS | A | 188 | 5.076 | 0.377 | 20.513 | 1.00 | 17.53 |
| ATOM | 1371 | O | LYS | A | 188 | 5.765 | 0.472 | 21.511 | 1.00 | 20.08 |
| ATOM | 1372 | N | ILE | A | 189 | 3.761 | 0.584 | 20.551 | 1.00 | 18.34 |
| ATOM | 1373 | CA | ILE | A | 189 | 3.063 | 0.924 | 21.781 | 1.00 | 18.37 |
| ATOM | 1374 | CB | ILE | A | 189 | 2.662 | 2.409 | 21.729 | 1.00 | 17.71 |
| ATOM | 1375 | CG1A | ILE | A | 189 | 2.140 | 2.932 | 23.051 | 0.50 | 18.61 |
| ATOM | 1376 | CG1B | ILE | A | 189 | 1.794 | 2.771 | 20.521 | 0.50 | 19.99 |
| ATOM | 1377 | CD1A | ILE | A | 189 | 1.758 | 4.385 | 22.938 | 0.50 | 20.42 |
| ATOM | 1378 | CD1B | ILE | A | 189 | 1.063 | 4.085 | 20.730 | 0.50 | 24.91 |
| ATOM | 1379 | CG2A | ILE | A | 189 | 1.579 | 2.616 | 20.661 | 0.50 | 18.62 |
| ATOM | 1380 | CG2B | ILE | A | 189 | 3.921 | 3.269 | 21.880 | 0.50 | 16.15 |
| ATOM | 1381 | C | ILE | A | 189 | 1.848 | -0.013 | 21.922 | 1.00 | 17.83 |
| ATOM | 1382 | O | ILE | A | 189 | 1.239 | -0.400 | 20.918 | 1.00 | 16.89 |
| ATOM | 1383 | N | CYS | A | 190 | 1.567 | -0.403 | 23.165 | 1.00 | 19.24 |
| ATOM | 1384 | CA | CYS | A | 190 | 0.313 | -1.068 | 23.547 | 1.00 | 19.00 |
| ATOM | 1385 | CB | CYS | A | 190 | 0.590 | -2.542 | 23.881 | 1.00 | 17.53 |
| ATOM | 1386 | SG | CYS | A | 190 | 1.496 | -3.470 | 22.591 | 1.00 | 25.53 |
| ATOM | 1387 | C | CYS | A | 190 | -0.258 | -0.402 | 24.791 | 1.00 | 18.76 |
| ATOM | 1388 | O | CYS | A | 190 | 0.428 | -0.293 | 25.789 | 1.00 | 18.93 |
| ATOM | 1389 | N | GLY | A | 191 | -1.534 | -0.004 | 24.757 | 1.00 | 18.32 |
| ATOM | 1390 | CA | GLY | A | 191 | -2.213 | 0.527 | 25.930 | 1.00 | 20.25 |
| ATOM | 1391 | C | GLY | A | 191 | -3.530 | -0.202 | 26.162 | 1.00 | 20.72 |
| ATOM | 1392 | O | GLY | A | 191 | -3.740 | -1.262 | 25.606 | 1.00 | 20.46 |
| ATOM | 1393 | N | GLU | A | 192 | -4.386 | 0.359 | 27.002 | 1.00 | 22.42 |
| ATOM | 1394 | CA | GLU | A | 192 | -5.677 | -0.253 | 27.279 | 1.00 | 24.91 |
| ATOM | 1395 | CB | GLU | A | 192 | -6.421 | 0.585 | 28.315 | 1.00 | 23.09 |
| ATOM | 1396 | CG | GLU | A | 192 | -7.854 | 0.111 | 28.537 | 1.00 | 29.54 |
| ATOM | 1397 | CD | GLU | A | 192 | -8.646 | 0.961 | 29.512 | 1.00 | 32.49 |
| ATOM | 1398 | OE1 | GLU | A | 192 | -8.290 | 2.150 | 29.745 | 1.00 | 31.32 |
| ATOM | 1399 | OE2 | GLU | A | 192 | -9.661 | 0.426 | 30.018 | 1.00 | 34.67 |
| ATOM | 1400 | C | GLU | A | 192 | -6.461 | -0.414 | 25.974 | 1.00 | 24.14 |
| ATOM | 1401 | O | GLU | A | 192 | -6.810 | 0.567 | 25.289 | 1.00 | 24.16 |
| ATOM | 1402 | N | GLU | A | 193 | -6.719 | -1.671 | 25.612 | 1.00 | 25.67 |
| ATOM | 1403 | CA | GLU | A | 193 | -7.236 | -1.978 | 24.284 | 1.00 | 26.65 |

| ATOM | 1404 | CB | GLU | A | 193 | -7.337 | -3.489 | 24.068 | 1.00 | 28.45 |
|------|------|------|-----|---|-----|--------|--------|--------|------|-------|
| ATOM | 1405 | CG | GLU | A | 193 | -7.767 | -3.843 | 22.648 | 1.00 | 29.15 |
| ATOM | 1406 | CD | GLU | A | 193 | -7.780 | -5.342 | 22.405 | 1.00 | 34.41 |
| ATOM | 1407 | OE1 | GLU | A | 193 | -7.163 | -6.077 | 23.211 | 1.00 | 33.00 |
| ATOM | 1408 | OE2 | GLU | A | 193 | -8.400 | -5.778 | 21.408 | 1.00 | 34.70 |
| ATOM | 1409 | C | GLU | A | 193 | -8.598 | -1.366 | 24.010 | 1.00 | 30.04 |
| ATOM | 1410 | O | GLU | A | 193 | -9.510 | -1.555 | 24.810 | 1.00 | 29.04 |
| ATOM | 1411 | N | GLN | A | 194 | -8.730 | -0.635 | 22.902 | 1.00 | 28.72 |
| ATOM | 1412 | CA | GLN | A | 194 | -10.054 | -0.254 | 22.417 | 1.00 | 30.57 |
| ATOM | 1413 | CB | GLN | A | 194 | -10.349 | 1.229 | 22.654 | 1.00 | 30.30 |
| ATOM | 1414 | CG | GLN | A | 194 | -10.354 | 1.700 | 24.097 | 1.00 | 38.21 |
| ATOM | 1415 | CD | GLN | A | 194 | -10.661 | 3.192 | 24.205 | 1.00 | 45.81 |
| ATOM | 1416 | OE1 | GLN | A | 194 | -11.766 | 3.629 | 23.868 | 1.00 | 47.74 |
| ATOM | 1417 | NE2 | GLN | A | 194 | -9.682 | 3.976 | 24.667 | 1.00 | 48.46 |
| ATOM | 1418 | C | GLN | A | 194 | -10.138 | -0.612 | 20.937 | 1.00 | 30.81 |
| ATOM | 1419 | O | GLN | A | 194 | -10.444 | -1.762 | 20.596 | 1.00 | 31.43 |
| ATOM | 1420 | N | LEU | A | 195 | -9.843 | 0.343 | 20.056 | 1.00 | 30.77 |
| ATOM | 1421 | CA | LEU | A | 195 | -9.869 | 0.103 | 18.620 | 1.00 | 31.53 |
| ATOM | 1422 | CB | LEU | A | 195 | -9.860 | 1.419 | 17.833 | 1.00 | 32.19 |
| ATOM | 1423 | CG | LEU | A | 195 | -11.132 | 2.254 | 17.673 | 1.00 | 37.67 |
| ATOM | 1424 | CD1 | LEU | A | 195 | -10.860 | 3.277 | 16.579 | 1.00 | 33.54 |
| ATOM | 1425 | CD2 | LEU | A | 195 | -12.359 | 1.404 | 17.322 | 1.00 | 36.45 |
| ATOM | 1426 | C | LEU | A | 195 | -8.692 | -0.729 | 18.144 | 1.00 | 31.71 |
| ATOM | 1427 | O | LEU | A | 195 | -8.796 | -1.454 | 17.159 | 1.00 | 32.54 |
| ATOM | 1428 | N | ASP | A | 196 | -7.554 | -0.607 | 18.821 | 1.00 | 29.57 |
| ATOM | 1429 | CA | ASP | A | 196 | -6.442 | -1.492 | 18.533 | 1.00 | 28.34 |
| ATOM | 1430 | CB | ASP | A | 196 | -5.424 | -0.868 | 17.558 | 1.00 | 26.58 |
| ATOM | 1431 | CG | ASP | A | 196 | -4.815 | 0.420 | 18.063 | 1.00 | 27.01 |
| ATOM | 1432 | OD1 | ASP | A | 196 | -5.145 | 0.869 | 19.183 | 1.00 | 27.13 |
| ATOM | 1433 | OD2 | ASP | A | 196 | -3.989 | 1.049 | 17.375 | 1.00 | 25.88 |
| ATOM | 1434 | C | ASP | A | 196 | -5.791 | -2.008 | 19.815 | 1.00 | 27.72 |
| ATOM | 1435 | O | ASP | A | 196 | -6.099 | -1.550 | 20.915 | 1.00 | 26.99 |
| ATOM | 1436 | N | ALA | A | 197 | -4.912 | -2.989 | 19.653 | 1.00 | 26.66 |
| ATOM | 1437 | CA | ALA | A | 197 | -4.279 | -3.646 | 20.792 | 1.00 | 26.48 |
| ATOM | 1438 | CB | ALA | A | 197 | -4.557 | -5.145 | 20.748 | 1.00 | 27.66 |
| ATOM | 1439 | C | ALA | A | 197 | -2.774 | -3.400 | 20.744 | 1.00 | 24.78 |
| ATOM | 1440 | O | ALA | A | 197 | -2.122 | -3.483 | 21.779 | 1.00 | 26.10 |
| ATOM | 1441 | N | HIS | A | 198 | -2.237 | -3.062 | 19.573 | 1.00 | 23.60 |
| ATOM | 1442 | CA | HIS | A | 198 | -0.811 | -2.715 | 19.465 | 1.00 | 24.08 |
| ATOM | 1443 | CB | HIS | A | 198 | 0.098 | -3.951 | 19.353 | 1.00 | 26.63 |
| ATOM | 1444 | CG | HIS | A | 198 | -0.227 | -4.848 | 18.198 | 1.00 | 31.90 |
| ATOM | 1445 | ND1 | HIS | A | 198 | -1.094 | -5.914 | 18.300 | 1.00 | 40.11 |
| ATOM | 1446 | CE1 | HIS | A | 198 | -1.186 | -6.519 | 17.128 | 1.00 | 38.77 |
| ATOM | 1447 | NE2 | HIS | A | 198 | -0.406 | -5.886 | 16.271 | 1.00 | 43.28 |
| ATOM | 1448 | CD2 | HIS | A | 198 | 0.215 | -4.844 | 16.918 | 1.00 | 33.37 |
| ATOM | 1449 | C | HIS | A | 198 | -0.679 | -1.841 | 18.217 | 1.00 | 22.55 |
| ATOM | 1450 | O | HIS | A | 198 | -1.523 | -1.964 | 17.329 | 1.00 | 24.31 |
| ATOM | 1451 | N | ARG | A | 199 | 0.343 | -0.980 | 18.167 | 1.00 | 20.23 |
| ATOM | 1452 | CA | ARG | A | 199 | 0.416 | 0.062 | 17.138 | 1.00 | 18.98 |
| ATOM | 1453 | CB | ARG | A | 199 | -0.341 | 1.295 | 17.651 | 1.00 | 17.45 |
| ATOM | 1454 | CG | ARG | A | 199 | -0.566 | 2.347 | 16.560 | 1.00 | 19.76 |
| ATOM | 1455 | CD | ARG | A | 199 | -1.165 | 3.621 | 17.129 | 1.00 | 19.36 |

FIGURE 280

| | | | | | | | | |
|---|---|---|---|---|---|---|---|---|
| ATOM | 1456 | NE | ARG | A | 199 | -2.420 | 3.326 | 17.842 | 1.00 | 18.91 |
| ATOM | 1457 | CZ | ARG | A | 199 | -2.944 | 4.092 | 18.798 | 1.00 | 18.52 |
| ATOM | 1458 | NH1 | ARG | A | 199 | -2.381 | 5.247 | 19.087 | 1.00 | 17.08 |
| ATOM | 1459 | NH2 | ARG | A | 199 | -4.066 | 3.733 | 19.428 | 1.00 | 19.74 |
| ATOM | 1460 | C | ARG | A | 199 | 1.858 | 0.488 | 16.894 | 1.00 | 19.23 |
| ATOM | 1461 | O | ARG | A | 199 | 2.642 | 0.507 | 17.836 | 1.00 | 20.70 |
| ATOM | 1462 | N | LEU | A | 200 | 2.183 | 0.809 | 15.639 | 1.00 | 19.23 |
| ATOM | 1463 | CA | LEU | A | 200 | 3.472 | 1.424 | 15.309 | 1.00 | 21.60 |
| ATOM | 1464 | CB | LEU | A | 200 | 4.021 | 0.867 | 13.984 | 1.00 | 22.49 |
| ATOM | 1465 | CG | LEU | A | 200 | 4.201 | -0.647 | 13.999 | 1.00 | 27.67 |
| ATOM | 1466 | CD1 | LEU | A | 200 | 4.779 | -1.119 | 12.672 | 1.00 | 28.09 |
| ATOM | 1467 | CD2 | LEU | A | 200 | 5.160 | -1.011 | 15.130 | 1.00 | 28.54 |
| ATOM | 1468 | C | LEU | A | 200 | 3.225 | 2.920 | 15.166 | 1.00 | 21.95 |
| ATOM | 1469 | O | LEU | A | 200 | 2.245 | 3.324 | 14.521 | 1.00 | 24.40 |
| ATOM | 1470 | N | ILE | A | 201 | 4.088 | 3.707 | 15.798 | 1.00 | 19.67 |
| ATOM | 1471 | CA | ILE | A | 201 | 4.022 | 5.165 | 15.845 | 1.00 | 22.82 |
| ATOM | 1472 | CB | ILE | A | 201 | 4.095 | 5.679 | 17.309 | 1.00 | 24.19 |
| ATOM | 1473 | CG1 | ILE | A | 201 | 2.877 | 5.227 | 18.090 | 1.00 | 31.22 |
| ATOM | 1474 | CD1 | ILE | A | 201 | 1.753 | 4.981 | 17.178 | 1.00 | 26.82 |
| ATOM | 1475 | CG2 | ILE | A | 201 | 4.104 | 7.245 | 17.358 | 1.00 | 27.78 |
| ATOM | 1476 | C | ILE | A | 201 | 5.295 | 5.667 | 15.190 | 1.00 | 20.99 |
| ATOM | 1477 | O | ILE | A | 201 | 6.374 | 5.155 | 15.492 | 1.00 | 21.91 |
| ATOM | 1478 | N | ARG | A | 202 | 5.216 | 6.709 | 14.376 | 1.00 | 19.22 |
| ATOM | 1479 | CA | ARG | A | 202 | 6.473 | 7.346 | 13.949 | 1.00 | 18.14 |
| ATOM | 1480 | CB | ARG | A | 202 | 6.517 | 7.524 | 12.440 | 1.00 | 19.80 |
| ATOM | 1481 | CG | ARG | A | 202 | 6.696 | 6.213 | 11.693 | 1.00 | 25.47 |
| ATOM | 1482 | CD | ARG | A | 202 | 7.194 | 6.457 | 10.291 | 1.00 | 32.91 |
| ATOM | 1483 | NE | ARG | A | 202 | 7.555 | 5.237 | 9.577 | 1.00 | 38.14 |
| ATOM | 1484 | CZ | ARG | A | 202 | 8.719 | 4.609 | 9.709 | 1.00 | 43.78 |
| ATOM | 1485 | NH1 | ARG | A | 202 | 9.646 | 5.051 | 10.552 | 1.00 | 42.73 |
| ATOM | 1486 | NH2 | ARG | A | 202 | 8.964 | 3.520 | 8.994 | 1.00 | 45.94 |
| ATOM | 1487 | C | ARG | A | 202 | 6.600 | 8.705 | 14.639 | 1.00 | 18.39 |
| ATOM | 1488 | O | ARG | A | 202 | 5.591 | 9.334 | 14.917 | 1.00 | 19.31 |
| ATOM | 1489 | N | HIS | A | 203 | 7.829 | 9.072 | 14.982 | 1.00 | 17.24 |
| ATOM | 1490 | CA | HIS | A | 203 | 8.142 | 10.319 | 15.694 | 1.00 | 16.77 |
| ATOM | 1491 | CB | HIS | A | 203 | 8.729 | 9.943 | 17.068 | 1.00 | 16.74 |
| ATOM | 1492 | CG | HIS | A | 203 | 8.980 | 11.095 | 17.996 | 1.00 | 17.60 |
| ATOM | 1493 | ND1 | HIS | A | 203 | 10.173 | 11.794 | 18.011 | 1.00 | 18.12 |
| ATOM | 1494 | CE1 | HIS | A | 203 | 10.133 | 12.706 | 18.970 | 1.00 | 17.49 |
| ATOM | 1495 | NE2 | HIS | A | 203 | 8.946 | 12.647 | 19.552 | 1.00 | 17.63 |
| ATOM | 1496 | CD2 | HIS | A | 203 | 8.221 | 11.629 | 18.985 | 1.00 | 18.26 |
| ATOM | 1497 | C | HIS | A | 203 | 9.178 | 11.090 | 14.880 | 1.00 | 16.45 |
| ATOM | 1498 | O | HIS | A | 203 | 10.257 | 10.574 | 14.537 | 1.00 | 16.92 |
| ATOM | 1499 | N | PHE | A | 204 | 8.811 | 12.326 | 14.542 | 1.00 | 17.22 |
| ATOM | 1500 | CA | PHE | A | 204 | 9.613 | 13.165 | 13.656 | 1.00 | 17.63 |
| ATOM | 1501 | CB | PHE | A | 204 | 8.780 | 13.662 | 12.478 | 1.00 | 17.15 |
| ATOM | 1502 | CG | PHE | A | 204 | 8.211 | 12.569 | 11.663 | 1.00 | 19.02 |
| ATOM | 1503 | CD1 | PHE | A | 204 | 6.914 | 12.146 | 11.891 | 1.00 | 17.04 |
| ATOM | 1504 | CE1 | PHE | A | 204 | 6.350 | 11.116 | 11.141 | 1.00 | 18.50 |
| ATOM | 1505 | CZ | PHE | A | 204 | 7.075 | 10.508 | 10.152 | 1.00 | 21.34 |
| ATOM | 1506 | CE2 | PHE | A | 204 | 8.386 | 10.932 | 9.889 | 1.00 | 22.09 |
| ATOM | 1507 | CD2 | PHE | A | 204 | 8.952 | 11.967 | 10.652 | 1.00 | 20.96 |

FIGURE 281

| | | | | | | | | |
|---|---|---|---|---|---|---|---|---|
| ATOM | 1508 | C | PHE | A | 204 | 10.142 | 14.333 | 14.466 | 1.00 | 18.46 |
| ATOM | 1509 | O | PHE | A | 204 | 9.382 | 15.198 | 14.850 | 1.00 | 19.13 |
| ATOM | 1510 | N | HIS | A | 205 | 11.448 | 14.343 | 14.733 | 1.00 | 19.90 |
| ATOM | 1511 | CA | HIS | A | 205 | 12.021 | 15.321 | 15.644 | 1.00 | 19.54 |
| ATOM | 1512 | CB | HIS | A | 205 | 12.825 | 14.610 | 16.716 | 1.00 | 21.35 |
| ATOM | 1513 | CG | HIS | A | 205 | 13.401 | 15.519 | 17.747 | 1.00 | 19.20 |
| ATOM | 1514 | ND1 | HIS | A | 205 | 14.407 | 15.127 | 18.610 | 1.00 | 24.56 |
| ATOM | 1515 | CE1 | HIS | A | 205 | 14.724 | 16.142 | 19.394 | 1.00 | 21.30 |
| ATOM | 1516 | NE2 | HIS | A | 205 | 13.962 | 17.173 | 19.071 | 1.00 | 21.10 |
| ATOM | 1517 | CD2 | HIS | A | 205 | 13.130 | 16.813 | 18.036 | 1.00 | 19.44 |
| ATOM | 1518 | C | HIS | A | 205 | 12.960 | 16.220 | 14.846 | 1.00 | 19.88 |
| ATOM | 1519 | O | HIS | A | 205 | 14.049 | 15.775 | 14.443 | 1.00 | 18.91 |
| ATOM | 1520 | N | TYR | A | 206 | 12.504 | 17.456 | 14.670 | 1.00 | 18.79 |
| ATOM | 1521 | CA | TYR | A | 206 | 13.205 | 18.483 | 13.897 | 1.00 | 18.49 |
| ATOM | 1522 | CB | TYR | A | 206 | 12.172 | 19.409 | 13.287 | 1.00 | 19.17 |
| ATOM | 1523 | CG | TYR | A | 206 | 12.754 | 20.435 | 12.354 | 1.00 | 19.28 |
| ATOM | 1524 | CD1 | TYR | A | 206 | 13.004 | 20.115 | 11.023 | 1.00 | 16.50 |
| ATOM | 1525 | CE1 | TYR | A | 206 | 13.540 | 21.052 | 10.141 | 1.00 | 17.88 |
| ATOM | 1526 | CZ | TYR | A | 206 | 13.831 | 22.327 | 10.588 | 1.00 | 22.43 |
| ATOM | 1527 | OH | TYR | A | 206 | 14.365 | 23.270 | 9.715 | 1.00 | 25.31 |
| ATOM | 1528 | CE2 | TYR | A | 206 | 13.594 | 22.666 | 11.904 | 1.00 | 23.08 |
| ATOM | 1529 | CD2 | TYR | A | 206 | 13.061 | 21.711 | 12.794 | 1.00 | 23.33 |
| ATOM | 1530 | C | TYR | A | 206 | 14.064 | 19.229 | 14.900 | 1.00 | 20.26 |
| ATOM | 1531 | O | TYR | A | 206 | 13.578 | 19.732 | 15.911 | 1.00 | 19.79 |
| ATOM | 1532 | N | THR | A | 207 | 15.368 | 19.199 | 14.661 | 1.00 | 21.64 |
| ATOM | 1533 | CA | THR | A | 207 | 16.318 | 19.479 | 15.717 | 1.00 | 23.75 |
| ATOM | 1534 | CB | THR | A | 207 | 17.403 | 18.361 | 15.771 | 1.00 | 23.14 |
| ATOM | 1535 | OG1 | THR | A | 207 | 17.900 | 18.102 | 14.449 | 1.00 | 24.97 |
| ATOM | 1536 | CG2 | THR | A | 207 | 16.813 | 17.010 | 16.198 | 1.00 | 25.49 |
| ATOM | 1537 | C | THR | A | 207 | 17.005 | 20.826 | 15.501 | 1.00 | 24.68 |
| ATOM | 1538 | O | THR | A | 207 | 17.894 | 21.182 | 16.291 | 1.00 | 26.32 |
| ATOM | 1539 | N | VAL | A | 208 | 16.588 | 21.554 | 14.473 | 1.00 | 24.44 |
| ATOM | 1540 | CA | VAL | A | 208 | 17.279 | 22.769 | 14.010 | 1.00 | 26.67 |
| ATOM | 1541 | CB | VAL | A | 208 | 17.996 | 22.597 | 12.627 | 1.00 | 24.93 |
| ATOM | 1542 | CG1 | VAL | A | 208 | 19.123 | 21.595 | 12.712 | 1.00 | 27.87 |
| ATOM | 1543 | CG2 | VAL | A | 208 | 17.022 | 22.243 | 11.490 | 1.00 | 27.01 |
| ATOM | 1544 | C | VAL | A | 208 | 16.420 | 24.039 | 14.032 | 1.00 | 26.34 |
| ATOM | 1545 | O | VAL | A | 208 | 16.647 | 24.972 | 13.252 | 1.00 | 29.43 |
| ATOM | 1546 | N | TRP | A | 209 | 15.419 | 24.083 | 14.903 | 1.00 | 25.54 |
| ATOM | 1547 | CA | TRP | A | 209 | 14.534 | 25.244 | 14.967 | 1.00 | 24.37 |
| ATOM | 1548 | CB | TRP | A | 209 | 13.080 | 24.768 | 14.863 | 1.00 | 25.75 |
| ATOM | 1549 | CG | TRP | A | 209 | 12.082 | 25.820 | 14.491 | 1.00 | 19.87 |
| ATOM | 1550 | CD1 | TRP | A | 209 | 12.153 | 27.174 | 14.694 | 1.00 | 22.45 |
| ATOM | 1551 | NE1 | TRP | A | 209 | 11.034 | 27.786 | 14.183 | 1.00 | 19.81 |
| ATOM | 1552 | CE2 | TRP | A | 209 | 10.202 | 26.822 | 13.663 | 1.00 | 25.00 |
| ATOM | 1553 | CD2 | TRP | A | 209 | 10.834 | 25.575 | 13.847 | 1.00 | 22.65 |
| ATOM | 1554 | CE3 | TRP | A | 209 | 10.185 | 24.414 | 13.399 | 1.00 | 23.01 |
| ATOM | 1555 | CZ3 | TRP | A | 209 | 8.951 | 24.531 | 12.793 | 1.00 | 19.01 |
| ATOM | 1556 | CH2 | TRP | A | 209 | 8.354 | 25.789 | 12.609 | 1.00 | 24.83 |
| ATOM | 1557 | CZ2 | TRP | A | 209 | 8.950 | 26.940 | 13.068 | 1.00 | 22.36 |
| ATOM | 1558 | C | TRP | A | 209 | 14.678 | 26.021 | 16.270 | 1.00 | 27.04 |
| ATOM | 1559 | O | TRP | A | 209 | 14.201 | 25.567 | 17.313 | 1.00 | 25.79 |

FIGURE 282

| ATOM | 1560 | N   | PRO | A | 210 | 15.303 | 27.198 | 16.230 | 1.00 | 28.07 |
| ATOM | 1561 | CA  | PRO | A | 210 | 15.452 | 28.000 | 17.454 | 1.00 | 28.03 |
| ATOM | 1562 | CB  | PRO | A | 210 | 16.386 | 29.140 | 17.022 | 1.00 | 29.50 |
| ATOM | 1563 | CG  | PRO | A | 210 | 16.944 | 28.740 | 15.657 | 1.00 | 31.17 |
| ATOM | 1564 | CD  | PRO | A | 210 | 15.880 | 27.869 | 15.050 | 1.00 | 27.52 |
| ATOM | 1565 | C   | PRO | A | 210 | 14.111 | 28.519 | 17.998 | 1.00 | 28.48 |
| ATOM | 1566 | O   | PRO | A | 210 | 13.268 | 28.944 | 17.216 | 1.00 | 28.98 |
| ATOM | 1567 | N   | ASP | A | 211 | 13.932 | 28.464 | 19.319 | 1.00 | 28.19 |
| ATOM | 1568 | CA  | ASP | A | 211 | 12.736 | 28.971 | 19.993 | 1.00 | 26.86 |
| ATOM | 1569 | CB  | ASP | A | 211 | 12.808 | 28.792 | 21.508 | 1.00 | 27.24 |
| ATOM | 1570 | CG  | ASP | A | 211 | 11.451 | 28.935 | 22.177 | 1.00 | 26.06 |
| ATOM | 1571 | OD1 | ASP | A | 211 | 10.461 | 29.156 | 21.452 | 1.00 | 26.31 |
| ATOM | 1572 | OD2 | ASP | A | 211 | 11.288 | 28.849 | 23.413 | 1.00 | 29.60 |
| ATOM | 1573 | C   | ASP | A | 211 | 12.585 | 30.448 | 19.661 | 1.00 | 28.25 |
| ATOM | 1574 | O   | ASP | A | 211 | 13.577 | 31.180 | 19.556 | 1.00 | 26.45 |
| ATOM | 1575 | N   | HIS | A | 212 | 11.348 | 30.872 | 19.435 | 1.00 | 25.98 |
| ATOM | 1576 | CA  | HIS | A | 212 | 11.107 | 32.260 | 19.072 | 1.00 | 28.34 |
| ATOM | 1577 | CB  | HIS | A | 212 | 11.743 | 33.153 | 20.145 | 1.00 | 29.66 |
| ATOM | 1578 | CG  | HIS | A | 212 | 11.094 | 34.492 | 20.283 | 1.00 | 36.64 |
| ATOM | 1579 | ND1 | HIS | A | 212 |  9.878 | 34.669 | 20.908 | 1.00 | 42.47 |
| ATOM | 1580 | CE1 | HIS | A | 212 |  9.553 | 35.951 | 20.875 | 1.00 | 42.76 |
| ATOM | 1581 | NE2 | HIS | A | 212 | 10.521 | 36.612 | 20.265 | 1.00 | 42.04 |
| ATOM | 1582 | CD2 | HIS | A | 212 | 11.501 | 35.724 | 19.892 | 1.00 | 41.28 |
| ATOM | 1583 | C   | HIS | A | 212 | 11.611 | 32.640 | 17.680 | 1.00 | 28.91 |
| ATOM | 1584 | O   | HIS | A | 212 | 11.494 | 33.799 | 17.275 | 1.00 | 30.92 |
| ATOM | 1585 | N   | GLY | A | 213 | 12.144 | 31.676 | 16.936 | 1.00 | 27.80 |
| ATOM | 1586 | CA  | GLY | A | 213 | 12.751 | 31.971 | 15.650 | 1.00 | 25.99 |
| ATOM | 1587 | C   | GLY | A | 213 | 12.192 | 31.153 | 14.511 | 1.00 | 26.04 |
| ATOM | 1588 | O   | GLY | A | 213 | 11.068 | 30.640 | 14.565 | 1.00 | 24.20 |
| ATOM | 1589 | N   | VAL | A | 214 | 13.012 | 31.066 | 13.470 | 1.00 | 26.25 |
| ATOM | 1590 | CA  | VAL | A | 214 | 12.724 | 30.274 | 12.296 | 1.00 | 26.25 |
| ATOM | 1591 | CB  | VAL | A | 214 | 12.213 | 31.170 | 11.158 | 1.00 | 27.10 |
| ATOM | 1592 | CG1 | VAL | A | 214 | 11.042 | 32.016 | 11.659 | 1.00 | 27.24 |
| ATOM | 1593 | CG2 | VAL | A | 214 | 13.347 | 32.040 | 10.628 | 1.00 | 28.86 |
| ATOM | 1594 | C   | VAL | A | 214 | 13.949 | 29.498 | 11.855 | 1.00 | 24.52 |
| ATOM | 1595 | O   | VAL | A | 214 | 15.095 | 29.866 | 12.167 | 1.00 | 24.97 |
| ATOM | 1596 | N   | PRO | A | 215 | 13.711 | 28.392 | 11.152 | 1.00 | 25.64 |
| ATOM | 1597 | CA  | PRO | A | 215 | 14.793 | 27.622 | 10.526 | 1.00 | 25.48 |
| ATOM | 1598 | CB  | PRO | A | 215 | 14.042 | 26.573 |  9.706 | 1.00 | 26.92 |
| ATOM | 1599 | CG  | PRO | A | 215 | 12.732 | 26.418 | 10.434 | 1.00 | 26.03 |
| ATOM | 1600 | CD  | PRO | A | 215 | 12.380 | 27.805 | 10.901 | 1.00 | 24.12 |
| ATOM | 1601 | C   | PRO | A | 215 | 15.609 | 28.518 |  9.612 | 1.00 | 27.43 |
| ATOM | 1602 | O   | PRO | A | 215 | 15.121 | 29.554 |  9.158 | 1.00 | 27.22 |
| ATOM | 1603 | N   | GLU | A | 216 | 16.841 | 28.111 |  9.315 | 1.00 | 28.05 |
| ATOM | 1604 | CA  | GLU | A | 216 | 17.721 | 28.985 |  8.553 | 1.00 | 28.65 |
| ATOM | 1605 | CB  | GLU | A | 216 | 19.161 | 28.486 |  8.661 | 1.00 | 30.42 |
| ATOM | 1606 | CG  | GLU | A | 216 | 19.771 | 28.747 | 10.023 | 1.00 | 35.56 |
| ATOM | 1607 | CD  | GLU | A | 216 | 21.219 | 29.169 |  9.904 | 1.00 | 42.95 |
| ATOM | 1608 | OE1 | GLU | A | 216 | 21.795 | 28.954 |  8.814 | 1.00 | 48.84 |
| ATOM | 1609 | OE2 | GLU | A | 216 | 21.765 | 29.715 | 10.889 | 1.00 | 45.41 |
| ATOM | 1610 | C   | GLU | A | 216 | 17.315 | 29.114 |  7.087 | 1.00 | 27.95 |
| ATOM | 1611 | O   | GLU | A | 216 | 17.649 | 30.113 |  6.448 | 1.00 | 27.93 |

FIGURE 283

| | | | | | | | | | |
|---|---|---|---|---|---|---|---|---|---|
| ATOM | 1612 | N   | THR | A | 217 | 16.652 | 28.099 | 6.537 | 1.00 25.57 |
| ATOM | 1613 | CA  | THR | A | 217 | 16.183 | 28.168 | 5.158 | 1.00 24.50 |
| ATOM | 1614 | CB  | THR | A | 217 | 16.913 | 27.146 | 4.270 | 1.00 23.44 |
| ATOM | 1615 | OG1 | THR | A | 217 | 16.712 | 25.831 | 4.821 | 1.00 23.33 |
| ATOM | 1616 | CG2 | THR | A | 217 | 18.430 | 27.370 | 4.323 | 1.00 25.77 |
| ATOM | 1617 | C   | THR | A | 217 | 14.697 | 27.816 | 5.082 | 1.00 22.97 |
| ATOM | 1618 | O   | THR | A | 217 | 14.161 | 27.138 | 5.964 | 1.00 23.20 |
| ATOM | 1619 | N   | THR | A | 218 | 14.037 | 28.246 | 4.013 | 1.00 22.43 |
| ATOM | 1620 | CA  | THR | A | 218 | 12.685 | 27.753 | 3.753 | 1.00 21.86 |
| ATOM | 1621 | CB  | THR | A | 218 | 12.003 | 28.563 | 2.637 | 1.00 22.40 |
| ATOM | 1622 | OG1 | THR | A | 218 | 12.807 | 28.503 | 1.448 | 1.00 23.58 |
| ATOM | 1623 | CG2 | THR | A | 218 | 11.911 | 30.047 | 3.006 | 1.00 25.57 |
| ATOM | 1624 | C   | THR | A | 218 | 12.759 | 26.291 | 3.315 | 1.00 21.64 |
| ATOM | 1625 | O   | THR | A | 218 | 11.897 | 25.483 | 3.667 | 1.00 21.31 |
| ATOM | 1626 | N   | GLN | A | 219 | 13.802 | 25.938 | 2.562 | 1.00 21.89 |
| ATOM | 1627 | CA  | GLN | A | 219 | 13.850 | 24.607 | 1.967 | 1.00 22.98 |
| ATOM | 1628 | CB  | GLN | A | 219 | 15.019 | 24.424 | 0.995 | 1.00 25.47 |
| ATOM | 1629 | CG  | GLN | A | 219 | 16.336 | 23.998 | 1.575 | 1.00 35.80 |
| ATOM | 1630 | CD  | GLN | A | 219 | 16.446 | 22.483 | 1.671 | 1.00 42.19 |
| ATOM | 1631 | OE1 | GLN | A | 219 | 17.144 | 21.962 | 2.541 | 1.00 48.46 |
| ATOM | 1632 | NE2 | GLN | A | 219 | 15.751 | 21.777 | 0.785 | 1.00 48.31 |
| ATOM | 1633 | C   | GLN | A | 219 | 13.831 | 23.550 | 3.060 | 1.00 22.41 |
| ATOM | 1634 | O   | GLN | A | 219 | 13.184 | 22.523 | 2.872 | 1.00 21.59 |
| ATOM | 1635 | N   | SER | A | 220 | 14.509 | 23.809 | 4.180 | 1.00 22.02 |
| ATOM | 1636 | CA  | SER | A | 220 | 14.554 | 22.828 | 5.260 | 1.00 21.83 |
| ATOM | 1637 | CB  | SER | A | 220 | 15.367 | 23.348 | 6.442 | 1.00 24.24 |
| ATOM | 1638 | OG  | SER | A | 220 | 15.366 | 22.396 | 7.489 | 1.00 28.06 |
| ATOM | 1639 | C   | SER | A | 220 | 13.157 | 22.477 | 5.785 | 1.00 21.60 |
| ATOM | 1640 | O   | SER | A | 220 | 12.768 | 21.309 | 5.802 | 1.00 20.80 |
| ATOM | 1641 | N   | LEU | A | 221 | 12.441 | 23.489 | 6.251 | 1.00 18.57 |
| ATOM | 1642 | CA  | LEU | A | 221 | 11.111 | 23.186 | 6.787 | 1.00 21.03 |
| ATOM | 1643 | CB  | LEU | A | 221 | 10.579 | 24.281 | 7.708 | 1.00 22.58 |
| ATOM | 1644 | CG  | LEU | A | 221 | 9.389  | 23.815 | 8.562 | 1.00 22.37 |
| ATOM | 1645 | CD1 | LEU | A | 221 | 9.934  | 22.943 | 9.698 | 1.00 22.41 |
| ATOM | 1646 | CD2 | LEU | A | 221 | 8.700  | 25.049 | 9.117 | 1.00 21.13 |
| ATOM | 1647 | C   | LEU | A | 221 | 10.114 | 22.722 | 5.737 | 1.00 21.34 |
| ATOM | 1648 | O   | LEU | A | 221 | 9.317  | 21.822 | 6.010 | 1.00 19.35 |
| ATOM | 1649 | N   | ILE | A | 222 | 10.165 | 23.274 | 4.524 | 1.00 17.11 |
| ATOM | 1650 | CA  | ILE | A | 222 | 9.335  | 22.740 | 3.456 | 1.00 17.94 |
| ATOM | 1651 | CB  | ILE | A | 222 | 9.569  | 23.524 | 2.130 | 1.00 17.12 |
| ATOM | 1652 | CG1 | ILE | A | 222 | 9.065  | 24.974 | 2.276 | 1.00 19.50 |
| ATOM | 1653 | CD1 | ILE | A | 222 | 9.548  | 25.933 | 1.171 | 1.00 19.49 |
| ATOM | 1654 | CG2 | ILE | A | 222 | 8.921  | 22.783 | 0.968 | 1.00 21.07 |
| ATOM | 1655 | C   | ILE | A | 222 | 9.601  | 21.260 | 3.217 | 1.00 19.20 |
| ATOM | 1656 | O   | ILE | A | 222 | 8.673  | 20.485 | 3.025 | 1.00 19.95 |
| ATOM | 1657 | N   | GLN | A | 223 | 10.869 | 20.854 | 3.207 | 1.00 16.23 |
| ATOM | 1658 | CA  | GLN | A | 223 | 11.123 | 19.449 | 2.988 | 1.00 18.60 |
| ATOM | 1659 | CB  | GLN | A | 223 | 12.616 | 19.228 | 2.715 | 1.00 19.15 |
| ATOM | 1660 | CG  | GLN | A | 223 | 12.941 | 17.766 | 2.467 | 1.00 22.79 |
| ATOM | 1661 | CD  | GLN | A | 223 | 12.643 | 17.290 | 1.061 | 1.00 33.15 |
| ATOM | 1662 | OE1 | GLN | A | 223 | 12.155 | 18.051 | 0.211 | 1.00 33.66 |
| ATOM | 1663 | NE2 | GLN | A | 223 | 12.917 | 16.006 | 0.817 | 1.00 35.76 |

FIGURE 284

```
ATOM  1664  C    GLN A 223    10.657  18.623   4.188  1.00 16.93
ATOM  1665  O    GLN A 223    10.199  17.502   3.988  1.00 18.36
ATOM  1666  N    PHE A 224    10.797  19.161   5.401  1.00 15.46
ATOM  1667  CA   PHE A 224    10.363  18.423   6.587  1.00 15.62
ATOM  1668  CB   PHE A 224    10.706  19.198   7.848  1.00 17.10
ATOM  1669  CG   PHE A 224    10.337  18.487   9.120  1.00 16.49
ATOM  1670  CD1  PHE A 224    10.836  17.215   9.398  1.00 17.51
ATOM  1671  CE1  PHE A 224    10.531  16.576  10.616  1.00 17.07
ATOM  1672  CZ   PHE A 224     9.717  17.205  11.544  1.00 16.55
ATOM  1673  CE2  PHE A 224     9.212  18.492  11.279  1.00 18.07
ATOM  1674  CD2  PHE A 224     9.544  19.125  10.054  1.00 19.46
ATOM  1675  C    PHE A 224     8.855  18.199   6.531  1.00 16.89
ATOM  1676  O    PHE A 224     8.380  17.078   6.751  1.00 16.66
ATOM  1677  N    VAL A 225     8.122  19.270   6.265  1.00 17.58
ATOM  1678  CA   VAL A 225     6.654  19.197   6.213  1.00 18.48
ATOM  1679  CB   VAL A 225     6.084  20.603   5.951  1.00 19.47
ATOM  1680  CG1  VAL A 225     4.635  20.522   5.473  1.00 20.27
ATOM  1681  CG2  VAL A 225     6.211  21.475   7.199  1.00 17.11
ATOM  1682  C    VAL A 225     6.241  18.203   5.122  1.00 19.13
ATOM  1683  O    VAL A 225     5.402  17.311   5.312  1.00 21.63
ATOM  1684  N    ARG A 226     6.829  18.331   3.941  1.00 19.30
ATOM  1685  CA   ARG A 226     6.514  17.393   2.871  1.00 20.41
ATOM  1686  CB   ARG A 226     7.276  17.776   1.594  1.00 20.66
ATOM  1687  CG   ARG A 226     6.656  18.990   0.916  1.00 22.30
ATOM  1688  CD   ARG A 226     7.410  19.483  -0.302  1.00 24.61
ATOM  1689  NE   ARG A 226     6.694  20.558  -0.983  1.00 24.83
ATOM  1690  CZ   ARG A 226     7.223  21.308  -1.948  1.00 31.14
ATOM  1691  NH1  ARG A 226     8.489  21.146  -2.306  1.00 30.48
ATOM  1692  NH2  ARG A 226     6.500  22.253  -2.526  1.00 34.90
ATOM  1693  C    ARG A 226     6.797  15.932   3.234  1.00 20.34
ATOM  1694  O    ARG A 226     6.060  15.004   2.879  1.00 19.67
ATOM  1695  N    THR A 227     7.910  15.717   3.920  1.00 19.65
ATOM  1696  CA   THR A 227     8.323  14.388   4.338  1.00 20.52
ATOM  1697  CB   THR A 227     9.715  14.485   4.977  1.00 22.22
ATOM  1698  OG1  THR A 227    10.673  14.679   3.930  1.00 22.33
ATOM  1699  CG2  THR A 227    10.110  13.143   5.586  1.00 24.52
ATOM  1700  C    THR A 227     7.310  13.786   5.339  1.00 20.30
ATOM  1701  O    THR A 227     6.886  12.642   5.191  1.00 20.93
ATOM  1702  N    VAL A 228     6.918  14.576   6.335  1.00 19.24
ATOM  1703  CA   VAL A 228     5.954  14.152   7.348  1.00 19.59
ATOM  1704  CB   VAL A 228     5.778  15.216   8.430  1.00 19.58
ATOM  1705  CG1  VAL A 228     4.631  14.832   9.353  1.00 20.61
ATOM  1706  CG2  VAL A 228     7.077  15.408   9.206  1.00 19.73
ATOM  1707  C    VAL A 228     4.609  13.877   6.690  1.00 21.77
ATOM  1708  O    VAL A 228     4.013  12.844   6.938  1.00 21.18
ATOM  1709  N    ARG A 229     4.183  14.774   5.805  1.00 22.98
ATOM  1710  CA   ARG A 229     2.866  14.626   5.179  1.00 25.81
ATOM  1711  CB   ARG A 229     2.546  15.904   4.402  1.00 23.29
ATOM  1712  CG   ARG A 229     1.423  15.881   3.384  1.00 28.30
ATOM  1713  CD   ARG A 229     0.053  15.877   3.972  1.00 30.57
ATOM  1714  NE   ARG A 229    -0.051  16.615   5.222  1.00 30.38
ATOM  1715  CZ   ARG A 229    -0.925  16.290   6.160  1.00 29.65
```

FIGURE 285

| ATOM | 1716 | NH1 | ARG | A | 229 | -1.763 | 15.279 | 5.941 | 1.00 | 32.05 |
|------|------|-----|-----|---|-----|--------|--------|-------|------|-------|
| ATOM | 1717 | NH2 | ARG | A | 229 | -0.987 | 16.980 | 7.291 | 1.00 | 29.06 |
| ATOM | 1718 | C | ARG | A | 229 | 2.879 | 13.378 | 4.301 | 1.00 | 26.73 |
| ATOM | 1719 | O | ARG | A | 229 | 1.879 | 12.653 | 4.242 | 1.00 | 27.86 |
| ATOM | 1720 | N | ASP | A | 230 | 4.015 | 13.108 | 3.658 | 1.00 | 26.22 |
| ATOM | 1721 | CA | ASP | A | 230 | 4.251 | 11.866 | 2.928 | 1.00 | 28.24 |
| ATOM | 1722 | CB | ASP | A | 230 | 5.621 | 11.877 | 2.251 | 1.00 | 28.67 |
| ATOM | 1723 | CG | ASP | A | 230 | 5.654 | 12.720 | 0.982 | 1.00 | 34.01 |
| ATOM | 1724 | OD1 | ASP | A | 230 | 4.609 | 13.162 | 0.469 | 1.00 | 39.53 |
| ATOM | 1725 | OD2 | ASP | A | 230 | 6.727 | 13.005 | 0.420 | 1.00 | 41.90 |
| ATOM | 1726 | C | ASP | A | 230 | 4.071 | 10.598 | 3.770 | 1.00 | 29.04 |
| ATOM | 1727 | O | ASP | A | 230 | 3.401 | 9.645 | 3.350 | 1.00 | 29.94 |
| ATOM | 1728 | N | TYR | A | 231 | 4.625 | 10.592 | 4.979 | 1.00 | 25.95 |
| ATOM | 1729 | CA | TYR | A | 231 | 4.433 | 9.452 | 5.871 | 1.00 | 26.50 |
| ATOM | 1730 | CB | TYR | A | 231 | 5.319 | 9.550 | 7.113 | 1.00 | 26.14 |
| ATOM | 1731 | CG | TYR | A | 231 | 6.748 | 9.078 | 6.927 | 1.00 | 23.97 |
| ATOM | 1732 | CD1 | TYR | A | 231 | 7.774 | 9.978 | 6.647 | 1.00 | 19.78 |
| ATOM | 1733 | CE1 | TYR | A | 231 | 9.081 | 9.547 | 6.522 | 1.00 | 22.19 |
| ATOM | 1734 | CZ | TYR | A | 231 | 9.390 | 8.211 | 6.654 | 1.00 | 23.00 |
| ATOM | 1735 | OH | TYR | A | 231 | 10.701 | 7.787 | 6.513 | 1.00 | 28.03 |
| ATOM | 1736 | CE2 | TYR | A | 231 | 8.401 | 7.304 | 6.947 | 1.00 | 27.25 |
| ATOM | 1737 | CD2 | TYR | A | 231 | 7.086 | 7.736 | 7.088 | 1.00 | 25.16 |
| ATOM | 1738 | C | TYR | A | 231 | 2.970 | 9.323 | 6.291 | 1.00 | 27.31 |
| ATOM | 1739 | O | TYR | A | 231 | 2.446 | 8.209 | 6.297 | 1.00 | 28.55 |
| ATOM | 1740 | N | ILE | A | 232 | 2.347 | 10.443 | 6.652 | 1.00 | 26.87 |
| ATOM | 1741 | CA | ILE | A | 232 | 0.914 | 10.502 | 6.996 | 1.00 | 27.98 |
| ATOM | 1742 | CB | ILE | A | 232 | 0.491 | 11.959 | 7.360 | 1.00 | 25.62 |
| ATOM | 1743 | CG1 | ILE | A | 232 | 1.038 | 12.361 | 8.727 | 1.00 | 26.35 |
| ATOM | 1744 | CD1 | ILE | A | 232 | 0.938 | 13.838 | 8.996 | 1.00 | 27.73 |
| ATOM | 1745 | CG2 | ILE | A | 232 | -1.058 | 12.159 | 7.424 | 1.00 | 25.67 |
| ATOM | 1746 | C | ILE | A | 232 | 0.046 | 9.935 | 5.875 | 1.00 | 32.06 |
| ATOM | 1747 | O | ILE | A | 232 | -0.767 | 9.022 | 6.107 | 1.00 | 33.57 |
| ATOM | 1748 | N | ASN | A | 233 | 0.245 | 10.451 | 4.663 | 1.00 | 33.34 |
| ATOM | 1749 | CA | ASN | A | 233 | -0.580 | 10.101 | 3.509 | 1.00 | 37.27 |
| ATOM | 1750 | CB | ASN | A | 233 | -0.320 | 11.037 | 2.313 | 1.00 | 36.54 |
| ATOM | 1751 | CG | ASN | A | 233 | -0.932 | 12.425 | 2.480 | 1.00 | 38.15 |
| ATOM | 1752 | OD1 | ASN | A | 233 | -1.648 | 12.712 | 3.442 | 1.00 | 42.42 |
| ATOM | 1753 | ND2 | ASN | A | 233 | -0.630 | 13.309 | 1.533 | 1.00 | 37.50 |
| ATOM | 1754 | C | ASN | A | 233 | -0.429 | 8.635 | 3.090 | 1.00 | 39.12 |
| ATOM | 1755 | O | ASN | A | 233 | -1.332 | 8.073 | 2.463 | 1.00 | 41.73 |
| ATOM | 1756 | N | ARG | A | 234 | 0.690 | 8.001 | 3.431 | 1.00 | 40.44 |
| ATOM | 1757 | CA | ARG | A | 234 | 0.962 | 6.653 | 2.945 | 1.00 | 42.23 |
| ATOM | 1758 | CB | ARG | A | 234 | 2.455 | 6.462 | 2.658 | 1.00 | 43.61 |
| ATOM | 1759 | CG | ARG | A | 234 | 2.949 | 7.205 | 1.408 | 1.00 | 43.04 |
| ATOM | 1760 | CD | ARG | A | 234 | 4.330 | 6.793 | 0.906 | 1.00 | 48.69 |
| ATOM | 1761 | NE | ARG | A | 234 | 5.341 | 6.796 | 1.963 | 1.00 | 51.23 |
| ATOM | 1762 | CZ | ARG | A | 234 | 6.283 | 7.724 | 2.115 | 1.00 | 54.19 |
| ATOM | 1763 | NH1 | ARG | A | 234 | 6.365 | 8.748 | 1.272 | 1.00 | 52.70 |
| ATOM | 1764 | NH2 | ARG | A | 234 | 7.144 | 7.630 | 3.122 | 1.00 | 51.22 |
| ATOM | 1765 | C | ARG | A | 234 | 0.400 | 5.566 | 3.863 | 1.00 | 42.06 |
| ATOM | 1766 | O | ARG | A | 234 | 0.337 | 4.379 | 3.512 | 1.00 | 42.43 |
| ATOM | 1767 | N | SER | A | 235 | -0.055 | 6.003 | 5.031 | 1.00 | 40.54 |

FIGURE 286

| | | | | | | | | | |
|---|---|---|---|---|---|---|---|---|---|
| ATOM | 1768 | CA | SER | A | 235 | -0.488 | 5.108 | 6.087 | 1.00 39.57 |
| ATOM | 1769 | CB | SER | A | 235 | -0.193 | 5.750 | 7.451 | 1.00 39.71 |
| ATOM | 1770 | OG | SER | A | 235 | -1.211 | 5.554 | 8.422 | 1.00 41.17 |
| ATOM | 1771 | C | SER | A | 235 | -1.964 | 4.744 | 5.925 | 1.00 38.09 |
| ATOM | 1772 | O | SER | A | 235 | -2.799 | 5.592 | 5.590 | 1.00 36.22 |
| ATOM | 1773 | N | PRO | A | 236 | -2.278 | 3.477 | 6.177 | 1.00 38.34 |
| ATOM | 1774 | CA | PRO | A | 236 | -3.661 | 2.979 | 6.083 | 1.00 39.35 |
| ATOM | 1775 | CB | PRO | A | 236 | -3.537 | 1.499 | 6.461 | 1.00 40.18 |
| ATOM | 1776 | CG | PRO | A | 236 | -2.214 | 1.375 | 7.150 | 1.00 39.24 |
| ATOM | 1777 | CD | PRO | A | 236 | -1.322 | 2.425 | 6.563 | 1.00 38.58 |
| ATOM | 1778 | C | PRO | A | 236 | -4.678 | 3.691 | 6.987 | 1.00 39.63 |
| ATOM | 1779 | O | PRO | A | 236 | -5.889 | 3.488 | 6.852 | 1.00 42.61 |
| ATOM | 1780 | N | GLY | A | 237 | -4.208 | 4.544 | 7.889 | 1.00 36.88 |
| ATOM | 1781 | CA | GLY | A | 237 | -5.069 | 5.079 | 8.938 | 1.00 34.20 |
| ATOM | 1782 | C | GLY | A | 237 | -4.178 | 5.738 | 9.970 | 1.00 30.76 |
| ATOM | 1783 | O | GLY | A | 237 | -3.532 | 5.037 | 10.733 | 1.00 29.45 |
| ATOM | 1784 | N | ALA | A | 238 | -4.150 | 7.071 | 9.986 | 1.00 28.97 |
| ATOM | 1785 | CA | ALA | A | 238 | -3.119 | 7.844 | 10.698 | 1.00 24.56 |
| ATOM | 1786 | CB | ALA | A | 238 | -2.656 | 9.019 | 9.834 | 1.00 27.03 |
| ATOM | 1787 | C | ALA | A | 238 | -3.564 | 8.342 | 12.077 | 1.00 23.45 |
| ATOM | 1788 | O | ALA | A | 238 | -2.759 | 8.476 | 12.986 | 1.00 21.78 |
| ATOM | 1789 | N | GLY | A | 239 | -4.853 | 8.620 | 12.242 | 1.00 21.70 |
| ATOM | 1790 | CA | GLY | A | 239 | -5.342 | 9.313 | 13.423 | 1.00 21.30 |
| ATOM | 1791 | C | GLY | A | 239 | -4.903 | 10.766 | 13.366 | 1.00 19.24 |
| ATOM | 1792 | O | GLY | A | 239 | -4.282 | 11.186 | 12.388 | 1.00 18.48 |
| ATOM | 1793 | N | PRO | A | 240 | -5.233 | 11.526 | 14.405 | 1.00 20.05 |
| ATOM | 1794 | CA | PRO | A | 240 | -4.740 | 12.907 | 14.530 | 1.00 19.68 |
| ATOM | 1795 | CB | PRO | A | 240 | -5.327 | 13.390 | 15.861 | 1.00 18.80 |
| ATOM | 1796 | CG | PRO | A | 240 | -6.393 | 12.393 | 16.247 | 1.00 21.11 |
| ATOM | 1797 | CD | PRO | A | 240 | -6.041 | 11.103 | 15.562 | 1.00 20.23 |
| ATOM | 1798 | C | PRO | A | 240 | -3.213 | 12.834 | 14.624 | 1.00 18.33 |
| ATOM | 1799 | O | PRO | A | 240 | -2.661 | 11.864 | 15.141 | 1.00 19.27 |
| ATOM | 1800 | N | THR | A | 241 | -2.548 | 13.832 | 14.071 | 1.00 16.60 |
| ATOM | 1801 | CA | THR | A | 241 | -1.090 | 13.930 | 14.185 | 1.00 15.99 |
| ATOM | 1802 | CB | THR | A | 241 | -0.593 | 14.614 | 12.919 | 1.00 15.63 |
| ATOM | 1803 | OG1 | THR | A | 241 | -0.797 | 13.696 | 11.849 | 1.00 17.20 |
| ATOM | 1804 | CG2 | THR | A | 241 | 0.941 | 14.788 | 12.984 | 1.00 15.00 |
| ATOM | 1805 | C | THR | A | 241 | -0.829 | 14.832 | 15.367 | 1.00 16.75 |
| ATOM | 1806 | O | THR | A | 241 | -1.343 | 15.938 | 15.418 | 1.00 17.15 |
| ATOM | 1807 | N | VAL | A | 242 | 0.031 | 14.387 | 16.274 | 1.00 16.56 |
| ATOM | 1808 | CA | VAL | A | 242 | 0.370 | 15.207 | 17.413 | 1.00 15.30 |
| ATOM | 1809 | CB | VAL | A | 242 | 0.777 | 14.315 | 18.586 | 1.00 13.91 |
| ATOM | 1810 | CG1 | VAL | A | 242 | 1.584 | 15.122 | 19.651 | 1.00 17.96 |
| ATOM | 1811 | CG2 | VAL | A | 242 | -0.473 | 13.828 | 19.205 | 1.00 14.74 |
| ATOM | 1812 | C | VAL | A | 242 | 1.537 | 16.089 | 17.002 | 1.00 15.85 |
| ATOM | 1813 | O | VAL | A | 242 | 2.491 | 15.610 | 16.401 | 1.00 17.01 |
| ATOM | 1814 | N | VAL | A | 243 | 1.421 | 17.375 | 17.295 | 1.00 15.52 |
| ATOM | 1815 | CA | VAL | A | 243 | 2.525 | 18.289 | 17.027 | 1.00 15.21 |
| ATOM | 1816 | CB | VAL | A | 243 | 2.223 | 19.311 | 15.915 | 1.00 13.92 |
| ATOM | 1817 | CG1 | VAL | A | 243 | 3.540 | 20.039 | 15.607 | 1.00 15.53 |
| ATOM | 1818 | CG2 | VAL | A | 243 | 1.710 | 18.648 | 14.624 | 1.00 15.61 |
| ATOM | 1819 | C | VAL | A | 243 | 2.848 | 19.042 | 18.309 | 1.00 13.38 |

FIGURE 287

```
ATOM  1820  O    VAL A 243    1.977  19.511  19.006  1.00  15.35
ATOM  1821  N    HIS A 244    4.127  19.115  18.681  1.00  13.84
ATOM  1822  CA   HIS A 244    4.487  19.880  19.875  1.00  13.12
ATOM  1823  CB   HIS A 244    4.399  19.034  21.167  1.00  11.87
ATOM  1824  CG   HIS A 244    5.560  18.115  21.377  1.00  15.41
ATOM  1825  ND1  HIS A 244    6.728  18.524  21.977  1.00  16.81
ATOM  1826  CE1  HIS A 244    7.566  17.503  22.042  1.00  16.27
ATOM  1827  NE2  HIS A 244    6.998  16.461  21.463  1.00  16.52
ATOM  1828  CD2  HIS A 244    5.726  16.808  21.067  1.00  14.38
ATOM  1829  C    HIS A 244    5.856  20.526  19.735  1.00  14.17
ATOM  1830  O    HIS A 244    6.688  20.046  18.970  1.00  16.93
ATOM  1831  N    CYS A 245    6.041  21.611  20.492  1.00  16.57
ATOM  1832  CA   CYS A 245    7.349  22.211  20.652  1.00  17.05
ATOM  1833  CB   CYS A 245    7.396  23.573  19.941  1.00  15.83
ATOM  1834  SG   CYS A 245    5.834  24.486  20.086  1.00  19.56
ATOM  1835  C    CYS A 245    7.521  22.283  22.151  1.00  17.57
ATOM  1836  O    CYS A 245    7.391  21.246  22.839  1.00  17.79
ATOM  1837  N    SER A 246    7.815  23.464  22.693  1.00  18.50
ATOM  1838  CA   SER A 246    7.937  23.554  24.159  1.00  16.87
ATOM  1839  CB   SER A 246    9.020  24.552  24.628  1.00  18.69
ATOM  1840  OG   SER A 246    9.228  24.422  26.031  1.00  18.18
ATOM  1841  C    SER A 246    6.573  23.942  24.722  1.00  17.49
ATOM  1842  O    SER A 246    6.046  23.238  25.580  1.00  17.21
ATOM  1843  N    ALA A 247    6.019  25.049  24.239  1.00  18.04
ATOM  1844  CA   ALA A 247    4.736  25.497  24.749  1.00  19.26
ATOM  1845  CB   ALA A 247    4.710  27.036  24.838  1.00  19.87
ATOM  1846  C    ALA A 247    3.573  25.010  23.903  1.00  17.94
ATOM  1847  O    ALA A 247    2.430  25.177  24.309  1.00  19.75
ATOM  1848  N    GLY A 248    3.848  24.439  22.729  1.00  20.22
ATOM  1849  CA   GLY A 248    2.806  24.174  21.748  1.00  18.63
ATOM  1850  C    GLY A 248    2.132  25.433  21.196  1.00  18.85
ATOM  1851  O    GLY A 248    0.898  25.475  21.017  1.00  19.05
ATOM  1852  N    VAL A 249    2.954  26.427  20.867  1.00  17.12
ATOM  1853  CA   VAL A 249    2.463  27.715  20.358  1.00  16.65
ATOM  1854  CB   VAL A 249    2.562  28.810  21.445  1.00  18.34
ATOM  1855  CG1  VAL A 249    2.075  30.142  20.845  1.00  21.79
ATOM  1856  CG2  VAL A 249    1.744  28.426  22.662  1.00  20.69
ATOM  1857  C    VAL A 249    3.164  28.180  19.070  1.00  17.87
ATOM  1858  O    VAL A 249    2.543  28.251  18.008  1.00  17.85
ATOM  1859  N    GLY A 250    4.453  28.487  19.140  1.00  19.22
ATOM  1860  CA   GLY A 250    5.039  29.253  18.055  1.00  19.94
ATOM  1861  C    GLY A 250    5.491  28.321  16.963  1.00  19.70
ATOM  1862  O    GLY A 250    5.086  28.456  15.808  1.00  19.01
ATOM  1863  N    ARG A 251    6.366  27.389  17.335  1.00  19.14
ATOM  1864  CA   ARG A 251    6.939  26.498  16.347  1.00  19.05
ATOM  1865  CB   ARG A 251    8.195  25.860  16.890  1.00  19.24
ATOM  1866  CG   ARG A 251    9.219  26.952  17.158  1.00  15.81
ATOM  1867  CD   ARG A 251   10.481  26.394  17.775  1.00  16.06
ATOM  1868  NE   ARG A 251   10.226  26.200  19.214  1.00  19.50
ATOM  1869  CZ   ARG A 251   11.094  25.704  20.078  1.00  22.30
ATOM  1870  NH1  ARG A 251   12.290  25.314  19.644  1.00  20.21
ATOM  1871  NH2  ARG A 251   10.758  25.569  21.366  1.00  23.16
```

FIGURE 288

```
ATOM   1872  C    ARG A 251      5.901  25.497  15.876  1.00 18.56
ATOM   1873  O    ARG A 251      5.813  25.250  14.680  1.00 17.43
ATOM   1874  N    THR A 252      5.111  24.941  16.794  1.00 18.19
ATOM   1875  CA   THR A 252      3.982  24.106  16.377  1.00 17.71
ATOM   1876  CB   THR A 252      3.217  23.628  17.607  1.00 17.40
ATOM   1877  OG1ATHR A 252      2.999  24.765  18.450  0.50 23.23
ATOM   1878  OG1BTHR A 252      4.029  22.684  18.306  0.50 13.92
ATOM   1879  CG2ATHR A 252      4.083  22.722  18.434  0.50 15.60
ATOM   1880  CG2BTHR A 252      1.947  22.833  17.252  0.50 10.20
ATOM   1881  C    THR A 252      3.019  24.851  15.484  1.00 17.17
ATOM   1882  O    THR A 252      2.600  24.297  14.475  1.00 15.23
ATOM   1883  N    GLY A 253      2.661  26.092  15.832  1.00 16.60
ATOM   1884  CA   GLY A 253      1.745  26.853  14.990  1.00 16.77
ATOM   1885  C    GLY A 253      2.300  27.075  13.599  1.00 17.58
ATOM   1886  O    GLY A 253      1.597  26.966  12.604  1.00 16.20
ATOM   1887  N    THR A 254      3.608  27.343  13.507  1.00 15.25
ATOM   1888  CA   THR A 254      4.197  27.626  12.216  1.00 14.32
ATOM   1889  CB   THR A 254      5.628  28.249  12.422  1.00 13.48
ATOM   1890  OG1  THR A 254      5.439  29.443  13.202  1.00 18.67
ATOM   1891  CG2  THR A 254      6.190  28.764  11.050  1.00 17.19
ATOM   1892  C    THR A 254      4.262  26.342  11.390  1.00 15.60
ATOM   1893  O    THR A 254      4.052  26.379  10.184  1.00 17.10
ATOM   1894  N    PHE A 255      4.576  25.222  12.032  1.00 15.48
ATOM   1895  CA   PHE A 255      4.640  23.944  11.321  1.00 15.29
ATOM   1896  CB   PHE A 255      5.043  22.832  12.304  1.00 17.14
ATOM   1897  CG   PHE A 255      4.977  21.465  11.674  1.00 17.46
ATOM   1898  CD1  PHE A 255      6.052  21.001  10.959  1.00 20.12
ATOM   1899  CE1  PHE A 255      6.001  19.759  10.330  1.00 19.80
ATOM   1900  CZ   PHE A 255      4.860  19.003  10.351  1.00 15.16
ATOM   1901  CE2  PHE A 255      3.755  19.457  11.013  1.00 16.37
ATOM   1902  CD2  PHE A 255      3.796  20.725  11.662  1.00 15.77
ATOM   1903  C    PHE A 255      3.271  23.608  10.725  1.00 15.30
ATOM   1904  O    PHE A 255      3.145  23.207   9.548  1.00 15.54
ATOM   1905  N    ILE A 256      2.256  23.693  11.568  1.00 13.96
ATOM   1906  CA   ILE A 256      0.914  23.321  11.106  1.00 14.62
ATOM   1907  CB   ILE A 256     -0.077  23.288  12.256  1.00 14.78
ATOM   1908  CG1  ILE A 256      0.284  22.166  13.221  1.00 16.14
ATOM   1909  CD1  ILE A 256     -0.671  22.068  14.439  1.00 16.04
ATOM   1910  CG2  ILE A 256     -1.497  23.016  11.695  1.00 14.89
ATOM   1911  C    ILE A 256      0.465  24.282   9.993  1.00 14.00
ATOM   1912  O    ILE A 256     -0.065  23.831   8.975  1.00 15.99
ATOM   1913  N    ALA A 257      0.637  25.588  10.195  1.00 14.29
ATOM   1914  CA   ALA A 257      0.292  26.539   9.130  1.00 13.84
ATOM   1915  CB   ALA A 257      0.571  27.988   9.530  1.00 14.99
ATOM   1916  C    ALA A 257      0.955  26.205   7.798  1.00 14.85
ATOM   1917  O    ALA A 257      0.328  26.208   6.746  1.00 16.25
ATOM   1918  N    LEU A 258      2.258  25.958   7.833  1.00 13.44
ATOM   1919  CA   LEU A 258      2.950  25.564   6.631  1.00 14.78
ATOM   1920  CB   LEU A 258      4.448  25.390   6.889  1.00 13.66
ATOM   1921  CG   LEU A 258      5.247  25.137   5.615  1.00 15.58
ATOM   1922  CD1  LEU A 258      5.050  26.284   4.593  1.00 17.44
ATOM   1923  CD2  LEU A 258      6.745  25.019   5.965  1.00 16.74
```

FIGURE 289

```
ATOM   1924  C    LEU A 258       2.391  24.297   6.013  1.00 14.93
ATOM   1925  O    LEU A 258       2.223  24.210   4.805  1.00 14.85
ATOM   1926  N    ASP A 259       2.105  23.290   6.838  1.00 15.85
ATOM   1927  CA   ASP A 259       1.470  22.081   6.314  1.00 16.95
ATOM   1928  CB   ASP A 259       1.186  21.146   7.501  1.00 18.21
ATOM   1929  CG   ASP A 259       0.834  19.718   7.102  1.00 22.66
ATOM   1930  OD1  ASP A 259       1.205  19.202   6.016  1.00 20.07
ATOM   1931  OD2  ASP A 259       0.217  18.996   7.920  1.00 33.57
ATOM   1932  C    ASP A 259       0.173  22.425   5.567  1.00 15.64
ATOM   1933  O    ASP A 259      -0.024  21.963   4.439  1.00 17.43
ATOM   1934  N    ARG A 260      -0.682  23.260   6.148  1.00 16.51
ATOM   1935  CA   ARG A 260      -1.947  23.632   5.504  1.00 16.62
ATOM   1936  CB   ARG A 260      -2.836  24.464   6.425  1.00 18.22
ATOM   1937  CG   ARG A 260      -3.435  23.668   7.571  1.00 25.51
ATOM   1938  CD   ARG A 260      -4.950  23.818   7.664  1.00 40.63
ATOM   1939  NE   ARG A 260      -5.428  25.199   7.581  1.00 49.41
ATOM   1940  CZ   ARG A 260      -5.919  25.797   6.491  1.00 52.56
ATOM   1941  NH1  ARG A 260      -6.025  25.176   5.311  1.00 50.50
ATOM   1942  NH2  ARG A 260      -6.310  27.059   6.592  1.00 53.49
ATOM   1943  C    ARG A 260      -1.685  24.431   4.233  1.00 16.45
ATOM   1944  O    ARG A 260      -2.247  24.131   3.165  1.00 18.96
ATOM   1945  N    ILE A 261      -0.767  25.394   4.310  1.00 15.77
ATOM   1946  CA   ILE A 261      -0.542  26.228   3.138  1.00 18.24
ATOM   1947  CB   ILE A 261       0.206  27.521   3.521  1.00 21.96
ATOM   1948  CG1AILE A 261       1.651  27.329   3.908  0.50 17.99
ATOM   1949  CG1BILE A 261      -0.685  28.609   4.112  0.50 19.62
ATOM   1950  CD1AILE A 261       2.215  28.633   4.442  0.50 20.12
ATOM   1951  CD1BILE A 261       0.000  29.266   5.315  0.50 24.86
ATOM   1952  CG2AILE A 261      -0.604  28.289   4.549  0.50 18.49
ATOM   1953  CG2BILE A 261       1.211  27.966   2.472  0.50 19.26
ATOM   1954  C    ILE A 261       0.067  25.456   1.973  1.00 19.50
ATOM   1955  O    ILE A 261      -0.278  25.684   0.799  1.00 17.34
ATOM   1956  N    LEU A 262       1.002  24.564   2.291  1.00 18.57
ATOM   1957  CA   LEU A 262       1.572  23.704   1.256  1.00 19.04
ATOM   1958  CB   LEU A 262       2.736  22.874   1.776  1.00 17.43
ATOM   1959  CG   LEU A 262       4.004  23.676   2.064  1.00 16.24
ATOM   1960  CD1  LEU A 262       5.114  22.827   2.635  1.00 18.88
ATOM   1961  CD2  LEU A 262       4.509  24.501   0.861  1.00 21.60
ATOM   1962  C    LEU A 262       0.533  22.831   0.568  1.00 18.56
ATOM   1963  O    LEU A 262       0.613  22.605  -0.649  1.00 19.59
ATOM   1964  N    GLN A 263      -0.423  22.344   1.350  1.00 16.77
ATOM   1965  CA   GLN A 263      -1.517  21.572   0.772  1.00 18.98
ATOM   1966  CB   GLN A 263      -2.359  20.878   1.850  1.00 21.56
ATOM   1967  CG   GLN A 263      -1.581  19.736   2.499  1.00 24.14
ATOM   1968  CD   GLN A 263      -2.322  19.083   3.652  1.00 30.60
ATOM   1969  OE1  GLN A 263      -3.120  18.178   3.445  1.00 37.41
ATOM   1970  NE2  GLN A 263      -2.058  19.540   4.868  1.00 34.60
ATOM   1971  C    GLN A 263      -2.383  22.438  -0.124  1.00 18.41
ATOM   1972  O    GLN A 263      -2.861  21.939  -1.165  1.00 19.16
ATOM   1973  N    GLN A 264      -2.585  23.692   0.286  1.00 17.80
ATOM   1974  CA   GLN A 264      -3.284  24.667  -0.547  1.00 19.17
ATOM   1975  CB   GLN A 264      -3.375  26.035   0.130  1.00 21.52
```

FIGURE 290

| | | | | | | | | |
|---|---|---|---|---|---|---|---|---|
| ATOM | 1976 | CG | GLN | A | 264 | -4.488 | 26.101 | 1.152 | 1.00 22.71 |
| ATOM | 1977 | CD | GLN | A | 264 | -4.485 | 27.392 | 1.924 | 1.00 27.25 |
| ATOM | 1978 | OE1 | GLN | A | 264 | -3.974 | 28.404 | 1.452 | 1.00 28.01 |
| ATOM | 1979 | NE2 | GLN | A | 264 | -5.062 | 27.364 | 3.126 | 1.00 32.99 |
| ATOM | 1980 | C | GLN | A | 264 | -2.569 | 24.866 | -1.856 | 1.00 17.97 |
| ATOM | 1981 | O | GLN | A | 264 | -3.195 | 24.854 | -2.914 | 1.00 18.97 |
| ATOM | 1982 | N | LEU | A | 265 | -1.243 | 25.044 | -1.807 | 1.00 16.73 |
| ATOM | 1983 | CA | LEU | A | 265 | -0.524 | 25.223 | -3.059 | 1.00 15.75 |
| ATOM | 1984 | CB | LEU | A | 265 | 0.944 | 25.599 | -2.792 | 1.00 16.04 |
| ATOM | 1985 | CG | LEU | A | 265 | 1.177 | 26.933 | -2.072 | 1.00 16.47 |
| ATOM | 1986 | CD1 | LEU | A | 265 | 2.699 | 27.094 | -1.977 | 1.00 23.16 |
| ATOM | 1987 | CD2 | LEU | A | 265 | 0.556 | 28.085 | -2.851 | 1.00 23.92 |
| ATOM | 1988 | C | LEU | A | 265 | -0.567 | 24.006 | -3.963 | 1.00 17.46 |
| ATOM | 1989 | O | LEU | A | 265 | -0.348 | 24.116 | -5.177 | 1.00 19.71 |
| ATOM | 1990 | N | ASP | A | 266 | -0.787 | 22.828 | -3.397 | 1.00 15.69 |
| ATOM | 1991 | CA | ASP | A | 266 | -0.767 | 21.626 | -4.210 | 1.00 16.88 |
| ATOM | 1992 | CB | ASP | A | 266 | -0.328 | 20.423 | -3.368 | 1.00 17.44 |
| ATOM | 1993 | CG | ASP | A | 266 | 1.156 | 20.375 | -3.149 | 1.00 21.62 |
| ATOM | 1994 | OD1 | ASP | A | 266 | 1.862 | 21.159 | -3.791 | 1.00 21.03 |
| ATOM | 1995 | OD2 | ASP | A | 266 | 1.680 | 19.586 | -2.335 | 1.00 25.07 |
| ATOM | 1996 | C | ASP | A | 266 | -2.163 | 21.343 | -4.768 | 1.00 16.49 |
| ATOM | 1997 | O | ASP | A | 266 | -2.320 | 20.469 | -5.624 | 1.00 18.65 |
| ATOM | 1998 | N | SER | A | 267 | -3.151 | 22.112 | -4.318 | 1.00 17.93 |
| ATOM | 1999 | CA | SER | A | 267 | -4.562 | 21.826 | -4.646 | 1.00 18.68 |
| ATOM | 2000 | CB | SER | A | 267 | -5.334 | 21.390 | -3.392 | 1.00 20.21 |
| ATOM | 2001 | OG A | SER | A | 267 | -4.827 | 20.179 | -2.869 | 0.50 22.09 |
| ATOM | 2002 | OG B | SER | A | 267 | -5.151 | 22.290 | -2.327 | 0.50 19.41 |
| ATOM | 2003 | C | SER | A | 267 | -5.375 | 22.910 | -5.354 | 1.00 19.44 |
| ATOM | 2004 | O | SER | A | 267 | -6.260 | 22.591 | -6.147 | 1.00 19.32 |
| ATOM | 2005 | N | LYS | A | 268 | -5.083 | 24.164 | -5.022 | 1.00 18.83 |
| ATOM | 2006 | CA | LYS | A | 268 | -5.848 | 25.354 | -5.377 | 1.00 20.16 |
| ATOM | 2007 | CB | LYS | A | 268 | -6.430 | 25.992 | -4.099 | 1.00 20.65 |
| ATOM | 2008 | CG | LYS | A | 268 | -7.498 | 25.094 | -3.470 | 1.00 26.76 |
| ATOM | 2009 | CD | LYS | A | 268 | -8.104 | 25.692 | -2.209 | 1.00 35.23 |
| ATOM | 2010 | CE | LYS | A | 268 | -9.065 | 26.845 | -2.493 | 1.00 39.80 |
| ATOM | 2011 | NZ | LYS | A | 268 | -9.302 | 27.654 | -1.258 | 1.00 42.30 |
| ATOM | 2012 | C | LYS | A | 268 | -4.995 | 26.373 | -6.115 | 1.00 20.26 |
| ATOM | 2013 | O | LYS | A | 268 | -3.762 | 26.340 | -6.077 | 1.00 20.14 |
| ATOM | 2014 | N | ASP | A | 269 | -5.653 | 27.329 | -6.766 | 1.00 20.67 |
| ATOM | 2015 | CA | ASP | A | 269 | -4.923 | 28.431 | -7.379 | 1.00 22.23 |
| ATOM | 2016 | CB | ASP | A | 269 | -5.354 | 28.695 | -8.824 | 1.00 21.86 |
| ATOM | 2017 | CG | ASP | A | 269 | -6.802 | 29.136 | -8.948 | 1.00 24.01 |
| ATOM | 2018 | OD1 | ASP | A | 269 | -7.478 | 29.270 | -7.910 | 1.00 23.82 |
| ATOM | 2019 | OD2 | ASP | A | 269 | -7.315 | 29.358 | -10.081 | 1.00 25.17 |
| ATOM | 2020 | C | ASP | A | 269 | -4.936 | 29.704 | -6.561 | 1.00 21.37 |
| ATOM | 2021 | O | ASP | A | 269 | -4.671 | 30.783 | -7.086 | 1.00 20.35 |
| ATOM | 2022 | N | SER | A | 270 | -5.235 | 29.557 | -5.272 | 1.00 22.33 |
| ATOM | 2023 | CA | SER | A | 270 | -5.009 | 30.638 | -4.323 | 1.00 20.47 |
| ATOM | 2024 | CB | SER | A | 270 | -6.278 | 31.451 | -4.075 | 1.00 24.06 |
| ATOM | 2025 | OG | SER | A | 270 | -7.314 | 30.640 | -3.578 | 1.00 26.40 |
| ATOM | 2026 | C | SER | A | 270 | -4.518 | 30.042 | -3.018 | 1.00 21.38 |
| ATOM | 2027 | O | SER | A | 270 | -4.735 | 28.852 | -2.739 | 1.00 22.73 |

FIGURE 291

| | | | | | | | | | |
|---|---|---|---|---|---|---|---|---|---|
| ATOM | 2028 | N | VAL | A | 271 | -3.885 | 30.903 | -2.225 | 1.00 22.36 |
| ATOM | 2029 | CA | VAL | A | 271 | -3.263 | 30.508 | -0.963 | 1.00 21.09 |
| ATOM | 2030 | CB | VAL | A | 271 | -1.709 | 30.463 | -1.115 | 1.00 19.31 |
| ATOM | 2031 | CG1 | VAL | A | 271 | -1.167 | 31.865 | -1.450 | 1.00 21.60 |
| ATOM | 2032 | CG2 | VAL | A | 271 | -1.082 | 29.972 | 0.200 | 1.00 21.85 |
| ATOM | 2033 | C | VAL | A | 271 | -3.688 | 31.549 | 0.072 | 1.00 20.22 |
| ATOM | 2034 | O | VAL | A | 271 | -3.787 | 32.736 | -0.240 | 1.00 22.08 |
| ATOM | 2035 | N | ASP | A | 272 | -3.917 | 31.112 | 1.310 | 1.00 20.16 |
| ATOM | 2036 | CA | ASP | A | 272 | -4.471 | 32.003 | 2.324 | 1.00 19.60 |
| ATOM | 2037 | CB | ASP | A | 272 | -5.965 | 31.714 | 2.437 | 1.00 19.30 |
| ATOM | 2038 | CG | ASP | A | 272 | -6.676 | 32.598 | 3.431 | 1.00 19.17 |
| ATOM | 2039 | OD1 | ASP | A | 272 | -6.077 | 33.593 | 3.891 | 1.00 21.60 |
| ATOM | 2040 | OD2 | ASP | A | 272 | -7.859 | 32.350 | 3.783 | 1.00 24.88 |
| ATOM | 2041 | C | ASP | A | 272 | -3.744 | 31.805 | 3.655 | 1.00 20.36 |
| ATOM | 2042 | O | ASP | A | 272 | -4.243 | 31.163 | 4.591 | 1.00 20.38 |
| ATOM | 2043 | N | ILE | A | 273 | -2.541 | 32.365 | 3.720 | 1.00 19.70 |
| ATOM | 2044 | CA | ILE | A | 273 | -1.760 | 32.311 | 4.942 | 1.00 19.19 |
| ATOM | 2045 | CB | ILE | A | 273 | -0.381 | 32.962 | 4.720 | 1.00 18.60 |
| ATOM | 2046 | CG1 | ILE | A | 273 | 0.333 | 32.288 | 3.548 | 1.00 21.27 |
| ATOM | 2047 | CD1 | ILE | A | 273 | 1.729 | 32.865 | 3.275 | 1.00 22.60 |
| ATOM | 2048 | CG2 | ILE | A | 273 | 0.464 | 32.875 | 5.999 | 1.00 20.66 |
| ATOM | 2049 | C | ILE | A | 273 | -2.477 | 32.966 | 6.107 | 1.00 20.28 |
| ATOM | 2050 | O | ILE | A | 273 | -2.472 | 32.424 | 7.218 | 1.00 18.55 |
| ATOM | 2051 | N | TYR | A | 274 | -3.100 | 34.117 | 5.869 | 1.00 18.83 |
| ATOM | 2052 | CA | TYR | A | 274 | -3.766 | 34.840 | 6.953 | 1.00 21.01 |
| ATOM | 2053 | CB | TYR | A | 274 | -4.367 | 36.112 | 6.356 | 1.00 19.87 |
| ATOM | 2054 | CG | TYR | A | 274 | -5.067 | 36.972 | 7.358 | 1.00 18.97 |
| ATOM | 2055 | CD1 | TYR | A | 274 | -4.394 | 38.025 | 7.954 | 1.00 21.35 |
| ATOM | 2056 | CE1 | TYR | A | 274 | -5.029 | 38.859 | 8.864 | 1.00 25.25 |
| ATOM | 2057 | CZ | TYR | A | 274 | -6.352 | 38.625 | 9.157 | 1.00 28.87 |
| ATOM | 2058 | OH | TYR | A | 274 | -6.978 | 39.454 | 10.070 | 1.00 34.66 |
| ATOM | 2059 | CE2 | TYR | A | 274 | -7.051 | 37.579 | 8.579 | 1.00 26.00 |
| ATOM | 2060 | CD2 | TYR | A | 274 | -6.413 | 36.757 | 7.669 | 1.00 22.43 |
| ATOM | 2061 | C | TYR | A | 274 | -4.875 | 33.977 | 7.550 | 1.00 21.55 |
| ATOM | 2062 | O | TYR | A | 274 | -4.991 | 33.834 | 8.776 | 1.00 22.52 |
| ATOM | 2063 | N | GLY | A | 275 | -5.625 | 33.326 | 6.671 | 1.00 19.33 |
| ATOM | 2064 | CA | GLY | A | 275 | -6.741 | 32.496 | 7.090 | 1.00 19.21 |
| ATOM | 2065 | C | GLY | A | 275 | -6.245 | 31.272 | 7.837 | 1.00 20.79 |
| ATOM | 2066 | O | GLY | A | 275 | -6.889 | 30.859 | 8.796 | 1.00 22.44 |
| ATOM | 2067 | N | ALA | A | 276 | -5.125 | 30.692 | 7.398 | 1.00 18.85 |
| ATOM | 2068 | CA | ALA | A | 276 | -4.558 | 29.525 | 8.094 | 1.00 20.03 |
| ATOM | 2069 | CB | ALA | A | 276 | -3.324 | 29.022 | 7.356 | 1.00 20.07 |
| ATOM | 2070 | C | ALA | A | 276 | -4.195 | 29.870 | 9.542 | 1.00 19.85 |
| ATOM | 2071 | O | ALA | A | 276 | -4.432 | 29.103 | 10.479 | 1.00 20.22 |
| ATOM | 2072 | N | VAL | A | 277 | -3.537 | 31.010 | 9.719 | 1.00 19.70 |
| ATOM | 2073 | CA | VAL | A | 277 | -3.115 | 31.387 | 11.057 | 1.00 19.31 |
| ATOM | 2074 | CB | VAL | A | 277 | -2.121 | 32.548 | 11.018 | 1.00 17.79 |
| ATOM | 2075 | CG1 | VAL | A | 277 | -1.820 | 32.967 | 12.458 | 1.00 18.22 |
| ATOM | 2076 | CG2 | VAL | A | 277 | -0.848 | 32.152 | 10.255 | 1.00 18.41 |
| ATOM | 2077 | C | VAL | A | 277 | -4.346 | 31.757 | 11.868 | 1.00 19.90 |
| ATOM | 2078 | O | VAL | A | 277 | -4.474 | 31.347 | 13.019 | 1.00 20.30 |
| ATOM | 2079 | N | HIS | A | 278 | -5.241 | 32.548 | 11.292 | 1.00 19.02 |

FIGURE 292

```
ATOM   2080  CA   HIS A 278      -6.516  32.865  11.948  1.00 19.17
ATOM   2081  CB   HIS A 278      -7.444  33.619  10.992  1.00 19.25
ATOM   2082  CG   HIS A 278      -8.751  33.994  11.601  1.00 18.26
ATOM   2083  ND1  HIS A 278      -9.794  33.105  11.749  1.00 23.05
ATOM   2084  CE1  HIS A 278     -10.818  33.721  12.311  1.00 21.29
ATOM   2085  NE2  HIS A 278     -10.478  34.980  12.522  1.00 22.86
ATOM   2086  CD2  HIS A 278      -9.189  35.176  12.093  1.00 20.74
ATOM   2087  C    HIS A 278      -7.203  31.605  12.495  1.00 17.84
ATOM   2088  O    HIS A 278      -7.537  31.525  13.680  1.00 18.09
ATOM   2089  N    ASP A 279      -7.350  30.601  11.635  1.00 18.49
ATOM   2090  CA   ASP A 279      -8.101  29.403  11.989  1.00 19.79
ATOM   2091  CB   ASP A 279      -8.327  28.536  10.749  1.00 21.91
ATOM   2092  CG   ASP A 279      -9.382  29.137   9.805  1.00 27.33
ATOM   2093  OD1  ASP A 279     -10.122  30.086  10.181  1.00 32.69
ATOM   2094  OD2  ASP A 279      -9.571  28.698   8.663  1.00 32.10
ATOM   2095  C    ASP A 279      -7.376  28.645  13.092  1.00 19.96
ATOM   2096  O    ASP A 279      -8.023  28.185  14.024  1.00 21.76
ATOM   2097  N    LEU A 280      -6.040  28.527  13.041  1.00 17.01
ATOM   2098  CA   LEU A 280      -5.330  27.942  14.182  1.00 16.07
ATOM   2099  CB   LEU A 280      -3.826  27.947  13.886  1.00 15.00
ATOM   2100  CG   LEU A 280      -3.422  27.038  12.707  1.00 18.81
ATOM   2101  CD1  LEU A 280      -1.913  27.070  12.480  1.00 18.81
ATOM   2102  CD2  LEU A 280      -3.882  25.608  12.945  1.00 25.24
ATOM   2103  C    LEU A 280      -5.569  28.675  15.513  1.00 16.26
ATOM   2104  O    LEU A 280      -5.712  28.053  16.564  1.00 16.85
ATOM   2105  N    ARG A 281      -5.589  30.004  15.476  1.00 15.08
ATOM   2106  CA   ARG A 281      -5.688  30.743  16.716  1.00 17.44
ATOM   2107  CB   ARG A 281      -5.378  32.206  16.447  1.00 17.50
ATOM   2108  CG   ARG A 281      -3.897  32.412  16.278  1.00 17.29
ATOM   2109  CD   ARG A 281      -3.452  33.863  16.134  1.00 16.44
ATOM   2110  NE   ARG A 281      -1.994  33.944  15.966  1.00 16.47
ATOM   2111  CZ   ARG A 281      -1.298  35.076  15.842  1.00 18.10
ATOM   2112  NH1  ARG A 281      -1.939  36.226  15.915  1.00 21.62
ATOM   2113  NH2  ARG A 281       0.034  35.066  15.648  1.00 18.29
ATOM   2114  C    ARG A 281      -7.060  30.626  17.353  1.00 17.49
ATOM   2115  O    ARG A 281      -7.199  30.854  18.553  1.00 19.29
ATOM   2116  N    LEU A 282      -8.062  30.261  16.560  1.00 18.15
ATOM   2117  CA   LEU A 282      -9.358  29.983  17.142  1.00 17.68
ATOM   2118  CB   LEU A 282     -10.396  29.682  16.062  1.00 16.99
ATOM   2119  CG   LEU A 282     -10.801  30.873  15.182  1.00 19.43
ATOM   2120  CD1  LEU A 282     -11.737  30.362  14.090  1.00 25.48
ATOM   2121  CD2  LEU A 282     -11.501  31.952  16.018  1.00 24.65
ATOM   2122  C    LEU A 282      -9.279  28.793  18.102  1.00 19.14
ATOM   2123  O    LEU A 282     -10.141  28.668  18.977  1.00 19.96
ATOM   2124  N    HIS A 283      -8.293  27.918  17.896  1.00 17.18
ATOM   2125  CA   HIS A 283      -8.277  26.637  18.601  1.00 18.07
ATOM   2126  CB   HIS A 283      -8.139  25.490  17.597  1.00 18.24
ATOM   2127  CG   HIS A 283      -9.231  25.476  16.585  1.00 19.11
ATOM   2128  ND1  HIS A 283     -10.466  24.910  16.822  1.00 23.60
ATOM   2129  CE1  HIS A 283     -11.231  25.064  15.756  1.00 19.21
ATOM   2130  NE2  HIS A 283     -10.545  25.722  14.844  1.00 24.32
ATOM   2131  CD2  HIS A 283      -9.296  26.007  15.343  1.00 23.68
```

FIGURE 293

| | | | | | | | | |
|---|---|---|---|---|---|---|---|---|
| ATOM | 2132 | C | HIS | A | 283 | -7.254 | 26.512 | 19.707 | 1.00 | 17.83 |
| ATOM | 2133 | O | HIS | A | 283 | -7.428 | 25.694 | 20.622 | 1.00 | 18.19 |
| ATOM | 2134 | N | ARG | A | 284 | -6.201 | 27.314 | 19.637 | 1.00 | 17.80 |
| ATOM | 2135 | CA | ARG | A | 284 | -5.240 | 27.348 | 20.746 | 1.00 | 18.49 |
| ATOM | 2136 | CB | ARG | A | 284 | -4.226 | 26.210 | 20.609 | 1.00 | 18.69 |
| ATOM | 2137 | CG | ARG | A | 284 | -3.276 | 26.099 | 21.796 | 1.00 | 18.21 |
| ATOM | 2138 | CD | ARG | A | 284 | -2.402 | 24.878 | 21.679 | 1.00 | 19.61 |
| ATOM | 2139 | NE | ARG | A | 284 | -1.291 | 24.852 | 22.639 | 1.00 | 17.43 |
| ATOM | 2140 | CZ | ARG | A | 284 | -1.355 | 24.269 | 23.836 | 1.00 | 15.60 |
| ATOM | 2141 | NH1 | ARG | A | 284 | -2.509 | 23.773 | 24.275 | 1.00 | 16.53 |
| ATOM | 2142 | NH2 | ARG | A | 284 | -0.290 | 24.237 | 24.619 | 1.00 | 17.46 |
| ATOM | 2143 | C | ARG | A | 284 | -4.530 | 28.695 | 20.752 | 1.00 | 17.37 |
| ATOM | 2144 | O | ARG | A | 284 | -4.367 | 29.323 | 19.707 | 1.00 | 16.68 |
| ATOM | 2145 | N | VAL | A | 285 | -4.142 | 29.123 | 21.941 | 1.00 | 16.77 |
| ATOM | 2146 | CA | VAL | A | 285 | -3.720 | 30.502 | 22.158 | 1.00 | 18.62 |
| ATOM | 2147 | CB | VAL | A | 285 | -3.294 | 30.774 | 23.616 | 1.00 | 18.24 |
| ATOM | 2148 | CG1 | VAL | A | 285 | -2.160 | 29.860 | 24.061 | 1.00 | 18.15 |
| ATOM | 2149 | CG2 | VAL | A | 285 | -2.946 | 32.249 | 23.792 | 1.00 | 21.76 |
| ATOM | 2150 | C | VAL | A | 285 | -2.599 | 30.925 | 21.225 | 1.00 | 19.42 |
| ATOM | 2151 | O | VAL | A | 285 | -1.503 | 30.358 | 21.256 | 1.00 | 20.43 |
| ATOM | 2152 | N | HIS | A | 286 | -2.914 | 31.919 | 20.395 | 1.00 | 21.27 |
| ATOM | 2153 | CA | HIS | A | 286 | -1.916 | 32.671 | 19.615 | 1.00 | 22.02 |
| ATOM | 2154 | CB | HIS | A | 286 | -1.237 | 33.690 | 20.547 | 1.00 | 20.50 |
| ATOM | 2155 | CG | HIS | A | 286 | -0.509 | 34.803 | 19.848 | 1.00 | 23.00 |
| ATOM | 2156 | ND1 | HIS | A | 286 | 0.558 | 34.583 | 19.001 | 1.00 | 22.19 |
| ATOM | 2157 | CE1 | HIS | A | 286 | 0.997 | 35.742 | 18.539 | 1.00 | 28.42 |
| ATOM | 2158 | NE2 | HIS | A | 286 | 0.299 | 36.711 | 19.104 | 1.00 | 23.08 |
| ATOM | 2159 | CD2 | HIS | A | 286 | -0.660 | 36.149 | 19.920 | 1.00 | 25.08 |
| ATOM | 2160 | C | HIS | A | 286 | -0.937 | 31.748 | 18.880 | 1.00 | 20.60 |
| ATOM | 2161 | O | HIS | A | 286 | 0.249 | 32.021 | 18.774 | 1.00 | 22.19 |
| ATOM | 2162 | N | MET | A | 287 | -1.425 | 30.634 | 18.328 | 1.00 | 19.66 |
| ATOM | 2163 | CA | MET | A | 287 | -0.622 | 29.854 | 17.395 | 1.00 | 20.00 |
| ATOM | 2164 | CB | MET | A | 287 | -1.505 | 28.919 | 16.577 | 1.00 | 21.36 |
| ATOM | 2165 | CG | MET | A | 287 | -2.213 | 27.872 | 17.401 | 1.00 | 22.55 |
| ATOM | 2166 | SD | MET | A | 287 | -1.075 | 26.566 | 17.823 | 1.00 | 40.15 |
| ATOM | 2167 | CE | MET | A | 287 | -1.223 | 27.071 | 19.109 | 1.00 | 6.08 |
| ATOM | 2168 | C | MET | A | 287 | 0.133 | 30.710 | 16.385 | 1.00 | 20.09 |
| ATOM | 2169 | O | MET | A | 287 | -0.471 | 31.515 | 15.681 | 1.00 | 20.94 |
| ATOM | 2170 | N | VAL | A | 288 | 1.422 | 30.424 | 16.237 | 1.00 | 19.63 |
| ATOM | 2171 | CA | VAL | A | 288 | 2.388 | 31.249 | 15.511 | 1.00 | 18.83 |
| ATOM | 2172 | CB | VAL | A | 288 | 1.962 | 31.725 | 14.093 | 1.00 | 17.58 |
| ATOM | 2173 | CG1 | VAL | A | 288 | 3.180 | 32.328 | 13.410 | 1.00 | 18.31 |
| ATOM | 2174 | CG2 | VAL | A | 288 | 1.542 | 30.563 | 13.204 | 1.00 | 17.78 |
| ATOM | 2175 | C | VAL | A | 288 | 2.758 | 32.425 | 16.439 | 1.00 | 18.47 |
| ATOM | 2176 | O | VAL | A | 288 | 1.937 | 33.283 | 16.710 | 1.00 | 20.51 |
| ATOM | 2177 | N | GLN | A | 289 | 3.970 | 32.397 | 16.978 | 1.00 | 20.96 |
| ATOM | 2178 | CA | GLN | A | 289 | 4.275 | 33.242 | 18.136 | 1.00 | 22.85 |
| ATOM | 2179 | CB | GLN | A | 289 | 5.360 | 32.573 | 18.989 | 1.00 | 23.05 |
| ATOM | 2180 | CG | GLN | A | 289 | 5.711 | 33.382 | 20.255 | 1.00 | 23.08 |
| ATOM | 2181 | CD | GLN | A | 289 | 6.940 | 32.853 | 20.982 | 1.00 | 24.28 |
| ATOM | 2182 | OE1 | GLN | A | 289 | 7.913 | 32.445 | 20.361 | 1.00 | 27.56 |
| ATOM | 2183 | NE2 | GLN | A | 289 | 6.888 | 32.843 | 22.309 | 1.00 | 23.63 |

FIGURE 294

| ATOM | 2184 | C | GLN | A | 289 | 4.723 | 34.660 | 17.707 | 1.00 | 24.40 |
|------|------|------|------|---|-----|--------|--------|--------|------|-------|
| ATOM | 2185 | O | GLN | A | 289 | 4.391 | 35.649 | 18.378 | 1.00 | 23.35 |
| ATOM | 2186 | N | THR | A | 290 | 5.492 | 34.737 | 16.617 | 1.00 | 26.49 |
| ATOM | 2187 | CA | THR | A | 290 | 6.172 | 35.968 | 16.207 | 1.00 | 25.39 |
| ATOM | 2188 | CB | THR | A | 290 | 7.702 | 35.856 | 16.359 | 1.00 | 26.91 |
| ATOM | 2189 | OG1 | THR | A | 290 | 8.244 | 35.042 | 15.307 | 1.00 | 28.99 |
| ATOM | 2190 | CG2 | THR | A | 290 | 8.109 | 35.128 | 17.629 | 1.00 | 27.48 |
| ATOM | 2191 | C | THR | A | 290 | 5.866 | 36.465 | 14.801 | 1.00 | 26.87 |
| ATOM | 2192 | O | THR | A | 290 | 5.512 | 35.692 | 13.896 | 1.00 | 25.17 |
| ATOM | 2193 | N | GLU | A | 291 | 6.023 | 37.770 | 14.595 | 1.00 | 25.95 |
| ATOM | 2194 | CA | GLU | A | 291 | 5.904 | 38.299 | 13.242 | 1.00 | 26.94 |
| ATOM | 2195 | CB | GLU | A | 291 | 6.101 | 39.818 | 13.221 | 1.00 | 28.49 |
| ATOM | 2196 | CG | GLU | A | 291 | 5.769 | 40.445 | 11.874 | 1.00 | 26.87 |
| ATOM | 2197 | CD | GLU | A | 291 | 6.009 | 41.941 | 11.858 | 1.00 | 36.69 |
| ATOM | 2198 | OE1 | GLU | A | 291 | 7.008 | 42.378 | 11.254 | 1.00 | 43.24 |
| ATOM | 2199 | OE2 | GLU | A | 291 | 5.212 | 42.677 | 12.471 | 1.00 | 40.46 |
| ATOM | 2200 | C | GLU | A | 291 | 6.910 | 37.609 | 12.314 | 1.00 | 26.09 |
| ATOM | 2201 | O | GLU | A | 291 | 6.577 | 37.275 | 11.174 | 1.00 | 25.81 |
| ATOM | 2202 | N | CYS | A | 292 | 8.123 | 37.346 | 12.792 | 1.00 | 27.35 |
| ATOM | 2203 | CA | CYS | A | 292 | 9.115 | 36.718 | 11.917 | 1.00 | 27.95 |
| ATOM | 2204 | CB | CYS | A | 292 | 10.448 | 36.520 | 12.615 | 1.00 | 29.85 |
| ATOM | 2205 | SG | CYS | A | 292 | 11.241 | 38.119 | 12.768 | 1.00 | 41.05 |
| ATOM | 2206 | C | CYS | A | 292 | 8.623 | 35.388 | 11.374 | 1.00 | 24.32 |
| ATOM | 2207 | O | CYS | A | 292 | 8.866 | 35.043 | 10.217 | 1.00 | 21.58 |
| ATOM | 2208 | N | GLN | A | 293 | 7.928 | 34.654 | 12.234 | 1.00 | 23.27 |
| ATOM | 2209 | CA | GLN | A | 293 | 7.384 | 33.358 | 11.845 | 1.00 | 22.22 |
| ATOM | 2210 | CB | GLN | A | 293 | 6.829 | 32.657 | 13.092 | 1.00 | 23.15 |
| ATOM | 2211 | CG | GLN | A | 293 | 7.935 | 32.014 | 13.943 | 1.00 | 22.95 |
| ATOM | 2212 | CD | GLN | A | 293 | 7.497 | 31.584 | 15.342 | 1.00 | 24.04 |
| ATOM | 2213 | OE1 | GLN | A | 293 | 6.342 | 31.765 | 15.721 | 1.00 | 21.47 |
| ATOM | 2214 | NE2 | GLN | A | 293 | 8.409 | 30.964 | 16.098 | 1.00 | 21.01 |
| ATOM | 2215 | C | GLN | A | 293 | 6.316 | 33.548 | 10.766 | 1.00 | 21.55 |
| ATOM | 2216 | O | GLN | A | 293 | 6.228 | 32.792 | 9.791 | 1.00 | 20.32 |
| ATOM | 2217 | N | TYR | A | 294 | 5.506 | 34.586 | 10.920 | 1.00 | 21.97 |
| ATOM | 2218 | CA | TYR | A | 294 | 4.537 | 34.924 | 9.888 | 1.00 | 21.49 |
| ATOM | 2219 | CB | TYR | A | 294 | 3.670 | 36.091 | 10.352 | 1.00 | 23.10 |
| ATOM | 2220 | CG | TYR | A | 294 | 2.400 | 36.319 | 9.556 | 1.00 | 21.89 |
| ATOM | 2221 | CD1 | TYR | A | 294 | 1.379 | 35.379 | 9.531 | 1.00 | 19.98 |
| ATOM | 2222 | CE1 | TYR | A | 294 | 0.185 | 35.606 | 8.862 | 1.00 | 22.15 |
| ATOM | 2223 | CZ | TYR | A | 294 | 0.045 | 36.772 | 8.138 | 1.00 | 24.71 |
| ATOM | 2224 | OH | TYR | A | 294 | -1.116 | 36.991 | 7.445 | 1.00 | 25.08 |
| ATOM | 2225 | CE2 | TYR | A | 294 | 1.059 | 37.703 | 8.118 | 1.00 | 22.86 |
| ATOM | 2226 | CD2 | TYR | A | 294 | 2.222 | 37.489 | 8.827 | 1.00 | 23.52 |
| ATOM | 2227 | C | TYR | A | 294 | 5.239 | 35.306 | 8.576 | 1.00 | 22.57 |
| ATOM | 2228 | O | TYR | A | 294 | 4.786 | 34.933 | 7.491 | 1.00 | 20.32 |
| ATOM | 2229 | N | VAL | A | 295 | 6.373 | 36.001 | 8.670 | 1.00 | 22.24 |
| ATOM | 2230 | CA | VAL | A | 295 | 7.104 | 36.358 | 7.454 | 1.00 | 20.86 |
| ATOM | 2231 | CB | VAL | A | 295 | 8.267 | 37.326 | 7.712 | 1.00 | 23.76 |
| ATOM | 2232 | CG1 | VAL | A | 295 | 9.018 | 37.568 | 6.381 | 1.00 | 23.08 |
| ATOM | 2233 | CG2 | VAL | A | 295 | 7.749 | 38.634 | 8.308 | 1.00 | 23.92 |
| ATOM | 2234 | C | VAL | A | 295 | 7.640 | 35.093 | 6.790 | 1.00 | 19.44 |
| ATOM | 2235 | O | VAL | A | 295 | 7.633 | 34.973 | 5.572 | 1.00 | 20.82 |

FIGURE 295

```
ATOM  2236  N    TYR A 296       8.078  34.149   7.611  1.00 21.43
ATOM  2237  CA   TYR A 296       8.763  32.971   7.121  1.00 19.39
ATOM  2238  CB   TYR A 296       9.281  32.156   8.298  1.00 19.80
ATOM  2239  CG   TYR A 296       9.911  30.860   7.902  1.00 18.43
ATOM  2240  CD1  TYR A 296      11.208  30.833   7.381  1.00 18.72
ATOM  2241  CE1  TYR A 296      11.823  29.631   7.077  1.00 22.90
ATOM  2242  CZ   TYR A 296      11.154  28.450   7.332  1.00 22.92
ATOM  2243  OH   TYR A 296      11.728  27.247   7.033  1.00 23.22
ATOM  2244  CE2  TYR A 296       9.873  28.447   7.854  1.00 21.43
ATOM  2245  CD2  TYR A 296       9.275  29.644   8.162  1.00 21.11
ATOM  2246  C    TYR A 296       7.771  32.136   6.320  1.00 18.46
ATOM  2247  O    TYR A 296       8.157  31.542   5.319  1.00 19.77
ATOM  2248  N    LEU A 297       6.509  32.096   6.767  1.00 19.80
ATOM  2249  CA   LEU A 297       5.478  31.346   6.056  1.00 17.52
ATOM  2250  CB   LEU A 297       4.148  31.412   6.825  1.00 19.78
ATOM  2251  CG   LEU A 297       4.110  30.542   8.092  1.00 16.59
ATOM  2252  CD1  LEU A 297       2.768  30.733   8.798  1.00 20.00
ATOM  2253  CD2  LEU A 297       4.304  29.063   7.757  1.00 18.37
ATOM  2254  C    LEU A 297       5.311  31.947   4.657  1.00 18.94
ATOM  2255  O    LEU A 297       5.174  31.247   3.654  1.00 19.58
ATOM  2256  N    HIS A 298       5.350  33.270   4.588  1.00 19.76
ATOM  2257  CA   HIS A 298       5.257  33.950   3.290  1.00 19.33
ATOM  2258  CB   HIS A 298       5.120  35.462   3.508  1.00 20.79
ATOM  2259  CG   HIS A 298       3.742  35.888   3.889  1.00 19.70
ATOM  2260  ND1  HIS A 298       3.242  35.727   5.165  1.00 20.71
ATOM  2261  CE1  HIS A 298       1.991  36.153   5.195  1.00 20.63
ATOM  2262  NE2  HIS A 298       1.672  36.608   3.998  1.00 23.44
ATOM  2263  CD2  HIS A 298       2.753  36.453   3.162  1.00 20.17
ATOM  2264  C    HIS A 298       6.475  33.665   2.410  1.00 18.63
ATOM  2265  O    HIS A 298       6.333  33.486   1.200  1.00 20.17
ATOM  2266  N    GLN A 299       7.667  33.627   2.990  1.00 21.31
ATOM  2267  CA   GLN A 299       8.868  33.309   2.226  1.00 20.83
ATOM  2268  CB   GLN A 299      10.128  33.492   3.082  1.00 22.50
ATOM  2269  CG   GLN A 299      10.312  34.954   3.499  1.00 25.27
ATOM  2270  CD   GLN A 299      11.423  35.135   4.525  1.00 28.26
ATOM  2271  OE1  GLN A 299      11.557  34.329   5.445  1.00 29.83
ATOM  2272  NE2  GLN A 299      12.188  36.219   4.403  1.00 26.71
ATOM  2273  C    GLN A 299       8.769  31.887   1.693  1.00 21.19
ATOM  2274  O    GLN A 299       9.147  31.646   0.552  1.00 20.84
ATOM  2275  N    CYS A 300       8.231  30.964   2.490  1.00 19.77
ATOM  2276  CA   CYS A 300       8.097  29.590   2.021  1.00 21.20
ATOM  2277  CB   CYS A 300       7.546  28.649   3.111  1.00 21.59
ATOM  2278  SG   CYS A 300       8.659  28.313   4.496  1.00 21.31
ATOM  2279  C    CYS A 300       7.227  29.549   0.778  1.00 18.38
ATOM  2280  O    CYS A 300       7.572  28.916  -0.213  1.00 19.58
ATOM  2281  N    VAL A 301       6.076  30.207   0.833  1.00 20.07
ATOM  2282  CA   VAL A 301       5.143  30.161  -0.279  1.00 19.34
ATOM  2283  CB   VAL A 301       3.831  30.847   0.087  1.00 19.69
ATOM  2284  CG1  VAL A 301       2.980  31.013  -1.147  1.00 19.02
ATOM  2285  CG2  VAL A 301       3.082  30.041   1.150  1.00 23.02
ATOM  2286  C    VAL A 301       5.730  30.824  -1.522  1.00 18.98
ATOM  2287  O    VAL A 301       5.634  30.294  -2.652  1.00 18.99
```

FIGURE 296

```
ATOM   2288  N   ARG A 302       6.361  31.968  -1.289  1.00 20.60
ATOM   2289  CA  ARG A 302       7.085  32.662  -2.365  1.00 22.52
ATOM   2290  CB  ARG A 302       7.807  33.876  -1.811  1.00 23.52
ATOM   2291  CG  ARG A 302       8.616  34.611  -2.872  1.00 24.32
ATOM   2292  CD  ARG A 302       9.710  35.455  -2.228  1.00 26.13
ATOM   2293  NE  ARG A 302      10.667  34.616  -1.520  1.00 31.05
ATOM   2294  CZ  ARG A 302      11.476  35.050  -0.558  1.00 36.30
ATOM   2295  NH1 ARG A 302      11.460  36.326  -0.192  1.00 37.18
ATOM   2296  NH2 ARG A 302      12.305  34.207   0.041  1.00 34.04
ATOM   2297  C   ARG A 302       8.087  31.777  -3.095  1.00 23.40
ATOM   2298  O   ARG A 302       8.103  31.755  -4.329  1.00 23.55
ATOM   2299  N   ASP A 303       8.903  31.055  -2.328  1.00 22.39
ATOM   2300  CA  ASP A 303       9.904  30.144  -2.863  1.00 22.73
ATOM   2301  CB  ASP A 303      10.892  29.686  -1.773  1.00 21.26
ATOM   2302  CG  ASP A 303      11.711  30.827  -1.192  1.00 28.53
ATOM   2303  OD1 ASP A 303      11.710  31.931  -1.789  1.00 27.62
ATOM   2304  OD2 ASP A 303      12.386  30.699  -0.137  1.00 26.66
ATOM   2305  C   ASP A 303       9.338  28.944  -3.632  1.00 20.36
ATOM   2306  O   ASP A 303       9.838  28.603  -4.712  1.00 21.25
ATOM   2307  N   VAL A 304       8.284  28.318  -3.106  1.00 20.24
ATOM   2308  CA  VAL A 304       7.656  27.200  -3.805  1.00 19.03
ATOM   2309  CB  VAL A 304       6.506  26.614  -2.948  1.00 21.99
ATOM   2310  CG1 VAL A 304       5.687  25.599  -3.724  1.00 21.81
ATOM   2311  CG2 VAL A 304       7.116  25.982  -1.713  1.00 22.11
ATOM   2312  C   VAL A 304       7.141  27.710  -5.149  1.00 19.92
ATOM   2313  O   VAL A 304       7.322  27.066  -6.197  1.00 21.24
ATOM   2314  N   LEU A 305       6.459  28.851  -5.112  1.00 18.22
ATOM   2315  CA  LEU A 305       5.836  29.364  -6.332  1.00 20.56
ATOM   2316  CB  LEU A 305       4.844  30.480  -6.012  1.00 17.57
ATOM   2317  CG  LEU A 305       3.557  30.008  -5.320  1.00 19.17
ATOM   2318  CD1 LEU A 305       2.712  31.253  -4.985  1.00 19.55
ATOM   2319  CD2 LEU A 305       2.691  28.974  -6.082  1.00 20.38
ATOM   2320  C   LEU A 305       6.824  29.794  -7.407  1.00 21.36
ATOM   2321  O   LEU A 305       6.574  29.576  -8.606  1.00 23.65
ATOM   2322  N   ARG A 306       7.947  30.358  -6.969  1.00 23.97
ATOM   2323  CA  ARG A 306       9.014  30.735  -7.913  1.00 23.57
ATOM   2324  CB  ARG A 306      10.171  31.436  -7.207  1.00 23.85
ATOM   2325  CG  ARG A 306       9.941  32.875  -6.733  1.00 26.18
ATOM   2326  CD  ARG A 306      11.158  33.484  -6.039  1.00 35.81
ATOM   2327  NE  ARG A 306      11.010  34.920  -5.779  1.00 36.91
ATOM   2328  CZ  ARG A 306      11.865  35.646  -5.060  1.00 37.77
ATOM   2329  NH1 ARG A 306      12.925  35.079  -4.500  1.00 36.45
ATOM   2330  NH2 ARG A 306      11.658  36.947  -4.882  1.00 37.40
ATOM   2331  C   ARG A 306       9.547  29.478  -8.604  1.00 25.69
ATOM   2332  O   ARG A 306       9.712  29.439  -9.834  1.00 23.35
ATOM   2333  N   ALA A 307       9.792  28.436  -7.811  1.00 23.29
ATOM   2334  CA  ALA A 307      10.314  27.185  -8.349  1.00 24.26
ATOM   2335  CB  ALA A 307      10.556  26.230  -7.205  1.00 24.03
ATOM   2336  C   ALA A 307       9.354  26.565  -9.344  1.00 22.10
ATOM   2337  O   ALA A 307       9.740  26.077 -10.410  1.00 22.72
ATOM   2338  N   ARG A 308       8.068  26.598  -9.008  1.00 20.80
ATOM   2339  CA  ARG A 308       7.092  25.915  -9.835  1.00 20.00
```

FIGURE 297

```
ATOM   2340  CB   ARG A 308       5.774  25.772  -9.075  1.00 21.72
ATOM   2341  CG   ARG A 308       5.870  24.610  -8.109  1.00 22.26
ATOM   2342  CD   ARG A 308       4.618  24.345  -7.299  1.00 19.97
ATOM   2343  NE   ARG A 308       4.902  23.149  -6.503  1.00 24.07
ATOM   2344  CZ   ARG A 308       4.025  22.542  -5.718  1.00 27.19
ATOM   2345  NH1  ARG A 308       2.791  23.003  -5.673  1.00 23.93
ATOM   2346  NH2  ARG A 308       4.377  21.464  -5.012  1.00 28.78
ATOM   2347  C    ARG A 308       6.876  26.662 -11.139  1.00 22.15
ATOM   2348  O    ARG A 308       6.699  26.030 -12.176  1.00 21.30
ATOM   2349  N    LYS A 309       6.953  27.992 -11.082  1.00 21.16
ATOM   2350  CA   LYS A 309       6.685  28.832 -12.253  1.00 22.32
ATOM   2351  CB   LYS A 309       6.801  30.333 -11.901  1.00 24.02
ATOM   2352  CG   LYS A 309       6.508  31.340 -13.040  1.00 29.43
ATOM   2353  CD   LYS A 309       6.215  32.737 -12.484  1.00 37.46
ATOM   2354  CE   LYS A 309       5.642  33.687 -13.538  1.00 44.02
ATOM   2355  NZ   LYS A 309       6.468  34.926 -13.712  1.00 43.80
ATOM   2356  C    LYS A 309       7.656  28.466 -13.367  1.00 22.56
ATOM   2357  O    LYS A 309       7.281  28.420 -14.539  1.00 23.42
ATOM   2358  N    LEU A 310       8.900  28.189 -12.999  1.00 22.00
ATOM   2359  CA   LEU A 310       9.906  27.866 -14.002  1.00 21.73
ATOM   2360  CB   LEU A 310      11.289  28.091 -13.409  1.00 21.13
ATOM   2361  CG   LEU A 310      11.536  29.517 -12.922  1.00 21.73
ATOM   2362  CD1  LEU A 310      12.995  29.640 -12.487  1.00 22.37
ATOM   2363  CD2  LEU A 310      11.167  30.510 -14.011  1.00 28.55
ATOM   2364  C    LEU A 310       9.830  26.446 -14.582  1.00 21.34
ATOM   2365  O    LEU A 310      10.478  26.145 -15.598  1.00 23.36
ATOM   2366  N    ARG A 311       9.067  25.580 -13.915  1.00 19.41
ATOM   2367  CA   ARG A 311       8.862  24.211 -14.373  1.00 19.13
ATOM   2368  CB   ARG A 311       9.162  23.298 -13.191  1.00 20.37
ATOM   2369  CG   ARG A 311      10.653  23.321 -12.863  1.00 21.47
ATOM   2370  CD   ARG A 311      11.008  22.805 -11.476  1.00 24.25
ATOM   2371  NE   ARG A 311      10.520  21.442 -11.254  1.00 23.85
ATOM   2372  CZ   ARG A 311      10.688  20.774 -10.127  1.00 22.32
ATOM   2373  NH1  ARG A 311      11.377  21.330  -9.126  1.00 25.69
ATOM   2374  NH2  ARG A 311      10.204  19.543  -9.993  1.00 18.91
ATOM   2375  C    ARG A 311       7.431  23.931 -14.838  1.00 21.21
ATOM   2376  O    ARG A 311       6.741  24.874 -15.241  1.00 25.92
ATOM   2377  O50  INH Z   1       4.605  33.376  23.736  1.00 26.83
ATOM   2378  C49  INH Z   1       4.231  34.382  24.326  1.00 26.06
ATOM   2379  O51  INH Z   1       2.962  34.991  23.967  1.00 27.49
ATOM   2380  C52  INH Z   1       1.903  34.307  23.285  1.00 26.93
ATOM   2381  C55  INH Z   1       0.784  35.332  23.198  1.00 23.29
ATOM   2382  C54  INH Z   1       2.396  33.902  21.890  1.00 27.36
ATOM   2383  C53  INH Z   1       1.427  33.119  24.127  1.00 26.28
ATOM   2384  N32  INH Z   1       4.935  34.973  25.294  1.00 24.59
ATOM   2385  C31  INH Z   1       6.210  34.438  25.733  1.00 26.22
ATOM   2386  C34  INH Z   1       6.924  35.626  26.369  1.00 30.49
ATOM   2387  C37  INH Z   1       7.645  36.501  25.365  1.00 33.76
ATOM   2388  C39  INH Z   1       7.034  37.645  24.864  1.00 38.94
ATOM   2389  C42  INH Z   1       7.713  38.450  23.950  1.00 41.70
ATOM   2390  C38  INH Z   1       9.011  38.126  23.555  1.00 44.11
ATOM   2391  O47  INH Z   1       9.671  38.890  22.679  1.00 44.40
```

FIGURE 298

```
ATOM   2392  C41  INH Z   1       9.626  36.988  24.070  1.00 42.62
ATOM   2393  C40  INH Z   1       8.945  36.181  24.978  1.00 40.44
ATOM   2394  C28  INH Z   1       5.891  33.469  26.827  1.00 26.18
ATOM   2395  O30  INH Z   1       4.821  33.476  27.419  1.00 28.17
ATOM   2396  N19  INH Z   1       6.822  32.576  27.106  1.00 25.35
ATOM   2397  C11  INH Z   1       6.586  31.591  28.149  1.00 22.00
ATOM   2398  C20  INH Z   1       7.939  31.279  28.733  1.00 28.32
ATOM   2399  N22  INH Z   1       8.016  31.042  30.046  1.00 29.86
ATOM   2400  C23  INH Z   1       9.185  30.716  30.864  1.00 32.68
ATOM   2401  O21  INH Z   1       8.902  31.256  27.987  1.00 30.70
ATOM   2402  C66  INH Z   1       5.982  30.345  27.471  1.00 23.98
ATOM   2403  C7   INH Z   1       6.449  29.951  26.074  1.00 24.27
ATOM   2404  C4   INH Z   1       5.750  30.388  24.950  1.00 22.11
ATOM   2405  C2   INH Z   1       6.147  30.039  23.651  1.00 23.96
ATOM   2406  C3   INH Z   1       7.564  29.129  25.869  1.00 22.36
ATOM   2407  C6   INH Z   1       7.945  28.794  24.569  1.00 19.47
ATOM   2408  C5   INH Z   1       7.273  29.237  23.440  1.00 24.64
ATOM   2409  N9   INH Z   1       7.676  28.877  22.190  1.00 20.59
ATOM   2410  S14  INH Z   1       7.262  27.472  21.482  1.00 19.91
ATOM   2411  O15  INH Z   1       7.837  26.333  22.230  1.00 20.79
ATOM   2412  O16  INH Z   1       7.744  27.509  20.095  1.00 20.74
ATOM   2413  O17  INH Z   1       5.777  27.520  21.588  1.00 19.08
ATOM   2414  O1   HOH W   1     -11.455  19.036  16.241  1.00 11.20
ATOM   2415  O1   HOH W   2      10.092  17.907  -7.247  1.00 15.97
ATOM   2416  O1   HOH W   3       6.980  17.279  36.265  1.00 18.93
ATOM   2417  O1   HOH W   4      12.344  25.665 -10.547  1.00 26.47
ATOM   2418  O1   HOH W   5      -0.391  18.120  30.610  1.00 15.54
ATOM   2419  O1   HOH W   6     -12.910  27.809  25.785  1.00 18.19
ATOM   2420  O1   HOH W   7      16.795  17.314  22.020  1.00 20.81
ATOM   2421  O1   HOH W   8      10.903  18.975  31.456  1.00 19.26
ATOM   2422  O1   HOH W   9      12.441  11.024  16.607  1.00 18.44
ATOM   2423  O1   HOH W  10      -5.476  27.892  24.187  1.00 18.18
ATOM   2424  O1   HOH W  11      -5.638  29.457 -12.183  1.00 22.91
ATOM   2425  O1   HOH W  12      -5.887  32.377  20.291  1.00 20.26
ATOM   2426  O1   HOH W  13      12.670   1.352  23.922  1.00 21.55
ATOM   2427  O1   HOH W  14      -2.209  18.671  -7.515  1.00 17.26
ATOM   2428  O1   HOH W  15      -7.454  18.582  28.843  1.00 18.21
ATOM   2429  O1   HOH W  16      -8.860  24.488  29.900  1.00 19.86
ATOM   2430  O1   HOH W  17      -2.830  35.618   3.268  1.00 21.86
ATOM   2431  O1   HOH W  18      18.579  15.179  13.609  1.00 26.92
ATOM   2432  O1   HOH W  19      -4.688  14.506  34.209  1.00 22.07
ATOM   2433  O1   HOH W  20       2.105  17.068  26.391  1.00 16.42
ATOM   2434  O1   HOH W  21       4.863  29.127  33.970  1.00 21.17
ATOM   2435  O1   HOH W  22      -3.568  19.852   7.077  1.00 22.18
ATOM   2436  O1   HOH W  23      -5.576   3.087  15.955  1.00 26.29
ATOM   2437  O1   HOH W  24     -12.917  17.205  18.619  1.00 22.65
ATOM   2438  O1   HOH W  25      18.698  13.470  17.368  1.00 27.43
ATOM   2439  O1   HOH W  26       1.962  17.321  29.108  1.00 20.96
ATOM   2440  O1   HOH W  27       2.295  24.954  29.144  1.00 19.64
ATOM   2441  O1   HOH W  28      -1.602  16.134  32.029  1.00 21.50
ATOM   2442  O1   HOH W  29      -0.729  38.734  15.728  1.00 29.29
ATOM   2443  O1   HOH W  30      -7.527  23.769  23.695  1.00 24.34
```

FIGURE 299

```
ATOM   2444  O1  HOH W  31    14.282  22.365  16.948  1.00 22.99
ATOM   2445  O1  HOH W  32    -1.604  32.781 -14.649  1.00 27.92
ATOM   2446  O1  HOH W  33    -8.734  34.148  26.134  1.00 25.36
ATOM   2447  O1  HOH W  34     8.370  30.039  18.987  1.00 21.01
ATOM   2448  O1  HOH W  35    14.794   1.864  27.548  1.00 28.16
ATOM   2449  O1  HOH W  36   -10.739  27.532  37.044  1.00 24.62
ATOM   2450  O1  HOH W  37    -7.059   1.474  21.471  1.00 25.62
ATOM   2451  O1  HOH W  38   -11.234  14.555  24.148  1.00 23.76
ATOM   2452  O1  HOH W  39     4.445  10.833  33.936  1.00 24.00
ATOM   2453  O1  HOH W  40     7.644  22.182  -5.700  1.00 31.73
ATOM   2454  O1  HOH W  41    -9.581  18.385  34.798  1.00 27.77
ATOM   2455  O1  HOH W  42    -3.762   2.958  27.993  1.00 25.67
ATOM   2456  O1  HOH W  43    16.682  28.017  20.896  1.00 27.72
ATOM   2457  O1  HOH W  44     1.889  20.014   3.611  1.00 25.02
ATOM   2458  O1  HOH W  45     1.627  25.550  -6.758  1.00 34.05
ATOM   2459  O1  HOH W  46     0.286   7.549   9.166  1.00 38.49
ATOM   2460  O1  HOH W  47    -3.896  24.915  37.139  1.00 26.95
ATOM   2461  O1  HOH W  48    15.746  30.134   2.550  1.00 25.69
ATOM   2462  O1  HOH W  49    -5.568  10.500  33.186  1.00 28.26
ATOM   2463  O1  HOH W  50    -1.650  34.023   1.496  1.00 26.31
ATOM   2464  O1  HOH W  51    -7.652  10.717  25.362  1.00 28.32
ATOM   2465  O1  HOH W  52     0.328   0.370  13.309  1.00 27.61
ATOM   2466  O1  HOH W  53    15.355   1.106  30.215  1.00 30.33
ATOM   2467  O1  HOH W  54    10.015  24.503  30.496  1.00 29.94
ATOM   2468  O1  HOH W  55   -11.943  35.367  17.617  1.00 28.12
ATOM   2469  O1  HOH W  56    -4.357  -4.311  17.098  1.00 30.10
ATOM   2470  O1  HOH W  57    -1.130  26.109  35.655  1.00 35.14
ATOM   2471  O1  HOH W  58     6.603  33.740  -5.667  1.00 34.26
ATOM   2472  O1  HOH W  59   -11.191  21.716  18.000  1.00 28.53
ATOM   2473  O1  HOH W  60     4.005  20.176  -0.974  1.00 28.49
ATOM   2474  O1  HOH W  61    15.234  25.407  33.117  1.00 33.69
ATOM   2475  O1  HOH W  62    16.720  13.787  18.961  1.00 30.06
ATOM   2476  O1  HOH W  63    17.985  26.085  10.889  1.00 35.47
ATOM   2477  O1  HOH W  64    -4.391  35.179  19.227  1.00 26.34
ATOM   2478  O1  HOH W  65   -10.126   3.407  31.678  1.00 37.24
ATOM   2479  O1  HOH W  66    13.041  23.718  -8.522  1.00 26.67
ATOM   2480  O1  HOH W  67    15.808  27.630   0.948  1.00 31.53
ATOM   2481  O1  HOH W  68    -5.194  14.828  38.851  1.00 32.15
ATOM   2482  O1  HOH W  69    -2.993  14.561  10.647  1.00 27.57
ATOM   2483  O1  HOH W  70     4.460  25.794 -13.772  1.00 29.85
ATOM   2484  O1  HOH W  71    -1.043  10.807  12.546  1.00 36.09
ATOM   2485  O1  HOH W  72     5.955  25.591 -17.688  1.00 35.00
ATOM   2486  O1  HOH W  73    -4.797  23.062   3.425  1.00 23.14
ATOM   2487  O1  HOH W  74    12.930  17.207  31.823  1.00 25.65
ATOM   2488  O1  HOH W  75    14.465  31.814   0.729  1.00 29.17
ATOM   2489  O1  HOH W  76    11.351   8.765  29.000  1.00 29.76
ATOM   2490  O1  HOH W  77    -3.463  15.346   8.038  1.00 33.01
ATOM   2491  O1  HOH W  78     9.188  38.767  15.085  1.00 31.31
ATOM   2492  O1  HOH W  79    -2.414   9.596  32.635  1.00 44.49
ATOM   2493  O1  HOH W  80    -4.993  26.536   9.601  1.00 32.37
ATOM   2494  O1  HOH W  81   -15.925  15.529  11.947  1.00 25.86
ATOM   2495  O1  HOH W  82   -12.382  18.790  35.935  1.00 34.44
```

FIGURE 300

```
ATOM   2496  O1  HOH W  83     2.705  48.628  10.273  1.00 40.15
ATOM   2497  O1  HOH W  84   -13.564  21.329  28.598  1.00 31.01
ATOM   2498  O1  HOH W  85     6.479  39.636  16.774  1.00 32.83
ATOM   2499  O1  HOH W  86    14.961   4.598  28.207  1.00 29.83
ATOM   2500  O1  HOH W  87    18.504  19.104  23.863  1.00 28.45
ATOM   2501  O1  HOH W  88    10.773  20.142  -0.695  1.00 35.21
ATOM   2502  O1  HOH W  89     3.708  16.397   0.920  1.00 38.22
ATOM   2503  O1  HOH W  90    -4.973  37.993  -5.374  1.00 31.06
ATOM   2504  O1  HOH W  91    22.103  24.540  26.314  1.00 35.14
ATOM   2505  O1  HOH W  92    10.864  34.785  14.518  1.00 48.98
ATOM   2506  O1  HOH W  93   -12.541  12.084  30.086  1.00 37.23
ATOM   2507  O1  HOH W  94    13.549  -1.341  30.361  1.00 38.12
ATOM   2508  O1  HOH W  95    -3.286  -3.603  24.358  1.00 30.37
ATOM   2509  O1  HOH W  96    -0.950  37.575   3.392  1.00 26.13
ATOM   2510  O1  HOH W  97     2.862  18.800   1.412  1.00 26.47
ATOM   2511  O1  HOH W  98     2.741   4.340  11.947  1.00 42.25
ATOM   2512  O1  HOH W  99     1.437  11.596  33.660  1.00 33.67
ATOM   2513  O1  HOH W 100    -4.898  17.123   5.233  1.00 30.59
ATOM   2514  O1  HOH W 101    -0.328  39.659  22.285  1.00 37.92
ATOM   2515  O1  HOH W 102     0.457  18.578  -0.352  1.00 32.32
ATOM   2516  O1  HOH W 103    15.238  15.465  29.462  1.00 35.78
ATOM   2517  O1  HOH W 104    12.139  22.090  -0.159  1.00 34.03
ATOM   2518  O1  HOH W 105   -14.864  19.163  30.964  1.00 32.43
ATOM   2519  O1  HOH W 106   -14.505  20.555  25.186  1.00 29.82
ATOM   2520  O1  HOH W 107     3.363  34.814  -7.718  1.00 34.48
ATOM   2521  O1  HOH W 108   -13.197  17.085  34.279  1.00 38.85
ATOM   2522  O1  HOH W 109    -1.443   5.382  31.117  1.00 38.54
ATOM   2523  O1  HOH W 110    -0.120  14.286  35.601  1.00 31.88
ATOM   2524  O1  HOH W 111     9.032  -5.844  19.709  1.00 36.70
ATOM   2525  O1  HOH W 112    11.379  24.876  -1.986  1.00 43.81
ATOM   2526  O1  HOH W 113    12.352  38.057   2.063  1.00 31.64
ATOM   2527  O1  HOH W 114    -5.579   7.024   7.334  1.00 39.14
ATOM   2528  O1  HOH W 115    -6.985  29.910  -0.433  1.00 41.07
ATOM   2529  O1  HOH W 116     5.045  33.328  -8.532  1.00 37.73
ATOM   2530  O1  HOH W 117     8.662  12.116   1.108  1.00 39.77
ATOM   2531  O1  HOH W 118    -6.293   5.912  32.542  1.00 30.14
ATOM   2532  O1  HOH W 119   -13.725  11.954  27.110  1.00 39.76
ATOM   2533  O1  HOH W 120    16.415   8.189  22.223  1.00 29.43
ATOM   2534  O1  HOH W 121   -12.645  19.481  23.348  1.00 31.08
ATOM   2535  O1  HOH W 122   -13.636  39.606   9.864  1.00 39.73
ATOM   2536  O1  HOH W 123   -11.065   7.560  40.828  1.00 45.73
ATOM   2537  O1  HOH W 124    -8.777   3.390  20.560  1.00 36.17
ATOM   2538  O1  HOH W 125     3.379  22.820  -2.032  1.00 27.89
ATOM   2539  O1  HOH W 126   -11.598  14.866  35.138  1.00 32.20
ATOM   2540  O1  HOH W 127    -0.940  19.672  39.788  1.00 33.34
ATOM   2541  O1  HOH W 128    15.163  -4.713  22.940  1.00 36.19
ATOM   2542  O1  HOH W 129    -0.987  26.949  -6.156  1.00 36.12
ATOM   2543  O1  HOH W 130    10.863  12.854   1.718  1.00 34.61
ATOM   2544  O1  HOH W 131    14.478  36.267   1.695  1.00 41.25
ATOM   2545  O1  HOH W 132    15.776  23.818  18.687  1.00 35.61
ATOM   2546  O1  HOH W 133    21.161   7.231  12.795  1.00 32.15
ATOM   2547  O1  HOH W 134    22.887  22.904  29.299  1.00 36.68
```

FIGURE 301

```
ATOM   2548  O1  HOH W 135       3.909  17.363  36.196  1.00 35.35
ATOM   2549  O1  HOH W 136     -12.046  11.064  22.456  1.00 35.04
ATOM   2550  O1  HOH W 137     -12.824  27.211  19.118  1.00 38.04
ATOM   2551  O1  HOH W 138      14.969  31.915   7.579  1.00 35.09
ATOM   2552  O1  HOH W 139      13.443  32.417  -3.827  1.00 44.74
ATOM   2553  O1  HOH W 140       2.776  12.732  37.520  1.00 41.66
ATOM   2554  O1  HOH W 141      -1.350  12.666  37.266  1.00 40.38
ATOM   2555  O1  HOH W 142       3.324   6.477  10.524  1.00 37.22
ATOM   2556  O1  HOH W 143     -16.166  29.270  31.100  1.00 36.51
ATOM   2557  O1  HOH W 144      16.001  -2.359  30.645  1.00 44.06
ATOM   2558  O1  HOH W 145       2.861  45.550  14.180  1.00 45.63
ATOM   2559  O1  HOH W 146       4.593  25.045  35.681  1.00 44.05
ATOM   2560  O1  HOH W 147      -5.762   3.453  30.636  1.00 34.95
ATOM   2561  O1  HOH W 148      -8.031  24.355  12.086  1.00 35.62
ATOM   2562  O1  HOH W 149      -6.652  22.984  -0.071  1.00 31.34
ATOM   2563  O1  HOH W 150      -9.852  26.486  11.576  1.00 53.30
ATOM   2564  O1  HOH W 151     -11.032  13.045  39.495  1.00 41.67
ATOM   2565  O1  HOH W 152      -5.662  -6.734  17.860  1.00 50.02
ATOM   2566  O1  HOH W 153     -14.654  10.777  19.722  1.00 39.18
ATOM   2567  O1  HOH W 154      11.452  35.739   9.234  1.00 31.71
ATOM   2568  O1  HOH W 155      -0.977   7.991  -0.542  1.00 45.59
ATOM   2569  O1  HOH W 156      11.447  44.304   4.341  1.00 42.42
ATOM   2570  O1  HOH W 157      20.425  25.089  10.825  1.00 38.33
ATOM   2571  O1  HOH W 158      -0.478  42.056  23.691  1.00 40.14
ATOM   2572  O1  HOH W 159     -13.365  36.694   5.529  1.00 49.14
ATOM   2573  O1  HOH W 160      15.601  29.777  23.845  1.00 36.82
ATOM   2574  O1  HOH W 161      10.807  30.311  34.040  1.00 40.96
ATOM   2575  O1  HOH W 162      -4.239  12.123  10.131  1.00 32.53
ATOM   2576  O1  HOH W 163     -15.155  30.501  26.593  1.00 34.26
ATOM   2577  O1  HOH W 164      17.868  18.293   5.518  1.00 38.35
ATOM   2578  O1  HOH W 165      -3.791   2.469  10.886  1.00 39.48
ATOM   2579  O1  HOH W 166     -13.791  14.215  31.432  1.00 38.00
ATOM   2580  O1  HOH W 167       0.432  17.497  39.137  1.00 42.73
ATOM   2581  O1  HOH W 168     -17.968  15.461  15.749  1.00 41.59
ATOM   2582  O1  HOH W 169       3.057  38.735  -8.809  1.00 36.15
ATOM   2583  O1  HOH W 170     -13.284  32.522  19.061  1.00 43.72
ATOM   2584  O1  HOH W 171       9.161  39.858  11.511  1.00 61.20
ATOM   2585  O1  HOH W 172      -8.076  25.214   1.277  1.00 34.46
ATOM   2586  O1  HOH W 173       2.413  -7.723  17.535  1.00 50.89
ATOM   2587  O1  HOH W 174       7.967  38.224  -3.285  1.00 35.96
ATOM   2588  O1  HOH W 175      10.930  20.638  33.730  1.00 35.38
ATOM   2589  O1  HOH W 176       4.602   2.675  11.036  1.00 36.17
ATOM   2590  O1  HOH W 177       4.229  47.562   3.051  1.00 39.90
ATOM   2591  O1  HOH W 178      15.151  17.822  29.427  1.00 40.53
ATOM   2592  O1  HOH W 179      -1.974  45.545   5.497  1.00 42.30
ATOM   2593  O1  HOH W 180     -11.790   5.702  19.435  1.00 46.01
ATOM   2594  O1  HOH W 181      -3.116  46.090  12.430  1.00 36.56
ATOM   2595  O1  HOH W 182      -2.855  17.252  -3.365  1.00 46.55
ATOM   2596  O1  HOH W 183      16.937  14.782  22.299  1.00 45.85
ATOM   2597  O1  HOH W 184      15.864  28.547  32.612  1.00 52.60
ATOM   2598  O1  HOH W 185     -12.223  41.151  11.021  1.00 46.56
ATOM   2599  O1  HOH W 186      -3.669  35.551 -11.268  1.00 45.80
```

FIGURE 302

```
ATOM   2600  O1  HOH W 187    -13.450   16.205   23.864  1.00 39.99
ATOM   2601  O1  HOH W 188     21.557    8.538    9.074  1.00 32.39
ATOM   2602  O1  HOH W 189      1.733   29.325  -10.520  1.00 44.58
ATOM   2603  O1  HOH W 190     -1.094   24.213   42.979  1.00 44.98
ATOM   2604  O1  HOH W 191     -6.827    4.971    4.805  1.00 47.90
ATOM   2605  O1  HOH W 192    -13.991   33.731   13.221  1.00 40.59
ATOM   2606  O1  HOH W 193     13.588   13.644   -1.450  1.00 40.18
ATOM   2607  O1  HOH W 194     -5.326   32.039   -9.354  1.00 38.33
ATOM   2608  O1  HOH W 195     13.465   33.762  -13.581  1.00 39.35
ATOM   2609  O1  HOH W 196     20.141   -1.476   26.767  1.00 58.47
ATOM   2610  O1  HOH W 197    -13.105   19.480   20.652  1.00 48.59
ATOM   2611  O1  HOH W 198      7.070    7.353   33.532  1.00 49.27
ATOM   2612  O1  HOH W 199      6.799   28.923  -16.944  1.00 51.04
ATOM   2613  O1  HOH W 200      0.389    6.026   29.372  1.00 35.03
ATOM   2614  O1  HOH W 201      8.386   25.655   32.893  1.00 37.20
ATOM   2615  O1  HOH W 202     17.615   -0.073   29.521  1.00 48.46
ATOM   2616  O1  HOH W 203     -6.124   28.880    4.959  1.00 35.61
ATOM   2617  O1  HOH W 204     13.941    6.496   29.759  1.00 53.62
ATOM   2618  O1  HOH W 205     16.954   -0.234   14.375  1.00 37.68
ATOM   2619  O1  HOH W 206      2.522   -7.489   20.961  1.00 44.59
ATOM   2620  O1  HOH W 207      5.703   49.354   10.543  1.00 44.22
ATOM   2621  O1  HOH W 208     -9.111   38.567   12.389  1.00 50.27
ATOM   2622  O1  HOH W 209     -7.236   20.258    6.492  1.00 35.19
ATOM   2623  O1  HOH W 210      8.786    5.463   31.949  1.00 35.74
ATOM   2624  O1  HOH W 211     -7.222   40.672   16.386  1.00 42.49
ATOM   2625  O1  HOH W 212     12.825   34.503    7.617  1.00 38.94
ATOM   2626  O1  HOH W 213      5.590   30.888   31.645  1.00 26.09
ATOM   2627  O1  HOH W 214      9.169   32.503   25.209  1.00 41.71
ATOM   2628  O1  HOH W 215     23.574   26.554   10.071  1.00 56.57
ATOM   2629  O1  HOH W 216     10.056   38.516   -1.760  1.00 38.36
ATOM   2630  O1  HOH W 217     -5.653   23.538   10.071  1.00 39.02
ATOM   2631  O1  HOH W 218     -9.772   39.888   16.597  1.00 39.89
ATOM   2632  O1  HOH W 219     -7.677   22.937    7.244  1.00 48.50
ATOM   2633  O1  HOH W 220     -8.099   10.871   39.914  1.00 44.93
ATOM   2634  O1  HOH W 221      9.902   31.834   22.653  1.00 46.40
ATOM   2635  O1  HOH W 222      3.536   38.208   17.936  1.00 39.89
ATOM   2636  O1  HOH W 223      5.427   12.563   -2.175  1.00 43.37
ATOM   2637  O1  HOH W 224     19.901   17.833    4.495  1.00 39.94
ATOM   2638  O1  HOH W 225    -12.027   36.815   13.817  1.00 44.07
ATOM   2639  O1  HOH W 226     -8.746   32.585   28.696  1.00 48.46
ATOM   2640  O1  HOH W 227     17.914   15.042   24.333  1.00 48.17
ATOM   2641  O1  HOH W 228    -15.428   28.994   22.176  1.00 32.12
ATOM   2642  O1  HOH W 229     -1.184   15.555   39.910  1.00 42.24
ATOM   2643  O1  HOH W 230      1.784   16.997    9.532  1.00 38.28
ATOM   2644  O1  HOH W 231     -4.431    5.259   30.630  1.00 57.46
ATOM   2645  O1  HOH W 232     14.418   34.885   17.296  1.00 49.40
ATOM   2646  O1  HOH W 233    -10.428   31.639    7.906  1.00 38.03
ATOM   2647  O1  HOH W 234     21.073    3.624   22.298  1.00 46.76
ATOM   2648  O1  HOH W 235      9.325   20.879   -6.720  1.00 46.19
ATOM   2649  O1  HOH W 236     10.266   24.192  -17.765  1.00 43.43
ATOM   2650  O1  HOH W 237      2.085   -3.234   15.986  1.00 49.75
ATOM   2651  O1  HOH W 238     -0.063    5.328   10.360  1.00 52.94
```

FIGURE 303

```
ATOM   2652  O1  HOH W 239    10.028   22.924   33.652  1.00 45.99
ATOM   2653  O1  HOH W 240    16.681   32.926   16.387  1.00 43.29
ATOM   2654  O1  HOH W 241     7.871   13.034   37.758  1.00 46.97
ATOM   2655  O1  HOH W 242    -7.500   33.136  -10.047  1.00 53.39
ATOM   2656  O1  HOH W 243    20.580   20.554    3.052  1.00 48.18
ATOM   2657  O1  HOH W 244    17.540   25.077    8.214  1.00 43.50
ATOM   2658  O1  HOH W 245    -5.445   39.439   24.106  1.00 43.55
ATOM   2659  O1  HOH W 246    10.166   40.681   14.159  1.00 41.16
ATOM   2660  O1  HOH W 247    19.127   23.993    6.155  1.00 40.29
ATOM   2661  O1  HOH W 248    -5.962   35.247  -11.325  1.00 64.60
ATOM   2662  O1  HOH W 249   -13.021   14.668    4.628  1.00 58.02
ATOM   2663  O1  HOH W 250   -15.666   12.941   32.852  1.00 45.95
ATOM   2664  O1  HOH W 251    -5.827    4.361   28.098  1.00 39.00
ATOM   2665  O1  HOH W 252    -4.508    4.229    4.028  1.00 58.76
ATOM   2666  O1  HOH W 253    -1.679   36.793  -11.023  1.00 54.88
ATOM   2667  O1  HOH W 254    -3.188   12.850   35.709  1.00 44.15
ATOM   2668  O1  HOH W 255    -4.863   46.499    9.267  1.00 47.64
ATOM   2669  O1  HOH W 256    -8.876   14.076   39.968  1.00 49.77
ATOM   2670  O1  HOH W 257    -7.413   15.403   42.092  1.00 56.43
ATOM   2671  O1  HOH W 258    15.526   32.542   13.982  1.00 38.82
ATOM   2672  O1  HOH W 259    16.627   29.755   30.106  1.00 59.92
ATOM   2673  O1  HOH W 260    -6.350   21.495   10.220  1.00 44.14
ATOM   2674  O1  HOH W 261   -10.475   11.052   40.121  1.00 46.63
ATOM   2675  O1  HOH W 262   -16.169   28.237   33.252  1.00 50.35
ATOM   2676  O1  HOH W 263    21.143   26.244    7.273  1.00 49.50
ATOM   2677  O1  HOH W 264    18.544    3.658   19.522  1.00 54.96
ATOM   2678  O1  HOH W 265   -13.057   36.485   10.921  1.00 57.92
ATOM   2679  O1  HOH W 266   -14.213   30.872    7.965  1.00 55.62
ATOM   2680  O1  HOH W 267    23.105   19.120    9.667  1.00 51.70
ATOM   2681  O1  HOH W 268    19.557   23.525   21.545  1.00 55.10
ATOM   2682  O1  HOH W 269    -6.887    8.335   40.062  1.00 53.82
ATOM   2683  O1  HOH W 270    12.547   34.227   22.521  1.00 60.24
ATOM   2684  O1  HOH W 271    -3.101   -0.406   15.411  1.00 43.16
ATOM   2685  O1  HOH W 272     2.686   50.220    2.020  1.00 56.09
ATOM   2686  O1  HOH W 273   -14.257   29.391   17.420  1.00 56.26
ATOM   2687  O1  HOH W 274    -7.269   25.617   22.970  1.00 58.39
ATOM   2688  O1  HOH W 275    -2.828    0.486    9.670  1.00 60.53
ATOM   2689  O1  HOH W 276     9.879   32.192  -10.785  1.00 50.33
ATOM   2690  O1  HOH W 277   -13.291   27.301   37.675  1.00 47.65
ATOM   2691  O1  HOH W 278     9.031   40.412   -7.375  1.00 59.24
ATOM   2692  O1  HOH W 279    21.333   22.702    9.534  1.00 50.34
ATOM   2693  O1  HOH W 280    10.062    2.181   11.069  1.00 63.85
ATOM   2694  O1  HOH W 281   -11.670   11.608   25.465  1.00 48.90
ATOM   2695  O1  HOH W 282     5.882   36.123   22.042  1.00 58.95
ATOM   2696  O1  HOH W 283    -4.121    5.854   34.338  1.00 54.24
ATOM   2697  O1  HOH W 284    -9.020    5.421   40.050  1.00 56.11
END
```

FIGURE 304

THREE DIMENSIONAL COORDINATES OF HPTPBETA

The disclosure of U.S. Provisional Application Ser. No. 60/413,547 filed 25 Sep. 2002, is herein incorporated by reference in its entirety.

FIELD OF THE INVENTION

The present invention relates to three-dimensional structures of the catalytic domain of HPTPbeta [SEQ ID NO: 7], and structures derived therefrom.

BACKGROUND OF THE INVENTION

HPTPbeta (Kruegar et al., EMBO J., 9, (1990)) has been suggested inter alia for modulating the activity of angiopoietin receptor-type tyrosine kinase Tie-2. See PCT Patent Application WO 00/65088. Inventors have shown in the present and concurrently filed patent applications that modulation of HPTPbeta modulates activities of both Tie-2 and VEGFR2. Therefore, HPTPbeta could be a target for the treatment of angiogenesis mediated disorders. However, the crystal structure of HPTPbeta has not been described. High-resolution 3D experimental models are needed to obtain insight into the mechanisms of HPTPbeta activation, the source of interactions between specific ligands and HPTPbeta, and to design better agonists and antagonists of HPTPbeta. Thus, there is a need for crystal structure of HPTPbeta.

SUMMARY OF THE INVENTION

The present invention attempts to address this need by providing a 3D structure of the catalytic domain of human HPTPbeta [SEQ ID NO: 7], and suitable means to design and identify potent and selective agonists or antagonist of the HPTPbeta for the treatment of angiogenesis mediated disorders.

In one aspect the invention provides for crystalline forms of the HPTPbeta catalytic domain [SEQ ID NO: 7] having unit cell dimensions of a=62±1 Å, b=72±1 Å, and c=70±1 Å, $\alpha$=90°, $\beta$=93±3°, $\gamma$=90° in the space group P2$_1$ (monoclinic form) and unit cell dimensions of a=39±1 Å, b=71±1 Å, and c=120±2 Å, $\alpha$=90°, $\beta$=90°, $\gamma$=90° in the space group P2$_1$2$_1$2$_1$ (orthorhombic form).

In another aspect the invention provides for a method of identifying a compound useful for the treatment of an angiogenesis mediated disorder, comprising the steps of using a three-dimensional (3D) structure of HPTPbeta as defined by the atomic coordinates of FIGS. 7-304, or combination thereof; and employing said 3D structure to design, modify, or select a compound that binds HPTPbeta in silico.

A method of identifying a compound useful for the treatment of an angiogenesis mediated disorder, comprising the steps of: providing a crystal of the complex between HPTPbeta and compound, or alternately exposing a crystal of HPTPbeta with a compound in aqueous media; exposing the complex to X-rays to generate a diffraction pattern; capturing the pattern to a recording device to generate diffraction data; processing the data to solve the complex structure; determining the locator of compound within complex structure; wherein the compound binding to the binding site of HPTPbeta, wherein the binding site is selected from the group consisting of P0, P+1, P−1, or mixtures thereof, indicates the compound is useful for the treatment of the HPTPbeta mediated disorder.

A method of identifying a compound useful for the treatment of an angiogenesis mediated disorder, comprising the steps of: selecting the compounds based on computer-aided drug design (CADD) using the coordinates from FIGS. 7-304; further analyzing if the compound binds HPTPbeta or modulates HPTPbeta activity in an in vitro, in vivo, or ex vivo assay; and identifying those compounds that bind HPTPbeta or modulate HPTPbeta activity as compounds useful for the treatment of an angiogenesis mediated disorder.

These and other objects, features, and advantages will become apparent to those of ordinary skill in the art from a reading of the following detailed description and the appended claims.

BRIEF DESCRIPTION OF THE DRAWINGS AND TABLES

FIG. 4 schematically represents interactions between Compound 1 and the HPTPbeta catalytic domain [SEQ ID NO: 7]: (a) hydrogen bonding and (b) Van der Waals interactions. The ligand is shown in magenta, the main body of the protein is colored blue, and the WPD loop residues are colored red.

Figure 5:
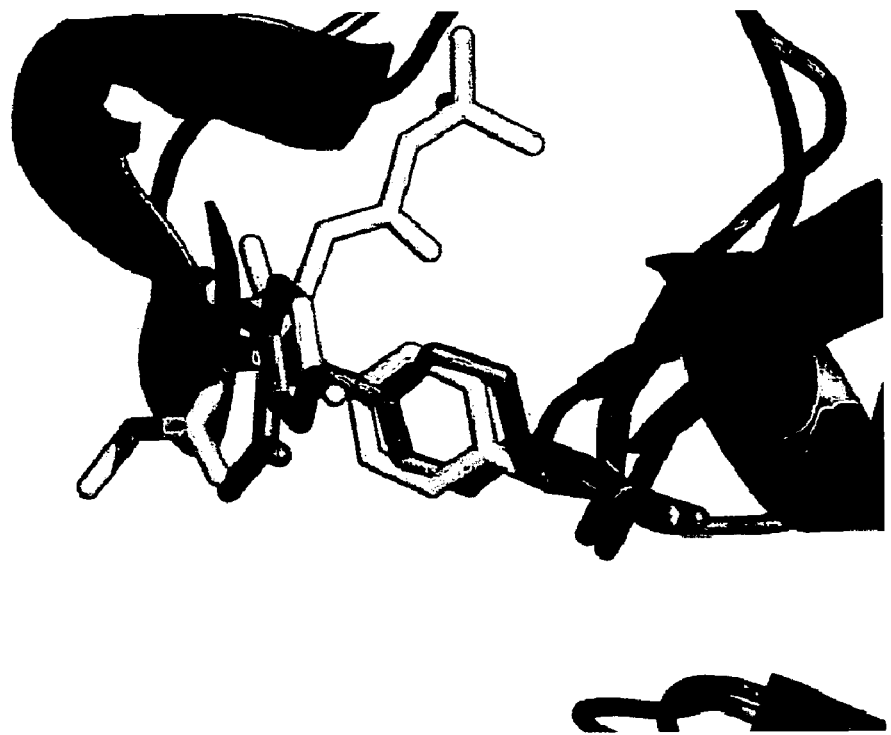

FIG. 5 shows an overlay of the phosphotyrosine (darker) bound to PTP-1B trap mutant and Compound 1 (lighter) bound to the HPTPbeta catalytic domain [SEQ ID NO: 7].

Figure 6:
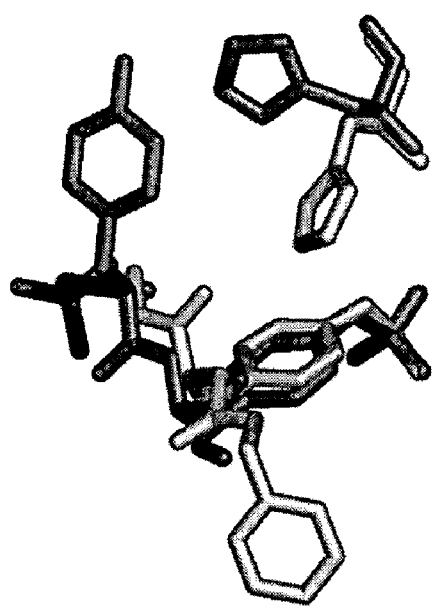

FIG. 6 shows Tyr212 conformation in enzyme complex with Compound 1 (lighter) and Compound 2 (darker).

FIGS. 7-102 show the atomic structure coordinates for HPTPbeta as derived from a monoclinic crystal of ligand-free HPTPbeta catalytic domain [SEQ ID NO: 7] polypeptide.

FIGS. 103-201 show the atomic structure coordinates for HPTPbeta and the inhibitor molecule as derived from a monoclinic crystal of HPTPbeta bound to the inhibitor Compound 1.

FIGS. 202-252 show the atomic structure coordinates for HPTPbeta as derived from an orthorhombic crystal of ligand-free HPTPbeta catalytic domain [SEQ ID NO: 7] polypeptide.

FIGS. 253-304 show the atomic structure coordinates for HPTPbeta and the inhibitor molecule as derived from an orthorhombic crystal of HPTPbeta bound to the inhibitor Compound 2.

The data shown in FIGS. 7-304 are expressed based on the Protein Data Bank (PDB) format: The PDB format is a format containing coordinates (X, Y, Z,), etc. of individual atoms, and is the standard formats in expressing coordinates of bipolymers. In FIGS. 7-304, the "ATOM" appearing in the utmost left column (1st column) denotes each atom of the atomic coordinates. The numbers (1, 2, 3, . . . etc.) appearing in the next column (2nd column) are serial numbers of individual atoms. Subsequently, in the left to right direction in these Figures, there are denoted the type of each atom and its position in the amino acid to which it belongs (e.g., "CB", "CG", "SD") (in the 3rd column); the amino acid residue to which each atom belongs (three-letter abbreviations for amino acids, e.g. "MET", "ASN") (In the 4th column); the sequence number of the residue counted from the N-terminal (in the 5th column); X-coordinate (in angstrom (Å) unit) (in the 6th column); Y-coordinate (in angstrom (Å) unit) (in the 7th column); Z-coordinate (in angstrom (Å) unit) (in the 8th column).

Sequence Listing Description

Each of the nucleotide or amino acid sequences in the sequence listing is shown in Table A.

TABLE A

| Sequence Description | SEQ ID NO: Nucleotide, Amino Acid | Species | Genbank (GB) or Derwent (D) Accession No. for Nucleotide Sequence | Related Genbank (GB) or Derwent (D) Accession Nos. |
| --- | --- | --- | --- | --- |
| HPTPbeta (HPTP-beta, PTPRB, PTPbeta, PTPB, R-PTP-beta) | 1 (nucleotide) | Homo Sapiens | X54131 | NM_002837 |
| HPTPbeta (HPTP-beta, PTPRB, PTPbeta, PTPB, R-PTP-beta) | 2 (amino acid) | Homo Sapiens | X54131 | NM_002837 |
| HPTPbeta intracellular domain (ICD) | 3 (nucleotide) | Homo Sapiens | | NM_002837 |
| HPTPbeta intracellular domain (ICD) | 4 (amino acid) | Homo Sapiens | | NM_002837 |
| HPTPbeta truncated ICD | 5 (nucleotide) | Homo Sapiens | | NM_002837 |
| HPTPbeta truncated ICD | 6 (amino acid) | Homo Sapiens | | NM_002837 |
| HPTPbeta crystallized ICD | 7 (amino acid) | Homo Sapiens | | NM_002837 |
| Intracellular domain forward primer | 8 | | | |
| Intracellular domain reverse primer | 9 | | | |
| Crystal domain forward primer | 10 | | | |
| Crystal domain reverse primer | 11 | | | |
| Crystal, His-tag forward primer | 12 | | | |
| Crystal, His-tag reverse primer | 13 | | | |
| Crystal TEV-site, forward primer | 14 | | | |
| Crystal TEV-site, reverse primer | 15 | | | |

DETAILED DESCRIPTION OF THE INVENTION

The present invention is directed to identifying or obtaining compounds useful for modulating HPTPbeta activity. Crystal structure information presented herein is useful in designing compounds and modeling them or their potential interaction with binding site(s) of HPTPbeta. Actual compounds may be identified from following design and model work performed in silico. A compound identified using the present invention may be effective for the treatment of an angiogenesis mediated disorder. These and other aspects and embodiments of the present invention are discussed below.

One aspect of the invention provides for the crystalline form of HPTPbeta. Four crystal structures of HPTPbeta are presented. FIGS. 7-102 show coordinates of HPTPbeta in the monoclinic crystal form having unit cell dimensions of a=61.89 Å, b=71.53 Å, and c=70.35 Å, $\alpha=90°$, $\beta=93.25°$, $\gamma=90°$ in the space group $P2_1$.

FIGS. 103-201 show coordinates of HPTPbeta in complex with Compound 1 in the monoclinic crystal form having unit cell dimensions of a=62.19 Å, b=71.80 Å, and c=70.45 Å, $\alpha=90°$, $\beta=93.56°$, $\gamma=90°$ in the space group $P2_1$.

FIGS. 202-252 show coordinates of HPTPbeta in the orthorhombic crystal form having unit cell dimensions of a=39.25 Å, b=71.13 Å, and c=119.91 Å, $\alpha=90°$, $\beta=90°$, $\gamma=90°$ in the space group $P2_12_12_1$.

FIGS. 253-304 show coordinates of HPTPbeta in complex with Compound 2 in the orthorhombic crystal form having unit cell dimensions of a=38.85 Å, b=69.61 Å, and c=117.78 Å, $\alpha=90°$, $\beta=90°$, $\gamma=90°$ in the space group $P2_12_12_1$. The structural data according to FIGS. 7-102; 103-201; 202-252; and 253-304 are at approximately 1.9, 1.8, 1.75, and 1.65 Angstrom (Å) resolution, respectively.

The coordinates of FIGS. 7-304 provide a measure of atomic location in Angstroms, to a first decimal place. The coordinates are a relative set of positions that define a shape in three dimensions. It is possible that an entirely different set of coordinates having a different origin and/or axes could define a similar or identical shape. Furthermore, varying the relative atomic positions of the atoms of the structure so that the root mean sqare deviation of the conserved residue backbone atoms (i.e. the nitrogen-carbon-carbon backbone atoms of the protein amino acid residues) is less than 1.5 Å, preferably less than 1.0 Å and more preferably less than 0.5 Å, when superimposed on the coordinates provided in FIGS. 7-304 for the conserved residue backbone atoms, will generally result in a structures which are substantially the same as the structures of FIGS. 7-304 in terms of both its structural characteristics and potency for structure-based drug design of HPTPbeta modulators. Likewise changing the number and/or positions of the water molecules of FIGS. 7-304 will not generally affect the potency of the structure for structure-based drug design of HPTPbeta modulators. Thus for the purposes described herein as being aspects of the present invention, it is within the scope of the invention if: the coordinates of FIGS. 7-304 are transposed to a different origin and/or axes; the relative atomic positions of the atoms of the structure are varied so that the root mean square deviation of conserved residue backbone atoms is less than 1.5 Å (preferably less than 1.0 Å and more preferably less than 0.5 Å) when superimposed on the coordinates provided in FIGS. 7-304, respectively, for the conserved residue backbone atoms; and/or the number and/or positions of water molecules is varied. Reference herein to the coordinates of FIGS. 7-304 thus includes the coordinates in which one or more individual values of the Figures are varied in this way.

Also, modifications in the HPTPbeta crystal structure due to e.g. mutations, additions, substitutions, and/or deletions of amino acid residues could account for variations in the HPTPbeta atomic coordinates. However, atomic coordinate data of HPTPbeta modified so that a ligand that bound to one or more binding sites of the HPTPbeta binding pocket would also be expected to bind to the corresponding binding sites of the modified HPTPbeta, and therefore are, for the purposes described herein as being aspects of the present invention, also within the scope of the invention. References herein to the coordinates of FIGS. 7-304 thus include the coordinates modified in this way. Preferably, the modified coordinate data define at least one HPTPbeta binding site.

Another aspect of the invention provides for the HPTPbeta binding pocket, wherein the binding pocket comprises at least the P(0), P(1) and P(-1) binding sites. The nomenclature of the binding sites is based on binding of phosphorylated peptides to PTPases, for example: P(0) is the active site of the enzyme, which accommodates the phosphotyrosine residue of the phosphopeptide; P(+1) is the site which accommodates the amino acid of the phosphopeptide that is adjacent to the phosphotyrosine in the direction of the carboxy terminus of the phosphopeptide; P(−1) accommodates the amino acid of the phosphopeptide that is adjacent to the phosphotyrosine in the direction of the amino terminus of the phosphopeptide. In HPTPbeta, P(0) is characterized by at least amino acid residues 152, 74-77, 209-214, 244-253, 288-290, and 293 of SEQ ID NO: 7; P(+1) is characterized by at least amino acid residues 76-80, 48-66, 284-292, and 212-214 of SEQ ID NO: 7; P−1 is characterized by at least amino acid residues 69-76, 119-123, and 149-154 of SEQ ID NO: 7.

In Silico Drug Design

For the first time, the present invention permits the use of virtual design techniques (i.e., computer modeling or "in silico") to design, select, and synthesize compounds capable of inhibiting/stimulating or binding HPTPbeta. In turn, these drug candidates may be effective in the treatment of an angiogenesis mediated disorder.

The term "angiogenesis mediated disorder" is defined as a disorder that involves a modulation in angiogenic activity resulting in the biological manifestation of a disease, disorder, and/or condition; in the biological cascade leading to the disorder; or as a symptom of the disorder. The Applicants have shown that the process of angiogenesis is modulated by HPTPbeta. This "involvement" of HPTPbeta in an angiogenesis mediated disorder includes, but is not limited to, the following: (1) The modulation of HPTPbeta activity as a "cause" of the angiogenesis mediated disorder or biological manifestation, whether the HPTPbeta is modulated genetically, by infection, by autoimmunity, trauma, biomechanical causes, lifestyle, or by some other causes; (2) The modulated HPTPbeta activity is part of the observable manifestation of the disease or disorder. That is, the disease or disorder is measurable in terms of the modulated HPTPbeta activity. From a clinical standpoint, modulated HPTPbeta activity indicates the disease, however, HPTPbeta activity need not be the "hallmark" of the disease or disorder; (3) The modulated HPTPbeta activity is part of the biochemical or cellular cascade that results in the disease or disorder. In this respect, inhibiting or stimulating of HPTPbeta (per the respective therapeutic goal) interrupts the cascade, and thus controls the disease; (4) The angiogenesis mediated disease or disorder is not the result of modulation in HPTPbeta activity, but modulation of the HPTPbeta activity would result in amelioration of the disease. "Modulation in HPTPbeta activity," as used herein, encompasses both unwanted or elevated HPTPbeta activity and desired or reduced HPTPbeta activity. As used herein, "angiogenesis mediated disorders" include: (1) those disorders, diseases and/or unwanted conditions which are characterized by unwanted or elevated angiogenesis, or (2) those disorders, diseases and/or unwanted conditions which are characterized by wanted or reduced angiogenesis.

Treatment of Angiogenesis Mediated Disorders

Treatment of disorders mediated by elevated angiogenesis

The agents screened by the present invention may be used in a method for the treatment of a disorder mediated by elevated angiogenesis. The agents identified by the present invention may be used to treat diseases like diabetic retinopathy, macular degeneration, sickle cell anemia, sarcoid, syphilis, pseudoxanthoma elasticum, Paget's disease, vein or artery occlusion, carotid obstructive disease, chronic uveitis/ vitritis, mycobacterial infections, Lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, diseases associated with rubeosis (neovascular iation of the angle) and diseases caused by the abnormal proliferation of fibrovasucular or fibrous tissue including all forms of proliferative viteroretinopathy. Agents screened by of the present invention can also treat diseases associated with chronic inflammation such as Crohn's disease and ulcerative colitis, psoriasis, sarcoidosis and rheumatoid arthritis. Other diseases that can be treated according to the present invention are hemangiomas, Osler-Weber-Rendu disease, or hereditary hemorrhagic telangiectasia, solid or blood borne tumors and acquired immune deficiency syndrome.

Treatment of Disorders Mediated by Reduced Angiogenesis

In one aspect, an agent may be used in a method for the treatment of a disorder mediated by reduced angiogenesis. As expected, this involves stimulated angiogenesis to treat a disease, disorder, or condition. It is likely that an agent that inhibits HPTPbeta would be used for treatment of an angiogenesis mediated disorder. The disorder is one characterized by tissue that is suffering from or is at risk of suffering from ischemic damage, infection, and/or poor healing, which results when the tissue is deprived of an adequate supply of oxygenated blood due to inadequate circulation (ischemic tissue).

In Silico Screening of Compounds

In the present invention, it is possible to carry out virtual screening for drugs using the above-described atomic coordinates or coordinates derived therefrom.

Briefly, the atomic coordinates of the three-dimensional structure elucidated by the invention are input into a computer so that images of the structure and various parameters are shown on the display. Then, other resultant data are input into a virtual compound library. Since a virtual compound library is contained in a virtual screening software such as DOCK-4 (Kuntz, UCSF), the above-described data may be input into such a software. Candidate drugs may be searched for, using a three-dimensional structure database of virtual or no-virtual drug candidate compounds, such as MDDR (Prous Science, Spain).

The potential stimulating/inhibitory or binding effect (i.e., interaction or association) of a compound may be analyzed prior to its actual synthesis and testing by the use of computer modeling techniques. If the theoretical structure of the given compound suggests insufficient interaction and association between it and HPTPbeta, synthesis and testing of the compound may be obviated. However, if computer modeling indicates a strong interaction, the molecule may then be synthesized and tested for its ability to bind to or stimulate/inhibit HPTPbeta using various methods known in the art or as described in the co-pending application. In this manner, synthesis of inoperative compounds may be avoided.

Agonist/antagonist or binding drug candidates of HPTPbeta may be computationally evaluated and designed by means of a series of steps in which chemical entities or fragments are screened and selected for their ability to bind with individual binding sites or combinations thereof (e.g., P0, P+1, and/or P−1) or other areas of HPTPbeta.

One skilled in the art may use any of several methods to screen chemical entities or fragments for their ability to associate with HPTPbeta and more particularly with the specific binding sites. This process may begin by visual inspection of, for example, the active site on the computer screen based on the HPTPbeta coordinates in any of the FIGS. 7-304. Selected fragments or chemical entities may then be positioned in a variety of orientations, or docked, within an individual binding site of HPTPbeta as defined supra. Docking may be accomplished using software such as QUANTA, SYBYL, followed by energy minimization and molecular dynamics with standard molecular mechanics forcefields, such as CHARMM and AMBER.

Specialized computer programs may also assist in the process of selecting fragments or chemical entities. These include: (1) GRID (Goodford, P. J., "A Computational Procedure for Determining Energetically Favorable Binding Sites on Biologically Important Macromolecules" J. Med. Chem., 28, pp. 849-857 (1985)), available from Oxford University, Oxford, UK; (2) MCSS (Miranker, A. and M. Karplus, "Functionality Maps of Binding Sites: A Multiple Copy Simultaneous Search Method" Proteins: Structure, Function and Genetics, 11, pp. 29-34 (1991)), available from Molecular Simulations, Burlington, Mass.; (3) AUTODOCK (Goodsell, D. S. and A. J. Olsen, "Automated Docking of Substrates to Proteins by Simulated Annealing" Proteins: Structure, Function, and Genetics, 8, pp. 195-202 (1990)), available from Scripps Research Institute, La Jolla, Calif.; and (4) DOCK (Kuntz, I. D. et al., "A Geometric Approach to Macromolecule-Ligand Interactions" J. Mol. Biol., 161, pp. 269-288 (1982)), available from University of California, San Francisco, Calif.; (5) GLIDE available from Schrodinger Inc.; (6) FlexX available from Tripos Inc; (7) GOLD (Jones et al., J. Mol. Biol., 245, 43-53, 1995), available from the Cambridge Crystallographic Data Centre.

Once suitable chemical entities or fragments have been selected, they can be assembled in silico or synthesized into a single drug candidate. In silico assembly may proceed by visual inspection of the relationship of the fragments to each other on the three-dimensional image displayed on a computer screen in relation to the structure coordinates of HPTPbeta. This would be followed by manual model building using software such as QUANTA or SYBYL. Chemical syntheses are by those methods well-known in the art.

Useful programs to aid one of skill in the art in connecting the individual chemical entities or fragments include the following: (1) CAVEAT (Bartlett, P. A. et al, "CAVEAT: A Program to Facilitate the Structure-Derived Design of Biologically Active Molecules". In Molecular Recognition in Chemical and Biological Problems", Special Pub., Royal Chem. Soc., 78, pp. 182-196 (1989)), available from the University of California, Berkeley, Calif.; (2) 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)); and (3) HOOK (available from Molecular Simulations, Burlington, Mass.).

Instead of proceeding to build an HPTPbeta agonist or antagonist in a step-wise fashion one fragment or chemical entity at a time as described above, drug candidates useful for the treatment of angiogenesis mediated disorders may be designed as a whole or "de novo" using either an empty active site or optionally including some portion(s) of a known agonist or antagonist. These methods include the following: (1) LUDI (Bohm, H. -J., "The Computer Program LUDI: A New Method for the De Novo Design of Enzyme Inhibitors", J. ComR. Aid. Molec. Design, 6, pp. 61-78 (1992)), available from Biosym Technologies, San Diego, Calif.; (2) LEGEND (Nishibata, Y. and A. Itai, Tetrahedron, 47, p. 8985 (1991)), available from Molecular Simulations, Burlington, Mass.; (3) LeapFrog (available from Tripos Associates, St. Louis, Mo.). Examples of known agonist or antagonists are described in WO 02/26774 A2.

Once a compound has been designed or selected by the above methods, the efficiency with which that compound may bind to HPTPbeta may be tested and optimized by computational evaluation. For example, an effective HPTPbeta agonist must preferably demonstrate a relatively small difference in energy between its bound and free states (i.e., a small deformation energy of binding). Thus, the most efficient HPTPbeta agonist should preferably be designed with deformation energy of binding of not greater that about 10 kcal/mole, preferably, not greater than 7 kcal/mole. HPTPbeta agonists may interact with the enzyme in more than one conformation that is similar in overall binding energy. In those cases, the deformation energy of binding is taken to be the difference between the energy of the free compound and the average energy of the conformations observed when the agonist binds to the enzyme.

A compound designed or selected, as binding to HPTPbeta may be further computationally optimized so that in its bound state it would preferably lack repulsive electrostatic interaction with the target enzyme. Such non-complementary (e.g., electrostatic) interactions include repulsive charge-charge, dipole-dipole, and charge-dipole interactions. Specifically, the sum of all electrostatic interactions between the compound and the enzyme when the compound is bound to HPTPbeta, preferably make a neutral or favorable contribution to the enthalpy of binding.

Specific computer softwares are available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A. Kollman, University of California at San Francisco, ©1994]; QUANTA/CHARMM [Molecular Simulations, Inc., Burlington, Mass. ©1994]; and Insight II/Discover (Biosym Technologies Inc., San Diego, Calif. ©1994). Other software packages will be known to those skilled in the art.

Once an HPTPbeta-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to HPTPbeta by the same computer methods described in detail, above.

Crystallographic Evaluation of Chemical Entities for Binding to HPTPbeta

For the first time, this invention allows one skilled in the art to study the binding of chemical entities to HPTPbeta by exposing either individual compounds or mixtures of compounds (such as may be obtained from combinatorial libraries) into HPTPbeta crystals, or, alternatively, by co-crystallization of the substances of interest with HPTPbeta, using methods known to those of ordinary skill in the art, and the crystallization conditions based on those described in the following examples. Acquisition and analysis of X-ray diffraction data from these crystals can be then performed using standard methods. If substance or substances bind to HPTPbeta then positive difference electron density will be observed in the Fourier maps calculated using the X-ray diffraction intensities and phases obtained from the HPTPbeta models presented in FIGS. 7-304. Models of the chemical entities can than be built into the electron density using standard methods and the resulting structures can be refined against the X-ray diffraction data, providing experimental data describing the interaction of the molecules of interest with the enzyme. Those skilled in the art can use these models to design HPTPbeta inhibitors based either on purely structural data or on combination of structural data with enzyme-activity based structure-activity relationship and in silico drug design.

EXAMPLES

1. Cloning and Expression of the Catalytic Domain of HPTPbeta [SEQ ID NO: 7]

The intracellular domain (ICD) of HPTPbeta (SEQ ID NO: 3) is cloned from human fetal heart cDNA containing the full gene of HPTPbeta (SEQ ID NO: 1) by PCR using Advantage Polymerase (Clontech) and the primers:

```
Beta-FOR2:   5'-GATCGACCATTATCTGTCCAC-3'   SEQ ID NO:8

Beta-REV2:   5'-CAGGAGCTCTTCAGGTACAT-3'    SEQ ID NO:9
``` under the following reaction conditions: 1 cycle at 95° C. for 1 minute, 30 cycles at 94° C. for 30 seconds and 62° C. for 2 minutes, and a final cycle of 62° C. for 3 minutes. PCR products are subcloned into pPCRScript vector (Stratagene) and sequenced, revealing 2 silent mutations in the HPTPbeta ICD clone, one at base pair (bp) 5372 (C to T, a Glycine residue) and the other a bp 5985 (C to T, a Tyrosine residue) (nucleotides are numbered from bp #1 in SEQ ID #1, which means that the initiator methionine in SEQ ID #2 corresponds to the codon beginning at base pair #31 in SEQ ID NO 1).

The sequence [SEQ ID NO: 5] encoding base pairs 5014 to 5949 of SEQ ID NO: 1 is cloned into the vector pMALc2x (New England Biolabs) using the following oligonucleotides:

```
5' primer:
5'-CGAGCATACGTAGATCGACCATTATCTGTCC-3'   SEQ ID NO:10

3' primer:
5'-CGAGCAAGCTTATTATTGTTCACTCCGTAGC-3'   SEQ ID NO:11
```

The HPTPbeta truncated gene [SEQ ID NO: 5] (Wang, Y. & Pallen, C. J. The journal of Biological Chemistry, 267(23), pp16696-16702, 1992) is amplified with these primers by PCR using the pPCRScript plasmid described above as the template, digested with SnaB1 and HindIII and ligated to pMAL-c2x that is pre-digested with Asp700 and HindIII to create plasmid pMAL-c2x-PTPbeta(5014-5949). The protein construct thus encoded is maltose-binding protein from *Escherichia coli* (MBP) followed by a Factor Xa cleavage site followed by base pairs 5014 to 5949 of HPTPbeta SEQ ID NO: 1. A six-histidine tag is added to the carboxy terminus using the QuikChange Site Directed Mutagenesis kit (Stratagene) and the following primers:

```
5'-GAAAGCTACGGAGTGAACAACATCATCATCATCATCATTAATAAGCTTGGCACTGG-3'   SEQ ID NO:12

5'-CCAGTGCCAAGCTTATTAATGATGATGATGATGATGTTGTTCACTCCGTAGCTTTC-3'   SEQ ID NO:13
```

The coding sequence of the clone (pMAL-c2x-PTPbeta (5014-5949)His6) is verified by DNA sequence analysis. Finally, the Factor Xa site is changed to a TEV protease cleavage site using the QuikChange Site Directed Mutagenesis kit and the following primers:

```
5'-AACAACAACCTCGGGGAGAATCTTTATTTTCAGGGCGATCGACCATTATCTG-3'   SEQ ID NO:14

5'-CAGATAATGGTCGATCGCCCTGAAAATAAAGATTCTCCCCGAGGTTGTTGTT-3'   SEQ ID NO:15
```

The protein construct thus encoded is maltose-binding protein from *Escherichia coli* (MBP) followed by a TEV protease cleavage site, followed by base pairs 5014 to 5949 of HPTPbeta SEQ ID NO: 1, followed by a six-histidine tag. After TEV protease cleavage, the resulting protein contains a non-native Glycine residue on the amino-terminus and a six-histidine tag on the carboxy-terminus (SEQ ID 7).

The coding sequence of the final clone (pMAL-TEV-PTP-beta(5014-5949)His6) is verified by DNA sequence analysis and used for recombinant protein production, *Escherichia coli* BL21-RIL cells (Strategene) are used as the host strain. Bacteria are grown in a 10-liter fermenter, using Super Broth medium (30 g tryptone, 20 g yeast extract, 7.5 g NaCl per liter) supplemented with 0.2% glucose and 100 mg/L, ampicillin at 22C to mid-log phase, at which point the bacteria are induced with 0.5 mM β-isopropyl thiogalactopyranoside and harvested by centrifugation 16 hours after induction.

2. Purification of the Catalytic Domain of HPTPbeta [SEQ ID NO: 7]

26 grams of cell pellet containing the overexpressed protein are suspended in 287.5 ml of 50 mM $NaH_2PO_4$, 300 mM NaCl, 10 mM imidazole, 5 mM β-mercaptoethanol, pH 8.0 (Buffer A) containing 4 "Complete-EDTA free" protease inhibitor tablets (Roche). Cells are lysed during 2 passes through a French press at 12000 psi, at 4° C. The lysate is centrifuged for 40 minutes at 17000 rpm, using a JA-17 (Sorvall) rotor at 4° C. Resulting supernatant (295 ml) is loaded at 10 ml/min, 4° C. on a 73 ml Ni-NTA column which is pre-equilibrated with Buffer A. The column is washed with 200 ml of 75 mM Imidazole in Buffer A and the protein is eluted with 175 mM of imidazole in Buffer A (6 ml fractions, 10 ml/min). Fractions containing the fusion protein are pooled based on Coomassie Blue-stained SDS-PAGE analysis. The pool is diluted to 515 ml with pure water to final conductivity of 10.42 mS/m (approximately 125-135 mM NaCl).

Diluted fusion protein is loaded onto a 150 ml Resource Q15 (Pharmacia) column pre-equilibrated with 10 mM Tris-HCl, 2 mM DTT, pH 7.2. The protein is eluted with a 22.5-29% linear gradient of 10 mM Tris-HCl, 2 mM DTT, 1 M NaCl, pH 7.2 (10 ml fractions are collected at 10 ml/min flow rate). Fractions are pooled based on SDS-PAGE analysis.

N-Octyl β-glycopyranoside (NOG) and dithiothreitol (DTT) are added to the pool resulting in final concentrations of 0.25% and 2 mM, respectively. Approximately 1.5 mg of recombinant Tobacco Etch Virus protease (TEV protease, Invitrogen) are added to the pool (using ~1/200 weight ratio of protease to substrate) and the reaction mixture is incubated with stirring for 17 hrs at 4° C. SDS-PAGE analysis reveals ~65% cleavage efficiency. Further addition of TEV protease does not result in additional cleavage.

Reaction mixture is adjusted to the final conductivity of 10.4 mS/cm by addition of 10 mM Tris-HCl, 2 mM DTT, 0.25% NOG, pH 7.2 (Buffer B) and loaded on a 150 ml Resource Q15 column pre-equilibrated with Buffer B. Proteins are eluted with a 19-24% linear gradient of 1M NaCl in Buffer B. Unfortunately, the fusion protein and the cleaved PTPβ catalytic domain [SEQ ID NO: 7] do not separate well using this method. Fractions containing the cleaved catalytic domain are pooled based on SDS-PAGE analysis.

The pool containing the PTPbeta catalytic domain [SEQ ID NO: 7] as well as some of the uncleaved fusion protein is concentrated down to 4.5 ml using a YM-10 membrane in an Amicon stirred cell and slowly passed through a 3 ml amylose resin (Quiagen) column pre-equilibrated with Buffer-B. Flow-through is collected and the column is washed with 3 ml of Buffer B. Combined flow-through and wash are loaded on a 48×5.0 cm Superdex 75 prep grade column, pre-equilibrated with Buffer B. The column is eluted with Buffer B at 2 ml/min while 10 ml fractions are collected. Two peaks are observed indicating good separation between the full-length fusion protein and the HPTPbeta catalytic domain [SEQ ID NO: 7]. Fractions are analyzed by SDS-PAGE and those found to contain pure protein are pooled. HPTPbeta catalytic domain [SEQ ID NO: 7] is concentrated to 9.8 mg/ml using an Amicon stirred cell equipped with YM-10 membrane. Total yield of HPTPbeta catalytic domain [SEQ ID NO: 7] is 58.6 mg based on the $OD_{280}$ measured in 6M guanidine-hydrochloride, pH 8.0.

3. Crystallization of the Catalytic Domain of HPTPbeta [SEQ ID NO: 7], collection of X-ray Diffraction Data, and Structure Solution HPTPbeta catalytic domain [SEQ ID NO: 7] is crystallized in hanging drops via the sparse-matrix approach using crystallization screens manufactured by Hampton Research and Emerald Biostructures (currently DeCode Genetics). Several polyethylene glycol (PEG)/magnesium chloride conditions are identified as crystallization leads, which are eventually refined to the following condition: 18% PEG8000, 100 mM TRIS-HCl pH 7.5, 1% β-mercaptoethanol (BME), 0.2 M MgCl2 in 6 µl drops containing equal amounts of protein and reservoir solutions. Under these conditions, crystals usually appear after 2-5 days, reach their maximum size of 0.2×0.2×0.3 mm in 6-8 days and decay within 3-4 weeks after set-up. The best crystals are grown by streak-seeding, which results in more reliable nucleation. For structural studies, individual protein crystals are cryoprotected by immersion into Paratone-N oil followed by flash cooling in a stream of nitrogen gas at 100K.

Two clearly different crystal morphologies are observed—one is subsequently identified as orthorhombic and the other as monoclinic crystal form. Laboratory X-ray source equipped with a CCD X-ray detector is used to collect 2.3 Å data from the orthorhombic crystals, which are found to belong to the space group $P2_12_12_1$ with unit cell dimensions of a=39.25 Å, b=71.13 Å, and c=119.91 Å, α=90°, β=90°, γ=90°, and one molecule in the asymmetric unit (a.u.). Programs of the HKL2000 suite are employed to index, integrate, and scale the diffraction data.

The crystal structure is solved via molecular replacement (CCP4 program AMoRe) (Collaborative Computational Project, Number 4. 199 Acta Cryst. D50, 760-763; and Navaza, J. *Act Cryst.* A50, 157-163 (1994) using the published structure of PTPµ from the Protein Data Bank (PDB), PDB code 1RPM as the search model. After multiple rounds of manual rebuilding (program O) and refinement (programs Refimac and SHELXL), the crystal structure of the enzyme contains residues 24 to 305, as well as 115 water molecules, and had the $R_{work}$ of 21.0% and $R_{free}$ of 26.2%. Concomitantly we are able to collect high-resolution data for both the orthorhombic and the monoclinic crystal forms of the enzyme using a synchrotron radiation source (beam lines 17-ID and 17-BM of the Advanced Photon Source at the Argon Naturation Laboratory—APS/ANL). The monoclinic form of the enzyme is found to belong to the space group $P2_1$ with unit cell dimensions of a=61.89 Å, b=71.53 Å, and c=70.35 Å, α=90°, β=93.25°, γ=90°. Using synchrotron data we are able to refine the structure of the enzyme in the orthorhombic crystal form to 1.75 Å resolution ($R_{work}$=19.0%, $R_{free}$=22.0%) and the monoclinic crystal form (which has two protein molecules in the a.u.) to 1.9 Å resolution ($R_{work}$=20.0%, $R_{free}$=24.0%). Validation of structures using programs PROCHECK and SFCHECK does not reveal any geometric abnormalities. Finished structures contain residues 19 to 310 as numerous water molecules.

Proprietary X-ray diffraction data were collected at beamlines 17-ID and 17-BM in the facilitates of the Industrial Macromolecular Crystallography Association Collaborative Access Team (IMCA-CAT) at the Advanced Photon Source. These facilities are supported by the companies of the Industrial Macromolecular Crystallography Association through a contract with Illinois Institute of Technology (IIT), executed through IIT's Center for Synchrotron Radiation Research and Instrumentation. Use of the Advanced Photon Source was supported by the U.S. Department of Energy, Basic Energy Sciences, Office of Science, under Contract No. W-31-109-Eng-38.

4. Exposing Inhibitors into HPTPbeta Catalytic Domain [SEQ ID NO: 7] Crystals, and Structure Solution of the Resulting Complexes To study the interaction of ligands with PTPβ we expose (soak) various molecules of interest into both the orthorhombic and the monoclinic crystals at a concentration of 1-10 mM in the crystallization buffer, using exposure times from 2 to 24 hours. Monoclinic crystals of the enzyme can be readily soaked (2-4 hours) with compounds of interest—and the resulting soaked crystals usually (with a notable exception that is outlined later) do not deteriorate. True ligands and/or inhibitors can be unambiguously identified, by analyzing electron density maps calculated using X-ray diffraction data collected from the soaked crystals. Interestingly, when molecules that belong to the family of Compound 2 are soaked into the monoclinic crystals, the latter deteriorate to the point where collection of X-ray diffraction data is impossible. Fortunately, the orthorhombic crystals of PTPbeta catalytic domain [SEQ ID NO: 7] can be successfully soaked with compounds of this class, which is particularly interesting in view of the fact that the orthorhombic crystals are nigh impossible to soak with many other classes of compounds—even 24-hr soaks do not result in small molecule penetration into the crystal lattice.

X-ray diffraction data from soaked crystals are collected and processed at APS/ANL in the same manner as described above, X-ray crystal structures of the complexes are solved via molecular replacement (AMoRe) using corresponding native structures for each crystal form as search models. Several rounds of manual rebuilding (O) and refinement (Refmac, SHELXL) are employed, after which the inhibitor molecules are built into the electron density (Quanta, SPARTAN) and refined. The geometry of the structures is analyzed using programs PROCHECK and SPFCHECK.

5. HPTPbeta Catalytic Domain [SEQ ID NO: 7] in Two Space Groups—Overview of the Unliganded Structure The two final models of the protein contain residues 19-310, which are clearly defined in the electron density maps of the orthorhombic and monoclinic forms, respectively. Loop 89-96 is entirely disordered in the orthorhombic form (and therefore is omitted from the final model) and is mostly disordered in the monoclinic form. The orthorhombic crystal form of the PTPbeta catalytic domain [SEQ ID NO: 7] contains one promoter in a.u. whereas the monoclinic form contains two promoters in the a.u. Root mean square deviation (rmsd) of the protein backbone atoms of the two molecules found in the monoclinic a.u. is 0.45 Å, whereas rmsd of the orthorhombic PTPbeta catalytic domain [SEQ ID NO: 7] and the monoclinic promoters is 0.55-0.66 A. Upon close inspection, it is evident that there are no major structural differences between the three molecules—the changes are confined to minor movements of the loops and rearrangements of conformationally unrestrained side chains of surface-exposed amino-acids. Therefore it is sufficient to supply the overall description of the unliganded PTPbeta catalytic domain [SEQ ID NO: 7] performed using the best-defined (highest resolution) promoter—the one found in the orthorhombic crystal form.

PTPbeta belongs to a broad family of PTPases that are extremely dissimilar in terms of their biological function, intracellular localization, and domain structure. These very diverse enzymes have one feature in common, namely their catalytic domain, the fold of which is preserved throughout this whole class of PTPases,. Historically, the first human PTPase to be discovered and studied is PTP-1B, which is a soluble single-domain phosphatase that was first identified in human placenta in 1989. Because of its early discovery and biological significance, PTP-1B is the most studied PTPase to-date, with over 40 X-ray crystal structures, both unliganded and liganded, available in the PDB. PTP-1B structure is therefore considered to be an archetype of the catalytic domain of this class of PTPases. Here, we use comparisons between PTPbeta catalytic domain [SEQ ID NO: 7] and PTP-1B (PDB code 2HNP) structures to illustrate the relationship between our crystal structure of the PTPbeta catalytic domain [SEQ ID NO: 7] and the rest of the PTPases of this class.

Figure 1:
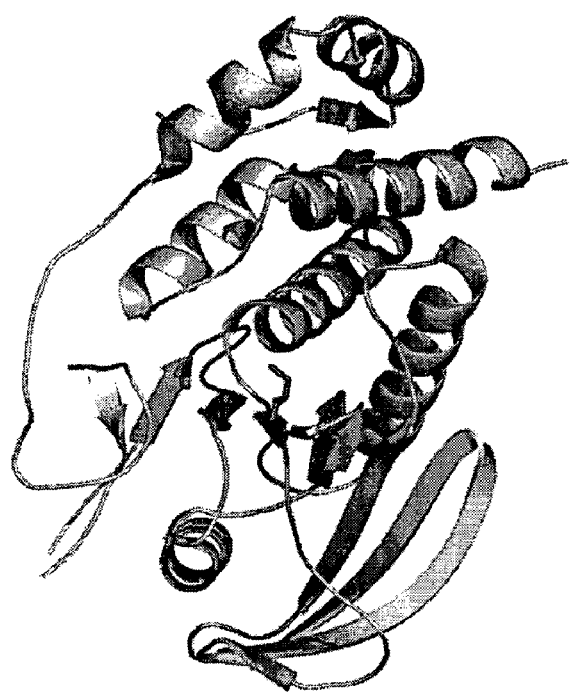
FIG. 1 shows a ribbon representation of the carbon-alpha trace of the HPTPbeta catalytic domain [SEQ ID NO:7].

Similar to PTP-1B, the crystal structure of PTPbeta catalytic domain [SEQ ID NO: 7] reveals a common PTPase fold, consisting of two closely-packed compartments: the alpha-helical domain and the beta-sheet one (FIG. 1). When the backbone atoms of the two enzymes are superimposed, the two structures fit with an rmsd of 1.3 A for the matching atoms. In this case, however, the rmsd does not adequately represent the dissimilarity of the two structures. The macroscopic and microscopic differences between PTP-1B and PTPbeta catalytic domain [SEQ ID NO: 7] are closely examined below. On the level of backbone, the differences between the two structures are:

The N-terminus—PTPbeta catalytic domain [SEQ ID NO: 7] structure has 12 more ordered residues (residues 19-31) than PTP-1B structure, and the first two alpha-helices (residues 32-55) of the two proteins occupy different positions.

The 106-111 loop of PTPbeta catalytic domain [SEQ ID NO: 7] is placed differently than the corresponding 74-80 loop of PTP-1B.

The first beta-strand and its beta-turn (residues 161-168 of PTPbeta catalytic domain [SEQ ID NO: 7]) are shifted with respect to their PTP-1B analogues (130-139)

The geometry of the 191-197 loop of PTPbeta catalytic domain [SEQ ID NO: 7] is very different from its PTP-1B analogue 162-167.

Loop 233-238 adopts a radically different conformation from its PTP-1B equivalent 202-209.

Residues 262-277 and the C-terminal a-helix 291-310 are shifted with respect to the position of their equivalents (residue 252-270 and a-helix 264-282) in PTP-1B.

Figure 2:
FIG. 2 shows the change that occurs in the WPD loop of the HPTPbeta catalytic domain [SEQ ID NO: 7] upon ligand binding (ligand-free structure is shown as darker trace).

The active site of the enzyme (residues 152-153, 244-253, 288-290, and 293) is located at the junction of the two domains and is occupied by four water molecules. A characteristic loop, containing a Trp-Pro-Asp triad (the WPD loop, residues 208-214) is located near the binding site. In PTP-1B and other phosphatases this loop is known to adopt a different conformation upon binding of ligands in the active site. As will be shown in the next example this conformation change also takes place when PTPbeta catalytic domain [SEQ ID NO: 7] binds to ligands (FIG. 2). The WPD loop of PTPbeta catalytic domain [SEQ ID NO: 7] contains a His212 instead of Phe181 in PTP-1B, and the orientation of PTPbeta catalytic domain [SEQ ID NO: 7] Trp209 is different from that of its PTP-1B analogue Trp179.

Additional small, but important distinctions between PTPbeta catalytic domain [SEQ ID NO: 7] and PTP-1B are further discussed in the example 7.

6. Synthesis of Compounds 1 ((S)-[1-Methylcarbamoyl-2-(4-sulfonamino-phenyl)-enthyl]-Carbamic Acid Benzyl Ester) and Compound 2 ({2-4-Hydroxy-phenyl)-1-[1-methylcarbamoyl-2-(4-sulfoamino-phenyl)-ethylcarbamoyl]-ethyl}-Carbamic Acid tert-butyl Ester)

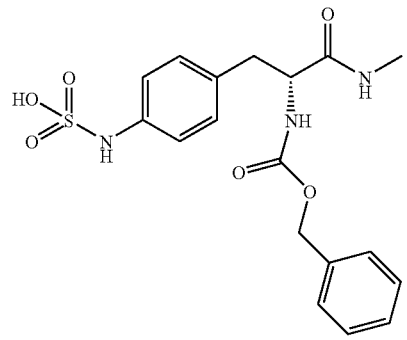

(S)-[1-Methylcarbamoyl-2-(4-sulfonamino-phenyl)-ethyl]-carbamic acid benzyl ester (Compound 1)

Boc-D-Phe(4-NO$_2$)-NMe: Boc-D-Phe(4-NO$_2$)-OH (4.0 g, 12.9 mmol) is dissolved in anhydrous tetrahydrofuran (20 mL) with 4-methylmorpholine (1.56 mL, 14.2 mmol). Isobutylchloroformate (1.84 mL, 14.2 mmol) is dropwise added at 0° C. and the mixture is stirred for 1 hr. at 0° C. Methylamine (12.9 mL, 2.0 M in tetrahydrofuran) is added dropwise at 0° C. and the mixture is stirred for 18 hr. at room temperature. The mixture is then recrystallized from 1:1 DCM:methanol to give a white solid.

H-D-Phe(4-NO$_2$)-NMe: Boc-D-Phe(4-NO$_2$)-NMe (1.5 g, 4.64 mmol) is dissolved in HCl (10 mL, 4.0 M in 1,4-dioxane), and the resulting mixture is stirred at room temperature for 1 hr. Ether (60 mL) is added to the mixture and the resulting precipitate is collected by filtration to yield pure white product.

CBZ-D-Phe(4-NO$_2$)-NMe: H-D-Phe(4-NO$_2$)-NMe (410 mg, 1.84 mmol) is dissolved in anhydrous DCM (10 mL) and diisopropylethylamine (0.352 mL, 2.02 mmol). Benzyl chloroformate (0.263 mL, 1.84 mmol) is added dropwise at 0° C., the mixture is allowed to warm to room temperature and is stirred for 72 hr. The solution is partitioned between DCM and 1N HCl. The organic layer is washed with brine, dried over MgSO$_4$, filtered and evaporated to give crude white solid.

CBZ-D Phe(4-NH$_2$)-NMe: CBZ-D-Phe(4-NO$_2$)-NMe (80 mg, 0.224 mmol) is dissolved in EtOAc:ethanol (1:1, 2 mL) and tin(II) chloride dihydrate (252 mg, 1.12 mmol) is added. The mixture is stirred at room temperature for 18 h. The reaction is partitioned between EtOAc (25 mL) and 1N NaOH (25 mL). The organic layer is washed twice more with 1N NaOH (25 mL). The combined organics were dried over MgSO$_4$, filtered and evaporated to give pure yellow oil.

(S)-[1-Methylcarbamoyl-2-(4-sulfoamino-phenyl)-ethyl]-carbamic acid benzyl ester: In a dry flask 0.107 g of the aniline compound is dissolved in 2 mL pyridine. To this solution is added 0.156 g of sulfurtrioxide-pyridine complex. The mixture is stirred 5 minutes then diluted with 25 mL of 7% ammonium hydroxide. The mixture is evaporated down to an off-white solid and purified to provide 0.056 g of product as its ammonium salt. $^1$H(D$_2$O): δ7.26-7.20 (m, 3H), 7.11-6.96 (m, 6H), 4.90-4.78 (m, 2H), 4.08 (t, 1H, J=8.3 Hz), 2.84-2.66 (m, 2H) 2.50 (s, 3H)

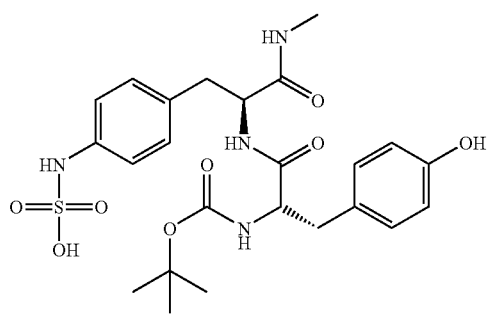

{2-(4-Hydroxy-phenyl)-1-[1-methylcarbamoyl-2-(4-sulfoamino-phenyl)-ethylcarbamoyl]-ethyl}-carbamic acid tert-butyl ester (Compound 2)

Boc-Phe(4-NO$_2$)-NMe: Boc-Phe(4-NO$_2$)-OH (10.0 g, 32.3 mmol) is dissolved in anhydrous tetrahydrofuran (32.2 mL) with 4-methylmorpholine (3.90 mL, 35.4 mmol). Isobutylchloroformate (4.18 mL, 32.3 mmol) is dropwise added at 0° C. and the mixture is stirred for 1 hr. at 0° C. Methylamine (332.3 mL, 2.0 M in tetrahydrofuran) is added dropwise at 0° C. and the mixture is stirred for 18 hr. at room temperature. The mixture is then recrystallized from 1:1 DCM:methanol to give 6.69 g pure white solid.

H-Phe(4-NO$_2$)-NMe: Boc-D-Phe(4-NO$_2$)-NMe (1.5 g, 4.64 mmol) is dissolved in HCl (10 mL, 4.0 M in 1,4-dioxane) and the resulting mixture is stirred at room temperature for 1 hr. Ether (60 mL) is added to the mixture and the resulting precipitate is collected by filtration to yield pure white product.

{2-(4-Hydroxy-phenyl)-1-[1-methylcarbamoyl-2-(4-nitro-phenyl)-ethylcarbamoyl]-ethyl} carbamic acid tert-butyl ester: H-L-Phe(4-NO$_2$)-NMe (200 mg, 0.770 mmol) is dissolved in 1 mL DMF. Diisopropylethylamine (209 mg, 1.62 mmol), EDC (162 mg, 0.847 mmol), HOBt.H$_2$O (130 mg, 0.847 mmol), and Boc-Tyr (238 mg, 0.847 mmol) are added and the mixture is stirred for 18 hr. at 20 ° C. The mixture is partitioned between water and EtOAc (2×60 mL). The organics are combined and washed with brine, dried over MgSO$_4$, filtered and evaporated to give crude product. Purification by flash chromatography, which is eluted with 97:3 DCM:methanol to give pure white solid.

{2-(4-Hydroxy-pyenyl)-1-[1-methylcarbamoyl-2-(4-amino-phenyl)-ethylcarbamoyl]-ethyl}-carbamic acid tert-butyl ester: {2-(4-Hyrdroxy-phenyl)-1-[1-methylcarbamoyl-2-(4-nitro-phenyl)-ethylcarbamoyl]-ethyl} carbamic acid tert-butyl ester (300, 0.617 mmol) is dissolved in methanol (10 mL). To this was added palladium on carbon (10% by weight, 100 mg). The reaction is placed under a hydrogen atmosphere until reaction is complete (tlc). The catalyst is removed by filtration and the filtrate is concentrated to provide the amine, which is used without purification.

{2-(4-Hydroxy-phenyl)-1-[1-methylcarbamoyl-2-(4-sulfoamino-phenyl)-ethylcarbamoyl]-ethyl}-carbamic acid tert-butyl ester: In a dry flask the aniline compound is dissolved in 2 mL pyridine. To this solution is added 0.295 g of sulfurtrioxide-pyridine complex. The mixture is stirred 5 minutes then diluted with 50 mL of 7% ammonium hydroxide. The mixture is evaporated down to an off-white solid and purified to provide 0.062 g of product as its ammonium salt. $^1$H(D$_2$O): δ7.00-6.87 (m, 6H), 6.69 and 6.66 (d, 2H, J=9.3 Hz), 4.28 (t, 1H, J=8.0), 4.05 (t, 1H, J=8.7 Hz), 2.81-2.65 (m, 4H), 2.47 (s, 3H), 1.21 (s, 9H)

7. HPTPbeta Catalytic Domain [SEQ ID NO: 7] in Complex with Ligands

Crystal structures are a very useful tool for design of PTP-beta inhibitors. As an illustration, we describe here two different modes of binding of PTPbeta inhibitors, determined through solving high-resolution crystal structures of PTPbeta catalytic domain [SEQ ID NO: 7] complexes with the representative members of these classes—Compound 1 and Compound 2.

Additional similarities and differences between the structure of the ligand-binding site of PTP-1B and PTPbeta catalytic domain [SEQ ID NO: 7] become apparent upon comparison of the ligand-bound structures of PTPbeta catalytic domain [SEQ ID NO: 7] with the ligand-bound structure of PTP-1B (PDB code 2HNP).

Figure 3:
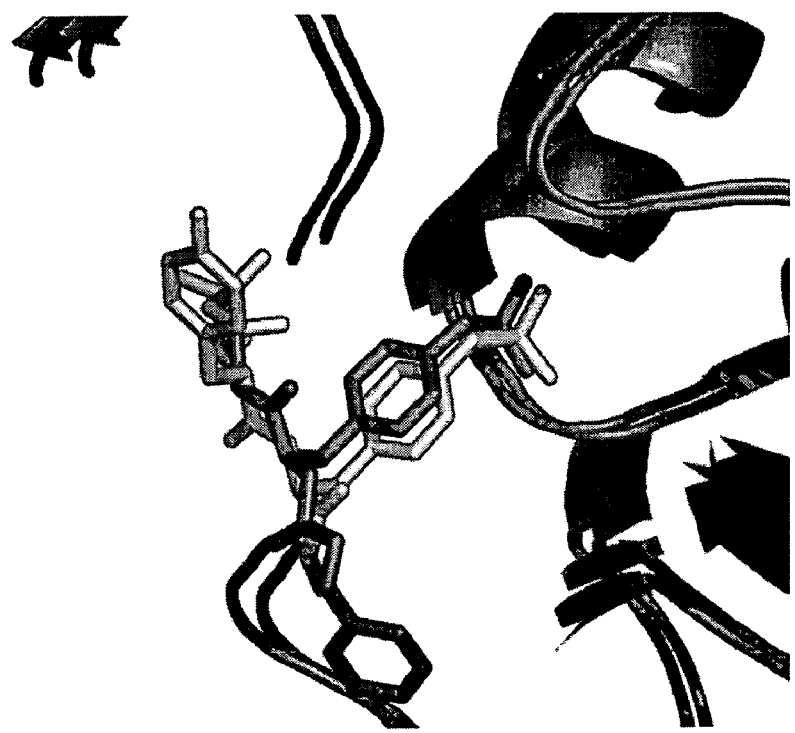
FIG. 3 shows a superposition between Compound 1 ((S)-[1-Methylcarbamoyl-2-(4-sulfoamino-phenyl)-ethyl]-carbamic acid benzyl ester) (darker) and Compound 2 ({2-(4-Hydroxy-phenyl)-1-[1-methylcarbamoyl-2-(4-sulfoamino-phenyl)-ethylcarbamoyl]-ethyl}-carbamic acid tert-butyl ester) (lighter) structures bound to HPTPbeta catalytic domain [SEQ ID NO: 7].

On the one hand, as can be seen from FIG. 3, the two sulfamic acid-based inhibitors described here bind with the phenyl sulfamic acid portion of the molecule occupying the P(0) pocket (the active site) of the enzyme. The sulfamic acid moiety is connected to the active site by an extensive network of hydrogen bonds (FIG. 4a), closely resembling the binding of phosphotyrosine phosphate group to previously studied PTPases, as exemplified in FIG. 5 showing superposition of phosphotyrosine bound in the active site of PTP-1B (PDB code 1PTV) with the sulfamic acid bound in the active site of PTPbeta catalytic domain [SEQ ID NO: 7]. The binding of sulfamic acids in P(0) pocket is accompanied by the closure of the WPD loop (FIG. 2) which brings Asp211 within hydrogen-bonding distance to sulfamic acid nitrogen and results in sandwiching of the phenyl between residues His212 and Ala247—again, resembling binding of phosphotyrosine to the active site of PTPases (e.g. PTP-1B). The phenyl group of the ligand participates Van der Waal's interactions with residues His286, His212, Ala247, Val249, and Gln289 (FIG. 4b). It is thus easy to assume that the phenyl sulfamic acid mimics the phosphotyrosine side chain that is the natural target of PTPbeta.

On the other hand, there are significant differences in the structure of the binding sites between PTPbeta catalytic domain [SEQ ID NO: 7] and PTP-1B. In particular these include:

Orientation of Gln289 is different from that of its PTP-1B analogue Gln262

Orientation of the side chain of His212 is different from that of its PTP-1B analogue Phe182

PTPbeta catalytic domain [SEQ ID NO: 7] has an Asn76-Asp75 instead of Asp48-Arg47 in PTP-1B, which results in different orientation of both amino acid side chains, as well as slight but significant difference in the geometry of the backbone in that region of the protein In PTPbeta catalytic domain [SEQ ID NO: 7], His286 occupies the month of the P(+1) pocket, instead of Gly259 in PTP-1B. This bulky amino acid is likely to modulate access to the P(+1) pocket of the enzyme Differences in the 147-155 stretch conformation as compared to its PTP-1B analogue are likely to result in different specificity of the P(−1) pocket Conformation of the 48-58 region of PTPbeta catalytic domain [SEQ ID NO: 7] is different from that of its equivalent in PTP-1B, likely resulting in altered specificity of the P(−1) pocket of the enzyme In both PTPbeta catalytic domain [SEQ ID NO: 7] complex structures presented here, the sulfamic acid moiety and the phenyl ring bind to the enzyme in a very similar manner, however the binding mode of the remainder of these two inhibitors to the protein is quite different, as follows:

P(0) pocket: Whereas Compound 1 interacts with His212 through the C-terminal amide carbonyl and through the phenyl ring, in the structure of the Compound 2 complex, His212 side chain is abstracted away from the binding site as a result of an interaction with the tyrosine side chain of the inhibitor (FIG. 6). The N-terminal amide carbonyl of Compound 2 forms a hydrogen bond with the nitrogen of the Asn76 side chain whereas there is no direct interaction between Asn76 and Compound 1.

P(−1) pocket: The N-terminal carbobenzoxy group of Compound 1 participates in extensive Van der Waal's contacts with Arg73 and Tyr74. In contrast, the C-terminal amide of Compound 2 interacts with Tyr74 and to a lesser extent with Arg150.

P(+1) pocket: The only interaction of Compound 1 with this pocket of the enzyme is a superficial VdW contact with Gin289Compound 2 interacts with the P(+1) pocket through hydrogen bonding of the t-BOC carbonyl with Gln289 side chain, and via extensive VdW interactions of the tert-butyl group with Ile77, Val249, Gln289, Val285, His286, and even Arg56. Notably, His286 is misplaced from its position in the both the unliganded enzyme and in the complex of PTPbeta catalytic domain [SEQ ID NO: 7] with Compound 1. In its new position, His286 pi-stacks with the guanidine of Arg281 and forms potential hydrogen bonds with main-chain carbonyls of Val288 and Lys52 or, depending on its protonation state, an ion-pair with Arg56.

In view of the above, it is not surprising that Compound 2, which forms an impressive array of interactions with the enzyme is a more potent inhibitor than Compound 1 which has a much more modest number of interactions with PTPbeta catalytic domain [SEQ ID NO: 7].

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope.

What is claimed is:

1. A method of identifying a drug candidate compound for the treatment of an angiogenic mediate disorder, comprising:
   a) employing the three-dimensional structural coordinates of the human protein tyrosine phosphatase beta (HPTPbeta) catalytic domain [SEQ ID NO:7] as set forth in FIGS. 202-252 to graphically image the HPTPbeta catalytic domain [SEQ ID NO: 7], and determining the binding mode of a compound within the catalytic domain;
   b) selecting one or more compounds which have the best fit with the HPTPbeta catalytic domain [SEQ ID NO:7] as a set forth in FIGS. 202-252 wherein the compounds are computationally positioned at one or more areas of said imaged HPTPbeta catalytic domain [SEQ ID NO:7] and
   c) assaying analyzing the ability of said drug candidate compound to bind or modulate HPTPbeta activity.

2. A method of identifying a drug candidate compound for the treatment of an angiogenic mediate disorder, comprising:
   a) employing the three-dimensional structural coordinates of the HPTPbeta catalytic domain [SEQ ID NO:7] as set forth in FIGS. 7-102 to graphically image the HPTPbeta catalytic domain [SEQ ID NO:7], and determining the binding mode of a compound within the catalytic domain;
   b) selecting one or more compounds which have the best fit with the HPTPbeta catalytic domain [SEQ ID NO:7] as set forth in FIGS. 7-102 wherein the compounds are computationally positioned positioning a drug candidate compound at one or more areas of said imaged HPTPbeta catalytic domain [SEQ ID NO:7]; and
   c) assaying the ability of said drug candidate compound to bind or modulate HPTPbeta activity.

3. The method according to claim 1 wherein said drug candidate compound is positioned at at least amino acid residues 152, 74-77, 209-214, 244-253, 288-290, and 293 of [SEQ ID NO:7].

4. The method according to claim 2 wherein said drug candidate compound is positioned at at least amino acid residues 152, 74-77, 209-214, 244-253, 288-290 , and 293 of [SEQ ID NO:7].

5. The method according to claim 1 wherein said drug candidate compound is positioned at at least amino acid residues 76-80, 48-66, 284-292 and 212-214 of [SEQ ID NO:7].

6. The method according to claim 2 wherein said drug candidate compound is positioned at at least amino acid residues 76-80, 48-66, 284-292 and 212-214 of [SEQ ID NO:7].

7. The method according to claim 1 wherein said drug candidate compound is positioned at at least amino acid residues 69-76, 119-123, and 149-154 of [SEQ ID NO:7].

8. The method according to claim 2, wherein said drug candidate compound is positioned at at least amino acid residues 69-76, 119-123, and 149-154 of [SEQ ID NO:7].

9. A method of identifying an inhibitor of an HPTPbeta molecule, comprising:
   a) providing a crystal of HPTPbeta comprising the amino acid residues of SEQ ID NO:7 which either has space group $P2_12_12_1$ and unit cell parameters a=39 Å, b=72 Å, c=120 Å and $\alpha=\beta=\gamma=90°$, or space group $P2_1$ with unit cell parameters of a=62 Å, b=70 Å, c=70 Å and $\alpha=90°$, $\beta=93°$, $\gamma=90°$;
   b) subjecting the crystal in (a) to X-ray diffraction and determining the three-dimensional structure coordinates of the HPTPbeta catalytic domain;
   c) employing the three-dimensional structure coordinates from (b) to graphically display the three-dimensional structure and identifying the active binding site residues of Asn74 Asn75 Ile76, Leu77, Cys152, Pro209, Asp210, His211, Gly212, Val213, Pro214, Cys244, Ser245, Ala246, Gly247, Val248, Gly249, Arg250, Thr251, Gly252, Thr253, Gin288, Thr289, Glu290, and Tyr293;

d) using the atomic coordinates of amino acids Asn74 Asn75 Ile76, Leu77, Cys 152, Pro209, Asp210, His211, Gly212, Val213, Pro214, Cys244, Ser245, Ala246, Gly247, Val248, Gly249, Arg250, Thr251, Gly252, Thr253, Gin288, Thr289, Glu290, and Tyr293 as determined in c) to generate a three-dimensional structure of a molecule comprising an HPTPbeta active site binding pocket so that the root mean square deviation of conserved residue backbone atoms is less than 1.5 Å as compared to the three-dimensional coordinates in a-c);

e) employing the three-dimensional structure from d) to design or select a potential drug candidate; and f) contacting the potential drug candidate with the molecule to determine the abilut of the potential inhibitor to associated with the molecule.

10. A method of identifying an inhibitor of an HPTPbeta molecule, comprising:

a) providing a crystal of HPTPbeta comprising the amino acid residues of SEQ ID NO:7 which either has space group $P2_12_12_1$ and unit cell parameters a=39 Å, b=72 Å, c=120 Å and $\alpha=\beta=\gamma=90°$, or space group $P2_1$ with unit cell parameters of a=62 Å, b=70 Å, c=70 Å and $\alpha=90°$, $\beta=93°$, $\gamma=90°$;

b) subjecting the crystal in (a) to X-ray diffraction and determining the three-dimensional structure coordinates of the HPTPbeta catalytic domain;

c) employing the three-dimensional structure coordinates from (b) to graphically display the three-dimensional structure and identifying the active binding site residues of Glu48, Glu49, Leu50, Lys51, Asp52, Val53, Gly54, Arg55, Asn56, Gln57, Ser58, Cys59, Asp60, Ile61, Ala62, Leu63, Leu64, Pro65, Glu66, Ile76, Leu77, Pro78, Tyr79, Asp80, Gly212, Val213, Pro214, Val284, His285, Met286, Val287, Gln288, Thr289, Glu290, Cys291, and Gln292;

d) using the atomic coordinates of amino acids Glu48, Glu49, Leu50, Lys51, Asp52, Val53, Gly54, Arg55, Asn56, Gln57, Ser58, Cys59, Asp60, Ile61, Ala62, Leu63, Leu64, Pro65, Glu66, Ile76, Leu77, Pro78, Tyr79, Asp80, Gly212, Val213, Pro214, Val284, His285, Met286, Val287, Gln288, Thr289, Glu290, Cys291, and Gln292 as determined in c) to generate a three-dimensional structure of a molecule comprising an HPTPbeta active site binding pocket so that the root mean square deviation of conserved residue backbone atoms is less than 1.5 Å as compared to the three-dimensional coordinates in a-c);

e) employing the three-dimensional structure from d) to design or select a potential drug candidate; and f) containing the potential drug candidate with the molecule to determine the ability of the potential inhibitor to associate with the molecule.

* * * * *

UNITED STATES PATENT AND TRADEMARK OFFICE
CERTIFICATE OF CORRECTION

PATENT NO. : 7,507,568 B2
APPLICATION NO. : 10/634027
DATED : March 24, 2009
INVENTOR(S) : Evdokimov et al.

It is certified that error appears in the above-identified patent and that said Letters Patent is hereby corrected as shown below:

On the cover page, Item (73) Assignee, please delete the word "Proctor," and substitute the following:

-- Procter --

On the cover page, under the section "References Cited," "Other Publications," please insert the following:

-- Wang et al., "Expressions and Characterization of Wild Type, Truncated, and Mutant Forms of the Intracellular Region of the Receptor-Like Protein Tyrosine Phosphatase HPTPβ," *J. Of Biological Chem.*, 267(23) (1992).

Wright et al., "Protein-Tyrosine Phophatases in the Vessel Wall Differential Expression After Acute Arterial Injury," *Arterioscler Thromb Vasc.*, 1189-1198 (2000).

Fachinger et al., "Functional Interaction of Vascular Endothelial-Protein-Tyrosine Phosphatase with the angiopoietin Receptor Tie-2," *Oncogene*, 18:5948-5953 (1999).

Gaits et al., "Increase in Receptor-Like Protein Tyrosine Phosphatase Activity and Expression Level on Density-Dependent Growth Arrest of Endothelial Cells," *Biochem. J.*, 311:97-103 (1995).

Harder et al., "Characterization and Kinetic Analysis of the Intracellular Domain of Human Protein Tyrosine Phosphatase β (HPTPβ) Using Synthetic Phosphopeptides," *Biochem. J.*, 296:395-401 (1994).

Krueger et al., "Structural Diversity and Evolution of Human Receptor-Like Protein Tyrosine Phosphatases," *The EMBRO J.*, 9(10):3241-3252 (1990).

UNITED STATES PATENT AND TRADEMARK OFFICE
CERTIFICATE OF CORRECTION

PATENT NO. : 7,507,568 B2
APPLICATION NO. : 10/634027
DATED : March 24, 2009
INVENTOR(S) : Evdokimov et al.

It is certified that error appears in the above-identified patent and that said Letters Patent is hereby corrected as shown below:

Martin, "3D Database Searching in Drug Design," *J. of Medicinal Chemistry*, 35(12):2145-2154 (1992).

Chanteau *et al.*, "Synthesis of Anthropomorphic Molecules: The NanoPutians," *J. Org. Chem.*, 68:8750-8766 (2003).

Hopkins *et al.*, "Inhibitors of Kinesin Activity from Structure-Based Computer Screening," *Biochemistry*, 39:2805-2814 (2000).

Rarey *et al.*, "A Fast Flexible Docking Method Using an Incremental Construction Algorithm," *J. Mol. Biol.*, 261:470-489 (1996).

Jones *et al.*, "Development and Validation of a Genetic Algorithm for Flexible Docking," *J. Mol. Biol.*, 267:727-748 (1997).

Stahl *et al.*, "Detailed Analysis of Scoring Functions for Virtual Screening," *J. Med. Chem.*, 44:1035-1042 (2001).

Skoichet *et al.*, "Lead Discovery Using Molecular Docking," *Chem. Biology*, 6:439-446 (2002). --

In claim 1, column 53, line 35, please delete the word "mediate" and substitute the following:

-- mediated --

In claim 2, column 53, line 51, please delete the word "mediate" and substitute the following:

-- mediated --

In claim 9, column 55, line 17, please delete the word "abilut" and substitute the following:

-- ability --

UNITED STATES PATENT AND TRADEMARK OFFICE
CERTIFICATE OF CORRECTION

PATENT NO. : 7,507,568 B2
APPLICATION NO. : 10/634027
DATED : March 24, 2009
INVENTOR(S) : Evdokimov et al.

It is certified that error appears in the above-identified patent and that said Letters Patent is hereby corrected as shown below:

In claim 10, column 56, line 25, please delete the wording "containing" and substitute the following:

-- contacting --

Signed and Sealed this

Twenty-sixth Day of May, 2009

JOHN DOLL
*Acting Director of the United States Patent and Trademark Office*

SEQUENCE LISTING

```
<160> NUMBER OF SEQ ID NOS: 15

<210> SEQ ID NO 1
<211> LENGTH: 6075
<212> TYPE: DNA
<213> ORGANISM: Homo sapiens
<220> FEATURE:
<221> NAME/KEY: CDS
<222> LOCATION: (31)..(6024)

<400> SEQUENCE: 1
gtctcctctg gatcttaact actgagcgca atg ctg agc cat gga gcc ggg ttg      54
                                Met Leu Ser His Gly Ala Gly Leu
                                 1               5 gcc ttg tgg atc aca ctg agc ctg ctg cag act gga ctg gcg gag cca     102
Ala Leu Trp Ile Thr Leu Ser Leu Leu Gln Thr Gly Leu Ala Glu Pro
     10                  15                  20 gag aga tgt aac ttc acc ctg gcg gag tcc aag gcc tcc agc cat tct     150
Glu Arg Cys Asn Phe Thr Leu Ala Glu Ser Lys Ala Ser Ser His Ser
 25                  30                  35                  40 gtg tct atc cag tgg aga att ttg ggc tca ccc tgt aac ttt agc ctc     198
Val Ser Ile Gln Trp Arg Ile Leu Gly Ser Pro Cys Asn Phe Ser Leu
                 45                  50                  55
```

-continued

| | |
|---|---|
| atc tat agc agt gac acc ctg ggg gcc gcg ttg tgc cct acc ttt cgg<br>Ile Tyr Ser Ser Asp Thr Leu Gly Ala Ala Leu Cys Pro Thr Phe Arg<br>　　　　　60　　　　　　　　　65　　　　　　　　　70 | 246 |
| ata gac aac acc aca tac gga tgt aac ctt caa gat tta caa gca gga<br>Ile Asp Asn Thr Thr Tyr Gly Cys Asn Leu Gln Asp Leu Gln Ala Gly<br>　　　75　　　　　　　　　80　　　　　　　　　85 | 294 |
| acc atc tat aac ttc aag att att tct ctg gat gaa gag aga act gtg<br>Thr Ile Tyr Asn Phe Lys Ile Ile Ser Leu Asp Glu Glu Arg Thr Val<br>90　　　　　　　　　95　　　　　　　　　100 | 342 |
| gtc ttg caa aca gat cct tta cct cct gct agg ttt gga gtc agt aaa<br>Val Leu Gln Thr Asp Pro Leu Pro Pro Ala Arg Phe Gly Val Ser Lys<br>105　　　　　　　　　110　　　　　　　　　115　　　　　　　　　120 | 390 |
| gag aag acg act tca acc ggc ttg cat gtt tgg tgg act cct tct tcc<br>Glu Lys Thr Thr Ser Thr Gly Leu His Val Trp Trp Thr Pro Ser Ser<br>　　　　　　　　　125　　　　　　　　　130　　　　　　　　　135 | 438 |
| gga aaa gtc acc tca tat gag gtg caa tta ttt gat gaa aat aac caa<br>Gly Lys Val Thr Ser Tyr Glu Val Gln Leu Phe Asp Glu Asn Asn Gln<br>　　　　　140　　　　　　　　　145　　　　　　　　　150 | 486 |
| aag ata cag ggg gtt caa att caa gaa agt act tca tgg aat gaa tac<br>Lys Ile Gln Gly Val Gln Ile Gln Glu Ser Thr Ser Trp Asn Glu Tyr<br>　　　　　　　155　　　　　　　　　160　　　　　　　　　165 | 534 |
| act ttt ttc aat ctc act gct ggt agt aaa tac aat att gcc atc aca<br>Thr Phe Phe Asn Leu Thr Ala Gly Ser Lys Tyr Asn Ile Ala Ile Thr<br>170　　　　　　　　　175　　　　　　　　　180 | 582 |
| gct gtt tct gga gga aaa cgt tct ttt tca gtt tat acc aat gga tca<br>Ala Val Ser Gly Gly Lys Arg Ser Phe Ser Val Tyr Thr Asn Gly Ser<br>185　　　　　　　　　190　　　　　　　　　195　　　　　　　　　200 | 630 |
| aca gtc cca tct cca gtg aaa gat att ggt att tcc aca aaa gcc aat<br>Thr Val Pro Ser Pro Val Lys Asp Ile Gly Ile Ser Thr Lys Ala Asn<br>　　　　　　　　　205　　　　　　　　　210　　　　　　　　　215 | 678 |
| tct ctc ctg att tcc tgg tcc cat ggt tct ggg aat gtg gaa cga tac<br>Ser Leu Leu Ile Ser Trp Ser His Gly Ser Gly Asn Val Glu Arg Tyr<br>　　　　　220　　　　　　　　　225　　　　　　　　　230 | 726 |
| cgg ctg atg cta atg gat aaa ggg atc cta gtt cat ggc ggt gtt gtg<br>Arg Leu Met Leu Met Asp Lys Gly Ile Leu Val His Gly Gly Val Val<br>　　　　　　　235　　　　　　　　　240　　　　　　　　　245 | 774 |
| gac aaa cat gct act tcc tat gct ttt cac ggg ctg tcc cct ggc tac<br>Asp Lys His Ala Thr Ser Tyr Ala Phe His Gly Leu Ser Pro Gly Tyr<br>250　　　　　　　　　255　　　　　　　　　260 | 822 |
| ctc tac aac ctc act gtt atg act gag gct gca ggg ctg caa aac tac<br>Leu Tyr Asn Leu Thr Val Met Thr Glu Ala Ala Gly Leu Gln Asn Tyr<br>265　　　　　　　　　270　　　　　　　　　275　　　　　　　　　280 | 870 |
| agg tgg aaa cta gtc agg aca gcc ccc atg gaa gtc tca aat ctg aag<br>Arg Trp Lys Leu Val Arg Thr Ala Pro Met Glu Val Ser Asn Leu Lys<br>　　　　　　　　　285　　　　　　　　　290　　　　　　　　　295 | 918 |
| gtg aca aat gat ggc agt ttg acc tct cta aaa gtc aaa tgg caa aga<br>Val Thr Asn Asp Gly Ser Leu Thr Ser Leu Lys Val Lys Trp Gln Arg<br>　　　　　300　　　　　　　　　305　　　　　　　　　310 | 966 |
| cct cct gga aat gtg gat tct tac aat atc acc ctg tct cac aaa ggg<br>Pro Pro Gly Asn Val Asp Ser Tyr Asn Ile Thr Leu Ser His Lys Gly<br>　　　　　　　315　　　　　　　　　320　　　　　　　　　325 | 1014 |
| acc atc aag gaa tcc aga gta tta gca cct tgg att act gaa act cac<br>Thr Ile Lys Glu Ser Arg Val Leu Ala Pro Trp Ile Thr Glu Thr His<br>330　　　　　　　　　335　　　　　　　　　340 | 1062 |
| ttt aaa gag tta gtc ccc ggt cga ctt tat caa gtt act gtc agc tgt<br>Phe Lys Glu Leu Val Pro Gly Arg Leu Tyr Gln Val Thr Val Ser Cys<br>345　　　　　　　　　350　　　　　　　　　355　　　　　　　　　360 | 1110 |
| gtc tct ggt gaa ctg tct gct cag aag atg gca gtg ggc aga aca ttt<br>Val Ser Gly Glu Leu Ser Ala Gln Lys Met Ala Val Gly Arg Thr Phe | 1158 |

-continued

```
                    365                 370                 375
cca gac aaa gtt gca aac ctg gag gca aac aat aat ggc agg atg agg    1206
Pro Asp Lys Val Ala Asn Leu Glu Ala Asn Asn Asn Gly Arg Met Arg
            380                 385                 390 tct ctt gta gtg agc tgg tcg ccc cct gct gga gac tgg gag cag tat    1254
Ser Leu Val Val Ser Trp Ser Pro Pro Ala Gly Asp Trp Glu Gln Tyr
        395                 400                 405 cgg atc cta ctc ttc aat gat tct gtg gtg ctg ctc aac atc act gtg    1302
Arg Ile Leu Leu Phe Asn Asp Ser Val Val Leu Leu Asn Ile Thr Val
    410                 415                 420 gga aag gaa gaa aca cag tat gtc atg gat gac acg ggg ctc gta ccg    1350
Gly Lys Glu Glu Thr Gln Tyr Val Met Asp Asp Thr Gly Leu Val Pro
425                 430                 435                 440 gga aga cag tat gag gtg gaa gtc att gtt gag agt gga aat ttg aag    1398
Gly Arg Gln Tyr Glu Val Glu Val Ile Val Glu Ser Gly Asn Leu Lys
            445                 450                 455 aat tct gag cgt tgc caa ggc agg aca gtc ccc ctg gct gtc ctc cag    1446
Asn Ser Glu Arg Cys Gln Gly Arg Thr Val Pro Leu Ala Val Leu Gln
        460                 465                 470 ctt cgt gtc aaa cat gcc aat gaa acc tca ctg agt atc atg tgg cag    1494
Leu Arg Val Lys His Ala Asn Glu Thr Ser Leu Ser Ile Met Trp Gln
    475                 480                 485 acc cct gta gca gaa tgg gag aaa tac atc att tcc cta gct gac aga    1542
Thr Pro Val Ala Glu Trp Glu Lys Tyr Ile Ile Ser Leu Ala Asp Arg
    490                 495                 500 gac ctc tta ctg atc cac aag tca ctc tcc aaa gat gcc aaa gaa ttc    1590
Asp Leu Leu Leu Ile His Lys Ser Leu Ser Lys Asp Ala Lys Glu Phe
505                 510                 515                 520 act ttt act gac ctg gtg cct gga cga aaa tac atg gct aca gtc acc    1638
Thr Phe Thr Asp Leu Val Pro Gly Arg Lys Tyr Met Ala Thr Val Thr
            525                 530                 535 agt att agt gga gac tta aaa aat tcc tct tca gta aaa gga aga aca    1686
Ser Ile Ser Gly Asp Leu Lys Asn Ser Ser Ser Val Lys Gly Arg Thr
        540                 545                 550 gtg cct gcc caa gtg act gac ttg cat gtg gcc aac caa gga atg acc    1734
Val Pro Ala Gln Val Thr Asp Leu His Val Ala Asn Gln Gly Met Thr
    555                 560                 565 agt agt ctg ttt act aac tgg acc cag gca caa gga gac gta gaa ttt    1782
Ser Ser Leu Phe Thr Asn Trp Thr Gln Ala Gln Gly Asp Val Glu Phe
    570                 575                 580 tac caa gtc tta ctg atc cat gaa aat gtg gtc att aaa aat gaa agc    1830
Tyr Gln Val Leu Leu Ile His Glu Asn Val Val Ile Lys Asn Glu Ser
585                 590                 595                 600 atc tcc agt gag acc agc aga tac agc ttc cac tct ctc aag tcc ggc    1878
Ile Ser Ser Glu Thr Ser Arg Tyr Ser Phe His Ser Leu Lys Ser Gly
            605                 610                 615 agc ctg tac tcc gtg gtg gta aca aca gtg agt gga ggg atc tct tcc    1926
Ser Leu Tyr Ser Val Val Val Thr Thr Val Ser Gly Gly Ile Ser Ser
        620                 625                 630 cga caa gtg gtt gtg gag gga aga aca gtc cct tcc agt gtg agt gga    1974
Arg Gln Val Val Val Glu Gly Arg Thr Val Pro Ser Ser Val Ser Gly
    635                 640                 645 gta acg gtg aac aat tcc ggt cgt aat gac tac ctc agc gtt tcc tgg    2022
Val Thr Val Asn Asn Ser Gly Arg Asn Asp Tyr Leu Ser Val Ser Trp
650                 655                 660 ctc gtg gcg ccc gga gat gtg gat aac tat gag gta aca ttg tct cat    2070
Leu Val Ala Pro Gly Asp Val Asp Asn Tyr Glu Val Thr Leu Ser His
            665                 670                 675                 680 gac ggc aag gtg gtt cag tcc ctt gtc att gcc aag tct gtc aga gaa    2118
```

-continued

```
                Asp Gly Lys Val Val Gln Ser Leu Val Ile Ala Lys Ser Val Arg Glu
                            685                 690                 695 tgt tcc ttc agc tcc ctc acc cca ggc cgc ctc tac acc gtg acc ata    2166
Cys Ser Phe Ser Ser Leu Thr Pro Gly Arg Leu Tyr Thr Val Thr Ile
        700                 705                 710 act aca agg agt ggc aag tat gaa aat cac tcc ttc agc caa gag cgg    2214
Thr Thr Arg Ser Gly Lys Tyr Glu Asn His Ser Phe Ser Gln Glu Arg
            715                 720                 725 aca gtg cct gac aaa gtc cag gga gtc agt gtt agc aac tca gcc agg    2262
Thr Val Pro Asp Lys Val Gln Gly Val Ser Val Ser Asn Ser Ala Arg
        730                 735                 740 agt gac tat tta agg gta tcc tgg gtg cat gcc act gga gac ttt gat    2310
Ser Asp Tyr Leu Arg Val Ser Trp Val His Ala Thr Gly Asp Phe Asp
745                 750                 755                 760 cac tat gaa gtc acc att aaa aac aaa aac aac ttc att caa act aaa    2358
His Tyr Glu Val Thr Ile Lys Asn Lys Asn Asn Phe Ile Gln Thr Lys
                765                 770                 775 agc att ccc aag tca gaa aac gaa tgt gta ttt gtt cag cta gtc cct    2406
Ser Ile Pro Lys Ser Glu Asn Glu Cys Val Phe Val Gln Leu Val Pro
            780                 785                 790 gga cgg ttg tac agt gtc act gtt act aca aaa agt gga caa tat gaa    2454
Gly Arg Leu Tyr Ser Val Thr Val Thr Thr Lys Ser Gly Gln Tyr Glu
        795                 800                 805 gcc aat gaa caa ggg aat ggg aga aca att cca gag cct gtt aag gat    2502
Ala Asn Glu Gln Gly Asn Gly Arg Thr Ile Pro Glu Pro Val Lys Asp
    810                 815                 820 cta aca ttg cgc aac agg agc act gag gac ttg cat gtg act tgg tca    2550
Leu Thr Leu Arg Asn Arg Ser Thr Glu Asp Leu His Val Thr Trp Ser
825                 830                 835                 840 gga gct aat ggg gat gtc gac caa tat gag atc cag ctg ctc ttc aat    2598
Gly Ala Asn Gly Asp Val Asp Gln Tyr Glu Ile Gln Leu Leu Phe Asn
                845                 850                 855 gac atg aaa gta ttt cct cct ttt cac ctt gta aat acc gca acc gag    2646
Asp Met Lys Val Phe Pro Pro Phe His Leu Val Asn Thr Ala Thr Glu
            860                 865                 870 tat cga ttt act tcc cta aca cca ggc cgc caa tac aaa att ctt gtc    2694
Tyr Arg Phe Thr Ser Leu Thr Pro Gly Arg Gln Tyr Lys Ile Leu Val
        875                 880                 885 ttg acg att agc ggg gat gta cag cag tca gcc ttc att gag ggc ttc    2742
Leu Thr Ile Ser Gly Asp Val Gln Gln Ser Ala Phe Ile Glu Gly Phe
    890                 895                 900 aca gtt cct agt gct gtc aaa aat att cac att tct ccc aat gga gca    2790
Thr Val Pro Ser Ala Val Lys Asn Ile His Ile Ser Pro Asn Gly Ala
905                 910                 915                 920 aca gat agc ctg acg gtg aac tgg act cct ggt ggg gga gac gtt gat    2838
Thr Asp Ser Leu Thr Val Asn Trp Thr Pro Gly Gly Gly Asp Val Asp
                925                 930                 935 tcc tac acg gtg tcg gca ttc agg cac agt caa aag gtt gac tct cag    2886
Ser Tyr Thr Val Ser Ala Phe Arg His Ser Gln Lys Val Asp Ser Gln
            940                 945                 950 act att ccc aag cac gtc ttt gag cac acg ttc cac aga ctg gag gcc    2934
Thr Ile Pro Lys His Val Phe Glu His Thr Phe His Arg Leu Glu Ala
        955                 960                 965 ggg gag cag tac cag atc atg att gcc tca gtc agc ggg tcc ctg aag    2982
Gly Glu Gln Tyr Gln Ile Met Ile Ala Ser Val Ser Gly Ser Leu Lys
    970                 975                 980 aat cag ata aat gtg gtt ggg cgg aca gtt cca gca tct gtc caa gga    3030
Asn Gln Ile Asn Val Val Gly Arg Thr Val Pro Ala Ser Val Gln Gly
985                 990                 995                 1000
```

```
gta att gca gac aat gca tac agc agt tat tcc tta ata gta agt       3075
Val Ile Ala Asp Asn Ala Tyr Ser Ser Tyr Ser Leu Ile Val Ser
             1005                1010                1015 tgg caa aaa gct gct ggt gtg gca gaa aga tat gat atc ctg ctt       3120
Trp Gln Lys Ala Ala Gly Val Ala Glu Arg Tyr Asp Ile Leu Leu
             1020                1025                1030 cta act gaa aat gga atc ctt ctg cgc aac aca tca gag cca gcc       3165
Leu Thr Glu Asn Gly Ile Leu Leu Arg Asn Thr Ser Glu Pro Ala
             1035                1040                1045 acc act aag caa cac aaa ttt gaa gat cta aca cca ggc aag aaa       3210
Thr Thr Lys Gln His Lys Phe Glu Asp Leu Thr Pro Gly Lys Lys
             1050                1055                1060 tac aag ata cag atc cta act gtc agt gga ggc ctc ttt agc aag       3255
Tyr Lys Ile Gln Ile Leu Thr Val Ser Gly Gly Leu Phe Ser Lys
             1065                1070                1075 gaa gcc cag act gaa ggc cga aca gtc cca gca gct gtc acc gac       3300
Glu Ala Gln Thr Glu Gly Arg Thr Val Pro Ala Ala Val Thr Asp
             1080                1085                1090 ctg agg atc aca gag aac tcc acc agg cac ctg tcc ttc cgc tgg       3345
Leu Arg Ile Thr Glu Asn Ser Thr Arg His Leu Ser Phe Arg Trp
             1095                1100                1105 acc gcc tca gag ggg gag ctc agc tgg tac aac atc ttt ttg tac       3390
Thr Ala Ser Glu Gly Glu Leu Ser Trp Tyr Asn Ile Phe Leu Tyr
             1110                1115                1120 aac cca gat ggg aat ctc cag gag aga gct caa gtt gac cca cta       3435
Asn Pro Asp Gly Asn Leu Gln Glu Arg Ala Gln Val Asp Pro Leu
             1125                1130                1135 gtc cag agc ttc tct ttc cag aac ttg cta caa ggc aga atg tac       3480
Val Gln Ser Phe Ser Phe Gln Asn Leu Leu Gln Gly Arg Met Tyr
             1140                1145                1150 aag atg gtg att gta act cac agt ggg gag ctg tct aat gag tct       3525
Lys Met Val Ile Val Thr His Ser Gly Glu Leu Ser Asn Glu Ser
             1155                1160                1165 ttc ata ttt ggt aga aca gtc cca gcc tct gtg agt cat ctc agg       3570
Phe Ile Phe Gly Arg Thr Val Pro Ala Ser Val Ser His Leu Arg
             1170                1175                1180 ggg tcc aat cgg aac acg aca gac agc ctt tgg ttc aac tgg agt       3615
Gly Ser Asn Arg Asn Thr Thr Asp Ser Leu Trp Phe Asn Trp Ser
             1185                1190                1195 cca gcc tct ggg gac ttt gac ttt tat gag ctg att ctc tat aat       3660
Pro Ala Ser Gly Asp Phe Asp Phe Tyr Glu Leu Ile Leu Tyr Asn
             1200                1205                1210 ccc aat ggc aca aag aag gaa aac tgg aaa gac aag gac ctg acg       3705
Pro Asn Gly Thr Lys Lys Glu Asn Trp Lys Asp Lys Asp Leu Thr
             1215                1220                1225 gag tgg cgg ttt caa ggc ctt gtt cct gga agg aag tac gtg ctg       3750
Glu Trp Arg Phe Gln Gly Leu Val Pro Gly Arg Lys Tyr Val Leu
             1230                1235                1240 tgg gtg gta act cac agt gga gat ctc agc aat aaa gtc aca gcg       3795
Trp Val Val Thr His Ser Gly Asp Leu Ser Asn Lys Val Thr Ala
             1245                1250                1255 gag agc aga aca gct cca agt cct ccc agt ctt atg tca ttt gct       3840
Glu Ser Arg Thr Ala Pro Ser Pro Pro Ser Leu Met Ser Phe Ala
             1260                1265                1270 gac att gca aac aca tcc ttg gcc atc acg tgg aaa ggg ccc cca       3885
Asp Ile Ala Asn Thr Ser Leu Ala Ile Thr Trp Lys Gly Pro Pro
             1275                1280                1285 gac tgg aca gac tac aac gac ttt gag ctg cag tgg ttg ccc aga       3930
Asp Trp Thr Asp Tyr Asn Asp Phe Glu Leu Gln Trp Leu Pro Arg
             1290                1295                1300
```

-continued

| | | |
|---|---|---|
| gat gca ctt act gtc ttc aac ccc tac aac aac aga aaa tca gaa<br>Asp Ala Leu Thr Val Phe Asn Pro Tyr Asn Asn Arg Lys Ser Glu<br>1305              1310              1315 | | 3975 |
| gga cgc att gtg tat ggt ctt cgt cca ggg aga tcc tat caa ttc<br>Gly Arg Ile Val Tyr Gly Leu Arg Pro Gly Arg Ser Tyr Gln Phe<br>1320              1325              1330 | | 4020 |
| aac gtc aag act gtc agt ggt gat tcc tgg aaa act tac agc aaa<br>Asn Val Lys Thr Val Ser Gly Asp Ser Trp Lys Thr Tyr Ser Lys<br>1335              1340              1345 | | 4065 |
| cca att ttt gga tct gtg agg aca aag cct gac aag ata caa aac<br>Pro Ile Phe Gly Ser Val Arg Thr Lys Pro Asp Lys Ile Gln Asn<br>1350              1355              1360 | | 4110 |
| ctg cat tgc cgg cct cag aac tcc acg gcc att gcc tgt tct tgg<br>Leu His Cys Arg Pro Gln Asn Ser Thr Ala Ile Ala Cys Ser Trp<br>1365              1370              1375 | | 4155 |
| atc cct cct gat tct gac ttt gat ggt tat agt att gaa tgc cgg<br>Ile Pro Pro Asp Ser Asp Phe Asp Gly Tyr Ser Ile Glu Cys Arg<br>1380              1385              1390 | | 4200 |
| aaa atg gac acc caa gaa gtt gag ttt tcc aga aag ctg gag aaa<br>Lys Met Asp Thr Gln Glu Val Glu Phe Ser Arg Lys Leu Glu Lys<br>1395              1400              1405 | | 4245 |
| gaa aaa tct ctg ctc aac atc atg atg cta gtg ccc cat aag agg<br>Glu Lys Ser Leu Leu Asn Ile Met Met Leu Val Pro His Lys Arg<br>1410              1415              1420 | | 4290 |
| tac ctg gtg tcc atc aaa gtg cag tcg gcc ggc atg acc agc gag<br>Tyr Leu Val Ser Ile Lys Val Gln Ser Ala Gly Met Thr Ser Glu<br>1425              1430              1435 | | 4335 |
| gtg gtt gaa gac agc act atc aca atg ata gac cgc ccc cct cct<br>Val Val Glu Asp Ser Thr Ile Thr Met Ile Asp Arg Pro Pro Pro<br>1440              1445              1450 | | 4380 |
| cca ccc cca cac att cgt gtg aat gaa aag gat gtg cta att agc<br>Pro Pro Pro His Ile Arg Val Asn Glu Lys Asp Val Leu Ile Ser<br>1455              1460              1465 | | 4425 |
| aag tct tcc atc aac ttt act gtc aac tgc agc tgg ttc agc gac<br>Lys Ser Ser Ile Asn Phe Thr Val Asn Cys Ser Trp Phe Ser Asp<br>1470              1475              1480 | | 4470 |
| acc aat gga gct gtg aaa tac ttc aca gtg gtg gtg aga gag gct<br>Thr Asn Gly Ala Val Lys Tyr Phe Thr Val Val Val Arg Glu Ala<br>1485              1490              1495 | | 4515 |
| gat ggc agt gat gag ctg aag cca gaa cag cag cac cct ctc cct<br>Asp Gly Ser Asp Glu Leu Lys Pro Glu Gln Gln His Pro Leu Pro<br>1500              1505              1510 | | 4560 |
| tcc tac ctg gag tac agg cac aat gcc tcc att cgg gtg tat cag<br>Ser Tyr Leu Glu Tyr Arg His Asn Ala Ser Ile Arg Val Tyr Gln<br>1515              1520              1525 | | 4605 |
| act aat tat ttt gcc agc aaa tgt gcc gaa aat cct aac agc aac<br>Thr Asn Tyr Phe Ala Ser Lys Cys Ala Glu Asn Pro Asn Ser Asn<br>1530              1535              1540 | | 4650 |
| tcc aag agt ttt aac att aag ctt gga gca gag atg gag agc tta<br>Ser Lys Ser Phe Asn Ile Lys Leu Gly Ala Glu Met Glu Ser Leu<br>1545              1550              1555 | | 4695 |
| ggt gga aaa cgc gat ccc act cag caa aaa ttc tgt gat gga cca<br>Gly Gly Lys Arg Asp Pro Thr Gln Gln Lys Phe Cys Asp Gly Pro<br>1560              1565              1570 | | 4740 |
| ctg aag cca cac act gcc tac aga atc agc att cga gct ttt aca<br>Leu Lys Pro His Thr Ala Tyr Arg Ile Ser Ile Arg Ala Phe Thr<br>1575              1580              1585 | | 4785 |
| cag ctc ttt gat gag gac ctg aag gaa ttc aca aag cca ctc tat<br>Gln Leu Phe Asp Glu Asp Leu Lys Glu Phe Thr Lys Pro Leu Tyr | | 4830 |

-continued

```
                 1590                    1595                     1600
tca gac aca ttt ttt tct tta ccc atc act act gaa tca gag ccc           4875
Ser Asp Thr Phe Phe Ser Leu Pro Ile Thr Thr Glu Ser Glu Pro
                 1605                    1610                    1615 ttg ttt gga gct att gaa ggt gtg agt gct ggt ctg ttt tta att           4920
Leu Phe Gly Ala Ile Glu Gly Val Ser Ala Gly Leu Phe Leu Ile
                 1620                    1625                    1630 ggc atg cta gtg gct gtt gtt gcc tta ttg atc tgc aga cag aaa           4965
Gly Met Leu Val Ala Val Val Ala Leu Leu Ile Cys Arg Gln Lys
                 1635                    1640                    1645 gtg agc cat ggt cga gaa aga ccc tct gcc cgt ctg agc att cgt           5010
Val Ser His Gly Arg Glu Arg Pro Ser Ala Arg Leu Ser Ile Arg
                 1650                    1655                    1660 agg gat cga cca tta tct gtc cac tta aac ctg ggc cag aaa ggt           5055
Arg Asp Arg Pro Leu Ser Val His Leu Asn Leu Gly Gln Lys Gly
                 1665                    1670                    1675 aac cgg aaa act tct tgt cca ata aaa ata aat cag ttt gaa ggg           5100
Asn Arg Lys Thr Ser Cys Pro Ile Lys Ile Asn Gln Phe Glu Gly
                 1680                    1685                    1690 cat ttc atg aag cta cag gct gac tcc aac tac ctt cta tcc aag           5145
His Phe Met Lys Leu Gln Ala Asp Ser Asn Tyr Leu Leu Ser Lys
                 1695                    1700                    1705 gaa tac gag gag tta aaa gac gtg ggc cga aac cag tca tgt gac           5190
Glu Tyr Glu Glu Leu Lys Asp Val Gly Arg Asn Gln Ser Cys Asp
                 1710                    1715                    1720 att gca ctc ttg ccg gag aat aga ggg aaa aat cga tac aac aat           5235
Ile Ala Leu Leu Pro Glu Asn Arg Gly Lys Asn Arg Tyr Asn Asn
                 1725                    1730                    1735 ata ttg ccc tat gat gcc acg cga gtg aag ctc tcc aat gta gat           5280
Ile Leu Pro Tyr Asp Ala Thr Arg Val Lys Leu Ser Asn Val Asp
                 1740                    1745                    1750 gat gat cct tgc tct gac tac atc aat gcc agc tac atc cct ggc           5325
Asp Asp Pro Cys Ser Asp Tyr Ile Asn Ala Ser Tyr Ile Pro Gly
                 1755                    1760                    1765 aac aac ttc aga aga gaa tac att gtc act cag gga ccg ctt cct           5370
Asn Asn Phe Arg Arg Glu Tyr Ile Val Thr Gln Gly Pro Leu Pro
                 1770                    1775                    1780 ggc acc aag gat gac ttc tgg aaa atg gtg tgg gaa caa aac gtt           5415
Gly Thr Lys Asp Asp Phe Trp Lys Met Val Trp Glu Gln Asn Val
                 1785                    1790                    1795 cac aac atc gtc atg gtg acc cag tgt gtt gag aag ggc cga gta           5460
His Asn Ile Val Met Val Thr Gln Cys Val Glu Lys Gly Arg Val
                 1800                    1805                    1810 aag tgt gac cat tac tgg cca gcg gac cag gat tcc ctc tac tat           5505
Lys Cys Asp His Tyr Trp Pro Ala Asp Gln Asp Ser Leu Tyr Tyr
                 1815                    1820                    1825 ggg gac ctc atc ctg cag atg ctc tca gag tcc gtc ctg cct gag           5550
Gly Asp Leu Ile Leu Gln Met Leu Ser Glu Ser Val Leu Pro Glu
                 1830                    1835                    1840 tgg acc atc cgg gag ttt aag ata tgc ggt gag gaa cag ctt gat           5595
Trp Thr Ile Arg Glu Phe Lys Ile Cys Gly Glu Glu Gln Leu Asp
                 1845                    1850                    1855 gca cac aga ctc atc cgc cac ttt cac tat acg gtg tgg cca gac           5640
Ala His Arg Leu Ile Arg His Phe His Tyr Thr Val Trp Pro Asp
                 1860                    1865                    1870 cat gga gtc cca gaa acc acc cag tct ctg atc cag ttt gtg aga           5685
His Gly Val Pro Glu Thr Thr Gln Ser Leu Ile Gln Phe Val Arg
                 1875                    1880                    1885 act gtc agg gac tac atc aac aga agc ccg ggt gct ggg ccc act           5730
```

-continued

```
Thr Val Arg Asp Tyr Ile Asn Arg Ser Pro Gly Ala Gly Pro Thr
            1890                1895                1900 gtg gtg cac tgc agt gct ggt gtg ggt agg act gga acc ttt att    5775
Val Val His Cys Ser Ala Gly Val Gly Arg Thr Gly Thr Phe Ile
            1905                1910                1915 gca ttg gac cga atc ctc cag cag tta gac tcc aaa gac tct gtg    5820
Ala Leu Asp Arg Ile Leu Gln Gln Leu Asp Ser Lys Asp Ser Val
            1920                1925                1930 gac att tat gga gca gtg cac gac cta aga ctt cac agg gtt cac    5865
Asp Ile Tyr Gly Ala Val His Asp Leu Arg Leu His Arg Val His
            1935                1940                1945 atg gtc cag act gag tgt cag tat gtc tac cta cat cag tgt gta    5910
Met Val Gln Thr Glu Cys Gln Tyr Val Tyr Leu His Gln Cys Val
            1950                1955                1960 aga gat gtc ctc aga gca aga aag cta cgg agt gaa caa gaa aac    5955
Arg Asp Val Leu Arg Ala Arg Lys Leu Arg Ser Glu Gln Glu Asn
            1965                1970                1975 ccc ttg ttt cca atc tat gaa aat gtg aat cca gag tat cac aga    6000
Pro Leu Phe Pro Ile Tyr Glu Asn Val Asn Pro Glu Tyr His Arg
            1980                1985                1990 gat cca gtc tat tca agg cat tga gaatgtacct gaagagctcc tggataaaaa  6054
Asp Pro Val Tyr Ser Arg His
            1995 ttattcactg tgtgatttgt t                                         6075

<210> SEQ ID NO 2
<211> LENGTH: 1997
<212> TYPE: PRT
<213> ORGANISM: Homo sapiens

<400> SEQUENCE: 2

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
                20                  25                  30

Glu Ser Lys Ala Ser Ser His Ser Val Ser Ile Gln Trp Arg Ile Leu
            35                  40                  45

Gly Ser Pro Cys Asn Phe Ser Leu Ile Tyr Ser Ser Asp Thr Leu Gly
        50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Lys Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Gly Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205
```

```
Ile Gly Ile Ser Thr Lys Ala Asn Ser Leu Leu Ile Ser Trp Ser His
    210                 215                 220
Gly Ser Gly Asn Val Glu Arg Tyr Arg Leu Met Leu Met Asp Lys Gly
225                 230                 235                 240
Ile Leu Val His Gly Val Val Asp Lys His Ala Thr Ser Tyr Ala
                245                 250                 255
Phe His Gly Leu Ser Pro Gly Tyr Leu Tyr Asn Leu Thr Val Met Thr
                260                 265                 270
Glu Ala Ala Gly Leu Gln Asn Tyr Arg Trp Lys Leu Val Arg Thr Ala
            275                 280                 285
Pro Met Glu Val Ser Asn Leu Lys Val Thr Asn Asp Gly Ser Leu Thr
290                 295                 300
Ser Leu Lys Val Lys Trp Gln Arg Pro Pro Gly Asn Val Asp Ser Tyr
305                 310                 315                 320
Asn Ile Thr Leu Ser His Lys Gly Thr Ile Lys Glu Ser Arg Val Leu
                325                 330                 335
Ala Pro Trp Ile Thr Glu Thr His Phe Lys Glu Leu Val Pro Gly Arg
                340                 345                 350
Leu Tyr Gln Val Thr Val Ser Cys Val Ser Gly Glu Leu Ser Ala Gln
            355                 360                 365
Lys Met Ala Val Gly Arg Thr Phe Pro Asp Lys Val Ala Asn Leu Glu
370                 375                 380
Ala Asn Asn Asn Gly Arg Met Arg Ser Leu Val Val Ser Trp Ser Pro
385                 390                 395                 400
Pro Ala Gly Asp Trp Glu Gln Tyr Arg Ile Leu Leu Phe Asn Asp Ser
                405                 410                 415
Val Val Leu Leu Asn Ile Thr Val Gly Lys Glu Thr Gln Tyr Val
                420                 425                 430
Met Asp Asp Thr Gly Leu Val Pro Gly Arg Gln Tyr Glu Val Glu Val
            435                 440                 445
Ile Val Glu Ser Gly Asn Leu Lys Asn Ser Glu Arg Cys Gln Gly Arg
450                 455                 460
Thr Val Pro Leu Ala Val Leu Gln Leu Arg Val Lys His Ala Asn Glu
465                 470                 475                 480
Thr Ser Leu Ser Ile Met Trp Gln Thr Pro Val Ala Glu Trp Glu Lys
                485                 490                 495
Tyr Ile Ile Ser Leu Ala Asp Arg Asp Leu Leu Leu Ile His Lys Ser
                500                 505                 510
Leu Ser Lys Asp Ala Lys Glu Phe Thr Phe Thr Asp Leu Val Pro Gly
            515                 520                 525
Arg Lys Tyr Met Ala Thr Val Thr Ser Ile Ser Gly Asp Leu Lys Asn
            530                 535                 540
Ser Ser Ser Val Lys Gly Arg Thr Val Pro Ala Gln Val Thr Asp Leu
545                 550                 555                 560
His Val Ala Asn Gln Gly Met Thr Ser Ser Leu Phe Thr Asn Trp Thr
                565                 570                 575
Gln Ala Gln Gly Asp Val Glu Phe Tyr Gln Val Leu Leu Ile His Glu
            580                 585                 590
Asn Val Val Ile Lys Asn Glu Ser Ile Ser Ser Glu Thr Ser Arg Tyr
                595                 600                 605
Ser Phe His Ser Leu Lys Ser Gly Ser Leu Tyr Ser Val Val Val Thr
            610                 615                 620
```

```
Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
            645                 650                 655

Asn Asp Tyr Leu Ser Val Ser Trp Leu Ala Pro Gly Asp Val Asp
        660                 665                 670

Asn Tyr Glu Val Thr Leu Ser His Asp Gly Lys Val Val Gln Ser Leu
    675                 680                 685

Val Ile Ala Lys Ser Val Arg Glu Cys Ser Phe Ser Ser Leu Thr Pro
690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
            740                 745                 750

Val His Ala Thr Gly Asp Phe Asp His Tyr Glu Val Thr Ile Lys Asn
        755                 760                 765

Lys Asn Asn Phe Ile Gln Thr Lys Ser Ile Pro Lys Ser Glu Asn Glu
770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
            820                 825                 830

Glu Asp Leu His Val Thr Trp Ser Gly Ala Asn Gly Asp Val Asp Gln
        835                 840                 845

Tyr Glu Ile Gln Leu Leu Phe Asn Asp Met Lys Val Phe Pro Pro Phe
    850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
            900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
    930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                965                 970                 975

Ala Ser Val Ser Gly Ser Leu Lys Asn Gln Ile Asn Val Val Gly Arg
            980                 985                 990

Thr Val Pro Ala Ser Val Gln Gly  Val Ile Ala Asp Asn  Ala Tyr Ser
        995                 1000                 1005

Ser Tyr  Ser Leu Ile Val Ser  Trp Gln Lys Ala Ala  Gly Val Ala
    1010                 1015                 1020

Glu Arg  Tyr Asp Ile Leu Leu  Leu Thr Glu Asn Gly  Ile Leu Leu
    1025                 1030                 1035

Arg Asn  Thr Ser Glu Pro Ala  Thr Thr Lys Gln His  Lys Phe Glu
```

-continued

```
            1040                1045                1050
Asp Leu Thr Pro Gly Lys Lys Tyr Lys Ile Gln Ile Leu Thr Val
    1055                1060                1065

Ser Gly Gly Leu Phe Ser Lys Glu Ala Gln Thr Glu Gly Arg Thr
    1070                1075                1080

Val Pro Ala Ala Val Thr Asp Leu Arg Ile Thr Glu Asn Ser Thr
    1085                1090                1095

Arg His Leu Ser Phe Arg Trp Thr Ala Ser Glu Gly Glu Leu Ser
    1100                1105                1110

Trp Tyr Asn Ile Phe Leu Tyr Asn Pro Asp Gly Asn Leu Gln Glu
    1115                1120                1125

Arg Ala Gln Val Asp Pro Leu Val Gln Ser Phe Ser Phe Gln Asn
    1130                1135                1140

Leu Leu Gln Gly Arg Met Tyr Lys Met Val Ile Val Thr His Ser
    1145                1150                1155

Gly Glu Leu Ser Asn Glu Ser Phe Ile Phe Gly Arg Thr Val Pro
    1160                1165                1170

Ala Ser Val Ser His Leu Arg Gly Ser Asn Arg Asn Thr Thr Asp
    1175                1180                1185

Ser Leu Trp Phe Asn Trp Ser Pro Ala Ser Gly Asp Phe Asp Phe
    1190                1195                1200

Tyr Glu Leu Ile Leu Tyr Asn Pro Asn Gly Thr Lys Lys Glu Asn
    1205                1210                1215

Trp Lys Asp Lys Asp Leu Thr Glu Trp Arg Phe Gln Gly Leu Val
    1220                1225                1230

Pro Gly Arg Lys Tyr Val Leu Trp Val Val Thr His Ser Gly Asp
    1235                1240                1245

Leu Ser Asn Lys Val Thr Ala Glu Ser Arg Thr Ala Pro Ser Pro
    1250                1255                1260

Pro Ser Leu Met Ser Phe Ala Asp Ile Ala Asn Thr Ser Leu Ala
    1265                1270                1275

Ile Thr Trp Lys Gly Pro Pro Asp Trp Thr Asp Tyr Asn Asp Phe
    1280                1285                1290

Glu Leu Gln Trp Leu Pro Arg Asp Ala Leu Thr Val Phe Asn Pro
    1295                1300                1305

Tyr Asn Asn Arg Lys Ser Glu Gly Arg Ile Val Tyr Gly Leu Arg
    1310                1315                1320

Pro Gly Arg Ser Tyr Gln Phe Asn Val Lys Thr Val Ser Gly Asp
    1325                1330                1335

Ser Trp Lys Thr Tyr Ser Lys Pro Ile Phe Gly Ser Val Arg Thr
    1340                1345                1350

Lys Pro Asp Lys Ile Gln Asn Leu His Cys Arg Pro Gln Asn Ser
    1355                1360                1365

Thr Ala Ile Ala Cys Ser Trp Ile Pro Pro Asp Ser Asp Phe Asp
    1370                1375                1380

Gly Tyr Ser Ile Glu Cys Arg Lys Met Asp Thr Gln Glu Val Glu
    1385                1390                1395

Phe Ser Arg Lys Leu Glu Lys Glu Lys Ser Leu Leu Asn Ile Met
    1400                1405                1410

Met Leu Val Pro His Lys Arg Tyr Leu Val Ser Ile Lys Val Gln
    1415                1420                1425

Ser Ala Gly Met Thr Ser Glu Val Val Glu Asp Ser Thr Ile Thr
    1430                1435                1440
```

-continued

```
Met Ile Asp Arg Pro Pro Pro Pro Pro His Ile Arg Val Asn
1445                1450                1455

Glu Lys Asp Val Leu Ile Ser Lys Ser Ser Ile Asn Phe Thr Val
1460                1465                1470

Asn Cys Ser Trp Phe Ser Asp Thr Asn Gly Ala Val Lys Tyr Phe
1475                1480                1485

Thr Val Val Val Arg Glu Ala Asp Gly Ser Asp Glu Leu Lys Pro
1490                1495                1500

Glu Gln Gln His Pro Leu Pro Ser Tyr Leu Glu Tyr Arg His Asn
1505                1510                1515

Ala Ser Ile Arg Val Tyr Gln Thr Asn Tyr Phe Ala Ser Lys Cys
1520                1525                1530

Ala Glu Asn Pro Asn Ser Asn Ser Lys Ser Phe Asn Ile Lys Leu
1535                1540                1545

Gly Ala Glu Met Glu Ser Leu Gly Gly Lys Arg Asp Pro Thr Gln
1550                1555                1560

Gln Lys Phe Cys Asp Gly Pro Leu Lys Pro His Thr Ala Tyr Arg
1565                1570                1575

Ile Ser Ile Arg Ala Phe Thr Gln Leu Phe Asp Glu Asp Leu Lys
1580                1585                1590

Glu Phe Thr Lys Pro Leu Tyr Ser Asp Thr Phe Phe Ser Leu Pro
1595                1600                1605

Ile Thr Thr Glu Ser Glu Pro Leu Phe Gly Ala Ile Glu Gly Val
1610                1615                1620

Ser Ala Gly Leu Phe Leu Ile Gly Met Leu Val Ala Val Val Ala
1625                1630                1635

Leu Leu Ile Cys Arg Gln Lys Val Ser His Gly Arg Glu Arg Pro
1640                1645                1650

Ser Ala Arg Leu Ser Ile Arg Arg Asp Arg Pro Leu Ser Val His
1655                1660                1665

Leu Asn Leu Gly Gln Lys Gly Asn Arg Lys Thr Ser Cys Pro Ile
1670                1675                1680

Lys Ile Asn Gln Phe Glu Gly His Phe Met Lys Leu Gln Ala Asp
1685                1690                1695

Ser Asn Tyr Leu Leu Ser Lys Glu Tyr Glu Glu Leu Lys Asp Val
1700                1705                1710

Gly Arg Asn Gln Ser Cys Asp Ile Ala Leu Leu Pro Glu Asn Arg
1715                1720                1725

Gly Lys Asn Arg Tyr Asn Asn Ile Leu Pro Tyr Asp Ala Thr Arg
1730                1735                1740

Val Lys Leu Ser Asn Val Asp Asp Pro Cys Ser Asp Tyr Ile
1745                1750                1755

Asn Ala Ser Tyr Ile Pro Gly Asn Asn Phe Arg Arg Glu Tyr Ile
1760                1765                1770

Val Thr Gln Gly Pro Leu Pro Gly Thr Lys Asp Asp Phe Trp Lys
1775                1780                1785

Met Val Trp Glu Gln Asn Val His Asn Ile Val Met Val Thr Gln
1790                1795                1800

Cys Val Glu Lys Gly Arg Val Lys Cys Asp His Tyr Trp Pro Ala
1805                1810                1815

Asp Gln Asp Ser Leu Tyr Tyr Gly Asp Leu Ile Leu Gln Met Leu
1820                1825                1830
```

-continued

```
Ser Glu Ser Val Leu Pro Glu Trp Thr Ile Arg Glu Phe Lys Ile
1835                1840                1845

Cys Gly Glu Glu Gln Leu Asp Ala His Arg Leu Ile Arg His Phe
    1850                1855                1860

His Tyr Thr Val Trp Pro Asp His Gly Val Pro Glu Thr Thr Gln
1865                1870                1875

Ser Leu Ile Gln Phe Val Arg Thr Val Arg Asp Tyr Ile Asn Arg
    1880                1885                1890

Ser Pro Gly Ala Gly Pro Thr Val Val His Cys Ser Ala Gly Val
    1895                1900                1905

Gly Arg Thr Gly Thr Phe Ile Ala Leu Asp Arg Ile Leu Gln Gln
    1910                1915                1920

Leu Asp Ser Lys Asp Ser Val Asp Ile Tyr Gly Ala Val His Asp
    1925                1930                1935

Leu Arg Leu His Arg Val His Met Val Gln Thr Glu Cys Gln Tyr
1940                1945                1950

Val Tyr Leu His Gln Cys Val Arg Asp Val Leu Arg Ala Arg Lys
    1955                1960                1965

Leu Arg Ser Glu Gln Glu Asn Pro Leu Phe Pro Ile Tyr Glu Asn
    1970                1975                1980

Val Asn Pro Glu Tyr His Arg Asp Pro Val Tyr Ser Arg His
1985                1990                1995
```

<210> SEQ ID NO 3
<211> LENGTH: 1011
<212> TYPE: DNA
<213> ORGANISM: Homo sapiens
<220> FEATURE:
<221> NAME/KEY: CDS
<222> LOCATION: (1)..(1011)

<400> SEQUENCE: 3

```
gat cga cca tta tct gtc cac tta aac ctg ggc cag aaa ggt aac cgg     48
Asp Arg Pro Leu Ser Val His Leu Asn Leu Gly Gln Lys Gly Asn Arg
1               5                   10                  15 aaa act tct tgt cca ata aaa ata aat cag ttt gaa ggg cat ttc atg     96
Lys Thr Ser Cys Pro Ile Lys Ile Asn Gln Phe Glu Gly His Phe Met
            20                  25                  30 aag cta cag gct gac tcc aac tac ctt cta tcc aag gaa tac gag gag    144
Lys Leu Gln Ala Asp Ser Asn Tyr Leu Leu Ser Lys Glu Tyr Glu Glu
        35                  40                  45 tta aaa gac gtg ggc cga aac cag tca tgt gac att gca ctc ttg ccg    192
Leu Lys Asp Val Gly Arg Asn Gln Ser Cys Asp Ile Ala Leu Leu Pro
    50                  55                  60 gag aat aga ggg aaa aat cga tac aac aat ata ttg ccc tat gat gcc    240
Glu Asn Arg Gly Lys Asn Arg Tyr Asn Asn Ile Leu Pro Tyr Asp Ala
65                  70                  75                  80 acg cga gtg aag ctc tcc aat gta gat gat gat cct tgc tct gac tac    288
Thr Arg Val Lys Leu Ser Asn Val Asp Asp Asp Pro Cys Ser Asp Tyr
                85                  90                  95 atc aat gcc agc tac atc cct ggc aac aac ttc aga aga gaa tac att    336
Ile Asn Ala Ser Tyr Ile Pro Gly Asn Asn Phe Arg Arg Glu Tyr Ile
            100                 105                 110 gtc act cag gga ccg ctt cct ggc acc aag gat gac ttc tgg aaa atg    384
Val Thr Gln Gly Pro Leu Pro Gly Thr Lys Asp Asp Phe Trp Lys Met
        115                 120                 125 gtg tgg gaa caa aac gtt cac aac atc gtc atg gtg acc cag tgt gtt    432
Val Trp Glu Gln Asn Val His Asn Ile Val Met Val Thr Gln Cys Val
    130                 135                 140
```

-continued

| | | |
|---|---|---|
| gag aag ggc cga gta aag tgt gac cat tac tgg cca gcg gac cag gat<br>Glu Lys Gly Arg Val Lys Cys Asp His Tyr Trp Pro Ala Asp Gln Asp<br>145                    150                    155                    160 | 480 |
| tcc ctc tac tat ggg gac ctc atc ctg cag atg ctc tca gag tcc gtc<br>Ser Leu Tyr Tyr Gly Asp Leu Ile Leu Gln Met Leu Ser Glu Ser Val<br>                    165                    170                    175 | 528 |
| ctg cct gag tgg acc atc cgg gag ttt aag ata tgc ggt gag gaa cag<br>Leu Pro Glu Trp Thr Ile Arg Glu Phe Lys Ile Cys Gly Glu Glu Gln<br>                180                    185                    190 | 576 |
| ctt gat gca cac aga ctc atc cgc cac ttt cac tat acg gtg tgg cca<br>Leu Asp Ala His Arg Leu Ile Arg His Phe His Tyr Thr Val Trp Pro<br>              195                    200                    205 | 624 |
| gac cat gga gtc cca gaa acc acc cag tct ctg atc cag ttt gtg aga<br>Asp His Gly Val Pro Glu Thr Thr Gln Ser Leu Ile Gln Phe Val Arg<br>210                    215                    220 | 672 |
| act gtc agg gac tac atc aac aga agc ccg ggt gct ggg ccc act gtg<br>Thr Val Arg Asp Tyr Ile Asn Arg Ser Pro Gly Ala Gly Pro Thr Val<br>225                    230                    235                    240 | 720 |
| gtg cac tgc agt gct ggt gtg ggt agg act gga acc ttt att gca ttg<br>Val His Cys Ser Ala Gly Val Gly Arg Thr Gly Thr Phe Ile Ala Leu<br>                    245                    250                    255 | 768 |
| gac cga atc ctc cag cag tta gac tcc aaa gac tct gtg gac att tat<br>Asp Arg Ile Leu Gln Gln Leu Asp Ser Lys Asp Ser Val Asp Ile Tyr<br>              260                    265                    270 | 816 |
| gga gca gtg cac gac cta aga ctt cac agg gtt cac atg gtc cag act<br>Gly Ala Val His Asp Leu Arg Leu His Arg Val His Met Val Gln Thr<br>                275                    280                    285 | 864 |
| gag tgt cag tat gtc tac cta cat cag tgt gta aga gat gtc ctc aga<br>Glu Cys Gln Tyr Val Tyr Leu His Gln Cys Val Arg Asp Val Leu Arg<br>290                    295                    300 | 912 |
| gca aga aag cta cgg agt gaa caa gaa aac ccc ttg ttt cca atc tat<br>Ala Arg Lys Leu Arg Ser Glu Gln Glu Asn Pro Leu Phe Pro Ile Tyr<br>305                    310                    315                    320 | 960 |
| gaa aat gtg aat cca gag tat cac aga gat cca gtc tat tca agg cat<br>Glu Asn Val Asn Pro Glu Tyr His Arg Asp Pro Val Tyr Ser Arg His<br>                    325                    330                    335 | 1008 |
| tga | 1011 |

```
<210> SEQ ID NO 4
<211> LENGTH: 336
<212> TYPE: PRT
<213> ORGANISM: Homo sapiens

<400> SEQUENCE: 4
```

Asp Arg Pro Leu Ser Val His Leu Asn Leu Gly Gln Lys Gly Asn Arg
1               5                   10                  15

Lys Thr Ser Cys Pro Ile Lys Ile Asn Gln Phe Glu Gly His Phe Met
            20                  25                  30

Lys Leu Gln Ala Asp Ser Asn Tyr Leu Leu Ser Lys Glu Tyr Glu Glu
        35                  40                  45

Leu Lys Asp Val Gly Arg Asn Gln Ser Cys Asp Ile Ala Leu Leu Pro
    50                  55                  60

Glu Asn Arg Gly Lys Asn Arg Tyr Asn Asn Ile Leu Pro Tyr Asp Ala
65                  70                  75                  80

Thr Arg Val Lys Leu Ser Asn Val Asp Asp Pro Cys Ser Asp Tyr
            85                  90                  95

Ile Asn Ala Ser Tyr Ile Pro Gly Asn Asn Phe Arg Arg Glu Tyr Ile
        100                 105                 110

```
Val Thr Gln Gly Pro Leu Pro Gly Thr Lys Asp Asp Phe Trp Lys Met
        115                 120                 125

Val Trp Glu Gln Asn Val His Asn Ile Val Met Val Thr Gln Cys Val
    130                 135                 140

Glu Lys Gly Arg Val Lys Cys Asp His Tyr Trp Pro Ala Asp Gln Asp
145                 150                 155                 160

Ser Leu Tyr Tyr Gly Asp Leu Ile Leu Gln Met Leu Ser Glu Ser Val
                165                 170                 175

Leu Pro Glu Trp Thr Ile Arg Glu Phe Lys Ile Cys Gly Glu Glu Gln
            180                 185                 190

Leu Asp Ala His Arg Leu Ile Arg His Phe His Tyr Thr Val Trp Pro
        195                 200                 205

Asp His Gly Val Pro Glu Thr Thr Gln Ser Leu Ile Gln Phe Val Arg
    210                 215                 220

Thr Val Arg Asp Tyr Ile Asn Arg Ser Pro Gly Ala Gly Pro Thr Val
225                 230                 235                 240

Val His Cys Ser Ala Gly Val Gly Arg Thr Gly Thr Phe Ile Ala Leu
                245                 250                 255

Asp Arg Ile Leu Gln Gln Leu Asp Ser Lys Asp Ser Val Asp Ile Tyr
            260                 265                 270

Gly Ala Val His Asp Leu Arg Leu His Arg Val His Met Val Gln Thr
        275                 280                 285

Glu Cys Gln Tyr Val Tyr Leu His Gln Cys Val Arg Asp Val Leu Arg
    290                 295                 300

Ala Arg Lys Leu Arg Ser Glu Gln Glu Asn Pro Leu Phe Pro Ile Tyr
305                 310                 315                 320

Glu Asn Val Asn Pro Glu Tyr His Arg Asp Pro Val Tyr Ser Arg His
                325                 330                 335

<210> SEQ ID NO 5
<211> LENGTH: 936
<212> TYPE: DNA
<213> ORGANISM: Homo sapiens
<220> FEATURE:
<221> NAME/KEY: CDS
<222> LOCATION: (1)..(936)

<400> SEQUENCE: 5 gat cga cca tta tct gtc cac tta aac ctg ggc cag aaa ggt aac cgg    48
Asp Arg Pro Leu Ser Val His Leu Asn Leu Gly Gln Lys Gly Asn Arg
1               5                   10                  15 aaa act tct tgt cca ata aaa ata aat cag ttt gaa ggg cat ttc atg    96
Lys Thr Ser Cys Pro Ile Lys Ile Asn Gln Phe Glu Gly His Phe Met
            20                  25                  30 aag cta cag gct gac tcc aac tac ctt cta tcc aag gaa tac gag gag   144
Lys Leu Gln Ala Asp Ser Asn Tyr Leu Leu Ser Lys Glu Tyr Glu Glu
        35                  40                  45 tta aaa gac gtg ggc cga aac cag tca tgt gac att gca ctc ttg ccg   192
Leu Lys Asp Val Gly Arg Asn Gln Ser Cys Asp Ile Ala Leu Leu Pro
    50                  55                  60 gag aat aga ggg aaa aat cga tac aac aat ata ttg ccc tat gat gcc   240
Glu Asn Arg Gly Lys Asn Arg Tyr Asn Asn Ile Leu Pro Tyr Asp Ala
65                  70                  75                  80 acg cga gtg aag ctc tcc aat gta gat gat gat cct tgc tct gac tac   288
Thr Arg Val Lys Leu Ser Asn Val Asp Asp Asp Pro Cys Ser Asp Tyr
                85                  90                  95 atc aat gcc agc tac atc cct ggc aac aac ttc aga aga gaa tac att   336
```

-continued

```
            Ile Asn Ala Ser Tyr Ile Pro Gly Asn Asn Phe Arg Arg Glu Tyr Ile
                        100                 105                 110 gtc act cag gga ccg ctt cct ggc acc aag gat gac ttc tgg aaa atg      384
Val Thr Gln Gly Pro Leu Pro Gly Thr Lys Asp Asp Phe Trp Lys Met
        115                 120                 125 gtg tgg gaa caa aac gtt cac aac atc gtc atg gtg acc cag tgt gtt      432
Val Trp Glu Gln Asn Val His Asn Ile Val Met Val Thr Gln Cys Val
130                 135                 140 gag aag ggc cga gta aag tgt gac cat tac tgg cca gcg gac cag gat      480
Glu Lys Gly Arg Val Lys Cys Asp His Tyr Trp Pro Ala Asp Gln Asp
145                 150                 155                 160 tcc ctc tac tat ggg gac ctc atc ctg cag atg ctc tca gag tcc gtc      528
Ser Leu Tyr Tyr Gly Asp Leu Ile Leu Gln Met Leu Ser Glu Ser Val
                165                 170                 175 ctg cct gag tgg acc atc cgg gag ttt aag ata tgc ggt gag gaa cag      576
Leu Pro Glu Trp Thr Ile Arg Glu Phe Lys Ile Cys Gly Glu Glu Gln
            180                 185                 190 ctt gat gca cac aga ctc atc cgc cac ttt cac tat acg gtg tgg cca      624
Leu Asp Ala His Arg Leu Ile Arg His Phe His Tyr Thr Val Trp Pro
        195                 200                 205 gac cat gga gtc cca gaa acc acc cag tct ctg atc cag ttt gtg aga      672
Asp His Gly Val Pro Glu Thr Thr Gln Ser Leu Ile Gln Phe Val Arg
    210                 215                 220 act gtc agg gac tac atc aac aga agc ccg ggt gct ggg ccc act gtg      720
Thr Val Arg Asp Tyr Ile Asn Arg Ser Pro Gly Ala Gly Pro Thr Val
225                 230                 235                 240 gtg cac tgc agt gct ggt gtg ggt agg act gga acc ttt att gca ttg      768
Val His Cys Ser Ala Gly Val Gly Arg Thr Gly Thr Phe Ile Ala Leu
                245                 250                 255 gac cga atc ctc cag cag tta gac tcc aaa gac tct gtg gac att tat      816
Asp Arg Ile Leu Gln Gln Leu Asp Ser Lys Asp Ser Val Asp Ile Tyr
            260                 265                 270 gga gca gtg cac gac cta aga ctt cac agg gtt cac atg gtc cag act      864
Gly Ala Val His Asp Leu Arg Leu His Arg Val His Met Val Gln Thr
        275                 280                 285 gag tgt cag tat gtc tac cta cat cag tgt gta aga gat gtc ctc aga      912
Glu Cys Gln Tyr Val Tyr Leu His Gln Cys Val Arg Asp Val Leu Arg
    290                 295                 300 gca aga aag cta cgg agt gaa caa                                      936
Ala Arg Lys Leu Arg Ser Glu Gln
305                 310

<210> SEQ ID NO 6
<211> LENGTH: 312
<212> TYPE: PRT
<213> ORGANISM: Homo sapiens

<400> SEQUENCE: 6

Asp Arg Pro Leu Ser Val His Leu Asn Leu Gly Gln Lys Gly Asn Arg
1               5                   10                  15

Lys Thr Ser Cys Pro Ile Lys Ile Asn Gln Phe Glu Gly His Phe Met
            20                  25                  30

Lys Leu Gln Ala Asp Ser Asn Tyr Leu Leu Ser Lys Glu Tyr Glu Glu
        35                  40                  45

Leu Lys Asp Val Gly Arg Asn Gln Ser Cys Asp Ile Ala Leu Leu Pro
    50                  55                  60

Glu Asn Arg Gly Lys Asn Arg Tyr Asn Asn Ile Leu Pro Tyr Asp Ala
65                  70                  75                  80

Thr Arg Val Lys Leu Ser Asn Val Asp Asp Asp Pro Cys Ser Asp Tyr
```

```
                    85                  90                  95
Ile Asn Ala Ser Tyr Ile Pro Gly Asn Asn Phe Arg Arg Glu Tyr Ile
            100                 105                 110

Val Thr Gln Gly Pro Leu Pro Gly Thr Lys Asp Asp Phe Trp Lys Met
            115                 120                 125

Val Trp Glu Gln Asn Val His Asn Ile Val Met Val Thr Gln Cys Val
            130                 135                 140

Glu Lys Gly Arg Val Lys Cys Asp His Tyr Trp Pro Ala Asp Gln Asp
145                 150                 155                 160

Ser Leu Tyr Tyr Gly Asp Leu Ile Leu Gln Met Leu Ser Glu Ser Val
                165                 170                 175

Leu Pro Glu Trp Thr Ile Arg Glu Phe Lys Ile Cys Gly Glu Glu Gln
            180                 185                 190

Leu Asp Ala His Arg Leu Ile Arg His Phe His Tyr Thr Val Trp Pro
            195                 200                 205

Asp His Gly Val Pro Glu Thr Thr Gln Ser Leu Ile Gln Phe Val Arg
            210                 215                 220

Thr Val Arg Asp Tyr Ile Asn Arg Ser Pro Gly Ala Gly Pro Thr Val
225                 230                 235                 240

Val His Cys Ser Ala Gly Val Gly Arg Thr Gly Thr Phe Ile Ala Leu
                245                 250                 255

Asp Arg Ile Leu Gln Gln Leu Asp Ser Lys Asp Ser Val Asp Ile Tyr
            260                 265                 270

Gly Ala Val His Asp Leu Arg Leu His Arg Val His Met Val Gln Thr
            275                 280                 285

Glu Cys Gln Tyr Val Tyr Leu His Gln Cys Val Arg Asp Val Leu Arg
            290                 295                 300

Ala Arg Lys Leu Arg Ser Glu Gln
305                 310

<210> SEQ ID NO 7
<211> LENGTH: 319
<212> TYPE: PRT
<213> ORGANISM: Homo sapiens

<400> SEQUENCE: 7

Gly Asp Arg Pro Leu Ser Val His Leu Asn Leu Gly Gln Lys Gly Asn
1               5                   10                  15

Arg Lys Thr Ser Cys Pro Ile Lys Ile Asn Gln Phe Glu Gly His Phe
            20                  25                  30

Met Lys Leu Gln Ala Asp Ser Asn Tyr Leu Leu Ser Lys Glu Tyr Glu
        35                  40                  45

Glu Leu Lys Asp Val Gly Arg Asn Gln Ser Cys Asp Ile Ala Leu Leu
    50                  55                  60

Pro Glu Asn Arg Gly Lys Asn Arg Tyr Asn Asn Ile Leu Pro Tyr Asp
65                  70                  75                  80

Ala Thr Arg Val Lys Leu Ser Asn Val Asp Asp Asp Pro Cys Ser Asp
                85                  90                  95

Tyr Ile Asn Ala Ser Tyr Ile Pro Gly Asn Asn Phe Arg Arg Glu Tyr
            100                 105                 110

Ile Val Thr Gln Gly Pro Leu Pro Gly Thr Lys Asp Asp Phe Trp Lys
            115                 120                 125

Met Val Trp Glu Gln Asn Val His Asn Ile Val Met Val Thr Gln Cys
        130                 135                 140
```

```
Val Glu Lys Gly Arg Val Lys Cys Asp His Tyr Trp Pro Ala Asp Gln
145                 150                 155                 160

Asp Ser Leu Tyr Tyr Gly Asp Leu Ile Leu Gln Met Leu Ser Glu Ser
                165                 170                 175

Val Leu Pro Glu Trp Thr Ile Arg Glu Phe Lys Ile Cys Gly Glu Glu
            180                 185                 190

Gln Leu Asp Ala His Arg Leu Ile Arg His Phe His Tyr Thr Val Trp
        195                 200                 205

Pro Asp His Gly Val Pro Glu Thr Thr Gln Ser Leu Ile Gln Phe Val
    210                 215                 220

Arg Thr Val Arg Asp Tyr Ile Asn Arg Ser Pro Gly Ala Gly Pro Thr
225                 230                 235                 240

Val Val His Cys Ser Ala Gly Val Gly Arg Thr Gly Thr Phe Ile Ala
                245                 250                 255

Leu Asp Arg Ile Leu Gln Gln Leu Asp Ser Lys Asp Ser Val Asp Ile
                260                 265                 270

Tyr Gly Ala Val His Asp Leu Arg Leu His Arg Val His Met Val Gln
            275                 280                 285

Thr Glu Cys Gln Tyr Val Tyr Leu His Gln Cys Val Arg Asp Val Leu
        290                 295                 300

Arg Ala Arg Lys Leu Arg Ser Glu Gln His His His His His His
305                 310                 315

<210> SEQ ID NO 8
<211> LENGTH: 21
<212> TYPE: DNA
<213> ORGANISM: Homo spaiens

<400> SEQUENCE: 8
gatcgaccat tatctgtcca c                                        21

<210> SEQ ID NO 9
<211> LENGTH: 20
<212> TYPE: DNA
<213> ORGANISM: Homo sapiens

<400> SEQUENCE: 9
caggagctct tcaggtacat                                          20

<210> SEQ ID NO 10
<211> LENGTH: 31
<212> TYPE: DNA
<213> ORGANISM: Homo sapiens

<400> SEQUENCE: 10
cgagcatacg tagatcgacc attatctgtc c                             31

<210> SEQ ID NO 11
<211> LENGTH: 31
<212> TYPE: DNA
<213> ORGANISM: Homo sapiens

<400> SEQUENCE: 11
cgagcaagct tattattgtt cactccgtag c                             31

<210> SEQ ID NO 12
<211> LENGTH: 56
<212> TYPE: DNA
<213> ORGANISM: Homo sapiens
```

-continued

```
<400> SEQUENCE: 12
gaaagctacg gagtgaacaa catcatcatc atcatcatta ataagcttgg cactgg          56

<210> SEQ ID NO 13
<211> LENGTH: 56
<212> TYPE: DNA
<213> ORGANISM: Homo sapiens

<400> SEQUENCE: 13
ccagtgccaa gcttattaat gatgatgatg atgatgttgt tcactccgta gctttc          56

<210> SEQ ID NO 14
<211> LENGTH: 52
<212> TYPE: DNA
<213> ORGANISM: Homo sapiens

<400> SEQUENCE: 14
aacaacaacc tcggggagaa tctttatttt cagggcgatc gaccattatc tg              52

<210> SEQ ID NO 15
<211> LENGTH: 52
<212> TYPE: DNA
<213> ORGANISM: Homo sapiens

<400> SEQUENCE: 15
cagataatgg tcgatcgccc tgaaaataaa gattctcccc gaggttgttg tt              52
```